US010435403B2

(12) United States Patent
Teller et al.

(10) Patent No.: US 10,435,403 B2
(45) Date of Patent: Oct. 8, 2019

(54) POSITIVE ALLOSTERIC MODULATORS OF MUSCARINIC M2 RECEPTOR

(71) Applicant: Bayer Pharma Aktiengesellschaft, Berlin (DE)

(72) Inventors: Henrik Teller, Schwaan (DE); Alexander Straub, Wuppertal (DE); Markus Brechmann, San Francisco, CA (US); Thomas Müller, Langenfeld (DE); Mark Meininghaus, Wuppertal (DE); Katrin Nowak-Reppel, Berlin (DE); Hanna Tinel, Wuppertal (DE); Klaus Münter, Wülfrath (DE); Daniela Fliegner, Berlin (DE); Thomas Mondritzki, Velbert (DE); Melissa Boultadakis Arapinis, Düsseldorf (DE); Tobias Marquardt, Wuppertal (DE); Alexandros Vakalopoulos, Hilden (DE); Anne-Sophie Rebstock, Champagne au Mont d'Or (FR); Matthias Beat Wittwer, Riehen (CH)

(73) Assignee: Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 15/735,138

(22) PCT Filed: Jun. 6, 2016

(86) PCT No.: PCT/EP2016/062737
§ 371 (c)(1),
(2) Date: Dec. 8, 2017

(87) PCT Pub. No.: WO2016/198342
PCT Pub. Date: Dec. 15, 2016

(65) Prior Publication Data
US 2018/0297994 A1 Oct. 18, 2018

(30) Foreign Application Priority Data

Jun. 9, 2015 (EP) .................................... 15171127
Feb. 22, 2016 (EP) .................................... 16156676

(51) Int. Cl.
| *C07D 471/04* | (2006.01) |
| *A61P 9/04* | (2006.01) |
| *A61K 31/4375* | (2006.01) |
| *A61K 31/4545* | (2006.01) |
| *A61K 31/496* | (2006.01) |
| *A61K 31/513* | (2006.01) |
| *A61K 31/5377* | (2006.01) |
| *A61K 45/06* | (2006.01) |
| *C07D 519/00* | (2006.01) |

(52) U.S. Cl.
CPC ........ *C07D 471/04* (2013.01); *A61K 31/4375* (2013.01); *A61K 31/4545* (2013.01); *A61K 31/496* (2013.01); *A61K 31/513* (2013.01); *A61K 31/5377* (2013.01); *A61K 45/06* (2013.01); *A61P 9/04* (2018.01); *C07D 519/00* (2013.01)

(58) Field of Classification Search
CPC .................................................... C07D 471/04
See application file for complete search history.

(56) References Cited

U.S. PATENT DOCUMENTS

| 4,990,517 A | 2/1991 | Petersen et al. |
| 5,496,947 A | 3/1996 | Yoon et al. |
| 7,488,739 B2 | 2/2009 | Watanuki et al. |

FOREIGN PATENT DOCUMENTS

| CA | 3030204 A1 | 1/2018 |
| CL | 200701360 | 11/2007 |
| CL | 201201605 | 6/2012 |
| CL | 201703138 | 6/2018 |
| CL | 201703147 | 6/2018 |
| EP | 0350733 A2 | 1/1990 |
| EP | 1650192 A1 | 4/2006 |
| EP | 3312177 A4 | 12/2018 |
| JP | 2005012561 | 1/2005 |
| WO | WO 2002/085886 A2 | 10/2002 |
| WO | WO 2003/050107 A1 | 6/2003 |
| WO | WO 2005/009971 A1 | 2/2005 |
| WO | WO 2005/049602 A1 | 2/2005 |
| WO | WO 2005/026145 A2 | 3/2005 |
| WO | WO 2005/026165 A1 | 3/2005 |
| WO | WO 2005/028451 A1 | 3/2005 |
| WO | WO 2005/056552 A1 | 6/2005 |
| WO | WO 2010/093341 A1 | 8/2010 |
| WO | WO2011084368 A1 | 7/2011 |

(Continued)

OTHER PUBLICATIONS

Bouzard et al. (1992). "Fluoronaphthyridines as Antibacterial Agents. 4. Synthesis and Structure- Activity Relationships of 5-Substituted-6-fluoro-7-(cycloalkylamino)-1,4-dihydro-4-oxo-1,8-naphthyridine-3-carboxylic Acids" *J. Med. Chem.* 35(3): 518-252.

(Continued)

*Primary Examiner* — Rebecca L Anderson
(74) *Attorney, Agent, or Firm* — Morrison & Foerster LLP

(57) ABSTRACT

The present application relates to positive allosteric modulators of the muscarinic M2 receptor, especially to novel 7-substituted 1-arylnaphthyridine-3-carboxamides, to processes for preparation thereof, to the use thereof, alone or in combinations, for treatment and/or prevention of diseases, and to the use thereof for production of medicaments for treatment and/or prevention of diseases, in particular for treatment and/or prevention of cardiovascular disorders and/or renal disorders.

8 Claims, No Drawings

(56) References Cited

FOREIGN PATENT DOCUMENTS

| WO | WO 2015/189560 A1 | 12/2015 |
|---|---|---|
| WO | WO 2016/071212 A1 | 5/2016 |
| WO | WO2016200851 A1 | 12/2016 |
| WO | WO2018011017 A1 | 1/2018 |
| WO | WO2018050510 A1 | 3/2018 |

OTHER PUBLICATIONS

Chen et al. (2014). "Role of the Autonomic Nervous System in Atrial Fibrillation" *Circ. Res.* 114(9): 1500-1515.

Christopoulos (2014). "Advances in G Protein-Coupled Receptor Allostery: From Function to Structure" *Mol. Pharmacol.* 86: 463-478.

Chu et al. (1992). "Synthesis and antibacterial activity of novel 6-fluoro-7-(gem-disubstituted piperazin-1-yl)-quinolines" *Can J. Chem.* 70: 1328-1337.

Clark et al. (1976). "The Inhibitory Effect of Gallamine on Muscarinic Receptors" *Br. J. Pharmac.* 58: 323-331.

Conn et al. (2009). "Allosteric modulators of GPCRs: a novel approach for the treatment of CNS disorders" *Nat. Rev. Drug. Discov.* 8(1): 41-54.

Conn et al. (2014). "Opportunities and challenges in the discovery of allosteric modulators of GPCRs for treating CNS disorders" *Nat. Rev. Drug Discov.* 13(9): 692-708.

Cooper et al. (1992). "Preparation and in Vitro and in Vivo Evaluation of Quinolones with Selective Activity against Gram-Positive Organisms" *J. Med. Chem.* 35(8): 1392-1398.

Croy et al. (2014). "Characterization of the Novel Positive Allosteric Modulator, LY2119620, at the Muscarinic $M_2$ and $M_4$ Receptors" *Molecular Pharmacology* 86: 106-115.

Davie et al. (2013). Development of $M_1$ mAChR Allosteric and Bitopic Ligands: Prospective Terapeutics for the Treatment of Cognitive Deficits: *ACS Chem. Neurosci.* 4: 1026-1048.

De Ferrari et al. (2011). "Chronic vagus nerve stimulation: a new and promising therapeutic approach for chronic heart failure" *Eur. Heart J.* 32: 847-855.

De Ferrari et al. (2014) "Vagal Stimulation in Heart Failure" *J. Cardiovasc.Transl. Res.* 7(3): 310-320.

European Search Report dated Oct. 20, 2016, for EP16188728.6, filed on Sep. 14, 2016, 9 pages.

Gold et al. (2016) "Vagus Nerve Stimulation for the Treatment of Heart Failure the INOVATE-HF Trial" *J Am Coll Cardiol* 68(2): 149-158.

Gregory et al. (2007) "Allosteric Modulation of Muscarinic Acetylcholine Receptors" *Current Neuropharmacol* 5(3): 157-167.

Halaris (2013) "Co-Morbidity between Cardiovascular Pathology and Depression: Role of Inflamation" *Mod Trends Pharmacopsychiatri.* 28: 144-161.

Hauptmann et al. (2012) "Rationale and study design of the Increase of Vagal TonE in Heart Failure study: INOVATE-HF" *Am Heart J* 163(6): 954-962.

He et al. (2014) "Novel strategies and underlying protective mechanisms of modulation of vagal activity in cardiovascular diseases" *Br. J. Pharmacol.* 12 pages.

International Search Report dated Aug. 22, 2016, for PCT/EP2016/062737, filed on Jun. 6, 2016, 8 pages. English translation included.

International Search Report & Written Opinion dated Sep. 22, 2017, for PCT/EP2017/066632, filed on Jul. 4, 2017, 14 pages. English translation of ISR included.

Klopman et al. (1996) "N-1-tert-Butyl-Substituted Quinolones: In Virto Anti-*Mycobacterium avium* Activities and Structure-Activity Relationship Studies" *Antimicrob. Agents Chemother.* 40(11): 2637-2643.

Kruse et al. (2013) "Muscarinic Receptors as Model Targets and Antitargets for Structure-Based Ligand Discovery" *Mol Pharmacol.* 84(4): 528-540.

Kruse et al. (2013) "Activation and allosteric modulation of a muscarinic acetylcholine receptor" *Nature* 504: 18 pages.

Leong-Sit et al. (2015) "Atrial fibrillation and heart failure: a bad combination" *Curr. Opin. Cardiol.* 7 pages.

Lewalter et al. (2011) "Pathophysiologie, Klinik ung Therapieoptionen bei Vorhofflimmern" *Fortbildungsprogramm Pharmazie* 5: 106-127. English translation of abstract only.

Maisel et al. (2003) "Atrial Fibrillation in Heart Failure: Epidemiology, Pathophysiology, and Rationale for Therapy" *Am. J. Cardiol.* 91(suppl): 2D-8D.

Mistry et al. (2013) "Synthesis and Pharmacological Profiling of Analogues of Benzyl Quinolone Carboxylic Acid (BQCA) as Allosteric Modulators of the $M_1$ Muscarinic Receptor" *J. Med. Chem.* 56: 5151-5172.

Neubig et al. (2003) "International Union of Pharmacology Committee on Receptor Nomenclature and Drug Classification. XXXVIII. Update on Terms and Symbols in Quantitative Pharmacology" *Pharmacol Rev.* 55(4): 597-606.

Premchand et al. (2014) "Autonomic Regulation Therapy via Left or Right Cervical Vagus Nerve Stimulation in Patients with Chronic Heart Failure: Results of the ANTHEM-HF Trial" *J. Card. Fail.* 20(11): 808-816.

Ranpuria et al. (2008) "Heart rate variability (HRV) in kidney failure: measurement and consequences of reduced HRV" *Nephrol Dial Transplant.* 23(2): 444-4499.

Rash et al. (2012) "Attention-deficit hyperactivity disorder and cardiac vagal control: a systematic review" *Atten Defic Hyperact Disord.* 4(4): 167-177.

Rosman et al. (1998) "Isotopic Compositions of the Elements 1997 (Technical Report)" *Pure Appl. Chem.* 70(1): 217-235.

Schober et al. (2014) "Development of a Radioligand, [$^3$H]LY2119620, to Probe the Human $M_2$ and $M_4$ Muscarinic Receptor Allosteric Binding Sites" *Molecular Pharmacology* 86:1: 116-123.

Schrage et al. (2014) "New insight into active muscarinic receptors with the novel radioagonist [$^3$H]iperoxo" *Biochem. Pharmacol.* 90(3): 307-319.

Sykora et al. (2009) "Baroreflex: A New Therapeutic Target in Human Stroke?" *Stroke* 40(12): e678-e682.

Wang et al. (2009) "Allosteric Modulators of G Protein-Coupled Receptors: Future Therapeutics for Complex Physiological Disorders" *J. Pharmacol. Exp. Therap.* 331(2): 340-348.

Zannad et al. (2015) "Chronic vagal stimulation for the treatment of low ejection fraction heart failure: results of the neural cardiac therapy for heart failure (NECTAR-HR) randomized controlled trial" *Eur. Heart J.* 36(7): 425-433.

Zhang et al. (2015) "Synthesis, antimycobacterial and antibacterial activity of fluoroquinolone derivatives containing an 3-alkoxyimino-4-(cycolpropylanimo)methylpyrrolidine moiety" *Eur J Med Chem* 104: 73-85.

International Preliminary Report on Patentability dated Jan. 24, 2019, for PCT Application No. PCT/EP2017/066632, filed on Jul. 4, 2017, 21 pages. German with English Translation.

Miao, Y. et al. (2016). "Accelerated structure-based design of chemically diverse allosteric modulators of a muscarinic 3 protein-coupled receptor," PNAS Early Edition, 113(38): E5675-E5684.

U.S. Appl. No. 16/317,322, filed Jan. 11, 2019, for Teller et al. (Copy not attached)(a copy of U.S. Patent Application is not submitted herewith pursuant to the waiver of 37C.F.R. § 1.98(a)(2)(iii) issued by the Office on Sep. 21, 2004.).

U.S. Appl. No. 16/333,079, filed Mar. 13, 2019, for Teller et al. (Copy not attached)(a copy of U.S. Patent Application is not submitted herewith pursuant to the waiver of 37C.F.R. § 1.98(a)(2)(iii) issued by the Office on Sep. 21, 2004.).

POSITIVE ALLOSTERIC MODULATORS OF MUSCARINIC M2 RECEPTOR

CROSS REFERENCE TO RELATED APPLICATIONS

This application is the national stage of International Application No. PCT/EP2016/062737, filed internationally on Jun. 6, 2016, which claims the benefit of European Application No. 16156676.5, filed Feb. 22, 2016, and European Application No. 15171127.2, filed Jun. 9, 2015.

The present application relates to positive allosteric modulators of the muscarinic M2 receptor, especially to novel 7-substituted 1-arylnaphthyridine-3-carboxamides, to processes for preparation thereof, to the use thereof, alone or in combinations, for treatment and/or prevention of diseases, and to the use thereof for production of medicaments for treatment and/or prevention of diseases, in particular for treatment and/or prevention of cardiovascular disorders and/or renal disorders.

Muscarinergic receptors are receptors which are positioned on the membrane and, as endogenous ligands, can bind the acetylcholine (ACh) neurotransmitter (acetylcholine receptors), but also be activated by muscarine. There are five subtypes of these G protein-coupled receptors (M1-M5) which are expressed in almost all kinds of tissue in the human organism. They are encountered both in the central and in the peripheral nervous system, and in many organs of the vegetative nervous system.

The M2 type (M2R) is expressed predominantly in the heart. At the cellular level, M2R stimulation by the acetylcholine agonist brings about inhibition of adenylcyclase and activation of the inwardly rectifying potassium channel (IKACh channel, GIRK (G protein activated inwardly rectifying K+ channel; also Kir3.x). This increases potassium conductivity, which leads to hyperpolarization of the muscle cells. Accordingly, the cells become more difficult to depolarize, which leads to an adverse chronotropic and dromotropic effect, and so the heart rate drops. M2R is the main mediator of the parasympathetic control of heart function, which is controlled by the vagus nerve. The right vagus nerve reduces the heart rate via the sinus node; the left vagus nerve predominantly increases the atrioventricular conduction time via the atrioventricular node (AV node). Overall, the influence of the vagus nerve on the resting heart rate is predominant compared to the sympathetic nerve. The effects of stimulation of M2R are thus opposed to those of beta-adrenergic stimulation.

The activation of the M2 receptor by the endogenous acetylcholine agonist, but also by synthetic analogues such as carbachol, oxotremorin-M or iperoxo (Schrage et al., Biochem. Phammcol. 2014, 90(3), 307-319), is effected by binding of the agonist to what is called the orthosteric binding site of the receptor and a resultant change in conformation of the receptor or stabilization of the active receptor confirmation. The conventional naturally occurring muscarine receptor agonists include, as well as the endogenous acetylcholine (ACh) agonist, various plant alkaloids such as arecoline, muscarine, and also pilocarpine (Neubig et al., Phammcol Rev., 2003, 55, 597-606). The orthosteric binding site of all muscarinic acetylcholine receptors is highly evolutionarily conserved and has a high sequence and structural homology between the various subtypes. Therefore, many of the known agonists are unselective with respect to the various subtypes of the muscarinic acetylcholine receptors (Kruse et al., Mol Pharmacol., 2013, 84(4), 528-540). M2R has, as well as an orthosteric binding site, an allosteric binding site as well (Gregory et al., Current Neurophannacol., 2007, 5(3), 157-167). The oldest known allosteric modulator is gallamine (Clark and Mitchelson, Br. J. Phammc., 1976, 58, 323-331).

Allosteric modulators have distinct differences from conventional orthosteric ligands. The allosteric modulator itself has no direct influence on receptor activation. The allosteric binding instead results in modulation of the binding affinity and/or effectiveness of the orthosteric agonist. The effect of an allosteric modulator can thus be displayed only in the presence of the endogenous ligand. This results in specificity in terms of space and time in the allosteric effect (Conn et al., Nat. Rev. Drug Disc., 2009, 8, 41-54; Conn et al, Nat. Rev. Drug. Disc., 2014, 13, 692-708). Furthermore, the effect of an allosteric modulator is self-limiting when it stabilizes the binding of the agonist in high concentrations. This in turn results, in principle, in a more favourable pharmacological safety profile compared to agonists, since toxic effects caused by receptor overactivation are limited (Christopoulos, Mol. Pharmacol., 2014, 86, 463-478).

The mutual influencing of allosteric and orthosteric ligands in terms of affinity and intrinsic activity, which is referred to as cooperativity, is determined by both ligands. In the case of a positive allosteric modulator of M2R, the effects of ACh (orthosteric ligand) are enhanced (positive cooperativity). Because of their ability to modulate receptor conformations in the presence of an orthosteric ligand, allosteric ligands can bring about fine adjustment of pharmacological effects (Wang et al., J. Pharmacol. Exp. Therap., 2009, 331, 340-348). In the case of the positive allosteric modulator of M2R, this suggests an advantageous effect profile, a reduced risk of side effects and a starting point for the development of more subtype-selective ligands compared to a full agonist.

The crystal structure of the positive allosteric M4R and M2R ligand LY2119620 (3-amino-5-chloro-N-cyclopropyl-4-methyl-6-[2-(4-methylpiperazin-1-yl)-2-oxoethoxy]thieno[2,3-b]pyridine-2-carboxamide) in a complex with M2R has been published. The allosteric binding site of M2R is spatially adjacent to but clearly delimited from the orthosteric binding site and, compared to the other muscarinic receptor subtypes, exhibits lower conservation, i.e. has greater differences in sequence (Kruse et al., Nature, 2013, 504, 101-106). LY2119620 was described as an unselective M2R/M4R positive allosteric modulator (Croy et al., Molecular Pharmacology, July 2014 86, 1, 106-115; Schober et al., Molecular Pharmacology, July 2014 86, 1, 116-123).

M2R as a constituent of the autonomic nervous system plays an important role in the pathogenesis and progression of cardiovascular disorders. Autonomic imbalance characterized by vagal (parasympathetic) weakening and dominance of the sympathetic nervous system is closely correlated to increased morbidity and mortality. The clinical and prognostic significance of autonomic imbalance is well-documented in various cardiovascular disorders, including heart failure (HF), heart rhythm disorders, ischaemia/reperfusion (I/R), hypertension (He et al., Br. J. Pharmacol. 2014, Epub) and chronic kidney disease (Ranpuria et al., Nephrol Dial Transplant. 2008, 23(2), 444-4499). Particularly in the case of patients having comorbidities such as diabetes, autonomic imbalance can contribute to increased morbidity and mortality (Vinik et al., Diabet Med., 2011, 28(6), 643-651). Baroreceptor reflex dysfunctions, such as hypertensive crises or variability in high blood pressure, as signs of a dysfunctional autonomic nervous system, often accompany the acute phase of ischaemic or haemorrhagic stroke (Sykora et al., *Stroke,* 2009, 40(12), 678-682).

The frequent observation of comorbidity between cardiovascular and psychological disorders, such as between heart failure and depression, is probably based on common pathomechanisms that accompany the autonomic imbalance (Halaris et al., *Mod Trends Phannacopsychiatri.,* 2013, 28, 144-161). Chronic stress shifts the homeostatic equilibrium of the autonomic nervous system. Reduced vagal tone contributes to pro-inflammatory status, with impairment of neurotransmitter regulation, especially serotonergic transmission. Other psychological disorders have also been connected to autonomic dysregulation, for example attention deficit/hyperactivity disorder (ADHD), which is characterized by loss of inhibition, lack of emotional self-control, inattentiveness and hyperactivity (Rash and Aguirre-Camacho, *Atten Defic Hyperact Disord.,* 2012, 4(4), 167-177).

Boosting parasympathetic activity by means of a positive allosteric modulator, including expected anti-inflammatory effects, elevation of nitrogen monoxide (NO), regulation of redox state, improvement of mitochondrial function and of calcium regulation, could therefore constitute a novel therapeutic principle, especially in the case of cardiovascular disorders. There are numerous pointers that the modulation of parasympathetic activity can be considered as a potential therapy target in the event of chronic heart failure. Vagal nerve stimulation in dogs that have recovered from myocardial infarction significantly lowered the incidence of sudden cardiac death, and mortality in rats suffering from chronic heart failure (De Ferrari, *J. Cardiovasc. Transl. Res.,* 2014, 7(3), 310-320). In a dog model with heart failure (LVEF 35%) and an implanted vagal stimulator, it was shown that, in the treatment group compared to the sham group, a significant improvement in the left-ventricular ejection fraction (LVEF) and reduction in the end-systolic and -diastolic volumes (LVESV, LVEDV) occurred, as did a significant reduction in heart rate within 3 months. The described effect of the VNS was additive to beta-blocker administration (De Ferrari, *J. Cardiovasc. Transl. Res.,* 2014, 7(3), 310-320). The plasma level for TNF-α and IL-6 and the myocardial protein expression thereof was lowered by vagal stimulation in this animal model, which suggests that boosting of the parasympathetic nervous system, as well as the effects on LV remodelling, also has positive effects on pro-inflammatory cytokines.

Based on experimental preclinical data, the first clinical studies on vagal stimulation in patients having chronic heart failure have now been done, as already established in the treatment of epilepsy and depression. The effect of boosting the parasympathetic system via direct vagal nerve stimulation (VNS) was assessed in a non-randomized observation study with 32 patients having left-ventricular (LV) systolic dysfunction, and the results suggest that vagal stimulation has a favourable effect on quality of life, stamina and LV remodelling (De Ferrari G M et al., *Eur. Heart J.,* 2011, 32, 847-855). In the multi-centre open-label feasibility study ANTHEM-HF, the safety, compatibility and efficacy of vagal stimulation in patients having chronic stable symptomatic heart failure with reduced ejection fraction (HFrEF) were examined in addition to the standard treatment (Premchand R K et al., *J. Card. Fail.,* 2014, 20(11), 808-816). The continuous vagal nerve stimulation employed in this study led to an improvement in the ejection fraction, variability of heart rate, NYHA class and quality of life. The first placebo-controlled clinical study NECTAR-HF, in contrast, did not show any significant effect of vagal nerve stimulation on the heart function of HF patients after 6 months (Zannad et al., *Eur. Heart J.,* 2015, 36(7), 425-433). The only improvement was in quality of life. The INOVATE-HF study with 650 HF patients was unable to show any effects of this treatment in relation to mortality and hospitalization. (Gold et al., *J Am Coll Cardiol.,* 2016, Mar. 29. pii: S0735-1097(16)32404-4. doi: 10.1016/j.jacc.2016.03.525). Quality of life and walking distance were significantly improved.

As well as the infection risk and the potential risks of a surgical intervention, treatment by means of electrical stimulation of the vagal nerve is limited by side effects such as dysphonia, coughing and oropharyngeal pain (Premchand R K et al., *J. Card. Fail.,* 2014, 20(11), 808-816). Medication-assisted boosting of the parasympathetic nervous system by a direct effect on M2R could constitute a novel therapy option.

Atrial fibrillation is the most common persistent heart rhythm disorder, and the prevalence thereof increases with age (Chen et al., *Circ. Res.,* 2014, 114(9), 1500-1515). Atrial fibrillation and heart failure often occur together in a mutually beneficial relationship. Thus, the prevalence of atrial fibrillation increases with the clinical severity of heart failure (Maisel and Stevenson, *Am. J. Cardiol.,* 2003, 91, (suppl) 2D-8D). Clinical data suggest that patients where heart failure is accompanied by atrial fibrillation have a poor prognosis. Both lethality (total lethality, sudden death and pump failure) and morbidity (hospitalization) were found to be significantly increased in this group of patients.

In the treatment of atrial fibrillation, there are two distinct treatment strategies: what is called rate control with adjustment and if at all possible normalization of ventricular frequency, and what is called rhythm control, comprising measures intended to establish or maintain a sinusoidal rhythm. An effective treatment consists of a combination of non-medication-assisted and medication-assisted or intervention measures (Levalter T, *Fortbildungsprogramm Pharmazie,* 2011, 5, 106-127).

For medication-assisted rhythm control after cardioversion, beta-blockers, class I and class III antiarrhythmics are used according to the underlying cardiac disorder and the extent of left-ventricular pumping function impairment. In patients having permanent atrial fibrillation and in oligosymptomatic (frequently older) patients having persistent or paroxysmal atrial fibrillation, simple rate control with retention and allowance of the atrial fibrillation is often the therapy of choice. Primarily medicaments that affect the refractory period or the conduction capacity of the AV node are used. In principle, this effect can be achieved by stimulation of the M2R, which plays the key physiological role at this point, for example with the aid of a positive allosteric modulator. The drugs available to date are beta-blockers, digitalis, calcium antagonists and, in individual cases, amiodarone, which are used with consideration of the lifestyle, underlying cardiac disorder and any secondary disorders. Especially in patients having reduced left ventricular pumping function and severe heart failure, however, the options for medication-assisted therapy are inadequate. Calcium antagonists are contraindicated in this group of patients. As the most recent studies have shown, treatment with digoxin leads to increased mortality of patients having atrial fibrillation (Leong-Sit and Tang, *Curr. Opin. Cardiol.,* 2015, Epub). For beta-blockers, a lack of effectiveness in patients having atrial fibrillation and heart failure was shown in a meta analysis (Leong-Sit and Tang, *Curr. Opin. Cardiol.,* 2015, Epub). The medical demand for novel efficient and safe treatments for rate control is correspondingly high. This could be achieved by medication-assisted stimulation of M2R.

The problem addressed by the present invention is that of identifying and providing novel substances which constitute potent, positive allosteric modulators of the muscarinic M2 receptor and as such are suitable for treatment and/or prevention particularly of cardiovascular disorders and/or renal disorders.

1-Benzyl-substituted 4-oxo-1,4-dihydroquinoline-3-carboxylic acids have been described as allosteric modulators of the M1 muscarine receptor for treatment of neurodegenerative disorders such as Alzheimer's and schizophrenia (Scammells et al., *ACS Chem. Neurosci.*, 2013, 4 (7), 1026-1048; Mistry et al., *J. Med. Chem.* 2013, 56, 5151-5172). Among other documents, EP 0945435 B1 discloses pyridonecarboxylic acid derivatives having antibacterial activity. WO 2002/085886-A2, WO 2003/050107-A1 and WO 2005/026145-A2 claim 7-piperidino-substituted quinolonecarboxylic acid derivatives, and WO 2005/026165-A1 and WO 2005/049602-A1 various 7-pyrrolidino-substituted quinolonecarboxylic acid derivatives, and EP 1650192-A1 specific 7-azetidinylquinolonecarboxylic acid derivatives having antimicrobial/antibacterial activity. WO 2005/009971-A1 and JP 2005012561 disclose quinolone derivatives which can be used as platelet aggregation inhibitors.

The present invention relates to positive allosteric modulators of the muscarinic M2 receptor for use in the treatment and/or prevention of disorders, especially of cardiovascular disorders and/or renal disorders.

The inventors have found that, surprisingly, the positive allosteric modulation of the muscarinic M2 receptor is particularly suitable for the treatment of cardiovascular disorders, preferably according to the aforementioned list of indications.

The positive allosteric M4R and M2R ligand LY2119620 is associated predominantly with neural and psychological disorders (Croy et al., *Molecular Pharmacology*, July 2014, 86, 1, 106-115). Molecules having a profile corresponding or similar to that of LY2119620 are thus unsuitable for a selected allosteric modification of the muscarinic M2 receptor, and hence treatment of cardiovascular disorders according to the aforementioned list of indications with a low level of side effects.

In an advantageous embodiment of the present invention, the inventive positive allosteric modulators of the muscarinic M2 receptor have subtype selectivity for the M2 receptor with regard to the positive allosteric effect.

In a particular embodiment, these have, within a concentration range of 1 μMAO μM, an identical or higher selectivity for the muscarinic M2 receptor than for the muscarinic M4 receptor. It is further preferable that the selectivity of the allosteric modulator for the muscarinic M2 receptor is at least 1.1 times, 1.2 times, 1.3 times or, more preferably, 1.4 times higher than that for the muscarinic M4 receptor.

In a further particular embodiment, these have, within a concentration range of 5 μM-20 μM, a selectivity at least 4 times higher for the muscarinic M2 receptor than for the muscarinic M1 receptor. It is preferably the case that the selectivity of the allosteric modulator for the muscarinic M2 receptor is at least 4.2 times, 4.3 times, 4.4 times, 4.5 times, 4.6 times, 4.7 times, 4.8 times, 4.9 times, 5 times, 5.1 times, 5.2 times, 5.3 times, 5.4 times, 5.5 times, 5.6 times, 5.7 times or, more preferably, 5.8 times higher than for the muscarinic M1 receptor.

The selectivity is determined here as the quotient of the respective modulator-related allosteric shift in the $EC_{50}$ value of the ACh dose-response curve for the M2 receptor relative to the respective other Mx receptor type. To determine said quotient, first of all, the $EC_{50}$ value of the ACh dose-response curve is determined for the particular receptors ("$EC_{50}$ ACh"). Subsequently, the allosteric shift in the $EC_{50}$ value of ACh ("shift $EC_{50}$") is determined after administration of 1 μM or 10 μM of the allosteric modulator to be tested. Especially suitable for this purpose is the protocol of the Eurofin functional $Ca^{2+}$ release test described on pages 610-612, section B-3. (GPCRProfiler® "Services in agonistic and allosteric mode for Mx Receptors"). Finally, quotients of the allosteric shift for the M2 receptor relative to the respective Mx receptor (e.g. M1R, M4R) are formed, which function in turn as a measure of the respective selectivity.

The invention especially relates to compounds of the general formula (I)

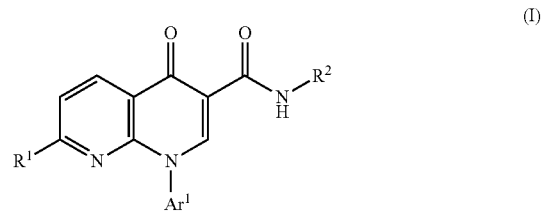

in which
$R^1$ is $NR^4R^5$,
in which
$R^4$ is hydrogen, methyl, $(C_2-C_4)$-alkyl or $(C_3-C_6)$-cycloalkyl,
  where $(C_2-C_4)$-alkyl may be substituted by hydroxyl or up to trisubstituted by fluorine and
$R^5$ is $(C_1-C_6)$-alkyl, $(C_3-C_6)$-cycloalkyl, 3- to 6-membered saturated heterocyclyl or $(C_1-C_4)$alkylsulphonyl,
  where $(C_1-C_6)$-alkyl, $(C_3-C_6)$-cycloalkyl and 3- to 6-membered saturated heterocyclyl may be up to trisubstituted, identically or differently, by methyl, difluoromethyl, trifluoromethyl, hydroxyl, hydroxycarbonyl, oxo, methoxy, difluoromethoxy, trifluoromethoxy and cyano, and additionally up to tetrasubstituted by fluorine,
or
$R^4$ and $R^5$ together with the nitrogen atom to which they are bonded form a saturated or partially unsaturated, 3- to 6-membered monocyclic or 6- to 10-membered bicyclic heterocycle which may contain one or two further, identical or different heteroatoms from the group of N, O, S, SO and/or $SO_2$ as ring members,
  where the 3- to 6-membered monocyclic and the 6- to 10-membered bicyclic heterocycle may each be substituted by 1 to 5 substituents independently selected from the group of $(C_1-C_4)$alkyl, difluoromethyl, trifluoromethyl, hydroxy, hydroxycarbonyl, oxo, $(C_1-C_3)$-alkoxy, difluoromethoxy, trifluoromethoxy, cyano, $(C_1-C_3)$-alkoxycarbonyl, aminocarbonyl, mono$(C_1-C_3)$-alkylaminocarbonyloxy, —NHC(=O)$R^{22A}$ and —$CH_2$NHC(=O)$R^{22B}$, and additionally up to tetrasubstituted by fluorine, in which $R^{22A}$ and $R^{22B}$ independently represent $(C_1-C_3)$-alkyl or cyclopropyl,
and
  in which $(C_1-C_4)$-alkyl may be mono- or disubstituted, identically or differently, by hydroxyl and $(C_1-C_3)$-alkoxy, and up to tetrasubstituted by fluorine, $R^2$ is a group of the formula

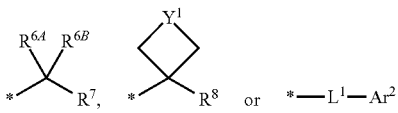

in which
* marks the bonding site to the nitrogen atom of the amide moiety,
$R^{6A}$ is hydrogen or $(C_1-C_4)$-alkyl,
$R^{6B}$ is hydrogen, $(C_1-C_4)$-alkyl, cyclopropyl, trifluoromethyl, methoxymethyl or trifluoromethoxymethyl,
$R^7$ is $(C_1-C_4)$-alkyl, cyclopropyl or cyclobutyl,
  where $(C_1-C_4)$-alkyl may be up to pentasubstituted and cyclopropyl and cyclobutyl up to tetrasubstituted by fluorine,
$Y^1$ is $-(CH_2)_k-$, $-CF_2-$, $-O-CH_2-$, $-CH_2-O-$ or $-CH_2-O-CH_2-$,
  in which
  k is 0, 1, 2 or 3,
$R^8$ is up to penta-fluorine-substituted $(C_1-C_2)$-alkyl or trifluoromethoxymethyl,
$L^1$ is a bond or a group of the formula $C(R^{9A}R^{9B})-(C(R^{10A}R^{10B}))_m-$,
  in which
  m represents 0 or 1,
  $R^{9A}$ represents hydrogen or methyl,
  $R^{9B}$ represents hydrogen, methyl, trifluoromethyl, pentafluoroethyl or trifluoromethoxymethyl,
  $R^{10A}$ and $R^{10B}$ independently represent hydrogen or methyl,
$Ar^2$ is phenyl,
  where phenyl may be mono- to trisubstituted, identically or differently, by fluorine, chlorine, $(C_1-C_3)$-alkyl, difluoromethoxymethyl, trifluoromethoxymethyl and/or trifluoromethyl,
or
is a 5- to 10-membered bicyclic or tricyclic carbocycle,
  where the 5- to 10-membered bicyclic or tricyclic carbocycle may be up to trisubstituted, identically or differently, by $(C_1-C_3)$-alkyl and trifluoromethyl, and additionally up to tetrasubstituted by fluorine,
$Ar^1$ is a group of the formula

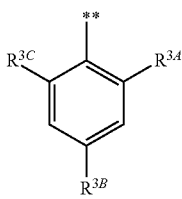

in which
** marks the bonding site to the nitrogen atom,
$R^{3A}$ is fluorine, chlorine or trifluoromethyl,
$R^{3B}$ is hydrogen or fluorine
and
$R^{3C}$ is hydrogen, fluorine or chlorine
and the N-oxides, salts, solvates, salts of the N-oxides and solvates of the N-oxides or salts thereof.

Compounds according to the invention are the compounds of the formula (I) and the salts, solvates and solvates of the salts thereof, the compounds that are encompassed by formula (I) and are of the formulae mentioned below and the salts, solvates and solvates of the salts thereof and the compounds that are encompassed by the formula (I) and are mentioned below as embodiments and the salts, solvates and solvates of the salts thereof if the compounds that are encompassed by the formula (I) and are mentioned below are not already salts, solvates and solvates of the salts.

Compounds according to the invention are likewise N-oxides of the compounds of the formula (I) and the salts, solvates and solvates of the salts thereof.

Preferred salts in the context of the present invention are physiologically acceptable salts of the compounds according to the invention. Also encompassed are salts which are not themselves suitable for pharmaceutical applications but can be used, for example, for the isolation, purification or storage of the compounds according to the invention.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically unacceptable salts of the compounds according to the invention also include salts of conventional bases, by way of example and with preference alkali metal salts (e.g. sodium and potassium salts), alkaline earth metal salts (e.g. calcium and magnesium salts), zinc salts and ammonium salts derived from ammonia or organic amines having 1 to 16 carbon atoms, by way of example and with preference ethylamine, diethylamine, triethylamine, DIPEA, monoethanolamine, diethanolamine, triethanolamine, dimethylaminoethanol, diethylaminoethanol, tris(hydroxymethyl)aminomethane, choline, procaine, dicyclohexylamine, dibenzylamine, N-methylmorpholine, N-methylpiperidine, arginine, lysine and 1,2-ethylenediamine.

Solvates in the context of the invention are described as those forms of the compounds according to the invention which form a complex in the solid or liquid state by coordination with solvent molecules. Hydrates are a specific form of the solvates in which the coordination is with water. Solvates preferred in the context of the present invention are hydrates.

The compounds according to the invention may, depending on their structure, exist in different stereoisomeric forms, i.e. in the form of configurational isomers or else, if appropriate, as conformational isomers (enantiomers and/or diastereomers, including those in the case of atropisomers). The present invention therefore encompasses the enantiomers and diastereomers, and the respective mixtures thereof. It is possible to isolate the stereoisomerically homogeneous constituents from such mixtures of enantiomers and/or diastereomers in a known manner Preference is given to employing chromatographic methods for this purpose, especially HPLC chromatography on achiral or chiral separation phases. In the case of carboxylic acids as intermediates or end products, separation is alternatively also possible via diastereomeric salts using chiral amine bases.

In the context of the present invention, the term "enantiomerically pure" is understood to the effect that the compound in question with respect to the absolute configuration of the chiral centres is present in an enantiomeric excess of more than 95%, preferably more than 98%. The enantiomeric excess, ee, is calculated here by evaluating an HPLC analysis chromatogram on a chiral phase using the formula below:

$$ee = \left| \frac{\text{Enantiomer 1 (area per cent)} - \text{Enantiomer 2 (area per cent)}}{\text{Enantiomer 1 (area per cent)} + \text{Enantiomer 2 (area per cent)}} \right| \times 100\%.$$

If the compounds according to the invention can occur in tautomeric forms, the present invention encompasses all the tautomeric forms.

The present invention also encompasses all suitable isotopic variants of the compounds according to the invention. An isotopic variant of a compound according to the invention is understood here to mean a compound in which at least one atom within the compound according to the invention has been exchanged for another atom of the same atomic number, but with a different atomic mass from the atomic mass which usually or predominantly occurs in nature ("unnatural fraction"). The expression "unnatural fraction" is understood to mean a fraction of such an isotope higher than its natural frequency. The natural frequencies of isotopes to be employed in this connection can be found in "Isotopic Compositions of the Elements 1997", Pure Appl. Chem., 70(1), 217-235, 1998. Examples of isotopes which can be incorporated into a compound according to the invention are those of hydrogen, carbon, nitrogen, oxygen, phosphorus, sulphur, fluorine, chlorine, bromine and iodine, such as $^2H$ (deuterium), $^3H$ (tritium), $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$. Particular isotopic variants of a compound according to the invention, especially those in which one or more radioactive isotopes have been incorporated, may be beneficial, for example, for the examination of the mechanism of action or of the drug distribution in the body; due to comparatively easy preparability and detectability, especially compounds labelled with $^3H$ or $^{14}C$ isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required; such modifications of the compounds according to the invention may therefore possibly also constitute a preferred embodiment of the present invention. With regard to the treatment and/or prophytaxis of the disorders specified here, the isotopic variant(s) of the compounds of the general formula (I) preferably contain deuterium ("deuterium-containing compounds of the general formula (I)"). Isotopic variants of the compounds of the general formula (I) into which one or more radioactive isotopes such as $^3H$ or $^{14}C$ have been incorporated are beneficial, for example, in medicament and/or substrate tissue distribution studies. Because of their easy incorporability and detectability, these isotopes are particularly preferred. It is possible to incorporate positron-emitting isotopes such as $^{18}F$ or $^{11}C$ into a compound of the general formula (I). These isotopic variants of the compounds of the general formula (I) are suitable for use in in vivo imaging applications. Deuterium-containing and $^{13}C$-containing compounds of the general formula (I) can be used within the scope of preclinical or clinical studies in mass spectrometry analyses (H. J. Leis et al., Curr. Org. Chem., 1998, 2, 131). Isotopic variants of the compounds according to the invention can be prepared by commonly used processes known to those skilled in the art, for example by the methods described further down and the procedures described in the working examples, by using corresponding isotopic modifications of the respective reagents and/or starting compounds.

Isotopic variants of the compounds of the general formula (I) can be prepared by processes known to those skilled in the art as described in the schemes and/or examples described here, by replacing a reagent with an isotopic variant of the reagent, preferably a deuterium-containing reagent. According to the deuteration sites desired, it is possible in some cases to incorporate deuterium from $D_2O$ directly into the compounds or into reagents which can be used for the synthesis of such compounds (Esaki et al., Tetrahedron, 2006, 62, 10954; Esaki et al., Chem. Eur. J., 2007, 13, 4052). Another useful reagent for incorporation of deuterium into molecules is deuterium gas. A rapid route for incorporation of deuterium is the catalytic deuteration of olefinic bonds (H. J. Leis et al., Curr. Org. Chem., 1998, 2, 131; J. R. Morandi et al., J. Org. Chem., 1969, 34 (6), 1889) and acetylenic bonds (N. H. Khan, J. Am. Chem. Soc., 1952, 74 (12), 3018; S. Chandrasekhar et al., Tetrahedron, 2011, 52, 3865). For direct exchange of hydrogen for deuterium in hydrocarbons containing functional groups, it is also possible to use metal catalysts (i.e. Pd, Pt and Rh) in the presence of deuterium gas (J. G. Atkinson et al., U.S. Pat. No. 3,966,781). Various deuterated reagents and synthesis units are commercially available from companies like, for example, C/D/N Isotopes, Quebec, Canada; Cambridge Isotope Laboratories Inc., Andover, Mass., USA; and CombiPhos Catalysts, Inc., Princeton, N.J., USA. Further information relating to the prior art with regard to deuterium-hydrogen exchange can be found, for example, in Hanzlik et al., J. Org. Chem., 1990, 55, 3992-3997; R. P. Hanzlik et al., Biochem. Biophys. Res. Commun., 1989, 160, 844; P. J. Reider et al., J. Org. Chem., 1987, 52, 3326-3334; M. Jarman et al., Carcinogenesis, 1993, 16(4), 683-688; J. Atzrodt et al., Angew. Chem., Int. Ed. 2007, 46, 7744; K. Matoishi et al., 2000, J. Chem. Soc, Chem. Commun., 1519-1520; K. Kassahun et al., WO 2012/112363.

The term "deuterium-containing compound of the general formula (I)" is defined as a compound of the general formula (I) in which one or more hydrogen atoms have been replaced by one or more deuterium atoms and in which the frequency of deuterium in every deuterated position in the compound of the general formula (I) is higher than the natural frequency of deuterium, which is about 0.015%. More particularly, in a deuterium-containing compound of the general formula (I), the frequency of deuterium in every deuterated position in the compound of the general formula (I) is higher than 10%, 20%, 30%, 40%, 50%, 60%, 70% or 80%, preferably higher than 90%, 95%, 96% or 97%, even further preferably higher than 98% or 99%, in this position or these positions. It will be apparent that the frequency of deuterium in every deuterated position is independent of the frequency of deuterium in other deuterated positions.

The selective incorporation of one or more deuterium atoms into a compound of the general formula (I) can alter the physicochemical properties (for example acidity [A. Streitwieser et al., J. Am. Chem. Soc., 1963, 85, 2759; C. L. Perrin et al., J. Am. Chem. Soc., 2007, 129, 4490], basicity [C. L. Perrin, et al., J. Am. Chem. Soc., 2003, 125, 15008; C. L. Perrin in Advances in Physical Organic Chemistry, 44, 144; C. L. Perrin et al., J. Am. Chem. Soc., 2005, 127, 9641], lipophilicity [B. Testa et al., Int. J. Pharm., 1984, 19(3), 271]) and/or the metabolic profile of the molecule, and cause changes in the ratio of parent compound to metabolites or the amounts of metabolites formed. Such changes may lead to particular therapeutic benefits and therefore be preferable under particular circumstances. Reduced rates of metabolism and metabolic switching, where the ratio of metabolites is changed, have been reported (D. J. Kushner et al., Can. J. Physiol. Pharmacol., 1999, 77, 79; A. E. Mutlib et al., Toxicol. Appl. Pharmacol., 2000, 169, 102). These changes in the exposure to parent drug and metabolites can have important consequences with respect to the pharmacodynamics, tolerability and efficacy of a deuterium-containing compound of the general formula (I). In some cases deuterium substitution reduces or eliminates the formation of an undesired or toxic metabolite and enhances the formation of a desired metabolite (e.g. Nevirapine: A. M. Sharma et al., Chem. Res. Toxicol., 2013, 26, 410; Uetrecht et al., Chemical Research in Toxicology, 2008, 21, 9, 1862; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. Indiplon (A. J. Morales et al., Abstract 285, The 15$^{th}$ North American Meeting of the International Society of Xenobiotics, San Diego, Calif., Oct. 12-16, 2008), ML-337 (C. J. Wenthur et al., J. Med. Chem., 2013, 56, 5208), and Odanacatib (K. Kassahun et al., WO2012/112363) are examples for this deuterium effect. Still other cases have been reported in which reduced rates of metabolism result in an increase in exposure of the drug without changing the rate of systemic clearance (e.g. Rofecoxib: F. Schneider et al., Arzneim. Forsch. Drug. Res., 2006, 56, 295; Telaprevir: F. Maltais et al., J. Med. Chem., 2009, 52, 7993). Deuterated drugs showing this effect may have reduced dosing requirements (e.g. lower number of doses or lower dosage to achieve the desired effect) and/or may produce lower metabolite loads.

A compound of general formula (I) may have multiple potential sites of attack for metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I), which are sites of attack for metabolizing enzymes such as e.g. cytochrome $P_{450}$.

In the context of the present invention, unless specified otherwise, the substituents are defined as follows:

Alkyl per se and "Alk" and "alkyl" in alkoxy, alkylsulphonyl, alkylaminocarbonyloxy and alkoxycarbonyl are a linear or branched alkyl radical having generally 1 to 6 and preferably 1 to 4 carbon atoms, by way of example and with preference methyl, ethyl, n-propyl, isopropyl, tert-butyl, isobutyl (2-methylprop-1-yl), n-pentyl and n-hexyl.

Alkoxy is, by way of example and with preference, methoxy, ethoxy, n-propoxy, isopropoxy, tert-butoxy, n-pentoxy and n-hexoxy.

Alkylaminocarbonyloxy is an alkylaminocarbonyloxy radical having one or two (independently chosen) alkyl substituents. $(C_1-C_3)$-Alkylaminocarbonyloxy is, for example, a monoalkylaminocarbonyloxy radical having 1 to 3 carbon atoms or a dialkylaminocarbonyloxy radical having 1 to 3 carbon atoms in each alkyl substituent. Preferred examples include: methylaminocarbonyloxy, ethylaminocarbonyloxy, n-propylaminocarbonyloxy, isopropylaminocarbonyloxy, tert-butylaminocarbonyloxy, n-pentylaminocarbonyloxy, n-hexylaminocarbonyloxy, N,N-dimethylaminocarbonyloxy, N,N-diethylaminocarbonyloxy, N-ethyl-N-methylaminocarbonyloxy, N-methyl-N-n-propylaminocarbonyloxy, N-isopropyl-N-n-propylaminocarbonyloxy, N-tert-butyl-N-methylaminocarbonyl, N-ethyl-N-n-pentylamino-carbonyl and N-n-hexyl-N-methylaminocarbonyloxy.

Alkylsulphonyl in the context of the invention is a straight-chain or branched alkyl radical which has 1 to 4 carbon atoms and is bonded via a sulphonyl group. Preferred examples include: methylsulphonyl, ethylsulphonyl, n-propylsulphonyl, isopropylsulphonyl, n-butylsulphonyl and tert-butylsulphonyl.

Alkoxycarbonyl is, by way of example and with preference, methoxycarbonyl, ethoxycarbonyl, n-propoxycarbonyl, isopropoxycarbonyl, tert-butoxycarbonyl, n-pentoxycarbonyl and n-hexoxycarbonyl.

Carbocycle in the context of the invention is a mono-, bi-, tri- or spirocyclic, saturated or partially unsaturated carbon cycle having a total of 3 to 10 ring atoms and up to 2 double bonds. A monocyclic saturated carbocycle is referred to synonymously as cycloalkyl. Examples include: cyclopropyl, cyclobutyl, cyclopentyl, cyclohexyl, cycloheptyl, cyclopentenyl, cyclohexenyl, cyclohexadienyl, cycloheptenyl, cycloheptadienyl, spiro[2.3]hexyl, spiro[2.4]heptyl, spiro[2.5]octyl, bicyclo[1.1.1]pentyl, bicyclo[2.2.1]heptyl, bicyclo[2.2.2]octyl, tricyclo[3.3.1.1$^{3,7}$]decyl. Preference is given to monocyclic cycloalkyl having 3 to 6 carbon atoms and bicyclic or tricyclic saturated carbocyclyl having 7 to 10 carbon atoms. Preferred examples include: cyclopropyl, cyclobutyl, cyclopentyl, cyclohexyl, bicyclo[1.1.1]pentyl, spiro[2.5]octyl, bicyclo[2.2.1]heptyl, bicyclo[2.2.2]octyl, tricyclo[3.3.1.1$^{3,7}$]decyl.

Cycloalkyl in the context of the invention is a monocyclic saturated cycloalkyl group having generally 3 to 8 and preferably 3 to 6 carbon atoms; preferred examples are cyclopropyl, cyclobutyl, cyclopentyl and cyclohexyl.

Heterocyclyl is a mono-, poly- or spirocyclic, preferably mono-, bi- or spirocyclic, nonaromatic heterocyclic radical having generally 3 to 10 ring atoms and up to 3, preferably up to 2, heteroatoms and/or hetero groups from the group of N, O, S, SO, $SO_2$. The heterocyclyl radicals may be saturated or partially unsaturated. Preference is given to 4- to 6-membered monocyclic saturated heterocyclyl radicals having one nitrogen atom and to those having one further heteroatom from the group of N, O, S, SO and $SO_2$, and 6- to 10-membered bicyclic saturated heterocyclyl radicals having one nitrogen atom and those having one further heteroatom from the group of N, O, S, SO and $SO_2$. Preferred examples include: aziridinyl, azetidinyl, pyrrolidinyl, piperidinyl, piperazinyl, oxazolidinyl, thiazolidinyl, thiadiazolidinyl, imidazolidinyl, imidazolidin-2-ylidene, morpholinyl, azaspiro[2.4]heptyl, azaspiro[3.3]heptyl, azabicyclo[3.1.0]hexyl, azabicyclo[3.2.1]octyl, perhydropyrrolo[3,4-c]pyrrolyl.

Halogen is fluorine, chlorine, bromine and iodine.

In the group of the formula that $R^2$, $Ar^1$ or Q may represent, the end point of the line marked by #$^1$, #$^2$, #$^2$; *,  and * is not a carbon atom or a $CH_2$ group, but is part of the bond to the respective atom to which $R^2$, $Ar^1$; $Ar^2$ or Q is bonded.

When radicals in the compounds according to the invention are substituted, the radicals may be mono- or polysubstituted, unless specified otherwise. In the context of the present invention, all radicals which occur more than once are defined independently of one another. When radicals in the compounds according to the invention are substituted, the radicals may be mono- or polysubstituted, unless specified otherwise. Substitution by one substituent or by two identical or different substituents is preferred.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" and "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

Preference is given in the context of the present invention to compounds of the formula (I) in which $R^1$ is $NR^4R^5$ in which $R^4$ is hydrogen, methyl, up to tri-fluorine-substituted $(C_2-C_4)$-alkyl or $(C_3-C_6)$-cycloalkyl, and $R^5$ is $(C_1-C_6)$-alkyl, $(C_3-C_6)$-cycloalkyl, 3- to 6-membered saturated heterocyclyl or $(C_1-C_4)$alkylsulphonyl, where $(C_1-C_6)$-alkyl, $(C_3-C_6)$-cycloalkyl and 3- to 6-membered saturated heterocyclyl may be up to trisubstituted, identically or differently, by methyl, difluoromethyl, trifluoromethyl, hydroxyl, oxo, methoxy, difluoromethoxy and trifluoromethoxy, and additionally up to tetrasubstituted by fluorine, or $R^4$ and $R^5$ together with the nitrogen atom to which they are bonded form a saturated or partially unsaturated, 3- to 6-membered monocyclic or 6- to 10-membered bicyclic heterocycle which may contain one or two further, identical or different heteroatoms from the group of N, O, S, SO and/or $SO_2$ as ring members, where the 3- to 6-membered monocyclic and the 6- to 10-membered bicyclic heterocycle may each be substituted by 1 to 5 substituents independently selected from the group of $(C_1-C_4)$-alkyl, difluoromethyl, trifluoromethyl, hydroxy, oxo, $(C_1-C_3)$-alkoxy, difluoromethoxy, trifluoromethoxy, cyano, $(C_1-C_3)$-alkoxycarbonyl, aminocarbonyl and mono-$(C_1-C_3)$ alkylaminocarbonyloxy, and additionally up to tetrasubstituted by fluorine, in which $(C_1-C_4)$-alkyl may be mono- or disubstituted, identically or differently, by hydroxyl and $(C_1-C_3)$-alkoxy, and up to tetrasubstituted by fluorine, $R^2$ is tert-butyl, 2-methylbutyl or is a group of the formula

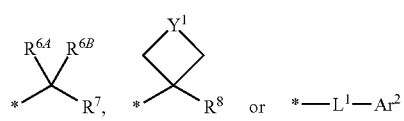

in which

\* marks the bonding site to the nitrogen atom of the amide moiety, $R^{6A}$ is hydrogen or $(C_1-C_4)$-alkyl, $R^{6B}$ is hydrogen, trifluoromethyl or trifluoromethoxymethyl, $R^7$ is $(C_1-C_4)$-alkyl or cyclopropyl, where $(C_1-C_4)$-alkyl may be up to pentasubstituted and cyclopropyl up to tetrasubstituted by fluorine, $Y^1$ is $—(CH_2)_k—$, $—O—CH_2—$, $—CH_2—O—$ or $—CH_2—O—CH_2—$, in which k is 1, 2 or 3, $R^8$ is up to penta-fluorine-substituted $(C_1-C_2)$-alkyl, $L^1$ is a bond or a group of the formula $—CR^{9A}R^{9B}—(CR^{10A}R^{10B})_m—$, in which m represents 0 or 1, $R^{9A}$ represents hydrogen or methyl, $R^{9B}$ represents hydrogen, methyl, trifluoromethyl, pentafluoroethyl or trifluoromethoxymethyl, $R^{10A}$ and $R^{10B}$ independently represent hydrogen or methyl, $Ar^2$ is phenyl, where phenyl may be mono- to trisubstituted, identically or differently, by fluorine, chlorine, $(C_1-C_3)$-alkyl, difluoromethoxymethyl, trifluoromethoxymethyl and/or trifluoromethyl, or is a 7- to 10-membered bicyclic or tricyclic carbocycle, where the 7- to 10-membered bicyclic or tricyclic carbocycle may be up to trisubstituted, identically or differently, by $(C_1-C_3)$-alkyl and trifluoromethyl, and additionally up to tetrasubstituted by fluorine, $Ar^1$ is a group of the formula

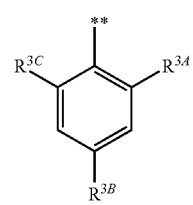

in which

\*\* marks the bonding site to the nitrogen atom, $R^{3A}$ is fluorine, chlorine or trifluoromethyl, $R^{3B}$ is hydrogen or fluorine and $R^{3C}$ is hydrogen, fluorine or chlorine and the N-oxides, salts, solvates, salts of the N-oxides and solvates of the N-oxides or salts thereof.

Preference is given in the context of the present invention to compounds of the formula (I)

in which $R^1$ is $NR^4R^5$, in which $R^4$ is hydrogen or methyl, and $R^5$ is $(C_1$-$C_4)$-alkyl or methylsulphonyl,
where $(C_1$-$C_4)$-alkyl may be up to disubstituted by hydroxyl and additionally up to trisubstituted by fluorine,
or
$R^4$ and $R^5$ together with the nitrogen atom to which they are bonded form a saturated or partially unsaturated, 4- to 6-membered monocyclic or 6- to 10-membered bicyclic heterocycle which may contain one or two further heteroatoms from the group of N, O, S, SO and $SO_2$ as ring member,
where the 4- to 6-membered monocyclic and the 6- to 10-membered bicyclic heterocycle may each be substituted by 1 to 5 substituents independently selected from the group of $(C_1$-$C_3)$alkyl, difluoromethyl, trifluoromethyl, hydroxymethyl, hydroxyethyl, hydroxyl, oxo, methoxy, difluoromethoxy, trifluoromethoxy, methoxymethyl, cyano, methoxycarbonyl, aminocarbonyl and monomethylaminocarbonyloxy, and additionally up to tetrasubstituted by fluorine,
$R^2$ is a group of the formula

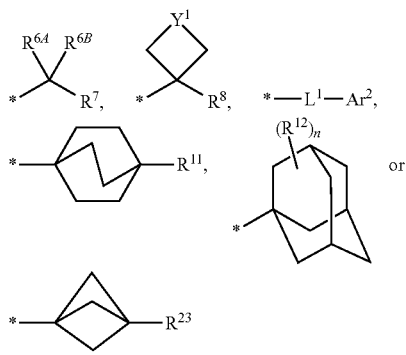

in which
* marks the bonding site to the nitrogen atom of the amide moiety,
$R^{6A}$ is hydrogen or methyl,
$R^{6B}$ is hydrogen, $(C_1$-$C_4)$-alkyl, cyclopropyl, trifluoromethyl or trifluoromethoxymethyl,
$R^7$ is $(C_1$-$C_4)$-alkyl, cyclopropyl or cyclobutyl,
where $(C_1$-$C_4)$-alkyl may be up to pentasubstituted by fluorine,
$Y^1$ is —$(CH_2)_k$—, —$CF_2$—, —O—$CH_2$—, —$CH_2$—O— or —$CH_2$—O—$CH_2$—,
in which
k is 0, 1, 2 or 3,
$R^8$ is methyl, trifluoromethyl or 2,2,2-trifluoroethyl,
$L^1$ is a bond or a group of the formula —$CR^{9A}R^{9B}$—,
in which
$R^{9A}$ represents hydrogen or methyl,
$R^{9B}$ represents hydrogen, methyl, trifluoromethyl or trifluoromethoxymethyl,
$Ar^2$ is phenyl,
which may be mono- or disubstituted, identically or differently, by fluorine, chlorine, methyl and/or trifluoromethyl,
$R^{11}$, $R^{12}$ and $R^{23}$ are each independently hydrogen, fluorine, methyl, ethyl or trifluoroethyl,
n is the number 1 or 2,
where, if one of the substituents $R^{11}$, $R^{12}$ or $R^{23}$ occurs twice in each case, its definitions may independently be the same or different, $Ar^1$ is a group of the formula

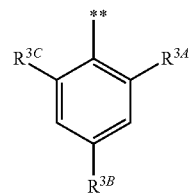

in which
** marks the bonding site to the nitrogen atom,
$R^{3A}$ is fluorine, chlorine or trifluoromethyl,
$R^{3B}$ is hydrogen or fluorine
and
$R^{3C}$ is hydrogen, fluorine or chlorine,
and the salts, solvates and solvates of the salts thereof.
Preference is given in the context of the present invention to compounds of the formula (I) in which
$R^1$ is $NR^4R^5$,
in which
$R^4$ is hydrogen or methyl,
and
$R^5$ is $(C_1$-$C_4)$-alkyl or methylsulphonyl,
where $(C_1$-$C_4)$-alkyl may be substituted by hydroxyl and additionally up to trisubstituted by fluorine,
or
$R^4$ and $R^5$ together with the nitrogen atom to which they are bonded form a saturated 4- to 6-membered monocyclic or 6- to 10-membered bicyclic heterocycle which may contain one further heteroatom from the group of N, O, S, SO and $SO_2$ as ring member, where the 4- to 6-membered monocyclic and the 6- to 10-membered bicyclic heterocycle may each be substituted by 1 to 4 substituents independently selected from the group of $(C_1$-$C_3)$-alkyl, difluoromethyl, trifluoromethyl, hydroxymethyl, hydroxyethyl, hydroxyl, oxo, methoxy, difluoromethoxy, trifluoromethoxy, methoxymethyl, cyano, methoxycarbonyl, aminocarbonyl and monomethylaminocarbonyloxy, and additionally up to tetrasubstituted by fluorine,
$R^2$ is tert-butyl
or
is a group of the formula

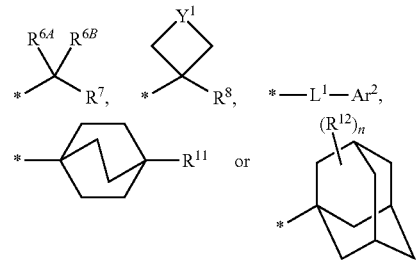

in which
*marks the bonding site to the nitrogen atom of the amide moiety,
$R^{6A}$ is hydrogen or methyl,
$R^{6B}$ is hydrogen, trifluoromethyl or trifluoromethoxymethyl, $R^7$ is $(C_1-C_4)$-alkyl or cyclopropyl,
where $(C_1-C_4)$-alkyl may be up to pentasubstituted by fluorine,
$Y^1$ is —$(CH_2)_k$—, —O—$CH_2$—, —$CH_2$—O— or —$CH_2$—O—$CH_2$—,
in which
k is 1, 2 or 3,
$R^8$ is methyl or trifluoromethyl,
$L^1$ is a bond or a group of the formula —$CR^{9A}R^{9B}$—,
in which
$R^{9A}$ represents hydrogen or methyl,
$R^{9B}$ represents hydrogen, methyl, trifluoromethyl or trifluoromethoxymethyl,
$Ar^2$ is phenyl,
which may be mono- or disubstituted, identically or differently, by fluorine, chlorine, methyl and/or trifluoromethyl,
$R^{11}$ and $R^{12}$ are independently hydrogen, fluorine, methyl, ethyl or trifluoromethyl,
n is the number 1 or 2,
where, if the substituent $R^{12}$ occurs twice, its definitions may be the same or different,
$Ar^1$ is a group of the formula

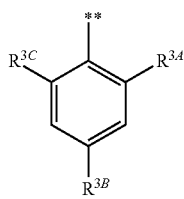

in which
** marks the bonding site to the nitrogen atom,
$R^{3A}$ is fluorine, chlorine or trifluoromethyl,
$R^{3B}$ is hydrogen or fluorine
and
$R^{3C}$ is hydrogen, fluorine or chlorine
and the salts, solvates and solvates of the salts thereof.

A particular embodiment of the present invention encompasses compounds of the formula (I) in which $R^1$ is a group of the formula

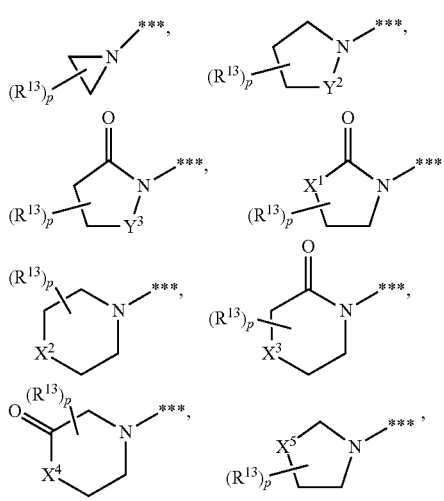
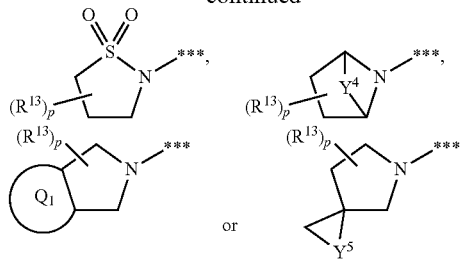

in which
** marks the bonding site to the carbon atom of the pyridine ring,
$Y^2$ and $Y^3$ are independently a bond, —$CH_2$— or —$(CH_2)_2$—,
$Y^4$ is —$(CH_2)_2$—, —$(CH_2)_3$— or —$CH_2$—O—$CH_2$—,
$Y^5$ is —$CF_2$—,
$X^1$, $X^3$ and $X^4$ are independently —O— or —NH—,
$X^2$ is —O— or —$NR^{14}$—
in which
$R^{14}$ is hydrogen, $(C_1-C_3)$-alkoxycarbonyl or aminocarbonyl,
$X^5$ is $S(O)_t$,
in which
t is 0, 1 or 2,
the ring $Q_1$ together with the atoms to which it is bonded forms a three-membered saturated carbocycle,
where the three-membered saturated carbocycle may be monosubstituted by hydroxyl or hydroxymethyl or up to disubstituted by fluorine,
or is a group of the formula

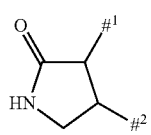

in which
$^1$ and #$^2$ mark the bonding site to the carbon atom of the pyrrolidine ring,
$R^{13}$ is fluorine, $(C_1-C_3)$-alkyl, difluoromethyl, trifluoromethyl, hydroxyl, hydroxymethyl, hydroxyethyl, methoxy, difluoromethoxy, trifluoromethoxy, methoxymethyl, cyano, methoxycarbonyl or monomethylaminocarbonyloxy,
p is the number 0, 1, 2, 3 or 4,
where, in the case that the substituents $R^{13D}$, $R^{13E}$ and $R^{13F}$ occur more than once, the definitions thereof may each be the same or different.

Preference is given in the context of the present invention to compounds of the formula (I) in which
$R^1$ is $NR^4R^5$,
in which
$R^4$ is hydrogen or methyl,
and
$R^5$ is methyl, isopropyl, 2,2-difluoroethyl, 2,2,2-trifluoroethyl, 2-hydroxyethyl or 2-hydroxypropyl,
or
is a 4- to 6-membered monocyclic or 6- to 8-membered bicyclic heterocycle which is bonded via a nitrogen atom and is of the formula

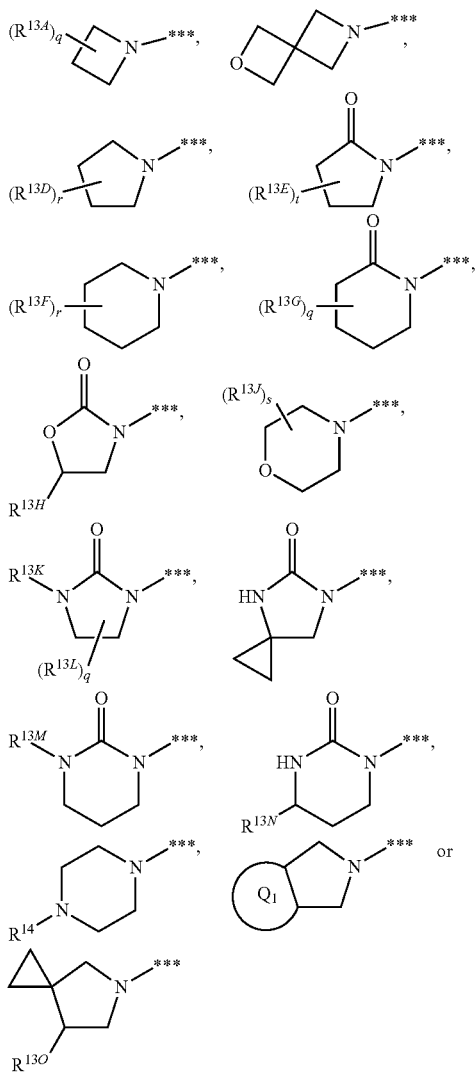

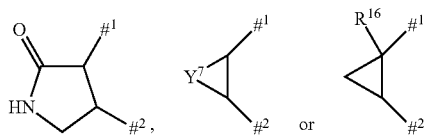

in which
*** marks the bonding site to the carbon atom of the pyridine ring,
the ring $Q_1$ is a group of the formula

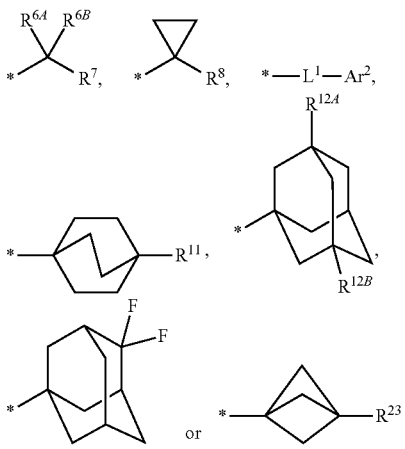

in which
$\#^1$ and $\#^2$ mark the bonding site to the carbon atom of the pyrrolidine ring,
and
$Y^7$ is —$CF_2$— or —$CHR^{15}$—,
in which
$R^{15}$ represents methoxymethyl,
and
$R^{16}$ is hydroxyl,
$R^{13A}$ is fluorine, hydroxyl, hydroxymethyl, methyl, trifluoromethyl or methoxy, $R^{13D}$ is hydrogen, fluorine, methyl, hydroxyl, hydroxymethyl, methoxy or difluoromethoxy,
$R^{13E}$ is hydrogen, fluorine, methyl, hydroxyl, hydroxymethyl or methoxy,
$R^{13F}$ is fluorine, methyl, hydroxyl, hydroxymethyl or cyano,
$R^{13G}$ is fluorine or hydroxyl,
$R^{13H}$ is hydrogen, methyl, hydroxymethyl, aminocarbonyl or methoxycarbonyl,
$R^{13J}$ is oxo, hydroxymethyl or difluoromethyl,
$R^{13K}$ is hydrogen, methyl or 2-hydroxyethyl,
$R^{13L}$ is hydrogen or methyl,
$R^{13M}$ is ethyl, 2-hydroxyethyl or cyano,
$R^{13N}$ is hydrogen or ethyl,
$R^{13O}$ is hydrogen or hydroxyl,
$R^{14}$ is methyl, methoxycarbonyl or aminocarbonyl,
q is the number 0, 1 or 2,
r is the number 0, 1, 2 or 3,
s is the number 0 or 1,
t is the number 0, 1, 2, 3 or 4,
where, in the case that the substituents $R^{13A}$, $R^{13D}$, $R^{13E}$, $R^{13F}$, $R^{13G}$, $R^{13J}$ and $R^{13L}$ occur more than once, the definitions thereof may each be the same or different,
$R^2$ is a group of the formula in which
*marks the bonding site to the nitrogen atom of the amide moiety,
$R^{6A}$ is hydrogen or methyl,
$R^{6B}$ is methyl, ethyl, cyclopropyl, trifluoromethyl or trifluoromethoxymethyl,
$R^7$ is methyl, ethyl, n-propyl, isopropyl, tert-butyl, 2-methylprop-1-yl, trifluoromethyl, difluoromethyl, pentafluoroethyl, 2,2,2-trifluoroethyl or cyclopropyl,
$R^8$ is 2,2,2-trifluoroethyl,
$L^1$ is a bond or a group of the formula —$CR^{9A}R^{9B}$—,
in which
$R^{9A}$ represents hydrogen or methyl,
$R^{9B}$ represents hydrogen, methyl, trifluoromethyl or trifluoromethoxymethyl,
$Ar^2$ is phenyl,
which may be mono- or disubstituted, identically or differently, by fluorine, chlorine, methyl and/or trifluoromethyl,
$R^{11}$ is hydrogen, fluorine or methyl,
$R^4$ is hydrogen, fluorine, methyl, ethyl or trifluoromethyl,
$R^{12B}$ is hydrogen or fluorine,
$R^{23}$ is hydrogen, fluorine or trifluoromethyl, and
Ar¹ is a group of the formula in which
** marks the bonding site to the nitrogen atom,
R³ᴬ is fluorine or chlorine,
R³ᴮ is hydrogen or fluorine,
and
R³ᶜ is hydrogen, fluorine or chlorine
and the salts, solvates and solvates of the salts thereof.

In the context of the present invention, particular preference is given to compounds of the formula (I) in which
R¹ is a group of the formula in which
*** marks the bonding site to the carbon atom of the pyridine ring,
R¹³ᴰᴬ is hydrogen or methyl,
R¹³ᴱᴬ is hydroxyl or hydroxymethyl,
R¹³ᴱᴮ is methyl or hydroxymethyl,
R¹³ᴱᶜ is hydrogen or methyl,
R¹³ᴸᴬ is hydrogen or methyl,
R² is a group of the formula in which
* marks the bonding site to the nitrogen atom of the amide moiety,
R⁶ᴮ is trifluoromethoxymethyl,
R⁷ᴬ is methyl, ethyl, trifluoromethyl or cyclopropyl,
R⁷ᴮ is trifluoromethyl, difluoromethyl or 2,2,2-trifluoroethyl,
R⁷ᶜ is methyl or ethyl,
R¹⁹ is chlorine,
and
Ar¹ is a group of the formula in which
** marks the bonding site to the nitrogen atom,
R³ᴬ is fluorine or chlorine, and
R³ᶜ is hydrogen or fluorine,
and the salts, solvates and solvates of the salts thereof.

In the context of the present invention, very particular preference is given to compounds of the formula (I) in which
R¹ is a group of the formula

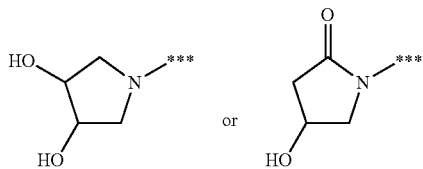

in which
*** marks the bonding site to the carbon atom of the pyridine ring,
$R^2$ is a group of the formula

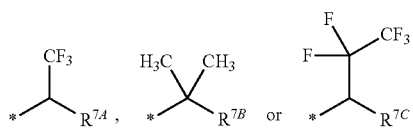

in which
*marks the bonding site to the nitrogen atom of the amide moiety,
$R^{7A}$ is ethyl, trifluoromethyl or cyclopropyl,
$R^{7B}$ is trifluoromethyl,
$R^{7C}$ is methyl or ethyl,
and
$Ar^1$ is a group of the formula

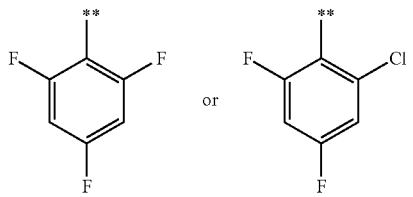

in which
** marks the bonding site to the nitrogen atom,
and the salts, solvates and solvates of the salts thereof.
Preference is given in the context of the present invention to compounds of the formula (I) in which
$R^1$ is $NR^4R^5$,
in which
$R^4$ is hydrogen or methyl,
and
$R^5$ is methyl, isopropyl, 2,2-difluoroethyl or 2,2,2-trifluoroethyl,
or
is a 4- to 6-membered monocyclic or 6- to 8-membered bicyclic heterocycle which is bonded via a nitrogen atom and is of the formula

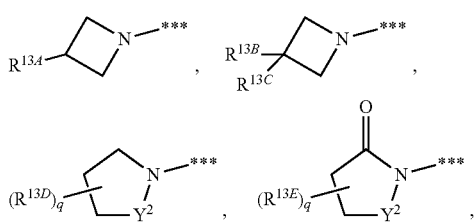

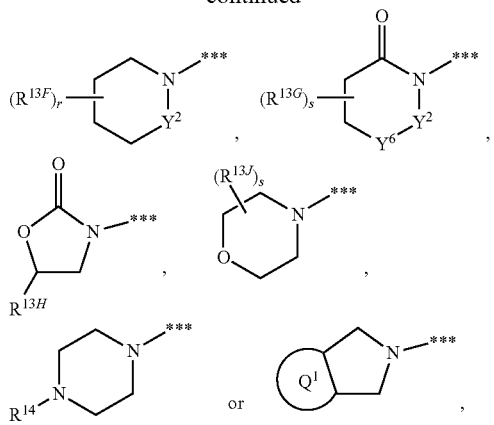

in which
*** marks the bonding site to the carbon atom of the pyridine ring,
$Y^2$ is $-CH_2-$,
$Y^6$ is $-CH_2-$ or $-CF_2-$,
the ring $Q_1$ is a group of the formula

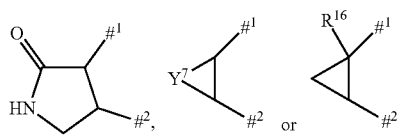

in which
$\#^1$ and $\#^2$ mark the bonding site to the carbon atom of the pyrrolidine ring,
$Y^7$ is $-CH_2-$ or $-CHR^{15}-$,
in which
$R^{15}$ represents methoxymethyl,
and
$R^{16}$ is hydroxyl,
$R^{13A}$ is fluorine, hydroxyl or hydroxymethyl,
$R^{13B}$ is hydroxyl,
$R^{13C}$ is trifluoromethyl,
$R^{13D}$ is fluorine, methyl, hydroxyl, hydroxymethyl, methoxy or difluoromethoxy,
$R^{13E}$ is fluorine, methyl, hydroxyl or methoxy,
$R^{13F}$ is fluorine, methyl, hydroxyl, hydroxymethyl or cyano,
$R^{13G}$ is hydroxyl,
$R^{13H}$ is hydrogen, methyl, hydroxymethyl or methoxycarbonyl,
$R^{13J}$ is hydroxymethyl or difluoromethyl,
$R^{14}$ is methoxycarbonyl or aminocarbonyl,
q is the number 0, 1 or 2,
r is the number 0, 1, 2 or 3,
s is the number 0 or 1,
where, in the case that the substituents $R^{13D}$, $R^{13E}$ and $R^{13F}$ occur more than once, the definitions thereof may each be the same or different, $R^2$ is tert-butyl
or
is a group of the formula

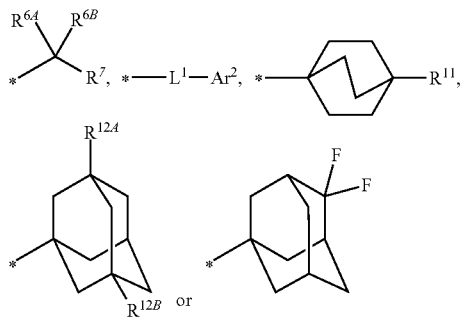

in which
* marks the bonding site to the nitrogen atom of the amide moiety,
$R^{6A}$ is hydrogen or methyl,
$R^{6B}$ is trifluoromethyl or trifluoromethoxymethyl,
$R^7$ is methyl, ethyl, n-propyl, isopropyl, tert-butyl, 2-methylprop-1-yl, trifluoromethyl or cyclopropyl,
$L^1$ is a bond or a group of the formula $-CR^{9A}R^{9B}-$,
in which
$R^{9A}$ represents hydrogen or methyl,
$R^{9B}$ represents hydrogen, methyl, trifluoromethyl or trifluoromethoxymethyl,
$Ar^2$ is phenyl,
which may be mono- or disubstituted, identically or differently, by fluorine, chlorine, methyl and/or trifluoromethyl,
$R^{11}$ is hydrogen, fluorine or methyl,
$R^{12A}$ is hydrogen, fluorine, methyl, ethyl or trifluoromethyl,
$R^{12B}$ is hydrogen or fluorine,
and
$Ar^1$ is a group of the formula

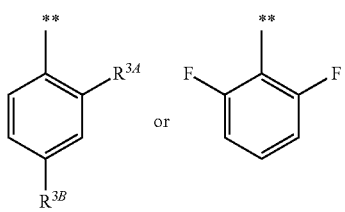

in which
** marks the bonding site to the nitrogen atom,
$R^{3A}$ is fluorine or chlorine,
and
$R^{3B}$ is hydrogen or fluorine,
and the salts, solvates and solvates of the salts thereof.
Preference is given in the context of the present invention to compounds of the formula (I) in which
$R^1$ is a group of the formula

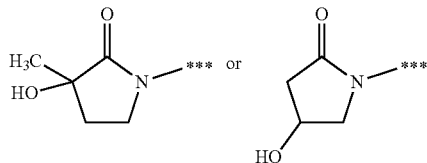

in which
*** marks the bonding site to the carbon atom of the pyridine ring,
$R^2$ is a group of the formula

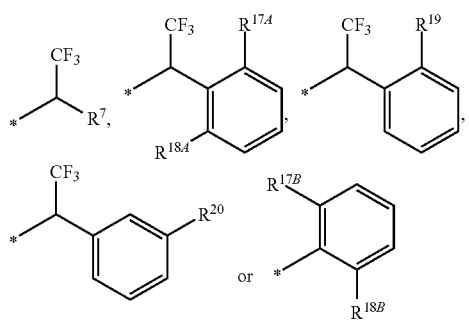

in which
* marks the bonding site to the nitrogen atom of the amide moiety,
$R^7$ is ethyl or cyclopropyl,
$R^{17A}$ is fluorine or chlorine,
$R^{18A}$ is fluorine,
$R^{17B}$ and $R^{18B}$ are each chlorine,
$R^{19}$ is fluorine or chlorine,
$R^{20}$ is fluorine,
and
$Ar^1$ is a group of the formula

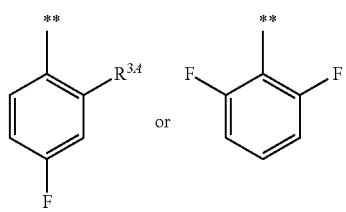

in which
** marks the bonding site to the nitrogen atom,
$R^{3A}$ is fluorine or chlorine,
and the salts, solvates and solvates of the salts thereof.
A further particular embodiment of the present invention encompasses compounds of the formula (I) in which
$R^2$ is tert-butyl
or
is a group of the formula

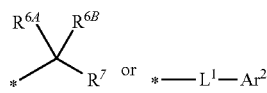

in which

* marks the bonding site to the nitrogen atom of the amide moiety,
$R^{6A}$ is hydrogen or methyl,
$R^{6B}$ is trifluoromethyl or trifluoromethoxymethyl,
$R^7$ is methyl, ethyl, n-propyl, isopropyl, tert-butyl, 2-methylprop-1-yl, trifluoromethyl or cyclopropyl,
$L^1$ is a bond or a group of the formula —$CR^{9A}R^{9B}$—,
in which
$R^{9A}$ represents hydrogen or methyl,
$R^{9B}$ represents hydrogen, methyl, trifluoromethyl or trifluoromethoxymethyl,
$Ar^2$ is phenyl,
which may be mono- or disubstituted, identically or differently, by fluorine, chlorine, methyl and/or trifluoromethyl,
and the salts, solvates and solvates of the salts thereof.

A further particular embodiment of the present invention encompasses compounds of the formula (I) in which
$R^2$ is a group of the formula

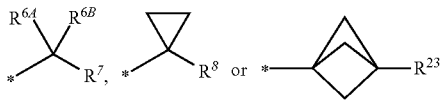

in which
* marks the bonding site to the nitrogen atom of the amide moiety,
$R^{6A}$ is hydrogen or methyl,
$R^{6B}$ is methyl, ethyl, cyclopropyl, trifluoromethyl or trifluoromethoxymethyl,
$R^7$ is methyl, ethyl, n-propyl, isopropyl, tert-butyl, 2-methylprop-1-yl, trifluoromethyl, difluoromethyl, pentafluoroethyl, 2,2,2-trifluoroethyl or cyclopropyl,
$R^8$ is 2,2,2-trifluoroethyl,
$R^{23}$ is hydrogen, fluorine or trifluoromethyl,
and the salts, solvates and solvates of the salts thereof.

A further particular embodiment of the present invention encompasses compounds of the formula (I) in which
$R^2$ is a group of the formula
*-L-$Ar^2$ in which
* marks the bonding site to the nitrogen atom of the amide moiety,
$L^1$ is a bond or a group of the formula —$CR^{9A}R^{9B}$—,
in which
$R^{9A}$ represents hydrogen,
$R^{9B}$ represents hydrogen, methyl, trifluoromethyl or trifluoromethoxymethyl,
$Ar^2$ is phenyl
or
a group of the formula

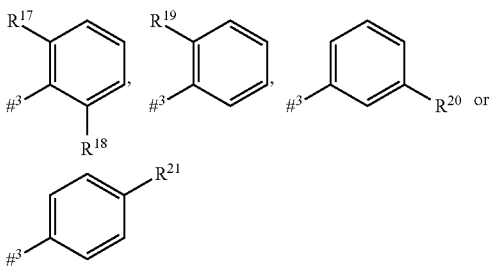

in which
$\#^3$ marks the bonding site
$R^{17}$ and $R^{19}$ independently represent fluorine, chlorine, methyl or trifluoromethyl,
$R^{18}$, $R^{20}$ and $R^{21}$ independently represent fluorine, chlorine or methyl,
and the salts, solvates and solvates of the salts thereof.

A further particular embodiment of the present invention encompasses compounds of the formula (I) in which
$R^2$ is a group of the formula
*-L-$Ar^2$ in which
* marks the bonding site to the nitrogen atom of the amide moiety,
$L^1$ is a bond or a group of the formula —$CR^{9A}R^{9B}$—,
in which
$R^{9A}$ represents hydrogen,
$R^{9B}$ represents methyl, trifluoromethyl or trifluoromethoxymethyl,
and the salts, solvates and solvates of the salts thereof.

A further particular embodiment of the present invention encompasses compounds of the formula (I) in which
$R^2$ is a group of the formula

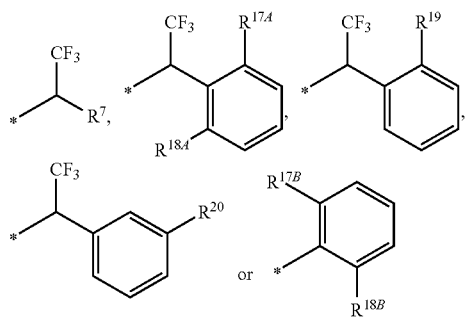

in which
* marks the bonding site to the nitrogen atom of the amide moiety,
$R^7$ is ethyl or cyclopropyl,
$R^{17A}$ is fluorine or chlorine,
$R^{18A}$ is fluorine,
$R^{17B}$ and $R^{18B}$ are each chlorine,
$R^{19}$ is fluorine or chlorine,
and
$R^{20}$ is fluorine,
and the salts, solvates and solvates of the salts thereof.

A further particular embodiment of the present invention encompasses compounds of the formula (I) in which
$R^2$ is a group of the formula

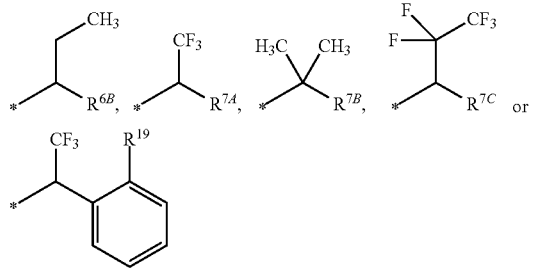

in which
* marks the bonding site to the nitrogen atom of the amide moiety,
$R^{6B}$ is trifluoromethoxymethyl,
$R^{7A}$ is methyl, ethyl, trifluoromethyl or cyclopropyl,
$R^{7B}$ is trifluoromethyl, difluoromethyl or 2,2,2-trifluoroethyl,
$R^{7C}$ is methyl or ethyl,
$R^{19}$ is chlorine,
and the salts, solvates and solvates of the salts thereof.

A further particular embodiment of the present invention encompasses compounds of the formula (I) in which
$R^2$ is a group of the formula

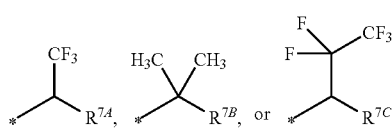

in which
* marks the bonding site to the nitrogen atom of the amide moiety,
$R^{7A}$ is ethyl, trifluoromethyl or cyclopropyl,
$R^{7B}$ is trifluoromethyl,
$R^{7C}$ is methyl or ethyl,
and the salts, solvates and solvates of the salts thereof.

A further particular embodiment of the present invention encompasses compounds of the formula (I) in which
$R^2$ is (2S)-1,1,1-trifluorobutan-2-yl of the formula

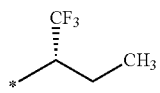

in which
* marks the bonding site to the nitrogen atom of the amide moiety,
and the salts, solvates and solvates of the salts thereof.

A further particular embodiment of the present invention encompasses compounds of the formula (I) in which
$R^2$ is (1S)-1-cyclopropyl-2,2,2-trifluoroethyl

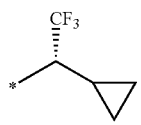

in which
* marks the bonding site to the nitrogen atom of the amide moiety,
and the salts, solvates and solvates of the salts thereof.

A further particular embodiment of the present invention encompasses compounds of the formula (I) in which
$R^2$ is 1,1,1,3,3,3-hexafluoropropan-2-yl,
and the salts, solvates and solvates of the salts thereof.

A further particular embodiment of the present invention encompasses compounds of the formula (I) in which
$R^2$ is 3,3,4,4,4-pentafluorobutan-2-yl,
and the salts, solvates and solvates of the salts thereof.

A further particular embodiment of the present invention encompasses compounds of the formula (I) in which $R^2$ is 1,1,1,2,2-pentafluoropentan-3-yl,
and the salts, solvates and solvates of the salts thereof.

A further particular embodiment of the present invention encompasses compounds of the formula (I) in which
$R^2$ is 1,1,1-trifluoro-2-methylpropan-2-yl,
and the salts, solvates and solvates of the salts thereof.

A further particular embodiment of the present invention encompasses compounds of the formula (I) in which
$R^2$ is a group of the formula

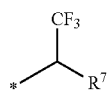

in which
* marks the bonding site to the nitrogen atom of the amide moiety,
$R^7$ is ethyl or cyclopropyl,
and the salts, solvates and solvates of the salts thereof.

A further particular embodiment of the present invention encompasses compounds of the formula (I) in which
$Ar^1$ is a group of the formula

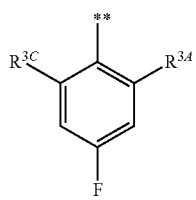

in which
** marks the bonding site to the nitrogen atom,
$R^{3A}$ is fluorine or chlorine, and
$R^{3C}$ is hydrogen or fluorine
and the salts, solvates and solvates of the salts thereof.

A further particular embodiment of the present invention encompasses compounds of the formula (I) in which
$Ar^1$ is a group of the formula

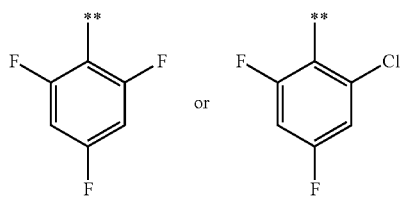

in which
** marks the bonding site to the nitrogen atom,
and the salts, solvates and solvates of the salts thereof.

A further particular embodiment of the present invention encompasses compounds of the formula (I) in which
$Ar^1$ is a group of the formula

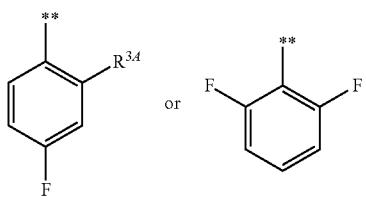

in which
** marks the bonding site to the nitrogen atom,
$R^{3A}$ is fluorine or chlorine,
and the salts, solvates and solvates of the salts thereof.

A further particular embodiment of the present invention encompasses compounds of the formula (I) in which
$Ar^1$ is a group of the formula

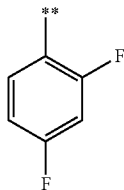

in which
** marks the bonding site to the nitrogen atom,
and the salts, solvates and solvates of the salts thereof.

A further particular embodiment of the present invention encompasses compounds of the formula (I) in which
$Ar^1$ is a group of the formula

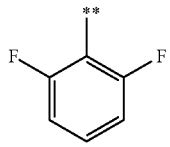

in which
** marks the bonding site to the nitrogen atom,
and the salts, solvates and solvates of the salts thereof.

A further particular embodiment of the present invention encompasses compounds of the formula (I) in which
$R^1$ is $NR^4R^5$,
in which
$R^4$ is hydrogen or methyl,
and
$R^5$ is methyl, isopropyl, 2,2-difluoroethyl or 2,2,2-trifluoroethyl,
and the salts, solvates and solvates of the salts thereof.

A further particular embodiment of the present invention encompasses compounds of the formula (I) in which
$R^1$ is a group of the formula

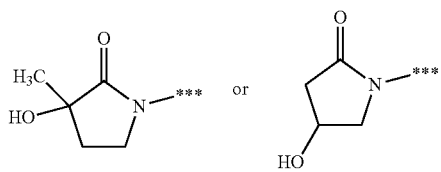

in which
*** marks the bonding site to the carbon atom of the pyridine ring,
and the salts, solvates and solvates of the salts thereof.

A further particular embodiment of the present invention encompasses compounds of the formula (I) in which
$R^1$ is a group of the formula

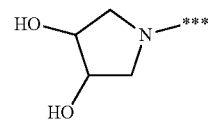

in which
*** marks the bonding site to the carbon atom of the pyridine ring,
and the salts, solvates and solvates of the salts thereof.

A further particular embodiment of the present invention encompasses compounds of the formula (I) in which
$R^1$ is trans-(3R,4R)-3,4-dihydroxypyrrolidin-1-yl of the formula

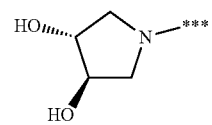

in which
*** marks the bonding site to the carbon atom of the pyridine ring,
and the salts, solvates and solvates of the salts thereof.

A further particular embodiment of the present invention encompasses compounds of the formula (I) in which
$R^1$ is cis-(R,S)-3,4-dihydroxypyrrolidin-1-yl of the formula

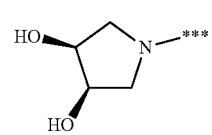

in which
*** marks the bonding site to the carbon atom of the pyridine ring,
and the salts, solvates and solvates of the salts thereof.

A further particular embodiment of the present invention encompasses compounds of the formula (I) in which
$R^1$ is a group of the formula

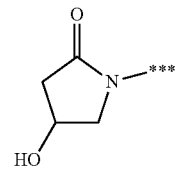

in which
*** marks the bonding site to the carbon atom of the pyridine ring,
and the salts, solvates and solvates of the salts thereof.

A further particular embodiment of the present invention encompasses compounds of the formula (I) in which R$^1$ is (4S)-4-hydroxy-2-oxopyrrolidin-1-yl of the formula

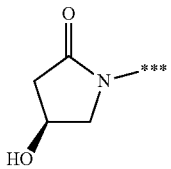

in which
*** marks the bonding site to the carbon atom of the pyridine ring,
and the salts, solvates and solvates of the salts thereof.

Irrespective of the particular combinations of the radicals specified, the individual radical definitions specified in the particular combinations or preferred combinations of radicals are also replaced as desired by radical definitions of other combinations.

Very particular preference is given to combinations of two or more of the abovementioned preferred ranges and embodiments.

The radical definitions specified as preferred, particularly preferred and very particularly preferred apply both to the compounds of the formula (I) and correspondingly toward all intermediates.

The invention further provides a process for preparing compounds of the formula (I) according to the invention, characterized in that

[A] a compound of the formula (II)

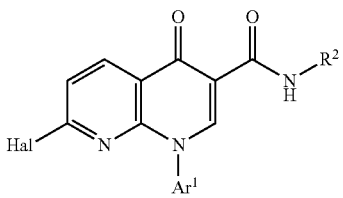

in which R$^2$ and Ar$^1$ have the definitions given above and
Hal is fluorine, chlorine, bromine or iodine, preferably chlorine,
is reacted with a compound of the formula (III)

R$^1$—H   (III)

in which R$^1$ has the definition given above
to give the inventive carboxamide of the formula (I)

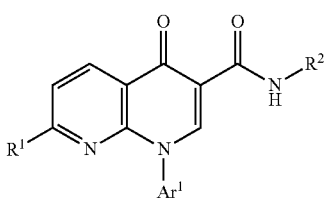

in which R$^1$, R$^2$ and Ar$^1$ have the definitions given above, or

[B] a compound of the formula (IV)

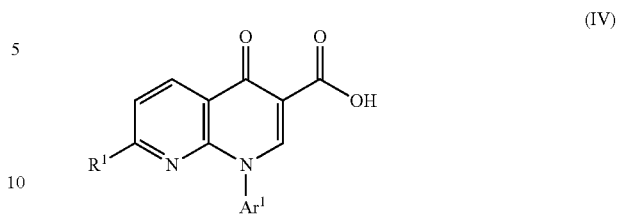

in which R$^1$ and Ar$^1$ have the definitions given above, is reacted with a compound of the formula (V)

R$^2$—NH$_2$   (V), in which R$^2$ has the definition given above,
to give the inventive carboxamide of the formula (I)

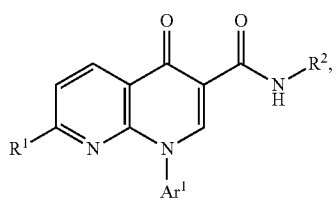

in which R$^1$, R$^2$ and Ar$^1$ have the definitions given above, and, if appropriate, the compounds of the formula (I) thus obtained are separated into their enantiomers and/or diastereomers and/or converted with the appropriate (i) solvents and/or (ii) bases or acids to their solvates, salts and/or solvates of the salts.

The reaction (II)+(III)→(I) can be effected via a nucleophilic substitution reaction or via a transition metal-mediated coupling reaction.

The nucleophilic substitution reaction is preferably conducted in the presence of a base. Suitable bases for the process step (II)+(III)→(I) are the customary inorganic or organic bases. These preferably include alkali metal hydroxides, for example lithium hydroxide, sodium hydroxide or potassium hydroxide, alkali metal or alkaline earth metal carbonates such as lithium carbonate, sodium carbonate, potassium carbonate or caesium carbonate, alkali metal alkoxides such as sodium methoxide or potassium methoxide, sodium ethoxide or potassium ethoxide or lithium tert-butoxide, sodium tert-butoxide or potassium tert-butoxide, alkali metal hydrides such as sodium hydride or potassium hydride, amides such as sodium amide, lithium bis(trimethylsilyl)amide or potassium bis(trimethylsilyl)amide or lithium diisopropylamide, or organic amines such as N,N-diisopropylethylamine (DIPEA), 1,5-diazabicyclo[4.3.0]non-5-ene (DBN) and 1,8-diazabicyclo[5.4.0]undec-7-ene (DBU). Preference is given to using N,N-diisopropylethylamine (DIPEA).

The reaction is effected generally within a temperature range from 0° C. to +100° C., preferably at +23° C. to +80° C.

Inert solvents for the process step (II)+(III)→(I) are, for example, ethers such as diethyl ether, dioxane, tetrahydrofuran, glycol dimethyl ether or diethylene glycol dimethyl ether, hydrocarbons such as benzene, toluene, xylene, hexane, cyclohexane or mineral oil fractions, halohydrocarbons such as dichloromethane, trichloromethane, tetrachloromethane, 1,2-dichloroethane, trichloroethylene or chlorobenzene, or other solvents such as acetone, ethyl acetate, acetonitrile, pyridine, dimethyl sulphoxide, N,N-dimethylformamide (DMF), N,N'-dimethylpropyleneurea (DMPU) or N-methylpyrrolidone (NMP). It is likewise possible to use mixtures of the solvents mentioned. Preference is given to using dimethylformamide (DMF) or N-methylpyrrolidone (NMP).

The transition metal-mediated coupling reaction for the process step (II)+(III)→(I), in a preferred embodiment, is conducted in the presence of a palladium catalyst. Suitable palladium catalysts are, for example, palladium(II) acetate, palladium(II) chloride, bis(triphenylphosphine)palladium (II) chloride, bis(acetonitrile)palladium(II) chloride, tetrakis(triphenylphosphine)palladium(0), bis(dibenzylideneacetone)palladium(0), tris(dibenzylideneacetone)palladium(0) or [1,1'-bis(diphenylphosphino)ferrocene]palladium(II) chloride, optionally in combination with a suitable phosphine ligand, for example triphenylphosphine, tri-tert-butylphosphine, 2-dicyclohexylphosphino-2',4',6'-triisopropylbiphenyl (X-Phos), 2-dicyclohexylphosphino-2',6'-dimethoxybiphenyl (S-Phos), 1,2,3,4,5-pentaphenyl-1'-(di-tert-butylphosphino)ferrocene (Q-Phos), 4,5-bis(diphenylphosphino)-9,9-dimethylxanthene (Xantphos), 2,2'-bis(diphenylphosphino)-1,1'-binaphthyl (BINAP), 2-dicyclohexylphosphino-2'-(N,N-dimethylamino)biphenyl or 2-di-tert-butylphosphino-2'-(N,N-dimethylamino)biphenyl.

The palladium-catalysed coupling reaction (II)+(III)→(I) is generally conducted in the presence of a base. Suitable bases are especially alkali metal carbonates such as sodium carbonate, potassium carbonate or caesium carbonate, alkali metal phosphates such as sodium phosphate or potassium phosphate, alkali metal fluorides such as potassium fluoride or caesium chloride, or alkali metal tert-butoxides such as sodium tert-butoxide or potassium tert-butoxide. The reaction is effected in an inert solvent, for example toluene, 1,2-dimethoxyethane, tetrahydrofuran, 1,4-dioxane, dimethyl sulphoxide (DMSO), N,N-dimethylformamide (DMF), N,N-dimethylacetamide (DMA) or mixtures thereof, within a temperature range from +80° C. to +200° C., preferably at +80° C. to +150° C., where heating by means of microwave apparatus may be advantageous.

Preference is given to using, for this coupling reaction, a catalystligand/base system consisting of palladium(II) acetate, 4,5-bis(diphenylphosphino)-9,9-dimethylxanthene (Xantphos) and caesium carbonate or potassium carbonate, and 1,4-dioxane as solvent.

The coupling reaction (II)+(III)→(I) may, in a further preferred embodiment, also be conducted with the aid of a copper(I) catalyst, such as copper(I) oxide, bromide or iodide, in the presence of a copper ligand such as trans-N,N'-dimethyl-1,2-cyclohexanediamine, 8-hydroxyquinoline or 1,10-phenanthroline, and of an inorganic or organic carbonate base, such as potassium carbonate, caesium carbonate or bis(tetraethylammonium) carbonate. Suitable inert solvents for this reaction are especially toluene, xylene, 1,4-dioxane, acetonitrile, dimethyl sulphoxide (DMSO), N,N-dimethylformamide (DMF) or mixtures thereof, optionally with addition of water. Preference is given to using a system consisting of copper(I) iodide, trans-N,N'-dimethyl-1,2-cyclohexanediamine and potassium carbonate in dimethylformamide. The reaction is effected generally within a temperature range from +50° C. to +200° C., preferably at +60° C. to +150° C.

The coupling reaction (IV)+(V)→(I) [amide formation] can be effected either by a direct route with the aid of a condensing or activating agent or via the intermediate stage of a carbonyl chloride, carboxylic ester or carbonyl imidazolide obtainable from (IV).

Suitable condensing or activating agents are, for example, carbodiimides such as N,N'-diethyl-, N,N'-dipropyl-, N,N'-diisopropyl-, N,N'-dicyclohexylcarbodiimide (DCC) or N-(3-dimethylaminopropyl)-N'-ethylcarbodiimide hydrochloride (EDC), phosgene derivatives such as N,N'-carbonyldiimidazole (CDI), isopropyl chloroformate or isobutyl chloroformate, 1,2-oxazolium compounds such as 2-ethyl-5-phenyl-1,2-oxazolium 3-sulphate or 2-tert-butyl-5-methylisoxazolium perchlorate, acylamino compounds such as 2-ethoxy-1-ethoxycarbonyl-1,2-dihydroquinoline, α-chloroenamines such as 1-chloro-N,N,2-trimethylprop-1-en-1-amine, 1,3,5-triazine derivatives such as 4-(4,6-dimethoxy-1,3,5-triazin-2-yl)-4-methylmorpholinium chloride, phosphorus compounds such as n-propanephosphonic anhydride (PPA), diethyl cyanophosphonate, diphenylphosphoryl azide (DPPA), bis(2-oxo-3-oxazolidinyl)phosphoryl chloride, benzotriazol-1-yloxytris(dimethylamino)phosphonium hexafluorophosphate or benzotriazol-1-yloxytris(pyrrolidino)phosphonium hexafluorophosphate (PyBOP), or uronium compounds such as O-(benzotriazol-1-yl)-N,N,N',N'-tetramethyluronium tetrafluoroborate (TBTU), O-(benzotriazol-1-yl)-N,N,N',N'-tetramethyluronium hexafluorophosphate (HBTU), O-(1H-6-chlorobenzotriazol-1-yl)-1,1,3,3-tetramethyluronium tetrafluoroborate (TCTU), O-(7-azabenzotriazol-1-yl)-N,N,N',N'-tetramethyluronium hexafluorophosphate (HATU) or 2-(2-oxo-1-(2H)-pyridyl)-1,1,3,3-tetramethyluronium tetrafluoroborate (TPTU), optionally in combination with further auxiliaries such as 1-hydroxybenzotriazole (HOBt) or N-hydroxysuccinimide (HOSu), and also, as bases, alkali metal carbonates, e.g. sodium carbonate or potassium carbonate, or tertiary amine bases such as triethylamine, N-methylmorpholine (NMM), N-methylpiperidine (NMP), N,N-diisopropylethylamine (DIPEA), pyridine or 4-N,N-dimethylaminopyridine (DMAP). Condensing or activating agents used with preference are O-(7-azabenzotriazol-1-yl)-N,N,N',N'-tetramethyluronium hexafluorophosphate (HATU) in combination with N,N-diisopropylethylamine (DIPEA), and isopropyl chloroformate in combination with N-methylmorpholine (NMM) and benzotriazol-1-yloxytris(pyrrolidino)phosphonium hexafluorophosphate (PyBOP) in combination with N,N-diisopropylethylamine (DIPEA).

In the case of a two-stage reaction regime via the carbonyl chlorides or carbonyl imidazolides obtainable from (IV), the coupling with the amine component (V) is conducted in the presence of a customary base, for example sodium carbonate or potassium carbonate, triethylamine, DIPEA, N-methylmorpholine (NMM), N-methylpiperidine (NMP), pyridine, 2,6-dimethylpyridine, 4-N,N-dimethylaminopyridine (DMAP), 1,8-diazabicyclo[5.4.0]undec-7-ene (DBU), 1,5-diazabicyclo[4.3.0]non-5-ene (DBN), sodium methoxide or potassium methoxide, sodium ethoxide or potassium ethoxide, sodium tert-butoxide or potassium tert-butoxide, or sodium hydride or potassium hydride.

The carbonyl imidazolides themselves are obtainable by known methods by reaction of (II) with N,N'-carbonyldiimidazole (CDI) at elevated temperature (+60° C. to +150° C.) in a correspondingly relatively high-boiling solvent such as N,N-dimethylformamide (DMF). The preparation of the carbonyl chlorides is accomplished in a customary manner by treating (II) with thionyl chloride or oxalyl chloride in an inert solvent such as dichloromethane or THF.

Inert solvents for the coupling reactions mentioned are—according to the method used—for example ethers such as diethyl ether, diisopropyl ether, methyl tert-butyl ether, tetrahydrofuran, 1,4-dioxane, 1,2-dimethoxyethane or bis(2-methoxyethyl) ether, hydrocarbons such as benzene, toluene, xylene, pentane, hexane or cyclohexane, halohydrocarbons such as dichloromethane, trichloromethane, carbon tetrachloride, 1,2-dichloroethane, trichloroethylene or chlorobenzene, or polar aprotic solvents such as acetone, methyl ethyl ketone, ethyl acetate, acetonitrile, butyronitrile, pyridine, dimethyl sulphoxide (DMSO), N,N-dimethylformamide (DMF), N,N'-dimethylpropyleneurea (DMPU) or N-methylpyrrolidinone (NMP). It is also possible to use mixtures of such solvents. Preference is given to using N,N-dimethylformamide (DMF). The couplings are generally conducted within a temperature range from 0° C. to +130° C., preferably at +20° C. to +30° C.

The preferred coupling method is the direct reaction of (II) with the amine compound (III) with the aid of a condensing or activating agent.

In the case of a two-stage reaction regime via the carboxylic esters obtainable from (IV), the coupling can be conducted with an activated amine component (V). The amine component (V) is preferably activated by the reaction with trimethylaluminium (cf. *Tetrahedron Lett.* 1977, 18, 4171-4174). Preference is given to using dichloromethane (DCM) as inert solvent. The couplings are generally conducted within a temperature range from 0° C. to +130° C., preferably at room temperature.

The compounds of the formula (II) can be prepared by reacting a carboxylic acid compound of the formula (VI)

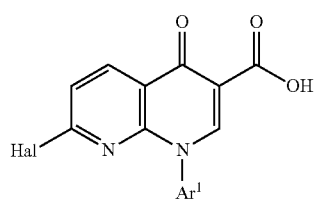

(VI)

in which Hal and Ar$^1$ have the definitions given above with a compound of the formula (V)

$$R^2\text{---}NH_2 \qquad (V)$$

in which R$^2$ has the definition given above
to give the inventive carboxamide of the formula (II)

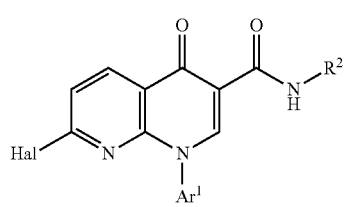

(II)

in which Hal, R$^1$, R$^2$ and Ar$^1$ have the definitions given above.

The coupling reaction (VI)+(V)→(II) [amide formation] can be effected either by a direct route with the aid of a condensing or activating agent or via the intermediate stage of a carbonyl chloride, carboxylic ester or carbonyl imidazolide obtainable from (VI), analogously to the conditions and reagents already described for the reaction (IV)+(V)→ (I).

If HATU is used as activating agent in the coupling reaction to give (II), it is possible that either an individual defined product of the general formula (II) is obtained, or else a mixture with a "HATU adduct". A "HATU adduct" in the present context refers to a pseudohalide compound where the Hal substituent in the general formula (II) is replaced by the 3H-[1,2,3]triazolo[4,5-b]pyridin-3-ol group, also referred to as 1-hydroxy-7-azabenzotriazole. Such a mixture of a halogen compound of the general formula (II) and a "HATU adduct" can likewise be used, analogously to the reaction described, as reactant for the further reaction (after (I) or (VIII)).

Depending on their respective substitution pattern, the compounds of the formula (IV) can be prepared by reacting either

[C] a compound of the formula (VII)

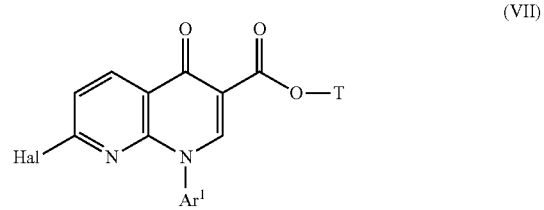

(VII)

in which Hal and Ar$^1$ have the definitions given above
and
T is (C$_1$-C$_4$)-alkyl or benzyl,
in a first step with a compound of the formula (III)

$$R^1\text{---}H \qquad (III)$$

in which R$^1$ has the definition given above
to give a compound of the formula (VIII)

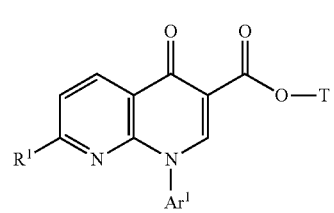

(VIII)

in which T, R$^1$ and Ar$^1$ have the definitions given above, and optionally, in a second step, detaching the ester radical T to give the inventive carboxylic acid of the formula (IV)

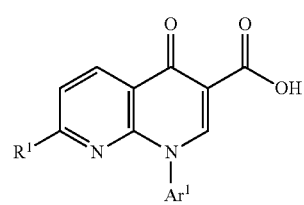

(IV)

in which R$^1$ and Ar$^1$ have the definitions given above
or
[D] a compound of the formula (VI)

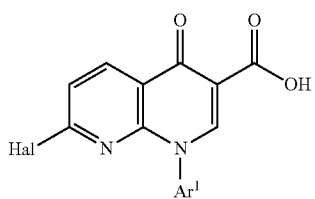

(VI)

in which Hal and Ar¹ have the definitions given above with a compound of the formula (III)

$R^1$—H    (III)

in which R¹ has the definition given above
to give the inventive carboxylic acid of the formula (IV)

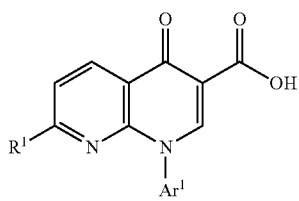

(IV)

in which R¹ and Ar¹ have the definitions given above.

The reaction (VII)+(III)→(VIII) [route C] or the reaction (VI)+(III)→(IV) [route D] can be effected via a nucleophilic substitution reaction or a transition metal-mediated coupling reaction analogously to the conditions already described for the reaction (II)+(III)→(I).

In a preferred embodiment, the reaction is conducted according to route C as a nucleophilic substitution reaction in the presence of a base, preference being given to using N,N-diisopropylethylamine (DIPEA).

Preference is given to using dimethylformamide (DMF), N-methylpyrrolidone (NMP) or acetonitrile as solvent.

In a preferred embodiment, the reaction is conducted according to route D as a transition metal-mediated coupling reaction in the presence of a suitable palladium catalyst or copper(I) catalyst. Preference is given to using a system consisting of palladium(II) acetate in combination with 4,5-bis(diphenylphosphino)-9,9-dimethylxanthene (Xantphos), caesium carbonate or potassium carbonate and 1,4-dioxane as solvent, or preference is likewise given to using a system consisting of copper(I) iodide, trans-N,N'-dimethyl-1,2-cyclohexanediamine and potassium carbonate in dimethylformamide as solvent.

The detachment of the ester group T in process step (VIII)→(IV) is conducted by customary methods, by treating the ester in an inert solvent with an acid or a base, with conversion of the salt of the carboxylic acid initially formed in the latter variant to the free carboxylic acid by subsequent treatment with acid. In the case of the tert-butyl esters, the ester cleavage is preferably effected with an acid. Benzyl esters can alternatively also be cleaved by hydrogenation (hydrogenolysis) in the presence of a suitable catalyst, for example palladium on activated carbon.

Suitable solvents for these reactions are water and the organic solvents customary for ester cleavage. These especially include alcohols such as methanol, ethanol, n-propanol, isopropanol, n-butanol or tert-butanol, ethers such as diethyl ether, tetrahydrofuran, 1,4-dioxane or 1,2-dimethoxyethane, or other solvents such as dichloromethane, acetonitrile, N,N-dimethylformamide or dimethyl sulphoxide. It is equally possible to use mixtures of these solvents. In the case of a basic ester hydrolysis, preference is given to using mixtures of water with tetrahydrofuran.

Suitable bases for a hydrolysis reaction are the customary inorganic bases. These especially include alkali metal or alkaline earth metal hydroxides, for example lithium hydroxide, sodium hydroxide, potassium hydroxide or barium hydroxide, or alkali metal or alkaline earth metal carbonates, such as sodium carbonate, potassium carbonate or calcium carbonate. Preference is given to using aqueous lithium hydroxide solution or sodium hydroxide solution in a mixture with THF as cosolvent.

Suitable acids for the ester cleavage are generally sulphuric acid, hydrogen chloride/hydrochloric acid, hydrogen bromide/hydrobromic acid, phosphoric acid, acetic acid, trifluoroacetic acid, toluenesulphonic acid, methanesulphonic acid or trifluoromethanesulphonic acid, or mixtures thereof, optionally with addition of water. Preference is given to using aqueous hydrochloric acid (18 percent) in a water/tetrahydrofuran mixture.

The ester cleavage is generally conducted within a temperature range from −20° C. to +100° C., preferably at 23° C. to +120° C.

Depending on the particular substitution pattern, the compounds of the formula (VI) and of the formula (VIIIL) can be prepared by, in analogy to known processes (see, for example, EP 0607825 A1, p. 25-26), reacting a 2,6-dichloronicotinoylacrylate derivative of the formula (IX)

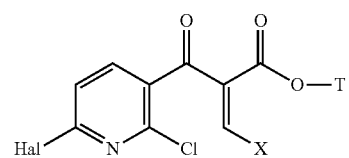

(IX)

in which Hal and T have the definitions given above
and
X is a leaving group such as dimethylamino, methoxy or ethoxy, and
in a first stage, preferably in the presence of a suitable base, with an aniline compound of the formula (X)

$Ar^1$—$NH_2$    (X)

in which Ar¹ has the definitions given above
to give an intermediate of the formula (XI)

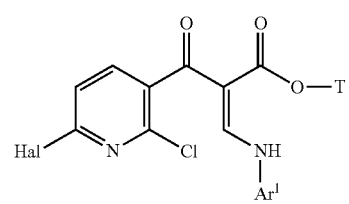

(XI)

in which Hal, Ar¹ and T have the definitions given above,
and then reacting the latter in the presence of a suitable base to give the ester compound of the formula (VII)

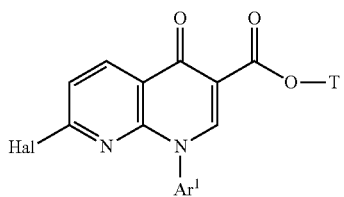

(VII)

in which Hal, Ar¹ and T have the definition given above, and then optionally converting the ester compound (VII) under hydrolysis conditions in a further step to the carboxylic acid compound (VI)

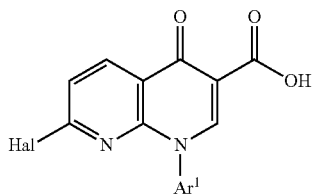

(VI)

in which Hal and Ar¹ have the definitions given above under the reaction conditions known in the literature.

The compounds of the formula (IX) are known from the literature (see, for example, EP 0607825 A1) or can be prepared in analogy to processes known from the literature.

The compounds of the formulae (III), (V) and (X) are commercially available or described as such in the literature, or they can be prepared in a way obvious to the person skilled in the art, in analogy to methods published in the literature. Numerous detailed methods and literature data for preparation of the respective starting materials can also be found in the Experimental Part in the section relating to the preparation of the starting compounds and intermediates.

The separation of stereoisomers (enantiomers and/or diastereomers) of the inventive compounds of the formula (I) can be achieved by customary methods familiar to those skilled in the art. Preference is given to employing chromatographic methods on achiral or chiral separation phases for this purpose.

Separation of the compounds according to the invention into the corresponding enantiomers and/or diastereomers can, if appropriate, also be conducted at the early stage of the intermediates (II), (IV) or (VIII), which are then reacted further in separated form in accordance with the reaction sequence described above. For such a separation of the stereoisomers of intermediates, preference is likewise given to employing chromatographic methods on achiral or chiral separation phases. Alternatively, separation can also be effected via diastereomeric salts of the carboxylic acids of the formula (IV) with chiral amine bases.

The preparation of the inventive compounds can be illustrated by way of example by the following reaction schemes:

Scheme 1

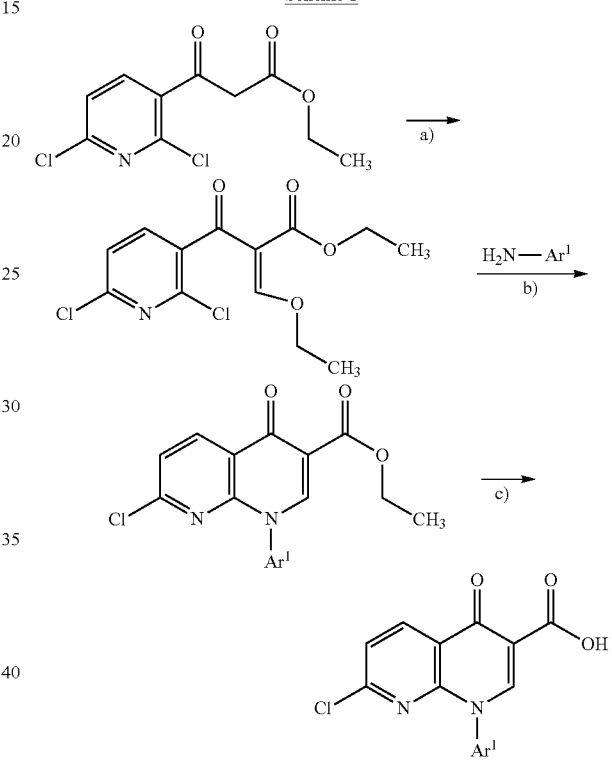

[a]: triethyl orthoformate, acetic anhydride; b): DIPEA, DCM, then K₂CO₃; c): aq. LiOH, THF or 18 per cent hydrochloric acid, THF, water].

Scheme 2

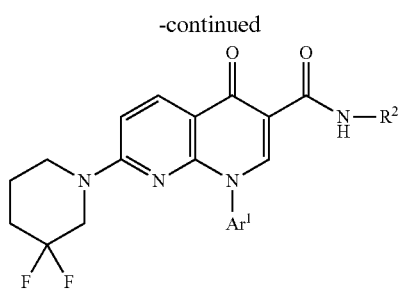
-continued
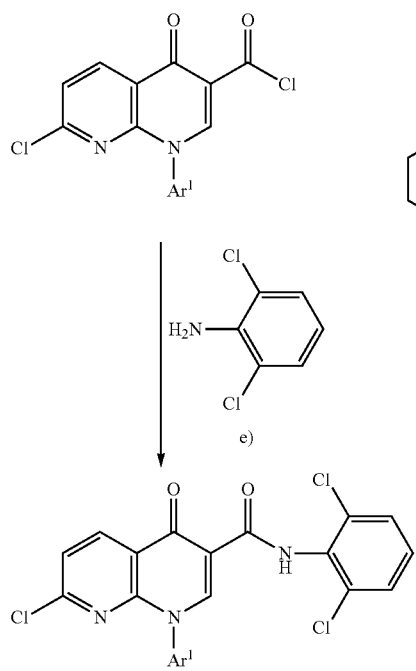
[a): ClCO₂iPr, NMM, NMP or HATU, DIPEA, DMF or PyBOP, DIPEA, DMF; b): Pd(OAc)₂, Xantphos, Cs₂CO₃, 1,4-dioxane; c): DIPEA, DMF; d): (COCl)₂, cat. DMF, THF; e): NaH, DMF or NEt₃, DCM].
Scheme 3
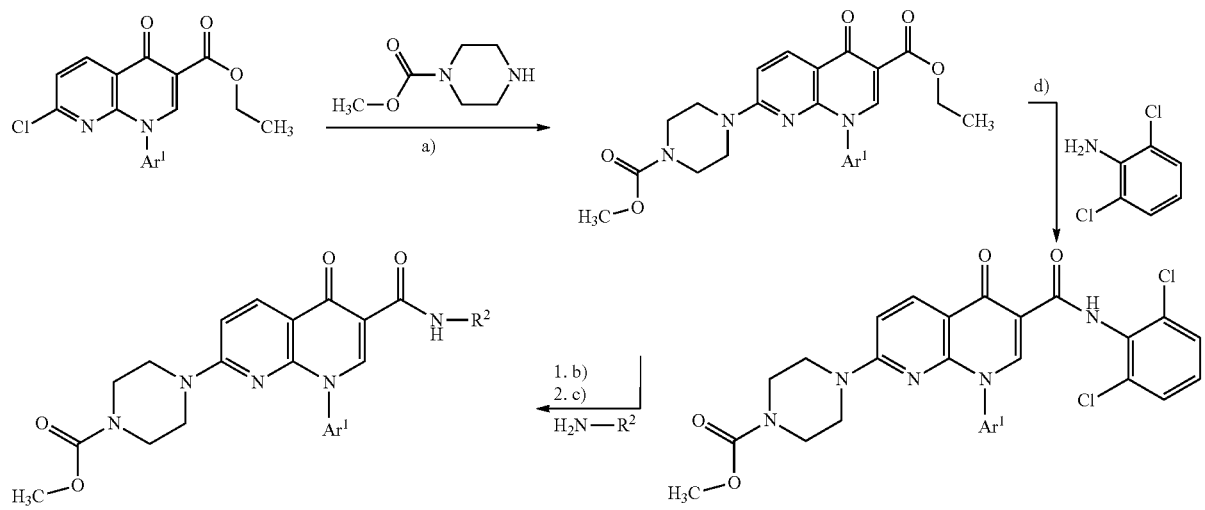
[a): DIPEA, DMF; b): aq. LiOH, THF or 18 per cent hydrochloric acid, THF, water; c): ClCO₂iPr, NMM, NMP or HATU, DIPEA, DMF or PyBOP, DIPEA, DMF; d): AlMe₃, DCM].
Scheme 4
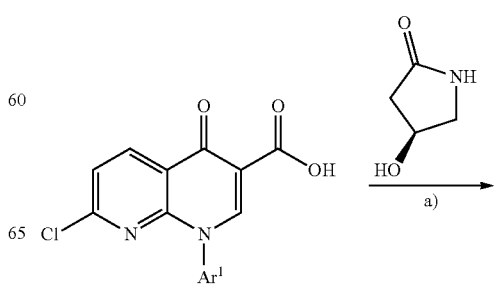

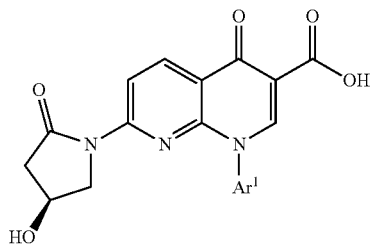

[a]: Pd(OAc)₂, Xantphos, Cs₂CO₃, 1,4-dioxane].

Scheme 5

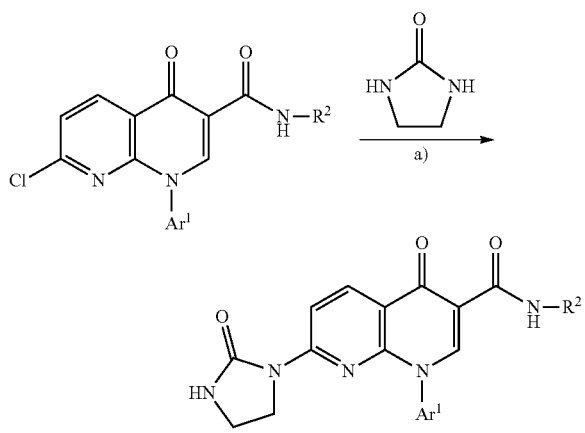

[a]: CuI, , K₂CO₃, trans-N,N'-dimethyl-1,2-cyclohexanediamine, DMF].

Further inventive compounds of the formula (I) can, if appropriate, also be prepared by transformations of functional groups of individual radicals or substituents, especially those listed under R and R, proceeding from other compounds of the formula (I) or precursors thereof obtained by the above processes. These transformations are conducted by customary methods familiar to the person skilled in the art and include, for example, reactions such as nucleophilic or electrophilic substitution reactions, transition-metal-mediated coupling reactions, preparation and addition reactions of metal organyls (e.g. Grignard compounds or lithium organyls), oxidation and reduction reactions, hydrogenation, halogenation (e.g. fluorination, bromination), dehalogenation, amination, alkylation and acylation, the formation of carboxylic esters, carboxamides and sulphonamides, ester cleavage and hydrolysis, and the introduction and removal of temporary protecting groups.

The invention relates, in a further aspect, to intermediates of the general formula (II)

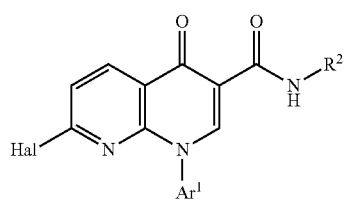

(II)

in which $R^2$ and $Ar^1$ have the definitions given above for compounds of the formula (I)

and

Hal is fluorine, chlorine, bromine or iodine, preferably chlorine.

The invention relates, in a further aspect, to intermediates of the general formula (IV)

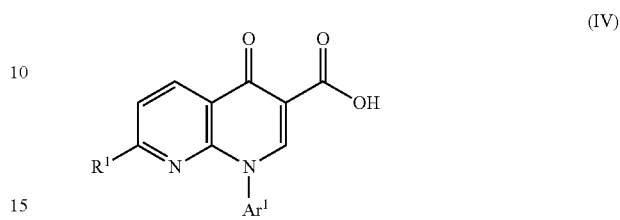

(IV)

in which $R^1$ and $Ar^1$ have the definitions given above for compounds of the formula (I).

The invention relates, in a further aspect, to the use of a compound of the general formula (II)

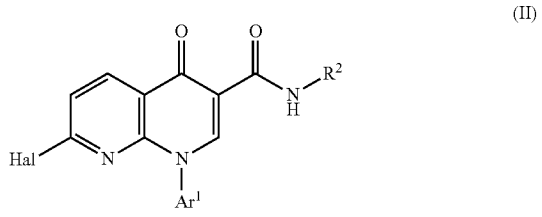

(II)

in which $R^2$ and $Ar^1$ have the definitions given above for compounds of the formula (I)

and

Hal is fluorine, chlorine, bromine or iodine, preferably chlorine.

or a compound of the general formula (IV)

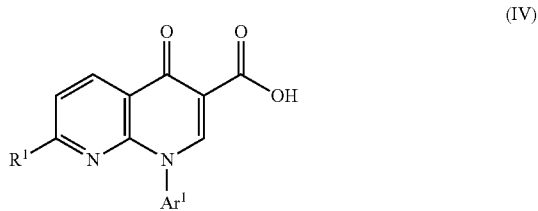

(IV)

in which $R^1$ and $Ar^1$ have the definitions given above for compounds of the formula (I) for preparation of a compound of the general formula (I) as defined above.

The compounds according to the invention have an unforeseeable useful spectrum of pharmacological and pharmacokinetic activity.

They are therefore suitable for use as medicaments for treatment and/or prophylaxis of diseases in humans and animals. The compounds according to the invention have valuable pharmacological properties and can be used for treatment and/or prophylaxis of disorders in humans and animals.

The compounds according to the invention are positive allosteric modulators of the muscarinic M2 receptor and are therefore suitable for treatment and/or prevention of disorders and pathological processes, especially cardiovascular disorders and/or renal disorders, wherein the M2 receptor is involved in dysregulation of the autonomic nervous system or an imbalance between the activity of the sympathetic and parasympathetic portion of the autonomic nervous system.

The present invention provides positive allosteric modulators of the muscarinic M2 receptor. Allosteric modulators have distinct differences from conventional orthosteric ligands. The effect of an allosteric modulator is self-limiting when it stabilizes the binding of the agonist in high concentrations. Furthermore, the effect of an allosteric modulator can be displayed only in the presence of the endogenous ligand. The allosteric modulator itself has no direct influence on receptor activation. This gives rise to specificity of the allosteric effect in terms of space and time. The mutual influencing of allosteric and orthosteric ligands in terms of affinity and intrinsic activity, which is referred to as cooperativity, is determined by both ligands. In the case of a positive allosteric modulator, the effects of the orthosteric ligand are enhanced (positive cooperativity). Because of its ability to modulate receptor combinations in the presence of an orthosteric ligand, allosteric ligands can bring about fine adjustment of pharmacological effects.

In the context of the present invention, disorders of the cardiovascular system or cardiovascular disorders are understood to mean, for example, the following disorders: acute and chronic heart failure, arterial hypertension, coronary heart disease, stable and unstable angina pectoris, myocardial ischaemia, myocardial infarction, shock, atherosclerosis, cardiac hypertrophy, cardiac fibrosis, atrial and ventricular arrhythmias, tachycardia, transitory and ischaemic attacks, stroke, pre-eclampsia, inflammatory cardiovascular disorders, peripheral and cardiac vascular disorders, peripheral perfusion disorders, arterial pulmonary hypertension, spasms of the coronary arteries and peripheral arteries, thromboses, thromboembolic disorders, oedema development, for example pulmonary oedema, cerebral oedema, renal oedema or heart failure-related oedema, and restenoses such as after thrombolysis treatments, percutaneous transluminal angioplasty (PTA), transluminal coronary angioplasty (PTCA), heart transplants and bypass operations, and micro- and macrovascular damage (vasculitis), reperfusion damage, arterial and venous thromboses, microalbuminuria, myocardial insufficiency, endothelial dysfunction, peripheral and cardiac vascular disorders, peripheral perfusion disorders, heart failure-related oedema, elevated levels of fibrinogen and of low-density LDL and elevated concentrations of plasminogen activator/inhibitor 1 (PAI 1).

In the context of the present invention, the term "heart failure" also includes more specific or related types of disease, such as acutely decompensated heart failure, right heart failure, left heart failure, global failure, ischaemic cardiomyopathy, dilated cardiomyopathy, congenital heart defects, heart valve defects, heart failure associated with heart valve defects, mitral valve stenosis, mitral valve insufficiency, aortic valve stenosis, aortic valve insufficiency, tricuspid stenosis, tricuspid insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders, and diastolic and systolic heart failure.

In the context of the present invention, the term atrial and ventricular arrhythmias also includes more specific or related types of disease, such as: atrial fibrillation, paroxysmal atrial fibrillation, intermittierent atrial fibrillation, permanent atrial fibrillation, atrial flutter, sinusoidal arrhythmia, sinusoidal tachycardia, passive heterotopia, active heterotopia, escape systoles, extra systoles, impulse conduction disorders, sick sinus syndrome, hypersensitive carotid sinus, tachycardias, AV node reentry tachycardia, atriventricular reentry tachycardia, WPW syndrome (Wolff-Parkinson-White), Mahaim tachycardia, hidden accessory conduction pathway, permanent junctional reentry tachycardia, focal atrial tachycardia, junctional ectopic tachycardia, atrial reentry tachycardia, ventricular tachycardia, ventricular flutter, ventricular fibrillation, sudden cardiac death.

In the context of the present invention, the term coronary heart disease also encompasses more specific or related types of disease, such as: ischaemic heart disease, stable angina pectoris, acute coronary syndrome, unstable angina pectoris, NSTEMI (non-ST elevation myocardial infarction), STEMI (ST elevation myocardial infarction), ischaemic heart muscle damage, heart rhythm dysfunctions and myocardial infarction.

The compounds according to the invention are further suitable for the prophylaxis and/or treatment of polycystic kidney disease (PCKD) and of the syndrome of inappropriate ADH secretion (SIADH).

The compounds according to the invention are also suitable for treatment and/or prophylaxis of renal disorders, in particular of acute and chronic renal insufficiency and acute and chronic renal failure.

In the context of the present invention, the term "acute renal insufficiency" encompasses acute manifestations of kidney disease, of kidney failure and/or renal insufficiency with and without the need for dialysis, and also underlying or related renal disorders such as renal hypoperfusion, intradialytic hypotension, volume deficiency (e.g. dehydration, blood loss), shock, acute glomerulonephritis, haemolytic-uraemic syndrome (HUS), vascular catastrophe (arterial or venous thrombosis or embolism), cholesterol embolism, acute Bence-Jones kidney in the event of plasmacytoma, acute supravesicular or subvesicular efflux obstructions, immunological renal disorders such as kidney transplant rejection, immune complex-induced renal disorders, tubular dilatation, hyperphosphataemia and/or acute renal disorders characterized by the need for dialysis, including in the case of partial resections of the kidney, dehydration through forced diuresis, uncontrolled blood pressure rise with malignant hypertension, urinary tract obstruction and infection and amyloidosis, and systemic disorders with glomerular factors, such as rheumatological-immunological systemic disorders, for example lupus erythematodes, renal artery thrombosis, renal vein thrombosis, analgesic nephropathy and renal tubular acidosis, and X-ray contrast agent- and medicament-induced acute interstitial renal disorders.

In the context of the present invention, the term "chronic renal insufficiency" encompasses chronic manifestations of kidney disease, of kidney failure and/or renal insufficiency with and without the need for dialysis, and also underlying or related renal disorders such as renal hypoperfusion, intradialytic hypotension, obstructive uropathy, glomerulopathy, glomerular and tubular proteinuria, renal oedema, haematuria, primary, secondary and chronic glomerulonephritis, membranous and membranoproliferative glomerulonephritis, Alport syndrome, glomerulosclerosis, tubulointerstitial disorders, nephropathic disorders such as primary and congenital kidney disease, renal inflammation, immunological renal disorders such as kidney transplant rejection, immune complex-induced renal disorders, diabetic and non-diabetic nephropathy, pyelonephritis, renal cysts, nephrosclerosis, hypertensive nephrosclerosis and nephrotic syndrome, which can be characterized diagnostically, for example, by abnormally reduced creatinine and/or water excretion, abnormally elevated blood concentrations of urea, nitrogen, potassium and/or creatinine, altered activity of renal enzymes, for example glutamyl synthetase, altered urine osmolarity or urine volume, elevated microalbuminuria, macroalbuminuria, glomerular and arteriolar lesions, tubular dilatation, hyperphosphataemia and/or the need for dialysis, and in the event of renal cell carcinoma, after partial resections of the kidney, dehydration through forced diuresis, uncontrolled blood pressure rise with malignant hypertension, urinary tract obstruction and infection and amyloidosis, and systemic disorders with glomerular factors, such as rheumatological-immunological systemic disorders, for example lupus erythematodes, and also renal artery stenosis, renal artery thrombosis, renal vein thrombosis, analgesic nephropathy and renal tubular acidosis. In addition, X-ray contrast agent- and medicament-induced chronic interstitial renal disorders, metabolic syndrome and dyslipidaemia. The present invention also encompasses the use of the compounds according to the invention for treatment and/or prophylaxis of sequelae of renal insufficiency, for example pulmonary oedema, heart failure, uraemia, anaemia, electrolyte disorders (for example hyperkalaemia, hyponatraemia) and disorders in bone and carbohydrate metabolism.

In addition, the compounds according to the invention are also suitable for treatment and/or prophylaxis of pulmonary arterial hypertension (PAH) and other forms of pulmonary hypertension (PH), of chronic obstructive pulmonary disease (COPD), of acute respiratory distress syndrome (ARDS), of acute lung injury (ALI), of alpha-1-antitrypsin deficiency (AATD), of pulmonary fibrosis, of pulmonary emphysema (for example pulmonary emphysema caused by cigarette smoke), of cystic fibrosis (CF), of acute coronary syndrome (ACS), heart muscle inflammations (myocarditis) and other autoimmune cardiac disorders (pericarditis, endocarditis, valvolitis, aortitis, cardiomyopathies), cardiogenic shock, aneurysms, sepsis (SIRS), multiple organ failure (MODS, MOF), inflammatory disorders of the kidney, chronic intestinal disorders (IBD, Crohn's Disease, UC), pancreatitis, peritonitis, rheumatoid disorders, inflammatory skin disorders and inflammatory eye disorders.

The compounds according to the invention can also be used for treatment and/or prophylaxis of asthmatic disorders of varying severity with intermittent or persistent characteristics (refractive asthma, bronchial asthma, allergic asthma, intrinsic asthma, extrinsic asthma, medicament- or dust-induced asthma), of various forms of bronchitis (chronic bronchitis, infectious bronchitis, eosinophilic bronchitis), of Bronchiolitis obliterans, bronchiectasis, pneumonia, idiopathic interstitial pneumonia, farmer's lung and related diseases, of coughs and colds (chronic inflammatory cough, iatrogenic cough), inflammation of the nasal mucosa (including medicament-related rhinitis, vasomotoric rhinitis and seasonal allergic rhinitis, for example hay fever) and of polyps.

The compounds described in the present invention are also active ingredients for control of central nervous system disorders characterized by disturbances of the NO/cGMP system. In particular, they are suitable for improving perception, concentration, learning or memory after cognitive impairments like those occurring in particular in association with situations/diseases/syndromes such as mild cognitive impairment, age-associated learning and memory impairments, age-associated memory losses, vascular dementia, craniocerebral trauma, stroke, dementia occurring after strokes (post-stroke dementia), post-traumatic craniocerebral trauma, general concentration impairments, concentration impairments in children with learning and memory problems, Alzheimer's disease, Lewy body dementia, dementia with degeneration of the frontal lobes including Pick's syndrome, Parkinson's disease, progressive nuclear palsy, dementia with corticobasal degeneration, amyolateral sclerosis (ALS), Huntington's disease, demyelinization, multiple sclerosis, thalamic degeneration, Creutzfeld-Jacob dementia, HIV dementia, schizophrenia with dementia or Korsakoff's psychosis. They are also suitable for treatment and/or prevention of central nervous system disorders such as states of anxiety, tension and depression, CNS-related sexual dysfunctions and sleep disturbances, and for controlling pathological disturbances of the intake of food, stimulants and addictive substances.

Because of their profile of biochemical and pharmacological properties, the compounds according to the invention are also especially suitable for treatment and/or prevention of heart failure, coronary heart disease, atrial and ventricular arrhythmia, kidney failure and nephropathy.

The compounds according to the invention can also be used for treatment and/or prophylaxis of primary and secondary Raynaud's phenomenon, microcirculation impairments, claudication, peripheral and autonomic neuropathies, diabetic microangiopathies, diabetic retinopathy, diabetic ulcers on the extremities, gangrene, CREST syndrome, erythematosis, onychomycosis, rheumatic disorders and for promoting wound healing.

The compounds according to the invention are additionally suitable for treatment and/or prevention of ophthalmologic disorders, for example glaucoma, age-related macular degeneration (AMD), of dry (nonexudative) AMD, wet (exudative, neovascular) AMD, choroidal neovascularization (CNV), diabetic retinopathy, atrophic changes to the retinal pigment epithelium (RPE), hypertrophic changes to the retinal pigment epithelium, macular oedema, diabetic macular oedema, retinal vein occlusion, choroidal retinal vein occlusion, macular oedema due to retinal vein occlusion, angiogenesis at the front of the eye, for example corneal angiogenesis, for example following keratitis, cornea transplant or keratoplasty, corneal angiogenesis due to hypoxia (as a result of extensive wearing of contact lenses), pterygium conjunctiva, subretinal oedema and intraretinal oedema. In addition, the compounds according to the invention are suitable for treatment and/or prevention of elevated and high intraocular pressure as a result of traumatic hyphaema, periorbital oedema, postoperative viscoelastic retention or intraocular inflammation.

Moreover, the compounds according to the invention are suitable for treatment and/or prophylaxis of hepatitis, neoplasms, osteoporosis, glaucoma and gastroparesis.

In addition, the compounds according to the invention are also suitable for controlling cerebral blood flow and are thus effective agents for controlling migraines. They are also suitable for the prophylaxis and control of sequelae of cerebral infarction (cerebral apoplexy) such as stroke, cerebral ischaemia and craniocerebral trauma. The compounds according to the invention can likewise be used for controlling states of pain and tinnitus.

The aforementioned well-characterized diseases in humans can also occur with comparable aetiology in other mammals and can likewise be treated therein with the compounds of the present invention.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" and "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

The present invention thus further provides for the use of the compounds according to the invention for treatment and/or prevention of disorders, especially of the aforementioned disorders.

The present invention further provides for the use of the compounds according to the invention for producing a medicament for the treatment and/or prevention of disorders, especially of the aforementioned disorders.

The present invention further provides a medicament comprising at least one of the compounds of the invention for treatment and/or prevention of disorders, especially of the aforementioned disorders.

The present invention further provides for the use of the compounds according to the invention in a method for treatment and/or prevention of disorders, especially of the aforementioned disorders.

The present invention further provides a method of treatment and/or prevention of disorders, especially of the aforementioned disorders, using an effective amount of at least one of the compounds according to the invention.

The present invention further provides the compounds according to the invention for use in a method of treatment and/or prevention of disorders, especially of the aforementioned disorders.

The compounds according to the invention can be used alone or, if required, in combination with one or more other pharmacologically active substances, provided that this combination does not lead to undesirable and unacceptable side effects. The present invention therefore further provides medicaments comprising at least one of the compounds according to the invention and one or more further active ingredients, especially for treatment and/or prevention of the aforementioned disorders. Preferred examples of combination active ingredients suitable for this purpose include:

active hypotensive ingredients, by way of example and with preference from the group of calcium antagonists, angiotensin AII antagonists, ACE inhibitors, NEP inhibitors, vasopeptidase inhibitors, endothelin antagonists, renin inhibitors, alpha-receptor blockers, beta-receptor blockers, mineralocorticoid receptor antagonists, and rho kinase inhibitors and the diuretics;

active antiarrhythmic ingredients, by way of example and with preference sodium channel blockers, beta receptor blockers, potassium channel blockers, calcium antagonists, If channel blockers, *digitalis*, parasympatholytics (vagolytics), sympathomimetics and other antiarrhythmics such as adenosine, adenosine receptor agonists and vernakalant.

vasopressin receptor antagonists, by way of example and with preference conivaptan, tolvaptan, lixivaptan, mozavaptan, satavaptan, SR-121463, RWJ 676070 or BAY 86-8050;

compounds which affect the energy metabolism of the heart, by way of example and with preference etomoxir, dichloroacetate, ranolazine or trimetazidine;

compounds which inhibit the degradation of cyclic guanosine monophosphate (cGMP) and/or cyclic adenosine monophosphate (cAMP), for example inhibitors of phosphodiesterases (PDE) 1, 2, 3, 4 and/or 5, especially PDE 5 inhibitors such as sildenafil, vardenafil and tadalafil;

antithrombotic agents, by way of example and with preference from the group of the platelet aggregation inhibitors, the anticoagulants or the profibrinolytic substances;

bronchodilatory agents, by way of example and with preference from the group of the beta-adrenergic receptor agonists, such as especially albuterol, isoproterenol, metaproterenol, terbutalin, formoterol or salmeterol, or from the group of the anticholinergics, such as especially ipratropium bromide;

anti-inflammatory agents, by way of example and with preference from the group of the glucocorticoids, such as especially prednisone, prednisolone, methylprednisolone, triamcinolone, dexamethasone, beclomethasone, betamethasone, flunisolide, budesonide or fluticasone;

* active ingredients which modulate lipid metabolism, by way of example and with preference from the group of the thyroid receptor agonists, cholesterol synthesis inhibitors such as, by way of example and preferably, HMG-CoA reductase inhibitors or squalene synthesis inhibitors, the ACAT inhibitors, CETP inhibitors, MTP inhibitors, PPAR-alpha, PPAR-gamma and/or PPAR-δ agonists, cholesterol absorption inhibitors, lipase inhibitors, polymeric bile acid adsorbents, bile acid reabsorption inhibitors and lipoprotein(a) antagonists.

compounds which inhibit the signal transduction cascade, by way of example and with preference from the group of the kinase inhibitors, especially from the group of the tyrosine kinase and/or serine/threonine kinase inhibitors;

compounds which inhibit the degradation and alteration of the extracellular matrix, by way of example and with preference inhibitors of the matrix metalloproteases (MMPs), especially inhibitors of chymase, stromelysin, collagenases, gelatinases and aggrecanases (in this context particularly of MMP-1, MMP-3, MMP-8, MMP-9, MMP-10, MMP-11 and MMP-13) and of metalloelastase (MMP-12);

compounds which block the binding of serotonin to its receptor, by way of example and with preference antagonists of the 5-HT$_{2b}$ receptor;

organic nitrates and NO donors, for example sodium nitroprusside, nitroglycerin, isosorbide mononitrate, isosorbide dinitrate, molsidomine or SIN-1, and inhaled NO;

NO-independent but haem-dependent stimulators of soluble guanylate cyclase, such as especially the compounds described in WO 00/06568, WO 00/06569, WO 02/42301 and WO 03/095451;

NO— and haem-independent activators of soluble guanylate cyclase, such as especially the compounds described in WO 01/19355, WO 01/19776, WO 01/19778, WO 01/19780, WO 02/070462 and WO 02/070510;

compounds which increase the synthesis of cGMP, for example sGC modulators such as, by way of example and with preference, riociguat, cinaciguat, vericiguat or BAY 1101042 prostacyclin analogues, by way of example and with preference iloprost, beraprost, treprostinil or epoprostenol;

* compounds which inhibit soluble epoxide hydrolase (sEH), for example N,N'-dicyclohexylurea, 12-(3-adamantan-1-ylureido)dodecanoic acid or 1-adamantan-1-yl-3-{5-[2-(2-ethoxyethoxy)ethoxy]pentyl}urea;

active ingredients which modulate glucose metabolism, for example insulins, sulphonylureas, acarbose, DPP4 inhibitors, GLP-1 analogues or SGLT-1 inhibitors.

In a preferred embodiment of the invention, the compounds according to the invention are used in combination with a kinase inhibitor, by way of example and with preference bortezomib, canertinib, erlotinib, gefitinib, imatinib, lapatinib, lestaurtinib, lonafarnib, pegaptinib, pelitinib, semaxanib, sorafenib, regorafenib, sunitinib, tandutinib, tipifarnib, vatalanib, fasudil, lonidamine, leflunomide, BMS-3354825 or Y-27632.

In a preferred embodiment of the invention, the compounds according to the invention are used in combination with a serotonin receptor antagonist, by way of example and with preference PRX-08066.

Antithrombotic agents are preferably understood to mean compounds from the group of the platelet aggregation inhibitors, the anticoagulants or the profibrinolytic substances.

In a preferred embodiment of the invention, the compounds according to the invention are administered in combination with a platelet aggregation inhibitor, by way of example and with preference aspirin, clopidogrel, ticlopidine or dipyridamole.

In a preferred embodiment of the invention, the compounds according to the invention are administered in combination with a thrombin inhibitor, by way of example and with preference ximelagatran, melagatran, bivalirudin or clexane.

In a preferred embodiment of the invention, the compounds according to the invention are administered in combination with a GPIIb/IIIa antagonist, by way of example and with preference tirofiban or abciximab.

In a preferred embodiment of the invention, the compounds according to the invention are administered in combination with a factor Xa inhibitor, by way of example and with preference rivaroxaban, DU-176b, fidexaban, razaxaban, fondaparinux, idraparinux, PMD-3112, YN-150, KFA-1982, EMD-503982, MCN-17, mLN-1021, DX 9065a, DPC 906, JTV 803, SSR-126512 or SSR-128428.

In a preferred embodiment of the invention, the compounds according to the invention are administered in combination with heparin or with a low molecular weight (LMW) heparin derivative.

In a preferred embodiment of the invention, the compounds according to the invention are administered in combination with a vitamin K antagonist, by way of example and with preference coumarin.

Hypotensive agents are preferably understood to mean compounds from the group of calcium antagonists, angiotensin AII antagonists, ACE inhibitors, endothelin antagonists, renin inhibitors, alpha-receptor blockers, beta-receptor blockers, mineralocorticoid receptor antagonists, rho kinase inhibitors, and the diuretics.

In a preferred embodiment of the invention, the compounds according to the invention are administered in combination with a calcium antagonist, by way of example and with preference nifedipine, amlodipine, verapamil or diltiazem.

In a preferred embodiment of the invention, the compounds according to the invention are administered in combination with an alpha-1-receptor blocker, by way of example and with preference prazosin.

In a preferred embodiment of the invention, the compounds according to the invention are administered in combination with a beta-receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII antagonist, by way of example and with preference losartan, candesartan, valsartan, telmisartan or embursatan, irbesartan, olmesartan, eprosartan or azilsartan or a dual angiotensin AII antagonist/NEP inhibitor, for example and with preference Entresto (LCZ696, valsartan/sacubitril).

In a preferred embodiment of the invention, the compounds according to the invention are administered in combination with an ACE inhibitor, by way of example and with preference enalapril, captopril, lisinopril, ramipril, delapril, fosinopril, quinopril, perindopril or trandopril.

In a preferred embodiment of the invention, the compounds according to the invention are administered in combination with an endothelin antagonist, by way of example and with preference bosentan, darusentan, ambrisentan or sitaxsentan.

In a preferred embodiment of the invention, the compounds according to the invention are administered in combination with a renin inhibitor, by way of example and with preference aliskiren, SPP-600 or SPP-800.

In a preferred embodiment of the invention, the compounds according to the invention are administered in combination with a mineralocorticoid receptor antagonist, by way of example and with preference spironolactone or eplerenone, finerenone.

In a preferred embodiment of the invention, the compounds according to the invention are administered in combination with a rho kinase inhibitor, by way of example and with preference fasudil, Y-27632, SLx-2119, BF-66851, BF-66852, BF-66853, KI-23095, SB-772077, GSK-269962A or BA-1049.

In a preferred embodiment of the invention, the compounds according to the invention are administered in combination with a diuretic, by way of example and with preference furosemide.

Lipid metabolism modifiers are preferably understood to mean compounds from the group of the CETP inhibitors, thyroid receptor agonists, cholesterol synthesis inhibitors such as HMG-CoA reductase inhibitors or squalene synthesis inhibitors, the ACAT inhibitors, MTP inhibitors, PPAR-alpha, PPAR-gamma and/or PPAR-δ agonists, cholesterol absorption inhibitors, polymeric bile acid adsorbents, bile acid reabsorption inhibitors, lipase inhibitors and the lipoprotein(a) antagonists.

In a preferred embodiment of the invention, the compounds according to the invention are administered in combination with a CETP inhibitor, by way of example and with preference torcetrapib (CP-529 414), JJT-705 or CETP vaccine (Avant).

In a preferred embodiment of the invention, the compounds according to the invention are administered in combination with a thyroid receptor agonist, by way of example and with preference D-thyroxine, 3,5,3'-triiodothyronine (T3), CGS 23425 or axitirome (CGS 26214).

In a preferred embodiment of the invention, the compounds according to the invention are administered in combination with an HMG-CoA reductase inhibitor from the class of statins, by way of example and with preference lovastatin, simvastatin, pravastatin, fluvastatin, atorvastatin, rosuvastatin or pitavastatin.

In a preferred embodiment of the invention, the compounds according to the invention are administered in combination with a squalene synthesis inhibitor, by way of example and with preference BMS-188494 or TAK-475.

In a preferred embodiment of the invention, the compounds according to the invention are administered in combination with an ACAT inhibitor, by way of example and with preference avasimibe, melinamide, pactimibe, eflucimibe or SMP-797.

In a preferred embodiment of the invention, the compounds according to the invention are administered in combination with an MTP inhibitor, by way of example and with preference implitapide, BMS-201038, R-103757 or JTT-130.

In a preferred embodiment of the invention, the compounds according to the invention are administered in combination with a PPAR-gamma agonist, by way of example and with preference pioglitazone or rosiglitazone.

In a preferred embodiment of the invention, the compounds according to the invention are administered in combination with a PPAR-δ agonist, by way of example and with preference GW 501516 or BAY 68-5042.

In a preferred embodiment of the invention, the compounds according to the invention are administered in combination with a cholesterol absorption inhibitor, by way of example and with preference ezetimibe, tiqueside or pamaqueside.

In a preferred embodiment of the invention, the compounds according to the invention are administered in combination with a lipase inhibitor, by way of example and with preference orlistat.

In a preferred embodiment of the invention, the compounds according to the invention are administered in combination with a polymeric bile acid adsorber, by way of example and with preference cholestyramine, colestipol, colesolvam, CholestaGel or colestimide.

In a preferred embodiment of the invention, the compounds according to the invention are administered in combination with a bile acid reabsorption inhibitor, by way of example and with preference ASBT (=IBAT) inhibitors, for example AZD-7806, S-8921, AK-105, BARI-1741, SC-435 or SC-635.

In a preferred embodiment of the invention, the compounds according to the invention are administered in combination with a lipoprotein(a) antagonist, by way of example and with preference gemcabene calcium (CI-1027) or nicotinic acid.

In a preferred embodiment of the invention, the compounds according to the invention are administered in combination with sGC modulators, by way of example and with preference riociguat, cinaciguat, vericiguat or BAY 1101042.

In a preferred embodiment of the invention, the compounds according to the invention are administered in combination with an active ingredient which modulates glucose metabolism, by way of example and with preference insulin, a sulphonylurea, acarbose, DPP4 inhibitors, GLP-1 analogues or SGLT-1 inhibitor.

Particular preference is given to combinations of the compounds according to the invention with one or more further active ingredients selected from the group consisting of active hypotensive ingredients, active antiarrhythmic ingredients, vasopressin receptor antagonists, PDE 5 inhibitors, platelet aggregation inhibitors, sGC activators and sGC stimulators.

The present invention further provides medicaments which comprise at least one compound according to the invention, typically together with one or more inert, non-toxic, pharmaceutically suitable excipients, and for the use thereof for the aforementioned purposes.

The compounds according to the invention can act systemically and/or locally. For this purpose, they can be administered in a suitable manner, for example by the oral, parenteral, pulmonal, nasal, sublingual, lingual, buccal, rectal, dermal, transdermal, conjunctival or otic route, or as an implant or stent.

The compounds according to the invention can be administered in administration forms suitable for these administration routes.

Suitable administration forms for oral administration are those which work according to the prior art and release the compounds according to the invention rapidly and/or in a modified manner and which contain the compounds according to the invention in crystalline and/or amorphized and/or dissolved form, for example tablets (uncoated or coated tablets, for example with gastric juice-resistant or retarded-dissolution or insoluble coatings which control the release of the compound according to the invention), tablets or films/oblates which disintegrate rapidly in the oral cavity, films/lyophilizates, capsules (for example hard or soft gelatin capsules), sugar-coated tablets, granules, pellets, powders, emulsions, suspensions, aerosols or solutions.

Parenteral administration can bypass an absorption step (e.g. take place intravenously, intraarterially, intracardially, intraspinally or intralumbally) or include an absorption (e.g. take place inhalatively, intramuscularly, subcutaneously, intracutaneously, percutaneously or intraperitoneally). Administration forms suitable for parenteral administration include preparations for injection and infusion in the form of solutions, suspensions, emulsions, lyophilizates or sterile powders.

For the other administration routes, suitable examples are inhalable medicament forms (including powder inhalers, nebulizers, metered aerosols), nasal drops, solutions or sprays, tablets, films/oblates or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents.

Oral and parenteral administration are preferred, especially oral, intravenous and intrapulmonary (inhalative) administration.

The compounds according to the invention can be converted to the administration forms mentioned. This can be accomplished in a manner known per se by mixing with inert non-toxic pharmaceutically suitable auxiliaries. These auxiliaries include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), colorants (e.g. inorganic pigments, for example iron oxides) and flavour and/or odour correctants.

In general, it has been found to be advantageous in the case of parenteral administration to administer amounts of about 0.001 to 1 mg/kg, preferably about 0.01 to 0.5 mg/kg, of body weight to achieve effective results. In the case of oral administration the dosage is about 0.01 to 100 mg/kg, preferably about 0.01 to 20 mg/kg and most preferably 0.1 to 10 mg/kg of body weight.

It may nevertheless be necessary in some cases to deviate from the stated amounts, specifically as a function of body weight, route of administration, individual response to the drug, nature of the preparation and time or interval over which administration takes place. Thus, in some cases less than the abovementioned minimum amount may be sufficient, while in other cases the upper limit mentioned must be exceeded. In the case of administration of greater amounts, it may be advisable to divide them into several individual doses over the day.

The working examples which follow illustrate the invention. The invention is not restricted to the examples.

A. EXAMPLES

Abbreviations and Acronyms

GP General Procedure
abs. absolute
aq. aqueous, aqueous solution
br. broad (in NMR signal)
Ex. Example
Bu butyl
c concentration
approx. circa, about
cat. catalytic
CI chemical ionization (in MS)
d doublet (in NMR)
d day(s)
DAST N,N-diethylaminosulphur trifluoride
DCI direct chemical ionization (in MS)
DCM dichloromethane
dd doublet of doublets (in NMR)
de diastereomeric excess
dist. distilled
DIPEA N,N-diisopropylethylamine
DMAP 4-N,N-dimethylaminopyridine
DMF N,N-dimethylformamide
DMSO dimethyl sulphoxide
dt doublet of triplets (in NMR)
of th. of theory (in chemical yield)
ee enantiomeric excess
EI electron impact ionization (in MS)
ent enantiomerically pure, enantiomer
eq. equivalent(s)
ESI electrospray ionization (in MS)
Et ethyl
GC gas chromatography
GC/MS gas chromatography-coupled mass spectrometry
h hour(s)
HATU O-(7-azabenzotriazol-1-yl)-N,N,N',N'-tetramethyluronium hexafluorophosphate
HPLC high-pressure, high-performance liquid chromatography
conc. concentrated (in the case of a solution)
LC liquid chromatography
LC/MS liquid chromatography-coupled mass spectrometry
Lit. literature (reference)
m multiplet (in NMR)
M molar (in solution)
Me methyl
min minute(s)
MS mass spectrometry
NMP N-methyl-2-pyrrolidone
NMR nuclear magnetic resonance spectrometry
OXONE® potassium peroxomonosulphate (2 $KHSO_5*KHSO_4*K_2SO_4$)
PyBOP 1-H-benzotriazol-1-yloxytris(pyrrolidino)phosphonium hexafluorophosphate
q (or quart) quartet (in NMR)
qd quartet of doublets (in NMR)
quant. quantitative (in chemical yield)
quint quintet (in NMR)
rac racemic, racemate
RP reverse phase (in HPLC)
RT room temperature
$R_t$ retention time (in HPLC, LC/MS)
s singlet (in NMR)
sept septet (in NMR)
SFC supercritical liquid chromatography
t triplet (in NMR)
tBu tert-butyl
td triplet of doublets (in NMR)
THF tetrahydrofuran
UV ultraviolet spectrometry
cf. see
v/v volume to volume ratio (of a solution)
Xantphos 9,9-dimethyl-4,5-bis(diphenylphosphino)xanthene
tog. together HPLC and LC-MS Methods:

Method 1 (LC/MS):
Instrument: Waters Acquity SQD UPLC System; column: Waters Acquity UPLC HSS T3 1.8 µm 50×1 mm; eluent A: 1 l water+0.25 ml 99% formic acid, eluent B: 1 l acetonitrile+0.25 ml 99% formic acid; gradient: 0.0 min 90% A→1.2 min 5% A→2.0 min 5% A; oven: 50° C.; flow rate: 0.40 ml/min; UV detection: 210-400 nm.

Method 2 (LC/MS):
MS instrument: Waters (Micromass) QM; HPLC instrument: Agilent 1100 series; column: Agilent ZORBAX Extend-C18 3.0×50 mm 3.5 µm; eluent A: 1 l water+0.01 mol ammonium carbonate, eluent B: 1 l acetonitrile; gradient: 0.0 min 98% A→0.2 min 98% A→3.0 min 5% A→4.5 min 5% A; oven: 40° C.; flow rate: 1.75 ml/min; UV detection: 210 nm Method 3 (LC/MS):
MS instrument type Thermo Scientific FT-MS; UHPLC+ instrument type Thermo Scientific UltiMate 3000; column Waters, HSST3, 2.1×75 mm, C18 1.8 µm; eluent A 1 l of water+0.01% formic acid; eluent B 1 l of acetonitrile+0.01% formic acid; gradient 0.0 min 10% B→2.5 min 95% B→3.5 min 95% B; oven 50° C.; flow rate 0.90 ml/min; UV detection 210 nm/optimum integration path 210-300 nm Method 4 (LC/MS):
Instrument: Waters ACQUITY SQD UPLC System; column: Waters Acquity UPLC HSS T3 1.8 µm 50×1 mm; eluent A: 1 l water+0.25 ml 99% formic acid, eluent B: 1 l acetonitrile+0.25 ml 99% formic acid; gradient: 0.0 min 95% A→6.0 min 5% A→7.5 min 5% A; oven: 50° C.; flow rate: 0.35 ml/min; UV detection: 210-400 nm.

Method 5 (LC/MS):

Instrument: Agilent MS Quad 6150; HPLC: Agilent 1290; column: Waters Acquity UPLC HSS T3 1.8μ 50×2.1 mm; eluent A: 1 l water+0.25 ml 99% formic acid, eluent B: 1 l acetonitrile+0.25 ml 99% formic acid; gradient: 0.0 min 90% A→0.3 min 90% A→1.7 min 5% A→3.0 min 5% A; oven: 50° C.; flow rate: 1.20 ml/min; UV detection: 205-305 nm.

Method 6 (GC-MS):

Instrument: Thermo DFS, Trace GC Ultra; column: Restek RTX-35, 15 m×200 μm×0.33 μm; constant flow rate of helium: 1.20 ml/min; oven: 60° C.; inlet: 220° C.; gradient: 60° C., 30° C./min→300° C. (hold for 3.33 min).

Method 7 (Preparative HPLC):

Column: Chromatorex C18, 250×30 mm; eluent A: water+0.1% formic acid, eluent B: acetonitrile; sample injection at 3.0 min, gradient: 0.0 min 10% B→5.0 min 10% B→25 min 80% B→30 min 95% B→35 min 10% B; flow rate: 50 ml/min, UV detection: 210 nm.

Further Details:

The percentages in the example and test descriptions which follow are, unless indicated otherwise, percentages by weight; parts are parts by weight. Solvent ratios, dilution ratios and concentration data for the liquid/liquid solutions are based in each case on volume.

In the case of purifications of compounds according to the invention by preparative HPLC by the above-described methods in which the eluents contain additives, for example trifluoroacetic acid, formic acid or ammonia, the compounds according to the invention can be obtained in salt form, for example as trifluoroacetate, formate or ammonium salt, if the compounds according to the invention contain a sufficiently basic or acidic functionality. Such a salt can be converted to the corresponding free base or acid by various methods known to the person skilled in the art.

Purity figures are generally based on corresponding peak integrations in the LC/MS chromatogram, but may additionally also have been determined with the aid of the $^1$H NMR spectrum. If no purity is indicated, the purity is generally 100% according to automated peak integration in the LC/MS chromatogram, or the purity has not been determined explicitly.

Stated yields in % of theory are generally corrected for purity if a purity of <100% is indicated. In solvent-containing or contaminated batches, the formal yield may be ">100%"; in these cases the yield is not corrected for solvent or purity.

The descriptions of the coupling patterns of $^1$H NMR signals that follow have in some cases been taken directly from the suggestions of the ACD SpecManager (ACD/Labs Release 12.00, Product version 12.5) and have not necessarily been strictly scrutinized. In some cases, the suggestions of the SpecManager were adjusted manually. Manually adjusted or assigned descriptions are generally based on the optical appearance of the signals in question and do not necessarily correspond to a strict, physically correct interpretation. In general, the stated chemical shift refers to the centre of the signal in question. In the case of broad multiplets, an interval is given. Signals obscured by solvent or water were either tentatively assigned or have not been listed. Significantly broadened signals—caused, for example, by rapid rotation of molecular moieties or because of exchanging protons—were likewise assigned tentatively (often referred to as a broad multiple or broad singlet) or are not listed.

The $^1$H NMR data of selected examples are stated in the form of $^1$H NMR peak lists. For each signal peak, first the δ value in ppm and then the signal intensity in round brackets are listed. The δ value/signal intensity number pairs for different signal peaks are listed with separation from one another by commas. The peak list for an example therefore takes the following form: $δ_1$ (intensity$_1$), $δ_2$ (intensity$_2$), . . . , $δ_i$ (intensity$_i$) . . . , $δ_n$ (intensity$_n$).

The intensity of sharp signals correlates with the height of the signals in a printed example of an NMR spectrum in cm and shows the true ratios of the signal intensities in comparison with other signals. In the case of broad signals, several peaks or the middle of the signal and the relative intensity thereof may be shown in comparison to the most intense signal in the spectrum. The lists of the $^1$H NMR peaks are similar to the conventional $^1$H-NMR printouts and thus usually contain all peaks listed in a conventional NMR interpretation. In addition, like conventional $^1$H NMR printouts, they may show solvent signals, signals of stereoisomers of the target compounds which likewise form part of the subject-matter of the invention, and/or peaks of impurities. The peaks of stereoisomers of the target compounds and/or peaks of impurities usually have a lower intensity on average than the peaks of the target compounds (for example with a purity of >90%). Such stereoisomers and/or impurities may be typical of the particular preparation process. Their peaks can thus help in identifying reproduction of our preparation process with reference to "byproduct fingerprints". An expert calculating the peaks of the target compounds by known methods (MestreC, ACD simulation, or using empirically evaluated expected values) can, if required, isolate the peaks of the target compounds, optionally using additional intensity filters. This isolation would be similar to the peak picking in question in conventional $^1$H NMR interpretation. A detailed description of the presentation of NMR data in the form of peak lists can be found in the publication "Citation of NMR Peaklist Data within Patent Applications" (cf. Research Disclosure Database Number 605005, 2014, 1 Aug. 2014 or http://www.research-disclosure.com/searching-disclosures). In the peak picking routine described in Research Disclosure Database Number 605005, the parameter "MinimumHeight" can be set between 1% and 4%. Depending on the type of chemical structure and/or depending on the concentration of the compound to be analysed, it may be advisable to set the parameters "MinimumHeight" of values<1%.

Melting points and melting-point ranges, if stated, are uncorrected.

All reactants or reagents whose preparation is not described explicitly hereinafter were purchased commercially from generally accessible sources. For all other reactants or reagents whose preparation likewise is not described hereinafter and which were not commercially obtainable or were obtained from sources which are not generally accessible, a reference is given to the published literature in which their preparation is described.

General Procedures

GP1

To a solution of the corresponding carboxylic acid (1-2 eq.) in DMF (0.08-0.12M) were added N,N-diisopropylethylamine (1.4-1.5 eq., or 2.4-3.0 eq. when the amine was used in hydrochloride form) and HATU (1.0-1.65 eq.), and the mixture was stirred at RT for 30 min. Subsequently, the appropriate amine (1.04-1.5 eq.) was added and the mixture was stirred at room temperature for a further 0.25-2 h. The reaction was then ended by the addition of water and 1 M aqueous hydrochloric acid. The precipitate was filtered off, taken up in DCM, dried over magnesium sulphate and filtered, and the solvent was removed under reduced pressure. Alternatively, the acidification was followed by extraction with ethyl acetate, drying of the combined organic phases over magnesium sulphate, filtration and removal of the solvent under reduced pressure. The crude product was then purified either by normal phase chromatography (eluent: cyclohexane/ethyl acetate mixtures or dichloromethane/methanol mixtures) or preparative RP-HPLC (water/acetonitrile gradient).

GP2

Potassium carbonate or caesium carbonate (1.5-2.5 eq.) was baked in a reaction vessel under reduced pressure. It was cooled to RT and flooded with argon. Palladium acetate (0.1-0.36 eq.), 9,9-dimethyl-4,5-bis(diphenylphosphino)xanthene (Xantphos, 0.18-0.36 eq.) and dioxane (0.04-0.12M) were added, and the suspension was degassed in an argon stream at room temperature for 10 min. Subsequently, the appropriate amide (1.0-1.2 eq.) and the appropriate 7-chloro-4-oxo-1,4-dihydro-1,8-naphthyridine (1.0 eq.) were added. The mixture was stirred at 80-110° C. for 1 h (or until conversion was complete by analytical HPLC or thin-layer chromatography with appropriate eluent mixtures). The mixture was cooled to RT and all volatile components were removed under reduced pressure, or alternatively the reaction mixture was poured into water, the pH was adjusted to pH 1 with 1M aqueous hydrochloric acid, the mixture was extracted with ethyl acetate, the combined organic phases were washed with saturated aqueous sodium chloride solution, dried over magnesium sulphate and filtered, and the solvent was removed under reduced pressure. The crude product was then purified either by normal phase chromatography (eluent: cyclohexane/ethyl acetate mixtures or dichloromethane/methanol mixtures) or preparative RP-HPLC (water/acetonitrile gradient).

GP3

To a solution of the appropriate 7-chloro-4-oxo-1,4-dihydro-1,8-naphthyridine in DMF (0.10-0.22 M) were successively added the appropriate amine (1.2 eq.) and DIPEA (1.5-3.5 eq.). The reaction solution was stirred at RT overnight. The crude product was then purified either by normal phase chromatography (eluent: cyclohexane/ethyl acetate mixtures or dichloromethane/methanol mixtures) or preparative RP-HPLC (water/acetonitrile gradient).

Starting Compounds and Intermediates

Example 1A rac-Methyl 5-methyl-1,2-oxazolidine-5-carboxylate

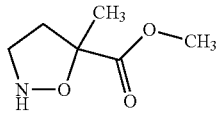

To a solution of 20.0 g (288 mmol) of hydroxylamine hydrochloride and 11.5 g (288 mmol) of sodium hydroxide in 20 ml of methanol and 40 ml of water were added dropwise 21.7 ml (290 mmol) of paraformaldehyde (37% in water), at a sufficiently slow rate that the temperature did not exceed 35° C. Subsequently, 31.0 ml (288 mmol) of methyl methacrylate were added and, on completion of addition, the mixture was stirred at 70° C. for 2 h. The mixture was cooled down to room temperature and extracted with DCM. The combined organic phases were dried over sodium sulphate and filtered, and the solvent was removed under reduced pressure. 3.70 g (8.5% of theory, 96% purity) of the title compound were obtained after vacuum distillation (0.7 mbar, 78-84° C.).

$^1$H-NMR (400 MHz, CDCl$_3$): δ [ppm]=6.05 (br. s, 1H), 3.76 (s, 3H), 3.27-3.36 (m, 1H), 3.12-3.24 (m, 1H), 2.45-2.57 (m, 1H), 2.07-2.17 (m, 1H), 1.55 (s, 3H).

GC/MS [Method 6]: R$_t$=3.51 min; MS: m/z=115.

Example 2A rac-3-Hydroxy-3-methylpyrrolidin-2-one

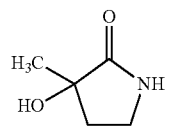

To a solution of 3.70 g (25.5 mmol) of the compound from Example 1A in 300 ml of ethanol were added 3.80 g (3.57 mmol) of palladium (10% on charcoal), and the mixture was stirred under a hydrogen atmosphere (standard pressure) overnight. The mixture was then filtered through Celite and the solvent was removed under reduced pressure. The solid obtained was then stirred with acetonitrile, and the precipitate was filtered off with suction, washed twice with 1 ml of acetonitrile and dried under high vacuum. 1.97 g (55% of theory; 82% purity) of the title compound were obtained.

$^1$H-NMR (400 MHz, CDCl$_3$): δ [ppm]=5.71 (br. s, 1H), 3.37-3.43 (m, 1H), 3.24-3.31 (m, 1H), 2.64 (s, 1H), 2.24-2.33 (m, 1H), 2.13-2.21 (m, 1H), 1.40 (s, 3H).

GC/MS [Method 6]: R$_t$=3.14 min; MS: m/z=145.

Example 3A

Ethyl 7-chloro-1-(2-fluorophenyl)-4-oxo-1,4-dihydro-1,8-naphthyridine-3-carboxylate

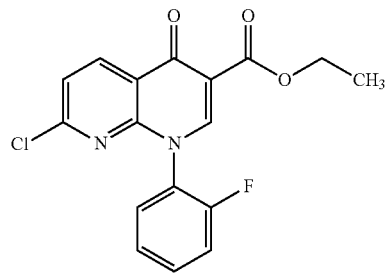 [SMILES: CCOC(=O)c1cn(-c2ccccc2F)c2nc(Cl)ccc2c1=O]

To a solution of 11.1 g (35.0 mmol) of ethyl 2-[(2,6-dichloropyridin-3-yl)carbonyl]-3-(dimethylamino)acrylate (CAS 635309-52-3) in 80 ml of ethanol were added 4.67 g (42.0 mmol) of 2-fluoroaniline in 21 ml of THF, and the mixture was stirred at RT overnight. Subsequently, the solvent was removed under reduced pressure, the residue was taken up in 110 ml of DMF, and 7.26 g (52.5 mmol) of potassium carbonate were added. The suspension was then stirred at 100° C. for 3 h, then cooled to RT and added to 200 ml of water. The precipitate was filtered off with suction, washed with water, then dissolved in 300 ml of ethyl acetate, washed three times with 50 ml of water, dried over sodium sulphate and filtered, and the solvent was removed under reduced pressure. The residue was taken up in a little DCM and purified by means of flash chromatography (ethyl acetate-cyclohexane gradient, then methanol-DCM, 5/95). 1.53 g (12% of theory, 99% purity) of the title compound were obtained. In addition, 1.33 g (11% of theory, 99% purity) of the title compound from Example 32A were obtained (for analysis see Example 32A).

$^1$H-NMR (400 MHz, DMSO-$d_6$): δ [ppm]=8.71 (s, 1H), 8.62 (d, 1H), 7.73-7.78 (m, 1H), 7.65-7.69 (m, 1H), 7.65 (d, 1H), 7.50-7.56 (m, 1H), 7.43-7.48 (m, 1H), 4.24 (q, 2H), 1.27 (t, 3H).

LC-MS (Method 1): $R_t$=0.94 min; 347 [M+H]$^+$.

Example 4A

Ethyl 7-chloro-1-(2-chlorophenyl)-4-oxo-1,4-dihydro-1,8-naphthyridine-3-carboxylate

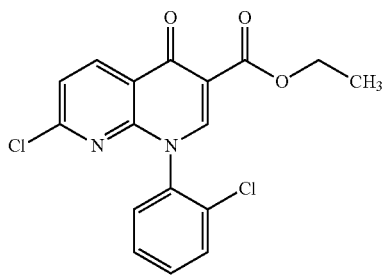 [SMILES: CCOC(=O)c1cn(-c2ccccc2Cl)c2nc(Cl)ccc2c1=O]

To a solution of 6.05 g (19.0 mmol) of ethyl 2-[(2,6-dichloropyridin-3-yl)carbonyl]-3-ethoxyacrylate (CAS 157373-27-8) and 3.39 g (26.6 mmol) of 2-chloroaniline in 30.2 ml DCM were added 23.2 ml (133 mmol) of DIPEA, and the mixture was stirred at RT for 4 h. Subsequently, 2.63 g (19.0 mmol) of potassium carbonate were added and the mixture was heated under reflux overnight. The mixture was diluted with 200 ml of DCM and washed twice with 75 ml of 1 M aqueous hydrochloric acid. The organic phase was dried over sodium sulphate and filtered, and the solvent was removed under reduced pressure. The suspension obtained was stirred with 40 ml of tert-butyl methyl ether, and the precipitate was filtered off with suction, washed with 10 ml of tert-butyl methyl ether and dried under high vacuum. 3.71 g (53% of theory, 99% purity) of the title compound were obtained.

$^1$H-NMR (400 MHz, DMSO-$d_6$): δ [ppm]=8.65 (s, 1H), 8.63 (d, 1H), 7.82-7.75 (m, 2H), 7.59-7.68 (m, 3H), 4.24 (q, 2H), 1.27 (t, 3H).

LC-MS (Method 3): $R_t$=1.81 min; 363 [M+H]$^+$.

Example 5A

Ethyl 7-chloro-1-(2-chloro-4-fluorophenyl)-4-oxo-1,4-dihydro-1,8-naphthyridine-3-carboxylate

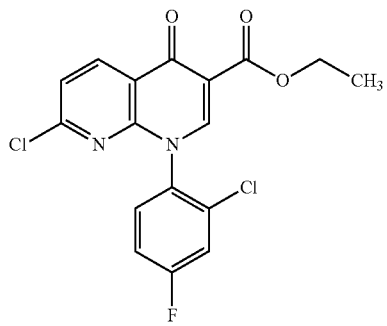 [SMILES: CCOC(=O)c1cn(-c2ccc(F)cc2Cl)c2nc(Cl)ccc2c1=O]

A mixture of 5 g (13.4 mmol) of ethyl 2-[(2,6-dichloropyridin-3-yl)carbonyl]-3-ethoxyacrylate (CAS 157373-27-8), 10.36 g (80.2 mmol) of DIPEA and 2.92 g (20.1 mmol) of 2-chloro-4-fluoroaniline in 50 ml of dichloromethane was stirred at 20° C. for 20 hours. Subsequently, the mixture was concentrated under reduced pressure, then taken up in ethyl acetate and washed three times with water and once with saturated sodium chloride solution. The organic phase was concentrated under reduced pressure and dried under high vacuum. The residue was then dissolved in 80 ml of dioxane, a solution of 1 g (9.3 mmol) of potassium tert-butoxide in 20 ml of dioxane was added while cooling with ice, and the mixture was stirred at 23° C. for 15 h. The solution was then added to ice-water, and the precipitated solid was filtered off with suction, washed with water and dried under high vacuum. 3.3 g (56% of theory, 87% purity) of the title compound were obtained.

LC-MS (Method 1): $R_t$=1.04 min; m/z=381.1 [M+H]$^+$.

Example 6A

Ethyl 1-(2,4-difluorophenyl)-7-(dimethylamino)-4-oxo-1,4-dihydro-1,8-naphthyridine-3-carboxylate

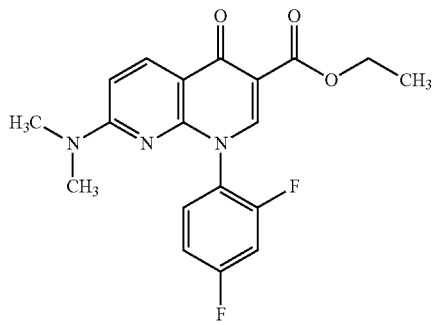 [SMILES: CCOC(=O)c1cn(-c2ccc(F)cc2F)c2nc(N(C)C)ccc2c1=O]

A mixture of 2 g (5.5 mmol) of ethyl 7-chloro-1-(2,4-difluorophenyl)-4-oxo-1,4-dihydro-1,8-naphthyridine-3-carboxylate (preparation described in DE 4301246, Example U, S.26), 894 mg (11 mmol) of dimethylamine hydrochloride and 2.48 g (19.2 mmol) of DIPEA in 50 ml of acetonitrile was stirred at 23° C. for 18 hours. Subsequently, the mixture was concentrated under reduced pressure, water was added and the aqueous phase was extracted with ethyl acetate. The combined organic phases were washed with saturated sodium chloride solution, dried over magnesium sulphate and concentrated under reduced pressure. This gave 1.92 g (94% of theory) of the title compound.

LC-MS (Method 1): $R_t$=0.95 min; m/z=374.1 [M+H]$^+$.

In analogy to Example 6A, the example compounds shown in Table 1A were prepared by reacting ethyl 7-chloro-1-(2,4-difluorophenyl)-4-oxo-1,4-dihydro-1,8-naphthyridine-3-carboxylate or the compound from Example 5A with the appropriate amines (or salts thereof) and DIPEA under the reaction conditions described. Differences are specified in the respective examples.

TABLE 1A

| Ex. | IUPAC name/structure/(yield) | Analytical data |
|---|---|---|
| 7A | Ethyl 1-(2,4-difluorophenyl)-7-(methylamino)-4-oxo-1,4-dihydro-1,8-naphthyridine-3-carboxylate<br />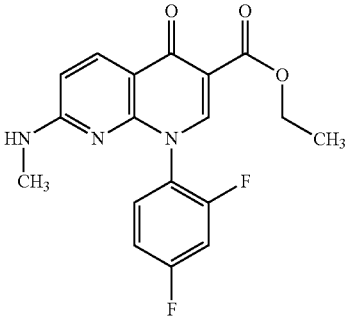<br />Solvent: THF/MeCN/NMP; 4 eq. methylamine (2 M in THF); 3.5 eq. DIPEA; 23° C. for 17 h, then 40°C. for 8h<br />(61% of theory) | LC-MS (Method 1): $R_t$ = 0.89 min<br />MS (ESpos): m/z = 360.2 [M + H]$^+$ |
| 8A | Ethyl 1-(2,4-difluorophenyl)-4-oxo-7-(propan-2-ylamino)-1,4-dihydro-1,8-naphthyridine-3-carboxylate<br />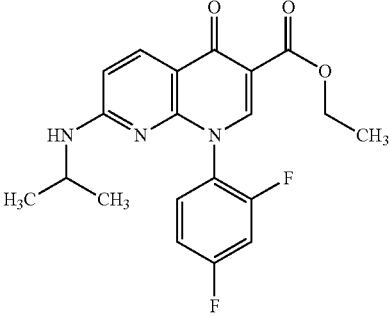<br />(68% of theory) | LC-MS (Method 1): $R_t$ = 0.99 min<br />MS (ESpos): m/z = 388.3 [M + H]$^+$ |
| 9A | Ethyl 1-(2,4-difluorophenyl)-7-[(2-hydroxyethyl)(methyl)amino]-4-oxo-1,4-dihydro-1,8-naphthyridine-3-carboxylate<br />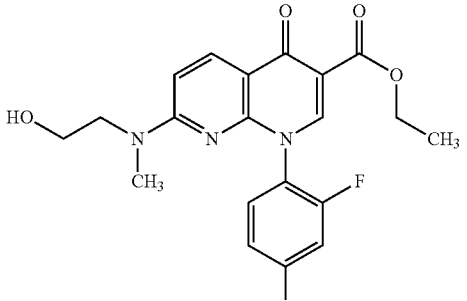<br />(93% of theory) | LC-MS (Method 1): $R_t$ = 0.85 min<br />MS (ESpos): m/z = 404.2. [M + H]$^+$ |

TABLE 1A-continued

| Ex. | IUPAC name/structure/(yield) | Analytical data |
|---|---|---|
| 10A | Ethyl 1-(2,4-difluorophenyl)-7-[(2-hydroxyethyl)amino]-4-oxo-1,4-dihydro-1,8-naphthyridine-3-carboxylate<br>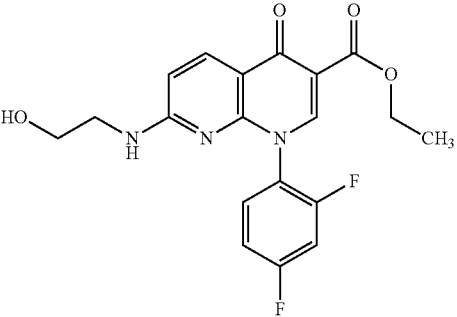<br>(63% of theory) | LC-MS (Method 1): $R_t$ = 0.80 min<br>MS (ESpos): m/z = 390.2 [M + H]$^+$ |
| 11A | Ethyl 1-(2,4-difluorophenyl)-7-[(2-fluoroethyl)amino]-4-oxo-1,4-dihydro-1,8-naphthyridine-3-carboxylate<br>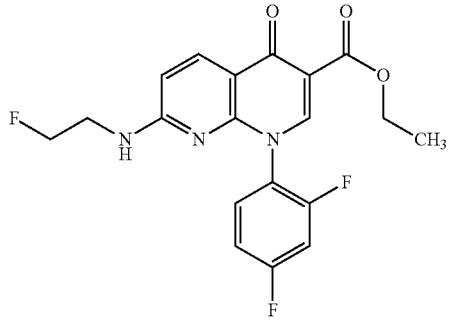<br>(38% of theory) | LC-MS (Method 1): $R_t$ = 0.90 min<br>MS (ESpos): m/z = 392.1 [M + H]$^+$ |
| 12A | Ethyl 1-(2,4-difluorophenyl)-7-[(2-fluoroethyl)(methyl)amino]-4-oxo-1,4-dihydro-1,8-naphthyridine-3-carboxylate<br>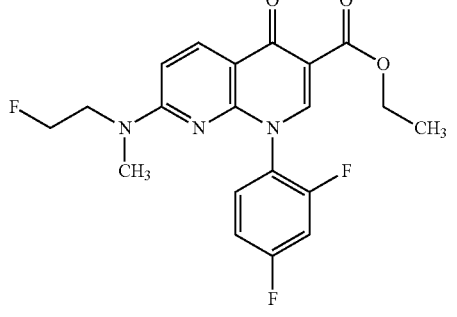<br>(64% of theory) | LC-MS (Method 1): $R_t$ = 0.96 min<br>MS (ESpos): m/z = 406.1 [M + H]$^+$ |

TABLE 1A-continued

| Ex. | IUPAC name/structure/(yield) | Analytical data |
|---|---|---|
| 13A | Ethyl 1-(2,4-difluorophenyl)-7-(3,3-difluoropyrrolidin-1-yl)-4-oxo-1,4-dihydro-1,8-naphthyridine-3-carboxylate<br>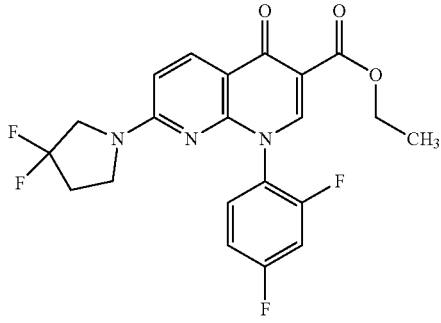<br>(83% of theory) | LC-MS (Method 1): $R_t$ = 1.02 min<br>MS (ESpos): m/z = 436.1 [M + H]$^+$ |
| 14A | Ethyl 1-(2,4-difluorophenyl)-7-[(3R)-3-fluoropyrrolidin-1-yl]-4-oxo-1,4-dihydro-1,8-naphthyridine-3-carboxylate<br>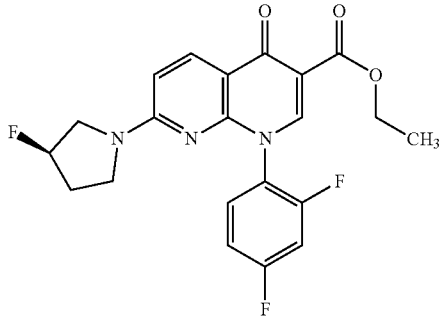<br>(72% of theory) | LC-MS (Method 1): $R_t$ = 0.97 min<br>MS (ESpos): m/z = 417.9 [M + H]$^+$ |
| 15A | Ethyl 1-(2,4-difluorophenyl)-7-[(3S)-3-fluoropyrrolidin-1-yl]-4-oxo-1,4-dihydro-1,8-naphthyridine-3-carboxylate<br>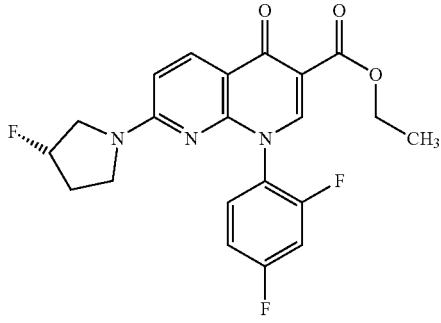<br>(90% of theory) | LC-MS (Method 1): $R_t$ = 0.97 min<br>MS (ESpos): m/z = 418.1 [M + H]$^+$ |

TABLE 1A-continued

| Ex. | IUPAC name/structure/(yield) | Analytical data |
|---|---|---|
| 16A | Ethyl 1-(2,4-difluorophenyl)-4-oxo-7-(3,3,4,4-tetrafluoropyrrolidin-1-yl)-1,4-dihydro-1,8-naphthyridine-3-carboxylate<br />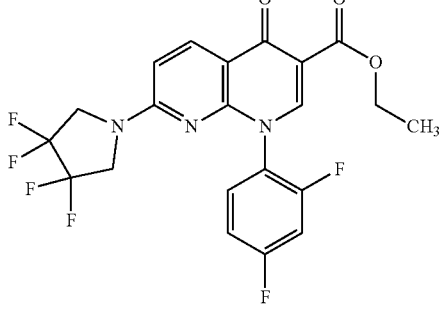<br />(50% of theory) | LC-MS (Method 1): $R_t$ = 1.05 min<br />MS (ESpos): m/z = 472.2 [M + H]$^+$ |
| 17A | Ethyl 7-[(2,2-difluoroethyl)(methyl)amino]-1-(2,4-difluorophenyl)-4-oxo-1,4-dihydro-1,8-naphthyridine-3-carboxylate<br />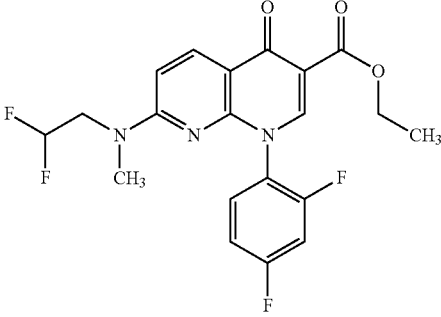<br />4 days at 23°C.<br />(84% of theory) | LC-MS (Method 1): $R_t$ = 0.98 min<br />MS (ESpos): m/z = 424.1 [M + H]$^+$ |
| 18A | Ethyl 7-[(2,2-difluoroethyl)amino]-1-(2,4-difluorophenyl)-4-oxo-1,4-dihydro-1,8-naphthyridine-3-carboxylate<br />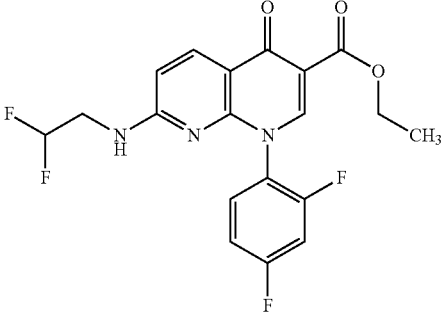<br />(47% of theory) | LC-MS (Method 1): $R_t$ = 0.93 min<br />MS (ESpos): m/z = 409.9 [M + H]$^+$ |

TABLE 1A-continued

| Ex. | IUPAC name/structure/(yield) | Analytical data |
|---|---|---|
| 19A | Ethyl 1-(2,4-difluorophenyl)-4-oxo-7-(1,3-thiazolidin-3-yl)-1,4-dihydro-1,8-naphthyridine-3-carboxylate<br>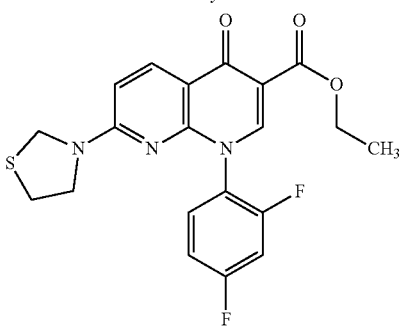<br>Solvent: DMF; 23° C. for 2 days;<br>then 50° C. for 18 h;<br>then 70° C. for 18 h;<br>(65% of theory) | LC-MS (Method 2): $R_t$ = 1.01 min<br>MS (ESpos): m/z = 418.2 [M + H]$^+$ |
| 20A | rac-Ethyl 1-(2,4-difluorophenyl)-7-[2-(hydroxymethyl)morpholin-4-yl]-4-oxo-1,4-dihydro-1,8-naphthyridine-3-carboxylate<br>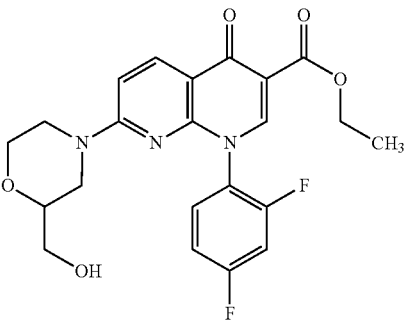<br>(20% of theory) | LC-MS (Method 1): $R_t$ = 0.79 min<br>MS (ESpos): m/z = 446.3 [M + H]$^+$ |
| 21A | rac-Ethyl 1-(2,4-difluorophenyl)-7-[2-(hydroxymethyl)pyrrolidin-1-yl]-4-oxo-1,4-dihydro-1,8-naphthyridine-3-carboxylate<br>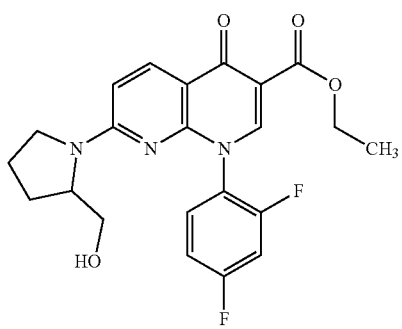<br>(76% of theory) | LC-MS (Method 1): $R_t$ = 0.87 min<br>MS (ESpos): m/z = 430.2 [M + H]$^+$ |

TABLE 1A-continued

| Ex. | IUPAC name/structure/(yield) | Analytical data |
|---|---|---|
| 22A | rac-Ethyl 1-(2,4-difluorophenyl)-7-[3-(hydroxymethyl)morpholin-4-yl]-4-oxo-1,4-dihydro-1,8-naphthyridine-3-carboxylate<br>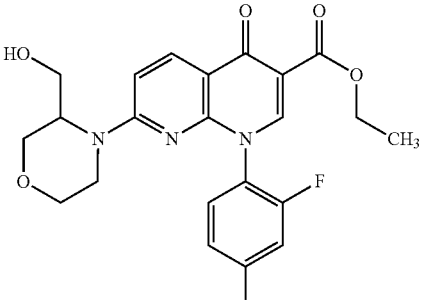<br>(30% of theory) | LC-MS (Method 1): $R_t$ = 0.81 min<br>MS (ESpos): m/z = 446.2 [M + H]$^+$ |
| 23A | rac-Ethyl 1-(2,4-difluorophenyl)-7-(3-hydroxy-3-methylpiperidin-1-yl)-4-oxo-1,4-dihydro-1,8-naphthyridine-3-carboxylate<br>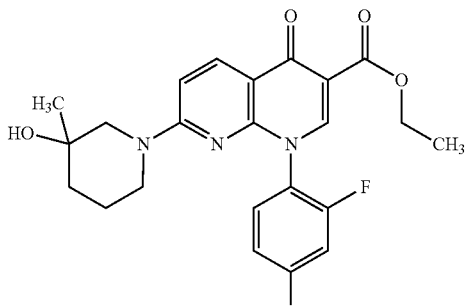<br>(37% of theory) | LC-MS (Method 1): $R_t$ = 0.91 min<br>MS (ESpos): m/z = 444.3 [M + H]$^+$ |
| 24A | Ethyl 1-(2,4-difluorophenyl)-7-[methyl(2,2,2-trifluoroethyl)amino]-4-oxo-1,4-dihydro-1,8-naphthyridine-3-carboxylate<br>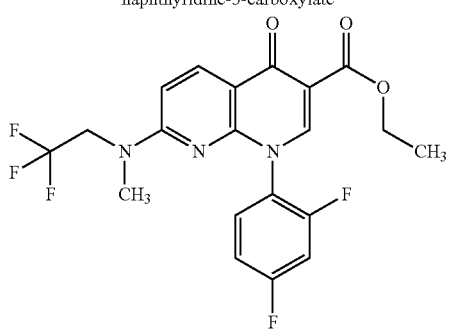<br>3.5 eq. 2,2,2-trifluoro-N-methylethylamine hydrochloride and 5.5 eq. DIPEA/60-70° C./4 days<br>(75% of theory) | LC-MS (Method 1): $R_t$ = 1.02 min<br>MS (ESpos): m/z = 442.2 [M + H]$^+$ |

TABLE 1A-continued

| Ex. | IUPAC name/structure/(yield) | Analytical data |
|---|---|---|
| 25A | Ethyl 1-(2,4-difluorophenyl)-7-(morpholin-4-yl)-4-oxo-1,4-dihydro-1,8-naphthyridine-3-carboxylate<br>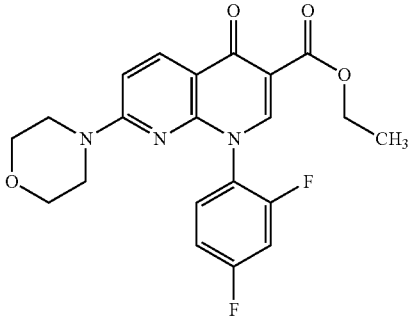<br>50%/4 h in acetonitrile<br>(82% of theory) | LC-MS (Method 1): $R_t$ = 0.93 min<br>MS (ESpos): m/z = 416.2 [M + H]$^+$ |
| 26A | Ethyl 1-(2,4-difluorophenyl)-4-oxo-7-(pyrrolidin-1-yl)-1,4-dihydro-1,8-naphthyridine-3-carboxylate<br>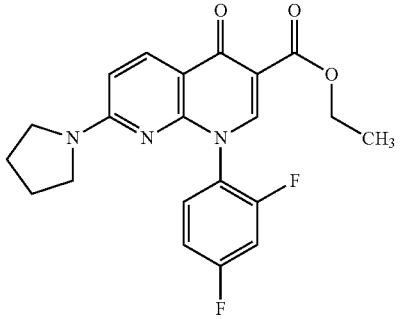<br>Solvent: DMF<br>(96% of theory) | LC-MS (Method 1): $R_t$ = 1.06 min<br>MS (ESpos): m/z = 400.2 [M + H]$^+$ |
| 27A | Ethyl 1-(2,4-difluorophenyl)-7-[4-hydroxy-4-(hydroxymethyl)piperidin-1-yl]-4-oxo-1,4-dihydro-1,8-naphthyridine-3-carboxylate<br>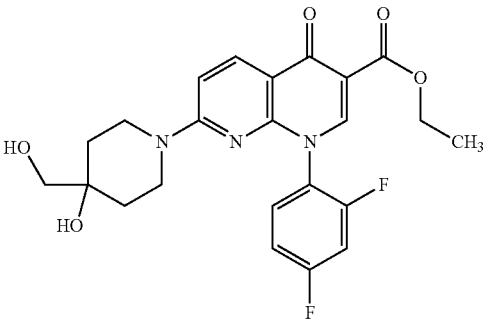<br>Solvent: NMP<br>(17% of theory) | LC-MS (Method 1): Rt = 0.76 min<br>MS (ESpos): m/z = 460.3 [M + H]+ |

TABLE 1A-continued

| Ex. | IUPAC name/structure/(yield) | Analytical data |
|---|---|---|
| 28A | Ethyl 1-(2-chloro-4-fluorophenyl)-7-(dimethylamino)-4-oxo-1,4-dihydro-1,8-naphthyridine-3-carboxylate<br><br>proceeding from the compound front Example 5A and dimethylamine hydrochloride; solvent: DMF; 17 h at 23° C.<br>(82% of theory) | LC-MS (Method 1): $R_t$ = 1.01 min<br>MS (ESpos): m/z = 390.2 [M + H]$^+$ |
| 29A | Ethyl 1-(2,4-difluorophenyl)-7-[4-(methoxycarbonyl)piperazin-1-yl]-4-oxo-1,4-dihydro-1,8-naphthyridine-3-carboxylate<br><br>Solvent: NMP; 4.5 days at 23° C.<br>(58% of theory) | LC-MS (Method 1): $R_t$ = 0.91 min<br>MS (ESpos): m/z = 473.3 [M + H]$^+$ |

Example 30A

Ethyl 1-(2,4-difluorophenyl)-4-oxo-7-[(2,2,2-trifluoroethyl)amino]-1,4-dihydro-1,8-naphthyridine-3-carboxylate

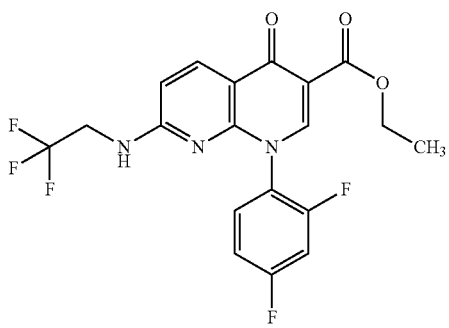 [SMILES: CCOC(=O)c1cn(-c2ccc(F)cc2F)c2nc(NCC(F)(F)F)ccc2c1=O]

A mixture of 1 g (2.7 mmol) of ethyl 7-chloro-1-(2,4-difluorophenyl)-4-oxo-1,4-dihydro-1,8-naphthyridine-3-carboxylate (preparation described in DE 4301246, Example U, S.26) and 1.9 g (19 mmol) of 2,2,2-trifluoroethylamine in 3.5 ml of acetonitrile was stirred in a microwave at 160° C. for one hour. Subsequently, the mixture was brought to pH 3 with 1 M aqueous hydrochloric acid, water was added, and the precipitated solid was filtered off with suction, washed with water and petroleum ether and dried under high vacuum. This gave 1.2 g (66% of theory) of the title compound.

$^1$H-NMR (400 MHz, DMSO-d$_6$): [ppm]=2.40 (s, 3H), 7.49-7.56 (m, 3H), 7.61-7.63 (m, 2H), 7.90-7.94 (m, 2H), 8.01 (d, 1H), 14.39 (br. s, 1H).

LC-MS (Method 1): $R_t$=0.91 min; MS (ESpos): m/z=428.1 [M+H]$^+$

Example 31A

Ethyl 1-(2,4-difluorophenyl)-7-(1,1-dioxido-1,3-thiazolidin-3-yl)-4-oxo-1,4-dihydro-1,8-naphthyridine-3-carboxylate

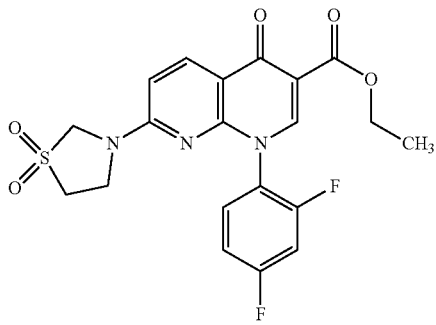 [SMILES: CCOC(=O)c1cn(-c2ccc(F)cc2F)c2nc(N3CCS(=O)(=O)C3)ccc2c1=O]

A mixture of 6.1 g (11.5 mmol; 79% purity) of the compound from Example 19A, 28.3 g (46 mmol) of OXONE® and 8 g (46 mmol) of dipotassium hydrogenphosphate in 88 ml of dioxane and 44 ml water was stirred at 23° C. for 8 hours and then left to stand for 13 h. Subsequently, 1 ml of 1 M aqueous hydrochloric acid and 100 ml of water were added, and the precipitated solid was filtered off with suction, washed with water and petroleum ether and dried under high vacuum. This gave 3.72 g (58% of theory) of the title compound.

LC-MS (Method 1): Rt=0.83 min; m/z=450.2 [M+H]+.

Example 32A

Ethyl 7-(dimethylamino)-1-(2-fluorophenyl)-4-oxo-1,4-dihydro-1,8-naphthyridine-3-carboxylate

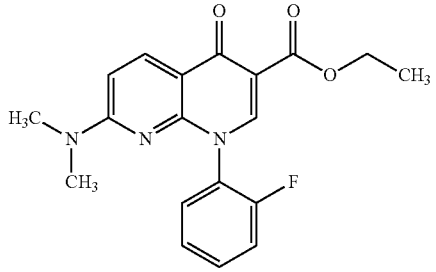 [SMILES: CCOC(=O)c1cn(-c2ccccc2F)c2nc(N(C)C)ccc2c1=O]

As described in the preparation of the compound from Example 3A, 11.1 g (35.0 mmol) of ethyl 2-[(2,6-dichloropyridin-3-yl)carbonyl]-3-(dimethylamino)acrylate were used to obtain 1.33 g (11% of theory, 99% purity) of the title compound.

$^1$H-NMR (400 MHz, DMSO-d$_6$): δ [ppm]=8.43 (s, 1H), 8.21 (d, 1H), 7.70-7.65 (m, 1H), 7.64-7.57 (m, 1H), 7.50-7.44 (m, 1H), 7.43-7.38 (m, 1H), 6.82 (d, 1H), 4.20 (q, 2H), 2.90 (br. s, 6H), 1.25 (t, 3H).

LC-MS (Method 3): R$_t$=1.64 min; 356 [M+H]+.

Example 33A

7-Chloro-1-(2-fluorophenyl)-4-oxo-1,4-dihydro-1,8-naphthyridine-3-carboxylic acid

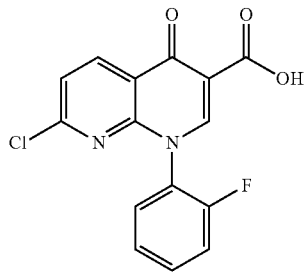 [SMILES: O=C(O)c1cn(-c2ccccc2F)c2nc(Cl)ccc2c1=O]

To a suspension of 1.52 g (4.38 mmol) of the compound from Example 3A in 21.7 ml of THF were added 8.8 ml of aqueous sodium hydroxide solution (1 M, 8.8 mmol), and the reaction mixture was stirred at room temperature for 3 h. The mixture was then diluted with 100 ml of water and the pH was adjusted to pH 1 with 1 M aqueous hydrochloric acid. The precipitate was filtered off with suction, washed with water and dried in a vacuum drying cabinet at 40° C. overnight. 1.22 g (86% of theory, 99% purity) of the title compound were obtained.

$^1$H-NMR (400 MHz, DMSO-d$_6$): δ [ppm]=14.1 (br. s, 1H), 9.02 (s, 1H), 8.80 (d, 1H), 7.81 (d, 1H), 7.79-7.74 (m, 1H), 7.72-7.66 (m, 1H), 7.58-7.52 (m, 1H), 7.50-7.44 (m, 1H).

LC-MS (Method 3): R$_t$=1.66 min; 319 [M+H]+.

Example 33B rac-1-(2-Fluorophenyl)-7-(3-hydroxy-2-oxopyrrolidin-1-yl)-4-oxo-1,4-dihydro-1,8-naphthyridine-3-carboxylic acid

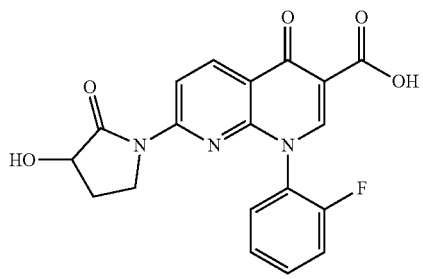 [SMILES: O=C(O)c1cn(-c2ccccc2F)c2nc(N3CCC(O)C3=O)ccc2c1=O]

According to GP2, 260 mg (816 μmol) of the compound from Example 33A were reacted with 82.5 mg (816 μmol) of 3-hydroxypyrrolidin-2-one (CAS: 15166-68-4) in the presence of 282 mg (2.04 mmol) of potassium carbonate, 33.0 mg (147 μmol) of palladium(II) acetate and 170 mg (294 μmol) of Xantphos in 8.24 ml of 1,4-dioxane at 80° C. The reaction mixture was poured into 30 ml of water and adjusted to pH 1 with 1 M aqueous hydrochloric acid. The mixture was extracted with dichloromethane. The combined organic phases were dried over sodium sulphate and filtered, and the solvent was removed under reduced pressure. The crude product was purified in two runs by means of preparative HPLC (column: Chromatorex C18, 10 μm, 125×30 mm, solvent: acetonitrile/0.05% formic acid gradient; (0 to 3 min. 10% acetonitrile to 35 min. 90% acetonitrile and a further 3 min. 90% acetonitrile), and 161.5 mg (50% of theory, 97.6% purity) of the title compound were obtained.

$^1$H-NMR (400 MHz, DMSO-$d_6$): δ [ppm]=14.63 (s, 1H), 8.99 (s, 1H), 8.78 (d, 1H), 8.58 (dd, 1H), 7.81-7.73 (m, 1H), 7.72-7.65 (m, 1H), 7.58-7.50 (m, 1H), 7.49-7.42 (m, 1H), 5.92 (d, 1H), 4.46-4.32 (m, 1H), 3.60-3.45 (m, 1H), 3.34-3.20 (m, 1H, partially under the water signal), 2.34-2.24 (m, 1H), 1.84-1.66 (m, 1H).

LC-MS (Method 3): $R_t$=1.28 min; 384 [M+H]$^+$.

Example 34A

7-Chloro-1-(2-chlorophenyl)-4-oxo-1,4-dihydro-1,8-naphthyridine-3-carboxylic acid

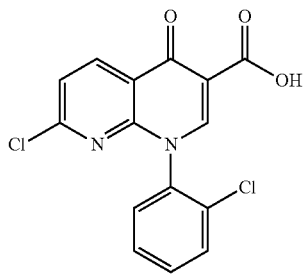 [SMILES: O=C(O)c1cn(-c2ccccc2Cl)c2nc(Cl)ccc2c1=O]

To a suspension of 3.70 g (10.2 mmol) of the compound from Example 4A in 50.5 ml of THF were added 20.4 ml of aqueous sodium hydroxide solution (1 M, 20.4 mmol), and the reaction mixture was stirred at room temperature for 3 h. The mixture was then diluted with 100 ml of water and the pH was adjusted to pH 1 with 1N aqueous hydrochloric acid. The precipitate was filtered off with suction, washed with water and dried in a vacuum drying cabinet at 40° C. overnight. 3.18 g (92% of theory, 99% purity) of the title compound were obtained.

$^1$H-NMR (400 MHz, DMSO-$d_6$): δ [ppm]=14.1 (br. s, 1H), 8.92 (s, 1H), 8.79 (d, 1H), 7.83-7.74 (m, 3H), 7.70-7.59 (m, 2H).

LC-MS (Method 3): $R_t$=1.79 min; 335 [M+H]$^+$.

Example 35A

7-Chloro-1-(2,4-difluorophenyl)-4-oxo-1,4-dihydro-1,8-naphthyridine-3-carboxylic acid

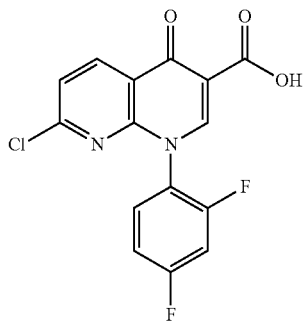 [SMILES: O=C(O)c1cn(-c2ccc(F)cc2F)c2nc(Cl)ccc2c1=O]

To 3 g (8.2 mmol) of ethyl 7-chloro-1-(2,4-difluorophenyl)-4-oxo-1,4-dihydro-1,8-naphthyridine-3-carboxylate (preparation described in DE 4301246, Example U, S.26) in 60 ml of THF were added 16.5 ml (16.4 mmol) of 1 M aqueous lithium hydroxide solution, and the mixture was stirred at 23° C. for 2 h. The mixture was diluted with 120 ml of water and then a pH of 1 was established with conc. hydrochloric acid. The precipitated solid was filtered off with suction, washed with water and dried under high vacuum. This gave 2.62 g (95% of theory) of the title compound.

LC-MS (Method 1): $R_t$=0.93 min; m/z=337.1 [M+H]$^+$.

Example 36A 1-(2,4-Difluorophenyl)-7-(dimethylamino)-4-oxo-1,4-dihydro-1,8-naphthyridine-3-carboxylic acid

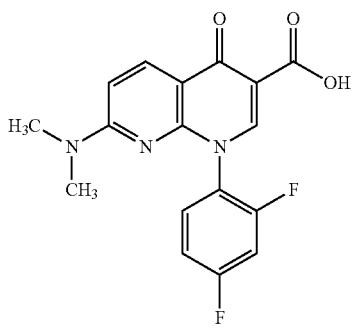 [SMILES: CN(C)c1ccc2c(=O)c(C(=O)O)cn(-c3ccc(F)cc3F)c2n1]

Method A:

A solution of 1.9 g (5.1 mmol) of the compound from Example 6A in 24 ml of 18 percent aqueous hydrochloric acid was stirred at 100° C. for 9 h. Subsequently, the mixture was filtered, and the filtercake was washed with 0.5 M aqueous hydrochloric acid and ethanol and dried under high vacuum. This gave 1.58 g (89% of theory) of the title compound.

Method B:

To 4.39 g (11.8 mmol) of the compound from Example 6A in 276 ml of THF were added 47 ml (47 mmol) of 1 M aqueous lithium hydroxide solution, and the mixture was stirred at 23° C. for 16 h. After 2.5 days, a pH of 3 was established by adding 1 M aqueous hydrochloric acid. After addition of water, the precipitated solid was filtered off with suction, washed with water and diethyl ether and dried under high vacuum. This gave 4 g (99% of theory) of the title compound.

LC-MS (Method 1): $R_t$=0.97 min; m/z=346.2 [M+H]$^+$.

In analogy to Example 36A, the example compounds shown in Table 2A were prepared by reacting the corresponding ester compounds from Examples 7A-31A with 18 percent aqueous hydrochloric acid or aqueous 1 to 2 M lithium hydroxide solution under the reaction conditions described. The reaction time was between 2 h and 16 h. Differences are specified in the respective examples.

TABLE 2A

| Ex. | IUPAC name/structure/(yield) | Analytical data |
|---|---|---|
| 37A | 1-(2,4-Difluorophenyl)-7-(methylamino)-4-oxo-1,4-dihydro-1,8-naphthyridine-3-carboxylic acid<br>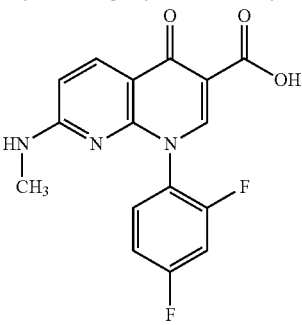<br>Method A; (80% of theory) | LC-MS (Method 1): $R_t$ = 0.84 min<br>MS (ESpos): m/z = 332.1 $[M + H]^+$ |
| 38A | 1-(2,4-Difluorophenyl)-4-oxo-7-(propan-2-ylamino)-1,4-dihydro-1,8-naphthyridine-3-carboxylic acid<br>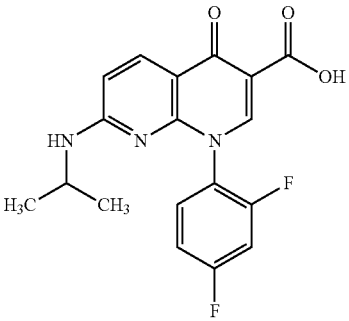<br>Method B; (79% of theory) | LC-MS (Method 1): $R_t$ = 0.98 min<br>MS (ESpos): m/z = 360.2 $[M + H]^+$ |
| 39A | 1-(2,4-Difluorophenyl)-7-[(2-hydroxyethyl)(methyl)amino]-4-oxo-1,4-dihydro-1,8-naphthyridine-3-carboxylic acid<br>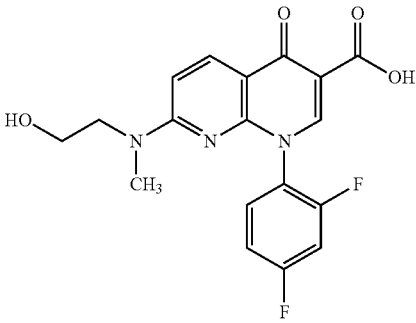<br>Method B; (98% of theory) | LC-MS (Method 1): $R_t$ = 0.80 min<br>MS (ESpos): m/z = 376.1 $[M + H]^+$ |

TABLE 2A-continued

| Ex. | IUPAC name/structure/(yield) | Analytical data |
|---|---|---|
| 40A | 1-(2,4-Difluorophenyl)-7-[(2-hydroxyethyl)amino]-4-oxo-1,4-dihydro-1,8-naphthyridine-3-carboxylic acid<br>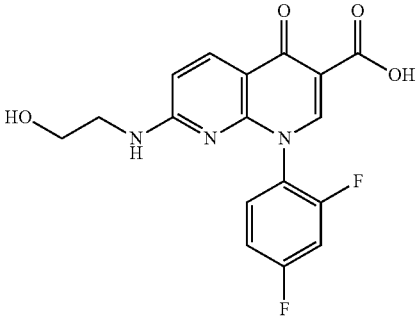<br>Method B; (84% of theory) | LC-MS (Method 1): $R_t$ = 1.34 min<br>MS (ESpos): m/z = 362.0 [M + H]$^+$ |
| 41A | 1-(2,4-Difluorophenyl)-7-[(2-fluoroethyl)amino]-4-oxo-1,4-dihydro-1,8-naphthyridine-3-carboxylic acid<br>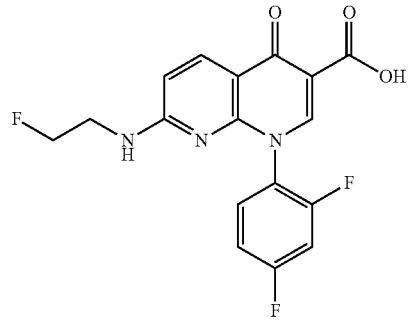<br>Method B; (100% of theory) | LC-MS (Method 1): $R_t$ = 0.87 min<br>MS (ESpos): m/z = 364.0 [M + H]$^+$ |
| 42A | 1-(2,4-Difluorophenyl)-7-[(2-flouroethyl)(methyl)amino]-4-oxo-1,4-dihydro-1,8-naphthyridinc-3-carboxylic acid<br>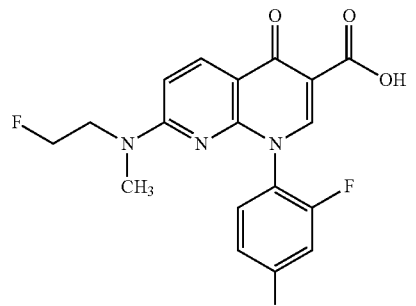<br>Method B; (89% of theory) | LC-MS (Method 1): $R_t$ = 0.87 min<br>MS (ESpos): m/z = 378.1 [M + H]$^+$ |

TABLE 2A-continued

| Ex. | IUPAC name/structure/(yield) | Analytical data |
| --- | --- | --- |
| 43A | 1-(2,4-Difluorophenyl)-7-(3,3-difluoropyrrolidin-1-yl)-4-oxo-1,4-dihydro-1,8-naphthyridine-3-carboxylic acid<br />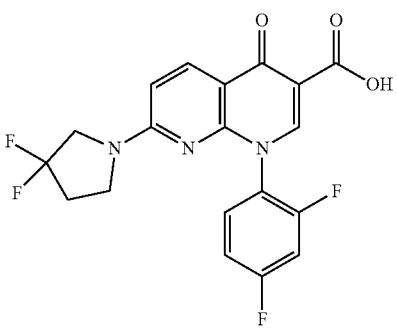<br />Method B; (89% of theory) | LC-MS (Method 1): $R_t$ = 1.01 min<br />MS (ESpos): m/z = 408.1 [M + H]$^+$ |
| 44A | 1-(2,4-Difluorophenyl)-7-[(3R)-3-fluoropyrrolidin-1-yl]-4-oxo-1,4-dihydro-1,8-naphthyridine-3-carboxylic acid<br />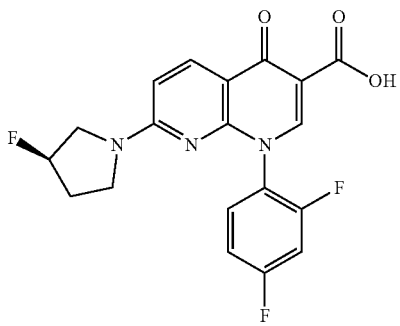<br />Method B; (88% of theory) | LC-MS (Method 1): $R_t$ = 0.95 min<br />MS (ESpos): m/z = 390.1 [M + H]$^+$ |
| 45A | 1-(2,4-Difluorophenyl)-7-[(3S)-3-fluoropyrrolidin-1-yl]-4-oxo-1,4-dihydro-1,8-naphthyridine-3-carboxylic acid<br />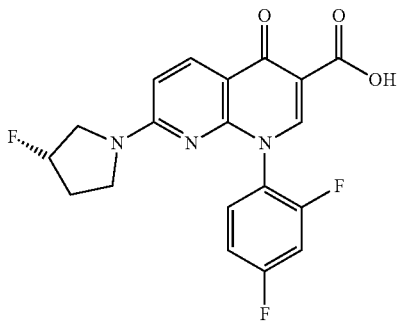<br />Method B; (82% of theory) | LC-MS (Method 1): $R_t$ = 0.95 min<br />MS (ESpos): m/z = 390.2 [M + H]$^+$ |

TABLE 2A-continued

| Ex. | IUPAC name/structure/(yield) | Analytical data |
|---|---|---|
| 46A | 1-(2,4-Difluorophenyl)-4-oxo-7-(3,3,4,4-tetrafluoropyrrolidin-1-yl)-1,4-dihydro-1,8-naphthyridine-3-carboxylic acid<br>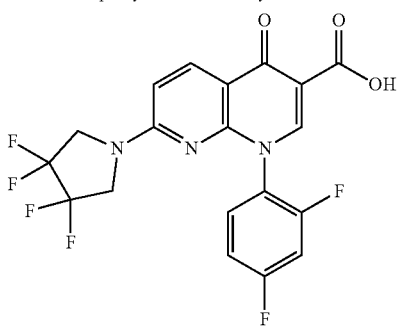<br>Method B; (59% of theory) | LC-MS (Method 1): $R_t$ = 1.05 min<br>MS (ESpos): m/z = 444.0 [M + H]$^+$ |
| 47A | 1-(2.4-Difluorophenyl)-4-oxo-7-[2,2,2-trifluoroethyl)amino]-1,4-dihydro-1,8-naphthyridine-3-carboxylic acid<br>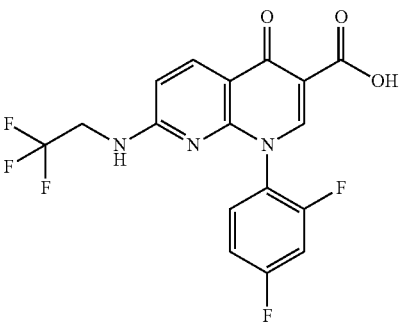<br>Method B; (75% of theory) | LC-MS (Method 1): $R_t$ = 0.88 min<br>MS (ESpos): m/z = 400.1 [M + H]$^+$ |
| 48A | 7-[(2,2-Difluoroethyl)(methyl)amino]-1-(2,4-difluorophenyl)-4-oxo-1,4-dihydro-1,8-naphthyridine-3-carboxylic acid<br>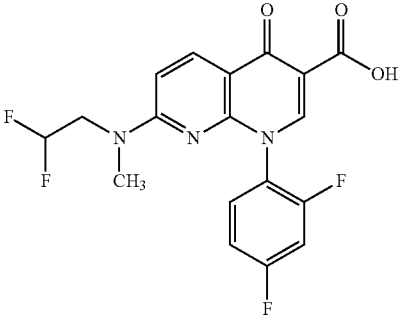<br>Method B; (91% of theory) | LC-MS (Method 1): $R_t$ = 0.96 min<br>MS (ESpos): m/z = 396.2 [M + H]$^+$ |

TABLE 2A-continued

| Ex. | IUPAC name/structure/(yield) | Analytical data |
|---|---|---|
| 49A | 7-[(2,2-Difluoroethyl)amino]-1-(2,4-difluorophenyl)-4-oxo-1,4-dihydro-1,8-naphthyridine-3-carboxylic acid<br />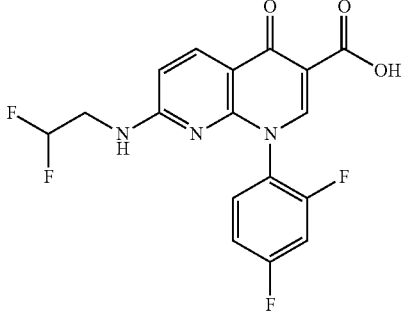<br />Method B; (96% of theory) | LC-MS (Method 2): $R_t$ = 0.88 min<br />MS (ESpos): m/z = 382.2 [M + H]⁺ |
| 50A | 1-(2,4-Difluorophenyl)-7-(1,1-dioxido-1,3-thiazolidin-3-yl)-4-oxo-1,4-dihydro-1,8-naphthyridine-3-carboxylic acid<br />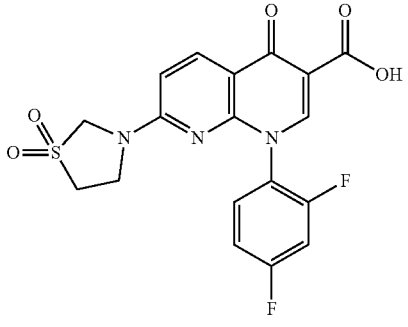<br />Method B; (45% of theory) | LC-MS (Method 1): $R_t$ = 0.70 min<br />MS (ESpos): m/z = 422.2 [M + H]⁺ |
| 51A | rac-1-(2,4-Difluorophenyl)-7-[2-(hydroxymethyl)morpholin-4-yl]-4-oxo-1,4-dihydro-1,8-naphthyridine-3-carboxylic acid<br />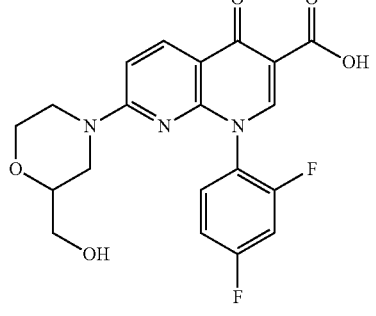<br />Method B; (100% of theory) | LC-MS (Method 1): $R_t$ = 0.70 min<br />MS (ESpos): m/z = 418.1 [M + H]⁺ |

TABLE 2A-continued

| Ex. | IUPAC name/structure/(yield) | Analytical data |
|---|---|---|
| 52A | rac-1-(2,4-Difluorophenyl)-7-[2-(hydroxymethyl)pyrrolidin-1-yl]-4-oxo-1,4-dihydro-1,8-naphthyridine-3-carboxylic acid 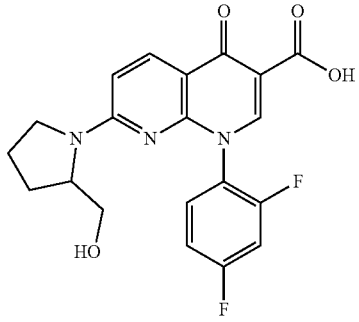 Method B; (89% of theory) | LC-MS (Method 1): $R_t$ = 0.85 min<br>MS (ESpos): m/z = 402.2 $[M + H]^+$ |
| 53A | rac-1-(2,4-difluorophenyl)-7-[3-(hydroxymethyl)morpholin-4-yl]-4-oxo-1,4-dihydro-1,8-naphthyridine-3-carboxylic acid 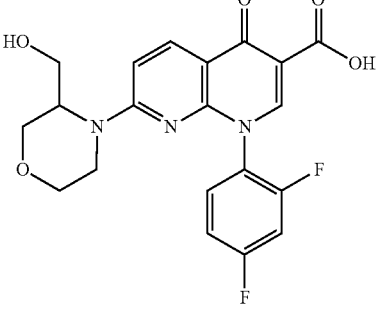 Method B; (16% of theory) | LC-MS (Method 1): $R_t$ = 0.76 min<br>MS (ESpos): m/z = 418.2 $[M + H]^+$ |
| 54A | rac-1-(2,4-Difluorophenyl)-7-(3-hydroxy-3-methylpiperidin-1-yl)-4-oxo-1,4-dihydro-1,8-naphthyridine-3-carboxylic acid 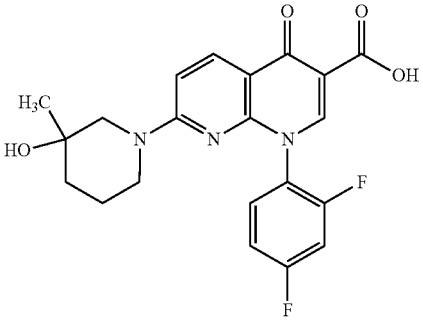 Method B; (68% of theory) | LC-MS (Method 1): $R_t$ = 0.90 min<br>MS (ESpos): m/z = 416.1 $[M + H]^+$ |

TABLE 2A-continued

| Ex. | IUPAC name/structure/(yield) | Analytical data |
|---|---|---|
| 55A | 1-(2,4-Difluorophenyl)-7-[methyl(2,2,2-trifluoroethyl)amino]-4-oxo-1,4-dihydro-1,8-naphthyridine-3-carboxylic acid<br>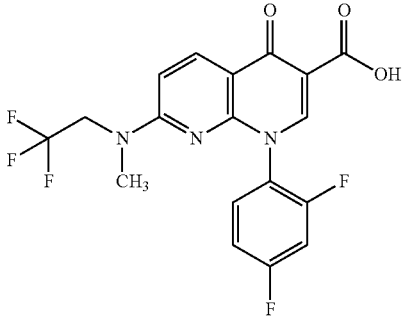<br>Method B; (100% of theory) | LC-MS (Method 1): $R_t$ = 1.00 min<br>MS (ESpos): m/z = 414.2 $[M + H]^+$ |
| 56A | 1-(2,4-Difluorophenyl)-7-(morpholin-4-yl)-4-oxo-1,4-dihydro-1,8-naphthyridine-3-carboxylic acid<br>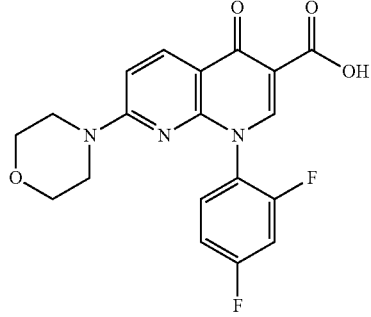<br>Method A; (99% of theory) | LC-MS (Method 1): $R_t$ = 0.90 min<br>MS (ESpos): m/z = 388.2 $[M + H]^+$ |
| 57A | 1-(2,4-Difluorophenyl)-4-oxo-7-(pyrrolidin-1-yl)-1,4-dihydro-1,8-naphthyridine-3-carboxylic acid<br>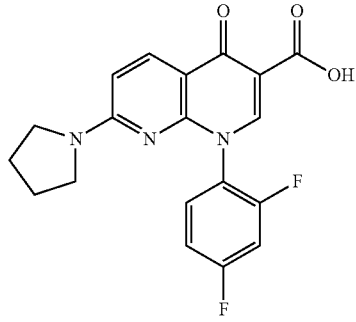<br>Method A; (89% of theory) | LC-MS (Method 1): $R_t$ = 1.05 min<br>MS (ESpos): m/z = 372.2 $[M + H]^+$ |

TABLE 2A-continued

| Ex. | IUPAC name/structure/(yield) | Analytical data |
| --- | --- | --- |
| 58A | 1-(2,4-Difluorophenyl)-7-[4-hydroxy-4-(hydroxymethyl)piperidin-1-yl]-4-oxo-1,4-dihydro-1,8-naphthyridine-3-carboxylic acid<br/>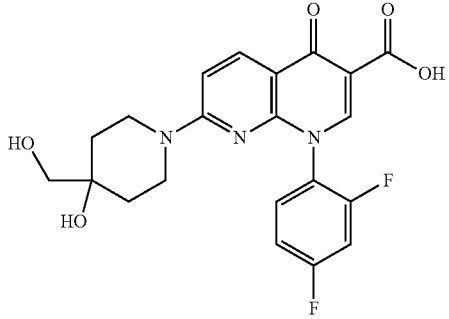<br/>Method B; (38% of theory) | |
| 59A | 1-(2,4-Difluorophenyl)-4-oxo-7-(1,3-thiazolidin-3-yl)-1,4-dihydro-1,8-naphthyridine-3-carboxylic acid<br/>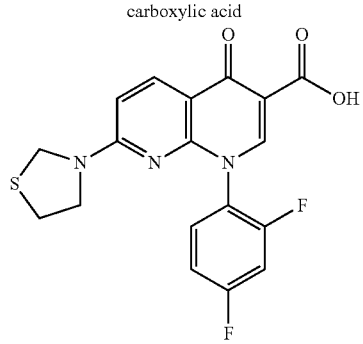<br/>Method B; (67% of theory) | LC-MS (Method 1): $R_t$ = 1.84 min<br/>MS (ESpos): m/z = 390.0 [M + H]$^+$ |
| 60A | 1-(2-Chloro-4-fluorophenyl)-7-(dimethylamino)-4-oxo-1,4-dihydro-1,8-naphthyridine-3-carboxylic acid<br/>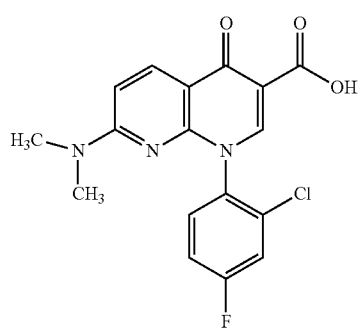<br/>Method A; (82% of theory) | LC-MS (Method 1): $R_t$ = 2.16 min<br/>MS (ESpos): m/z = 362.1 [M + H]$^+$ |

Example 61A 1-(2,4-Difluorophenyl)-4-oxo-7-(2-oxo-1,3-oxazolidin-3-yl)-1,4-dihydro-1,8-naphthyridine-3-carboxylic acid

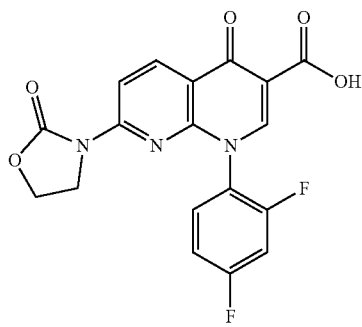 [SMILES: O=C(O)c1cn(-c2ccc(F)cc2F)c2nc(N3CCOC3=O)ccc2c1=O]

A mixture of 300 mg (0.67 mmol) of ethyl 7-chloro-1-(2,4-difluorophenyl)-4-oxo-1,4-dihydro-1,8-naphthyridine-3-carboxylate (preparation described in DE 4301246, Example U, S.26), 232 mg (2.7 mmol) of 2-oxazolidinone, 184 mg (1.3 mmol) of potassium carbonate, 129 mg (0.68 mmol) of copper(I) iodide and 51 mg (0.69 mmol) of trans-N,N'-dimethyl-1,2-cyclohexanediamine in 7.5 ml of DMF was stirred at 110° C. for 3 h and then at 23° C. for a further 13 h. Subsequently, 127 mg (0.67 mmol) of copper(I) iodide and 40 mg (0.66 mmol) of trans-N,N'-dimethyl-1,2-cyclohexanediamine were added and the mixture was stirred at 130° C. for a further 10 h, the mixture was filtered and the filtrate was concentrated by preparative HPLC (eluent: acetonitrile/water gradient with 0.1% formic acid). This gave 28 mg (6% of theory, 59% purity (HPLC)) of the target compound, which was used for the next stage without further purification.

LC-MS (Method 1): Rt=2.38 min; m/z=388.0 [M+H]$^+$.

Example 62A 7-(Dimethylamino)-1-(2-fluorophenyl)-4-oxo-1,4-dihydro-1,8-naphthyridine-3-carboxylic acid

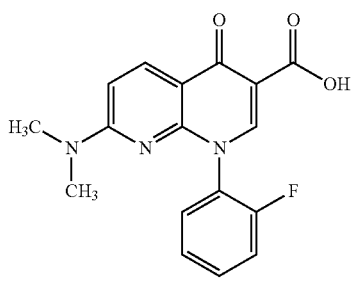 [SMILES: CN(C)c1ccc2c(=O)c(C(=O)O)cn(-c3ccccc3F)c2n1]

To a suspension of 1.33 g (3.74 mmol) of the compound from Example 32A in 18.5 ml of THF were added 7.5 ml of aqueous sodium hydroxide solution (1 M, 7.5 mmol), and the reaction mixture was stirred at room temperature for 3 h. The mixture was then diluted with 100 ml of water and the pH was adjusted to pH 1 with 1 M aqueous hydrochloric acid. The precipitate was filtered off with suction, washed with water and dried in a vacuum drying cabinet at 40° C. overnight. 1.13 g (91% of theory, 99% purity) of the title compound were obtained.

$^1$H-NMR (400 MHz, DMSO-d$_6$): δ [ppm]=15.4 (br. s, 1H), 8.73 (s, 1H), 8.32 (d, 1H), 7.75-7.70 (m, 1H), 7.67-7.61 (m, 1H), 7.53-7.46 (m, 1H), 7.45-7.40 (m, 1H), 7.02 (d, 1H), 2.95 (br. s, 6H).

LC-MS (Method 3): R$_t$=1.62 min; 328 [M+H]$^+$.

Example 63A 1-(2,4-Difluorophenyl)-7-[(4S)-4-hydroxy-2-oxopyrrolidin-1-yl)]-4-oxo-1,4-dihydro-1,8-naphthyridine-3-carboxylic acid

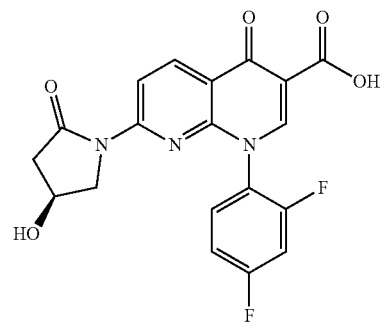 [SMILES: O=C(O)c1cn(-c2ccc(F)cc2F)c2nc(N3C[C@@H](O)CC3=O)ccc2c1=O]

According to GP2, 2.50 g (7.43 mmol) of the compound from Example 35A were reacted with 750 mg (7.43 mmol) of (4S)-4-hydroxypyrrolidin-2-one in the presence of 4.84 g (14.9 mmol) of caesium carbonate, 300 mg (1.34 mmol) of palladium(II) acetate and 773 mg (1.34 mmol) of Xantphos in 75 ml of dioxane at 80° C. The reaction mixture was cooled to room temperature and poured into 300 ml of water. The pH was adjusted to 1 with 1N aqueous hydrochloric acid and the precipitate was filtered off with suction, washed with n-hexane and dried under high vacuum. The crude product was purified by means of flash chromatography (dichloromethane/methanol gradient), and 292 mg (6.4% of theory; 65% purity) of the title compound were obtained.

LC-MS (Method 1): R$_t$=0.73 min; 402 [M+H]$^+$.

Example 64A 1-(2-Chlorophenyl)-7-[(4S)-4-hydroxy-2-oxopyrrolidin-1-yl)]-4-oxo-1,4-dihydro-1,8-naphthyridine-3-carboxylic acid

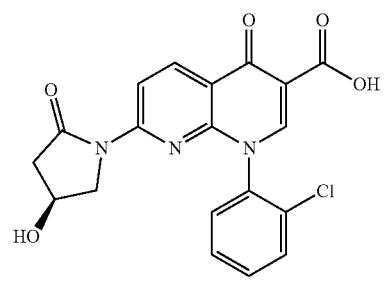 [SMILES: O=C(O)c1cn(-c2ccccc2Cl)c2nc(N3C[C@@H](O)CC3=O)ccc2c1=O]

According to GP2, 500 mg (1.49 mmol) of the compound from Example 34A were reacted with 150 mg (1.49 mmol)

of (4S)-4-hydroxypyrrolidin-2-one in the presence of 515 mg (3.73 mmol) of potassium carbonate, 60.3 mg (269 µmol) of palladium(II) acetate and 311 mg (537 µmol) of Xantphos in 15 ml of dioxane at 90° C. The crude product was purified by flash chromatography (dichloromethane/methanol gradient) and preparative HPLC (column: Kromasil C18, 10 µm, 125×30 mm, solvent: acetonitrile/0.05% formic acid gradient (0 to 3 min 10% acetonitrile, to 35 min 90% acetonitrile and for a further 3 min 90% acetonitrile). 67.4 mg (11% of theory, 99% purity) of the title compound were obtained (as an atropisomer mixture).

¹H-NMR (400 MHz, DMSO-d₆): δ [ppm]=14.66 (br. s, 1H), 8.92 (s, 1H), 8.76 (d, 1H), 8.57 (dd, 1H), 7.82-7.75 (m, 2H), 7.70-7.59 (m, 2H), 5.32 (dd, 1H), 4.27-4.20 (m, 1H), 3.60-3.52 (m, 1H), 3.40-3.33 (m, 1H), 2.99-2.88 (m, 1H), 2.40-2.32 (m, 1H).

LC-MS (Method 3): $R_t$=1.30/1.36 min; 400 [M+H]⁺.

Example 65A

7-Chloro-1-(2,4-difluorophenyl)-4-oxo-N-(tricyclo[3.3.1.1³,⁷]dec-1-yl)-1,4-dihydro-1,8-naphthyridine-3-carboxamide

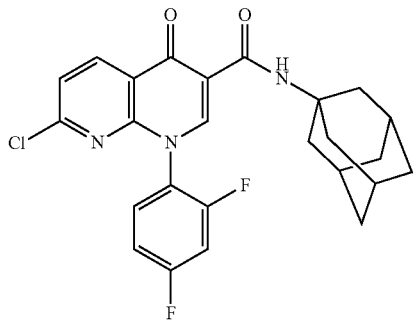 [SMILES: O=C(NC12CC3CC(CC(C3)C1)C2)c1cn(-c2ccc(F)cc2F)c2nc(Cl)ccc2c1=O]

To 90 mg (0.27 mmol) of the compound from Example 35A and 68 mg (0.67 mmol) of N-methylmorpholine in 3.3 ml of DMF was added, at 0° C., 0.54 ml (0.54 mmol) of isopropyl chloroformate (1 M in toluene), and the mixture was then stirred at 0° C. for 1 h. Then, at 0° C., 53 mg (0.35 mmol) of 1-adamantanamine were added and the mixture was stirred at 20° C. for 2 h. The mixture was purified via preparative HPLC (eluent: acetonitrile/water gradient with 0.1% formic acid). This gave 48 mg (36% of theory) of the title compound.

LC-MS (Method 1): $R_t$=1.46 min; m/z=470.2 [M+H]⁺.

In analogy to Example 65A, the example compounds shown in Table 3A were prepared by reacting the compound from Example 35A with the appropriate amines (or salts thereof) under the reaction conditions described. Differences are specified in the respective examples.

Illustrative Workup of the Reaction Mixture:

The reaction mixture was then added to water and adjusted to pH 1 with 1 M aqueous hydrochloric acid. The solvent (toluene) was removed under reduced pressure and the precipitate formed was filtered off and dried under reduced pressure. The purification was effected, by way of example, by column chromatography (silica gel, cyclohexane→cyclohexane/ethyl acetate 10:1) or preparative thin-layer chromatography (silica gel, DCM).

TABLE 3A

| Ex. | IUPAC name/structure/(yield) | Analytical data |
|---|---|---|
| 66A | rac-7-Chloro-1-(2,4-difluorophenyl)-4-oxo-N-(1,1,1-trifluorobutan-2-yl)-1,4-dihydro-1,8-naphthyridine-3-carboxamide<br><br>Solvent: NMP<br>(62% of theory) | LC-MS (Method 1): $R_t$ = 1.21 min<br>MS (ESpos): m/z = 446.2 [M + H]⁺ |

TABLE 3A-continued

| Ex. | IUPAC name/structure/(yield) | Analytical data |
|---|---|---|
| 67A | 7-Chloro-1-(2,4-difluorophenyl)-4-oxo-)-N-[(2R)-1,1,1-trifluorobutan-2-yl)-1,4-dihydro-1,8-naphthyridine-3-carboxamide<br><br>Workup: The mixture was added to water and adjusted to pH 1 with aqueous 1 M hydrochloric acid. Then the toluene was removed under reduced pressure, and the precipitate was filtered off, dried under high vacuum and purified by silica gel chromatography (cyclohexane ⟶ cyclohexane/ethyl acetate 10:1).<br>(59% of theory) | LC-MS (Method 1): $R_t$ = 1.16 min<br>MS (ESpos): m/z = 446.1 [M + H]$^+$ |
| 68A | 7-Chloro-1-(2,4-difluorophenyl)-4-oxo-)-N-[(2R)-1,1,1-trifluorobutan-2-yl)-1,4-dihydro-1,8-naphthyridine-3-carboxamide<br><br>Workup: The mixture was added to water and adjusted to pH 1 with aqueous 1 M hydrochloric acid. Then the toluene was removed under reduced pressure, and the precipitate was filtered off, dried under high vacuum and purified by silica gel chromatography (cyclohexane ⟶ cyclohexane/ethyl acetate 10:1).<br>(70% of theory) | LC-MS (Method 1): $R_t$ = 1.20 min<br>MS (ESpos): m/z = 446.2 [M + H]$^+$ |
| 69A | rac-7-Chloro-1-(2,4-difluorophenyl)-4-oxo-N-(1,1,1-trifluoropropan-2-yl)-1,4-dihydro-1,8-naphthyridine-3-carboxamide<br><br>(76% of theory) | LC-MS (Method 1): $R_t$ = 1.16 min<br>MS (ESpos): m/z = 432.0 [M + H]$^+$ |

TABLE 3A-continued

| Ex. | IUPAC name/structure/(yield) | Analytical data |
|---|---|---|
| 70A | 7-Chloro-1-(2,4-difluorophenyl)-N-(4-methylbicyclo[2.2.2]oct-1-yl)-4-oxo-1,4-dihydro-1,8-naphthyridine-3-carboxamide<br>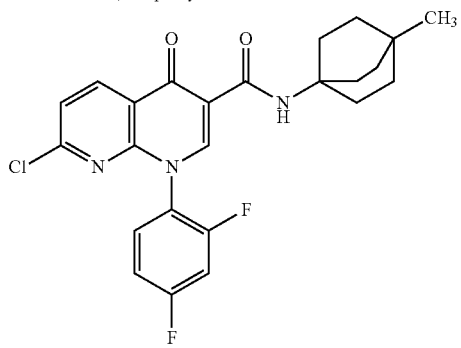<br>Purification by preparative thin-layer chromatography (silica gel, DCM)<br>(23% of theory) | LC-MS (Method 1): $R_t$ = 1.39 min<br>MS (ESpos): m/z = 458.3 [M + H]$^+$ |
| 71A | 7-Chloro-1-(2,4-difluorophenyl)-N-[2-(2,6-difluorophenyl)propan-2-yl]-4-oxo-1,4-dihydro-1,8-naphthyridine-3-carboxamide<br>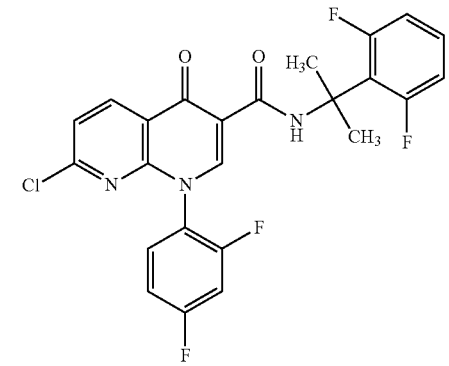<br>Purification via preparative thin-layer chromatography (silica gel, DCM)<br>(22% of theory) | LC-MS (Method 1): $R_t$ = 1.26 min<br>MS (ESpos): m/z = 490.3 [M + H]$^+$ |
| 72A | 7-Chloro-N-(2,6-dichlorobenzyl)-1-(2,4-difluorophenyl)-4-oxo-1,4-dihydro-1,8-naphthyridine-3-carboxamide<br>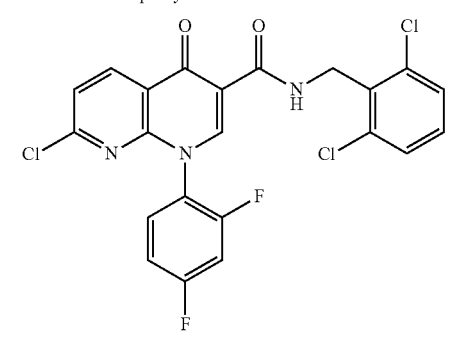<br>(88% of theory) | LC-MS (Method 1): $R_t$ = 1.24 min<br>MS (ESpos): m/z = 494.1 [M + H]$^+$ |

Example 73A rac-7-Chloro-N-[1-(2-chlorophenyl)-2,2,2-trifluoroethyl]-1-(2,4-difluorophenyl)-4-oxo-1,4-dihydro-1,8-naphthyridine-3-carboxamide

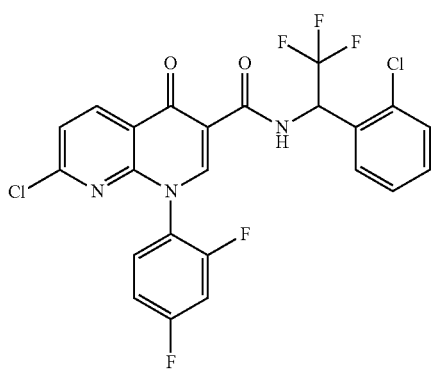 [SMILES: O=C(NC(c1ccccc1Cl)C(F)(F)F)c1cn(-c2ccc(F)cc2F)c2nc(Cl)ccc2c1=O]

According to GP1, 1.50 g (4.46 mmol) of the compound from Example 35A were reacted with 1.40 mg (6.68 mmol) of rac-1-(2-chlorophenyl)-2,2,2-trifluoroethanamine in the presence of 1.69 g (4.46 mmol) of HATU and 1.09 ml (6.24 mmol) of N,N-diisopropylethylamine in 45 ml of dimethylformamide. The crude product was purified by means of flash chromatography (cyclohexane/ethyl acetate gradient), and 1.73 g (71% of theory; 96% purity) of the title compound were obtained.

$^1$H-NMR (400 MHz, DMSO-$d_6$): δ [ppm]=11.05 (d, 1H), 8.92 (s, 1H), 8.79 (d, 1H), 7.91-7.75 (m, 1H), 7.77 (d, 1H), 7.68-7.48 (m, 5H), 7.41-7.33 (m, 1H), 6.53-6.42 (m, 1H).

LC-MS (Method 1): $R_t$=1.30 min; 528 [M+H]$^+$.

Example 74A rac-7-Chloro-1-(2,4-difluorophenyl)-4-oxo-N-[1-(trifluoromethoxy)propan-2-yl]-1,4-dihydro-1,8-naphthyridine-3-carboxamide

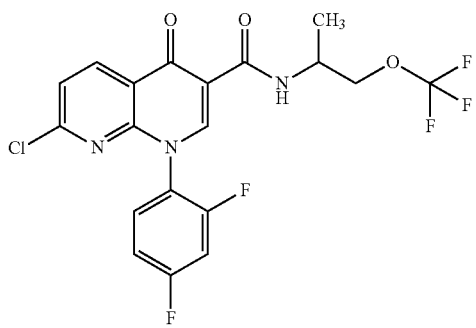 [SMILES: CC(COC(F)(F)F)NC(=O)c1cn(-c2ccc(F)cc2F)c2nc(Cl)ccc2c1=O]

According to GP1, 2.50 g (7.43 mmol) of the compound from Example 35A were reacted with 1.28 mg (6.68 mmol) of rac-1-(trifluoromethoxy)propan-2-amine in the presence of 3.11 g (8.17 mmol) of HATU and 1.29 ml (7.43 mmol) of N,N-diisopropylethylamine in 90 ml of dimethylformamide. After monitoring the reaction overnight, a further 1.55 g (4.08 mmol) of HATU and 647 μl (3.71 mmol) of N,N-diisopropylethylamine were added and the mixture was stirred at room temperature overnight. The crude product was purified by means of flash chromatography (cyclohexane/ethyl acetate gradient), and 2.38 g (69% of theory; 99% purity) of the title compound were obtained.

$^1$H-NMR (400 MHz, DMSO-$d_6$): δ [ppm]=9.72 (d, 1H), 8.83 (s, 1H), 8.74 (d, 1H), 7.90-7.82 (m, 1H), 7.73 (d, 1H), 7.67-7.60 (m, 1H), 7.41-7.34 (m, 1H), 4.42-4.33 (m, 1H), 4.24-4.15 (m, 2H), 1.26 (d, 3H).

LC-MS (Method 3): $R_t$=2.18 min; 462 [M+H]$^+$.

Example 75A

7-Chloro-1-(2,4-difluorophenyl)-4-oxo-N-[1-phenyl-2-(trifluoromethoxy)ethyl]-1,4-dihydro-1,8-naphthyridine-3-carboxamide

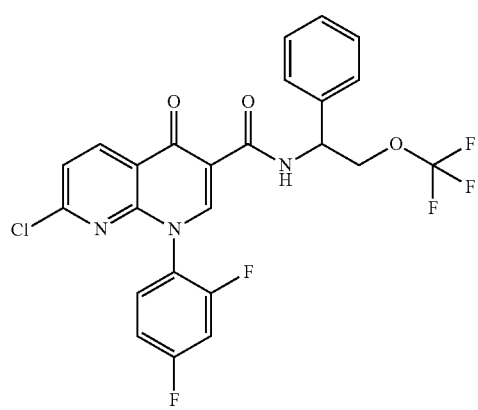 [SMILES: O=C(NC(COC(F)(F)F)c1ccccc1)c1cn(-c2ccc(F)cc2F)c2nc(Cl)ccc2c1=O]

According to GP1, 1.1 g (3.3 mmol) of the compound from Example 35A were reacted with 1.22 g (4.90 mmol) of (−)-1-phenyl-2-(trifluoromethoxy)ethanamine hydrochloride (97% purity, optical rotation: −21.13° in methanol c=0.5300 g/100 ml, 589 nm, 20° C.) in the presence of 1.24 g (3.27 mmol) of HATU and 1.14 ml (6.53 mmol) of N,N-diisopropylethylamine in 33 ml of dimethylformamide. The crude product was purified by means of flash chromatography (cyclohexane/ethyl acetate gradient), and 880 mg (49% of theory; 95% purity) of the title compound (non-racemic mixture) were obtained.

$^1$H-NMR (400 MHz, DMSO-$d_6$): δ [ppm]=10.37 (d, 1H), 8.84 (s, 1H), 8.78 (d, 1H), 7.91-7.77 (m, 1H), 7.74 (d, 1H), 7.67-7.59 (m, 1H), 7.51-7.29 (m, 6H), 5.56-5.48 (m, 1H), 4.55-4.41 (m, 2H).

LC-MS (Method 3): $R_t$=2.36 min; 524 [M+H]$^+$.

Example 76A rac-7-Chloro-1-(2,4-difluorophenyl)-4-oxo-N-[1-(trifluoromethoxy)butan-2-yl]-1,4-dihydro-1,8-naphthyridine-3-carboxamide (racemate)

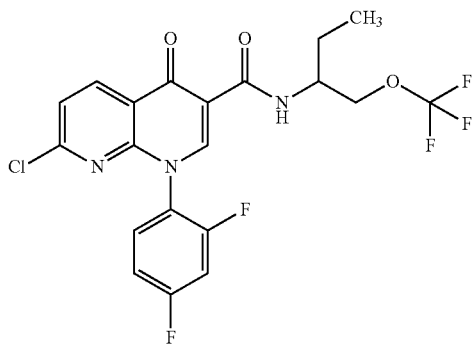 [SMILES: CCC(COC(F)(F)F)NC(=O)c1cn(-c2ccc(F)cc2F)c2nc(Cl)ccc2c1=O]

According to GP1, 100 mg (285 µmol) of the compound from Example 35A (96% purity) were reacted with 82.8 g (428 µmol) of rac-1-(trifluoromethoxy)butan-2-amine hydrochloride in the presence of 108 mg (285 µmol) of HATU and 119 µl (684 µmol) of N,N-diisopropylethylamine in 3 ml of dimethylformamide. The crude product was purified by means of flash chromatography (cyclohexane/ethyl acetate gradient), and 101 mg (75% of theory; 100% purity) of the title compound were obtained.

$^1$H-NMR (400 MHz, DMSO-$d_6$): δ [ppm]=9.69 (d, 1H), 8.83 (s, 1H), 8.74 (d, 1H), 7.90-7.83 (m, 1H), 7.73 (d, 1H), 7.67-7.60 (m, 1H), 7.41-7.34 (m, 1H), 4.27-4.13 (m, 3H), 1.76-1.52 (m, 2H), 0.94 (t, 3H).

LC-MS (Method 1): $R_t$=1.25 min; 476 [M+H]$^+$.

Example 77A rac-7-Chloro-1-(2,4-difluorophenyl)-N-[1-(2-fluorophenyl)ethyl]-4-oxo-1,4-dihydro-1,8-naphthyridine-3-carboxamide

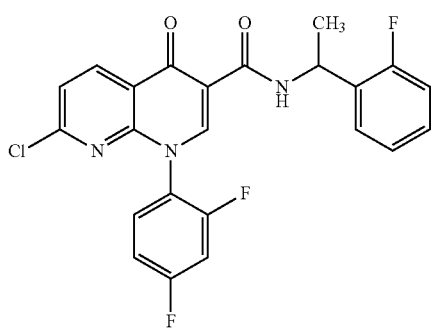 [SMILES: CC(NC(=O)c1cn(-c2ccc(F)cc2F)c2nc(Cl)ccc2c1=O)c1ccccc1F]

According to GP1, 100 mg (285 µmol) of the compound from Example 35A (96% purity) were reacted with 59.5 g (428 µmol) of rac-1-(2-fluorophenyl)ethylamine in the presence of 108 mg (285 µmol) of HATU and 70 µl (0.40 mmol) of N,N-diisopropylethylamine in 3 ml of dimethylformamide. The crude product was purified by means of flash chromatography (cyclohexane/ethyl acetate gradient), and 97.3 mg (75% of theory; 100% purity) of the title compound were obtained.

$^1$H-NMR (400 MHz, DMSO-$d_6$): δ [ppm]=10.12 (d, 1H), 8.79 (s, 1H), 8.75 (d, 1H), 7.89-7.78 (m, 1H), 7.74 (d, 1H), 7.67-7.58 (m, 1H), 7.49-7.41 (m, 1H), 7.40-7.29 (m, 2H), 7.24-7.17 (m, 2H), 5.44-5.34 (m, 1H), 1.52 (d, 3H).

LC-MS (Method 1): $R_t$=1.23 min; 458 [M+H]$^+$.

Example 78A rac-7-Chloro-1-(2,4-difluorophenyl)-4-oxo-N-(1,1,1-trifluoro-3-methoxy-2-methylpropan-2-yl)-1,4-dihydro-1,8-naphthyridine-3-carboxamide

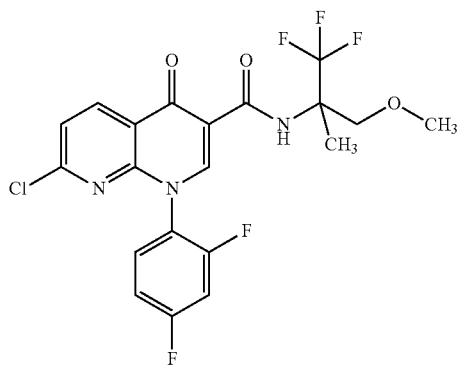 [SMILES: COCC(C)(NC(=O)c1cn(-c2ccc(F)cc2F)c2nc(Cl)ccc2c1=O)C(F)(F)F]

According to GP1, 100 mg (285 µmol) of the compound from Example 35A (96% purity) were reacted with 87.2 mg (428 µmol) of rac-1,1,1-trifluoro-3-methoxy-2-methylpropan-2-amine hydrochloride in the presence of 108 mg (285 µmol) of HATU and 119 µl (684 µmol) of N,N-diisopropylethylamine in 3 ml of dimethylformamide. The crude product was purified by means of flash chromatography (cyclohexane/ethyl acetate gradient), and 112 mg (82% of theory; 100% purity) of the title compound were obtained.

$^1$H-NMR (400 MHz, DMSO-$d_6$): δ [ppm]=10.28 (br. s, 1H), 8.84 (s, 1H), 8.75 (d, 1H), 7.90-7.82 (m, 1H), 7.74 (d, 1H), 7.67-7.60 (m, 1H), 7.41-7.34 (m, 1H), 3.90-3.84 (m, 1H), 3.77-3.67 (m, 1H), 3.36 (s, 3H), 1.64 (s, 3H).

LC-MS (Method 1): $R_t$=1.20 min; 476 [M+H]$^+$.

Example 79A

7-Chloro-1-(2,4-difluorophenyl)-4-oxo-N-[4-(trifluoromethyl)tetrahydro-2H-pyran-4-yl]-1,4-dihydro-1,8-naphthyridine-3-carboxamide

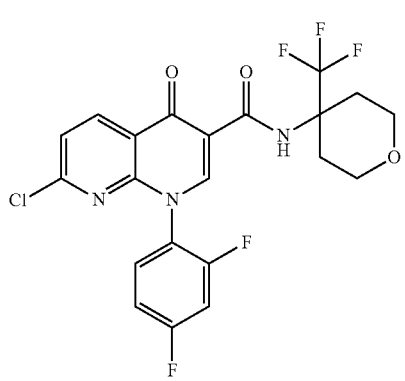 [SMILES: O=C(NC1(C(F)(F)F)CCOCC1)c1cn(-c2ccc(F)cc2F)c2nc(Cl)ccc2c1=O]

According to GP1, 100 mg (285 µmol) of the compound from Example 35A (96% purity) were reacted with 87.9 g (428 µmol) of 4-(trifluoromethyl)tetrahydro-2H-pyran-4-amine hydrochloride in the presence of 108 mg (285 µmol) of HATU and 119 µl (684 µmol) of N,N-diisopropylethylamine in 3 ml of dimethylformamide. The crude product was purified by means of flash chromatography (cyclohexane/ethyl acetate gradient), and 108 mg (77% of theory; 100% purity) of the title compound were obtained.

$^1$H-NMR (400 MHz, DMSO-$d_6$): δ [ppm]=10.08 (s, 1H), 8.87 (s, 1H), 8.76 (d, 1H), 7.90-7.83 (m, 1H), 7.76 (d, 1H), 7.68-7.61 (m, 1H), 7.41-7.34 (m, 1H), 3.95-3.85 (m, 2H), 3.57-3.45 (m, 2H), 2.47-2.39 (m, 1H), 1.95-1.83 (m, 2H).

LC-MS (Method 1): $R_t$=1.17 min; 488 [M+H]$^+$.

Example 80A rac-7-Chloro-1-(2,4-difluorophenyl)-N-[1-(2,6-difluorophenyl)-2,2,2-trifluoroethyl]-4-oxo-1,4-dihydro-1,8-naphthyridine-3-carboxamide

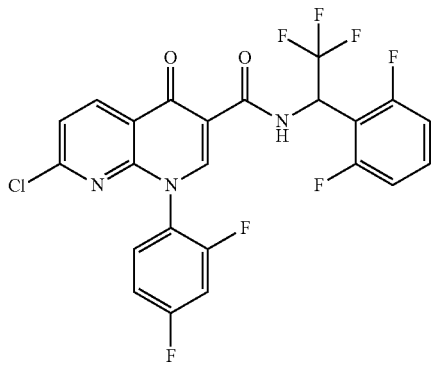 [SMILES: O=C(NC(c1c(F)cccc1F)C(F)(F)F)c1cn(-c2ccc(F)cc2F)c2nc(Cl)ccc2c1=O]

According to GP1, 3.00 g (8.91 mmol) of the compound from Example 35A were reacted with 1.96 g (9.27 mmol) of rac-1-(2,6-difluorophenyl)-2,2,2-trifluoroethanamine in the presence of 3.39 g (8.91 mmol) of HATU and 2.17 ml (12.5 mmol) of N,N-diisopropylethylamine in 90 ml of dimethylformamide. The crude product was purified by means of flash chromatography (cyclohexane/ethyl acetate mixture, 5:1), and 2.10 g (44% of theory; 100% purity) of the title compound were obtained.

$^1$H NMR (400 MHz, DMSO-$d_6$) δ [ppm]=11.14 (d, 1H), 8.93 (s, 1H), 8.79 (d, 1H), 7.93-7.75 (m, 1H), 7.76 (d, 1H), 7.68-7.59 (m, 2H), 7.42-7.27 (m, 3H), 6.50-6.38 (m, 1H).

LC-MS (Method 1): $R_t$=1.29 min; 530.1 [M+H]$^+$.

Example 81A

7-Chloro-N-(2,6-dichlorophenyl)-1-(2,4-difluorophenyl)-4-oxo-1,4-dihydro-1,8-naphthyridine-3-carboxamide

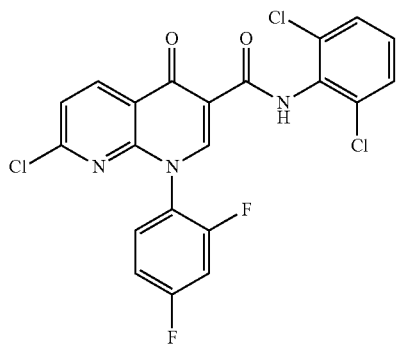 [SMILES: O=C(Nc1c(Cl)cccc1Cl)c1cn(-c2ccc(F)cc2F)c2nc(Cl)ccc2c1=O]

To a suspension of 1.00 g (2.97 mmol) of the compound from Example 35A in 10 ml of THF were added 0.29 ml (3.3 mmol) of oxalyl chloride and catalytic amounts of dimethylformamide. After the evolution of gas had ended, the reaction mixture was heated at 60° C. for 1 h and then cooled down to RT. All the volatile components were removed under reduced pressure and the residue was taken up in 20 ml of DMF. In parallel, 481 mg (2.97 mmol) of 2,6-dichloroaniline were dissolved in 10 ml of DMF, and 119 mg (2.97 mmol) of sodium hydride (60% in mineral oil) were added. The mixture was stirred at RT for 30 min. Subsequently, the above solution was added rapidly and the reaction mixture was stirred at RT overnight. The reaction was ended by adding water and ethyl acetate, and the phases were separated. The organic phase was washed twice with water and with saturated aqueous sodium chloride solution, dried over magnesium sulphate and filtered, and the solvent was removed under reduced pressure. The crude product was taken up in a little DCM and purified by means of flash chromatography (cyclohexane/ethyl acetate gradient). 298 mg (18% of theory, 88% purity) of the title compound were obtained.

LC-MS (Method 3): $R_t$=2.30 min; 480 [M+H]$^+$.

Example 82A

7-Chloro-1-(2-fluorophenyl)-4-oxo-N-[(2R)-1,1,1-trifluorobutan-2-yl]-1,4-dihydro-1,8-naphthyridine-3-carboxamide

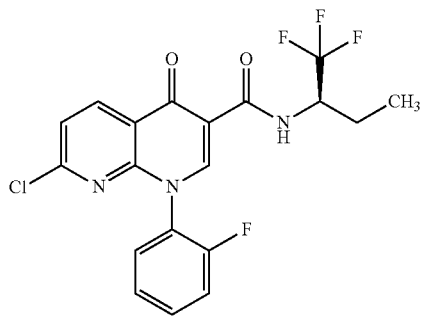 [SMILES: CC[C@@H](NC(=O)c1cn(-c2ccccc2F)c2nc(Cl)ccc2c1=O)C(F)(F)F]

According to GP1, 250 mg (784 µmol) of the compound from Example 33A were reacted with 192 mg (1.18 mmol) of (R)-1-trifluoromethylpropylamine hydrochloride in the presence of 298 mg (784 µmol) of HATU and 410 µl (2.35 mmol) of N,N-diisopropylethylamine in 8.1 ml of dimethylformamide. The crude product was purified by means of flash chromatography (cyclohexane/ethyl acetate gradient), and 139 mg (41% of theory; 99% purity) of the title compound were obtained.

$^1$H-NMR (400 MHz, DMSO-$d_6$): δ [ppm]=10.00 (d, 1H), 8.86 (s, 1H), 8.76 (d, 1H), 7.83-7.65 (m, 3H), 7.58-7.51 (m, 1H), 7.50-7.44 (m, 1H), 4.85-4.69 (m, 1H), 1.96-1.82 (m, 1H), 1.75-1.60 (m, 1H), 0.98 (t, 3H).

LC-MS (Method 1): $R_t$=1.17 min; 428 [M+H]$^+$.

Example 83A tert-Butyl 5-[8-(2,4-difluorophenyl)-5-oxo-6-{[(2R)-1,1,1-trifluorobutan-2-yl]carbamoyl}-5,8-dihydro-1,8-naphthyridin-2-yl]-1-oxohexahydropyrrol[3,4-c]pyrrole-2(1H)-carboxylate (diastereomer mixture)

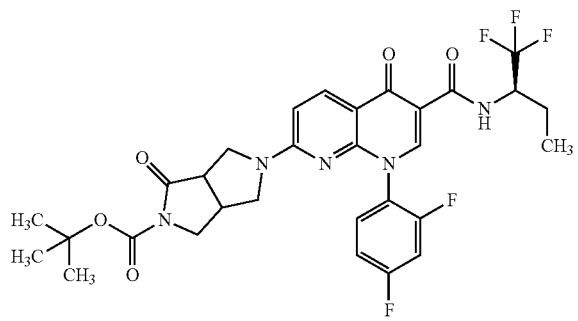 [SMILES: CC[C@@H](NC(=O)c1cn(-c2ccc(F)cc2F)c2nc(N3CC4CN(C(=O)OC(C)(C)C)C(=O)C4C3)ccc2c1=O)C(F)(F)F]

According to GP3, 200 mg (449 µmol) of the compound from Example 67A were reacted with 128 mg (538 µmol) of rac-tert-butyl 1-oxooctahydropyrrolo[3,4-c]pyrrole-2-carboxylate in the presence of 117 µl (673 µmol) of N,N-diisopropylethylamine in 4.4 ml of dimethylformamide. The crude product was diluted with acetonitrile and purified by means of preparative HPLC (column: Chromatorex C18, 10 µm, 125×30 mm, solvent: acetonitrile/0.05% formic acid gradient; (0 to 3 min. 10% acetonitrile to 35 min. 90% acetonitrile and a further 3 min. 90% acetonitrile), and 224 mg (79% of theory, 100% purity) of the title compound were obtained.

$^1$H-NMR (400 MHz, DMSO-$d_6$): δ [ppm]=10.47 (d, 1H), 8.62 (s, 1H), 8.32 (d, 1H), 7.77-7.86 (m, 1H), 7.54-7.65 (m, 1H), 7.28-7.38 (m, 1H), 6.65-6.90 (br. s, 1H), 4.68-4.80 (m, 1H), 2.97-3.90 (m, 8H), 1.82-1.94 (m, 1H), 1.57-1.70 (m, 1H), 1.43 (s, 9H), 0.96 (t, 3H).

LC-MS (Method 3): $R_t$=2.20 min; 636 [M+H]$^+$.

Example 84A

Ethyl 7-chloro-1-(2,6-difluorophenyl)-4-oxo-1,4-dihydro-1,8-naphthyridine-3-carboxylate

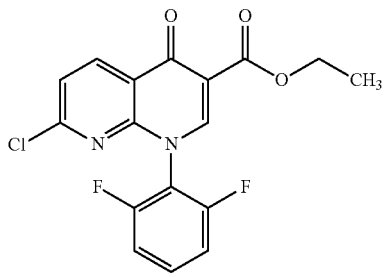 [SMILES: CCOC(=O)c1cn(-c2c(F)cccc2F)c2nc(Cl)ccc2c1=O]

To a solution of 6.05 g (19.0 mmol) of ethyl 2-[(2,6-dichloropyridin-3-yl)carbonyl]-3-ethoxyacrylate (CAS 157373-27-8) and 3.44 g (26.6 mmol) of 2,6-difluoroaniline in 30.2 ml of DCM were added 23.2 ml (133 mmol) of DIPEA, and the mixture was stirred at room temperature for 4 h. The mixture was diluted with 200 ml of DCM and washed twice with 75 ml of 1 M aqueous hydrochloric acid. The organic phase was dried over sodium sulphate and filtered, and the solvent was removed under reduced pressure. The residue was stirred with 40 ml of tert-butyl methyl ether and the precipitate was washed with 10 ml of tert-butyl methyl ether. Subsequently, the precipitate was admixed with 30 ml of DCM and 2.63 g (19.0 mmol) of potassium carbonate, and the mixture was heated under reflux overnight. The mixture was cooled to RT, diluted with 200 ml of DCM and washed twice with 75 ml of 1 M aqueous hydrochloric acid. The organic phase was dried over magnesium sulphate and filtered, and the solvent was removed under reduced pressure. The residue was taken up in 100 ml of acetonitrile and 30 ml of DMF, and heated to 50° C. 1.66 g (12.0 mmol) of potassium carbonate were added at 50° C. and the mixture was stirred for a further 1 h. The reaction mixture was cooled down to RT and poured into 200 ml of aqueous 1 M hydrochloric acid. The mixture was extracted three times with 150 ml of DCM. The combined organic phases were dried over magnesium sulphate and filtered, and the solvent was removed under reduced pressure. The residue was stirred with 200 ml of water and the precipitate was filtered off with suction and dried under high vacuum. 4.19 g (60% of theory, 100% purity) of the title compound were obtained.

$^1$H-NMR (400 MHz, DMSO-d6): δ [ppm]=8.92 (s, 1H), 8.63 (d, 1H), 7.78-7.70 (m, 1H), 7.68 (d, 1H), 7.49-7.43 (m, 2H), 4.25 (q, 2H), 1.28 (t, 3H).

LC-MS (Method 3): $R_t$=1.78 min; 365 [M+H]$^+$.

Example 85A

7-Chloro-1-(2,6-difluorophenyl)-4-oxo-1,4-dihydro-1,8-naphthyridine-3-carboxylic acid

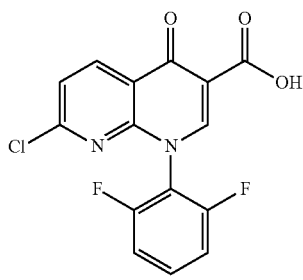 [SMILES: O=C(O)c1cn(-c2c(F)cccc2F)c2nc(Cl)ccc2c1=O]

To a suspension of 3.83 g (10.5 mmol) of the compound from Example 84A in 31.5 ml of water were successively added 31.5 ml of concentrated hydrochloric acid and 31.5 ml of tetrahydrofuran. The resulting suspension was stirred vigorously at 120° C. for 4 h and subsequently cooled down to RT. The mixture was diluted with 100 ml of water, and the precipitate was filtered off with suction and dried under high vacuum. 3.39 g (95% of theory, 98.9% purity) of the title compound were obtained.

$^1$H-NMR (400 MHz, DMSO-$d_6$): δ [ppm]=13.86 (s, 1H), 9.25 (s, 1H), 8.79 (d, 1H), 7.82 (d, 1H), 7.80-7.72 (m, 1H), 7.51-7.43 (m, 2H).

LC-MS (Method 3): $R_t$=1.74 min; 337 [M+H]$^+$.

Example 86A

7-Chloro-1-(2,6-difluorophenyl)-4-oxo-N-[(2R)-1,1,1-trifluorobutan-2-yl]-1,4-dihydro-1,8-naphthyridine-3-carboxamide

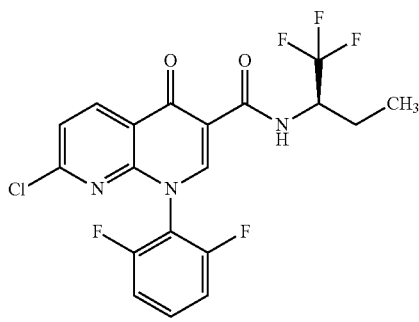 [SMILES: CC[C@@H](NC(=O)c1cn(-c2c(F)cccc2F)c2nc(Cl)ccc2c1=O)C(F)(F)F]

According to GP1, 500 mg (1.43 mmol) of the compound from Example 85A were reacted with 350 mg (2.14 mmol) of (R)-1-trifluoromethylpropylamine hydrochloride in the presence of 542 mg (1.43 mmol) of HATU and 596 µl (3.42 mmol) of DIPEA in 14.3 ml of DMF. The crude product was purified by means of flash chromatography (cyclohexane/ethyl acetate gradient), and 493 mg (77% of theory; 99% purity) of the title compound were obtained.

$^1$H-NMR (400 MHz, DMSO-$d_6$): δ [ppm]=9.89 (d, 1H), 9.09 (s, 1H), 8.76 (d, 1H), 7.78 (d, 1H), 7.80-7.71 (m, 1H), 7.50-7.43 (m, 2H), 4.84-4.71 (m, 1H), 1.96-1.84 (m, 1H), 1.75-1.61 (m, 1H), 0.98 (t, 3H).

LC-MS (Method 3): $R_t$=2.30 min; 446 [M+H]$^+$.

Example 87A rac-Ethyl 1-(2,4-difluorophenyl)-7-(3-hydroxypyrrolidin-1-yl)-4-oxo-1,4-dihydro-1,8-naphthyridine-3-carboxylate

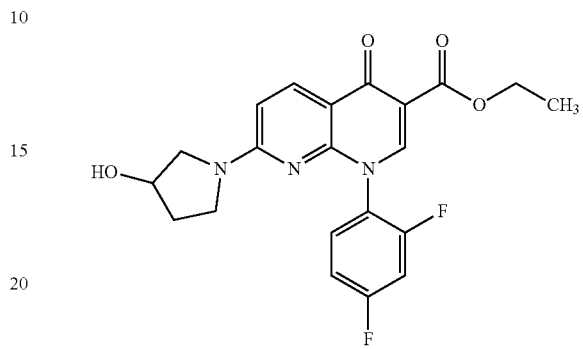

To a solution of 3.00 g (8.23 mmol) of ethyl 7-chloro-1-(2,4-difluorophenyl)-4-oxo-1,4-dihydro-1,8-naphthyridine-3-carboxylate (preparation described in DE 4301246, Example U, S.26) in 20.8 ml of DMF were successively added 1.33 ml (16.5 mmol) of rac-3-pyrrolidinol and 5.01 ml (28.8 ml) of DIPEA. The mixture was stirred at RT overnight. The reaction was ended by adding water and the precipitate was filtered off with suction, washed with water and dried under high vacuum. 3.33 g (97.5% of theory, 100% purity) of the title compound were obtained.

LC-MS (Method 1): $R_t$=0.83 min; 416 [M+H]$^+$.

Example 88A rac-1-(2,4-Difluorophenyl)-7-(3-hydroxypyrrolidin-1-yl)-4-oxo-1,4-dihydro-1,8-naphthyridine-3-carboxylic acid

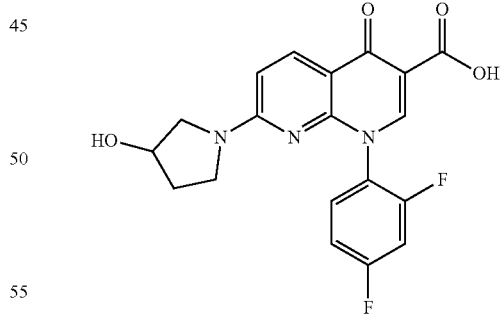

3.30 g (8.02 mmol) of the compound from Example 87A were partly dissolved and partly suspended in 25 ml of water, 25 ml of concentrated hydrochloric acid were added and the mixture was heated under reflux for 6 h. The reaction mixture was left to stand at RT over the weekend. The precipitate was subsequently filtered off with suction, washed with aqueous 0.5 M hydrochloric acid and ethanol, and dried under high vacuum. 2.14 g (67% of theory, 97% purity) of the title compound were obtained.

LC-MS (Method 1): $R_t$=0.80 min; 388 [M+H]$^+$.

¹H-NMR (400 MHz, DMSO-d6): δ [ppm]=8.77 (s, 1H), 8.33-8.27 (m, 1H), 7.85-7.76 (m, 1H), 7.62-7.54 (m, 1H), 7.37-7.29 (m, 1H), 6.88-6.79 (m, 1H), 4.43-3.01 (m, 6H, partially under the water peak), 2.07-1.73 (m, 2H).

Example 89A

Ethyl 7-chloro-4-oxo-1-[2-(trifluoromethyl)phenyl]-1,4-dihydro-1,8-naphthyridine-3-carboxylate

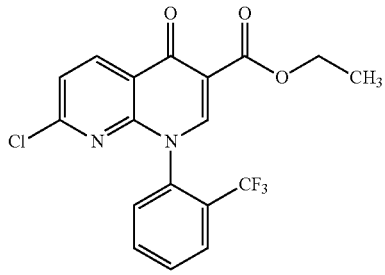 [SMILES: CCOC(=O)c1cn(-c2ccccc2C(F)(F)F)c2nc(Cl)ccc2c1=O]

To a solution of 6.05 g (19.0 mmol) of ethyl 2-[(2,6-dichloropyridin-3-yl)carbonyl]-3-ethoxyacrylate (CAS 157373-27-8) and 4.59 g (28.5 mmol) of 2-trifluoromethylaniline in 30 ml DCM were added 23.2 ml (133 mmol) of DIPEA, and the mixture was stirred at RT for 4 h. Subsequently, 2.63 g (19.0 mmol) of potassium carbonate were added and the mixture was heated under reflux overnight. The mixture was diluted with 400 ml of DCM and washed twice with 150 ml of 1 M aqueous hydrochloric acid. The organic phase was dried over sodium sulphate and filtered, and the solvent was removed under reduced pressure. The suspension obtained was stirred with 40 ml of tert-butyl methyl ether, and the precipitate was filtered off with suction, washed with 10 ml of tert-butyl methyl ether and dried under high vacuum. 4.21 g (55% of theory, 99% purity) of the title compound were obtained.

LC-MS (Method 3): $R_t$=1.81 min; 397 [M+H]⁺.
¹H-NMR (400 MHz, DMSO-d6): δ [ppm]=8.71 (s, 1H), 8.62 (d, 1H), 8.04-8.00 (m, 1H), 7.99-7.93 (m, 1H), 7.89-7.83 (m, 2H), 7.63 (d, 1H), 4.23 (q, 2H), 1.26 (t, 3H).

Example 90A

7-Chloro-4-oxo-1-[2-(trifluoromethyl)phenyl]-1,4-dihydro-1,8-naphthyridine-3-carboxylic acid

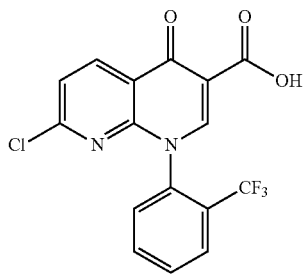 [SMILES: O=C(O)c1cn(-c2ccccc2C(F)(F)F)c2nc(Cl)ccc2c1=O]

To a suspension of 4.10 g (10.3 mmol) of the compound from Example 89A in 51 ml of THF were added 20.7 ml of aqueous sodium hydroxide solution (20.7 mmol), and the reaction mixture was stirred at RT for 3 h. The mixture was then diluted with 250 ml of water and the pH was adjusted to pH 1 with 1N aqueous hydrochloric acid. The precipitate was filtered off with suction, washed with water and dried in a vacuum drying cabinet at 40° C. overnight. 3.77 g (98% of theory, 99% purity) of the title compound were obtained.

LC-MS (Method 3): $R_t$=1.84 min; 369 [M+H]⁺.
¹H-NMR (400 MHz, DMSO-d₆): δ [ppm]=14.03 (br. s, 1H), 9.08 (s, 1H), 8.80 (d, 1H), 8.06-8.01 (m, 1H), 8.00-7.94 (m, 1H), 7.92-7.84 (m, 2H), 7.79 (d, 1H).

Example 91A

7-Chloro-4-oxo-N-[(2R)-1,1,1-trifluorobutan-2-yl]-1-[2-(trifluoromethyl)phenyl]-1,4-dihydro-1,8-naphthyridine-3-carboxamide

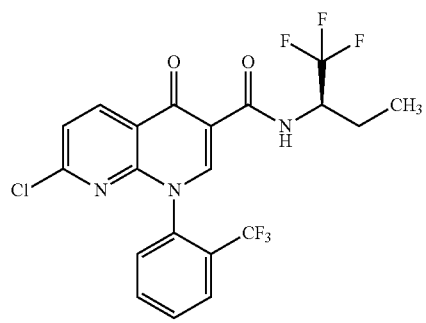 [SMILES: CC[C@@H](NC(=O)c1cn(-c2ccccc2C(F)(F)F)c2nc(Cl)ccc2c1=O)C(F)(F)F]

According to GP1, 250 mg (678 µmol) of the compound from Example 90A were reacted with 166 mg (1.02 mmol) of (R)-1-trifluoromethylpropylamine hydrochloride in the presence of 258 mg (678 µmol) of HATU and 354 µl (2.03 mmol) of DIPEA in 7 ml of DMF. The crude product was purified by means of flash chromatography (25 g, silica cartridge, flow rate: 25 ml/min, detection: 220 nm and 270 nm, cyclohexane/ethyl acetate gradient (0% ethyl acetate, then 20% ethyl acetate, then 30% ethyl acetate). The two atropisomers were separated, and 56.6 mg (17% of theory, 99% purity, atropisomer 1, Example 92A) and 58.8 mg (18% of theory, 99% purity, atropisomer 2, Example 93A) of the title compound were obtained as atropisomers.

Example 92A

7-Chloro-4-oxo-N-[(2R)-1,1,1-trifluorobutan-2-yl]-1-[2-(trifluoromethyl)phenyl]-1,4-dihydro-1,8-naphthyridine-3-carboxamide (atropisomer 1)

LC-MS (Method 3): $R_t$=2.32 min; 478 [M+H]⁺.
¹H-NMR (400 MHz, DMSO-d₆): δ [ppm]=9.99 (d, 1H), 8.86 (s, 1H), 8.75 (d, 1H), 8.06-8.02 (m, 1H), 8.00-7.95 (m, 1H), 7.91-7.85 (m, 2H), 7.73 (d, 1H), 4.83-4.70 (m, 1H), 1.96-1.84 (m, 1H), 1.76-1.62 (m, 1H), 0.99 (t, 3H).

Example 93A

7-Chloro-4-oxo-N-[(2R)-1,1,1-trifluorobutan-2-yl]-1-[2-(trifluoromethyl)phenyl]-1,4-dihydro-1,8-naphthyridine-3-carboxamide (atropisomer 2)

LC-MS (Method 3): $R_t$=2.31 min; 478 [M+H]⁺.
¹H-NMR (400 MHz, DMSO-d₆): δ [ppm]=9.99 (d, 1H), 8.87 (s, 1H), 8.76 (d, 1H), 8.06-8.02 (m, 1H), 8.00-7.95 (m, 1H), 7.91-7.85 (m, 2H), 7.74 (d, 1H), 4.83-4.70 (m, 1H), 1.96-1.83 (m, 1H), 1.74-1.61 (m, 1H), 0.96 (t, 3H).

Example 94A (3R)-2,5-Dioxotetrahydrofuran-3-yl trifluoroacetate

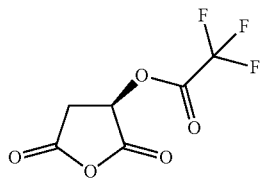 [SMILES: O=C1C[C@@H](OC(=O)C(F)(F)F)C(=O)O1]

At 0° C., 12.0 ml (85.0 mmol) of trifluoroacetic anhydride were added to 5.70 g (42.5 mmol) of (2R)-2-hydroxysuccinic acid, and the mixture was stirred at 0° C. for 1 h and at room temperature for 2 h. Subsequently, all volatile components were removed under reduced pressure at room temperature. The crude product was used in Example 95A without further purification.

Example 95A (3R)-3-Hydroxy-4-methoxy-4-oxobutanoic acid

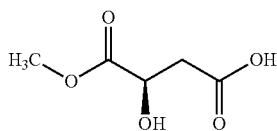

5.17 ml (128 mmol) of methanol were added to 9.02 g (42.5 mmol) of the compound from Example 94A, and the mixture was stirred at room temperature for 4 h. Subsequently, excess methanol was removed under reduced pressure and the residue was recrystallized from diethyl ether/cyclohexane. The solid was dried under high vacuum. This gave 5.84 g (92.8% of theory) of the title compound.

$^1$H-NMR (400 MHz, DMSO-d$_6$): δ [ppm]=12.31 (br. s, 1H), 5.68 (br. s, 1H), 4.35 (dd, 1H), 3.63 (s, 3H), 2.63 (dd, 1H), 2.52-2.45 (m, 1H).

Example 96A

Methyl (5S)-2-oxo-1,3-oxazolidine-5-carboxylate

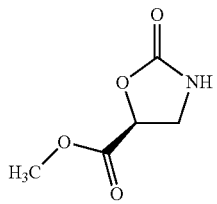

To a solution of 5.84 g (39.4 mmol) of the compound from Example 95A in 159 ml of tert-butanol were added 11.9 g (43.4 mmol) of diphenylphosphoryl azide and 6.05 ml (43.4 mmol) of triethylamine, and then the mixture was heated under reflux for 4 h. The mixture was cooled down to room temperature and the solvent was removed under reduced pressure. The residue was purified by means of flash chromatography (ethyl acetate/cyclohexane gradient). Finally, recrystallization was effected from ethyl acetate/cyclohexane, the solid was dried under high vacuum and 3.29 g (57.7% of theory) of the title compound were obtained.

$^1$H-NMR (400 MHz, DMSO-d$_6$): δ [ppm]=7.79 (s, 1H), 5.15 (dd, 1H), 3.80-3.74 (m, 1H), 3.73 (s, 3H), 3.52-3.46 (m, 1H).

Example 97A (3S)-2,5-Dioxotetrahydrofuran-3-yl trifluoroacetate

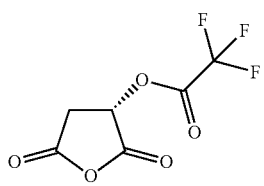 [SMILES: O=C1C[C@H](OC(=O)C(F)(F)F)C(=O)O1]

At 0° C., 12.0 ml (85.0 mmol) of trifluoroacetic anhydride were added to 5.70 g (42.5 mmol) of (2S)-2-hydroxysuccinic acid, and the mixture was stirred at 0° C. for 1 h and at room temperature for 2 h. Subsequently, all volatile components were removed under reduced pressure at room temperature. The crude product was used in Example 98A without further purification.

Example 98A (3S)-3-Hydroxy-4-methoxy-4-oxobutanoic acid

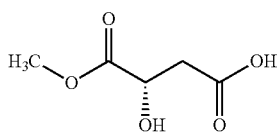

5.17 ml (128 mmol) of methanol were added to 9.02 g (42.5 mmol) of the compound from Example 97A, and the mixture was stirred at room temperature for 4 h. Subsequently, excess methanol was removed under reduced pressure and the residue was recrystallized from diethyl ether/cyclohexane. The solid was dried under high vacuum. This gave 5.95 g (94.5% of theory) of the title compound.

$^1$H-NMR (400 MHz, DMSO-d$_6$): δ [ppm]=12.31 (br. s, 1H), 5.67 (br. s, 1H), 4.38-4.31 (m, 1H), 3.63 (s, 3H), 2.63 (dd, 1H), 2.52-2.45 (m, 1H).

Example 99A

Methyl (5R)-2-oxo-1,3-oxazolidine-5-carboxylate

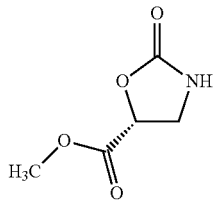

To a solution of 5.95 g (39.4 mmol) of the compound from Example 98A in 160 ml of tert-butanol were added 12.2 g (44.2 mmol) of diphenylphosphoryl azide and 6.16 ml (44.2 mmol) of triethylamine, and then the mixture was heated under reflux for 4 h. The mixture was cooled down to room temperature and the solvent was removed under reduced pressure. The residue was purified by means of flash chromatography (ethyl acetate/cyclohexane gradient). Finally, recrystallization was effected from ethyl acetate/cyclohexane, the solid was dried under high vacuum and 3.48 g (59.7% of theory) of the title compound were obtained.

$^1$H-NMR (400 MHz, DMSO-$d_6$): δ [ppm]=7.79 (s, 1H), 5.15 (dd, 1H), 3.80-3.74 (m, 1H), 3.73 (s, 3H), 3.52-3.46 (m, 1H).

Example 100A

Ethyl 7-chloro-4-oxo-1-(2,4,6-trifluorophenyl)-1,4-dihydro-1,8-naphthyridine-3-carboxylate

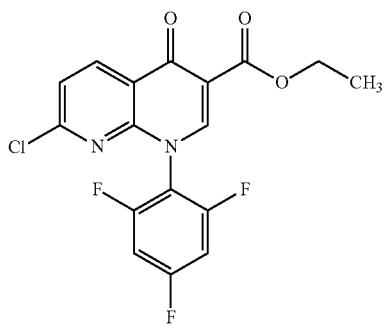 [SMILES: CCOC(=O)c1cn(-c2c(F)cc(F)cc2F)c2nc(Cl)ccc2c1=O]

To a solution of 12.1 g (38.0 mmol) of ethyl 2-[(2,6-dichloropyridin-3-yl)carbonyl]-3-ethoxyacrylate (CAS 157373-27-8) and 7.83 g (53.2 mmol) of 2,4,6-trifluoroaniline in 60.5 ml of DCM were added 46.4 ml (266 mmol) of DIPEA, and the mixture was stirred at RT for 4 h. Subsequently, 5.26 g (38.0 mmol) of potassium carbonate were added and the mixture was heated under reflux overnight. The mixture was diluted with 200 ml of DCM and washed twice with 150 ml of 1 M aqueous hydrochloric acid. The organic phase was dried over sodium sulphate and filtered, and the solvent was removed under reduced pressure. The suspension obtained was stirred with 80 ml of tert-butyl methyl ether, and the precipitate was filtered off with suction, washed with 10 ml of tert-butyl methyl ether and dried under high vacuum. 8.60 g (58% of theory, 99% purity) of the title compound were obtained.

LC-MS (Method 1): $R_t$=0.97 min; 383 [M+H]$^+$.

Example 100B

7-Chloro-4-oxo-1-(2,4,6-trifluorophenyl)-1,4-dihydro-1,8-naphthyridine-3-carboxylic acid

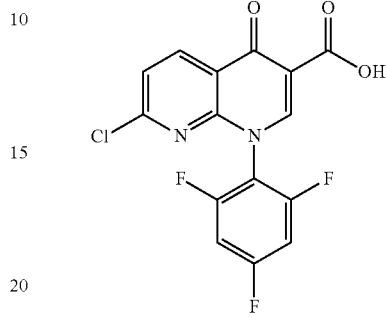

To an initial charge of 8.60 g (22.5 mmol) of ethyl 7-chloro-4-oxo-1-(2,4,6-trifluorophenyl)-1,4-dihydro-1,8-naphthyridine-3-carboxylate (Example 100A) in 67.7 ml of water were added 67.7 ml of 36 percent aqueous hydrochloric acid and 67.7 ml of THF, and the mixture was stirred at 110° C. for 4.5 h. The reaction mixture was cooled down to RT. The precipitate was filtered off with suction, washed with water and dried under high vacuum. 7.87 g (98% of theory, 99% purity) of the title compound were obtained.

LC-MS (Method 1): $R_t$=0.95 min; MS (ESIpos): m/z=355 [M+H]$^+$.

$^1$H NMR (400 MHz, DMSO-d6): δ [ppm]=13.83 (s, 1H), 9.27 (s, 1H), 8.78 (d, 1H), 7.82 (d, 1H), 7.67-7.59 (m, 2H).

Example 100C

7-Chloro-4-oxo-N-[(2R)-1,1,1-trifluorobutan-2-yl]-1-(2,4,6-trifluorophenyl)-1,4-dihydro-1,8-naphthyridine-3-carboxamide

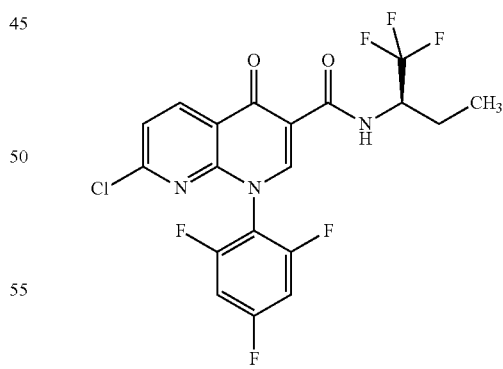

According to GP1, 1.00 g (2.82 mmol) of 7-chloro-4-oxo-1-(2,4,6-trifluorophenyl)-1,4-dihydro-1,8-naphthyridine-3-carboxylic acid (Example 100B) were reacted with 692 mg (4.23 mmol) of (2R)-1,1,1-trifluorobutan-2-amine hydrochloride in the presence of 1.07 g (2.82 mmol) of HATU and 1.18 ml (6.77 mmol) of N,N-diisopropylethylamine in 28.3 ml of dimethylformamide. The reaction was ended by adding 40 ml of water and 60 ml of ethyl acetate, and the phases were separated. The aqueous phase was extracted three times with 20 ml of ethyl acetate, and the combined organic phases were washed with 40 ml of a mixture (1:1, v/v) of saturated aqueous sodium chloride solution and aqueous 1N hydrochloric acid. The organic phase was washed three times with 30 ml of saturated aqueous sodium chloride solution, dried over sodium sulphate and filtered, and the solvent was removed under reduced pressure. The residue was purified by means of normal phase chromatography (cyclohexane-ethyl acetate gradient), and 1.16 g (88% of theory; 99% purity) of the title compound were obtained.

$^1$H NMR (400 MHz, DMSO-d$_6$) δ [ppm]=9.88 (d, 1H), 9.13 (s, 1H), 8.75 (d, 1H), 7.78 (d, 1H), 7.66-7.58 (m, 2H), 4.83-4.72 (m, 1H), 1.95-1.84 (m, 1H), 1.74-1.61 (m, 1H), 0.98 (t, 3H).

LC-MS (Method 3): R$_t$=2.35 min; 464 [M+H]$^+$.

Example 101A rac-7-Chloro-N-(1-cyclopropyl-2,2,2-trifluoroethyl)-1-(2,4-difluorophenyl)-4-oxo-1,4-dihydro-1,8-naphthyridine-3-carboxamide

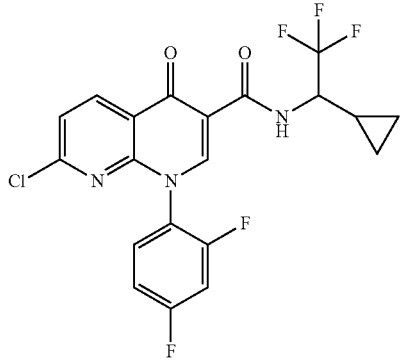 [SMILES: O=C(NC(C1CC1)C(F)(F)F)c1cn(-c2ccc(F)cc2F)c2nc(Cl)ccc2c1=O]

According to GP1, 500 mg (1.49 mmol) of 7-chloro-4-oxo-1-(2,4-difluorophenyl)-1,4-dihydro-1,8-naphthyridine-3-carboxylic acid (Example 35A) were reacted with 391 mg (2.23 mmol) of 1-cyclopropyl-2,2,2-trifluoroethanamine hydrochloride (racemate, CAS: 75702-99-7) in the presence of 565 mg (1.49 mmol) of HATU and 621 μl (3.56 mmol) of N,N-diisopropylethylamine in 15 ml of dimethylformamide. The reaction was ended by adding 20 ml of water and 30 ml of ethyl acetate, and the phases were separated. The aqueous phase was extracted three times with 10 ml of ethyl acetate, and the combined organic phases were washed with 40 ml of a mixture (1:1, v/v) of saturated aqueous sodium chloride solution and aqueous 1N hydrochloric acid. The organic phase was washed three times with 15 ml of saturated aqueous sodium chloride solution, dried over sodium sulphate and filtered, and the solvent was removed under reduced pressure. The residue was purified by means of normal phase chromatography (cyclohexane-ethyl acetate gradient), and 564 mg (82% of theory; 99% purity) of the title compound were obtained.

$^1$H NMR (400 MHz, DMSO-d$_6$) δ [ppm]=10.14 (d, 1H), 8.89 (s, 1H), 8.75 (d, 1H), 7.91-7.81 (m, 1H), 7.76 (d, 1H), 7.68-7.59 (m, 1H), 7.41-7.33 (m, 1H), 4.47-4.33 (m, 1H), 1.29-1.19 (m, 1H), 0.71-0.51 (m, 3H), 0.37-0.28 (m, 1H).

LC-MS (Method 1): R$_t$=1.20 min; 458 [M+H]$^+$.

Example 102A rac-7-Chloro-N-(1-cyclopropyl-2,2,2-trifluoroethyl)-1-(2,6-difluorophenyl)-4-oxo-1,4-dihydro-1,8-naphthyridine-3-carboxamide

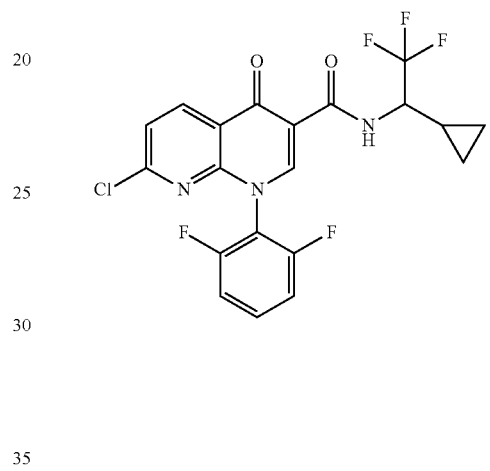

According to GP1, 1.00 g (2.97 mmol) of 7-chloro-4-oxo-1-(2,6-difluorophenyl)-1,4-dihydro-1,8-naphthyridine-3-carboxylic acid (Example 85A) were reacted with 782 mg (4.46 mmol) of 1-cyclopropyl-2,2,2-trifluoroethanamine hydrochloride (racemate, CAS: 75702-99-7) in the presence of 1.13 g (2.97 mmol) of HATU and 1.24 ml (7.13 mmol) of N,N-diisopropylethylamine in 30 ml of dimethylformamide. The reaction was ended by adding 20 ml of water and 30 ml of ethyl acetate, and the phases were separated. The aqueous phase was extracted three times with 10 ml of ethyl acetate, and the combined organic phases were washed with 20 ml of a mixture (1:1, v/v) of saturated aqueous sodium chloride solution and aqueous 1N hydrochloric acid. The organic phase was washed three times with 15 ml of saturated aqueous sodium chloride solution, dried over sodium sulphate and filtered, and the solvent was removed under reduced pressure. The residue was purified by means of normal phase chromatography (cyclohexane-ethyl acetate gradient), and 1.11 g (81% of theory; 99% purity) of the title compound were obtained.

$^1$H NMR (400 MHz, DMSO-d$_6$) δ [ppm]=10.05 (d, 1H), 9.08 (s, 1H), 8.77 (d, 1H), 7.81-7.70 (m, 2H), 7.50-7.42 (m, 2H), 4.45-4.33 (m, 1H), 1.30-1.20 (m, 1H), 0.72-0.54 (m, 3H), 0.38-0.30 (m, 1H).

LC-MS (Method 3): R$_t$=2.32 min; 458 [M+H]$^+$.

Example 103A

7-Chloro-N-[(1R)-1-cyclopropyl-2,2,2-trifluoroethyl]-1-(2,6-difluorophenyl)-4-oxo-1,4-dihydro-1,8-naphthyridine-3-carboxamide

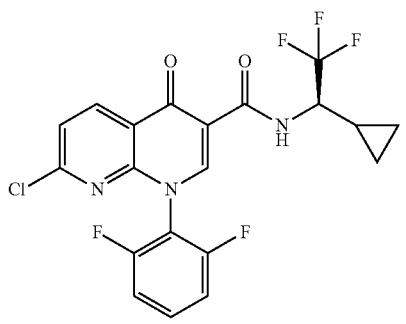 [SMILES: O=C(N[C@H](C1CC1)C(F)(F)F)c1cn(-c2c(F)cccc2F)c2nc(Cl)ccc2c1=O]

According to GP1, 1.00 g (2.94 mmol) of the compound from Example 85A were reacted with 774 mg (4.41 mmol) of (R)-1-trifluoromethylpropylamine hydrochloride in the presence of 1.12 g (2.94 mmol) of HATU and 1.23 ml (7.06 mmol) of DIPEA in 29.5 ml of DMF. The reaction was ended by adding 40 ml of water and 60 ml of ethyl acetate, and the phases were separated. The aqueous phase was extracted three times with 20 ml of ethyl acetate, and the combined organic phases were washed with 40 ml of a mixture (1:1, v/v) of saturated aqueous sodium chloride solution and aqueous 1N hydrochloric acid. The organic phase was washed three times with 30 ml of saturated aqueous sodium chloride solution, dried over sodium sulphate and filtered, and the solvent was removed under reduced pressure. The residue was purified by means of normal phase chromatography (cyclohexane-ethyl acetate gradient), and 840 mg (62% of theory; 99% purity) of the title compound were obtained.

$^1$H-NMR (400 MHz, DMSO-d$_6$): δ [ppm]=10.05 (d, 1H), 9.08 (s, 1H), 8.76 (d, 1H), 7.81-7.70 (m, 2H), 7.50-7.42 (m, 2H), 4.46-4.33 (m, 1H), 1.29-1.18 (m, 1H), 0.73-0.52 (m, 3H), 0.39-0.30 (m, 1H).

LC-MS (Method 3): R$_t$=2.31 min; 458 [M+H]$^+$.

Example 104A

7-Chloro-N-[(1S)-1-cyclopropyl-2,2,2-trifluoroethyl]-1-(2,6-difluorophenyl)-4-oxo-1,4-dihydro-1,8-naphthyridine-3-carboxamide

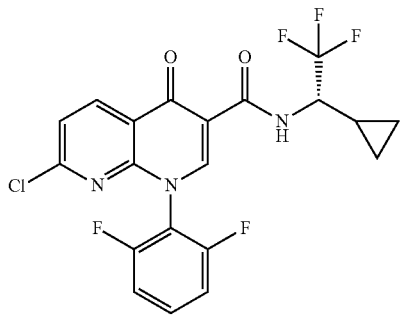 [SMILES: O=C(N[C@@H](C1CC1)C(F)(F)F)c1cn(-c2c(F)cccc2F)c2nc(Cl)ccc2c1=O]

According to GP1, 350 mg (1.03 mmol) of the compound from Example 85A were reacted with 217 mg (1.24 mmol) of (S)-1-trifluoromethylpropylamine hydrochloride in the presence of 391 mg (1.03 mmol) of HATU and 430 µl (2.47 mmol) of DIPEA in 10 ml of DMF. The mixture was poured into a mixture of 30 ml of water and 5 ml of 1N aqueous hydrochloric acid, and the precipitate was filtered off with suction. The precipitate was taken up in a little dichloromethane and purified by means of normal phase chromatography (cyclohexane-ethyl acetate gradient), and 325 mg (69% of theory; 100% purity) of the title compound were obtained.

$^1$H-NMR (400 MHz, DMSO-d$_6$): δ [ppm]=10.05 (d, 1H), 9.08 (s, 1H), 8.76 (d, 1H), 7.81-7.70 (m, 2H), 7.50-7.42 (m, 2H), 4.46-4.33 (m, 1H), 1.30-1.20 (m, 1H), 0.72-0.53 (m, 3H), 0.39-0.29 (m, 1H).

LC-MS (Method 1): R$_t$=1.20 min; 458 [M+H]$^+$.

Example 105A

Ethyl 7-chloro-1-(2-chloro-6-fluorophenyl)-4-oxo-1,4-dihydro-1,8-naphthyridine-3-carboxylate

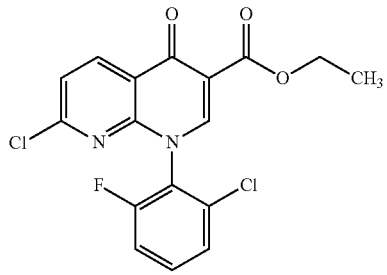

To a solution of 6.05 g (19.0 mmol) of ethyl 2-[(2,6-dichloropyridin-3-yl)carbonyl]-3-ethoxyacrylate (CAS 157373-27-8) and 3.88 g (26.6 mmol) of 2-chloro-6-fluoroaniline in 30.3 ml dichloromethane were added 23.2 ml (133 mmol) of DIPEA, and the mixture was stirred at RT for 4 h. Subsequently, 2.63 g (19.0 mmol) of potassium carbonate were added and the mixture was heated under reflux overnight. The mixture was diluted with 200 ml of DCM and washed twice with 75 ml of 1 M aqueous hydrochloric acid. The organic phase was dried over sodium sulphate and filtered, and the solvent was removed under reduced pressure. The suspension obtained was stirred with 40 ml of tert-butyl methyl ether, and the precipitate was filtered off with suction, washed with 10 ml of tert-butyl methyl ether and dried under high vacuum. 5.70 g (64% of theory, 81% purity) of the title compound were obtained.

$^1$H-NMR (400 MHz, DMSO-d$_6$): δ [ppm]=8.88 (s, 1H), 8.64 (d, 1H), 7.76-7.57 (m, 4H), 4.25 (q, 2H), 1.28 (t, 3H).

LC-MS (Method 3): R$_t$=1.86 min; 381 [M+H]$^+$.

Example 105B

7-Chloro-1-(2-chloro-6-fluorophenyl)-4-oxo-1,4-dihydro-1,8-naphthyridine-3-carboxylic acid

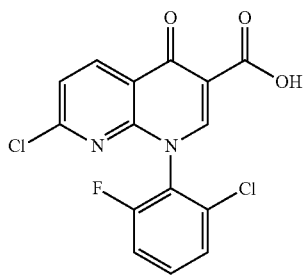 [SMILES: O=C(O)c1cn(-c2c(F)cccc2Cl)c2nc(Cl)ccc2c1=O]

To an initial charge of 5.70 g (14.9 mmol) of ethyl 7-chloro-1-(2-chloro-6-fluorophenyl)-4-oxo-1,4-dihydro-1,8-naphthyridine-3-carboxylate in 45 ml of water were added 45 ml of 36 percent aqueous hydrochloric acid and 45 ml of THF, and the mixture was stirred at 120° C. for 4.5 h. The reaction mixture was cooled down to RT. The precipitate was filtered off with suction, washed with water and dried under high vacuum. 4.12 g (77% of theory, 99% purity) of the title compound were obtained.

$^1$H NMR (400 MHz, DMSO-d6): δ [ppm]=13.84 (s, 1H), 9.23 (s, 1H), 8.80 (d, 1H), 7.82 (d, 1H), 7.78-7.57 (m, 3H).

LC-MS (Method 3): $R_t$=1.84 min; MS (ESIpos): m/z=352.9 [M+H]$^+$.

Example 105C

7-Chloro-1-(2-chloro-6-fluorophenyl)-4-oxo-N-[(2R)-1,1,1-trifluorobutan-2-yl]-1,4-dihydro-1,8-naphthyridine-3-carboxamide

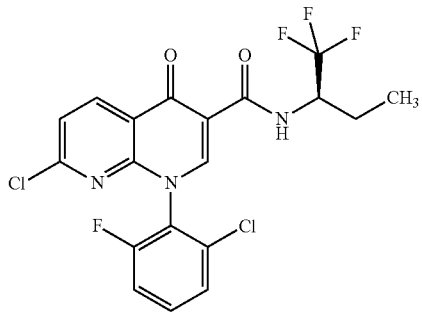 [SMILES: CC[C@@H](NC(=O)c1cn(-c2c(F)cccc2Cl)c2nc(Cl)ccc2c1=O)C(F)(F)F]

According to GP1, 1.00 g (2.83 mmol) of 7-chloro-1-(2-chloro-6-fluorophenyl)-4-oxo-1,4-dihydro-1,8-naphthyridine-3-carboxylic acid were reacted with 695 mg (4.25 mmol) of (2R)-1,1,1-trifluorobutan-2-amine hydrochloride in the presence of 1.08 g (2.83 mmol) of HATU and 1.18 ml (6.80 mmol) of N,N-diisopropylethylamine in 28.4 ml of dimethylformamide. The reaction was ended by adding 40 ml of water and 60 ml of ethyl acetate, and the phases were separated. The aqueous phase was extracted three times with 20 ml of ethyl acetate, and the combined organic phases were washed with 40 ml of a mixture (1:1, v/v) of saturated aqueous sodium chloride solution and aqueous 1N hydrochloric acid. The organic phase was washed three times with 30 ml of saturated aqueous sodium chloride solution, dried over sodium sulphate and filtered, and the solvent was removed under reduced pressure. The residue was purified by means of normal phase chromatography (cyclohexane-ethyl acetate gradient), and 1.09 g (82% of theory; 99% purity) of the title compound were obtained.

$^1$H NMR (400 MHz, DMSO-d$_6$) δ [ppm]=9.90 (d, 1H), 9.07-9.06 (m, 1H), 8.77 (d, 1H), 7.79 (d, 1H), 7.77-7.57 (m, 3H), 4.83-4.71 (m, 1H), 1.96-1.84 (m, 1H), 1.75-1.62 (m, 1H), 1.02-0.95 (m, 3H).

LC-MS (Method 1): $R_t$=1.31 min; 462 [M+H]$^+$.

Example 106A

7-Chloro-1-(2,6-difluorophenyl)-4-oxo-N-[(2S)-1,1,1-trifluoropropan-2-yl]-1,4-dihydro-1,8-naphthyridine-3-carboxamide

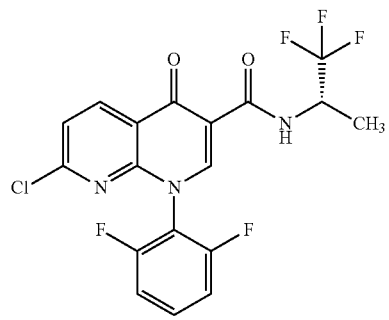 [SMILES: C[C@H](NC(=O)c1cn(-c2c(F)cccc2F)c2nc(Cl)ccc2c1=O)C(F)(F)F]

According to GP1, 880 mg (2.61 mmol) of the compound from Example 85A were reacted with 443 mg (3.92 mmol) of (2S)-1,1,1-trifluoropropan-2-amine in the presence of 994 mg (2.61 mmol) of HATU and 1.09 ml (6.27 mmol) of DIPEA in 26.4 ml of DMF. The reaction was ended by adding 20 ml of water and 30 ml of ethyl acetate, and the phases were separated. The aqueous phase was extracted three times with 10 ml of ethyl acetate, and the combined organic phases were washed with 20 ml of a mixture (1:1, v/v) of saturated aqueous sodium chloride solution and aqueous 1N hydrochloric acid. The organic phase was washed three times with 15 ml of saturated aqueous sodium chloride solution, dried over sodium sulphate and filtered, and the solvent was removed under reduced pressure. The crude product was purified by means of flash chromatography (cyclohexane/ethyl acetate gradient), and 773 mg (68% of theory; 99% purity) of the title compound were obtained.

$^1$H-NMR (400 MHz, DMSO-d$_6$): δ [ppm]=9.94 (d, 1H), 9.08 (s, 1H), 8.75 (d, 1H), 7.80-7.71 (m, 2H), 7.50-7.43 (m, 2H), 4.99-4.88 (m, 1H), 1.40 (d, 3H).

LC-MS (Method 3): $R_t$=2.19 min; 432 [M+H]$^+$.

Example 107A

7-Chloro-1-(2,4,6-trifluorophenyl)-4-oxo-N-[(2S)-1,1,1-trifluoropropan-2-yl]-1,4-dihydro-1,8-naphthyridine-3-carboxamide

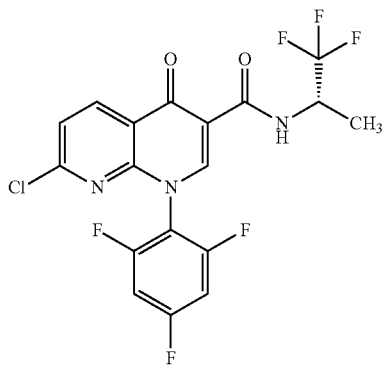 [SMILES: C[C@H](NC(=O)c1cn(-c2c(F)cc(F)cc2F)c2nc(Cl)ccc2c1=O)C(F)(F)F]

According to GP1, 1.00 g (2.82 mmol) of the compound from Example 100B were reacted with 478 mg (4.23 mmol) of (2S)-1,1,1-trifluoropropan-2-amine in the presence of 1.07 g (2.82 mmol) of HATU and 1.18 ml (6.77 mmol) of DIPEA in 28.5 ml of DMF. The reaction was ended by adding 25 ml of water and 35 ml of ethyl acetate, and the phases were separated. The aqueous phase was extracted three times with 15 ml of ethyl acetate, and the combined organic phases were washed with 25 ml of a mixture (1:1, v/v) of saturated aqueous sodium chloride solution and aqueous 1N hydrochloric acid. The organic phase was washed three times with 20 ml of saturated aqueous sodium chloride solution, dried over sodium sulphate and filtered, and the solvent was removed under reduced pressure. The crude product was purified by means of flash chromatography (cyclohexane/ethyl acetate gradient), and 751 mg (59% of theory; 99% purity) of the title compound were obtained.

$^1$H-NMR (400 MHz, DMSO-$d_6$): δ [ppm]=9.93 (d, 1H), 9.13 (s, 1H), 8.75 (d, 1H), 7.78 (d, 1H), 7.66-7.58 (m, 2H), 5.00-4.86 (m, 1H), 1.40 (d, 3H).

LC-MS (Method 1): $R_t$=1.26 min; 450 [M+H]$^+$.

Example 108A

Ethyl 7-chloro-1-(2-chloro-4,6-difluorophenyl)-4-oxo-1,4-dihydro-1,8-naphthyridine-3-carboxylate

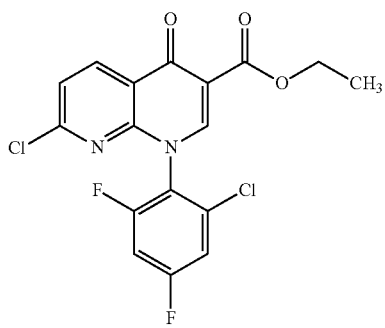 [SMILES: CCOC(=O)c1cn(-c2c(F)cc(F)cc2Cl)c2nc(Cl)ccc2c1=O]

To a solution of 13.8 g (43.4 mmol) of ethyl 2-[(2,6-dichloropyridin-3-yl)carbonyl]-3-ethoxyacrylate (CAS 157373-27-8) and 9.93 g (60.7 mmol) of 2-chloro-4,6-difluoroaniline in 68.2 ml of dichloromethane were added 52.9 ml (304 mmol) of DIPEA, and the mixture was stirred at RT for 4 h. Subsequently, 6.00 g (43.4 mmol) of potassium carbonate were added and the mixture was heated under reflux overnight. The mixture was diluted with 600 ml of DCM and washed twice with 200 ml of 1 M aqueous hydrochloric acid. The organic phase was dried over sodium sulphate and filtered, and the solvent was removed under reduced pressure. The suspension obtained was stirred with 80 ml of tert-butyl methyl ether, and the precipitate was filtered off with suction, washed with 20 ml of tert-butyl methyl ether and dried under high vacuum. 15.0 g (72% of theory, 83% purity) of the title compound were obtained.

LC-MS (Method 3): $R_t$=1.91 min; 399 [M+H]$^+$.

Example 108B

7-Chloro-1-(2-chloro-4,6-difluorophenyl)-4-oxo-1,4-dihydro-1,8-naphthyridine-3-carboxylic acid

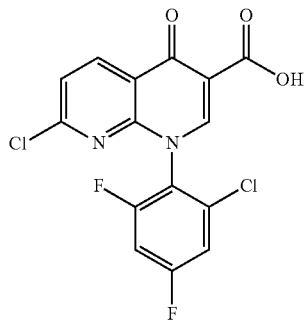 [SMILES: O=C(O)c1cn(-c2c(F)cc(F)cc2Cl)c2nc(Cl)ccc2c1=O]

To an initial charge of 15.0 g (37.6 mmol) of ethyl 7-chloro-1-(2-chloro-4,6-difluorophenyl)-4-oxo-1,4-dihydro-1,8-naphthyridine-3-carboxylate in 131 ml of water were added 131 ml of 36 percent aqueous hydrochloric acid and 131 ml of THF, and the mixture was stirred at 110° C. for 4.5 h. The reaction mixture was cooled down to RT. The precipitate was filtered off with suction, washed with water and dried under high vacuum. 10.2 g (72% of theory, 99% purity) of the title compound were obtained.

$^1$H NMR (400 MHz, DMSO-d6): δ [ppm]=13.81 (s, 1H), 9.25 (s, 1H), 8.80 (d, 1H), 7.84-7.73 (m, 3H).

LC-MS (Method 3): $R_t$=1.87 min; MS (ESIpos): m/z=370.9 [M+H]$^+$.

Example 108C

7-Chloro-1-(2-chloro-4,6-difluorophenyl)-4-oxo-N-[(2R)-1,1,1-trifluorobutan-2-yl]-1,4-dihydro-1,8-naphthyridine-3-carboxamide

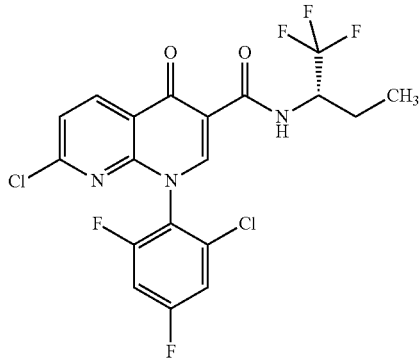 [SMILES: CC[C@H](NC(=O)c1cn(-c2c(F)cc(F)cc2Cl)c2nc(Cl)ccc2c1=O)C(F)(F)F]

According to GP1, 1.00 g (2.69 mmol) of 7-chloro-1-(2-chloro-4,6-difluorophenyl)-4-oxo-1,4-dihydro-1,8-naphthyridine-3-carboxylic acid were reacted with 513 mg (4.04 mmol) of (2S)-1,1,1-trifluorobutan-2-amine hydrochloride in the presence of 1.02 g (2.69 mmol) of HATU and 657 µl (3.77 mmol) of N,N-diisopropylethylamine in 27 ml of dimethylformamide. The reaction was ended by adding 40 ml of water and 60 ml of ethyl acetate, and the phases were separated. The aqueous phase was extracted three times with 20 ml of ethyl acetate, and the combined organic phases were washed with 40 ml of a mixture (1:1, v/v) of saturated aqueous sodium chloride solution and aqueous 1N hydrochloric acid. The organic phase was washed three times with 30 ml of saturated aqueous sodium chloride solution, dried over sodium sulphate and filtered, and the solvent was removed under reduced pressure. The residue was purified by means of normal phase chromatography (cyclohexane-ethyl acetate gradient), and 914 mg (71% of theory; 100% purity) of the title compound were obtained.

$^1$H NMR (400 MHz, DMSO-d$_6$) δ [ppm]=9.88 (d, 1H), 9.11 (s, 1H), 8.77 (d, 1H), 7.81-7.72 (m, 3H), 4.83-4.71 (m, 1H), 1.96-1.84 (m, 1H), 1.74-1.61 (m, 1H), 1.01-0.94 (m, 3H).

LC-MS (Method 3): R$_t$=2.40 min; 480 [M+H]$^+$.

Example 109A

7-Chloro-1-(2-chloro-4,6-difluorophenyl)-4-oxo-N-(4,4,4-trifluoro-2-methylbutan-2-yl)-1,4-dihydro-1,8-naphthyridine-3-carboxamide

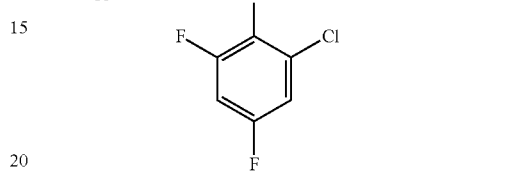

According to GP1, 255 mg (680 µmol) of 7-chloro-1-(2-chloro-4,6-difluorophenyl)-4-oxo-1,4-dihydro-1,8-naphthyridine-3-carboxylic acid were reacted with 181 mg (1.02 mmol) of 4,4,4-trifluoro-2-methylbutan-2-amine hydrochloride in the presence of 259 mg (680 µmol) of HATU and 415 µl (2.38 mmol) of N,N-diisopropylethylamine in 7 ml of dimethylformamide. The reaction mixture was adjusted to pH 1 with 1N aqueous hydrochloric acid and purified in several runs by means of preparative HPLC (column: Chromatorex C18, 10 µm, 125×30 mm, solvent: acetonitrile/0.05% formic acid gradient (0 to 3 min 15% acetonitrile, to 15 min 90% acetonitrile and for a further 3 min 90% acetonitrile). 202 mg (60% of theory, 100% purity) of the title compound were obtained.

$^1$H NMR (400 MHz, DMSO-d$_6$) δ [ppm]=9.70 (s, 1H), 9.00 (s, 1H), 8.75 (d, 1H), 7.80-7.72 (m, 3H), 3.03-2.89 (m, 2H), 1.50 (s, 6H).

LC-MS (Method 3): R$_t$=2.41 min; 494 [M+H]$^+$.

Example 110A

7-Chloro-1-(2-chloro-4,6-difluorophenyl)-N-[(1S)-1-cyclopropyl-2,2,2-trifluoroethyl]-4-oxo-1,4-dihydro-1,8-naphthyridine-3-carboxamide

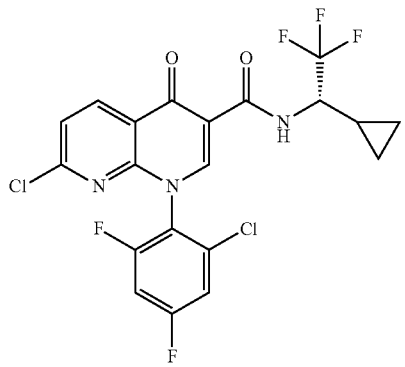 [SMILES: O=C(N[C@@H](C1CC1)C(F)(F)F)c1cn(-c2c(F)cc(F)cc2Cl)c2nc(Cl)ccc2c1=O]

According to GP1, 600 mg (1.62 mmol) of 7-chloro-1-(2-chloro-4,6-difluorophenyl)-4-oxo-1,4-dihydro-1,8-naphthyridine-3-carboxylic acid were reacted with 426 mg (2.43 mmol) of (1S)-1-cyclopropyl-2,2,2-trifluoroethanamine hydrochloride in the presence of 615 mg (1.62 mmol) of HATU and 676 µl (3.88 mmol) of N,N-diisopropylethylamine in 16.2 ml of dimethylformamide. The reaction mixture was stirred into a mixture of 200 ml of water and 16 ml of 1N aqueous hydrochloric acid, and the precipitate was filtered off with suction. The precipitate was taken up in a little dichloromethane and purified by means of normal phase chromatography (cyclohexane-ethyl acetate gradient). 633 mg (79% of theory, 99% purity) of the title compound were obtained.

$^1$H NMR (400 MHz, DMSO-d$_6$) δ [ppm]=10.05 (d, 1H), 9.11 (s, 1H), 8.78 (d, 1H), 7.81-7.72 (m, 3H), 4.46-4.32 (m, 1H), 1.30-1.19 (m, 1H), 0.71-0.53 (m, 3H), 0.40-0.29 (m, 1H).

LC-MS (Method 1): R$_t$=1.23 min; 492 [M+H]$^+$.

Example 111A

7-Chloro-1-(2-chloro-4,6-difluorophenyl)-4-oxo-N-[(2S)-1,1,1-trifluoropropan-2-yl]-1,4-dihydro-1,8-naphthyridine-3-carboxamide

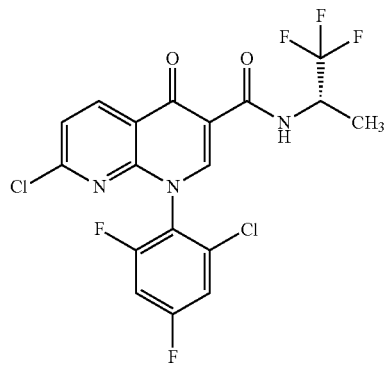 [SMILES: C[C@H](NC(=O)c1cn(-c2c(F)cc(F)cc2Cl)c2nc(Cl)ccc2c1=O)C(F)(F)F]

According to GP1, 5.00 g (13.5 mmol) of 7-chloro-1-(2-chloro-4,6-difluorophenyl)-4-oxo-1,4-dihydro-1,8-naphthyridine-3-carboxylic acid were reacted with 1.83 g (16.2 mmol) of (2S)-1,1,1-trifluoropropan-2-amine hydrochloride in the presence of 5.12 g (13.5 mmol) of HATU and 5.63 ml (32.3 mmol) of N,N-diisopropylethylamine in 135 ml of dimethylformamide. The reaction mixture was stirred into a mixture of 600 ml of water and 135 ml of 1N aqueous hydrochloric acid, and the precipitate was filtered off with suction. The precipitate was taken up in 12 ml of dichloromethane and purified by means of normal phase chromatography (cyclohexane-ethyl acetate gradient). 4.12 g (65% of theory, 99% purity) of the title compound were obtained.

$^1$H NMR (400 MHz, DMSO-d$_6$) δ [ppm]=9.94 (d, 1H), 9.11 (d, 1H), 8.76 (d, 1H), 7.81-7.72 (m, 3H), 4.98-4.86 (m, 1H), 1.42-1.38 (m, 3H).

LC-MS (Method 1): R$_t$=1.21 min; 466 [M+H]$^+$.

Example 112A

7-Chloro-1-(2-chloro-4,6-difluorophenyl)-4-oxo-N-[(2S)-1-(trifluoromethoxy)propan-2-yl]-1,4-dihydro-1,8-naphthyridine-3-carboxamide

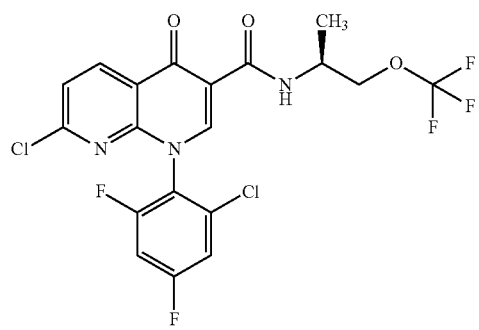 [SMILES: C[C@@H](COC(F)(F)F)NC(=O)c1cn(-c2c(F)cc(F)cc2Cl)c2nc(Cl)ccc2c1=O]

According to GP1, 264 mg (704 µmol) of 7-chloro-1-(2-chloro-4,6-difluorophenyl)-4-oxo-1,4-dihydro-1,8-naphthyridine-3-carboxylic acid were reacted with 190 mg (1.06 mmol) of (2S)-1-(trifluoromethoxy)propan-2-amine hydrochloride in the presence of 268 mg (704 µmol) of HATU and 294 µl (1.69 mmol) of N,N-diisopropylethylamine in 7 ml of dimethylformamide. The reaction mixture was stirred into a mixture of 42 ml of water and 6 ml of 1N aqueous hydrochloric acid, and the precipitate was filtered off with suction. The precipitate was taken up in dichloromethane, the phases were separated, the organic phase was dried over magnesium sulphate and filtered and the solvent was removed under reduced pressure. The residue was purified by means of normal phase chromatography (cyclohexane-ethyl acetate gradient), and 299 mg (86% of theory; 100% purity) of the title compound were obtained.

$^1$H NMR (400 MHz, DMSO-d$_6$) δ [ppm]=9.76-9.61 (m, 1H), 9.03 (s, 1H), 8.76 (d, 1H), 7.80-7.72 (m, 3H), 4.43-4.31 (m, 1H), 4.24-4.14 (m, 2H), 1.30-1.22 (m, 3H).

LC-MS (Method 3): R$_t$=2.32 min; 496 [M+H]$^+$.

Example 113A

4-Oxo-7-(2-oxoimidazolidin-1-yl)-1-(2,4,6-trifluorophenyl)-1,4-dihydro-1,8-naphthyridine-3-carboxylic acid

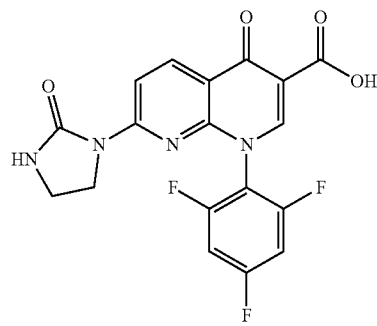 [SMILES: O=C(O)c1cn(-c2c(F)cc(F)cc2F)c2nc(N3CCNC3=O)ccc2c1=O]

According to GP2, 15.0 g (42.3 mmol) of the compound from Example 100B were reacted with 25.5 g (296 mmol) of imidazolin-2-one in the presence of 14.6 g (106 mmol) of potassium carbonate, 190 mg (846 µmol) of palladium(II) acetate and 979 mg (1.69 mmol) of Xantphos in 400 ml of 1,4-dioxane. The mixture was stirred at 90° C. for 2.5 h and then cooled down to RT. The suspension was stirred into water and adjusted to pH 2 with dilute aqueous hydrochloric acid. The precipitate was filtered off with suction and washed with water. The residue was stirred in acetonitrile, filtered off with suction, washed and dried under high vacuum. This gave 15.0 g (88% of theory) of the title compound.

$^1$H-NMR (400 MHz, DMSO-d$_6$): δ [ppm]=14.7 (s, 1H), 9.20 (s, 1H), 8.63-8.47 (m, 2H), 7.75 (s, 1H), 7.64-7.54 (m, 2H), 3.64-3.55 (m, 2H).

LC-MS (Method 3): R$_t$=1.37 min; 405 [M+H]$^+$.

Example 114A

7-Chloro-1-(2,6-difluorophenyl)-4-oxo-N-[(2)-1,1,1-trifluorobutan-2-yl)-1,4-dihydro-1,8-naphthyridine-3-carboxamide

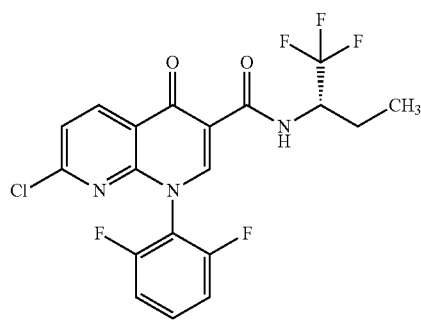 [SMILES: CC[C@H](NC(=O)c1cn(-c2c(F)cccc2F)c2nc(Cl)ccc2c1=O)C(F)(F)F]

According to GP1, 1.00 g (2.97 mmol) of the compound from Example 85A were reacted with 566 mg (4.46 mmol) of (2S)-1,1,1-trifluorobutan-2-amine in the presence of 1.13 g (2.97 mmol) of HATU and 1.24 ml (7.13 mmol) of N,N-diisopropylethylamine in 30 ml of dimethylformamide. The reaction mixture was diluted with 20 ml of water and 30 ml of ethyl acetate, and the phases were separated. The aqueous phase was extracted three times with 10 ml of ethyl acetate, and the combined organic phases were washed with 20 ml of a mixture of 1N aqueous hydrochloric acid and saturated aqueous ammonium chloride solution. This was followed by washing three times with 15 ml of saturated aqueous sodium chloride solution, drying over sodium sulphate and filtration, and removal of the solvent under reduced pressure. The residue was taken up in 10 ml of dichloromethane and purified by means of normal phase chromatography (cyclohexane-ethyl acetate gradient). 884 mg (66% of theory, 99% purity) of the title compound were obtained.

$^1$H NMR (400 MHz, DMSO-d$_6$) δ [ppm]=9.89 (d, 1H), 9.09 (s, 1H), 8.76 (d, 1H), 7.80-7.71 (m, 2H), 7.50-7.43 (m, 2H), 4.84-4.70 (m, 1H), 1.96-1.84 (m, 1H), 1.75-1.61 (m, 1H), 0.98 (t, 3H).

LC-MS (Method 1): R$_t$=1.20 min; MS (ESIpos) m/z 446 [M+H]$^+$.

Example 115A

7-Chloro-1-(2,4,6-trifluorophenyl)-4-oxo-N-[(2S)-1,1,1-trifluorobutan-2-yl)-1,4-dihydro-1,8-naphthyridine-3-carboxamide

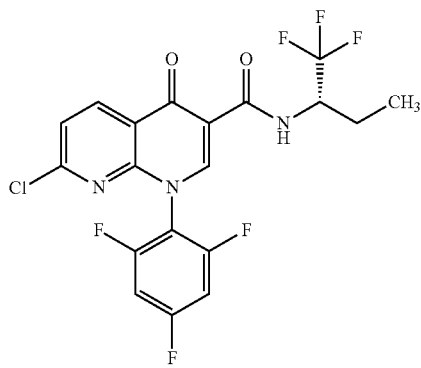 [SMILES: CC[C@H](NC(=O)c1cn(-c2c(F)cc(F)cc2F)c2nc(Cl)ccc2c1=O)C(F)(F)F]

According to GP1, 2.00 g (5.64 mmol) of the compound from Example 100B were reacted with 1.11 g (6.77 mmol) of (2S)-1,1,1-trifluorobutan-2-amine in the presence of 2.14 g (5.64 mmol) of HATU and 3.34 ml (19.2 mmol) of N,N-diisopropylethylamine in 57 ml of dimethylformamide. The reaction mixture was diluted with 75 ml of water and 100 ml of ethyl acetate, and the phases were separated. The aqueous phase was extracted three times with 50 ml of ethyl acetate, and the combined organic phases were washed with 60 ml of a mixture of 1N aqueous hydrochloric acid and saturated aqueous ammonium chloride solution. This was followed by washing three times with 20 ml of saturated aqueous sodium chloride solution, drying over magnesium sulphate and filtration, and removal of the solvent under reduced pressure. The residue was taken up in dichloromethane and purified by means of normal phase chromatography (cyclohexane-ethyl acetate gradient). 1.28 g (49% of theory, 100% purity) of the title compound were obtained.

$^1$H NMR (400 MHz, DMSO-d$_6$) δ [ppm]=9.88 (d, 1H), 9.13 (s, 1H), 8.75 (d, 1H), 7.78 (m, 1H), 7.66-7.58 (m, 2H), 4.84-4.71 (m, 1H), 1.96-1.84 (m, 1H), 1.74-1.62 (m, 1H), 0.98 (t, 3H).

LC-MS (Method 3): R$_t$=2.30 min; MS (ESIpos) m/z 464 [M+H]$^+$.

Example 116A (3S,5R)-3,5-Dimethylpyrrolidin-3-ol trifluoroacetic acid

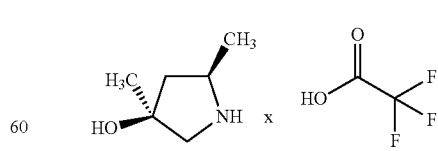

To a solution of 100 mg (464 µmol) of tert-butyl (2R, 4S)-4-hydroxy-2,4-dimethylpyrrolidine-1-carbamate in 1.5 ml of dichloromethane were added 500 µl (6.49 mmol) of trifluoroacetic acid, and the mixture was stirred at room temperature for 2 h. The solvent was removed under reduced pressure and the residue was coevaporated three times with 5 ml of dichloromethane. 98.6 mg (88% of theory, 95% purity) of the title compound were obtained.

$^1$H NMR (400 MHz, DMSO-$d_6$) δ [ppm]=9.10 (br. s, 1H), 8.68 (br. s, 1H), 5.22 (br. s, 1H), 3.76-3.63 (m, 1H), 3.10-3.03 (m, 1H), 3.00-2.91 (m, 1H), 2.12 (dd, 1H), 1.62 (ddd, 1H), 1.34 (d, 3H), 1.32 (s, 3H).

Example 117A

7-[(4S)-4-Hydroxy-2-oxopyrrolidin-1-yl]-4-oxo-1-(2,4,6-trifluorophenyl)-1,4-dihydro-1,8-naphthyridine-3-carboxylic acid

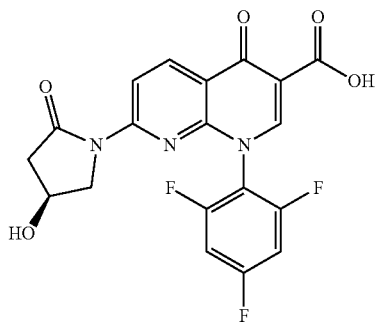 [SMILES: O=C(O)c1cn(-c2c(F)cc(F)cc2F)c2nc(N3C[C@@H](O)CC3=O)ccc2c1=O]

According to GP2, 50.0 g (141 mmol) of the compound from Example 100B were reacted with 17.1 g (169 mmol) of (4S)-4-hydroxypyrrolidin-2-one in the presence of 29.2 g (211 mmol) of potassium carbonate, 6.33 g (28.2 mmol) of palladium(II) acetate and 16.3 g (28.2 mmol) of Xantphos in 1000 ml of 1,4-dioxane at 80° C. for 1.5 h. The mixture was cooled down and extracted by stirring in a mixture of ice-water, hydrochloric acid and ethyl acetate. The mixture was filtered with suction through kieselguhr, and the organic phase was washed with water and saturated aqueous sodium chloride solution, dried and finally concentrated. The residue was admixed with acetonitrile, cooled and filtered off with suction, and the precipitate was washed with cold acetonitrile. 48 g (81% of theory, 97% purity) of the title compound were obtained.

LC-MS (Method 3): $R_t$=1.33 min; MS (ESIpos) m/z 420 [M+H]$^+$.

Example 118A

7-Chloro-1-(2,4,6-trifluorophenyl)-4-oxo-N-[(2S)-1-(trifluoromethoxy)propan-2-yl]-1,4-dihydro-1,8-naphthyridine-3-carboxamide

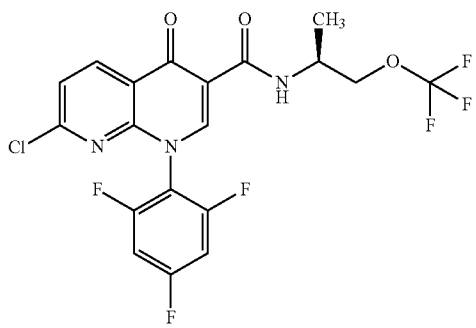 [SMILES: C[C@@H](COC(F)(F)F)NC(=O)c1cn(-c2c(F)cc(F)cc2F)c2nc(Cl)ccc2c1=O]

According to GP1, 250 mg (698 µmol) of the compound from Example 100B were reacted with 188 mg (1.05 mmol) of (2S)-1-(trifluoromethoxy)propan-2-amine hydrochloride in the presence of 265 mg (698 µmol) of HATU and 292 µl (1.68 mmol) of N,N-diisopropylethylamine in 7 ml of dimethylformamide. The reaction mixture was stirred into a mixture of 42 ml of water and 6 ml of 1N aqueous hydrochloric acid, and the precipitate was filtered off with suction. The precipitate was taken up in dichloromethane, the phases were separated, the organic phase was dried over magnesium sulphate and filtered and the solvent was removed under reduced pressure. The residue was purified by means of normal phase chromatography (cyclohexane-ethyl acetate gradient), and 226 mg (68% of theory; 100% purity) of the title compound were obtained.

$^1$H NMR (400 MHz, DMSO-$d_6$) δ [ppm]=9.63 (d, 1H), 9.06 (s, 1H), 8.74 (d, 1H), 7.76 (d, 1H), 7.65-7.57 (m, 2H), 4.43-4.32 (m, 1H), 4.24-4.15 (m, 2H), 1.26 (d, 3H).

LC-MS (Method 1): $R_t$=1.21 min; MS (ESIpos) m/z 480 [M+H]$^+$.

Example 119A

7-Chloro-1-(2-chloro-6-fluorophenyl)-4-oxo-N-[(2S)-1,1,1-trifluorobutan-2-yl]-1,4-dihydro-1,8-naphthyridine-3-carboxamide

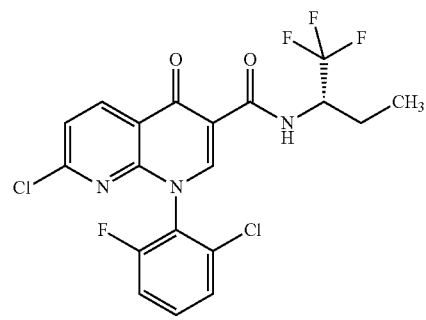 [SMILES: CC[C@H](NC(=O)c1cn(-c2c(F)cccc2Cl)c2nc(Cl)ccc2c1=O)C(F)(F)F]

According to GP1, 500 mg (1.42 mmol) of the compound from Example 105B were reacted with 347 mg (2.12 mmol) of (2S)-1,1,1-trifluorobutan-2-amine hydrochloride in the presence of 538 mg (1.42 mmol) of HATU and 592 µl (3.40 mmol) of N,N-diisopropylethylamine in 14.2 ml of dimethylformamide. The reaction mixture was stirred into a solution of 50 ml of water and 15 ml of 1N aqueous hydrochloric acid, and the precipitate was filtered off with suction, washed with water and dried. The precipitate was dissolved in 10 ml of dichloromethane and purified by means of normal phase chromatography (cyclohexane-ethyl acetate gradient). 496 mg (75% of theory, 99% purity) of the title compound were obtained.

$^1$H NMR (400 MHz, DMSO-$d_6$) δ [ppm]=9.90 (d, 1H), 9.07 (s, 1H), 8.77 (d, 1H), 7.81-7.56 (m, 4H), 4.84-4.70 (m, 1H), 1.96-1.83 (m, 1H), 1.76-1.62 (m, 1H), 1.02-0.94 (m, 3H).

LC-MS (Method 3): $R_t$=2.33 min; 462 [M+H]$^+$.

Example 120A

7-Chloro-1-(2-chloro-6-fluorophenyl)-N-[(1S)-1-cyclopropyl-2,2,2-trifluoroethyl]-4-oxo-1,4-dihydro-1,8-naphthyridine-3-carboxamide

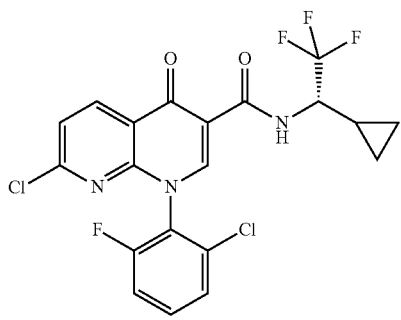 [SMILES: O=C(N[C@@H](C1CC1)C(F)(F)F)c1cn(-c2c(F)cccc2Cl)c2nc(Cl)ccc2c1=O]

According to GP1, 250 mg (708 μmol) of the compound from Example 105B were reacted with 186 mg (1.06 mmol) of (1S)-1-cyclopropyl-2,2,2-trifluoroethanamine hydrochloride in the presence of 269 mg (708 μmol) of HATU and 296 μl (1.70 mmol) of N,N-diisopropylethylamine in 7.1 ml of dimethylformamide. The reaction mixture was stirred into a solution of 25 ml of water and 8 ml of 1N aqueous hydrochloric acid, and the precipitate was filtered off with suction, washed with water and dried. The precipitate was dissolved in 8 ml of dichloromethane and purified by means of normal phase chromatography (cyclohexane-ethyl acetate gradient). 250 mg (74% of theory, 99% purity) of the title compound were obtained.

$^1$H NMR (400 MHz, DMSO-$d_6$) δ [ppm]=10.06 (d, 1H), 9.06 (s, 1H), 8.78 (d, 1H), 7.79 (d, 1H), 7.77-7.57 (m, 3H), 4.45-4.32 (m, 1H), 1.31-1.20 (m, 1H), 0.73-0.53 (m, 3H), 0.40-0.30 (m, 1H).

LC-MS (Method 3): $R_t$=2.35 min; 474 [M+H]$^+$.

Example 121A

7-[(3R,4R)-3,4-Dihydroxypyrrolidin-1-yl]-4-oxo-1-(2,4,6-trifluorophenyl)-1,4-dihydro-1,8-naphthyridine-3-carboxylic acid

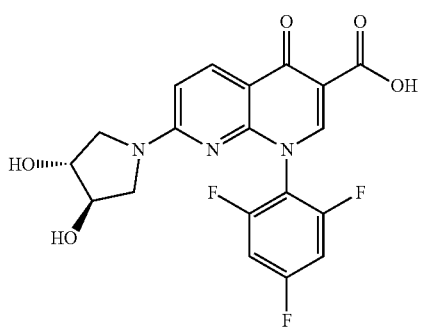 [SMILES: O=C(O)c1cn(-c2c(F)cc(F)cc2F)c2nc(N3C[C@@H](O)[C@H](O)C3)ccc2c1=O]

According to GP3, 10.0 g (28.2 mmol) of the compound from Example 100B were reacted with 4.46 g (31.0 mmol, 97% purity) of (3R,4R)-pyrrolidine-3,4-diol hydrochloride and 17.2 ml (98.7 mmol) of N,N-diisopropylethylamine in 150 ml of dimethylformamide. The mixture was diluted with 350 ml of water, 150 ml of 1N aqueous hydrochloric acid and 250 ml of ethyl acetate. The phases were separated and the aqueous phase was extracted three times with 250 ml of ethyl acetate. The combined organic phases were washed twice with 250 ml of phosphate buffer solution (3.52 g potassium dihydrogenphosphate, 7.26 g of disodium hydrogenphosphate dihydrate in 1000 ml of water, pH 7) and 250 ml of saturated aqueous sodium chloride solution, dried over magnesium sulphate, filtered and concentrated to a volume of about 100 ml. 250 ml of tert-butyl methyl ether were slowly added dropwise while stirring. The precipitate was filtered off with suction and dried under high vacuum. 10.8 g (91% of theory, 100% by LC/MS) of the title compound were obtained. By NMR, the product still contained traces of ethyl acetate, but was used without further purification.

$^1$H NMR (400 MHz, DMSO-$d_6$) δ [ppm]=15.23 (s, 1H), 9.02 (s, 1H), 8.30 (d, 1H), 7.62-7.54 (m, 2H), 6.87 (d, 1H), 5.26 (d, 1H), 5.17 (d, 1H), 4.06 (br. s, 1H, partly beneath a resonance of ethyl acetate), 3.94 (br. s, 1H), 3.64 (dd, 1H), 3.37 (d, 1H), 3.27 (dd, 1H), 3.08 (d, 1H).

LC-MS (Method 3): $R_t$=1.68 min; m/z=563 [M+H]$^+$.

Example 122A 1-(2-{[tert-Butyl(dimethyl) silyl]oxy}ethyl)imidazolidin-2-one

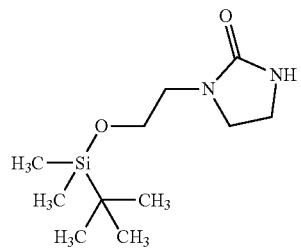 [SMILES: CC(C)(C)[Si](C)(C)OCCN1CCNC1=O]

To a solution of 1.00 g (7.68 mmol) of 1-(2-hydroxyethyl)imidazolidin-2-one (CAS: 3699-54-5) and 628 mg (9.22 mmol) of imidazole in 7.75 ml of dimethylformamide at 0° C. were added 1.27 g (8.45 mmol) of tert-butyldimethylsilyl chloride, and the mixture was stirred at room temperature overnight. All volatile constituents were removed under reduced pressure and 10 ml of water were added to the residue. The mixture was extracted three times with 20 ml of ethyl acetate. The combined organic phases were washed with saturated aqueous sodium chloride solution, dried over magnesium sulphate and filtered, and the solvent was removed under reduced pressure. 1.24 g (66% of theory, 100% purity) of the title compound were obtained.

$^1$H NMR (400 MHz, DMSO-$d_6$) δ [ppm]=6.24 (br. s, 1H), 3.64 (t, 2H), 3.41-3.36 (m, 2H), 3.22-3.17 (m, 2H), 3.11 (t, 2H), 0.86 (s, 9H), 0.04 (s, 6H).

LC-MS (Method 3): $R_t$=1.78 min; m/z=245 [M+H]$^+$.

Example 123A

7-[3-(2-Hydroxyethyl)-2-oxoimidazolidin-1-yl]-4-oxo-1-(2,4,6-trifluorophenyl)-1,4-dihydro-1,8-naphthyridine-3-carboxylic acid

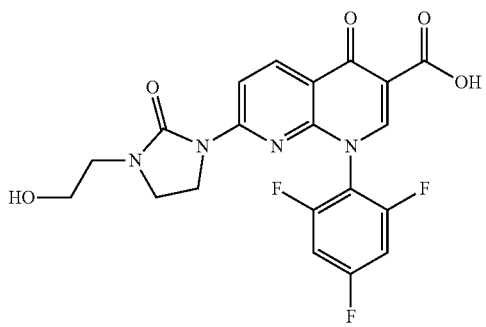 [SMILES: O=C(O)c1cn(-c2c(F)cc(F)cc2F)c2nc(N3CCN(CCO)C3=O)ccc2c1=O]

According to General Procedure 2, 250 mg (705 µmol) of the compound from Example 100B were reacted with 190 mg (775 µmol) of the compound from Example 122A in the presence of 244 mg (1.76 mmol) of potassium carbonate, 7.9 mg (35 µmol) of palladium(II) acetate and 41 mg (70 µmol) of Xantphos in 10 ml of dioxane at 90° C. for 90 min. The reaction mixture was poured into 15 ml of aqueous 1N hydrochloric acid and 15 ml of saturated aqueous sodium chloride solution and stirred. The mixture was extracted twice with 50 ml of ethyl acetate and the combined organic phases were concentrated. The residue was purified in three runs by means of preparative HPLC (column: Chromatorex C18, 10 µm, 125×30 mm, solvent: acetonitrile/0.1% formic acid gradient; 0 to 5 min 10% acetonitrile, over 14 min to 90% acetonitrile and for a further 4 min 90% acetonitrile). The collected fractions of the silylated intermediate were admixed again with 10 ml of aqueous 1N hydrochloric acid and stirred at 40° C. for 30 minutes. This was followed by concentration and separation of the residue in three runs by means of preparative HPLC (column: Chromatorex C18, 10 µm, 125×30 mm, solvent: acetonitrile/0.1% formic acid gradient; 0 to 5 min 10% acetonitrile, over 14 min to 90% acetonitrile and for a further 4 min 90% acetonitrile). The product fractions were combined and 269 mg (85% of theory, 100% purity) of the title compound were obtained.

$^1$H NMR (400 MHz, DMSO-d6): δ [ppm]=14.66 (br. s, 1H), 9.20 (s, 1H), 8.61 (d, 1H), 8.51 (d, 1H), 7.64-7.56 (m, 2H), 4.75 (br. s, 1H), 3.58-3.46 (m, 6H), 3.28 (t, 2H).

LC-MS (Method 3): $R_t$=1.18 min; MS (ESIpos): m/z=449 [M+H]$^+$.

Example 124A 1-(2-{[tert-Butyl(dimethyl)silyl]oxy}ethyl)tetrahydropyrimidin-2(1H)-one

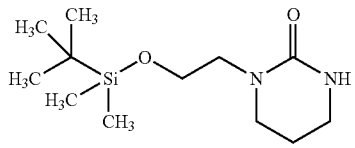

To a solution of 600 mg (4.16 mmol) of 1-(2-hydroxyethyl)tetrahydropyrimidin-2(1H)-one (DE1121617, 1962) and 690 mg (4.58 mmol) of tert-butyl(chloro)dimethylsilane in 4.2 ml of DMF were added, at 0° C., 340 mg (4.99 mmol) of imidazole. The mixture was stirred at 0° C. for 30 min and at RT overnight. Subsequently, all volatile constituents were removed under reduced pressure and the residue was admixed with 10 ml of water and extracted three times with 20 ml of ethyl acetate. The combined organic phases were washed with 30 ml of saturated aqueous sodium chloride solution, dried with magnesium sulphate and filtered, and the solvent was removed under reduced pressure. 732 mg (68% of theory, 100% purity) of the title compound were obtained.

$^1$H NMR (400 MHz, DMSO-d6): δ [ppm]=6.11 (s, 1H), 3.63 (t, 2H), 3.30-3.21 (m, 4H), 3.11-3.04 (m, 2H), 1.80-1.72 (m, 2H), 0.86 (s, 9H), 0.03 (s, 6H).

LC-MS (Method 3): $R_t$=1.83 min; MS (ESIpos): m/z=259 [M+H]$^+$.

Example 125A

7-[3-(2-Hydroxyethyl)-2-oxotetrahydropyrimidin-1(2H)-yl]-4-oxo-1-(2,4,6-trifluorophenyl)-1,4-dihydro-1,8-naphthyridine-3-carboxylic acid

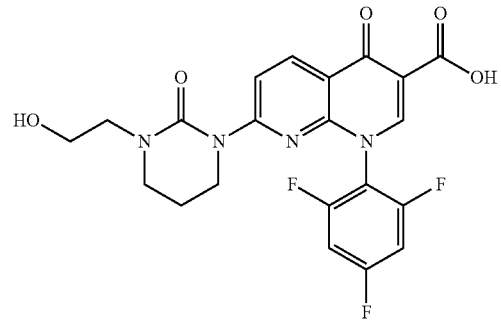 [SMILES: O=C(O)c1cn(-c2c(F)cc(F)cc2F)c2nc(N3CCCN(CCO)C3=O)ccc2c1=O]

According to General Procedure 2, 250 mg (705 µmol) of the compound from Example 100B were reacted with 166 mg (641 µmol) of the compound from Example 124A in the presence of 221 mg (1.60 mmol) of potassium carbonate, 7.2 mg (32 µmol) of palladium(II) acetate and 37 mg (64 µmol) of Xantphos in 6.4 ml of dioxane at 90° C. for 90 min. The reaction mixture was diluted with 15 ml of dioxane, poured into 15 ml of aqueous 1N hydrochloric acid and 15 ml of saturated aqueous sodium chloride solution and stirred at 40° C. The mixture was extracted three times with 30 ml of ethyl acetate and the combined organic phases were concentrated. The residue was purified in two runs by means of preparative HPLC (column: Chromatorex C18, 10 µm, 125×30 mm, solvent: acetonitrile/0.1% formic acid gradient; 0 to 5 min 10% acetonitrile, over 14 min to 90% acetonitrile and for a further 4 min 90% acetonitrile). 110 mg (26% of theory, 78% purity) of the title compound were obtained.

$^1$H NMR (400 MHz, DMSO-d6): δ [ppm]=14.61 (br. s, 1H), 9.22 (s, 1H), 8.55 (d, 1H), 8.24 (d, 1H), 7.65-7.57 (m, 2H), 4.71 (t, 1H), 3.58-3.48 (m, 4H), 3.42-3.36 (m, 4H), 1.95-1.86 (m, 2H).

LC-MS (Method 3): $R_t$=1.36 min; MS (ESIpos): m/z=463 [M+H]$^+$.

Example 126A

7-Chloro-N-[(1S)-1-cyclopropyl-2,2,2-trifluoro-ethyl]-4-oxo-1-(2,4,6-trifluorophenyl)-1,4-dihydro-1,8-naphthyridine-3-carboxamide

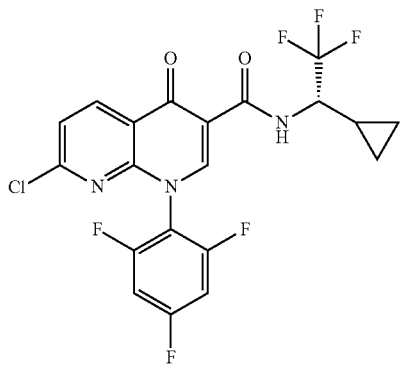 [SMILES: O=C(N[C@@H](C1CC1)C(F)(F)F)c1cn(-c2c(F)cc(F)cc2F)c2nc(Cl)ccc2c1=O]

According to GP1, 2.00 g (5.64 mmol) of the compound from Example 100B were reacted with 1.09 g (6.20 mmol) of (1S)-1-cyclopropyl-2,2,2-trifluoroethanamine hydrochloride in the presence of 2.14 g (5.64 mmol) of HATU and 2.36 ml (13.5 mmol) of N,N-diisopropylethylamine in 50 ml of dimethylformamide.

The mixture was stirred at room temperature for a further 5 min and then the reaction mixture was poured into 20 ml of water. 3 ml of 1N aqueous hydrochloric acid were added, and the precipitate was filtered off with suction and washed with water. The residue was taken up in 10 ml of dichloromethane and purified by means of normal phase chromatography (cyclohexane-ethyl acetate gradient). 1.82 g (68% of theory, 100% purity) of the title compound were obtained.

$^1$H NMR (400 MHz, DMSO-$d_6$) δ [ppm]=10.04 (d, 1H), 9.13 (s, 1H), 8.76 (d, 1H), 7.79 (d, 1H), 7.65-7.58 (m, 2H), 4.46-4.33 (m, 1H), 1.30-1.19 (m, 1H), 0.73-0.52 (m, 3H), 0.38-0.29 (m, 1H).

LC-MS (Method 3): $R_t$=2.31 min; MS (ESIpos) m/z 476 [M+H]$^+$.

Example 127A 7-(5-Benzyl-1,1-dioxido-1,2,5-thiadiazolidin-2-yl)-N-[(1S)-1-cyclopropyl-2,2,2-trifluoroethyl]-4-oxo-1-(2,4,6-trifluorophenyl)-1,4-dihydro-1,8-naphthyridine-3-carboxamide

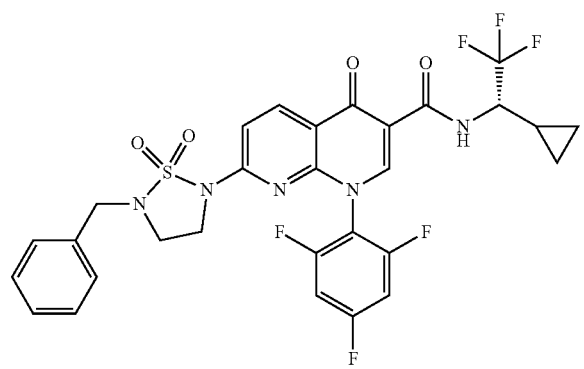 [SMILES: O=C(N[C@@H](C1CC1)C(F)(F)F)c1cn(-c2c(F)cc(F)cc2F)c2nc(N3CCN(Cc4ccccc4)S3(=O)=O)ccc2c1=O]

According to GP2, 100 mg (210 µmol) of the compound from Example 126A were reacted with 53.5 mg (252 µmol) of 2-benzyl-1,2,5-thiadiazolidine 1,1-dioxide in the presence of 43.6 mg (315 µmol) of potassium carbonate, 4.7 mg (21 µmol) of palladium(II) acetate and 24 mg (42 µmol) of Xantphos in 1.5 ml of 1,4-dioxane. Subsequently, the volume of the mixture was reduced under reduced pressure, and the residue was taken up with 1 ml of aqueous 1N hydrochloric acid and 1 ml of acetonitrile and separated by means of preparative HPLC (column: Chromatorex C18, 10 µm, 125×30 mm, solvent: acetonitrile/0.1% formic acid gradient; 0 to 5 min 10% acetonitrile, over 14 min to 90% acetonitrile and for a further 4 min 90% acetonitrile). The product fractions were combined and 104 mg (75% of theory, 98.5% purity) of the title compound were obtained.

LC-MS (Method 3): $R_t$=2.39 min; MS (ESIpos) m/z 652 [M+H]$^+$.

Example 128A

7-[(2-Aminoethyl)amino]-4-oxo-N-[(2S)-1,1,1-trifluorobutan-2-yl]-1-(2,4,6-trifluorophenyl)-1,4-dihydro-1,8-naphthyridine-3-carboxamide hydrochloride

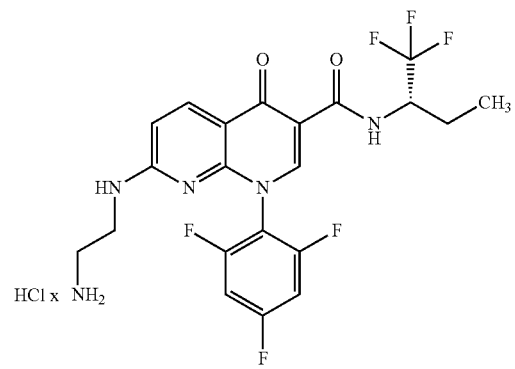 [SMILES: CC[C@H](NC(=O)c1cn(-c2c(F)cc(F)cc2F)c2nc(NCCN)ccc2c1=O)C(F)(F)F]

To a solution of 500 mg (1.08 mmol) of the compound from Example 115A in 11 ml of dimethylformamide were added 1.44 ml (21.6 mmol) of ethane-1,2-diamine. The mixture was stirred at room temperature for a further 45 min. The mixture was concentrated by rotary evaporation and taken up with 6 ml of aqueous hydrochloric acid and 4 ml of acetonitrile, and purified in two runs by means of preparative HPLC (column: Chromatorex C18, 10 µm, 125×30 mm, eluent: acetonitrile/0.1% formic acid gradient; 0 to 5 min 10% acetonitrile, over 14 min to 90% acetonitrile and for a further 4 min 90% acetonitrile). 426 mg (81% of theory, 100% purity) of the title compound were obtained. The yield is based on the free amine.

$^1$H NMR (400 MHz, DMSO-$d_6$) δ [ppm]=10.44 (d, 1H), 8.79 (s, 1H), 8.38 (br. s, 1H), 8.30 (s, 1H), 8.19 (d, 1H), 7.58-7.50 (m, 2H), 6.73 (d, 1H), 4.80-4.66 (m, 1H), 3.15-3.03 (m, 2H), 2.71-2.59 (m, 2H), 1.95-1.80 (m, 1H), 1.71-1.56 (m, 1H), 0.96 (t, 3H).

LC-MS (Method 1): $R_t$=0.67 min; MS (ESIpos) m/z 488 [M+H]$^+$.

Example 129A

Ethyl 7-({(2R)-2-[(tert-butoxycarbonyl)amino]propyl}amino)-4-oxo-1-(2,4,6-trifluorophenyl)-1,4-dihydro-1,8-naphthyridine-3-carboxylate

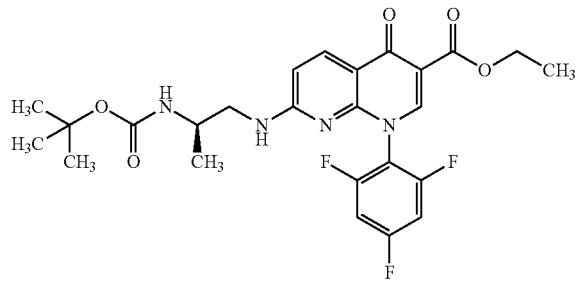 [SMILES: CCOC(=O)c1cn(-c2c(F)cc(F)cc2F)c2nc(NC[C@@H](C)NC(=O)OC(C)(C)C)ccc2c1=O]

To a solution of 1.50 g (3.92 mmol) of the compound from Example 100A in 25 ml of dimethylformamide were successively added 991 mg (4.70 mmol) of tert-butyl [(2R)-1-aminopropan-2-yl]carbamate hydrochloride and 2.39 ml (13.7 mmol) of N,N-diisopropylethylamine. The mixture was stirred at room temperature overnight and at 60° C. for 37 h. Subsequently, the reaction solution was poured into 250 ml of water and adjusted to pH 5 with aqueous 1N hydrochloric acid. The precipitate was filtered off with suction, washed with water and dried under high vacuum. 1.81 g (85% of theory, 95% purity) of the title compound were obtained.

LC-MS (Method 3): $R_t$=1.82 min; MS (ESIpos) m/z 521 [M+H]$^+$.

Example 129B

Ethyl 7-{[(2R)-2-aminopropyl]amino}-4-oxo-1-(2,4,6-trifluorophenyl)-1,4-dihydro-1,8-naphthyridine-3-carboxylate trifluoroacetate

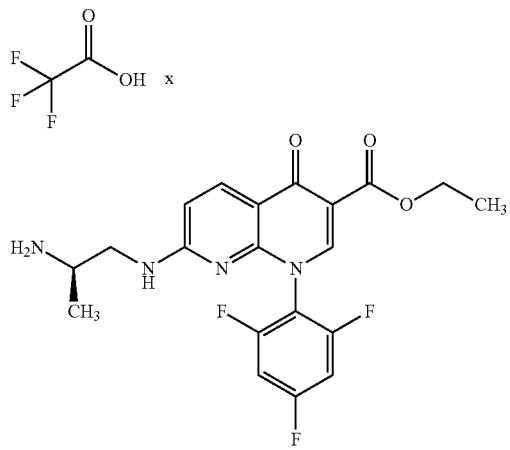

To a solution of 1.80 g (3.46 mmol) of the compound from Example 129A in 100 ml of dichloromethane were added 5.33 ml (69.2 mmol) of trifluoroacetic acid. The mixture was stirred at room temperature for a further 2.5 h. Subsequently, all volatile constituents were removed under reduced pressure and the residue was codistilled with toluene and lyophilized. 2.50 g (quantitative, 99% purity) of the title compound were obtained.

LC-MS (Method 3): $R_t$=0.92 min; MS (ESIpos) m/z 421 [M+H]$^+$.

Example 129C

Ethyl 7-[(4R)-4-methyl-2-oxoimidazolidin-1-yl]-4-oxo-1-(2,4,6-trifluorophenyl)-1,4-dihydro-1,8-naphthyridine-3-carboxylate

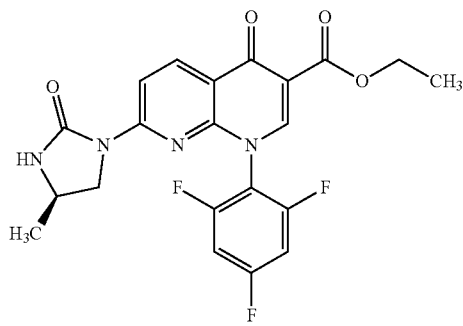 [SMILES: CCOC(=O)c1cn(-c2c(F)cc(F)cc2F)c2nc(N3C[C@@H](C)NC3=O)ccc2c1=O]

To a solution of 2.50 g (4.68 mmol) of the compound from Example 129B in 103 ml of dimethylformamide were successively added 647 mg (4.68 mmol) of potassium carbonate and 1.90 g (11.7 mmol) of 1,1'-carbonyldiimidazole. The mixture was stirred at room temperature for a further 6 h. The reaction solution was poured into 600 ml of water, and 5 ml of aqueous 1N hydrochloric acid were added. The precipitate was filtered off with suction, washed with water and dried under high vacuum. 1.20 g (59% of theory, 99% purity) of the title compound were obtained.

$^1$H NMR (400 MHz, DMSO-d$_6$) δ [ppm]=8.79 (s, 1H), 8.44 (d, 1H), 8.34 (d, 1H), 7.76 (s, 1H), 7.63-7.53 (m, 2H), 4.23 (q, 2H), 3.80-3.67 (m, 2H), 3.12-3.02 (m, 1H), 1.28 (t, 3H), 1.12 (d, 3H).

LC-MS (Method 1): $R_t$=0.86 min; MS (ESIpos) m/z 447 [M+H]$^+$.

Example 129D

7-[(4R)-4-Methyl-2-oxoimidazolidin-1-yl]-4-oxo-1-(2,4,6-trifluorophenyl)-1,4-dihydro-1,8-naphthyridine-3-carboxylic acid

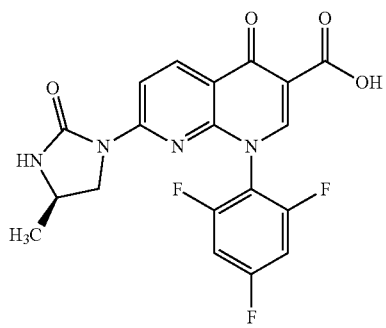 [SMILES: C[C@@H]1CN(c2ccc3c(=O)c(C(=O)O)cn(-c4c(F)cc(F)cc4F)c3n2)C(=O)N1]

To an initial charge of 1.19 g (2.67 mmol) of the compound from Example 129C in 8 ml of water were added 8 ml of 36 percent aqueous hydrochloric acid and 8 ml of THF, and the mixture was stirred at 110° C. for 3 h. The reaction mixture was cooled to RT and 100 ml of water were added. The precipitate was filtered off with suction, washed with water and dried under high vacuum. 994 mg (87% of theory, 97% purity) of the title compound were obtained.

LC-MS (Method 3): $R_t$=1.49 min; MS (ESIpos): m/z=419 [M+H]$^+$.

$^1$H NMR (400 MHz, DMSO-d6): δ [ppm]=14.65 (s, 1H), 9.19 (s, 1H), 8.60 (d, 1H), 8.50 (d, 1H), 7.91 (s, 1H), 7.65-7.55 (m, 2H), 3.81-3.70 (m, 2H), 3.13-3.07 (m, 1H), 1.13 (d, 3H).

Example 130A

Ethyl 7-chloro-1-(2,6-dichloro-4-fluorophenyl)-4-oxo-1,4-dihydro-1,8-naphthyridine-3-carboxylate

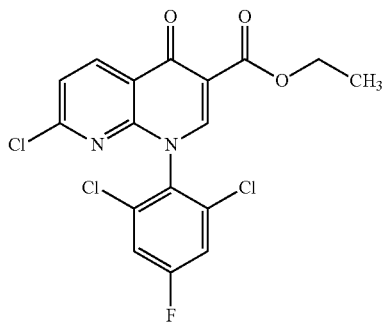 [SMILES: CCOC(=O)c1cn(-c2c(Cl)cc(F)cc2Cl)c2nc(Cl)ccc2c1=O]

To a solution of 6.07 g (19.1 mmol) of ethyl 2-[(2,6-dichloropyridin-3-yl)carbonyl]-3-ethoxyacrylate (CAS 157373-27-8) and 4.81 g (26.7 mmol) of 2,6-dichloro-4-fluoroaniline in 30 ml DCM were added 23.3 ml (134 mmol) of DIPEA, and the mixture was stirred at RT for 4 h. Subsequently, 2.64 g (19.1 mmol) of potassium carbonate were added and the mixture was heated under reflux overnight. The mixture was diluted with 200 ml of DCM and washed twice with 75 ml of 1 M aqueous hydrochloric acid.

The organic phase was dried over sodium sulphate and filtered, and the solvent was removed under reduced pressure. The suspension obtained was stirred with 40 ml of tert-butyl methyl ether, and the precipitate was filtered off with suction, washed with 10 ml of tert-butyl methyl ether and dried under high vacuum. 3.81 g (45% of theory, 94% purity) of the title compound were obtained.

LC-MS (Method 1): $R_t$=1.04 min; MS (ESIpos) m/z 415 [M+H]$^+$.

$^1$H NMR (400 MHz, DMSO-d6): δ [ppm]=8.88 (s, 1H), 8.65 (d, 1H), 7.92 (d, 2H), 7.69 (d, 1H), 4.25 (q, 2H), 1.28 (t, 3H).

Example 130B

7-Chloro-1-(2,6-dichloro-4-fluorophenyl)-4-oxo-1,4-dihydro-1,8-naphthyridine-3-carboxylic acid

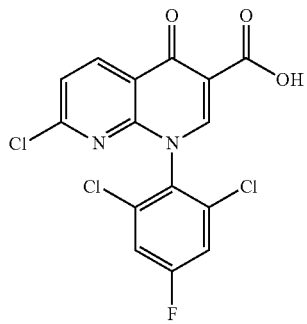 [SMILES: O=C(O)c1cn(-c2c(Cl)cc(F)cc2Cl)c2nc(Cl)ccc2c1=O]

To an initial charge of 3.81 g (8.62 mmol, 94% purity) of the compound from Example 130A in 38 ml of water were added 38 ml of 36 percent aqueous hydrochloric acid and 38 ml of THF, and the mixture was stirred at 110° C. for 4.5 h. The reaction mixture was cooled to RT and diluted with 200 ml of water. The precipitate was filtered off with suction, washed with water and dried under high vacuum. 3.36 g (quantitative, 100% purity) of the title compound were obtained.

LC-MS (Method §): $R_t$=1.96 min; MS (ESIpos): m/z=387 [M+H]$^+$.

Example 130C

7-Chloro-N-[(1R)-1-cyclopropyl-2,2,2-trifluoroethyl]-1-(2,6-dichloro-4-fluorophenyl)-4-oxo-1,4-dihydro-1,8-naphthyridine-3-carboxamide

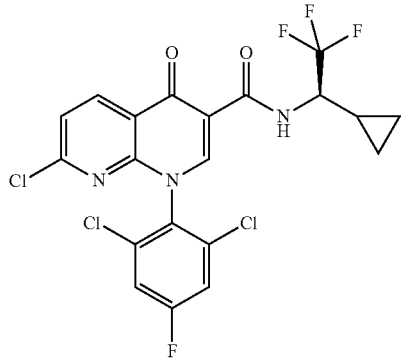 [SMILES: O=C(N[C@H](C1CC1)C(F)(F)F)c1cn(-c2c(Cl)cc(F)cc2Cl)c2nc(Cl)ccc2c1=O]

According to GP1, 460 mg (1.18 mmol) of the compound from Example 130B were reacted with 313 mg (1.76 mmol) of (1S)-1-cyclopropyl-2,2,2-trifluoroethanamine hydrochloride in the presence of 447 mg (1.18 mmol) of HATU and 491 μl (2.82 mmol) of N,N-diisopropylethylamine in 12 ml of dimethylformamide. The reaction was ended by adding 40 ml of water and 60 ml of ethyl acetate, and the phases were separated. The aqueous phase was extracted three times with 20 ml of ethyl acetate, and the combined organic phases were washed with 40 ml of a mixture (1:1, v/v) of saturated aqueous sodium chloride solution and aqueous 1N hydrochloric acid. The organic phase was washed three times with 30 ml of saturated aqueous sodium chloride solution, dried over sodium sulphate and filtered, and the solvent was removed under reduced pressure. The residue was purified by means of normal phase chromatography (cyclohexane-ethyl acetate gradient), and 369 mg (61% of theory; 99% purity) of the title compound were obtained.

$^1$H NMR (400 MHz, DMSO-$d_6$) δ [ppm]=10.6 (d, 1H), 9.09 (s, 1H), 8.79 (d, 1H), 7.92 (d, 2H), 7.80 (d, 1H), 4.44-4.31 (m, 1H), 1.30-1.20 (m, 1H), 0.73-0.52 (m, 3H), 0.39-0.30 (m, 1H).

LC-MS (Method 1): $R_t$=1.29 min; MS (ESIpos) m/z 464 [M+H]$^+$.

Example 131A

7-Chloro-1-(2,6-dichloro-4-fluorophenyl)-4-oxo-N-[(2R)-1,1,1-trifluorobutan-2-yl]-1,4-dihydro-1,8-naphthyridine-3-carboxamide

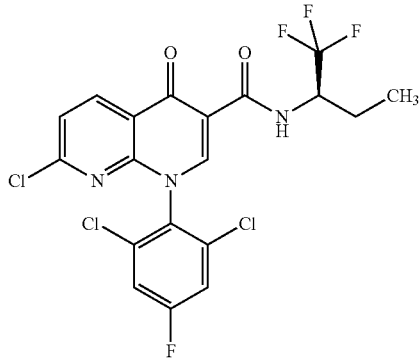 [SMILES: CC[C@@H](NC(=O)c1cn(-c2c(Cl)cc(F)cc2Cl)c2nc(Cl)ccc2c1=O)C(F)(F)F]

According to GP1, 1.00 g (2.58 mmol) of the compound from Example 130B were reacted with 633 mg (3.87 mmol) of (2R)-1,1,1-trifluorobutan-2-amine hydrochloride in the presence of 981 mg (2.58 mmol) of HATU and 1.08 ml (6.19 mmol) of N,N-diisopropylethylamine in 26 ml of dimethylformamide. The reaction was ended by adding 40 ml of water and 60 ml of ethyl acetate, and the phases were separated. The aqueous phase was extracted three times with 20 ml of ethyl acetate, and the combined organic phases were washed with 40 ml of a mixture (1:1, v/v) of saturated aqueous sodium chloride solution and aqueous 1N hydrochloric acid. The organic phase was washed three times with 30 ml of saturated aqueous sodium chloride solution, dried over sodium sulphate and filtered, and the solvent was removed under reduced pressure. The residue was purified by means of normal phase chromatography (cyclohexane-ethyl acetate gradient), and 1.07 g (83% of theory; 99% purity) of the title compound were obtained.

$^1$H NMR (400 MHz, DMSO-$d_6$) δ [ppm]=9.90 (d, 1H), 9.10 (s, 1H), 8.78 (d, 1H), 7.92 (d, 2H), 7.79 (d, 1H), 4.84-4.71 (m, 1H), 1.96-1.84 (m, 1H), 1.75-1.62 (m, 1H), 0.98 (t, 3H).

LC-MS (Method 1): $R_t$=1.28 min; MS (ESIpos) m/z 496 [M+H]$^+$.

Example 132A

7-Chloro-1-(2,6-dichloro-4-fluorophenyl)-4-oxo-N-[(2S)-1,1,1-trifluorobutan-2-yl]-1,4-dihydro-1,8-naphthyridine-3-carboxamide

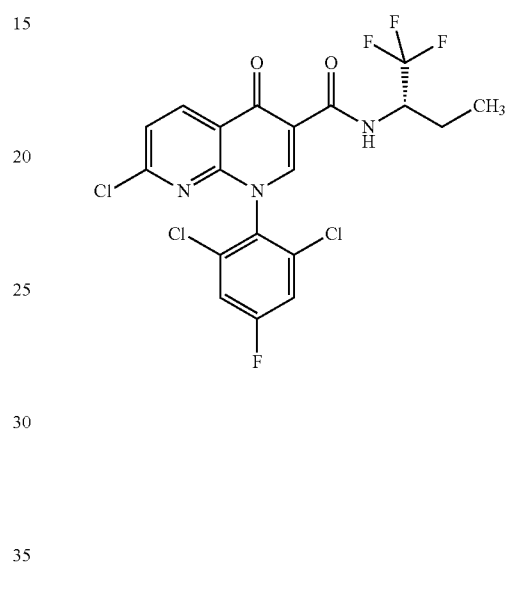

According to GP1, 900 mg (2.30 mmol) of the compound from Example 130B were reacted with 438 mg (3.45 mmol) of (2S)-1,1,1-trifluorobutan-2-amine in the presence of 874 mg (2.30 mmol) of HATU and 561 µl (3.22 mmol) of N,N-diisopropylethylamine in 23 ml of dimethylformamide. The reaction was ended by adding 40 ml of water and 60 ml of ethyl acetate, and the phases were separated. The aqueous phase was extracted three times with 20 ml of ethyl acetate, and the combined organic phases were washed with 40 ml of a mixture (1:1, v/v) of saturated aqueous sodium chloride solution and aqueous 1N hydrochloric acid. The organic phase was washed three times with 30 ml of saturated aqueous sodium chloride solution, dried over sodium sulphate and filtered, and the solvent was removed under reduced pressure. The residue was purified by means of normal phase chromatography (cyclohexane-ethyl acetate gradient), and 425 mg (37% of theory; 99% purity) of the title compound were obtained.

$^1$H NMR (400 MHz, DMSO-$d_6$) δ [ppm]=9.90 (d, 1H), 9.10 (s, 1H), 8.79 (d, 1H), 7.92 (d, 2H), 7.80 (d, 1H), 4.84-4.72 (m, 1H), 1.96-1.84 (m, 1H), 1.76-1.62 (m, 1H), 0.99 (t, 3H).

LC-MS (Method 1): $R_t$=1.28 min; MS (ESIpos) m/z 496 [M+H]$^+$.

Example 133A 1-(2-Chloro-4,6-difluorophenyl)-7-[(4S)-4-hydroxy-2-oxopyrrolidin-1-yl)]-4-oxo-1,4-dihydro-1,8-naphthyridine-3-carboxylic acid

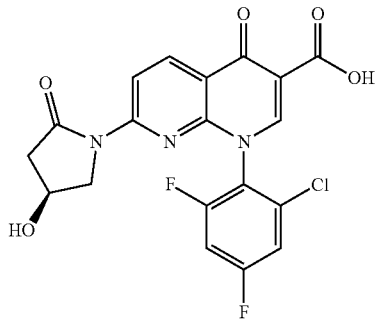 [SMILES: O=C(O)c1cn(-c2c(F)cc(F)cc2Cl)c2nc(N3C[C@@H](O)CC3=O)ccc2c1=O]

According to GP2, 1.40 g (3.77 mmol) of the compound from Example 108B were reacted with 458 mg (4.53 mmol) of (4S)-4-hydroxypyrrolidin-2-one in the presence of 782 mg (5.66 mmol) of potassium carbonate, 169 mg (754 μmol) of palladium(II) acetate and 437 mg (754 μmol) of Xantphos in 26.8 ml of 1,4-dioxane at 80° C. for 1.5 h. The mixture was cooled down and extracted by stirring in a mixture of ice-water, hydrochloric acid and ethyl acetate. The mixture was filtered with suction through kieselguhr, and the organic phase was washed with water and saturated aqueous sodium chloride solution, dried and finally concentrated. 152 mg of the residue were purified by means of preparative HPLC (column: Chromatorex C18, 10 μm, 125×30 mm, solvent: acetonitrile/0.1% formic acid gradient; 0 to 5 min. 10% acetonitrile, over 14 min. 90% acetonitrile and a further 4 min. 90% acetonitrile), and 84.2 mg (5% of theory, 99% purity) of the title compound were obtained. The majority of the residue was extracted with tert-butyl methyl ether in a Soxhlet apparatus for 22 h and concentrated by rotary evaporation. The residue was stirred with 3 ml of acetonitrile, and the precipitate was filtered off with suction, washed three times with 0.5 ml of acetonitrile and dried under high vacuum. 1.01 g (51% of theory, 83% purity) of the title compound were obtained.

LC-MS (Method 1): $R_t$=0.76 min; MS (ESIpos) m/z 436 [M+H]$^+$.

$^1$H NMR (400 MHz, DMSO-d$_6$) δ [ppm]=14.41 (s, 1H), 9.24 (s, 1H), 8.77 (d, 1H), 8.60 (d, 1H), 7.84-7.74 (m, 2H), 5.35 (d, 1H), 4.32-4.26 (m, 1H), 3.70-3.61 (m, 1H), 3.47-3.38 (m, 1H), 2.95 (dd, 1H), 2.38 (d, 1H).

Example 134A 1-(2-Chloro-4,6-difluorophenyl)-7-[(3R,4R)-3,4-dihydroxypyrrolidin-1-yl]-4-oxo-1,4-dihydro-1,8-naphthyridine-3-carboxylic acid

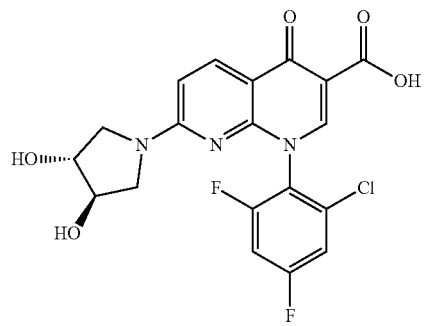 [SMILES: O=C(O)c1cn(-c2c(F)cc(F)cc2Cl)c2nc(N3C[C@@H](O)[C@H](O)C3)ccc2c1=O]

To a solution of 150 mg (404 μmol) of the compound from Example 108B in 4 ml of dimethylformamide were added, at room temperature, 69.8 mg (485 μmol) of (3R,4R)-pyrrolidine-3,4-diol hydrochloride and 246 μl (1.42 mmol) of N,N-diisopropylethylamine. On completion of conversion, the mixture was acidified to pH 1 with 1N aqueous hydrochloric acid, concentrated and purified by means of preparative HPLC (column: Chromatorex C18, 10 μm, 125×30 mm, eluent: acetonitrile/0.05% formic acid gradient; 0 to 3 min 10% acetonitrile to 15 min 90% acetonitrile and for a further 3 min 90% acetonitrile). 161 mg (90% of theory, 99% purity) of the title compound were obtained.

LC-MS (Method 3): $R_t$=1.21 min; MS (ESIpos) m/z 438 [M+H]$^+$.

$^1$H NMR (400 MHz, DMSO-d$_6$) δ [ppm]=15.23 (br. s, 1H), 8.98 (s, 1H), 8.31 (d, 1H), 7.78-7.67 (m, 2H), 6.86 (d, 1H), 5.28-5.23 (m, 1H), 5.20-5.15 (m, 1H), 4.05 (br. s, 1H), 3.93 (br. s, 1H), 3.64 (dd, 1H), 3.37 (d, 1H), 3.27-3.18 (m, 1H), 3.08-2.98 (m, 1H).

Example 135A

7-Chloro-N-[(1R)-1-cyclopropyl-2,2,2-trifluoroethyl]-4-oxo-1-(2,4,6-trifluorophenyl)-1,4-dihydro-1,8-naphthyridine-3-carboxamide

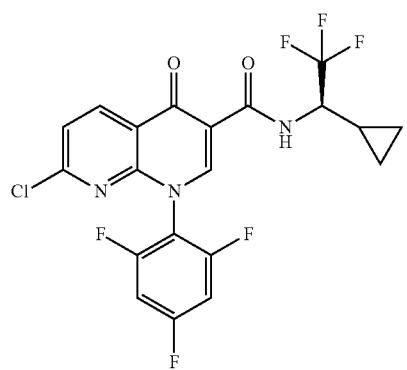 [SMILES: O=C(N[C@H](C1CC1)C(F)(F)F)c1cn(-c2c(F)cc(F)cc2F)c2nc(Cl)ccc2c1=O]

According to GP1, 500 mg (1.40 mmol) of the compound from Example 100B were reacted with 368 mg (2.09 mmol)

of (1R)-1-cyclopropyl-2,2,2-trifluoroethanamine hydrochloride in the presence of 531 mg (1.40 mmol) of HATU and 583 µl (3.35 mmol) of N,N-diisopropylethylamine in 14 ml of dimethylformamide. The reaction was ended by adding 20 ml of water and 30 ml of ethyl acetate, and the phases were separated. The aqueous phase was extracted three times with 20 ml of ethyl acetate, and the combined organic phases were washed with 20 ml of a mixture (1:1, v/v) of saturated aqueous sodium chloride solution and aqueous 1N hydrochloric acid. The organic phase was washed three times with 15 ml of saturated aqueous sodium chloride solution, dried over sodium sulphate and filtered, and the solvent was removed under reduced pressure. The residue was taken up in 10 ml of dichloromethane and purified by means of normal phase chromatography (cyclohexane-ethyl acetate gradient), and 510 mg (76% of theory; 99% purity) of the title compound were obtained.

$^1$H NMR (400 MHz, DMSO-$d_6$) δ [ppm]=10.04 (d, 1H), 9.13 (s, 1H), 8.76 (d, 1H), 7.79 (d, 1H), 7.66-7.58 (m, 2H), 4.43-4.35 (m, 1H), 1.29-1.19 (m, 1H), 0.71-0.52 (m, 3H), 0.37-0.31 (m, 1H).

LC-MS (Method 1): $R_t$=1.23 min; MS (ESIpos) m/z 476 [M+H]$^+$.

Example 136A

7-Chloro-1-(2-chloro-4,6-difluorophenyl)-4-oxo-N-[(2R)-1,1,1-trifluorobutan-2-yl]-1,4-dihydro-1,8-naphthyridine-3-carboxamide

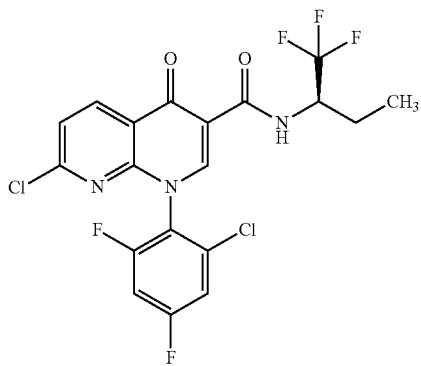 [SMILES: CC[C@@H](NC(=O)c1cn(-c2c(F)cc(F)cc2Cl)c2nc(Cl)ccc2c1=O)C(F)(F)F]

According to GP1, 1.00 g (2.69 mmol) of the compound from Example 108B were reacted with 661 mg (4.04 mmol) of (2R)-1,1,1-trifluorobutan-2-amine hydrochloride in the presence of 1.02 g (2.69 mmol) of HATU and 1.13 ml (6.47 mmol) of N,N-diisopropylethylamine in 27 ml of dimethylformamide. The reaction was ended by adding 40 ml of water and 60 ml of ethyl acetate, and the phases were separated. The aqueous phase was extracted three times with 20 ml of ethyl acetate, and the combined organic phases were washed with 40 ml of a mixture (1:1, v/v) of saturated aqueous sodium chloride solution and aqueous 1N hydrochloric acid. The organic phase was washed three times with 30 ml of saturated aqueous sodium chloride solution, dried over magnesium sulphate and filtered, and the solvent was removed under reduced pressure. The residue was taken up in dichloromethane and purified by means of normal phase chromatography (cyclohexane-ethyl acetate gradient), and 1.01 g (78% of theory; 100% purity) of the title compound were obtained.

$^1$H NMR (400 MHz, DMSO-$d_6$) δ [ppm]=9.92-9.85 (m, 1H), 9.13-9.08 (m, 1H), 8.80-8.74 (m, 1H), 7.83-7.72 (m, 3H), 4.83-4.72 (m, 1H), 1.95-1.85 (m, 1H), 1.75-1.63 (m, 1H), 1.02-0.94 (m, 3H).

LC-MS (Method 3): $R_t$=2.40 min; MS (ESIpos) m/z 480 [M+H]$^+$.

Example 137A

7-Chloro-4-oxo-N-[1-(trifluoromethoxy)butan-2-yl]-1-(2,4,6-trifluorophenyl)-1,4-dihydro-1,8-naphthyridine-3-carboxamide (racemate)

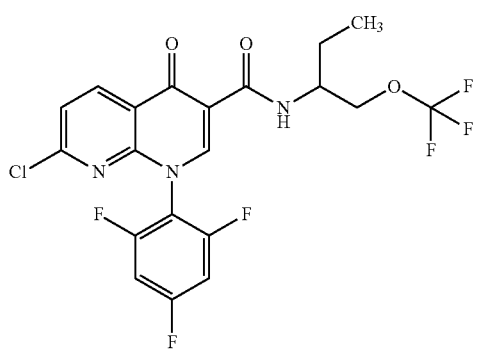 [SMILES: CCC(COC(F)(F)F)NC(=O)c1cn(-c2c(F)cc(F)cc2F)c2nc(Cl)ccc2c1=O]

According to GP1, 200 mg (564 µmol) of the compound from Example 100B were reacted with 120 mg (620 µmol) of 1-(trifluoromethoxy)butan-2-amine hydrochloride in the presence of 241 mg (564 µmol) of HATU and 236 µl (1.35 mmol) of N,N-diisopropylethylamine in 5.7 ml of dimethylformamide. The reaction was ended by adding 10 ml of water and 15 ml of ethyl acetate, and the phases were separated. The aqueous phase was extracted three times with 20 ml of ethyl acetate, and the combined organic phases were washed with 40 ml of a mixture (1:1, v/v) of saturated aqueous sodium chloride solution and aqueous 1N hydrochloric acid. The organic phase was washed three times with 30 ml of saturated aqueous sodium chloride solution, dried over magnesium sulphate and filtered, and the solvent was removed under reduced pressure. The residue was taken up in dichloromethane and purified by means of normal phase chromatography (cyclohexane-ethyl acetate gradient), and 188 mg (67% of theory; 99% purity) of the title compound were obtained.

$^1$H NMR (400 MHz, DMSO-$d_6$) δ [ppm]=9.60 (d, 1H), 9.06 (s, 1H), 8.75 (d, 1H), 7.76 (d, 1H), 7.66-7.57 (m, 2H), 4.28-4.14 (m, 3H), 1.76-1.53 (m, 2H), 0.95 (t, 3H).

LC-MS (Method 1): $R_t$=1.23 min; MS (ESIpos) m/z 494 [M+H]$^+$.

Example 138A

7-Chloro-1-(2-chloro-4,6-difluorophenyl)-N-[(1R)-1-cyclopropyl-2,2,2-trifluoroethyl]-4-oxo-1,4-dihydro-1,8-naphthyridine-3-carboxamide

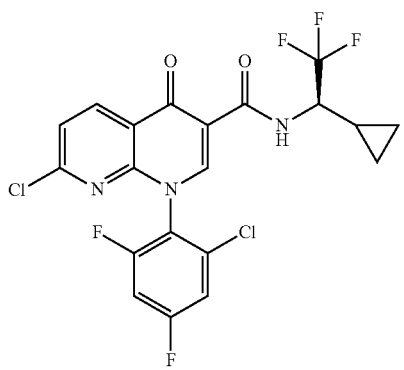 [SMILES: O=C(N[C@H](C1CC1)C(F)(F)F)c1cn(-c2c(F)cc(F)cc2Cl)c2nc(Cl)ccc2c1=O]

According to GP1, 640 mg (1.72 mmol) of the compound from Example 108B were reacted with 459 mg (2.59 mmol) of (1R)-1-cyclopropyl-2,2,2-trifluoroethanamine hydrochloride in the presence of 656 mg (1.72 mmol) of HATU and 721 μl (4.14 mmol) of N,N-diisopropylethylamine in 17.3 ml of dimethylformamide. The reaction was ended by adding 40 ml of water and 60 ml of ethyl acetate, and the phases were separated. The aqueous phase was extracted three times with 20 ml of ethyl acetate, and the combined organic phases were washed with 40 ml of a mixture (1:1, v/v) of saturated aqueous sodium chloride solution and aqueous 1N hydrochloric acid. The organic phase was washed three times with 30 ml of saturated aqueous sodium chloride solution, dried over magnesium sulphate and filtered, and the solvent was removed under reduced pressure. The residue was taken up in dichloromethane and purified by means of normal phase chromatography (cyclohexane-ethyl acetate gradient), and 635 mg (75% of theory; 100% purity) of the title compound were obtained.

$^1$H NMR (400 MHz, DMSO-$d_6$) δ [ppm]=10.04 (d, 1H), 9.11 (s, 1H), 8.77 (d, 1H), 7.82-7.71 (m, 3H), 4.46-4.32 (m, 1H), 1.29-1.19 (m, 1H), 0.73-0.52 (m, 3H), 0.39-0.29 (m, 1H).

LC-MS (Method 3): $R_t$=2.41 min; 492 [M+H]$^+$.

Example 139A (5R)-5-({[tert-Butyl(dimethyl)silyl]oxy}methyl)pyrrolidin-2-one

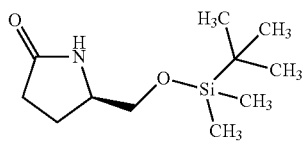

To a solution of 1.03 g (8.95 mmol) of (5R)-5-(hydroxymethyl)pyrrolidin-2-one and 914 mg (13.4 mmol) of imidazole in 20 ml of dimethylformamide were added, at 0° C., 1.39 g (8.95 mmol) of tert-butyldimethylsilyl chloride. The mixture was stirred at 0° C. for 30 min and at room temperature overnight. Subsequently, all volatile constituents were removed under reduced pressure and the residue was admixed with 100 ml of water and extracted three times with 30 ml of ethyl acetate. The combined organic phases were washed with 30 ml of saturated aqueous sodium chloride solution, dried over magnesium sulphate and filtered, and the solvent was removed under reduced pressure. 1.56 g (76% of theory, 100% purity) of the title compound were obtained.

$^1$H NMR (400 MHz, CDCl$_3$) δ [ppm]=5.70 (br. s, 1H), 3.79-3.72 (m, 1H), 3.63 (dd, 1H), 3.44 (dd, 1H), 2.38-2.31 (m, 2H), 2.23-2.12 (m, 1H), 1.78-1.67 (m, 1H), 0.89 (s, 9H), 0.06 (s, 6H).

LC-MS (Method 1): $R_t$=0.97 min; 230 [M+H]$^+$.

Example 140A

N-(Cyclopropylmethylene)-2-methylpropane-2-(R)-sulphinamide

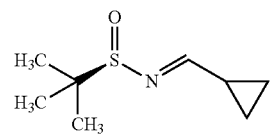

To a solution of 1.73 g (14.3 mmol) of (R)-2-methylpropane-2-sulphinamide and 2.00 g (28.5 mmol) of cyclopropanecarbaldehyde in 85.6 ml of dichloromethane were added 6.83 g (42.8 mmol) of copper(II) sulphate (dry). The mixture was stirred at room temperature for a further 18 h and then filtered through 3 cm of Celite and washed through with dichloromethane. The organic phase was washed twice with 10 ml of a 10% aqueous ammonium chloride solution, dried over sodium sulphate and filtered, and the solvent was removed under reduced pressure. 2.47 g (86% of theory, 86% purity) of the title compound were obtained.

LC-MS (Method 3): $R_t$=1.37 min; 174 [M+H]$^+$.

Example 140B

N-[(1S)-1-Cyclopropyl-2,2-difluoro-2-(phenylsulphonyl)ethyl]-2-methylpropane-2-(R)-sulphinamide

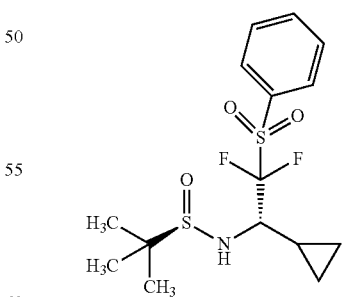

To a solution of 728 mg (4.20 mmol) of the compound from Example 140A and 769 mg (4.00 mmol) of difluoromethyl phenyl sulphone were added, at −78° C., 4.8 ml (4.8 mmol, 1 M in THF) of lithium hexamethyldisilazide, and the mixture was stirred for a further 20 min. The reaction was ended by adding 20 ml of saturated aqueous sodium chloride solution and the mixture was extracted three times with 50 ml of ethyl acetate. The combined organic phases were dried over sodium sulphate, filtered and concentrated by rotary evaporation. The residue was dissolved in 4 ml of dichloromethane and purified by means of normal phase chromatography (cyclohexane-ethyl acetate gradient). Recovered reactant from compound 140A was converted once again in an analogous manner and the product fractions were combined. 897 mg (58%) of the title compound were obtained.

$^1$H NMR (400 MHz, DMSO-$d_6$) δ [ppm]=7.98-7.88 (m, 3H), 7.79-7.73 (m, 2H), 5.80 (d, 1H), 3.43-3.33 (m, 1H), 1.33-1.22 (m, 1H), 0.77-0.48 (m, 4H).

LC-MS (Method 1): $R_t$=0.93 min; MS (ESIpos) m/z 366 [M+H]$^+$.

Example 140C

N-[(1S)-1-Cyclopropyl-2,2-difluoroethyl]-2-methylpropane-2-(R)-sulphinamide

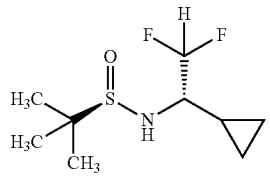

To a suspension of 650 mg (1.78 mmol) of the compound from Example 140B and 1.79 g (12.6 mmol) of sodium hydrogenphosphate in 23 ml of methanol were added, at −20° C., 4.02 g of sodium amalgam (5% sodium). The mixture was stirred for a further 4.5 h, the liquid was decanted off and all volatile constituents were removed under reduced pressure. 15 ml of saturated aqueous sodium chloride solution were added and the mixture was extracted three times with 15 ml of ethyl acetate. The combined organic phases were dried over sodium sulphate and filtered, and the solvent was removed under reduced pressure. 397 mg (98% of theory, 99% purity) of the title compound were obtained.

LC-MS (Method 1): $R_t$=0.79 min; MS (ESIpos) m/z 226 [M+H]$^+$.

Example 140D (1S)-1-Cyclopropyl-2,2-difluoroethanamine hydrochloride

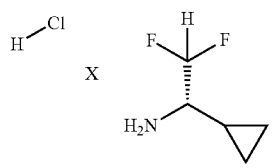

To a solution of 396 mg (1.76 mmol) of the compound from Example 140C in 24.8 ml of methanol were added 6.20 ml (24.8 mmol, 4N in dioxane) of hydrochloric acid, and the mixture was stirred for a further 30 min. Subsequently, the mixture was concentrated to dryness by rotary evaporation and stirred with 8 ml of diethyl ether, centrifuged and decanted, and the residue was dried under high vacuum. 209 mg (75% of theory, 99% purity) of the title compound were obtained.

$^1$H NMR (400 MHz, D$_2$O-$d_2$) δ [ppm]=6.28 (t, 1H), 3.03-2.93 (m, 1H), 1.13-1.04 (m, 1H), 0.84-0.76 (m, 2H), 0.62-0.46 (m, 2H).

Optical rotation: MeOH, conc. 0.4850 g/100 ml, λ: 365 nm [−15.12°]

Example 141A tert-Butyl [(2R)-1-{[6-{[(1S)-1-cyclopropyl-2,2,2-trifluoroethyl]carbamoyl}-5-oxo-8-(2,4,6-trifluorophenyl)-5,8-dihydro-1,8-naphthyridin-2-yl]amino}propan-2-yl]carbamate

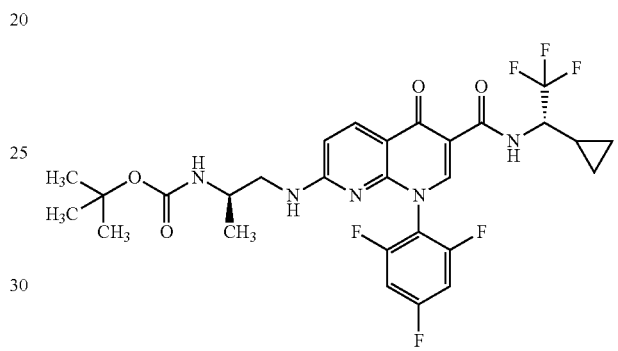

To a solution of 150 mg (315 μmol) of the compound from Example 126A in 3.1 ml of dimethylformamide were added, at room temperature, 93.0 mg (441 μmol) of tert-butyl [(2R)-1-aminopropan-2-yl]carbamate hydrochloride and 225 μl (1.29 mmol) of N,N-diisopropylethylamine. The mixture was stirred for a further 72 h. The reaction solution was diluted with 1 ml of acetonitrile and 0.5 ml of water and separated by means of preparative HPLC (column: Chromatorex C18, 10 μm, 125×30 mm, solvent: acetonitrile/0.1% formic acid gradient; 0 to 5 min 10% acetonitrile, over 14 min to 90% acetonitrile and for a further 4 min 90% acetonitrile). 161 mg (83% of theory, 99% purity) of the title compound were obtained.

LC-MS (Method 3): $R_t$=2.24 min; MS (ESIpos) m/z 614 [M+H]$^+$.

Example 141B

7-{[(2R)-2-Aminopropyl]amino}-N-[(1S)-1-cyclopropyl-2,2,2-trifluoroethyl)-4-oxo-1-(2,4,6-trifluorophenyl)-1,4-dihydro-1,8-naphthyridine-3-carboxamide trifluoroacetic acid

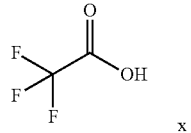

-continued

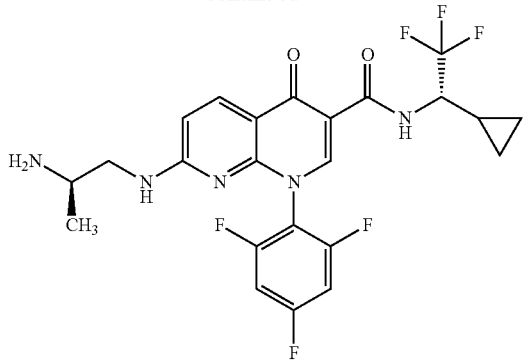

To a solution of 166 mg (271 µmol) of the compound from Example 141A in 10 ml of dichloromethane were added 5.00 ml (64.9 mmol) of trifluoroacetic acid while cooling with an ice bath. The mixture was stirred at room temperature for a further 2 h and then all volatile components were removed under reduced pressure. The residue was codistilled with toluene and dried under high vacuum. 170 mg (99% of theory, 99% purity) of the title compound were obtained.

LC-MS (Method 3): $R_t$=1.32 min; MS (ESIpos) m/z 514 [M+H]$^+$.

Example 142A

N-[(1S)-1-Cyclopropyl-2,2,2-trifluoroethyl]-7-{[(2S)-2-hydroxypropyl]amino}-4-oxo-1-(2,4,6-trifluorophenyl)-1,4-dihydro-1,8-naphthyridine-3-carboxamide

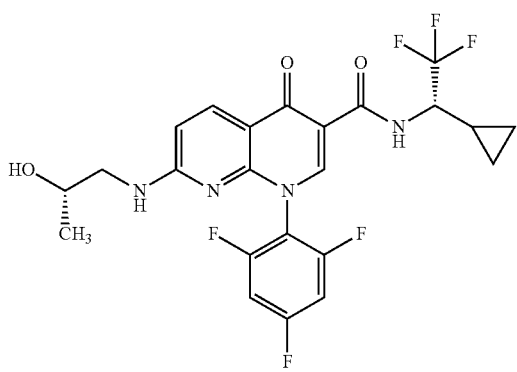 [SMILES: C[C@H](O)CNc1ccc2c(=O)c(C(=O)N[C@@H](C3CC3)C(F)(F)F)cn(-c3c(F)cc(F)cc3F)c2n1]

To a solution of 150 mg (315 µmol) of the compound from Example 126A in 3.1 ml of dimethylformamide were added, at room temperature, 33.2 mg (441 µmol) of (2S)-1-aminopropan-2-ol and 192 µl (1.10 mmol) of N,N-diisopropylethylamine. The mixture was stirred for a further 48 h. The reaction solution was diluted with 1 ml of acetonitrile, 0.5 ml of water and 0.1 ml of 1N aqueous hydrochloric acid and separated by means of preparative HPLC (column: Chromatorex C18, 10 µm, 125×30 mm, solvent: acetonitrile/0.1% formic acid gradient; 0 to 5 min 10% acetonitrile, over 14 min to 90% acetonitrile and for a further 4 min 90% acetonitrile). 136 mg (83% of theory, 99% purity) of the title compound were obtained.

$^1$H-NMR (400 MHz, DMSO-d$_6$) δ [ppm]=10.60 (d, 1H), 8.77 (s, 1H), 8.21-8.11 (m, 2H), 7.60-7.51 (m, 2H), 6.74 (d, 1H), 4.65 (d, 1H), 4.44-4.32 (m, 1H), 3.62-3.50 (m, 1H), 3.06-2.96 (m, 1H), 2.84-2.75 (m, 1H), 1.25-1.15 (m, 1H), 0.83 (d, 3H), 0.69-0.47 (m, 3H), 0.38-0.30 (m, 1H).

LC-MS (Method 3): $R_t$=1.88 min; MS (ESIpos) m/z 515 [M+H]$^+$.

Example 143A tert-Butyl [(2S)-1-{[6-{[(1S)-1-cyclopropyl-2,2,2-trifluoroethyl]carbamoyl}-5-oxo-8-(2,4,6-trifluorophenyl)-5,8-dihydro-1,8-naphthyridin-2-yl]amino]}propan-2-yl]carbamate

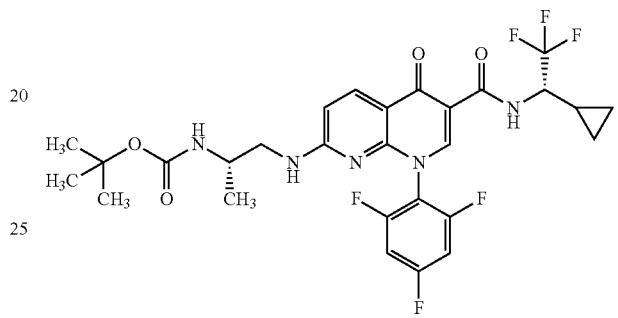

To a solution of 150 mg (315 µmol) of the compound from Example 126A in 3.1 ml of dimethylformamide were added, at room temperature, 93.0 mg (441 µmol) of tert-butyl [(2S)-1-aminopropan-2-yl]carbamate hydrochloride and 225 µl (1.29 mmol) of N,N-diisopropylethylamine. The mixture was stirred for a further 72 h. The reaction solution was diluted with 0.2 ml of acetonitrile and 0.5 ml of water and separated by means of preparative HPLC (column: Chromatorex C18, 10 µm, 125×30 mm, solvent: acetonitrile/0.1% formic acid gradient; 0 to 5 min 10% acetonitrile, over 14 min to 90% acetonitrile and for a further 4 min 90% acetonitrile). 174 mg (89% of theory, 99% purity) of the title compound were obtained.

LC-MS (Method 3): $R_t$=2.22 min; MS (ESIpos) m/z 614 [M+H]$^+$.

Example 143B

7-{[(2S)-2-Aminopropyl]amino}-N-[(1S)-1-cyclopropyl-2,2,2-trifluoroethyl)-4-oxo-1-(2,4,6-trifluorophenyl)-1,4-dihydro-1,8-naphthyridine-3-carboxamide trifluoroacetic acid

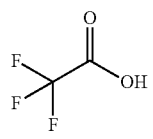

-continued

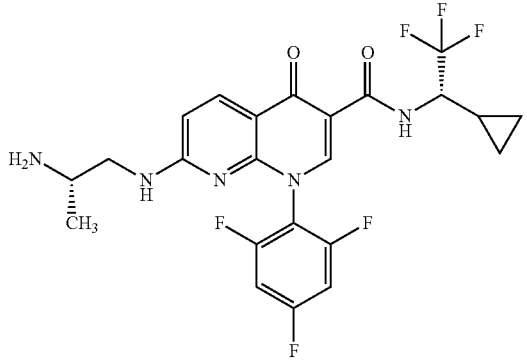

To a solution of 174 mg (283 µmol) of the compound from Example 143A in 10 ml of dichloromethane were added 436 µl (5.66 mmol) of trifluoroacetic acid while cooling with an ice bath. The mixture was stirred at room temperature for 3 h and then a further 10 equivalents of trifluoroacetic acid were added and the mixture was stirred at room temperature for a further hour. All volatile components were removed under reduced pressure, and the residue was codistilled twice with 20 ml of toluene and dried under high vacuum. 185 mg (quantitative, 100% purity) of the title compound were obtained.

LC-MS (Method 3): $R_t$=1.29 min; MS (ESIpos) m/z 514 $[M+H]^+$.

Example 144A tert-Butyl [1-({[6-{[(1S)-1-cyclopropyl-2,2,2-trifluoroethyl]carbamoyl}-5-oxo-8-(2,4,6-trifluorophenyl)-5,8-dihydro-1,8-naphthyridin-2-yl]amino}methyl)cyclopropyl]carbamate

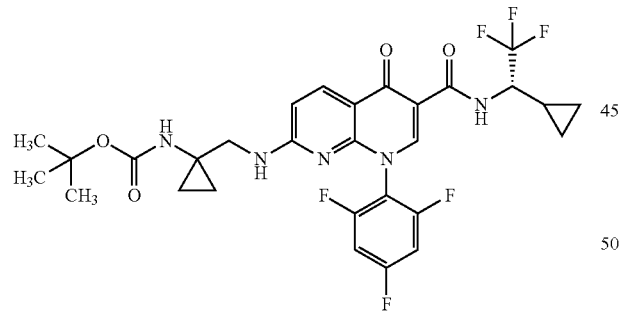

To a solution of 150 mg (315 µmol) of the compound from Example 126A in 3.1 ml of dimethylformamide were added, at room temperature, 98.3 mg (441 µmol) of tert-butyl [1-(aminomethyl)cyclopropyl]carbamate hydrochloride and 225 µl (1.29 mmol) of N,N-diisopropylethylamine. The mixture was stirred for a further 48 h. The reaction solution was diluted with 0.2 ml of acetonitrile and 0.5 ml of water and separated by means of preparative HPLC (column: Chromatorex C18, 10 µm, 125×30 mm, solvent: acetonitrile/ 0.05% formic acid gradient; 0 to 3 min 10% acetonitrile, to 35 min 90% acetonitrile and for a further 3 min 90% acetonitrile). 171 mg (86% of theory, 99% purity) of the title compound were obtained.

LC-MS (Method 3): $R_t$=2.30 min; MS (ESIpos) m/z 626 $[M+H]^+$.

Example 144B

7-{[(1-Aminocyclopropyl)methyl]amino}-N-[(1S)-1-cyclopropyl-2,2,2-trifluoroethyl]-4-oxo-1-(2,4,6-trifluorophenyl)-1,4-dihydro-1,8-naphthyridine-3-carboxamide bis(trifluoroacetate)

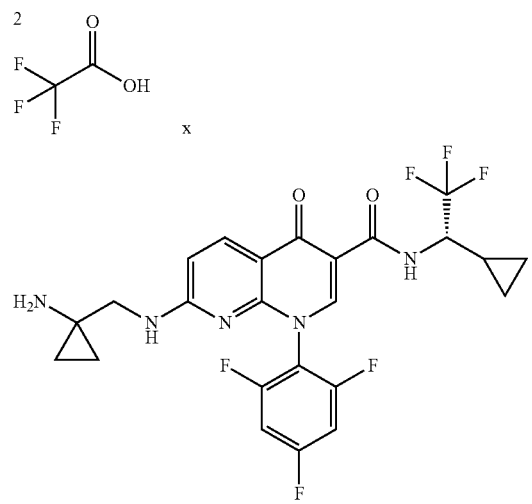

To a solution of 170 mg (272 µmol) of the compound from Example 144A in 7.9 ml of dichloromethane were added 419 µl (5.44 mmol) of trifluoroacetic acid while cooling with an ice bath. The mixture was stirred at room temperature for a further 2.5 h. All volatile components were removed under reduced pressure, and the residue was codistilled with toluene and finally lyophilized. 185 mg (89% of theory, 99% purity) of the title compound were obtained.

LC-MS (Method 3): $R_t$=1.31 min; MS (ESIpos) m/z 526 $[M+H]^+$.

Example 145A tert-Butyl (1-{[6-{[(1S)-1-cyclopropyl-2,2,2-trifluoroethyl]carbamoyl}-5-oxo-8-(2,4,6-trifluorophenyl)-5,8-dihydro-1,8-naphthyridin-2-yl]amino}-2-methylpropan-2-yl)carbamate

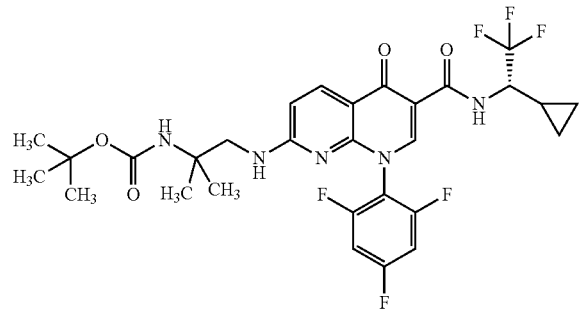 [SMILES: CC(C)(CNc1ccc2c(=O)c(C(=O)N[C@@H](C3CC3)C(F)(F)F)cn(-c3c(F)cc(F)cc3F)c2n1)NC(=O)OC(C)(C)C]

To a solution of 150 mg (315 µmol) of the compound from Example 126A in 3.1 ml of dimethylformamide were added, at room temperature, 99.2 mg (441 μmol) of tert-butyl (1-amino-2-methylpropan-2-yl)carbamate hydrochloride and 225 μl (1.29 mmol) of N,N-diisopropylethylamine. The mixture was stirred for a further 48 h. The reaction solution was diluted with 0.2 ml of acetonitrile and 0.5 ml of water and separated by means of preparative HPLC (column: Chromatorex C18, 10 μm, 125×30 mm, solvent: acetonitrile/ 0.1% formic acid gradient; 0 to 5 min 10% acetonitrile, over 14 min to 90% acetonitrile and for a further 4 min 90% acetonitrile). 174 mg (87% of theory, 99% purity) of the title compound were obtained.

LC-MS (Method 3): $R_t$=2.40 min; MS (ESIpos) m/z 628 [M+H]$^+$.

Example 145B

7-[(2-Amino-2-methylpropyl)amino]-N-[(1S)-1-cyclopropyl-2,2,2-trifluoroethyl]-4-oxo-1-(2,4,6-trifluorophenyl)-1,4-dihydro-1,8-naphthyridine-3-carboxamide bis(trifluoroacetate)

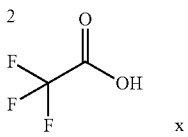

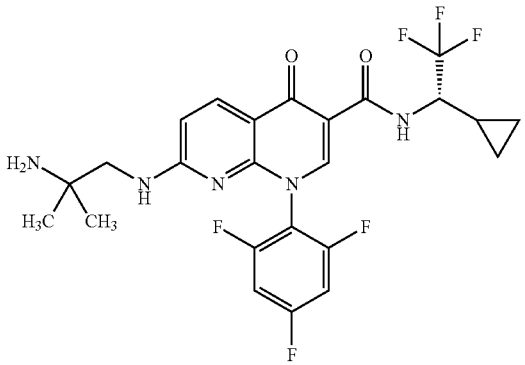

To a solution of 172 mg (274 μmol) of the compound from Example 145A in 7.9 ml of dichloromethane were added 422 μl (5.48 mmol) of trifluoroacetic acid while cooling with an ice bath. The mixture was stirred at room temperature for a further 2.5 h. All volatile components were removed under reduced pressure, and the residue was codistilled with toluene and finally lyophilized. 185 mg (91% of theory, 99% purity) of the title compound were obtained.

LC-MS (Method 3): $R_t$=1.33 min; MS (ESIpos) m/z 528 [M+H]$^+$.

Example 146A

Ethyl 7-({(2R)-2-[(tert-butoxycarbonyl)amino] propyl}amino)-4-oxo-1-(2,4,6-trifluorophenyl)-1,4-dihydro-1,8-naphthyridine-3-carboxylate

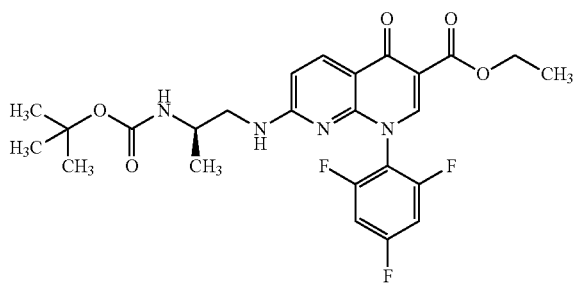 [SMILES: CCOC(=O)c1cn(-c2c(F)cc(F)cc2F)c2nc(NC[C@@H](C)NC(=O)OC(C)(C)C)ccc2c1=O]

To a solution of 1.50 g (3.92 mmol) of the compound from Example 100A in 25 ml of dimethylformamide were added, at room temperature, 991 mg (4.70 mmol) of tert-butyl [(2R)-1-aminopropan-2-yl]carbamate hydrochloride and 2.39 ml (13.7 mmol) of N,N-diisopropylethylamine. The mixture was stirred at room temperature for 12 h and at 60° C. for 37 h. The reaction solution was added to 250 ml of water and adjusted to pH 5 with 1N aqueous hydrochloric acid. The precipitate was filtered off with suction, washed with water and dried under high vacuum. 1.81 g (85% of theory, 95% purity) of the title compound were obtained.

LC-MS (Method 3): $R_t$=1.82 min; MS (ESIpos) m/z 521 [M+H]$^+$.

Example 146B

Ethyl 7-{[(2R)-2-aminopropyl]amino}-4-oxo-1-(2,4,6-trifluorophenyl)-1,4-dihydro-1,8-naphthyridine-3-carboxylate trifluoroacetate

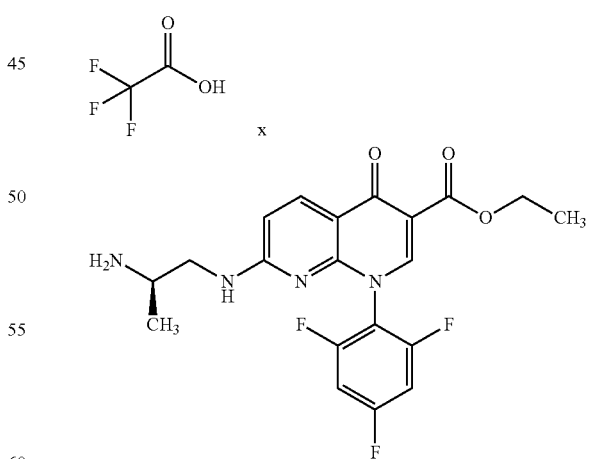

To a solution of 1.80 g (3.46 mmol) of the compound from Example 146A in 100 ml of dichloromethane were added 5.33 ml (69.2 mmol) of trifluoroacetic acid while cooling with an ice bath. The mixture was stirred at room temperature for a further 2.5 h. All volatile components were removed under reduced pressure, and the residue was codistilled with toluene and finally lyophilized. 2.50 g (quantitative, 99% purity) of the title compound were obtained.

LC-MS (Method 3): $R_t$=0.92 min; MS (ESIpos) m/z 421 [M+H]$^+$.

Example 146C

Ethyl 7-[(4R)-4-methyl-2-oxoimidazolidin-1-yl]-4-oxo-1-(2,4,6-trifluorophenyl)-1,4-dihydro-1,8-naphthyridine-3-carboxylate

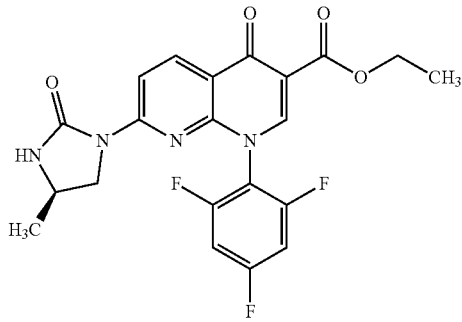

To a solution of 2.50 g (4.68 mmol) of the compound from Example 146B in 103 ml of dimethylformamide were added, at room temperature, 647 mg (4.68 mmol) of potassium carbonate and 1.89 g (11.7 mmol) of 1,1'-carbonyldiimidazole. The mixture was stirred for a further 6 h. Subsequently, the reaction solution was added to 600 ml of water, 5 ml of 1N aqueous hydrochloric acid were added, and the precipitate was filtered off with suction, washed with water and dried under high vacuum. 1.20 g (57% of theory, 99% purity) of the title compound were obtained.

LC-MS (Method 1): $R_t$=0.86 min; MS (ESIpos) m/z 447 [M+H]$^+$.

Example 146D

7-[(4R)-4-Methyl-2-oxoimidazolidin-1-yl]-4-oxo-1-(2,4,6-trifluorophenyl)-1,4-dihydro-1,8-naphthyridine-3-carboxylic acid

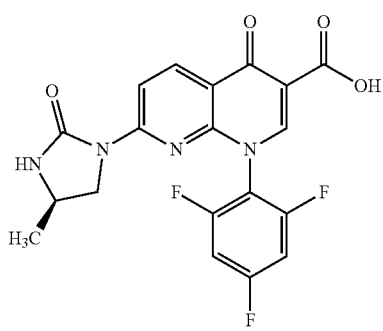

To an initial charge of 1.19 g (2.67 mmol) of the compound from Example 146C in 8 ml of water were added 8 ml of 36 percent aqueous hydrochloric acid and 8 ml of THF, and the mixture was stirred at 110° C. for 4 h. The reaction mixture was cooled to RT and diluted with 100 ml of water. The precipitate was filtered off with suction, washed with water and dried under high vacuum. 995 mg (87% of theory, 97% purity) of the title compound were obtained.

LC-MS (Method 3): $R_t$=1.49 min; MS (ESIpos): m/z=419 [M+H]$^+$.

$^1$H NMR (400 MHz, DMSO-d6): δ [ppm]=14.65 (s, 1H), 9.19 (s, 1H), 8.60 (d, 1H), 8.50 (d, 1H), 7.91 (s, 1H), 7.65-7.55 (m, 2H), 3.81-3.70 (m, 2H), 3.14-3.06 (m, 1H), 1.13 (d, 3H).

Example 147A

N-Benzyl-1,1,1,2,2-pentafluorobutan-3-amine (racemate)

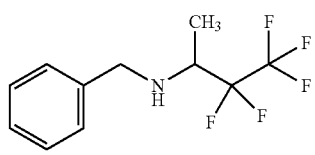 [SMILES: CC(NCc1ccccc1)C(F)(F)C(F)(F)F]

To a solution of 2.00 g (12.2 mmol) of 3,3,4,4,4-pentafluorobutan-2-one in 10 ml of dichloromethane were added, at 0° C., 5.40 ml (18.3 mmol) of titanium tetraisopropoxide and 2.66 ml (24.4 mmol) of benzylamine. The mixture was stirred at RT for a further 90 min before being cooled down again to 0° C. Subsequently, 2.14 g (34.1 mmol) of sodium cyanoborohydride, 36 ml of methanol and 3 Å molecular sieve were added. The mixture was warmed to RT and stirred for a further 2 d. The reaction solution was admixed with a little water and ethyl acetate and filtered. The filtrate was washed twice with saturated aqueous sodium hydrogencarbonate solution and once with saturated aqueous sodium chloride solution. The organic phase was dried over sodium sulphate and filtered, and the solvent was removed under reduced pressure. The residue was purified twice by means of normal phase chromatography (ethyl acetate/cyclohexane 1/20), and 1.65 g (48% of theory; 91% purity) of the title compound were obtained.

LC-MS (Method 6): $R_t$=2.17 min; MS (ESIpos): m/z=254 [M+H]$^+$.

$^1$H NMR (500 MHz, DMSO-d6): δ [ppm]=7.28-7.36 (m, 4H), 7.20-7.27 (m, 1H), 3.83 (dd, 1H), 3.72 (dd, 1H), 3.22-3.30 (m, 1H), 2.43-2.48 (m, 1H), 1.20 (d, 3H).

Example 147B 1,1,1,2,2-Pentafluorobutan-3-amine hydrochloride (racemate)

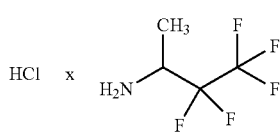

To a solution of 1.50 g (5.92 mmol) of N-benzyl-1,1,1,2,2-pentafluoropentan-3-amine in 27.4 ml of methanol were added 150 mg of palladium on charcoal (10%), and hydrogenation was effected at standard pressure and room temperature for 6 h. The reaction mixture was then filtered through a Millipore filter and the solvent was removed under reduced pressure. The receiver containing the solvent distilled off was then transferred to a flask and admixed with 4 N aqueous hydrochloric acid in dioxane and concentrated again. The residue was stirred with diethyl ether and the precipitate was filtered off with suction and dried under high vacuum. 456 mg (39% of theory, 100% purity) of the title compound were obtained.

$^1$H NMR (500 MHz, DMSO-d6): δ [ppm]=9.21 (br. s, 3H), 4.40-4.29 (m, 1H), 1.41 (d, 3H).

Example 148A 3-({[tert-Butyl(dimethyl)silyl]oxy}methyl)pyrrolidin-2-one (racemate)

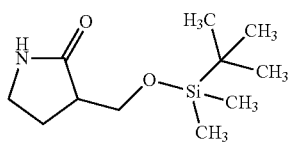

To a solution of 110 mg (955 μmol) of 3-(hydroxymethyl)pyrrolidin-2-one and 97.6 mg (1.43 mmol) of imidazole in 5 ml of dimethylformamide were added, at 0° C., 148 mg (955 μmol) of tert-butyldimethylsilyl chloride. The mixture was stirred at 0° C. for 30 min and at room temperature overnight. Subsequently, all volatile constituents were removed under reduced pressure and the residue was admixed with 10 ml of water and extracted three times with 20 ml of ethyl acetate. The combined organic phases were washed with 30 ml of saturated aqueous sodium chloride solution, dried over magnesium sulphate and filtered, and the solvent was removed under reduced pressure. 115 mg (52% of theory, 100% purity) of the title compound were obtained.

$^1$H NMR (400 MHz, CDCl$_3$) δ [ppm]=5.44 (br. s, 1H), 3.84 (dd, 1H), 3.75 (dd, 1H), 3.35-3.22 (m, 2H), 2.48-2.40 (m, 1H), 2.26-2.06 (m, 2H), 0.82 (s, 9H), 0.00 (d, 6H).

LC-MS (Method 3): R$_t$=1.81 min; MS (ESIpos) m/z 230 [M+H]$^+$.

Example 149A

7-[(3R)-3-Hydroxy-2-oxopyrrolidin-1-yl]-4-oxo-1-(2,4,6-trifluorophenyl)-1,4-dihydro-1,8-naphthyridine-3-carboxylic acid

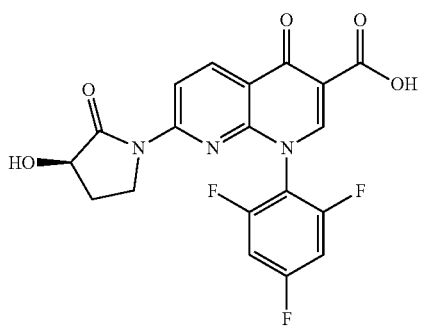 [SMILES: O=C(O)c1cn(-c2c(F)cc(F)cc2F)c2nc(N3CC[C@@H](O)C3=O)ccc2c1=O]

According to GP2, 270 mg (761 μmol) of the compound from Example 100B were reacted with 92.4 mg (914 μmol) of (3R)-3-hydroxypyrrolidin-2-one in the presence of 158 mg (1.14 mmol) of potassium carbonate, 17 mg (76 μmol) of palladium(II) acetate and 88.1 mg (152 μmol) of Xantphos in 6 ml of 1,4-dioxane at 80° C. for 12 h. Catalyst was added to the mixture once again, and the mixture was stirred at 80° C. for a further 5 h. Subsequently, the reaction mixture was extracted by stirring in a mixture of ice-water, hydrochloric acid and ethyl acetate. The mixture was filtered with suction through kieselguhr, and the organic phase was washed with water and saturated aqueous sodium chloride solution, dried over sodium sulphate, filtered and concentrated. The residue was dissolved in 6.5 ml of acetonitrile and 0.5 ml of water and purified by means of preparative HPLC (column: Chromatorex C18, 10 μm, 125×30 mm, solvent: acetonitrile/0.1% formic acid gradient; 0 to 5 min 10% acetonitrile, over 14 min to 90% acetonitrile and for a further 4 min 90% acetonitrile). 159 mg (49% of theory, 99% purity) of the title compound were obtained.

$^1$H NMR (400 MHz, DMSO-d$_6$) δ [ppm]=14.37 (br. s, 1H), 9.25 (s, 1H), 8.77 (d, 1H), 8.60 (d, 1H), 7.66-7.56 (m, 2H), 5.93 (d, 1H), 4.45-4.36 (m, 1H), 3.62-3.53 (m, 1H), 2.38-2.26 (m, 1H), 1.85-1.71 (m, 1H), one resonance partially under the water signal.

LC-MS (Method 1): R$_t$=0.73 min; MS (ESIpos) m/z 420 [M+H]$^+$.

Example 151A tert-Butyl (5-oxopyrrolidin-3-yl)carbamate (racemate)

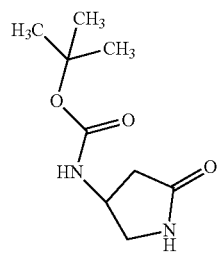

To a solution of 100 mg (732 μmol) of 4-aminopyrrolidin-2-one hydrochloride (racemate) in 1.5 ml of water and 3.5 ml of dioxane were added, at room temperature, 185 mg (2.19 mmol) of sodium hydrogencarbonate and 168 mg (769 μmol) of di-tert-butyl dicarbonate. The mixture was stirred overnight. The mixture was then admixed with water and extracted three times with ethyl acetate. The combined organic phases were dried over magnesium sulphate and concentrated, and the residue was dried under high vacuum. 69.2 mg (47% of theory, 100% purity) of the title compound were obtained.

LC-MS (Method 1): R$_t$=0.48 min; MS (ESIpos): m/z=201 [M+H]$^+$

Example 151B tert-Butyl {5-oxo-1-[5-oxo-6-{[(2S)-1,1,1-trifluorobutan-2-yl]carbamoyl}-8-(2,4,6-trifluorophenyl)-5,8-dihydro-1,8-naphthyridin-2-yl]pyrrolidin-3-yl}carbamate (diastereomer mixture)

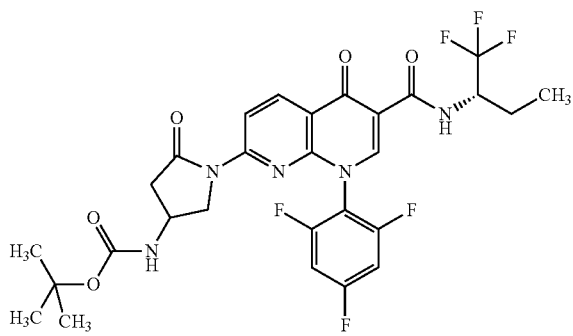 [SMILES: CC[C@H](NC(=O)c1cn(-c2c(F)cc(F)cc2F)c2nc(N3CC(NC(=O)OC(C)(C)C)CC3=O)ccc2c1=O)C(F)(F)F]

Potassium carbonate (17.9 mg, 129 µmol), palladium(II) acetate (3.87 mg, 17.2 µmol) and 9,9-dimethyl-4,5-bis(diphenylphosphino)xanthene (9.98 mg, 17.2 µmol) were stirred in 4.0 ml of dioxane under argon at RT for 10 minutes. Then the compound from Example 115A (40.0 mg, 86.2 µmol) and the compound from Example 151A (20.7 mg, 103 µmol) were added and the mixture was stirred at 80° C. for 4 h. The mixture was purified directly by preparative RP-HPLC (column: Reprosil 125×30; 10µ, flow rate: 50 ml/min, MeCN/water, 0.1% TFA). The volatile constituents were removed under reduced pressure and the residue was dried under high vacuum. This gave 30.7 mg (79% pure, 45% of theory) of the title compound.

LC-MS (Method 1): $R_t$=1.20 min; MS (ESIpos): m/z=628 [M+H]$^+$.

Example 151C

7-[4-Amino-2-oxopyrrolidin-1-yl]-4-oxo-N-[(2S)-1,1,1-trifluorobutan-2-yl]-1-(2,4,6-trifluorophenyl)-1,4-dihydro-1,8-naphthyridine-3-carboxamide (bis)trifluoroacetate (diastereomer mixture)

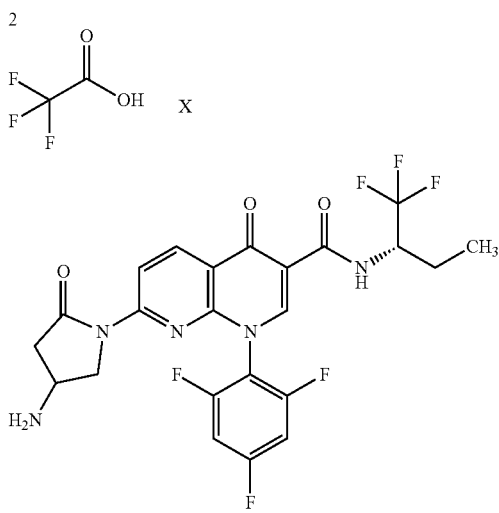

The compound from Example 151B (30.7 mg, 79% purity, 38.5 µmol) was dissolved in 2.0 ml of dichloromethane, trifluoroacetic acid (150 µl, 1.9 mmol) was added, and the mixture was stirred at RT for 5 h. The volatile constituents were removed under reduced pressure and the residue was purified by means of preparative RP-HPLC (column: Reprosil 125×30; 10µ, flow rate: 50 ml/min, MeCN/water/0.1% TFA). The volatile constituents were removed under reduced pressure and the residue was dried under high vacuum. This gave 25.7 mg (95% purity, 84% of theory) of the title compound.

LC-MS (Method 1): $R_t$=0.72 in; MS (ESIpos): m/z=528 [M+H]$^+$

Example 152A

N-[(5-Oxopyrrolidin-3-yl)methyl]acetamide (racemate)

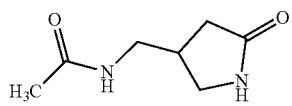

To an initial charge of 4-(aminomethyl)pyrrolidin-2-one hydrochloride (racemate) (30.0 mg, 199 mol) in 1.0 ml of dichloromethane was added triethylamine (83 µl, 600 µmol). Acetyl chloride (17 µl, 240 µmol) was added to the reaction mixture at 0° C., and the reaction mixture was stirred at RT overnight. The organic phase was washed once with water and dried over magnesium sulphate. The volatile constituents were removed under reduced pressure and the residue was dried under high vacuum. This gave 11.7 mg of the title compound, which was used immediately in the next reaction stage without further purification.

Example 153A

N-Benzyl-1,1,1,2,2-pentafluoropentan-3-amine (racemate)

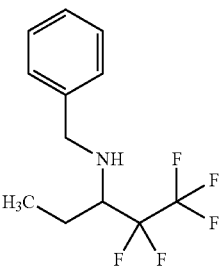 [SMILES: CCC(NCc1ccccc1)C(F)(F)C(F)(F)F]

To a solution of 2.00 g (11.4 mmol) of 1,1,1,2,2-pentafluoropentan-3-one in 10 ml of dichloromethane were added, at 0° C., 5.03 ml (17.0 mmol) of titanium tetraisopropoxide and 2.48 ml (22.7 mmol) of benzylamine. The mixture was stirred at RT for a further 90 min before being cooled down again to 0° C. Subsequently, 2.00 g (31.8 mmol) of sodium cyanoborohydride, 36 ml of methanol and 3 Å molecular sieve were added. The mixture was warmed to RT and stirred for a further 2 d. The reaction solution was then admixed with a little water and ethyl acetate and filtered. The filtrate was washed twice with saturated aqueous sodium hydrogencarbonate solution and once with saturated aqueous sodium chloride solution. The organic phase was dried over sodium sulphate and filtered, and the solvent was removed under reduced pressure. The residue was purified by means of normal phase chromatography (ethyl acetate/cyclohexane 1/20), and 989 mg (25% of theory; 76% purity) of the title compound were obtained.

LC-MS (Method 1): R$_t$=1.27 min; MS (ESIpos): m/z=268 [M+H]$^+$ $^1$H NMR (400 MHz, DMSO-d6): δ [ppm]=7.21-7.36 (m, 5H), 3.73-3.85 (m, 2H), 3.05-3.20 (m, 1H), 1.63-1.75 (m, 1H), 1.49-1.61 (m, 1H), 1.15-1.20 (m, 1H), 0.96 (t, 3H).

Example 153B 1,1,1,2,2-Pentafluoropentan-3-amine hydrochloride (racemate)

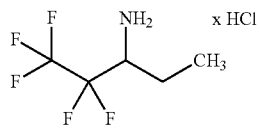

To a solution of 980 g (2.75 mmol) of the compound from Example 153A in 11.3 ml of methanol were added 75 mg of palladium on charcoal (10%), and hydrogenation was effected at standard pressure and room temperature for 6 h. The reaction mixture was then filtered through a Millipore filter and the solvent was removed under reduced pressure. The receiver containing the solvent distilled off was then transferred to a flask and admixed with 4 N aqueous hydrochloric acid in dioxane and concentrated again. The residue was stirred with diethyl ether and the precipitate was filtered off with suction and dried under high vacuum. 379 mg (65% of theory, 100% purity) of the title compound were obtained.

$^1$H NMR (400 MHz, DMSO-d6): δ [ppm]=8.97 (br. s, 3H), 4.16-4.28 (m, 1H), 1.67-1.94 (m, 2H), 1.05 (t, 3H).

Example 154A

7-Chloro-N-(1,1,1,3,3,3-hexafluoropropan-2-yl)-4-oxo-1-(2,4,6-trifluorophenyl)-1,4-dihydro-1,8-naphthyridine-3-carboxamide

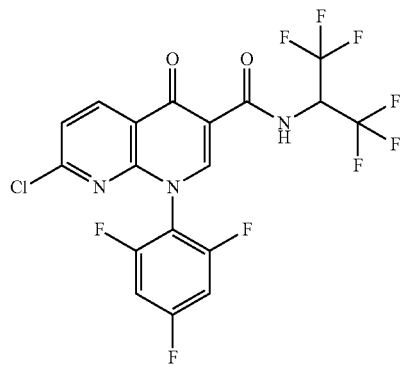 [SMILES: O=C(NC(C(F)(F)F)C(F)(F)F)c1cn(-c2c(F)cc(F)cc2F)c2nc(Cl)ccc2c1=O]

To a solution of 500 mg (1.41 mmol) of the compound from Example 100B, 259 mg (1.55 mmol) of 1,1,1,3,3,3-hexafluoropropan-2-amine and 740 μl (4.20 mmol) of DIPEA in 13 ml of ethyl acetate were added dropwise 3.30 ml (5.60 mmol) of 2,4,6-tripropyl-1,3,5,2,4,6-trioxatriphosphorinane 2,4,6-trioxide (T3P, 50% in DMF). The mixture was stirred at 80° C. overnight. The reaction mixture was poured into water and ethyl acetate, and the phases were separated. The organic phase was washed three times with water and once with saturated aqueous sodium chloride solution, dried over sodium sulphate and filtered, and the solvent was removed under reduced pressure. The residue was dissolved in a little acetonitrile, filtered through a Millipore filter and purified by means of preparative HPLC (column: Chromatorex C18, 10 μm, 125*40 mm, solvent: acetonitrile, water, 0.1% formic acid). The substance was recrystallized from acetonitrile, filtered off with suction, washed with a little acetonitrile and dried. 432 mg (61% of theory, 100% purity) of the title compound were obtained.

LC-MS (Method 3): R$_t$=2.39 min; MS (ESIpos): m/z=504 [M+H]$^+$ $^1$H NMR (400 MHz, DMSO-d$_6$): δ ppm=10.76 (d, 1H), 9.26 (s, 1H), 8.78 (d, 1H), 7.81 (d, 1H), 7.59-7.66 (m, 2H), 6.36-6.47 (m, 1H).

Example 155A

7-[7-Hydroxy-5-azaspiro[2.4]hept-5-yl]-4-oxo-1-(2,4,6-trifluorophenyl)-1,4-dihydro-1,8-naphthyridine-3-carboxylic acid (racemate)

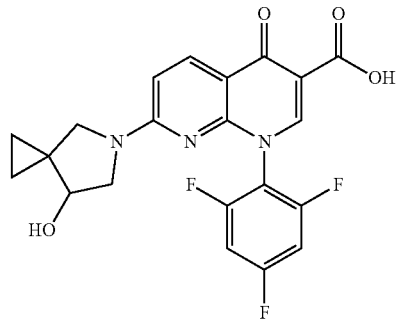 [SMILES: O=C(O)c1cn(-c2c(F)cc(F)cc2F)c2nc(N3CC(O)C4(CC4)C3)ccc2c1=O]

According to GP3, 500 mg (1.41 mmol) of the compound from Example 100B were reacted with 239 mg (1.55 mmol, 97% purity) of 5-azaspiro[2.4]heptan-7-ol hydrochloride in the presence of 860 μl (4.90 mmol) of DIPEA in 14 ml of DMF. The mixture was diluted with water, 1 M aqueous hydrochloric acid and ethyl acetate. The phases were separated and the aqueous phase was extracted three times with ethyl acetate. The combined organic phases were washed with saturated aqueous sodium chloride solution, dried over sodium sulphate and filtered, and the solvent was removed under reduced pressure. The crude product was purified by means of preparative HPLC (column: Chromatorex C18, 10 μm, 125*40 mm, solvent: acetonitrile, water, 0.1% formic acid), and 422 mg (63% of theory, 90% purity) of the title compound were obtained.

LC-MS (Method 3): R$_t$=1.60 min; MS (ESIpos): m/z=432 [M+H]$^+$ $^1$H NMR (400 MHz, DMSO-d$_6$): δ ppm=15.19 (br s, 1H), 8.99-9.04 (m, 1H), 8.31 (d, 1H), 7.51-7.62 (m, 2H), 6.89 (d, 0.40H), 6.76 (d, 0.60H), 5.04 (br s, 1H), 3.61-3.80 (m, 2H), 3.13-3.53 (m, 2.60H), 2.89 (d, 0.40H), 0.78-0.87 (m, 1H), 0.45-0.63 (m, 3H).

Example 156A

7-[(3R,4S)-3,4-Dihydroxypyrrolidin-1-yl]-4-oxo-1-(2,4,6-trifluorophenyl)-1,4-dihydro-1,8-naphthyridine-3-carboxylic acid

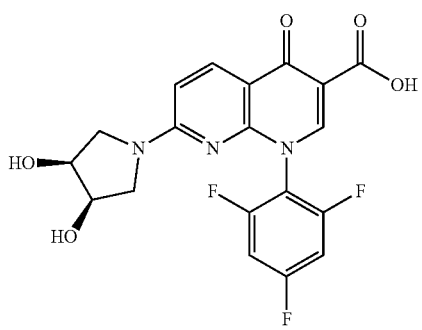 [SMILES: O=C(O)c1cn(-c2c(F)cc(F)cc2F)c2nc(N3C[C@@H](O)[C@@H](O)C3)ccc2c1=O]

According to GP3, 500 mg (1.41 mmol) of the compound from Example 100B were reacted with 236 mg (1.69 mmol) of (3R,4S)-pyrrolidine-3,4-diol hydrochloride in the presence of 860 µl (4.90 mmol) of DIPEA in 6.3 ml of DMF. The mixture was diluted with water, 1 M aqueous hydrochloric acid and ethyl acetate. The phases were separated and the aqueous phase was extracted three times with ethyl acetate. The combined organic phases were washed with saturated aqueous sodium chloride solution, dried over sodium sulphate and filtered, and the solvent was removed under reduced pressure. The crude product was crystallized from ethyl acetate and cyclohexane, filtered off with suction, washed with a little ethyl acetate/cyclohexane and dried. 459 mg (77% of theory) of the title compound were obtained.

LC-MS (Method 3): $R_t$=1.19 min; MS (ESIpos): m/z=422 [M+H]$^+$ $^1$H NMR (400 MHz, DMSO-d$_6$): δ ppm=15.21 (s, 1H), 9.02 (s, 1H), 8.29 (d, 1H), 7.54-7.62 (m, 2H), 6.84 (d, 1H), 5.07 (d, 1H), 4.97 (d, 1H), 4.10-4.20 (m, 1H), 4.00-4.07 (m, 1H), 3.63 (dd, 1H), 3.24 (dd, 1H), 3.01 (dd, 1H).

Example 157A

7-[4-(Methoxycarbonyl)piperazin-1-yl]-4-oxo-1-(2,4,6-trifluorophenyl)-1,4-dihydro-1,8-naphthyridine-3-carboxylic acid

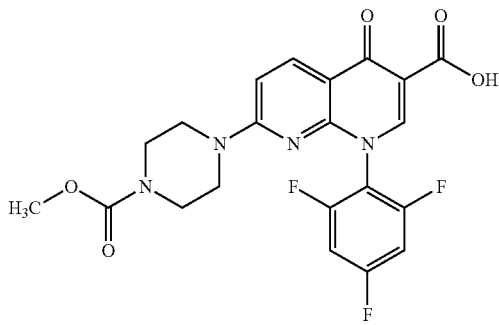 [SMILES: COC(=O)N1CCN(c2ccc3c(=O)c(C(=O)O)cn(-c4c(F)cc(F)cc4F)c3n2)CC1]

According to GP3, 500 mg (1.41 mmol) of the compound from Example 100B were reacted with 244 mg (1.69 mmol) of methyl piperazine-1-carboxylate in the presence of 860 µl (4.90 mmol) of DIPEA in 6.3 ml of DMF. The mixture was diluted with acetonitrile, a little water and formic acid. The substance was purified by means of preparative HPLC (acetonitrile/water/0.1% formic acid). 380 mg (58% of theory, 98% purity) of the title compound were obtained.

LC-MS (Method 3): $R_t$=1.63 min; MS (ESIpos): m/z=463 [M+H]$^+$ $^1$H NMR (400 MHz, DMSO-d$_6$): δ ppm=15.06 (br s, 1H), 9.04 (s, 1H), 8.35 (d, 1H), 7.58 (t, 2H), 7.21 (d, 1H), 3.61 (s, 3H), 3.51-3.59 (m, 4H), 3.37-3.44 (m, 4H).

Example 158A

Ethyl 4-{[(benzyloxy)carbonyl]amino}-3-oxobutanoate

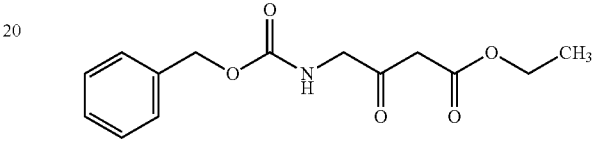

To a solution of 15.0 g (71.7 mmol) of N-[(benzyloxy)carbonyl]glycine in 534 ml of THF were added 9.24 g (57.0 mmol) of carbonyldiimidazole (CDI), and the mixture was stirred at RT for 2.5 h. Subsequently, while cooling with an ice bath, 9.76 g (57.4 mmol) of potassium 3-ethoxy-3-oxopropanoate and 4.95 g (52.0 mmol) of magnesium chloride were added. On completion of addition, stirring was continued at 50° C. for a further 48 h. The solvent was removed under reduced pressure, the residue was taken up with ethyl acetate and saturated aqueous ammonium chloride solution, and the phases were separated. The organic phase was washed with saturated aqueous sodium chloride solution, dried over sodium sulphate and filtered, and the solvent was removed under reduced pressure. The residue was purified by means of normal phase chromatography (ethyl acetate-cyclohexane gradient), and 12.7 g (60% of theory; 95% purity) of the title compound were obtained.

LC-MS (Method 1): $R_t$=0.83 min; MS (ESIneg): m/z=278 [M–H]$^-$ $^1$H NMR (400 MHz, DMSO-d6): δ [ppm]=7.56 (br t, 1H), 7.25-7.41 (m, 5H), 5.04 (s, 2H), 4.09 (q, 2H), 3.97 (d, 2H), 3.60 (s, 2H), 1.19 (t, 3H).

Example 158B

Ethyl 4-{[(benzyloxy)carbonyl]amino}-2-methyl-3-oxobutanoate (racemate)

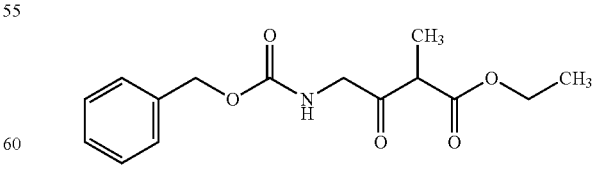

A suspension of 1.00 g (3.58 mmol) of ethyl 4-{[(benzyloxy)carbonyl]amino}-3-oxobutanoate, 669 µl (10.7 mmol) of iodomethane and 990 mg (7.16 mmol) of potassium carbonate in 15 ml of acetone was reacted in a microwave at 50° C. for 2 h. Microwave irradiation was continued, while monitoring the reaction, at 45° C. for a further 2 h. The reaction mixture was poured into water and extracted three times with ethyl acetate. The combined organic phases were washed with saturated aqueous sodium chloride solution, dried over sodium sulphate and filtered, and the solvent was removed under reduced pressure. The residue was dissolved in a little acetonitrile, filtered through a Millipore filter and separated in two runs by means of preparative HPLC (column: Chromatorex C18, 10 µm, 125*40 mm, solvent: acetonitrile, water, 0.1% formic acid). 536 mg (51% of theory, 100% purity) of the title compound were obtained.

LC-MS (Method 1): $R_t$=0.87 min; MS (ESIneg): m/z=292 [M-H]$^-$ $^1$H NMR (400 MHz, DMSO-d6): δ [ppm]=7.57 (br t, 1H), 7.24-7.40 (m, 5H), 5.04 (s, 2H), 4.09 (q, 2H), 4.03 (d, 2H), 3.80 (q, 1H), 1.22-1.09 (m, 6H).

Example 158C

Ethyl 4-{[(benzyloxy)carbonyl]amino}-3-hydroxy-2-methylbutanoate (diastereomer mixture)

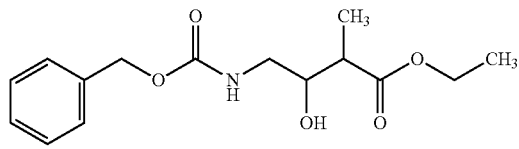 [SMILES: CCOC(=O)C(C)C(O)CNC(=O)OCc1ccccc1]

To a solution of 533 mg (1.82 mmol) of ethyl 4-{[(benzyloxy)carbonyl]amino}-2-methyl-3-oxobutanoate in 9.2 ml of methanol were added, at −78° C., 96.2 mg (2.54 mmol) of sodium borohydride. The mixture was warmed gradually to −15° C. while monitoring the reaction. At −15° C., the reaction was ended by adding saturated aqueous ammonium chloride solution. The mixture was extracted three times with ethyl acetate. The combined organic phases were washed with saturated aqueous sodium chloride solution, dried over sodium sulphate and filtered, and the solvent was removed under reduced pressure. The residue was taken up in a little acetonitrile and purified in two runs by means of preparative HPLC (column: Chromatorex C18, 10 µm, 125*40 mm, solvent: acetonitrile, water, 0.1% formic acid). 398 mg (74% of theory, 100% purity) of the title compound were obtained.

LC-MS (Method 1): $R_t$=0.80 min; MS (ESIpos): m/z=296 [M+H]$^+$ $^1$H NMR (400 MHz, DMSO-d6): δ [ppm]=7.26-7.45 (m, 5H), 7.20-7.25 (m, 0.3H), 7.11 (br t, 0.7H), 5.01 (s, 2H), 4.90-4.97 (m, 1H), 3.98-4.08 (m, 2H), 3.81-3.88 (m, 0.3H), 3.63-3.71 (m, 0.7H), 3.11-3.20 (m, 0.7H), 2.93-3.07 (m, 1.3H), 2.40-2.49 (m, 1H), 1.17 (t, 3H), 1.00-1.05 (m, 3H).

Example 158D

4-Hydroxy-3-methylpyrrolidin-2-one (diastereomer mixture)

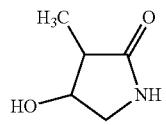

To a solution of 397 mg (1.34 mmol) of ethyl 4-{[(benzyloxy)carbonyl]amino}-3-hydroxy-2-methylbutanoate in 7.2 ml of methanol were added 40 mg of palladium on charcoal (10%), and hydrogenation was effected at standard pressure and room temperature for 6 h. The reaction mixture was then filtered through a Millipore filter and the solvent was removed under reduced pressure. 211 mg (quantitative) of the target compound were obtained, which were used without further purification in the next step. $^1$H-NMR (400 MHz, DMSO-d6) δ[ppm]: −0.008 (0.80), 0.936 (15.27), 0.954 (16.00), 0.985 (4.68), 1.002 (5.72), 1.010 (9.61), 1.021 (1.34), 1.028 (9.33), 1.038 (1.50), 1.055 (2.69), 1.073 (1.35), 1.158 (4.92), 1.176 (10.33), 1.194 (5.03), 2.004 (1.14), 2.022 (1.44), 2.039 (1.10), 2.225 (1.59), 2.239 (1.71), 2.243 (1.63), 2.257 (1.57), 2.479 (1.15), 2.854 (1.16), 2.868 (1.22), 2.878 (1.29), 2.893 (1.32), 2.958 (1.71), 2.962 (2.91), 2.966 (1.63), 2.984 (1.89), 2.988 (3.22), 2.992 (1.80), 3.317 (5.99), 3.329 (6.86), 3.333 (5.11), 3.336 (4.95), 3.343 (6.27), 3.350 (4.61), 3.355 (6.03), 3.360 (3.76), 3.374 (3.03), 3.377 (2.85), 3.414 (1.25), 3.431 (1.52), 3.449 (1.35), 3.847 (1.23), 3.862 (1.17), 4.018 (1.05), 4.035 (2.89), 4.053 (2.81), 4.071 (0.94), 4.194 (1.14), 4.207 (1.95), 4.219 (1.09), 7.419 (1.14).

Example 159A

7-Chloro-N-(1,1,1,3,3,3-hexafluoro-2-methylpropan-2-yl)-4-oxo-1-(2,4,6-trifluorophenyl)-1,4-dihydro-1,8-naphthyridine-3-carboxamide

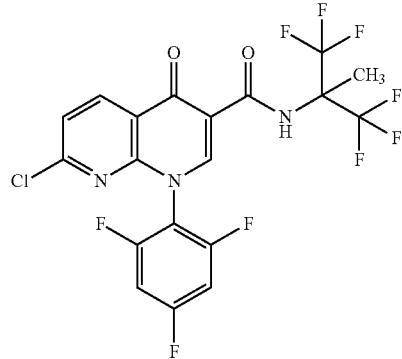 [SMILES: CC(NC(=O)c1cn(-c2c(F)cc(F)cc2F)c2nc(Cl)ccc2c1=O)(C(F)(F)F)C(F)(F)F]

To a solution of 150 mg (423 µmol) of the compound from Example 100B, 91.9 mg (508 µmol) of 1,1,1,3,3,3-hexafluoro-2-methylpropan-2-amine and 220 µl (1.30 mmol) of DIPEA in 1.6 ml of ethyl acetate were added dropwise 740 µl (1.30 mmol) of 2,4,6-tripropyl-1,3,5,2,4,6-trioxatriphosphorinane 2,4,6-trioxide (T3P, 50% in DMF). The mixture was stirred at 80° C. overnight and another 370 µl (0.65 mmol) of 2,4,6-tripropyl-1,3,5,2,4,6-trioxatriphosphorinane 2,4,6-trioxide (T3P, 50% in DMF) were added. The reaction mixture was stirred at 80° C. for a further 64 h and the solvent was then removed under reduced pressure. The residue was dissolved in acetonitrile, a little water and formic acid, filtered through a Millipore filter and purified by means of preparative HPLC (column: Chromatorex C18, 10 µm, 125*40 mm, solvent: acetonitrile, water, 0.1% formic acid). 76.3 mg (35% of theory) of the title compound were obtained.

LC-MS (Method 3): $R_t$=2.46 min; MS (ESIpos): m/z=518 [M+H]$^+$

¹H NMR (400 MHz, DMSO-d₆): δ ppm=10.96 (s, 1H), 9.18 (s, 1H), 8.79 (d, 1H), 7.80 (d, 1H), 7.62 (t, 2H), 2.08 (s, 3H).

Example 160A

7-Chloro-4-oxo-1-(2,4,6-trifluorophenyl)-1,4-dihydro-1,8-naphthyridine-3-carbonyl chloride

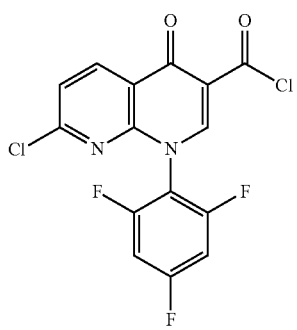 [SMILES: O=C(Cl)c1cn(-c2c(F)cc(F)cc2F)c2nc(Cl)ccc2c1=O]

To a solution of 800 mg (2.26 mmol) of the compound from Example 100B in 18 ml of THF were added 490 µl (6.70 mmol) of thionyl chloride and the mixture was stirred under reflux for a further 2 h, and then all the volatile components were removed under reduced pressure. The crude product was used in the next step without further workup (conversion was assumed to be quantitative).

Example 160B

7-Chloro-N-(2,6-dichlorophenyl)-4-oxo-1-(2,4,6-trifluorophenyl)-1,4-dihydro-1,8-naphthyridine-3-carboxamide

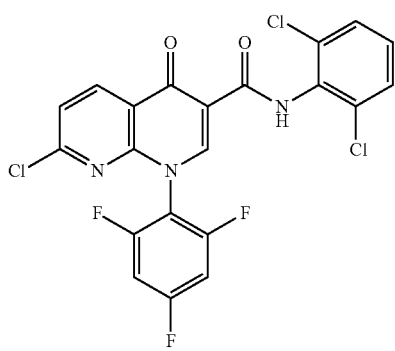 [SMILES: O=C(Nc1c(Cl)cccc1Cl)c1cn(-c2c(F)cc(F)cc2F)c2nc(Cl)ccc2c1=O]

To a solution of 840 mg (2.25 mmol) of 7-chloro-4-oxo-1-(2,4,6-trifluorophenyl)-1,4-dihydro-1,8-naphthyridine-3-carbonyl chloride in 47 ml of dichloromethane were added, at RT, 940 µl (6.80 mmol) of triethylamine and 438 mg (2.70 mmol) of 2,6-dichloroaniline. The mixture was stirred at RT for 30 min and at 50° C. overnight. The reaction mixture was concentrated and taken up in dichloromethane, washed twice with 1 M aqueous hydrochloric acid, dried over magnesium sulphate and filtered, and the solvent was removed under reduced pressure. The crude product was purified by means of normal phase chromatography (ethyl acetate/cyclohexane=1/1). 544 mg (48% of theory, 99% purity) of the title compound were obtained.

LC-MS (Method 3): R$_t$=2.35 min; MS (ESIpos): m/z=498 [M+H]⁺

¹H NMR (400 MHz, DMSO-d₆): δ ppm=11.34 (s, 1H), 9.22 (s, 1H), 8.81 (d, 1H), 7.81 (d, 1H), 7.58-7.65 (m, 4H), 7.36-7.43 (m, 1H).

Example 161A 7-(3-Methoxy-3-methylazetidin-1-yl)-4-oxo-1-(2,4,6-trifluorophenyl)-1,4-dihydro-1,8-naphthyridine-3-carboxylic acid

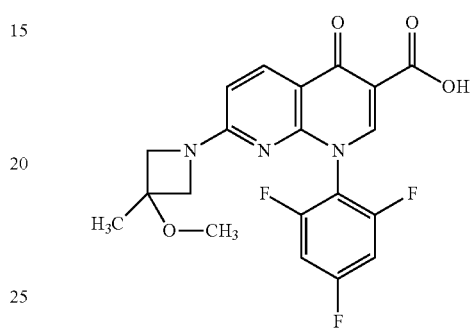

According to GP3, 91.3 mg (257 µmol) of the compound from Example 100B were reacted with 42.5 mg (309 µmol) of 3-methoxy-3-methylazetidine hydrochloride in the presence of 160 µl (900 µmol) of DIPEA in 1.2 ml of DMF. The reaction was ended by adding acetonitrile, a little water and formic acid, the mixture was filtered through a Millipore filter, the crude solution was purified by means of preparative HPLC (column: Chromatorex C18, 10 µm, 125*40 mm, solvents: acetonitrile, water, 0.1% formic acid), and 72.4 mg (63% of theory, 93% purity) of the title compound were obtained.

LC-MS (Method 3): R$_t$=1.83 min; MS (ESIpos): m/z=420 [M+H]⁺

¹H NMR (400 MHz, DMSO-d₆): δ ppm=15.14 (br s, 1H), 9.01 (s, 1H), 8.32 (d, 1H), 7.52-7.60 (m, 2H), 6.70 (d, 1H), 3.48-4.18 (m, 4H), 3.16 (s, 3H), 1.41 (s, 3H).

Example 162A (3S,4S)-1-Benzyl-3,4-bis{[tert-butyl(dimethyl)silyl]oxy}pyrrolidine-2,5-dione

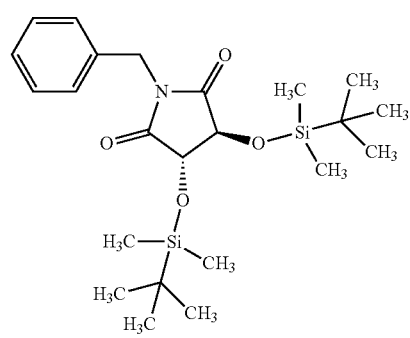 [SMILES: CC(C)(C)[Si](C)(C)O[C@@H]1C(=O)N(Cc2ccccc2)C(=O)[C@H]1O[Si](C)(C)C(C)(C)C]

To a solution of 1.03 g (4.65 mmol) of (3S,4S)-1-benzyl-3,4-dihydroxypyrrolidine-2,5-dione and 949 mg (13.9 mmol) of imidazole in 19.2 ml of DMF were added 1.76 g (11.7 mmol) of tert-butyldimethylsilyl chloride, and the reaction mixture was stirred at room temperature for 3 h. The reaction was admixed with water and extracted three times with dichloromethane. The organic phase was washed with water, dried over magnesium sulphate and filtered, and the solvent was removed under reduced pressure. The residue was purified by means of normal phase chromatography (ethyl acetate/cyclohexane=1/4). This gave 1.57 g (75% of theory) of the title compound.

$^1$H NMR (400 MHz, DMSO-d6): δ [ppm]=7.25-7.36 (m, 5H), 4.80 (s, 2H), 4.53 (dd, 2H), 0.91 (s, 18H), 0.17 (s, 6H), 0.13 (s, 6H).

Example 162B (3R,4R)-1-Benzyl-3,4-bis {[tert-butyl(dimethyl) silyl]oxy}pyrrolidine

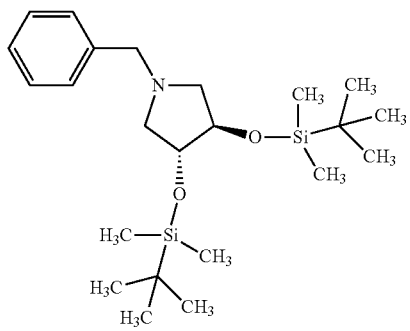 [SMILES: CC(C)(C)[Si](C)(C)O[C@@H]1CN(Cc2ccccc2)C[C@H]1O[Si](C)(C)C(C)(C)C]

To a solution of 1.57 g (3.49 mmol) of (3S,4S)-1-benzyl-3,4-bis {[tertbutyl(dimethyl)silyl]oxy}pyrrolidine-2,5-dione in 11.3 ml of THF at 0° C. were added dropwise 9.1 ml (1.00 M, 9.10 mmol) of borane-tetrahydrofuran complex, and the reaction mixture was stirred at room temperature for 2.5 h and under reflux for 2 h. The solvent was removed on a rotary evaporator and the residue was dissolved in 7 ml of ethanol. The mixture was stirred under reflux for 21 h. Subsequently, the mixture was concentrated by evaporation on a rotary evaporator, and water and diethyl ether were added. The organic phase was extracted three times with diethyl ether. The combined organic phases were washed with saturated sodium chloride solution, dried over sodium sulphate and concentrated. The residue was purified by means of normal phase chromatography (ethyl acetate-cyclohexane gradient). 711 mg (46% of theory, 95% purity) of the title compound were obtained.

LC-MS (Method 1): R$_t$=1.07 min; MS (ESIpos): m/z=422 [M+H]$^+$ $^1$H NMR (400 MHz, CDCl3): δ [ppm]=7.22-7.35 (m, 5H), 4.07-4.15 (m, 2H), 3.62 (dd, 2H), 2.87 (dd, 2H), 2.43-2.48 (m, 2H), 0.87-0.90 (m, 18H), 0.06 (s, 6H), 0.01-0.05 (m, 6H).

Example 162C (3R,4R)-3,4-Bis {[tert-butyl(dimethyl)silyl] oxy}pyrrolidine

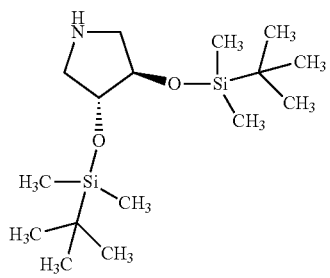 [SMILES: CC(C)(C)[Si](C)(C)O[C@@H]1CNC[C@H]1O[Si](C)(C)C(C)(C)C]

To a solution of 711 mg (1.69 mmol) of (3R,4R)-1-benzyl-3,4-bis {[tertbutyl(dimethyl)silyl]oxy}pyrrolidine in 7.7 ml of ethanol were added 71.1 mg (506 μmol) of palladium(II) hydroxide, and hydrogenation was effected at standard pressure and room temperature for 2.5 h. The reaction mixture was then filtered through kieselguhr and the solvent was removed under reduced pressure. 582 mg (quantitative) of the title compound were obtained, which were used without further purification in the next step.

$^1$H NMR (400 MHz, DMSO-d6): δ [ppm]=4.26-4.39 (m, 1H), 3.90-3.94 (m, 2H), 3.40-3.49 (m, 1H), 2.94-3.01 (m, 2H), 0.85 (s, 18H), 0.05 (s, 6H), 0.04 (s, 6H).

Example 163A

Ethyl 4-{[(benzyloxy)carbonyl]amino}-3-oxopentanoate (racemate)

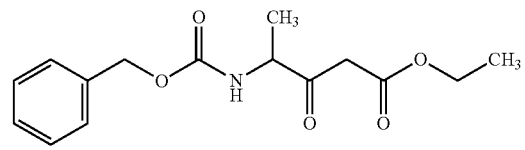 [SMILES: CCOC(=O)CC(=O)C(C)NC(=O)OCc1ccccc1]

To a solution of 15.0 g (71.7 mmol) of N-[(benzyloxy) carbonyl]-DL-alanine in 200 ml of THF were added 3.46 g (21.3 mmol) of carbonyldiimidazole (CDI), and the mixture was stirred at RT for a further 2.5 h.

Subsequently, while cooling with an ice bath, 3.63 g (21.3 mmol) of potassium 3-ethoxy-3-oxopropanoate and 1.86 g (19.5 mmol) of magnesium chloride were added. On completion of addition, stirring was continued at 50° C. overnight. Ethyl acetate and saturated aqueous ammonium chloride solution were added, and the phases were separated. The organic phase was washed with saturated aqueous sodium chloride solution, dried over sodium sulphate and filtered, and the solvent was removed under reduced pressure. The residue was purified by means of normal phase chromatography (ethyl acetate-cyclohexane gradient), and 2.90 g (37% of theory) of the title compound were obtained.

LC-MS (Method 3): R$_t$=1.63 min; MS (ESIneg): m/z=292 [M−H]$^-$ $^1$H NMR (400 MHz, DMSO-d$_6$): δ ppm=7.74 (br d, 1H), 7.25-7.43 (m, 5H), 5.04 (s, 2H), 4.12-4.21 (m, 1H), 4.00-4.12 (m, 2H), 3.54-3.67 (m, 2H), 1.14-1.22 (m, 6H).

Example 163B

Ethyl 4-{[(benzyloxy)carbonyl]amino}-3-hydroxy-pentanoate (diastereomer mixture)

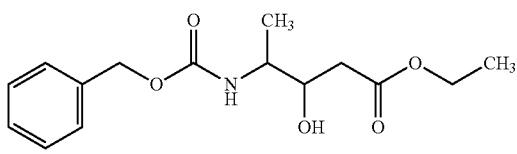 [SMILES: CCOC(=O)CC(O)C(C)NC(=O)OCc1ccccc1]

To a solution of 1.0 g (3.41 mmol) of ethyl 4-{[(benzyloxy)carbonyl]amino}-3-oxopentanoate in 18 ml of methanol were added, at 0° C., 181 mg (4.77 mmol) of sodium borohydride. The mixture was warmed gradually to RT and stirred at RT for a further 2 h. The reaction was ended by adding saturated aqueous ammonium chloride solution. The organic phase was extracted three times with ethyl acetate. The combined organic phases were washed with saturated aqueous sodium chloride solution, dried over magnesium sulphate and filtered, and the solvent was removed under reduced pressure. The residue was taken up in a little acetonitrile and purified by means of preparative HPLC (column: Chromatorex C18, 10 μm, 125*40 mm, solvent: acetonitrile, water, 0.1% formic acid). 398 mg (40% of theory) of the title compound were obtained.

LC-MS (Method 1): $R_t$=0.79 min; MS (ESIpos): m/z=296 [M+H]$^+$ $^1$H NMR (400 MHz, DMSO-d$_6$): δ ppm=7.27-7.39 (m, 5H), 7.08 (br d, 0.75H), 6.97 (br d, 0.25H), 4.97-5.04 (m, 2H), 4.89-4.97 (m, 1H), 4.04 (q, 2H), 3.84-3.90 (m, 0.25H), 3.72-3.80 (m, 0.75H), 3.55-3.65 (m, 0.25H), 3.38-3.50 (m, 0.75H), 2.39-2.47 (m, 2H), 2.16-2.25 (m, 1H), 1.17 (t, 3H), 0.98-1.06 (m, 3H).

Example 163C

4-Hydroxy-5-methylpyrrolidin-2-one (diastereomer mixture)

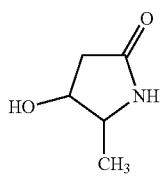

To a solution of 398 mg (1.35 mmol) of ethyl 4-{[(benzyloxy)carbonyl]amino}-3-hydroxypentanoate in 6.8 ml of methanol were added 34 mg of palladium on charcoal (10%), and hydrogenation was effected at standard pressure and room temperature for 5 h. The reaction mixture was then filtered through a Millipore filter and the solvent was removed under reduced pressure. 152 mg (98% of theory) of the title compound were obtained, which were used without further purification in the next step.

$^1$H-NMR (400 MHz, DMSO-d6) δ[ppm]: 0.922 (1.20), 0.938 (1.18), 1.022 (4.00), 1.038 (5.02), 1.054 (16.00), 1.071 (15.05), 1.162 (0.96), 1.180 (1.95), 1.198 (0.96), 1.911 (2.63), 1.922 (2.66), 1.928 (0.88), 1.936 (0.72), 1.953 (3.08), 1.964 (3.16), 1.969 (1.02), 1.977 (0.79), 2.358 (0.76), 2.373 (0.78), 2.399 (0.72), 2.412 (3.05), 2.429 (2.91), 2.454 (2.51), 2.471 (2.81), 3.272 (1.56), 3.274 (1.65), 3.280 (1.80), 3.282 (1.89), 3.288 (2.04), 3.290 (2.15), 3.296 (2.48), 3.298 (2.71), 3.313 (14.07), 3.793 (1.26), 3.801 (1.51), 3.810 (1.48), 3.819 (1.12), 4.038 (0.90), 4.056 (0.89), 4.923 (0.86), 4.934 (0.81), 5.163 (2.76), 5.174 (2.65), 7.588 (1.18).

Example 164A

Ethyl 4-{[(benzyloxy)carbonyl]amino}-2,2-dimethyl-3-oxopentanoate (racemate)

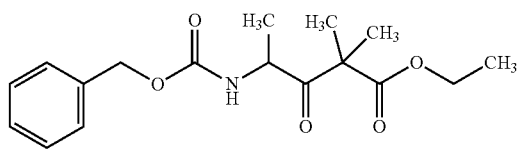 [SMILES: CCOC(=O)C(C)(C)C(=O)C(C)NC(=O)OCc1ccccc1]

A suspension of 500 mg (1.70 mmol) of ethyl 4-{[(benzyloxy)carbonyl]amino}-3-oxopentanoate, 320 μl (5.10 mmol) of iodomethane and 471 mg (3.41 mmol) of potassium carbonate in 7.2 ml of acetone was reacted in a microwave at 60° C. for 16 h. The reaction mixture was poured into water and extracted three times with ethyl acetate. The combined organic phases were washed with saturated aqueous sodium chloride solution, dried over sodium sulphate and filtered, and the solvent was removed under reduced pressure. The residue was dissolved in a little acetonitrile, filtered through a Millipore filter and separated in two runs by means of preparative HPLC (column: Chromatorex C18, 10 μm, 125*40 mm, solvent: acetonitrile, water, 0.1% formic acid). 260 mg (47% of theory) of the title compound were obtained.

LC-MS (Method 3): $R_t$=1.92 min; MS (ESIpos): m/z=322 [M+H]$^+$ $^1$H NMR (400 MHz, DMSO-d$_6$): δ ppm=7.65 (br d, 1H), 7.26-7.42 (m, 5H), 5.01 (s, 2H), 4.51 (quint., 1H), 4.06 (q, 2H), 1.35 (s, 3H), 1.29 (s, 3H), 1.11-1.18 (m, 6H).

Example 164B

Ethyl 4-{[(benzyloxy)carbonyl]amino}-2,2-dimethyl-3-hydroxypentanoate (diastereomer 2)

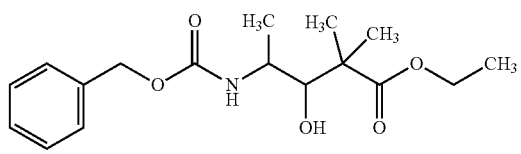 [SMILES: CCOC(=O)C(C)(C)C(O)C(C)NC(=O)OCc1ccccc1]

To a solution of 260 mg (809 μmol) of ethyl 4-{[(benzyloxy)carbonyl]amino}-2,2-dimethyl-3-oxopentanoate in 4.5 ml of methanol were added, at 0° C., 42.9 mg (1.13 mmol) of sodium borohydride. The mixture was warmed gradually to RT and stirred at RT for a further 17 h. The reaction was ended by adding saturated aqueous ammonium chloride solution. The organic phase was extracted three times with ethyl acetate. The combined organic phases were washed with saturated aqueous sodium chloride solution, dried over magnesium sulphate and filtered, and the solvent was removed under reduced pressure. The residue was taken up in a little acetonitrile and purified by means of preparative HPLC (column: Chromatorex C18, 10 µm, 125*40 mm, solvent: acetonitrile, water, 0.1% formic acid). 64.0 mg (24% of theory, 100% purity) of the title compound (diastereomer 2) were obtained. 95.0 mg (34% of theory, 93% purity) of diastereomer 1 were obtained.

LC-MS (Method 3): $R_t$=1.71 min; MS (ESIpos): m/z=324 [M+H]$^+$

Example 164C

4-Hydroxy-3,3,5-trimethylpyrrolidin-2-one (racemate)

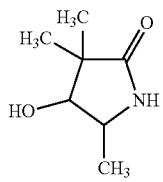

To a solution of 64.0 mg (198 µmol) of ethyl 4-{[(benzyloxy)carbonyl]amino}-2,2-dimethyl-3-hydroxypentanoate (diastereomer 2) in 1.0 ml of methanol were added 5 mg of palladium on charcoal (10%), and hydrogenation was effected at standard pressure and room temperature for 6 h. The reaction mixture was then filtered through a Millipore filter and the solvent was removed under reduced pressure. 20.0 mg (71% of theory) of the title compound were obtained, which were used without further purification in the next step.

$^1$H NMR (400 MHz, CDCl3): δ ppm=5.54 (br s, 1H), 3.85-3.92 (m, 2H), 2.62 (s, 1H), 1.27 (d, 3H), 1.20 (s, 3H), 1.19 (s, 3H).

Example 165A

7-[(3R,4R)-3,4-Bis{[tert-butyl(dimethyl)silyl]oxy}pyrrolidin-1-yl]-1-(2,6-difluorophenyl)-4-oxo-N-[(2R)-1,1,1-trifluorobutan-2-yl]-1,4-dihydro-1,8-naphthyridine-3-carboxamide

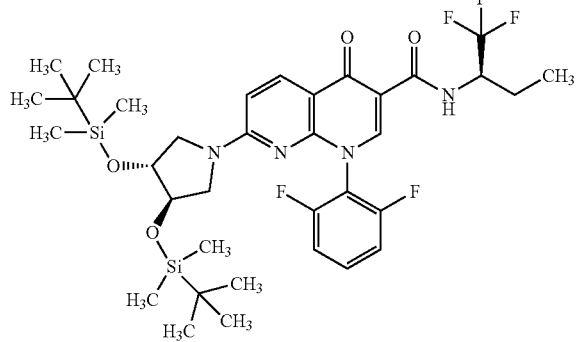

According to GP3, 75.0 mg (168 µmol) of the compound from Example 86A were reacted with 67.0 mg (202 µmol) of the compound from Example 162C in the presence of 100 µl (590 µmol) of DIPEA in 750 µl of DMF. The solvent was removed under reduced pressure and the crude product was purified by means of normal phase chromatography (ethyl acetate-cyclohexane gradient). 119 mg (95% of theory, 95% purity) of the title compound were obtained.

$^1$H NMR (400 MHz, DMSO-d$_6$): δ ppm=10.42 (d, 1H), 8.78 (s, 1H), 8.30 (d, 1H), 7.70 (tt, 1H), 7.32-7.43 (m, 2H), 6.82 (d, 1H), 4.69-4.80 (m, 1H), 4.15-4.21 (m, 1H), 4.00-4.07 (m, 1H), 3.68 (br dd, 1H), 3.21-3.29 (m, 2H), 3.03-3.11 (m, 1H), 1.83-1.93 (m, 1H), 1.58-1.70 (m, 1H), 0.97 (t, 3H), 0.83 (s, 9H), 0.79 (s, 9H), 0.08 (s, 6H).

Example 166A

Ethyl 7-chloro-1-(2,6-dichlorophenyl)-4-oxo-1,4-dihydro-1,8-naphthyridine-3-carboxylate

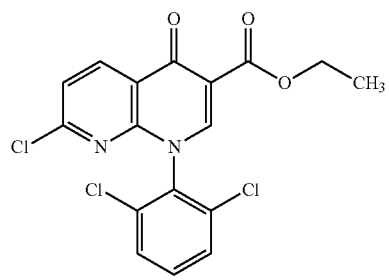 [SMILES: CCOC(=O)c1cn(-c2c(Cl)cccc2Cl)c2nc(Cl)ccc2c1=O]

To a solution of 6.07 g (19.1 mmol) of ethyl 2-[(2,6-dichloropyridin-3-yl)carbonyl]-3-ethoxyacrylate (CAS 157373-27-8) and 4.33 g (26.7 mmol) of 2,6-dichloroaniline in 30 ml DCM were added 23 ml (130 mmol) of N,N-diisopropylethylamine, and the mixture was stirred at room temperature for 4 h. Subsequently, 2.64 g (19.1 mmol) of potassium carbonate were added to the reaction mixture and the reaction was heated under reflux for 4 d. The mixture was cooled down to RT, diluted with dichloromethane, and washed twice with 1 M aqueous hydrochloric acid and once with saturated aqueous sodium chloride solution. The organic phase was dried over sodium sulphate and filtered, and the solvent was removed under reduced pressure. The residue was stirred with diethyl ether and the precipitate was filtered off with suction and dried under high vacuum. Dichloromethane and methanol (1:1, v/v) were added to the substance. The mixture was boiled briefly and the precipitate was filtered off with suction. The mother liquor was concentrated and precipitating solid was filtered off with suction once again. 2.83 g (37% of theory, 100% purity) of the title compound were obtained.

LC-MS (Method 3): $R_t$=1.89 min; MS (ESIpos): m/z=396 [M+H]$^+$ $^1$H NMR (400 MHz, DMSO-d$_6$): δ ppm=8.85 (s, 1H), 8.65 (d, 1H), 7.77-7.82 (m, 2H), 7.65-7.72 (m, 2H), 4.25 (q, 2H), 1.28 (t, 3H).

Example 166B

7-Chloro-1-(2,6-dichlorophenyl)-4-oxo-1,4-dihydro-1,8-naphthyridine-3-carboxylic acid

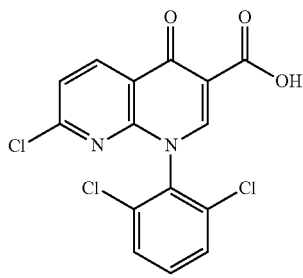 [SMILES: O=C(O)c1cn(-c2c(Cl)cccc2Cl)c2nc(Cl)ccc2c1=O]

To a suspension of 2.78 g (7.00 mmol) of the compound from Example 166A in 23 ml of water were successively added 23 ml of concentrated hydrochloric acid and 23 ml of tetrahydrofuran. The resulting suspension was stirred vigorously at 120° C. for 30 h and subsequently cooled down to RT. The mixture was diluted with 150 ml of water, and the precipitate was filtered off with suction and dried under high vacuum. 2.49 g (96% of theory, 100% purity) of the title compound were obtained.

LC-MS (Method 3): $R_t$=1.91 min; MS (ESIpos): m/z=368 [M+H]$^+$ $^1$H NMR (400 MHz, DMSO-d$_6$): δ ppm=13.82 (br s, 1H), 9.22 (s, 1H), 8.81 (d, 1H), 7.78-7.84 (m, 3H), 7.70 (dd, 1H).

Example 166C

7-Chloro-1-(2,6-dichlorophenyl)-4-oxo-N-[(2R)-1,1,1-trifluorobutan-2-yl]-1,4-dihydro-1,8-naphthyridine-3-carboxamide

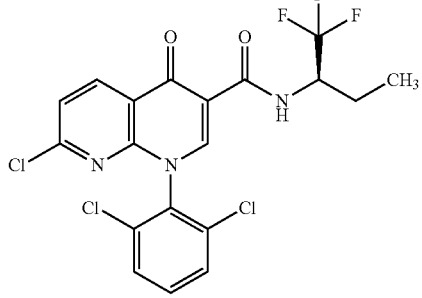

According to GP1, 400 mg (1.08 mmol) of 7-chloro-1-(2,6-dichlorophenyl)-4-oxo-1,4-dihydro-1,8-naphthyridine-3-carboxylic acid were reacted with 266 mg (1.62 mmol) of (2R)-1,1,1-trifluorobutan-2-amine hydrochloride in the presence of 494 mg (1.30 mmol) of HATU and 570 µl (3.20 mmol) of DIPEA in 6.0 ml of DMF. The mixture was diluted with water, 1 M aqueous hydrochloric acid and ethyl acetate. The phases were separated and the organic phase was removed under reduced pressure. The crude product was suspended in acetonitrile and the precipitate (116.5 mg of the title compound) was filtered off. The mother liquor was purified by means of preparative HPLC (column: Chromatorex C18, 10 µm, 125*40 mm, solvent: acetonitrile, water, 0.1% formic acid), and, combined with the precipitate, a total of 304 mg (59% of theory, 99% purity) of the title compound were obtained.

LC-MS (Method 3): $R_t$=2.40 min; MS (ESIpos): m/z=478 [M+H]$^+$ $^1$H-NMR (400 MHz, DMSO-d$_6$): δ ppm=9.91 (d, 1H), 9.04 (s, 1H), 8.78 (d, 1H), 7.77-7.83 (m, 3H), 7.67-7.73 (m, 1H), 4.70-4.83 (m, 1H), 1.85-1.95 (m, 1H), 1.60-1.75 (m, 1H), 0.98 (t, 3H).

Example 167A

7-[(3R,4R)-3,4-Bis{[tert-butyl(dimethyl)silyl]oxy}pyrrolidin-1-yl]-1-(2,4-difluorophenyl)-4-oxo-N-[(2R)-1,1,1-trifluorobutan-2-yl]-1,4-dihydro-1,8-naphthyridine-3-carboxamide

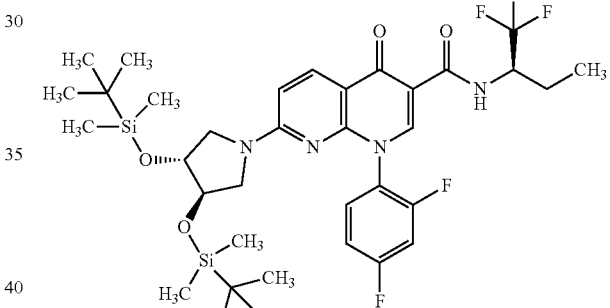

According to General Procedure 3, 100 mg (224 µmol) of the compound from Example 67A were reacted with 89.3 mg (269 µmol) of the compound from Example 162C in the presence of 140 µl (790 µmol) of DIPEA in 1.0 ml of DMF. The solvent was removed under reduced pressure and the crude product was purified by means of normal phase chromatography (ethyl acetate-cyclohexane gradient). 166 mg (quantitative) of the title compound were obtained.

$^1$H NMR (400 MHz, DMSO-d$_6$): δ ppm=10.50 (d, 1H), 8.64 (d, 1H), 8.29 (d, 1H), 7.74-7.86 (m, 1H), 7.42-7.58 (m, 1H), 7.26-7.35 (m, 1H), 6.80 (d, 1H), 4.68-4.79 (m, 1H), 4.18 (br s, 1H), 4.05 (br s, 1H), 3.63-3.73 (m, 1H), 3.22-3.30 (m, 2H), 2.95-3.17 (m, 1H), 1.83-1.93 (m, 1H), 1.58-1.69 (m, 1H), 0.96 (t, 3H), 0.76-0.86 (m, 18H), 0.08 (s, 6H), −0.03-0.05 (m, 6H).

Example 168A 7-(4-Carbamoylpiperazin-1-yl)-4-oxo-1-(2,4,6-trifluorophenyl)-1,4-dihydro-1,8-naphthyridine-3-carboxylic acid

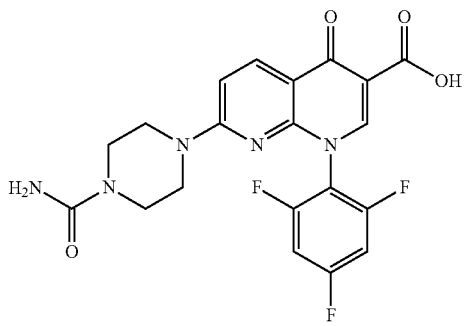 [SMILES: NC(=O)N1CCN(c2ccc3c(=O)c(C(=O)O)cn(-c4c(F)cc(F)cc4F)c3n2)CC1]

According to General Procedure 3, 500 g (1.41 mmol) of 7-chloro-4-oxo-1-(2,4,6-trifluorophenyl)-1,4-dihydro-1,8-naphthyridine-3-carboxylic acid (Example 100B) were reacted with 219 mg (1.69 mmol) of piperazine-1-carboxamide in the presence of 860 µl (4.90 mmol) of DIPEA in 6.3 ml of DMF. The precipitate (358 mg of the title compound) was filtered out of the reaction mixture and the mother liquor was purified by means of preparative HPLC (acetonitrile/water/0.1% formic acid). Combined with the precipitate, 418 mg (67% of theory, 100% purity) of the title compound were obtained.

LC-MS (Method 1): $R_t$=0.70 min; MS (ESIpos): m/z=448 [M+H]$^+$ $^1$H NMR (400 MHz, DMSO-d$_6$): δ ppm=15.09 (br s, 1H), 9.04 (s, 1H), 8.34 (d, 1H), 7.59 (t, 2H), 7.23 (d, 1H), 6.04 (s, 2H), 3.44-3.59 (m, 4H).

Example 169A (5S)-3-[6-{[(1S)-1-Cyclopropyl-2,2,2-trifluoroethyl]carbamoyl}-5-oxo-8-(2,4,6-trifluorophenyl)-5,8-dihydro-1,8-naphthyridin-2-yl]-2-oxo-1,3-oxazolidine-5-carbonyl chloride

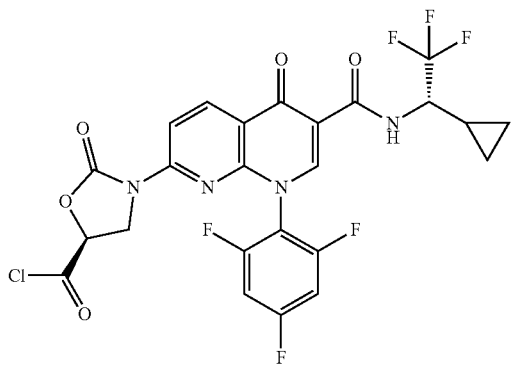 [SMILES: O=C(N[C@@H](C1CC1)C(F)(F)F)c1cn(-c2c(F)cc(F)cc2F)c2nc(N3C[C@@H](C(=O)Cl)OC3=O)ccc2c1=O]

To a solution of 317 mg (556 µmol) of the compound from Example 667 in 7.0 ml of dichloromethane were added 410 µl (5.60 mmol) of thionyl chloride, the mixture was stirred under reflux for a further 3 h, and another 820 µl (11.2 mmol) of thionyl chloride were added. The reaction mixture was stirred under reflux overnight and then all volatile components were removed under reduced pressure. The crude product was used in the next step without further workup (conversion was assumed to be quantitative).

Example 170A (5R)-3-[6-{[(1S)-1-Cyclopropyl-2,2,2-trifluoroethyl]carbamoyl}-5-oxo-8-(2,4,6-trifluorophenyl)-5,8-dihydro-1,8-naphthyridin-2-yl]-2-oxo-1,3-oxazolidine-5-carbonyl chloride

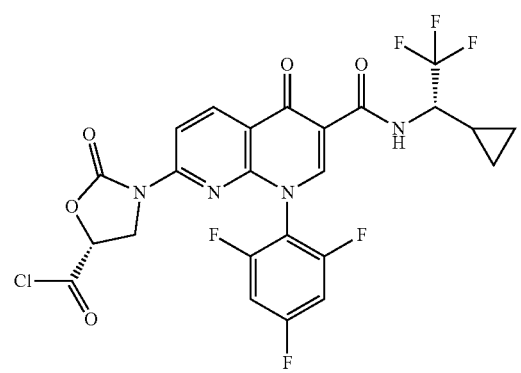 [SMILES: O=C(N[C@@H](C1CC1)C(F)(F)F)c1cn(-c2c(F)cc(F)cc2F)c2nc(N3C[C@H](C(=O)Cl)OC3=O)ccc2c1=O]

To a solution of 440 mg (771 µmol) of the compound from Example 670 in 10 ml of dichloromethane were added 560 µl (7.70 mmol) of thionyl chloride, the mixture was stirred under reflux for a further 3 h, and another 1.12 ml (15.4 mmol) of thionyl chloride were added. The reaction mixture was stirred under reflux overnight and then all volatile components were removed under reduced pressure. The crude product was used in the next step without further workup (conversion was assumed to be quantitative).

WORKING EXAMPLES

Example 1

1-(2,4-Difluorophenyl)-7-(3,3-difluoropiperidin-1-yl)-4-oxo-N-(tricyclo[3.3.1.1$^{3,7}$]dec-1-yl)-1,4-dihydro-1,8-naphthyridine-3-carboxamide

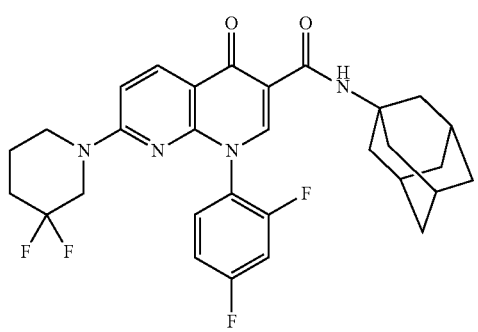 [SMILES: O=C(NC12CC3CC(CC(C3)C1)C2)c1cn(-c2ccc(F)cc2F)c2nc(N3CCCC(F)(F)C3)ccc2c1=O]

A mixture of 80 mg (0.17 mmol) of the compound from Example 65A, 54 mg (0.34 mmol) of 3,3-difluoropiperidine hydrochloride and 88 mg (0.68 mmol) of DIPEA in 1.5 ml of NMP was stirred at 23° C. for 2 h. Subsequently, the mixture was purified via preparative HPLC (Method 7). This gave 43 mg (45% of theory) of the title compound.

$^1$H-NMR (400 MHz, DMSO-d$_6$) δ [ppm]: −0.008 (1.85), 0.008 (1.65), 1.609 (0.87), 1.620 (1.04), 1.673 (7.07), 2.011 (0.49), 2.029 (0.86), 2.058 (16.00), 2.073 (2.19), 2.366 (0.53), 2.710 (0.50), 3.534 (0.91), 3.546 (1.26), 3.562 (0.86), 3.824 (0.46), 3.841 (0.59), 3.855 (0.75), 3.885 (0.41), 7.185 (1.64), 7.208 (1.68), 7.339 (0.69), 7.348 (0.66), 7.568 (0.46), 7.575 (0.47), 7.590 (0.61), 7.597 (0.72), 7.600 (0.63), 7.616 (0.46), 7.623 (0.45), 7.779 (0.44), 7.795 (0.53), 7.802 (0.90), 7.816 (0.89), 7.823 (0.51), 7.839 (0.42), 8.295 (2.38), 8.318 (2.19), 8.514 (4.49), 9.883 (2.53).

LC-MS (Method 1): R$_t$=1.34 min; m/z=479.2 [M+H]$^+$.

In analogy to Example 1, the example compounds shown in Table 1 were prepared by reacting the compound from Example 65A with the appropriate amines (or salts thereof) under the reaction conditions described. Differences are specified in the respective examples.

TABLE 1

| Ex. | | Analytical data |
|---|---|---|
| 2 | 7-(6,6-Difluoro-3-azabicyclo[3.1.0]hex-3-yl)-1-(2,4-difluorophenyl)-4-oxo-N-(tricyclo[3.3.1.1$^{3,7}$]dec-1-yl)-1,4-dihydro-1,8-naphthyridine-3-carboxamide<br>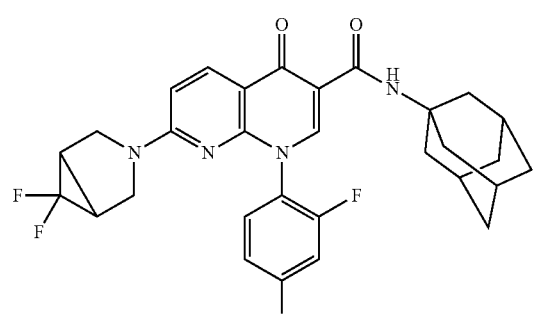<br>(92% of theory) | LC-MS (Method 1): R$_t$ = 1.42 min<br>MS (ESpos): m/z = 553.4 [M + H]$^+$<br>$^1$H-NMR (400 MHz, DMSO-d$_6$): δ = 1.67 (m, 6 H), 2.06 (m, 9H), 2.58-2.77 (m, 2H, partially overlapping with DMSO signal), 3.44 (br. s, 2H), 3.80 (br. s, 2H), 6.74 (d, 1H), 7.29-7.36 (m, 1H), 7.53-7.64 (m, 1H), 7.76-7.84 (m, 1H), 8.30 (d, 1H), 8.50 (s, 1H), 9.91 (br.s, 1H). |
| 3 | 1-(2,4-Difluorophenyl)-7-[(3R,4R)-4-fluoro-3-hydroxypiperidin-1-yl]-4-oxo-N-(tricyclo[3.3.1.1$^{3,7}$]dec-1-yl)-1,4-dihydro-1,8-naphthyridine-3-carboxamide<br>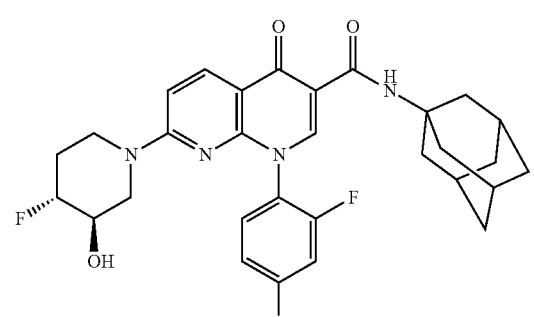<br>(80% of theory) | LC-MS (Method 1): R$_t$ = 1.26 min<br>MS (ESpos): m/z = 553.4 [M + H]$^+$<br>$^1$H-NMR (400 MHz, DMSO-d$_6$): δ = 1.39-1.55 (m, 1H), 1.68 (s, 6 H), 1.88-2.01 (m, 1H), 2.06 (m, 9H), 2.90-3.09 (m, 1H), 3.11-3.27 (m, 2H), 3.38-3.51 (m, 2H), 4.36-4.45 (m, 1H), 4.48-4.59 (m, 1H), 5.41-5.49 (m, 2H), 7.11 (d, 1H), 7.29-7.36 (m, 1H), 7.52-7.62 (m, 1H), 7.77-7.84 (m, 1H), 8.28 (d, 1H), 8.49 (s, 1H), 9.91 (br. s, 1H). |

TABLE 1-continued

| Ex. | | Analytical data |
|---|---|---|
| 4 | Methyl 4-[8-(2,4-difluorophenyl)-5-oxo-6-(tricyclo[3.3.1.1³,⁷]dec-1-ylcarbamoyl)-5,8-dihydro-1,8-naphthyridin-2-yl]piperazine-1-carboxylate<br><br>(74% of theory) | LC-MS (Method 1): $R_t$ = 1.30 min<br>MS (ESpos): m/z = 578.2 [M + H]⁺<br>¹H-NMR (400 MHz, DMSO-d₆) δ [ppm]: −0.008 (1.17), 0.008 (0.97), 1.157 (1.26), 1.175 (2.57), 1.193 (1.30), 1.672 (7.47), 1.988 (4.65), 2.055 (16.00), 3.360 (1.42), 3.374 (3.07), 3.388 (2.46), 3.493 (2.28), 3.506 (2.93), 3.520 (1.59), 3.603 (13.90), 4.021 (1.08), 4.038 (1.07), 7.070 (2.00), 7.093 (2.02), 7.308 (0.42), 7.325 (0.78), 7.332 (0.76), 7.334 (0.61), 7.344 (0.41), 7.348 (0.43), 7.351 (0.45), 7.354 (0.40), 7.555 (0.52), 7.562 (0.55), 7.578 (0.70), 7.581 (0.76), 7.585 (0.78), 7.589 (0.65), 7.604 (0.54), 7.611 (0.52), 7.761 (0.51), 7.775 (0.61), 7.782 (1.00), 7.797 (1.01), 7.804 (0.56), 7.819 (0.49), 8.297 (2.65), 8.319 (2.43), 8.503 (5.19), 9.897 (2.86). |
| 5 | 1-(2,4-Difluorophenyl)-7-(4-fluoropiperidin-1-yl)-4-oxo-N-(tricyclo[3.3.1.1³,⁷]dec-1-yl)-1,4-dihydro-1,8-naphthyridine-3-carboxamide<br><br>(81% of theory) | LC-MS (Method 1): $R_t$ = 1.38 min<br>MS (ESpos): m/z = 537.5 [M + H]⁺<br>¹H-NMR (400 MHz, DMSO-d₆) δ [ppm]: 1.670 (8.34), 1.828 (0.58), 2.055 (16.00), 2.365 (0.20), 2.710 (0.19), 3.494 (1.01), 3.602 (0.95), 4.797 (0.41), 4.919 (0.41), 7.124 (1.42), 7.147 (1.47), 7.309 (0.45), 7.330 (0.88), 7.351 (0.49), 7.562 (0.47), 7.584 (0.83), 7.604 (0.48), 7.772 (0.40), 7.794 (0.82), 7.809 (0.82), 7.830 (0.38), 8.272 (1.60), 8.295 (1.52), 8.493 (3.05), 9.909 (2.30) |
| 6 | 7-(3,3-Difluoro-4,4-dihydroxypiperidin-1-yl)-1-(2,4-difluorophenyl)-4-oxo-N-(tricyclo[3.3.1.1³,⁷]dec-1-yl)-1,4-dihydro-1,8-naphthyridine-3-carboxamide<br><br>(18% of theory) | LC-MS (Method 1): $R_t$ = 1.17 min<br>MS (ESpos): m/z = 587.4 [M + H]⁺<br>¹H-NMR (400 MHz, DMSO-d₆) δ [ppm]: 1.003 (5.12), 1.020 (4.58), 1.174 (1.24), 1.671 (8.60), 1.987 (2.21), 2.057 (16.00), 3.560 (1.43), 3.824 (0.84), 6.433 (1.52), 7.197 (1.18), 7.220 (1.24), 7.346 (0.81), 7.594 (0.81), 7.798 (0.93), 7.813 (0.94), 8.191 (1.88), 8.294 (2.21), 8.317 (2.03), 8.516 (4.68), 9.880 (2.69). |

TABLE 1-continued

| Ex. | | Analytical data |
|---|---|---|
| 7 | 1-(2,4-Difluorophenyl)-7-[(3R)-3-fluoro-4,4-dihydroxypiperidin-1-yl]-4-oxo-N-(tricyclo[3.3.1.1$^{3,7}$]dec-1-yl)-1,4-dihydro-1,8-naphthyridine-3-carboxamide 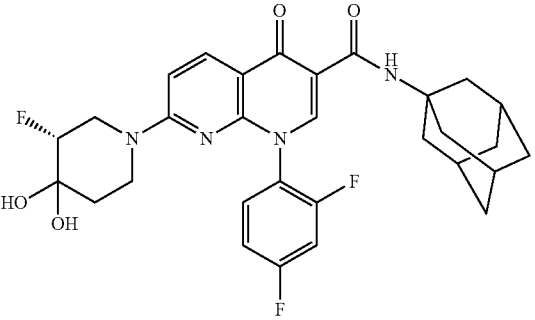 [SMILES: O=C(NC12CC3CC(CC(C3)C1)C2)c1cn(-c2ccc(F)cc2F)c2nc(N3CCC(O)(O)[C@H](F)C3)ccc2c1=O] (10% of theory) | LC-MS (Method 1): $R_t$ = 1.10 min<br>MS (ESpos): m/z = 569.5 [M + H]$^+$<br>$^1$H-NMR (400 MHz, DMSO-d$_6$) δ [ppm]:<br>0.976 (1.80), 0.992 (1.66), 1.507 (0.39),<br>1.537 (0.33), 1.671 (8.13), 2.057 (16.00),<br>2.328 (0.30), 2.366 (0.39), 2.670 (0.34),<br>2.711 (0.38), 3.026 (0.31), 3.168 (0.84),<br>3.934 (0.41), 3.964 (0.41), 4.152 (0.42),<br>4.229 (0.43), 4.264 (0.69), 5.946 (0.85),<br>5.959 (0.93), 6.045 (1.02), 7.105 (1.27),<br>7.128 (1.32), 7.317 (0.44), 7.337 (0.85),<br>7.354 (0.47), 7.559 (0.44), 7.566 (0.48),<br>7.585 (0.77), 7.608 (0.46), 7.615 (0.43),<br>7.782 (0.45), 7.799 (0.65), 7.815 (0.42),<br>8.209 (0.39), 8.247 (1.41), 8.270 (1.34),<br>8.486 (2.39), 9.915 (2.26). |
| 8 | 1-(2,4-Difluorophenyl)-4-oxo-7-(piperidin-1-yl)-N-(tricyclo[3.3.1.1$^{3,7}$]dec-1-yl)-1,4-dihydro-1,8-naphthyridine-3-carboxamide 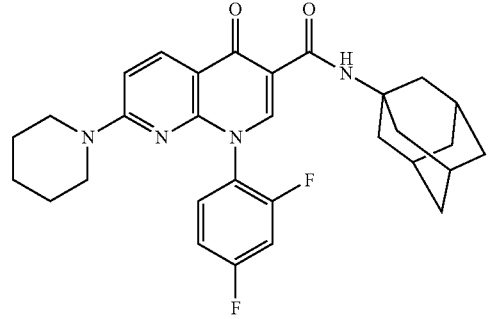 [SMILES: O=C(NC12CC3CC(CC(C3)C1)C2)c1cn(-c2ccc(F)cc2F)c2nc(N3CCCCC3)ccc2c1=O] (73% of theory) | LC-MS (Method 1): $R_t$ = 1.48 min<br>MS (ESpos): m/z = 519.4 [M + H]$^+$<br>$^1$H-NMR (400 MHz, DMSO-d$_6$) δ [ppm]:<br>−0.001 (14.80), 0.938 (0.69), 0.953 (0.65),<br>1.427 (2.32), 1.578 (1.22), 1.670 (7.45),<br>2.054 (16.00), 2.365 (0.41), 2.694 (0.59),<br>2.709 (0.44), 3.470 (2.58), 7.048 (1.93),<br>7.071 (1.98), 7.301 (0.42), 7.323 (0.81),<br>7.343 (0.44), 7.545 (0.51), 7.552 (0.54),<br>7.574 (0.76), 7.593 (0.52), 7.600 (0.49),<br>7.760 (0.50), 7.782 (0.99), 7.797 (0.99),<br>7.819 (0.49), 8.227 (2.51), 8.250 (2.35),<br>8.466 (5.28), 9.935 (2.69). |
| 9 | rac-1-(2,4-Difluorophenyl)-7-(3-fluoro-3-methylpyrrolidin-1-yl)-4-oxo-N-(tricyclo[3.3.1.1$^{3,7}$]dec-1-yl)-1,4-dihydro-1,8-naphthyridine-3-carboxamide 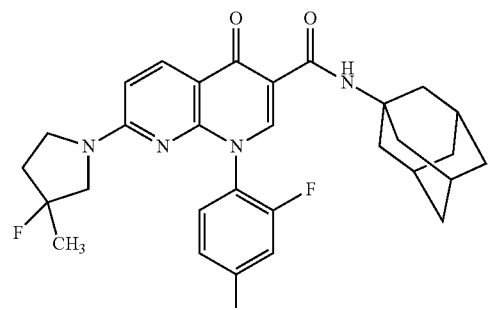 (85% of theory) | LC-MS (Method 1): $R_t$ = 1.43 min<br>MS (ESpos): m/z = 537.4 [M + H]$^+$<br>$^1$H-NMR (400 MHz, DMSO-d$_6$) δ [ppm]:<br>−0.150 (0.31), −0.009 (2.72), 0.007 (2.36),<br>0.146 (0.29), 1.243 (0.52), 1.258 (0.65),<br>1.272 (0.33), 1.508 (0.80), 1.671 (7.35),<br>1.987 (0.32), 2.056 (16.00), 2.212 (0.24),<br>2.322 (0.25), 2.327 (0.34), 2.365 (1.68),<br>2.560 (0.88), 2.562 (0.73), 2.564 (0.52),<br>2.567 (0.41), 2.569 (0.47), 2.577 (0.26),<br>2.580 (0.27), 2.660 (0.25), 2.665 (0.33),<br>2.669 (0.45), 2.674 (0.29), 2.694 (0.21),<br>2.709 (1.76), 3.144 (0.22), 3.161 (0.59),<br>3.174 (0.64), 3.195 (0.19), 3.217 (0.19),<br>3.380 (0.28), 3.431 (0.22), 3.448 (0.25),<br>3.459 (0.24), 3.472 (0.21), 3.507 (0.25),<br>3.681 (0.22), 6.722 (0.27), 7.301 (0.33),<br>7.322 (0.64), 7.341 (0.38), 7.550 (0.25),<br>7.573 (0.46), 7.764 (0.29), 7.786 (0.62),<br>7.800 (0.60), 7.823 (0.27), 8.283 (0.75),<br>8.305 (0.75), 8.482 (3.76), 9.934 (2.64). |

TABLE 1-continued

| Ex. | | Analytical data |
|---|---|---|
| 10 | 7-(3-Cyanopiperidin-1-yl)-1-(2,4-difluorophenyl)-4-oxo-N-(tricyclo[3.3.1.1$^{3,7}$]dec-1-yl)-1,4-dihydro-1,8-naphthyridine-3-carboxamide<br>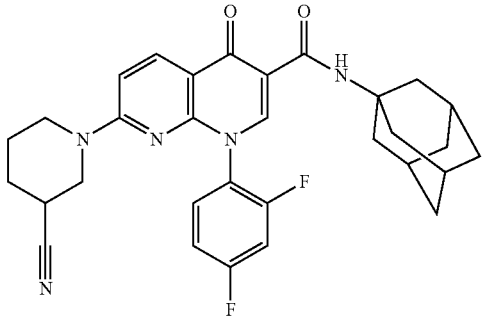 [SMILES: N#CC1CCCN(c2ccc3c(=O)c(C(=O)NC45CC6CC(CC(C6)C4)C5)cn(-c4ccc(F)cc4F)c3n2)C1]<br>(87% of theory) | LC-MS (Method 1): $R_t$ = 1.27 min<br>MS (ESpos): m/z = 544.3 [M + H]$^+$<br>$^1$H-NMR (400 MHz, DMSO-d$_6$) δ [ppm]:<br>0.936 (1.41), 0.951 (1.34), 1.235 (0.32),<br>1.475 (0.40), 1.558 (0.43), 1.672 (7.37),<br>1.862 (0.58), 1.882 (1.03), 1.901 (1.49),<br>1.920 (1.32), 1.937 (0.61), 2.057 (16.00),<br>2.155 (1.02), 2.176 (1.43), 2.195 (0.76),<br>2.327 (0.29), 2.669 (0.31), 2.694 (6.05),<br>2.961 (0.60), 3.285 (2.06), 3.477 (0.41),<br>3.561 (0.38), 3.680 (0.35), 3.713 (0.77),<br>3.743 (0.54), 3.760 (0.53), 7.166 (1.68),<br>7.189 (1.72), 7.321 (0.53), 7.555 (0.54),<br>7.575 (0.53), 7.786 (0.49), 7.802 (0.58),<br>7.822 (0.46), 8.292 (2.36), 8.315 (2.20),<br>8.514 (3.44), 9.891 (2.51). |
| 11 | 1-(2,4-Difluorophenyl)-7-[(2R,4S)-4-fluoro-2-methylpyrrolidin-1-yl]-4-oxo-N-(tricyclo[3.3.1.1$^{3,7}$]dec-1-yl)-1,4-dihydro-1,8-naphthyridine-3-carboxamide<br>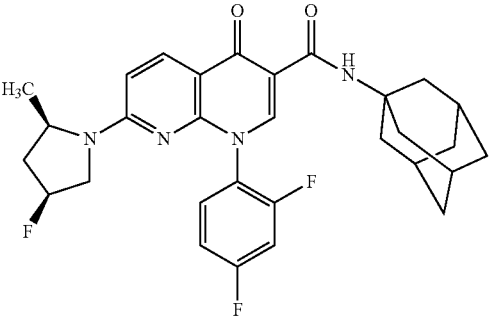 [SMILES: C[C@@H]1C[C@H](F)CN1c1ccc2c(=O)c(C(=O)NC34CC5CC(CC(C5)C3)C4)cn(-c3ccc(F)cc3F)c2n1]<br>(70% of theory) | LC-MS (Method 1): $R_t$ = 1.43 min<br>MS (ESpos): m/z = 537.4 [M + H]$^+$<br>1H-NMR (400 MHz, DMSO-d$_6$) δ [ppm]:<br>−0.150 (0.18), 0.145 (0.20), 0.840 (0.16),<br>0.889 (0.59), 0.919 (0.47), 0.934 (2.34),<br>0.951 (2.23), 1.066 (0.31), 1.146 (0.27),<br>1.234 (0.18), 1.672 (7.79), 1.901 (0.20),<br>1.959 (0.24), 2.058 (16.00), 2.218 (0.20),<br>2.327 (0.34), 2.366 (1.39), 2.408 (0.22),<br>2.427 (0.23), 2.669 (0.35), 2.694 (0.24),<br>2.709 (1.39), 2.960 (0.19), 3.584 (0.17),<br>3.915 (0.17), 5.326 (0.24), 5.457 (0.24),<br>6.737 (0.27), 7.322 (0.66), 7.344 (0.38),<br>7.569 (0.46), 7.592 (0.47), 7.767 (0.28),<br>7.788 (0.62), 7.804 (0.62), 7.825 (0.27),<br>8.281 (1.86), 8.303 (1.78), 8.498 (1.45),<br>9.940 (2.44). |
| 12 | 7-(4-Carbamoylpiperazin-1-yl)-1-(2,4-difluorophenyl)-4-oxo-N-(tricyclo[3.3.1.1$^{3,7}$]dec-1-yl)-1,4-dihydro-1,8-naphthyridine-3-carboxamide<br>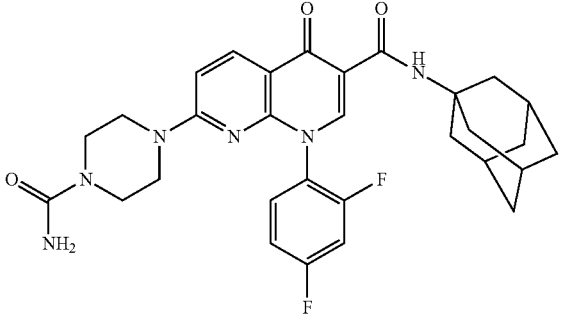 [SMILES: NC(=O)N1CCN(c2ccc3c(=O)c(C(=O)NC45CC6CC(CC(C6)C4)C5)cn(-c4ccc(F)cc4F)c3n2)CC1]<br>(quant. yield) | LC-MS (Method 1): $R_t$ = 1.10 min<br>MS (ESpos): m/z = 563.4 [M + H]$^+$<br>$^1$H-NMR (400 MHz, DMSO-d$_6$) δ [ppm]:<br>−0.001 (0.96), 1.669 (1.15), 1.861 (0.09),<br>1.881 (0.29), 1.901 (0.34), 1.916 (0.24),<br>1.919 (0.30), 1.937 (0.12), 2.055 (2.40),<br>2.155 (0.34), 2.175 (0.47), 2.195 (0.24),<br>2.694 (2.11), 3.284 (0.84), 3.302 (1.37),<br>3.315 (16.00), 3.453 (0.43), 6.021 (0.47),<br>7.083 (0.28), 7.106 (0.28), 7.314 (0.07),<br>7.335 (0.12), 7.356 (0.07), 7.560 (0.08),<br>7.567 (0.09), 7.586 (0.12), 7.608 (0.08),<br>7.615 (0.08), 7.770 (0.08), 7.785 (0.10),<br>7.792 (0.15), 7.807 (0.15), 7.814 (0.08),<br>7.829 (0.07), 8.280 (0.38), 8.303 (0.35),<br>8.497 (0.81), 9.907 (0.41). |

TABLE 1-continued

| Ex. | | Analytical data |
|---|---|---|
| 13 | 7-(1,1-Difluoro-5-azaspiro[2.4]hept-5-yl)-1-(2,4-difluorophenyl)-4-oxo-N-(tricyclo[3.3.1.1³,⁷]dec-1-yl)-1,4-dihydro-1,8-naphthyridine-3-carboxamide<br />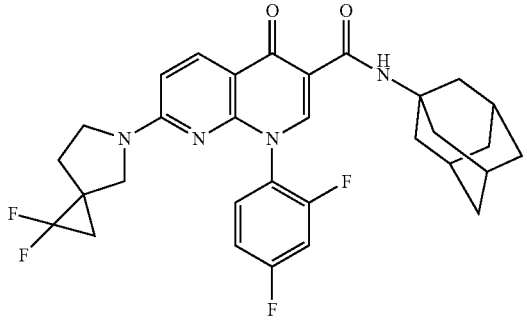 [SMILES: O=C(NC12CC3CC(CC(C3)C1)C2)c1cn(-c2ccc(F)cc2F)c2nc(N3CCC4(C3)CC4(F)F)ccc2c1=O]<br />(95% of theory) | LC-MS (Method 1): $R_t$ = 1.46 min<br />MS (ESpos): m/z = 567.4 [M + H]⁺<br />¹H-NMR (400 MHz, DMSO-d₆) δ [ppm]:<br />−0.150 (0.85), −0.009 (8.08), 0.008 (6.51),<br />0.146 (0.85), 1.147 (0.31), 1.156 (0.33),<br />1.174 (0.66), 1.192 (0.37), 1.240 (0.31),<br />1.258 (0.33), 1.616 (0.81), 1.622 (0.76),<br />1.636 (0.85), 1.672 (7.46), 1.988 (1.36),<br />2.056 (16.00), 2.131 (0.39), 2.156 (0.37),<br />2.177 (0.37), 2.327 (0.66), 2.366 (3.16),<br />2.608 (0.25), 2.669 (0.74), 2.673 (0.54),<br />2.694 (1.07), 2.709 (3.12), 3.285 (1.30),<br />3.461 (0.33), 3.505 (0.29), 4.020 (0.31),<br />4.038 (0.31), 6.742 (0.48), 6.765 (0.50),<br />7.293 (0.37), 7.307 (0.76), 7.330 (0.43),<br />7.526 (0.39), 7.533 (0.37), 7.555 (0.68),<br />7.575 (0.39), 7.760 (0.35), 7.780 (0.72),<br />7.796 (0.70), 7.816 (0.33), 8.291 (1.90),<br />8.313 (1.84), 8.488 (4.22), 9.928 (2.71). |
| 14 | rac-1-(2,4-Difluorophenyl)-7-(3-hydroxypiperidin-1-yl)-4-oxo-N-(tricyclo[3.3.1.1³,⁷]dec-1-yl)-1,4-dihydro-1,8-naphthyridine-3-carboxamide<br />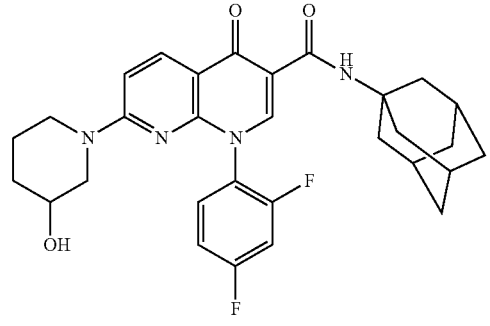 [SMILES: O=C(NC12CC3CC(CC(C3)C1)C2)c1cn(-c2ccc(F)cc2F)c2nc(N3CCCC(O)C3)ccc2c1=O]<br />(96% of theory) | LC-MS (Method 1): $R_t$ = 1.19 min<br />MS (ESpos): m/z = 535.3 [M + H]⁺<br />¹H-NMR (400 MHz, DMSO-d₆) δ [ppm]:<br />−0.009 (1.19), 0.007 (1.22), 0.942 (0.31),<br />1.263 (0.83), 1.391 (0.47), 1.669 (7.58),<br />1.803 (0.43), 1.881 (0.20), 1.901 (0.21),<br />1.920 (0.19), 2.054 (16.00), 2.155 (0.20),<br />2.176 (0.27), 2.195 (0.16), 2.327 (0.18),<br />2.366 (0.33), 2.669 (0.23), 2.694 (1.18),<br />2.709 (0.39), 2.949 (0.25), 3.030 (0.21),<br />3.057 (0.30), 3.090 (0.23), 3.126 (0.30),<br />3.154 (0.21), 3.285 (0.44), 3.370 (0.20),<br />3.429 (0.42), 3.670 (0.32), 3.806 (0.27),<br />3.839 (0.46), 3.869 (0.25), 4.796 (1.50),<br />4.808 (1.49), 7.027 (1.79), 7.050 (1.83),<br />7.296 (0.38), 7.300 (0.42), 7.322 (0.82),<br />7.339 (0.44), 7.343 (0.46), 7.558 (0.45),<br />7.757 (0.30), 7.779 (0.66), 7.795 (0.66),<br />7.816 (0.29), 8.222 (1.38), 8.245 (1.32),<br />8.464 (4.15), 9.934 (2.51). |
| 15 | 1-(2,4-Difluorophenyl)-7-[(2S)-2-(hydroxymethyl)piperidin-1-yl]-4-oxo-N-(tricyclo[3.3.1.1³,⁷]dec-1-yl)-1,4-dihydro-1,8-naphthyridine-3-carboxamide<br />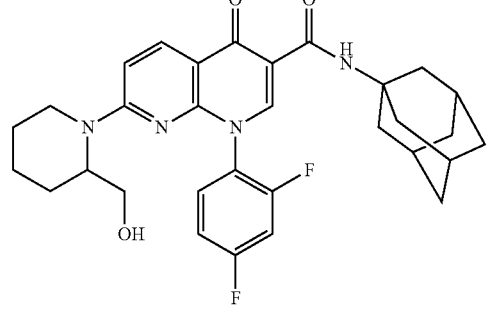<br />(30% of theory) | LC-MS (Method 1): $R_t$ = 1.29 min<br />MS (ESpos): m/z = 549.5 [M + H]⁺<br />¹H-NMR (400 MHz, DMSO-d₆) δ [ppm]:<br />−0.150 (0.21), −0.009 (1.84), 0.007 (1.70),<br />1.236 (0.37), 1.482 (0.76), 1.535 (0.66),<br />1.567 (0.70), 1.670 (7.53), 1.764 (0.57),<br />1.796 (0.50), 2.054 (16.00), 2.072 (5.28),<br />2.365 (0.29), 2.709 (0.31), 2.797 (0.25),<br />3.502 (0.84), 4.064 (0.44), 4.098 (0.42),<br />4.216 (0.54), 4.660 (0.70), 7.023 (1.61),<br />7.046 (1.69), 7.290 (0.40), 7.312 (0.79),<br />7.332 (0.44), 7.538 (0.42), 7.564 (0.41),<br />7.751 (0.44), 7.773 (0.89), 7.788 (0.89),<br />7.810 (0.43), 8.207 (2.03), 8.230 (1.91),<br />8.457 (4.04), 9.953 (2.51). |

TABLE 1-continued

| Ex. | | Analytical data |
|---|---|---|
| 16 | 1-(2,4-Difluorophenyl)-7-[4-fluoro-4-(hydroxymethyl)piperidin-1-yl]-4-oxo-N-(tricyclo[3.3.1.1³,⁷]dec-1-yl)-1,4-dihydro-1,8-naphthyridine-3-carboxamide<br/>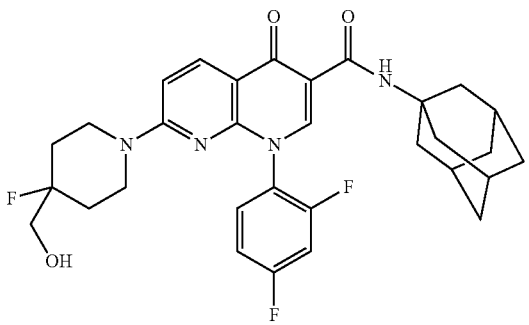 [SMILES: O=C(NC12CC3CC(CC(C3)C1)C2)c1cn(-c2ccc(F)cc2F)c2nc(N3CCC(F)(CO)CC3)ccc2c1=O]<br/>(85% of theory) | LC-MS (Method 1): $R_t$ = 1.28 min<br/>MS (ESpos): m/z = 567.4 [M + H]⁺<br/>¹H-NMR (500 MHz, DMSO-$d_6$) δ [ppm]: −0.004 (1.82), 1.158 (0.27), 1.172 (0.55), 1.187 (0.28), 1.226 (0.04), 1.493 (0.22), 1.517 (0.43), 1.538 (0.34), 1.588 (0.43), 1.608 (0.33), 1.666 (7.42), 1.921 (0.06), 1.986 (1.03), 2.052 (16.00), 2.180 (0.05), 3.171 (0.46), 3.357 (1.33), 3.369 (1.34), 3.397 (1.31), 3.408 (1.34), 3.968 (0.84), 3.989 (0.79), 4.020 (0.26), 4.034 (0.24), 4.049 (0.08), 4.942 (0.95), 4.954 (2.16), 4.965 (0.91), 7.113 (1.93), 7.131 (1.95), 7.305 (0.40), 7.309 (0.43), 7.322 (0.78), 7.326 (0.80), 7.339 (0.43), 7.343 (0.43), 7.552 (0.50), 7.558 (0.53), 7.573 (0.76), 7.576 (0.77), 7.591 (0.51), 7.596 (0.49), 7.771 (0.48), 7.783 (0.58), 7.788 (0.95), 7.800 (0.94), 7.806 (0.54), 7.818 (0.45), 8.266 (2.80), 8.284 (2.54), 8.492 (5.72), 9.913 (2.79). |
| 17 | 1-(2,4-Difluorophenyl)-7-[3-(2-hydroxyethyl)piperidin-1-yl]-4-oxo-N-(tricyclo[3.3.1.1³,⁷]dec-1-yl)-1,4-dihydro-1,8-naphthyridine-3-carboxamide<br/>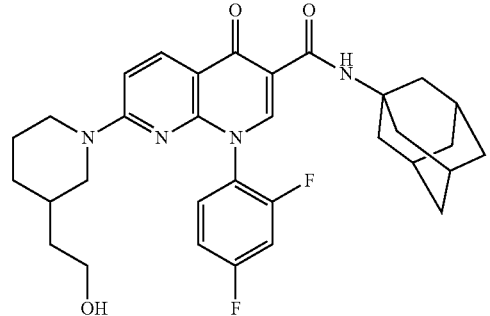 [SMILES: O=C(NC12CC3CC(CC(C3)C1)C2)c1cn(-c2ccc(F)cc2F)c2nc(N3CCCC(CCO)C3)ccc2c1=O]<br/>Workup: add water and then 1M aq. hydrochloric acid. The precipitate formed was filtered off.<br/>(86% of theory) | LC-MS (Method 1): $R_t$ = 1.27 min<br/>MS (ESpos): m/z = 563.3 [M + H]⁺<br/>¹H-NMR (400 MHz, DMSO-$d_6$) δ [ppm]: −0.009 (0.83), 0.007 (0.78), 0.935 (3.19), 0.951 (2.99), 1.145 (0.47), 1.172 (0.53), 1.242 (1.02), 1.258 (1.12), 1.447 (0.35), 1.583 (0.44), 1.669 (7.61), 1.741 (0.45), 1.881 (0.30), 1.901 (0.37), 1.920 (0.32), 1.937 (0.14), 2.053 (16.00), 2.155 (0.33), 2.176 (0.46), 2.195 (0.25), 2.327 (0.13), 2.366 (0.20), 2.409 (0.36), 2.426 (0.36), 2.669 (0.16), 2.694 (1.84), 2.709 (0.23), 2.944 (0.40), 2.960 (0.40), 3.284 (0.93), 4.019 (0.87), 4.346 (0.46), 4.359 (0.56), 7.043 (1.77), 7.067 (1.81), 7.298 (0.38), 7.320 (0.75), 7.340 (0.41), 7.549 (0.51), 7.568 (0.52), 7.756 (0.47), 7.771 (0.56), 7.778 (0.91), 7.793 (0.91), 7.799 (0.53), 7.814 (0.44), 8.224 (2.04), 8.246 (1.89), 8.463 (3.15), 9.938 (2.76) |
| 18 | 1-(2,4-Difluorophenyl)-4-oxo-7-(3-oxopiperazin-1-yl)-N-(tricyclo[3.3.1.1³,⁷]dec-1-yl)-1,4-dihydro-1,8-naphthyridine-3-carboxamide<br/>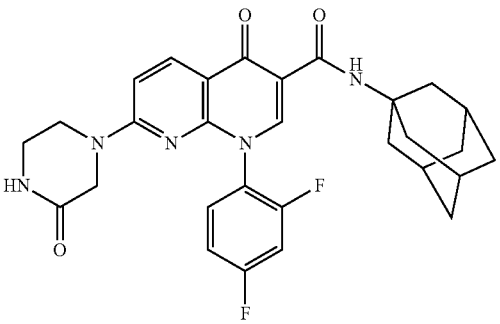 [SMILES: O=C1CN(c2ccc3c(=O)c(C(=O)NC45CC6CC(CC(C6)C4)C5)cn(-c4ccc(F)cc4F)c3n2)CCN1]<br/>(96% of theory) | LC-MS (Method 1): $R_t$ = 1.11 min<br/>MS (ESpos): m/z = 534.4 [M + H]⁺<br/>¹H-NMR (400 MHz, DMSO-$d_6$) δ [ppm]: −0.013 (0.90), 0.003 (0.81), 0.915 (0.58), 0.930 (4.33), 0.946 (4.10), 1.666 (7.41), 1.877 (0.19), 1.897 (0.25), 1.915 (0.21), 2.052 (16.00), 2.151 (0.23), 2.171 (0.30), 2.191 (0.17), 2.322 (0.13), 2.361 (0.17), 2.386 (0.18), 2.404 (0.48), 2.421 (0.47), 2.439 (0.17), 2.664 (0.14), 2.689 (1.26), 2.705 (0.18), 2.939 (0.26), 2.955 (0.35), 2.972 (0.26), 3.219 (1.44), 3.280 (0.50), 3.631 (1.43), 3.896 (2.24), 7.041 (1.72), 7.064 (1.76), 7.315 (0.41), 7.337 (0.79), 7.358 (0.44), 7.562 (0.50), 7.569 (0.52), 7.591 (0.74), 7.610 (0.52), 7.617 (0.50), 7.773 (0.50), 7.788 (0.58), 7.794 (0.96), 7.809 (0.96), 7.816 (0.54), 7.831 (0.47), 8.138 (1.26), 8.309 (2.58), 8.332 (2.40), 8.503 (4.84), 9.886 (2.76). |

Example 19

1-(2,4-Difluorophenyl)-7-[(3R)-3-methoxypyrrolidin-1-yl]-N-(4-methylbicyclo[2.2.2]oct-1-yl)-4-oxo-1,4-dihydro-1,8-naphthyridine-3-carboxamide

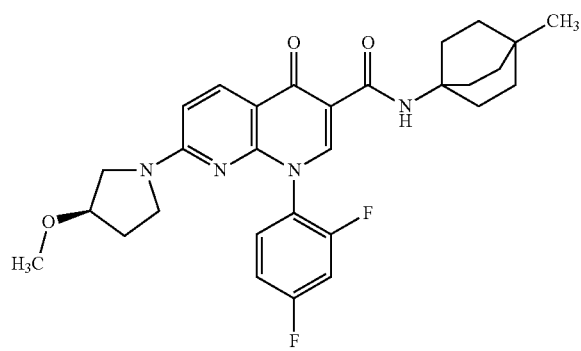

A mixture of 100 mg (0.18 mmol) of the compound from Example 70A, 50 mg (0.23 mmol) of (3R)-3-methoxypyrrolidine trifluoroacetate and 114 mg (0.89 mmol) of DIPEA in 3.6 ml of NMP was stirred at 23° C. for 24 h. Subsequently, the mixture was purified via preparative HPLC (Method 7). This gave 61 mg (66% of theory) of the title compound.

LC-MS (Method 1): $R_t$=1.38 min; m/z=523.3 [M+H]$^+$.

$^1$H-NMR (400 MHz, DMSO-d$_6$) δ [ppm]: −0.150 (0.80), −0.009 (7.08), 0.007 (6.82), 0.146 (0.80), 0.786 (16.00), 0.824 (0.73), 0.947 (0.63), 0.965 (0.63), 1.147 (0.53), 1.156 (0.75), 1.174 (1.49), 1.192 (0.80), 1.235 (0.53), 1.447 (4.65), 1.467 (6.04), 1.487 (5.65), 1.893 (5.84), 1.906 (5.88), 1.914 (6.31), 1.933 (5.14), 1.987 (2.90), 2.327 (1.20), 2.366 (2.84), 2.520 (3.49), 2.523 (3.78), 2.525 (3.98), 2.559 (1.63), 2.562 (1.22), 2.569 (0.71), 2.573 (0.55), 2.664 (0.98), 2.669 (1.27), 2.673 (0.90), 2.709 (2.86), 3.203 (3.51), 3.369 (0.53), 3.510 (0.75), 4.020 (0.69), 4.038 (0.75), 4.056 (0.53), 6.713 (4.24), 6.735 (4.29), 7.290 (0.65), 7.309 (1.27), 7.335 (0.75), 7.559 (0.86), 7.747 (0.67), 7.769 (1.33), 7.784 (1.31), 7.805 (0.55), 8.246 (3.49), 8.268 (3.25), 8.465 (8.24), 9.893 (4.82).

In analogy to Example 19, the example compounds shown in Table 2 were prepared by reacting the compound from Example 70A with (R)-(−)-3-hydroxypyrrolidine hydrochloride.

TABLE 2

| Ex. | | Analytical data |
|---|---|---|
| 20 | 1-(2,4-Difluorophenyl)-7-[(3R)-3-hydroxypyrrolidin-1-yl]-N-(4-methylbicyclo[2.2.2]oct-1-yl)-4-oxo-1,4-dihydro-1,8-naphthyridine-3-carboxamide <br><br> (69% of theory) | LC-MS (Method 1): $R_t$ = 1.21 min<br>MS (ESpos): m/z = 509.3 [M + H]$^+$<br>$^1$H-NMR (400 MHz, DMSO-d$_6$) δ [ppm]:<br>−0.150 (0.42), 0.146 (0.38), 0.786 (12.69), 1.156 (4.38), 1.174 (8.48), 1.192 (4.27), 1.448 (4.66), 1.467 (6.21), 1.487 (5.27), 1.782 (0.40), 1.893 (6.18), 1.914 (6.62), 1.933 (4.80), 1.987 (16.00), 2.327 (0.72), 2.366 (0.96), 2.669 (0.74), 2.710 (1.01), 3.054 (0.40), 3.149 (0.75), 3.498 (0.91), 4.002 (1.32), 4.020 (3.89), 4.038 (3.86), 4.056 (1.25), 4.248 (0.53), 4.370 (0.46), 4.894 (0.37), 4.954 (0.34), 5.007 (0.35), 6.707 (1.01), 7.288 (0.71), 7.309 (1.31), 7.328 (0.77), 7.538 (0.71), 7.560 (1.28), 7.579 (0.66), 7.745 (0.53), 7.765 (1.05), 7.780 (1.03), 7.802 (0.51), 8.237 (1.63), 8.259 (1.67), 8.458 (5.07), 9.902 (4.00). |

Example 21

1-(2,4-Difluorophenyl)-N-[2-(2,6-difluorophenyl)propan-2-yl]-7-[(3R)-3-hydroxypyrrolidin-1-yl]-4-oxo-1,4-dihydro-1,8-naphthyridine-3-carboxamide

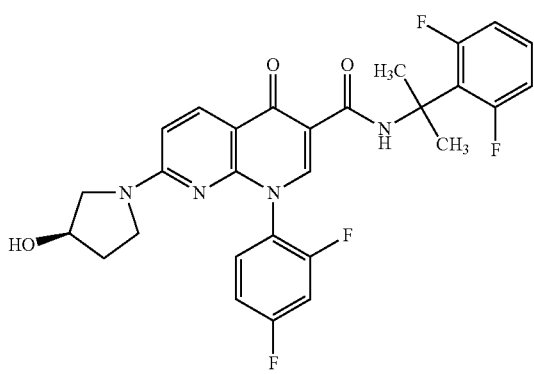 [SMILES: CC(C)(NC(=O)c1cn(-c2ccc(F)cc2F)c2nc(N3CC[C@@H](O)C3)ccc2c1=O)c1c(F)cccc1F]

A mixture of 400 mg (0.61 mmol) of the compound from Example 71A, 151 mg (1.2 mmol) of (R)-(−)-3-hydroxypyrrolidine hydrochloride and 396 mg (3.0 mmol) of DIPEA in 12.5 ml of NMP was stirred at 23° C. for 24 h. Subsequently, the mixture was concentrated under reduced pressure and purified via preparative HPLC (Method 7). This gave 201 mg (59% of theory) of the title compound.

LC-MS (Method 1): $R_t$=1.10 min; m/z=541.3 [M+H]$^+$.

1H-NMR (400 MHz, DMSO-d$_6$) δ [ppm]: −0.009 (2.16), −0.007 (1.87), 0.007 (2.12), 1.156 (3.27), 1.174 (6.61), 1.192 (3.31), 1.824 (16.00), 1.899 (0.99), 1.987 (12.10), 2.327 (0.40), 2.366 (0.62), 2.520 (1.01), 2.523 (1.08), 2.525 (1.05), 2.558 (0.48), 2.560 (0.39), 2.563 (0.35), 2.665 (0.32), 2.669 (0.41), 2.673 (0.33), 2.709 (0.62), 3.047 (0.34), 3.154 (0.68), 3.507 (0.82), 4.002 (0.92), 4.020 (2.74), 4.038 (2.73), 4.055 (0.88), 4.252 (0.52), 4.379 (0.44), 4.892 (0.29), 4.953 (0.32), 5.007 (0.29), 6.733 (0.92), 6.756 (0.59), 6.923 (0.37), 6.935 (2.26), 6.957 (3.14), 6.982 (2.65), 6.995 (0.39), 7.226 (0.48), 7.241 (1.09), 7.247 (1.04), 7.262 (2.30), 7.277 (2.05), 7.283 (2.06), 7.298 (1.07), 7.510 (0.64), 7.515 (0.68), 7.537 (1.19), 7.557 (0.67), 7.563 (0.64), 7.730 (0.45), 7.751 (0.96), 7.767 (0.93), 7.788 (0.41), 8.148 (0.29), 8.274 (1.68), 8.297 (1.63), 8.398 (6.56), 10.700 (4.58).

In analogy to Example 21, the example compounds shown in Table 3 were prepared by reacting the compound from Example 71A with (3R)-3-methoxypyrrolidine trifluoroacetate.

Example 23 rac-Methyl 4-{8-(2,4-difluorophenyl)-5-oxo-6-[(1,1,1-trifluorobutan-2-yl)carbamoyl]-5,8-dihydro-1,8-naphthyridin-2-yl}piperazine-1-carboxylate

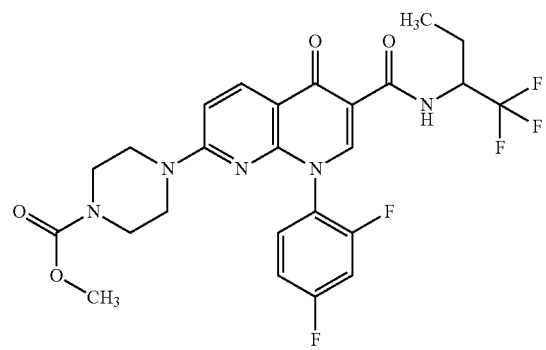 [SMILES: CCC(NC(=O)c1cn(-c2ccc(F)cc2F)c2nc(N3CCN(C(=O)OC)CC3)ccc2c1=O)C(F)(F)F]

TABLE 3

| Ex. | | Analytical data |
|---|---|---|
| 22 | 1-(2,4-Difluorophenyl)-N-[2-(2,6-difluorophenyl)propan-2-yl]-7-[(3R)-3-methoxypyrrolidin-1-yl]-4-oxo-1,4-dihydro-1,8-naphthyridine-3-carboxamide<br><br>(80% of theory) | LC-MS (Method 1): $R_t$ = 1.19 min<br>MS (ESpos): m/z = 541.3 [M + H]$^+$<br>$^1$H-NMR (400 MHz, DMSO-d$_6$) δ [ppm]: −0.009 (1.27), 0.007 (1.11), 1.156 (4.13), 1.174 (8.37), 1.192 (4.22), 1.824 (11.59), 1.907 (1.33), 1.936 (1.03), 1.987 (16.00), 3.205 (2.05), 3.444 (0.43), 3.526 (0.53), 3.573 (0.41), 4.002 (1.30), 4.020 (3.76), 4.038 (3.78), 4.055 (1.40), 6.739 (2.53), 6.761 (2.58), 6.935 (1.64), 6.957 (2.30), 6.982 (1.93), 7.242 (0.81), 7.248 (0.82), 7.262 (1.61), 7.278 (1.49), 7.283 (1.44), 7.299 (0.73), 7.515 (0.40), 7.538 (0.66), 7.555 (0.46), 7.733 (0.43), 7.755 (0.85), 7.770 (0.86), 8.284 (2.18), 8.306 (2.06), 8.379 (0.40), 8.406 (5.65), 8.426 (0.41), 10.691 (3.02). |

A mixture of 100 mg (0.2 mmol) of the compound from Example 66A, 65 mg (0.45 mmol) of methyl piperazine-1-carboxylate and 116 mg (0.9 mmol) of DIPEA in 4.6 ml of NMP was stirred at 23° C. for 24 h. The mixture was then diluted with water and brought to pH 7 with 1 M aqueous hydrochloric acid, and the precipitated solid was filtered off. The solid obtained was washed with water and petroleum ether. This gave 98 mg (76% of theory) of the title compound.

LC-MS (Method 1): $R_t$=1.11 min; m/z=554.2 [M+H]$^+$.

$^1$H-NMR (400 MHz, DMSO-d$_6$) δ [ppm]: −0.009 (2.77), 0.007 (2.54), 0.946 (2.28), 0.964 (5.05), 0.983 (2.47), 1.156 (1.15), 1.174 (2.29), 1.192 (1.16), 1.615 (0.44), 1.632 (0.54), 1.641 (0.48), 1.650 (0.45), 1.658 (0.53), 1.859 (0.47), 1.868 (0.46), 1.878 (0.54), 1.884 (0.47), 1.894 (0.42), 1.987 (4.10), 2.523 (0.64), 3.381 (3.36), 3.394 (2.76), 3.508 (2.37), 3.519 (3.03), 3.594 (1.16), 3.604 (16.00), 4.020 (0.95), 4.038 (0.96), 4.734 (0.46), 4.754 (0.43), 7.108 (2.25), 7.131 (2.32), 7.312 (0.43), 7.329 (0.82), 7.334 (0.85), 7.350 (0.46), 7.355 (0.46), 7.560 (0.51), 7.567 (0.54), 7.586 (0.80), 7.589 (0.80), 7.609 (0.54), 7.616 (0.52), 7.801 (0.54), 7.811 (0.55), 7.825 (0.53), 8.321 (3.02), 8.344 (2.79), 8.641 (1.92), 8.647 (1.77), 10.431 (1.61), 10.455 (1.56).

660 mg of the racemic title compound were separated into the enantiomers by chiral HPLC (preparative HPLC: column: Daicel® Chiralpak AD-H, 5 µm, 250×20 mm; eluent: 85% CO$_2$/15% isopropanol; flow rate 70 ml/min; 40° C., detection: 210 nm).

This gave (in the sequence of elution from the column) 252 mg of enantiomer A $R_t$=2.24 min and 230 mg of enantiomer B $R_t$=2.51 min.

[Analytical HPLC: column: SFC Daicel® Chiralpak AD-3, 3 ml/min; eluent A: CO$_2$, eluent B: isopropanol, gradient 5% B→50% B]

Example 24 ent-Methyl 4-{8-(2,4-difluorophenyl)-5-oxo-6-[(1,1,1-trifluorobutan-2-yl)carbamoyl]-5,8-dihydro-1,8-naphthyridin-2-yl}piperazine-1-carboxylate (enantiomer A)

Example 25 ent-Methyl 4-{8-(2,4-difluorophenyl)-5-oxo-6-[(1,1,1-trifluorobutan-2-yl)carbamoyl]-5,8-dihydro-1,8-naphthyridin-2-yl}piperazine-1-carboxylate (enantiomer B)

In analogy to Example 23, the example compounds shown in Table 4 were prepared by reacting the compound from Example 66A or 67A with the appropriate amines (or salts thereof) under the reaction conditions described. Differences are specified in the respective examples.

TABLE 4

| Ex. | | Analytical data |
|---|---|---|
| 26 | rac-1-(2,4-Difluorophenyl)-7-[3-(hydroxymethyl)azetidin-1-yl]-4-oxo-N-[1,1,1-trifluorobutan-2-yl]-1,4-dihydro-1,8-naphthyridine-3-carboxamide<br />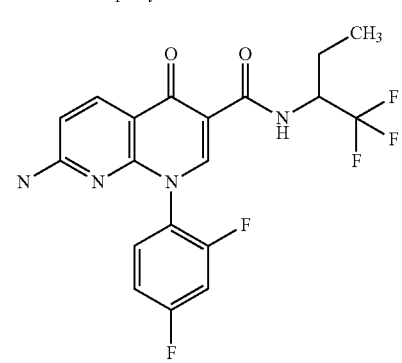<br />(80% of theory) | LC-MS (Method 1): $R_t$ = 0.98 min<br />MS (ESpos): m/z = 497.2 [M + H]$^+$<br />$^1$H-NMR (400 MHz, DMSO-d$_6$) δ [ppm ]: −0.009 (2.48), 0.007 (2.54), 0.943 (7.17), 0.961 (16.00), 0.979 (7.83), 1.156 (2.16), 1.174 (4.31), 1.192 (2.20), 1.592 (1.08), 1.610 (1.44), 1.617 (1.31), 1.627 (1.76), 1.635 (1.60), 1.645 (1.56), 1.652 (1.71), 1.671 (1.29), 1.845 (1.29), 1.855 (1.50), 1.864 (1.51), 1.873 (1.71), 1.880 (1.53), 1.890 (1.34), 1.899 (1.16), 1.908 (1.03), 1.987 (7.76), 2.709 (0.66), 2.722 (0.66), 2.736 (1.22), 2.742 (1.47), 2.756 (2.11), 2.770 (1.55), 2.776 (1.32), 2.791 (0.75), 3.499 (5.39), 3.513 (9.07), 3.527 (5.29), 3.777 (0.78), 4.002 (1.02), 4.020 (2.25), 4.037 (2.22), 4.055 (0.99), 4.703 (0.79), 4.718 (1.35), 4.726 (1.43), 4.747 (1.44), 4.764 (3.32), 4.777 (5.94), 4.790 (2.69), 6.559 (9.51), 6.581 (9.58), 7.280 (1.33), 7.284 (1.45), 7.287 (1.39), 7.301 (2.68), 7.306 (2.81), 7.322 (1.50), 7.327 (1.54), 7.329 (1.42), 7.524 (1.63), 7.530 (1.72), 7.549 (2.56), 7.553 (2.59), 7.572 (1.72), 7.579 (1.66), 7.761 (0.88), 7.782 (1.90), 7.798 (1.86), 7.818 (0.79), 8.254 (9.96), 8.276 (9.63), 8.593 (10.07), 10.486 (5.14), 10.510 (4.93). |

TABLE 4-continued

| Ex. | | Analytical data |
|---|---|---|
| 27 | 1-(2,4-Difluorophenyl)-7-[(2-fluoroethyl)amino]-4-oxo-N-[(2R)-1,1,1-trifluorobutan-2-yl]-1,4-dihydro-1,8-naphthyridine-3-carboxamide<br><br>Compound from Ex. 67A and 2-fluoroethylamine hydrochloride (28% of theory) | LC-MS (Method 1): $R_t$ = 1.08 min<br>MS (ESpos): m/z = 473.3 [M + H]$^+$<br>$^1$H-NMR (400 MHz, DMSO-d$_6$) δ [ppm]: −0.010 (1.41), 0.943 (7.22), 0.961 (16.00), 0.980 (7.84), 1.594 (1.08), 1.612 (1.45), 1.619 (1.30), 1.628 (1.78), 1.637 (1.59), 1.647 (1.52), 1.654 (1.72), 1.672 (1.30), 1.846 (1.27), 1.856 (1.47), 1.864 (1.51), 1.875 (1.70), 1.881 (1.52), 1.891 (1.34), 1.900 (1.15), 1.908 (1.18), 3.161 (5.33), 3.174 (5.48), 3.241 (1.95), 4.075 (1.84), 4.088 (1.80), 4.248 (2.71), 4.366 (2.71), 4.727 (1.47), 4.743 (1.38), 6.728 (4.34), 6.750 (4.47), 7.298 (1.44), 7.319 (2.88), 7.336 (1.53), 7.340 (1.58), 7.539 (1.60), 7.546 (1.68), 7.565 (2.66), 7.568 (2.69), 7.587 (1.71), 7.594 (1.66), 7.805 (1.94), 7.813 (1.70), 7.827 (1.93), 8.199 (5.46), 8.221 (5.11), 8.602 (5.92), 10.503 (4.35), 10.527 (4.24). |
| 28 | 7-(6,6-Difluoro-3-azabicyclo[3.1.0]hex-3-yl)-1-(2,4-difluorophenyl)-4-oxo-N-[(2R)-1,1,1-trifluorobutan-2-yl]-1,4-dihydro-1,8-naphthyridine-3-carboxamide<br><br>Compound from Ex. 67A and 6,6-difluoro-3-azabicylo[3.1.0]hexane hydrochloride (81% of theory) | LC-MS (Method 1): $R_t$ = 1.14 min<br>MS (ESpos): m/z = 529.2 [M + H]$^+$<br>$^1$H-NMR (400 MHz, DMSO-d$_6$) δ [ppm]: −0.009 (5.85), 0.007 (5.33), 0.946 (5.73), 0.965 (12.67), 0.983 (6.30), 1.156 (4.25), 1.174 (8.61), 1.192 (4.36), 1.615 (1.09), 1.623 (0.95), 1.632 (1.35), 1.641 (1.24), 1.650 (1.18), 1.658 (1.35), 1.676 (0.99), 1.849 (1.00), 1.858 (1.19), 1.867 (1.21), 1.877 (1.36), 1.884 (1.23), 1.894 (1.09), 1.987 (16.00), 2.365 (1.97), 2.519 (3.11), 2.522 (3.24), 2.561 (1.42), 2.563 (1.28), 2.623 (1.10), 2.669 (1.19), 2.709 (2.96), 2.730 (1.03), 3.438 (1.56), 3.818 (2.15), 4.002 (1.31), 4.020 (3.85), 4.038 (3.83), 4.055 (1.28), 4.733 (1.15), 4.747 (1.10), 6.772 (5.99), 6.794 (6.14), 7.309 (1.00), 7.329 (1.92), 7.346 (1.08), 7.581 (1.05), 7.815 (1.42), 7.831 (1.36), 8.318 (6.82), 8.340 (6.51), 8.638 (6.35), 10.443 (3.83), 10.467 (3.73). |
| 29 | 7-(1,1-Difluoro-5-azaspiro[2.4]hept-5-yl)-1-(2,4-difluorophenyl)-4-oxo-N-[(2R)-1,1,1-trifluorobutan-2-yl]-1,4-dihydro-1,8-naphthyridine-3-carboxamide (diastereomer mixture)<br><br>Compound from Ex. 67A and 1,1-difluoro-5-azaspiro[2.4]heptane hydrochloride (74% of theory) | LC-MS (Method 1): $R_t$ = 1.23 min<br>MS (ESpos): m/z = 543.2 [M + H]$^+$<br>$^1$H-NMR (400 MHz, DMSO-d$_6$) δ [ppm]: −0.150 (2.00), 0.007 (16.00), 0.146 (1.96), 0.948 (5.32), 0.967 (10.79), 0.986 (5.25), 1.156 (3.44), 1.174 (6.39), 1.192 (3.21), 1.237 (0.78), 1.618 (3.03), 1.634 (2.73), 1.860 (1.18), 1.870 (1.26), 1.879 (1.29), 1.896 (1.18), 1.987 (12.34), 2.127 (0.96), 2.327 (1.74), 2.366 (6.87), 2.671 (1.81), 2.710 (6.54), 3.599 (0.92), 4.002 (1.18), 4.020 (2.85), 4.038 (2.85), 4.055 (0.92), 4.735 (1.22), 6.783 (1.18), 7.297 (1.22), 7.316 (2.11), 7.333 (1.18), 7.539 (1.07), 7.558 (1.81), 7.580 (0.96), 7.805 (1.55), 7.819 (1.59), 8.315 (3.92), 8.338 (3.77), 8.629 (5.54), 10.468 (3.21), 10.492 (3.07). |

TABLE 4-continued

| Ex. | | Analytical data |
|---|---|---|
| 30 | 1-(2,4-Difluorophenyl)-7-(3-fluoro-3-methylpyrrolidin-1-yl)-4-oxo-N-[(2R)-1,1,1-trifluorobutan-2-yl]-1,4-dihydro-1,8-naphthyridine-3-carboxamide (diastereomer mixture)<br>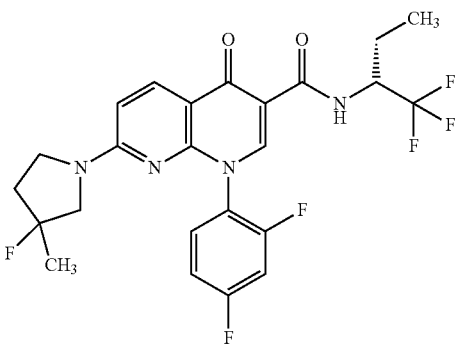<br>Compound from Ex. 67A and 3-fluoro-3-methylpyrrolidine para-toluenesulphonic acid salt<br>(85% of theory) | LC-MS (Method 1): $R_t$ = 1.26 min<br>MS (ESpos): m/z = 513.3 [M + H]$^+$<br>$^1$H-NMR (400 MHz, DMSO-d$_6$) δ [ppm]:<br>−0.002 (16.00), 0.948 (5.01), 0.967 (11.10),<br>0.985 (5.46), 1.156 (1.21), 1.173 (2.44),<br>1.191 (1.23), 1.459 (1.19), 1.511 (2.33),<br>1.565 (1.27), 1.599 (0.91), 1.617 (1.07),<br>1.624 (0.94), 1.633 (1.24), 1.642 (1.13),<br>1.652 (1.06), 1.659 (1.21), 1.677 (0.91),<br>1.695 (0.26), 1.850 (0.89), 1.860 (1.04),<br>1.868 (1.07), 1.878 (1.19), 1.885 (1.05),<br>1.895 (0.94), 1.903 (0.82), 1.913 (0.70),<br>1.987 (4.81), 2.137 (0.61), 2.366 (0.59),<br>2.709 (0.59), 3.166 (7.39), 3.532 (0.58),<br>3.699 (0.58), 4.001 (0.41), 4.019 (1.16),<br>4.037 (1.20), 4.055 (0.66), 4.077 (1.28),<br>4.089 (1.19), 4.733 (1.03), 4.752 (0.97),<br>6.755 (0.65), 6.797 (0.60), 7.305 (0.82),<br>7.325 (1.62), 7.343 (0.96), 7.575 (1.25),<br>7.595 (0.87), 7.810 (1.27), 7.826 (1.24),<br>8.309 (1.63), 8.330 (1.59), 8.625 (5.70),<br>10.476 (3.51), 10.500 (3.39). |
| 31 | 1-(2,4-Difluorophenyl)-7-[(2R,4S)-4-fluoro-2-methylpyrrolidin-1-yl]-4-oxo-N-[(2R)-1,1,1-trifluorobutan-2-yl]-1,4-dihydro-1,8-naphthyridine-3-carboxamide<br>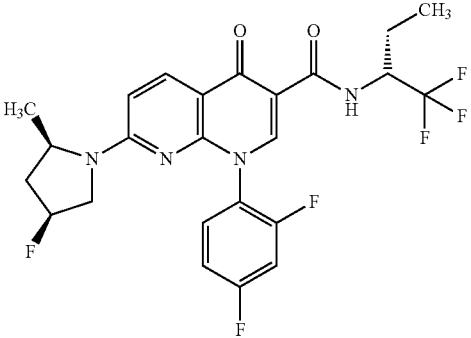<br>Compound from Ex. 67A and (2R,4S)-4-fluoro-2-methylpyrrolidine para-toluenesulphonic acid salt<br>(70% of theory) | LC-MS (Method 1): $R_t$ = 1.27 min<br>MS (ESpos): m/z = 513.3 [M + H]$^+$<br>$^1$H-NMR (400 MHz, DMSO-d$_6$) δ [ppm]:<br>−0.150 (0.90), −0.009 (8.02), 0.007 (7.82),<br>0.145 (0.90), 0.891 (0.90), 0.949 (7.45),<br>0.968 (16.00), 0.986 (8.02), 1.047 (1.02),<br>1.133 (0.70), 1.146 (0.90), 1.156 (0.94),<br>1.174 (1.51), 1.192 (0.98), 1.235 (0.57),<br>1.600 (1.06), 1.618 (1.43), 1.625 (1.35),<br>1.635 (1.68), 1.643 (1.60), 1.653 (1.47),<br>1.660 (1.72), 1.679 (1.35), 1.698 (0.37),<br>1.851 (1.35), 1.861 (1.51), 1.870 (1.64),<br>1.880 (1.88), 1.886 (1.72), 1.896 (1.64),<br>1.904 (1.51), 1.914 (1.43), 1.987 (2.58),<br>2.226 (0.53), 2.251 (0.53), 2.322 (1.15),<br>2.327 (1.47), 2.331 (1.19), 2.347 (0.57),<br>2.365 (6.55), 2.454 (0.45), 2.518 (6.51),<br>2.564 (2.25), 2.567 (2.13), 2.575 (1.15),<br>2.585 (0.65), 2.589 (0.49), 2.594 (0.49),<br>2.596 (0.49), 2.611 (0.41), 2.665 (0.90),<br>2.669 (1.19), 2.674 (0.86), 2.709 (6.38),<br>3.161 (2.46), 3.174 (2.70), 3.443 (0.37),<br>3.456 (0.49), 3.820 (0.53), 3.916 (0.53),<br>4.002 (0.41), 4.020 (0.57), 4.038 (0.61),<br>4.061 (0.37), 4.074 (0.70), 4.087 (0.70),<br>4.712 (0.82), 4.735 (1.39), 4.754 (1.35),<br>5.331 (0.70), 5.462 (0.70), 6.759 (0.82),<br>7.307 (1.27), 7.328 (2.58), 7.348 (1.43),<br>7.574 (1.47), 7.591 (1.64), 7.792 (1.15),<br>7.813 (2.33), 7.829 (2.25), 7.850 (1.06),<br>8.306 (7.53), 8.328 (7.12), 8.644 (9.49),<br>10.479 (5.07), 10.503 (4.87). |

TABLE 4-continued

| Ex. | | Analytical data |
|---|---|---|
| 32 | 1-(2,4-Difluorophenyl)-7-(3-fluoroazetidin-1-yl)-4-oxo-N-[(2R)-1,1,1-trifluorobutan-2-yl]-1,4-dihydro-1,8-naphthyridine-3-carboxamide<br>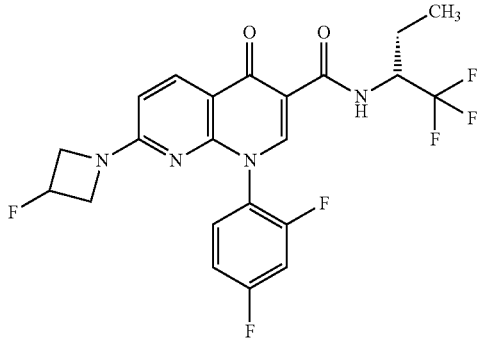<br>Compound from Ex. 67A and 3-fluoroazetidine hydrochloride<br>(37% of theory) | LC-MS (Method 1): $R_t$ = 1.19 min<br>MS (ESpos): m/z = 485.3 [M + H]$^+$<br>$^1$H-NMR (400 MHz, DMSO-d$_6$) δ [ppm]:<br>−0.013 (4.92), 0.003 (4.10), 0.851 (3.11),<br>0.869 (6.83), 0.887 (3.72), 0.940 (7.25),<br>0.959 (16.00), 0.977 (7.76), 1.083 (1.53),<br>1.103 (2.06), 1.123 (1.81), 1.276 (1.29),<br>1.295 (2.23), 1.313 (2.25), 1.573 (1.82),<br>1.592 (2.84), 1.611 (2.42), 1.628 (1.99),<br>1.636 (1.74), 1.646 (1.61), 1.653 (1.84),<br>1.671 (1.50), 1.844 (1.34), 1.854 (1.55),<br>1.863 (1.53), 1.872 (1.73), 1.879 (1.53),<br>1.889 (1.38), 1.983 (1.34), 4.016 (1.51),<br>4.033 (1.42), 4.260 (1.47), 4.728 (1.44),<br>4.748 (1.39), 5.365 (1.42), 5.372 (1.67),<br>5.379 (1.36), 5.508 (1.35), 5.515 (1.72),<br>5.522 (1.36), 6.654 (9.23), 6.676 (9.40),<br>7.289 (1.50), 7.306 (2.80), 7.311 (2.88),<br>7.328 (1.57), 7.332 (1.64), 7.527 (1.81),<br>7.534 (1.84), 7.553 (2.73), 7.556 (2.77),<br>7.576 (1.81), 7.582 (1.71), 7.792 (2.02),<br>7.808 (1.97), 8.320 (9.70), 8.342 (9.33),<br>8.629 (10.09), 10.427 (4.92), 10.450 (4.79). |
| 33 | 1-(2,4-Difluorophenyl)-7-[(3R,4R)-4-fluoro-3-hydroxypiperidin-1-yl]-4-oxo-N-[(2R)-1,1,1-trifluorobutan-2-yl]-1,4-dihydro-1,8-naphthyridine-3-carboxamide<br>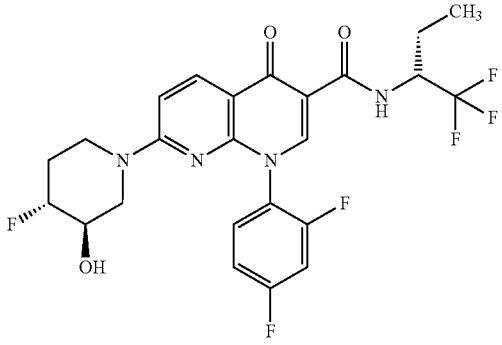<br>Compound from Ex. 67A and (4R)-fluoro-(3R)-piperidinol (HCl salt)<br>(75% of theory) | LC-MS (Method 1): $R_t$ = 1.07 min<br>MS (ESpos): m/z = 529.3 [M + H]$^+$<br>$^1$H-NMR (500 MHz, DMSO-d$_6$) δ [ppm]:<br>−0.005 (6.51), 0.949 (7.71), 0.964 (16.00),<br>0.978 (7.85), 1.483 (1.21), 1.605 (1.14),<br>1.611 (0.61), 1.620 (1.52), 1.626 (1.37),<br>1.633 (1.76), 1.640 (1.60), 1.648 (1.52),<br>1.654 (1.65), 1.668 (1.22), 1.840 (0.49),<br>1.855 (1.29), 1.862 (1.50), 1.869 (1.53),<br>1.877 (1.72), 1.882 (1.56), 1.890 (1.39),<br>1.897 (1.19), 1.905 (1.04), 1.977 (1.18),<br>1.986 (1.37), 3.044 (0.64), 3.172 (1.08),<br>3.180 (1.05), 3.207 (0.72), 3.216 (0.73),<br>3.242 (1.01), 3.262 (0.72), 3.458 (1.12),<br>3.800 (0.90), 3.879 (0.84), 3.910 (1.36),<br>3.940 (0.77), 4.427 (0.95), 4.525 (0.97),<br>4.733 (1.48), 4.745 (1.40), 4.761 (0.80),<br>5.444 (1.68), 5.454 (2.00), 5.463 (2.46),<br>5.473 (2.06), 7.144 (6.66), 7.162 (6.72),<br>7.314 (1.45), 7.331 (2.76), 7.345 (1.54),<br>7.539 (0.72), 7.561 (1.54), 7.582 (1.53),<br>7.602 (0.74), 7.811 (1.41), 7.822 (1.95),<br>7.834 (1.51), 8.289 (3.51), 8.293 (3.42),<br>8.307 (3.42), 8.311 (3.20), 8.636 (6.64),<br>10.447 (4.07), 10.466 (3.95). |

| Ex. | | Analytical data |
|---|---|---|
| 34 | 1-(2,4-Difluorophenyl)-7-[3-fluoro-4,4-dihydroxypiperidin-1-yl]-4-oxo-N-[(2R)-1,1,1-trifluorobutan-2-yl]-1,4-dihydro-1,8-naphthyridine-3-carboxamide (diastereomer mixture)<br>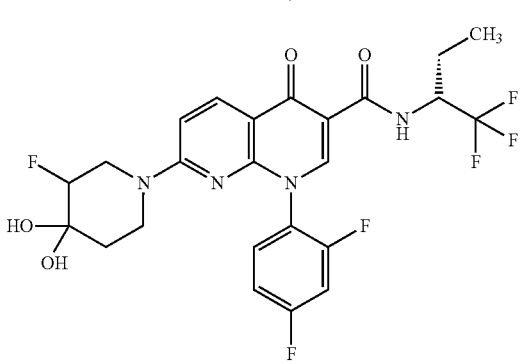<br>Compound from Ex. 67A and rac. 3-fluoropiperidin-4-one hydrochloride. Purification by preparative HPLC (eluent: acetonitrile/water gradient with 0.1% formic acid). (10% of theory) | LC-MS (Method 1): $R_t$ = 0.95 min<br>MS (ESpos): m/z = 545.4 [M + H]$^+$<br>$^1$H-NMR (400 MHz, DMSO-$d_6$) δ [ppm]: −0.150 (1.60), −0.009 (15.46), 0.007 (13.56), 0.146 (1.68), 0.824 (0.88), 0.841 (2.18), 0.857 (3.04), 0.875 (1.57), 0.946 (7.18), 0.964 (16.00), 0.982 (8.24), 1.052 (0.41), 1.073 (0.52), 1.146 (0.93), 1.235 (1.42), 1.291 (1.44), 1.551 (1.16), 1.597 (1.83), 1.614 (2.50), 1.631 (3.47), 1.641 (3.64), 1.649 (3.77), 1.658 (3.02), 1.675 (1.98), 1.849 (1.38), 1.858 (1.98), 1.867 (2.13), 1.876 (2.22), 1.884 (2.29), 1.893 (1.94), 1.911 (1.25), 1.919 (0.95), 2.327 (2.16), 2.366 (3.80), 2.406 (1.08), 2.669 (2.24), 2.709 (3.13), 2.992 (0.58), 3.173 (8.88), 3.935 (0.80), 4.055 (0.71), 4.087 (0.73), 4.151 (0.60), 4.277 (1.90), 4.387 (0.67), 4.466 (0.56), 4.563 (0.97), 4.745 (1.94), 4.930 (0.37), 5.041 (0.39), 5.960 (1.49), 5.974 (1.79), 6.061 (1.51), 6.271 (1.01), 6.322 (1.08), 7.144 (2.37), 7.155 (2.05), 7.167 (2.67), 7.179 (2.05), 7.320 (1.81), 7.341 (3.47), 7.355 (3.82), 7.378 (2.54), 7.394 (1.83), 7.468 (0.37), 7.565 (1.55), 7.590 (3.13), 7.613 (2.18), 7.817 (2.11), 7.830 (2.35), 7.853 (1.90), 8.271 (2.74), 8.281 (2.72), 8.294 (2.85), 8.303 (2.46), 8.406 (5.13), 8.428 (4.72), 8.630 (5.80), 8.708 (2.98), 8.715 (3.39), 10.386 (2.67), 10.409 (2.46), 10.443 (2.44), 10.451 (2.31), 10.468 (2.50). |
| 35 | 7-(3,3-Difluoro-4,4-dihydroxypiperidin-1-yl)-1-(2,4-difluorophenyl)-4-oxo-N-[(2R)-1,1,1-trifluorobutan-2-yl]-1,4-dihydro-1,8-naphthyridine-3-carboxamide<br>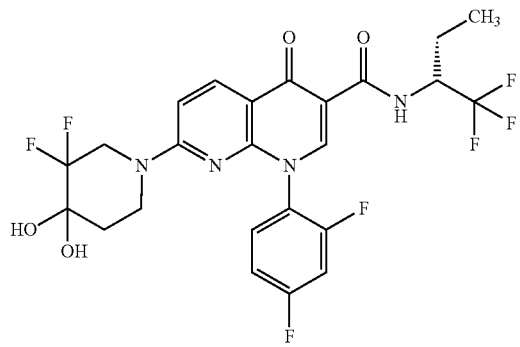<br>Compound from Ex. 67A and 3,3-difluoropiperidin-4-one hydrochloride, purified via preparative HPLC (eluent: acetonitrile/water gradient with 0.1% formic acid. (62% of theory) | LC-MS (Method 1): $R_t$ = 0.97 min<br>MS (ESpos): m/z = 563.4 [M + H]$^+$<br>$^1$H-NMR (400 MHz, DMSO-$d_6$) δ [ppm]: −0.009 (3.57), 0.007 (3.08), 0.878 (1.06), 0.897 (2.32), 0.915 (1.20), 0.946 (7.02), 0.964 (15.55), 0.983 (7.62), 1.156 (3.54), 1.174 (7.22), 1.191 (3.64), 1.599 (1.09), 1.617 (1.49), 1.624 (1.38), 1.634 (1.87), 1.643 (1.90), 1.652 (2.23), 1.660 (3.02), 1.677 (3.45), 1.719 (1.10), 1.725 (1.09), 1.735 (1.10), 1.743 (1.04), 1.753 (0.94), 1.851 (1.22), 1.860 (1.42), 1.869 (1.41), 1.879 (1.61), 1.885 (1.45), 1.896 (1.25), 1.904 (1.15), 1.914 (0.91), 1.987 (13.10), 2.523 (1.19), 3.243 (14.94), 3.563 (2.61), 3.842 (1.83), 4.001 (1.06), 4.019 (3.06), 4.037 (3.03), 4.055 (1.02), 4.736 (1.36), 4.751 (1.28), 5.752 (2.70), 6.432 (16.00), 6.787 (5.50), 7.238 (2.48), 7.253 (2.10), 7.261 (2.70), 7.275 (1.77), 7.329 (1.38), 7.350 (2.70), 7.366 (1.42), 7.371 (1.44), 7.574 (1.36), 7.580 (1.33), 7.599 (2.36), 7.622 (1.39), 7.628 (1.22), 7.818 (1.57), 7.830 (1.84), 7.842 (1.61), 8.320 (5.05), 8.330 (3.54), 8.343 (4.70), 8.353 (3.13), 8.658 (4.55), 8.661 (4.61), 8.665 (4.83), 10.399 (2.31), 10.408 (3.19), 10.424 (2.26), 10.432 (2.93). |

Example 36

1-(2,4-Difluorophenyl)-7-(dimethylamino)-4-oxo-N-(tricyclo[3.3.1.1³,⁷]dec-1-yl)-1,4-dihydro-1,8-naphthyridine-3-carboxamide

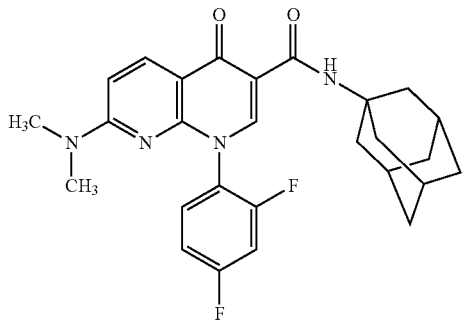 [SMILES: CN(C)c1ccc2c(=O)c(C(=O)NC34CC5CC(CC(C5)C3)C4)cn(-c3ccc(F)cc3F)c2n1]

80 mg (0.23 mmol) of the compound from example 36A were initially charged in 2.3 ml of DMF, 106 mg (0.28 mmol) of HATU and 99 mg (0.77 mmol) of DIPEA were added, and the mixture was stirred at 20° C. for 30 minutes. Then 49 mg (0.32 mmol) of 1-adamantanamine were added and the mixture was stirred at 20° C. for 2 hours. Subsequently, the mixture was purified via preparative HPLC (eluent: acetonitrile/water gradient with 0.1% formic acid). This gave 63 mg (57% of theory) of the title compound.

LC-MS (Method 1): $R_t$=1.34 min; m/z=479 [M+H]$^+$.

$^1$H-NMR (400 MHz, DMSO-$d_6$) δ [ppm]: −0.008 (2.42), 0.009 (2.27), 1.671 (7.70), 2.054 (16.00), 2.076 (1.22), 2.936 (2.35), 6.892 (2.41), 6.915 (2.39), 7.304 (0.41), 7.319 (0.71), 7.327 (0.84), 7.340 (0.41), 7.346 (0.47), 7.350 (0.41), 7.554 (0.53), 7.560 (0.54), 7.575 (0.69), 7.580 (0.79), 7.586 (0.68), 7.602 (0.55), 7.609 (0.52), 7.767 (0.50), 7.781 (0.59), 7.789 (1.00), 7.803 (0.99), 7.810 (0.55), 7.825 (0.46), 8.251 (2.69), 8.275 (2.54), 8.477 (5.26), 9.952 (2.61).

In analogy to Example 36, the example compounds shown in Table 5 were prepared by reacting the compound from Example 36A or 60A with the appropriate amines (or salts thereof) under the reaction conditions described. Differences are specified in the respective examples.

TABLE 5

| Ex. | | Analytical data |
|---|---|---|
| 37 | 1-(2,4-Difluorophenyl)-7-(dimethylamino)-N-(3-fluorotricyclo[3.3.1.1³,⁷]dec-1-yl)-4-oxo-1,4-dihydro-1,8-naphthyridine-3-carboxamide<br><br>(33% of theory) | LC-MS (Method 1): $R_t$ = 1.29 min<br>MS (ESpos): m/z = 497.3 [M + H]$^+$<br>$^1$H-NMR (400 MHz, CDCl$_3$) δ [ppm]: 0.009 (6.24), 0.017 (0.22), 0.078 (0.31), 1.576 (16.00), 1.631 (0.21), 1.889 (0.30), 1.944 (0.26), 2.015 (0.21), 2.053 (0.18), 2.083 (0.35), 2.137 (0.30), 2.379 (0.60), 2.450 (0.15), 2.795 (0.16), 2.993 (1.92), 3.500 (0.66), 6.656 (0.74), 6.679 (0.75), 7.007 (0.28), 7.022 (0.32), 7.028 (0.30), 7.041 (0.32), 7.047 (0.28), 7.059 (0.15), 7.351 (0.15), 7.372 (0.19), 7.386 (0.20), 7.394 (0.14), 7.409 (0.12), 7.529 (0.15), 8.407 (0.75), 8.429 (0.73), 8.627 (1.17), 10.134 (0.34). |
| 38 | 1-(2,4-Difluorophenyl)-N-(3,5-difluorotricyclo[3.3.1.1³,⁷]dec-1-yl)-7-(dimethylamino)-4-oxo-1,4-dihydro-1,8-naphthyridine-3-carboxamide]<br><br>(61% of theory) | LC-MS (Method 1): $R_t$ = 1.16 min<br>MS (ESpos): m/z = 515.3 [M + H]$^+$<br>$^1$H-NMR (400 MHz, DMSO-$d_6$) δ [ppm]: −0.009 (9.96), 0.007 (6.42), 1.803 (11.32), 1.899 (7.42), 2.072 (2.34), 2.138 (3.86), 2.317 (4.06), 2.939 (8.32), 3.161 (10.82), 3.174 (10.98), 4.062 (1.20), 4.075 (3.14), 4.088 (3.06), 6.902 (7.86), 6.925 (7.90), 7.303 (1.50), 7.325 (2.64), 7.341 (1.46), 7.554 (1.88), 7.576 (2.60), 7.595 (1.78), 7.766 (1.76), 7.788 (3.30), 7.803 (3.20), 7.825 (1.56), 8.256 (8.82), 8.279 (8.28), 8.512 (16.00), 10.263 (7.66). |

TABLE 5-continued

| Ex. | | Analytical data |
|---|---|---|
| 39 | 1-(2,4-Difluorophenyl)-N-(4,4-difluorotricyclo[3.3.1.1³,⁷]dec-1-yl)-7-(dimethylamino)-4-oxo-1,4-dihydro-1,8-naphthyridine-3-carboxamide<br>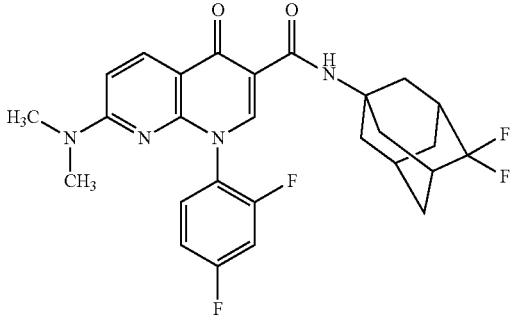<br>(28% of theory) | LC-MS (Method 1): $R_t$ = 1.26 min<br>MS (ESpos): m/z = 515.3 [M + H]⁺<br>¹H-NMR (400 MHz, DMSO-$d_6$) δ [ppm]: 1.785 (9.36), 2.065 (16.00), 2.277 (8.35), 2.362 (2.47), 2.932 (8.32), 6.892 (5.42), 6.914 (5.67), 7.318 (2.44), 7.571 (2.32), 7.778 (2.38), 8.246 (5.88), 8.269 (5.64), 8.483 (10.54), 10.042 (6.95). |
| 40 | 1-(2-Chloro-4-fluorophenyl)-N-(4,4-difluorotricyclo[3.3.1.1³,⁷]dec-1-yl)-7-(dimethylamino)-4-oxo-1,4-dihydro-1,8-naphthyridine-3-carboxamide<br>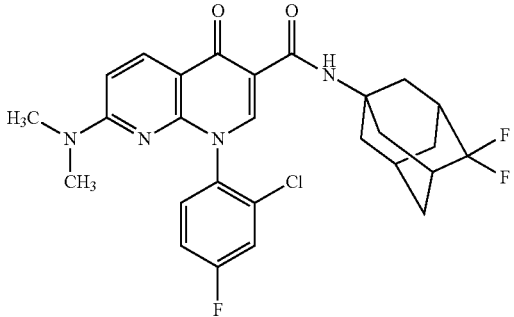 [SMILES: CN(C)c1ccc2c(=O)c(C(=O)NC34CC5CC(C3)C(F)(F)C(C5)C4)cn(-c3ccc(F)cc3Cl)c2n1]<br>Compound from Ex. 60A<br>(45% of theory) | LC-MS (Method 1): $R_t$ = 1.30 min<br>MS (ESpos): m/z = 531.2 [M + H]⁺<br>¹H-NMR (400 MHz, DMSO-$d_6$) δ [ppm]: 1.790 (8.79), 2.068 (16.00), 2.280 (7.81), 2.366 (2.24), 2.709 (2.36), 2.906 (6.43), 6.882 (6.22), 6.905 (6.28), 7.473 (2.99), 7.494 (1.91), 7.773 (4.13), 7.787 (4.64), 7.809 (2.78), 8.250 (6.52), 8.272 (6.22), 8.410 (12.62), 10.064 (7.15). |
| 41 | 1-(2,4-Difluorophenyl)-7-(dimethylamino)-N-(3-methyltricyclo[3.3.1.1³,⁷]dec-1-yl)-4-oxo-1,4-dihydro-1,8-naphthyridine-3-carboxamide<br>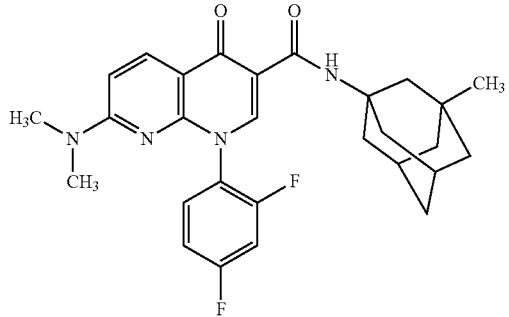<br>(67% of theory) | LC-MS (Method 1): $R_t$ = 1.41 min<br>MS (ESpos): m/z = 493.3 [M + H]⁺<br>¹H-NMR (400 MHz, DMSO-$d_6$) δ [ppm]: 0.836 (16.00), 1.415 (9.74), 1.516 (1.11), 1.546 (1.92), 1.599 (1.99), 1.630 (1.04), 1.761 (7.37), 1.912 (2.13), 1.940 (3.65), 1.999 (3.82), 2.027 (2.14), 2.092 (4.16), 2.366 (0.43), 2.936 (6.28), 6.890 (3.74), 6.912 (3.75), 7.302 (0.93), 7.318 (1.65), 7.339 (0.89), 7.553 (0.98), 7.572 (1.58), 7.595 (0.96), 7.758 (0.93), 7.779 (1.71), 7.794 (1.68), 7.816 (0.79), 8.247 (3.92), 8.269 (3.64), 8.467 (6.71), 9.958 (4.38). |

| Ex. | | Analytical data |
|---|---|---|
| 42 | 1-(2,4-Difluorophenyl)-7-(dimethylamino)-N-(4-methylbicyclo[2.2.2]oct-1-yl)-4-oxo-1,4-dihydro-1,8-naphthyridine-3-carboxamide 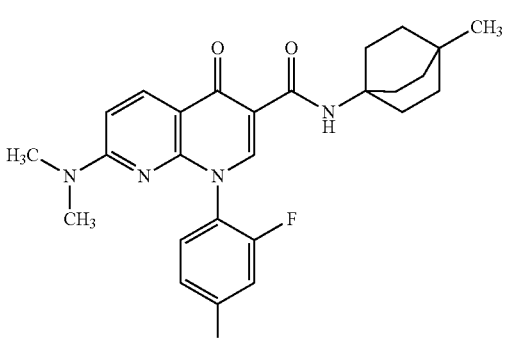 (96% of theory) | LC-MS (Method 1): $R_t$ = 1.38 min<br>MS (ESpos): m/z = 467.3 [M + H]$^+$<br>$^1$H-NMR (400 MHz, DMSO-d$_6$) δ [ppm]: −0.014 (1.72), 0.003 (1.72), 0.781 (16.00), 1.442 (4.66), 1.461 (6.05), 1.481 (5.60), 1.888 (5.60), 1.900 (5.04), 1.909 (5.99), 1.928 (4.77), 2.726 (8.77), 2.885 (12.33), 2.928 (4.93), 6.879 (4.49), 6.902 (4.55), 7.285 (0.67), 7.289 (0.74), 7.292 (0.70), 7.306 (1.37), 7.311 (1.42), 7.328 (0.78), 7.332 (0.80), 7.335 (0.72), 7.534 (0.90), 7.541 (0.95), 7.560 (1.32), 7.563 (1.35), 7.582 (0.94), 7.589 (0.92), 7.748 (0.89), 7.763 (1.05), 7.769 (1.78), 7.784 (1.76), 7.791 (1.00), 7.806 (0.87), 7.947 (1.22), 8.238 (4.90), 8.260 (4.64), 8.462 (8.75), 9.879 (4.75). |
| 43 | N-tert-Butyl-1-(2,4-difluorophenyl)-7-(dimethylamino)-4-oxo-1,4-dihydro-1,8-naphthyridine-3-carboxamide 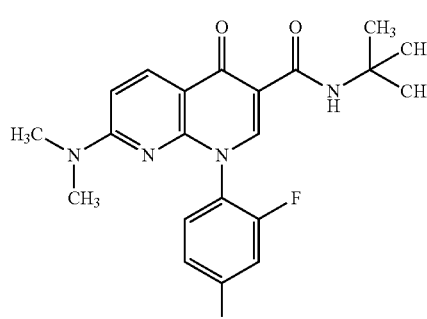 (88% of theory) | LC-MS (Method 1): $R_t$ = 1.12 min<br>MS (ESpos): m/z = 401.1 [M + H]$^+$<br>$^1$H-NMR (400 MHz, DMSO-d$_6$) δ [ppm]: −0.009 (0.52), 0.007 (0.34), 1.388 (16.00), 2.523 (0.72), 2.890 (0.41), 2.938 (1.24), 6.894 (1.26), 6.916 (1.25), 7.317 (0.34), 7.321 (0.34), 7.552 (0.25), 7.568 (0.32), 7.571 (0.33), 7.574 (0.33), 7.578 (0.29), 7.759 (0.24), 7.774 (0.29), 7.780 (0.46), 7.795 (0.46), 7.802 (0.26), 8.253 (1.33), 8.276 (1.27), 8.501 (2.21), 10.014 (1.06). |
| 44 | 1-(2,4-Difluorophenyl)-7-(dimethylamino)-4-oxo-N-[(2S)-1,1,1-trifluoropropan-2-yl]-1,4-dihydro-1,8-naphthyridine-3-carboxamide 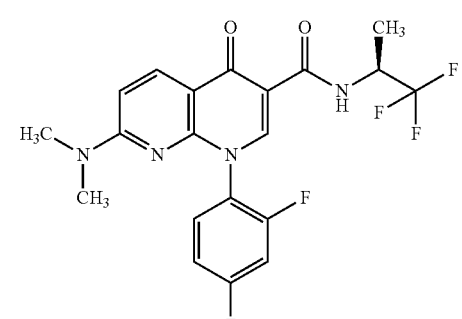 (35% of theory) | LC-MS (Method 1): $R_t$ = 1.13 min<br>MS (ESpos): m/z = 441.1 [M + H]$^+$<br>$^1$H-NMR (400 MHz, DMSO-d$_6$) δ [ppm]: −0.150 (1.10), −0.008 (11.13), 0.007 (9.84), 0.146 (1.10), 1.360 (15.85), 1.377 (16.00), 2.365 (0.82), 2.709 (0.88), 2.945 (6.97), 4.860 (1.15), 4.880 (1.78), 4.901 (1.81), 4.919 (1.13), 6.927 (7.86), 6.949 (8.04), 7.306 (1.38), 7.326 (2.83), 7.348 (1.53), 7.558 (1.54), 7.580 (2.58), 7.599 (1.57), 7.808 (1.47), 8.267 (8.65), 8.290 (8.27), 8.607 (6.53), 10.543 (3.31), 10.566 (3.23). |

TABLE 5-continued

| Ex. | | Analytical data |
|---|---|---|
| 45 | 1-(2,4-Difluorophenyl)-7-(dimethylamino)-4-oxo-N-[(2S)-1,1,1-trifluorobutan-2-yl]-1,4-dihydro-1,8-naphthyridine-3-carboxamide<br />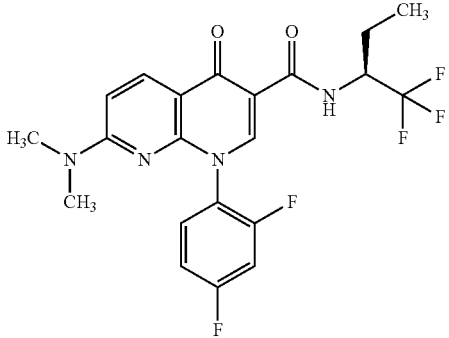 [SMILES: CC[C@H](NC(=O)c1cn(-c2ccc(F)cc2F)c2nc(N(C)C)ccc2c1=O)C(F)(F)F]<br />(74% of theory) | LC-MS (Method 1): $R_t$ = 1.21 min<br />MS (ESpos): m/z = 455.2 [M + H]$^+$<br />$^1$H-NMR (400 MHz, DMSO-d$_6$) δ [ppm]: −0.009 (4.23), 0.007 (4.21), 0.946 (7.18), 0.965 (16.00), 0.983 (7.72), 1.613 (1.53), 1.630 (1.75), 1.639 (1.51), 1.648 (1.41), 1.655 (1.78), 1.858 (1.43), 1.867 (1.52), 1.876 (1.65), 1.883 (1.44), 2.669 (1.34), 2.947 (6.45), 4.732 (1.34), 4.747 (1.36), 6.929 (9.58), 6.952 (9.93), 7.304 (1.41), 7.327 (2.80), 7.343 (1.55), 7.551 (1.78), 7.558 (1.87), 7.576 (2.74), 7.599 (1.90), 7.606 (1.86), 7.805 (1.90), 7.827 (1.83), 8.275 (11.06), 8.298 (10.59), 8.614 (7.21), 10.490 (4.78), 10.514 (4.65). |
| 46 | rac-1-(2,4-Difluorophenyl)-7-(dimethylamino)-4-oxo-N-[4,4,4-trifluorobutan-2-yl]-1,4-dihydro-1,8-naphthyridine-3-carboxamide<br />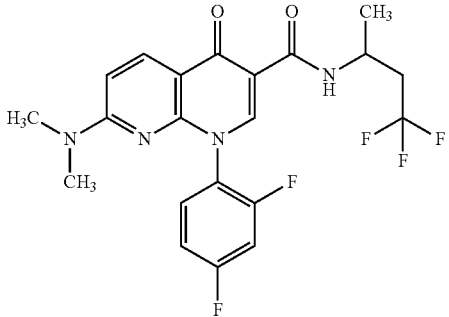 [SMILES: CC(CC(F)(F)F)NC(=O)c1cn(-c2ccc(F)cc2F)c2nc(N(C)C)ccc2c1=O]<br />(82% of theory) | LC-MS (Method 1): $R_t$ = 1.10 min<br />MS (ESpos): m/z = 455.3 [M + H]$^+$<br />$^1$H-NMR (400 MHz, DMSO-d$_6$) δ [ppm]: 1.272 (15.86), 1.289 (15.96), 2.522 (1.97), 2.560 (2.34), 2.573 (1.89), 2.589 (1.88), 2.602 (1.76), 2.653 (1.74), 2.672 (1.77), 2.939 (10.25), 4.357 (1.92), 4.373 (2.32), 4.388 (1.85), 6.900 (7.38), 6.923 (7.55), 7.317 (2.97), 7.322 (3.10), 7.343 (1.66), 7.546 (1.71), 7.553 (1.80), 7.572 (2.88), 7.594 (1.79), 7.601 (1.69), 7.791 (2.15), 8.252 (8.40), 8.275 (8.03), 8.534 (16.00), 10.126 (4.93), 10.147 (4.79). |
| 47 | 1-(2,4-Difluorophenyl)-7-(dimethylamino)-N-(4-fluorobicyclo[2.2.2]oct-1-yl)-4-oxo-1,4-dihydro-1,8-naphthyridine-3-carboxamide<br />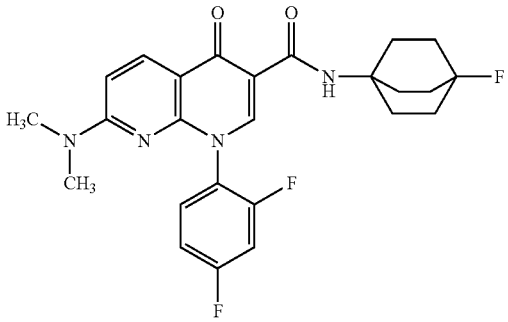 [SMILES: CN(C)c1ccc2c(=O)c(C(=O)NC34CCC(F)(CC3)CC4)cn(-c3ccc(F)cc3F)c2n1]<br />(85% of theory) | LC-MS (Method 1): $R_t$ = 1.19 min<br />MS (ESpos): m/z = 471.3 [M + H]$^+$<br />$^1$H-NMR (400 MHz, CDCl$_3$) δ [ppm]: 0.001 (0.16), 0.017 (0.15), 0.078 (0.09), 1.576 (16.00), 1.935 (0.16), 1.950 (0.30), 1.965 (0.31), 1.976 (0.33), 1.990 (0.21), 2.235 (0.37), 2.247 (0.28), 2.257 (0.35), 2.275 (0.28), 2.634 (0.10), 2.966 (0.08), 2.988 (0.82), 6.651 (0.35), 6.674 (0.36), 7.006 (0.15), 7.022 (0.15), 7.027 (0.14), 7.041 (0.15), 7.046 (0.12), 7.051 (0.09), 7.059 (0.07), 7.343 (0.07), 7.357 (0.08), 7.364 (0.08), 7.377 (0.09), 8.392 (0.37), 8.415 (0.36), 8.607 (0.58), 10.007 (0.15). |

TABLE 5-continued

| Ex. | | Analytical data |
|---|---|---|
| 48 | rac-N-[1-(2-Chlorophenyl)-2,2,2-trifluoroethyl]-1-(2,4-difluorophenyl)-7-(dimethylamino)-4-oxo-1,4-dihydro-1,8-naphthyridine-3-carboxamide<br />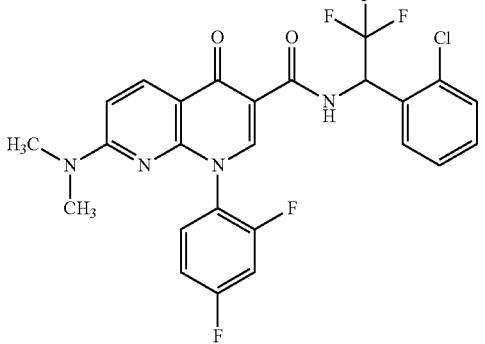<br />(74% of theory) | LC-MS (Method 1): $R_t$ = 1.19 min<br />MS (ESpos): m/z = 471.3 [M + H]$^+$<br />$^1$H-NMR (400 MHz, DMSO-d$_6$) δ [ppm]: −0.013 (6.67), 0.003 (6.02), 2.322 (0.99), 2.361 (1.40), 2.664 (1.24), 2.705 (1.56), 2.944 (4.69), 6.425 (1.75), 6.446 (2.37), 6.466 (1.61), 6.943 (8.07), 6.966 (8.08), 7.306 (1.62), 7.325 (1.64), 7.471 (1.19), 7.475 (1.31), 7.490 (3.28), 7.494 (3.47), 7.508 (3.26), 7.513 (3.29), 7.525 (2.21), 7.544 (4.34), 7.561 (3.07), 7.594 (7.00), 7.598 (7.38), 7.613 (5.54), 7.617 (4.99), 7.738 (0.97), 7.753 (0.91), 7.812 (0.95), 7.827 (0.96), 8.312 (9.17), 8.335 (8.61), 8.620 (16.00), 11.614 (2.88), 11.637 (2.62). |
| 49 | N-(2,6-Dichlorobenzyl)-1-(2,4-difluorophenyl)-7-(dimethylamino)-4-oxo-1,4-dihydro-1,8-naphthyridine-3-carboxamide<br />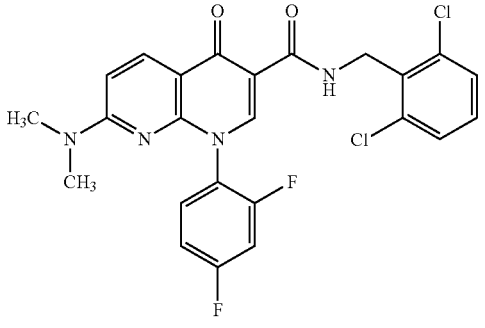 [SMILES: CN(C)c1ccc2c(=O)c(C(=O)NCc3c(Cl)cccc3Cl)cn(-c3ccc(F)cc3F)c2n1]<br />(73% of theory) | LC-MS (Method 1): $R_t$ = 1.22 min<br />MS (ESpos): m/z = 503.0 [M + H]$^+$<br />$^1$H-NMR (400 MHz, DMSO-d$_6$) δ [ppm]: 2.726 (3.73), 2.886 (6.85), 2.927 (11.71), 4.786 (4.36), 4.800 (4.64), 4.812 (4.61), 4.825 (4.28), 6.879 (8.07), 6.902 (8.27), 7.315 (3.57), 7.374 (3.40), 7.395 (6.06), 7.414 (5.77), 7.520 (16.00), 7.540 (12.58), 7.565 (3.42), 7.773 (3.72), 7.788 (3.61), 8.217 (8.38), 8.240 (8.00), 8.565 (14.86), 10.336 (2.96), 10.350 (5.68), 10.362 (2.79). |
| 50 | N-(2,4-Difluorobenzyl)-1-(2,4-difluorophenyl)-7-(dimethylamino)-4-oxo-1,4-dihydro-1,8-naphthyridine-3-carboxamide<br />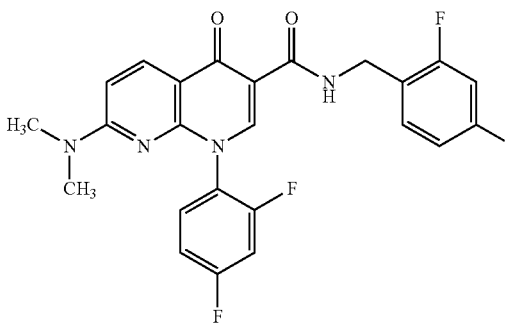<br />(78% of theory) | LC-MS (Method 1): $R_t$ = 1.15 min<br />MS (ESpos): m/z = 471.1 [M + H]$^+$<br />$^1$H-NMR (400 MHz, DMSO-d$_6$) δ [ppm]: −0.009 (7.30), 0.007 (6.62), 2.939 (8.43), 4.558 (4.82), 4.567 (4.86), 6.898 (7.29), 6.921 (7.44), 7.048 (1.32), 7.054 (1.43), 7.070 (2.82), 7.075 (2.95), 7.091 (1.54), 7.097 (1.58), 7.218 (1.78), 7.225 (1.74), 7.243 (2.60), 7.248 (2.50), 7.268 (1.90), 7.274 (1.76), 7.301 (1.33), 7.315 (2.57), 7.321 (2.64), 7.336 (1.40), 7.341 (1.43), 7.413 (1.64), 7.435 (3.27), 7.451 (3.31), 7.473 (1.48), 7.545 (1.64), 7.552 (1.70), 7.575 (2.53), 7.594 (1.75), 7.601 (1.63), 7.756 (1.66), 7.771 (1.95), 7.778 (3.29), 7.793 (3.27), 7.799 (1.86), 7.814 (1.57), 8.255 (8.00), 8.278 (7.61), 8.555 (16.00), 10.346 (2.21), 10.361 (4.55), 10.376 (2.15). |

TABLE 5-continued

| Ex. | | Analytical data |
|---|---|---|
| 51 | 1-(2,4-Difluorophenyl)-7-(dimethylamino)-N-(2,6-dimethylbenzyl)-4-oxo-1,4-dihydro-1,8-naphthyridine-3-carboxamide<br>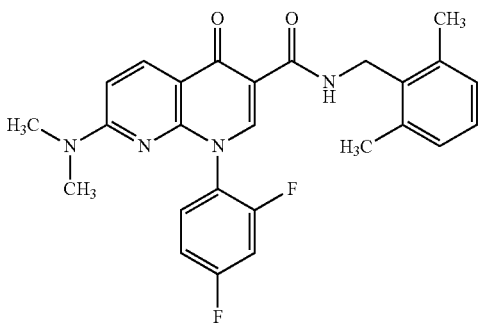 [SMILES: Cc1cccc(C)c1CNC(=O)c1cn(-c2ccc(F)cc2F)c2nc(N(C)C)ccc2c1=O]<br>(41% of theory) | LC-MS (Method 1): $R_t$ = 1.22 min<br>MS (ESpos): m/z = 463.2 [M + H]$^+$<br>$^1$H-NMR (400 MHz, DMSO-d$_6$) δ [ppm]: −0.013 (1.23), 0.003 (1.03), 2.068 (0.40), 2.393 (16.00), 2.922 (1.87), 4.526 (0.91), 4.540 (1.40), 4.554 (0.82), 6.869 (1.65), 6.892 (1.65), 7.043 (0.92), 7.060 (2.86), 7.084 (1.56), 7.099 (0.78), 7.106 (0.56), 7.121 (0.34), 7.294 (0.32), 7.311 (0.56), 7.337 (0.29), 7.540 (0.39), 7.547 (0.39), 7.566 (0.55), 7.588 (0.37), 7.595 (0.35), 7.750 (0.38), 7.771 (0.70), 7.786 (0.69), 7.808 (0.32), 8.198 (1.92), 8.221 (1.79), 8.564 (3.61), 10.077 (0.52), 10.090 (0.94), 10.102 (0.43). |
| 52 | 1-(2,4-Difluorophenyl)-N-(2,6-difluorophenyl)-7-(dimethylamino)-4-oxo-1,4-dihydro-1,8-naphthyridine-3-carboxamide<br>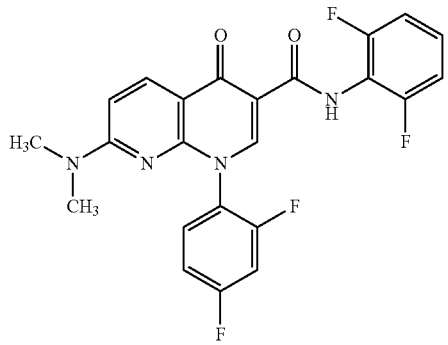 [SMILES: CN(C)c1ccc2c(=O)c(C(=O)Nc3c(F)cccc3F)cn(-c3ccc(F)cc3F)c2n1]<br>(62% of theory) | LC-MS (Method 1): $R_t$ = 1.13 min<br>MS (ESpos): m/z = 457.2 [M + H]$^+$<br>$^1$H-NMR (400 MHz, DMSO-d$_6$) δ [ppm]: −0.009 (2.92), 0.007 (2.64), 2.962 (5.97), 6.953 (7.45), 6.976 (7.64), 7.188 (4.26), 7.209 (9.81), 7.229 (6.29), 7.328 (2.60), 7.336 (3.06), 7.354 (3.59), 7.374 (3.14), 7.395 (1.60), 7.558 (1.60), 7.565 (1.68), 7.584 (2.45), 7.588 (2.46), 7.607 (1.70), 7.614 (1.64), 7.808 (1.66), 7.823 (1.94), 7.830 (3.26), 7.845 (3.24), 7.852 (1.81), 7.867 (1.58), 8.327 (8.17), 8.350 (7.85), 8.690 (16.00), 11.813 (9.92). |
| 53 | 1-(2,4-Difluorophenyl)-N-[2-(2,6-difluorophenyl)propan-2-yl]-7-(dimethylamino)-4-oxo-1,4-dihydro-1,8-naphthyridine-3-carboxamide<br>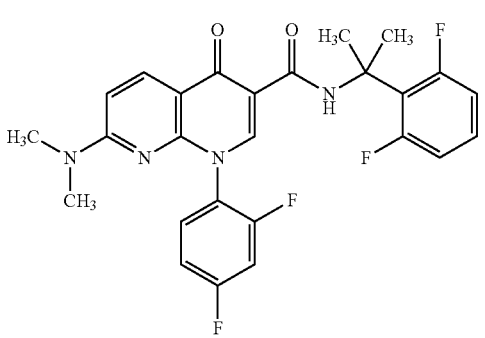 [SMILES: CN(C)c1ccc2c(=O)c(C(=O)NC(C)(C)c3c(F)cccc3F)cn(-c3ccc(F)cc3F)c2n1]<br>(100% of theory) | LC-MS (Method 1): $R_t$ = 1.22 min<br>MS (ESpos): m/z = 499.2 [M + H]$^+$<br>$^1$H-NMR (400 MHz, DMSO-d$_6$) δ [ppm]: −0.013 (8.59), 0.003 (7.77), 1.819 (16.00), 2.934 (4.18), 6.906 (4.62), 6.929 (6.51), 6.953 (3.18), 6.977 (2.76), 7.257 (2.44), 7.278 (2.11), 7.539 (1.48), 7.755 (1.87), 7.770 (1.85), 8.276 (5.32), 8.299 (4.95), 8.402 (10.08), 10.676 (4.51). |

| Ex. | | Analytical data |
|---|---|---|
| 54 | 1-(2,4-Difluorophenyl)-7-(dimethylamino)-N-(2,6-dimethylphenyl)-4-oxo-1,4-dihydro-1,8-naphthyridine-3-carboxamide<br>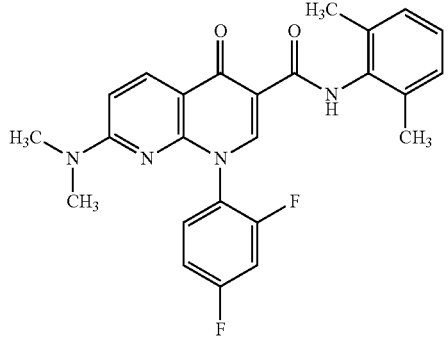 [SMILES: Cc1cccc(C)c1NC(=O)c1cn(-c2ccc(F)cc2F)c2nc(N(C)C)ccc2c1=O]<br>(72% of theory) | LC-MS (Method 1): $R_t$ = 1.20 min<br>MS (ESpos): m/z = 449.2 [M + H]$^+$<br>$^1$H-NMR (400 MHz, DMSO-$d_6$) δ [ppm]: −0.001 (3.96), 2.211 (16.00), 2.889 (0.60), 2.962 (1.78), 6.939 (1.47), 6.962 (1.47), 7.114 (6.25), 7.321 (0.66), 7.326 (0.65), 7.580 (0.61), 7.832 (0.70), 7.847 (0.69), 8.339 (1.66), 8.362 (1.57), 8.657 (3.43), 11.593 (1.96). |

Example 55

N-(2,6-Dichlorophenyl)-1-(2,4-difluorophenyl)-7-(dimethylamino)-4-oxo-1,4-dihydro-1,8-naphthyridine-3-carboxamide

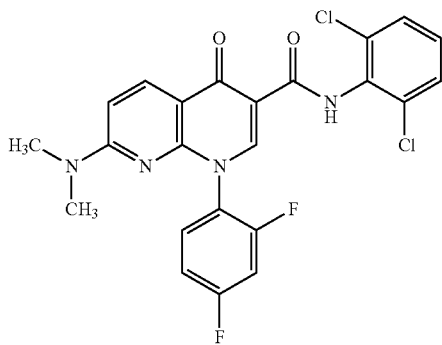 [SMILES: CN(C)c1ccc2c(=O)c(C(=O)Nc3c(Cl)cccc3Cl)cn(-c3ccc(F)cc3F)c2n1]

100 mg (0.29 mmol) of the compound from example 36A were initially charged in 3 ml of DMF, 132 mg (0.35 mmol) of HATU and 119 mg (0.93 mmol) of DIPEA were added, and the mixture was stirred at 20° C. for 30 minutes. Then a mixture of 66 mg (0.4 mmol) of 2,6-dichloroaniline and 29 mg (0.72 mmol) of NaH (60 percent in paraffin) was added and the mixture was stirred at 23° C. for 18 hours. Subsequently, the mixture was purified via preparative RP-HPLC (eluent: acetonitrile/water gradient with 0.1% formic acid). This gave 27 mg (19% of theory) of the title compound.

LC-MS (Method 1): $R_t$=1.38 min; m/z=523.3 [M+H]$^+$.

$^1$H-NMR (400 MHz, DMSO-$d_6$) δ [ppm]: −0.009 (1.63), 0.007 (1.55), 2.689 (15.32), 2.730 (12.82), 2.889 (16.00), 2.965 (4.17), 6.953 (6.16), 6.976 (6.30), 7.328 (2.09), 7.352 (3.89), 7.372 (5.08), 7.392 (4.16), 7.563 (1.58), 7.575 (15.18), 7.586 (2.51), 7.595 (12.02), 7.605 (1.69), 7.837 (1.53), 7.844 (2.57), 7.859 (2.51), 7.951 (1.95), 8.332 (6.93), 8.355 (6.69), 8.685 (13.85), 12.019 (7.76).

Example 56 rac-N-[1-(2,6-Dichlorophenyl)-2,2,2-trifluoroethyl]-1-(2,4-difluorophenyl)-7-(dimethylamino)-4-oxo-1,4-dihydro-1,8-naphthyridine-3-carboxamide

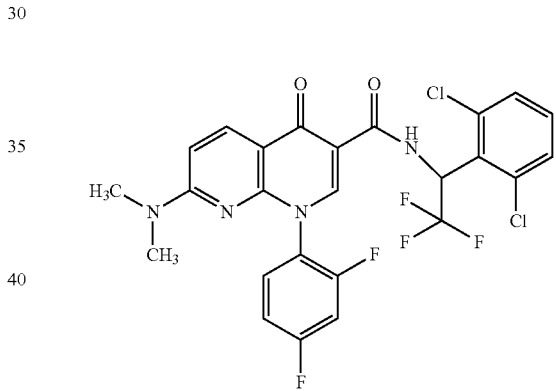

200 mg (0.58 mmol) of the compound from example 36A und 283 mg (1.2 mmol) of 1-(2,6-dichlorophenyl)-2,2,2-trifluoroethanamine were initially charged in 4 ml of DMF, 210 mg (1.6 mmol) of DIPEA and 422 mg (0.81 mmol) of PyBOP were added, and the mixture was stirred at 23° C. for 40 minutes. The reaction mixture was then adjusted to pH 1 with 1 M aqueous hydrochloric acid, and the precipitated solid was then filtered off with suction and washed with water and petroleum ether. This gave 300 mg (86% of theory, containing 0.25 eq. of DMF) of the title compound.

LC-MS (Method 1): $R_t$=1.36 min; m/z=571.0 [M+H]$^+$.

$^1$H-NMR (400 MHz, DMSO-$d_6$) δ [ppm]: −0.001 (16.00), 0.006 (0.72), 1.242 (0.19), 1.258 (0.19), 1.713 (0.27), 1.722 (0.31), 1.730 (0.67), 1.737 (0.27), 1.746 (0.25), 2.731 (2.00), 2.890 (2.47), 2.946 (0.87), 2.991 (0.45), 3.001 (0.49), 3.007 (0.62), 3.017 (0.60), 3.024 (0.38), 3.034 (0.25), 6.922 (0.96), 6.945 (0.97), 7.028 (0.15), 7.052 (0.20), 7.067 (0.21), 7.310 (0.24), 7.329 (0.27), 7.423 (0.17), 7.443 (0.14), 7.489 (0.45), 7.509 (1.14), 7.529 (0.87), 7.564 (0.36), 7.591 (0.82), 7.611 (0.50), 7.645 (0.69), 7.665 (0.52), 7.735 (0.15), 7.754 (0.15), 7.815 (0.15), 7.830 (0.15), 7.951 (0.33), 8.315 (1.18), 8.338 (1.08), 8.621 (0.72), 11.803 (0.29), 11.822 (0.27).

In analogy to Example 56, the example compounds shown in Table 6 were prepared by reacting the compound from Example 36A with the appropriate amines (or salts thereof) under the reaction conditions described. Differences are specified in the respective examples.

TABLE 6

| Ex. | | Analytical data |
|---|---|---|
| 57 | 1-(2,4-Difluorophenyl)-7-(dimethylamino)-4-oxo-N-[2-(trifluoromethyl)phenyl]-1,4-dihydro-1,8-naphthyridine-3-carboxamide<br>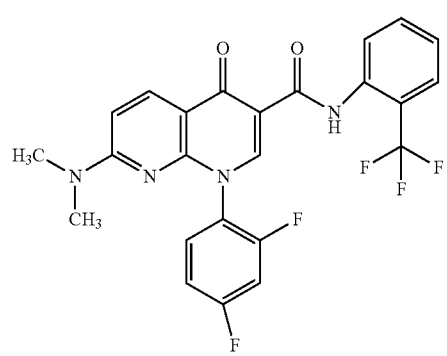<br>3 d at 23° C.; purification by preparative HPLC (eluent: acetonitrile/water gradient with 0.1% formic acid).<br>(27% of theory) | LC-MS (Method 1): $R_t$ = 1.29 min; m/z = 469.3 $[M + H]^+$.<br>$^1$H-NMR (400 MHz, DMSO-$d_6$) δ [ppm]: −0.009 (0.87), −0.001 (16.00), 0.005 (0.30), 0.007 (0.48), 2.958 (0.27), 6.938 (0.37), 6.961 (0.36), 7.322 (0.17), 7.343 (0.31), 7.361 (0.18), 7.594 (0.12), 7.673 (0.10), 7.693 (0.17), 7.712 (0.10), 7.746 (0.20), 7.765 (0.18), 7.824 (0.10), 7.830 (0.16), 7.845 (0.16), 8.311 (0.22), 8.331 (0.21), 8.347 (0.44), 8.369 (0.41), 8.724 (0.83), 12.669 (0.40). |
| 58 | N-[2-Chloro-6-(trifluoromethyl)benzyl]-1-(2,4-difluorophenyl)-7-(dimethylamino)-4-oxo-1,4-dihydro-1,8-naphthyridine-3-carboxamide<br>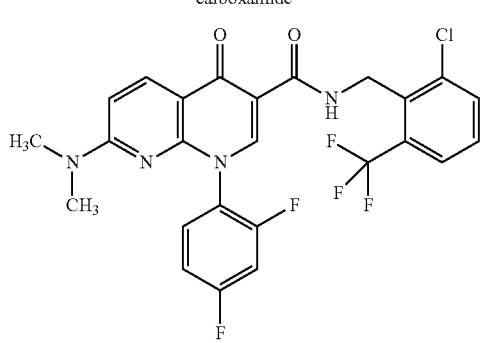<br>(86% of theory) | LC-MS (Method 1): $R_t$ = 1.23 min; m/z = 537.3 $[M + H]^+$.<br>$^1$H-NMR (400 MHz, DMSO-$d_6$) δ [ppm]: 1.244 (3.96), 1.259 (5.15), 1.275 (2.54), 2.889 (3.79), 2.928 (9.26), 4.791 (6.78), 6.873 (6.91), 6.896 (7.09), 7.318 (2.92), 7.323 (3.02), 7.572 (2.88), 7.619 (2.39), 7.639 (5.38), 7.659 (3.27), 7.790 (3.43), 7.805 (3.57), 7.818 (6.03), 7.838 (4.78), 7.905 (5.21), 7.925 (4.46), 8.188 (7.85), 8.211 (7.45), 8.588 (16.00), 10.251 (2.62), 10.264 (5.29), 10.276 (2.47). |
| 59 | 1-(2,4-Difluorophenyl)-7-(dimethylamino)-4-oxo-N-[2-(trifluoromethyl)benzyl]-1,4-dihydro-1,8-naphthyridine-3-carboxamide<br>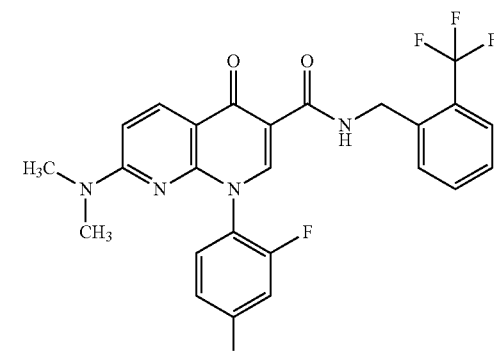<br>(75% of theory) | LC-MS (Method 1): $R_t$ = 1.21 min; m/z = 503.4 $[M + H]^+$.<br>$^1$H-NMR (400 MHz, DMSO-$d_6$) δ [ppm]: −0.010 (2.01), 0.007 (1.99), 2.940 (7.80), 4.728 (5.35), 4.743 (5.41), 6.899 (7.30), 6.922 (7.44), 7.317 (2.38), 7.322 (2.51), 7.484 (1.65), 7.503 (3.70), 7.522 (2.30), 7.548 (1.63), 7.555 (1.70), 7.573 (2.43), 7.577 (2.54), 7.580 (2.51), 7.588 (3.28), 7.596 (2.10), 7.607 (5.24), 7.657 (2.95), 7.676 (3.89), 7.741 (4.52), 7.761 (4.24), 7.779 (1.88), 7.786 (3.19), 7.801 (3.15), 7.808 (1.76), 8.263 (8.28), 8.286 (7.89), 8.573 (16.00), 10.449 (2.12), 10.464 (4.38), 10.479 (2.00). |

TABLE 6-continued

| Ex. | | Analytical data |
|---|---|---|
| 60 | 1-(2,4-Difluorophenyl)-7-(dimethylamino)-N-[2-fluoro-6-(trifluoromethyl)benzyl]-4-oxo-1,4-dihydro-1,8-naphthyridine-3-carboxamide 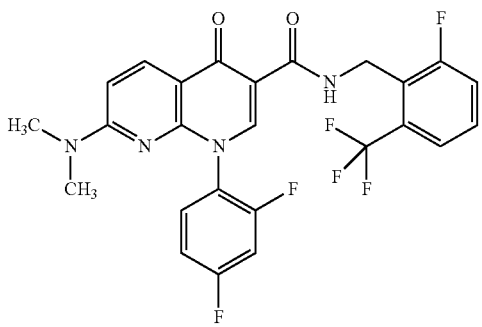 (81% of theory) | LC-MS (Method 1): $R_t$ = 1.22 min; m/z = 521.3 [M + H]$^+$.<br>$^1$H-NMR (400 MHz, DMSO-$d_6$) δ [ppm]: 0.007 (3.36), 2.366 (2.57), 2.709 (2.59), 2.730 (0.61), 2.929 (6.92), 4.744 (3.85), 6.878 (6.28), 6.901 (6.36), 7.298 (1.15), 7.320 (2.22), 7.341 (1.24), 7.543 (1.40), 7.550 (1.41), 7.573 (2.16), 7.592 (1.56), 7.599 (1.38), 7.628 (2.72), 7.641 (5.46), 7.657 (16.00), 7.758 (1.32), 7.773 (1.58), 7.779 (2.63), 7.794 (2.62), 7.801 (1.49), 7.816 (1.25), 8.209 (6.65), 8.232 (6.36), 8.571 (11.91), 10.338 (1.95), 10.351 (3.90), 10.364 (1.83). |

Example 61

1-(2,4-Difluorophenyl)-7-[(3S)-3-fluoropyrrolidin-1-yl]-4-oxo-N-(tricyclo[3.3.1.1$^{3,7}$]dec-1-yl)-1,4-dihydro-1,8-naphthyridine-3-carboxamide

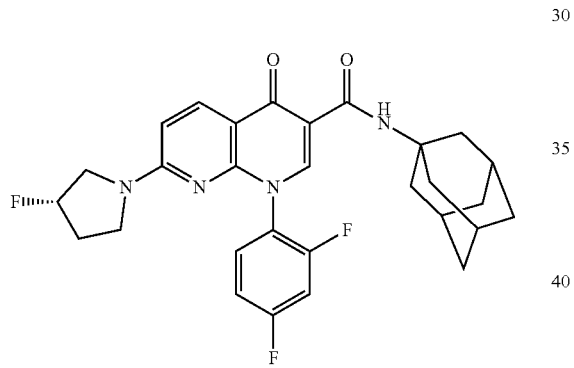

100 mg (0.26 mmol) of the compound from example 45A were initially charged in 2.9 ml of DMF, 117 mg (0.31 mmol) of HATU and 106 mg (0.82 mmol) of DIPEA were added, and the mixture was stirred at 20° C. for 30 minutes. Then 54 mg (0.36 mmol) of 1-adamantanamine were added and the mixture was then stirred at 20° C. for 2 hours. Subsequently, the mixture was purified via preparative HPLC (eluent: acetonitrile/water gradient with 0.1% formic acid). This gave 103 mg (77% of theory) of the title compound.

LC-MS (Method 1): $R_t$=1.38 min; m/z=523.3 [M+H]$^+$.
$^1$H-NMR (400 MHz, DMSO-$d_6$) δ [ppm]: −0.008 (1.49), 0.008 (1.35), 1.157 (2.39), 1.175 (4.83), 1.193 (2.46), 1.356 (0.71), 1.674 (7.25), 1.988 (8.83), 2.058 (16.00), 4.003 (0.70), 4.021 (2.07), 4.038 (2.06), 4.056 (0.68), 6.763 (0.54), 6.785 (0.56), 7.323 (0.65), 7.782 (0.40), 7.790 (0.66), 7.805 (0.66), 8.138 (1.19), 8.292 (1.32), 8.314 (1.29), 8.491 (4.34), 9.938 (2.58).

In analogy to Example 61, the example compounds shown in Table 7 were prepared by reacting the compound from Example 45A with the appropriate amines (or salts thereof) under the reaction conditions described. Differences are specified in the respective examples.

TABLE 7

| Ex. | | Analytical data |
|---|---|---|
| 62 | 1-(2,4-Difluorophenyl)-7-[(3S)-3-fluoropyridin-1-yl]-N-(3-fluorotricyclo[3.3.1.1³,⁷]dec-1-yl)-4-oxo-1,4-dihydro-1,8-naphthyridine-3-carboxamide<br><br>(87% of theory) | LC-MS (Method 1): $R_t$ = 1.24 min<br>MS (ESpos): m/z = 541.3 [M + H]⁺<br>¹H-NMR (400 MHz, CDCl₃) δ [ppm]: 0.000 (1.22), 0.016 (1.21), 0.077 (0.68), 1.231 (0.26), 1.296 (1.42), 1.309 (1.45), 1.441 (0.77), 1.592 (16.00), 1.733 (0.25), 1.754 (0.25), 1.889 (1.68), 1.950 (1.39), 2.053 (1.22), 2.083 (2.24), 2.138 (1.82), 2.169 (0.98), 2.324 (0.52), 2.378 (3.30), 2.449 (0.56), 2.794 (0.45), 2.812 (0.99), 2.892 (3.80), 2.965 (4.40), 3.488 (0.35), 3.601 (0.79), 5.242 (0.24), 5.370 (0.24), 6.540 (0.62), 6.561 (0.61), 7.006 (0.79), 7.026 (1.24), 7.046 (1.69), 7.065 (0.86), 7.348 (0.51), 7.368 (0.89), 7.383 (0.88), 7.404 (0.39), 7.528 (0.44), 8.025 (0.47), 8.442 (3.20), 8.464 (3.08), 8.639 (5.60), 10.109 (1.88). |
| 63 | 1-(2,4-Difluorophenyl)-N-(4-fluorobicyclo[2.2.2]oct-1-yl)-7-[(3S)-3-fluoropyrrolidin-1-yl]-4-oxo-1,4-dihydro-1,8-naphthyridine-3-carboxamide<br><br>(100% of theory) | LC-MS (Method 1): $R_t$ = 1.18 min<br>MS (ESpos): m/z = 515.3 [M + H]⁺<br>¹H-NMR (400 MHz, CDCl₃) δ [ppm]: −0.140 (0.04), 0.001 (0.37), 0.017 (0.29), 0.078 (0.19), 0.155 (0.04), 1.421 (0.08), 1.441 (0.12), 1.576 (16.00), 1.937 (0.28), 1.951 (0.53), 1.967 (0.53), 1.977 (0.58), 1.992 (0.37), 2.132 (0.03), 2.236 (0.64), 2.258 (0.61), 2.276 (0.48), 2.373 (0.04), 2.449 (0.13), 2.794 (0.12), 2.812 (0.13), 2.893 (0.28), 2.965 (0.35), 3.177 (0.03), 3.594 (0.10), 5.243 (0.03), 5.377 (0.03), 6.536 (0.08), 6.556 (0.08), 7.006 (0.17), 7.027 (0.16), 7.046 (0.23), 7.065 (0.11), 7.340 (0.07), 7.361 (0.12), 7.375 (0.12), 7.395 (0.06), 7.529 (0.12), 8.027 (0.04), 8.429 (0.48), 8.451 (0.47), 8.620 (0.81), 9.983 (0.29). |
| 64 | 1-(2,4-Difluorophenyl)-7-[(3S)-3-fluoropyrrolidin-1-yl]-4-oxo-N-[(2S)-1,1,1-trifluorobutan-2-yl]-1,4-dihydro-1,8-naphthyridine-3-carboxamide<br><br>Workup: Precipitate the product with 1M aqueous hydrochloric acid and water and then filter off the precipitate.<br>(86% of theory) | LC-MS (Method 2): $R_t$ = 2.82 min<br>MS (ESpos): m/z = 499.0 [M + H]⁺<br>¹H-NMR (400 MHz, DMSO-d₆) δ [ppm]: −0.150 (0.56), −0.048 (0.52), −0.042 (0.74), −0.038 (0.83), −0.035 (0.90), −0.033 (0.93), −0.031 (1.01), −0.028 (1.10), −0.026 (1.26), −0.023 (1.40), −0.021 (1.53), −0.018 (1.77), −0.016 (2.10), −0.014 (2.33), −0.012 (3.16), −0.009 (6.86), −0.007 (6.14), −0.006 (7.26), 0.004 (4.31), 0.006 (3.08), 0.007 (4.66), 0.010 (1.10), 0.013 (0.63), 0.015 (0.47), 0.018 (0.40), 0.145 (0.56), 0.950 (7.53), 0.968 (16.00), 0.987 (7.73), 1.146 (0.34), 1.156 (0.33), 1.169 (0.46), 1.174 (0.59), 1.581 (0.39), 1.599 (1.18), 1.617 (1.60), 1.624 (1.41), 1.634 (1.83), 1.643 (1.66), 1.652 (1.56), 1.660 (1.77), 1.678 (1.30), 1.697 (0.38), 1.833 (0.51), 1.852 (1.38), 1.861 (1.57), 1.870 (1.57), 1.880 (1.73), 1.886 (1.53), 1.896 (1.36), 1.904 (1.17), 1.914 (1.01), 1.987 (0.93), 2.166 (0.83), 2.327 (0.76), 2.332 (0.60), 2.366 (0.84), 2.519 (3.20), 2.521 (3.13), 2.523 (3.42), 2.526 (3.67), 2.558 (0.99), 2.560 (0.80), 2.563 (0.66), 2.565 (0.58), 2.568 (0.53), 2.570 (0.50), 2.573 (0.42), 2.575 (0.33), 2.578 (0.33), 2.587 (0.33), 2.665 (0.55), 2.669 (0.69), 2.674 (0.52), 2.709 (0.89), 3.132 (0.37), 3.496 (0.81), 3.690 (0.92), 4.735 (1.51), 4.747 (1.40), 4.771 (0.78), 5.278 (0.44), 5.402 (0.55), 5.510 (0.34), 5.753 (4.85), 6.807 (1.77), 7.324 (2.28), 7.546 (0.78), 7.569 (1.54), 7.587 (1.29), 7.812 (1.76), 7.831 (1.67), 8.136 (0.79), 8.316 (4.26), 8.338 (4.02), 8.631 (10.61), 10.479 (4.79), 10.503 (4.55). |

| Ex. | | Analytical data |
|---|---|---|
| 65 | 1-(2,4-Difluorophenyl)-7-[(3S)-3-fluoropyrrolidin-1-yl]-4-oxo-N-[1,1,1-trifluoro-4-methylpentan-2-yl]-1,4-dihydro-1,8-naphthyridine-3-carboxamide (diastereomer mixture)<br>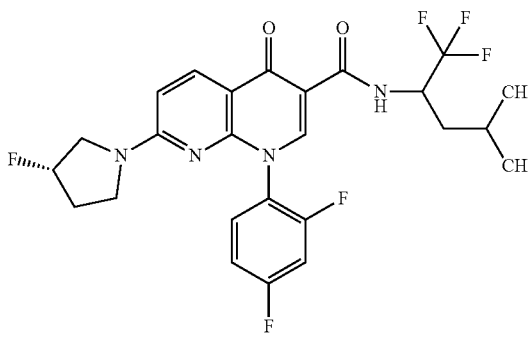<br>(92% of theory) | LC-MS (Method 1): $R_t$ = 1.29 min<br>MS (ESpos): m/z = 527.3 [M + H]$^+$<br>$^1$H-NMR (400 MHz, CDCl$_3$) δ [ppm]: 0.001 (0.58), 0.017 (0.41), 0.078 (0.30), 0.959 (1.73), 0.975 (1.96), 0.984 (3.35), 1.001 (3.17), 1.232 (0.09), 1.379 (0.07), 1.396 (0.06), 1.442 (0.38), 1.459 (0.11), 1.492 (0.12), 1.508 (0.13), 1.518 (0.12), 1.576 (16.00), 1.602 (0.52), 1.611 (0.65), 1.619 (0.37), 1.636 (0.42), 1.645 (0.30), 1.714 (0.32), 1.724 (0.41), 1.742 (0.32), 1.752 (0.52), 1.758 (0.35), 1.768 (0.16), 1.778 (0.40), 1.786 (0.49), 1.795 (0.26), 1.802 (0.22), 1.811 (0.26), 1.821 (0.16), 1.826 (0.16), 1.837 (0.09), 2.069 (0.08), 2.153 (0.08), 2.280 (0.06), 2.384 (0.11), 2.450 (0.21), 2.634 (0.36), 2.795 (0.16), 2.813 (0.23), 2.893 (0.24), 2.966 (0.30), 3.612 (0.30), 4.877 (0.15), 4.895 (0.24), 4.920 (0.24), 4.929 (0.16), 4.939 (0.13), 4.947 (0.10), 5.245 (0.08), 5.379 (0.09), 6.560 (0.22), 7.006 (0.26), 7.040 (0.52), 7.060 (0.68), 7.078 (0.35), 7.280 (0.28), 7.364 (0.21), 7.385 (0.36), 7.399 (0.36), 7.421 (0.17), 7.529 (0.22), 8.450 (1.52), 8.472 (1.49), 8.697 (1.99), 10.362 (0.46), 10.386 (0.46). |
| 66 | 1-(2,4-Difluorophenyl)-7-[(3S)-3-fluoropyrrolidin-1-yl]-4-oxo-N-[1,1,1-trifluoropentan-2-yl]-1,4-dihydro-1,8-naphthyridine-3-carboxamide (diastereomer mixture)<br>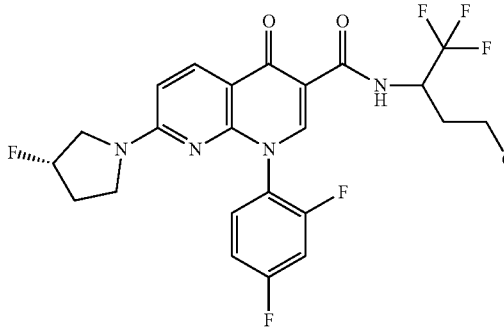<br>Workup: Precipitate the product with 1M aqueous hydrochloric acid and water and then filter off the precipitate.<br>(90% of theory) | LC-MS (Method 2): $R_t$ = 2.95 min<br>MS (ESpos): m/z = 513.1 [M + H]$^+$<br>$^1$H-NMR (400 MHz, DMSO-d$_6$) δ [ppm]: −0.151 (0.40), −0.009 (3.50), 0.007 (3.30), 0.144 (0.41), 0.866 (0.27), 0.894 (7.06), 0.912 (16.00), 0.930 (8.28), 0.998 (0.63), 1.067 (0.57), 1.146 (0.48), 1.168 (0.59), 1.231 (0.25), 1.280 (0.26), 1.299 (0.59), 1.317 (0.99), 1.335 (1.38), 1.355 (2.83), 1.373 (1.58), 1.391 (1.13), 1.410 (0.91), 1.433 (1.07), 1.444 (1.40), 1.464 (1.26), 1.480 (0.73), 1.497 (0.45), 1.594 (0.59), 1.606 (0.60), 1.621 (0.88), 1.629 (1.55), 1.641 (1.14), 1.655 (1.61), 1.667 (1.09), 1.678 (0.85), 1.690 (0.65), 1.739 (0.85), 1.748 (1.00), 1.765 (1.39), 1.772 (1.51), 1.781 (1.19), 1.790 (1.30), 1.796 (0.94), 1.815 (0.53), 1.823 (0.45), 2.182 (0.85), 2.225 (0.67), 2.322 (0.46), 2.326 (0.53), 2.331 (0.40), 2.365 (0.64), 2.522 (1.03), 2.664 (0.37), 2.669 (0.45), 2.689 (0.62), 2.709 (0.66), 2.730 (0.62), 2.889 (0.78), 3.090 (0.45), 3.136 (0.33), 3.486 (0.70), 3.697 (0.77), 4.773 (0.73), 4.797 (1.25), 4.816 (1.27), 4.835 (0.70), 5.283 (0.36), 5.409 (0.46), 5.512 (0.26), 6.804 (1.49), 6.821 (1.46), 7.302 (1.11), 7.324 (2.12), 7.342 (1.19), 7.546 (0.65), 7.566 (1.37), 7.588 (1.15), 7.792 (0.91), 7.813 (1.86), 7.829 (1.85), 7.850 (0.81), 8.311 (3.82), 8.334 (3.68), 8.629 (9.55), 10.474 (4.44), 10.498 (4.28). |

TABLE 7-continued

| Ex. | | Analytical data |
|---|---|---|
| 67 | 1-(2,4-Difluorophenyl)-7-[(3S)-3-fluoropyrrolidin-1-yl]-4-oxo-N-(2,2,2-trifluoroethyl)-1,4-dihydro-1,8-naphthyridine-3-carboxamide<br>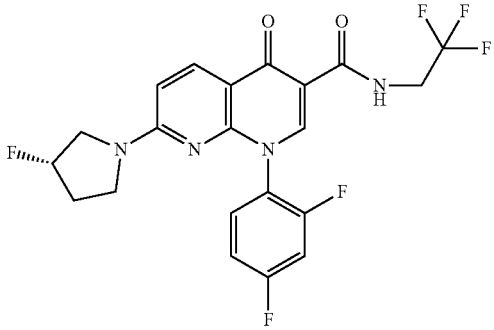<br>Workup: Precipitate the product with 1M aqueous hydrochloric acid and water and then filter off the precipitate.<br>(91% of theory) | LC-MS (Method 1): $R_t$ = 1.07 min<br>MS (ESpos): m/z = 471.2 [M + H]$^+$<br>$^1$H-NMR (400 MHz, CDCl$_3$) δ [ppm]: 0.001 (0.23), 0.017 (0.25), 0.079 (0.15), 1.442 (0.09), 1.571 (16.00), 2.156 (0.04), 2.390 (0.06), 2.450 (0.09), 2.794 (0.06), 2.894 (0.08), 2.966 (0.09), 3.608 (0.16), 4.098 (0.11), 4.118 (0.14), 4.137 (0.17), 4.158 (0.14), 4.177 (0.10), 5.243 (0.05), 5.375 (0.05), 6.575 (0.12), 7.006 (0.11), 7.047 (0.27), 7.066 (0.35), 7.086 (0.18), 7.365 (0.11), 7.386 (0.19), 7.400 (0.19), 7.421 (0.08), 7.529 (0.11), 8.460 (0.82), 8.470 (0.06), 8.482 (0.80), 8.492 (0.04), 8.694 (1.41), 8.705 (0.06), 10.563 (0.14), 10.579 (0.25), 10.594 (0.13). |
| 68 | 1-(2,4-Difluorophenyl)-7-[(3S)-3-fluoropyridin-1-yl]-4-oxo-N-[1-(trifluormethyl)cyclopropyl]-1,4-dihydro-1,8-naphthyridine-3-carboxamide<br>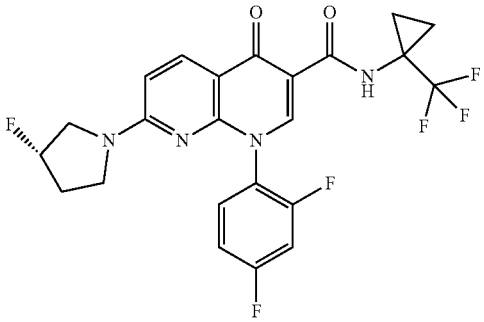<br>(94% of theory) | LC-MS (Method 1): $R_t$ = 1.12 min<br>MS (ESpos): m/z = 497.3 [M + H]$^+$<br>$^1$H-NMR (400 MHz, CDCl$_3$) δ [ppm]: 0.016 (0.30), 0.078 (0.15), 1.234 (0.52), 1.354 (0.11), 1.371 (0.17), 1.391 (1.08), 1.416 (0.12), 1.431 (0.07), 1.441 (0.18), 1.502 (0.05), 1.580 (16.00), 2.059 (0.06), 2.150 (0.06), 2.380 (0.08), 2.450 (0.14), 2.794 (0.10), 2.893 (0.23), 2.965 (0.27), 3.607 (0.23), 5.237 (0.06), 5.368 (0.07), 6.554 (0.18), 6.570 (0.17), 7.006 (0.13), 7.039 (0.36), 7.058 (0.48), 7.078 (0.24), 7.353 (0.15), 7.373 (0.26), 7.388 (0.27), 7.409 (0.13), 7.529 (0.10), 8.438 (0.91), 8.460 (0.88), 8.469 (0.07), 8.677 (1.57), 8.704 (0.07), 10.627 (0.63). |
| 69 | 1-(2,4-Difluorophenyl)-7-[(3S)-3-fluoropyrrolidin-1-yl]-4-oxo-N-[1,1,1-trifluoro-3-methylbutan-2-yl]-1,4-dihydro-1,8-naphthyridine-3-carboxamide (diastereomer mixture)<br>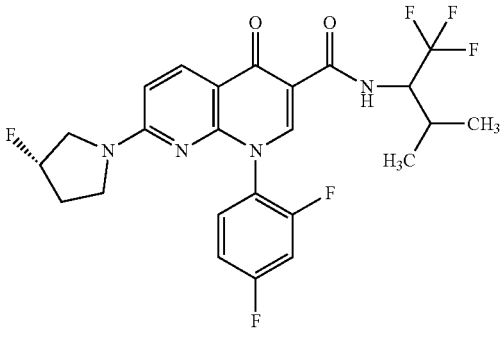<br>Workup: Precipitate the product with 1M aqueous hydrochloric acid and water and then filter off the precipitate.<br>(98% of theory) | LC-MS (Method 1): $R_t$ = 1.23 min<br>MS (ESpos): m/z = 513.3 [M + H]$^+$<br>$^1$H-NMR (400 MHz, CDCl$_3$) δ [ppm]: 0.000 (0.84), 0.017 (0.61), 0.078 (0.50), 0.863 (0.16), 0.976 (0.27), 0.995 (0.27), 1.063 (4.55), 1.081 (4.67), 1.138 (4.58), 1.155 (4.44), 1.232 (0.20), 1.267 (0.14), 1.284 (0.14), 1.293 (0.13), 1.441 (0.48), 1.584 (16.00), 2.064 (0.15), 2.089 (0.14), 2.268 (0.22), 2.285 (0.47), 2.295 (0.51), 2.302 (0.62), 2.313 (0.65), 2.320 (0.51), 2.330 (0.50), 2.347 (0.28), 2.384 (0.18), 2.450 (0.34), 2.793 (0.23), 2.812 (0.60), 2.893 (1.00), 2.965 (1.23), 3.609 (0.52), 4.754 (0.11), 4.765 (0.33), 4.775 (0.36), 4.790 (0.46), 4.797 (0.44), 4.811 (0.34), 4.822 (0.32), 5.242 (0.15), 5.372 (0.15), 6.560 (0.39), 7.006 (0.33), 7.044 (0.86), 7.063 (1.17), 7.082 (0.60), 7.366 (0.35), 7.386 (0.62), 7.401 (0.63), 7.422 (0.29), 7.529 (0.30), 8.027 (0.13), 8.480 (2.49), 8.502 (2.40), 8.700 (3.93), 10.580 (0.77), 10.605 (0.76). |

TABLE 7-continued

| Ex. | | Analytical data |
|---|---|---|
| 70 | 1-(2,4-Difluorophenyl)-7-[(3S)-3-fluoropyridin-1-yl]-N-(1,1,1,3,3,3-hexafluoropropan-2-yl)-4-oxo-1,4-dihydro-1,8-naphthyridine-3-carboxamide<br />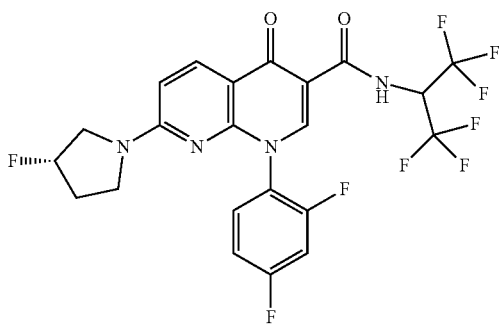<br />Workup: Precipitate the product with 1M aqueous hydrochloric acid and water and then filter off the precipitate.<br />(11% of theory) | LC-MS (Method 1): $R_t$ = 1.24 min<br />MS (ESpos): m/z = 539.2 [M + H]$^+$<br />$^1$H-NMR (400 MHz, CDCl$_3$) δ [ppm]: −0.140 (0.11), 0.001 (0.99), 0.017 (0.82), 0.079 (0.21), 0.155 (0.11), 1.265 (0.11), 1.557 (16.00), 2.101 (0.10), 2.152 (0.11), 2.430 (0.12), 2.449 (0.24), 2.794 (0.16), 3.376 (0.10), 3.496 (0.21), 3.505 (0.21), 3.624 (0.35), 5.235 (0.09), 5.371 (0.09), 5.554 (0.15), 5.572 (0.35), 5.579 (0.18), 5.589 (0.44), 5.597 (0.38), 5.607 (0.33), 5.614 (0.46), 5.625 (0.16), 5.632 (0.32), 5.650 (0.13), 6.586 (0.25), 7.006 (0.21), 7.059 (0.55), 7.079 (0.75), 7.098 (0.37), 7.371 (0.24), 7.391 (0.40), 7.407 (0.40), 7.426 (0.17), 7.529 (0.20), 8.469 (1.94), 8.492 (1.89), 8.691 (2.87), 11.305 (0.64), 11.330 (0.63). |
| 71 | 1-(2,4-Difluorophenyl)-7-[(3S)-3-fluoropyrrolidin-1-yl]-4-oxo-N-[1,1,1-trifluorobutan-2-yl]-1,4-dihydro-1,8-naphthyridine-3-carboxamide<br />(diastereomer mixture)<br />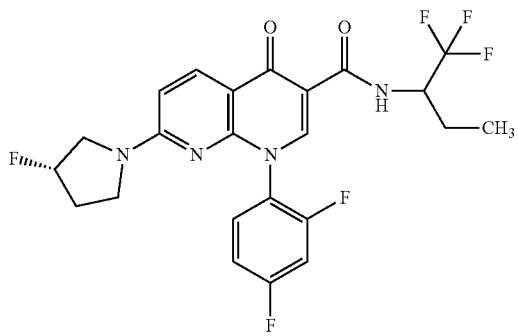<br />Workup: Precipitate the product with 1M aqueous hydrochloric acid and water and then filter off the precipitate.<br />(86% of theory) | LC-MS (Method 1): $R_t$ = 1.18 min<br />MS (ESpos): m/z = 499.3 [M + H]$^+$<br />$^1$H-NMR (400 MHz, CDCl$_3$) δ [ppm]: 0.000 (0.22), 0.016 (0.19), 0.078 (0.13), 1.057 (0.57), 1.076 (1.25), 1.094 (0.62), 1.231 (0.04), 1.440 (0.17), 1.457 (0.05), 1.485 (0.06), 1.501 (0.06), 1.511 (0.06), 1.590 (16.00), 1.687 (0.05), 1.705 (0.10), 1.712 (0.05), 1.723 (0.12), 1.731 (0.11), 1.740 (0.15), 1.749 (0.13), 1.759 (0.13), 1.766 (0.15), 1.778 (0.05), 1.784 (0.12), 1.803 (0.04), 1.913 (0.04), 1.932 (0.11), 1.942 (0.12), 1.950 (0.12), 1.961 (0.13), 1.967 (0.11), 1.977 (0.11), 1.986 (0.09), 1.996 (0.09), 2.005 (0.05), 2.014 (0.04), 2.072 (0.03), 2.126 (0.03), 2.399 (0.05), 2.451 (0.08), 2.795 (0.06), 2.812 (0.09), 2.893 (0.08), 2.965 (0.10), 3.611 (0.14), 4.726 (0.05), 4.735 (0.06), 4.750 (0.10), 4.759 (0.10), 4.769 (0.10), 4.778 (0.10), 4.785 (0.07), 4.794 (0.06), 4.804 (0.04), 5.237 (0.04), 5.379 (0.04), 6.565 (0.10), 7.006 (0.10), 7.045 (0.22), 7.064 (0.29), 7.083 (0.15), 7.364 (0.09), 7.385 (0.15), 7.399 (0.15), 7.420 (0.07), 7.529 (0.09), 8.456 (0.66), 8.478 (0.65), 8.694 (0.97), 10.419 (0.20), 10.443 (0.20). |

Example 72

1-(2,4-Difluorophenyl)-7-[(3R)-3-fluoropyrrolidin-1-yl]-4-oxo-N-(tricyclo[3.3.1.1$^{3,7}$]dec-1-yl)-1,4-dihydro-1,8-naphthyridine-3-carboxamide

Example 73

1-(2,4-Difluorophenyl)-7-(3,3-difluoropyrrolidin-1-yl)-4-oxo-N-(tricyclo[3.3.1.1$^{3,7}$]dec-1-yl)-1,4-dihydro-1,8-naphthyridine-3-carboxamide

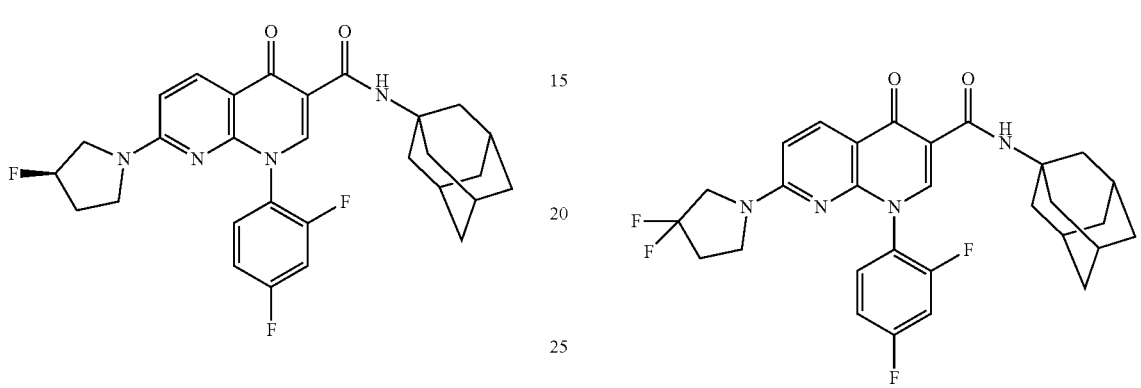

100 mg (0.26 mmol) of the compound from example 44A were initially charged in 2.9 ml of DMF, 117 mg (0.31 mmol) of HATU and 106 mg (0.82 mmol) of DIPEA were added, and the mixture was stirred at 20° C. for 30 minutes. Then 54 mg (0.36 mmol) of 1-adamantanamine were added and the mixture was stirred at 20° C. for 2 hours. Subsequently, the mixture was purified directly via preparative HPLC (eluent: acetonitrile/water gradient with 0.1% formic acid). This gave 103 mg (77% of theory) of the title compound.

LC-MS (Method 1): R$_t$=1.38 min; m/z=523.3 [M+H]$^+$.

$^1$H-NMR (400 MHz, DMSO-d$_6$) δ [ppm]: −0.150 (0.23), −0.041 (0.10), −0.023 (0.69), −0.018 (0.95), −0.009 (3.93), −0.007 (3.54), 0.006 (1.08), 0.007 (1.84), 0.011 (0.32), 0.013 (0.18), 0.016 (0.13), 0.146 (0.25), 1.156 (1.38), 1.174 (2.79), 1.192 (1.39), 1.234 (0.24), 1.355 (0.69), 1.672 (7.42), 1.825 (0.14), 1.988 (4.88), 2.057 (16.00), 2.182 (0.33), 2.215 (0.29), 2.322 (0.25), 2.327 (0.32), 2.332 (0.22), 2.366 (0.28), 2.519 (1.27), 2.521 (1.30), 2.523 (1.58), 2.558 (0.24), 2.560 (0.20), 2.563 (0.17), 2.565 (0.13), 2.568 (0.14), 2.570 (0.12), 2.573 (0.13), 2.575 (0.11), 2.665 (0.25), 2.669 (0.30), 2.674 (0.22), 2.709 (0.30), 3.161 (1.88), 3.174 (1.86), 3.467 (0.26), 3.675 (0.25), 4.002 (0.39), 4.020 (1.11), 4.038 (1.09), 4.056 (0.43), 4.073 (0.52), 4.086 (0.49), 4.099 (0.18), 5.323 (0.11), 5.412 (0.14), 6.764 (0.58), 6.785 (0.57), 7.300 (0.36), 7.321 (0.67), 7.339 (0.38), 7.565 (0.42), 7.585 (0.38), 7.767 (0.35), 7.789 (0.69), 7.804 (0.68), 7.826 (0.30), 8.149 (0.45), 8.291 (1.37), 8.313 (1.30), 8.490 (4.58), 8.519 (0.13), 9.937 (2.54).

100 mg (0.26 mmol) of the compound from example 43A were initially charged in 2.8 ml of DMF, 112 mg (0.3 mmol) of HATU and 101 mg (0.79 mmol) of DIPEA were added, and the mixture was stirred at 20° C. for 30 minutes. Then 52 mg (0.34 mmol) of 1-adamantanamine were added and the mixture was stirred at 20° C. for 2 hours. Subsequently, the mixture was purified via preparative HPLC (eluent: acetonitrile/water gradient with 0.1% formic acid). This gave 76 mg (57% of theory) of the title compound.

LC-MS (Method 1): R$_t$=1.41 min; m/z=541.3 [M+H]$^+$.

$^1$H-NMR (400 MHz, DMSO-d$_6$) δ [ppm]: −0.009 (0.75), 0.007 (0.74), 1.232 (0.33), 1.672 (7.44), 2.057 (16.00), 2.365 (0.15), 2.709 (0.15), 3.161 (2.40), 3.174 (2.48), 3.546 (0.24), 4.060 (0.26), 4.073 (0.71), 4.086 (0.69), 4.099 (0.24), 6.791 (0.59), 6.813 (0.61), 7.306 (0.40), 7.328 (0.78), 7.349 (0.43), 7.557 (0.41), 7.563 (0.43), 7.586 (0.69), 7.605 (0.43), 7.612 (0.41), 7.770 (0.49), 7.785 (0.57), 7.791 (0.97), 7.806 (0.96), 7.813 (0.55), 7.828 (0.46), 8.336 (1.86), 8.358 (1.78), 8.519 (4.96), 9.897 (2.61).

In analogy to Example 73, the example compounds shown in Table 8 were prepared by reacting the compound from Example 43A with the appropriate amines (or salts thereof) under the reaction conditions described. Differences are specified in the respective examples.

TABLE 8

| Ex. | | Analytical data |
|---|---|---|
| 74 | rac-1-(2,4-Difluorophenyl)-7-(3,3-difluoropyrrolidin-1-yl)-4-oxo-N-[1,1,1-trifluorobutan-2-yl]-1,4-dihydro-1,8-naphthyridine-3-carboxamide<br />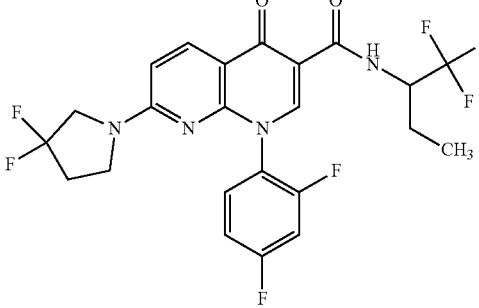<br />(88% of theory) | LC-MS (Method 1): $R_t$ = 1.22 min<br />MS (ESpos): m/z = 517.2 [M + H]$^+$<br />$^1$H-NMR (400 MHz, CDCl$_3$) δ [ppm]: 0.079 (1.42), 1.057 (7.39), 1.076 (15.90), 1.095 (7.93), 1.232 (5.14), 1.572 (16.00), 1.705 (1.42), 1.723 (1.66), 1.740 (1.97), 1.766 (1.94), 1.784 (1.50), 1.964 (1.56), 2.450 (2.28), 3.619 (2.76), 4.753 (1.34), 6.541 (2.25), 6.563 (2.32), 7.006 (1.26), 7.045 (2.37), 7.065 (3.90), 7.078 (3.60), 7.360 (1.50), 7.380 (2.31), 7.394 (2.41), 7.529 (1.20), 8.505 (8.37), 8.528 (7.99), 8.712 (12.30), 10.344 (2.52), 10.368 (2.49). |
| 75 | 1-(2,4-Difluorophenyl)-7-(3,3-difluoropyrrolidin-1-yl)-4-oxo-N-[(2S)-1,1,1-trifluorobutan-2-yl]-1,4-dihydro-1,8-naphthyridine-3-carboxamide<br />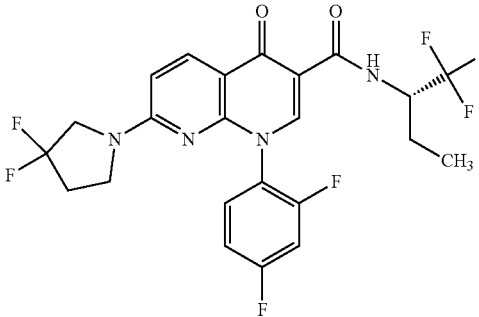<br />(90% of theory) | LC-MS (Method 1): $R_t$ = 1.22 min<br />MS (ESpos): m/z = 517.2 [M + H]$^+$<br />$^1$H-NMR (400 MHz, CDCl$_3$) δ [ppm]: 0.001 (3.23), 0.017 (2.20), 0.079 (1.12), 1.057 (7.43), 1.075 (16.00), 1.094 (7.94), 1.253 (5.33), 1.442 (1.10), 1.587 (6.32), 1.705 (1.64), 1.723 (1.85), 1.730 (1.63), 1.740 (2.10), 1.748 (1.79), 1.758 (1.81), 1.765 (2.06), 1.784 (1.62), 1.935 (1.36), 1.945 (1.43), 1.953 (1.47), 1.963 (1.58), 1.980 (1.25), 2.450 (2.19), 2.471 (2.26), 3.000 (0.76), 3.622 (2.74), 4.761 (1.35), 6.541 (2.20), 6.563 (2.21), 7.006 (1.01), 7.045 (2.38), 7.059 (3.52), 7.065 (3.84), 7.077 (3.64), 7.084 (3.12), 7.359 (1.55), 7.380 (2.28), 7.394 (2.36), 7.416 (1.18), 7.529 (0.88), 8.505 (8.69), 8.527 (8.30), 8.712 (12.29), 10.344 (2.49), 10.368 (2.49). |
| 76 | rac-1-(2,4-Difluorophenyl)-7-(3,3-difluoropyrrolidin-1-yl)-4-oxo-N-[1,1,1-trifluoropentan-2-yl]-1,4-dihydro-1,8-naphthyridine-3-carboxamide<br />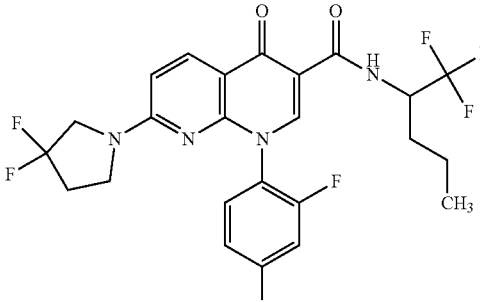<br />(82% of theory) | LC-MS (Method 1): $R_t$ = 1.28 min<br />MS (ESpos): m/z = 531.2 [M + H]$^+$<br />$^1$H-NMR (400 MHz, CDCl$_3$) δ [ppm]: 0.001 (3.68), 0.017 (2.94), 0.079 (1.31), 0.957 (7.45), 0.975 (16.00), 0.994 (8.03), 1.161 (4.06), 1.233 (1.72), 1.442 (2.18), 1.461 (1.88), 1.479 (2.03), 1.497 (1.61), 1.583 (14.64), 1.686 (1.15), 1.721 (1.97), 1.733 (1.47), 1.747 (2.16), 1.759 (1.56), 1.770 (1.26), 1.782 (1.01), 1.841 (1.54), 1.859 (1.34), 2.450 (2.21), 2.470 (2.11), 3.618 (2.48), 4.859 (1.21), 6.539 (2.05), 6.562 (2.05), 7.006 (1.29), 7.043 (2.11), 7.063 (3.49), 7.076 (3.17), 7.358 (1.38), 7.379 (2.09), 7.393 (2.17), 7.415 (1.10), 7.529 (1.23), 8.502 (8.83), 8.524 (8.43), 8.710 (11.39), 10.325 (2.44), 10.349 (2.44). |

Example 77

1-(2,4-Difluorophenyl)-4-oxo-7-(3,3,4,4-tetrafluoro-pyrrolidin-1-yl)-N-(tricyclo[3.3.1.1$^{3,7}$]dec-1-yl)-1,4-dihydro-1,8-naphthyridine-3-carboxamide

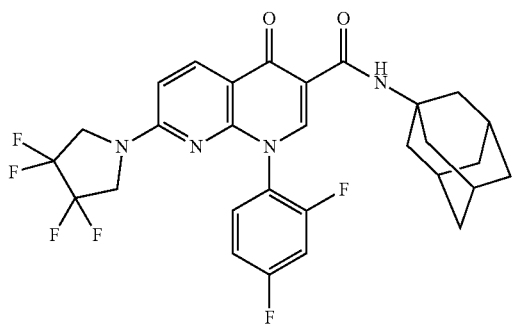 [SMILES: O=C(NC12CC3CC(CC(C3)C1)C2)c1cn(-c2ccc(F)cc2F)c2nc(N3CC(F)(F)C(F)(F)C3)ccc2c1=O]

110 mg (0.21 mmol, 86% purity) of the compound from example 46A were initially charged in 2.4 ml of DMF, 97 mg (0.26 mmol) of HATU and 88 mg (0.68 mmol) of DIPEA were added, and the mixture was stirred at 20° C. for 30 minutes. Then 45 mg (0.3 mmol) of 1-adamantanamine were added and the mixture was stirred at 20° C. for 2 hours. Subsequently, the mixture was purified via preparative HPLC (eluent: acetonitrile/water gradient with 0.1% formic acid). This gave 61 mg (50% of theory) of the title compound.

LC-MS (Method 1): R$_t$=1.41 min; m/z=577.3 [M+H]$^+$.

$^1$H-NMR (400 MHz, DMSO-d$_6$) δ [ppm]: 0.000 (16.00), 1.235 (0.38), 1.674 (4.18), 2.060 (8.85), 3.161 (0.98), 3.175 (1.04), 4.069 (0.63), 4.083 (0.61), 6.877 (1.25), 6.899 (1.26), 7.337 (0.45), 7.570 (0.31), 7.589 (0.43), 7.612 (0.30), 7.787 (0.29), 7.809 (0.54), 7.823 (0.54), 7.846 (0.27), 8.433 (1.51), 8.455 (1.40), 8.562 (2.73), 9.835 (1.41).

Example 78

1-(2,4-Difluorophenyl)-7-(1,1-dioxido-1,3-thiazolidin-3-yl)-4-oxo-N-[1,1,1-trifluoro-4-methylpentan-2-yl]-1,4-dihydro-1,8-naphthyridine-3-carboxamide

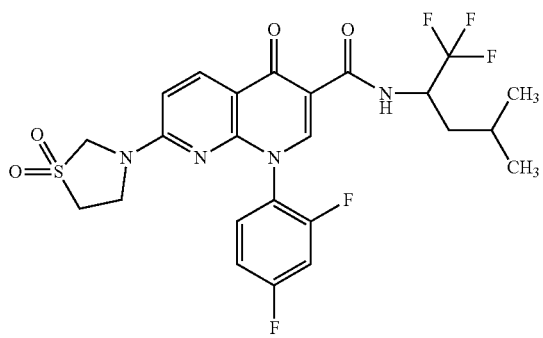 [SMILES: CC(C)CC(NC(=O)c1cn(-c2ccc(F)cc2F)c2nc(N3CCS(=O)(=O)C3)ccc2c1=O)C(F)(F)F]

80 mg (0.15 mmol, 80% purity) of the compound from example 50A were initially charged in 1.7 ml of DMF, 70 mg (0.18 mmol) of HATU and 63 mg (0.49 mmol) of DIPEA were added, and the mixture was stirred at 20° C. for 30 minutes. Then 59 mg (0.39 mmol) of 1,1,1-trifluoro-4-methylpentan-2-amine hydrochloride were added and the mixture was stirred at 20° C. for 2 hours. Then 1 ml of 1 M aqueous hydrochloric acid and 2 ml of water were added, and the precipitated solid was filtered off, washed with 2 ml of water and 1 ml of petroleum ether and dried under high vacuum. This gave 72 mg (84% of theory) of the title compound.

LC-MS (Method 1): R$_t$=1.15 min; m/z=559.3 [M+H]$^+$.

$^1$H-NMR (400 MHz, CDCl$_3$) δ [ppm]: −0.140 (0.90), 0.001 (7.91), 0.017 (7.32), 0.079 (2.03), 0.155 (0.80), 0.937 (0.81), 0.957 (6.31), 0.965 (6.32), 0.973 (7.22), 0.982 (7.57), 0.988 (9.90), 1.004 (9.53), 1.233 (1.77), 1.343 (3.73), 1.430 (0.86), 1.442 (2.01), 1.580 (16.00), 1.621 (4.52), 1.647 (2.46), 1.708 (1.59), 1.718 (1.97), 1.737 (1.56), 1.746 (2.37), 1.773 (1.76), 1.799 (1.17), 2.450 (1.53), 2.602 (0.92), 2.794 (1.57), 2.894 (1.25), 2.965 (1.59), 2.999 (0.85), 3.179 (0.78), 3.379 (3.94), 3.397 (8.19), 3.414 (4.27), 3.986 (4.62), 4.003 (8.47), 4.021 (3.86), 4.390 (4.78), 4.893 (0.90), 4.918 (0.94), 6.685 (5.10), 6.708 (5.24), 7.006 (1.92), 7.064 (1.40), 7.084 (3.11), 7.104 (2.61), 7.370 (1.09), 7.385 (1.41), 7.391 (1.53), 7.405 (1.57), 7.427 (0.86), 7.529 (1.90), 8.616 (5.68), 8.639 (5.59), 8.757 (5.70), 10.146 (1.87), 10.170 (1.82).

Example 79

1-(2,4-Difluorophenyl)-7-[(2-hydroxyethyl)amino]-4-oxo-N-(tricyclo[3.3.1.1$^{3,7}$]dec-1-yl)-1,4-dihydro-1,8-naphthyridine-3-carboxamide

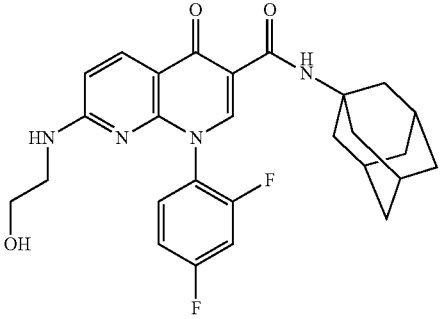 [SMILES: O=C(NC12CC3CC(CC(C3)C1)C2)c1cn(-c2ccc(F)cc2F)c2nc(NCCO)ccc2c1=O]

100 mg (0.28 mmol) of the compound from example 40A were initially charged in 3.1 ml of DMF, 126 mg (0.33 mmol) of HATU and 114 mg (0.89 mmol) of DIPEA were added, and the mixture was stirred at 20° C. for 30 minutes. Then 59 mg (0.39 mmol) of 1-adamantanamine were added and the mixture was stirred at 20° C. for 2 hours. Subsequently, the mixture was purified via preparative HPLC (eluent: acetonitrile/water gradient with 0.1% formic acid). This gave 77 mg (56% of theory) of the title compound.

LC-MS (Method 1): R$_t$=1.20 min; m/z=495.3 [M+H]$^+$.

$^1$H-NMR (400 MHz, DMSO-d$_6$) δ [ppm]: −0.013 (0.84), −0.005 (16.00), 0.003 (1.54), 0.011 (1.70), 1.665 (1.85), 2.047 (3.60), 3.025 (0.21), 3.305 (14.58), 3.320 (2.20), 4.595 (0.20), 6.661 (0.24), 6.684 (0.27), 7.302 (0.21), 7.541 (0.19), 7.760 (0.23), 7.775 (0.25), 7.940 (0.14), 8.132 (0.18), 8.425 (0.71), 9.985 (0.44).

In analogy to Example 79, the example compounds shown in Table 9 were prepared by reacting the compound from Example 40A with the appropriate amines (or salts thereof) under the reaction conditions described. Differences are specified in the respective examples.

TABLE 9

| Ex. | | Analytical data |
|---|---|---|
| 80 | 1-(2,4-Difluorophenyl)-7-[(2-hydroxyethyl)amino]-4-oxo-N-[1,1,1-trifluoro-4-methylpentan-2-yl]-1,4-dihydro-1,8-naphthyridine-3-carboxamide<br>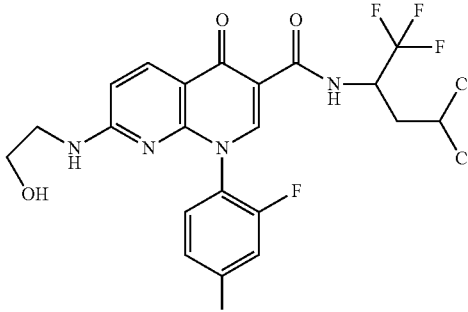<br>(52% of theory) | LC-MS (Method 1): $R_t$ = 1.08 min<br>MS (ESpos): m/z = 499.3 [M + H]$^+$<br>$^1$H-NMR (400 MHz, CDCl$_3$) δ [ppm]: 0.000 (0.62), 0.009 (16.00), 0.017 (0.54), 0.078 (1.39), 0.953 (1.91), 0.969 (2.16), 0.975 (2.17), 0.981 (3.89), 0.997 (3.76), 1.590 (8.07), 1.635 (1.25), 1.709 (0.55), 1.719 (0.66), 1.737 (0.54), 1.747 (0.83), 1.753 (0.57), 1.779 (0.61), 1.791 (0.40), 1.801 (0.44), 2.449 (0.72), 2.599 (0.31), 2.601 (0.42), 2.604 (0.53), 2.633 (1.92), 2.635 (1.25), 2.637 (0.96), 2.639 (0.83), 2.641 (0.61), 2.644 (0.43), 2.646 (0.29), 2.649 (0.34), 2.794 (0.78), 3.321 (0.51), 3.334 (1.26), 3.345 (1.44), 3.359 (0.71), 3.650 (0.95), 3.662 (1.38), 3.674 (0.74), 4.889 (0.31), 4.913 (0.32), 5.459 (0.38), 5.474 (0.66), 5.488 (0.38), 6.535 (1.92), 6.557 (1.98), 7.006 (0.49), 7.032 (0.37), 7.052 (1.16), 7.073 (1.04), 7.091 (0.32), 7.282 (0.47), 7.285 (0.32), 7.364 (0.46), 7.379 (0.49), 7.386 (0.61), 7.400 (0.59), 7.407 (0.41), 7.421 (0.34), 7.529 (0.50), 8.379 (1.44), 8.401 (1.39), 8.671 (2.40), 10.330 (0.62), 10.353 (0.60). |
| 81 | 1-(2,4-Difluorophenyl)-7-[(2-hydroxyethyl)amino]-4-oxo-N-[1,1,1-trifluoropentan-2-yl]-1,4-dihydro-1,8-naphthyridine-3-carboxamide<br>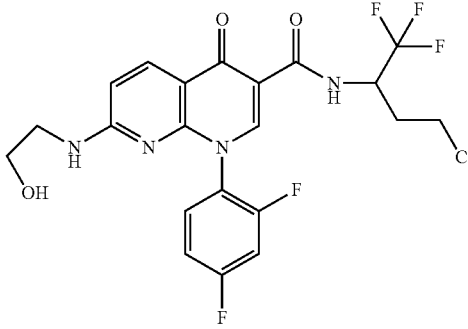<br>(66% of theory) | LC-MS (Method 1): $R_t$ = 1.03 min<br>MS (ESpos): m/z = 485.1 [M + H]$^+$<br>$^1$H-NMR (400 MHz, CDCl$_3$) δ [ppm]: 0.009 (16.00), 0.078 (1.32), 0.953 (2.90), 0.972 (6.47), 0.990 (3.32), 1.268 (0.49), 1.456 (0.71), 1.473 (0.75), 1.592 (5.81), 1.718 (0.94), 1.730 (0.71), 1.744 (0.98), 1.756 (0.76), 1.768 (0.62), 1.828 (0.76), 2.053 (0.81), 2.450 (0.67), 2.795 (0.70), 3.334 (2.18), 3.345 (2.48), 3.359 (1.19), 3.499 (2.54), 3.650 (1.68), 3.662 (2.43), 4.853 (0.54), 5.478 (1.10), 6.535 (3.40), 6.557 (3.46), 7.006 (0.52), 7.034 (0.80), 7.054 (2.29), 7.074 (2.10), 7.092 (0.63), 7.362 (0.56), 7.383 (0.82), 7.397 (0.84), 7.529 (0.52), 8.381 (2.56), 8.403 (2.49), 8.665 (5.40), 10.366 (1.05), 10.390 (1.04). |

Example 82

1-(2,4-Difluorophenyl)-7-[(2-hydroxyethyl)(methyl)amino]-4-oxo-N-(tricyclo[3.3.1.1$^{3,7}$]dec-1-yl)-1,4-dihydro-1,8-naphthyridine-3-carboxamide

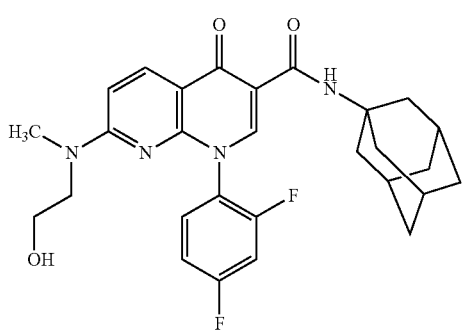 [SMILES: CN(CCO)c1ccc2c(=O)c(C(=O)NC34CC5CC(CC(C5)C3)C4)cn(-c3ccc(F)cc3F)c2n1]

100 mg (0.27 mmol) of the compound from example 39A were initially charged in 3 ml of DMF, 121 mg (0.32 mmol) of HATU and 110 mg (0.85 mmol) of DIPEA were added, and the mixture was stirred at 20° C. for 30 minutes. Then 56 mg (0.37 mmol) of 1-adamantanamine were added and the mixture was stirred at 20° C. for 2 hours. Subsequently, the mixture was purified via preparative HPLC (eluent: acetonitrile/water gradient with 0.1% formic acid). This gave 92 mg (68% of theory) of the title compound.

LC-MS (Method 1): $R_t$=1.19 min; m/z=509.2 [M+H]$^+$.

$^1$H-NMR (400 MHz, DMSO-d$_6$) δ [ppm]: −0.150 (0.24), −0.023 (0.16), −0.020 (0.15), −0.009 (2.07), 0.007 (1.93), 0.145 (0.23), 1.146 (0.09), 1.168 (0.83), 1.174 (0.20), 1.233 (0.21), 1.270 (0.15), 1.671 (7.32), 1.987 (0.25), 2.055 (16.00), 2.322 (0.13), 2.327 (0.20), 2.365 (0.17), 2.523 (0.40), 2.669 (0.21), 2.674 (0.16), 2.709 (0.18), 3.020 (0.25), 3.162 (2.25), 3.173 (2.27), 4.073 (0.44), 4.087 (0.43), 4.648 (0.12), 6.578 (0.11), 6.903 (0.34), 7.285 (0.37), 7.290 (0.40), 7.306 (0.74), 7.312 (0.77), 7.328 (0.40), 7.332 (0.42), 7.526 (0.38), 7.533 (0.39), 7.556 (0.66), 7.574 (0.40), 7.581 (0.38), 7.747 (0.44), 7.762 (0.54), 7.769 (0.88), 7.784 (0.86), 7.790 (0.51), 7.805 (0.43), 8.143 (1.20), 8.231 (0.74), 8.254 (0.73), 8.473 (5.19), 9.954 (2.53).

Example 83

1-(2,4-Difluorophenyl)-7-[(2-fluoroethyl)amino]-4-oxo-N-(tricyclo[3.3.1.1³,⁷]dec-1-yl)-1,4-dihydro-1,8-naphthyridine-3-carboxamide

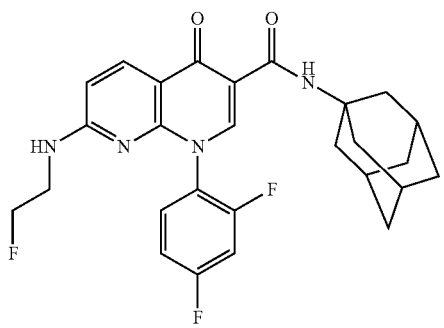 [SMILES: O=C(NC12CC3CC(CC(C3)C1)C2)c1cn(-c2ccc(F)cc2F)c2nc(NCCF)ccc2c1=O]

100 mg (0.17 mmol, 77% purity) of the compound from example 41A were initially charged in 2.4 ml of DMF, 96 mg (0.25 mmol) of HATU and 87 mg (0.68 mmol) of DIPEA were added, and the mixture was stirred at 20° C. for 30 minutes. Then 45 mg (0.3 mmol) of 1-adamantanamine were added and the mixture was stirred at 20° C. for 2 hours. Subsequently, the mixture was purified via preparative HPLC (eluent: acetonitrile/water gradient with 0.1% formic acid). This gave 92 mg (87% of theory) of the title compound. In addition, 11 mg (11% of theory) of the title compound from Example 84 were obtained (for analysis see Example 84).

LC-MS (Method 1): $R_t$=1.25 min; m/z=497.1 [M+H]⁺.

¹H-NMR (400 MHz, DMSO-d₆) δ [ppm]: −0.009 (1.89), 0.007 (1.26), 1.174 (0.32), 1.669 (7.54), 1.988 (0.63), 2.053 (16.00), 4.243 (0.76), 4.362 (0.77), 5.753 (3.13), 6.692 (1.39), 6.714 (1.40), 7.293 (0.46), 7.316 (0.83), 7.336 (0.45), 7.535 (0.54), 7.542 (0.55), 7.564 (0.77), 7.583 (0.54), 7.590 (0.53), 7.763 (0.52), 7.778 (0.73), 7.785 (1.00), 7.800 (1.00), 7.822 (0.48), 8.126 (0.44), 8.173 (1.35), 8.195 (1.26), 8.262 (0.52), 8.459 (4.10), 9.957 (2.41).

Example 84

7-(Aziridin-1-yl)-1-(2,4-difluorophenyl)-4-oxo-N-(tricyclo[3.3.1.1³,⁷]dec-1-yl)-1,4-dihydro-1,8-naphthyridine-3-carboxamide

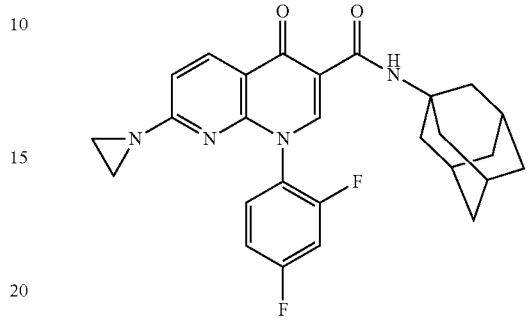

As described in the preparation of the compound from Example 83, 100 mg (0.17 mmol) of the compound from Example 41A were used to obtain 11 mg (11% of theory) of the title compound.

LC-MS (Method 1): $R_t$=1.34 min; m/z=479.2 [M+H]⁺.

¹H-NMR (400 MHz, DMSO-d₆) δ [ppm]: −0.150 (1.66), −0.061 (0.29), −0.009 (16.00), 0.007 (12.85), 0.146 (1.63), 1.147 (0.73), 1.670 (4.93), 2.055 (10.44), 2.322 (1.15), 2.327 (1.55), 2.331 (1.20), 2.365 (1.43), 2.664 (1.49), 2.669 (1.88), 2.709 (1.75), 2.934 (1.81), 3.285 (1.03), 3.460 (0.27), 5.753 (5.19), 6.890 (1.66), 6.912 (1.65), 7.302 (0.31), 7.322 (0.58), 7.342 (0.34), 7.552 (0.36), 7.571 (0.50), 7.600 (0.38), 7.761 (0.39), 7.783 (0.61), 7.799 (0.61), 7.820 (0.29), 8.251 (1.83), 8.274 (1.69), 8.474 (3.26), 9.944 (1.67).

In analogy to Example 83, the example compounds shown in Table 10 were prepared by reacting the compound from Example 41A with the appropriate amines (or salts thereof) under the reaction conditions described. Differences are specified in the respective examples.

TABLE 10

| Ex. | | Analytical data |
|---|---|---|
| 85 | rac-1-(2,4-Difluorophenyl)-7-[(2-fluoroethyl)amino]-4-oxo-N-[1,1,1-trifluorobutan-2-yl]-1,4-dihydro-1,8-naphthyridine-3-carboxamide<br><br>(62% of theory) | LC-MS (Method 1): $R_t$ = 1.09 min<br>MS (ESpos): m/z = 473.2 [M + H]⁺<br>¹H-NMR (400 MHz, CDCl3) δ [ppm]: 0.001 (0.93), 0.017 (0.79), 1.054 (1.69), 1.073 (3.70), 1.091 (1.86), 1.570 (16.00), 1.722 (0.35), 1.729 (0.30), 1.739 (0.43), 1.748 (0.36), 1.758 (0.35), 1.765 (0.42), 1.783 (0.35), 1.933 (0.29), 1.943 (0.31), 1.951 (0.33), 1.961 (0.35), 1.969 (0.30), 1.978 (0.28), 3.422 (0.41), 3.434 (0.57), 3.447 (0.46), 3.488 (0.39), 3.501 (0.48), 3.514 (0.36), 4.338 (0.59), 4.455 (0.57), 4.749 (0.32), 4.758 (0.32), 4.768 (0.29), 4.777 (0.30), 5.308 (0.55), 5.325 (0.36), 5.339 (0.64), 5.353 (0.34), 6.551 (2.21), 6.573 (2.25), 7.022 (0.32), 7.029 (0.45), 7.050 (1.36), 7.070 (1.29), 7.091 (0.34), 7.363 (0.34), 7.378 (0.45), 7.385 (0.53), 7.399 (0.54), 7.405 (0.33), 8.408 (1.71), 8.430 (1.64), 8.690 (2.98), 10.367 (0.57), 10.391 (0.56). |

TABLE 10-continued

| Ex. | | Analytical data |
|---|---|---|
| 86 | rac-1-(2,4-Difluorophenyl)-7-[(2-fluoroethyl)amino]-4-oxo-N-[(2R)-1,1,1-trifluoropentan-2-yl]-1,4-dihydro-1,8-naphthyridine-3-carboxamide<br><br>(80% of theory) | LC-MS (Method 1): $R_t$ = 1.18 min<br>MS (ESpos): m/z = 487.2 [M + H]$^+$<br>$^1$H-NMR (400 MHz, DMSO-d$_6$) δ [ppm]: 0.890 (4.26), 0.908 (9.54), 0.926 (4.93), 1.156 (4.22), 1.174 (8.57), 1.191 (4.34), 1.293 (0.33), 1.311 (0.65), 1.329 (0.91), 1.348 (1.13), 1.366 (1.05), 1.385 (0.71), 1.403 (0.59), 1.437 (0.98), 1.457 (0.87), 1.589 (0.40), 1.601 (0.41), 1.624 (1.05), 1.636 (0.79), 1.650 (1.11), 1.662 (0.77), 1.673 (0.58), 1.685 (0.45), 1.735 (0.57), 1.744 (0.68), 1.768 (1.06), 1.777 (0.82), 1.786 (0.91), 1.987 (16.00), 3.238 (1.12), 4.001 (1.31), 4.019 (3.90), 4.037 (3.86), 4.055 (1.27), 4.248 (1.63), 4.365 (1.62), 4.787 (0.88), 4.809 (0.90), 6.727 (2.72), 6.750 (2.78), 7.296 (0.91), 7.318 (1.80), 7.339 (0.95), 7.537 (1.01), 7.544 (1.05), 7.563 (1.65), 7.586 (1.05), 7.592 (1.00), 7.788 (0.71), 7.809 (1.46), 7.825 (1.47), 7.846 (0.65), 8.195 (3.34), 8.217 (3.32), 8.601 (4.68), 10.499 (2.74), 10.523 (2.63). |
| 87 | 1-(2,4-Difluorophenyl)-7-[(2-fluoroethyl)amino]-4-oxo-N-[(2S)-1,1,1-trifluorobutan-2-yl]-1,4-dihydro-1,8-naphthyridine-3-carboxamide<br><br>(88% of theory) | LC-MS (Method 1): $R_t$ = 1.10 min<br>MS (ESpos): m/z = 473.1 [M + H]$^+$<br>$^1$H-NMR (400 MHz, CDCl3) δ [ppm]: 0.001 (0.70), 0.017 (0.67), 1.054 (2.82), 1.073 (6.18), 1.091 (3.08), 1.269 (0.84), 1.571 (16.00), 1.704 (0.44), 1.722 (0.57), 1.730 (0.49), 1.739 (0.70), 1.748 (0.60), 1.758 (0.60), 1.765 (0.71), 1.783 (0.56), 1.933 (0.48), 1.943 (0.53), 1.952 (0.56), 1.962 (0.60), 1.969 (0.51), 1.979 (0.47), 2.054 (1.54), 3.422 (0.69), 3.435 (0.96), 3.448 (0.77), 3.488 (0.65), 3.502 (0.81), 3.515 (0.60), 4.338 (0.98), 4.456 (0.97), 4.749 (0.52), 4.758 (0.53), 4.767 (0.50), 4.777 (0.51), 5.322 (0.60), 5.336 (1.10), 5.350 (0.59), 6.551 (3.52), 6.573 (3.59), 7.022 (0.52), 7.029 (0.73), 7.050 (2.28), 7.070 (2.18), 7.091 (0.57), 7.363 (0.60), 7.378 (0.75), 7.385 (0.95), 7.399 (0.92), 7.405 (0.56), 7.420 (0.47), 8.408 (2.76), 8.430 (2.69), 8.690 (4.93), 10.368 (0.96), 10.393 (0.94). |
| 88 | 1-(2,4-Difluorophenyl)-7-[(2-fluoroethyl)amino]-4-oxo-N-[1,1,1-trifluoro-4-methylpentan-2-yl]-1,4-dihydro-1,8-naphthyridine-3-carboxamide<br><br>(81% of theory) | LC-MS (Method 1): $R_t$ = 1.21 min<br>MS (ESpos): m/z = 501.1 [M + H]$^+$<br>$^1$H-NMR (400 MHz, CDCl3) δ [ppm]: 0.002 (1.23), 0.018 (0.96), 0.954 (3.69), 0.961 (3.35), 0.970 (4.10), 0.977 (3.90), 0.983 (6.77), 1.000 (6.52), 1.251 (1.45), 1.269 (2.97), 1.287 (1.48), 1.562 (16.00), 1.605 (0.50), 1.613 (0.98), 1.621 (0.57), 1.638 (0.74), 1.711 (0.73), 1.721 (0.95), 1.739 (0.76), 1.749 (1.28), 1.755 (0.82), 1.784 (0.91), 1.793 (0.54), 1.803 (0.60), 2.054 (5.63), 3.422 (0.69), 3.434 (0.94), 3.447 (0.77), 3.487 (0.65), 3.501 (0.78), 3.514 (0.58), 4.123 (1.22), 4.140 (1.19), 4.338 (0.99), 4.455 (0.98), 4.892 (0.54), 4.897 (0.51), 4.916 (0.55), 5.308 (0.65), 5.322 (1.19), 5.336 (0.63), 6.548 (3.79), 6.570 (3.87), 7.024 (0.60), 7.045 (1.87), 7.066 (1.71), 7.089 (0.51), 7.364 (0.78), 7.378 (0.90), 7.385 (1.10), 7.399 (1.12), 7.406 (0.70), 7.420 (0.61), 8.402 (2.82), 8.424 (2.74), 8.693 (4.00), 10.314 (1.02), 10.338 (1.01). |

TABLE 10-continued

| Ex. | | Analytical data |
|---|---|---|
| 89 | 1-(2,4-Difluorophenyl)-7-[(2-fluoroethyl)amino]-N-(1,1,1,3,3,3-hexafluoropropan-2-yl)-4-oxo-1,4-dihydro-1,8-naphthyridine-3-carboxamide<br>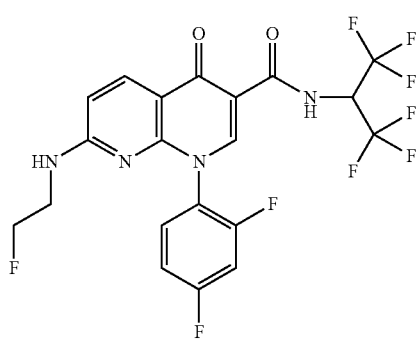<br>Workup: Precipitate the product from water/ 1M aqueous hydrochloric acid and filter off the precipitate.<br>(49% of theory) | LC-MS (Method 1): $R_t$ = 1.16 min<br>MS (ESpos): m/z = 513.0 [M + H]$^+$<br>$^1$H-NMR (400 MHz, DMSO-$d_6$) δ [ppm]: −0.009 (7.65), 0.007 (6.55), 2.520 (2.86), 2.523 (3.34), 2.525 (3.18), 3.244 (2.42), 4.249 (3.34), 4.367 (3.31), 6.293 (1.94), 6.298 (1.86), 6.317 (2.05), 6.750 (5.02), 6.772 (5.07), 7.302 (2.00), 7.306 (2.17), 7.309 (2.15), 7.322 (3.87), 7.328 (4.05), 7.344 (2.18), 7.348 (2.17), 7.351 (2.07), 7.547 (2.40), 7.554 (2.64), 7.572 (3.49), 7.576 (3.71), 7.595 (2.54), 7.602 (2.55), 7.799 (2.53), 7.814 (3.05), 7.821 (4.81), 7.836 (5.18), 7.843 (2.65), 7.857 (2.68), 8.216 (4.87), 8.239 (4.83), 8.278 (2.50), 8.290 (3.13), 8.705 (16.00), 11.489 (5.43), 11.515 (5.18). |

Example 90

1-(2,4-Difluorophenyl)-4-oxo-N-(tricyclo[3.3.1.1$^{3,7}$]dec-1-yl)-7-[(2,2,2-trifluoroethyl)amino]-1,4-dihydro-1,8-naphthyridine-3-carboxamide 73 mg (0.18 mmol) of the compound from example 47A were initially charged in 2 ml of DMF, 83 mg (0.22 mmol) of HATU and 76 mg (0.58 mmol) of DIPEA were added, and the mixture was stirred at 20° C. for 30 minutes. Then 39 mg (0.26 mmol) of 1-adamantanamine were added and the mixture was stirred at 20° C. for 2 hours. Subsequently, the mixture was purified via preparative HPLC (eluent: acetonitrile/water gradient with 0.1% formic acid). This gave 86 mg (88% of theory) of the title compound.

LC-MS (Method 1): $R_t$=1.35 min; m/z=533.3 [M+H]$^+$.
$^1$H-NMR (400 MHz, DMSO-$d_6$) δ [ppm]: −0.150 (0.27), −0.009 (2.24), 0.007 (2.13), 0.145 (0.26), 1.671 (7.23), 2.056 (16.00), 2.327 (0.23), 2.365 (0.31), 2.669 (0.25), 2.709 (0.31), 3.842 (0.52), 6.782 (1.04), 6.804 (1.05), 7.302 (0.41), 7.323 (0.76), 7.344 (0.42), 7.529 (0.49), 7.536 (0.52), 7.554 (0.73), 7.577 (0.51), 7.584 (0.50), 7.754 (0.48), 7.769 (0.58), 7.776 (0.96), 7.791 (0.95), 7.798 (0.54), 7.813 (0.47), 8.149 (0.31), 8.271 (2.14), 8.293 (2.02), 8.387 (0.42), 8.511 (4.59), 9.896 (2.62).

In analogy to Example 90, the example compounds shown in Table 11 were prepared by reacting the compound from Example 47A or the compound from Example 55A with the appropriate amines (or salts thereof) under the reaction conditions described. Differences are specified in the respective examples.

TABLE 11

| Ex. | | Analytical data |
|---|---|---|
| 91 | 1-(2,4-Difluorophenyl)-N-(3-fluorotricyclo[3.3.1.1$^{3,7}$]dec-1-yl)-4-oxo-7-[(2,2,2-trifluoroethyl)amino]-1,4-dihydro-1,8-naphthyridine-3-carboxamide<br>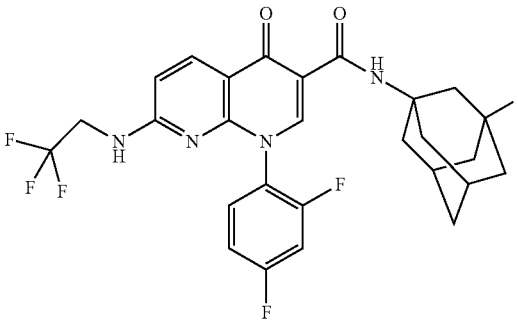<br>(62% of theory) | LC-MS (Method 1): R$_t$ = 1.21 min<br>MS (ESpos): m/z = 551.2 [M + H]$^+$<br>$^1$H-NMR (400 MHz, CDCl3) δ [ppm]:<br>0.009 (2.02), 0.078 (0.26), 1.250 (0.62),<br>1.268 (1.29), 1.286 (0.65), 1.576 (16.00),<br>1.631 (0.40), 1.891 (0.69), 1.940 (0.58),<br>2.053 (2.80), 2.083 (0.82), 2.132 (0.59),<br>2.376 (1.07), 2.894 (0.75), 2.966 (0.89),<br>3.798 (0.25), 3.820 (0.77), 3.837 (0.87),<br>3.842 (0.82), 3.859 (0.79), 3.881 (0.25),<br>4.104 (0.18), 4.122 (0.52), 4.140 (0.53),<br>4.158 (0.17), 5.245 (0.48), 6.600 (1.56),<br>6.622 (1.58), 7.006 (0.15), 7.024 (0.24),<br>7.031 (0.41), 7.044 (0.67), 7.051 (0.65),<br>7.063 (0.74), 7.070 (0.59), 7.076 (0.40),<br>7.081 (0.37), 7.351 (0.32), 7.365 (0.37),<br>7.372 (0.42), 7.385 (0.42), 7.394 (0.30),<br>7.408 (0.24), 7.529 (0.15), 8.465 (1.55),<br>8.487 (1.50), 8.674 (2.56), 9.991 (0.80). |
| 92 | 1-(2,4-Difluorophenyl)-N-(3,5-difluorotricyclo[3.3.1.1$^{3,7}$]dec-1-yl)-4-oxo-7-[(2,2,2-trifluoroethyl)amino]-1,4-dihydro-1,8-naphthyridine-3-carboxamide<br>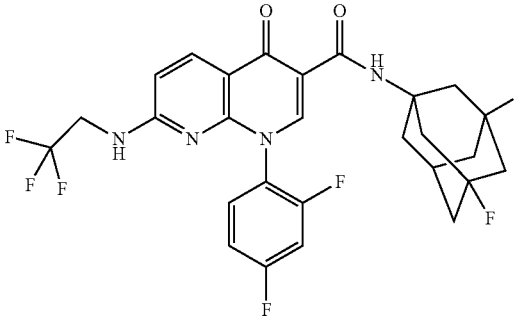<br>(33% of theory) | LC-MS (Method 1): R$_t$ = 1.13 min<br>MS (ESpos): m/z = 569.3 [M + H]$^+$<br>$^1$H-NMR (400 MHz, DMSO-d$_6$) δ [ppm]:<br>−0.150 (0.90), −0.009 (7.71), 0.007 (7.47),<br>0.145 (0.97), 1.156 (2.58), 1.174 (5.20),<br>1.192 (2.65), 1.804 (9.58), 1.902 (6.37),<br>1.987 (9.51), 2.072 (1.78), 2.112 (1.99),<br>2.171 (3.19), 2.327 (3.45), 2.448 (1.58),<br>2.669 (1.05), 2.709 (1.19), 3.161 (15.44),<br>3.174 (16.00), 3.842 (1.60), 4.020 (2.24),<br>4.038 (2.24), 4.062 (1.58), 4.075 (4.33),<br>4.088 (4.28), 4.101 (1.51), 6.795 (2.89),<br>6.818 (3.02), 7.305 (1.19), 7.326 (2.31),<br>7.347 (1.31), 7.532 (1.36), 7.538 (1.51),<br>7.561 (2.24), 7.580 (1.53), 7.586 (1.51),<br>7.759 (1.41), 7.774 (1.65), 7.781 (2.82),<br>7.796 (2.84), 7.817 (1.41), 8.279 (6.13),<br>8.301 (5.84), 8.419 (1.26), 8.551 (13.67),<br>10.210 (6.91). |
| 93 | 1-(2,4-Difluorophenyl)-4-oxo-7-[(2,2,2-trifluoroethyl)amino]-N-[1,1,1-trifluoropropan-2-yl]-1,4-dihydro-1,8-naphthyridine-3-carboxamide<br>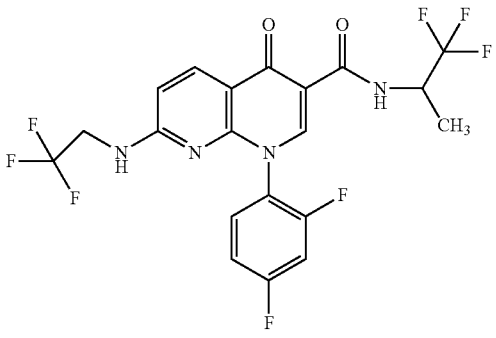<br>(45% of theory) | LC-MS (Method 1): R$_t$ = 1.09 min<br>MS (ESpos): m/z = 495.1 [M + H]$^+$<br>$^1$H-NMR (400 MHz, CDCl$_3$) δ [ppm]: 0.001<br>(0.87), 0.016 (0.49), 0.017 (0.80), 1.251<br>(0.34), 1.269 (0.71), 1.287 (0.37), 1.451<br>(2.80), 1.468 (2.83), 1.566 (16.00), 2.054<br>(1.26), 2.630 (0.83), 2.634 (0.30), 2.637<br>(0.20), 3.818 (0.41), 3.827 (0.36), 3.835<br>(0.40), 3.842 (0.52), 3.849 (0.38), 3.857<br>(0.36), 3.866 (0.41), 4.122 (0.27), 4.140<br>(0.27), 4.918 (0.24), 4.937 (0.24), 5.265<br>(0.36), 6.621 (1.63), 6.643 (1.66), 7.042<br>(0.21), 7.049 (0.33), 7.065 (0.67), 7.068<br>(0.60), 7.084 (0.69), 7.093 (0.41), 7.102<br>(0.30), 7.259 (0.24), 7.261 (0.42), 7.276<br>(0.51), 7.280 (0.23), 7.382 (0.30), 7.401<br>(0.29), 8.479 (1.56), 8.501 (1.52), 8.722<br>(1.17), 10.364 (0.37), 10.388 (0.36). |

TABLE 11-continued

| Ex. | | Analytical data |
|---|---|---|
| 94 | 1-(2,4-Difluorophenyl)-4-oxo-N-[(2R)-1,1,1-trifluorobutan-2-yl]-7-[(2,2,2-trifluoroethyl)amino]-1,4-dihydro-1,8-naphthyridine-3-carboxamide 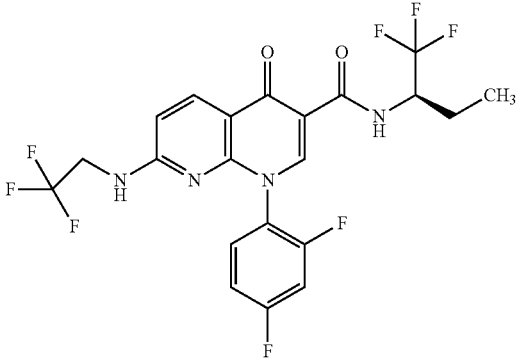 (45% of theory) | LC-MS (Method 1): $R_t$ = 1.10 min<br>MS (ESpos): m/z = 509.2 [M + H]$^+$<br>$^1$H-NMR (400 MHz, DMSO-d$_6$) δ [ppm]:<br>−0.009 (7.83), 0.007 (6.82), 0.945 (7.20),<br>0.963 (16.00), 0.982 (7.83), 1.617 (1.49),<br>1.624 (1.37), 1.634 (1.79), 1.643 (1.63),<br>1.652 (1.56), 1.659 (1.75), 1.678 (1.35),<br>1.850 (1.25), 1.860 (1.49), 1.868 (1.53),<br>1.878 (1.70), 1.885 (1.49), 1.895 (1.30),<br>1.903 (1.13), 2.523 (2.31), 3.851 (1.98),<br>3.869 (1.96), 3.892 (1.42), 4.735 (1.44),<br>4.754 (1.37), 6.819 (3.40), 6.841 (3.45),<br>7.306 (1.39), 7.328 (2.81), 7.345 (1.53),<br>7.534 (1.56), 7.542 (1.63), 7.560 (2.64),<br>7.565 (2.69), 7.583 (1.68), 7.590 (1.63),<br>7.796 (1.86), 7.805 (1.86), 7.819 (1.84),<br>8.300 (7.29), 8.322 (6.91), 8.467 (1.63),<br>8.655 (6.11), 8.662 (5.52), 10.426 (4.88),<br>10.450 (4.72). |
| 95 | rac-1-(2,4-Difluorophenyl)-4-oxo-7-[(2,2,2-trifluoroethyl)amino]-N-[1,1,1-trifluoro-4-methylpentan-2-yl]-1,4-dihydro-1,8-naphthyridine-3-carboxamide 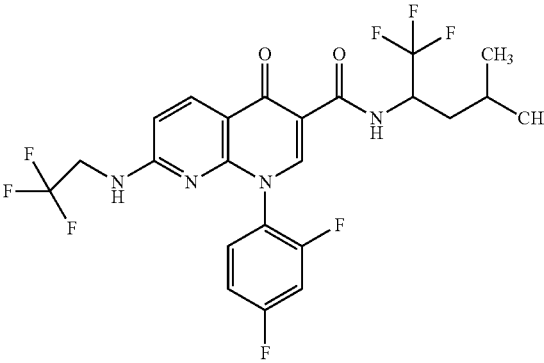 (54% of theory) | LC-MS (Method 1): $R_t$ = 1.25 min<br>MS (ESpos): m/z = 537.1 [M + H]$^+$<br>$^1$H-NMR (400 MHz, CDCl$_3$) δ [ppm]: 0.002<br>(1.21), 0.018 (0.98), 0.957 (3.49), 0.973<br>(3.84), 0.984 (6.39), 1.001 (6.32), 1.251<br>(0.59), 1.269 (1.24), 1.287 (0.60), 1.559<br>(16.00), 1.609 (0.40), 1.617 (0.79), 1.625<br>(0.46), 1.643 (0.60), 1.708 (0.56), 1.718<br>(0.76), 1.736 (0.61), 1.746 (1.03), 1.752<br>(0.70), 1.775 (0.71), 1.797 (0.39), 2.054<br>(2.17), 3.818 (0.79), 3.831 (0.85), 3.835<br>(0.89), 3.841 (0.82), 3.848 (0.86), 3.853<br>(0.88), 3.857 (0.85), 3.870 (0.78), 4.123<br>(0.47), 4.141 (0.46), 4.892 (0.42), 4.897<br>(0.39), 4.917 (0.43), 5.210 (0.48), 5.226<br>(0.89), 5.242 (0.47), 6.619 (3.06), 6.641<br>(3.12), 7.044 (0.47), 7.063 (1.28), 7.082<br>(1.15), 7.369 (0.62), 7.383 (0.69), 7.390<br>(0.77), 7.404 (0.80), 7.411 (0.52), 7.426<br>(0.42), 8.478 (2.53), 8.500 (2.48), 8.735<br>(3.20), 10.235 (0.79), 10.259 (0.78). |
| 96 | 1-(2,4-Difluorophenyl)-4-oxo-7-[(2,2,2-trifluoroethyl)amino]-N-[1-(trifluoromethyl)cyclopentyl]-1,4-dihydro-1,8-naphthyridine-3-carboxamide 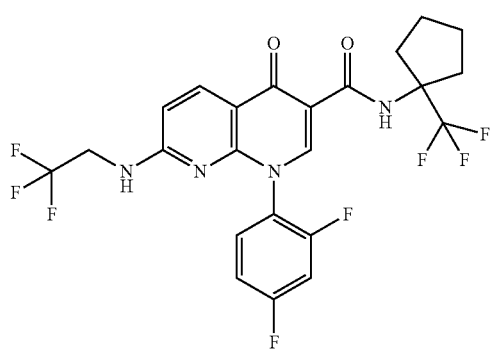 (50% of theory) | LC-MS (Method 1): $R_t$ = 1.21 min<br>MS (ESpos): m/z = 535.1 [M + H]$^+$<br>$^1$H-NMR (400 MHz, DMSO-d$_6$) δ [ppm]:<br>−0.009 (2.42), 0.007 (1.94), 1.174 (2.34),<br>1.731 (3.38), 1.749 (4.42), 1.773 (4.61),<br>1.790 (3.12), 1.987 (4.41), 2.026 (2.74),<br>2.044 (3.04), 2.061 (3.19), 2.350 (1.72),<br>2.365 (2.67), 2.384 (2.86), 2.418 (1.36),<br>3.823 (1.37), 3.847 (1.84), 3.867 (1.87),<br>6.807 (3.27), 6.829 (3.31), 7.299 (1.38),<br>7.304 (1.50), 7.321 (2.76), 7.326 (2.90),<br>7.342 (1.55), 7.347 (1.55), 7.532 (1.76),<br>7.539 (1.85), 7.557 (2.72), 7.561 (2.71),<br>7.580 (1.80), 7.587 (1.75), 7.762 (1.74),<br>7.777 (2.08), 7.784 (3.42), 7.799 (3.34),<br>7.805 (1.86), 7.820 (1.63), 8.293 (6.84),<br>8.315 (6.47), 8.454 (1.57), 8.604 (16.00),<br>10.523 (9.58). |

TABLE 11-continued

| Ex. | | Analytical data |
|---|---|---|
| 97 | 1-(2,4-Difluorophenyl)-N-(4-fluorobicylco[2.2.2]oct-1-yl)-4-oxo-7-[(2,2,2-trifluoroethyl)amino]-1,4-dihydro-1,8-naphthyridine-3-carboxamide<br>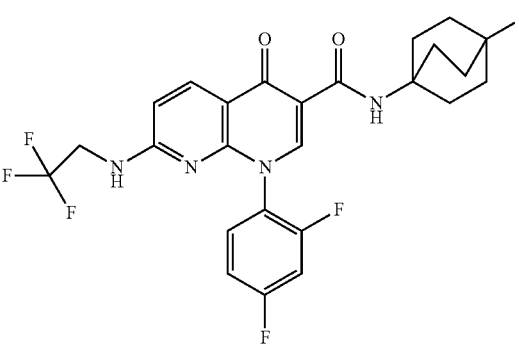<br>(59% of theory) | LC-MS (Method 1): $R_t$ = 1.16 min<br>MS (ESpos): m/z = 525.1 [M + H]$^+$<br>$^1$H-NMR (400 MHz, CDCl$_3$) δ [ppm]: 0.010 (3.66), 0.079 (0.26), 1.233 (0.17), 1.251 (0.35), 1.269 (0.74), 1.287 (0.37), 1.566 (16.00), 1.939 (0.49), 1.953 (0.93), 1.969 (0.95), 1.980 (1.01), 1.993 (0.63), 2.054 (1.38), 2.234 (1.14), 2.246 (0.89), 2.255 (1.03), 2.274 (0.83), 3.811 (0.21), 3.816 (0.49), 3.833 (0.54), 3.838 (0.50), 3.855 (0.48), 4.123 (0.29), 4.140 (0.29), 5.205 (0.26), 6.594 (1.02), 6.616 (1.03), 7.031 (0.24), 7.045 (0.44), 7.051 (0.41), 7.055 (0.26), 7.065 (0.43), 7.070 (0.38), 7.076 (0.25), 7.082 (0.21), 7.344 (0.20), 7.358 (0.22), 7.365 (0.25), 7.378 (0.26), 7.387 (0.19), 8.454 (0.99), 8.476 (0.95), 8.657 (1.56), 9.864 (0.47). |
| 98 | 1-(2,4-Difluorophenyl)-N-(4-methylbicylco[2.2.2]oct-1-yl)-4-oxo-7-[(2,2,2-trifluoroethyl)amino]-1,4-dihydro-1,8-naphthyridine-3-carboxamide<br>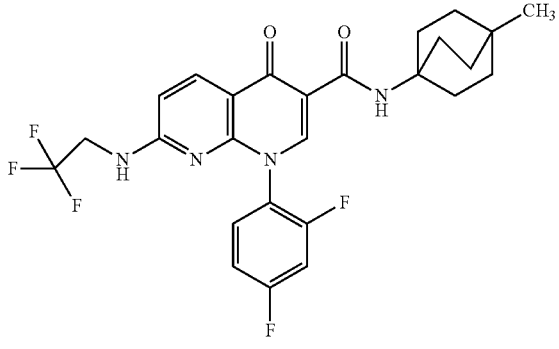<br>(56% of theory) | LC-MS (Method 1): $R_t$ = 1.28 min<br>MS (ESpos): m/z = 521.2 [M + H]$^+$<br>$^1$H-NMR (400 MHz, CDCl$_3$) δ [ppm]: 0.001 (0.28), 0.017 (0.22), 0.816 (1.69), 1.507 (0.44), 1.527 (0.51), 1.547 (0.58), 1.564 (16.00), 2.021 (0.50), 2.041 (0.48), 2.061 (0.42), 3.816 (0.20), 3.832 (0.22), 3.838 (0.20), 3.855 (0.20), 5.174 (0.10), 6.582 (0.44), 6.604 (0.46), 7.006 (0.11), 7.023 (0.10), 7.037 (0.19), 7.044 (0.18), 7.056 (0.19), 7.062 (0.16), 7.342 (0.09), 7.363 (0.11), 7.376 (0.12), 7.399 (0.08), 7.529 (0.10), 8.464 (0.43), 8.486 (0.42), 8.674 (0.69), 9.766 (0.19). |
| 99 | rac-1-(2,4-Difluorophenyl)-7-[methyl(2,2,2-trifluoroethyl)amino]-4-oxo-N-[1,1,1-trifluoropropan-2-yl]-1,4-dihydro-1,8-naphthyridine-3-carboxamide<br>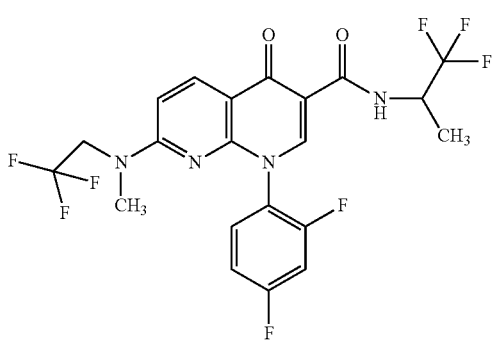<br>Compound from Example 55A and 1,1,1-trifluoropropan-2-amine | LC-MS (Method 1): $R_t$ = 1.18 min<br>MS (ESpos): m/z = 509.2 [M + H]$^+$<br>$^1$H-NMR (400 MHz, DMSO-d$_6$) δ [ppm]: 1.168 (1.57), 1.232 (1.49), 1.269 (1.09), 1.368 (15.88), 1.385 (16.00), 3.094 (6.92), 4.238 (0.99), 4.872 (1.17), 4.892 (1.82), 4.911 (1.83), 4.930 (1.13), 7.099 (1.62), 7.120 (1.64), 7.306 (1.51), 7.311 (1.61), 7.328 (2.88), 7.333 (3.00), 7.349 (1.64), 7.354 (1.69), 7.547 (1.45), 7.570 (2.64), 7.595 (1.43), 7.777 (1.34), 7.792 (1.49), 7.800 (1.54), 7.808 (1.57), 7.823 (1.38), 8.408 (4.61), 8.431 (4.41), 8.692 (6.39), 8.700 (5.51), 10.428 (2.96), 10.451 (2.92). |

TABLE 11-continued

| Ex. | | Analytical data |
|---|---|---|
| 100 | rac-1-(2,4-Difluorophenyl)-7-[methyl(2,2,2-trifluoroethyl)amino]-4-oxo-N-[1,1,1-trifluorobutan-2-yl]-1,4-dihydro-1,8-naphthyridine-3-carboxamide<br>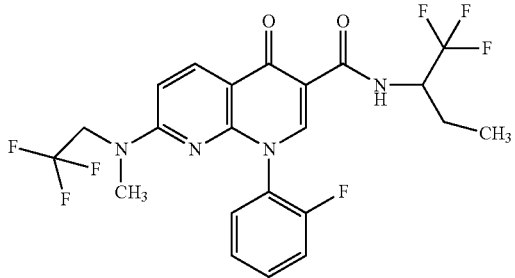<br>(100% of theory) | LC-MS (Method 1): Rt = 1.22 min<br>MS (ESpos): m/z = 523.2 [M + H]$^+$<br>1H-NMR (400 MHz, DMSO-d6) δ [ppm]:<br>−0.009 (6.06), 0.007 (4.96), 0.950 (7.55),<br>0.968 (16.00), 0.987 (7.84), 1.168 (1.87),<br>1.233 (1.40), 1.269 (1.13), 1.604 (1.17),<br>1.622 (1.56), 1.630 (1.41), 1.639 (1.87),<br>1.648 (1.62), 1.657 (1.61), 1.665 (1.81),<br>1.683 (1.39), 1.854 (1.34), 1.864 (1.54),<br>1.873 (1.55), 1.883 (1.71), 1.889 (1.50),<br>1.899 (1.34), 1.908 (1.20), 1.918 (0.98),<br>2.327 (0.87), 2.365 (1.13), 2.523 (1.71),<br>2.669 (0.82), 2.709 (1.03), 3.094 (5.27),<br>4.232 (0.96), 4.718 (0.86), 4.742 (1.43),<br>4.762 (1.30), 7.102 (1.57), 7.123 (1.59),<br>7.312 (1.54), 7.333 (2.90), 7.349 (1.59),<br>7.543 (1.60), 7.550 (1.63), 7.568 (2.65),<br>7.592 (1.70), 7.598 (1.57), 7.803 (1.81),<br>7.813 (1.79), 7.827 (1.76), 8.418 (4.92),<br>8.440 (4.73), 8.699 (6.82), 8.707 (6.06),<br>10.377 (4.66), 10.401 (4.47). |

Example 101

1-(2,4-Difluorophenyl)-7-[(2-fluoroethyl)(methyl)amino]-4-oxo-N-(tricyclo[3.3.1.1$^{3,7}$]dec-1-yl)-1,4-dihydro-1,8-naphthyridine-3-carboxamide

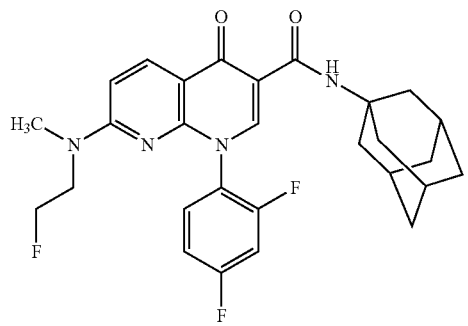 [SMILES: CN(CCF)c1ccc2c(=O)c(C(=O)NC34CC5CC(CC(C5)C3)C4)cn(-c3ccc(F)cc3F)c2n1]

100 mg (0.27 mmol) of the compound from example 42A were initially charged in 3 ml of DMF, 121 mg (0.32 mmol) of HATU and 110 mg (0.85 mmol) of DIPEA were added, and the mixture was stirred at 20° C. for 30 minutes. Then 56 mg (0.37 mmol) of 1-adamantanamine were added and the mixture was stirred at 20° C. for 2 hours. Subsequently, the mixture was purified via preparative HPLC (eluent: acetonitrile/water gradient with 0.1% formic acid). This gave 46 mg (34% of theory) of the title compound.

LC-MS (Method 1): R$_t$=1.38 min; m/z=511.3 [M+H]$^+$.
$^1$H-NMR (400 MHz, DMSO-d$_6$) δ [ppm]: −0.013 (1.34), 0.003 (1.24), 1.229 (0.37), 1.667 (7.41), 1.983 (0.28), 2.052 (16.00), 2.322 (0.18), 2.664 (0.20), 3.021 (0.65), 3.157 (1.10), 3.170 (1.12), 3.612 (0.28), 4.069 (0.29), 4.082 (0.29), 4.328 (0.22), 4.438 (0.22), 5.749 (0.29), 6.938 (0.82), 6.961 (0.82), 7.291 (0.38), 7.295 (0.41), 7.311 (0.76), 7.316 (0.78), 7.331 (0.42), 7.337 (0.42), 7.536 (0.48), 7.543 (0.50), 7.562 (0.74), 7.566 (0.74), 7.585 (0.49), 7.592 (0.47), 7.761 (0.47), 7.776 (0.58), 7.783 (0.93), 7.798 (0.91), 7.804 (0.52), 7.819 (0.43), 8.279 (1.06), 8.302 (1.01), 8.495 (4.56), 9.916 (2.39).

In analogy to Example 101, the example compounds shown in Table 12 were prepared by reacting the compound from Example 42A with the appropriate amines (or salts thereof) under the reaction conditions described. Differences are specified in the respective examples.

TABLE 12

| Ex. | | Analytical data |
|---|---|---|
| 102 | 1-(2,4-Difluorophenyl)-7-[(2-fluoroethyl)(methyl)amino]-N-(3-fluorotricyclo[3.3.1.1$^{3,7}$]dec-1-yl)-4-oxo-1,4-dihydro-1,8-naphthyridine-3-carboxamide 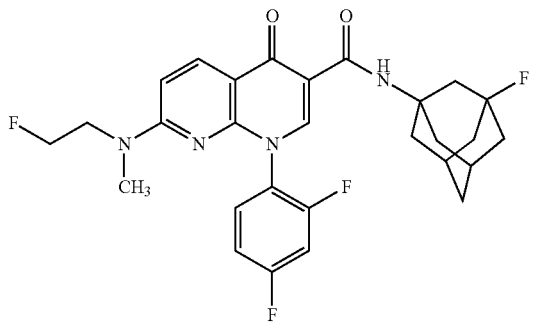 (90% of theory) | LC-MS (Method 1): $R_t$ = 1.24 min<br>MS (ESpos): m/z = 529.3 [M + H]$^+$<br>$^1$H-NMR (400 MHz, CDCl3) δ [ppm]:<br>0.017 (0.33), 0.078 (0.23), 1.043 (1.05),<br>1.059 (1.12), 1.232 (0.17), 1.581 (16.00),<br>1.632 (0.29), 1.890 (0.44), 1.948 (0.36),<br>2.051 (0.26), 2.081 (0.54), 2.137 (0.36),<br>2.380 (0.77), 2.450 (0.14), 2.794 (0.14),<br>2.893 (0.23), 2.965 (0.30), 3.136 (1.37),<br>3.607 (0.16), 4.304 (0.19), 4.421 (0.19),<br>6.695 (0.88), 6.718 (0.90), 7.006 (0.36),<br>7.027 (0.73), 7.047 (0.71), 7.066 (0.19),<br>7.333 (0.20), 7.347 (0.23), 7.355 (0.27),<br>7.369 (0.27), 7.529 (0.15), 8.453 (0.81),<br>8.476 (0.78), 8.636 (1.49), 10.081 (0.46). |
| 103 | 1-(2,4-Difluorophenyl)-7-[(2-fluoroethyl)(methyl)amino]-4-oxo-N-[(2S)-1,1,1-trifluorobutan-2-yl]-1,4-dihydro-1,8-naphthyridine-3-carboxamide 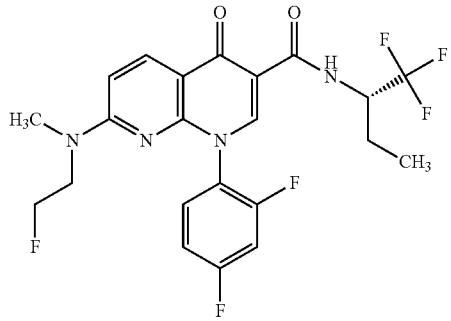 (80% of theory) | LC-MS (Method 2): $R_t$ = 2.81 min<br>MS (ESpos): m/z = 487.0 [M + H]$^+$<br>$^1$H-NMR (400 MHz, DMSO-d$_6$) δ [ppm]:<br>−0.150 (1.09), −0.047 (1.29), −0.039 (1.70),<br>−0.036 (1.79), −0.034 (1.99), −0.031 (2.08),<br>−0.029 (2.31), −0.027 (2.43), −0.024 (2.68),<br>−0.022 (2.95), −0.019 (3.40), −0.017 (3.89),<br>−0.014 (4.70), −0.012 (5.89), −0.009 (12.50),<br>−0.007 (10.42), 0.004 (3.50), 0.006 (2.85),<br>0.007 (6.27), 0.009 (1.14), 0.146 (0.86),<br>0.948 (7.98), 0.966 (16.00), 0.985 (7.56),<br>1.146 (0.53), 1.169 (1.42), 1.243 (0.90),<br>1.598 (1.25), 1.617 (1.59), 1.624 (1.49),<br>1.633 (1.96), 1.642 (1.69), 1.652 (1.62),<br>1.659 (1.78), 1.677 (1.33), 1.851 (1.53),<br>1.860 (1.67), 1.869 (1.65), 1.879 (1.82),<br>1.885 (1.52), 1.895 (1.39), 1.904 (1.20),<br>1.913 (1.01), 2.322 (0.87), 2.327 (1.15),<br>2.332 (0.91), 2.366 (1.73), 2.403 (0.53),<br>2.416 (0.72), 2.424 (0.89), 2.518 (4.50),<br>2.521 (4.24), 2.665 (0.61), 2.669 (0.87),<br>2.674 (0.60), 2.709 (1.31), 3.040 (1.83),<br>3.324 (1.08), 3.327 (0.74), 3.624 (1.00),<br>4.334 (0.70), 4.424 (0.70), 4.710 (0.98),<br>4.726 (1.44), 4.749 (1.41), 6.984 (2.44),<br>7.007 (2.46), 7.304 (1.49), 7.326 (2.78),<br>7.342 (1.53), 7.347 (1.53), 7.547 (1.66),<br>7.554 (1.78), 7.573 (2.58), 7.576 (2.63),<br>7.595 (1.85), 7.602 (1.70), 7.808 (1.96),<br>7.816 (1.71), 7.823 (1.76), 7.830 (1.89),<br>8.309 (3.08), 8.331 (3.03), 8.641 (5.53),<br>8.647 (5.09), 10.458 (4.33), 10.482 (4.24). |

TABLE 12-continued

| Ex. | | Analytical data |
|---|---|---|
| 104 | rac-1-(2,4-Difluorophenyl)-7-[(2-fluoroethyl)(methyl)amino]-4-oxo-N-[1,1,1-trifluorobutan-2-yl]-1,4-dihydro-1,8-naphthyridine-3-carboxamide<br>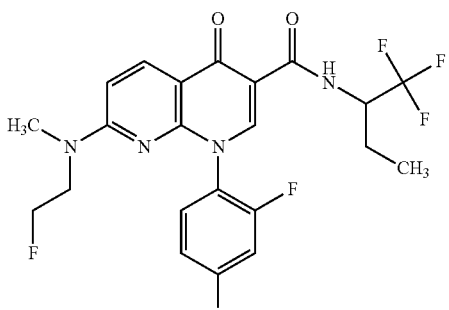<br>(70% of theory) | LC-MS (Method 3): $R_t$ = 2.80 min<br>MS (ESpos): m/z = 487.1 $[M + H]^+$<br>$^1$H-NMR (400 MHz, DMSO-$d_6$) δ [ppm]:<br>−0.150 (1.38), −0.009 (11.87), 0.007 (11.12),<br>0.146 (1.29), 0.948 (7.35), 0.966 (16.00),<br>0.985 (7.63), 1.148 (0.57), 1.169 (1.25),<br>1.259 (0.90), 1.599 (1.06), 1.617 (1.43),<br>1.624 (1.37), 1.633 (1.78), 1.642 (1.54),<br>1.651 (1.62), 1.659 (1.74), 1.677 (1.47),<br>1.850 (1.25), 1.860 (1.53), 1.868 (1.43),<br>1.879 (1.72), 1.894 (1.21), 1.914 (1.00),<br>2.327 (1.59), 2.331 (1.26), 2.365 (2.15),<br>2.669 (1.51), 2.709 (1.91), 3.034 (1.72),<br>3.622 (1.03), 4.346 (0.78), 4.427 (0.72),<br>4.731 (1.51), 4.754 (1.38), 6.984 (2.40),<br>7.008 (2.40), 7.305 (1.50), 7.320 (2.79),<br>7.340 (1.60), 7.547 (1.68), 7.554 (1.91),<br>7.573 (2.75), 7.595 (1.78), 7.602 (1.60),<br>7.808 (1.96), 7.830 (1.90), 8.309 (3.31),<br>8.331 (3.10), 8.641 (6.21), 8.647 (5.57),<br>10.458 (4.46), 10.482 (4.09). |
| 105 | rac-1-(2,4-Difluorophenyl)-7-[(2-fluoroethyl)(methyl)amino]-4-oxo-N-[1,1,1-trifluoropropan-2-yl]-1,4-dihydro-1,8-naphthyridine-3-carboxamide<br>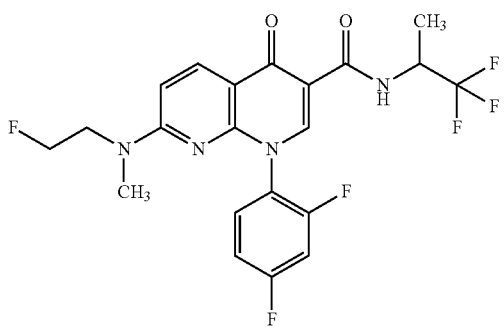<br>Workup: Add water/1M aqueous hydrochloric acid and filter off the precipitate.<br>(72% of theory) | LC-MS (Method 2): $R_t$ = 2.71 min<br>MS (ESpos): m/z = 473.1 $[M + H]^+$<br>$^1$H-NMR (400 MHz, DMSO-$d_6$) δ [ppm]:<br>−0.150 (0.75), −0.009 (9.82), 0.007 (6.09),<br>0.146 (0.75), 1.169 (1.04), 1.242 (1.12),<br>1.259 (1.01), 1.272 (0.81), 1.322 (0.61),<br>1.339 (0.97), 1.363 (16.00), 1.381 (15.67),<br>2.322 (0.61), 2.327 (0.85), 2.331 (0.61),<br>2.365 (1.09), 2.665 (0.64), 2.669 (0.83),<br>2.674 (0.59), 2.709 (1.06), 2.890 (0.61),<br>3.037 (1.81), 3.632 (0.98), 4.338 (0.71),<br>4.435 (0.72), 4.863 (1.19), 4.883 (1.81),<br>4.904 (1.75), 4.923 (1.05), 6.982 (2.40),<br>7.005 (2.44), 7.300 (1.48), 7.304 (1.57),<br>7.321 (2.73), 7.326 (2.74), 7.343 (1.50),<br>7.347 (1.52), 7.547 (1.47), 7.554 (1.57),<br>7.573 (2.53), 7.595 (1.57), 7.602 (1.39),<br>7.781 (1.24), 7.796 (1.44), 7.804 (1.47),<br>7.812 (1.50), 7.827 (1.27), 8.300 (3.07),<br>8.323 (2.86), 8.634 (5.56), 8.639 (4.62),<br>10.509 (2.89), 10.532 (2.72). |
| 106 | 1-(2,4-Difluorophenyl)-7-[(2-fluoroethyl)(methyl)amino]-4-oxo-N-[1,1,1-trifluoropentan-2-yl]-1,4-dihydro-1,8-naphthyridine-3-carboxamide<br>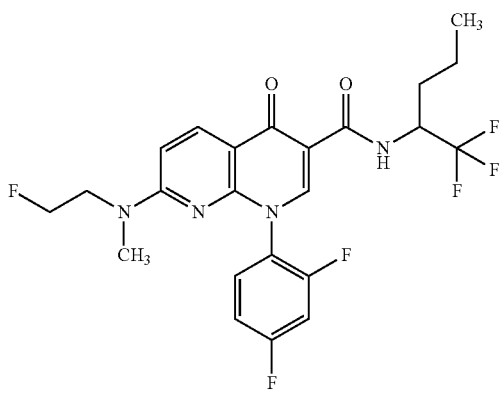<br>Workup: Add water/1M aqueous hydrochloric acid and filter off the precipitate.<br>(83% of theory) | LC-MS (Method 2): $R_t$ = 2.93 min<br>MS (ESpos): m/z = 501.1 $[M + H]^+$<br>$^1$H-NMR (400 MHz, DMSO-$d_6$) δ [ppm]:<br>−0.009 (3.94), 0.007 (3.37), 0.881 (0.92),<br>0.893 (7.30), 0.912 (16.00), 9.30 (8.22),<br>1.168 (1.40), 1.243 (1.28), 1.259 (1.19),<br>1.273 (1.01), 1.298 (0.80), 1.316 (1.26),<br>1.322 (1.31), 1.338 (1.79), 1.353 (1.95),<br>1.371 (1.81), 1.389 (1.27), 1.409 (1.09),<br>1.430 (1.25), 1.442 (1.60), 1.462 (1.43),<br>1.594 (0.71), 1.606 (0.76), 1.621 (1.05),<br>1.628 (1.78), 1.640 (1.35), 1.654 (1.83),<br>1.667 (1.25), 1.677 (0.98), 1.690 (0.77),<br>1.739 (1.00), 1.748 (1.15), 1.765 (1.62),<br>1.772 (1.74), 1.780 (1.38), 1.790 (1.48),<br>1.796 (1.09), 2.523 (0.94), 2.890 (0.90),<br>3.040 (1.77), 3.616 (0.94), 3.626 (0.96),<br>4.324 (0.71), 4.443 (0.69), 4.773 (0.86),<br>4.792 (1.43), 4.816 (1.45), 4.834 (0.81),<br>6.983 (2.47), 7.006 (2.53), 7.298 (1.43),<br>7.302 (1.51), 7.319 (2.85), 7.324 (2.87),<br>7.340 (1.55), 7.345 (1.59), 7.545 (1.73),<br>7.551 (1.83), 7.570 (2.71), 7.574 (2.69),<br>7.593 (1.86), 7.600 (1.73), 7.790 (1.08),<br>7.810 (2.21), 7.828 (2.23), 7.847 (0.94),<br>8.305 (3.19), 8.327 (3.09), 8.641 (6.69),<br>10.453 (4.58), 10.477 (4.39). |

TABLE 12-continued

| Ex. | | Analytical data |
|---|---|---|
| 107 | rac-1-(2,4-Difluorophenyl)-7-[(2-fluoroethyl)(methyl)amino]-4-oxo-N-[1,1,1-trifluoro-4-methylpentan-2-yl]-1,4-dihydro-1,8-naphthyridine-3-carboxamide<br>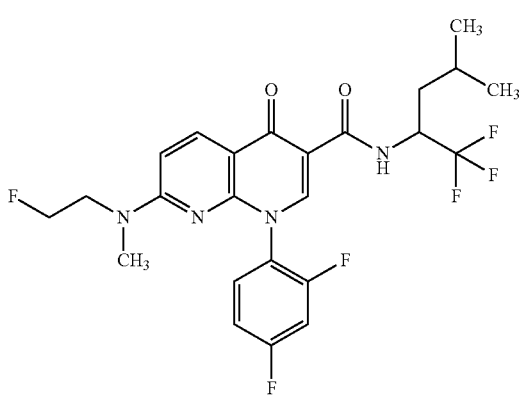<br>Workup: Add water/1M aqueous hydrochloric acid and filter off the precipitate.<br>(80% of theory) | LC-MS (Method 3): $R_t$ = 3.04 min<br>MS (ESpos): m/z = 515.1 [M + H]$^+$<br>$^1$H-NMR (400 MHz, DMSO-d$_6$) δ [ppm]:<br>−0.009 (6.42), 0.007 (4.09), 0.883 (13.44),<br>0.895 (14.22), 0.941 (15.51), 0.956 (16.00),<br>1.168 (2.55), 1.562 (3.80), 1.589 (3.13),<br>1.644 (4.16), 1.671 (5.56), 1.698 (2.43),<br>2.365 (0.82), 2.669 (0.70), 2.709 (0.89),<br>3.040 (2.45), 3.617 (1.28), 4.438 (0.95),<br>4.816 (1.94), 6.982 (3.12), 7.005 (3.15),<br>7.301 (2.00), 7.322 (3.69), 7.338 (1.98),<br>7.542 (2.15), 7.549 (2.23), 7.568 (3.47),<br>7.591 (2.21), 7.597 (2.11), 7.794 (1.99),<br>7.816 (3.88), 7.831 (3.84), 7.853 (1.76),<br>8.302 (4.18), 8.324 (4.00), 8.648 (13.72),<br>10.450 (5.71), 10.474 (5.53). |
| 108 | 1-(2,4-Difluorophenyl)-7-[(2-fluoroethyl)(methyl)amino]-4-oxo-N-[1,1,1-trifluoro-3-methylbutan-2-yl]-1,4-dihydro-1,8-naphthyridine-3-carboxamide<br>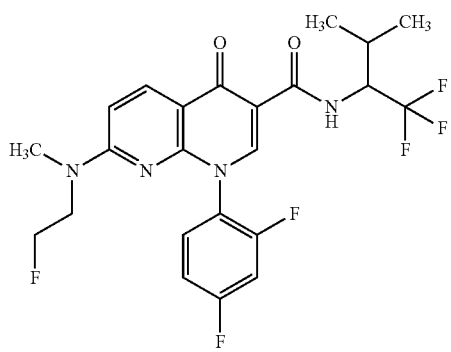<br>Workup: Add water/1M aqueous hydrochloric acid and filter off the precipitate.<br>(99% of theory) | LC-MS (Method 1): $R_t$ = 1.22 min<br>MS (ESpos): m/z = 501.3 [M + H]$^+$<br>$^1$H-NMR (400 MHz, CDCl3) δ [ppm]:<br>−0.000 (0.10), 0.016 (0.10), 0.077 (0.05),<br>1.061 (0.15), 1.079 (0.15), 1.136 (0.13),<br>1.153 (0.13), 1.587 (16.00), 2.285 (0.01),<br>2.302 (0.02), 2.312 (0.02), 2.329 (0.01),<br>2.450 (0.03), 2.794 (0.03), 2.892 (0.13),<br>2.965 (0.16), 3.144 (0.11), 3.612 (0.01),<br>3.641 (0.01), 4.309 (0.02), 4.419 (0.02),<br>4.783 (0.02), 4.806 (0.01), 6.711 (0.09),<br>6.734 (0.09), 7.006 (0.04), 7.022 (0.02),<br>7.043 (0.05), 7.063 (0.05), 7.085 (0.01),<br>7.352 (0.02), 7.366 (0.02), 7.374 (0.03),<br>7.387 (0.03), 7.394 (0.02), 7.409 (0.01),<br>7.529 (0.04), 8.025 (0.02), 8.490 (0.08),<br>8.513 (0.07), 8.697 (0.13), 10.550 (0.02),<br>10.575 (0.02). |
| 109 | 1-(2,4-Difluorophenyl)-7-[(2-fluoroethyl)(methyl)amino]-4-oxo-N-[1-(trifluoromethyl)cyclopropyl]-1,4-dihydro-1,8-naphthyridine-3-carboxamide<br>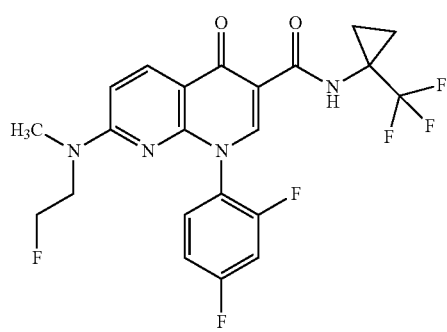<br>Workup: Add water/1M aqueous hydrochloric acid and filter off the precipitate.<br>(75% of theory) | LC-MS (Method 1): $R_t$ = 1.11 min<br>MS (ESpos): m/z = 485.3 [M + H]$^+$<br>$^1$H-NMR (400 MHz, CDCl$_3$) δ [ppm]: 0.001<br>(0.018), 0.017 (0.17), 0.078 (0.11), 1.223<br>(0.13), 1.237 (0.14), 1.267 (0.05), 1.355<br>(0.04), 1.371 (0.06), 1.392 (0.32), 1.417<br>(0.04), 1.573 (16.00), 2.449 (0.06), 2.794<br>(0.06), 2.893 (0.04), 2.965 (0.05), 3.140<br>(0.36), 3.607 (0.05), 3.620 (0.05), 3.633<br>(0.05), 4.307 (0.06), 4.419 (0.06), 6.705<br>(0.26), 6.728 (0.27), 7.006 (0.08), 7.016<br>(0.07), 7.030 (0.07), 7.039 (0.18), 7.048<br>(0.04), 7.059 (0.19), 7.080 (0.06), 7.339<br>(0.06), 7.353 (0.07), 7.361 (0.09), 7.375<br>(0.09), 7.528 (0.06), 8.449 (0.23), 8.472<br>(0.22), 8.673 (0.43), 10.596 (0.15). |

TABLE 12-continued

| Ex. | | Analytical data |
|---|---|---|
| 110 | 1-(2,4-Difluorophenyl)-N-(4-fluorobicyclo[2.2.2]oct-1-yl)-7-[(2-fluoroethyl)(methyl)amino]-4-oxo-1,4-dihydro-1,8-naphthyridine-3-carboxamide<br>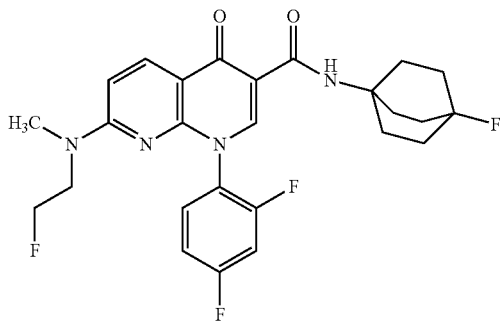<br>Workup: Add water/1M aqueous hydrochloric acid and filter off the precipitate.<br>(88% of theory) | LC-MS (Method 1): $R_t$ = 1.18 min<br>MS (ESpos): m/z = 503.3 [M + H]$^+$<br>$^1$H-NMR (400 MHz, CDCl3) δ [ppm]: 0.000 (0.20), 0.017 (0.21), 0.078 (0.12), 1.041 (0.05), 1.576 (16.00), 1.937 (0.17), 1.952 (0.31), 1.967 (0.31), 1.978 (0.34), 1.992 (0.22), 2.235 (0.38), 2.246 (0.30), 2.257 (0.35), 2.276 (0.29), 2.450 (0.07), 2.602 (0.03), 2.635 (0.12), 2.639 (0.07), 2.641 (0.05), 2.644 (0.05), 2.794 (0.06), 2.965 (0.03), 3.132 (0.41), 3.565 (0.04), 3.602 (0.05), 3.613 (0.05), 3.627 (0.04), 3.667 (0.04), 4.298 (0.06), 4.415 (0.06), 6.690 (0.33), 6.713 (0.33), 6.998 (0.05), 7.006 (0.14), 7.018 (0.07), 7.026 (0.24), 7.034 (0.05), 7.046 (0.25), 7.053 (0.08), 7.066 (0.06), 7.075 (0.04), 7.256 (0.06), 7.260 (0.13), 7.281 (0.08), 7.290 (0.04), 7.294 (0.03), 7.325 (0.07), 7.339 (0.08), 7.347 (0.10), 7.361 (0.09), 7.382 (0.05), 7.529 (0.08), 8.439 (0.32), 8.462 (0.30), 8.618 (0.60), 9.956 (0.16). |
| 111 | 1-(2,4-Difluorophenyl)-7-[(2-fluoroethyl)(methyl)amino]-N-(1,1,1,3,3,3-hexafluoropropan-2-yl)-4-oxo-1,4-dihydro-1,8-naphthyridine-3-carboxamide<br>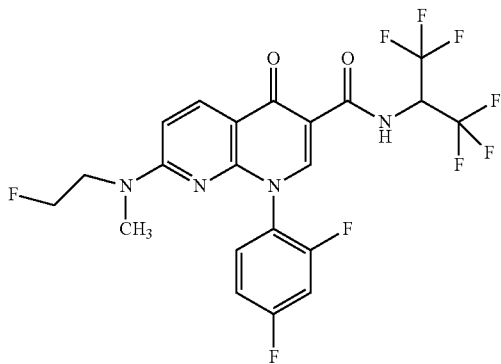<br>(17% of theory) | LC-MS (Method 1): $R_t$ = 1.23 min<br>MS (ESpos): m/z = 527.1 [M + H]$^+$<br>$^1$H-NMR (400 MHz, CDCl$_3$) δ [ppm]: 0.002 (0.57), 0.018 (0.49), 0.079 (0.13), 1.557 (16.00), 2.450 (0.09), 2.794 (0.09), 3.151 (0.37), 3.613 (0.07), 3.648 (0.07), 4.305 (0.07), 4.432 (0.06), 5.309 (0.16), 5.568 (0.07), 5.586 (0.08), 5.593 (0.07), 5.603 (0.06), 5.611 (0.09), 5.628 (0.07), 6.733 (0.46), 6.756 (0.47), 7.006 (0.13), 7.032 (0.08), 7.039 (0.11), 7.053 (0.09), 7.060 (0.30), 7.081 (0.32), 7.088 (0.10), 7.100 (0.08), 7.357 (0.09), 7.372 (0.11), 7.379 (0.13), 7.394 (0.13), 7.529 (0.14), 8.481 (0.36), 8.503 (0.35), 8.689 (0.72), 11.267 (0.13), 11.293 (0.12). |

Example 112

7-[(2,2-Difluoroethyl)(methyl)amino]-1-(2,4-difluorophenyl)-4-oxo-N-(tricyclo[3.3.1.1³,⁷]dec-1-yl)-1,4-dihydro-1,8-naphthyridine-3-carboxamide

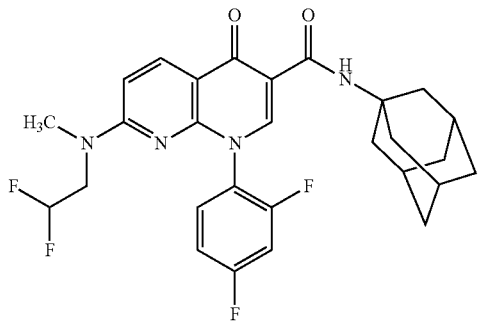 [SMILES: CN(CC(F)F)c1ccc2c(=O)c(C(=O)NC34CC5CC(CC(C5)C3)C4)cn(-c3ccc(F)cc3F)c2n1]

278 mg (0.7 mmol) of the compound from example 48A were initially charged in 7.9 ml of DMF, 321 mg (0.84 mmol) of HATU and 291 mg (2.3 mmol) of DIPEA were added, and the mixture was stirred at 20° C. for 30 minutes. Then 149 mg (1.0 mmol) of 1-adamantanamine were added and the mixture was stirred at 20° C. for 1 hour. Subsequently, 1 ml of 1 M aqueous hydrochloric acid was added and the mixture was purified via preparative HPLC (eluent: acetonitrile/water gradient with 0.1% formic acid). This gave 65 mg (18% of theory) of the title compound.

LC-MS (Method 1): $R_t$=1.35 min; m/z=529.2 [M+H]⁺.
¹H-NMR (400 MHz, DMSO-d₆) δ [ppm]: 1.669 (7.89), 1.946 (0.40), 1.983 (0.31), 2.055 (16.00), 3.077 (0.90), 3.157 (2.88), 3.170 (2.96), 3.725 (0.36), 4.056 (0.31), 4.069 (0.86), 4.082 (0.84), 4.095 (0.30), 6.993 (0.69), 7.016 (0.72), 7.297 (0.40), 7.319 (0.79), 7.336 (0.55), 7.540 (0.45), 7.547 (0.47), 7.569 (0.76), 7.589 (0.47), 7.595 (0.45), 7.770 (0.42), 7.786 (0.53), 7.792 (0.85), 7.807 (0.85), 7.814 (0.51), 7.829 (0.39), 8.339 (1.00), 8.361 (0.98), 8.531 (3.55), 9.880 (2.28).

In analogy to Example 112, the example compounds shown in Table 13 were prepared by reacting the compound from Example 48A with the appropriate amines (or salts thereof) under the reaction conditions described. Differences are specified in the respective examples.

TABLE 13

| Ex. | | Analytical data |
|---|---|---|
| 113 | rac-7-[(2,2-Difluoroethyl)(methyl)amino]-1-(2,4-difluorophenyl)-4-oxo-N-[1,1,1-trifluoropropan-2-yl]-1,4-dihydro-1,8-naphthyridine-3-carboxamide<br>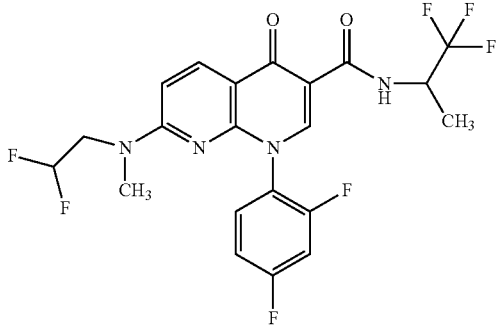<br>(6% of theory) | LC-MS (Method 1): $R_t$ = 1.15 min<br>MS (ESpos): m/z = 491.3 [M + H]⁺<br>¹H-NMR (500 MHz, DMSO-d₆) δ [ppm]:<br>−0.120 (1.57), −0.007 (16.00), 0.006 (12.71), 0.116 (1.53), 1.235 (0.81), 1.368 (14.07), 1.382 (14.02), 2.361 (1.27), 2.635 (1.20), 3.101 (1.58), 3.725 (0.75), 4.890 (1.59), 4.907 (1.60), 5.753 (2.66), 7.038 (1.51), 7.311 (1.38), 7.328 (2.64), 7.340 (1.37), 7.559 (1.33), 7.577 (2.44), 7.597 (1.28), 7.790 (1.10), 7.802 (1.56), 7.820 (1.63), 7.833 (1.19), 8.362 (2.37), 8.380 (2.31), 8.672 (5.13), 8.679 (4.44), 10.466 (2.23), 10.483 (2.24). |

TABLE 13-continued

| Ex. | | Analytical data |
|---|---|---|
| 114 | rac-7-[(2,2-Difluoroethyl)(methy)amino]-1-(2,4-difluorophenyl)-4-oxo-N-[1,1,1-trifluorobutan-2-yl]-1,4-dihydro-1,8-naphthyridine-3-carboxamide<br>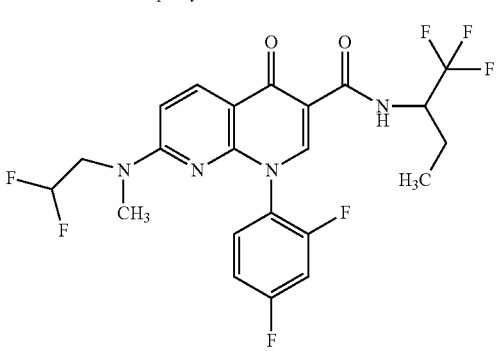<br>(92% of theory) | LC-MS (Method 1): $R_t$ = 1.19 min<br>MS (ESpos): m/z = 505.3 [M + H]$^+$<br>$^1$H-NMR (400 MHz, DMSO-$d_6$) δ [ppm]:<br>−0.009 (9.63), 0.007 (5.71), 0.949 (7.95),<br>0.968 (16.00), 0.986 (7.83), 1.168 (1.61),<br>1.233 (1.29), 1.602 (1.28), 1.620 (1.68),<br>1.627 (1.58), 1.637 (1.99), 1.645 (1.79),<br>1.655 (1.61), 1.662 (1.90), 1.680 (1.38),<br>1.853 (1.46), 1.862 (1.53), 1.871 (1.72),<br>1.881 (1.90), 1.897 (1.44), 1.907 (1.21),<br>1.916 (1.03), 2.327 (1.14), 2.365 (1.46),<br>2.669 (0.91), 2.709 (1.20), 2.730 (1.72),<br>2.890 (2.25), 3.091 (5.58), 3.217 (0.83),<br>3.709 (1.38), 4.739 (1.64), 4.754 (1.48),<br>7.038 (2.31), 7.060 (2.27), 7.307 (1.80),<br>7.328 (3.19), 7.344 (1.75), 7.550 (1.92),<br>7.556 (2.06), 7.576 (3.05), 7.598 (1.88),<br>7.605 (1.79), 7.792 (1.12), 7.814 (2.41),<br>7.837 (2.18), 8.368 (3.55), 8.390 (3.37),<br>8.680 (6.43), 8.686 (5.75), 10.412 (4.34),<br>10.436 (4.22). |
| 115 | 7-[(2,2-Difluoroethyl)(methyl)amino]-1-(2,4-difluorophenyl)-N-(1,1,1,3,3,3-hexafluoropropan-2-yl)-4-oxo-1,4-dihydro-1,8-naphthyridine-3-carboxamide<br>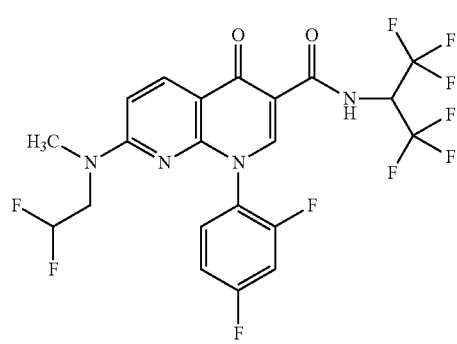<br>(17% of theory) | LC-MS (Method 1): $R_t$ = 1.24 min<br>MS (ESpos): m/z = 545.0 [M + H]$^+$<br>$^1$H-NMR (400 MHz, CDCl$_3$) δ [ppm]: 1.269<br>(0.10), 1.557 (16.00), 2.054 (0.15), 3.190<br>(1.17), 3.597 (0.09), 3.667 (0.09), 5.611<br>(0.17), 6.766 (0.51), 6.789 (0.52), 7.065<br>(0.14), 7.083 (0.36), 7.102 (0.33), 7.120<br>(0.12), 7.350 (0.12), 7.371 (0.15), 7.385<br>(0.17), 8.536 (0.49), 8.558 (0.47), 8.723<br>(0.89), 11.191 (0.17), 11.215 (0.18). |

Example 116

1-(2,4-Difluorophenyl)-7-[4-hydroxy-4-(hydroxymethyl)piperidin-1-yl]-4-oxo-N-(tricyclo[3.3.1.1$^{3,7}$]dec-1-yl)-1,4-dihydro-1,8-naphthyridine-3-carboxamide

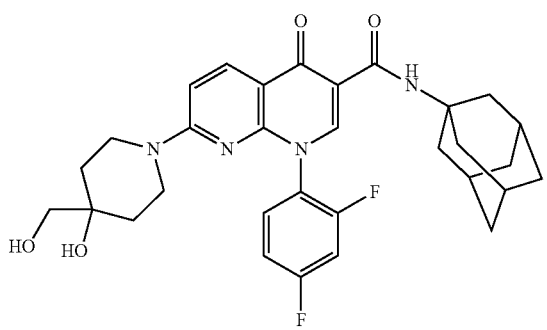 [SMILES: O=C(NC12CC3CC(CC(C3)C1)C2)c1cn(-c2ccc(F)cc2F)c2nc(N3CCC(O)(CO)CC3)ccc2c1=O]

30 mg (0.07 mmol) of the compound from example 58A were initially charged in 0.8 ml of DMF, 32 mg (0.08 mmol) of HATU and 29 mg (0.22 mmol) of DIPEA were added, and the mixture was stirred at 20° C. for 30 minutes. Then 15 mg (0.1 mmol) of 1-adamantanamine were added and the mixture was stirred at 20° C. for 2 hours. Subsequently, the mixture was purified via preparative HPLC (eluent: acetonitrile/water gradient with 0.1% formic acid). This gave 6 mg (15% of theory) of the title compound.

LC-MS (Method 1): $R_t$=1.14 min; m/z=565.2 [M+H]$^+$.
$^1$H-NMR (400 MHz, DMSO-$d_6$) δ [ppm]: −0.150 (0.51), −0.009 (4.42), 0.007 (3.91), 0.146 (0.50), 1.146 (0.38), 1.234 (0.81), 1.322 (0.81), 1.450 (0.78), 1.670 (7.49), 2.055 (16.00), 2.327 (0.82), 2.365 (1.03), 2.669 (0.87), 2.709 (1.05), 3.083 (0.65), 3.136 (2.56), 3.150 (2.63), 3.899 (0.89), 4.287 (2.59), 4.550 (1.22), 5.753 (5.06), 7.062 (1.93), 7.085 (1.95), 7.302 (0.43), 7.324 (0.82), 7.348 (0.44), 7.553 (0.53), 7.576 (0.76), 7.595 (0.52), 7.602 (0.53), 7.760 (0.50), 7.781 (1.00), 7.796 (1.00), 7.818 (0.47), 8.225 (2.67), 8.248 (2.48), 8.468 (5.33), 9.938 (2.87).

Example 117

1-(2,4-Difluorophenyl)-7-[(3R)-3-(hydroxymethyl)morpholin-4-yl]-4-oxo-N-(tricyclo[3.3.1.1³,⁷]dec-1-yl)-1,4-dihydro-1,8-naphthyridine-3-carboxamide

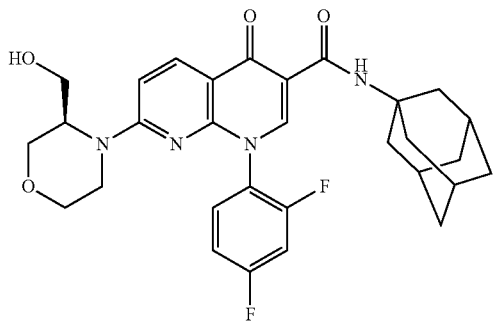 [SMILES: O=C(NC12CC3CC(CC(C3)C1)C2)c1cn(-c2ccc(F)cc2F)c2nc(N3CCOC[C@H]3CO)ccc2c1=O]

117 mg (0.28 mmol) of the compound from example 53A were initially charged in 3.2 ml of DMF, 128 mg (0.34 mmol) of HATU and 116 mg (0.9 mmol) of DIPEA were added, and the mixture was stirred at 20° C. for 30 minutes. Then 60 mg (0.4 mmol) of 1-adamantanamine were added and the mixture was stirred at 20° C. for 2 hours. Subsequently, 1 ml of 1 M aqueous hydrochloric acid was added and the mixture was purified via preparative HPLC (eluent: acetonitrile/water gradient with 0.1% formic acid). This gave 24 mg (15% of theory) of the title compound.

LC-MS (Method 1): $R_t$=1.18 min; m/z=551.2 [M+H]⁺.
¹H-NMR (400 MHz, CDCl₃) δ [ppm]: 0.001 (0.73), 0.017 (0.73), 1.233 (2.05), 1.430 (0.33), 1.562 (16.00), 1.693 (0.38), 1.724 (1.25), 1.745 (1.30), 1.775 (0.35), 2.120 (1.10), 2.180 (3.88), 3.262 (0.20), 3.537 (0.28), 3.564 (0.26), 3.594 (0.26), 3.780 (0.43), 3.949 (0.23), 4.028 (0.38), 4.059 (0.53), 5.309 (0.70), 6.568 (0.24), 6.764 (0.32), 6.787 (0.33), 7.006 (0.26), 7.040 (0.58), 7.060 (0.66), 7.078 (0.27), 7.375 (0.24), 7.529 (0.23), 8.470 (1.03), 8.493 (0.99), 8.650 (0.95), 9.856 (0.49).

Example 118 rac-1-(2,4-Difluorophenyl)-7-[2-(hydroxymethyl)morpholin-4-yl]-4-oxo-N-(tricyclo[3.3.1.1³,⁷]dec-1-yl)-1,4-dihydro-1,8-naphthyridine-3-carboxamide

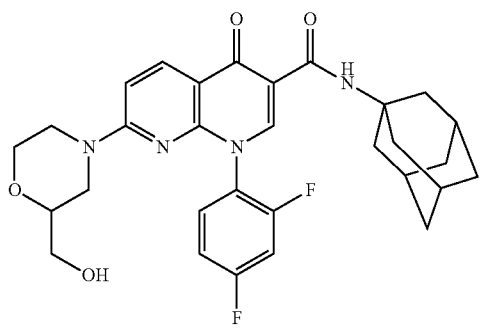 [SMILES: O=C(NC12CC3CC(CC(C3)C1)C2)c1cn(-c2ccc(F)cc2F)c2nc(N3CCOC(CO)C3)ccc2c1=O]

60 mg (0.14 mmol) of the compound from example 51A were initially charged in 1.6 ml of DMF, 66 mg (0.17 mmol) of HATU and 60 mg (0.46 mmol) of DIPEA were added, and the mixture was stirred at 20° C. for 30 minutes. Then 30 mg (0.2 mmol) of 1-adamantanamine were added and the mixture was stirred at 20° C. for 2 hours. Subsequently, 1 ml of 1 M aqueous hydrochloric acid was added and the mixture was purified via preparative HPLC (eluent: acetonitrile/water gradient with 0.1% formic acid). This gave 28 mg (35% of theory) of the title compound.

LC-MS (Method 1): $R_t$=1.18 min; m/z=551.2 [M+H]⁺.
¹H-NMR (400 MHz, CDCl₃) δ [ppm]: −0.139 (0.05), 0.002 (0.46), 0.018 (0.36), 0.079 (0.09), 0.156 (0.04), 1.233 (0.14), 1.251 (0.34), 1.269 (0.70), 1.287 (0.34), 1.560 (16.00), 1.693 (0.12), 1.724 (0.41), 1.745 (0.42), 1.776 (0.12), 1.830 (0.08), 2.054 (1.26), 2.121 (0.37), 2.181 (1.27), 2.450 (0.04), 2.865 (0.05), 2.886 (0.05), 3.003 (0.05), 3.037 (0.05), 3.568 (0.12), 3.580 (0.12), 3.595 (0.15), 3.609 (0.15), 3.624 (0.10), 3.651 (0.07), 3.907 (0.10), 3.941 (0.14), 3.957 (0.14), 3.986 (0.13), 4.105 (0.10), 4.123 (0.29), 4.140 (0.28), 4.159 (0.09), 6.746 (0.31), 6.769 (0.32), 7.006 (0.14), 7.031 (0.21), 7.051 (0.21), 7.069 (0.07), 7.349 (0.08), 7.364 (0.08), 7.371 (0.11), 7.384 (0.10), 7.392 (0.06), 7.406 (0.05), 7.529 (0.10), 8.469 (0.34), 8.492 (0.33), 8.659 (0.60), 9.865 (0.20).

Example 119 rac-1-(2,4-Difluorophenyl)-7-(3-hydroxy-3-methylpiperidin-1-yl)-4-oxo-N-(tricyclo[3.3.1.1³,⁷]dec-1-yl)-1,4-dihydro-1,8-naphthyridine-3-carboxamide

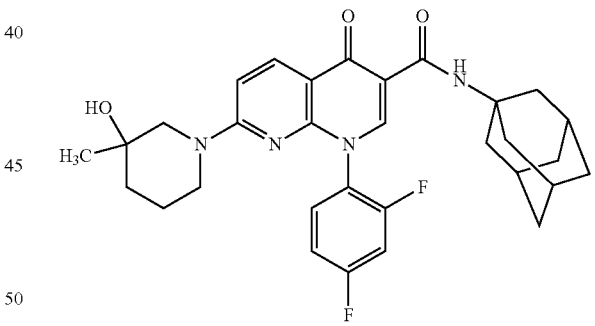

100 mg (0.23 mmol) of the compound from example 54A were initially charged in 2.6 ml of DMF, 103 mg (0.3 mmol) of HATU and 94 mg (0.73 mmol) of DIPEA were added, and the mixture was stirred at 20° C. for 30 minutes. Then 48 mg (0.32 mmol) of 1-adamantanamine were added and the mixture was stirred at 20° C. for 2 hours. Subsequently, the mixture was adjusted to pH 7 with 1 M aqueous hydrochloric acid and purified via preparative HPLC (eluent: acetonitrile/water gradient with 0.1% formic acid).

This gave 110 mg (88% of theory) of the title compound.
LC-MS (Method 1): $R_t$=1.28 min; m/z=549.4 [M+H]⁺.
¹H-NMR (400 MHz, DMSO-d₆) δ [ppm]: −0.009 (1.67), 0.007 (1.02), 0.992 (1.31), 1.017 (1.70), 1.086 (0.32), 1.094

(0.32), 1.104 (0.31), 1.146 (0.33), 1.168 (1.13), 1.236 (0.84), 1.269 (0.74), 1.521 (1.16), 1.584 (0.75), 1.615 (0.51), 1.669 (7.59), 1.746 (0.53), 1.826 (0.43), 2.053 (16.00), 2.366 (0.23), 2.523 (0.75), 2.689 (0.26), 2.709 (0.23), 2.730 (1.08), 2.890 (1.46), 3.085 (0.20), 3.150 (0.25), 3.228 (0.50), 3.263 (0.70), 3.407 (0.23), 3.615 (0.34), 4.366 (0.89), 4.379 (1.15), 7.021 (1.80), 7.044 (1.80), 7.305 (0.43), 7.324 (0.76), 7.343 (0.41), 7.547 (0.47), 7.554 (0.49), 7.572 (0.73), 7.595 (0.44), 7.602 (0.39), 7.756 (0.31), 7.772 (0.59), 7.793 (0.57), 8.185 (2.02), 8.208 (1.86), 8.453 (4.93), 8.464 (0.25), 9.935 (0.21), 9.957 (2.41).

Example 120

7-[(2,2-Difluoroethyl)amino]-1-(2,4-difluorophenyl)-4-oxo-N-(tricyclo[3.3.1.1$^{3,7}$]dec-1-yl)-1,4-dihydro-1,8-naphthyridine-3-carboxamide

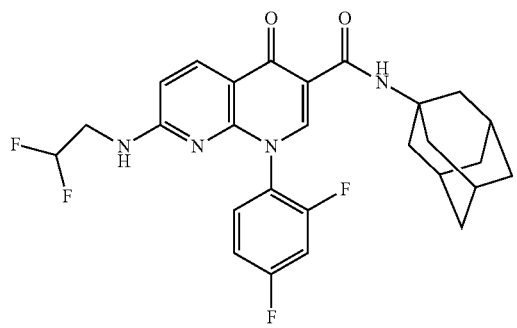 [SMILES: O=C(NC12CC3CC(CC(C3)C1)C2)c1cn(-c2ccc(F)cc2F)c2nc(NCC(F)F)ccc2c1=O]

130 mg (0.23 mmol, 67% purity) of the compound from example 49A were initially charged in 2.6 ml of DMF, 105 mg (0.28 mmol) of HATU and 95 mg (0.73 mmol) of DIPEA were added, and the mixture was stirred at 20° C. for 30 minutes. Then 49 mg (0.32 mmol) of 1-adamantanamine were added and the mixture was stirred at 20° C. for 2 hours. Subsequently, 1 ml of 1 M aqueous hydrochloric acid was added and the mixture was purified via preparative HPLC (eluent: acetonitrile/water gradient with 0.1% formic acid). This gave 99 mg (84% of theory) of the title compound.

LC-MS (Method 1): $R_t$=1.28 min; m/z=515.3 [M+H]$^+$.

$^1$H-NMR (400 MHz, CDCl$_3$) δ [ppm]: 0.002 (1.20), 0.018 (1.39), 0.921 (0.24), 0.935 (0.24), 1.557 (16.00), 1.694 (0.36), 1.725 (1.30), 1.746 (1.36), 1.778 (0.36), 2.054 (0.23), 2.122 (1.14), 2.182 (4.00), 3.495 (1.71), 3.507 (1.69), 3.529 (0.20), 3.540 (0.21), 5.195 (0.31), 5.542 (0.21), 5.672 (0.22), 5.683 (0.42), 5.693 (0.20), 5.824 (0.20), 6.561 (1.16), 6.583 (1.18), 7.006 (0.25), 7.033 (0.30), 7.048 (0.53), 7.053 (0.54), 7.067 (0.57), 7.072 (0.46), 7.085 (0.26), 7.259 (0.44), 7.342 (0.24), 7.356 (0.27), 7.363 (0.33), 7.376 (0.36), 7.385 (0.24), 7.398 (0.20), 7.529 (0.25), 8.441 (1.07), 8.463 (1.04), 8.678 (1.99), 9.832 (0.56).

In analogy to Example 120, the example compounds shown in Table 14 were prepared by reacting the compound from Example 49A with the appropriate amines (or salts thereof) under the reaction conditions described. Differences are specified in the respective examples.

TABLE 14

| Ex. | | Analytical data |
|---|---|---|
| 121 | rac-7-[(2,2-Difluoroethyl)amino]-1-(2,4-difluorophenyl)-4-oxo-N-[1,1,1-trifluoropropan-2-yl]-1,4-dihydro-1,8-naphthyridine-3-carboxamide<br><br>(90% of theory) | LC-MS (Method 1): $R_t$ = 1.06 min<br>MS (ESpos): m/z = 477.2 [M + H]$^+$<br>$^1$H-NMR (400 MHz, CDCl$_3$) δ [ppm]: 0.017 (1.03), 0.079 (0.26), 1.251 (0.34), 1.269 (0.70), 1.287 (0.39), 1.451 (6.74), 1.469 (6.79), 1.568 (16.00), 2.054 (1.31), 2.451 (0.23), 3.499 (0.63), 3.536 (0.64), 4.122 (0.29), 4.140 (0.28), 4.899 (0.41), 4.918 (0.64), 4.937 (0.63), 4.955 (0.39), 5.279 (1.13), 5.309 (0.61), 5.542 (0.54), 5.673 (0.56), 5.683 (1.08), 5.693 (0.54), 5.824 (0.52), 6.593 (3.50), 6.615 (3.54), 7.006 (0.26), 7.049 (0.54), 7.056 (0.78), 7.075 (2.30), 7.094 (2.15), 7.112 (0.69), 7.377 (0.78), 7.398 (0.72), 7.529 (0.24), 8.444 (3.15), 8.466 (3.09), 8.713 (3.35), 10.386 (0.98), 10.410 (0.97). |

| Ex. | | Analytical data |
|---|---|---|
| 122 | rac-7-[(2,2-Difluoroethyl)amino]-1-(2,4-difluorophenyl)-4-oxo-N-[1,1,1-trifluorobutan-2-yl]-1,4-dihydro-1,8-naphthyridine-3-carboxamide<br>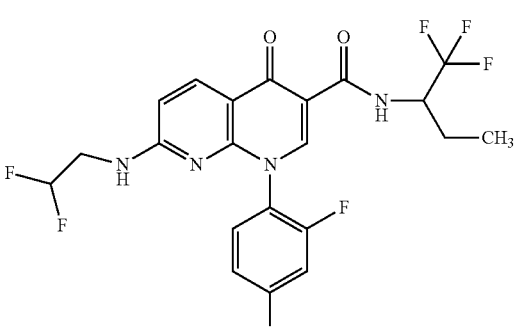<br>(82% of theory) | LC-MS (Method 1): $R_t$ = 1.11 min<br>MS (ESpos): m/z = 491.2 [M + H]$^+$<br>$^1$H-NMR (400 MHz, CDC$_{l3}$) δ [ppm]: 0.001 (0.67), 0.017 (0.70), 0.079 (0.19), 1.055 (0.55), 1.074 (1.22), 1.092 (0.61), 1.563 (16.00), 1.704 (0.09), 1.723 (0.11), 1.730 (0.10), 1.740 (0.14), 1.748 (0.12), 1.758 (0.12), 1.765 (0.14), 1.784 (0.11), 1.936 (0.09), 1.947 (0.10), 1.954 (0.11), 1.966 (0.11), 1.982 (0.09), 2.449 (0.13), 2.794 (0.14), 3.507 (0.13), 3.538 (0.12), 4.751 (0.11), 4.761 (0.10), 4.769 (0.10), 4.779 (0.11), 5.259 (0.11), 5.272 (0.18), 5.309 (0.26), 5.544 (0.10), 5.674 (0.11), 5.685 (0.21), 5.695 (0.11), 5.825 (0.11), 6.594 (0.73), 6.616 (0.76), 7.006 (0.16), 7.050 (0.10), 7.056 (0.14), 7.076 (0.41), 7.095 (0.35), 7.101 (0.21), 7.113 (0.12), 7.365 (0.12), 7.386 (0.15), 7.400 (0.16), 7.406 (0.12), 7.529 (0.16), 8.450 (0.69), 8.471 (0.67), 8.722 (0.95), 10.309 (0.19), 10.332 (0.19). |
| 123 | 7-[(2,2-Difluoroethyl)amino]-1-(2,4-difluorophenyl)-4-oxo-N-[(2R)-1,1,1-trifluorobutan-2-yl]-1,4-dihydro-1,8-naphthyridine-3-carboxamide<br>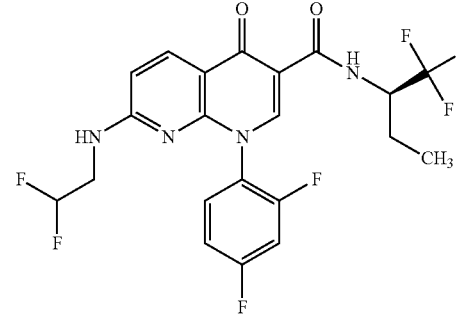<br>(57% of theory) | LC-MS (Method 1): $R_t$ = 1.07 min<br>MS (ESpos): m/z = 491.2 [M + H]$^+$<br>$^1$H-NMR (400 MHz, DMSO-d$_6$) δ [ppm]: −0.150 (0.74), −0.009 (10.07), 0.007 (5.25), 0.145 (0.82), 0.944 (7.49), 0.963 (16.00), 0.981 (7.84), 1.156 (1.80), 1.174 (3.56), 1.192 (1.78), 1.597 (1.15), 1.615 (1.63), 1.623 (1.41), 1.632 (1.89), 1.641 (1.58), 1.650 (1.56), 1.658 (1.75), 1.676 (1.37), 1.849 (1.38), 1.859 (1.62), 1.867 (1.55), 1.877 (1.76), 1.883 (1.53), 1.894 (1.40), 1.903 (1.14), 1.913 (0.95), 1.987 (6.41), 2.327 (0.95), 2.365 (0.89), 2.558 (0.69), 2.664 (0.75), 2.669 (1.03), 2.709 (0.91), 3.402 (2.56), 4.020 (1.51), 4.038 (1.49), 4.732 (1.51), 4.746 (1.41), 5.640 (0.74), 5.779 (1.39), 5.922 (0.72), 6.782 (4.45), 6.805 (4.51), 7.305 (1.56), 7.327 (2.88), 7.343 (1.55), 7.549 (1.71), 7.556 (1.80), 7.575 (2.74), 7.598 (1.73), 7.604 (1.59), 7.815 (2.18), 7.824 (1.83), 7.829 (1.78), 7.837 (2.02), 8.254 (6.67), 8.276 (6.39), 8.321 (1.84), 8.641 (5.85), 8.646 (5.13), 10.457 (4.94), 10.481 (4.71). |
| 124 | 7-[(2,2-Difluoroethyl)amino]-1-(2,4-difluorophenyl)-4-oxo-N-[1,1,1-trifluoropentan-2-yl]-1,4-dihydro-1,8-naphthyridine-3-carboxamide<br>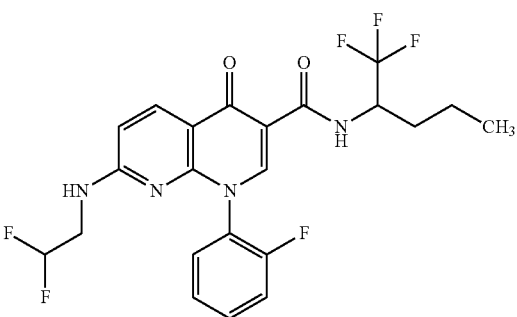<br>(71% of theory) | LC-MS (Method 1): $R_t$ = 1.20 min<br>MS (ESpos): m/z = 505.2 [M + H]$^+$<br>$^1$H-NMR (400 MHz, DMSO-d$_6$) δ [ppm]: 0.005 (1.90), 0.890 (6.75), 0.909 (15.05), 0.927 (7.74), 1.156 (4.23), 1.173 (8.48), 1.191 (4.30), 1.312 (0.96), 1.329 (1.40), 1.348 (1.72), 1.367 (1.56), 1.385 (1.04), 1.404 (0.88), 1.424 (1.11), 1.437 (1.48), 1.457 (1.31), 1.472 (0.74), 1.592 (0.61), 1.604 (0.65), 1.618 (0.92), 1.627 (1.59), 1.639 (1.22), 1.653 (1.70), 1.664 (1.18), 1.676 (0.88), 1.688 (0.67), 1.737 (0.88), 1.746 (1.04), 1.763 (1.53), 1.769 (1.62), 1.779 (1.26), 1.787 (1.38), 1.812 (0.55), 1.987 (16.00), 3.366 (1.27), 3.403 (1.27), 3.438 (1.27), 4.001 (1.31), 4.019 (3.84), 4.037 (3.80), 4.055 (1.25), 4.771 (0.78), 4.790 (1.36), 4.814 (1.37), 4.832 (0.75), 5.638 (0.66), 5.780 (1.31), 5.921 (0.65), 6.781 (4.18), 6.803 (4.27), 7.299 (1.29), 7.303 (1.36), 7.320 (2.62), 7.325 (2.71), 7.341 (1.46), 7.346 (1.44), 7.546 (1.54), 7.553 (1.57), 7.572 (2.53), 7.576 (2.52), 7.594 (1.60), 7.601 (1.51), 7.797 (1.02), 7.817 (2.15), 7.835 (2.14), 7.854 (0.92), 8.250 (6.07), 8.272 (5.87), 8.319 (1.69), 8.640 (6.16), 10.453 (4.66), 10.477 (4.50). |

TABLE 14-continued

| Ex. | | Analytical data |
|---|---|---|
| 125 | rac-7-[(2,2-Difluoroethyl)amino]-1-(2,4-difluorophenyl)-4-oxo-N-[1,1,1-trifluoro-4-methylpentan-2-yl]-1,4-dihydro-1,8-naphthyridine-3-carboxamide<br><br>(96% of theory) | LC-MS (Method 1): $R_t$ = 1.22 min<br>MS (ESpos): m/z = 519.1 [M + H]$^+$<br>$^1$H-NMR (400 MHz, CDCl$_3$) δ [ppm]:<br>0.001 (0.59), 0.017 (0.56), 0.954 (2.22), 0.963 (2.28), 0.970 (2.57), 0.984 (4.16), 1.001 (3.93), 1.251 (1.68), 1.269 (3.42), 1.287 (1.71), 1.568 (16.00), 1.616 (0.64), 1.625 (0.38), 1.643 (0.48), 1.708 (0.48), 1.719 (0.63), 1.737 (0.50), 1.747 (0.87), 1.753 (0.56), 1.766 (0.35), 1.775 (0.61), 1.782 (0.64), 1.790 (0.37), 1.799 (0.40), 2.054 (6.64), 3.502 (0.44), 3.538 (0.43), 3.546 (0.42), 3.553 (0.36), 4.104 (0.50), 4.122 (1.47), 4.140 (1.45), 4.158 (0.48), 4.892 (0.37), 4.897 (0.34), 4.916 (0.37), 5.255 (0.47), 5.270 (0.87), 5.285 (0.44), 5.542 (0.38), 5.673 (0.38), 5.683 (0.74), 5.693 (0.38), 5.824 (0.37), 6.592 (2.49), 6.614 (2.55), 7.051 (0.40), 7.071 (1.29), 7.091 (1.19), 7.109 (0.35), 7.364 (0.49), 7.379 (0.56), 7.386 (0.68), 7.400 (0.67), 7.407 (0.44), 7.421 (0.34), 8.442 (2.11), 8.464 (2.05), 8.725 (2.43), 10.256 (0.68), 10.280 (0.67). |
| 126 | 7-[(2,2-Difluoroethyl)amino]-1-(2,4-difluorophenyl)-N-(1,1,1,3,3,3-hexafluoropropan-2-yl)-4-oxo-1,4-dihydro-1,8-naphthyridine-3-carboxamide<br><br>Purification via preparative HPLC (eluent: acetonitrile/water gradient with 0.1% formic acid).<br>(70% of theory) | LC-MS (Method 1): $R_t$ = 1.17 min<br>MS (ESpos): m/z = 531.2 [M + H]$^+$<br>$^1$H-NMR (400 MHz, CDCl3) δ [ppm]:<br>0.002 (1.44), 0.018 (1.22), 1.251 (0.71), 1.269 (1.54), 1.287 (0.74), 1.557 (16.00), 2.054 (2.72), 3.479 (0.46), 3.493 (0.41), 3.501 (0.69), 3.516 (0.89), 3.528 (0.69), 3.537 (0.74), 3.547 (0.81), 3.552 (0.81), 3.563 (0.70), 3.583 (0.40), 3.589 (0.39), 4.123 (0.59), 4.141 (0.59), 5.294 (1.00), 5.309 (1.40), 5.544 (0.71), 5.554 (0.41), 5.566 (0.63), 5.584 (0.82), 5.591 (0.71), 5.601 (0.65), 5.609 (0.84), 5.626 (0.60), 5.674 (0.67), 5.685 (1.33), 5.695 (0.66), 5.825 (0.65), 6.615 (4.34), 6.637 (4.44), 7.065 (0.66), 7.071 (1.01), 7.089 (2.38), 7.096 (1.19), 7.108 (2.23), 7.116 (1.30), 7.126 (0.83), 7.129 (0.72), 7.133 (0.46), 7.136 (0.50), 7.371 (0.88), 7.385 (0.97), 7.393 (1.05), 7.407 (1.17), 7.414 (0.71), 7.428 (0.61), 8.465 (3.85), 8.486 (3.76), 8.720 (6.71), 11.176 (1.18), 11.201 (1.17). |

Example 127 rac-1-(2,4-Difluorophenyl)-7-[2-(hydroxymethyl)pyrrolidin-1-yl]-4-oxo-N-(tricyclo[3.3.1.1$^{3,7}$]dec-1-yl)-1,4-dihydro-1,8-naphthyridine-3-carboxamide

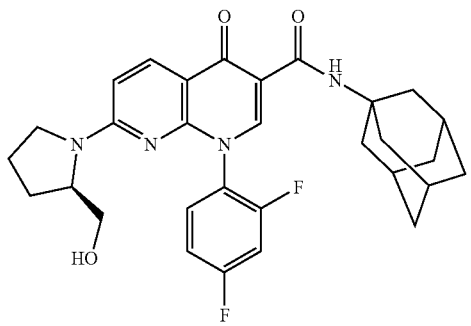 [SMILES: O=C(NC12CC3CC(CC(C3)C1)C2)c1cn(-c2ccc(F)cc2F)c2nc(N3CCC[C@@H]3CO)ccc2c1=O]

100 mg (0.25 mmol) of the compound from example 52A were initially charged in 2.8 ml of DMF, 114 mg (0.3 mmol) of HATU and 103 mg (0.8 mmol) of DIPEA were added, and the mixture was stirred at 20° C. for 30 minutes. Then 49 mg (0.32 mmol) of 1-adamantanamine were added and the mixture was stirred at 20° C. for 2 hours. Subsequently, 1 ml of 1 M aqueous hydrochloric acid was added and the mixture was purified via preparative HPLC (eluent: acetonitrile/water gradient with 0.1% formic acid). This gave 76 mg (57% of theory) of the title compound.

LC-MS (Method 1): $R_t$=1.27 min; m/z=535.3 [M+H]$^+$.

$^1$H-NMR (400 MHz, DMSO-d$_6$) δ [ppm]: −0.150 (1.22), −0.009 (14.65), 0.007 (10.98), 0.018 (0.98), 0.025 (0.54), 0.058 (0.18), 0.083 (0.13), 0.146 (1.22), 1.146 (0.44), 1.168 (0.21), 1.225 (0.57), 1.243 (2.78), 1.259 (2.59), 1.273 (1.71), 1.355 (0.26), 1.586 (0.40), 1.670 (7.56), 1.752 (0.51), 1.827 (0.87), 1.926 (0.77), 2.055 (16.00), 2.137 (0.14), 2.274 (0.14), 2.322 (0.73), 2.327 (0.95), 2.332 (0.68), 2.365 (1.41), 2.390 (0.22), 2.523 (4.43), 2.559 (0.82), 2.669 (0.94), 2.674 (0.67), 2.689 (0.41), 2.709 (1.31), 2.730 (0.71), 2.890 (1.05), 3.129 (0.49), 3.139 (0.52), 3.147 (0.50), 3.157 (0.47), 3.427 (0.20), 3.466 (0.24), 3.600 (0.16), 3.616 (0.21), 3.625 (0.18), 3.958 (0.15), 4.340 (0.14), 4.462 (0.13), 6.705 (0.26), 6.867 (0.15), 7.278 (0.46), 7.299 (0.76), 7.317 (0.42), 7.547 (0.39), 7.731 (0.37), 7.753 (0.65), 7.769 (0.65), 7.889 (0.12), 7.954 (0.13), 8.019 (0.12), 8.239 (0.99), 8.261 (0.85), 8.471 (2.45), 9.962 (2.29)

Example 128

1-(2,4-Difluorophenyl)-4-oxo-7-(2-oxo-1,3-oxazolidin-3-yl)-N-(tricyclo[3.3.1.1$^{3,7}$]dec-1-yl)-1,4-dihydro-1,8-naphthyridine-3-carboxamide

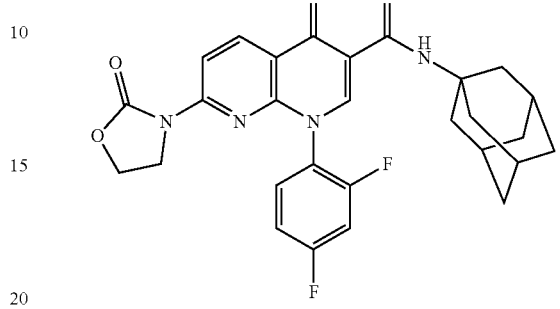

28 mg (0.04 mmol, 59% purity (HPLC)) of the compound from example 61A were initially charged in 1 ml of DMF, 24 mg (0.06 mmol) of HATU and 18 mg (0.14 mmol) of DIPEA were added, and the mixture was stirred at 20° C. for 30 minutes. Then 12 mg (0.08 mmol) of 1-adamantanamine were added and the mixture was stirred at 23° C. for 9 hours. The mixture was left to stand for 13 h and then purified via preparative HPLC (eluent: acetonitrile/water gradient with 0.1% formic acid). This gave 12 mg (54% of theory) of the title compound.

LC-MS (Method 1): $R_t$=1.30 min; m/z=521.2 [M+H]$^+$.

$^1$H-NMR (400 MHz, DMSO-d$_6$) δ [ppm]: −0.150 (1.16), −0.009 (10.40), 0.007 (9.44), 0.016 (0.60), 0.021 (0.38), 0.146 (1.19), 1.680 (5.04), 2.072 (16.00), 2.322 (0.58), 2.327 (0.93), 2.331 (0.68), 2.366 (1.10), 2.520 (1.96), 2.523 (2.04), 2.525 (1.76), 2.558 (0.72), 2.560 (0.57), 2.563 (0.46), 2.565 (0.45), 2.660 (0.41), 2.664 (0.63), 2.669 (0.93), 2.674 (0.61), 2.709 (1.14), 3.285 (0.67), 3.711 (0.38), 3.730 (0.79), 3.753 (0.82), 3.771 (0.39), 4.356 (0.52), 4.377 (0.83), 4.385 (0.86), 4.397 (0.50), 4.405 (0.50), 7.353 (0.60), 7.565 (0.42), 7.598 (0.52), 7.613 (0.40), 7.620 (0.40), 7.827 (0.41), 7.842 (0.43), 7.849 (0.71), 7.864 (0.73), 7.871 (0.38), 8.265 (2.34), 8.287 (2.47), 8.678 (2.58), 8.700 (2.77), 8.703 (4.30), 9.720 (1.95).

Example 129

1-(2,4-Difluorophenyl)-4-oxo-7-(1,3-thiazolidin-3-yl)-N-(tricyclo[3.3.1.1$^{3,7}$]dec-1-yl)-1,4-dihydro-1,8-naphthyridine-3-carboxamide

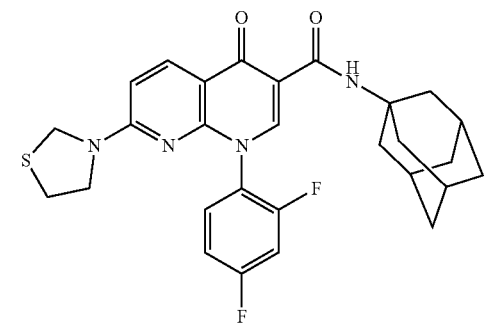 [SMILES: O=C(NC12CC3CC(CC(C3)C1)C2)c1cn(-c2ccc(F)cc2F)c2nc(N3CCSC3)ccc2c1=O]

200 mg (0.26 mmol) of the compound from example 59A were initially charged in 5.8 ml of DMF, 235 mg (0.62 mmol) of HATU and 212 mg (1.64 mmol) of DIPEA were added, and the mixture was stirred at 20° C. for 30 minutes. Then 109 mg (0.72 mmol) of 1-adamantanamine were added and the mixture was stirred at 20° C. for 2 hours. Subsequently, the mixture was purified via preparative HPLC (eluent: acetonitrile/water gradient with 0.1% formic acid). This gave 130 mg (48% of theory) of the title compound.

LC-MS (Method 1): $R_t$=1.48 min; m/z=523.2 [M+H]$^+$.

1H-NMR (400 MHz, DMSO-d$_6$) δ [ppm]: −0.009 (1.08), −0.001 (16.00), 0.007 (0.50), 1.672 (1.96), 1.987 (0.08), 2.058 (4.16), 3.084 (0.32), 3.099 (0.63), 3.115 (0.32), 3.161 (0.22), 3.174 (0.23), 3.614 (0.33), 4.419 (0.44), 6.885 (0.59), 6.907 (0.60), 7.303 (0.12), 7.319 (0.21), 7.346 (0.11), 7.546 (0.14), 7.553 (0.15), 7.572 (0.20), 7.594 (0.14), 7.601 (0.13), 7.775 (0.14), 7.789 (0.17), 7.796 (0.26), 7.811 (0.25), 7.833 (0.12), 8.330 (0.74), 8.353 (0.68), 8.515 (1.27), 9.898 (0.67).

Example 130

1-(2,4-Difluorophenyl)-7-(1,1-dioxido-1,3-thiazolidin-3-yl)-4-oxo-N-(tricyclo[3.3.1.1$^{3,7}$]dec-1-yl)-1,4-dihydro-1,8-naphthyridine-3-carboxamide

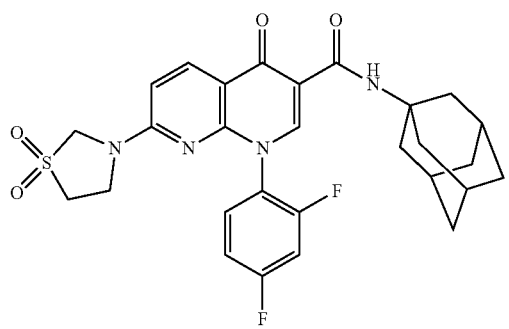 [SMILES: O=C(NC12CC3CC(CC(C3)C1)C2)c1cn(-c2ccc(F)cc2F)c2nc(N3CCS(=O)(=O)C3)ccc2c1=O]

98 mg (0.19 mmol) of the compound from Example 129 were initially charged in 1.4 ml of dioxane and 0.7 ml of water, 98 mg (0.56 mmol) of dipotassium hydrogenphosphate and 344 mg (0.56 mmol) of OXONE® were added, and the mixture was stirred at 23° C. for 8 h and then left to stand for 13 h. Water was added to the mixture, the precipitated solid was filtered off and the latter was then purified via preparative HPLC (eluent: acetonitrile/water gradient with 0.1% formic acid). This gave 67 mg (64% of theory) of the title compound. In addition, 12 mg (12% of theory) of the title compound from Example 131 were obtained (for analysis see Example 131).

LC-MS (Method 1): $R_t$=1.20 min; m/z=555.3 [M+H]$^+$.

$^1$H-NMR (400 MHz, DMSO-d$_6$) δ [ppm]: −0.009 (1.95), 0.007 (1.22), 1.673 (7.35), 2.061 (16.00), 2.072 (4.15), 3.526 (1.04), 3.544 (2.15), 3.562 (1.26), 3.799 (0.98), 4.560 (1.05), 6.963 (1.49), 6.985 (1.48), 7.318 (0.45), 7.340 (0.78), 7.361 (0.44), 7.564 (0.55), 7.571 (0.57), 7.590 (0.76), 7.613 (0.53), 7.620 (0.49), 7.791 (0.53), 7.806 (0.64), 7.813 (1.01), 7.828 (0.98), 7.835 (0.55), 7.850 (0.47), 8.420 (2.63), 8.442 (2.44), 8.562 (5.10), 9.841 (2.67).

Example 131

1-(2,4-Difluorophenyl)-7-(1-oxido-1,3-thiazolidin-3-yl)-4-oxo-N-(tricyclo[3.3.1.1$^{3,7}$]dec-1-yl)-1,4-dihydro-1,8-naphthyridine-3-carboxamide

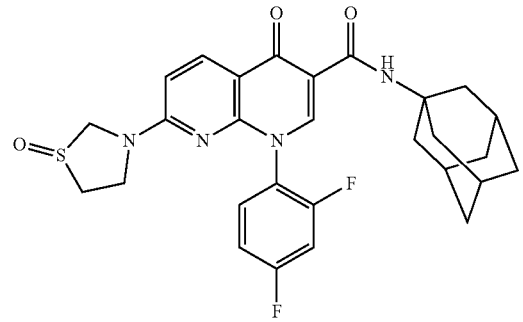 [SMILES: O=C(NC12CC3CC(CC(C3)C1)C2)c1cn(-c2ccc(F)cc2F)c2nc(N3CCS(=O)C3)ccc2c1=O]

As described in the preparation of the compound from Example 130, 98 mg (0.19 mmol) of the compound from Example 129 were used to obtain 12 mg (12% of theory) of the title compound.

LC-MS (Method 1): $R_t$=1.09 min; m/z=539.3 [M+H]$^+$.

$^1$H-NMR (400 MHz, DMSO-d$_6$) δ [ppm]: −0.009 (2.26), 0.007 (1.41), 1.026 (1.00), 1.043 (0.87), 1.234 (0.36), 1.673 (7.26), 2.061 (16.00), 2.522 (1.08), 3.072 (0.45), 3.923 (0.56), 4.312 (0.41), 4.622 (0.35), 6.964 (2.06), 6.986 (2.07), 7.338 (0.60), 7.578 (0.45), 7.809 (0.56), 8.177 (2.22), 8.377 (2.66), 8.399 (2.45), 8.534 (4.78), 9.883 (2.63).

Example 132

1-(2,4-Difluorophenyl)-7-(dimethylamino)-4-oxo-N-[(2S)-1,1,1-trifluoro-3,3-dimethylbutan-2-yl]-1,4-dihydro-1,8-naphthyridine-3-carboxamide

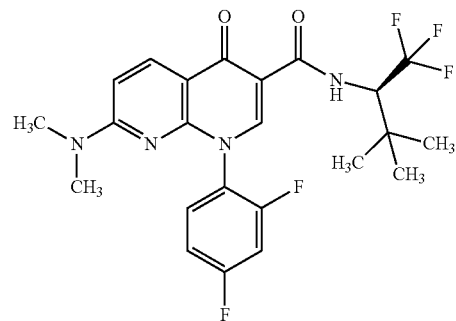 [SMILES: CN(C)c1ccc2c(=O)c(C(=O)N[C@H](C(C)(C)C)C(F)(F)F)cn(-c3ccc(F)cc3F)c2n1]

To 100 mg (0.29 mmol) of the compound from Example 36A and 73 mg (0.72 mmol) of N-methylmorpholine in 3.1 ml of DMF was added, at 0° C., 0.58 ml (0.58 mmol) of isopropyl chloroformate (1 M in toluene), and the mixture was stirred at 0° C. for 1 h. Then, at 0° C., 58 mg (0.38 mmol) of (R)-2,2-dimethyl-1-trifluoromethylpropylamine were added and the mixture was stirred at 20° C. for 16 hours. Subsequently, the mixture was concentrated and purified via preparative HPLC (eluent: acetonitrile/water gradient with 0.1% formic acid). This gave 20 mg (15% of theory) of the title compound.

LC-MS (Method 1): $R_t$=1.26 min; m/z=483.2 [M+H]$^+$.

1H-NMR (400 MHz, CDCl3) δ [ppm]: 0.080 (0.08), 1.174 (1.07), 1.266 (0.04), 1.551 (16.00), 3.000 (0.35), 4.651 (0.04), 4.675 (0.05), 4.698 (0.04), 6.669 (0.13), 6.692 (0.13), 7.006 (0.07), 7.042 (0.07), 7.061 (0.07), 7.371 (0.03), 7.385 (0.04), 7.392 (0.05), 7.407 (0.04), 7.528 (0.07), 8.449 (0.12), 8.472 (0.12), 8.688 (0.20), 10.742 (0.04), 10.768 (0.04).

In analogy to Example 132, the example compounds shown in Table 15 were prepared by reacting the compound from Example 36A with the appropriate amines (or salts thereof) under the reaction conditions described. Differences are specified in the respective examples.

TABLE 15

| Ex. | | Analytical data |
|---|---|---|
| 133 | 1-(2,4-Difluorophenyl)-7-(dimethylamino)-4-oxo-N-[(2R)-1,1,1-trifluoro-4-methylpentan-2-yl]-1,4-dihydro-1,8-naphthyridine-3-carboxamide 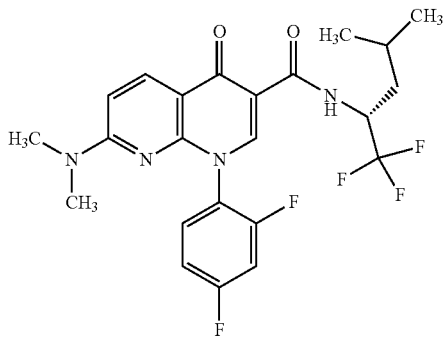 (23% of theory) | LC-MS (Method 1): $R_t$ = 1.29 min<br>MS (ESpos): m/z = 483.2 [M + H]$^+$<br>$^1$H-NMR (400 MHz, CDCl3) δ [ppm]: −0.139 (0.03), 0.156 (0.03), 0.958 (0.19), 0.974 (0.22), 0.983 (0.32), 0.999 (0.28), 1.266 (0.06), 1.551 (16.00), 1.609 (0.06), 1.634 (0.04), 1.713 (0.03), 1.723 (0.04), 1.752 (0.04), 1.787 (0.05), 3.000 (0.35), 4.894 (0.03), 6.671 (0.13), 6.694 (0.13), 7.006 (0.07), 7.038 (0.08), 7.059 (0.07), 7.367 (0.04), 7.388 (0.05), 7.402 (0.05), 7.424 (0.02), 7.528 (0.07), 8.415 (0.13), 8.438 (0.13), 8.684 (0.18), 10.389 (0.04), 10.415 (0.04). |
| 134 | 1-(2,4-Difluorophenyl)-7-(dimethylamino)-4-oxo-N-[(2S)-1,1,1-trifluoro-3-methylbutan-2-yl]-1,4-dihydro-1,8-naphthyridine-3-carboxamide 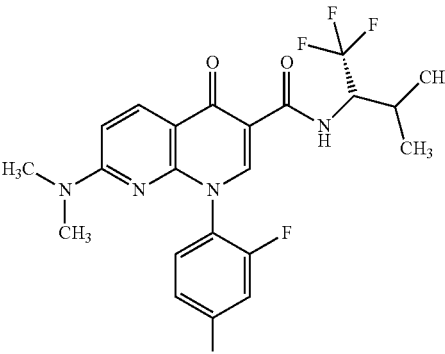 (49% of theory) | LC-MS (Method 1): $R_t$ = 1.23 min<br>MS (ESpos): m/z = 469.2 [M + H]$^+$<br>$^1$H-NMR (400 MHz, CDCl3) δ [ppm]: 0.000 (0.22), 0.017 (0.20), 0.078 (0.13), 1.062 (0.81), 1.079 (0.83), 1.137 (0.70), 1.154 (0.72), 1.265 (0.08), 1.576 (16.00), 2.300 (0.10), 2.310 (0.11), 2.450 (0.07), 2.793 (0.07), 3.000 (1.08), 4.789 (0.08), 6.670 (0.59), 6.693 (0.60), 7.006 (0.09), 7.023 (0.11), 7.042 (0.23), 7.062 (0.21), 7.367 (0.11), 7.382 (0.13), 7.389 (0.14), 7.403 (0.14), 7.425 (0.08), 7.529 (0.09), 8.444 (0.57), 8.467 (0.55), 8.687 (0.79), 10.606 (0.13), 10.632 (0.12). |

Example 135

1-(2,4-Difluorophenyl)-4-oxo-7-(pyrrolidin-1-yl)-N-(tricyclo[3.3.1.1³,⁷]dec-1-yl)-1,4-dihydro-1,8-naphthyridine-3-carboxamide

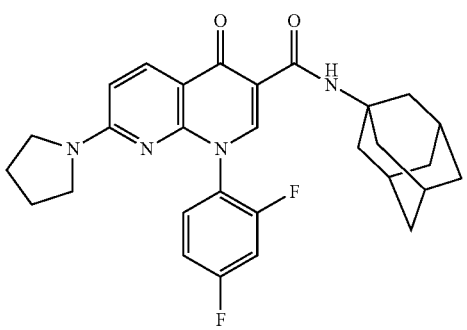 [SMILES: O=C(NC12CC3CC(CC(C3)C1)C2)c1cn(-c2ccc(F)cc2F)c2nc(N3CCCC3)ccc2c1=O]

To 80 mg (0.22 mmol) of the compound from Example 57A and 54.5 mg (0.54 mmol) of N-methylmorpholine in 2.6 ml of DMF was added, at 0° C., 0.43 ml (0.43 mmol) of isopropyl chloroformate (1 M in toluene), and the mixture was stirred at 0° C. for 1 h. Then, at 0° C., 42 mg (0.28 mmol) of 1-adamantanamine were added and the mixture was stirred at 20° C. for 2 hours. After 12 h at 20° C., the mixture was purified via preparative HPLC (eluent: acetonitrile/water gradient with 0.1% formic acid). This gave 20 mg (19% of theory) of the title compound.

LC-MS (Method 1): $R_t$=1.47 min; m/z=505.3 [M+H]⁺.

¹H-NMR (400 MHz, DMSO-$d_6$): δ=1.67 (m, 6H), 1.74-1.99 (m, 4H), 2.06 (m, 9H), 2.99-3.23 (m, 2H), 3.34-3.48 (m, 2H), 6.70 (d, 1H), 7.28-7.34 (m, 1H), 7.53-7.60 (m, 1H), 7.74-7.81 (m, 1H), 8.25 (d, 1H), 8.47 (s, 1H), 9.97 (br. s, 1H).

Example 136

1-(2,4-Difluorophenyl)-7-(morpholin-4-yl)-4-oxo-N-(tricyclo[3.3.1.1³,⁷]dec-1-yl)-1,4-dihydro-1,8-naphthyridine-3-carboxamide

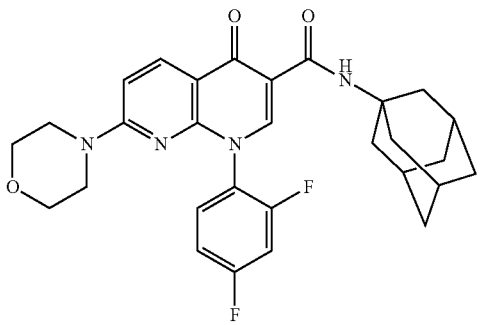 [SMILES: O=C(NC12CC3CC(CC(C3)C1)C2)c1cn(-c2ccc(F)cc2F)c2nc(N3CCOCC3)ccc2c1=O]

To 80 mg (0.17 mmol, 83% purity) of the compound from Example 56A and 43 mg (0.43 mmol) of N-methylmorpholine in 2 ml of DMF was added, at 0° C., 0.34 ml (0.34 mmol) of isopropyl chloroformate (1 M in toluene), and the mixture was stirred at 0° C. for 1 h. Then, at 0° C., 34 mg (0.22 mmol) of 1-adamantanamine were added and the mixture was stirred at 20° C. for 2 hours. The mixture was purified via preparative HPLC (eluent: acetonitrile/water gradient with 0.1% formic acid). This gave 29 mg (33% of theory) of the title compound.

LC-MS (Method 1): $R_t$=1.47 min; m/z=521.2 [M+H]⁺.

¹H-NMR (400 MHz, DMSO-$d_6$) δ [ppm]: 0.000 (16.00), 1.671 (3.77), 2.055 (7.92), 3.443 (1.72), 3.454 (1.40), 3.574 (1.56), 3.587 (1.91), 7.064 (0.97), 7.087 (0.98), 7.301 (0.21), 7.323 (0.42), 7.340 (0.22), 7.550 (0.28), 7.572 (0.40), 7.592 (0.28), 7.763 (0.25), 7.785 (0.50), 7.800 (0.49), 7.821 (0.23), 8.296 (1.30), 8.318 (1.21), 8.491 (2.61), 9.897 (1.31).

Example 137

1-(2,4-Difluorophenyl)-7-(dimethylamino)-4-oxo-N-[(2S)-1,1,1-trifluoro-4-methylpentan-2-yl]-1,4-dihydro-1,8-naphthyridine-3-carboxamide

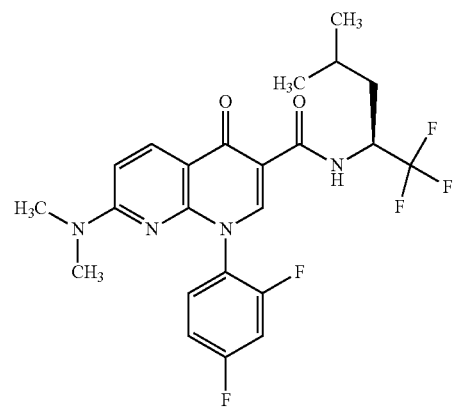 [SMILES: CC(C)C[C@H](NC(=O)c1cn(-c2ccc(F)cc2F)c2nc(N(C)C)ccc2c1=O)C(F)(F)F]

To 100 mg (0.29 mmol) of the compound from Example 36A and 73 mg (0.72 mmol) of N-methylmorpholine in 3.1 ml of DMF was added, at 0° C., 0.58 ml (0.58 mmol) of isopropyl chloroformate (1 M in toluene), and the mixture was stirred at 0° C. for 1 h. Then, at 0° C., 58 mg (0.38 mmol) of (S)-1,1,1-trifluoro-4-methyl-2-pentylamine were added and the mixture was stirred at 20° C. for 16 hours. Then the mixture was purified via preparative HPLC (eluent: acetonitrile/water gradient with 0.1% formic acid). This gave 104 mg (74% of theory) of the title compound.

LC-MS (Method 1): $R_t$=1.28 min; m/z=483.2 [M+H]⁺.

¹H-NMR (400 MHz, CDCl₃) δ [ppm]: 0.958 (4.49), 0.975 (5.14), 0.983 (6.83), 0.999 (6.13), 1.266 (0.96), 1.564 (16.00), 1.609 (1.34), 1.635 (0.88), 1.713 (0.67), 1.723 (0.84), 1.751 (1.06), 1.786 (1.05), 2.999 (7.99), 4.919 (0.54), 6.671 (2.93), 6.693 (3.01), 7.019 (0.67), 7.039 (1.67), 7.058 (1.54), 7.367 (0.65), 7.387 (0.97), 7.402 (0.99), 7.424 (0.49), 8.414 (2.85), 8.437 (2.78), 8.683 (4.11), 10.391 (0.96), 10.415 (0.98).

In analogy to Example 137, the example compounds shown in Table 16 were prepared by reacting the compound from Example 36A or 60A with the appropriate amines (or salts thereof) under the reaction conditions described. Differences are specified in the respective examples.

TABLE 16

| Ex. | | Analytical data |
|---|---|---|
| 138 | rac-1-(2,4-Difluorophenyl)-7-(dimethylamino)-4-oxo-N-[2,2,2-trifluoro-1-(3-methylphenyl)ethyl]-1,4-dihydro-1,8-naphthyridine-3-carboxamide<br>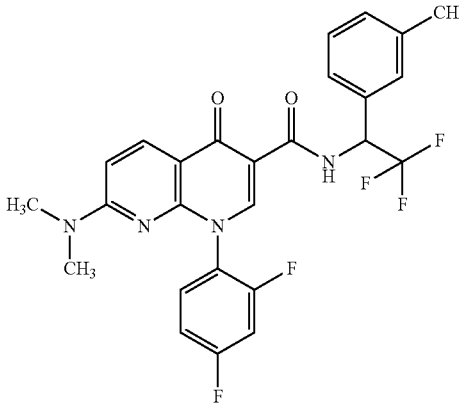<br>(35% of theory) | LC-MS (Method 1): $R_t$ = 1.36 min<br>MS (ESpos): m/z = 517.2 $[M + H]^+$<br>$^1$H-NMR (400 MHz, DMSO-$d_6$) δ [ppm]:<br>−0.009 (2.14), 0.007 (1.88), 1.387 (4.58),<br>2.351 (16.00), 2.522 (0.44), 2.890 (0.83),<br>2.950 (2.67), 5.962 (0.92), 5.984 (1.25),<br>6.006 (0.84), 6.942 (4.11), 6.965 (4.18),<br>7.245 (1.22), 7.262 (1.92), 7.310 (0.79),<br>7.332 (1.20), 7.355 (7.81), 7.371 (2.23),<br>7.391 (0.56), 7.553 (0.46), 7.573 (0.79),<br>7.750 (0.44), 7.769 (0.66), 7.783 (0.53),<br>7.791 (0.49), 7.819 (0.49), 7.834 (0.47),<br>8.326 (4.55), 8.349 (4.33), 8.424 (0.68),<br>8.618 (8.10), 11.425 (2.01), 11.449 (1.94). |
| 139 | rac-1-(2,4-Difluorophenyl)-7-(dimethylamino)-4-oxo-N-[2,2,2-trifluoro-1-(4-fluorophenyl)ethyl]-1,4-dihydro-1,8-naphthyridine-3-carboxamide<br>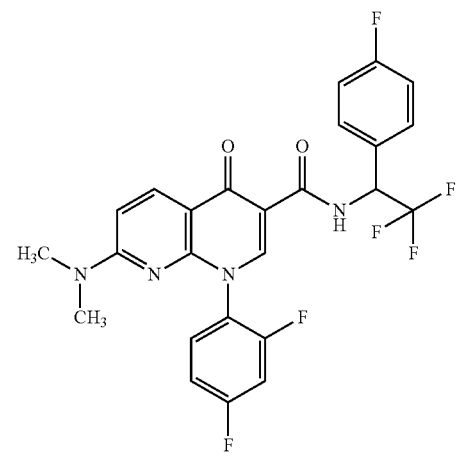<br>(37% of theory) | LC-MS (Method 1): $R_t$ = 1.32 min<br>MS (ESpos): m/z = 521.2 $[M + H]^+$<br>$^1$H-NMR (400 MHz, DMSO-$d_6$) δ [ppm]:<br>0.007 (4.07), 2.072 (1.25), 2.951 (5.22),<br>6.091 (1.85), 6.113 (2.53), 6.134 (1.71),<br>6.946 (7.80), 6.969 (7.93), 7.308 (6.62),<br>7.330 (12.46), 7.352 (6.41), 7.574 (1.76),<br>7.608 (4.02), 7.622 (4.54), 7.641 (3.07),<br>7.753 (0.93), 7.768 (0.94), 7.818 (1.05),<br>7.833 (1.00), 8.322 (8.62), 8.345 (8.23),<br>8.622 (16.00), 11.479 (4.76), 11.503 (4.56) |

TABLE 16-continued

| Ex. | | Analytical data |
|---|---|---|
| 140 | rac-1-(2,4-Difluorophenyl)-7-(dimethylamino)-4-oxo-N-[2,2,2-trifluoro-1-(3-fluorophenyl)ethyl]-1,4-dihydro-1,8-naphthyridine-3-carboxamide<br>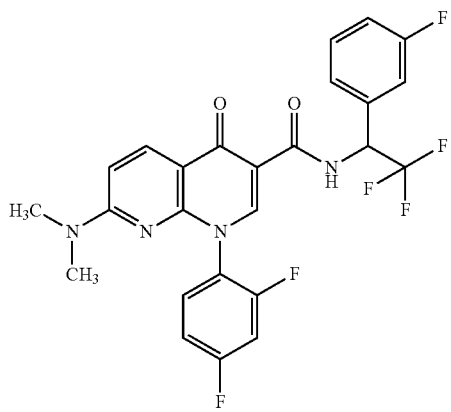<br>(34% of theory) | LC-MS (Method 1): $R_t$ = 1.25 min<br>MS (ESpos): m/z = 521.2 [M + H]$^+$<br>$^1$H-NMR (400 MHz, DMSO-d$_6$) δ [ppm]:<br>−0.009 (12.35), 0.004 (4.35), 0.006 (3.57),<br>0.007 (5.74), 2.072 (2.45), 2.366 (0.89),<br>2.526 (7.91), 2.669 (0.95), 2.709 (0.99),<br>2.954 (4.94), 6.134 (1.60), 6.156 (2.15),<br>6.177 (1.39), 6.950 (7.54), 6.973 (7.35),<br>7.285 (1.95), 7.299 (3.43), 7.306 (3.99),<br>7.321 (2.88), 7.326 (2.96), 7.413 (3.90),<br>7.431 (4.16), 7.528 (2.24), 7.544 (3.21),<br>7.549 (4.29), 7.564 (4.14), 7.569 (2.98),<br>7.584 (2.43), 7.753 (0.97), 7.769 (0.91),<br>7.819 (0.98), 7.835 (0.95), 8.331 (8.79),<br>8.353 (8.26), 8.627 (16.00), 11.500 (4.07),<br>11.523 (3.81). |
| 141 | rac-1-(2,4-Difluorophenyl)-7-(dimethylamino)-4-oxo-N-[2,2,2-trifluoro-1-(4-methylphenyl)ethyl]-1,4-dihydro-1,8-naphthyridine-3-carboxamide<br>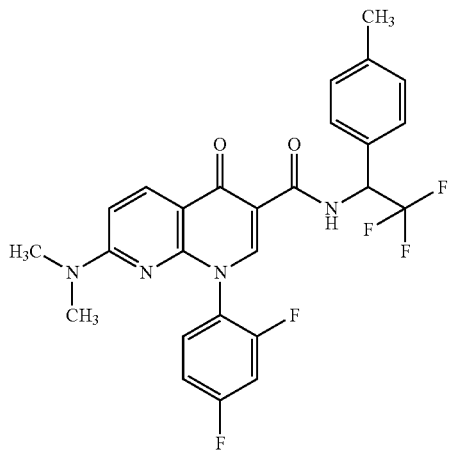<br>(39% of theory) | LC-MS (Method 1): $R_t$ = 1.36 min<br>MS (ESpos): m/z = 517.2 [M + H]$^+$<br>$^1$H-NMR (400 MHz, DMSO-d$_6$) δ [ppm]:<br>−0.009 (5.89), 0.007 (3.81), 2.072 (0.71),<br>2.324 (16.00), 2.523 (1.41), 2.948 (2.94),<br>5.962 (0.99), 5.983 (1.29), 6.005 (0.83),<br>6.943 (4.65), 6.966 (4.56), 7.275 (4.04),<br>7.295 (5.29), 7.326 (0.91), 7.427 (3.90),<br>7.447 (2.96), 7.572 (0.93), 7.753 (0.49),<br>7.766 (0.52), 7.819 (0.53), 7.833 (0.52),<br>8.322 (5.43), 8.345 (5.01), 8.617 (9.31),<br>11.420 (2.08), 11.443 (1.96). |

TABLE 16-continued

| Ex. | | Analytical data |
|---|---|---|
| 142 | rac-1-(2,4-Difluorophenyl)-7-(dimethylamino)-4-oxo-N-[2,2,2-trifluoro-1-(2-methylphenyl)ethyl]-1,4-dihydro-1,8-naphthyridine-3-carboxamide<br>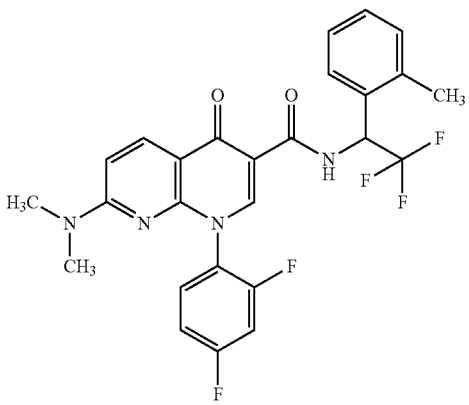<br>(39% of theory) | LC-MS (Method 1): $R_t$ = 1.24 min<br>MS (ESpos): m/z = 517.1 [M + H]$^+$<br>$^1$H-NMR (400 MHz, DMSO-d$_6$) δ [ppm]:<br>−0.009 (2.71), 0.007 (2.25), 2.072 (2.19),<br>2.443 (16.00), 2.523 (0.78), 2.946 (4.02),<br>3.287 (0.69), 6.149 (1.47), 6.170 (2.06),<br>6.192 (1.37), 6.937 (6.45), 6.960 (6.55),<br>7.291 (1.26), 7.297 (1.95), 7.314 (6.35),<br>7.329 (4.65), 7.346 (2.90), 7.361 (2.05),<br>7.379 (0.78), 7.460 (1.86), 7.568 (1.13),<br>7.739 (0.68), 7.755 (0.71), 7.814 (0.75),<br>7.830 (0.71), 8.307 (7.18), 8.330 (6.80),<br>8.615 (11.47), 11.459 (3.56), 11.482 (3.44). |
| 143 | rac-1-(2,4-Difluorophenyl)-7-(dimethylamino)-4-oxo-N-(1,1,1-trifluoro-3-phenylpropan-2-yl)-1,4-dihydro-1,8-naphthyridine-3-carboxamide<br>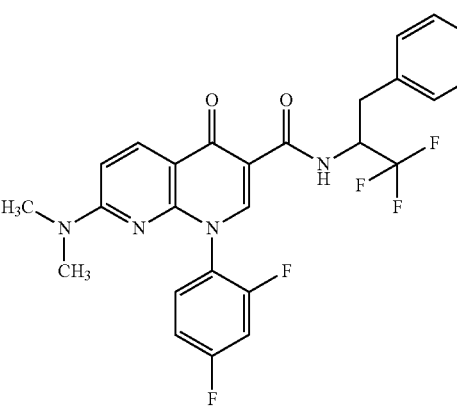<br>(35% of theory) | LC-MS (Method 1): $R_t$ = 1.35 min<br>MS (ESpos): m/z = 517.2 [M + H]$^+$<br>$^1$H-NMR (400 MHz, DMSO-d$_6$) δ [ppm]:<br>−0.009 (8.70), 0.007 (3.77), 2.072 (2.06),<br>2.085 (3.79), 2.730 (7.16), 2.890 (12.47),<br>2.901 (7.59), 2.936 (13.83), 2.963 (8.00),<br>3.219 (4.15), 3.246 (3.55), 5.082 (2.18),<br>6.915 (12.58), 6.938 (12.45), 7.201 (3.83),<br>7.273 (8.46), 7.310 (10.19), 7.547 (3.56),<br>7.767 (2.90), 8.268 (16.00), 8.291 (14.62),<br>8.479 (7.19), 8.489 (5.88), 10.590 (7.45),<br>10.614 (6.89). |
| 144 | rac-1-(2,4-Difluorophenyl)-7-(dimethylamino)-4-oxo-N-(1,1,1-trifluoropentan-2-yl)-1,4-dihydro-1,8-naphthyridine-3-carboxamide<br>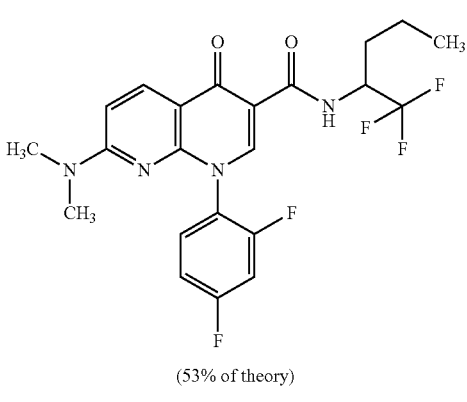<br>(53% of theory) | LC-MS (Method 1): $R_t$ = 1.30 min<br>MS (ESpos): m/z = 469.2 [M + H]$^+$<br>$^1$H-NMR (400 MHz, DMSO-d$_6$) δ [ppm]:<br>−0.013 (4.68), 0.003 (4.35), 0.887 (7.06),<br>0.906 (16.00), 0.924 (8.19), 1.327 (1.40),<br>1.345 (1.67), 1.365 (1.60), 1.384 (1.10),<br>1.436 (1.51), 1.620 (1.70), 1.647 (1.76),<br>1.765 (1.63), 2.942 (6.60), 4.807 (1.43),<br>6.923 (9.13), 6.946 (9.28), 7.298 (1.43),<br>7.320 (2.82), 7.341 (1.57), 7.544 (1.76),<br>7.551 (1.83), 7.570 (2.68), 7.593 (1.82),<br>7.599 (1.70), 7.803 (2.27), 7.819 (2.25),<br>8.266 (10.01), 8.289 (9.57), 8.608 (8.67),<br>10.482 (4.88), 10.505 (4.71). |

TABLE 16-continued

| Ex. | | Analytical data |
|---|---|---|
| 145 | rac-1-(2,4-Difluorophenyl)-7-(dimethylamino)-4-oxo-N-(1,1,1-trifluoro-4-methylpentan-2-yl)-1,4-dihydro-1,8-naphthyridine-3-carboxamide<br><br>(57% of theory) | LC-MS (Method 1): $R_t$ = 1.35 min<br>MS (ESpos): m/z = 483.3 [M + H]$^+$<br>$^1$H-NMR (400 MHz, DMSO-d$_6$) δ [ppm]:<br>−0.150 (1.26), −0.009 (16.00), 0.007 (10.57), 0.146 (1.29), 0.880 (5.73), 0.895 (5.90), 0.941 (6.27), 0.957 (6.46), 1.146 (0.73), 1.560 (1.57), 1.587 (1.17), 1.642 (1.65), 1.669 (2.24), 1.696 (1.06), 2.072 (1.51), 2.322 (1.23), 2.327 (1.62), 2.331 (1.26), 2.366 (1.23), 2.562 (0.81), 2.669 (1.73), 2.709 (1.45), 2.946 (3.80), 4.829 (0.84), 6.928 (5.15), 6.950 (5.20), 7.301 (0.87), 7.318 (1.71), 7.344 (0.98), 7.547 (1.01), 7.553 (1.01), 7.574 (1.54), 7.594 (0.90), 7.602 (0.84), 7.792 (0.98), 7.813 (1.79), 7.828 (1.68), 7.850 (0.84), 8.268 (5.62), 8.291 (5.29), 8.619 (7.16), 10.483 (2.69), 10.507 (2.69). |
| 146 | rac-1-(2,4-Difluorophenyl)-7-(dimethylamino)-4-oxo-N-(1,1,1-trifluorobutan-2-yl)-1,4-dihydro-1,8-naphthyridine-3-carboxamide<br><br>(62% of theory) | LC-MS (Method 1): $R_t$ = 1.24 min<br>MS (ESpos): m/z = 455.2 [M + H]$^+$<br>$^1$H-NMR (400 MHz, DMSO-d$_6$) δ [ppm]:<br>−0.001 (4.33), 0.946 (7.55), 0.965 (16.00), 0.983 (7.69), 1.595 (1.19), 1.613 (1.56), 1.620 (1.42), 1.630 (1.86), 1.638 (1.67), 1.648 (1.59), 1.655 (1.75), 1.673 (1.41), 1.848 (1.44), 1.858 (1.61), 1.867 (1.61), 1.876 (1.78), 2.947 (7.03), 4.730 (1.52), 6.929 (9.36), 6.951 (9.37), 7.304 (1.59), 7.321 (2.83), 7.347 (1.51), 7.550 (1.86), 7.557 (1.92), 7.576 (2.68), 7.598 (1.83), 7.605 (1.69), 7.804 (1.92), 8.275 (10.57), 8.297 (10.00), 8.614 (6.93), 10.490 (4.90), 10.514 (4.63). |
| 147 | rac-1-(2,4-Difluorophenyl)-7-(dimethylamino)-4-oxo-N-(1,1,1-trifluoropropan-2-yl)-1,4-dihydro-1,8-naphthyridine-3-carboxamide<br><br>(19% of theory) | LC-MS (Method 1): $R_t$ = 1.12 min<br>MS (ESpos): m/z = 441.2 [M + H]$^+$<br>$^1$H-NMR (400 MHz, DMSO-d$_6$) δ [ppm]:<br>−0.150 (1.12), −0.020 (3.11), −0.018 (3.55), −0.016 (4.21), −0.013 (5.41), −0.009 (14.12), 0.006 (5.28), 0.007 (8.66), 0.012 (1.18), 0.145 (1.10), 1.360 (16.00), 1.377 (15.75), 2.520 (2.59), 2.523 (2.85), 2.526 (2.97), 2.890 (1.83), 2.943 (6.81), 4.860 (1.18), 4.880 (1.75), 4.901 (1.76), 4.919 (1.11), 6.927 (8.83), 6.949 (8.89), 7.301 (1.35), 7.305 (1.53), 7.308 (1.40), 7.322 (2.65), 7.327 (2.68), 7.344 (1.47), 7.348 (1.54), 7.351 (1.34), 7.551 (1.61), 7.558 (1.67), 7.576 (2.49), 7.599 (1.58), 7.606 (1.51), 7.777 (1.17), 7.791 (1.44), 7.799 (1.42), 7.808 (1.45), 7.823 (1.18), 8.267 (10.58), 8.290 (9.97), 8.607 (6.25), 10.543 (3.19), 10.566 (3.05). |

TABLE 16-continued

| Ex. | | Analytical data |
|---|---|---|
| 148 | rac-N-(1-Cyclopropyl-2,2,2-trifluoroethyl)-1-(2,4-difluorophenyl)-7-(dimethylamino)-4-oxo-1,4-dihydro-1,8-naphthyridine-3-carboxamide<br>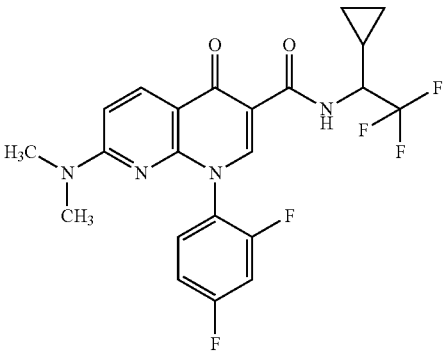<br>(74% of theory) | LC-MS (Method 1): $R_t$ = 1.19 min<br>MS (ESpos): m/z = 467.1 [M + H]$^+$<br>$^1$H-NMR (400 MHz, DMSO-d$_6$) δ [ppm]:<br>−0.009 (4.53), 0.007 (4.41), 0.327 (2.82), 0.497 (2.60), 0.509 (3.84), 0.521 (3.29), 0.531 (2.72), 0.542 (2.82), 0.562 (3.54), 0.573 (3.26), 0.583 (2.87), 0.593 (2.39), 0.645 (2.81), 0.657 (2.81), 0.667 (2.39), 1.182 (2.22), 1.194 (3.92), 1.203 (2.68), 1.206 (2.53), 1.215 (3.80), 2.072 (3.10), 2.949 (9.68), 4.383 (3.15), 4.405 (3.10), 6.930 (14.26), 6.953 (14.42), 7.302 (2.24), 7.305 (2.12), 7.319 (4.12), 7.324 (4.25), 7.341 (2.27), 7.345 (2.40), 7.348 (2.24), 7.548 (2.78), 7.555 (2.90), 7.574 (4.04), 7.578 (4.12), 7.580 (3.77), 7.597 (2.92), 7.603 (2.87), 7.802 (3.38), 7.818 (3.35), 8.278 (16.00), 8.301 (15.12), 8.603 (14.27), 10.622 (4.05), 10.644 (3.96). |
| 149 | 1-(2,4-Difluorophenyl)-7-(dimethylamino)-N-(1,1,1,3,3,3-hexafluoropropan-2-yl)-4-oxo-1,4-dihydro-1,8-naphthyridine-3-carboxamide<br>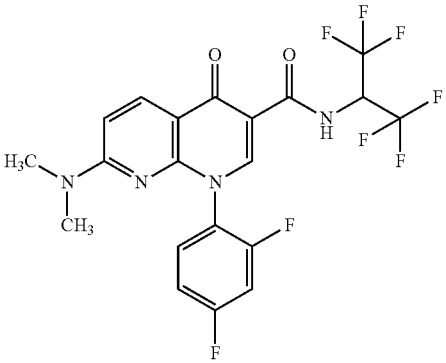<br>(24% of theory) | LC-MS (Method 1): $R_t$ = 1.33 min<br>MS (ESpos): m/z = 495.2 [M + H]$^+$<br>$^1$H-NMR (400 MHz, DMSO-d$_6$) δ [ppm]:<br>−0.009 (5.51), 0.007 (5.59), 2.322 (1.36), 2.327 (1.80), 2.332 (1.30), 2.366 (1.80), 2.669 (2.09), 2.710 (1.92), 2.956 (4.44), 6.294 (1.45), 6.318 (1.56), 6.955 (8.61), 6.978 (8.77), 7.312 (1.37), 7.334 (2.59), 7.355 (1.58), 7.558 (1.81), 7.565 (1.71), 7.588 (2.61), 7.606 (1.75), 7.613 (1.76), 7.799 (1.84), 7.814 (2.03), 7.820 (3.27), 7.835 (3.25), 7.842 (1.91), 7.857 (1.68), 8.293 (9.07), 8.316 (8.62), 8.716 (16.00), 11.478 (4.79), 11.503 (4.49). |
| 150 | rac-1-(2,4-Difluorophenyl)-7-(dimethylamino)-4-oxo-N-(1,1,1-trifluoro-3-methylbutan-2-yl)-1,4-dihydro-1,8-naphthyridine-3-carboxamide<br>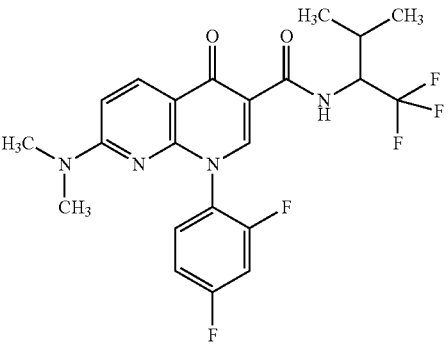<br>(37% of theory) | LC-MS (Method 1): $R_t$ = 1.22 min<br>MS (ESpos): m/z = 469.2 [M + H]$^+$<br>$^1$H-NMR (400 MHz, DMSO-d$_6$) δ [ppm]:<br>−0.150 (1.70), −0.009 (16.00), 0.007 (14.74), 0.146 (1.81), 0.951 (8.74), 0.968 (8.97), 1.021 (7.68), 1.038 (7.74), 2.245 (1.16), 2.949 (3.60), 4.769 (1.02), 6.929 (5.45), 6.952 (5.59), 7.326 (1.56), 7.557 (1.03), 7.576 (1.53), 7.599 (1.02), 7.812 (1.31), 7.828 (1.28), 8.300 (6.15), 8.323 (5.88), 8.622 (4.12), 10.677 (2.77), 10.702 (2.67). |

TABLE 16-continued

| Ex. | | Analytical data |
|---|---|---|
| 151 | 1-(2,4-Difluorophenyl)-7-(dimethylamino)-4-oxo-N-[1-(trifluoromethyl)cyclopentyl]-1,4-dihydro-1,8-naphthyridine-3-carboxamide<br />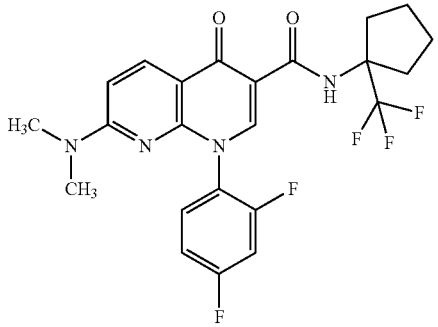<br />(28% of theory) | LC-MS (Method 1): $R_t$ = 1.33 min<br />MS (ESpos); m/z = 481.2 [M + H]$^+$<br />$^1$H-NMR (400 MHz, DMSO-d$_6$) δ [ppm]:<br />−0.001 (16.00), 1.773 (0.24), 2.056 (0.17),<br />2.366 (0.17), 2.942 (0.38), 6.920 (0.41),<br />6.942 (0.42), 7.325 (0.15), 7.578 (0.14),<br />7.791 (0.18), 7.806 (0.18), 8.271 (0.46),<br />8.294 (0.44), 8.563 (0.84), 10.583 (0.47). |
| 152 | N-(Bicyclo[2.2.2]oct-1-yl)-1-(2-chloro-4-fluorophenyl)-7-(dimethylamino)-4-oxo-1,4-dihydro-1,8-naphthyridine-3-carboxamide<br />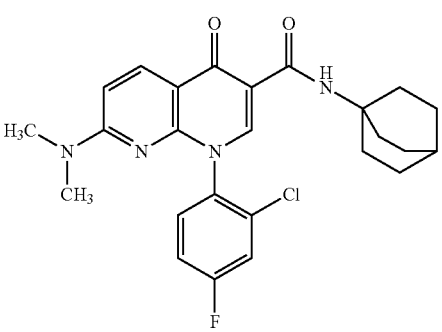<br />Compound from Ex. 60A and bicyclo[2.2.1]oct-1-ylamine<br />(34% of theory) | LC-MS (Method 1): $R_t$ = 1.30 min<br />MS (ESpos): m/z = 469.1 [M + H]$^+$<br />$^1$H-NMR (400 MHz, DMSO-d$_6$) δ [ppm]:<br />−0.013 (6.24), 0.003 (6.28), 1.540 (2.38),<br />1.547 (3.51), 1.555 (3.25), 1.632 (9.41),<br />1.638 (9.20), 1.650 (8.75), 1.865 (10.16),<br />1.877 (8.30), 1.887 (10.18), 1.905 (7.68),<br />2.885 (6.02), 2.900 (7.48), 6.867 (7.56),<br />6.890 (7.82), 7.456 (3.08), 7.463 (3.36),<br />7.752 (3.65), 7.759 (6.96), 7.773 (7.07),<br />7.781 (7.29), 7.795 (3.43), 8.239 (8.11),<br />8.261 (7.78), 8.386 (16.00), 9.878 (7.48). |
| 153 | 1-(2-Chloro-4-fluorophenyl)-7-(dimethylamino)-4-oxo-N-[3-(trifluoromethyl)tricyclo[3.3.1.1$^{3,7}$]dec-1-yl]-1,4-dihydro-1,8-naphthyridine-3-carboxamide<br />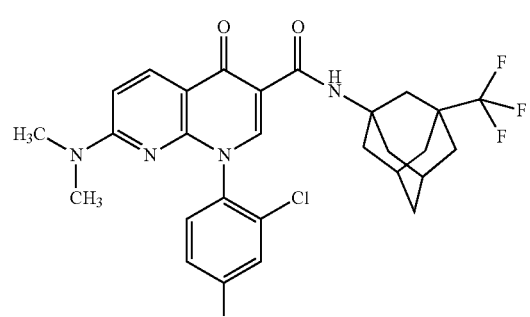<br />Compound from Ex. 60A and 3-(trifluoromethyl)tricyclo[3.3.1.1$^{3,7}$]decan-1-amine hydrochloride<br />(33% of theory) | LC-MS (Method 1): $R_t$ = 1.39 min<br />MS (ESpos): m/z = 563.1 [M + H]$^+$<br />$^1$H-NMR (400 MHz, DMSO-d$_6$) δ [ppm]:<br />1.639 (2.93), 1.671 (4.03), 1.713 (10.59),<br />1.914 (3.34), 1.945 (4.32), 2.106 (4.81),<br />2.129 (13.92), 2.231 (5.97), 2.908 (5.71),<br />6.886 (6.89), 6.909 (6.87), 7.457 (1.72),<br />7.471 (3.06), 7.478 (3.24), 7.500 (2.00),<br />7.773 (5.39), 7.796 (5.10), 7.810 (3.24),<br />8.249 (7.62), 8.271 (7.26), 8.411 (16.00),<br />10.124 (7.70). |

TABLE 16-continued

| Ex. | | Analytical data |
|---|---|---|
| 154 | 1-(2-Chloro-4-fluorophenyl)-7-(dimethylamino)-4-oxo-N-(spiro[2.5]oct-1-yl)-1,4-dihydro-1,8-naphthyridine-3-carboxamide<br>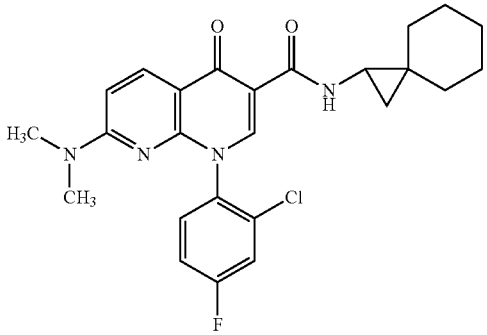<br>Compound from Ex. 60A and spiro[2.5]octan-1-amine<br>(13% of theory) | LC-MS (Method 1): $R_t$ = 1.36 min<br>MS (ESpos): m/z = 469.2 [M + H]$^+$<br>$^1$H-NMR (400 MHz, DMSO-$d_6$) δ [ppm]: −0.009 (5.56), 0.007 (3.50), 0.337 (1.60), 0.350 (3.09), 0.362 (2.78), 0.375 (1.28), 0.725 (1.89), 0.739 (2.80), 0.757 (1.66), 1.269 (1.62), 1.328 (1.59), 1.440 (3.49), 1.470 (6.97), 2.669 (0.55), 2.721 (1.33), 2.732 (2.29), 2.751 (2.17), 2.763 (1.19), 2.909 (6.10), 6.877 (7.56), 6.900 (7.61), 7.445 (1.59), 7.453 (1.80), 7.467 (2.80), 7.474 (2.89), 7.488 (1.78), 7.495 (1.91), 7.764 (3.55), 7.771 (5.42), 7.786 (6.06), 7.793 (5.35), 7.802 (1.98), 7.807 (2.24), 7.824 (1.44), 8.254 (8.13), 8.277 (7.61), 8.437 (0.53), 8.468 (16.00), 10.048 (2.79), 10.062 (2.29). |
| 155 | N-tert-Butyl-1-(2-chloro-4-fluorophenyl)-7-(dimethylamino)-4-oxo-1,4-dihydro-1,8-naphthyridine-3-carboxamide<br>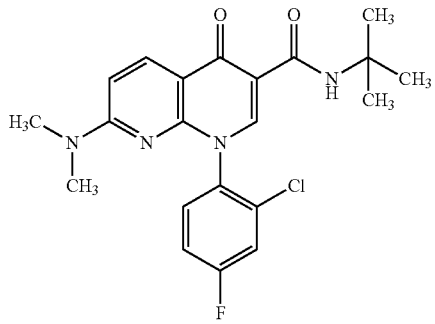<br>Compound from Ex. 60A and tert-butylamine<br>(42% of theory) | LC-MS (Method 1): $R_t$ = 1.22 min<br>MS (ESpos): m/z = 417.2 [M + H]$^+$<br>$^1$H-NMR (400 MHz, DMSO-$d_6$) δ [ppm]: −0.009, (1.09), 0.007 (1.06), 1.387 (16.00), 1.405 (0.38), 2.522 (0.31), 2.908 (1.02), 6.880 (1.21), 6.903 (1.22), 7.445 (0.26), 7.452 (0.29), 7.466 (0.45), 7.473 (0.49), 7.487 (0.30), 7.494 (0.34), 7.763 (0.54), 7.769 (1.06), 7.784 (1.13), 7.791 (1.06), 7.805 (0.53), 8.253 (1.27), 8.275 (1.20), 8.423 (2.46), 10.033 (1.08). |
| 156 | 1-(2-Chloro-4-fluorophenyl)-7-(dimethylamino)-N-(1-methylcyclohexyl)-4-oxo-1,4-dihydro-1,8-naphthyridine-3-carboxamide<br>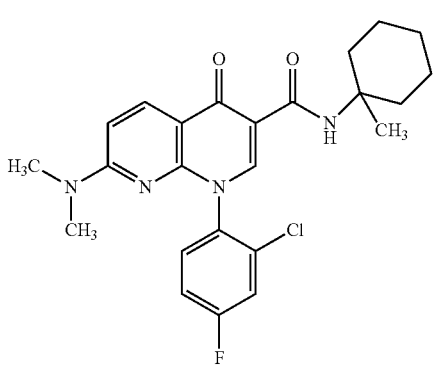<br>Compound from Ex. 60A and (1-methylcyclohexyl)amine hydrochloride<br>(22% of theory) | LC-MS (Method 1): $R_t$ = 1.28 min<br>MS (ESpos): m/z = 457.1 [M + H]$^+$<br>$^1$H-NMR (400 MHz, DMSO-$d_6$) δ [ppm]: −0.150 (0.51), −0.009 (4.50), 0.007 (3.96), 0.146 (0.48), 1.225 (0.49), 1.240 (0.53), 1.343 (1.13), 1.382 (16.00), 1.459 (0.75), 1.495 (2.35), 1.505 (2.20), 1.558 (0.57), 2.072 (0.55), 2.105 (0.98), 2.322 (0.45), 2.327 (0.59), 2.331 (0.44), 2.366 (0.57), 2.523 (1.30), 2.664 (0.52), 2.669 (0.68), 2.674 (0.50), 2.709 (0.65), 2.911 (2.70), 6.882 (3.55), 6.905 (3.65), 7.444 (0.76), 7.451 (0.90), 7.465 (1.31), 7.472 (1.48), 7.486 (0.91), 7.493 (1.02), 7.762 (1.52), 7.769 (1.68), 7.776 (1.81), 7.784 (1.75), 7.791 (3.15), 7.798 (1.70), 7.812 (1.59), 8.276 (3.96), 8.299 (3.71), 8.419 (8.02), 10.045 (2.98). |

TABLE 16-continued

| Ex. | | Analytical data |
|---|---|---|
| 157 | 1-(2-Chloro-4-fluorophenyl)-7-(dimethylamino)-N-(3-ethyltricyclo[3.3.1.1$^{3,7}$]dec-1-yl)-4-oxo-1,4-dihydro-1,8-naphthyridine-3-carboxamide<br>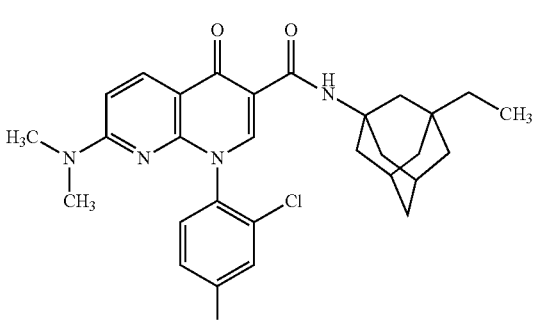<br>Compound from Ex. 60A and (3-ethyl-1-adamantyl)amine hydrochloride<br>(43% of theory) | LC-MS (Method 1): $R_t$ = 1.59 min<br>MS (ESpos): m/z = 523.3 [M + H]$^+$<br>$^1$H-NMR (400 MHz, DMSO-$d_6$) δ [ppm]:<br>−0.150 (1.83), −0.009 (16.00), 0.007 (14.17),<br>0.146 (1.83), 0.766 (3.31), 0.785 (8.94),<br>0.803 (4.23), 1.125 (1.12), 1.144 (3.75),<br>1.163 (3.04), 1.182 (0.90), 1.403 (6.87),<br>1.528 (0.66), 1.560 (1.24), 1.613 (1.23),<br>1.644 (0.71), 1.742 (5.91), 1.959 (2.01),<br>2.016 (2.78), 2.044 (1.35), 2.108 (2.98),<br>2.322 (1.08), 2.326 (1.39), 2.331 (1.04),<br>2.365 (1.34), 2.664 (1.16), 2.669 (1.54),<br>2.674 (1.12), 2.709 (1.39), 2.904 (3.63),<br>6.878 (4.36), 6.901 (4.54), 7.446 (0.93),<br>7.453 (1.12), 7.467 (1.66), 7.475 (1.90),<br>7.488 (1.08), 7.495 (1.29), 7.764 (2.14),<br>7.771 (4.16), 7.785 (4.35), 7.792 (4.13),<br>7.806 (1.99), 8.248 (5.12), 8.270 (4.82),<br>8.392 (10.95), 9.982 (4.20). |

Example 158

1-(2,4-Difluorophenyl)-4-oxo-7-(propan-2-ylamino)-N-(tricyclo[3.3.1.1$^{3,7}$]dec-1-yl)-1,4-dihydro-1,8-naphthyridine-3-carboxamide

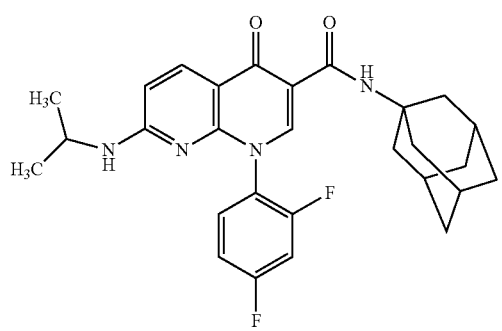 [SMILES: CC(C)Nc1ccc2c(=O)c(C(=O)NC34CC5CC(CC(C5)C3)C4)cn(-c3ccc(F)cc3F)c2n1]

To 100 mg (0.28 mmol) of the compound from Example 38A and 70 mg (0.7 mmol) of N-methylmorpholine in 2.5 ml of DMF was added, at 0° C., 0.56 ml (0.56 mmol) of isopropyl chloroformate (1 M in toluene), and the mixture was stirred at 0° C. for 1 h. Then, at 0° C., 34 mg (0.22 mmol) of 1-adamantanamine were added and the mixture was stirred at 20° C. for 2 hours. After 12 h, the mixture was purified via preparative HPLC (eluent: acetonitrile/water gradient with 0.1% formic acid). This gave 2 mg (2% of theory) of the title compound.

LC-MS (Method 1): $R_t$=1.39 min; m/z=493.3 [M+H]$^+$.
$^1$H-NMR (400 MHz, CDCl$_3$) δ [ppm]: 1.098 (4.13), 1.117 (4.71), 1.132 (3.93), 1.265 (2.61), 1.567 (12.87), 1.691 (1.63), 1.721 (5.40), 1.745 (5.60), 1.775 (1.65), 2.015 (1.00), 2.117 (5.05), 2.185 (16.00), 3.500 (0.95), 3.693 (0.81), 3.710 (1.29), 3.727 (1.30), 3.743 (0.82), 4.797 (1.15), 4.814 (1.12), 6.410 (2.16), 6.432 (2.22), 6.997 (1.04), 7.015 (2.62), 7.036 (2.60), 7.052 (1.03), 7.336 (0.81), 7.357 (1.29), 7.371 (1.35), 7.393 (0.61), 8.344 (2.01), 8.365 (1.98), 8.624 (6.01), 9.938 (2.22).

In analogy to Example 158, the example compound shown in Table 17 was prepared, by reacting the compound from Example 38A with the appropriate amines (or salts thereof) under the reaction conditions described. Differences are specified in the respective examples.

TABLE 17

| Ex. | | Analytical data |
|---|---|---|
| 159 | N-(Bicyclo[2.2.2]oct-1-yl)-1-(2,4-difluorophenyl)-4-oxo-7-(propan-2-ylamino)-1,4-dihydro-1,8-naphthyridine-3-carboxamide<br />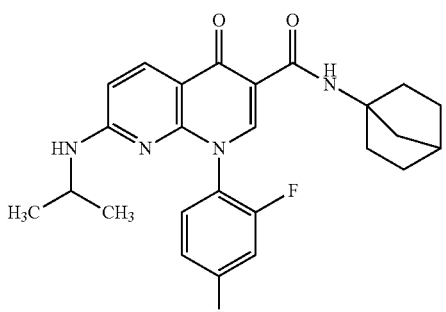<br />(10% of theory) | LC-MS (Method 1): $R_t$ = 1.27 min<br />MS (ESpos): m/z = 467.2 [M + H]$^+$<br />$^1$H-NMR (400 MHz, DMSO-d$_6$) δ [ppm]:<br />−0.019 (1.74), −0.016 (2.07), −0.009 (6.78),<br />0.005 (3.03), 0.007 (4.37), 0.949 (9.89),<br />0.963 (11.01), 0.995 (13.19), 1.011 (11.80),<br />1.542 (3.78), 1.549 (5.44), 1.557 (4.95),<br />1.583 (1.41), 1.633 (15.56), 1.639 (15.24),<br />1.651 (14.55), 1.8181 (3.29), 1.839 (3.03),<br />1.867 (16.00), 1.878 (13.44), 1.888 (15.97),<br />1.906 (11.40), 2.0721 (2.38), 2.523 (3.78),<br />2.526 (4.13), 3.497 (1.95), 3.513 (1.94),<br />6.586 (5.23), 6.608 (5.28), 7.278 (2.03),<br />7.282 (2.25), 7.285 (2.19), 7.299 (3.89),<br />7.303 (4.11), 7.321 (2.28), 7.325 (2.35),<br />7.328 (2.17), 7.336 (2.29), 7.356 (2.15),<br />7.524 (2.49), 7.531 (2.79), 7.550 (3.94),<br />7.554 (4.11), 7.572 (2.66), 7.579 (2.48),<br />7.742 (4.31), 7.757 (3.59), 7.764 (5.12),<br />7.779 (4.76), 7.786 (2.93), 7.801 (2.21),<br />8.098 (4.22), 8.120 (4.08), 8.427 (15.57),<br />8.447 (2.59), 9.912 (9.63), 10.202 (1.52). |

Example 160

1-(2,4-Difluorophenyl)-7-(methylamino)-4-oxo-N-[3-(trifluoromethyl)tricyclo[3.3.1.1$^{3,7}$]dec-1-yl]-1,4-dihydro-1,8-naphthyridine-3-carboxamide

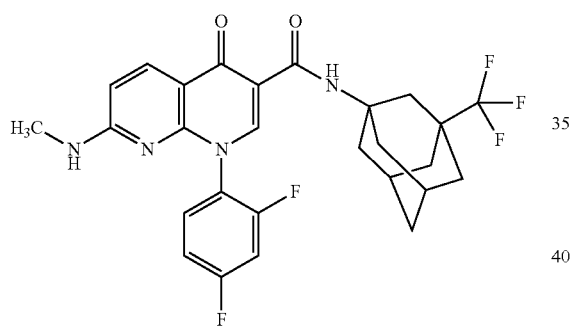

To 80 mg (0.24 mmol) of the compound from Example 37A and 61 mg (0.6 mmol) of N-methylmorpholine in 2.2 ml of DMF was added, at 0° C., 0.48 ml (0.48 mmol) of isopropyl chloroformate (1 M in toluene), and the mixture was stirred at 0° C. for 1 h. Then, at 0° C., 34 mg (0.22 mmol) of 1-(3-trifluoromethyl)adamantanamine were added and the mixture was stirred at 20° C. for 2 hours. After 12 h, the mixture was purified via preparative HPLC (eluent: acetonitrile/water gradient with 0.1% formic acid).

This gave 57 mg (42% of theory) of the title compound.
LC-MS (Method 1): $R_t$=1.27 min; m/z=533.1 [M+H]$^+$.
$^1$H-NMR (400 MHz, DMSO-d$_6$) δ [ppm]: −0.009 (6.50), 0.007 (6.34), 1.639 (3.23), 1.668 (4.16), 1.714 (11.64), 1.915 (4.17), 1.942 (5.42), 2.107 (6.21), 2.128 (16.00), 2.230 (6.76), 3.672 (1.64), 5.753 (4.27), 6.622 (5.65), 6.645 (5.71), 7.295 (1.67), 7.317 (3.10), 7.338 (1.74), 7.538 (2.09), 7.544 (2.19), 7.567 (3.02), 7.586 (2.14), 7.593 (2.09), 7.756 (2.14), 7.778 (4.13), 7.793 (4.26), 7.815 (2.78), 8.141 (1.63), 8.447 (11.87), 10.142 (6.07).

In analogy to Example 160, the example compounds shown in Table 18 were prepared by reacting the compound from Example 37A with the appropriate amines (or salts thereof) under the reaction conditions described. Differences are specified in the respective examples.

TABLE 18

| Ex. | | Analytical data |
|---|---|---|
| 161 | 1-(2,4-Difluorophenyl)-N-(4,4-difluorotricyclo[3.3.1.1^{3,7}]dec-1-yl)-7-(methylamino)-4-oxo-1,4-dihydro-1,8-naphthyridine-3-carboxamide<br><br>(56% of theory) | LC-MS (Method 1): $R_t$ = 1.16 min<br>MS (ESpos): m/z = 501.3 [M + H]$^+$<br>$^1$H-NMR (400 MHz, DMSO-$d_6$) δ [ppm]:<br>−0.005 (16.00), 1.740 (1.03), 1.783 (7.48),<br>1.820 (1.02), 2.061 (12.90), 2.272 (6.60),<br>2.297 (4.96), 6.615 (3.10), 6.637 (3.14),<br>7.287 (1.11), 7.309 (2.02), 7.329 (1.05),<br>7.530 (1.11), 7.537 (1.20), 7.559 (1.89),<br>7.578 (1.13), 7.585 (1.13), 7.754 (1.14),<br>7.769 (1.46), 7.775 (2.28), 7.790 (2.33),<br>7.797 (1.64), 7.812 (1.67), 8.116 (1.04),<br>8.136 (1.04), 8.442 (5.93), 10.085 (3.75). |
| 162 | N-(Bicyclo[2.2.2]oct-1-yl)-1-(2,4-difluorophenyl)-7-(methylamino)-4-oxo-1,4-dihydro-1,8-naphthyridine-3-carboxamide<br><br>(9% of theory) | LC-MS (Method 1): $R_t$ = 1.17 min<br>MS (ESpos): m/z = 439.1 [M + H]$^+$<br>$^1$H-NMR (400 MHz, DMSO-$d_6$) δ [ppm]:<br>1.546 (5.04), 1.631 (14.89), 1.863 (15.35),<br>1.885 (16.00), 1.903 (11.48), 2.068 (2.97),<br>6.605 (5.86), 6.627 (5.97), 7.304 (3.93),<br>7.531 (2.28), 7.555 (3.73), 7.573 (2.19),<br>7.768 (4.61), 7.783 (4.99), 7.805 (3.68),<br>8.111 (2.11), 8.423 (11.13), 9.900 (7.11). |

Example 163

N-(2,6-Dichlorophenyl)-1-(2,4-difluorophenyl)-4-oxo-7-[(2,2,2-trifluoroethyl)amino]-1,4-dihydro-1,8-naphthyridine-3-carboxamide

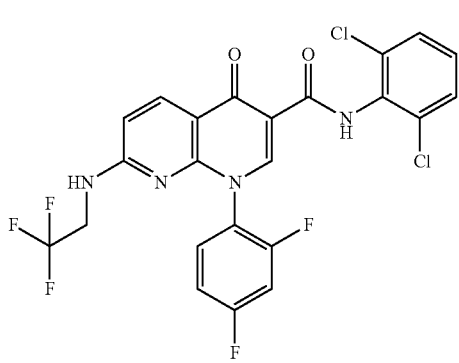 [SMILES: O=C(Nc1c(Cl)cccc1Cl)c1cn(-c2ccc(F)cc2F)c2nc(NCC(F)(F)F)ccc2c1=O]

152 mg (0.94 mmol) of 2,6-dichloroaniline were dissolved in 10 ml of dichloromethane, 0.94 ml (0.94 mmol) of trimethylaluminium (1 M solution in toluene) was added and the mixture was stirred at 23° C. (under argon) for one hour. Then 200 mg (0.47 mmol) of the compound from Example 30A were added and the mixture was stirred at 23° C. for 16 h. 5 ml of water were added, then the mixture was filtered through kieselguhr and washed with ethyl acetate and methanol, and the combined eluates were concentrated under reduced pressure. The residue was purified by preparative HPLC (Method 7). This gave 57 mg (22% of theory) of the title compound.

LC-MS (Method 1): $R_t$=1.11 min; m/z=543.1 [M+H]$^+$.
$^1$H-NMR (400 MHz, DMSO-$d_6$) δ [ppm]: −0.031 (2.20), −0.020 (3.38), −0.017 (3.92), −0.009 (13.57), 0.005 (4.57), 0.007 (7.84), 1.156 (3.89), 1.174 (7.63), 1.192 (3.94), 1.249 (2.03), 1.987 (12.97), 2.520 (4.06), 2.523 (4.45), 3.863 (1.67), 3.885 (1.55), 4.020 (3.06), 4.037 (2.99), 6.844 (2.50), 6.866 (2.42), 7.324 (2.25), 7.330 (2.28), 7.355 (4.12), 7.375 (5.28), 7.396 (4.49), 7.540 (1.76), 7.547 (1.79), 7.577 (16.00), 7.589 (2.18), 7.597 (12.49), 7.815 (1.39), 7.830 (1.72), 7.837 (2.62), 7.852 (2.82), 7.859 (1.49), 8.359 (5.18), 8.381 (4.91), 8.500 (1.33), 8.730 (11.18), 11.946 (7.80).

Example 164

Methyl 4-{6-[(2,6-dichlorophenyl)carbamoyl]-8-(2,4-difluorophenyl)-5-oxo-5,8-dihydro-1,8-naphthyridin-2-yl}piperazine-1-carboxylate

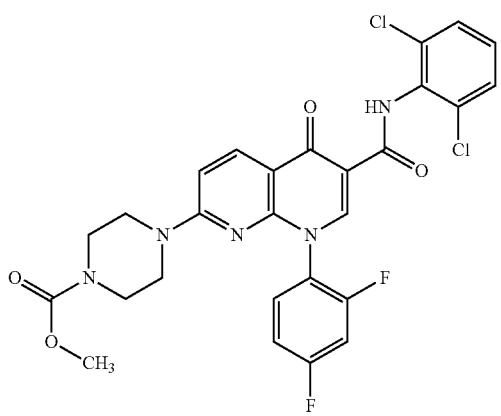 [SMILES: COC(=O)N1CCN(c2ccc3c(=O)c(C(=O)Nc4c(Cl)cccc4Cl)cn(-c4ccc(F)cc4F)c3n2)CC1]

77 mg (0.47 mmol) of 2,6-dichloroaniline were dissolved in dichloromethane, 0.47 ml (0.47 mmol) of trimethylaluminium (1 M solution in toluene) was added and the mixture was stirred at 23° C. (under argon) for one hour. Then 120 mg (0.24 mmol) of the compound from Example 29A were added and the mixture was stirred at 23° C. for 16 h. The mixture was purified by preparative HPLC (Method 7). This gave 80 mg (57% of theory) of the title compound.

LC-MS (Method 1): $R_t$=1.10 min; m/z=588.1 [M+H]$^+$.

$^1$H-NMR (400 MHz, DMSO-$d_6$) δ [ppm]: -0.009 (2.56), 0.007 (2.34), 1.156 (2.57), 1.174 (5.27), 1.192 (2.63), 1.987 (9.53), 2.522 (1.04), 2.524 (0.92), 3.394 (3.43), 3.407 (2.81), 3.536 (3.09), 3.610 (16.00), 4.002 (0.76), 4.020 (2.20), 4.038 (2.22), 4.055 (0.75), 7.132 (2.23), 7.155 (2.27), 7.336 (0.99), 7.354 (1.74), 7.375 (2.28), 7.395 (1.92), 7.576 (6.94), 7.597 (6.13), 7.840 (1.12), 7.855 (1.12), 8.381 (3.02), 8.403 (2.84), 8.713 (6.16), 11.950 (3.67).

Example 165

1-(2,4-Difluorophenyl)-4-oxo-7-(2-oxopiperidin-1-yl)-N-(tricyclo[3.3.1.1$^{3,7}$]dec-1-yl)-1,4-dihydro-1,8-naphthyridine-3-carboxamide

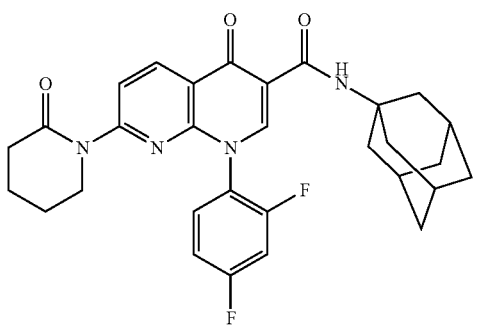 [SMILES: O=C(NC12CC3CC(CC(C3)C1)C2)c1cn(-c2ccc(F)cc2F)c2nc(N3CCCCC3=O)ccc2c1=O]

104 mg (0.32 mmol) of caesium carbonate, 5 mg (0.02 mmol) of palladium(II) acetate and 12 mg (0.02 mmol) of Xantphos were stirred in 5 ml of dioxane under argon at 20° C. for 10 minutes. Then 100 mg (0.21 mmol) of the compound from Example 65A and 25 mg (0.26 mmol) of 6-valerolactam were added and the mixture was stirred at 80° C. for 1 h. Subsequently, the mixture was added to 30 ml of water and brought to pH 1 with 1 M aqueous hydrochloric acid. The precipitated solid was filtered off with suction and washed with water, petroleum ether and acetonitrile. The residue was then dissolved in DCM, activated carbon was added and then the mixture was stirred at RT. The mixture was filtered through kieselguhr and the volatile constituents were then removed under reduced pressure. The residue was purified via preparative thin-layer chromatography (eluent: THF; extractant: ethyl acetate). The product-containing fractions were concentrated under reduced pressure and the residue was then stirred with 1 M aqueous hydrochloric acid. The precipitate was then filtered off, washed with water, acetonitrile and ethyl acetate and dried under high vacuum. This gave 12 mg (10% of theory) of the title compound.

LC-MS (Method 1): $R_t$=1.35 min; m/z=533.5 [M+H]$^+$.

$^1$H-NMR (400 MHz, CDCl$_3$) δ [ppm]: 1.265 (0.20), 1.442 (0.16), 1.567 (16.00), 1.730 (0.51), 1.750 (0.51), 1.852 (0.42), 2.129 (0.45), 2.187 (1.47), 3.597 (0.23), 7.040 (0.12), 7.060 (0.35), 7.079 (0.32), 7.394 (0.12), 7.409 (0.12), 8.176 (0.45), 8.198 (0.48), 8.672 (0.49), 8.694 (0.44), 8.807 (0.77), 9.701 (0.22).

Example 166

1-(2,4-Difluorophenyl)-4-oxo-7-(2-oxopyrrolidin-1-yl)-N-(tricyclo[3.3.1.1$^{3,7}$]dec-1-yl)-1,4-dihydro-1,8-naphthyridine-3-carboxamide

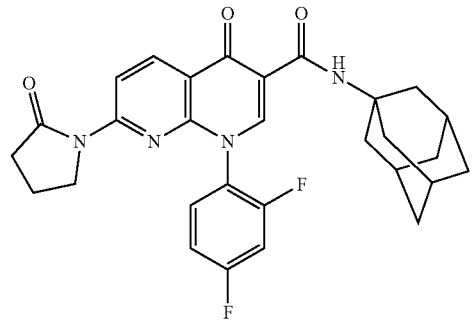 [SMILES: O=C(NC12CC3CC(CC(C3)C1)C2)c1cn(-c2ccc(F)cc2F)c2nc(N3CCCC3=O)ccc2c1=O]

208 mg (0.64 mmol) of caesium carbonate, 10 mg (0.04 mmol) of palladium(II) acetate and 25 mg (0.04 mmol) of Xantphos were stirred in 5.6 ml of dioxane (under argon) at 20° C. for 10 minutes. Then 200 mg (0.43 mmol) of the compound from Example 65A and 36 mg (0.43 mmol) of 2-pyrrolidinone were added and the mixture was stirred at 110° C. for 22 h. Subsequently, the mixture was filtered and the filtrate was purified via preparative HPLC (eluent: acetonitrile/water gradient with 0.1% formic acid). This gave 13 mg (6% of theory) of the title compound.

LC-MS (Method 1): $R_t$=1.33 min; m/z=519.2 [M+H]$^+$.

$^1$H-NMR (400 MHz, DMSO-$d_6$) δ [ppm]: -0.150 (1.78), -0.009 (16.00), 0.008 (15.04), 0.146 (1.89), 1.146 (0.80), 1.235 (0.55), 1.679 (4.33), 1.956 (0.66), 1.976 (0.50), 2.072 (9.96), 2.322 (1.13), 2.327 (1.68), 2.331 (1.16), 2.365 (1.94), 2.523 (4.23), 2.525 (3.79), 2.558 (2.30), 2.575 (1.51), 2.582 (1.43), 2.595 (0.88), 2.665 (1.49), 2.669 (1.89), 2.674 (1.46), 2.709 (2.20), 3.286 (1.67), 3.426 (0.36), 3.549 (0.83), 3.570

(0.83), 3.587 (0.49), 7.354 (0.52), 7.616 (0.53), 7.642 (0.36), 7.845 (0.57), 7.860 (0.58), 8.464 (1.62), 8.486 (1.97), 8.658 (1.94), 8.680 (1.65), 8.705 (2.97), 9.725 (1.56).

In analogy to Example 166, the example compounds shown in Table 19 were prepared by reacting the compound from Example 65A with the appropriate amines (or salts thereof) under the reaction conditions described. Differences are specified in the respective examples.

TABLE 19

| Ex. | | Analytical data |
|---|---|---|
| 167 | 1-(2,4-Difluorophenyl)-7-(1,1-dioxido-1,2-thiazolidin-2-yl)-4-oxo-N-(tricyclo[3.3.1.1$^{3,7}$]dec-1-yl)-1,4-dihydro-1,8-naphthyridine-3-carboxamide<br />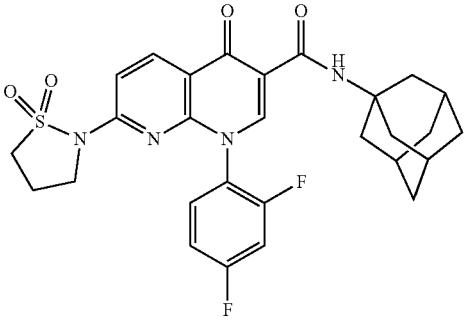<br />(52% of theory) | LC-MS (Method 1): $R_t$ = 1.26 min<br />MS (ESpos): m/z = 555.2 [M + H]$^+$<br />$^1$H-NMR (400 MHz, DMSO-d$_6$) δ [ppm]: −0.013 (1.19), 0.003 (1.16), 1.672 (7.13), 2.063 (16.00), 2.067 (13.86), 2.091 (0.91), 2.297 (1.24), 2.315 (1.97), 2.332 (1.36), 3.575 (0.95), 3.594 (2.09), 3.606 (2.00), 3.616 (1.55), 3.634 (0.64), 7.320 (0.73), 7.325 (0.76), 7.340 (2.97), 7.362 (2.60), 7.537 (0.49), 7.555 (0.69), 7.559 (0.70), 7.578 (0.50), 7.813 (0.54), 7.820 (0.91), 7.835 (0.91), 7.842 (0.52), 8.612 (2.64), 8.634 (2.52), 8.653 (4.54), 9.730 (2.56). |
| 168 | 1-(2,4-Difluorophenyl)-4-oxo-7-(2-oxoazetidin-1-yl)-N-(tricyclo[3.3.1.1$^{3,7}$]dec-1-yl)-1,4-dihydro-1,8-naphthyridine-3-carboxamide<br />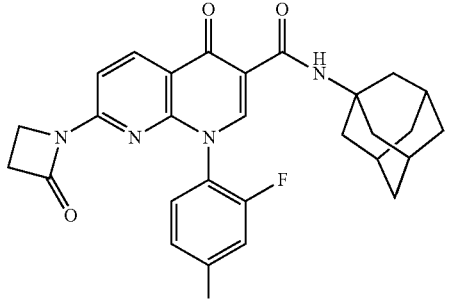<br />(9% of theory) | LC-MS (Method 1): $R_t$ = 1.31 min<br />MS (ESpos): m/z = 505.4 [M + H]$^+$<br />$^1$H-NMR (400 MHz, DMSO-d$_6$) δ [ppm]: 1.156 (0.38), 1.174 (0.71), 1.192 (0.39), 1.234 (0.73), 1.676 (7.37), 1.987 (1.27), 2.067 (16.00), 2.327 (0.39), 2.365 (0.42), 2.669 (0.41), 2.709 (0.40), 3.088 (1.46), 3.100 (1.49), 3.386 (1.28), 4.020 (0.29), 4.038 (0.29), 7.327 (0.44), 7.349 (0.82), 7.366 (0.61), 7.576 (0.50), 7.598 (0.77), 7.618 (0.50), 7.696 (2.27), 7.717 (2.38), 7.810 (0.46), 7.832 (0.88), 7.847 (0.90), 7.869 (0.46), 8.654 (2.35), 8.675 (2.58), 8.681 (4.17), 9.709 (2.41). |
| 169 | 1-(2,4-Difluorophenyl)-7-[methyl(methylsulphonyl)amino]-4-oxo-N-(tricyclo[3.3.1.1$^{3,7}$]dec-1-yl)-1,4-dihydro-1,8-naphthyridine-3-carboxamide<br />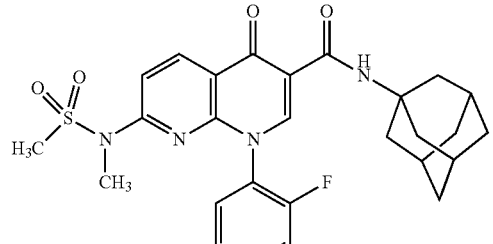<br />(45% of the theory) | LC-MS (Method 1): $R_t$ = 1.26 min<br />MS (ESpos): m/z = 543.2 [M + H]$^+$<br />$^1$H-NMR (400 MHz, DMSO-d$_6$) δ [ppm]: −0.154 (0.08), −0.005 (16.00), 0.141 (0.08), (2.57), 2.068 (8.74), 3.036 (4.34), (4.18), 7.329 (0.13), 7.351 (0.27), (0.14), 7.540 (0.80), 7.562 (0.83), (0.17), 7.594 (0.25), 7.617 (0.17), (0.16), 7.823 (0.15), 7.845 (0.31), (0.31), 7.867 (0.18), 7.881 (0.15), (0.81), 8.653 (0.77), 8.699 (1.49), 9.689 (0.87). |

TABLE 19-continued

| Ex. | | Analytical data |
|---|---|---|
| 170 | 1-(2,4-Difluorophenyl)-7-[(4S)-4-hydroxy-2-oxopyrrolidin-1-yl]-4-oxo-N-(tricyclo[3.3.1.1$^{3,7}$]dec-1-yl)-1,4-dihydro-1,8-naphthyridine-3-carboxamide<br>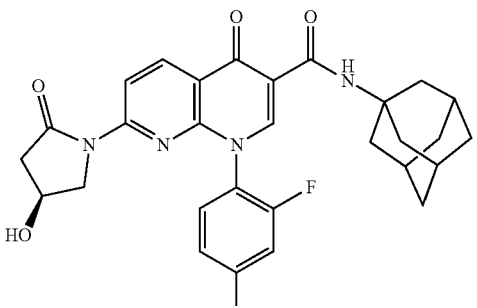<br>(34% of theory) | LC-MS (Method 1): $R_t$ = 1.16 min<br>MS (ESpos): m/z = 535.2 [M + H]$^+$<br>$^1$H-NMR (400 MHz, DMSO-d$_6$) δ [ppm]:<br>−0.149 (1.21), −0.008 (10.86), 0.008 (9.92), 0.146 (1.23), 1.147 (0.47), 1.676 (8.65), 2.059 (8.89), 2.072 (16.00), 2.327 (1.28), 2.366 (1.28), 2.391 (0.39), 2.524 (2.59), 2.670 (1.06), 2.674 (0.83), 2.710 (1.13), 2.899 (0.30), 2.932 (0.38), 3.288 (1.29), 3.441 (0.36), 3.466 (0.65), 3.499 (0.39), 3.637 (0.32), 3.667 (0.50), 4.284 (0.71), 5.283 (0.52), 5.343 (0.51), 7.368 (0.63), 7.601 (0.62), 7.621 (0.76), 7.649 (0.38), 7.845 (0.52), 7.864 (0.57), 8.365 (0.43), 8.467 (0.57), 8.481 (0.65), 8.503 (0.80), 8.666 (2.59), 8.688 (2.08), 8.704 (4.17), 9.725 (2.21). |
| 171 | 7-(5,5-Difluoro-2-oxopiperidin-1-yl)-1-(2,4-difluorophenyl)-4-oxo-N-(tricyclo[3.3.1.1$^{3,7}$]dec-1-yl)-1,4-dihydro-1,8-naphthyridine-3-carboxamide<br>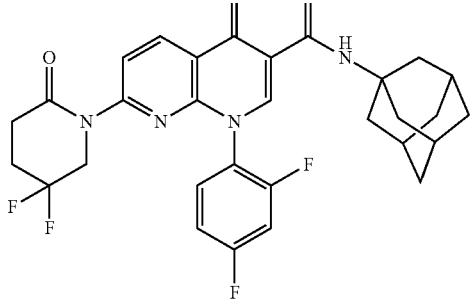<br>(77% of theory) | LC-MS (Method 1): $R_t$ = 1.31 min<br>MS (ESpos): m/z = 569.3 [M + H]$^+$<br>$^1$H-NMR (400 MHz, DMSO-d$_6$) δ [ppm]:<br>1.680 (7.72), 2.075 (16.00), 2.366 (1.00), 2.387 (0.85), 2.406 (1.26), 2.424 (0.94), 2.444 (0.66), 2.720 (1.48), 2.738 (2.68), 2.756 (1.18), 3.955 (1.20), 3.987 (2.25), 4.019 (1.16), 7.388 (0.84), 7.641 (0.46), 7.661 (0.78), 7.683 (0.45), 7.857 (0.42), 7.878 (0.82), 7.894 (0.81), 7.915 (0.40), 8.155 (1.85), 8.177 (2.01), 8.670 (2.00), 8.692 (1.84), 8.749 (3.57), 9.679 (2.44). |

TABLE 19-continued

| Ex. | | Analytical data |
|---|---|---|
| 172 | 1-(2,4-Difluorophenyl)-4-oxo-7-(3-oxomorpholin-4-yl)-1-(tricyclo[3.3.1.1$^{3,7}$]dec-1-yl)-1,4-dihydro-1,8-naphthyridine-3-carboxamide<br>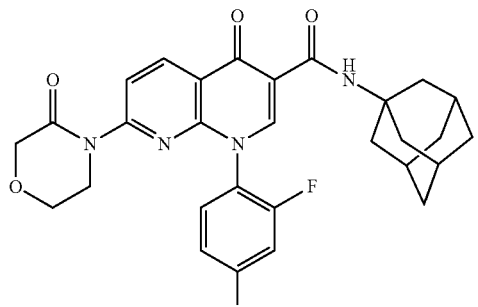<br>(17% of theory) | LC-MS (Method 1): R$_t$ = 1.28 min<br>MS (ESpos): m/z = 535.2 [M + H]$^+$<br>$^1$H-NMR (400 MHz, DMSO-d$_6$) δ [ppm]:<br>−0.150 (1.50), −0.009 (13.61), 0.007 (12.45),<br>0.146 (1.55), 1.146 (0.70), 1.590 (0.77),<br>1.681 (7.53), 2.075 (16.00), 2.322 (1.13),<br>2.327 (1.57), 2.331 (1.05), 2.366 (1.89),<br>2.522 (3.55), 2.665 (1.16), 2.669 (1.59),<br>2.673 (1.17), 2.709 (1.95), 3.544 (1.38),<br>3.558 (2.29), 3.570 (1.65), 3.898 (1.63),<br>4.277 (3.49), 4.284 (3.49), 7.355 (0.77),<br>7.605 (0.85), 7.861 (0.97), 7.876 (0.88),<br>8.339 (2.75), 8.361 (3.02), 8.681 (3.13),<br>8.703 (2.70), 8.739 (4.78), 9.687 (2.58). |
| 173 | rac-1-(2,4-Difluorophenyl)-7-[4-hydroxy-2-oxopiperidin-1-yl]-4-oxo-N-(tricyclo[3.3.1.1$^{3,7}$]dec-1-yl)-1,4-dihydro-1,8-naphthyridine-3-carboxamide<br>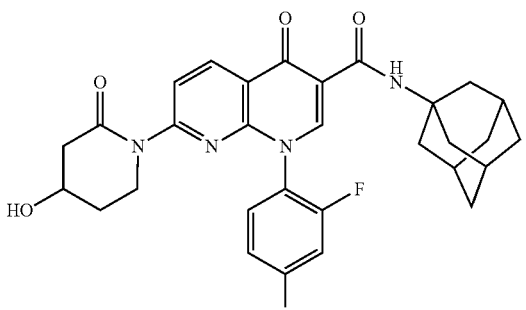<br>(15% of theory) | LC-MS (Method 1): R$_t$ = 1.12 min<br>MS (ESpos): m/z = 549.3 [M + H]$^+$<br>$^1$H-NMR (400 MHz, DMSO-d$_6$) δ [ppm]:<br>−0.150 (1.72), −0.009 (14.59), 0.007 (14.85),<br>0.083 (0.31), 0.146 (1.85), 1.146 (0.73),<br>1.156 (0.94), 1.174 (1.95), 1.192 (0.90),<br>1.237 (0.44), 1.672 (7.27), 1.987 (3.59),<br>2.059 (16.00), 2.322 (1.28), 2.327 (1.93),<br>2.365 (2.81), 2.523 (5.04), 2.669 (2.18),<br>2.673 (1.72), 2.709 (2.92), 3.432 (0.48),<br>3.682 (0.31), 4.020 (1.01), 4.037 (0.80),<br>4.056 (0.34), 6.840 (0.42), 7.319 (0.42),<br>7.337 (0.82), 7.360 (0.57), 7.575 (0.55),<br>7.606 (0.86), 7.631 (0.52), 7.821 (0.76),<br>7.837 (0.59), 8.470 (0.46), 8.519 (1.15),<br>9.805 (0.84), 12.106 (1.28). |

Example 174

1-(2,4-Difluorophenyl)-7-[(4S)-4-hydroxy-2-oxopyrrolidin-1-yl]-4-oxo-N-[(2S)-1,1,1-trifluorobutan-2-yl]-1,4-dihydro-1,8-naphthyridine-3-carboxamide

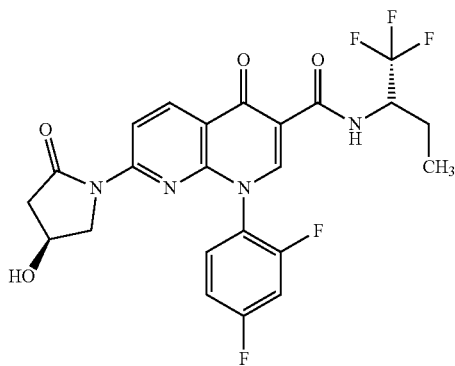

412 mg (1.3 mmol) of caesium carbonate, 34 mg (0.15 mmol) of palladium(II) acetate and 88 mg (0.15 mmol) of Xantphos were stirred in dioxane (under an argon atmosphere) at 20° C. for 10 minutes. Then 400 mg (0.84 mmol) of the compound from Example 68A and 85 mg (0.84 mmol) of (4S)-4-hydroxypyrrolidin-2-one were added and the mixture was stirred at 80° C. for 40 min. Subsequently, the mixture was added to water and brought to pH 1 with 1 M aqueous hydrochloric acid. The precipitated solid was filtered off with suction, washed with water and petroleum ether, and then purified by column chromatography (silica gel cartridge; cyclohexane/ethyl acetate gradient (5:1-2:1-1:1). This gave 169 mg (38% of theory) of the title compound.

LC-MS (Method 1): R$_t$=1.01 min; m/z=511.3 [M+H]$^+$.

$^1$H-NMR (400 MHz, DMSO-d$_6$) δ [ppm]: −0.001 (16.00), 0.958 (1.16), 0.976 (2.31), 0.995 (1.20), 1.174 (0.23), 1.234 (0.33), 1.565 (0.20), 1.686 (0.37), 1.894 (0.30), 1.987 (0.32), 2.336 (0.30), 2.379 (0.33), 2.943 (0.26), 3.437 (0.27), 3.469 (0.43), 3.503 (0.26), 3.674 (0.30), 4.288 (0.45), 4.764 (0.26), 5.293 (0.38), 5.343 (0.30), 7.373 (0.37), 7.629 (0.42), 7.877 (0.31), 8.516 (0.39), 8.538 (0.45), 8.698 (1.21), 8.720 (1.05), 8.849 (0.86), 10.208 (0.55), 10.232 (0.57).

In analogy to Example 174, the example compounds shown in Table 20 were prepared by reacting the respective compounds from Examples 66A-70A with the appropriate amines (or salts thereof) under the reaction conditions described. Differences are specified in the respective examples.

TABLE 20

| Ex. | | Analytical data |
|---|---|---|
| 175 | 1-(2,4-Difluorophenyl)-7-[(4S)-4-hydroxy-2-oxopyrrolidin-1-yl]-4-oxo-N-[(2R)-1,1,1-trifluorobutan-2-yl]-1,4-dihydro-1,8-naphthyridine-3-carboxamide<br><br>Compound from Ex. 67A and (4S)-4-hydroxypyrrolidin-2-one<br>(48% of theory) | LC-MS (Method 1): $R_t$ = 0.99 min; m/z = 511.4 [M + H]$^+$.<br>$^1$H-NMR (500 MHz, DMSO-d$_6$) δ [ppm]: −0.009 (0.77), −0.003 (16.00), 0.004 (0.49), 0.964 (5.50), 0.979 (11.59), 0.994 (5.60), 1.634 (0.80), 1.640 (0.40), 1.649 (1.07), 1.654 (0.94), 1.662 (1.26), 1.669 (1.12), 1.677 (1.07), 1.683 (1.16), 1.697 (0.87), 1.865 (0.40), 1.872 (0.89), 1.879 (1.04), 1.886 (1.06), 1.894 (1.17), 1.899 (1.06), 1.908 (0.94), 1.914 (0.79), 1.922 (0.66), 2.342 (1.02), 2.362 (1.10), 2.376 (1.18), 2.397 (1.08), 2.898 (0.72), 2.910 (0.78), 2.933 (1.41), 2.945 (1.40), 2.967 (0.70), 2.979 (0.64), 3.444 (0.98), 3.468 (1.29), 3.479 (1.06), 3.503 (1.12), 3.632 (0.76), 3.642 (0.89), 3.656 (0.78), 3.667 (1.25), 3.677 (0.91), 3.692 (0.70), 3.701 (0.60), 4.286 (2.23), 4.759 (0.98), 4.765 (1.02), 4.778 (0.96), 4.793 (0.54), 5.294 (0.49), 5.348 (0.44), 5.752 (2.39), 7.354 (0.90), 7.371 (1.72), 7.388 (0.93), 7.608 (1.00), 7.627 (1.78), 7.646 (0.98), 7.869 (1.43), 7.880 (1.22), 7.886 (1.37), 8.503 (1.49), 8.520 (2.77), 8.537 (1.79), 8.700 (8.73), 8.718 (7.10), 8.850 (3.69), 8.857 (3.69), 10.211 (3.77), 10.230 (3.59). |
| 176 | 1-(2,4-Difluorophenyl)-7-[(4S)-4-hydroxy-2-oxopyrrolidin-1-yl]-4-oxo-N-[1,1,1-trifluorobutan-2-yl]-1,4-dihydro-1,8-naphthyridine-3-carboxamide<br>(diastereomer mixture)<br><br>Compound from Ex. 66A and (4R)-4-hydroxypyrrolidin-2-one; 110°C. for 6 h<br>(44% of theory) | LC-MS (Method 1): $R_t$ = 1.01 min; m/z = 511.1 [M + H]$^+$.<br>$^1$H-NMR (400 MHz, DMSO-d$_6$) δ [ppm]: −0.009 (6.49), 0.007 (6.13), 0.898 (1.89), 0.960 (7.36), 0.978 (15.05), 0.996 (7.39), 1.156 (3.78), 1.174 (7.50), 1.192 (3.75), 1.625 (1.27), 1.643 (1.78), 1.650 (1.47), 1.660 (1.95), 1.669 (1.81), 1.679 (1.62), 1.686 (1.92), 1.704 (1.44), 1.866 (1.43), 1.876 (1.62), 1.885 (1.74), 1.894 (1.69), 1.901 (1.72), 1.908 (1.51), 1.987 (14.10), 2.335 (1.77), 2.357 (1.34), 2.378 (1.74), 2.400 (1.55), 2.906 (1.12), 2.942 (1.40), 3.439 (1.38), 3.470 (2.50), 3.503 (1.70), 3.640 (1.26), 3.664 (1.63), 4.020 (3.12), 4.038 (3.14), 4.280 (2.69), 4.764 (1.63), 4.778 (1.57), 5.287 (2.24), 5.295 (2.18), 5.344 (1.88), 5.354 (1.85), 5.753 (16.00), 7.373 (2.43), 7.607 (1.71), 7.630 (2.72), 7.653 (1.31), 7.870 (1.88), 8.502 (2.22), 8.516 (2.66), 8.524 (2.78), 8.539 (2.90), 8.699 (12.77), 8.721 (10.04), 8.849 (5.98), 8.855 (5.41), 10.209 (4.47), 10.233 (4.26). |
| 177 | rac-1-(2,4-Difluorophenyl)-4-oxo-7-(2-oxopyrrolidin-1-yl)-N-[1,1,1-trifluorobutan-2-yl]-1,4-dihydro-1,8-naphthyridine-3-carboxamide<br><br>Compound from Ex. 66A and pyrrolidin-2-one; 110°C. for 6 h<br>(10% of theory) | LC-MS (Method 1): $R_t$ = 1.15 min; m/z = 495.3 [M + H]$^+$.<br>$^1$H-NMR (400 MHz, DMSO-d$_6$) δ [ppm]: −0.150 (1.83), −0.009 (16.00), 0.007 (15.91), 0.146 (1.93), 0.958 (5.12), 0.977 (11.28), 0.995 (5.59), 1.156 (2.03), 1.174 (3.85), 1.192 (2.09), 1.234 (2.67), 1.642 (1.04), 1.659 (1.22), 1.685 (1.20), 1.703 (0.89), 1.894 (1.21), 1.947 (2.11), 1.962 (2.97), 1.987 (5.90), 2.327 (1.10), 2.366 (1.85), 2.563 (3.59), 2.582 (4.46), 2.590 (4.72), 2.602 (2.58), 2.610 (2.36), 2.669 (1.47), 2.709 (2.18), 3.533 (1.53), 3.550 (2.74), 3.573 (2.86), 3.591 (1.58), 4.020 (1.08), 4.038 (1.03), 4.764 (1.01), 7.339 (0.95), 7.360 (1.97), 7.381 (1.09), 7.598 (1.36), 7.620 (1.88), 7.639 (1.26), 7.646 (1.22), 7.878 (1.35), 8.500 (6.13), 8.522 (7.62), 8.690 (7.51), 8.713 (6.15), 8.850 (3.94), 10.209 (3.35), 10.232 (3.25). |

TABLE 20-continued

| Ex. | | Analytical data |
|---|---|---|
| 178 | 1-(2,4-Difluorophenyl)-4-oxo-7-(2-oxopiperidin-1-yl)-N-[(2R)-1,1,1-trifluorobutan-2-yl]-1,4-dihydro-1,8-naphthyridine-3-carboxamide<br>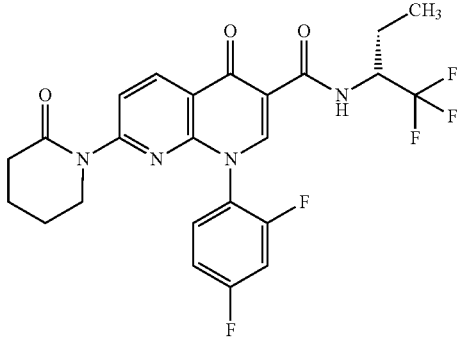<br>Compound from Ex. 67A and piperidin-2-one<br>(35% of theory) | LC-MS (Method 1): $R_t$ = 1.15 min; m/z = 509.4 $[M + H]^+$.<br>$^1$H-NMR (400 MHz, DMSO-$d_6$) δ [ppm]: 0.959 (8.20), 0.978 (16.00), 0.996 (7.69), 1.662 (2.25), 1.755 (15.41), 1.894 (1.98), 3.526 (7.02), 4.765 (1.79), 7.342 (1.95), 7.363 (3.27), 7.602 (2.15), 7.624 (3.24), 7.643 (1.92), 7.869 (2.39), 8.133 (8.33), 8.155 (8.74), 8.624 (8.95), 8.646 (8.06), 8.860(6.39), 10.191 (4.92), 10.214 (4.57). |
| 179 | rac-1-(2,4-Difluorophenyl)-4-oxo-7-(2-oxopyrrolidin-1-yl)-N-[1,1,1-trifluoropropan-2-yl]-1,4-dihydro-1,8-naphthyridine-3-carboxamide<br>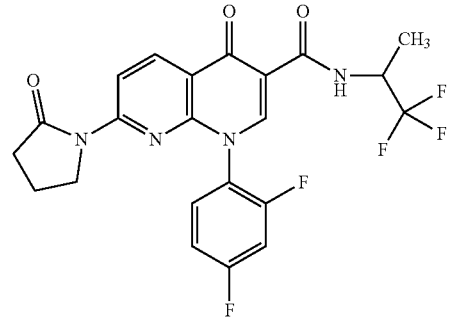<br>Compound from Ex. 69A and 2-pyrrolidinone; 110°C. for 6 h<br>(15% of theory) | LC-MS (Method 1): $R_t$ = 1.12 min; m/z = 481.2 $[M + H]^+$.<br>$^1$H-NMR (400 MHz, DMSO-$d_6$) δ [ppm]: −0.150 (1.18), −0.009 (10.63), 0.007 (10.36), 0.145 (1.32), 1.381 (15.86), 1.399 (16.00), 1.946 (2.60), 1.960 (3.95), 1.981 (3.04), 2.365 (1.72), 2.561 (4.22), 2.580 (5.74), 2.588 (6.01), 2.601 (3.24), 2.608 (2.87), 2.669 (1.28), 2.709 (1.89), 3.531 (2.16), 3.549 (3.95), 3.570 (3.71), 4.912 (1.69), 4.933 (1.69), 7.339 (1.49), 7.361 (2.84), 7.382 (1.99), 7.598 (1.65), 7.620 (2.46), 7.639 (1.69), 7.855 (1.59), 8.496 (8.78), 8.518 (10.67), 8.681 (11.27), 8.703 (9.08), 8.843 (5.97), 10.258 (3.24), 10.281 (3.07). |
| 180 | rac-1-(2,4-Difluorophenyl)-7-(1,1-dioxido-1,2-thiazolidin-2-yl)-4-oxo-N-[1,1,1-trifluorobutan-2-yl]-1,4-dihydro-1,8-naphthyridine-3-carboxamide<br>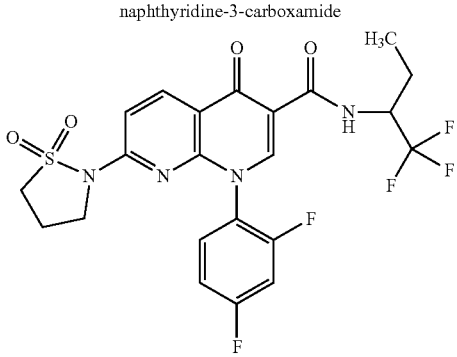<br>Compound from Ex. 66A and 1,3-propane sultam; 110°C. for 6 h<br>(44% of theory) | LC-MS (Method 1): $R_t$ = 1.09 min; m/z = 531.1 $[M + H]^+$.<br>$^1$H-NMR (400 MHz, DMSO-$d_6$) δ [ppm]: −0.009 (4.11), 0.007 (2.26), 0.957 (7.72), 0.975 (16.00), 0.993 (7.78), 1.620 (1.16), 1.638 (1.63), 1.646 (1.74), 1.655 (1.95), 1.663 (1.71), 1.673 (1.65), 1.680 (1-79), 1.698 (1.35), 1.862 (1.46), 1.872 (1.66), 1.881 (1.67), 1.890 (1.83), 1.897 (1.61), 1.907 (1.46), 1.915 (1.14), 1.925 (0.98), 1.987 (1.19), 2.290 (1.50), 2.307 (5.22), 2.325 (8.04), 2.342 (5.26), 2.359 (1.49), 3.593 (4.45), 3.603 (8.33), 3.610 (8.78), 3.619 (8.50), 3.629 (6.96), 3.647 (2.73), 4.757 (1.58), 4.774 (1.48), 7.310 (1.63), 7.326 (2.99), 7.331 (3.06), 7.347 (1.80), 7.352 (1.81), 7.374 (8.75), 7.396 (8.90), 7.537 (1.80), 7.543 (1.86), 7.562 (2.84), 7.566 (2.80), 7.585 (1.80), 7.592 (1.66), 7.818 (1.14), 7.838 (2.25), 7.854 (2.25), 7.875 (1.01), 8.647 (8.78), 8.669 (8.39), 8.804 (8.06), 10.221 (5.01), 10.245 (4.79). |

TABLE 20-continued

| Ex. | | Analytical data |
|---|---|---|
| 181 | 1-(2,4-Difluorophenyl)-7-[(4S)-4-hydroxy-2-oxopyrrolidin-1-yl]-N-(4-methylbicyclo[2.2.2]oct-1-yl)-4-oxo-1,4-dihydro-1,8-naphthyridine-3-carboxamide 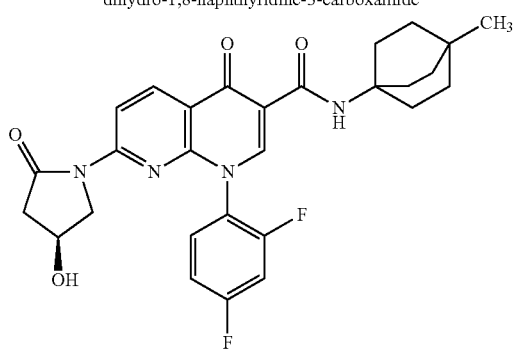 Compound from Ex. 70A and (4R)-4-hydroxypyrrolidin-2-one; 110°C. for 17 h (2% of theory) | LC-MS (Method 1): $R_t$ = 1.15 min; m/z = 523.4 $[M + H]^+$. $^1$H-NMR (400 MHz, DMSO-$d_6$) δ [ppm]: 0.8 (s, 3H), 1.43-1.52 (m, 6H), 1.89-1.98 (m, 6H), 3.41-3.52 (m, 1H), 3.59-3.72 (m, 1H), 4.24-4.30 (m, 2H), 5.26-5.30 (m, 0.5H), 5.32-5.35 (m, 0.5H), 7.32-7.40 (m, 1H), 7.54-7.66 (m, 1H), 7.77-7.90 (m, 1H), 8.45-8.51 (m, 1H), 8.67 (d, 1H), 8.70 (s, 1H), 9.66 (s, 1H). |

Example 182

N-(2,6-Dichlorobenzyl)-1-(2,4-difluorophenyl)-7-(1,1-dioxido-1,2-thiazolidin-2-yl)-4-oxo-1,4-dihydro-1,8-naphthyridine-3-carboxamide

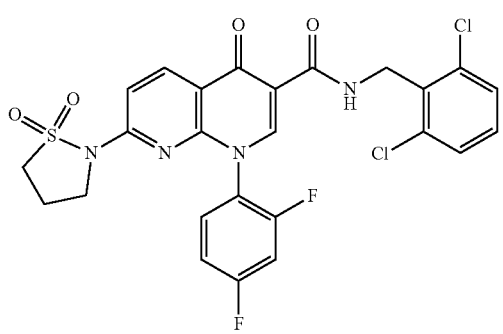 [SMILES: O=C(NCc1c(Cl)cccc1Cl)c1cn(-c2ccc(F)cc2F)c2nc(N3CCCS3(=O)=O)ccc2c1=O]

7 mg (0.03 mmol) of palladium(II) acetate and 18 mg (0.03 mmol) of Xantphos were stirred in 3.6 ml of dioxane under an argon atmosphere at 20° C. for 10 minutes. Then 150 mg (0.3 mmol) of the compound from Example 72A, 74 mg (0.06 mmol) of 1,3-propane sultam and 148 mg (0.46 mmol) of caesium carbonate were added and the mixture was stirred at 110° C. for 6 h. After cooling down to 23° C., the mixture was purified via preparative HPLC (eluent: acetonitrile/water gradient with 0.1% formic acid). This gave 95 mg (51% of theory) of the title compound.

LC-MS (Method 1): $R_t$=1.15 min; m/z=579.2 $[M+H]^+$.

$^1$H-NMR (400 MHz, DMSO-$d_6$) δ [ppm]: 1.156 (4.54), 1.174 (8.71), 1.192 (4.39), 1.987 (16.00), 2.297 (4.76), 2.314 (6.89), 2.331 (5.14), 3.577 (4.62), 3.590 (8.77), 3.606 (8.06), 3.634 (2.43), 4.020 (4.03), 4.037 (3.96), 4.815 (3.11), 4.827 (3.16), 4.845 (3.08), 4.859 (2.88), 7.325 (3.46), 7.334 (7.37), 7.356 (6.87), 7.380 (2.99), 7.399 (5.75), 7.420 (4.45), 7.526 (13.43), 7.546 (9.83), 7.555 (3.20), 7.811 (2.87), 7.826 (2.86), 8.595 (6.46), 8.617 (6.25), 8.754 (11.28), 10.157 (2.54), 10.171 (4.84).

In analogy to Example 182, the example compound shown in Table 21 was prepared, by reacting the compound from Example 72A with the appropriate amines (or salts thereof) under the reaction conditions described. Differences are specified in the respective examples.

TABLE 21

| Ex. | | Analytical data |
|---|---|---|
| 183 | N-(2,6-Dichlorobenzyl)-1-(2,4-difluorophenyl)-7-[(4S)-4-hydroxy-2-oxopyrrolidin-1-yl]-4-oxo-1,4-dihydro-1,8-naphthyridine-3-carboxamide 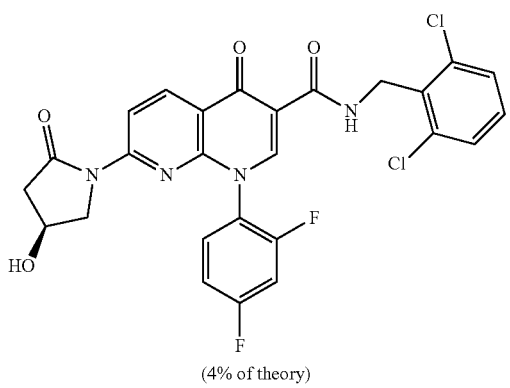 (4% of theory) | LC-MS (Method 1): $R_t$ = 1.00 min; m/z = 559.1 [M + H]$^+$. $^1$H-NMR (400 MHz, DMSO-$d_6$) δ [ppm]: 2.83-3.00 (m, 1H), 3.42-3.52 (m, 1H), 3.56-3.73 (m, 1H), 4.24-4.30 (m, 1H), 4.78-4.90 (m, 2H), 5.25-5.29 (m, 0.5H), 5.31-5.36 (m, 0.5H), 7.33-7.43 (m, 2H), 7.54 (d, 1H), 7.56-7.66 (m, 1H), 8.44-8.52 (m, 1H), 8.66 (d, 1H), 8.79 (s, 1H), 10.13-10.19 (m, 1H). |

Example 184

1-(2,4-Difluorophenyl)-N-[2-(2,6-difluorophenyl)propan-2-yl]-4-oxo-7-(2-oxoimidazolidin-1-yl)-1,4-dihydro-1,8-naphthyridine-3-carboxamide

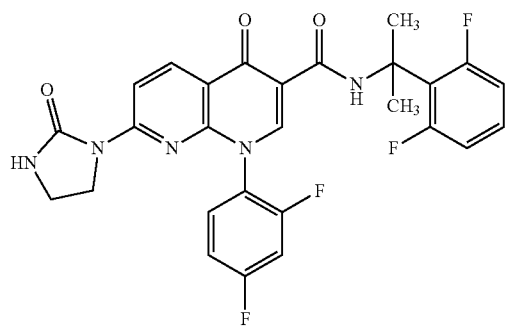 [SMILES: CC(C)(NC(=O)c1cn(-c2ccc(F)cc2F)c2nc(N3CCNC3=O)ccc2c1=O)c1c(F)cccc1F]

5 mg (0.02 mmol) of palladium(II) acetate and 13 mg (0.02 mmol) of Xantphos were stirred in 2.7 ml of dioxane under an argon atmosphere at 20° C. for 10 minutes. Then 150 mg (0.23 mmol, 75% purity) of the compound from Example 71A, 40 mg (0.46 mmol) of 2-imidazolidinone and 112 mg (0.35 mmol) of caesium carbonate were added and the mixture was stirred at 110° C. for 6 h. After cooling down to 23° C., the mixture was purified via preparative HPLC (eluent: acetonitrile/water gradient with 0.1% formic acid).

This gave 45 mg (35% of theory) of the title compound.

LC-MS (Method 1): $R_t$=1.00 min; m/z=540.2 [M+H]$^+$.
$^1$H-NMR (400 MHz, DMSO-$d_6$) δ [ppm]: 1.839 (16.00), 1.987 (1.18), 3.534 (1.12), 3.555 (1.83), 3.576 (1.84), 6.942 (2.23), 6.963 (3.18), 6.989 (2.62), 7.248 (1.08), 7.269 (1.75), 7.275 (1.24), 7.284 (1.63), 7.289 (1.21), 7.304 (1.85), 7.556 (1.46), 7.607 (3.76), 7.810 (1.62), 7.825 (1.63), 8.387 (3.80), 8.409 (4.82), 8.546 (4.78), 8.568 (4.25), 8.575 (7.71), 10.534 (4.55).

In analogy to Example 184, the example compound shown in Table 22 was prepared, by reacting the compound from Example 71A with the appropriate amines (or salts thereof) under the reaction conditions described. Differences are specified in the respective examples.

TABLE 22

| Ex. | | Analytical data |
|---|---|---|
| 185 | 1-(2,4-Difluorophenyl)-N-[2-(2,6-difluorophenyl)propan-2-yl]-7-(1,1-dioxido-1,2-thiazolidin-2-yl)-4-oxo-1,4-dihydro-1,8-naphthyridine-3-carboxamide 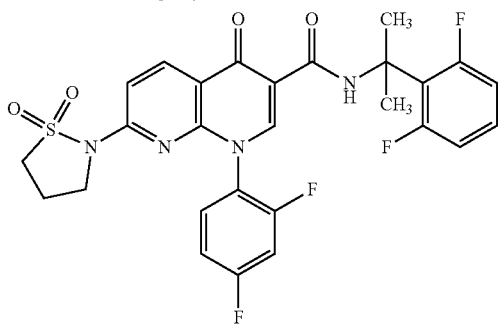 and 1,3-propane sultam (68% of theory) | LC-MS (Method 1): $R_t$ = 1.16 min<br>MS (ESpos): m/z = 575.3 [M + H]$^+$<br>$^1$H-NMR (400 MHz, DMSO-d$_6$) δ [ppm]:<br>1.157 (4.28), 1.175 (8.38), 1.193 (4.21),<br>1.842 (10.49), 1.989 (16.00), 2.302 (1.66),<br>2.319 (2.48), 2.336 (1.72), 3.576 (1.42),<br>3.595 (2.93), 3.613 (2.62), 3.624 (1.78),<br>3.642 (0.79), 4.003 (1.40), 4.021 (3.96),<br>4.039 (3.85), 4.057 (1.24), 6.946 (1.55),<br>6.967 (2.19), 6.992 (1.69), 7.251 (0.78),<br>7.256 (0.76), 7.271 (1.60), 7.292 (1.53),<br>7.309 (0.73), 7.363 (2.74), 7.385 (2.84),<br>7.507 (0.64), 7.513 (0.65), 7.535 (0.99),<br>7.555 (0.61), 7.562 (0.57), 7.795 (0.70),<br>7.801 (1.09), 7.816 (1.08), 7.823 (0.60),<br>8.597 (5.07), 8.650 (2.78), 8.672 (2.60),<br>10.470 (2.95). |

Example 186

1-(2,4-Difluorophenyl)-4-oxo-7-(2-oxoimidazolidin-1-yl)-N-(tricyclo[3.3.1.1$^{3,7}$]dec-1-yl)-1,4-dihydro-1,8-naphthyridine-3-carboxamide

Example 187

1-(2,4-Difluorophenyl)-7-[4-fluoro-2-oxopyrrolidin-1-yl]-4-oxo-N-(tricyclo[3.3.1.1$^{3,7}$]dec-1-yl)-1,4-dihydro-1,8-naphthyridine-3-carboxamide

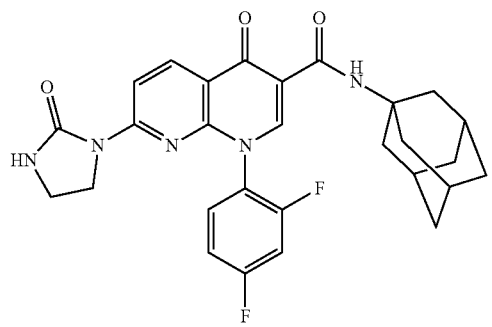 [SMILES: O=C(NC12CC3CC(CC(C3)C1)C2)c1cn(-c2ccc(F)cc2F)c2nc(N3CCNC3=O)ccc2c1=O]

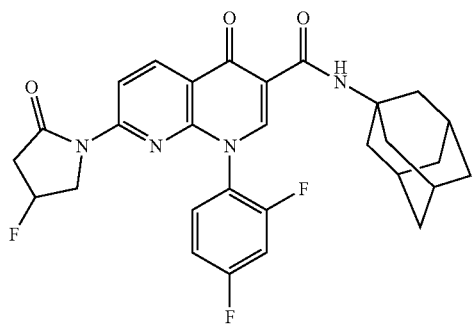 [SMILES: O=C(NC12CC3CC(CC(C3)C1)C2)c1cn(-c2ccc(F)cc2F)c2nc(N3CC(F)CC3=O)ccc2c1=O]

A mixture of 200 mg (0.4 mmol) of the compound from Example 65A, 147 mg (1.7 mmol) of 2-imidazolidinone, 118 mg (0.9 mmol) of potassium carbonate, 83 mg (0.4 mmol) of copper(I) iodide and 32 mg (0.4 mmol) of trans-N,N'-dimethyl-1,2-cyclohexanediamine in 5 ml of DMF was stirred at 110° C. for 22 h. Subsequently, the mixture was filtered and the filtrate was purified via preparative HPLC (eluent: acetonitrile/water gradient with 0.1% formic acid). This gave 7 mg (3% of theory) of the title compound.

$^1$H-NMR (400 MHz, DMSO-d$_6$) δ [ppm]: −0.150 (1.07), −0.009 (9.84), 0.007 (8.65), 0.146 (1.15), 1.677 (7.23), 2.068 (16.00), 2.327 (0.71), 2.365 (0.96), 2.669 (0.75), 2.709 (0.97), 3.563 (0.92), 7.341 (0.77), 7.601 (2.15), 7.836 (0.93), 7.851 (0.93), 8.144 (0.84), 8.368 (2.57), 8.391 (3.21), 8.515 (3.29), 8.537 (2.43), 8.638 (4.84), 9.797 (2.58).

LC-MS (Method 1): $R_t$=1.21 min
MS (ESpos): m/z=520.2 [M+H]$^+$

To 150 mg (0.28 mmol) of the compound from Example 170 in 5 ml of DCM at −78° C. were added dropwise 143 mg (0.84 mmol) of DAST, and the mixture was stirred at −78° C. for 3 hours. Then the mixture was warmed to 20° C. and saturated aqueous sodium chloride solution was added. The product was extracted with ethyl acetate. The solvent was removed under reduced pressure and the residue was purified directly via preparative HPLC (eluent: acetonitrile/water gradient with 0.1% formic acid). This gave 6 mg (4% of theory) of the title compound.

LC-MS (Method 1): $R_t$=1.31 min; m/z=537.4 [M+H]$^+$.

$^1$H-NMR (400 MHz, DMSO-d$_6$): δ=1.67 (br. s, 6H), 2.07 (br.s, 9H), 2.73-2.83 (m), 3.7-3.9 (m), 3.94-4.04 (m), 4.48-4.59 (m, 1H), 5.30-5.36 (m), 5.43-5.48 (m), 7.11 (d, 1H), 7.31-7.42 (m, 1H), 7.57-7.73 (m, 1H), 7.83-7.91 (m, 1H), 8.44-8.49 (m, 1H), 8.69-8.74 (m, 2H), 9.70 (br. s, 1H).

Example 188

7-[(3R)-3-(Difluoromethoxy)pyrrolidin-1-yl]-1-(2,4-difluorophenyl)-N-[2-(2,6-difluorophenyl)propan-2-yl]-4-oxo-1,4-dihydro-1,8-naphthyridine-3-carboxamide

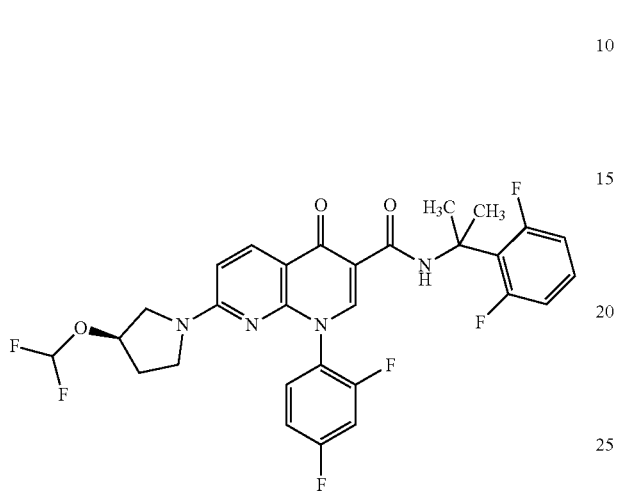

400 mg (0.74 mmol) of the compound from Example 21 and 71 mg (0.37 mmol) of copper(I) iodide were initially charged in 11 ml of acetonitrile under an argon atmosphere. Added dropwise to this mixture at 55° C. were a solution of 264 mg (1.48 mmol) of 2,2-difluoro-2-(fluorosulphonyl)acetic acid in 6 ml of acetonitrile, and the mixture was then stirred at 55° C. for 20 minutes. Then a further 528 mg (3 mmol) of 2,2-difluoro-2-(fluorosulphonyl)acetic acid in 29 ml of acetonitrile were added dropwise, and the mixture was then stirred at 55° C. for 6 hours. The solvent was removed under reduced pressure and the residue was purified by preparative HPLC (in three portions; eluent: acetonitrile/water gradient with 0.1% formic acid).

This gave 121 mg (28% of theory) of the title compound.

LC-MS (Method 1): $R_t$=1.24 min; m/z=591.4 [M+H]$^+$.

$^1$H-NMR (400 MHz, DMSO-d$_6$) δ [ppm]: 0.006 (0.90), 1.156 (1.80), 1.174 (3.60), 1.192 (1.83), 1.826 (16.00), 1.987 (6.86), 2.147 (0.58), 2.365 (0.31), 2.709 (0.28), 3.493 (0.35), 3.590 (0.46), 4.002 (0.54), 4.020 (1.61), 4.037 (1.60), 4.055 (0.52), 4.844 (0.36), 4.933 (0.27), 6.549 (0.46), 6.739 (0.96), 6.771 (1.40), 6.793 (1.37), 6.936 (2.38), 6.958 (3.19), 6.983 (2.59), 6.995 (0.39), 7.227 (0.45), 7.242 (1.03), 7.248 (1.00), 7.263 (2.26), 7.278 (2.13), 7.283 (2.14), 7.299 (1.07), 7.508 (0.75), 7.514 (0.77), 7.536 (1.28), 7.556 (0.76), 7.563 (0.71), 7.739 (0.59), 7.760 (1.20), 7.776 (1.19), 7.797 (0.54), 8.132 (0.39), 8.314 (2.17), 8.336 (2.09), 8.420 (6.84), 10.672 (4.67).

Example 189

1-(2,4-Difluorophenyl)-7-[(3S)-3-fluoropyrrolidin-1-yl]-4-oxo-N-[(2R)-1,1,1-trifluorobutan-2-yl]-1,4-dihydro-1,8-naphthyridine-3-carboxamide

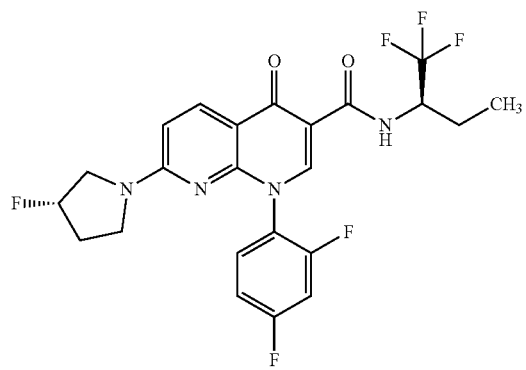 [SMILES: CC[C@@H](NC(=O)c1cn(-c2ccc(F)cc2F)c2nc(N3CC[C@H](F)C3)ccc2c1=O)C(F)(F)F]

According to GP3, 100 mg (224 μmol) of the compound from Example 67A were reacted with 34 mg (0.27 mmol) of (S)-3-fluoropyrrolidine hydrochloride and 0.14 ml (0.79 mmol) of N,N-diisopropylethylamine in 1 ml of dimethylformamide. The crude product was diluted with 0.5 ml of acetonitrile and purified by means of preparative HPLC (column: Chromatorex C18, 10 μm, 125×30 mm, solvent: acetonitrile/0.05% formic acid gradient; (0 to 3 min. 10% acetonitrile to 35 min. 90% acetonitrile and a further 3 min. 90% acetonitrile), and 97.5 mg (86% of theory, 99% purity) of the title compound were obtained.

$^1$H-NMR (400 MHz, DMSO-d$_6$): δ [ppm]=10.49 (d, 1H), 8.63 (s, 1H), 8.33 (d, 1H), 7.86-7.78 (m, 1H), 7.63-7.53 (m, 1H), 7.36-7.29 (m, 1H), 6.85-6.77 (m, 1H), 5.55-5.23 (m, 1H), 4.80-4.67 (m, 1H), 3.85-3.05 (m, 4H), 2.33-1.97 (m, 2H), 1.93-1.82 (m, 1H), 1.70-1.57 (m, 1H), 0.97 (t, 3H).

LC-MS (Method 1): $R_t$=1.22 min; 499 [M+H]$^+$.

Example 190

1-(2,4-Difluorophenyl)-7-[(1R,5S)-6-(methoxymethyl)-3-azabicyclo[3.1.0]hex-3-yl]-4-oxo-N-[(2R)-1,1,1-trifluorobutan-2-yl]-1,4-dihydro-1,8-naphthyridine-3-carboxamide

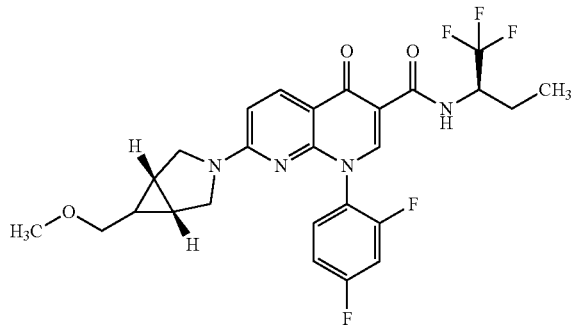 [SMILES: CC[C@@H](NC(=O)c1cn(-c2ccc(F)cc2F)c2nc(N3C[C@@H]4C(COC)[C@@H]4C3)ccc2c1=O)C(F)(F)F]

According to GP3, 100 mg (224 μmol) of the compound from Example 67A were reacted with 44 mg (0.27 mmol) of (1R,5S)-6-(methoxymethyl)-3-azabicyclo[3.1.]hexane

Example 191

1-(2,4-Difluorophenyl)-7-[3-methoxy-3-methylpyr-rolidin-1-yl]-4-oxo-N-[(2R)-1,1,1-trifluorobutan-2-yl]-1,4-dihydro-1,8-naphthyridine-3-carboxamide (diastereomer mixture)

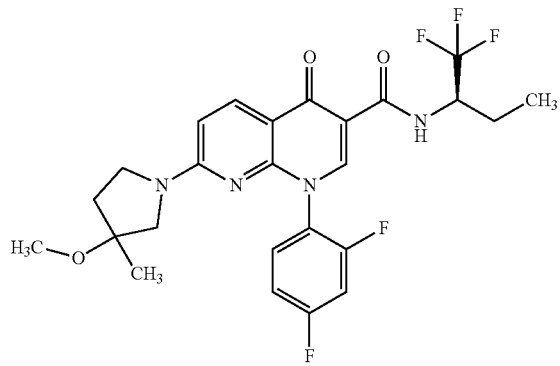 [SMILES: CC[C@@H](NC(=O)c1cn(-c2ccc(F)cc2F)c2nc(N3CCC(C)(OC)C3)ccc2c1=O)C(F)(F)F]

According to GP3, 100 mg (224 µmol) of the compound from Example 67A were reacted with 43 mg (0.27 mmol) of rac-3-methoxy-3-methylpyrrolidine hydrochloride and 0.14 ml (0.79 mmol) of N,N-diisopropylethylamine in 2.2 ml of dimethylformamide. The crude product was diluted with acetonitrile and purified by means of preparative HPLC (column: Chromatorex C18, 10 µm, 125×30 mm, solvent: acetonitrile/0.05% formic acid gradient; (0 to 3 min. 10% acetonitrile to 35 min. 90% acetonitrile and a further 3 min. 90% acetonitrile), and 107 mg (89% of theory, 99% purity) of the title compound were obtained.

$^1$H-NMR (400 MHz, DMSO-d6): δ [ppm]=10.49 (d, 1H), 8.62 (s, 1H), 8.28 (d, 1H), 7.84-7.76 (i, 1H), 7.64-7.53 (i, 1H), 7.36-7.28 (i, 1H), 6.73 (d, 1H), 4.79-4.66 (i, 1H), 3.73-3.11 (i, 6H), 3.20 (s, 3H), 1.94-1.82 (i, 1H), 1.71-1.50 (i, 3H), 0.96 (t, 3H), 0.85-0.74 (i, 1H).

LC-MS (Method 3): R$_t$ =2.29 min; 537 [M+H]$^+$.

Example 191

1-(2,4-Difluorophenyl)-7-[3-methoxy-3-methylpyrrolidin-1-yl]-4-oxo-N-[(2R)-1,1,1-trifluorobutan-2-yl]-1,4-dihydro-1,8-naphthyridine-3-carboxamide (diastereomer mixture)

According to GP3, 100 mg (224 µmol) of the compound from Example 67A were reacted with 43 mg (0.27 mmol) of rac-3-methoxy-3-methylpyrrolidine hydrochloride and 0.14 ml (0.79 mmol) of N,N-diisopropylethylamine in 2.2 ml of dimethylformamide. The crude product was diluted with acetonitrile and purified by means of preparative HPLC (column: Chromatorex C18, 10 µm, 125×30 mm, solvent: acetonitrile/0.05% formic acid gradient; (0 to 3 min. 10% acetonitrile to 35 min. 90% acetonitrile and a further 3 min. 90% acetonitrile), and 105 mg (89% of theory, 99% purity) of the title compound were obtained.

$^1$H-NMR (400 MHz, DMSO-d$_6$): δ [ppm]=10.51 (d, 1H), 8.61 (s, 1H), 8.31-8.24 (m, 1H), 7.86-7.76 (m, 1H), 7.64-7.52 (m, 1H), 7.37-7.28 (m, 1H), 6.74 (d, 1H), 4.80-4.67 (m, 1H), 3.63-2.83 (m, 7H), 2.24-2.01 (m, 1H), 1.94-1.57 (m, 3H), 1.35-1.20 (2×s, 3H), 0.97 (t, 3H).

LC-MS (Method 3): R$_t$=2.30 min; 525 [M+H]$^+$.

Example 192

1-(2,4-Difluorophenyl)-4-oxo-7-(pyrrolidin-1-yl)-N-[(2R)-1,1,1-trifluorobutan-2-yl]-1,4-dihydro-1,8-naphthyridine-3-carboxamide

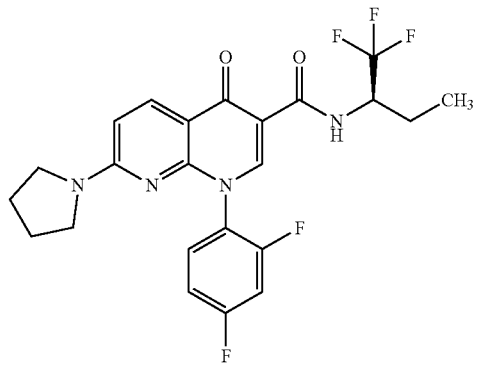 [SMILES: CC[C@@H](NC(=O)c1cn(-c2ccc(F)cc2F)c2nc(N3CCCC3)ccc2c1=O)C(F)(F)F]

According to GP1, 100 mg (269 µmol) of the compound from Example 57A were reacted with 66.1 mg (40.4 µmol) of (2R)-1,1,1-trifluorobutan-2-amine hydrochloride in the presence of 102 mg (269 µmol) of HATU and 153 µl (876 µmol) of N,N-diisopropylethylamine in 2.7 ml of dimethylformamide. After purification by means of preparative HPLC (column: Chromatorex C18, 10 µm, 125×30 mm, solvent: acetonitrile/0.05% formic acid gradient; (0 to 3 min. 10% acetonitrile to 35 min. 90% acetonitrile and a further 3 min. 90% acetonitrile), 24 mg (19% of theory, 100% purity) of the title compound were obtained.

$^1$H-NMR (400 MHz, DMSO-d$_6$): δ [ppm]=10.53 (d, 1H), 8.60 (s, 1H), 8.28 (d, 1H), 7.85-7.75 (m, 1H), 7.61-7.52 (m, 1H), 7.35-7.27 (m, 1H), 6.75 (d, 1H), 4.80-4.68 (m, 1H), 3.51-3.34 (br. s, 2H), 3.21-3.02 (br. s, 2H), 1.99-1.74 (m, 5H), 1.70-1.56 (m, 1H), 0.97 (t, 3H).

LC-MS (Method 1): R$_t$=1.31 min; 481 [M+H]$^+$.

Example 193

1-(2,4-Difluorophenyl)-7-[(4S)-4-methoxy-2-oxopyrrolidin-1-yl]-4-oxo-N-[(2R)-1,1,1-trifluorobutan-2-yl]-1,4-dihydro-1,8-naphthyridine-3-carboxamide

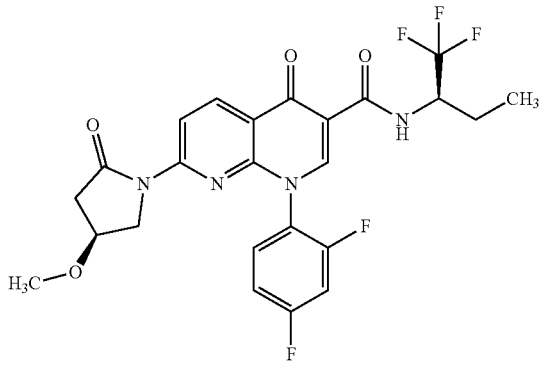 [SMILES: CC[C@@H](NC(=O)c1cn(-c2ccc(F)cc2F)c2nc(N3C[C@@H](OC)CC3=O)ccc2c1=O)C(F)(F)F]

To a solution of 50 mg (98 µmol) of the compound from Example 175 in 1 ml of DCM were added 24 µl (0.39 mmol, 4 eq.) of methyl iodide and 270 mg (2.11 mmol, 21.5 eq.) of silver(I) oxide, and the resulting suspension was stirred at room temperature for 1 d and under reflux for 3 d. Subsequently, the mixture was cooled to RT and the crude product was purified by means of preparative HPLC (column: Chromatorex C18, 10 μm, 125×30 mm, solvent: acetonitrile/0.05% formic acid gradient; (0 to 3 min. 10% acetonitrile to 35 min. 90% acetonitrile and a further 3 min. 90% acetonitrile)), and 28.4 mg (55% of theory, 99% purity) of the title compound were obtained.

$^1$H-NMR (400 MHz, DMSO-$d_6$): δ [ppm]=10.21 (d, 1H), 8.87 (d, 1H), 8.72 (d, 1H), 8.49 (d, 1H), 7.92-7.84 (m, 1H), 7.71-7.59 (m, 1H), 7.42-7.33 (m, 1H), 4.83-4.71 (m, 1H), 4.06-4.00 (m, 1H), 3.74-3.54 (m, 2H), 3.22/3.17 (2×s, 3H), 3.01-2.90 (m, 1H), 2.64-2.56 (m, 1H), 1.96-1.83 (m, 1H), 1.73-1.60 (m, 1H), 0.98 (t, 3H).

LC-MS (Method 1): $R_t$=1.11 min; 525 [M+H]$^+$.

Example 194

1-(2,4-Difluorophenyl)-7-[3-hydroxy-3-methyl-2-oxopyrrolidin-1-yl]-4-oxo-N-[(2R)-1,1,1-trifluorobutan-2-yl]-1,4-dihydro-1,8-naphthyridine-3-carboxamide (diastereomer mixture)

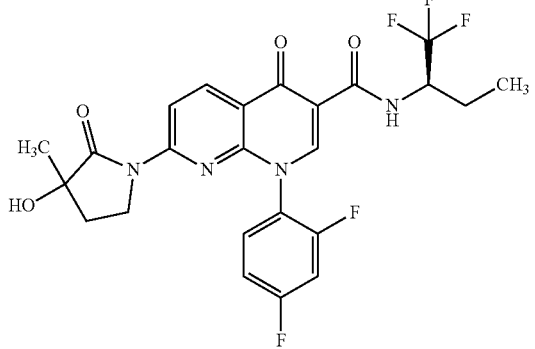

According to GP2, 163 mg (366 μmol) of the compound from Example 67A were reacted with 42.1 mg (366 μmol) of the compound from Example 2A in the presence of 179 mg (548 μmol) of caesium carbonate, 15 mg (66 μmol) of palladium(II) acetate and 38 mg (66 μmol) of Xantphos in 8.2 ml of dioxane. After purification by means of flash chromatography (twice, ethyl acetate/cyclohexane gradient), 153.6 mg (75% of theory, 94% purity) of the title compound were obtained.

$^1$H-NMR (400 MHz, DMSO-$d_6$): δ [ppm]=10.21 (d, 1H), 8.87 (s, 1H), 8.74 (d, 1H), 8.54 (d, 1H), 7.92-7.84 (m, 1H), 7.66-7.58 (m, 1H), 7.40-7.30 (m, 1H), 5.72 (d, 1H), 4.84-4.70 (m, 1H), 3.60-3.49 (m, 1H), 3.45-3.34 (m, 1H), 2.06-1.85 (m, 3H), 1.72-1.62 (m, 1H), 1.29/1.27 (2×s, 3H), 0.98 (t, 3H).

LC-MS (Method 3): $R_t$=1.95 min; 525 [M+H]$^+$.

130 mg of the title compound (diastereomer mixture) were separated into the diastereomers by chiral HPLC (preparative HPLC: column: Daicel® Chiralpak AD-H, 5 μm, 250×20 mm; eluent: 85% $CO_2$/15% isopropanol; flow rate 80 ml/min; 40° C., detection: 210 nm).

This gave (in the sequence of elution from the column) 37.2 mg of diastereomer 1 (99% de) $R_t$=6.04 min and 32.7 mg (99% de) of diastereomer 2 $R_t$=7.33 min.

[Analytical HPLC: column: SFC Daicel® Chiralpak AD, 3 ml/min; 90% $CO_2$/10% isopropanol]

Diastereomer 1 was additionally purified by means of preparative HPLC (column: Chromatorex C18, 10 μm, 125×30 mm, solvent: acetonitrile/0.05% formic acid gradient; (0 to 3 min. 10% acetonitrile to 35 min. 90% acetonitrile and a further 3 min. 90% acetonitrile)), and 24.6 mg (13% of theory, 99% purity) of the title compound from Example 196 were obtained.

Diastereomer 2 was additionally purified by means of preparative HPLC (column: Chromatorex C18, 10 μm, 125×30 mm, solvent: acetonitrile/0.05% formic acid gradient; (0 to 3 min. 10% acetonitrile to 35 min. 90% acetonitrile and a further 3 min. 90% acetonitrile)), and 20.6 mg (11% of theory, 99% purity) of the title compound from Example 197 were obtained.

Example 195

1-(2,4-Difluorophenyl)-7-[3-hydroxy-3-methyl-2-oxopyrrolidin-1-yl]-4-oxo-N-[(2R)-1,1,1-trifluorobutan-2-yl]-1,4-dihydro-1,8-naphthyridine-3-carboxamide (diastereomer 1)

$^1$H-NMR (400 MHz, DMSO-$d_6$): δ [ppm]=10.21 (d, 1H), 8.86 (s, 1H), 8.74 (d, 1H), 8.54 (d, 1H), 7.92-7.84 (m, 1H), 7.67-7.58 (m, 1H), 7.40-7.32 (m, 1H), 5.72 (d, 1H), 4.83-4.71 (m, 1H), 3.60-3.49 (m, 1H), 3.45-3.34 (m, 1H), 2.07-1.84 (m, 3H), 1.74-1.60 (m, 1H), 1.29/1.27 (2×s, 3H), 0.98 (t, 3H).

LC-MS (Method 1): $R_t$=1.04 min; 525 [M+H]$^+$.

Example 196

1-(2,4-Difluorophenyl)-7-[3-hydroxy-3-methyl-2-oxopyrrolidin-1-yl]-4-oxo-N-[(2R)-1,1,1-trifluorobutan-2-yl]-1,4-dihydro-1,8-naphthyridine-3-carboxamide (diastereomer 2)

$^1$H-NMR (400 MHz, DMSO-$d_6$): δ [ppm]=10.21 (d, 1H), 8.86 (s, 1H), 8.74 (d, 1H), 8.54 (d, 1H), 7.92-7.84 (m, 1H), 7.66-7.59 (m, 1H), 7.39-7.33 (m, 1H), 5.72 (d, 1H), 4.82-4.72 (m, 1H), 3.60-3.49 (m, 1H), 3.45-3.34 (m, 1H), 2.05-1.85 (m, 3H), 1.71-1.59 (m, 1H), 1.29/1.27 (2×s, 3H), 0.98 (t, 3H).

LC-MS (Method 1): $R_t$=1.04 min; 525 [M+H]$^+$.

Example 197

1-(2,4-Difluorophenyl)-7-[3-methoxy-3-methyl-2-oxopyrrolidin-1-yl]-4-oxo-N-[(2R)-1,1,1-trifluorobutan-2-yl]-1,4-dihydro-1,8-naphthyridine-3-carboxamide (diastereomer mixture)

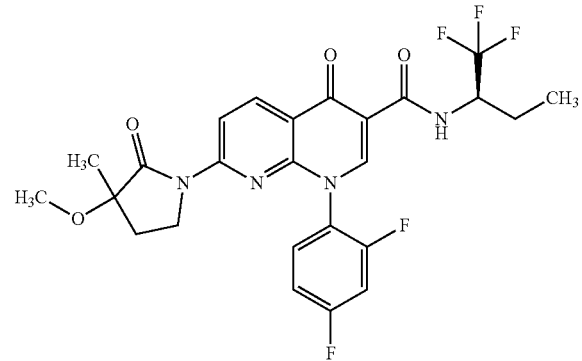 [SMILES: CC[C@@H](NC(=O)c1cn(-c2ccc(F)cc2F)c2nc(N3CCC(C)(OC)C3=O)ccc2c1=O)C(F)(F)F]

To a solution of 30 mg (57 µmol) of the diastereomer mixture from Example 194 in 1 ml of DCM were added 28 µl (0.46 mmol, 8 eq.) of methyl iodide and 170 mg (1.37 mmol, 24 eq.) of silver(I) oxide, and the resulting suspension was stirred under reflux for 3 d. Subsequently, the mixture was cooled to RT and filtered, and 30.0 mg (96% of theory, 99% purity) of the title compound were obtained.

¹H-NMR (400 MHz, DMSO-d₆): δ [ppm]=10.20 (d, 1H), 8.87 (s, 1H), 8.75 (d, 1H), 8.54 (d, 1H), 7.91-7.83 (m, 1H), 7.66-7.58 (m, 1H), 7.41-7.33 (m, 1H), 4.83-4.73 (m, 1H), 3.53-3.39 (m, 2H), 3.21/3.18 (2×s, 3H), 2.29-2.17 (m, 1H), 2.01-2.84 (m, 2H), 1.73-1.61 (m, 1H), 1.33/1.31 (2×s, 3H), 0.98 (t, 3H).

LC-MS (Method 3): $R_t$=2.24 min; 539 [M+H]⁺.

30 mg of the title compound (diastereomer mixture) were separated into the diastereomers by chiral HPLC (preparative HPLC: Chiralpak-IF 5 µm 250×20 mm; eluent: 100% methanol, 0.2% diethylamine; temperature: 30° C.; flow rate: 15 ml/min; UV detection: 220 nm).

This gave (in the sequence of elution from the column) 11 mg of diastereomer 1 (99% de) $R_t$=7.26 min and 6 mg (97.4% de) of diastereomer 2 $R_t$=8.36 min.

[Analytical HPLC: column: Chiralpak IF 5 µm 250×4.6 mm; eluent: 100% methanol, 0.2% diethylamine; temperature: 40° C.; flow rate: 1 ml/min; UV detection: 235 nm]

Diastereomer 1 was additionally purified (column: Chromatorex C18, 10 µm, 125×30 mm, solvent: acetonitrile/0.05% formic acid gradient; (0 to 3 min. 10% acetonitrile to 35 min. 90% acetonitrile and a further 3 min. 90% acetonitrile)), and 6.4 mg (21% of theory, 99% purity) of the title compound from Example 198 were obtained.

Diastereomer 2 was additionally purified by means of preparative HPLC (column: Chromatorex C18, 10 µm, 125×30 mm, solvent: acetonitrile/0.05% formic acid gradient; (0 to 3 min. 10% acetonitrile to 35 min. 90% acetonitrile and a further 3 min. 90% acetonitrile)), and 3.6 mg (12% of theory, 99% purity) of the title compound from Example 199 were obtained.

Example 198

1-(2,4-Difluorophenyl)-7-[3-methoxy-3-methyl-2-oxopyrrolidin-1-yl]-4-oxo-N-[(2R)-1,1,1-trifluorobutan-2-yl]-1,4-dihydro-1,8-naphthyridine-3-carboxamide (diastereomer 1)

¹H-NMR (400 MHz, DMSO-d₆): δ [ppm]=10.19 (d, 1H), 8.87 (s, 1H), 8.75 (d, 1H), 8.54 (d, 1H), 7.91-7.83 (m, 1H), 7.66-7.58 (m, 1H), 7.39-7.33 (m, 1H), 4.84-4.70 (m, 1H), 3.60-3.38 (m, 2H), 3.20/3.18 (2×s, 3H), 2.28-2.17 (m, 1H), 2.02-1.84 (m, 2H), 1.74-1.60 (m, 1H), 1.33/1.31 (2×s, 3H), 0.98 (t, 3H).

LC-MS (Method 3): $R_t$=2.26 min; 539 [M+H]⁺.

Example 199

1-(2,4-Difluorophenyl)-7-[3-methoxy-3-methyl-2-oxopyrrolidin-1-yl]-4-oxo-N-[(2R)-1,1,1-trifluorobutan-2-yl]-1,4-dihydro-1,8-naphthyridine-3-carboxamide (diastereomer 2)

¹H-NMR (400 MHz, DMSO-d₆): δ [ppm]=10.19 (d, 1H), 8.87 (s, 1H), 8.75 (d, 1H), 8.54 (d, 1H), 7.91-7.83 (m, 1H), 7.65-7.59 (m, 1H), 7.39-7.33 (m, 1H), 4.83-4.72 (m, 1H), 3.60-3.37 (m, 2H), 3.21/3.18 (2×s, 3H), 2.28-2.17 (m, 1H), 2.01-1.84 (m, 2H), 1.72-1.60 (m, 1H), 1.33/1.31 (2×s, 3H), 0.98 (t, 3H).

LC-MS (Method 3): $R_t$=2.24 min; 539 [M+H]⁺.

Example 200

(3S)-1-[8-(2,4-Difluorophenyl)-5-oxo-6-{[(2R)-1,1,1-trifluorobutan-2-yl]carbamoyl}-5,8-dihydro-1,8-naphthyridin-2-yl]-5-oxopyrrolidin-3-yl methyl carbamate

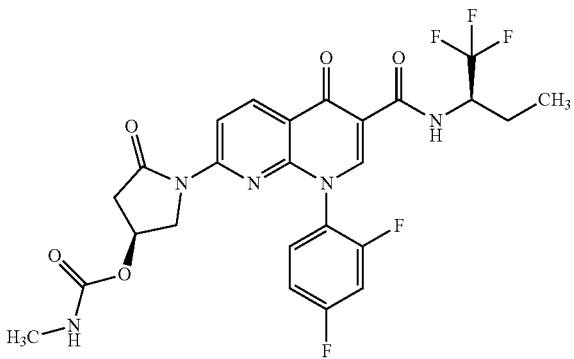 [SMILES: CC[C@@H](NC(=O)c1cn(-c2ccc(F)cc2F)c2nc(N3C[C@@H](OC(=O)NC)CC3=O)ccc2c1=O)C(F)(F)F]

To a solution of 100 mg (196 µmol) of the compound from Example 175 in 4 ml of DCM were added 18.3 mg (196 µmol) of methylcarbamoyl chloride, 4.8 mg (39 µmol) of 4-dimethylaminopyridine and 30 µl (0.22 mmol) of triethylamine, and the mixture was stirred at RT overnight. The solvent was then removed under reduced pressure and the residue was purified by means of preparative HPLC (column: Kromasil C18, 10 µm, 125×30 mm, solvent: acetonitrile/0.05% formic acid gradient (0 to 3 min 10% acetonitrile, to 35 min 90% acetonitrile and for a further 3 min 90% acetonitrile)). 31.9 mg (28% of theory, 99% purity) of the title compound were obtained.

¹H-NMR (400 MHz, DMSO-d₆): δ [ppm]=10.20 (d, 1H), 8.88-8.85 (m, 1H), 8.73 (d, 1H), 8.51-8.45 (m, 1H), 7.91-7.81 (m, 1H), 7.66-7.55 (m, 1H), 7.41-7.32 (m, 1H), 7.22-7.08 (m, 1H), 5.15-5.09 (m, 1H), 4.84-4.71 (m, 1H), 3.89-3.77 (m, 1H), 3.68-3.54 (m, 1H), 3.20-3.09 (m, 1H), 1.96-1.84 (m, 1H), 1.73-1.60 (m, 1H), 0.98 (t, 3H).

LC-MS (Method 4): $R_t$=3.27 min; 568 [M+H]⁺.

Example 201

N-(2,6-Dichlorophenyl)-1-(2,4-difluorophenyl)-7-[(4S)-4-hydroxy-2-oxopyrrolidin-1-yl]-4-oxo-1,4-dihydro-1,8-naphthyridine-3-carboxamide

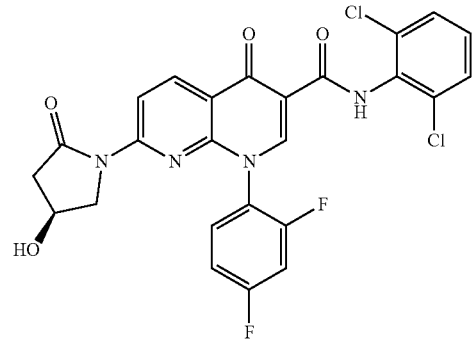 [SMILES: O=C(Nc1c(Cl)cccc1Cl)c1cn(-c2ccc(F)cc2F)c2nc(N3C[C@@H](O)CC3=O)ccc2c1=O]

According to GP2, 100 mg (153 µmol, 73.6% purity) of the compound from Example 81A were reacted with 15.5 mg (153 µmol) of (4S)-4-hydroxypyrrolidin-2-one in the presence of 74.8 mg (230 µmol) of caesium carbonate, 6.2 mg (28 µmol) of palladium(II) acetate and 16 mg (28 µmol) of Xantphos in 2 ml of dioxane. The residue was purified by means of flash chromatography (cyclohexane/ethyl acetate gradient) and finally by preparative thin-layer chromatography (dichloromethane/methanol=95/5, 20×20 cm plates, 1 mm of silica). The product fraction was visualized by UV detection and scratched off, and eluted from the silica gel with ethyl acetate. The mixture was filtered through Celite and the solvent was removed under reduced pressure. The residue was lyophilized from water/acetonitrile, and 27.3 mg (33% of theory; 100% purity) of the title compound were obtained.

$^1$H-NMR (400 MHz, DMSO-d6): δ [ppm]=11.7 (s, 1H), 8.92 (s, 1H), 8.77 (d, 1H), 8.57-8.52 (m, 1H), 7.96-7.86 (m, 1H), 7.67-7.57 (m, 3H), 7.42-7.33 (m, 2H), 5.33 (dd, 1H), 4.32-4.25 (m, 1H), 3.74-3.63 (m, 1H), 3.54-3.43 (m, 1H), 3.01-2.89 (m, 1H), 2.43-2.31 (m, 1H).

LC-MS (Method 1): $R_t$=1.03 min; 545 [M+H]$^+$.

Example 202

N-(2,6-Dichlorophenyl)-1-(2,4-difluorophenyl)-7-[(3S)-3-hydroxy-2-oxopyrrolidin-1-yl]-4-oxo-1,4-dihydro-1,8-naphthyridine-3-carboxamide

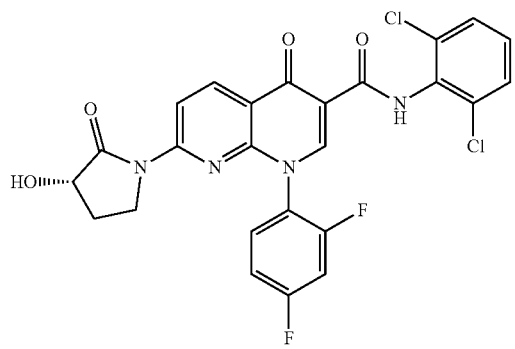 [SMILES: O=C(Nc1c(Cl)cccc1Cl)c1cn(-c2ccc(F)cc2F)c2nc(N3CC[C@H](O)C3=O)ccc2c1=O]

According to GP2, 150 mg (275 µmol, 88% purity) of the compound from Example 81A were reacted with 27.8 mg (275 µmol) of (3S)-3-hydroxypyrrolidin-2-one in the presence of 56.9 mg (412 µmol) of potassium carbonate, 6.2 mg (27 µmol) of palladium(II) acetate and 32 mg (55 µmol) of Xantphos in 2.8 ml of dioxane. The crude product was purified twice by means of preparative HPLC (column: Chromatorex C18, 10 µm, 125×30 mm, solvent: acetonitrile/0.05% formic acid gradient (0 to 3 min 10% acetonitrile, to 35 min 90% acetonitrile and for a further 3 min 90% acetonitrile). 49.2 mg (33% of theory, 100% purity) of the title compound were obtained.

$^1$H-NMR (400 MHz, DMSO-d$_6$): δ [ppm]=11.69 (s, 1H), 8.93 (s, 1H), 8.79 (d, 1H), 8.58-8.52 (m, 1H), 7.94-7.85 (m, 1H), 7.66-7.57 (m, 3H), 7.42-7.32 (m, 2H), 5.91 (d, 1H), 4.46-4.34 (m, 1H), 3.64-3.51 (m, 1H), 3.39-3.27 (m, 1H), 2.38-2.27 (m, 1H), 1.86-1.69 (m, 1H).

LC-MS (Method 3): $R_t$=1.83 min; 545 [M+H]$^+$.

Example 203

7-(Dimethylamino)-1-(2-fluorophenyl)-4-oxo-N-[(2S)-1,1,1-trifluorobutan-2-yl]-1,4-dihydro-1,8-naphthyridine-3-carboxamide

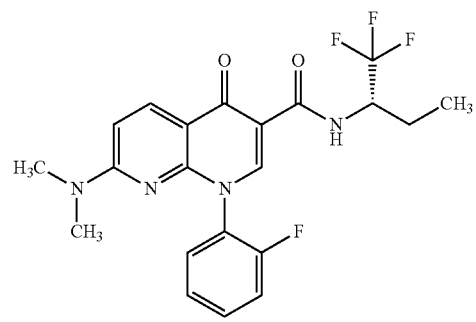 [SMILES: CC[C@H](NC(=O)c1cn(-c2ccccc2F)c2nc(N(C)C)ccc2c1=O)C(F)(F)F]

According to GP1, 100 mg (306 µmol) of the compound from Example 62A were reacted with 58.3 mg (458 µmol) of (S)-2-trifluoromethylpropylamine in the presence of 116 mg (306 µmol) of HATU and 160 µl (917 µmol) of N,N-diisopropylethylamine in 3.2 ml of dimethylformamide. The reaction was ended by adding aqueous 1 M hydrochloric acid and 10 ml of water, and the precipitate was filtered off with suction. The precipitated solid was washed with water and dried under high vacuum overnight. The residue was taken up in 2 ml of dichloromethane and purified by means of flash chromatography (cyclohexane/ethyl acetate gradient), and 87.4 mg (65% of theory; 99% purity) of the title compound were obtained.

$^1$H-NMR (400 MHz, DMSO-d$_6$): δ [ppm]=10.51 (d, 1H), 8.59 (s, 1H), 8.29 (d, 1H), 7.77-7.69 (m, 1H), 7.66-7.59 (m, 1H), 7.52-7.46 (m, 1H), 7.45-7.39 (m, 1H), 6.94 (d, 1H), 4.80-4.66 (m, 1H), 2.93 (br. s, 6H), 1.94-1.82 (m, 1H), 1.71-1.56 (m, 1H), 0.97 (t, 3H).

LC-MS (Method 3): $R_t$=2.18 min; 437 [M+H]$^+$.

Example 204 rac-7-(Dimethylamino)-1-(2-fluorophenyl)-4-oxo-N-[1,1,1-trifluorobutan-2-yl]-1,4-dihydro-1,8-naphthyridine-3-carboxamide

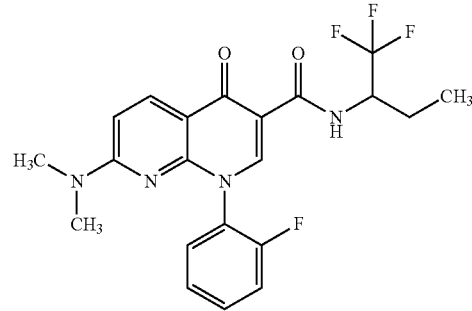 [SMILES: CCC(NC(=O)c1cn(-c2ccccc2F)c2nc(N(C)C)ccc2c1=O)C(F)(F)F]

According to GP1, 100 mg of the compound from Example 62A were reacted with 75.0 mg (458 µmol) of rac-2-trifluoromethylpropylamine hydrochloride in the presence of 116 mg (306 µmol) of HATU and 160 µl (917 µmol)

of N,N-diisopropylethylamine in 3.2 ml of dimethylformamide. The reaction was ended by adding aqueous 1 M hydrochloric acid and 10 ml of water, and the precipitate was filtered off with suction. The precipitated solid was washed with water and dried under high vacuum overnight. The residue was taken up in 2 ml of dichloromethane and purified by means of flash chromatography (cyclohexane/ethyl acetate gradient), and 98.6 mg (73% of theory; 99% purity) of the title compound were obtained.

$^1$H-NMR (400 MHz, DMSO-d$_6$): δ [ppm]=10.51 (d, 1H), 8.59 (s, 1H), 8.29 (d, 1H), 7.76-7.69 (m, 1H), 7.66-7.59 (m, 1H), 7.52-7.46 (m, 1H), 7.45-7.39 (m, 1H), 6.94 (d, 1H), 4.80-4.68 (m, 1H), 2.93 (br. s, 6H), 1.93-1.84 (m, 1H), 1.69-1.58 (m, 1H), 0.97 (t, 3H).

LC-MS (Method 3): R$_t$=2.14 min; 437 [M+H]$^+$.

Example 205

1-(2,4-Difluorophenyl)-4-oxo-7-(2-oxoazetidin-1-yl)-N-[(2R)-1,1,1-trifluorobutan-2-yl]-1,4-dihydro-1,8-naphthyridine-3-carboxamide

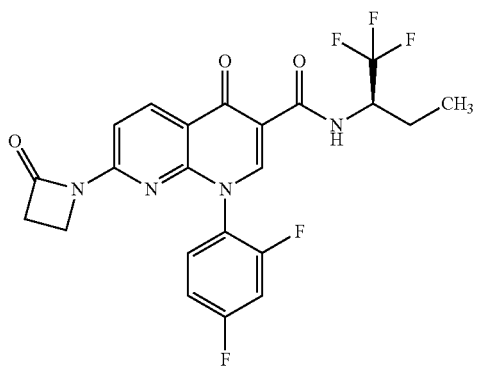 [SMILES: CC[C@@H](NC(=O)c1cn(-c2ccc(F)cc2F)c2nc(N3CCC3=O)ccc2c1=O)C(F)(F)F]

According to GP2, 100 mg (224 μmol) of the compound from Example 67A were reacted with 15.9 mg (224 μmol) of azetidinone in the presence of 11.6 mg (0.011 mmol) of tris(dibenzylidenacetone)dipalladium-chloroform complex and 19 mg (34 μmol) of Xantphos in 5 ml of toluene at 90° C. The crude product was purified by flash chromatography (cyclohexane/ethyl acetate gradient) and preparative HPLC (column: Chromatorex C18, 10 μm, 125×30 mm, solvent: acetonitrile/0.05% formic acid gradient (0 to 3 min 10% acetonitrile, to 35 min 90% acetonitrile and for a further 3 min 90% acetonitrile). 18.5 mg (17% of theory, 99% purity) of the title compound were obtained.

$^1$H-NMR (400 MHz, DMSO-d6): δ [ppm]=10.20 (d, 1H), 8.83 (s, 1H), 8.69 (d, 1H), 7.90-7.82 (m, 1H), 7.74 (d, 1H), 7.64-7.57 (m, 1H), 7.39-7.31 (m, 1H), 4.83-4.71 (m, 1H), 3.45-3.35 (m, 2H), 3.14-3.07 (m, 2H), 1.95-1.83 (m, 1H), 1.73-1.59 (m, 1H), 0.97 (t, 3H).

LC-MS (Method 3): R$_t$=2.15 min; 481 [M+H]$^+$.

Example 206 rac-N-[(1R)-1-(2-Chlorophenyl)-2,2,2-trifluoroethyl]-1-(2,4-difluorophenyl)-7-[3-hydroxy-2-oxopiperidin-1-yl]-4-oxo-1,4-dihydro-1,8-naphthyridine-3-carboxamide (diastereomer mixture)

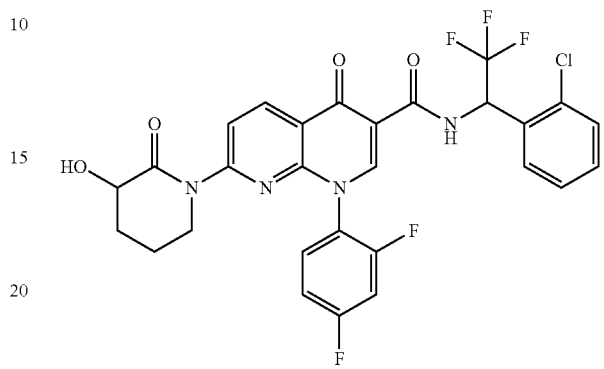

According to GP2, 150 mg (273 μmol, 96% purity) of the compound from Example 73A were reacted with 31.4 mg (273 μmol) of 3-hydroxy-2-piperidone in the presence of 56.5 mg (409 μmol) of potassium carbonate, 6.1 mg (27 μmol) of palladium(II) acetate and 32 mg (55 μmol) of Xantphos in 2.7 ml of dioxane. The residue was purified by flash chromatography (cyclohexane/ethyl acetate gradient) and preparative HPLC (column: Chromatorex C18, 10 μm, 125×30 mm, solvent: acetonitrile/0.05% formic acid gradient (0 to 3 min 10% acetonitrile, to 35 min 90% acetonitrile and for a further 3 min 90% acetonitrile). 69.8 mg (42% of theory, 100% purity) of the title compound were obtained.

$^1$H-NMR (400 MHz, DMSO-d$_6$): δ [ppm]=11.29 (d, 1H), 8.88 (s, 1H), 8.70 (d, 1H), 8.19-8.10 (m, 1H), 7.93-7.77 (m, 1H), 7.67-7.48 (m, 5H), 7.40-7.31 (m, 1H), 6.53-6.42 (m, 1H), 5.53-5.46 (m, 1H), 4.27-4.18 (m, 1H), 3.71-3.59 (m, 1H), 3.54-3.41 (m, 1H), 2.12-2.02 (m, 1H), 1.84-1.73 (m, 2H), 1.71-1.58 (m, 1H).

LC-MS (Method 3): R$_t$=2.18 min; 607 [M+H]$^+$.

58 mg of the title compound (racemic diastereomer mixture) were separated into the enantiomeric diastereomers by chiral HPLC (preparative HPLC: column: Chiralcel OZ-H 5 μm 250×20 mm; eluent: 75% ethanol, 25% isohexane; temperature: 40° C.; flow rate: 15 ml/min; UV detection: 220 nm).

This gave (in the sequence of elution from the column) 14 mg of diastereomer 1 (enantiomer A) (99% de) R$_t$=6.63 min, 12 mg (99% de) of diastereomer 2 (enantiomer A) R$_t$=7.71 min, 11 mg (99% de) of diastereomer 1 (enantiomer B) R$_t$=12.9 min, and 18 mg (99% de) of diastereomer 2 (enantiomer B) R$_t$=18.3 min.

[Analytical HPLC: column: Chiralcel OZ-H 5 μm 250× 4.6 mm; eluent: 75% ethanol, 25% isohexane; temperature: 40° C.; flow rate: 1 ml/min; UV detection: 220 nm]

Diastereomer 1 (enantiomer A) was additionally purified by means of preparative HPLC (column: Chromatorex C18, 10 μm, 125×30 mm, solvent: acetonitrile/0.05% formic acid gradient; (0 to 3 min. 10% acetonitrile to 35 min. 90% acetonitrile and a further 3 min. 90% acetonitrile)), and 10.4 mg (6.2% of theory, 99% purity) of the title compound from Example 207 were obtained.

Diastereomer 2 (enantiomer A) was additionally purified by means of preparative HPLC (column: Chromatorex C18, 10 µm, 125×30 mm, solvent: acetonitrile/0.05% formic acid gradient; (0 to 3 min. 10% acetonitrile to 35 min. 90% acetonitrile and a further 3 min. 90% acetonitrile)), and 8.4 mg (5% of theory, 99% purity) of the title compound from Example 208 were obtained.

Diastereomer 1 (enantiomer B) was additionally purified by means of preparative HPLC (column: Chromatorex C18, 10 µm, 125×30 mm, solvent: acetonitrile/0.05% formic acid gradient; (0 to 3 min. 10% acetonitrile to 35 min. 90% acetonitrile and a further 3 min. 90% acetonitrile)), and 8.7 mg (5% of theory, 99% purity) of the title compound from Example 209 were obtained.

Diastereomer 2 (enantiomer B) was additionally purified by means of preparative HPLC (column: Chromatorex C18, 10 µm, 125×30 mm, solvent: acetonitrile/0.05% formic acid gradient; (0 to 3 min. 10% acetonitrile to 35 min. 90% acetonitrile and a further 3 min. 90% acetonitrile)), and 11.4 mg (6.8% of theory, 99% purity) of the title compound from Example 210 were obtained.

Example 207

N-[(1R)-1-(2-Chlorophenyl)-2,2,2-trifluoroethyl]-1-(2,4-difluorophenyl)-7-[3-hydroxy-2-oxopiperidin-1-yl]-4-oxo-1,4-dihydro-1,8-naphthyridine-3-carboxamide (diastereomer 1, enantiomer A)

$^1$H-NMR (400 MHz, DMSO-d$_6$): δ [ppm]=11.29 (d, 1H), 8.88 (s, 1H), 8.70 (d, 1H), 8.18-8.11 (m, 1H), 7.92-7.77 (m, 1H), 7.67-7.48 (m, 5H), 7.40-7.31 (m, 1H), 6.53-6.43 (m, 1H), 5.52-5.47 (m, 1H), 4.26-4.18 (m, 1H), 3.72-3.59 (m, 1H), 3.52-3.41 (m, 1H), 2.11-2.02 (m, 1H), 1.84-1.73 (m, 2H), 1.71-1.58 (m, 1H).

LC-MS (Method 3): R$_t$=2.21 min; 607 [M+H]$^+$.

Example 208

N-[(1R)-1-(2-Chlorophenyl)-2,2,2-trifluoroethyl]-1-(2,4-difluorophenyl)-7-[3-hydroxy-2-oxopiperidin-1-yl]-4-oxo-1,4-dihydro-1,8-naphthyridine-3-carboxamide (diastereomer 2, enantiomer A)

$^1$H-NMR (400 MHz, DMSO-d$_6$): δ [ppm]=11.29 (d, 1H), 8.88 (s, 1H), 8.70 (d, 1H), 8.18-8.11 (m, 1H), 7.91-7.78 (m, 1H), 7.67-7.48 (m, 5H), 7.40-7.31 (m, 1H), 6.53-6.43 (m, 1H), 5.52-5.47 (m, 1H), 4.26-4.18 (m, 1H), 3.72-3.59 (m, 1H), 3.52-3.41 (m, 1H), 2.11-2.02 (m, 1H), 1.84-1.73 (m, 2H), 1.71-1.58 (m, 1H).

LC-MS (Method 3): R$_t$=2.21 min; 607 [M+H]$^+$.

Example 209

N-[(1R)-1-(2-Chlorophenyl)-2,2,2-trifluoroethyl]-1-(2,4-difluorophenyl)-7-[3-hydroxy-2-oxopiperidin-1-yl]-4-oxo-1,4-dihydro-1,8-naphthyridine-3-carboxamide (diastereomer 1, enantiomer B)

$^1$H-NMR (400 MHz, DMSO-d$_6$): δ [ppm]=11.29 (d, 1H), 8.88 (s, 1H), 8.70 (d, 1H), 8.18-8.11 (m, 1H), 7.91-7.78 (m, 1H), 7.67-7.48 (m, 5H), 7.40-7.31 (m, 1H), 6.53-6.43 (m, 1H), 5.52-5.47 (m, 1H), 4.26-4.18 (m, 1H), 3.72-3.59 (m, 1H), 3.52-3.41 (m, 1H), 2.11-2.02 (m, 1H), 1.84-1.73 (m, 2H), 1.71-1.58 (m, 1H).

LC-MS (Method 3): R$_t$=2.20 min; 607 [M+H]$^+$.

Example 210

N-[(1R)-1-(2-Chlorophenyl)-2,2,2-trifluoroethyl]-1-(2,4-difluorophenyl)-7-[3-hydroxy-2-oxopiperidin-1-yl]-4-oxo-1,4-dihydro-1,8-naphthyridine-3-carboxamide (diastereomer 2, enantiomer B)

$^1$H-NMR (400 MHz, DMSO-d$_6$): δ [ppm]=11.29 (d, 1H), 8.88 (s, 1H), 8.70 (d, 1H), 8.18-8.11 (m, 1H), 7.92-7.77 (m, 1H), 7.67-7.48 (m, 5H), 7.40-7.31 (m, 1H), 6.53-6.43 (m, 1H), 5.52-5.47 (m, 1H), 4.26-4.18 (m, 1H), 3.72-3.59 (m, 1H), 3.52-3.41 (m, 1H), 2.11-2.02 (m, 1H), 1.84-1.73 (m, 2H), 1.71-1.58 (m, 1H).

LC-MS (Method 3): R$_t$=2.21 min; 607 [M+H]$^+$.

Example 211

N-[1-(2-Chlorophenyl)-2,2,2-trifluoroethyl]-1-(2,4-difluorophenyl)-7-[(4S)-4-hydroxy-2-oxopyrrolidin-1-yl]-4-oxo-1,4-dihydro-1,8-naphthyridine-3-carboxamide (diastereomer mixture)

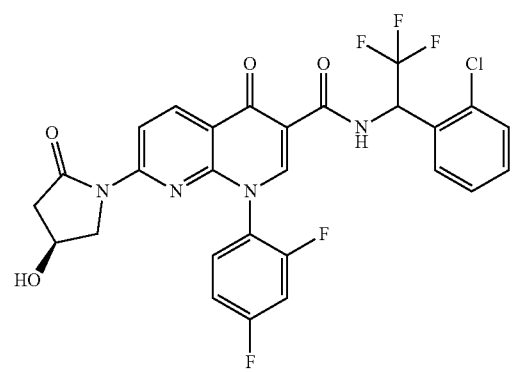 [SMILES: O=C(NC(c1ccccc1Cl)C(F)(F)F)c1cn(-c2ccc(F)cc2F)c2nc(N3C[C@@H](O)CC3=O)ccc2c1=O]

According to GP2, 750 mg (1.36 mmol, 96% purity) of the compound from Example 73A were reacted with 138 mg (1.36 mmol) of (4S)-4-hydroxypyrrolidin-2-one in the presence of 283 mg (2.04 mmol) of potassium carbonate, 30.6 mg (136 µmol) of palladium(II) acetate and 158 mg (273 µmol) of Xantphos in 14 ml of dioxane. The mixture was filtered, washed through with acetonitrile and concentrated, and the crude product was purified by means of flash chromatography (cyclohexane/ethyl acetate gradient). 555 mg (65% of theory, 95% purity) of the title compound were obtained.

$^1$H-NMR (400 MHz, DMSO-d$_6$): δ [ppm]=11.33 (d, 1H), 8.86 (s, 1H), 8.75 (d, 1H), 8.57-8.51 (m, 1H), 7.93-7.76 (m, 1H), 7.67-7.48 (m, 5H), 7.41-7.32 (m, 1H), 6.53-6.42 (m, 1H), 5.37-5.27 (m, 1H), 4.31-4.25 (m, 1H), 3.72-3.61 (m, 1H), 3.51-3.42 (m, 1H), 3.00-2.88 (m, 1H), 2.42-2.31 (m, 1H).

LC-MS (Method 3): R$_t$=2.13 min; 593 [M+H]$^+$.

550 mg of the title compound (diastereomer mixture) were separated into the diastereomers by chiral HPLC (preparative HPLC: column: Chiralpak AZ-H 5 µm 250×20 mm; eluent: 50% isopropanol, 50% isohexane; temperature: 25° C.; flow rate: 15 ml/min; UV detection: 210 nm).

This gave (in the sequence of elution from the column) 229 mg of diastereomer 1 (99% de) R$_t$=0.96 min and 235 mg (99% de) of diastereomer 2 R$_t$=1.44 min.

[Analytical HPLC: column: Chiralcel AZ-3 3 μm 50×4.6 mm; eluent: 50% isopropanol, 50% isohexane; flow rate: 1 ml/min; UV detection: 220 nm]

Diastereomer 1 was additionally purified by means of preparative HPLC (column: Chromatorex C18, 10 μm, 125×30 mm, solvent: acetonitrile/0.05% formic acid gradient; (0 to 3 min. 10% acetonitrile to 35 min. 90% acetonitrile and a further 3 min. 90% acetonitrile)), and 151.6 mg (19% of theory, 100% purity) of the title compound from Example 212 were obtained.

Diastereomer 2 was additionally purified by means of preparative HPLC (column: Chromatorex C18, 10 μm, 125×30 mm, solvent: acetonitrile/0.05% formic acid gradient; (0 to 3 min. 10% acetonitrile to 35 min. 90% acetonitrile and a further 3 min. 90% acetonitrile)), and 151.7 mg (19% of theory, 100% purity) of the title compound from Example 213 were obtained.

Example 212

N-[1-(2-Chlorophenyl)-2,2,2-trifluoroethyl]-1-(2,4-difluorophenyl)-7-[(4S)-4-hydroxy-2-oxopyrrolidin-1-yl]-4-oxo-1,4-dihydro-1,8-naphthyridine-3-carboxamide (diastereomer A)

$^1$H-NMR (400 MHz, DMSO-d$_6$): δ [ppm]=11.33 (d, 1H), 8.86 (s, 1H), 8.75 (d, 1H), 8.57-8.51 (m, 1H), 7.91-7.78 (m, 1H), 7.67-7.48 (m, 5H), 7.41-7.33 (m, 1H), 6.52-6.42 (m, 1H), 5.32 (dd, 1H), 4.31-4.25 (m, 1H), 3.72-3.61 (m, 1H), 3.51-3.41 (m, 1H), 3.00-2.88 (m, 1H), 2.41-2.31 (m, 1H).

LC-MS (Method 3): R$_t$=2.07 min; 593 [M+H]$^+$.

Example 213

N-[1-(2-Chlorophenyl)-2,2,2-trifluoroethyl]-1-(2,4-difluorophenyl)-7-[(4S)-4-hydroxy-2-oxopyrrolidin-1-yl]-4-oxo-1,4-dihydro-1,8-naphthyridine-3-carboxamide (diastereomer B)

$^1$H-NMR (400 MHz, DMSO-d$_6$): δ [ppm]=11.33 (d, 1H), 8.86 (s, 1H), 8.75 (d, 1H), 8.57-8.51 (m, 1H), 7.93-7.76 (m, 1H), 7.67-7.48 (m, 5H), 7.42-7.32 (m, 1H), 6.52-6.42 (m, 1H), 5.32 (dd, 1H), 4.31-4.25 (m, 1H), 3.71-3.61 (m, 1H), 3.52-3.42 (m, 1H), 3.00-2.88 (m, 1H), 2.42-2.32 (m, 1H).

LC-MS (Method 3): R$_t$=2.07 min; 593 [M+H]$^+$.

Example 214

1-(2,4-Difluorophenyl)-N-[1-(2,6-difluorophenyl)ethyl]-7-[(4S)-4-hydroxy-2-oxopyrrolidin-1-yl]-4-oxo-1,4-dihydro-1,8-naphthyridine-3-carboxamide (diastereomer mixture)

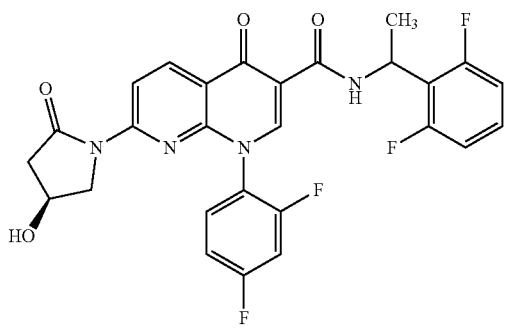 [SMILES: CC(NC(=O)c1cn(-c2ccc(F)cc2F)c2nc(N3C[C@@H](O)CC3=O)ccc2c1=O)c1c(F)cccc1F]

According to GP1, 90 mg (0.15 mmol, 65% purity) of the compound from Example 63A were reacted with 34.4 mg (219 μmol) of rac-1-(2,6-difluorophenyl)ethylamine in the presence of 55.4 mg (146 μmol) of HATU and 35.5 μl (204 μmol) of N,N-diisopropylethylamine in 1.44 ml of dimethylformamide. The crude product was purified by means of flash chromatography (cyclohexane/ethyl acetate gradient), and 51.2 mg (65% of theory; 100% purity) of the title compound were obtained.

$^1$H-NMR (400 MHz, DMSO-d$_6$): δ [ppm]=10.54-10.48 (m, 1H), 8.75-8.67 (m, 2H), 8.53-8.46 (m, 1H), 7.89-7.75 (m, 1H), 7.66-7.55 (m, 1H), 7.43-7.30 (m, 2H), 7.16-7.05 (m, 2H), 5.68-5.56 (m, 1H), 5.35-5.26 (m, 1H), 4.31-4.24 (m, 1H), 3.71-3.60 (m, 1H), 3.52-3.40 (m, 1H), 2.99-2.87 (m, 1H), 2.40-2.31 (m, 1H), 1.57 (d, 3H).

LC-MS (Method 1): R$_t$=1.02 min; 541 [M+H]$^+$.

39 mg of the title compound (diastereomer mixture) were separated into the diastereomers by chiral HPLC (preparative HPLC: column: Chiralpak AZ-H 5 μm 250×20 mm; eluent: 50% isopropanol, 50% isohexane; temperature: 25° C.; flow rate: 15 ml/min; UV detection: 210 nm).

This gave (in the sequence of elution from the column) 14.9 mg of diastereomer 1 (99% de) R$_t$=1.14 min and 12.9 mg (99% de) of diastereomer 2 R$_t$=1.81 min.

[Analytical HPLC: column: Chiralcel AZ-3 3 μm 50×4.6 mm; eluent: 50% isopropanol, 50% isohexane; flow rate: 1 ml/min; UV detection: 220 nm].

Diastereomer 1 was additionally purified by means of flash chromatography (cyclohexane/ethyl acetate gradient), and 14.3 mg (18% of theory; 100% purity) of the compound from Example 215 were obtained.

Diastereomer 2 was additionally purified by means of flash chromatography (cyclohexane/ethyl acetate gradient), and 9.8 mg (12% of theory; 100% purity) of the compound from Example 216 were obtained.

Example 215

1-(2,4-Difluorophenyl)-N-[1-(2,6-difluorophenyl)ethyl]-7-[(4S)-4-hydroxy-2-oxopyrrolidin-1-yl]-4-oxo-1,4-dihydro-1,8-naphthyridine-3-carboxamide (diastereomer 1)

$^1$H-NMR (400 MHz, DMSO-d$_6$): δ [ppm]=10.54-10.49 (m, 1H), 8.75-8.69 (m, 2H), 8.52-8.47 (min, 1H), 7.87-7.78 (m, 1H), 7.65-7.58 (m, 1H), 7.43-7.32 (m, 2H), 7.15-7.07 (m, 2H), 5.68-5.56 (m, 1H), 5.35-5.25 (m, 1H), 4.31-4.24 (m, 1H), 3.71-3.60 (m, 1H), 3.51-3.41 (m, 1H), 2.99-2.87 (m, 1H), 2.40-2.31 (m, 1H), 1.57 (d, 3H).

LC-MS (Method 1): R$_t$=0.99 min; 541 [M+H]$^+$.

Example 216

1-(2,4-Difluorophenyl)-N-[1-(2,6-difluorophenyl)ethyl]-7-[(4S)-4-hydroxy-2-oxopyrrolidin-1-yl]-4-oxo-1,4-dihydro-1,8-naphthyridine-3-carboxamide (diastereomer 2)

$^1$H-NMR (400 MHz, DMSO-d$_6$): δ [ppm]=10.54-10.48 (m, 1H), 8.75-8.69 (m, 2H), 8.53-8.47 (m, 1H), 7.90-7.76 (m, 1H), 7.66-7.56 (m, 1H), 7.43-7.31 (m, 2H), 7.16-7.07 (m, 2H), 5.68-5.57 (m, 1H), 5.31 (dd, 1H), 4.31-4.24 (m, 1H), 3.71-3.60 (m, 1H), 3.52-3.41 (m, 1H), 2.99-2.86 (m, 1H), 2.41-2.31 (m, 1H), 1.57 (d, 3H).

LC-MS (Method 1): R$_t$=0.98 min; 541 [M+H]$^+$.

Example 217

N-[1-(2-Chlorophenyl)-2,2,2-trifluoroethyl]-1-(2,4-difluorophenyl)-7-[(3S)-3-fluoropyrrolidin-1-yl]-4-oxo-1,4-dihydro-1,8-naphthyridine-3-carboxamide (diastereomer mixture)

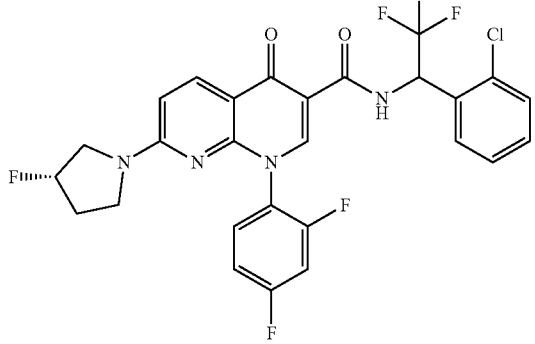

According to GP3, 150 mg (273 µmol, 96% purity) of the compound from Example 73A were reacted with 41 mg (0.33 mmol) of (S)-3-fluoropyrrolidine hydrochloride and 0.21 ml (1.2 mmol) of N,N-diisopropylethylamine in 2.7 ml of dimethylformamide. The crude product was diluted with acetonitrile and purified by means of preparative HPLC (column: Chromatorex C18, 10 µm, 125×30 mm, solvent: acetonitrile/0.05% formic acid gradient; (0 to 3 min. 10% acetonitrile to 35 min. 90% acetonitrile and a further 3 min. 90% acetonitrile), and 142 mg (90% of theory, 100% purity) of the title compound were obtained.

$^1$H-NMR (400 MHz, DMSO-$d_6$): δ [ppm]=11.62 (d, 1H), 8.64 (s, 1H), 8.37 (d, 1H), 7.88-7.70 (m, 1H), 7.65-7.45 (m, 1H), 7.37-7.26 (m, 1H), 6.88-6.77 (m, 1H), 6.50-6.40 (m, 1H), 5.55-5.23 (m, 1H), 3.84-3.06 (m, 4H), 2.34-1.96 (m, 2H).

LC-MS (Method 3): $R_t$=2.40 min; 581 [M+H]$^+$.

Example 218

1-(2,4-Difluorophenyl)-7-[3-hydroxypyrrolidin-1-yl]-4-oxo-N-[(2S)-1,1,1-trifluorobutan-2-yl]-1,4-dihydro-1,8-naphthyridine-3-carboxamide (diastereomer mixture)

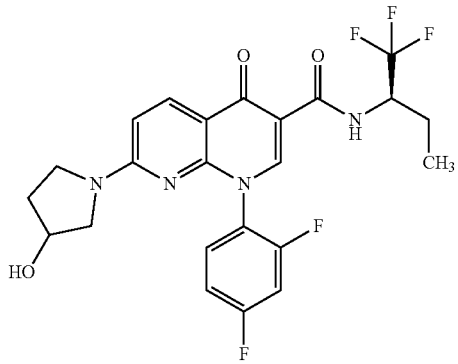 [SMILES: CC[C@@H](NC(=O)c1cn(-c2ccc(F)cc2F)c2nc(N3CCC(O)C3)ccc2c1=O)C(F)(F)F]

According to GP1, 250 mg (626 µmol) of the compound from Example 88A were reacted with 154 mg (939 µmol) of (2R)-1,1,1-trifluorobutan-2-amine hydrochloride in the presence of 238 mg (626 µmol) of HATU and 153 µl (876 µmol) of N,N-diisopropylethylamine in 6.3 ml of dimethylformamide. After purification by means of flash chromatography (cyclohexane/ethyl acetate gradient), 204 mg (66% of theory, 100% purity) of the title compound were obtained.

$^1$H-NMR (400 MHz, DMSO-$d_6$): δ [ppm]=10.53 (d, 1H), 8.61 (s, 1H), 8.28 (d, 1H), 7.86-7.75 (m, 1H), 7.61-7.53 (m, 1H), 7.36-7.28 (m, 1H), 6.80-6.70 (m, 1H), 5.10-4.87 (m, 1H), 4.80-4.67 (m, 1H), 4.43.4.21 (m, 1H), 3.60-3.01 (m, 4H), 2.09-1.56 (m, 4H), 0.97 (t, 3H).

LC-MS (Method 1): $R_t$=1.05 min; 497 [M+H]$^+$.

169.9 mg of the title compound (diastereomer mixture) were separated into the diastereomers by chiral HPLC (preparative HPLC: separation method: column: Chiralcel OZ-H 5 m 250×20 mm; eluent: 25% isopropanol, 75% isohexane; temperature: 30° C.; flow rate: 15 ml/min; UV detection: 270 nm).

This gave (in the sequence of elution from the column) 88 mg of diastereomer 1 (99% de) $R_t$=5.35 min and 75 mg (97% de) of diastereomer 2 $R_t$=5.91 min.

[Analytical HPLC: column: Chiralcel OZ-H 5 µm 250× 4.6 mm; eluent: 30% isopropanol, 70% isohexane; temperature: 30° C.; flow rate: 1 ml/min; UV detection: 270 nm]

Diastereomer 1 was additionally purified by means of flash chromatography (cyclohexane/ethyl acetate gradient), and 60 mg (19% of theory; 97% purity) of the title compound from Example 219 were obtained.

Diastereomer 2 was additionally purified by means of flash chromatography (cyclohexane/ethyl acetate gradient), and 46 mg (14% of theory; 98% purity) of the title compound from Example 220 were obtained.

Example 219

1-(2,4-Difluorophenyl)-7-[3-hydroxypyrrolidin-1-yl]-4-oxo-N-[(2S)-1,1,1-trifluorobutan-2-yl]-1,4-dihydro-1,8-naphthyridine-3-carboxamide (diastereomer 1)

$^1$H-NMR (400 MHz, DMSO-$d_6$): δ [ppm]=10.52 (d, 1H), 8.61 (s, 1H), 8.28 (d, 1H), 7.85-7.76 (m, 1H), 7.61-7.51 (m, 1H), 7.36-7.27 (m, 1H), 6.80-6.70 (m, 1H), 5.09-4.88 (m, 1H), 4.80-4.67 (m, 1H), 4.42.4.21 (m, 1H), 3.60-2.98 (m, 4H), 2.08-1.55 (m, 4H), 0.97 (t, 3H).

LC-MS (Method 1): $R_t$=1.01 min; 497 [M+H]$^+$.

Example 220

1-(2,4-Difluorophenyl)-7-[3-hydroxypyrrolidin-1-yl]-4-oxo-N-[(2S)-1,1,1-trifluorobutan-2-yl]-1,4-dihydro-1,8-naphthyridine-3-carboxamide (diastereomer 2)

$^1$H-NMR (400 MHz, DMSO-$d_6$): δ [ppm]=10.53 (d, 1H), 8.61 (s, 1H), 8.28 (d, 1H), 7.86-7.76 (m, 1H), 7.61-7.53 (m, 1H), 7.36-7.28 (m, 1H), 6.80-6.71 (m, 1H), 5.08-4.87 (m, 1H), 4.80-4.67 (m, 1H), 4.43.4.22 (m, 1H), 3.58-3.00 (m, 4H), 2.08-1.57 (m, 4H), 0.97 (t, 3H).

LC-MS (Method 1): $R_t$=1.05 min; 497 [M+H]$^+$.

Example 221

1-(2,4-Difluorophenyl)-4-oxo-7-[4-oxohexahydropyrrolo[3,4-c]pyrrol-2(1H)-yl]-N-[(2R)-1,1,1-trifluorobutan-2-yl]-1,4-dihydro-1,8-naphthyridine-3-carboxamide (diastereomer mixture)

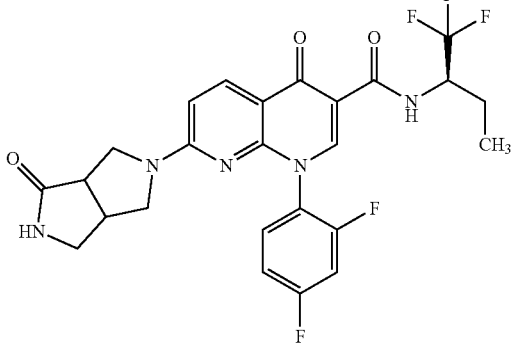

To a solution of 242 mg (381 µmol) of the diastereomer mixture from Example 83A in 3 ml of THF were added, at 0° C., 476 µl (1.90 mmol) of hydrochloric acid (4M in dioxane). The mixture was stirred at 0° C. for 30 min and at RT overnight. The solvent was removed under reduced pressure and the residue was purified by means of preparative HPLC (column: Chromatorex C18, 10 µm, 125×30 mm, solvent: acetonitrile/0.05% formic acid gradient; (0 to 3 min. 10% acetonitrile to 35 min. 90% acetonitrile and a further 3 min. 90% acetonitrile), and 168 mg (83% of theory, 100% purity) of the title compound were obtained.

$^1$H-NMR (400 MHz, DMSO-d$_6$): δ [ppm]=10.48 (d, 1H), 8.62 (s, 1H), 8.31 (d, 1H), 7.87-7.70 (m, 2H), 7.63-7.52 (m, 1H), 7.37-7.27 (m, 1H), 6.87-6.70 (br. s, 1H), 4.80-4.66 (m, 1H), 3.92-2.88 (br. m, 8H), 1.94-1.81 (m, 1H), 1.70-1.56 (m, 1H), 0.97 (t, 3H).

LC-MS (Method 3): R$_t$=1.74 min; 536 [M+H]$^+$.

167 mg of the title compound (diastereomer mixture) were separated into the diastereomers by chiral HPLC (preparative HPLC: column: Chiralpak AD-H 5 µm 250×20 mm; eluent: 30% isopropanol, 70% isohexane; temperature: 25° C.; flow rate: 20 ml/min; UV detection: 230 nm).

This gave (in the sequence of elution from the column) 63.6 mg of diastereomer 1 (99% de) R$_t$=3.46 min and 67.9 mg (99% de) of diastereomer 2 R$_t$=6.09 min.

[Analytical HPLC: column: Daicel AD-3 3 µm 30×4.6 mm; eluent: 70% isopropanol, 50% isohexane; UV detection: 220 nm].

Diastereomer 1 was additionally purified by means of preparative HPLC (column: Chromatorex C18, 10 µm, 125×30 mm, solvent: acetonitrile/0.05% formic acid gradient; (0 to 3 min. 10% acetonitrile to 35 min. 90% acetonitrile and a further 3 min. 90% acetonitrile)), and 41 mg (20% of theory, 100% purity) of the title compound from Example 222 were obtained.

Diastereomer 2 was additionally purified by means of preparative HPLC (column: Chromatorex C18, 10 µm, 125×30 mm, solvent: acetonitrile/0.05% formic acid gradient; (0 to 3 min. 10% acetonitrile to 35 min. 90% acetonitrile and a further 3 min. 90% acetonitrile)), and 38 mg (18% of theory, 100% purity) of the title compound from Example 223 were obtained.

Example 222

1-(2,4-Difluorophenyl)-4-oxo-7-[4-oxohexahydropyrrolo[3,4-c]pyrrol-2(1H)-yl]-N-[(2R)-1,1,1-trifluorobutan-2-yl]-1,4-dihydro-1,8-naphthyridine-3-carboxamide (diastereomer 1)

$^1$H-NMR (400 MHz, DMSO-d$_6$): δ [ppm]=10.48 (d, 1H), 8.62 (s, 1H), 8.31 (d, 1H), 7.86-7.73 (m, 2H), 7.63-7.53 (m, 1H), 7.37-7.28 (m, 1H), 6.87-6.71 (br. s, 1H), 4.80-4.68 (m, 1H), 3.93-2.89 (br. m, 8H), 1.94-1.81 (m, 1H), 1.70-1.57 (m, 1H), 0.97 (t, 3H).

LC-MS (Method 1): R$_t$=0.97 min; 536 [M+H]$^+$.

Example 223

1-(2,4-Difluorophenyl)-4-oxo-7-[4-oxohexahydropyrrolo[3,4-c]pyrrol-2(1H)-yl]-N-[(2R)-1,1,1-trifluorobutan-2-yl]-1,4-dihydro-1,8-naphthyridine-3-carboxamide (diastereomer 2)

$^1$H-NMR (400 MHz, DMSO-d$_6$): δ [ppm]=10.48 (d, 1H), 8.62 (s, 1H), 8.31 (d, 1H), 7.86-7.73 (m, 2H), 7.63-7.54 (m, 1H), 7.37-7.28 (m, 1H), 6.87-6.70 (br. s, 1H), 4.81-4.67 (m, 1H), 3.93-2.89 (br. m, 8H), 1.94-1.82 (m, 1H), 1.70-1.57 (m, 1H), 0.97 (t, 3H).

LC-MS (Method 1): R$_t$=0.97 min; 536 [M+H]$^+$.

Example 224

1-(2,4-Difluorophenyl)-7-[3-hydroxy-2-oxopyrrolidin-1-yl]-4-oxo-N-[(2R)-1,1,1-trifluorobutan-2-yl]-1,4-dihydro-1,8-naphthyridine-3-carboxamide (diastereomer mixture)

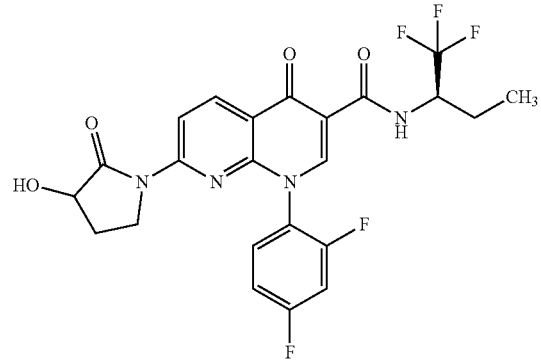 [SMILES: CC[C@@H](NC(=O)c1cn(-c2ccc(F)cc2F)c2nc(N3CCC(O)C3=O)ccc2c1=O)C(F)(F)F]

According to GP2, 150 mg (326 µmol) of the compound from Example 67A (97% purity) were reacted with 33.0 mg (326 µmol) of rac-3-hydroxy-2-pyrrolidin-2-one in the presence of 67.7 mg (490 µmol) of potassium carbonate, 7.3 mg (33 µmol) of palladium(II) acetate and 38 mg (65 µmol) of Xantphos in 3 ml of dioxane. The reaction mixture was filtered, washed through with acetonitrile and concentrated, and the residue was purified by means of flash chromatography (cyclohexane/ethyl acetate gradient). 92.5 mg (55% of theory, 99% purity) of the title compound were obtained.

$^1$H-NMR (400 MHz, DMSO-d$_6$): δ [ppm]=10.21 (d, 1H), 8.86 (s, 1H), 8.73 (d, 1H), 8.56-8.49 (m, 1H), 7.92-7.82 (m, 1H), 7.67-7.56 (m, 1H), 7.40-7.31 (m, 1H), 5.90 (d, 1H), 4.84-4.70 (m, 1H), 4.44-4.32 (m, 1H), 3.63-3.49 (m, 1H), 3.37-3.23 (m, 1H), 2.37-2.26 (m, 1H), 1.96-1.59 (m, 3H), 0.98 (t, 3H).

LC-MS (Method 3): $R_t$=1.88 min; 511 [M+H]⁺.

90 mg of the title compound (diastereomer mixture) were separated into the diastereomers by chiral HPLC (preparative HPLC: column: Chiralcel OX-H 5 µm 250×20 mm; eluent: 40% ethanol, 60% isohexane; temperature: 30° C.; flow rate: 15 ml/min; UV detection: 220 nm).

This gave (in the sequence of elution from the column) 43 mg of diastereomer 1 (99% de) $R_t$=8.76 min and 46 mg (99% de) of diastereomer 2 $R_t$=10.65 min.

[Analytical HPLC: column: Chiralcel OX-H 5 µm 250× 4.6 mm; eluent: 40% ethanol, 60% isohexane; temperature: 30° C.; flow rate: 1 ml/min; UV detection: 220 nm]

Diastereomer 1 was additionally purified by means of preparative HPLC (column: Chromatorex C18, 10 µm, 125× 30 mm, solvent: acetonitrile/0.05% formic acid gradient; (0 to 3 min. 10% acetonitrile to 35 min. 90% acetonitrile and a further 3 min. 90% acetonitrile)), and 36.6 mg (22% of theory, 100% purity) of the title compound from Example 225 were obtained.

Diastereomer 2 was additionally purified by means of preparative HPLC (column: Chromatorex C18, 10 µm, 125× 30 mm, solvent: acetonitrile/0.05% formic acid gradient; (0 to 3 min. 10% acetonitrile to 35 min. 90% acetonitrile and a further 3 min. 90% acetonitrile)), and 36.7 mg (22% of theory, 100% purity) of the title compound from Example 226 were obtained.

Example 225

1-(2,4-Difluorophenyl)-7-[3-hydroxy-2-oxopyrrolidin-1-yl]-4-oxo-N-[(2R)-1,1,1-trifluorobutan-2-yl]-1,4-dihydro-1,8-naphthyridine-3-carboxamide (diastereomer 1)

¹H-NMR (400 MHz, DMSO-d₆): δ [ppm]=10.21 (d, 1H), 8.86 (s, 1H), 8.73 (d, 1H), 8.56-8.50 (m, 1H), 7.92-7.82 (m, 1H), 7.66-7.57 (m, 1H), 7.40-7.32 (m, 1H), 5.90 (d, 1H), 4.84-4.70 (m, 1H), 4.44-4.33 (m, 1H), 3.63-3.51 (m, 1H), 3.38-3.25 (m, 1H), 2.38-2.26 (m, 1H), 1.96-1.60 (m, 3H), 0.98 (t, 3H).

LC-MS (Method 3): $R_t$=1.86 min; 511 [M+H]⁺.

Example 226

1-(2,4-Difluorophenyl)-7-[3-hydroxy-2-oxopyrrolidin-1-yl]-4-oxo-N-[(2R)-1,1,1-trifluorobutan-2-yl]-1,4-dihydro-1,8-naphthyridine-3-carboxamide (diastereomer 2)

¹H-NMR (400 MHz, DMSO-d₆): δ [ppm]=10.21 (d, 1H), 8.86 (s, 1H), 8.73 (d, 1H), 8.56-8.49 (m, 1H), 7.91-7.83 (m, 1H), 7.66-7.57 (m, 1H), 7.39-7.33 (m, 1H), 5.90 (d, 1H), 4.83-4.70 (m, 1H), 4.44-4.33 (m, 1H), 3.63-3.50 (m, 1H), 3.38-3.24 (m, 1H), 2.37-2.26 (m, 1H), 1.96-1.60 (m, 3H), 0.98 (t, 3H).

LC-MS (Method 3): $R_t$=1.87 min; 511 [M+H]⁺.

Example 227

1-(2,4-Difluorophenyl)-7-[(3S)-3-fluoropyrrolidin-1-yl]-4-oxo-N-[1-(trifluoromethoxy)propan-2-yl]-1,4-dihydro-1,8-naphthyridine-3-carboxamide (diastereomer mixture)

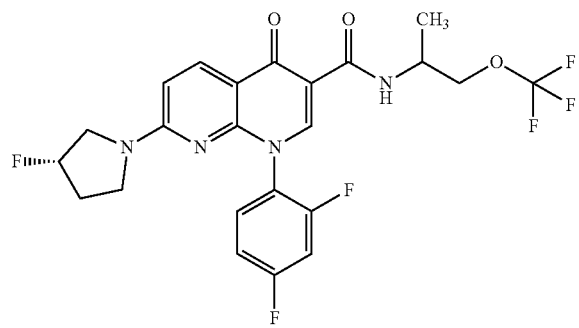 [SMILES: CC(COC(F)(F)F)NC(=O)c1cn(-c2ccc(F)cc2F)c2nc(N3CC[C@H](F)C3)ccc2c1=O]

According to GP3, 150 mg (325 µmol) of the compound from Example 74A were reacted with 48.9 g (390 µmol) of (S)-3-fluoropyrrolidine hydrochloride and 0.20 ml (1.1 mmol) of N,N-diisopropylethylamine in 1.45 ml of dimethylformamide. The crude product was diluted with acetonitrile and purified by means of preparative HPLC (column: Chromatorex C18, 10 µm, 125×30 mm, solvent: acetonitrile/0.05% formic acid gradient; (0 to 3 min. 10% acetonitrile to 35 min. 90% acetonitrile and a further 3 min. 90% acetonitrile), and 141 mg (84% of theory, 99% purity) of the title compound were obtained.

¹H-NMR (400 MHz, DMSO-d₆): δ [ppm]=10.15 (d, 1H), 8.57 (s, 1H), 8.32 (d, 1H), 7.85-7.74 (m, 1H), 7.64-7.51 (m, 1H), 7.37-7.27 (m, 1H), 6.84-6.74 (m, 1H), 5.56-5.22 (m, 1H), 4.39-4.28 (m, 1H), 4.21-4.11 (m, 2H), 3.88-3.03 (m, 4H), 2.38-1.92 (m, 2H), 1.25 (d, 3H).

LC-MS (Method 3): $R_t$=2.13 min; 515 [M+H]⁺.

135 mg of the title compound (diastereomer mixture) were separated into the diastereomers by chiral HPLC (preparative HPLC: column: OZ-H 5 µm 250×20 mm; eluent: 50% ethanol (with 2% diethylamine), 50% isohexane; temperature: 25° C.; flow rate: 15 ml/min; UV detection: 210 nm).

This gave (in the sequence of elution from the column) 50 mg of diastereomer 1 (99% de) $R_t$=1.02 min and 57 mg (92.3% de) of diastereomer 2 $R_t$=1.33 min.

[Analytical HPLC: column: Chiralpak OZ-3 3 µm 50×4.6 mm; eluent: 50% ethanol (with 2% diethylamine), 50% isohexane; flow rate: 1 ml/min; UV detection: 220 nm]

Diastereomer 1 was additionally purified by means of preparative HPLC (column: Chromatorex C18, 10 µm, 125× 30 mm, solvent: acetonitrile/0.05% formic acid gradient; (0 to 3 min. 10% acetonitrile to 35 min. 90% acetonitrile and a further 3 min. 90% acetonitrile)), and 40.5 mg (24% of theory, 99% purity) of the title compound from Example 228 were obtained.

Diastereomer 2 was additionally purified by means of preparative HPLC (column: Chromatorex C18, 10 µm, 125× 30 mm, solvent: acetonitrile/0.05% formic acid gradient; (0 to 3 min. 10% acetonitrile to 35 min. 90% acetonitrile and a further 3 min. 90% acetonitrile)), and 46.7 mg (28% of theory, 99% purity) of the title compound from Example 229 were obtained.

Example 228

1-(2,4-Difluorophenyl)-7-[(3S)-3-fluoropyrrolidin-1-yl]-4-oxo-N-[1-(trifluoromethoxy)propan-2-yl]-1,4-dihydro-1,8-naphthyridine-3-carboxamide (diastereomer 1)

$^1$H-NMR (400 MHz, DMSO-d$_6$): δ [ppm]=10.15 (d, 1H), 8.57 (s, 1H), 8.32 (d, 1H), 7.84-7.76 (m, 1H), 7.63-7.52 (m, 1H), 7.37-7.28 (m, 1H), 6.83-6.75 (m, 1H), 5.55-5.24 (m, 1H), 4.39-4.29 (m, 1H), 4.20-4.12 (m, 2H), 3.82-3.05 (m, 4H), 2.35-1.99 (m, 2H), 1.25 (d, 3H).
LC-MS (Method 3): R$_t$=2.09 min; 515 [M+H]$^+$.

Example 229

1-(2,4-Difluorophenyl)-7-[(3S)-3-fluoropyrrolidin-1-yl]-4-oxo-N-[1-(trifluoromethoxy)propan-2-yl]-1,4-dihydro-1,8-naphthyridine-3-carboxamide (diastereomer 2)

$^1$H-NMR (400 MHz, DMSO-d$_6$): δ [ppm]=10.15 (d, 1H), 8.57 (s, 1H), 8.32 (d, 1H), 7.84-7.75 (m, 1H), 7.64-7.53 (m, 1H), 7.37-7.27 (m, 1H), 6.84-6.74 (m, 1H), 5.57-5.22 (m, 1H), 4.39-4.29 (m, 1H), 4.21-4.12 (m, 2H), 3.83-3.03 (m, 4H), 2.36-1.92 (m, 2H), 1.25 (d, 3H).
LC-MS (Method 3): R$_t$=2.08 min; 515 [M+H]$^+$.

Example 230 rac-1-(2,4-Difluorophenyl)-4-oxo-7-(2-oxopyrrolidin-1-yl)-N-[1-(trifluoromethoxy)propan-2-yl]-1,4-dihydro-1,8-naphthyridine-3-carboxamide

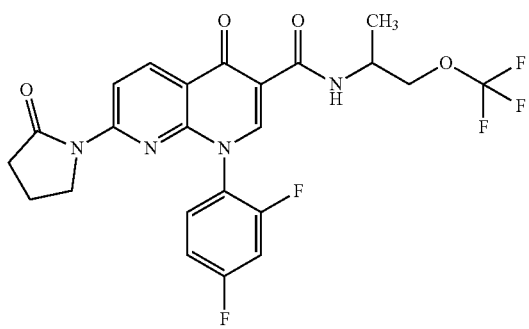 [SMILES: CC(COC(F)(F)F)NC(=O)c1cn(-c2ccc(F)cc2F)c2nc(N3CCCC3=O)ccc2c1=O]

According to GP2, 150 mg (325 μmol) of the compound from Example 74A were reacted with 27.6 mg (325 μmol) of pyrrolidin-2-one in the presence of 67.3 mg (487 μmol) of potassium carbonate, 13 mg (58 μmol) of palladium(II) acetate and 34 mg (58 μmol) of Xantphos in 4 ml of dioxane. The crude product was dissolved in 3 ml of acetonitrile and 0.5 ml of water and purified by means of preparative HPLC (column: Chromatorex C18, 10 μm, 125×30 mm, solvent: acetonitrile/0.05% formic acid gradient; (0 to 3 min. 10% acetonitrile to 35 min. 90% acetonitrile and a further 3 min. 90% acetonitrile), and 3.3 mg (2% of theory, 99% purity) of the title compound were obtained.
$^1$H-NMR (400 MHz, DMSO-d$_6$): δ [ppm]=9.92 (d, 1H), 8.78 (s, 1H), 8.69 (d, 1H), 8.49 (d, 1H), 7.89-7.91 (m, 1H), 7.65-7.58 (m, 1H), 7.39-7.33 (m, 1H), 4.41-4.32 (m, 1H), 4.22-4.14 (m, 2H), 3.61-3.50 (m, 2H), 2.00-1.91 (m, 2H), 1.26 (d, 3H).
LC-MS (Method 3): R$_t$=2.04 min; 511 [M+H]$^+$.

Example 231

1-(2,4-Difluorophenyl)-7-(dimethylamino)-4-oxo-N-[1-(trifluoromethoxy)propan-2-yl]-1,4-dihydro-1,8-naphthyridine-3-carboxamide

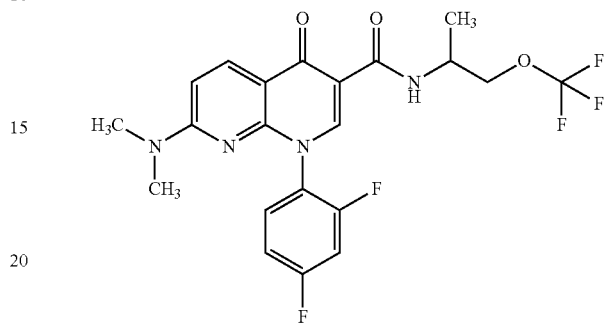

According to GP1, 100 mg (290 μmol) of the compound from Example 36A were reacted with 78.0 mg (434 μmol) of (+)-1-(trifluoromethoxy)propan-2-amine hydrochloride (optical rotation: +10°, c=0.4000 g/100 ml, MeOH, 20° C.) in the presence of 110 mg (290 μmol) of HATU and 151 μl (869 μmol) of N,N-diisopropylethylamine in 3 ml of dimethylformamide. 1 ml of aqueous 1M hydrochloric acid and 10 ml of water were added, and the precipitate was filtered off with suction and dried under high vacuum overnight. The crude product was purified by means of flash chromatography (cyclohexane/ethyl acetate gradient), and 80 mg (58% of theory; 99% purity) of the title compound (non-racemic mixture) were obtained.
$^1$H-NMR (400 MHz, DMSO-d$_6$): δ [ppm]=10.15 (d, 1H), 8.55 (s, 1H), 8.28 (d, 1H), 7.83-7.75 (m, 1H), 7.61-7.54 (m, 1H), 7.35-7.29 (m, 1H), 6.92 (d, 1H), 4.39-4.29 (m, 1H), 4.20-4.12 (m, 2H), 2.94 (br. s, 6H); 1.25 (d, 3H).
LC-MS (Method 1): R$_t$=1.12 min; 471 [M+H]$^+$.

Example 232

1-(2,4-Difluorophenyl)-4-oxo-7-(pyrrolidin-1-yl)-N-[1-(trifluoromethoxy)propan-2-yl]-1,4-dihydro-1,8-naphthyridine-3-carboxamide

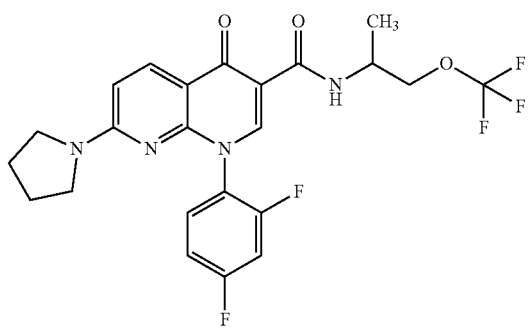 [SMILES: CC(COC(F)(F)F)NC(=O)c1cn(-c2ccc(F)cc2F)c2nc(N3CCCC3)ccc2c1=O]

According to GP1, 100 mg of the compound from Example 57A were reacted with 72.5 mg (404 μmol) of (+)-1-(trifluoromethoxy)propan-2-amine hydrochloride (optical rotation: +10°, c=0.4000 g/100 ml, MeOH, 20° C.) in the presence of 102 mg (269 µmol) of HATU and 141 µl (808 µmol) of N,N-diisopropylethylamine in 3 ml of dimethylformamide. 1 ml of aqueous 1M hydrochloric acid and 10 ml of water were added, and the precipitate was filtered off with suction and dried under high vacuum overnight. The crude product was purified by means of flash chromatography (cyclohexane/ethyl acetate gradient), and 97 mg (72% of theory; 99% purity) of the title compound (non-racemic mixture) were obtained.

$^1$H-NMR (400 MHz, DMSO-d$_6$): δ [ppm]=10.17 (d, 1H), 8.54 (s, 1H), 8.27 (d, 1H), 7.82-7.74 (m, 1H), 7.60-7.53 (m, 1H), 7.34-7.28 (m, 1H), 6.73 (d, 1H), 4.39-4.29 (m, 1H), 4.21-4.12 (m, 2H), 3.50-3.35 (br. s, 2H), 3.23-3.02 (br. s, 2H), 2.01-1.73 (m, 4H), 1.25 (d, 3H).

LC-MS (Method 1): R$_t$=1.21 min; 497 [M+H]$^+$.

Example 233

1-(2,4-Difluorophenyl)-7-[(4S)-4-hydroxy-2-oxopyrrolidin-1-yl]-4-oxo-N-[1-phenyl-2-(trifluoromethoxy)ethyl]-1,4-dihydro-1,8-naphthyridine-3-carboxamide

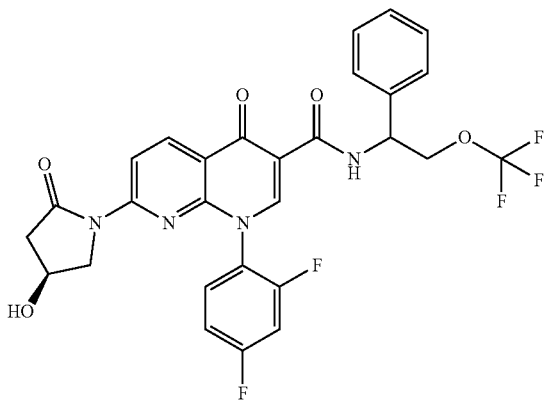 [SMILES: O=C(NC(COC(F)(F)F)c1ccccc1)c1cn(-c2ccc(F)cc2F)c2nc(N3C[C@@H](O)CC3=O)ccc2c1=O]

According to GP2, 200 mg (363 µmol) of the compound from Example 75A (95% purity) were reacted with 36.7 mg (363 µmol) of (S)-(−)-4-hydroxy-2-pyrrolidinone in the presence of 75.2 mg (544 µmol) of potassium carbonate, 8.1 mg (36 µmol) of palladium(II) acetate and 42 mg (73 µmol) of Xantphos in 3.6 ml of dioxane. The crude product was purified twice by means of preparative HPLC (column: Chromatorex C18, 10 µm, 125×30 mm, solvent: acetonitrile/ 0.05% formic acid gradient; (0 to 3 min. 10% acetonitrile to 35 min. 90% acetonitrile and a further 3 min. 90% acetonitrile)), and 37.8 mg (18% of theory, 100% purity) of the title compound (non-racemic mixture) were obtained.

$^1$H-NMR (400 MHz, DMSO-d$_6$): δ [ppm]=10.60 (d, 1H), 8.80 (s, 1H), 8.74 (d, 1H), 8.55-8.48 (m, 1H), 7.90-7.81 (m, 1H), 7.66-7.58 (m, 1H), 7.51-7.29 (m, 6H), 5.55-5.48 (m, 1H), 5.32 (dd, 1H), 4.53-4.40 (m, 2H), 4.31-4.25 (m, 1H), 3.72-3.61 (m, 1H), 3.52-3.42 (m, 1H), 3.00-2.88 (m, 1H), 2.42-2.29 (m, 1H).

LC-MS (Method 3): R$_t$=1.94 min; 589 [M+H]$^+$.

Example 234

1-(2,4-Difluorophenyl)-7-[(4S)-4-hydroxy-2-oxopyrrolidin-1-yl]-4-oxo-N-[1-(trifluoromethoxy)butan-2-yl]-1,4-dihydro-1,8-naphthyridine-3-carboxamide (diastereomer mixture)

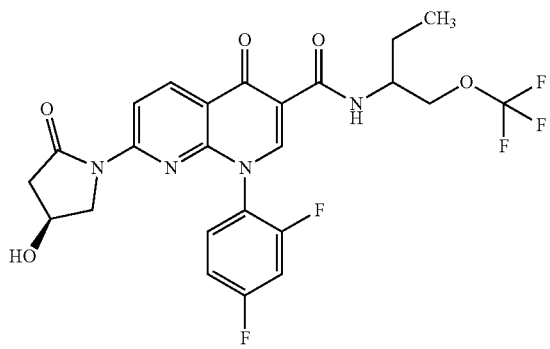 [SMILES: CCC(COC(F)(F)F)NC(=O)c1cn(-c2ccc(F)cc2F)c2nc(N3C[C@@H](O)CC3=O)ccc2c1=O]

According to GP2, 100 mg (210 µmol) of the compound from Example 76A were reacted with 21.2 mg (210 µmol) of (S)-(−)-4-hydroxy-2-pyrrolidinone in the presence of 103 mg (315 µmol) of caesium carbonate, 8.5 mg (38 µmol) of palladium(II) acetate and 18 mg (31 µmol) of Xantphos in 2.1 ml of dioxane. The crude product was purified by means of flash chromatography (cyclohexane/ethyl acetate gradient) and preparative thin-layer chromatography (1 mm silica plates, 20×20 cm, cyclohexane/ethyl acetate=35/65). The product fraction was visualized by UV detection and scratched off, and eluted from the silica gel with ethyl acetate. The mixture was filtered through Celite and the solvent was removed under reduced pressure. The residue was lyophilized from water/acetonitrile, and 17 mg (15% of theory; 100% purity) of the title compound were obtained.

$^1$H-NMR (400 MHz, DMSO-d$_6$): δ [ppm]=9.90 (d, 1H), 8.79 (s, 1H), 8.70 (d, 1H), 8.53-8.47 (m, 1H), 7.92-7.81 (m, 1H), 7.67-7.58 (m, 1H), 7.41-7.33 (m, 1H), 5.32 (dd, 1H), 4.31-4.13 (m, 4H), 3.72-3.62 (m, 1H), 3.52-3.43 (m, 1H), 3.00-2.88 (m, 1H), 2.41-2.32 (m, 1H), 1.76-1.53 (m, 2H), 0.95 (t, 3H).

LC-MS (Method 1): R$_t$=0.99 min; 541 [M+H]$^+$.

Example 235

1-(2,4-Difluorophenyl)-N-[1-(2-fluorophenyl)ethyl]-7-[(4S)-4-hydroxy-2-oxopyrrolidin-1-yl]-4-oxo-1,4-dihydro-1,8-naphthyridine-3-carboxamide (diastereomer mixture)

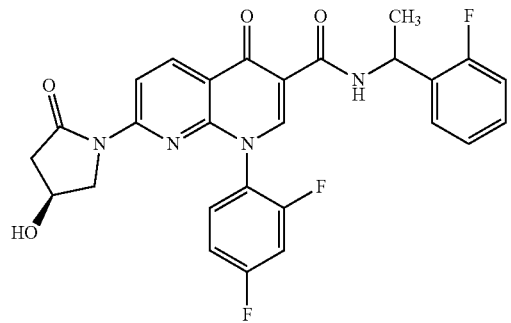 [SMILES: CC(NC(=O)c1cn(-c2ccc(F)cc2F)c2nc(N3C[C@@H](O)CC3=O)ccc2c1=O)c1ccccc1F]

According to GP2, 97.0 mg (212 µmol) of the compound from Example 77A were reacted with 21.4 mg (212 µmol) of (S)-(−)-4-hydroxy-2-pyrrolidinone in the presence of 104 mg (318 µmol) of caesium carbonate, 8.6 mg (38 µmol) of palladium(II) acetate and 18 mg (31 µmol) of Xantphos in 2 ml of dioxane. The crude product was purified by means of flash chromatography (cyclohexane/ethyl acetate gradient) and lyophilized from acetonitrile/water. 45.8 mg (41% of theory, 100% purity) of the title compound were obtained.

$^1$H-NMR (400 MHz, DMSO-$d_6$): δ [ppm]=10.33 (d, 1H), 8.74 (s, 1H), 8.71 (d, 1H), 8.54-8.48 (m, 1H), 7.90-7.78 (m, 1H), 7.66-7.57 (m, 1H), 7.48-7.42 (m, 1H), 7.41-7.29 (m, 2H), 7.24-7.16 (m, 2H), 5.44-5.26 (m, 2H), 4.31-4.24 (m, 1H), 3.72-3.60 (m, 1H), 3.52-3.42 (m, 1H), 2.99-2.87 (m, 1H), 2.42-2.31 (m, 1H), 1.52 (d, 3H).

LC-MS (Method 1): $R_t$=0.97 min; 523 [M+H]$^+$.

Example 236

1-(2,4-Difluorophenyl)-7-[(4S)-4-hydroxy-2-oxopyr-rolidin-1-yl]-4-oxo-N-[1,1,1-trifluoro-3-methoxy-2-methylpropan-2-yl]-1,4-dihydro-1,8-naphthyridine-3-carboxamide (diastereomer mixture)

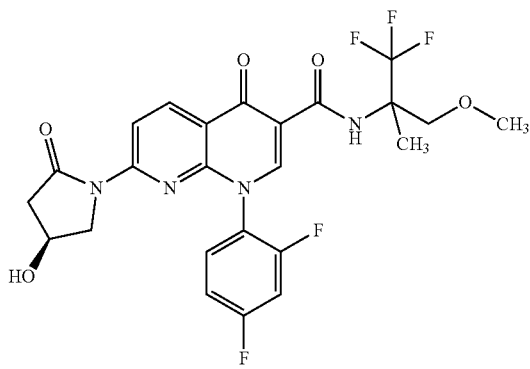 [SMILES: COCC(C)(NC(=O)c1cn(-c2ccc(F)cc2F)c2nc(N3C[C@@H](O)CC3=O)ccc2c1=O)C(F)(F)F]

According to GP2, 110 mg (231 µmol) of the compound from Example 78A were reacted with 23.3 mg (231 µmol) of (S)-(−)-4-hydroxy-2-pyrrolidinone in the presence of 96.9 mg (297 µmol) of caesium carbonate, 8.0 mg (36 µmol) of palladium(II) acetate and 18 mg (31 µmol) of Xantphos in 2.3 ml of dioxane.

The crude product was purified by means of flash chromatography (cyclohexane/ethyl acetate gradient) and preparative thin-layer chromatography (1 mm silica plates, 20×20 cm, dichloromethane/methanol=95/5). The product fraction was visualized by UV detection and scratched off, and eluted from the silica gel with ethyl acetate. The mixture was filtered through Celite and the solvent was removed under reduced pressure. The residue was lyophilized from water/acetonitrile, and 49 mg (39% of theory; 100% purity) of the title compound were obtained.

$^1$H-NMR (400 MHz, DMSO-$d_6$): δ [ppm]=10.50 (br. s, 1H), 8.79 (s, 1H), 8.71 (d, 1H), 8.54-8.48 (m, 1H), 7.91-7.81 (m, 1H), 7.67-7.59 (m, 1H), 7.41-7.33 (m, 1H), 5.32 (dd, 1H), 4.31-4.26 (m, 1H), 3.91-3.84 (m, 1H), 3.77-3.61 (m, 2H), 3.52-3.42 (m, 1H), 3.36 (s, 3H), 2.99-2.88 (m, 1H), 2.41-2.31 (m, 1H), 1.64 (s, 3H).

LC-MS (Method 1): $R_t$=0.96 min; 541 [M+H]$^+$.

Example 237

1-(2,4-Difluorophenyl)-7-[(4S)-4-hydroxy-2-oxopyr-rolidin-1-yl]-4-oxo-N-[4-(trifluoromethyl)tetra-hydro-2H-pyran-4-yl]-1,4-dihydro-1,8-naphthyri-dine-3-carboxamide

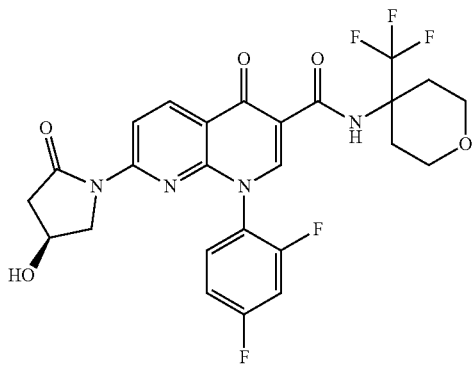 [SMILES: O=C(NC1(C(F)(F)F)CCOCC1)c1cn(-c2ccc(F)cc2F)c2nc(N3C[C@@H](O)CC3=O)ccc2c1=O]

According to GP2, 106 mg (217 µmol) of the compound from Example 79A were reacted with 21.9 mg (217 µmol) of (S)-(−)-4-hydroxy-2-pyrrolidinone in the presence of 106 mg (326 µmol) of caesium carbonate, 8.8 mg (39 µmol) of palladium(II) acetate and 23 mg (39 µmol) of Xantphos in 2.3 ml of dioxane. The crude product was purified by means of flash chromatography (cyclohexane/ethyl acetate gradient) and twice by means of preparative thin-layer chromatography (1 mm silica plates, 20×20 cm, cyclohexane/ethyl acetate=1/1, then dichloromethane/methanol=90/10). The product fraction was visualized by UV detection and scratched off, and eluted from the silica gel with ethyl acetate or dichloromethane. The mixture was filtered through a fine filter and the solvent was removed under reduced pressure. The residue was lyophilized from water/acetonitrile, and 42.8 mg (35% of theory; 99% purity) of the title compound were obtained.

$^1$H-NMR (400 MHz, DMSO-$d_6$): δ [ppm]=10.34 (s, 1H), 8.82 (s, 1H), 8.72 (d, 1H), 8.55-8.50 (m, 1H), 7.92-7.83 (m, 1H), 7.67-7.59 (m, 1H), 7.41-7.33 (m, 1H), 5.32 (dd, 1H), 4.31-4.25 (m, 1H), 3.94-3.85 (m, 2H), 3.72-3.62 (m, 1H), 3.58-3.42 (m, 3H), 3.00-2.89 (m, 1H), 2.45-2.31 (m, 2H), 1.95-1.83 (m, 2H).

LC-MS (Method 4): $R_t$=2.83 min; 553 [M+H]$^+$.

Example 238

1-(2,4-Difluorophenyl)-7-[(4S)-4-hydroxy-2-oxopyrrolidin-1-yl]-4-oxo-N-[3-(trifluoromethyl)tetrahydrofuran-3-yl]-1,4-dihydro-1,8-naphthyridine-3-carboxamide (diastereomer mixture)

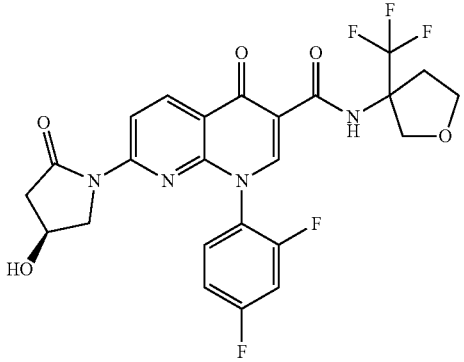 [SMILES: O=C(NC1(C(F)(F)F)CCOC1)c1cn(-c2ccc(F)cc2F)c2nc(N3C[C@@H](O)CC3=O)ccc2c1=O]

According to GP1, 82 mg (0.13 mmol, 65% purity) of the compound from Example 63A were reacted with 30.9 mg (199 µmol) of rac-3-(trifluoromethyl)tetrahydrofuran-3-amine in the presence of 50.5 mg (133 µmol) of HATU and 32.0 µl (186 µmol) of N,N-diisopropylethylamine in 1.3 ml of dimethylformamide. The crude product was purified by means of flash chromatography (cyclohexane/ethyl acetate gradient), and 39.8 mg (56% of theory; 100% purity) of the title compound were obtained.

$^1$H-NMR (400 MHz, DMSO-$d_6$): δ [ppm]=10.62 (s, 1H), 8.83 (s, 1H), 8.71 (d, 1H), 8.55-8.50 (m, 1H), 7.91-7.81 (m, 1H), 7.67-7.59 (m, 1H), 7.41-7.33 (m, 1H), 5.32 (dd, 1H), 4.34-4.25 (m, 2H), 4.16-4.09 (m, 1H), 4.01-3.93 (m, 1H), 3.92-3.83 (m, 1H), 3.71-3.61 (m, 1H), 3.52-3.41 (m, 1H), 3.00-2.88 (m, 1H), 2.41-2.31 (m, 1H).

LC-MS (Method 1): $R_t$=0.90 min; 539 [M+H]$^+$.

Example 239

1-(2-Fluorophenyl)-7-[(4S)-4-hydroxy-2-oxopyrrolidin-1-yl]-4-oxo-N-[(2R)-1,1,1-trifluorobutan-2-yl]-1,4-dihydro-1,8-naphthyridine-3-carboxamide

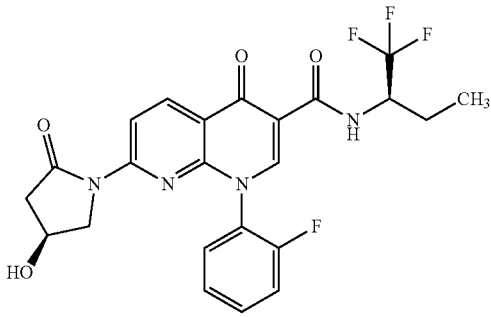 [SMILES: CC[C@@H](NC(=O)c1cn(-c2ccccc2F)c2nc(N3C[C@@H](O)CC3=O)ccc2c1=O)C(F)(F)F]

According to GP2, 130 mg (304 µmol) of the compound from Example 82A were reacted with 30.7 mg (304 µmol) of (S)-(−)-4-hydroxy-2-pyrrolidinone in the presence of 149 mg (456 µmol) of caesium carbonate, 12 mg (55 µmol) of palladium(II) acetate and 63.3 mg (109 µmol) of Xantphos in 6 ml of dioxane. The crude product was diluted with 3 ml of acetonitrile and 0.5 ml of water and purified by means of preparative HPLC (column: Chromatorex C18, 10 µm, 125× 30 mm, solvent: acetonitrile/0.05% formic acid gradient; (0 to 3 min. 10% acetonitrile to 35 min. 90% acetonitrile and a further 3 min. 90% acetonitrile), and 51.3 mg (35% of theory, 99% purity) of the title compound were obtained.

$^1$H-NMR (400 MHz, DMSO-$d_6$): δ [ppm]=10.23 (d, 1H), 8.82 (s, 1H), 8.72 (d, 1H), 8.55-8.49 (m, 1H), 7.82-7.76 (m, 1H), 7.72-7.65 (m, 1H), 7.57-7.43 (m, 2H), 5.32 (dd, 1H), 4.84-4.70 (m, 1H), 4.29-4.22 (m, 1H), 3.69-3.57 (m, 1H), 3.50-3.39 (m, 1H), 2.99-2.87 (m, 1H), 2.41-2.30 (m, 1H), 1.96-1.84 (m, 1H), 1.73-1.59 (m, 1H), 0.98 (t, 3H).

LC-MS (Method 1): $R_t$=0.96 min; 493 [M+H]$^+$.

Example 240

1-(2-Chlorophenyl)-7-[(4S)-4-hydroxy-2-oxopyrrolidin-1-yl]-4-oxo-N-[(2R)-1,1,1-trifluorobutan-2-yl]-1,4-dihydro-1,8-naphthyridine-3-carboxamide (atropisomer mixture)

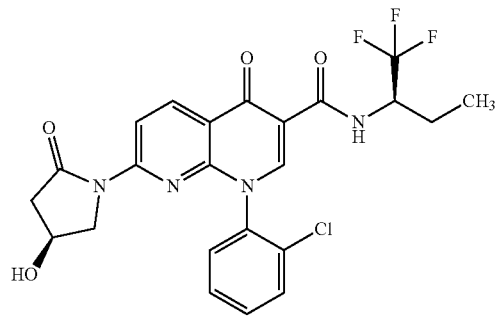 [SMILES: CC[C@@H](NC(=O)c1cn(-c2ccccc2Cl)c2nc(N3C[C@@H](O)CC3=O)ccc2c1=O)C(F)(F)F]

According to GP1, 30 mg (75 µmol) of the compound from Example 64A were reacted with 18.4 mg (113 µmol) of (R)-1,1,1-trifluoro-2-butylamine hydrochloride in the presence of 29 mg (75 µmol) of HATU and 39 µl (0.23 mmol) of N,N-diisopropylethylamine in 0.8 ml of dimethylformamide. The mixture was diluted with 1 ml of acetonitrile and 0.5 ml of water and the solution was purified by means of preparative HPLC (column: Chromatorex C18, 10 µm, 125× 30 mm, solvent: acetonitrile/0.05% formic acid gradient; 0 to 3 min 10% acetonitrile, to 35 min 90% acetonitrile and for a further 3 min 90% acetonitrile). 23 mg (60% of theory, 99% purity) of the title compound were obtained (as an atropisomer mixture).

$^1$H-NMR (400 MHz, DMSO-$d_6$): δ [ppm]=10.25 (d, 1H), 8.75 (d, 1H), 8.72 (d, 1H), 8.51 (dd, 1H), 7.84-7.76 (m, 2H), 7.70-7.59 (m, 2H), 5.31 (dd, 1H), 4.84-4.70 (m, 1H), 4.27-4.20 (m, 1H), 3.61-3.52 (m, 1H), 3.41-3.34 (m, 1H), 2.97-2.87 (m, 1H), 2.40-2.30 (m, 1H), 1.96-1.84 (m, 1H), 1.75-1.60 (m, 1H), 1.02-0.95 (m, 3H).

LC-MS (Method 1): $R_t$=1.00 min; 509 [M+H]$^+$.

Example 241

1-(2,4-Difluorophenyl)-N-[1-(2,6-difluorophenyl)-2,2,2-trifluoroethyl]-7-[(3S)-3-fluoropyrrolidin-1-yl]-4-oxo-1,4-dihydro-1,8-naphthyridine-3-carboxamide (diastereomer mixture)

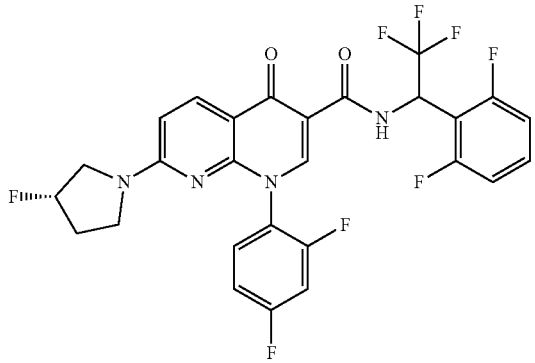 [SMILES: O=C(NC(c1c(F)cccc1F)C(F)(F)F)c1cn(-c2ccc(F)cc2F)c2nc(N3CC[C@H](F)C3)ccc2c1=O]

According to GP3, 150 mg (283 μmol) of the compound from Example 80A were reacted with 43 mg (0.28 mmol) of (S)-3-fluoropyrrolidine hydrochloride and 0.17 ml (0.99 mmol) of N,N-diisopropylethylamine in 1.3 ml of dimethylformamide. The crude product was purified by means of preparative HPLC (column: Chromatorex C18, 10 μm, 125×40 mm, solvent: acetonitrile/0.05% formic acid gradient; (0 to 3 min. 10% acetonitrile to 40 min. 90% acetonitrile and a further 3 min. 90% acetonitrile), and 119 mg (72% of theory, 100% purity) of the title compound were obtained.

$^1$H NMR (400 MHz, DMSO-$d_6$) δ [ppm]=11.61 (d, 1H), 8.65 (s, 1H), 8.36 (d, 1H), 7.89-7.69 (m, 1H), 7.67-7.51 (m, 2H), 7.38-7.25 (m, 3H), 6.82 (br. d, 1H), 6.49-6.38 (m, 1H), 5.57-5.23 (m, 1H), 3.86-3.44 (m, 3H), 3.25-3.01 (m, 1H), 2.32-2.08 (m, 2H).

LC-MS (Method 1): $R_t$=1.31 min; 583 [M+H]$^+$.

131 mg of the title compound (diastereomer mixture) were separated into the diastereomers by chiral HPLC (preparative HPLC: column: Daicel Chiralpak IC 5 μm 250×20 mm; eluent: 50% isohexane, 50% ethanol+0.2% diethylamine; temperature: 40° C.; flow rate: 20 ml/min; UV detection: 220 nm).

This gave (in the sequence of elution from the column) 57 mg of diastereomer 1 (99% de) $R_t$=4.13 min and 58 mg (99% de) of diastereomer 2 $R_t$=5.55 min.

[Analytical HPLC: column: Daicel Chiralpak IC 5 μm 250×4.6 mm; eluent: 50% isohexane, 50% ethanol+0.2% diethylamine; temperature: 40° C.; flow rate: 1 ml/min; UV detection: 235 nm]

Example 242

1-(2,4-Difluorophenyl)-N-[1-(2,6-difluorophenyl)-2,2,2-trifluoroethyl]-7-[(3S)-3-fluoropyrrolidin-1-yl]-4-oxo-1,4-dihydro-1,8-naphthyridine-3-carboxamide (diastereomer 1)

$^1$H NMR (400 MHz, DMSO-$d_6$) δ [ppm]=11.61 (d, 1H), 8.65 (s, 1H), 8.36 (d, 1H), 7.89-7.69 (m, 1H), 7.68-7.51 (m, 2H), 7.37-7.23 (m, 3H), 6.88-6.73 (m, 1H), 6.50-6.34 (m, 1H), 5.57-5.21 (m, 1H), 3.87-3.34 (m, 3H), 3.22-3.01 (m, 1H), 2.34-1.94 (m, 2H).

LC-MS (Method 3): $R_t$=2.36 min; 583 [M+H]$^+$.

Example 243

1-(2,4-Difluorophenyl)-N-[1-(2,6-difluorophenyl)-2,2,2-trifluoroethyl]-7-[(3S)-3-fluoropyrrolidin-1-yl]-4-oxo-1,4-dihydro-1,8-naphthyridine-3-carboxamide (diastereomer 2)

$^1$H NMR (400 MHz, DMSO-$d_6$) δ [ppm]=11.61 (d, 1H), 8.65 (s, 1H), 8.36 (d, 1H), 7.90-7.69 (m, 1H), 7.67-7.49 (m, 2H), 7.38-7.26 (m, 3H), 6.82 (br. d, 1H), 6.49-6.37 (m, 1H), 5.58-5.21 (m, 1H), 3.86-3.34 (m, 3H), 3.24-3.00 (m, 1H), 2.34-1.97 (m, 2H).

LC-MS (Method 3): $R_t$=2.34 min; 583 [M+H]$^+$.

Example 244

1-(2,4-Difluorophenyl)-N-[1-(2,6-difluorophenyl)-2,2,2-trifluoroethyl]-7-[(4S)-4-hydroxy-2-oxopyrrolidin-1-yl]-4-oxo-1,4-dihydro-1,8-naphthyridine-3-carboxamide (diastereomer mixture)

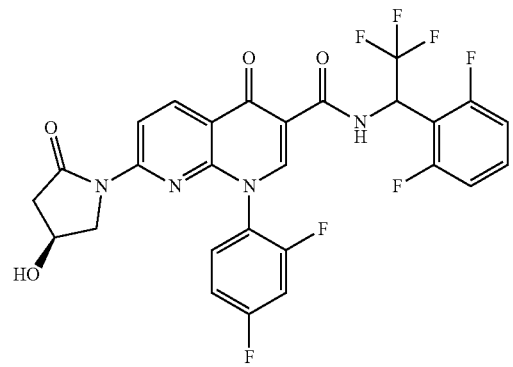 [SMILES: O=C(NC(c1c(F)cccc1F)C(F)(F)F)c1cn(-c2ccc(F)cc2F)c2nc(N3C[C@@H](O)CC3=O)ccc2c1=O]

According to GP2, 200 mg (377 μmol) of the compound from Example 80A were reacted with 45.8 mg (453 μmol) of (4S)-4-hydroxypyrrolidin-2-one in the presence of 78.3 mg (566 μmol) of potassium carbonate, 17 mg (75 μmol) of palladium(II) acetate and 44 mg (75 μmol) of Xantphos in 3.4 ml of dioxane.

The crude product was purified by means of preparative HPLC (column: Chromatorex C18, 10 μm, 125×40 mm, solvent: acetonitrile/0.1% formic acid gradient; (0 to 3 min. 10% acetonitrile to 40 min. 90% acetonitrile and a further 3 min. 90% acetonitrile), and 168 mg (75% of theory, 100% purity) of the title compound were obtained.

$^1$H NMR (400 MHz, DMSO-$d_6$) δ [ppm]=11.37 (d, 1H), 8.87 (s, 1H), 8.75 (d, 1H), 8.52 (dd, 1H), 7.94-7.75 (m, 1H), 7.68-7.57 (m, 2H), 7.42-7.26 (m, 3H), 6.50-6.39 (m, 1H), 5.37-5.26 (m, 1H), 4.28 (br. d, 1H), 3.73-3.60 (m, 1H), 3.53-3.40 (m, 1H), 3.01-2.87 (m, 1H), 2.42-2.31 (m, 1H).

LC-MS (Method 3): $R_t$=2.01 min; 595 [M+H]$^+$.

133 mg of the title compound (diastereomer mixture) were separated into the diastereomers by chiral HPLC (preparative HPLC: column: Daicel Chiralpak ID 5 μm 250×20 mm; eluent: 80% isohexane, 20% ethanol; temperature: 23° C.; flow rate: 30 ml/min; UV detection: 220 nm).

This gave (in the sequence of elution from the column) 53.9 mg of diastereomer 1 (99% de) $R_t$=2.12 min and 52.2 mg (99% de) of diastereomer 2 $R_t$=3.03 min.

[Analytical HPLC: column: Daicel Chiralpak ID-3 3 μm 50×4.6 mm; eluent: 80% isohexane, 20% ethanol; temperature: 30° C.; flow rate: 1 ml/min; UV detection: 220 nm]

Example 245

1-(2,4-Difluorophenyl)-N-[1-(2,6-difluorophenyl)-2,2,2-trifluoroethyl]-7-[(4S)-4-hydroxy-2-oxopyrrolidin-1-yl]-4-oxo-1,4-dihydro-1,8-naphthyridine-3-carboxamide (diastereomer 1)

$^1$H NMR (400 MHz, DMSO-d$_6$) δ [ppm]=11.37 (d, 1H), 8.88 (s, 1H), 8.75 (d, 1H), 8.52 (dd, 1H), 7.92-7.76 (m, 1H), 7.68-7.57 (m, 2H), 7.41-7.25 (m, 3H), 6.50-6.39 (m, 1H), 5.32 (dd, 1H), 4.28 (br. d, 1H), 3.72-3.60 (m, 1H), 3.46 (t, 1H), 3.00-2.87 (m, 1H), 2.37 (dd, 1H).

LC-MS (Method 3): R$_t$=2.01 min; 595 [M+H]$^+$.

Example 246

1-(2,4-Difluorophenyl)-N-[1-(2,6-difluorophenyl)-2,2,2-trifluoroethyl]-7-[(4S)-4-hydroxy-2-oxopyrrolidin-1-yl]-4-oxo-1,4-dihydro-1,8-naphthyridine-3-carboxamide (diastereomer 2)

$^1$H NMR (400 MHz, DMSO-d$_6$) δ [ppm]=11.37 (dd, 1H), 8.87 (s, 1H), 8.75 (d, 1H), 8.52 (dd, 1H), 7.95-7.75 (m, 1H), 7.68-7.57 (m, 2H), 7.41-7.26 (m, 3H), 6.50-6.38 (m, 1H), 5.32 (dd, 1H), 4.31-4.25 (br. d, 1H), 3.71-3.60 (m, 1H), 3.52-3.41 (m, 1H), 3.00-2.88 (m, 1H), 2.37 (dd, 1H).

LC-MS (Method 3): R$_t$=2.00 min; 595 [M+H]$^+$.

Example 247

1-(2,4-Difluorophenyl)-N-[1-(2,6-difluorophenyl)-2,2,2-trifluoroethyl]-7-[3-hydroxy-2-oxopiperidin-1-yl]-4-oxo-1,4-dihydro-1,8-naphthyridine-3-carboxamide (diastereomer mixture)

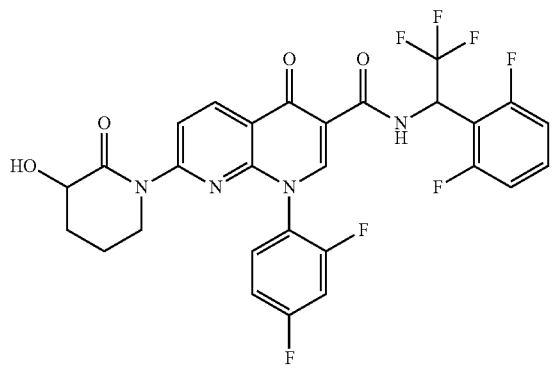 [SMILES: O=C(NC(c1c(F)cccc1F)C(F)(F)F)c1cn(-c2ccc(F)cc2F)c2nc(N3CCCC(O)C3=O)ccc2c1=O]

According to GP2, 150 mg (283 μmol) of the compound from Example 80A were reacted with 39.1 mg (340 μmol) of rac-3-hydroxypiperidin-2-one in the presence of 58.7 mg (425 μmol) of potassium carbonate, 13 mg (57 μmol) of palladium(II) acetate and 33 mg (57 μmol) of Xantphos in 2.5 ml of dioxane. The crude product was purified by means of preparative HPLC (column: Chromatorex C18, 10 μm, 125×40 mm, solvent: acetonitrile/0.1% formic acid gradient; (0 to 3 min. 10% acetonitrile to 40 min. 90% acetonitrile and a further 3 min. 90% acetonitrile), and 102 mg (59% of theory, 100% purity) of the title compound were obtained.

$^1$H NMR (400 MHz, DMSO-d$_6$) δ [ppm]=11.34 (br. d, 1H), 8.89 (s, 1H), 8.70 (d, 1H), 8.17-8.09 (m, 1H), 7.94-7.75 (m, 1H), 7.68-7.56 (m, 2H), 7.41-7.27 (m, 3H), 6.51-6.39 (m, 1H), 5.52-5.46 (m, 1H), 4.27-4.17 (m, 1H), 3.71-3.58 (m, 1H), 3.54-3.40 (m, 1H), 2.12-2.01 (m, 1H), 1.86-1.71 (m, 1H), 1.71-1.57 (m, 1H).

LC-MS (Method 3): R$_t$=2.11 min; 609 [M+H]$^+$. 91.2 mg of the title compound (racemic diastereomer mixture) were separated into the enantiomeric diastereomers by chiral HPLC (preparative HPLC: column: Daicel Chiralpak AZ-H 5 μm 250×30 mm; eluent: 50% isohexane, 20% ethanol; temperature: 25° C.; flow rate: 50 ml/min; UV detection: 220 nm).

This gave (in the sequence of elution from the column) 17.8 mg of diastereomer 1 (96.5% de) R$_t$=3.19 min, 14.5 mg (95% de) of diastereomer 2 R$_t$=4.21 min, 17.4 mg (97% de) of diastereomer 3 R$_t$=6.11 min, and 14.5 mg (97% de) of diastereomer 4 R$_t$=10.80 min.

[Analytical HPLC: column: Daicel AZ-3 3 μm 50×4.6 mm; eluent: 50% isohexane, 50% ethanol; temperature: 30° C.; flow rate: 1 ml/min; UV detection: 220 nm]

Example 248

1-(2,4-Difluorophenyl)-N-[1-(2,6-difluorophenyl)-2,2,2-trifluoroethyl]-7-[3-hydroxy-2-oxopiperidin-1-yl]-4-oxo-1,4-dihydro-1,8-naphthyridine-3-carboxamide (diastereomer 1)

$^1$H NMR (400 MHz, DMSO-d$_6$) δ [ppm]=11.34 (br. d, 1H), 8.89 (s, 1H), 8.70 (d, 1H), 8.17-8.10 (m, 1H), 7.93-7.76 (m, 1H), 7.68-7.57 (m, 2H), 7.40-7.27 (m, 3H), 6.51-6.39 (m, 1H), 5.52-5.46 (m, 1H), 4.27-4.18 (m, 1H), 3.71-3.59 (m, 1H), 3.54-3.41 (m, 1H), 2.12-2.01 (m, 1H), 1.83-1.73 (m, 2H), 1.71-1.58 (m, 1H).

LC-MS (Method 3): R$_t$=2.12 min; 609 [M+H]$^+$.

Example 249

1-(2,4-Difluorophenyl)-N-[1-(2,6-difluorophenyl)-2,2,2-trifluoroethyl]-7-[3-hydroxy-2-oxopiperidin-1-yl]-4-oxo-1,4-dihydro-1,8-naphthyridine-3-carboxamide (diastereomer 2)

$^1$H NMR (400 MHz, DMSO-d$_6$) δ [ppm]=11.37-11.31 (m, 1H), 8.89 (s, 1H), 8.70 (d, 1H), 8.13 (dd, 1H), 7.94-7.75 (m, 1H), 7.68-7.56 (m, 2H), 7.41-7.26 (m, 3H), 6.51-6.38 (m, 1H), 5.52-5.46 (m, 1H), 4.27-4.16 (m, 1H), 3.72-3.58 (m, 1H), 3.53-3.39 (m, 1H), 2.12-2.01 (m, 1H), 1.83-1.73 (m, 2H), 1.72-1.57 (m, 1H).

LC-MS (Method 3): R$_t$=2.13 min; 609 [M+H]$^+$.

Example 250

1-(2,4-Difluorophenyl)-N-[1-(2,6-difluorophenyl)-2,2,2-trifluoroethyl]-7-[3-hydroxy-2-oxopiperidin-1-yl]-4-oxo-1,4-dihydro-1,8-naphthyridine-3-carboxamide (3rd diastereomer)

$^1$H NMR (400 MHz, DMSO-d$_6$) δ [ppm]=11.37-11.31 (m, 1H), 8.89 (s, 1H), 8.70 (d, 1H), 8.13 (dd, 1H), 7.94-7.75 (m, 1H), 7.68-7.56 (m, 2H), 7.40-7.26 (m, 3H), 6.51-6.39 (m, 1H), 5.52-5.46 (m, 1H), 4.26-4.17 (m, 1H), 3.72-3.59 (m, 1H), 3.52-3.40 (m, 1H), 2.12-2.01 (m, 1H), 1.84-1.73 (m, 2H), 1.72-1.58 (m, 1H).

LC-MS (Method 3): $R_t$=2.12 min; 609 [M+H]$^+$.

Example 251

1-(2,4-Difluorophenyl)-N-[1-(2,6-difluorophenyl)-2,2,2-trifluoroethyl]-7-[3-hydroxy-2-oxopiperidin-1-yl]-4-oxo-1,4-dihydro-1,8-naphthyridine-3-carboxamide (4th diastereomer)

$^1$H NMR (400 MHz, DMSO-d$_6$) δ [ppm]=11.34 (br. d, 1H), 8.89 (s, 1H), 8.70 (d, 1H), 8.17-8.09 (m, 1H), 7.93-7.76 (m, 1H), 7.68-7.57 (m, 2H), 7.40-7.28 (m, 3H), 6.51-6.39 (m, 1H), 5.52-5.46 (m, 1H), 4.27-4.18 (m, 1H), 3.70-3.59 (m, 1H), 3.54-3.41 (m, 1H), 2.12-2.02 (m, 1H), 1.83-1.73 (m, 2H), 1.70-1.58 (m, 1H).
LC-MS (Method 3): $R_t$=2.13 min; 609 [M+H]$^+$.

Example 252 rac-1-(2,4-Difluorophenyl)-N-[1-(2,6-difluorophenyl)-2,2,2-trifluoroethyl]-7-[4-hydroxy-2-oxopiperidin-1-yl]-4-oxo-1,4-dihydro-1,8-naphthyridine-3-carboxamide (diastereomer mixture)

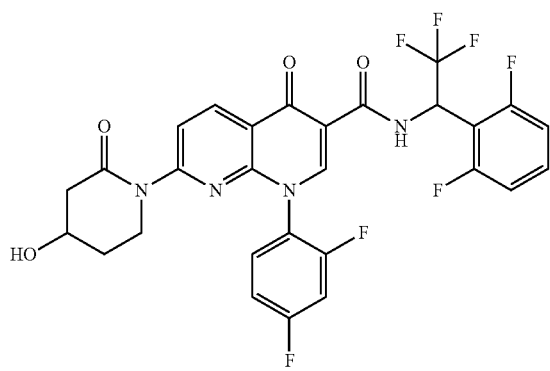 [SMILES: O=C(NC(c1c(F)cccc1F)C(F)(F)F)c1cn(-c2ccc(F)cc2F)c2nc(N3CCC(O)CC3=O)ccc2c1=O]

According to GP2, 150 mg (283 µmol) of the compound from Example 80A were reacted with 39.1 mg (340 µmol) of rac-4-hydroxypiperidin-2-one in the presence of 58.7 mg (425 µmol) of potassium carbonate, 13 mg (57 µmol) of palladium(II) acetate and 33 mg (57 µmol) of Xantphos in 2.5 ml of dioxane. The crude product was purified by means of preparative HPLC (column: Chromatorex C18, 10 µm, 125×40 mm, solvent: acetonitrile/0.1% formic acid gradient; (0 to 3 min. 10% acetonitrile to 40 min. 90% acetonitrile and a further 3 min. 90% acetonitrile), and 113 mg (65% of theory, 100% purity) of the title compound were obtained.

$^1$H NMR (400 MHz, DMSO-d$_6$) δ [ppm]=11.38-11.31 (m, 1H), 8.89 (s, 1H), 8.67 (d, 1H), 8.15-8.08 (m, 1H), 7.94-7.76 (m, 1H), 7.68-7.56 (m, 2H), 7.41-7.24 (m, 3H), 6.51-6.38 (m, 1H), 5.10-5.01 (m, 1H), 4.11-4.01 (m, 1H), 3.69-3.57 (m, 1H), 3.50-3.38 (m, 1H), 2.84-2.72 (m, 1H), 2.46-2.37 (m, 1H), 1.99-1.87 (m, 1H), 1.78-1.66 (m, 1H).
LC-MS (Method 3): $R_t$=2.12 min; 609 [M+H]$^+$.

100 mg of the title compound (racemic diastereomer mixture) were separated into the enantiomeric diastereomers by chiral HPLC (preparative HPLC: column: Daicel Chiralpak ID 5 µm 250×50 mm; eluent: 50% isohexane, 20% ethanol; temperature: 40° C.; flow rate: 15 ml/min; UV detection: 220 nm).

This gave (in the sequence of elution from the column) 22 mg of diastereomer 1 (99% de) $R_t$=8.70 min, 24 mg (99% de) of diastereomer 2 $R_t$=11.80 min, 24 mg (99.5% de) of diastereomer 3 $R_t$=6.47 min, and 24 mg (99.5% de) of diastereomer 4 $R_t$=5.94 min.

[Analytical HPLC: column: Daicel Chiralcel OZ-H 5 µm 250×4.6 mm; eluent: 50% isohexane, 50% ethanol; temperature: 40° C.; flow rate: 1 ml/min; UV detection: 220 nm]

Example 253

1-(2,4-Difluorophenyl)-N-[1-(2,6-difluorophenyl)-2,2,2-trifluoroethyl]-7-[4-hydroxy-2-oxopiperidin-1-yl]-4-oxo-1,4-dihydro-1,8-naphthyridine-3-carboxamide (diastereomer 1)

$^1$H NMR (400 MHz, DMSO-d$_6$) δ [ppm]=11.39-11.31 (m, 1H), 8.89 (s, 1H), 8.67 (d, 1H), 8.15-8.09 (m, 1H), 7.94-7.76 (m, 1H), 7.68-7.57 (m, 2H), 7.41-7.27 (m, 3H), 6.51-6.39 (m, 1H), 5.10-5.04 (m, 1H), 4.12-4.01 (m, 1H), 3.69-3.59 (m, 1H), 3.48-3.38 (m, 1H), 2.83-2.72 (m, 1H), 2.47-2.37 (m, 1H), 1.99-1.88 (m, 1H), 1.79-1.67 (m, 1H).
LC-MS (Method 3): $R_t$=1.99 min; 609 [M+H]$^+$.

Example 254

1-(2,4-Difluorophenyl)-N-[1-(2,6-difluorophenyl)-2,2,2-trifluoroethyl]-7-[4-hydroxy-2-oxopiperidin-1-yl]-4-oxo-1,4-dihydro-1,8-naphthyridine-3-carboxamide (diastereomer 2)

$^1$H NMR (400 MHz, DMSO-d$_6$) δ [ppm]=11.34 (br. d, 1H), 8.89 (s, 1H), 8.67 (d, 1H), 8.15-8.09 (m, 1H), 7.93-7.76 (m, 1H), 7.68-7.57 (m, 2H), 7.40-7.26 (m, 3H), 6.50-6.39 (m, 1H), 5.10-5.02 (m, 1H), 4.12-4.01 (m, 1H), 3.68-3.57 (m, 1H), 3.50-3.39 (m, 1H), 2.84-2.72 (m, 1H), 2.47-2.37- (m, 1H), 2.00-1.88 (m, 1H), 1.78-1.66 (m, 1H).
LC-MS (Method 3): $R_t$=2.00 min; 609 [M+H]$^+$.

Example 255

1-(2,4-Difluorophenyl)-N-[1-(2,6-difluorophenyl)-2,2,2-trifluoroethyl]-7-[4-hydroxy-2-oxopiperidin-1-yl]-4-oxo-1,4-dihydro-1,8-naphthyridine-3-carboxamide (3rd diastereomer)

$^1$H NMR (400 MHz, DMSO-d$_6$) δ [ppm]=11.38-11.32 (m, 1H), 8.89 (s, 1H), 8.67 (d, 1H), 8.16-8.07 (m, 1H), 7.95-7.75 (m, 1H), 7.68-7.57 (m, 2H), 7.41-7.26 (m, 3H), 6.51-6.39 (m, 1H), 5.11-5.02 (m, 1H), 4.11-4.01 (m, 1H), 3.69-3.58 (m, 1H), 3.48-3.38 (m, 1H), 2.84-2.72 (m, 1H), 2.48-2.37 (m, 1H), 2.00-1.88 (m, 1H), 1.79-1.67 (m, 1H).
LC-MS (Method 3): $R_t$=1.99 min; 609 [M+H]$^+$.

Example 256

1-(2,4-Difluorophenyl)-N-[1-(2,6-difluorophenyl)-2,2,2-trifluoroethyl]-7-[4-hydroxy-2-oxopiperidin-1-yl]-4-oxo-1,4-dihydro-1,8-naphthyridine-3-carboxamide (4th diastereomer)

$^1$H NMR (400 MHz, DMSO-d$_6$) δ [ppm]=11.35 (d, 1H), 8.89 (s, 1H), 8.67 (d, 1H), 8.15-8.09 (m, 1H), 7.93-7.77 (m, 1H), 7.68-7.58 (m, 2H), 7.40-7.28 (m, 3H), 6.50-6.39 (m, 1H), 5.10-5.04 (m, 1H), 4.11-4.02 (m, 1H), 3.68-3.58 (m, 1H), 3.50-3.39 (m, 1H), 2.83-2.73 (m, 1H), 2.47-2.37 (m, 1H), 1.99-1.88 (m, 1H), 1.78-1.67 (m, 1H).

LC-MS (Method 3): $R_t$=2.00 min; 609 [M+H]$^+$.

Example 257

Methyl (5S)-3-[8-(2,4-difluorophenyl)-5-oxo-6-{[(2R)-1,1,1-trifluorobutan-2-yl]carbamoyl}-5,8-dihydro-1,8-naphthyridin-2-yl]-2-oxo-1,3-oxazolidine-5-carboxylate

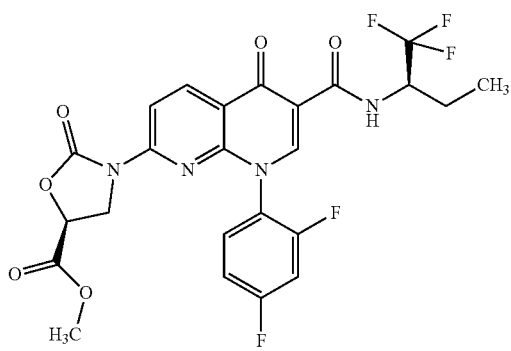 [SMILES: CC[C@@H](NC(=O)c1cn(-c2ccc(F)cc2F)c2nc(N3C[C@@H](C(=O)OC)OC3=O)ccc2c1=O)C(F)(F)F]

According to GP2, 100 mg (224 µmol) of the compound from Example 67A were reacted with 39.1 mg (269 µmol) of the compound from Example 96 in the presence of 46.5 mg (269 µmol) of potassium carbonate, 10 mg (45 µmol) of palladium(II) acetate and 26 mg (45 µmol) of Xantphos in 2 ml of 1,4-dioxane. The crude product was diluted with acetonitrile and water and purified by means of preparative HPLC (column: Chromatorex C18, 10 µm, 125×40 mm, solvent: acetonitrile/0.05% formic acid gradient; (0 to 3 min. 10% acetonitrile to 40 min. 90% acetonitrile and a further 3 min. 90% acetonitrile), and 101 mg (81% of theory, 100% purity) of the title compound were obtained.

$^1$H NMR (400 MHz, DMSO-d$_6$): δ [ppm]=0.98 (t, 3H), 1.60-1.72 (m, 1H), 1.84-1.95 (m, 1H), 3.73 (d, 3H), 3.77-3.89 (m, 1H), 3.96-4.08 (m, 1H), 4.70-4.83 (m, 1H), 5.23-5.32 (m, 1H), 7.37 (td, 1H), 7.63 (br. t, 1H), 7.82-7.93 (m, 1H), 8.26 (dd, 1H), 8.75 (d, 1H), 8.86 (d, 1H), 10.18 (d, 1H).

LC-MS (Method 2): $R_t$=2.07 min; 555 [M+H]$^+$.

Example 258

Methyl (5S)-3-[8-(2,4-difluorophenyl)-5-oxo-6-{[(2S)-1,1,1-trifluorobutan-2-yl]carbamoyl}-5,8-dihydro-1,8-naphthyridin-2-yl]-2-oxo-1,3-oxazolidine-5-carboxylate

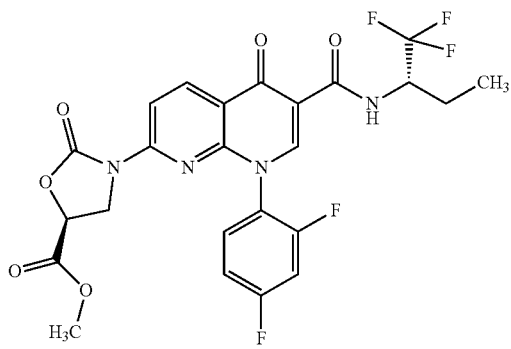 [SMILES: CC[C@H](NC(=O)c1cn(-c2ccc(F)cc2F)c2nc(N3C[C@@H](C(=O)OC)OC3=O)ccc2c1=O)C(F)(F)F]

According to GP2, 500 mg (1.12 mmol, 94% purity) of the compound from Example 68A were reacted with 195 mg (1.35 mmol) of the compound from Example 96 in the presence of 233 mg (1.68 mmol) of potassium carbonate, 50.4 mg (224 µmol) of palladium(II) acetate and 130 mg (224 µmol) of Xantphos in 10 ml of 1,4-dioxane. The crude product was diluted with acetonitrile and water and purified by means of preparative HPLC (column: Chromatorex C18, 10 µm, 125×40 mm, solvent: acetonitrile/0.05% formic acid gradient; (0 to 3 min. 10% acetonitrile to 40 min. 90% acetonitrile and a further 3 min. 90% acetonitrile), and 504 mg (81% of theory, 100% purity) of the title compound were obtained.

$^1$H NMR (400 MHz, DMSO-d$_6$): δ [ppm]=0.98 (t, 3H), 1.60-1.74 (m, 1H), 1.83-1.97 (m, 1H), 3.73 (d, 3H), 3.77-3.89 (m, 1H), 3.96-4.08 (m, 1H), 4.70-4.85 (m, 1H), 5.22-5.31 (m, 1H), 7.32-7.41 (m, 1H), 7.63 (td, 1H), 7.88 (td, 1H), 8.26 (t, 1H), 8.75 (d, 1H), 8.86 (s, 1H), 10.18 (d, 1H).

LC-MS (Method 1): $R_t$=1.13 min; 555 [M+H]$^+$.

Example 259

Methyl (5R)-3-[8-(2,4-difluorophenyl)-5-oxo-6-{[(2S)-1,1,1-trifluorobutan-2-yl]carbamoyl}-5,8-dihydro-1,8-naphthyridin-2-yl]-2-oxo-1,3-oxazolidine-5-carboxylate

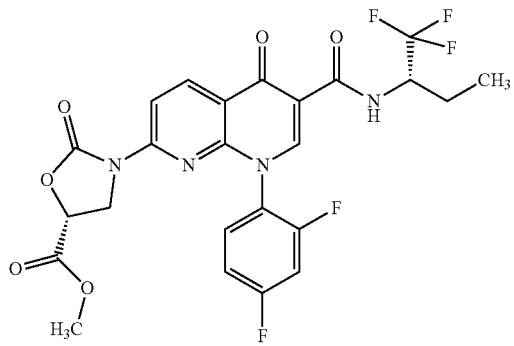 [SMILES: CC[C@H](NC(=O)c1cn(-c2ccc(F)cc2F)c2nc(N3C[C@H](C(=O)OC)OC3=O)ccc2c1=O)C(F)(F)F]

According to GP2, 500 mg (1.12 mmol, 94% purity) of the compound from Example 68A were reacted with 195 mg (1.35 mmol) of the compound from Example 99 in the presence of 233 mg (1.68 mmol) of potassium carbonate, 50.4 mg (224 µmol) of palladium(II) acetate and 130 mg (224 µmol) of Xantphos in 10 ml of 1,4-dioxane. The crude product was diluted with acetonitrile and water and purified by means of preparative HPLC (column: Chromatorex C18, 10 µm, 125×40 mm, solvent: acetonitrile/0.05% formic acid gradient; (0 to 3 min. 10% acetonitrile to 40 min. 90% acetonitrile and a further 3 min. 90% acetonitrile), and 497 mg (80% of theory, 100% purity) of the title compound were obtained.

$^1$H NMR (400 MHz, DMSO-d$_6$): δ [ppm]=0.98 (t, 3H), 1.59-1.74 (m, 1H), 1.83-1.96 (m, 1H), 3.73 (d, 3H), 3.77-3.89 (m, 1H), 3.96-4.09 (m, 1H), 4.70-4.84 (m, 1H), 5.23-5.32 (m, 1H), 7.32-7.41 (m, 1H), 7.57-7.68 (m, 1H), 7.82-7.94 (m, 1H), 8.26 (dd, 1H), 8.75 (d, 1H), 8.86 (d, 1H), 10.18 (d, 1H).

LC-MS (Method 1): $R_t$=1.14 min; 555 [M+H]$^+$.

Example 260 rac-1-(2,6-Difluorophenyl)-7-[5-(hydroxymethyl)-2-oxo-1,3-oxazolidin-3-yl]-4-oxo-N-[(2R)-1,1,1-trifluorobutan-2-yl]-1,4-dihydro-1,8-naphthyridine-3-carboxamide

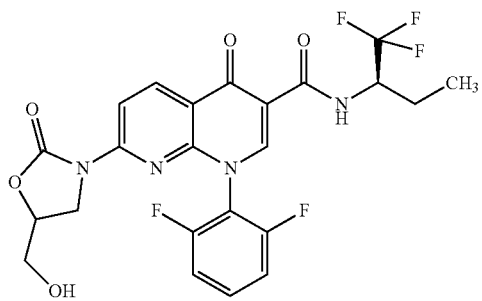 [SMILES: CC[C@@H](NC(=O)c1cn(-c2c(F)cccc2F)c2nc(N3CC(CO)OC3=O)ccc2c1=O)C(F)(F)F]

According to GP2, 40 mg (89.7 µmol, 99% purity) of the compound from Example 86A were reacted with 12.6 mg (108 µmol) of rac-5-(hydroxymethyl)-1,3-oxazolidin-2-one in the presence of 18.6 mg (135 µmol) of potassium carbonate, 4.0 mg (18 µmol) of palladium(II) acetate and 10 mg (18 µmol) of Xantphos in 1 ml of 1,4-dioxane. The reaction mixture was diluted with acetonitrile and water, filtered and purified by means of preparative HPLC (column: Chromatorex C18, 10 µm, 125×40 mm, solvent: acetonitrile/0.05% formic acid gradient; 0 to 3 min. 10% acetonitrile to 40 min. 90% acetonitrile and a further 3 min. 90% acetonitrile) and additionally by means of flash chromatography (cyclohexane/ethyl acetate gradient), and 10 mg (21% of theory, 100% purity) of the title compound were obtained.

$^1$H NMR (400 MHz, DMSO-d$_6$): δ [ppm]=0.98 (t, 3H), 1.59-1.75 (m, 1H), 1.83-1.96 (m, 1H), 3.42-3.55 (m, 2H), 3.56-3.66 (m, 1H), 3.75 (t, 1H), 4.62-4.71 (m, 1H), 4.72-4.83 (m, 1H), 5.18 (t, 1H), 7.39-7.50 (m, 2H), 7.69-7.80 (m, 1H), 8.34 (d, 1H), 8.73 (d, 1H), 9.01 (s, 1H), 10.12 (d, 1H).

LC-MS (Method 2): R$_t$=1.88 min; 527 [M+H]$^+$.

Example 261

1-(2,4-Difluorophenyl)-7-(3-hydroxyazetidin-1-yl)-4-oxo-N-[(2R)-1,1,1-trifluorobutan-2-yl]-1,4-dihydro-1,8-naphthyridine-3-carboxamide

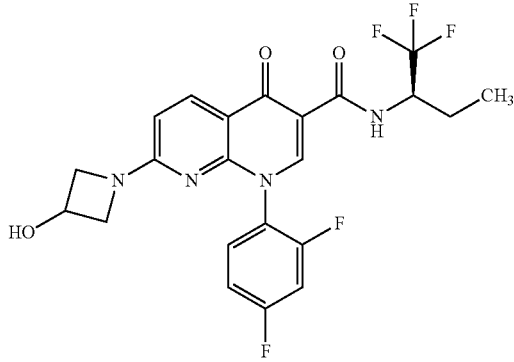 [SMILES: CC[C@@H](NC(=O)c1cn(-c2ccc(F)cc2F)c2nc(N3CC(O)C3)ccc2c1=O)C(F)(F)F]

According to GP3, 50.0 mg (112 µmol) of the compound from Example 67A were reacted with 14.7 mg (135 µmol) of 3-hydroxyazetidine hydrochloride and 68 µl (0.39 mmol) of N,N-diisopropylamine in 0.5 ml of dimethylformamide. The reaction solution was diluted with 0.5 ml each of acetonitrile and water and purified by means of preparative HPLC (column: Chromatorex C18, 10 µm, 125×30 mm, solvent: acetonitrile/0.05% formic acid gradient; 0 to 3 min 10% acetonitrile, to 40 min 90% acetonitrile and for a further 3 min 90% acetonitrile). 50.7 mg (93% of theory, 99% purity) of the title compound were obtained.

$^1$H NMR (400 MHz, DMSO-d$_6$): δ [ppm]=0.96 (t, 3H), 1.57-1.70 (m, 1H), 1.82-1.94 (m, 1H), 3.50-3.81 (br. m, 2H), 3.89-4.32 (br. m, 2H), 4.49-4.57 (m, 1H), 4.67-4.80 (m, 1H), 5.72 (d, 1H), 6.60 (d, 1H), 7.28-7.34 (m, 1H), 7.52-7.60 (m, 1H), 7.75-7.84 (m, 1H), 8.28 (d, 1H), 8.61 (s, 1H), 10.48 (d, 1H).

LC-MS (Method 1): R$_t$=1.00 min; 483 [M+H]$^+$.

Example 262

1-(2,4-Difluorophenyl)-7-[3-hydroxy-3-(trifluoromethyl)azetidin-1-yl]-4-oxo-N-[(2R)-1,1,1-trifluorobutan-2-yl]-1,4-dihydro-1,8-naphthyridine-3-carboxamide

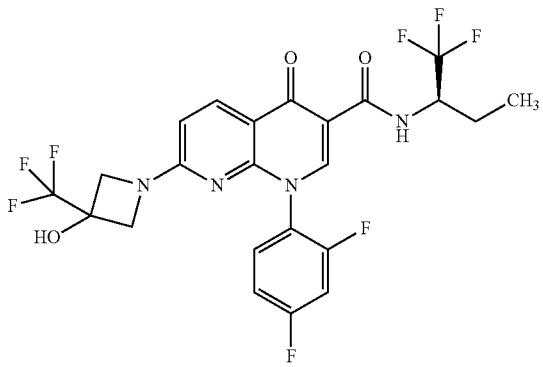 [SMILES: CC[C@@H](NC(=O)c1cn(-c2ccc(F)cc2F)c2nc(N3CC(O)(C(F)(F)F)C3)ccc2c1=O)C(F)(F)F]

According to GP3, 50.0 mg (112 µmol) of the compound from Example 67A were reacted with 19.0 mg (135 µmol) of 3-(trifluoromethyl)azetidin-3-ol and 68 µl (0.39 mmol) of N,N-diisopropylethylamine in 0.5 ml of dimethylformamide. The reaction solution was diluted with 0.5 ml of acetonitrile and purified by means of preparative HPLC (column: Chromatorex C18, 10 µm, 125×30 mm, solvent: acetonitrile/0.05% formic acid gradient; (0 to 3 min. 10% acetonitrile to 40 min. 90% acetonitrile and a further 3 min. 90% acetonitrile), and 51.9 mg (83% of theory, 99% purity) of the title compound were obtained.

$^1$H NMR (400 MHz, DMSO-d$_6$): δ [ppm]=0.97 (t, 3H), 1.57-1.71 (m, 1H), 1.82-1.94 (m, 1H), 3.67-4.51 (br. m, 4H), 4.68-4.81 (m, 1H), 6.75 (d, 1H), 7.29-7.36 (m, 1H), 7.43 (s, 1H), 7.54-7.62 (m, 1H), 7.77-7.86 (m, 1H), 8.38 (d, 1H), 8.66 (s, 1H), 10.42 (d, 1H).

LC-MS (Method 3): R$_t$=2.14 min; 551 [M+H]$^+$.

Example 263

7-[2-(Difluoromethyl)morpholin-4-yl]-1-(2,4-difluorophenyl)-4-oxo-N-[(2R)-1,1,1-trifluorobutan-2-yl]-1,4-dihydro-1,8-naphthyridine-3-carboxamide (diastereomer mixture)

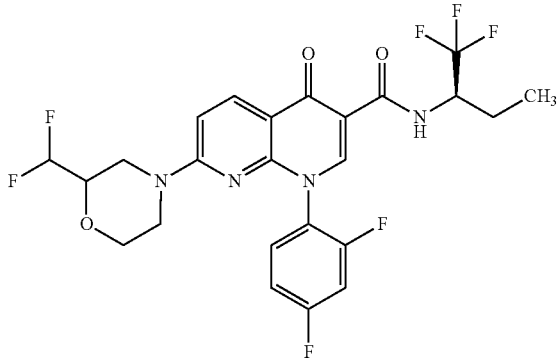 [SMILES: CC[C@@H](NC(=O)c1cn(-c2ccc(F)cc2F)c2nc(N3CCOC(C(F)F)C3)ccc2c1=O)C(F)(F)F]

According to GP3, 100 mg (224 µmol) of the compound from Example 67A were reacted with 36.9 mg (269 µmol) of rac-2-(difluoromethyl)morpholine and 137 µl (785 µmol) of N,N-diisopropylethylamine in 1 ml of dimethylformamide. The reaction solution was purified by means of preparative HPLC (column: Chromatorex C18, 10 µm, 125×30 mm, solvent: acetonitrile/0.05% formic acid gradient; (0 to 3 min. 10% acetonitrile to 40 min. 90% acetonitrile and a further 3 min. 90% acetonitrile), and 103 mg (83% of theory, 99% purity) of the title compound were obtained.

$^1$H NMR (400 MHz, DMSO-d$_6$): δ [ppm]=0.97 (t, 3H), 1.57-1.71 (m, 1H), 1.83-1.94 (m, 1H), 2.83-2.96 (m, 1H), 3.05-3.16 (m, 1H), 3.48-3.58 (m, 1H), 3.63-3.74 (m, 1H), 3.91-4.04 (m, 2H), 4.07-4.16 (m, 1H), 4.70-4.79 (m, 1H), 6.02 (t, 1H), 7.16 (d, 1H), 7.27-7.35 (m, 1H), 7.48-7.70 (m, 1H), 7.77-7.86 (m, 1H), 8.36 (d, 1H), 8.66-8.69 (m, 1H), 10.43 (d, 1H).

LC-MS (Method 3): R$_t$=2.19 min; 547 [M+H]$^+$.

98 mg of the title compound (diastereomer mixture) were separated into the diastereomers by chiral HPLC (preparative HPLC: column: Daicel Chiralcel OX-H 5 µm 250×20 mm; eluent: 25% ethanol, 75% isohexane; temperature: 40° C.; flow rate: 15 ml/min; UV detection: 220 nm).

This gave (in the sequence of elution from the column) 46 mg of diastereomer 1 (99% de) R$_t$=6.27 min and 46 mg (99% de) of diastereomer 2 R$_t$=7.92 min.

[Analytical HPLC: column: Chiralcel OX-3 5 µm 50×4.6 mm; eluent: 30% ethanol, 70% isohexane; temperature: 30° C.; flow rate: 1.0 ml/min; UV detection: 220 nm]

Diastereomer 1 (Example 264) was additionally purified by means of preparative HPLC (column: Chromatorex C18, 10 µm, 125×30 mm, solvent: acetonitrile/0.05% formic acid gradient; (0 to 3 min. 10% acetonitrile to 35 min. 90% acetonitrile and a further 3 min. 90% acetonitrile)), and 38.4 mg (31% of theory, 99% purity) of the title compound from Example 264 were obtained.

Diastereomer 2 (Example 265) was additionally purified by means of preparative HPLC (column: Chromatorex C18, 10 µm, 125×30 mm, solvent: acetonitrile/0.05% formic acid gradient; (0 to 3 min. 10% acetonitrile to 35 min. 90% acetonitrile and a further 3 min. 90% acetonitrile)), and 40.1 mg (32% of theory, 99% purity) of the title compound from Example 265 were obtained.

Example 264

7-[2-(Difluoromethyl)morpholin-4-yl]-1-(2,4-difluorophenyl)-4-oxo-N-[(2R)-1,1,1-trifluorobutan-2-yl]-1,4-dihydro-1,8-naphthyridine-3-carboxamide (diastereomer 1)

$^1$H NMR (400 MHz, DMSO-d$_6$): δ [ppm]=0.97 (t, 3H), 1.57-1.71 (m, 1H), 1.82-1.95 (m, 1H), 2.82-2.97 (m, 1H), 3.04-3.17 (m, 1H), 3.47-3.59 (m, 1H), 3.63-3.75 (m, 1H), 3.91-4.04 (m, 2H), 4.07-4.16 (m, 1H), 4.68-4.81 (m, 1H), 6.02 (t, 1H), 7.16 (d, 1H), 7.27-7.36 (m, 1H), 7.48-7.60 (m, 1H), 7.77-7.85 (m, 1H), 8.36 (d, 1H), 8.67 (d, 1H), 10.43 (d, 1H).

LC-MS (Method 3): Rt=2.20 min; 547 [M+H]$^+$.

Example 265

7-[2-(Difluoromethyl)morpholin-4-yl]-1-(2,4-difluorophenyl)-4-oxo-N-[(2R)-1,1,1-trifluorobutan-2-yl]-1,4-dihydro-1,8-naphthyridine-3-carboxamide (diastereomer 2)

$^1$H NMR (400 MHz, DMSO-d$_6$): δ [ppm]=0.97 (t, 3H), 1.57-1.71 (m, 1H), 1.81-1.95 (m, 1H), 2.82-2.96 (m, 1H), 3.04-3.16 (m, 1H), 3.46-3.58 (m, 1H), 3.62-3.75 (m, 1H), 3.89-4.04 (m, 2H), 4.07-4.16 (m, 1H), 4.67-4.81 (m, 1H), 6.02 (t, 1H), 7.16 (d, 1H), 7.26-7.36 (m, 1H), 7.47-7.60 (m, 1H), 7.77-7.86 (m, 1H), 8.36 (d, 1H), 8.67 (d, 1H), 10.43 (d, 1H).

LC-MS (Method 3): Rt=2.20 min; 547 [M+H]$^+$.

Example 266

1-(2,4-Difluorophenyl)-7-[5-methyl-2-oxo-1,3-oxazolidin-3-yl]-4-oxo-N-[(2R)-1,1,1-trifluorobutan-2-yl]-1,4-dihydro-1,8-naphthyridine-3-carboxamide (diastereomer mixture)

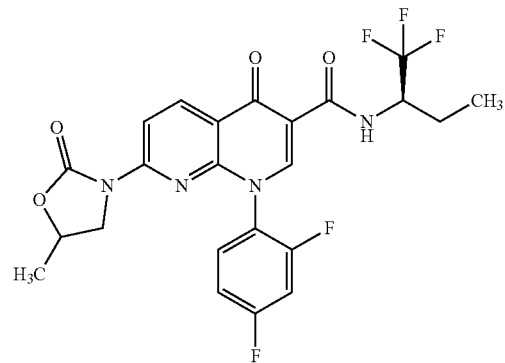 [SMILES: CC[C@@H](NC(=O)c1cn(-c2ccc(F)cc2F)c2nc(N3CC(C)OC3=O)ccc2c1=O)C(F)(F)F]

According to GP2, 100 mg (222 µmol) of the compound from Example 67A were reacted with 26.9 mg (266 µmol) of rac-5-methyl-1,3-oxazolidin-2-one in the presence of 36.8 mg (266 µmol) of potassium carbonate, 3.5 mg (16 µmol) of palladium(II) acetate and 26 mg (44 µmol) of Xantphos in 2 ml of 1,4-dioxane. The solvent was removed under reduced pressure and the residue was taken up in 3 ml of acetonitrile and 1 ml of DMSO. The precipitate was filtered off with suction and dried under high vacuum, and 24.5 mg (21.6% of theory, 100% purity) of the title compound were obtained.

$^1$H-NMR (400 MHz, DMSO-d6): δ [ppm]=0.98 (t, 3H), 1.31-1.40 (m, 3H), 1.60-1.72 (m, 1H), 1.83-1.93 (m, 1H), 3.83-3.95 (m, 1H), 4.69-4.84 (m, 2H), 7.31-7.39 (m, 1H), 7.55-7.66 (m, 1H), 7.82-7.92 (m, 1H), 8.32 (d, 1H), 8.72 (d, 1H), 8.84 (s, 1H), 10.21 (d, 1H).

LC-MS (Method 1): $R_t$=1.14 min; 511 [M+H]$^+$.

Example 267

1-(2,4-Difluorophenyl)-7-[1-hydroxy-3-azabicyclo[3.1.0]hex-3-yl]-4-oxo-N-[(2R)-1,1,1-trifluorobutan-2-yl]-1,4-dihydro-1,8-naphthyridine-3-carboxamide (diastereomer mixture)

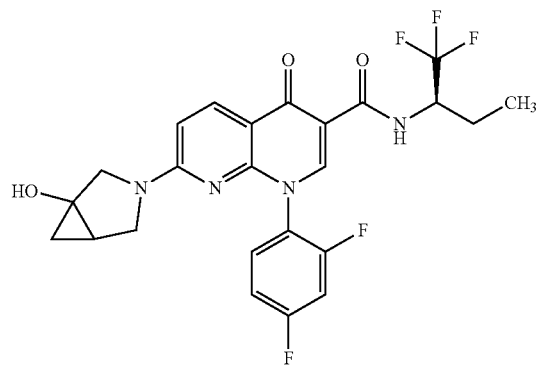 [SMILES: CC[C@@H](NC(=O)c1cn(-c2ccc(F)cc2F)c2nc(N3CC4CC4(O)C3)ccc2c1=O)C(F)(F)F]

According to GP3, 50.0 mg (112 µmol) of the compound from Example 67A were reacted with 19.2 mg (135 µmol) of rac-3-azabicyclo[3.1.0]hexan-1-ol hydrochloride and 68.0 µl (393 µmol) of N,N-diisopropylamine in 0.5 ml of dimethylformamide. The reaction solution was diluted with 0.5 ml of acetonitrile and purified by means of preparative HPLC (column: Chromatorex C18, 10 µm, 125×30 mm, solvent: acetonitrile/0.05% formic acid gradient; (0 to 3 min. 10% acetonitrile to 40 min. 90% acetonitrile and a further 3 min. 90% acetonitrile), and 41.4 mg (72% of theory, 99% purity) of the title compound were obtained.

$^1$H NMR (400 MHz, DMSO-d$_6$): δ [ppm]=0.32-0.50 (m, 1H), 0.89-1.09 (m, 4H), 1.50-1.72 (m, 2H), 1.81-1.94 (m, 1H), 3.04-3.95 (m, 4H), 4.66-4.81 (m, 1H), 6.01 (d, 1H), 6.66-6.82 (m, 1H), 7.27-7.38 (m, 1H), 7.52-7.66 (m, 1H), 7.75-7.86 (m, 1H), 8.28 (d, 1H), 8.62 (s, 1H), 10.48 (d, 1H).

LC-MS (Method 3): $R_t$=1.98 min; 509 [M+H]$^+$.

35 mg of the title compound (diastereomer mixture) were separated into the diastereomers by chiral HPLC (preparative HPLC: column: Daicel Chiralcel OZ-H 5 µm 250×20 mm; eluent: 25% 2-propanol, 75% isohexane; temperature: 25° C.; flow rate: 15 ml/min; UV detection: 210 nm).

This gave (in the sequence of elution from the column) 15.4 mg of diastereomer 1 (100% de) $R_t$=1.34 min and 20.1 mg (97% de) of diastereomer 2 $R_t$=1.59 min.

[Analytical HPLC: column: Daicel Chiralpak OZ-3 3 µm 50×4.6 mm; eluent: 20% ethanol, 80% isohexane; flow rate: 1 ml/min; UV detection: 220 nm].

Diastereomer 1 was additionally purified by means of preparative HPLC (column: Chromatorex C18, 10 µm, 125×30 mm, solvent: acetonitrile/0.05% formic acid gradient; (0 to 3 min. 10% acetonitrile to 35 min. 90% acetonitrile and a further 3 min. 90% acetonitrile)), and 8.8 mg (15% of theory, 99% purity) of the title compound from Example 314 were obtained.

Diastereomer 2 was additionally purified by means of preparative HPLC (column: Chromatorex C18, 10 µm, 125×30 mm, solvent: acetonitrile/0.05% formic acid gradient; (0 to 3 min. 10% acetonitrile to 35 min. 90% acetonitrile and a further 3 min. 90% acetonitrile)), and 8.4 mg (15% of theory, 99% purity) of the title compound from Example 315 were obtained.

Example 268

7-[(4S)-4-Hydroxy-2-oxopyrrolidin-1-yl]-4-oxo-N-[(2R)-1,1,1-trifluorobutan-2-yl]-1-[2-(trifluoromethyl)phenyl]-1,4-dihydro-1,8-naphthyridine-3-carboxamide (atropisomer mixture)

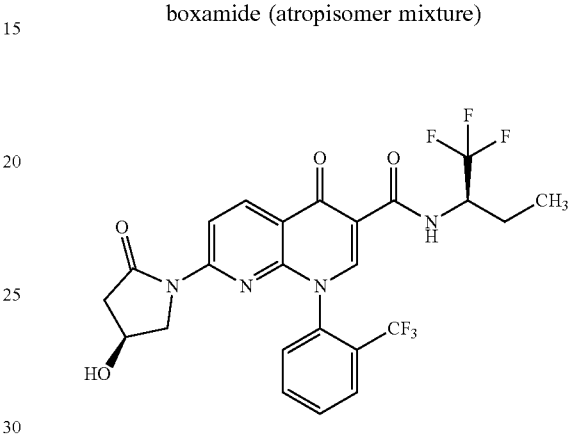

According to GP2, 55.0 mg (115 µmol) of the compound from Example 92A were reacted with 11.6 mg (115 µmol) of (4S)-4-hydroxypyrrolidin-2-one in the presence of 56.3 mg (173 µmol) of caesium carbonate, 4.7 mg (21 µmol) of palladium(II) acetate and 24 mg (41 µmol) of Xantphos in 2.3 ml of 1,4-dioxane. Subsequently, the mixture was diluted with 3 ml of acetonitrile and 0.5 ml of water, filtered and purified by means of preparative HPLC (column: Chromatorex C18, 10 µm, 125×30 mm, solvent: acetonitrile/0.05% formic acid gradient; 0 to 3 min 10% acetonitrile, to 35 min 90% acetonitrile and for a further 3 min 90% acetonitrile). 22 mg (35% of theory, 99% purity) of the title compound were obtained as a mixture of the atropisomers.

In analogy to the experimental procedure described in A, 56 mg (117 µmol) of the compound from Example 93A were reacted with 11.9 mg (117 µmol) of (4S)-4-hydroxypyrrolidin-2-one in the presence of 57.3 mg (176 µmol) of caesium carbonate, 4.7 mg (21 µmol) of palladium(II) acetate and 24 mg (41 µmol) of Xantphos in 2.3 ml of 1,4-dioxane. Subsequently, the mixture was diluted with 3 ml of acetonitrile and 0.5 ml of water, filtered and purified by means of preparative HPLC (column: Chromatorex C18, 10 µm, 125×30 mm, solvent: acetonitrile/0.05% formic acid gradient; 0 to 3 min 10% acetonitrile, to 35 min 90% acetonitrile and for a further 3 min 90% acetonitrile). 27 mg (42% of theory, 99% purity) of the title compound were obtained as a mixture of the atropisomers.

The mixture of the atropisomers A and B was combined and the combined batch was then separated into the atropisomers by chiral HPLC (preparative HPLC: column: Daicel Chiralcel OZ-H 5 µm 250×20 mm; eluent: 30% ethanol, 70% isohexane; temperature: 25° C.; flow rate: 15 ml/min; UV detection: 220 nm).

This gave (in the sequence of elution from the column) 22 mg of atropisomer 1 (90% de) $R_t$=3.99 min and 18 mg (83% de) of atropisomer 2 $R_t$=4.79 min.

[Analytical HPLC: column: Daicel Chiralpak AZ-H 5 μm 250×4.6 mm; eluent: 30% ethanol, 70% isohexane with 0.2% diethylamine; temperature: 50° C.; flow rate: 1.0 ml/min; UV detection: 270 nm]

Atropisomer 1 was additionally purified by means of preparative HPLC (column: Chromatorex C18, 10 μm, 125×30 mm, solvent: acetonitrile/0.05% formic acid gradient; (0 to 3 min. 10% acetonitrile to 35 min. 90% acetonitrile and a further 3 min. 90% acetonitrile)), and 16.8 mg (26.6% of theory, 99% purity) of the title compound from Example 269 were obtained.

Atropisomer 2 was additionally purified by means of preparative HPLC (column: Chromatorex C18, 10 μm, 125×30 mm, solvent: acetonitrile/0.05% formic acid gradient; (0 to 3 min. 10% acetonitrile to 35 min. 90% acetonitrile and a further 3 min. 90% acetonitrile)), and 20.1 mg (32% of theory, 99% purity) of the title compound from Example 270 were obtained.

Example 269

7-[(4S)-4-Hydroxy-2-oxopyrrolidin-1-yl]-4-oxo-N-[(2R)-1,1,1-trifluorobutan-2-yl]-1-[2-(trifluoromethyl)phenyl]-1,4-dihydro-1,8-naphthyridine-3-carboxamide (atropisomer 1)

$^1$H-NMR (400 MHz, DMSO-d$_6$): δ [ppm]=0.97 (t, 3H), 1.59-1.73 (m, 1H), 1.83-1.95 (m, 1H), 2.32 (d, 1H), 2.93 (dd, 1H), 3.47 (dd, 1H), 4.17-4.23 (m, 1H), 4.70-4.82 (m, 1H), 5.27 (d, 1H), 7.91-7.84 (m, 2H), 7.95-8.00 (m, 1H), 8.02-8.07 (m, 1H), 8.51 (d, 1H), 8.71 (d, 1H), 8.82 (s, 1H), 10.24 (d, 1H).

LC-MS (Method 3): R$_t$=1.88 min; 543 [M+H]$^+$.

Example 270

7-[(4S)-4-Hydroxy-2-oxopyrrolidin-1-yl]-4-oxo-N-[(2R)-1,1,1-trifluorobutan-2-yl]-1-[2-(trifluoromethyl)phenyl]-1,4-dihydro-1,8-naphthyridine-3-carboxamide (atropisomer 2)

$^1$H-NMR (400 MHz, DMSO-d$_6$): δ [ppm]=0.99 (t, 3H), 1.61-1.75 (m, 1H), 1.84-1.96 (m, 1H), 2.34 (d, 1H), 2.89 (dd, 1H), 3.25 (d, 1H), 3.47 (dd, 1H), 4.17-4.24 (m, 1H), 4.69-4.83 (m, 1H), 5.29 (d, 1H), 7.82-7.91 (m, 2H), 7.93-7.99 (m, 1H), 8.02-8.07 (m, 1H), 8.49 (d, 1H), 8.71 (d, 1H), 8.81 (s, 1H), 10.23 (d, 1H).

LC-MS (Method 3): R$_t$=1.87 min; 543 [M+H]$^+$.

Example 271

N-[(1R)-1-Cyclopropyl-2,2,2-trifluoroethyl]-1-(2,4-difluorophenyl)-7-[(4S)-4-hydroxy-2-oxopyrrolidin-1-yl]-4-oxo-1,4-dihydro-1,8-naphthyridine-3-carboxamide

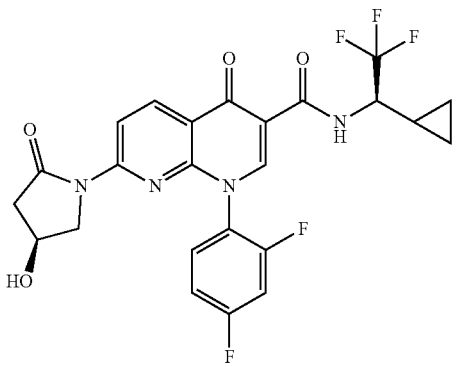 [SMILES: O=C(N[C@H](C1CC1)C(F)(F)F)c1cn(-c2ccc(F)cc2F)c2nc(N3C[C@@H](O)CC3=O)ccc2c1=O]

According to GP1, 74.0 mg (167 μmol, 90.8% purity) of the compound from Example 63A were reacted with 32.3 mg (184 μmol) of (R)-1-cyclopropyl-2,2,2-trifluoroethanamine hydrochloride (*J. Med. Chem.* 2011, 54, 7334-7349) in the presence of 63.7 mg (167 μmol) of HATU and 70 μl (0.40 mmol) of N,N-diisopropylethylamine in 0.9 ml of dimethylformamide. 1 ml of 1M aqueous hydrochloric acid and 10 ml of water were added and the mixture was extracted three times with 10 ml of ethyl acetate. The combined organic phases were dried over magnesium sulphate and filtered, and the solvent was removed under reduced pressure. The residue was taken up in a little DCM and purified by means of flash chromatography (cyclohexane/ethyl acetate gradient). 75.3 mg (86% of theory, 100% purity) of the title compound were obtained.

$^1$H-NMR (400 MHz, DMSO-d$_6$): δ [ppm]=0.29-0.38 (m, 1H). 0.51-0.71 (m, 3H), 1.18-1.28 (m, 1H), 2.31-2.42 (m, 1H), 2.87-3.00 (m, 1H), 3.42-3.52 (m, 1H), 3.61-3.72 (m, 1H), 4.25-4.32 (m, 1H), 4.34-4.49 (m, 1H), 5.32 (dd, 1H), 7.41-7.33 (m, 1H), 7.59-7.67 (m, 1H), 7.83-7.92 (m, 1H), 8.49-8.55 (m, 1H), 8.71 (d, 1H), 8.84 (s, 1H), 10.36 (dd, 1H).

LC-MS (Method 3): R$_t$=1.89 min; 523 [M+H]$^+$.

Example 272

1-(2,4-Difluorophenyl)-7-[(4S)-4-hydroxy-2-oxopyrrolidin-1-yl]-4-oxo-N-[2,2,2-trifluoro-1-(3-fluorophenyl)ethyl]-1,4-dihydro-1,8-naphthyridine-3-carboxamide (diastereomer mixture)

According to GP1, 170 mg (352 µmol, 83% purity) of the compound from Example 63A were reacted with 102 mg (527 µmol) of rac-2,2,2-trifluoro-1-(3-fluorophenyl)ethanamine in the presence of 134 mg (352 µmol) of HATU and 86 µl (0.49 mmol) of N,N-diisopropylethylamine in 3.5 ml of dimethylformamide. 1 ml of 1M aqueous hydrochloric acid and 10 ml of water were added and the mixture was extracted three times with 10 ml of ethyl acetate. The combined organic phases were dried over magnesium sulphate and filtered, and the solvent was removed under reduced pressure. The residue was taken up in a little DCM and purified by means of flash chromatography (cyclohexane/ethyl acetate gradient). 107 mg (53% of theory, 100% purity) of the title compound were obtained.

$^1$H-NMR (400 MHz, DMSO-d$_6$): δ [ppm]=2.31-2.42, 2.88-3.00 (m, 1H), 3.41-3.52 (m, 1H), 3.61-3.72 (m, 1H), 4.25-4.32 (m, 1H), 5.32 (d, 1H), 6.15-6.25 (m, 1H), 7.27-7.49 (m, 4H), 7.52-7.68 (m, 2H), 7.76-7.94 (m, 1H), 8.51-8.57 (m, 1H), 8.77 (d, 1H), 8.87 (s, 1H), 11.21 (d, 1H).

LC-MS (Method 3): R$_t$=2.04 min; 577 [M+H]$^+$.

Example 273

1-(2,4-Difluorophenyl)-7-[(4S)-4-hydroxy-2-oxopyrrolidin-1-yl]-4-oxo-N-[2,2,2-trifluoro-1-(4-fluorophenyl)ethyl]-1,4-dihydro-1,8-naphthyridine-3-carboxamide (diastereomer mixture)

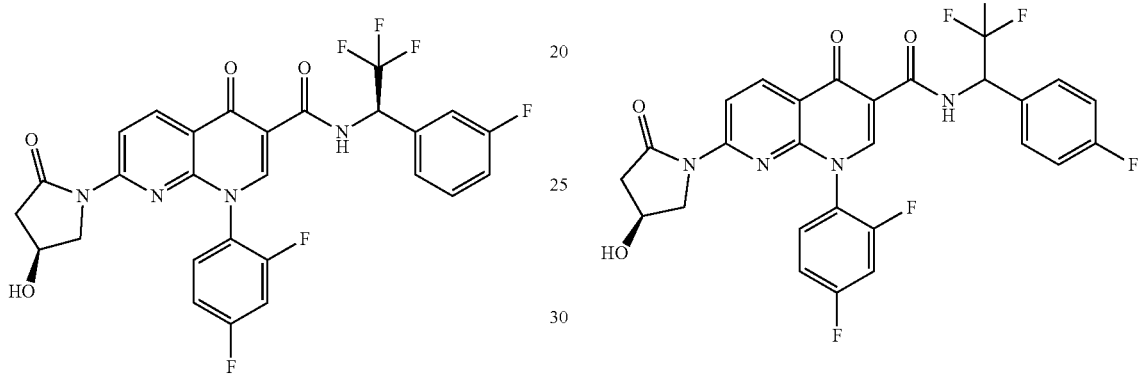

According to GP1, 170 mg (352 µmol, 83% purity) of the compound from Example 63A were reacted with 81.5 mg (422 µmol) of rac-2,2,2-trifluoro-1-(4-fluorophenyl)ethanamine in the presence of 134 mg (352 µmol) of HATU and 86 µl (0.49 mmol) of N,N-diisopropylethylamine in 3.5 ml of dimethylformamide. 1 ml of 1M aqueous hydrochloric acid and 10 ml of water were added and the mixture was extracted three times with 10 ml of ethyl acetate. The combined organic phases were washed with saturated aqueous sodium chloride solution, dried over magnesium sulphate and filtered, and the solvent was removed under reduced pressure. The residue was taken up in a little dichloromethane and purified by means of flash chromatography (cyclohexane/ethyl acetate gradient). 98 mg (48% of theory, 100% purity) of the title compound were obtained.

$^1$H-NMR (400 MHz, DMSO-d$_6$): δ [ppm]=2.32-2.42 (m, 1H). 2.88-3.00 (m, 1H), 3.42-3.52 (m, 1H), 3.61-3.72 (m, 1H), 4.25-4.32 (m, 1H), 5.32 (d, 1H), 6.09-6.21 (m, 1H), 7.30-7.42 (m, 3H), 7.58-7.68 (m, 3H), 7.77-7.93 (m, 1H), 8.51-8.57 (m, 1H), 8.76 (d, 1H), 8.86 (s, 1H), 11.20 (d, 1H).

LC-MS (Method 3): R$_t$=2.03 min; 577 [M+H]$^+$.

Example 274

N-[1-(3-Chlorophenyl)-2,2,2-trifluoroethyl]-1-(2,4-difluorophenyl)-7-[(4S)-4-hydroxy-2-oxopyrrolidin-1-yl]-4-oxo-1,4-dihydro-1,8-naphthyridine-3-carboxamide (diastereomer mixture)

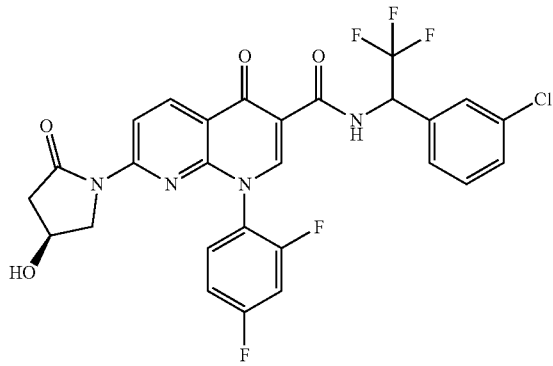 [SMILES: O=C(NC(c1cccc(Cl)c1)C(F)(F)F)c1cn(-c2ccc(F)cc2F)c2nc(N3C[C@@H](O)CC3=O)ccc2c1=O]

According to GP1, 170 mg (352 µmol, 83% purity) of the compound from Example 63A were reacted with 88.4 mg (422 µmol) of rac-1-(3-chlorophenyl)-2,2,2-trifluoroethanamine in the presence of 134 mg (352 µmol) of HATU and 86 µl (0.49 mmol) of N,N-diisopropylethylamine in 3.5 ml of dimethylformamide. 1 ml of 1 M aqueous hydrochloric acid and 10 ml of water were added and the mixture was extracted three times with 10 ml of ethyl acetate. The combined organic phases were washed with saturated aqueous sodium chloride solution, dried over magnesium sulphate and filtered, and the solvent was removed under reduced pressure. The residue was taken up in a little dichloromethane and purified by means of flash chromatography (cyclohexane/ethyl acetate gradient). 127 mg (61% of theory, 100% purity) of the title compound were obtained.

$^1$H-NMR (400 MHz, DMSO-$d_6$): δ [ppm]=2.31-2.42 (m, 1H), 2.87-3.01 (m, 1H), 3.42-3.53 (m, 1H), 3.60-3.73 (m, 1H), 4.25-4.32 (m, 1H), 5.32 (d, 1H), 6.15-6.25 (m, 1H), 7.31-7.41 (m, 1H), 7.51-7.71 (m, 5H), 7.77-7.94 (m, 1H), 8.51-8.57 (m, 1H), 8.77 (d, 1H), 8.86 (s, 1H), 11.22 (d, 1H).

LC-MS (Method 3): $R_t$=2.15 min; 593 [M+H]$^+$.

Example 275

1-(2,6-Difluorophenyl)-7-[(4S)-4-hydroxy-2-oxopyrrolidin-1-yl]-4-oxo-N-[(2R)-1,1,1-trifluorobutan-2-yl]-1,4-dihydro-1,8-naphthyridine-3-carboxamide

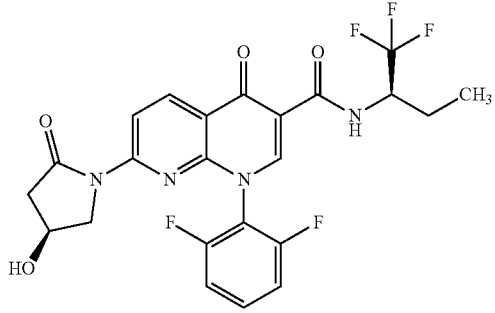 [SMILES: CC[C@@H](NC(=O)c1cn(-c2c(F)cccc2F)c2nc(N3C[C@@H](O)CC3=O)ccc2c1=O)C(F)(F)F]

According to GP2, 100 mg (224 µmol) of the compound from Example 86A were reacted with 22.7 mg (224 µmol) of (4S)-4-hydroxypyrrolidin-2-one in the presence of 109 mg (336 µmol) of caesium carbonate, 9.1 mg (40 µmol) of palladium(II) acetate and 47 mg (81 µmol) of Xantphos in 5 ml of 1,4-dioxane. This was followed by dilution with 2 ml of acetonitrile and 0.5 ml of water, filtration and purification by means of preparative HPLC (column: Chromatorex C18, 10 µm, 125×30 mm, solvent: acetonitrile/0.05% formic acid gradient; (0 to 3 min. 10% acetonitrile to 35 min. 90% acetonitrile and a further 3 min. 90% acetonitrile), and 33.2 mg (29% of theory, 99% purity) of the title compound were obtained.

$^1$H-NMR (400 MHz, DMSO-$d_6$): δ [ppm]=0.99 (t, 3H). 1.60-1.74 (m, 1H), 1.84-1.96 (m, 1H), 2.37 (d, 1H), 2.93 (dd, 1H), 3.43 (d, 1H), 3.64 (dd, 1H), 4.21-4.30 (m, 1H), 4.70-4.83 (m, 1H), 5.32 (d, 1H), 7.42-7.50 (m, 2H), 7.72-7.81 (m, 1H), 8.54 (d, 1H), 8.72 (d, 1H), 9.02 (s, 1H), 10.13 (d, 1H).

LC-MS (Method 3): $R_t$=1.86 min; 511 [M+H]$^+$.

Example 276

1-(2,6-Difluorophenyl)-7-[3-hydroxy-3-methylpyrrolidin-1-yl]-4-oxo-N-[(2R)-1,1,1-trifluorobutan-2-yl]-1,4-dihydro-1,8-naphthyridine-3-carboxamide (diastereomer mixture)

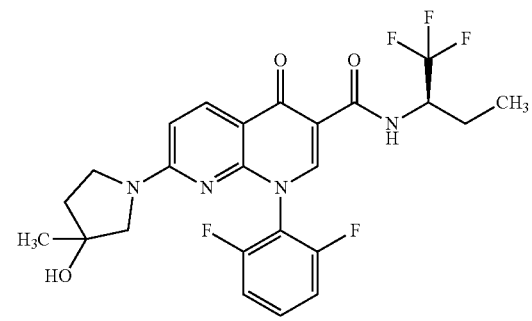 [SMILES: CC[C@@H](NC(=O)c1cn(-c2c(F)cccc2F)c2nc(N3CCC(C)(O)C3)ccc2c1=O)C(F)(F)F]

According to GP3, 100 mg (224 µmol) of the compound from Example 86A were reacted with 41.2 mg (269 µmol, 90% purity) of rac-3-methylpyrrolidin-3-ol hydrochloride and 137 µl (785 µmol) of N,N-diisopropylethylamine in 1 ml of dimethylformamide. The mixture was diluted with 0.5 ml of acetonitrile and the crude solution was purified by means of preparative HPLC (column: Chromatorex C18, 10 µm, 125×30 mm, solvent: acetonitrile/0.05% formic acid gradient; (0 to 3 min. 10% acetonitrile to 40 min. 90% acetonitrile and a further 3 min. 90% acetonitrile), and 96.4 mg (83% of theory, 99% purity) of the title compound were obtained.

$^1$H NMR (400 MHz, DMSO-$d_6$): δ [ppm]=0.97 (t, 3H), 1.22/1.31 (2×s, 3H), 1.57-1.72 (m, 1H), 1.72-1.80 (m, 1H), 1.82-1.95 (m, 2H), 2.90/3.09 (2×d, 1H), 3.13-3.21 (m, 1H), 3.23-3.40 (m, 1H, partially under the DMSO peak), 3.49-3.59 (m, 1H), 4.67-4.79 (m, 1H), 4.84 (d, 1H), 6.74 (dd, 1H), 7.36-7.46 (m, 2H), 7.65-7.76 (m, 1H), 8.24-8.31 (m, 1H), 8.73 (d, 1H), 10.45 (d, 1H).

LC-MS (Method 3): $R_t$=2.00 min; 511 [M+H]$^+$.

90 mg of the title compound (diastereomer mixture) were separated into the diastereomers by chiral HPLC (preparative HPLC: column: Daicel Chiralpak IE-H 5 µm 250×20 mm; eluent: 20% ethanol, 80% isohexane; temperature: 25° C.; flow rate: 15 ml/min; UV detection: 220 nm).

This gave (in the sequence of elution from the column) 43 mg of diastereomer 1 (99% de) $R_t$=6.98 min and 45 mg (94% de) of diastereomer 2 $R_t$=7.36 min.

[Analytical HPLC: column: Chiralpak IE-3 5 μm 250×4.6 mm; eluent: 25% ethanol, 75% isohexane; temperature: 30° C.; flow rate: 1.0 ml/min; UV detection: 220 nm]

Diastereomer 1 was additionally purified by means of preparative HPLC (column: Chromatorex C18, 10 μm, 125× 30 mm, solvent: acetonitrile/0.05% formic acid gradient; (0 to 3 min. 10% acetonitrile to 35 min. 90% acetonitrile and a further 3 min. 90% acetonitrile)), and 35.8 mg (31% of theory, 99% purity) of the title compound from Example 276 were obtained.

Diastereomer 2 was additionally purified by means of preparative HPLC (column: Chromatorex C18, 10 μm, 125× 30 mm, solvent: acetonitrile/0.05% formic acid gradient; (0 to 3 min. 10% acetonitrile to 35 min. 90% acetonitrile and a further 3 min. 90% acetonitrile)), and 36.0 mg (31% of theory, 99% purity) of the title compound from Example 277 were obtained.

Example 277

1-(2,6-Difluorophenyl)-7-[3-hydroxy-3-methylpyrrolidin-1-yl]-4-oxo-N-[(2R)-1,1,1-trifluorobutan-2-yl]-1,4-dihydro-1,8-naphthyridine-3-carboxamide (diastereomer 1)

$^1$H NMR (400 MHz, DMSO-$d_6$): δ [ppm]=0.97 (t, 3H), 1.22/1.31 (2×s, 3H), 1.58-1.71 (m, 1H), 1.73-1.80 (m, 1H), 1.83-1.94 (m, 2H), 2.91/3.09 (2×d, 1H), 3.13-3.21 (m, 1H), 3.27-3.39 (m, 1H, partially under the DMSO peak), 3.51-3.58 (m, 1H), 4.67-4.78 (m, 1H), 4.85 (d, 1H), 6.74 (dd, 1H), 7.37-7.45 (m, 2H), 7.65-7.76 (m, 1H), 8.24-8.31 (m, 1H), 8.74 (d, 1H), 10.45 (d, 1H).

LC-MS (Method 3): $R_t$=2.01 min; 511 [M+H]$^+$.

Example 278

1-(2,6-Difluorophenyl)-7-[3-hydroxy-3-methylpyrrolidin-1-yl]-4-oxo-N-[(2R)-1,1,1-trifluorobutan-2-yl]-1,4-dihydro-1,8-naphthyridine-3-carboxamide (diastereomer 2)

$^1$H NMR (400 MHz, DMSO-$d_6$): δ [ppm]=0.97 (t, 3H). 1.22/1.31 (2×s, 3H), 1.57-1.71 (m, 1H), 1.73-1.80 (m, 1H), 1.82-1.95 (m, 2H), 2.91/3.09 (2×d, 1H), 3.13-3.21 (m, 1H), 3.26-3.39 (m, 1H, partially under the DMSO peak), 3.50-3.57 (m, 1H), 4.67-4.79 (m, 1H), 4.85 (d, 1H), 6.74 (dd, 1H), 7.37-7.46 (m, 2H), 7.65-7.76 (m, 1H), 8.24-8.32 (m, 1H), 8.74 (d, 1H), 10.45 (d, 1H), LC-MS (Method 3): $R_t$=2.01 min; 511 [M+H]$^+$.

Example 279

1-(2-Chlorophenyl)-N-[1-cyclopropyl-2,2,2-trifluoroethyl]-7-[(4S)-4-hydroxy-2-oxopyrrolidin-1-yl]-4-oxo-1,4-dihydro-1,8-naphthyridine-3-carboxamide (diastereomer mixture)

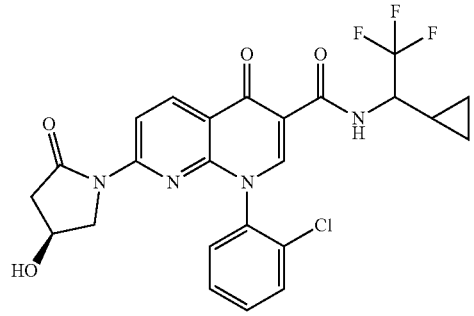 [SMILES: O=C(NC(C1CC1)C(F)(F)F)c1cn(-c2ccccc2Cl)c2nc(N3C[C@@H](O)CC3=O)ccc2c1=O]

According to GP1, 30 mg (75 μmol) of the compound from Example 64A were reacted with 19.8 mg (11.3 μmol) of rac-1-cyclopropyl-2,2,2-trifluoroethanamine hydrochloride in the presence of 29 mg (75 μmol) of HATU and 39 μl (0.23 mmol) of N,N-diisopropylethylamine in 0.77 ml of dimethylformamide. The mixture was diluted with 1 ml of acetonitrile and 0.5 ml of water and the solution was purified by means of preparative HPLC (column: Chromatorex C18, 10 μm, 125×30 mm, solvent: acetonitrile/0.05% formic acid gradient; 0 to 3 min 10% acetonitrile, to 35 min 90% acetonitrile and for a further 3 min 90% acetonitrile). 25.8 mg (65% of theory, 99% purity) of the title compound were obtained.

$^1$H-NMR (400 MHz, DMSO-$d_6$): δ [ppm]=0.30-0.40 (m, 1H), 0.50-0.71 (m, 3H), 1.18-1.29 (m, 1H), 2.31-2.39 (m, 1H), 2.86-2.97 (m, 1H), 3.33-3.41 (m, 1H), 3.52-3.61 (m, 1H), 4.20-4.26 (m, 1H), 4.35-4.47 (m, 1H), 5.31 (dd. 1H), 7.58-7.70 (m, 2H), 7.76-7.83 (m, 2H), 8.51 (dd, 1H), 8.70-8.75 (min, 2H), 10.38 (dd, 1H).

LC-MS (Method 1): $R_t$=1.02 min; 521 [M+H]$^+$.

Example 280

7-[3-Hydroxy-2-oxopyrrolidin-1-yl]-4-oxo-N-[(2R)-1,1,1-trifluorobutan-2-yl]-1-(2,4,6-trifluorophenyl)-1,4-dihydro-1,8-naphthyridine-3-carboxamide (diastereomer mixture)

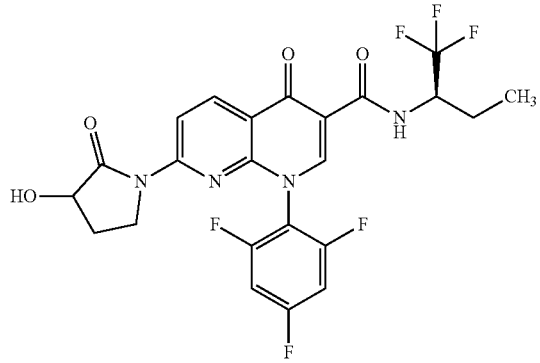 [SMILES: CC[C@@H](NC(=O)c1cn(-c2c(F)cc(F)cc2F)c2nc(N3CCC(O)C3=O)ccc2c1=O)C(F)(F)F]

According to GP2, 150 mg (323 µmol) of the compound from Example 100C were reacted with 32.7 mg (323 µmol) of 3-hydroxypyrrolidin-2-one (CAS: 15166-68-4) in the presence of 67.1 mg (485 µmol) of potassium carbonate, 13 mg (58 µmol) of palladium(II) acetate and 67.4 mg (116 µmol) of Xantphos in 2.97 ml of 1,4-dioxane. Subsequently, the volume of the mixture was reduced under reduced pressure and it was diluted with 3 ml of acetonitrile and 1 ml of aqueous hydrochloric acid, filtered and purified by means of preparative HPLC (column: Chromatorex C18, 10 µm, 125×30 mm, solvent: acetonitrile/0.05% formic acid gradient; (0 to 3 min. 10% acetonitrile to 35 min. 90% acetonitrile and a further 3 min. 90% acetonitrile), and 118.4 mg (69% of theory, 99% purity) of the title compound were obtained.

$^1$H-NMR (400 MHz, DMSO-$d_6$): δ [ppm]=10.11 (d, 1H), 9.08 (s, 1H), 8.74 (d, 1H), 8.55 (d, 1H), 7.64-7.56 (m, 2H), 5.91 (d, 1H), 4.83-4.71 (min, 1H), 4.43-4.35 (m, 1H), 3.62-3.54 (m, 1H), 3.38-3.32 (m, 1H), 2.36-2.27 (m, 1H), 1.95-1.60 (min, 3H), 0.98 (t, 3H).

LC-MS (Method 1): $R_t$=1.00 min; 529 [M+H]$^+$.

110 mg of the title compound (diastereomer mixture) were separated into the diastereomers by chiral HPLC (preparative HPLC: column: Daicel Chiralcel OZ-H 5 µm 250×20 mm; eluent: 20% ethanol, 80% isohexane; temperature: 23° C.; flow rate: 20 ml/min; UV detection: 220 nm).

This gave (in the sequence of elution from the column) 41.4 mg of diastereomer 1 (100% de) $R_t$=2.27 min and 44.8 mg (93% de) of diastereomer 2 $R_t$=2.67 min.

[Analytical HPLC: column: Chiralcel OZ-3 3 µm; eluent: 20% ethanol, 80% isohexane; flow rate: 1.0 ml/min; UV detection: 220 nm].

Diastereomer 1 was additionally purified by means of preparative HPLC (column: Chromatorex C18, 10 µm, 125×30 mm, solvent: acetonitrile/0.05% formic acid gradient; 0 to 3 min. 10% acetonitrile to 35 min. 90% acetonitrile and a further 3 min. 90% acetonitrile)), and 37.0 mg (22% of theory, 99% purity) of the title compound from Example 281 were obtained.

Diastereomer 2 was additionally purified by means of preparative HPLC (column: Chromatorex C18, 10 µm, 125×30 mm, solvent: acetonitrile/0.05% formic acid gradient; (0 to 3 min. 10% acetonitrile to 35 min. 90% acetonitrile and a further 3 min. 90% acetonitrile)), and 39.8 mg (23% of theory, 99% purity) of the title compound from Example 282 were obtained.

Example 281

7-[3-Hydroxy-2-oxopyrrolidin-1-yl]-4-oxo-N-[(2R)-1,1,1-trifluorobutan-2-yl]-1-(2,4,6-trifluorophenyl)-1,4-dihydro-1,8-naphthyridine-3-carboxamide (diastereomer 1)

$^1$H-NMR (400 MHz, DMSO-$d_6$): δ [ppm]=10.11 (d, 1H), 9.08 (s, 1H), 8.74 (d, 1H), 8.55 (d, 1H), 7.64-7.56 (m, 2H), 5.91 (d, 1H), 4.82-4.72 (m, 1H), 4.43-4.35 (m, 1H), 3.62-3.54 (m, 1H), 3.38-3.32 (m, 1H), 2.37-2.27 (m, 1H), 1.97-1.61 (m, 3H), 0.98 (t, 3H).

LC-MS (Method 3): $R_t$=1.89 min; 529 [M+H]$^+$.

Example 282

7-[3-Hydroxy-2-oxopyrrolidin-1-yl]-4-oxo-N-[(2R)-1,1,1-trifluorobutan-2-yl]-1-(2,4,6-trifluorophenyl)-1,4-dihydro-1,8-naphthyridine-3-carboxamide (diastereomer 2)

$^1$H-NMR (400 MHz, DMSO-$d_6$): δ [ppm]=10.11 (d, 1H), 9.08 (s, 1H), 8.74 (d, 1H), 8.55 (d, 1H), 7.64-7.56 (m, 2H), 5.91 (d, 1H), 4.84-4.70 (m, 1H), 4.43-4.35 (m, 1H), 3.62-3.53 (m, 1H), 3.38-3.32 (m, 1H), 2.36-2.26 (m, 1H), 1.96-1.60 (m, 3H), 0.98 (t, 3H).

LC-MS (Method 3): $R_t$=1.89 min; 529 [M+H]$^+$.

Example 283

N-[(1-Cyclopropyl-2,2,2-trifluoroethyl]-1-(2,4-difluorophenyl)-7-[(4S)-4-hydroxy-2-oxopyrrolidin-1-yl]-4-oxo-1,4-dihydro-1,8-naphthyridine-3-carboxamide (diastereomer mixture)

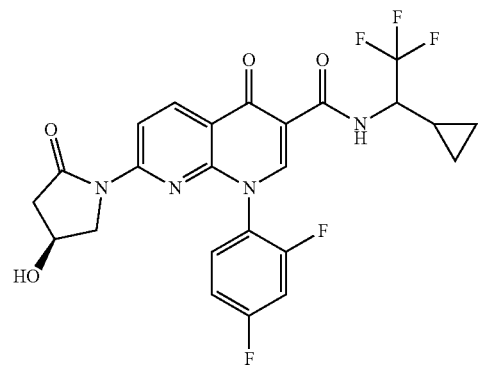 [SMILES: O=C(NC(C1CC1)C(F)(F)F)c1cn(-c2ccc(F)cc2F)c2nc(N3C[C@@H](O)CC3=O)ccc2c1=O]

According to GP2, 560 mg (1.22 mmol) of the compound from Example 101A were reacted with 124 mg (1.22 mmol) of (4S)-4-hydroxypyrrolidin-2-one (CAS: 68108-18-9) in the presence of 254 mg (1.84 mmol) of potassium carbonate, 49.4 mg (220 µmol) of palladium(II) acetate and 255 mg (440 µmol) of Xantphos in 11.2 ml of 1,4-dioxane. Subsequently, the volume of the mixture was reduced under reduced pressure, and the residue was acidified with 1N aqueous hydrochloric acid and dichloromethane. The crude product was purified by means of normal phase chromatography (cyclohexane-ethyl acetate gradient), and 316 mg (49% of theory; 99% purity) of the title compound were obtained.

$^1$H-NMR (400 MHz, DMSO-$d_6$): δ [ppm]=10.36 (d, 1H), 8.84 (s, 1H), 8.71 (d, 1H), 8.52 (dd, 1H), 7.92-7.82 (m, 1H), 7.66-7.59 (m, 1H), 7.41-7.33 (m, 1H), 5.32 (dd, 1H), 4.48-4.35 (m, 1H), 4.31-4.26 (m, 1H), 3.72-3.61 (m, 1H), 3.52-3.42 (m, 1H), 3.00-2.87 (m, 1H), 2.42-2.32 (m, 1H), 1.29-1.19 (m, 1H), 0.71-0.50 (m, 3H), 0.39-0.30 (m, 1H).

LC-MS (Method 1): $R_t$=1.06 min; 523 [M+H]$^+$.

310 mg of the title compound (diastereomer mixture) were separated into the diastereomers by chiral HPLC (preparative HPLC: column: Daicel Chiralpak IE 5 µm 250×20 mm; eluent: 50% ethanol, 50% isohexane; temperature: 25° C.; flow rate: 15 ml/min; UV detection: 210 nm).

This gave (in the sequence of elution from the column) 145 mg of diastereomer 1 (100% de) $R_t$=2.95 min and 128 mg (100% de) of diastereomer 2 $R_t$=5.61 min.

[Analytical HPLC: column: Chiraltek IE-3 3 µm; eluent: 50% ethanol, 50% isohexane; UV detection: 220 nm].

Diastereomer 1 was additionally purified by means of preparative HPLC (column: Chromatorex C18, 10 µm, 125×30 mm, solvent: acetonitrile/0.05% formic acid gradient; (0 to 3 min. 10% acetonitrile to 35 min. 90% acetonitrile and a further 3 min. 90% acetonitrile)), and 129.7 mg (20% of theory, 99% purity) of the title compound from Example 284 were obtained.

Diastereomer 2 was additionally purified by means of preparative HPLC (column: Chromatorex C18, 10 μm, 125×30 mm, solvent: acetonitrile/0.05% formic acid gradient; (0 to 3 min. 10% acetonitrile to 35 min. 90% acetonitrile and a further 3 min. 90% acetonitrile)), and 112 mg (17% of theory, 99% purity) of the title compound from Example 271 were obtained.

Example 284

N-[(1S)-1-cyclopropyl-2,2,2-trifluoroethyl]-1-(2,4-difluorophenyl)-7-[(4S)-4-hydroxy-2-oxopyrrolidin-1-yl]-4-oxo-1,4-dihydro-1,8-naphthyridine-3-carboxamide (diastereomer 1)

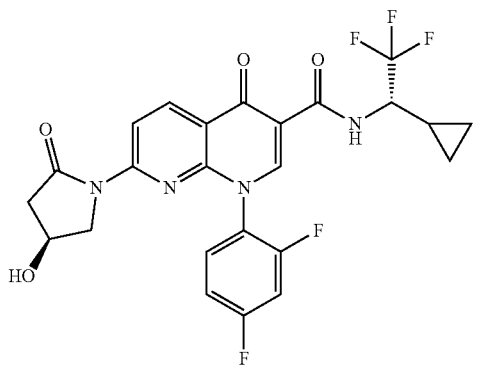 [SMILES: O=C(N[C@@H](C1CC1)C(F)(F)F)c1cn(-c2ccc(F)cc2F)c2nc(N3C[C@@H](O)CC3=O)ccc2c1=O]

$^1$H-NMR (400 MHz, DMSO-$d_6$): δ [ppm]=10.11 (d, 1H), 9.08 (s, 1H), 8.74 (d, 1H), 8.55 (d, 1H), 7.64-7.56 (m, 2H), 5.91 (d, 1H), 4.84-4.70 (m, 1H), 4.43-4.35 (m, 1H), 3.62-3.53 (m, 1H), 3.38-3.32 (m, 1H), 2.36-2.26 (m, 1H), 1.96-1.60 (m, 3H), 0.98 (t, 3H).
LC-MS (Method 3): $R_t$=1.89 min; 529 [M+H]$^+$.

Example 285

1-(2,4-Difluorophenyl)-7-[(4R)-4-hydroxy-2-oxopyrrolidin-1-yl]-4-oxo-N-[(2S)-1,1,1-trifluorobutan-2-yl]-1,4-dihydro-1,8-naphthyridine-3-carboxamide

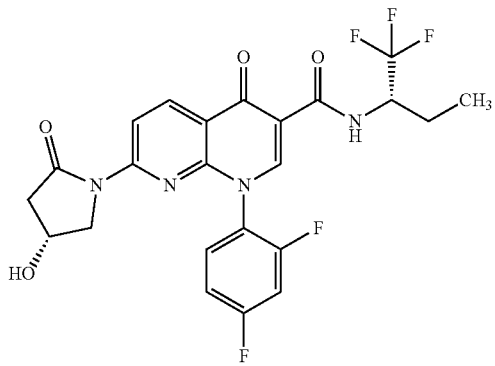 [SMILES: CC[C@H](NC(=O)c1cn(-c2ccc(F)cc2F)c2nc(N3C[C@H](O)CC3=O)ccc2c1=O)C(F)(F)F]

According to GP2, 140 mg (314 μmol) of the compound from Example 68A were reacted with 38.1 mg (377 μmol) of (4R)-4-hydroxypyrrolidin-2-one (CAS: 22677-21-0) in the presence of 65.1 mg (471 μmol) of potassium carbonate, 7.1 mg (31 μmol) of palladium(II) acetate and 18 mg (31 μmol) of Xantphos in 3.1 ml of 1,4-dioxane. After a reaction at 80° C. overnight, another 0.1 eq. of palladium(II) acetate and 0.1 eq. of Xantphos were added and the mixture was stirred for a further 3 h. Subsequently, the volume of the mixture was concentrated under reduced pressure, the residue was taken up with 0.5 ml of water and 3 ml of acetonitrile and filtered, and the crude product was separated by means of preparative HPLC (column: Chromatorex C18, 10 μm, 125×30 mm, eluent: acetonitrile/0.05% formic acid gradient (0 to 3 min 10% acetonitrile, to 35 min to 90% acetonitrile and for a further 3 min 90% acetonitrile)). 63.2 mg (39% of theory, 100% purity) of the title compound were obtained.

$^1$H-NMR (400 MHz, DMSO-$d_6$): δ [ppm]=10.22 (d, 1H), 8.87-8.83 (m, 1H), 8.71 (d, 1H), 8.52 (dd, 1H), 7.92-7.83 (m, 1H), 7.67-7.58 (m, 1H), 7.41-7.33 (m, 1H), 5.32 (dd, 1H), 4.84-4.70 (m, 1H), 4.32-4.24 (m, 1H), 3.72-3.61 (m, 1H), 3.52-3.42 (m, 1H), 3.00 (m, 1H), 2.41-2.31 (m, 1H), 1.96-1.83 (m, 1H), 1.73-1.59 (m, 1H), 0.98 (t, 3H).
LC-MS (Method 3): $R_t$=1.83 min; 511 [M+H]$^+$.

Example 286

1-(2,4-Difluorophenyl)-4-oxo-7-(2-oxo-2,5-dihydro-1H-pyrrol-1-yl)-N-[(2S)-1,1,1-trifluorobutan-2-yl]-1,4-dihydro-1,8-naphthyridine-3-carboxamide

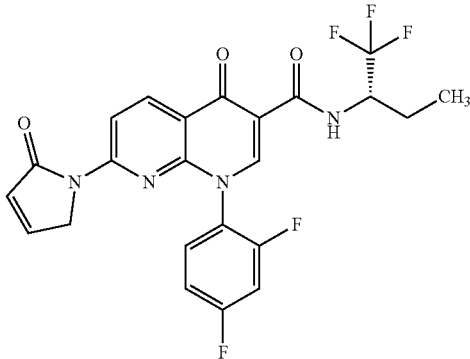 [SMILES: CC[C@H](NC(=O)c1cn(-c2ccc(F)cc2F)c2nc(N3CC=CC3=O)ccc2c1=O)C(F)(F)F]

To a solution of 47 mg (92 μmol) of the compound from Example 285 in 737 μl of toluene were added 40 mg (74 μmol) of tetrabutylammonium triphenyldifluorosilicate and 40.0 μl (230 μmol) of diisopropylethylamine. The mixture was stirred at room temperature for a further 5 min and then 61.2 mg (203 μmol) of perfluorobutane-1-sulphonyl fluoride were added. The mixture was stirred at room temperature for a further 20 min and then all volatile constituents were removed under reduced pressure. The residue was stirred with 4 ml of acetonitrile and 2 ml of water. The precipitate was filtered off with suction and dried under high vacuum. 19.6 mg (37% of theory, 85% purity) of the title compound were obtained.

$^1$H-NMR (400 MHz, DMSO-$d_6$): δ [ppm]=10.22 (d, 1H), 8.85 (s, 1H), 8.73 (d, 1H), 8.53 (d, 1H), 7.93-7.84 (m, 1H), 7.64-7.58 (m, 1H), 7.53 (d, 1H), 7.41-7.31 (m, 1H), 6.29 (d, 1H), 4.82-4.71 (m, 1H), 4.24 (s, 2H), 1.96-1.84 (m, 1H), 1.72-1.61 (m, 1H), 0.98 (t, 3H).
LC-MS (Method 3): $R_t$=2.13 min; 493 [M+H]$^+$.

Example 287

N-[1-(2-Chlorophenyl)-2,2,2-trifluoroethyl]-1-(2-fluorophenyl)-7-[3-hydroxy-2-oxopyrrolidin-1-yl]-4-oxo-1,4-dihydro-1,8-naphthyridine-3-carboxamide (racemic diastereomer mixture)

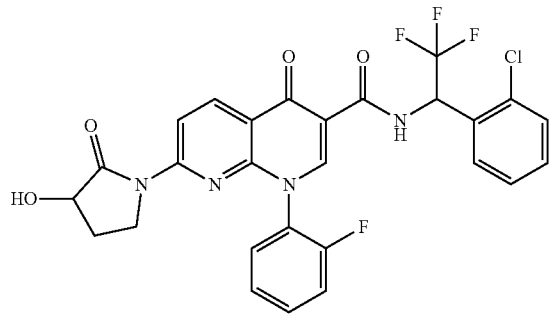 [SMILES: O=C(NC(c1ccccc1Cl)C(F)(F)F)c1cn(-c2ccccc2F)c2nc(N3CCC(O)C3=O)ccc2c1=O]

According to GP1, 75.0 mg (196 μmol) of the compound from Example 33B were reacted with 61.5 mg (293 μmol) of rac-1-(2-chlorophenyl)-2,2,2-trifluoroethanamine in the presence of 74.4 mg (196 μmol) of HATU and 102 μl (587 μmol) of N,N-diisopropylethylamine in 2 ml of dimethylformamide. The mixture was diluted with 1 ml of acetonitrile and 0.5 ml of water and the solution was purified by means of preparative HPLC (column: Chromatorex C18, 10 μm, 125×30 mm, solvent: acetonitrile/0.05% formic acid gradient; 0 to 3 min 10% acetonitrile, to 35 min 90% acetonitrile and for a further 3 min 90% acetonitrile). 94.5 mg (83% of theory, 99% purity) of the title compound were obtained.

$^1$H-NMR (400 MHz, DMSO-d$_6$): δ [ppm]=11.33 (d, 1H), 8.84 (s, 1H), 8.78 (d, 1H), 8.58-8.52 (m, 1H), 7.82-7.41 (m, 8H), 6.53-6.43 (m, 1H), 5.90 (d, 1H), 4.45-4.32 (m, 1H), 3.60-3.46 (m, 1H), 3.36-3.20 (m, 1H partially under the water signal), 2.34-2.24 (m, 1H), 1.83-1.66 (m, 1H).

LC-MS (Method 3): $R_t$=2.11 min; 575 [M+H]$^+$.

90 mg of the title compound (diastereomer mixture) were separated into the diastereomers by two chiral HPLC operations (preparative HPLC: column: Daicel Chiralcel OX-H 5 μm 250×20 mm; eluent: 100% ethanol, temperature: 45° C.; flow rate: 15 ml/min; UV detection: 220 nm, and column: Daicel Chiralpak IF 5 μm 250×20 mm; eluent: 35% ethanol, 65% isohexane, temperature: 45° C.; flow rate: 15 ml/min; UV detection: 220 nm).

This gave (in the sequence of elution from the column) 12 mg (enantiomer 1 of diastereomer 1, (93% de) $R_t$=6.29 min, 15 mg (enantiomer 1 of diastereomer 2, 100% de) $R_t$=6.93 min, 15 mg (enantiomer 2 of diastereomer 2, 80% de) $R_t$=10.88 min, and 19 mg (enantiomer 2 of diastereomer 1, 100% de) $R_t$=13.11 min.

[Analytical HPLC: column: Chiralcel OX-H 5 μm 250×4.6 mm; eluent: 100% ethanol; flow rate: 1 ml/min; temperature: 45° C.; UV detection: 220 nm]

Enantiomer 1 of diastereomer 1 was additionally purified by means of preparative HPLC (column: Chromatorex C18, 10 μm, 125×30 mm, solvent: acetonitrile/0.05% formic acid gradient; (0 to 3 min. 10% acetonitrile to 35 min. 90% acetonitrile and a further 3 min. 90% acetonitrile)), and 11.3 mg (10% of theory, 99% purity) of the title compound from Example 288 were obtained.

Enantiomer 1 of diastereomer 2 was additionally purified by means of preparative HPLC (column: Chromatorex C18, 10 μm, 125×30 mm, solvent: acetonitrile/0.05% formic acid gradient; (0 to 3 min. 10% acetonitrile to 35 min. 90% acetonitrile and a further 3 min. 90% acetonitrile)), and 12.8 mg (11% of theory, 99% purity) of the title compound from Example 289 were obtained.

Enantiomer 2 of diastereomer 2 was additionally purified by means of preparative HPLC (column: Chromatorex C18, 10 μm, 125×30 mm, solvent: acetonitrile/0.05% formic acid gradient; (0 to 3 min. 10% acetonitrile to 35 min. 90% acetonitrile and a further 3 min. 90% acetonitrile)), and 14.2 mg (13% of theory, 99% purity) of the title compound from Example 290 were obtained.

Enantiomer 2 of diastereomer 1 was additionally purified by means of preparative HPLC (column: Chromatorex C18, 10 μm, 125×30 mm, solvent: acetonitrile/0.05% formic acid gradient; (0 to 3 min. 10% acetonitrile to 35 min. 90% acetonitrile and a further 3 min. 90% acetonitrile)), and 15.7 mg (14% of theory, 99% purity) of the title compound from Example 291 were obtained.

Example 288

$^1$H-NMR (400 MHz, DMSO-d$_6$): δ [ppm]=11.33 (d, 1H), 8.84 (s, 1H), 8.78 (d, 1H), 8.57-8.57 (m, 1H), 7.82-7.40 (m, 8H), 6.52-6.42 (m, 1H), 5.90 (d, 1H), 4.43-4.32 (m, 1H), 3.60-3.46 (m, 1H), 3.34-3.20 (m, 1H partially under the water signal), 2.34-2.24 (m, 1H), 1.83-1.66 (m, 1H).

LC-MS (Method 3): $R_t$=2.11 min; 575 [M+H]$^+$.

Example 289

$^1$H-NMR (400 MHz, DMSO-d$_6$): δ [ppm]=11.33 (d, 1H), 8.84 (s, 1H), 8.78 (d, 1H), 8.57-8.51 (m, 1H), 7.81-7.42 (m, 8H), 6.53-6.42 (m, 1H), 5.90 (d, 1H), 4.44-4.31 (m, 1H), 3.59-3.45 (m, 1H), 3.36-3.19 (m, 1H partially under the water signal), 2.33-2.23 (m, 1H), 1.83-1.65 (m, 1H).

LC-MS (Method 3): $R_t$=2.14 min; 575 [M+H]$^+$.

Example 290

$^1$H-NMR (400 MHz, DMSO-d$_6$): δ [ppm]=11.33 (d, 1H), 8.84 (s, 1H), 8.78 (d, 1H), 8.57-8.51 (m, 1H), 7.81-7.41 (m, 8H), 6.53-6.42 (m, 1H), 5.90 (d, 1H), 4.44-4.31 (m, 1H), 3.58-3.46 (m, 1H), 2.34-2.23 (m, 1H), 1.82-1.66 (m, 1H). One proton resonance under the water signal.

LC-MS (Method 3): $R_t$=2.11 min; 575 [M+H]$^+$.

Example 291

$^1$H-NMR (400 MHz, DMSO-d$_6$): δ [ppm]=11.33 (d, 1H), 8.84 (s, 1H), 8.78 (d, 1H), 8.58-8.52 (m, 1H), 7.82-7.40 (m, 8H), 6.53-6.42 (m, 1H), 5.90 (d, 1H), 4.45-4.32 (m, 1H), 3.60-3.45 (m, 1H), 3.35-3.19 (m, 1H partially under the water signal), 2.34-2.23 (m, 1H), 1.82-1.67 (m, 1H).

LC-MS (Method 3): $R_t$=2.11 min; 575 [M+H]$^+$.

Example 292

1-(2,6-Difluorophenyl)-7-[3-hydroxy-2-oxopyrrolidin-1-yl]-4-oxo-N-[(2R)-1,1,1-trifluorobutan-2-yl]-1,4-dihydro-1,8-naphthyridine-3-carboxamide (diastereomer mixture)

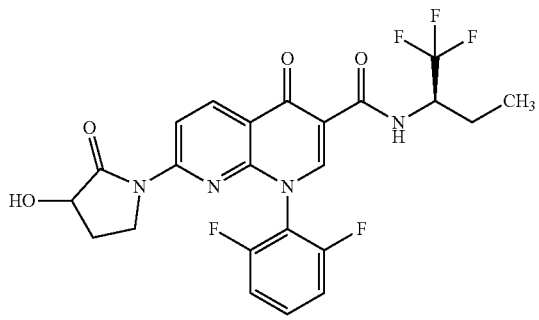 [SMILES: CC[C@@H](NC(=O)c1cn(-c2c(F)cccc2F)c2nc(N3CCC(O)C3=O)ccc2c1=O)C(F)(F)F]

According to GP2, 150 mg (336 µmol) of the compound from Example 86A were reacted with 34.0 mg (336 µmol) of 3-hydroxypyrrolidin-2-one (CAS: 15166-68-4) in the presence of 69.8 mg (505 µmol) of potassium carbonate, 14 mg (61 µmol) of palladium(II) acetate and 70.1 mg (121 µmol) of Xantphos in 3.09 ml of 1,4-dioxane. Subsequently, the volume of the mixture was reduced under reduced pressure and it was diluted with 3 ml of acetonitrile and acidified with 1 ml of water, filtered and purified by means of preparative HPLC (column: Chromatorex C18, 10 µm, 125×30 mm, solvent: acetonitrile/0.05% formic acid gradient; (0 to 3 min. 10% acetonitrile to 35 min. 90% acetonitrile and a further 3 min. 90% acetonitrile), and 127.3 mg (73% of theory, 99% purity) of the title compound were obtained.

$^1$H-NMR (400 MHz, DMSO-$d_6$): δ [ppm]=10.12 (d, 1H), 9.03 (s, 1H), 8.74 (d, 1H), 8.55 (d, 1H), 7.79-7.70 (m, 1H), 7.49-7.41 (m, 2H), 5.90 (d, 1H), 4.83-4.71 (m, 1H), 4.42-4.34 (m, 1H), 3.55-3.49 (m, 1H), 3.33-3.23 (m, 1H partially under the water signal), 2.34-2.23 (m, 1H), 1.95-1.61 (m, 3H), 0.98 (t, 3H).

LC-MS (Method 3): $R_t$=1.87 min; 511 [M+H]$^+$.

120 mg of the title compound (diastereomer mixture) were separated into the diastereomers by chiral HPLC (preparative HPLC: column: Daicel Chiralcel OX-H 5 µm 250×45 mm; eluent: 20% ethanol, 55% isohexane; temperature: 23° C.; flow rate: 20 ml/min; UV detection: 220 nm).

This gave (in the sequence of elution from the column) 52.5 mg of diastereomer 1 (100% de) $R_t$=1.13 min and 45.5 mg (94% de) of diastereomer 2 $R_t$=1.25 min.

[Analytical HPLC: column: Daicel Chiralpak OX-3 3 µm 50×4.6 mm; eluent: 50% ethanol, 50% isohexane; flow rate: 1 ml/min; UV detection: 220 nm].

Diastereomer 1 was additionally purified by means of preparative HPLC (column: Chromatorex C18, 10 µm, 125×30 mm, solvent: acetonitrile/0.05% formic acid gradient; (0 to 3 min. 10% acetonitrile to 35 min. 90% acetonitrile and a further 3 min. 90% acetonitrile)), and 40.7 mg (23% of theory, 99% purity) of the title compound from Example 293 were obtained.

Diastereomer 2 was additionally purified by means of preparative HPLC (column: Chromatorex C18, 10 µm, 125×30 mm, solvent: acetonitrile/0.05% formic acid gradient; (0 to 3 min. 10% acetonitrile to 35 min. 90% acetonitrile and a further 3 min. 90% acetonitrile)), and 41.1 mg (24% of theory, 99% purity) of the title compound from Example 294 were obtained.

Example 293

$^1$H-NMR (400 MHz, DMSO-$d_6$): δ [ppm]=10.12 (d, 1H), 9.03 (s, 1H), 8.74 (d, 1H), 8.55 (d, 1H), 7.79-7.70 (m, 1H), 7.50-7.41 (m, 2H), 5.90 (d, 1H), 4.84-4.70 (m, 1H), 4.43-4.34 (m, 1H), 3.56-3.48 (m, 1H), 3.34-3.24 (m, 1H partially under the water signal), 2.33-2.23 (m, 1H), 1.96-1.61 (m, 3H), 0.98 (t, 3H).

LC-MS (Method 1): $R_t$=0.98 min; 511 [M+H]$^+$.

Example 294

$^1$H-NMR (400 MHz, DMSO-$d_6$): δ [ppm]=10.13 (d, 1H), 9.03 (s, 1H), 8.74 (d, 1H), 8.55 (d, 1H), 7.79-7.70 (m, 1H), 7.50-7.41 (m, 2H), 5.91 (d, 1H), 4.84-4.70 (m, 1H), 4.43-4.34 (m, 1H), 3.56-3.47 (m, 1H), 3.33-3.24 (m, 1H partially under the water signal), 2.34-2.23 (m, 1H), 1.96-1.60 (m, 3H), 0.99 (t, 3H).

LC-MS (Method 1): $R_t$=0.98 min; 511 [M+H]$^+$.

Example 295

N-[1-Cyclopropyl-2,2,2-trifluoroethyl]-1-(2,6-difluorophenyl)-7-[(4S)-4-hydroxy-2-oxopyrrolidin-1-yl]-4-oxo-1,4-dihydro-1,8-naphthyridine-3-carboxamide (diastereomer mixture)

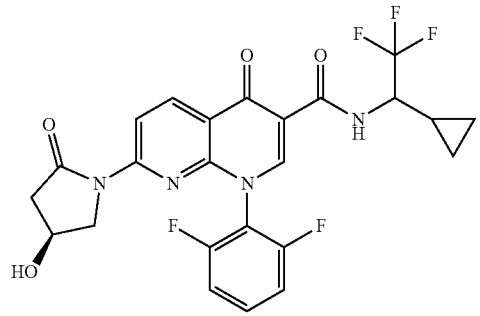 [SMILES: O=C(NC(C1CC1)C(F)(F)F)c1cn(-c2c(F)cccc2F)c2nc(N3C[C@@H](O)CC3=O)ccc2c1=O]

According to GP2, 100 mg (218 µmol) of the compound from Example 102A were reacted with 22.1 mg (218 µmol) of (4S)-4-hydroxypyrrolidin-2-one (CAS: 68108-18-9) in the presence of 45.3 mg (328 µmol) of potassium carbonate, 8.8 mg (39 µmol) of palladium(II) acetate and 46 mg (79 µmol) of Xantphos in 2 ml of 1,4-dioxane. Subsequently, the volume of the mixture was concentrated under reduced pressure, the residue was acidified with 1N aqueous hydrochloric acid, diluted with 5 ml of acetonitrile and filtered, and the crude product was purified by means of preparative HPLC (column: Chromatorex C18, 10 µm, 125×30 mm, solvent: acetonitrile/0.05% formic acid gradient (0 to 3 min 10% acetonitrile, to 35 min to 90% acetonitrile and for a further 3 min 90% acetonitrile)). 68.9 mg (60% of theory, 99% purity) of the title compound were obtained.

$^1$H-NMR (400 MHz, DMSO-$d_6$): δ [ppm]=10.28 (d, 1H), 9.02 (s, 1H), 8.73 (d, 1H), 8.54 (d, 1H), 7.81-7.72 (m, 1H), 7.50-7.42 (m, 2H), 5.33 (d, 1H), 4.47-4.34 (m, 1H), 4.29-4.22 (m, 1H), 3.64 (dd, 1H), 3.43 (d, 1H), 2.93 (dd, 1H), 2.37 (d, 1H), 1.29-1.18 (m, 1H), 0.71-0.51 (m, 3H), 0.40-0.31 (m, 1H).

LC-MS (Method 1): $R_t$=1.05 min; 523 [M+H]$^+$.

65 mg of the title compound (diastereomer mixture) were separated into the diastereomers by chiral HPLC (preparative HPLC: column: Daicel Chiralcel OX-H 250×20 mm; eluent: 30% ethanol, 70% isohexane; temperature: 23° C.; flow rate: 20 ml/min; UV detection: 220 nm).

This gave (in the sequence of elution from the column) 17.3 mg of diastereomer 1 (100% de) $R_t$=2.16 min and 17.9 mg (100% de) of diastereomer 2 $R_t$=3.39 min.

[Analytical HPLC: column: Daicel Chiralpak OX-3 3 µm 50×4.6 mm; eluent: 20% ethanol, 80% isohexane; flow rate: 1 ml/min; temperature: 30° C.; UV detection: 220 nm].

Diastereomer 1 was additionally purified by means of preparative HPLC (column: Chromatorex C18, 10 µm, 125×30 mm, solvent: acetonitrile/0.05% formic acid gradient; (0 to 3 min. 10% acetonitrile to 35 min. 90% acetonitrile and a further 3 min. 90% acetonitrile)), and 16.9 mg (15% of theory, 99% purity) of the title compound from Example 296 were obtained.

Diastereomer 2 was additionally purified by means of preparative HPLC (column: Chromatorex C18, 10 µm, 125×30 mm, solvent: acetonitrile/0.05% formic acid gradient; (0 to 3 min. 10% acetonitrile to 35 min. 90% acetonitrile and a further 3 min. 90% acetonitrile)), and 17.7 mg (15% of theory, 99% purity) of the title compound from Example 297 were obtained.

Example 296

N-[(1R)-1-cyclopropyl-2,2,2-trifluoroethyl]-1-(2,6-difluorophenyl)-7-[(4S)-4-hydroxy-2-oxopyrrolidin-1-yl]-4-oxo-1,4-dihydro-1,8-naphthyridine-3-carboxamide (diastereomer 1)

$^1$H-NMR (400 MHz, DMSO-d$_6$): δ [ppm]=10.27 (d, 1H), 9.02 (s, 1H), 8.73 (d, 1H), 8.54 (d, 1H), 7.80-7.71 (m, 1H), 7.50-7.42 (m, 2H), 5.33 (d, 1H), 4.46-4.36 (m, 1H), 4.29-4.23 (m, 1H), 3.64 (dd, 1H), 3.43 (d, 1H), 2.93 (dd, 1H), 2.37 (d, 1H), 1.28-1.19 (m, 1H), 0.71-0.52 (m, 3H), 0.40-0.31 (m, 1H).

LC-MS (Method 3): $R_t$=1.84 min; 523 [M+H]$^+$.

Alternatively, the title compound can also be obtained according to GP2 by reacting the compound from Example 103A with (4S)-4-hydroxypyrrolidin-2-one (CAS: 68108-18-9).

Example 297

N-[(1S)-1-cyclopropyl-2,2,2-trifluoroethyl]-1-(2,6-difluorophenyl)-7-[(4S)-4-hydroxy-2-oxopyrrolidin-1-yl]-4-oxo-1,4-dihydro-1,8-naphthyridine-3-carboxamide (diastereomer 2)

$^1$H-NMR (400 MHz, DMSO-d$_6$): δ [ppm]=10.28 (d, 1H), 9.02 (s, 1H), 8.73 (d, 1H), 8.54 (d, 1H), 7.81-7.71 (m, 1H), 7.50-7.41 (m, 2H), 5.33 (d, 1H), 4.47-4.34 (m, 1H), 4.29-4.22 (m, 1H), 3.64 (dd, 1H), 3.43 (d, 1H), 2.93 (dd, 1H), 2.37 (d, 1H), 1.30-1.18 (m, 1H), 0.71-0.51 (m, 3H), 0.39-0.30 (m, 1H).

LC-MS (Method 3): $R_t$=1.84 min; 523 [M+H]$^+$.

Alternatively, the title compound can also be obtained according to GP2 by reacting the compound from Example 104A with (4S)-4-hydroxypyrrolidin-2-one (CAS: 68108-18-9).

Example 298

N-[1-(2-Chlorophenyl)-2,2,2-trifluoroethyl]-1-(2,4-difluorophenyl)-7-[(3S)-3-hydroxy-2-oxopyrrolidin-1-yl]-4-oxo-1,4-dihydro-1,8-naphthyridine-3-carboxamide (diastereomer mixture)

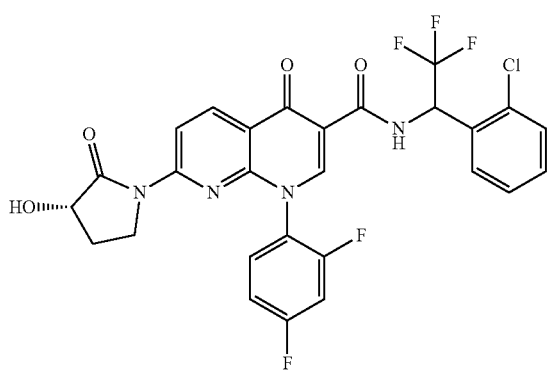 [SMILES: O=C(NC(c1ccccc1Cl)C(F)(F)F)c1cn(-c2ccc(F)cc2F)c2nc(N3CC[C@H](O)C3=O)ccc2c1=O]

According to GP2, 439 mg (798 µmol, 96% purity) of the compound from Example 73A were reacted with 99.8 mg (957 µmol) of (3S)-3-hydroxypyrrolidin-2-one (CAS: 34368-52-0) in the presence of 132 mg (957 µmol) of potassium carbonate, 18 mg (80 µmol) of palladium(II) acetate and 92.3 mg (160 µmol) of Xantphos in 79 ml of 1,4-dioxane. Subsequently, the mixture was admixed with 50 ml of water and extracted three times with 30 ml of ethyl acetate. The aqueous phase was acidified with 1N aqueous hydrochloric acid and extracted again with ethyl acetate. The combined organic phases were washed with saturated aqueous sodium chloride solution, dried over magnesium sulphate, filtered and purified by means of normal phase chromatography (cyclohexane-ethyl acetate gradient). 280 mg (59% of theory, 100% purity) of the title compound were obtained.

$^1$H-NMR (400 MHz, DMSO-d$_6$): δ [ppm]=11.32 (d, 1H), 8.87 (s, 1H), 8.78 (d, 1H), 8.54 (dd, 1H), 7.92-7.77 (m, 1H), 7.68-7.48 (m, 5H), 7.40-7.31 (m, 1H), 6.53-6.42 (m, 1H), 5.91 (d, 1H), 4.45-4.33 (m, 1H), 3.63-3.50 (m, 1H), 2.36-2.26 (m, 1H), 1.83-1.67 (m, 1H).

LC-MS (Method 1): $R_t$=1.20 min; 593 [M+H]$^+$.

Example 299

N-[1-(2-Chlorophenyl)-2,2,2-trifluoroethyl]-1-(2,4-difluorophenyl)-7-[(3R)-3-hydroxy-2-oxopyrrolidin-1-yl]-4-oxo-1,4-dihydro-1,8-naphthyridine-3-carboxamide (diastereomer mixture)

Example 300

1-(2,4-Difluorophenyl)-N-[1-(2,6-difluorophenyl)-2,2,2-trifluoroethyl]-7-[(3R)-3-hydroxy-2-oxopyrrolidin-1-yl]-4-oxo-1,4-dihydro-1,8-naphthyridine-3-carboxamide (diastereomer mixture)

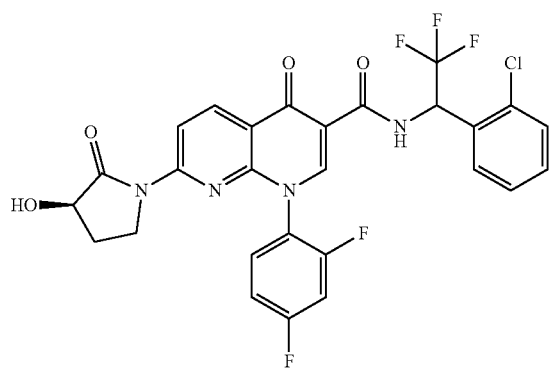 [SMILES: O=C(NC(c1ccccc1Cl)C(F)(F)F)c1cn(-c2ccc(F)cc2F)c2nc(N3CC[C@@H](O)C3=O)ccc2c1=O]

According to GP2, 606 mg (987 μmol, 86% purity) of the compound from Example 73A were reacted with 123 mg (1.18 mmol) of (3R)-3-hydroxypyrrolidin-2-one (CAS: 77510-50-0) in the presence of 164 mg (1.18 mmol) of potassium carbonate, 22 mg (99 μmol) of palladium(II) acetate and 114 mg (197 μmol) of Xantphos in 99 ml of 1,4-dioxane. After reaction overnight, a further 0.1 eq. of palladium(II) acetate and 0.2 eq. of Xantphos were added and the mixture was stirred at 80° C. for 2.5 h. Subsequently, the mixture was admixed with 50 ml of water, acidified with 1N aqueous hydrochloric acid and extracted three times with 30 ml of ethyl acetate. The combined organic phases were washed with saturated aqueous sodium chloride solution, dried over magnesium sulphate, filtered and purified by means of normal phase chromatography (cyclohexane-ethyl acetate gradient). 284 mg (49% of theory, 100% purity) of the title compound were obtained.

$^1$H-NMR (400 MHz, DMSO-d$_6$): δ [ppm]=11.32 (d, 1H), 8.87 (s, 1H), 8.77 (d, 1H), 8.54 (dd, 1H), 7.92-7.76 (m, 1H), 7.67-7.47 (m, 5H), 7.40-7.30 (m, 1H), 6.53-6.41 (m, 1H), 5.91 (d, 1H), 4.45-4.32 (m, 1H), 3.62-3.49 (m, 1H), 2.35-2.27 (m, 1H), 1.84-1.68 (m, 1H).

LC-MS (Method 4): R$_t$=3.69 min; 593 [M+H]$^+$.

According to GP2, 428 mg (719 μmol, 89% purity) of the compound from Example 80A were reacted with 89.9 mg (863 μmol) of (3R)-3-hydroxypyrrolidin-2-one (CAS: 77510-50-0) in the presence of 123 mg (863 μmol) of potassium carbonate, 16 mg (72 μmol) of palladium(II) acetate and 83.2 mg (144 μmol) of Xantphos in 72 ml of 1,4-dioxane. Subsequently, the mixture was admixed with 50 ml of water, acidified with 1N aqueous hydrochloric acid and extracted three times with 30 ml of ethyl acetate. The combined organic phases were washed with saturated aqueous sodium chloride solution, dried over magnesium sulphate, filtered and purified by means of normal phase chromatography (cyclohexane-ethyl acetate gradient). 266 mg (62% of theory, 100% purity) of the title compound were obtained.

$^1$H-NMR (400 MHz, DMSO-d$_6$): δ [ppm]=11.36 (d, 1H), 8.89 (s, 1H), 8.77 (d, 1H), 8.56-8.50 (m, 1H), 7.93-7.74 (m, 1H), 7.68-7.57 (m, 2H), 7.40-7.28 (m, 3H), 6.50-6.39 (m, 1H), 5.91 (d, 1H), 4.45-4.32 (m, 1H), 3.62-3.50 (m, 1H), 2.36-2.27 (m, 1H), 1.84-1.70 (m, 1H).

LC-MS (Method 1): R$_t$=1.08 min; 595 [M+H]$^+$.

Example 301

1-(2,4-Difluorophenyl)-7-[4-methyl-2-oxopyrrolidin-1-yl]-4-oxo-N-[(2R)-1,1,1-trifluorobutan-2-yl]-1,4-dihydro-1,8-naphthyridine-3-carboxamide (diastereomer mixture)

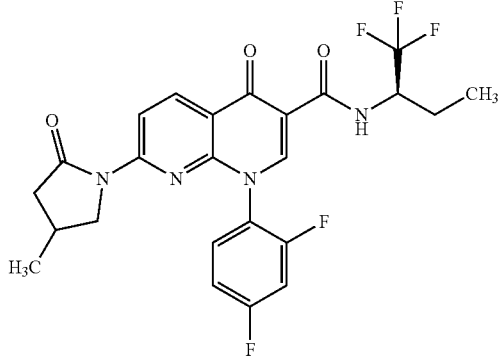

According to GP2, 200 mg (449 µmol) of the compound from Example 67A were reacted with 49.2 mg (471 µmol) of 4-methyl-2-pyrrolidinone (racemate) in the presence of 93.0 mg (673 µmol) of potassium carbonate, 18 mg (81 µmol) of palladium(II) acetate and 93.5 mg (162 µmol) of Xantphos in 4 ml of 1,4-dioxane. Subsequently, the volume of the mixture was concentrated under reduced pressure, and the residue was taken up with 2 ml of 1N aqueous hydrochloric acid and 8 ml of acetonitrile and purified by means of preparative HPLC (column: Chromatorex C18, 10 µm, 125×30 mm, solvent: acetonitrile/0.05% formic acid gradient; 0 to 3 min 10% acetonitrile, to 35 min 90% acetonitrile and for a further 3 min 90% acetonitrile). 92.9 mg (40% of theory, 99% purity) of the title compound were obtained.

$^1$H-NMR (400 MHz, DMSO-d$_6$): δ [ppm]=10.22 (d, 1H), 8.85 (s, 1H), 8.70 (d, 1H), 8.49 (d, 1H), 7.92-7.82 (m, 1H), 7.68-7.59 (m, 1H), 7.40-7.33 (m, 1H), 4.84-4.70 (m, 1H), 3.76-3.65 (m, 1H), 3.18-3.06 (m, 1H), 2.79-2.65 (m, 1H), 2.46-2.23 (m, 2H), 1.95-1.83 (m, 1H), 1.73-1.59 (m, 1H), 1.06-0.94 (m, 6H).

LC-MS (Method 1): R$_t$=1.19 min; 509 [M+H]$^+$.

89 mg of the title compound (diastereomer mixture) were separated into the diastereomers by chiral HPLC (preparative HPLC: column: Daicel Chiralpak AZ-H 5 µm 250×20 mm; eluent: 25% ethanol, 75% isohexane; temperature: 25° C.; flow rate: 20.2 ml/min; UV detection: 265 nm).

This gave (in the sequence of elution from the column) 45.4 mg of diastereomer 1 (100% de) R$_t$=3.42 min and 37.1 mg (100% de) of diastereomer 2 R$_t$=3.93 min.

[Analytical HPLC: column: Daicel Chiralpak AZ-3 3 µm 50×4.6 mm; eluent: 20% ethanol, 80% isohexane; flow rate: 1 ml/min; UV detection: 220 nm].

Diastereomer 1 was additionally purified by means of preparative HPLC (column: Chromatorex C18, 10 µm, 125×30 mm, solvent: acetonitrile/0.05% formic acid gradient; (0 to 3 min. 10% acetonitrile to 35 min. 90% acetonitrile and a further 3 min. 90% acetonitrile)), and 33.6 mg (15% of theory, 99% purity) of the title compound from Example 302 were obtained.

Diastereomer 2 was additionally purified by means of preparative HPLC (column: Chromatorex C18, 10 µm, 125×30 mm, solvent: acetonitrile/0.05% formic acid gradient; (0 to 3 min. 10% acetonitrile to 35 min. 90% acetonitrile and a further 3 min. 90% acetonitrile)), and 26.9 mg (12% of theory, 99% purity) of the title compound from Example 303 were obtained.

Example 302

1-(2,4-Difluorophenyl)-7-[4-methyl-2-oxopyrrolidin-1-yl]-4-oxo-N-[(2R)-1,1,1-trifluorobutan-2-yl]-1,4-dihydro-1,8-naphthyridine-3-carboxamide (diastereomer 1)

$^1$H-NMR (400 MHz, DMSO-d$_6$): δ [ppm]=10.22 (d, 1H), 8.85 (s, 1H), 8.70 (d, 1H), 8.49 (d, 1H), 7.92-7.83 (m, 1H), 7.68-7.59 (m, 1H), 7.41-7.33 (m, 1H), 4.84-4.70 (m, 1H), 3.76-3.65 (m, 1H), 3.18-3.06 (m, 1H), 2.78-2.65 (m, 1H), 2.46-2.23 (m, 2H), 1.96-1.83 (m, 1H), 1.73-1.60 (m, 1H), 1.07-0.94 (m, 6H).

LC-MS (Method 3): R$_t$=2.27 min; 509 [M+H]$^+$.

Example 303

1-(2,4-Difluorophenyl)-7-[4-methyl-2-oxopyrrolidin-1-yl]-4-oxo-N-[(2R)-1,1,1-trifluorobutan-2-yl]-1,4-dihydro-1,8-naphthyridine-3-carboxamide (diastereomer 2)

$^1$H-NMR (400 MHz, DMSO-d$_6$): δ [ppm]=10.22 (d, 1H), 8.85 (s, 1H), 8.70 (d, 1H), 8.49 (d, 1H), 7.92-7.82 (m, 1H), 7.68-7.59 (m, 1H), 7.41-7.32 (m, 1H), 4.83-4.70 (m, 1H), 3.77-3.64 (m, 1H), 3.18-3.07 (m, 1H), 2.78-2.65 (m, 1H), 2.46-2.22 (m, 2H), 1.96-1.84 (m, 1H), 1.73-1.59 (m, 1H), 1.06-0.93 (m, 6H).

LC-MS (Method 3): R$_t$=2.27 min; 509 [M+H]$^+$.

Example 304

1-(2,6-Difluorophenyl)-7-[1-hydroxy-3-azabicyclo[3.1.0]hex-3-yl]-4-oxo-N-[(2R)-1,1,1-trifluorobutan-2-yl]-1,4-dihydro-1,8-naphthyridine-3-carboxamide (diastereomer mixture)

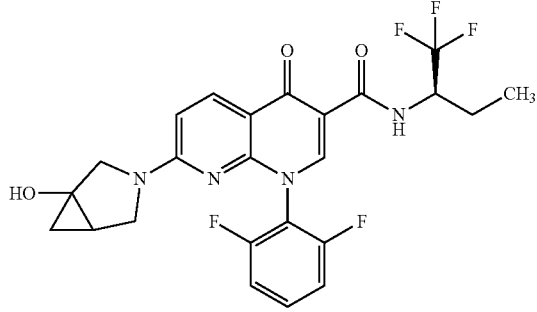 [SMILES: CC[C@@H](NC(=O)c1cn(-c2c(F)cccc2F)c2nc(N3CC4CC4(O)C3)ccc2c1=O)C(F)(F)F]

According to GP3, 240 mg (538 µmol) of the compound from Example 86A were reacted with 80.7 mg (565 µmol) of 3-azabicyclo[3.1.0]hexan-1-ol hydrochloride (racemate, 95% purity) and 328 µl (1.88 mmol) of N,N-diisopropylethylamine in 2.4 ml of dimethylformamide. The crude product was diluted with 0.5 ml of acetonitrile and 0.5 ml of 1N aqueous hydrochloric acid and purified by means of preparative HPLC (column: Chromatorex C18, 10 µm, 125×30 mm, solvent: acetonitrile/0.05% formic acid gradient; 0 to 3 min 10% acetonitrile, to 35 min 90% acetonitrile and for a further 3 min 90% acetonitrile). 158.6 mg (57% of theory, 98.7% purity) of the title compound were obtained.

$^1$H-NMR (400 MHz, DMSO-d$_6$): δ [ppm]=10.41 (d, 1H), 8.76 (s, 1H), 8.29 (d, 1H), 7.77-7.65 (m, 1H), 7.49-7.37 (m, 2H), 6.83-6.68 (m, 1H), 6.01 (d, 1H), 4.81-4.67 (m, 1H), 3.94-3.83 (m, 0.5H), 3.72-3.60 (m, 0.5H), 3.56-3.39 (m, 1.5H), 3.27-3.18 (m, 0.5H), 3.17-3.02 (m, 1H), 1.94-1.81 (m, 1H), 1.71-1.47 (m, 2H), 1.07-0.92 (m, 4H), 0.48-0.37 (m, 1H).

LC-MS (Method 3): R$_t$=1.99 min; 509 [M+H]$^+$.

150 mg of the title compound (diastereomer mixture) were separated into the diastereomers by chiral HPLC (preparative HPLC: column: Daicel Chiralcel OZ-H 5 μm 250×20 mm; eluent: 20% ethanol, 80% isohexane; temperature: 23° C.; flow rate: 20 ml/min; UV detection: 220 nm).

This gave (in the sequence of elution from the column) 69.0 mg of diastereomer 1 (100% de) R$_t$=1.74 min and 50.9 mg (98% de) of diastereomer 2 R$_t$=2.48 min.

[Analytical HPLC: column: Daicel Chiralpak OX-3 3 μm 50×4.6 mm; eluent: 20% 2-propanol, 80% isohexane; flow rate: 1 ml/min; temperature: 30° C.; UV detection: 220 nm].

Diastereomer 1 was additionally purified by means of preparative HPLC (column: Chromatorex C18, 10 μm, 125×30 mm, solvent: acetonitrile/0.05% formic acid gradient; (0 to 3 min. 10% acetonitrile to 35 min. 90% acetonitrile and a further 3 min. 90% acetonitrile)), and 48.6 mg (18% of theory, 99% purity) of the title compound from Example 305 were obtained.

Diastereomer 2 was additionally purified by means of preparative HPLC (column: Chromatorex C18, 10 μm, 125×30 mm, solvent: acetonitrile/0.05% formic acid gradient; (0 to 3 min. 10% acetonitrile to 35 min. 90% acetonitrile and a further 3 min. 90% acetonitrile)), and 41.5 mg (15% of theory, 99% purity) of the title compound from Example 306 were obtained.

Example 305

1-(2,6-Difluorophenyl)-7-[1-hydroxy-3-azabicyclo [3.1.0]hex-3-yl]-4-oxo-N-[(2R)-1,1,1-trifluorobutan-2-yl]-1,4-dihydro-1,8-naphthyridine-3-carboxamide (diastereomer 1)

$^1$H-NMR (400 MHz, DMSO-d$_6$): δ [ppm]=10.41 (d, 1H), 8.76 (s, 1H), 8.28 (d, 1H), 7.77-7.65 (m, 1H), 7.49-7.36 (m, 2H), 6.84-6.69 (m, 1H), 6.00 (d, 1H), 4.80-4.67 (m, 1H), 3.92-3.82 (m, 0.5H), 3.69-3.60 (m, 0.5H), 3.56-3.39 (m, 1.5H), 3.16-3.02 (m, 1H), 1.94-1.82 (m, 1H), 1.71-1.48 (m, 2H), 1.05-0.90 (m, 4H), 0.47-0.36 (m, 1H).

LC-MS (Method 3): R$_t$=1.96 min; 509 [M+H]$^+$.

Example 306

1-(2,6-Difluorophenyl)-7-[1-hydroxy-3-azabicyclo [3.1.0]hex-3-yl]-4-oxo-N-[(2R)-1,1,1-trifluorobutan-2-yl]-1,4-dihydro-1,8-naphthyridine-3-carboxamide (diastereomer 2)

$^1$H-NMR (400 MHz, DMSO-d$_6$): δ [ppm]=10.41 (d, 1H), 8.76 (s, 1H), 8.28 (d, 1H), 7.77-7.65 (m, 1H), 7.48-7.36 (m, 2H), 6.83-6.68 (m, 1H), 6.00 (d, 1H), 4.80-4.67 (m, 1H), 3.92-3.82 (m, 0.5H), 3.69-3.59 (m, 0.5H), 3.54-3.39 (m, 1.5H), 3.16-3.02 (m, 1H), 1.94-1.81 (m, 1H), 1.71-1.47 (m, 2H), 1.05-0.90 (m, 4H), 0.46-0.38 (m, 1H).

LC-MS (Method 3): R$_t$=1.96 min; 509 [M+H]$^+$.

Example 307

1-(2-Chloro-6-fluorophenyl)-7-[(4S)-4-hydroxy-2-oxopyrrolidin-1-yl]-4-oxo-N-[(2R)-1,1,1-trifluorobutan-2-yl]-1,4-dihydro-1,8-naphthyridine-3-carboxamide

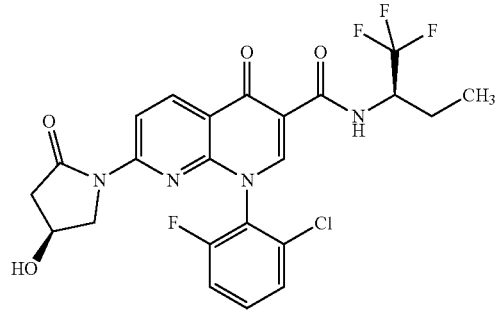 [SMILES: CC[C@@H](NC(=O)c1cn(-c2c(F)cccc2Cl)c2nc(N3C[C@@H](O)CC3=O)ccc2c1=O)C(F)(F)F]

According to GP2, 100 mg (216 μmol) of the compound from Example 105C were reacted with 21.9 mg (216 μmol) of (S)-4-hydroxypyrrolidinone in the presence of 44.8 mg (325 μmol) of potassium carbonate, 8.7 mg (39 μmol) of palladium(II) acetate and 45 mg (78 μmol) of Xantphos in 1.98 ml of 1,4-dioxane.

Subsequently, the volume of the mixture was concentrated under reduced pressure, the residue was acidified with 1N aqueous hydrochloric acid and taken up with 3 ml of acetonitrile, filtered and purified by means of preparative HPLC (column: Chromatorex C18, 10 μm, 125×30 mm, solvent: acetonitrile/0.05% formic acid gradient (0 to 3 min 10% acetonitrile, to 35 min to 90% acetonitrile and for a further 3 min 90% acetonitrile)). 57.1 mg (50% of theory, 99% purity) of the title compound were obtained.

$^1$H-NMR (400 MHz, DMSO-d$_6$): δ [ppm]=10.15 (d, 1H), 8.99 (s, 1H), 8.73 (d, 1H), 8.54 (d, 1H), 7.78-7.56 (m, 3H), 5.32 (d, 1H), 4.82-4.71 (m, 1H), 4.28-4.22 (m, 1H), 3.63-3.55 (m, 1H), 3.41-3.34 (m, 1H), 2.93 (dd, 1H), 2.40-2.31 (m, 1H), 1.95-1.83 (m, 1H), 1.74-1.60 (m, 1H), 1.02-0.95 (m, 3H).

LC-MS (Method 1): R$_t$=1.01 min; 527 [M+H]$^+$.

Example 308

1-(2-Chloro-6-fluorophenyl)-7-[(3R)-3-hydroxy-2-oxopyrrolidin-1-yl]-4-oxo-N-[(2R)-1,1,1-trifluorobutan-2-yl]-1,4-dihydro-1,8-naphthyridine-3-carboxamide

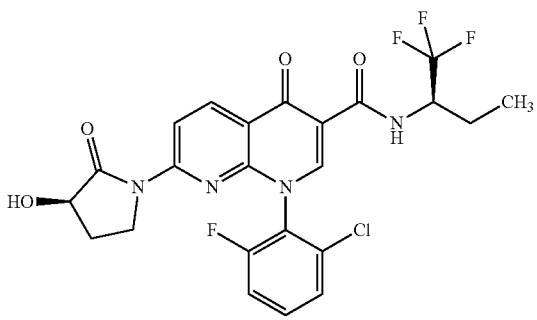 [SMILES: CC[C@@H](NC(=O)c1cn(-c2c(F)cccc2Cl)c2nc(N3CC[C@@H](O)C3=O)ccc2c1=O)C(F)(F)F]

According to GP2, 100 mg (216 µmol) of the compound from Example 105C were reacted with 21.9 mg (216 µmol) of (R)-3-hydroxypyrrolidinone in the presence of 44.8 mg (325 µmol) of potassium carbonate, 8.7 mg (39 µmol) of palladium(II) acetate and 45 mg (78 µmol) of Xantphos in 1.98 ml of 1,4-dioxane.

Subsequently, the volume of the mixture was concentrated under reduced pressure, the residue was acidified with 1N aqueous hydrochloric acid and taken up with 5 ml of acetonitrile, filtered and purified by means of preparative HPLC (column: Chromatorex C18, 10 µm, 125×30 mm, solvent: acetonitrile/0.05% formic acid gradient (0 to 3 min 10% acetonitrile, to 35 min to 90% acetonitrile and for a further 3 min 90% acetonitrile)). 57.5 mg (58% of theory, 99% purity) of the title compound were obtained.

$^1$H-NMR (400 MHz, DMSO-d$_6$): δ [ppm]=10.17-10.11 (m, 1H), 9.00 (s, 1H), 8.75 (d, 1H), 8.54 (d, 1H), 7.76-7.55 (m, 3H), 5.90 (d, 1H), 4.83-4.71 (m, 1H), 4.41-4.33 (m, 1H), 3.51-3.42 (m, 1H), 3.27-3.18 (m, 1H), 2.31-2.22 (m, 1H), 1.96-1.84 (m, 1H), 1.80-1.61 (m, 2H), 1.03-0.94 (m, 1H).

LC-MS (Method 3): R$_t$=1.91 min; 527 [M+H]$^+$.

Example 309

1-(2-Chloro-6-fluorophenyl)-7-[(3S)-3-hydroxy-2-oxopyrrolidin yl]-4-oxo-N-[(2R)-1,1,1-trifluorobutan-2-yl]-1,4-dihydro-1,8-naphthyridine-3-carboxamide

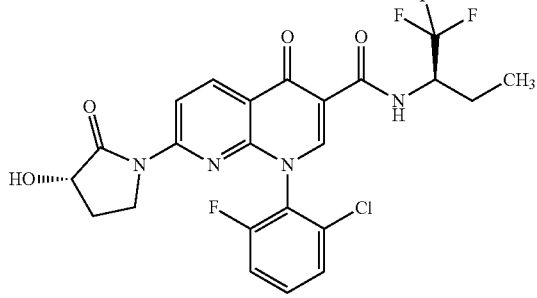

According to GP2, 100 mg (216 µmol) of the compound from Example 105C were reacted with 21.9 mg (216 µmol) of (S)-3-hydroxypyrrolidinone in the presence of 44.8 mg (325 µmol) of potassium carbonate, 8.7 mg (39 µmol) of palladium(II) acetate and 45 mg (78 µmol) of Xantphos in 1.98 ml of 1,4-dioxane. Subsequently, the volume of the mixture was concentrated under reduced pressure, the residue was acidified with 1N aqueous hydrochloric acid and taken up with 3 ml of acetonitrile, filtered and purified by means of preparative HPLC (column: Chromatorex C18, 10 µm, 125×30 mm, solvent: acetonitrile/0.05% formic acid gradient (0 to 3 min 10% acetonitrile, to 35 min to 90% acetonitrile and for a further 3 min 90% acetonitrile)). 63.3 mg (55% of theory, 99% purity) of the title compound were obtained.

$^1$H-NMR (400 MHz, DMSO-d$_6$): δ [ppm]=10.14 (d, 1H), 9.00 (d, 1H), 8.75 (d, 1H), 8.54 (d, 1H), 7.76-7.54 (m, 3H), 5.90 (d, 1H), 4.83-4.70 (m, 1H), 4.42-4.33 (m, 1H), 3.52-3.41 (m, 1H), 3.28-3.18 (m, 1H), 2.32-2.23 (m, 1H), 1.96-1.84 (m, 1H), 1.80-1.61 (m, 2H), 1.02-0.94 (m, 1H).

LC-MS (Method 3): R$_t$=1.91 min; 527 [M+H]$^+$.

Example 310

1-(2-Chloro-6-fluorophenyl)-7-[1-hydroxy-3-azabicyclo[3.1.0]hex-3-yl]-4-oxo-N-[(2R)-1,1,1-trifluorobutan-2-yl]-1,4-dihydro-1,8-naphthyridine-3-carboxamide (diastereomer mixture)

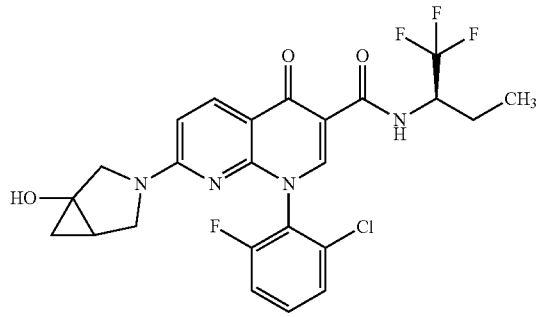 [SMILES: CC[C@@H](NC(=O)c1cn(-c2c(F)cccc2Cl)c2nc(N3CC4CC4(O)C3)ccc2c1=O)C(F)(F)F]

According to GP3, 100 mg (216 µmol) of the compound from Example 105C were reacted with 35.5 mg (238 µmol) of 3-azabicyclo[3.1.0]hexan-1-ol hydrochloride (racemate, 91% purity) and 132 µl (757 µmol) of N,N-diisopropylethylamine in 2 ml of dimethylformamide. The crude product was diluted with 0.5 ml of acetonitrile and was purified by means of preparative HPLC (column: Chromatorex C18, 10 µm, 125×30 mm, solvent: acetonitrile/0.05% formic acid gradient; 0 to 3 min 10% acetonitrile, to 35 min 90% acetonitrile and for a further 3 min 90% acetonitrile). 74.7 mg (66% of theory, 100% purity) of the title compound were obtained.

$^1$H-NMR (400 MHz, DMSO-d$_6$): δ [ppm]=10.43 (d, 1H), 8.71 (s, 1H), 8.28 (d, 1H), 7.75-7.50 (m, 3H), 6.83-6.69 (m, 1H), 5.99 (d, 1H), 4.80-4.67 (m, 1H), 3.92-3.82 (m, 0.5H), 3.69-3.60 (m, 0.5H), 3.54-3.37 (m, 1.5H), 3.24-2.97 (m, 1.5H), 1.94-1.82 (m, 1H), 1.72-1.46 (m, 2H), 1.05-0.92 (m, 4H), 0.48-0.35 (m, 1H).

LC-MS (Method 3): R$_t$=2.04 min; 525 [M+H]$^+$.

Example 311

1-(2,6-Difluorophenyl)-7-[1-hydroxy-3-azabicyclo[3.1.0]hex-3-yl]-4-oxo-N-[(2S)-1,1,1-trifluoropropan-2-yl]-1,4-dihydro-1,8-naphthyridine-3-carboxamide (diastereomer mixture)

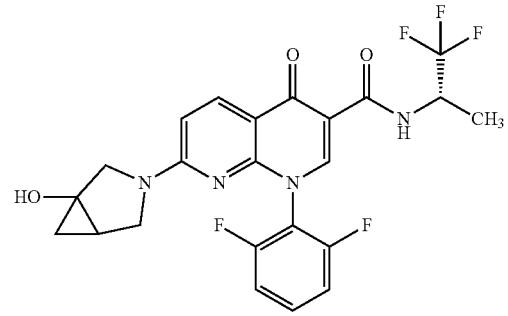 [SMILES: C[C@H](NC(=O)c1cn(-c2c(F)cccc2F)c2nc(N3CC4CC4(O)C3)ccc2c1=O)C(F)(F)F]

According to GP3, 100 mg (232 µmol) of the compound from Example 106A were reacted with 37.9 mg (255 µmol)

of 3-azabicyclo[3.1.0]hexan-1-ol hydrochloride (racemate, 91% purity) and 141 µl (811 µmol) of N,N-diisopropylethylamine in 1 ml of dimethylformamide. The crude product was diluted with 0.5 ml of acetonitrile and was purified by means of preparative HPLC (column: Chromatorex C18, 10 µm, 125×30 mm, solvent: acetonitrile/0.05% formic acid gradient; 0 to 3 min 10% acetonitrile, to 35 min 90% acetonitrile and for a further 3 min 90% acetonitrile). 72.1 mg (63% of theory, 100% purity) of the title compound were obtained.

$^1$H-NMR (400 MHz, DMSO-$d_6$): δ [ppm]=10.46 (d, 1H), 8.75 (s, 1H), 8.27 (d, 1H), 7.77-7.65 (m, 1H), 7.48-7.36 (m, 2H), 6.83-6.69 (m, 1H), 6.00 (d, 1H), 4.95-4.81 (m, 1H), 3.91-3.83 (m, 0.5H), 3.69-3.60 (m, 0.5H), 3.55-3.38 (m, 1.5H), 3.26-3.02 (m, 1.5H), 1.69-1.47 (m, 1H), 1.37 (d, 3H), 1.05-0.98 (m, 1H), 0.46-0.39 (m, 1H).

LC-MS (Method 3): $R_t$=1.89 min; 495 [M+H]$^+$.

70 mg of the title compound (diastereomer mixture) were separated into the diastereomers by chiral HPLC (preparative HPLC: column: Daicel Chiralpak AZ-H 5 µm 250×20 mm; eluent: 15% ethanol, 85% isohexane; temperature: 25° C.; flow rate: 20 ml/min; UV detection: 265 nm).

This gave (in the sequence of elution from the column) 34.4 mg of diastereomer 1 (100% de) $R_t$=2.29 min and 37.5 mg (100% de) of diastereomer 2 $R_t$=2.48 min.

[Analytical HPLC: column: Daicel Chiralpak AZ-3 3 µm 50×4.6 mm; eluent: 10% ethanol, 90% isohexane; flow rate: 1 ml/min; UV detection: 220 nm].

Diastereomer 1 was additionally purified by means of preparative HPLC (column: Chromatorex C18, 10 µm, 125× 30 mm, solvent: acetonitrile/0.05% formic acid gradient; (0 to 3 min. 10% acetonitrile to 35 min. 90% acetonitrile and a further 3 min. 90% acetonitrile)), and 17.3 mg (15% of theory, 100% purity) of the title compound from Example 312 were obtained.

Diastereomer 2 was additionally purified by means of preparative HPLC (column: Chromatorex C18, 10 µm, 125× 30 mm, solvent: acetonitrile/0.05% formic acid gradient; (0 to 3 min. 10% acetonitrile to 35 min. 90% acetonitrile and a further 3 min. 90% acetonitrile)), and 16.7 mg (15% of theory, 100% purity) of the title compound from Example 313 were obtained.

Example 312

1-(2,6-Difluorophenyl)-7-[1-hydroxy-3-azabicyclo [3.1.0]hex-3-yl]-4-oxo-N-[(2S)-1,1,1-trifluoropropan-2-yl]-1,4-dihydro-1,8-naphthyridine-3-carboxamide (diastereomer 1)

$^1$H-NMR (400 MHz, DMSO-$d_6$): δ [ppm]=10.46 (d, 1H), 8.75 (s, 1H), 8.27 (d, 1H), 7.76-7.65 (m, 1H), 7.48-7.36 (m, 2H), 6.83-6.69 (m, 1H), 6.01 (d, 1H), 4.93-4.83 (m, 1H), 3.91-3.83 (m, 0.5H), 3.69-3.60 (m, 0.5H), 3.54-3.41 (m, 1.5H), 3.25-3.02 (m, 1.5H), 1.68-1.48 (m, 1H), 1.37 (d, 3H), 1.04-0.98 (m, 1H), 0.46-0.39 (m, 1H).

LC-MS (Method 3): $R_t$=1.96 min; 495 [M+H]$^+$.

Example 313

1-(2,6-Difluorophenyl)-7-[1-hydroxy-3-azabicyclo [3.1.0]hex-3-yl]-4-oxo-N-[(2S)-1,1,1-trifluoropropan-2-yl]-1,4-dihydro-1,8-naphthyridine-3-carboxamide (diastereomer 2)

$^1$H-NMR (400 MHz, DMSO-$d_6$): δ [ppm]=10.46 (d, 1H), 8.75 (s, 1H), 8.27 (d, 1H), 7.76-7.65 (m, 1H), 7.47-7.37 (m, 2H), 6.81-6.69 (m, 1H), 6.00 (d, 1H), 4.93-4.83 (m, 1H), 3.91-3.84 (m, 0.5H), 3.68-3.60 (m, 0.5H), 3.53-3.41 (m, 1.5H), 3.25-3.04 (m, 1.5H), 1.68-1.48 (m, 1H), 1.37 (d, 3H), 1.04-0.99 (m, 1H), 0.47-0.38 (m, 1H).

LC-MS (Method 3): $R_t$=1.88 min; 495 [M+H]$^+$.

Example 314

1-(2,4-Difluorophenyl)-7-[1-hydroxy-3-azabicyclo [3.1.0]hex-3-yl]-4-oxo-N-[(2R)-1,1,1-trifluorobutan-2-yl]-1,4-dihydro-1,8-naphthyridine-3-carboxamide (diastereomer 1)

$^1$H NMR (400 MHz, DMSO-$d_6$): δ [ppm]=10.48 (d, 1H), 8.62 (s, 1H), 8.28 (d, 1H), 7.85-7.75 (m, 1H), 7.65-7.53 (m, 1H), 7.38-7.28 (m, 1H), 6.81-6.66 (m, 1H), 6.00 (d, 1H), 4.80-4.67 (m, 1H), 3.94-3.04 (m, 4H partially under the water signal), 1.93-1.82 (m, 1H), 1.69-1.51 (m, 2H), 1.07-0.92 (m, 4H), 0.48-0.35 (m, 1H).

LC-MS (Method 3): $R_t$=1.99 min; 509 [M+H]$^+$.

Example 315

1-(2,4-Difluorophenyl)-7-[1-hydroxy-3-azabicyclo [3.1.0]hex-3-yl]-4-oxo-N-[(2R)-1,1,1-trifluorobutan-2-yl]-1,4-dihydro-1,8-naphthyridine-3-carboxamide (diastereomer 2)

$^1$H NMR (400 MHz, DMSO-$d_6$): δ [ppm]=10.48 (d, 1H), 8.62 (s, 1H), 8.28 (d, 1H), 7.86-7.74 (m, 1H), 7.66-7.52 (m, 1H), 7.38-7.27 (m, 1H), 6.81-6.67 (m, 1H), 6.00 (d, 1H), 4.80-4.67 (m, 1H), 3.93-3.06 (m, 4H partially under the water signal), 1.93-1.81 (m, 1H), 1.71-1.50 (m, 2H), 1.06-0.91 (m, 4H), 0.47-0.35 (m, 1H).

LC-MS (Method 3): $R_t$=1.99 min; 509 [M+H]$^+$.

Example 316

7-[1-Hydroxy-3-azabicyclo[3.1.0]hex-3-yl]-4-oxo-1-(2,4,6-trifluorophenyl)-N-[(2S)-1,1,1-trifluoropropan-2-yl]-1,4-dihydro-1,8-naphthyridine-3-carboxamide (diastereomer mixture)

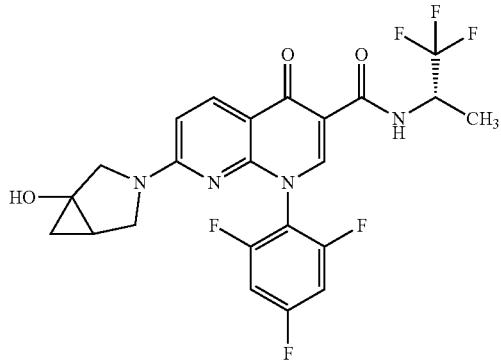 [SMILES: C[C@H](NC(=O)c1cn(-c2c(F)cc(F)cc2F)c2nc(N3CC4CC4(O)C3)ccc2c1=O)C(F)(F)F]

According to GP3, 150 mg (334 µmol) of the compound from Example 107A were reacted with 54.7 mg (367 µmol) of 3-azabicyclo[3.1.0]hexan-1-ol hydrochloride (racemate, 91% purity) and 203 µl (1.17 mmol) of N,N-diisopropylethylamine in 1.5 ml of dimethylformamide. The crude product was diluted with 0.5 ml of acetonitrile and was purified by means of preparative HPLC (column: Chromatorex C18, 10 μm, 125×30 mm, solvent: acetonitrile/0.05% formic acid gradient; 0 to 3 min 10% acetonitrile, to 35 min 90% acetonitrile and for a further 3 min 90% acetonitrile). 123.8 mg (72% of theory, 99% purity) of the title compound were obtained.

¹H-NMR (400 MHz, DMSO-d₆): δ [ppm]=10.45 (d, 1H), 8.81 (s, 1H), 8.27 (d, 1H), 7.64-7.50 (m, 2H), 6.83-6.68 (m, 1H), 6.02 (d, 1H), 4.95-4.82 (m, 1H), 3.92-3.84 (m, 0.5H), 3.69-3.39 (m, 2H), 3.19-3.08 (m, 1H), 1.69-1.50 (m, 1H), 1.37 (d, 3H), 1.06-0.98 (m, 1H), 0.48-0.39 (m, 1H).

LC-MS (Method 1): $R_t$=1.01 min; 513 [M+H]⁺.

120 mg of the title compound (diastereomer mixture) were separated into the diastereomers by chiral SFC (preparative SFC: column: Daicel Chiralpak IA 5 μm 250×20 mm; eluent: 7% ethanol, 93% carbon dioxide; temperature: 40° C.; flow rate: 100 ml/min; UV detection: 210 nm).

This gave (in the sequence of elution from the column) 42.0 mg of diastereomer 1 (100% de) $R_t$=1.48 min and 47.2 mg (87% de) of diastereomer 2 $R_t$=1.57 min.

[Analytical SFC: column: Daicel Chiralpak IA; eluent: 10% ethanol, 90% carbon dioxide; flow rate: 3 ml/min; UV detection: 220 nm].

Diastereomer 1 was additionally purified by means of preparative HPLC (column: Chromatorex C18, 10 μm, 125×30 mm, solvent: acetonitrile/0.05% formic acid gradient; (0 to 3 min. 10% acetonitrile to 35 min. 90% acetonitrile and a further 3 min. 90% acetonitrile)), and 26.9 mg (16% of theory, 100% purity) of the title compound from Example 317 were obtained.

Diastereomer 2 was additionally purified by means of preparative HPLC (column: Chromatorex C18, 10 μm, 125×30 mm, solvent: acetonitrile/0.05% formic acid gradient; (0 to 3 min. 10% acetonitrile to 35 min. 90% acetonitrile and a further 3 min. 90% acetonitrile)), and 38.8 mg (22% of theory, 100% purity) of the title compound from Example 318 were obtained.

Example 317

7-[1-Hydroxy-3-azabicyclo[3.1.0]hex-3-yl]-4-oxo-1-(2,4,6-trifluorophenyl)-N-[(2S)-1,1,1-trifluoropropan-2-yl]-1,4-dihydro-1,8-naphthyridine-3-carboxamide (diastereomer 1)

¹H-NMR (400 MHz, DMSO-d₆): δ [ppm]=10.45 (d, 1H), 8.81 (s, 1H), 8.27 (d, 1H), 7.63-7.51 (m, 2H), 6.83-6.68 (m, 1H), 6.01 (d, 1H), 4.95-4.81 (m, 1H), 3.92-3.84 (m, 0.5H), 3.70-3.40 (m, 2H), 3.20-3.08 (m, 1H), 1.69-1.51 (m, 1H), 1.37 (d, 3H), 1.06-0.98 (m, 1H), 0.46-0.39 (m, 1H).

LC-MS (Method 3): $R_t$=1.92 min; 513 [M+H]⁺.

Example 318

7-[1-Hydroxy-3-azabicyclo[3.1.0]hex-3-yl]-4-oxo-1-(2,4,6-trifluorophenyl)-N-[(2S)-1,1,1-trifluoropropan-2-yl]-1,4-dihydro-1,8-naphthyridine-3-carboxamide (diastereomer 2)

¹H-NMR (400 MHz, DMSO-d₆): δ [ppm]=10.45 (d, 1H), 8.81 (s, 1H), 8.27 (d, 1H), 7.64-7.50 (m, 2H), 6.82-6.69 (m, 1H), 6.02 (d, 1H), 4.94-4.83 (m, 1H), 3.92-3.83 (m, 0.5H), 3.69-3.40 (m, 2H), 3.20-3.09 (m, 1H), 1.69-1.50 (m, 1H), 1.37 (d, 3H), 1.06-0.99 (m, 1H), 0.49-0.39 (m, 1H).

LC-MS (Method 3): $R_t$=1.92 min; 513 [M+H]⁺.

Example 319

N-[(1R)-1-Cyclopropyl-2,2,2-trifluoroethyl]-1-(2,6-difluorophenyl)-7-[1-hydroxy-3-azabicyclo[3.1.0]hex-3-yl]-4-oxo-1,4-dihydro-1,8-naphthyridine-3-carboxamide (diastereomer mixture)

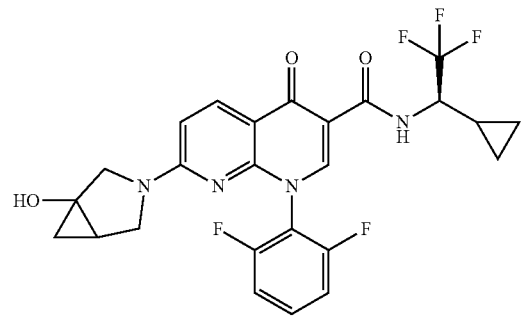 [SMILES: O=C(N[C@H](C1CC1)C(F)(F)F)c1cn(-c2c(F)cccc2F)c2nc(N3CC4CC4(O)C3)ccc2c1=O]

According to GP3, 150 mg (328 μmol) of the compound from Example 103A were reacted with 53.7 mg (360 μmol) of 3-azabicyclo[3.1.0]hexan-1-ol hydrochloride (racemate, 91% purity) and 200 μl (1.15 mmol) of N,N-diisopropylethylamine in 1.5 ml of dimethylformamide. The crude product was diluted with 5 ml of acetonitrile and 0.5 ml of 1N aqueous hydrochloric acid, filtered and purified by means of preparative HPLC (column: Chromatorex C18, 10 μm, 125×30 mm, solvent: acetonitrile/0.05% formic acid gradient; 0 to 3 min 10% acetonitrile, to 35 min 90% acetonitrile and for a further 3 min 90% acetonitrile). 119.3 mg (69% of theory, 98.4% purity) of the title compound were obtained.

¹H-NMR (400 MHz, DMSO-d₆): δ [ppm]=10.54 (d, 1H), 8.75 (s, 1H), 8.29 (d, 1H), 7.77-7.65 (m, 1H), 7.47-7.35 (m, 2H), 6.83-6.69 (m, 1H), 6.00 (d, 1H), 4.43-4.31 (m, 1H), 3.92-3.82 (m, 0.5H), 3.70-3.59 (m, 0.5H), 3.55-3.39 (m, 1.5H), 3.27-3.18 (m, 0.5H), 3.16-3.03 (m, 1H), 1.69-1.48 (m, 1H), 1.26-1.14 (m, 1H), 1.05-0.97 (m, 1H), 0.70-0.48 (m, 3H), 0.47-0.39 (m, 1H), 0.37-0.30 (m, 1H).

LC-MS (Method 3): $R_t$=2.01 min; 521 [M+H]⁺.

Example 320

1-(2,4-Difluorophenyl)-4-oxo-7-(2-oxoimidazolidin-1-yl)-N-[(2R)-1,1,1-trifluorobutan-2-yl]-1,4-dihydro-1,8-naphthyridine-3-carboxamide

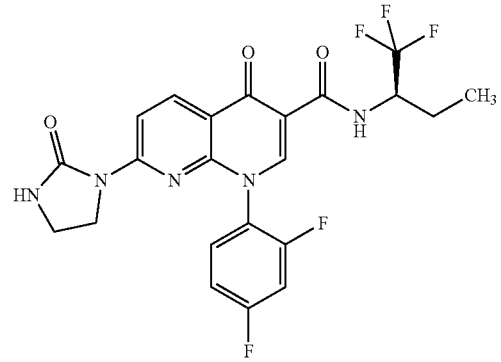 [SMILES: CC[C@@H](NC(=O)c1cn(-c2ccc(F)cc2F)c2nc(N3CCNC3=O)ccc2c1=O)C(F)(F)F]

According to GP2, 300 mg (673 µmol) of the compound from Example 67A were reacted with 64.0 mg (707 µmol) of imidazolidinone in the presence of 140 mg (1.01 mmol) of potassium carbonate, 27.2 mg (121 µmol) of palladium (II) acetate and 140 mg (242 µmol) of Xantphos in 6 ml of 1,4-dioxane. Subsequently, the mixture was admixed with 10 ml of ethyl acetate, washed with 1N aqueous hydrochloric acid and concentrated to dryness by rotary evaporation. The residue was taken up in 10 ml of THF, 250 mg of N-acetylcysteine were added and the mixture was stirred at room temperature for 30 min. The mixture was diluted with 30 ml of ethyl acetate and washed with saturated aqueous sodium hydrogencarbonate solution, dried over sodium sulphate and filtered, and the solvent was removed under reduced pressure. The residue was stirred in 6 ml of acetonitrile and 1 ml of water, the precipitate was filtered off with suction and the mother liquor was purified by means of preparative HPLC (column: Chromatorex C18, 10 µm, 125×30 mm, solvent: acetonitrile/0.05% formic acid gradient; 0 to 3 min 10% acetonitrile, to 35 min 90% acetonitrile and for a further 3 min 90% acetonitrile). 20.2 mg (5.9% of theory, 97.1% purity) of the title compound were obtained.

$^1$H-NMR (400 MHz, DMSO-d$_6$): δ [ppm]=10.31 (d, 1H), 8.78 (s, 1H), 8.56 (d, 1H), 8.42 (d, 1H), 7.91-7.82 (m, 1H), 7.66-7.55 (m, 2H), 7.38-7.31 (m, 1H), 4.80-4.72 (m, 1H), 3.65-3.50 (m, 2H), 3.39-3.33 (m, 2H partially under the water signal), 1.95-1.82 (m, 1H), 1.72-1.59 (m, 1H), 0.98 (t, 3H).

LC-MS (Method 3): R$_t$=1.89 min; 496 [M+H]$^+$.

Example 321

1-(2,4-Difluorophenyl)-7-(3-methyl-2-oxoimidazolidin-1-yl)-4-oxo-N-[(2R)-1,1,1-trifluorobutan-2-yl]-1,4-dihydro-1,8-naphthyridine-3-carboxamide

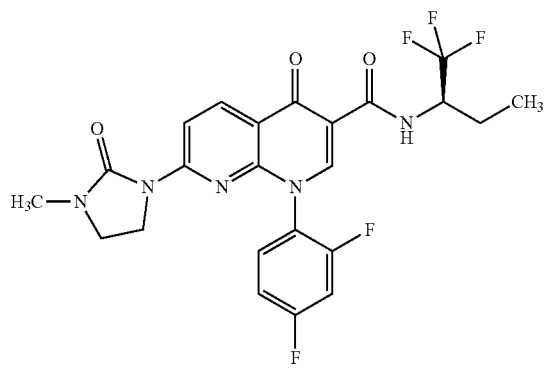 [SMILES: CC[C@@H](NC(=O)c1cn(-c2ccc(F)cc2F)c2nc(N3CCN(C)C3=O)ccc2c1=O)C(F)(F)F]

To a solution of 20 mg (40 µmol) of the compound from Example 320 in 1 ml of 1,2-dimethoxyethane were added, while cooling with an ice bath, 2.4 mg (61 µmol, 60% in mineral oil) of sodium hydride, and the mixture was stirred for a further 30 min. The mixture was warmed to room temperature, 5.0 µl (81 µmol) of iodomethane were added and the mixture was stirred at 80° C. overnight. Subsequently, the volume of the mixture was concentrated under reduced pressure, and the residue was taken up in 3 ml of acetonitrile, 0.5 ml of water and 1 ml of DMSO, and purified by means of preparative HPLC (column: Chromatorex C18, 10 µm, 125×30 mm, solvent: acetonitrile/0.05% formic acid gradient; 0 to 3 min 10% acetonitrile, to 35 min 90% acetonitrile and for a further 3 min 90% acetonitrile). 5.4 mg (26% of theory, 99% purity) of the title compound were obtained.

$^1$H-NMR (400 MHz, DMSO-d$_6$): δ [ppm]=10.31 (d, 1H), 8.78 (s, 1H), 8.57 (d, 1H), 8.43 (d, 1H), 7.91-7.81 (m, 1H), 7.63-7.56 (m, 1H), 7.38-7.31 (m, 1H), 4.81-4.71 (m, 1H), 3.57-3.36 (m, 4H), 2.79 (s, 3H), 1.94-1.84 (m, 1H), 1.72-1.59 (m, 1H), 0.98 (t, 3H).

LC-MS (Method 1): R$_t$=1.16 min; 510 [M+H]$^+$.

Example 322

1-(2-Chloro-4,6-difluorophenyl)-7-[(3R,4R)-3,4-dihydroxypyrrolidin-1-yl]-4-oxo-N-[(2S)-1-(trifluoromethoxy)propan-2-yl]-1,4-dihydro-1,8-naphthyridine-3-carboxamide

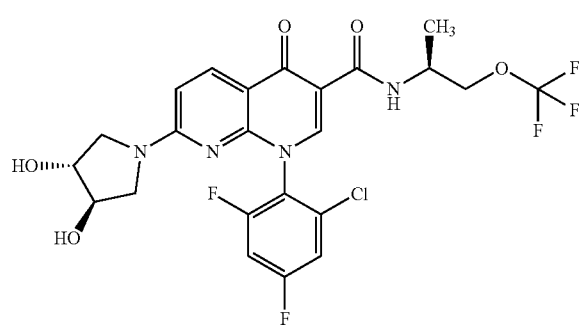 [SMILES: C[C@@H](COC(F)(F)F)NC(=O)c1cn(-c2c(F)cc(F)cc2Cl)c2nc(N3C[C@@H](O)[C@H](O)C3)ccc2c1=O]

According to GP3, 51.7 mg (104 µmol) of the compound from Example 112A were reacted with 16.0 mg (115 µmol) of (3R,4R)-pyrrolidine-3,4-diol hydrochloride and 63.5 µl (365 µmol) of N,N-diisopropylethylamine in 1 ml of dimethylformamide. The crude product was acidified with 2 ml of acetonitrile and 1N aqueous hydrochloric acid and purified by means of preparative HPLC (column: Chromatorex C18, 10 µm, 125×30 mm, solvent: acetonitrile/0.05% formic acid gradient; 0 to 3 min 10% acetonitrile, to 35 min 90% acetonitrile and for a further 3 min 90% acetonitrile). 48 mg (82% of theory, 100% purity) of the title compound were obtained.

$^1$H-NMR (400 MHz, DMSO-d$_6$): δ [ppm]=10.14-10.09 (m, 1H), 8.66 (s, 1H), 8.27 (d, 1H), 7.75-7.65 (m, 2H), 6.75 (d, 1H), 5.24-5.20 (m, 1H), 5.15-5.11 (m, 1H), 4.38-4.29 (m, 1H), 4.21-4.13 (m, 2H), 4.06-4.02 (m, 1H), 3.93-3.88 (m, 1H), 3.64-3.57 (m, 1H), 3.24-3.16 (m, 1H), 3.06-2.98 (m, 1H), 1.28-1.21 (m, 3H).

LC-MS (Method 3): R$_t$=1.68 min; m/z=563 [M+H]$^+$.

Example 323

N-[(1S)-1-Cyclopropyl-2,2,2-trifluoroethyl]-4-oxo-7-(2-oxoimidazolidin-1-yl)-1-(2,4,6-trifluorophenyl)-1,4-dihydro-1,8-naphthyridine-3-carboxamide

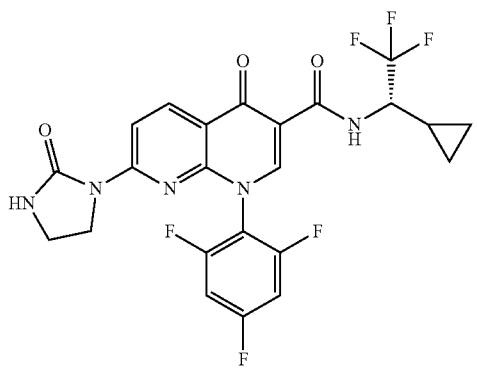 [SMILES: O=C(N[C@@H](C1CC1)C(F)(F)F)c1cn(-c2c(F)cc(F)cc2F)c2nc(N3CCNC3=O)ccc2c1=O]

According to GP1, 15.0 g (37.1 mmol) of the compound from Example 113A were reacted with 7.82 g (44.5 mmol) of (1S)1-cyclopropyl-2,2,2-trifluoroethanamine hydrochloride in the presence of 16.9 g (44.5 mmol) of HATU and 16.2 ml (92.8 mmol) of N,N-diisopropylethylamine in 400 ml of dimethylformamide. On completion of conversion, the reaction solution was stirred into water and adjusted to pH 3. The mixture was extracted with ethyl acetate and the phases were separated. The organic phase was washed with water, dried over sodium sulphate, filtered and concentrated. The residue was stirred in acetonitrile, filtered off with suction after 1 h, washed and dried under high vacuum. 9.3 g (48% of theory, 99% purity) of the title compound were obtained.

$^1$H-NMR (400 MHz, DMSO-d$_6$): δ [ppm]=10.36 (d, 1H), 8.99 (s, 1H), 8.57 (d, 1H), 8.44 (d, 1H), 7.67 (s, 1H), 7.62-7.53 (m, 2H), 4.47-4.34 (m, 1H), 3.64-3.56 (m, 2H), 3.39-3.32 (m, 2H), 1.28-1.17 (m, 1H), 0.71-0.50 (m, 3H), 0.39-0.31 (m, 1H).

LC-MS (Method 3): R$_t$=1.94 min; m/z=526 [M+H]$^+$.

Example 324

7-[3-Hydroxy-3-methylpyrrolidin-1-yl]-4-oxo-N-[(2R)-1,1,1-trifluorobutan-2-yl]-1-(2,4,6-trifluorophenyl)-1,4-dihydro-1,8-naphthyridine-3-carboxamide (diastereomer mixture)

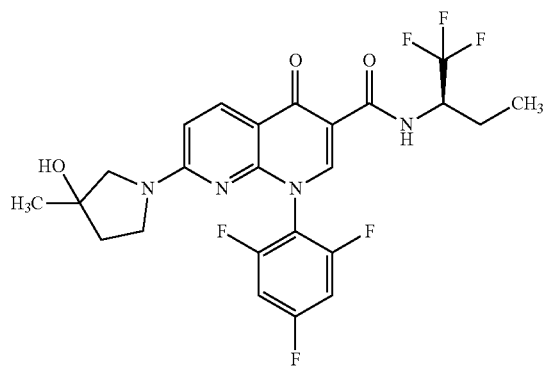 [SMILES: CC[C@@H](NC(=O)c1cn(-c2c(F)cc(F)cc2F)c2nc(N3CCC(C)(O)C3)ccc2c1=O)C(F)(F)F]

According to GP3, 100 mg (216 µmol) of the compound from Example 100C and 39.6 mg (90% purity, 259 µmol) of 3-methylpyrrolidin-3-ol hydrochloride were reacted in the presence of 130 µl (750 µmol) of N,N-diisopropylethylamine in 1.0 ml of DMF. The reaction mixture was diluted with 0.5 ml of acetonitrile and was purified by means of preparative HPLC (column: Chromatorex C18, 10 µm, 125×30 mm, solvent: acetonitrile/0.05% formic acid gradient; 0 to 3 min 10% acetonitrile, to 35 min 90% acetonitrile and for a further 3 min 90% acetonitrile). 93.5 mg (81% of theory, 99% purity) of the title compound were obtained.

$^1$H-NMR (400 MHz, DMSO-d6) δ[ppm]: −0.008 (2.44), 0.008 (1.51), 0.952 (7.58), 0.970 (16.00), 0.988 (7.79), 1.249 (9.47), 1.323 (10.19), 1.602 (1.14), 1.621 (1.57), 1.627 (1.40), 1.637 (1.85), 1.646 (1.66), 1.655 (1.60), 1.663 (1.71), 1.681 (1.29), 1.795 (2.67), 1.814 (1.90), 1.832 (0.86), 1.850 (1.62), 1.859 (1.90), 1.868 (1.90), 1.878 (2.33), 1.885 (2.43), 1.895 (2.50), 1.904 (2.87), 1.913 (3.39), 1.929 (1.83), 2.941 (1.33), 2.971 (1.75), 3.119 (1.67), 3.150 (1.26), 3.223 (2.27), 3.239 (1.69), 3.288 (2.21), 3.341 (2.64), 3.364 (2.32), 3.391 (0.81), 3.548 (2.35), 3.566 (1.53), 4.732 (1.56), 4.752 (1.44), 4.820 (3.48), 4.893 (3.76), 6.703 (2.03), 6.725 (2.13), 6.762 (1.95), 6.785 (1.84), 7.533 (1.97), 7.554 (3.99), 7.574 (3.36), 8.247 (2.36), 8.270 (4.17), 8.293 (1.97), 8.792 (5.29), 8.799 (5.47), 10.424 (5.03), 10.448 (4.79).

LC-MS Method 3): R$_t$=2.06 min; MS (ESIpos): m/z=529 [M+H]$^+$

Example 325

7-[(4S)-4-Hydroxy-2-oxopyrrolidin-1-yl]-4-oxo-N-[(2R)-1,1,1-trifluorobutan-2-yl]-1-(2,4,6-trifluorophenyl)-1,4-dihydro-1,8-naphthyridine-3-carboxamide

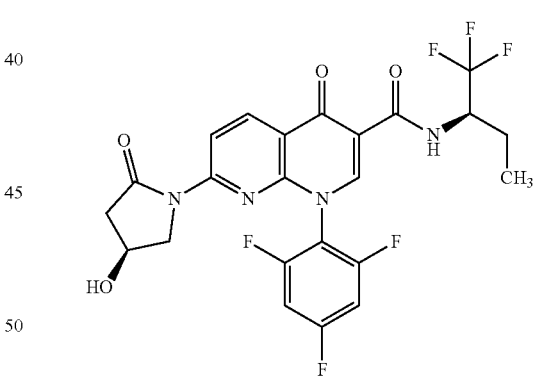

According to GP2, 100 mg (216 µmol) of the compound from Example 100C were reacted with 26.2 mg (259 µmol) of (4S)-4-hydroxypyrrolidin-2-one in the presence of 44.7 mg (323 µmol) of potassium carbonate, 8.71 mg (38.8 µmol) of palladium(II) acetate and 44.9 mg (77.6 µmol) of Xantphos in 2.0 ml of 1,4-dioxane. Subsequently, the reaction mixture was concentrated. It was acidified with 1N aqueous hydrochloric acid, admixed with 3 ml of acetonitrile and filtered. The filtrate was purified by means of preparative HPLC (column: Chromatorex C18, 10 µm, 125×30 mm, solvent: acetonitrile/0.05% formic acid gradient; 0 to 3 min. 10% acetonitrile to 35 min. 90% acetonitrile and a further 3 min. 90% acetonitrile), and 87.9 mg (76% of theory, 99% purity) of the title compound were obtained.

¹H-NMR (400 MHz, DMSO-d6) δ[ppm]: −0.008 (3.32), 0.008 (3.18), 0.965 (7.20), 0.984 (16.00), 1.002 (7.81), 1.632 (1.07), 1.649 (1.52), 1.666 (1.70), 1.675 (1.50), 1.692 (1.78), 1.710 (1.36), 1.866 (1.31), 1.877 (1.46), 1.884 (1.48), 1.895 (1.68), 2.355 (3.56), 2.399 (4.11), 2.711 (0.71), 2.916 (3.44), 2.931 (3.68), 2.959 (3.12), 2.974 (3.03), 3.287 (4.13), 3.463 (3.72), 3.493 (4.43), 3.673 (3.24), 3.686 (3.90), 3.703 (2.95), 3.715 (2.59), 4.290 (2.79), 4.763 (1.42), 5.331 (7.89), 5.340 (7.81), 7.595 (2.27), 7.602 (2.65), 7.617 (4.31), 7.625 (4.51), 7.639 (2.65), 7.645 (2.27), 8.532 (10.26), 8.554 (12.42), 8.707 (12.88), 8.729 (9.97), 9.072 (15.90), 10.103 (5.12), 10.127 (4.94).

LC-MS (Method 3): Rt=1.90 min; MS (ESIpos): m/z=529 [M+H]$^+$

Example 326

N-[1-Cyclopropyl-2,2,2-trifluoroethyl]-1-(2,6-difluorophenyl)-7-[3-hydroxy-3-methylpyrrolidin-1-yl]-4-oxo-1,4-dihydro-1,8-naphthyridine-3-carboxamide (racemic diastereomer mixture)

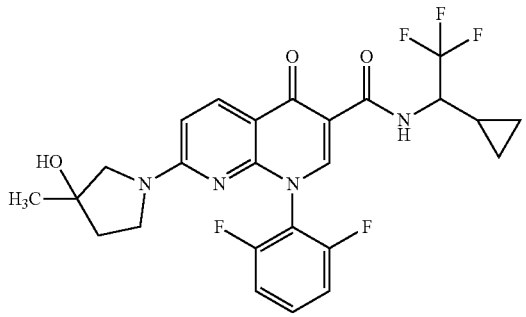 [SMILES: CC1(O)CCN(c2ccc3c(=O)c(C(=O)NC(C4CC4)C(F)(F)F)cn(-c4c(F)cccc4F)c3n2)C1]

According to GP3, 150 mg (328 μmol) of the compound from Example 102A and 60.1 mg (90% purity, 393 μmol) of 3-methylpyrrolidin-3-ol hydrochloride were reacted in the presence of 200 μl (1.15 mmol) of N,N-diisopropylethylamine in 1.5 ml of DMF. The reaction mixture was diluted with 0.5 ml of acetonitrile and was purified by means of preparative HPLC (column: Chromatorex C18, 10 μm, 125× 30 mm, solvent: acetonitrile/0.05% formic acid gradient; 0 to 3 min 10% acetonitrile, to 35 min 90% acetonitrile and for a further 3 min 90% acetonitrile). 147 mg (85% of theory, 99% purity) of the title compound were obtained.

¹H-NMR (400 MHz, DMSO-d6) δ[ppm]: −0.008 (2.22), 0.008 (2.01), 0.325 (2.15), 0.336 (3.45), 0.349 (3.49), 0.361 (2.61), 0.373 (1.29), 0.509 (2.38), 0.520 (3.47), 0.532 (3.03), 0.547 (2.85), 0.556 (2.52), 0.568 (3.35), 0.578 (2.96), 0.589 (2.71), 0.599 (2.27), 0.612 (1.41), 0.626 (1.71), 0.637 (1.90), 0.648 (3.05), 0.658 (2.82), 0.663 (2.80), 0.671 (2.75), 0.683 (1.22), 0.693 (0.88), 1.166 (0.72), 1.179 (1.48), 1.187 (2.19), 1.199 (3.96), 1.220 (16.00), 1.240 (2.11), 1.314 (13.09), 1.769 (3.67), 1.786 (2.27), 1.900 (3.26), 1.917 (2.19), 2.891 (1.81), 2.922 (2.43), 3.079 (2.24), 3.107 (1.74), 3.169 (3.01), 3.186 (2.19), 3.289 (3.10), 3.335 (3.65), 3.357 (3.14), 3.385 (1.15), 3.542 (3.08), 4.353 (1.85), 4.374 (3.17), 4.396 (3.12), 4.416 (1.64), 4.806 (4.85), 4.886 (4.93), 6.703 (2.56), 6.724 (2.64), 6.760 (2.57), 6.783 (2.48), 7.386 (4.04), 7.408 (8.42), 7.431 (4.69), 7.694 (2.63), 7.714 (2.48), 7.729 (1.34), 8.258 (2.85), 8.280 (5.59), 8.303 (2.71), 8.724 (5.94), 8.736 (6.08), 10.574 (7.24), 10.598 (6.96).

LC-MS (Method 1): Rt=1.14 min; MS (ESIpos): m/z=523 [M+H]$^+$

Example 327

1-(2,6-Difluorophenyl)-7-[3-hydroxy-3-methylpyrrolidin-1-yl]-4-oxo-N-[(2S)-1,1,1-trifluorobutan-2-yl]-1,4-dihydro-1,8-naphthyridine-3-carboxamide (diastereomer mixture)

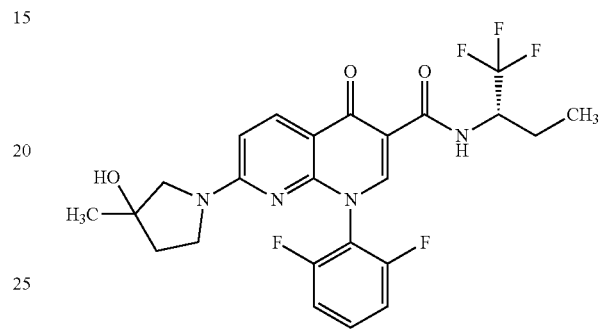

According to GP3, 150 mg (336 μmol) of the compound from Example 114A and 61.7 mg (90% purity, 404 μmol) of 3-methylpyrrolidin-3-ol hydrochloride were reacted in the presence of 205 μl (1.18 mmol) of N,N-diisopropylethylamine in 1.6 ml of DMF. The reaction mixture was diluted with 0.5 ml of acetonitrile and was purified by means of preparative HPLC (column: Chromatorex C18, 10 μm, 125× 30 mm, solvent: acetonitrile/0.05% formic acid gradient; 0 to 3 min 10% acetonitrile, to 35 min 90% acetonitrile and for a further 3 min 90% acetonitrile). 148 mg (85% of theory, 99% purity) of the title compound were obtained.

¹H-NMR (400 MHz, DMSO-d6) δ[ppm]: −0.008 (1.74), 0.008 (1.59), 0.953 (7.22), 0.972 (16.00), 0.990 (7.86), 1.221 (9.41), 1.314 (9.55), 1.604 (1.11), 1.622 (1.51), 1.629 (1.32), 1.639 (1.80), 1.647 (1.62), 1.657 (1.53), 1.664 (1.74), 1.683 (1.31), 1.752 (1.35), 1.769 (2.70), 1.786 (1.71), 1.842 (0.74), 1.851 (1.53), 1.861 (1.80), 1.870 (2.02), 1.879 (2.75), 1.886 (2.65), 1.897 (3.47), 1.904 (3.28), 1.915 (2.43), 2.074 (2.15), 2.892 (1.28), 2.922 (1.76), 3.078 (1.63), 3.108 (1.27), 3.171 (2.19), 3.187 (1.57), 3.289 (2.34), 3.335 (2.76), 3.357 (2.27), 3.384 (0.79), 3.541 (2.31), 3.559 (1.53), 4.706 (0.81), 4.730 (1.48), 4.750 (1.39), 4.765 (0.81), 4.806 (3.46), 4.885 (3.51), 6.701 (1.85), 6.723 (1.98), 6.759 (1.91), 6.782 (1.87), 7.389 (2.83), 7.411 (5.95), 7.433 (3.33), 7.680 (1.06), 7.697 (1.88), 7.714 (1.77), 7.734 (0.89), 8.254 (1.99), 8.276 (3.83), 8.299 (1.88), 8.733 (3.67), 8.745 (3.76), 10.440 (4.71), 10.464 (4.56).

LC-MS (Method 1): R$_t$=1.12 min; MS (ESIpos): m/z=511 [M+H]$^+$

Example 328

1-(2,4-Difluorophenyl)-7-(3-methoxy-3-methylazetidin-1-yl)-4-oxo-N-[(2R)-1,1,1-trifluorobutan-2-yl]-1,4-dihydro-1,8-naphthyridine-3-carboxamide

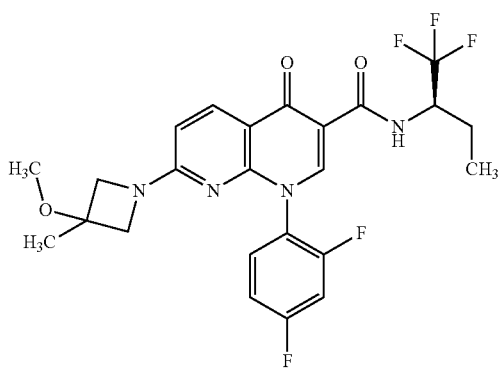 [SMILES: CC[C@@H](NC(=O)c1cn(-c2ccc(F)cc2F)c2nc(N3CC(C)(OC)C3)ccc2c1=O)C(F)(F)F]

According to GP3, 80.0 mg (179 µmol) of the compound from Example 67A and 29.6 mg (215 µmol) of 3-methoxy-3-methylazetidine hydrochloride were reacted in the presence of 110 µl (628 µmol) of N,N-diisopropylethylamine in 0.83 ml of DMF. The reaction mixture was diluted with 0.5 ml of acetonitrile and was purified by means of preparative HPLC (column: Chromatorex C18, 10 µm, 125×30 mm, solvent: acetonitrile/0.05% formic acid gradient; 0 to 3 min 10% acetonitrile, to 35 min 90% acetonitrile and for a further 3 min 90% acetonitrile). 74.2 mg (80% of theory, 99% purity) of the title compound were obtained.

$^1$H-NMR (400 MHz, DMSO-d6) δ[ppm]: 0.945 (1.92), 0.964 (4.32), 0.982 (2.11), 1.408 (8.86), 3.155 (16.00), 6.612 (2.62), 6.634 (2.63), 8.293 (2.95), 8.315 (2.81), 8.610 (3.06), 10.461 (1.38), 10.484 (1.33).

LC-MS (Method 3): $R_t$=2.29 min; MS (ESIpos): m/z=511 [M+H]$^+$

Example 329

1-(2,6-Difluorophenyl)-7-[(4S)-4-hydroxy-2-oxopyrrolidin-1-yl]-4-oxo-N-[(2S)-1,1,1-trifluoropropan-2-yl]-1,4-dihydro-1,8-naphthyridine-3-carboxamide

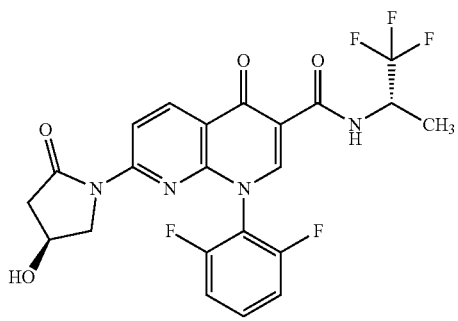 [SMILES: C[C@H](NC(=O)c1cn(-c2c(F)cccc2F)c2nc(N3C[C@@H](O)CC3=O)ccc2c1=O)C(F)(F)F]

According to GP2, 100 mg (232 µmol) of the compound from Example 106A were reacted with 25.8 mg (255 µmol) of (4S)-4-hydroxypyrrolidin-2-one in the presence of 48.0 mg (347 µmol) of potassium carbonate, 5.2 mg (23 µmol) of palladium(II) acetate and 26.6 mg (46.3 µmol) of Xantphos in 3.0 ml of 1,4-dioxane. Subsequently, the reaction mixture was concentrated. The residue was dissolved with 0.5 ml of water and with 3 ml of acetonitrile and purified by means of preparative HPLC (column: Chromatorex C18, 10 µm, 125×30 mm, solvent: acetonitrile/0.05% formic acid gradient; 0 to 3 min. 10% acetonitrile to 35 min. 90% acetonitrile and a further 3 min. 90% acetonitrile), and 77.9 mg (68% of theory, 100% purity) of the title compound were obtained.

$^1$H-NMR (400 MHz, DMSO-d6) δ[ppm]: -0.008 (4.64), 0.008 (4.39), 0.146 (0.56), 1.388 (15.95), 1.405 (16.00), 2.074 (1.46), 2.346 (3.39), 2.367 (0.65), 2.389 (3.97), 2.711 (0.60), 2.901 (3.40), 2.916 (3.51), 2.944 (3.10), 2.959 (3.05), 3.288 (3.83), 3.415 (3.37), 3.445 (4.29), 3.615 (3.18), 3.627 (3.85), 3.644 (2.88), 3.656 (2.54), 4.241 (1.11), 4.254 (2.54), 4.262 (2.49), 4.277 (1.01), 4.890 (1.13), 4.913 (1.59), 4.931 (1.71), 4.950 (1.13), 5.322 (7.78), 5.332 (7.60), 7.433 (2.03), 7.445 (2.54), 7.456 (4.16), 7.467 (4.37), 7.478 (2.84), 7.490 (2.29), 7.724 (0.88), 7.740 (1.87), 7.746 (1.94), 7.756 (1.31), 7.762 (3.37), 7.768 (1.31), 7.778 (1.82), 7.783 (1.82), 7.800 (0.83), 8.527 (10.07), 8.549 (12.17), 8.704 (12.31), 8.726 (9.65), 9.018 (12.68), 10.169 (4.80), 10.192 (4.62).

LC-MS (Method 3): $R_t$=1.73 min; MS (ESIpos): m/z=497 [M+H]$^+$

Example 330

7-[(4S)-4-Hydroxy-2-oxopyrrolidin-1-yl]-4-oxo-1-(2,4,6-trifluorophenyl)-N-[(2S)-1,1,1-trifluoropropan-2-yl]-1,4-dihydro-1,8-naphthyridine-3-carboxamide

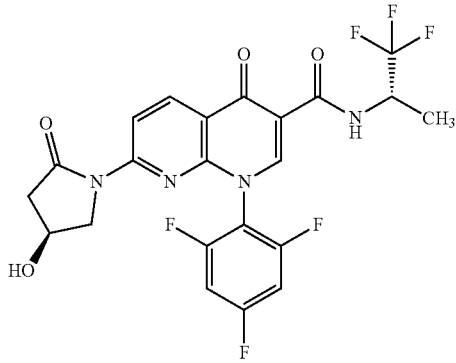 [SMILES: C[C@H](NC(=O)c1cn(-c2c(F)cc(F)cc2F)c2nc(N3C[C@@H](O)CC3=O)ccc2c1=O)C(F)(F)F]

According to GP2, 300 mg (667 µmol) of the compound from Example 107A were reacted with 74.2 mg (734 µmol) of (4S)-4-hydroxypyrrolidin-2-one in the presence of 138 mg (1.00 mmol) of potassium carbonate, 15 mg (67 µmol) of palladium(II) acetate and 27 mg (46 µmol) of Xantphos in 8.6 ml of 1,4-dioxane. Subsequently, the reaction mixture was concentrated. Subsequently, the mixture was acidified with 5 ml of 1N aqueous hydrochloric acid and the pH was monitored. 140 mg of N-acetylcysteine were added and the mixture was stirred at RT for a further 15 min. The mixture was introduced into a separating funnel and diluted with 15 ml of saturated aqueous sodium hydrogencarbonate solution and 20 ml of ethyl acetate. The phases were separated and the aqueous phase was extracted three times with ethyl acetate.

The combined organic phases were dried over magnesium sulphate and filtered, and the solvent was removed under reduced pressure. The residue was dissolved in 9 ml of acetonitrile and 3 ml of DMSO and purified in four runs by means of preparative HPLC (column: Chromatorex C18, 10 μm, 125×30 mm, solvent: acetonitrile/0.05% formic acid gradient; 0 to 3 min. 15% acetonitrile to 35 min. 85% acetonitrile and a further 3 min. 85% acetonitrile), and 208.4 mg (60% of theory, 99% purity) of the title compound were obtained.

$^1$H-NMR (400 MHz, DMSO-d$_6$): δ [ppm]=10.17 (d, 1H), 9.07 (s, 1H), 8.71 (d, 1H), 8.54 (d, 1H), 7.66-7.57 (m, 2H), 5.34 (d, 1H), 4.99-4.86 (m, 1H), 4.32-4.26 (m, 1H), 3.69 (dd, 1H), 3.48 (d, 1H), 2.94 (dd, 1H), 2.38 (d, 1H), 1.39 (d, 3H).

LC-MS (Method 3): R$_t$=1.74 min; MS (ESIpos): m/z=515 [M+H]$^+$

Example 331

7-[(2R,4S)-4-Hydroxy-2,4-dimethylpyrrolidin-1-yl]-4-oxo-N-[(2S)-1,1,1-trifluorobutan-2-yl]-1-(2,4,6-trifluorophenyl)-1,4-dihydro-1,8-naphthyridine-3-carboxamide

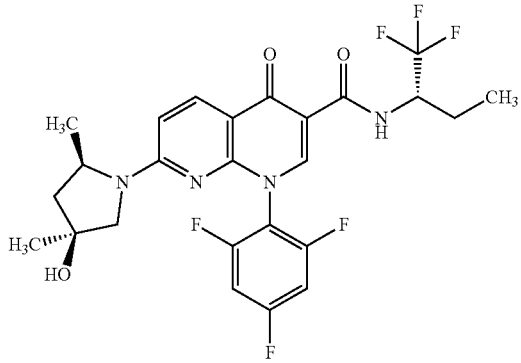 [SMILES: CC[C@H](NC(=O)c1cn(-c2c(F)cc(F)cc2F)c2nc(N3C[C@@](C)(O)C[C@H]3C)ccc2c1=O)C(F)(F)F]

According to GP3, 30.8 mg (66.4 μmol) of the compound from Example 115A and 24.0 mg (95% purity, 99.6 μmol) of the compound from Example 116A were reacted in the presence of 40.0 μl (232 μmol) of N,N-di-iso-propylethylamine in 640 μl of DMF. The reaction mixture was diluted with 0.5 ml of acetonitrile and was purified by means of preparative HPLC (column: Chromatorex C18, 10 μm, 125× 30 mm, solvent: acetonitrile/0.05% formic acid gradient; 0 to 3 min 15% acetonitrile, to 35 min 85% acetonitrile and for a further 3 min 85% acetonitrile). 30.1 mg (83% of theory, 99% purity) of the title compound were obtained.

$^1$H-NMR (400 MHz, DMSO-d6) δ[ppm]: −0.150 (0.64), −0.008 (5.62), 0.008 (5.53), 0.146 (0.72), 0.951 (7.19), 0.970 (16.00), 0.988 (8.00), 1.046 (4.51), 1.147 (0.98), 1.271 (7.87), 1.603 (1.19), 1.620 (2.00), 1.628 (2.26), 1.637 (2.64), 1.646 (2.21), 1.655 (2.51), 1.663 (3.02), 1.681 (1.74), 1.850 (1.28), 1.860 (1.57), 1.869 (1.53), 1.879 (1.87), 1.884 (1.57), 1.895 (1.40), 1.904 (1.23), 1.913 (0.98), 2.019 (1.02), 2.328 (0.60), 2.367 (1.02), 2.670 (0.72), 2.710 (1.15), 3.288 (6.51), 3.337 (2.51), 3.483 (1.49), 3.794 (1.11), 4.722 (1.36), 4.877 (2.94), 6.711 (1.53), 7.546 (3.40), 7.569 (6.00), 7.589 (3.23), 8.251 (4.38), 8.273 (4.30), 8.817 (5.11), 10.416 (5.45), 10.440 (5.32).

LC-MS (Method 3): Rt=2.13 min; MS (ESIpos): m/z=543 [M+H]$^+$

Example 332

7-[(4S)-4-Hydroxy-2-oxopyrrolidin-1-yl]-4-oxo-N-[(2S)-1,1,1-trifluorobutan-2-yl]-1-(2,4,6-trifluorophenyl)-1,4-dihydro-1,8-naphthyridine-3-carboxamide

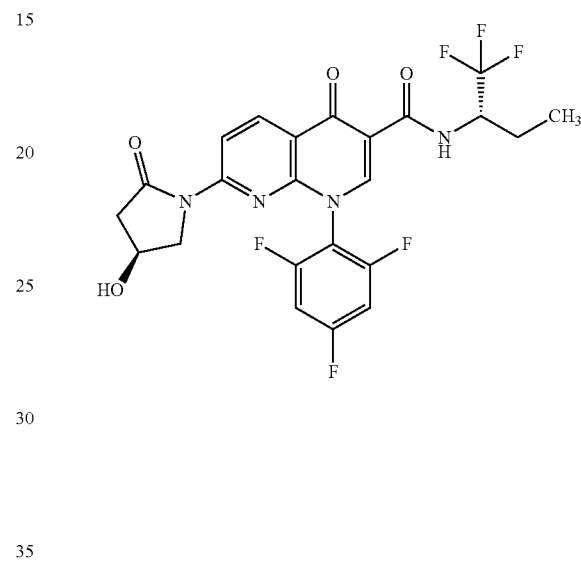

According to GP1, 20.0 g (47.7 mmol) of the compound from Example 117A were reacted with 9.36 g (57.2 mmol) of (2S)-1,1,1-trifluorobutan-2-amine hydrochloride in the presence of 27.2 g (71.5 mmol) of HATU and 20.8 ml (119 mmol) of N,N-diisopropylethylamine in 250 ml of dimethylformamide. The reaction mixture was extracted by stirring in ice-water and a little aqueous hydrochloric acid, and the precipitate was filtered off with suction and washed with water. The crude product was combined with a second batch which proceeded from 2.00 g of the compound from Example 117A in an analogous mode of operation. The combined residue was purified twice by means of normal phase chromatography (dichloromethane-methanol 95:5 v/v and petroleum ether-ethyl acetate 1:1, v/v toward dichloromethane-methanol 9:1, v/v). Finally, the product was stirred with tert-butyl methyl ether and the precipitate was filtered off with suction and washed with tert-butyl methyl ether. 20.3 g (81% of theory, 100% purity) of the title compound were obtained.

$^1$H-NMR (400 MHz, DMSO-d$_6$): δ [ppm]=10.11 (d, 1H), 8.72 (d, 1H), 8.54 (d, 1H), 7.66-7.58 (m, 2H), 5.35-5.31 (m, 1H), 4.83-4.70 (m, 1H), 4.33-4.26 (m, 1H), 3.69 (dd, 1H), 3.47 (d, 1H), 2.95 (dd, 1H), 2.38 (d, 1H), 1.95-1.84 (m, 1H), 1.74-1.60 (m, 1H), 0.98 (t, 3H).

LC-MS (Method 3): R$_t$=1.86 min; 529 [M+H]$^+$.

Example 333

1-(2,6-Difluorophenyl)-7-[(4S)-4-hydroxy-2-oxopyrrolidin-1-yl]-4-oxo-N-[(2S)-1,1,1-trifluorobutan-2-yl]-1,4-dihydro-1,8-naphthyridine-3-carboxamide

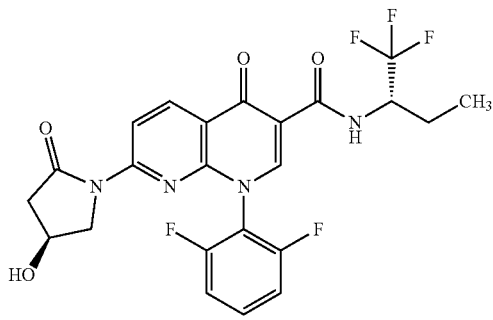 [SMILES: CC[C@H](NC(=O)c1cn(-c2c(F)cccc2F)c2nc(N3C[C@@H](O)CC3=O)ccc2c1=O)C(F)(F)F]

According to GP2, 150 mg (336 μmol) of the compound from Example 114A were reacted with 34.0 mg (336 μmol) of (4S)-4-hydroxypyrrolidin-2-one in the presence of 69.8 mg (505 μmol) of potassium carbonate, 13.6 mg (60.6 μmol) of palladium(II) acetate and 70.1 mg (121 μmol) of Xantphos in 3.1 ml of 1,4-dioxane. Subsequently, the reaction mixture was concentrated. The residue was diluted in 0.5 ml of acetonitrile and was purified by means of preparative HPLC (column: Chromatorex C18, 10 μm, 125×30 mm, solvent: acetonitrile/0.05% formic acid gradient; 0 to 3 min 15% acetonitrile, to 35 min 85% acetonitrile and for a further 3 min 85% acetonitrile). 91.7 mg (52% of theory, 98% purity) of the title compound were obtained.

$^1$H-NMR (400 MHz, DMSO-d$_6$) δ [ppm]: −0.150 (0.56), −0.008 (4.35), 0.008 (4.37), 0.965 (7.27), 0.983 (16.00), 1.002 (7.82), 1.147 (0.70), 1.633 (1.04), 1.651 (1.43), 1.658 (1.32), 1.668 (1.70), 1.677 (1.64), 1.694 (1.72), 1.712 (1.37), 1.868 (1.33), 1.877 (1.66), 1.886 (1.59), 1.896 (1.80), 1.902 (1.61), 1.921 (1.18), 1.931 (1.03), 2.074 (2.86), 2.347 (3.58), 2.390 (4.26), 2.712 (0.60), 2.905 (3.75), 2.920 (3.83), 2.948 (3.25), 2.963 (3.15), 3.288 (4.57), 3.414 (3.64), 3.444 (4.51), 3.619 (3.35), 3.631 (3.95), 3.649 (3.06), 3.661 (2.75), 4.255 (2.75), 4.783 (1.37), 5.322 (7.99), 5.331 (7.85), 7.434 (2.17), 7.447 (2.84), 7.455 (4.53), 7.469 (4.89), 7.479 (3.23), 7.492 (2.57), 7.725 (0.91), 7.741 (2.07), 7.747 (2.07), 7.763 (3.68), 7.779 (1.86), 7.784 (1.95), 7.800 (0.99), 8.530 (10.39), 8.553 (12.44), 8.712 (12.73), 8.734 (9.89), 9.023 (14.97), 10.118 (4.99), 10.142 (4.86).

LC-MS (Method 3): R$_t$=1.85 min; MS (ESIpos): m/z=511 [M+H]$^+$

Example 334

1-(2-Chloro-4,6-difluorophenyl)-7-[(2R,4S)-4-hydroxy-2,4-dimethylpyrrolidin-1-yl]-4-oxo-N-[(2S)-1,1,1-trifluorobutan-2-yl]-1,4-dihydro-1,8-naphthyridine-3-carboxamide

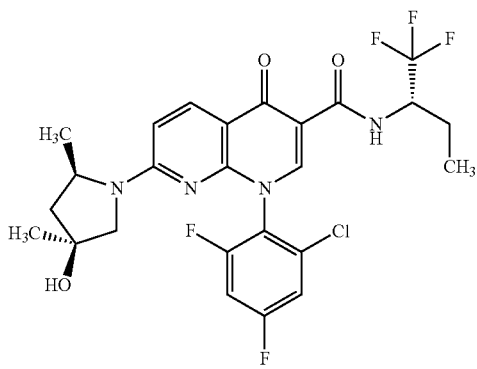 [SMILES: CC[C@H](NC(=O)c1cn(-c2c(F)cc(F)cc2Cl)c2nc(N3C[C@@](C)(O)C[C@H]3C)ccc2c1=O)C(F)(F)F]

According to GP3, 19.0 mg (39.7 μmol) of the compound from Example 108C and 10.5 mg (95% purity, 43.6 μmol) of the compound from Example 116A were reacted in the presence of 24.0 μl (140 μmol) of N,N-diisopropylethylamine in 1.5 ml of DMF. The reaction mixture was diluted with 4 ml of acetonitrile and 0.5 ml of water and purified by means of preparative HPLC (column: Kromasil C18, 10 μm, 250×20 mm, solvent: acetonitrile/0.05% formic acid gradient; 0 to 3 min 10% acetonitrile, to 35 min 90% acetonitrile and for a further 3 min 90% acetonitrile). 15.1 mg (67% of theory, 99% purity) of the title compound were obtained.

$^1$H-NMR (400 MHz, DMSO-d6) δ[ppm]: −0.149 (0.94), −0.008 (16.00), 0.008 (6.41), 0.146 (0.76), 0.949 (3.46), 0.968 (7.24), 0.978 (8.76), 0.996 (5.30), 1.266 (6.27), 1.648 (2.13), 1.886 (1.12), 2.000 (0.86), 2.710 (0.76), 3.288 (13.91), 3.334 (2.74), 3.740 (1.05), 4.733 (1.23), 4.869 (2.34), 6.682 (1.26), 7.712 (2.74), 7.734 (2.92), 8.253 (2.81), 8.275 (2.63), 8.768 (2.70), 10.438 (3.53), 10.462 (3.28).

LC-MS (Method 3): R$_t$=2.16 min; MS (ESIpos): m/z=559 [M+H]$^+$

Example 335

1-(2-Chloro-4,6-difluorophenyl)-7-(3,3-dimethyl-2-oxopyrrolidin-1-yl)-4-oxo-N-[(2S)-1,1,1-trifluoropropan-2-yl]-1,4-dihydro-1,8-naphthyridine-3-carboxamide

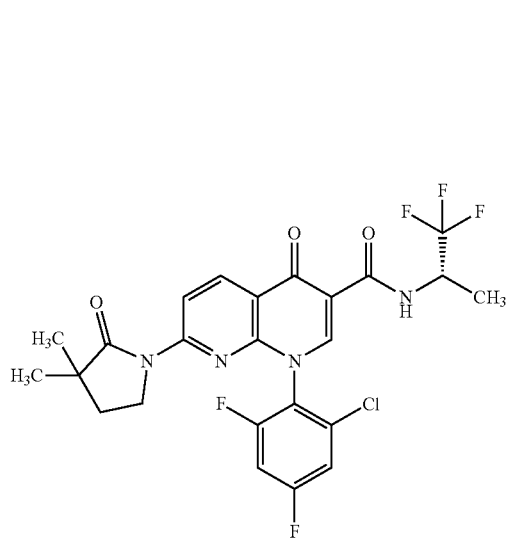 [SMILES: C[C@H](NC(=O)c1cn(-c2c(F)cc(F)cc2Cl)c2nc(N3CCC(C)(C)C3=O)ccc2c1=O)C(F)(F)F]

According to GP2, 50.0 mg (107 µmol) of the compound from Example 111A were reacted with 12.1 mg (107 µmol) of 3,3-dimethylpyrrolidin-2-one in the presence of 22.2 mg (161 µmol) of potassium carbonate, 4.3 mg (19 µmol) of palladium(II) acetate and 22.3 mg (38.6 µmol) of Xantphos in 980 µl of 1,4-dioxane. Subsequently, the reaction mixture was acidified with 0.5 ml of 1N aqueous hydrochloric acid and concentrated. The residue was purified by means of normal phase chromatography (cyclohexane-ethyl acetate gradient). 34.0 mg (58% of theory, 99% purity) of the title compound were obtained.

$^1$H-NMR (400 MHz, DMSO-$d_6$) δ [ppm]: −0.008 (1.16), 0.008 (0.85), 1.136 (16.00), 1.385 (2.51), 1.391 (2.58), 1.403 (2.55), 1.409 (2.44), 1.861 (1.36), 1.879 (2.82), 1.896 (1.41), 3.288 (1.97), 3.469 (0.75), 3.487 (1.42), 3.499 (1.18), 7.738 (0.64), 7.745 (0.94), 7.760 (0.98), 7.769 (0.99), 7.781 (0.72), 8.548 (2.50), 8.570 (3.07), 8.704 (3.06), 8.726 (2.32), 9.033 (2.57), 9.037 (2.49), 10.166 (1.26), 10.189 (1.19).

LC-MS (Method 1): $R_t$=1.26 min; MS (ESIpos): m/z=543 [M+H]$^+$

Example 336

1-(2-Chloro-4,6-difluorophenyl)-7-(3,3-dimethyl-2-oxopyrrolidin-1-yl)-4-oxo-N-[(2S)-1,1,1-trifluorobutan-2-yl]-1,4-dihydro-1,8-naphthyridine-3-carboxamide

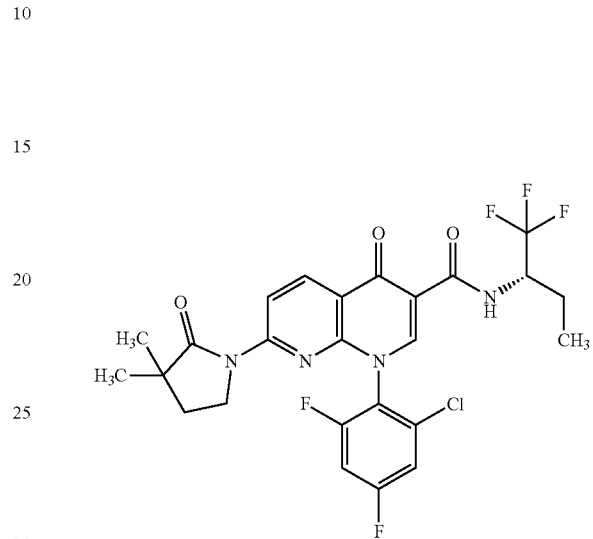

According to GP2, 50.0 mg (104 µmol) of the compound from Example 108C were reacted with 11.8 mg (104 µmol) of 3,3-dimethylpyrrolidin-2-one in the presence of 21.6 mg (156 µmol) of potassium carbonate, 4.2 mg (19 µmol) of palladium(II) acetate and 21.7 mg (37.5 µmol) of Xantphos in 950 µl of 1,4-dioxane. Subsequently, the reaction mixture was acidified with 0.5 ml of aqueous 1N hydrochloric acid and concentrated. The residue was dissolved in 8 ml of dichloromethane and purified by means of normal phase chromatography (cyclohexane-ethyl acetate gradient). 33.7 mg (58% of theory, 99% purity) of the title compound were obtained.

$^1$H-NMR (400 MHz, DMSO-$d_6$) δ [ppm]: −0.008 (0.66), 0.008 (0.63), 0.961 (0.88), 0.971 (1.05), 0.980 (2.05), 0.990 (2.04), 0.998 (1.10), 1.008 (0.96), 1.138 (16.00), 1.863 (1.33), 1.880 (2.84), 1.898 (1.63), 3.288 (1.03), 3.482 (0.71), 3.490 (1.11), 3.500 (1.33), 3.518 (0.64), 7.747 (0.84), 7.763 (0.85), 7.770 (0.93), 8.551 (2.23), 8.574 (2.77), 8.711 (2.67), 8.734 (2.08), 9.040 (3.76), 10.112 (0.77), 10.116 (0.79), 10.136 (0.76), 10.140 (0.74).

LC-MS (Method 1): $R_t$=1.31 min; MS (ESIpos): m/z=557 [M+H]$^+$

Example 337

1-(2,4-Difluorophenyl)-4-oxo-7-(2-oxopyrrolidin-1-yl)-N-[(2R)-1,1,1-trifluorobutan-2-yl]-1,4-dihydro-1,8-naphthyridine-3-carboxamide

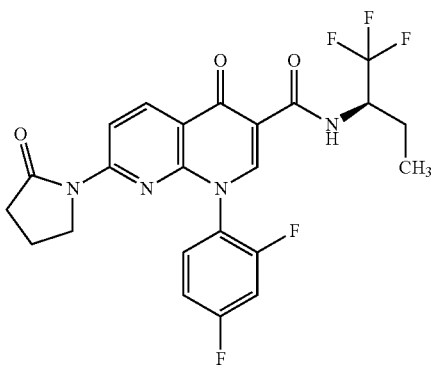 [SMILES: CC[C@@H](NC(=O)c1cn(-c2ccc(F)cc2F)c2nc(N3CCCC3=O)ccc2c1=O)C(F)(F)F]

According to GP2, 100 mg (224 μmol) of the compound from Example 67A were reacted with 21.0 mg (224 μmol) of pyrrolidin-2-one in the presence of 46.5 mg (336 μmol) of potassium carbonate, 2.5 mg (11 μmol) of palladium(II) acetate and 13.0 mg (22.4 μmol) of Xantphos in 2.0 μl of 1,4-dioxane. Subsequently, the reaction mixture was acidified with 0.5 ml of aqueous 1N hydrochloric acid and concentrated. The residue was dissolved in 8 ml of dichloromethane and purified by means of normal phase chromatography (cyclohexane-ethyl acetate gradient). Finally, the residue was stirred with 4 ml of acetonitrile, 3 ml of water and 2 ml of DMSO, and the precipitate was filtered off with suction, washed with water and dried under high vacuum. 60.4 mg (52% of theory, 95% purity) of the title compound were obtained.

$^1$H-NMR (400 MHz, DMSO-$d_6$) δ [ppm]: −0.149 (0.63), −0.008 (4.86), 0.008 (4.78), 0.146 (0.63), 0.959 (7.14), 0.978 (16.00), 0.996 (7.84), 1.148 (0.86), 1.175 (0.71), 1.233 (0.86), 1.398 (1.41), 1.625 (1.10), 1.643 (1.41), 1.651 (1.25), 1.660 (1.73), 1.669 (1.57), 1.678 (1.49), 1.686 (1.73), 1.704 (1.33), 1.867 (1.33), 1.876 (1.49), 1.885 (1.57), 1.895 (1.73), 1.901 (1.49), 1.911 (1.41), 1.920 (1.49), 1.930 (1.80), 1.948 (3.06), 1.962 (4.24), 1.988 (3.53), 2.001 (1.18), 2.328 (0.71), 2.366 (1.18), 2.564 (3.69), 2.569 (3.76), 2.582 (5.65), 2.591 (6.12), 2.603 (3.14), 2.610 (2.82), 2.670 (0.71), 2.710 (1.25), 3.289 (7.69), 3.533 (2.04), 3.551 (3.76), 3.574 (3.84), 3.591 (2.04), 4.765 (1.41), 7.343 (1.33), 7.362 (2.75), 7.383 (1.49), 7.591 (1.80), 7.598 (1.88), 7.614 (2.43), 7.617 (2.59), 7.621 (2.67), 7.624 (2.35), 7.640 (1.88), 7.647 (1.80), 7.860 (1.88), 7.880 (1.80), 8.500 (9.25), 8.522 (11.22), 8.690 (11.37), 8.713 (9.18), 8.850 (5.65), 10.209 (4.78), 10.233 (4.63).

LC-MS (Method 1): $R_t$=1.13 min; MS (ESIpos): m/z=495 [M+H]$^+$

Example 338

1-(2-Chloro-4,6-difluorophenyl)-N-[(1S)-1-cyclopropyl-2,2,2-trifluoroethyl]-7-[(4S)-4-hydroxy-2-oxopyrrolidin-1-yl]-4-oxo-1,4-dihydro-1,8-naphthyridine-3-carboxamide

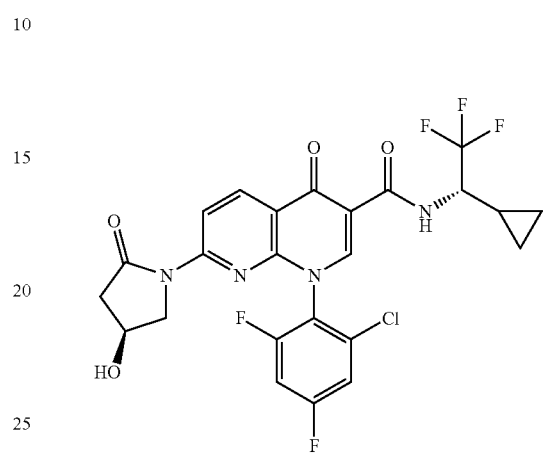

According to GP2, 100 mg (203 μmol) of the compound from Example 110A were reacted with 22.6 mg (223 μmol) of pyrrolidin-2-one in the presence of 42.1 mg (305 μmol) of potassium carbonate, 2.3 mg (10 μmol) of palladium(II) acetate and 11.8 mg (20.3 μmol) of Xantphos in 1.8 μl of 1,4-dioxane. On completion of conversion, N-acetylcysteine was added and the mixture was stirred at room temperature for a further 0.5 h. The mixture was diluted with 20 ml of ethyl acetate and extracted with saturated aqueous sodium hydrogencarbonate solution. The organic phase was concentrated and stirred in 4 ml of acetonitrile and 3 ml of water. The precipitate was filtered off with suction and dried under high vacuum. The mother liquor was purified by means of preparative HPLC (column: Kromasil C18, 10 μm, 250×20 mm, solvent: acetonitrile/0.05% formic acid gradient; 0 to 3 min 10% acetonitrile, to 35 min 90% acetonitrile and for a further 3 min 90% acetonitrile) and the product fractions were combined with the precipitate. Finally, by normal phase chromatography (cyclohexane-ethyl acetate gradient), 43.2 mg (36% of theory; 95% purity) of the title compound were obtained.

$^1$H-NMR (400 MHz, DMSO-$d_6$) δ [ppm]=10.27 (d, 1H), 9.03 (s, 1H), 8.73 (d, 1H), 8.54 (d, 1H), 7.82-7.72 (m, 2H), 5.33 (d, 1H), 4.46-4.34 (m, 1H), 4.31-4.25 (m, 1H), 3.69-3.60 (m, 1H), 3.46-3.38 (m, 1H), 2.94 (dd, 1H), 2.37 (d, 1H), 1.28-1.19 (m, 1H), 0.71-0.51 (m, 3H), 0.39-0.30 (m, 1H).

LC-MS (Method 3): $R_t$=1.94 min; MS (ESIpos): m/z=557 [M+H]$^+$

Example 339

7-[(4S)-4-Hydroxy-2-oxopyrrolidin-1-yl]-4-oxo-N-[(2S)-1-(trifluoromethoxy)propan-2-yl]-1-(2,4,6-trifluorophenyl)-1,4-dihydro-1,8-naphthyridine-3-carboxamide

Example 340

1-(2-Chloro-4,6-difluorophenyl)-4-oxo-7-(2-oxoimidazolidin-1-yl)-N-[(2S)-1,1,1-trifluorobutan-2-yl]-1,4-dihydro-1,8-naphthyridine-3-carboxamide

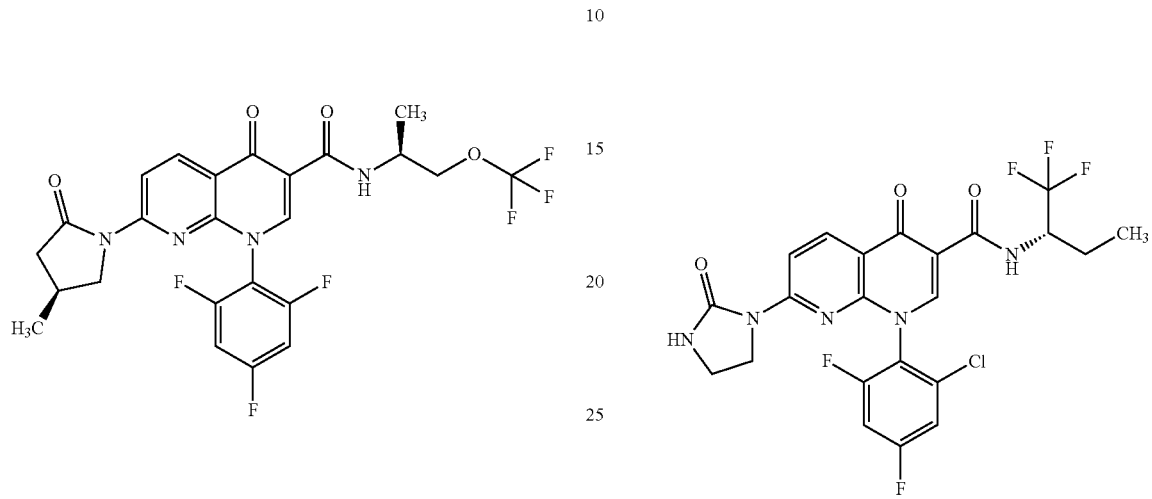

According to GP2, 80 mg (167 µmol) of the compound from Example 118A were reacted with 18.5 mg (183 µmol) of (4S)-4-hydroxypyrrolidin-2-one in the presence of 34.6 mg (250 µmol) of potassium carbonate, 1.9 mg (8.3 µmol) of palladium(II) acetate and 9.65 mg (16.7 µmol) of Xantphos in 1.7 ml of 1,4-dioxane. 80 mg of N-acetylcysteine were added and the mixture was stirred at RT for 30 min. The reaction mixture was admixed with 30 ml of ethyl acetate, washed with saturated aqueous sodium hydrogencarbonate solution, dried over sodium sulphate, filtered and concentrated. The residue was purified by means of preparative HPLC (column: Chromatorex C18, 10 µm, 125×30 mm, solvent: acetonitrile/0.05% formic acid gradient; 0 to 3 min 10% acetonitrile, to 35 min 90% acetonitrile and for a further 3 min 90% acetonitrile). 12.5 mg (14% of theory, 100% purity) of the title compound were obtained.

$^1$H-NMR (400 MHz, DMSO-d6) δ[ppm]: −0.149 (0.63), −0.008 (5.28), 0.008 (5.09), 0.146 (0.59), 1.258 (15.87), 1.275 (16.00), 2.053 (0.86), 2.353 (2.84), 2.396 (3.32), 2.912 (2.80), 2.926 (2.94), 2.955 (2.59), 2.970 (2.52), 3.291 (2.86), 3.462 (2.92), 3.492 (3.55), 3.670 (2.57), 3.682 (3.15), 3.700 (2.40), 3.712 (2.10), 4.158 (0.69), 4.169 (1.05), 4.183 (4.77), 4.189 (5.49), 4.194 (5.66), 4.201 (5.45), 4.214 (0.90), 4.226 (0.95), 4.296 (2.19), 4.351 (1.26), 4.369 (1.77), 4.386 (1.24), 5.329 (4.44), 5.338 (4.42), 7.588 (1.96), 7.595 (2.23), 7.608 (3.28), 7.618 (3.36), 7.625 (1.89), 7.631 (2.21), 7.638 (1.77), 8.511 (7.76), 8.533 (9.40), 8.693 (9.48), 8.716 (7.55), 8.990 (11.46), 9.825 (4.04), 9.845 (3.93).

LC-MS (Method 1): R$_t$=0.97 min; MS (ESIpos): m/z=545 [M+H]$^+$

According to GP2, 100 mg (208 µmol) of the compound from Example 108C were reacted with 89.6 mg (1.04 mmol) of imidazolidin-2-one in the presence of 43.2 mg (312 µmol) of potassium carbonate, 2.3 mg (10 µmol) of palladium(II) acetate and 12.0 mg (20.8 µmol) of Xantphos in 6.0 ml of 1,4-dioxane. Subsequently, the reaction mixture was acidified with 0.5 ml of 1N aqueous hydrochloric acid and concentrated.

The residue was dissolved in 8 ml of dichloromethane and purified by means of normal phase chromatography (cyclohexane-ethyl acetate gradient). 50.0 mg (43% of theory, 95% purity) of the title compound were obtained.

$^1$H-NMR (400 MHz, DMSO-d6) δ[ppm]: −0.149 (0.90), −0.008 (7.68), 0.008 (7.59), 0.146 (0.93), 0.958 (3.13), 0.968 (3.74), 0.977 (7.30), 0.986 (7.36), 0.995 (3.94), 1.005 (3.45), 1.234 (0.99), 1.398 (0.81), 1.657 (1.22), 1.668 (1.10), 1.676 (1.22), 1.685 (0.93), 1.693 (0.96), 1.872 (1.01), 1.891 (1.16), 2.074 (1.80), 2.367 (0.67), 2.711 (0.70), 3.288 (4.46), 3.340 (6.90), 3.360 (4.38), 3.514 (0.93), 3.523 (2.41), 3.534 (2.67), 3.542 (4.14), 3.553 (3.10), 3.574 (1.74), 4.757 (1.10), 7.663 (6.00), 7.691 (1.28), 7.698 (1.80), 7.713 (1.97), 7.721 (3.16), 7.738 (3.16), 7.744 (3.77), 7.759 (2.26), 8.427 (8.20), 8.449 (10.75), 8.554 (10.61), 8.577 (7.65), 8.959 (16.00), 10.215 (2.72), 10.219 (2.78), 10.239 (2.72), 10.244 (2.64).

LC-MS (Method 3): R$_t$=1.98 min; MS (ESIpos): m/z=530 [M+H]$^+$

Example 341

4-Oxo-7-(2-oxoimidazolidin-1-yl)-1-(2,4,6-trifluorophenyl)-N-[(2S)-1,1,1-trifluoropropan-2-yl]-1,4-dihydro-1,8-naphthyridine-3-carboxamide

Example 342

N-[(1R)-1-Cyclopropyl-2,2,2-trifluoroethyl]-4-oxo-7-(2-oxoimidazolidin-1-yl)-1-(2,4,6-trifluorophenyl)-1,4-dihydro-1,8-naphthyridine-3-carboxamide

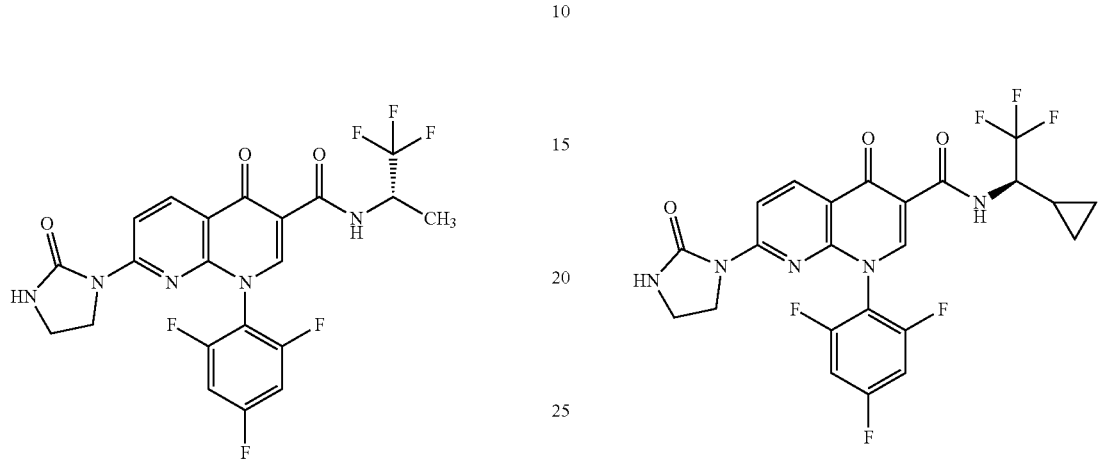

According to GP2, 51.0 mg (113 µmol) of the compound from Example 107A were reacted with 97.6 mg (1.13 mmol) of imidazolidin-2-one in the presence of 23.5 mg (170 µmol) of potassium carbonate, 2.6 mg (11 µmol) of palladium(II) acetate and 13.1 mg (22.7 µmol) of Xantphos in 1.1 ml of 1,4-dioxane. 50 mg of N-acetylcysteine were added and the mixture was stirred at RT for 30 min. The reaction mixture was admixed with 30 ml of ethyl acetate, washed with saturated aqueous sodium hydrogencarbonate solution, dried over sodium sulphate, filtered and concentrated. The residue was purified by means of preparative HPLC (column: Chromatorex C18, 10 µm, 125×30 mm, solvent: acetonitrile/0.05% formic acid gradient; 0 to 3 min 10% acetonitrile, to 35 min 90% acetonitrile and for a further 3 min 90% acetonitrile). 18.4 mg (32% of theory, 100% purity) of the title compound were obtained.

$^1$H-NMR (400 MHz, DMSO-d6) δ[ppm]: −0.008 (3.27), 0.008 (2.98), 1.381 (15.90), 1.398 (16.00), 2.074 (0.99), 2.367 (1.03), 2.711 (1.03), 3.288 (4.49), 3.329 (4.49), 3.348 (6.38), 3.368 (4.68), 3.576 (5.10), 3.592 (4.33), 3.598 (6.22), 3.616 (3.43), 4.881 (1.12), 4.900 (1.64), 4.923 (1.67), 4.941 (1.06), 7.546 (1.22), 7.554 (4.33), 7.569 (1.92), 7.576 (8.05), 7.584 (1.92), 7.598 (4.42), 7.607 (1.31), 7.667 (6.64), 8.426 (9.14), 8.449 (12.60), 8.541 (12.86), 8.557 (0.90), 8.563 (8.88), 8.993 (12.99), 10.250 (4.75), 10.273 (4.52).

LC-MS (Method 1): $R_t$=1.00 min; MS (ESIpos): m/z=500 [M+H]$^+$

According to GP1, 150 mg (371 µmol) of the compound from Example 113A were reacted with 78.2 mg (445 µmol) of (1R)-1-cyclopropyl-2,2,2-trifluoroethanamine hydrochloride in the presence of 169 mg (445 µmol) of HATU and 160 µl (930 µmol) of N,N-diisopropylethylamine in 5.0 ml of dimethylformamide.

The mixture was diluted with 1 ml of 1N aqueous hydrochloric acid and 1 ml of dimethyl sulphoxide and the solution was purified by means of preparative HPLC (column: Chromatorex C18, 10 µm, 125×30 mm, solvent: acetonitrile/0.05% formic acid gradient; 0 to 3 min 10% acetonitrile, to 35 min 90% acetonitrile and for a further 3 min 90% acetonitrile). Finally, the crude product was suspended in 20 ml of acetonitrile and diluted with 100 ml of water. Acetonitrile was removed under reduced pressure, and the precipitate was filtered off with suction and dried under high vacuum. 85.3 mg (44% of theory, 100% purity) of the title compound were obtained.

$^1$H-NMR (400 MHz, DMSO-d6) δ[ppm]: 0.341 (2.94), 0.354 (2.82), 0.576 (3.29), 0.657 (2.82), 1.217 (2.63), 1.238 (2.90), 2.327 (2.08), 2.670 (2.20), 2.710 (1.65), 3.349 (6.98), 3.370 (5.25), 3.578 (5.57), 3.599 (7.10), 3.617 (3.76), 4.395 (2.39), 4.414 (2.55), 7.553 (5.18), 7.575 (9.37), 7.597 (5.22), 7.669 (7.69), 8.430 (8.67), 8.453 (11.45), 8.552 (11.92), 8.575 (8.04), 8.988 (16.00), 10.340 (5.33), 10.363 (5.37).

LC-MS (Method 1): $R_t$=1.03 min; MS (ESIpos): m/z=526 [M+H]$^+$

Example 343

4-Oxo-7-(2-oxoimidazolidin-1-yl)-N-[(2S)-1,1,1-trifluorobutan-2-yl]-1-(2,4,6-trifluorophenyl)-1,4-dihydro-1,8-naphthyridine-3-carboxamide

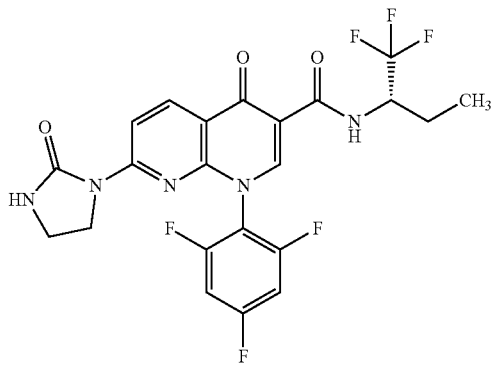 [SMILES: CC[C@H](NC(=O)c1cn(-c2c(F)cc(F)cc2F)c2nc(N3CCNC3=O)ccc2c1=O)C(F)(F)F]

According to GP2, 100 mg (216 µmol) of the compound from Example 115A were reacted with 186 mg (2.16 mmol) of imidazolidin-2-one in the presence of 44.7 mg (323 µmol) of potassium carbonate, 4.8 mg (22 µmol) of palladium(II) acetate and 25.0 mg (43.1 µmol) of Xantphos in 2.2 ml of 1,4-dioxane. 100 mg of N-acetylcysteine were added and the mixture was stirred at RT for 30 min. The reaction mixture was admixed with 30 ml of ethyl acetate, washed with saturated aqueous sodium hydrogencarbonate solution, dried over magnesium sulphate, filtered and concentrated. The residue was purified by means of preparative HPLC (column: Chromatorex C18, 10 µm, 125×30 mm, solvent: acetonitrile/0.05% formic acid gradient; 0 to 3 min 10% acetonitrile, to 35 min 90% acetonitrile and for a further 3 min 90% acetonitrile).

Product fractions that were still contaminated were concentrated and repurified by means of normal phase chromatography (cyclohexane-ethyl acetate gradient). The product fractions from the two separations were combined and 46.6 mg (42% of theory, 100% purity) of the title compound were obtained.

$^1$H-NMR (400 MHz, DMSO-d6) δ[ppm]: −0.008 (2.95), 0.008 (2.68), 0.960 (7.15), 0.978 (16.00), 0.997 (7.87), 1.148 (0.85), 1.623 (1.07), 1.641 (1.56), 1.648 (1.70), 1.658 (1.74), 1.666 (1.61), 1.676 (1.56), 1.683 (1.70), 1.701 (1.30), 1.862 (1.25), 1.872 (1.52), 1.881 (1.43), 1.890 (1.74), 1.897 (1.52), 1.906 (1.21), 1.915 (1.16), 2.367 (1.39), 2.670 (0.76), 2.710 (1.39), 3.287 (7.51), 3.330 (4.83), 3.350 (6.53), 3.370 (5.05), 3.578 (5.27), 3.600 (6.75), 3.618 (3.80), 4.746 (1.39), 7.556 (4.74), 7.578 (8.45), 7.600 (4.69), 7.668 (7.28), 8.429 (9.97), 8.452 (13.27), 8.549 (13.77), 8.571 (9.34), 8.996 (15.28), 10.199 (5.14), 10.223 (4.87).

LC-MS (Method 1): $R_t$=1.02 min; MS (ESIpos): m/z=514 [M+H]$^+$

Example 344

1-(2,4-Difluorophenyl)-7-(3-ethyl-2-oxotetrahydropyrimidin-1(2H)-yl)-4-oxo-N-[(2R)-1,1,1-trifluorobutan-2-yl]-1,4-dihydro-1,8-naphthyridine-3-carboxamide

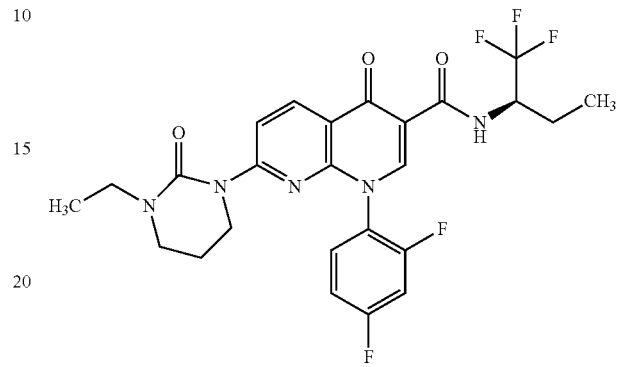

According to GP2, 200 mg (449 µmol) of the compound from Example 67A were reacted with 63.3 mg (494 µmol) of 1-ethyltetrahydropyrimidin-2(1H)-one in the presence of 93.0 mg (673 µmol) of potassium carbonate, 5.0 mg (22 µmol) of palladium(II) acetate and 26.0 mg (44.9 µmol) of Xantphos in 4.0 ml of 1,4-dioxane. Subsequently, the reaction mixture was acidified with aqueous 1N hydrochloric acid and concentrated. The residue was dissolved in 10 ml of dichloromethane and purified by means of normal phase chromatography (cyclohexane-ethyl acetate gradient). 191.2 mg (76% of theory, 96% purity) of the title compound were obtained.

$^1$H-NMR (400 MHz, DMSO-d6) δ[ppm]=10.29 (d, 1H), 8.81-8.78 (m, 1H), 8.50 (d, 1H), 8.15 (d, 1H), 7.91-7.83 (m, 1H), 7.65-7.57 (m, 1H), 7.39-7.32 (m, 1H), 4.83-4.70 (m, 1H), 3.58-3.43 (m, 2H), 3.30-3.27 (m, 4H, partly under the water resonance), 1.95-1.83 (m, 3H), 1.72-1.60 (m, 1H), 1.07 (t, 3H), 0.98 (t, 3H).

LC-MS (Method 3): $R_t$=2.22 min; MS (ESIpos): m/z=538 [M+H]$^+$

Example 345

N-[(1S)-1-Cyclopropyl-2,2,2-trifluoroethyl]-1-(2,6-difluorophenyl)-7-[(3R,4R)-3,4-dihydroxypyrrolidin-1-yl]-4-oxo-1,4-dihydro-1,8-naphthyridine-3-carboxamide

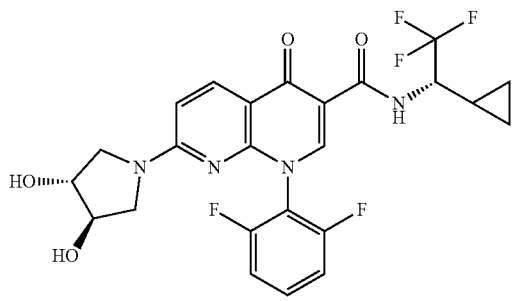 [SMILES: O=C(N[C@@H](C1CC1)C(F)(F)F)c1cn(-c2c(F)cccc2F)c2nc(N3C[C@@H](O)[C@H](O)C3)ccc2c1=O]

According to GP3, 50.0 mg (109 μmol) of the compound from Example 104A were reacted with 16.8 mg (120 μmol) of (3R,4R)-pyrrolidine-3,4-diol hydrochloride in the presence of 67.0 μl (380 μmol) of N,N-diisopropylethylamine in 2.0 ml of dimethylformamide. The reaction mixture was adjusted to pH 1 with aqueous 1 M hydrochloric acid and separated by means of preparative HPLC (column: Chromatorex C18, 10 μm, 125×30 mm, solvent: acetonitrile/ 0.05% formic acid gradient (0 to 3 min 10% acetonitrile, to 35 min 90% acetonitrile and for a further 3 min 90% acetonitrile). The product fractions were combined and concentrated. 50.9 mg (89% of theory, 100% purity) of the title compound were obtained.

$^1$H-NMR (400 MHz, DMSO-d6) δ[ppm]: −0.149 (0.90), −0.011 (4.62), −0.008 (11.14), 0.008 (6.98), 0.146 (0.94), 0.316 (0.83), 0.327 (1.80), 0.338 (2.71), 0.350 (2.71), 0.362 (2.01), 0.373 (1.04), 0.498 (0.83), 0.510 (1.94), 0.522 (2.81), 0.534 (2.50), 0.549 (2.22), 0.557 (2.12), 0.569 (2.85), 0.579 (2.36), 0.589 (2.15), 0.600 (1.77), 0.614 (1.15), 0.627 (1.46), 0.637 (1.77), 0.648 (2.46), 0.652 (2.05), 0.658 (2.29), 0.663 (2.22), 0.672 (2.15), 0.680 (1.01), 0.684 (0.94), 0.693 (0.69), 1.179 (1.28), 1.188 (1.77), 1.200 (2.98), 1.208 (2.12), 1.212 (1.84), 1.220 (2.85), 1.232 (1.49), 1.241 (1.04), 2.367 (1.11), 2.710 (1.11), 3.010 (3.12), 3.042 (4.13), 3.174 (2.53), 3.184 (2.81), 3.206 (2.05), 3.216 (1.77), 3.288 (7.05), 3.347 (3.85), 3.592 (2.29), 3.602 (2.53), 3.620 (2.08), 3.630 (1.84), 3.893 (3.68), 4.039 (3.71), 4.356 (1.49), 4.376 (2.39), 4.399 (2.33), 4.419 (1.28), 5.125 (5.48), 5.134 (5.34), 5.219 (5.55), 5.228 (5.24), 6.769 (9.65), 6.792 (9.75), 7.395 (5.17), 7.415 (10.72), 7.437 (5.83), 7.672 (1.15), 7.687 (2.33), 7.693 (2.19), 7.703 (1.70), 7.709 (3.99), 7.714 (1.53), 7.725 (1.98), 7.731 (2.05), 7.746 (0.94), 8.278 (12.08), 8.300 (11.04), 8.742 (16.00), 10.573 (5.93), 10.596 (5.55).

LC-MS (Method 3): $R_t$=1.67 min; MS (ESIpos): m/z=525 [M+H]$^+$

Example 346

1-(2-Chloro-6-fluorophenyl)-7-[(3R,4R)-3,4-dihydroxypyrrolidin-1-yl]-4-oxo-N-[(2S)-1,1,1-trifluorobutan-2-yl]-1,4-dihydro-1,8-naphthyridine-3-carboxamide

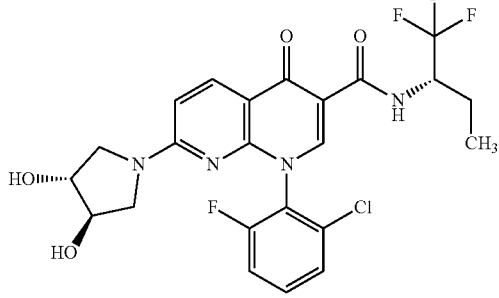

According to GP3, 50.0 mg (108 μmol) of the compound from Example 119A and 16.6 mg (119 μmol) of (3R,4R)-pyrrolidine-3,4-diol hydrochloride were reacted in the presence of 53.0 μl (380 μmol) of N,N-diisopropylethylamine in 1.0 ml of DMF. The reaction mixture was adjusted to pH 1 with aqueous 1M hydrochloric acid and separated by means of preparative HPLC (column: Chromatorex C18, 10 μm, 125×30 mm, solvent: acetonitrile/0.05% formic acid gradient (0 to 3 min 10% acetonitrile, to 35 min 90% acetonitrile and for a further 3 min 90% acetonitrile). 46.1 mg (80% of theory, 99% purity) of the title compound were obtained.

$^1$H-NMR (400 MHz, DMSO-d6) δ[ppm]: −0.008 (1.98), 0.008 (1.84), 0.952 (3.72), 0.963 (4.56), 0.971 (8.66), 0.981 (8.89), 0.989 (4.80), 1.000 (4.09), 1.622 (0.99), 1.633 (1.04), 1.639 (1.46), 1.649 (1.32), 1.657 (1.46), 1.668 (1.08), 1.674 (1.13), 1.854 (1.08), 1.864 (1.27), 1.871 (1.32), 1.883 (1.46), 1.899 (1.18), 1.907 (0.94), 2.367 (1.08), 2.711 (1.08), 2.950 (1.51), 2.980 (2.54), 3.007 (1.98), 3.124 (1.18), 3.133 (1.46), 3.143 (1.32), 3.154 (1.98), 3.165 (1.04), 3.174 (1.04), 3.291 (4.24), 3.339 (4.42), 3.585 (2.02), 3.595 (2.26), 3.612 (1.93), 3.623 (1.69), 3.883 (3.34), 4.034 (3.34), 4.733 (1.36), 4.752 (1.27), 5.126 (3.48), 5.130 (3.91), 5.135 (3.95), 5.222 (3.95), 5.227 (3.86), 6.762 (8.52), 6.784 (8.75), 7.522 (1.08), 7.527 (1.79), 7.531 (1.27), 7.543 (1.79), 7.547 (3.34), 7.551 (2.78), 7.566 (1.51), 7.570 (2.26), 7.575 (1.60), 7.620 (2.26), 7.623 (2.35), 7.627 (1.27), 7.641 (4.80), 7.643 (5.08), 7.647 (2.21), 7.665 (3.01), 7.680 (3.01), 7.686 (3.72), 7.700 (3.76), 7.706 (1.46), 7.721 (1.36), 8.275 (9.88), 8.297 (9.27), 8.695 (16.00), 10.458 (3.29), 10.462 (3.34), 10.482 (3.25), 10.486 (3.20).

LC-MS (Method 3): $R_t$=1.68 min; MS (ESIpos): m/z=529 [M+H]$^+$

Example 347

1-(2-Chloro-6-fluorophenyl)-N-[(1S)-1-cyclopropyl-2,2,2-trifluoroethyl]-7-[(3R,4R)-3,4-dihydroxypyrrolidin-1-yl]-4-oxo-1,4-dihydro-1,8-naphthyridine-3-carboxamide

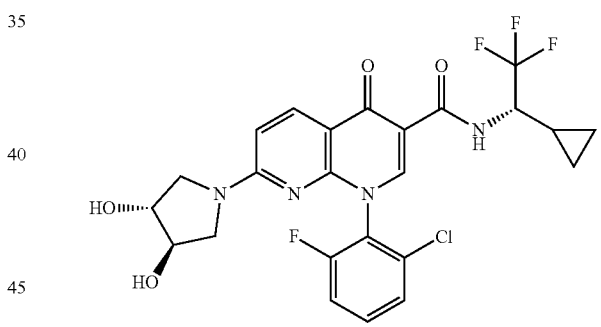

According to GP3, 50.0 mg (105 μmol) of the compound from Example 120A and 16.2 mg (116 μmol) of (3R,4R)-pyrrolidine-3,4-diol hydrochloride were reacted in the presence of 52.0 μl (370 μmol) of N,N-diisopropylethylamine in 1.0 ml of DMF. The reaction mixture was adjusted to pH 1 with aqueous 1N hydrochloric acid and purified by means of preparative HPLC (column: Chromatorex C18, 10 μm, 125×30 mm, solvent: acetonitrile/0.05% formic acid gradient (0 to 3 min 10% acetonitrile, to 35 min 90% acetonitrile and for a further 3 min 90% acetonitrile). 48.3 mg (84% of theory, 99% purity) of the title compound were obtained.

$^1$H-NMR (400 MHz, DMSO-d6) δ[ppm]=10.61 (d, 1H), 8.69 (s, 1H), 8.29 (d, 1H), 7.73-7.51 (m, 3H), 6.77 (d, 1H), 5.24-5.20 (m, 1H), 5.14-5.11 (m, 1H), 4.43-4.32 (m, 1H), 4.03 (br. s, 1H), 3.88 (br. s, 1H), 3.64-3.56 (m, 1H), 3.20-3.10 (m, 1H), 3.02-2.93 (m, 1H), 1.26-1.16 (m, 1H), 0.71-0.47 (m, 3H), 0.39-0.29 (m, 1H).

LC-MS (Method 3): $R_t$=1.72 min; MS (ESIpos): m/z=541 [M+H]$^+$

Example 348

1-(2,6-Difluorophenyl)-7-[(3R,4R)-3,4-dihydroxy-pyrrolidin-1-yl]-4-oxo-N-[(2S)-1,1,1-trifluorobutan-2-yl]-1,4-dihydro-1,8-naphthyridine-3-carboxamide

Example 349

7-[(3R,4R)-3,4-Dihydroxypyrrolidin-1-yl]-4-oxo-N-[(2R)-1,1,1-trifluoro-3,3-dimethylbutan-2-yl]-1-(2,4,6-trifluorophenyl)-1,4-dihydro-1,8-naphthyridine-3-carboxamide

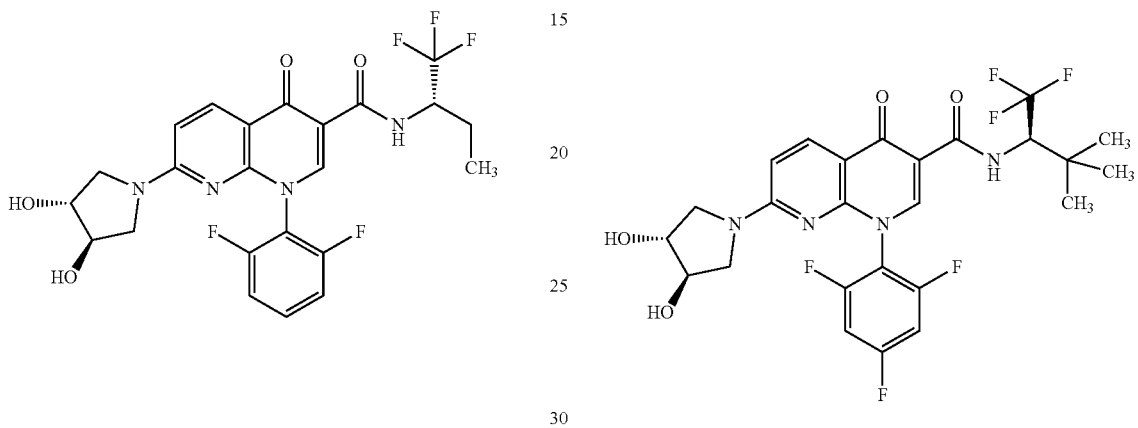

According to GP3, 50.0 mg (111 µmol) of the compound from Example 114A were reacted with 17.0 mg (122 µmol) of (3R,4R)-pyrrolidine-3,4-diol hydrochloride in the presence of 68.0 µl (390 µmol) of N,N-diisopropylethylamine in 1.1 ml of dimethylformamide. The reaction mixture was diluted with 2 ml of acetonitrile, acidified with 1N aqueous hydrochloric acid and purified by means of preparative HPLC (column: Chromatorex C18, 10 µm, 125×30 mm, solvent: acetonitrile/0.05% formic acid gradient; 0 to 3 min 10% acetonitrile, to 35 min 90% acetonitrile and for a further 3 min 90% acetonitrile). 50.9 mg (89% of theory, 100% purity) of the title compound were obtained.

$^1$H-NMR (500 MHz, DMSO-d6) δ[ppm]: 0.960 (7.49), 0.974 (16.00), 0.989 (7.72), 1.614 (1.16), 1.629 (1.43), 1.634 (1.34), 1.642 (1.76), 1.649 (1.57), 1.657 (1.48), 1.662 (1.62), 1.677 (1.25), 1.859 (1.29), 1.867 (1.48), 1.874 (1.48), 1.882 (1.66), 1.887 (1.48), 1.894 (1.29), 1.902 (1.16), 1.909 (0.97), 3.017 (2.82), 3.043 (3.61), 3.180 (2.13), 3.188 (2.36), 3.205 (1.76), 3.213 (1.57), 3.344 (3.75), 3.596 (1.99), 3.603 (2.22), 3.618 (1.90), 3.626 (1.66), 3.895 (3.24), 4.043 (3.24), 4.735 (1.29), 4.743 (1.20), 5.130 (4.21), 5.137 (4.21), 5.226 (4.16), 5.233 (3.93), 6.771 (8.92), 6.789 (9.02), 7.402 (3.47), 7.419 (6.94), 7.437 (3.61), 7.682 (0.88), 7.694 (1.85), 7.699 (1.90), 7.707 (1.43), 7.712 (3.28), 7.716 (1.29), 7.724 (1.76), 7.729 (1.71), 7.741 (0.79), 8.278 (11.05), 8.296 (10.27), 8.751 (15.72), 10.442 (5.18), 10.462 (4.90).

LC-MS (Method 1): $R_t$=1.63 min; MS (ESIpos): m/z=513 [M+H]$^+$

According to GP1, 55.0 mg (131 µmol) of the compound from Example 121A were reacted with 24.3 mg (157 µmol) of (2R)-1,1,1-trifluoro-3,3-dimethylbutan-2-amine in the presence of 74.5 mg (196 µmol) of HATU and 57.0 µl (330 µmol) of N,N-diisopropylethylamine in 2.0 ml of dimethylformamide. The mixture was diluted with 1 ml of water and 2 ml of acetonitrile and the solution was purified by means of preparative HPLC (column: Chromatorex C18, 10 µm, 125×30 mm, solvent: acetonitrile/0.05% formic acid gradient; 0 to 3 min 10% acetonitrile, to 35 min 90% acetonitrile and for a further 3 min 90% acetonitrile). 55.9 mg (77% of theory, 100% purity) of the title compound were obtained.

$^1$H-NMR (400 MHz, DMSO-d6) δ[ppm]: −0.008 (0.77), 0.008 (0.71), 1.090 (16.00), 3.057 (0.73), 3.089 (0.96), 3.241 (0.64), 3.289 (0.78), 3.331 (0.87), 3.360 (0.89), 3.611 (0.58), 3.931 (0.86), 4.050 (0.86), 4.622 (0.74), 5.145 (1.36), 5.154 (1.36), 5.229 (1.36), 5.238 (1.34), 6.771 (2.11), 6.793 (2.16), 7.544 (0.97), 7.567 (1.61), 7.587 (0.93), 8.297 (2.61), 8.319 (2.43), 8.816 (4.01), 10.765 (1.26), 10.790 (1.19).

LC-MS (Method 3): $R_t$=1.86 min; MS (ESIpos): m/z=559 [M+H]$^+$

Example 350

7-[(3R,4R)-3,4-Dihydroxypyrrolidin-1-yl]-4-oxo-N-[1-(trifluoromethyl)cyclopentyl]-1-(2,4,6-trifluorophenyl)-1,4-dihydro-1,8-naphthyridine-3-carboxamide

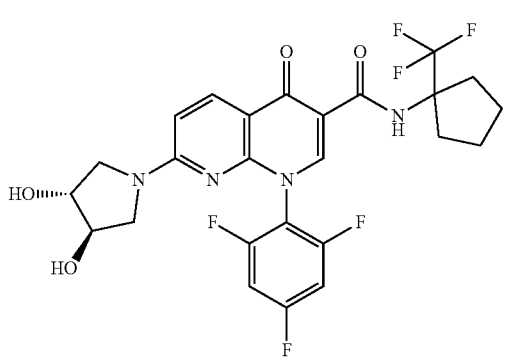 [SMILES: O=C(NC1(C(F)(F)F)CCCC1)c1cn(-c2c(F)cc(F)cc2F)c2nc(N3C[C@@H](O)[C@H](O)C3)ccc2c1=O]

According to GP1, 55.0 mg (131 µmol) of the compound from Example 121A were reacted with 29.7 mg (157 µmol) of 1-(trifluoromethyl)cyclopentanamine hydrochloride in the presence of 74.5 mg (196 µmol) of HATU and 79.6 µl (460 µmol) of N,N-diisopropylethylamine in 2.0 ml of dimethylformamide. The mixture was diluted with 1 ml of water and 2 ml of acetonitrile and the solution was purified by means of preparative HPLC (column: Chromatorex C18, 10 µm, 125×30 mm, solvent: acetonitrile/0.05% formic acid gradient; 0 to 3 min 10% acetonitrile, to 35 min 90% acetonitrile and for a further 3 min 90% acetonitrile). 63.4 mg (87% of theory, 100% purity) of the title compound were obtained.

$^1$H-NMR (400 MHz, DMSO-d6) δ[ppm]: −0.008 (4.57), 0.008 (4.33), 1.708 (1.76), 1.729 (3.67), 1.747 (3.47), 1.765 (3.35), 1.784 (3.71), 1.794 (3.02), 1.803 (3.27), 1.824 (1.96), 2.012 (1.84), 2.029 (3.10), 2.045 (3.63), 2.063 (3.67), 2.073 (16.00), 2.079 (2.12), 2.353 (2.61), 2.367 (4.73), 2.382 (2.90), 2.400 (2.82), 2.711 (1.43), 3.052 (3.14), 3.083 (4.20), 3.225 (2.37), 3.235 (2.73), 3.256 (2.04), 3.267 (1.96), 3.288 (4.53), 3.349 (4.08), 3.593 (2.20), 3.603 (2.57), 3.621 (2.08), 3.632 (1.92), 3.926 (3.76), 4.046 (3.76), 5.135 (5.67), 5.144 (5.76), 5.227 (5.76), 5.236 (5.67), 6.760 (9.55), 6.782 (9.76), 7.541 (2.61), 7.545 (2.94), 7.553 (1.96), 7.561 (5.02), 7.564 (5.02), 7.567 (5.14), 7.576 (2.00), 7.584 (3.02), 7.599 (0.98), 8.263 (11.02), 8.286 (10.49), 8.741 (15.39), 10.513 (11.71).

LC-MS (Method 3): $R_t$=1.83 min; MS (ESIpos): m/z=557 [M+H]$^+$

Example 351

1-(2-Chloro-6-fluorophenyl)-7-[(4S)-4-hydroxy-2-oxopyrrolidin-1-yl]-4-oxo-N-[(2S)-1,1,1-trifluorobutan-2-yl]-1,4-dihydro-1,8-naphthyridine-3-carboxamide

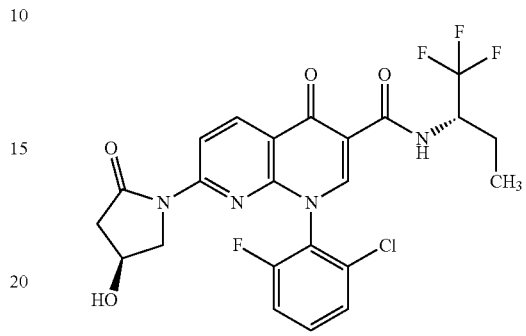

According to GP2, 100 mg (216 µmol) of the compound from Example 119A were reacted with 24.1 mg (238 µmol) of (4S)-4-hydroxypyrrolidin-2-one in the presence of 44.8 mg (325 µmol) of potassium carbonate, 2.4 mg (11 µmol) of palladium(II) acetate and 12.5 mg (21.6 µmol) of Xantphos in 1.9 ml of 1,4-dioxane. Subsequently, 100 mg of N-acetylcysteine were added and the mixture was stirred at RT for a further 0.5 h. After adding 20 ml of ethyl acetate, the mixture was extracted with saturated aqueous sodium hydrogencarbonate solution. The organic phase was concentrated and the residue was purified by means of preparative HPLC (column: Chromatorex C18, 10 µm, 125×30 mm, eluent: acetonitrile/0.05% formic acid gradient; 0 to 3 min 10% acetonitrile, to 35 min 90% acetonitrile and for a further 3 min 90% acetonitrile). 54.1 mg (47% of theory, 98% purity) of the title compound were obtained.

$^1$H-NMR (500 MHz, DMSO-d6) δ[ppm]: 0.968 (5.41), 0.979 (6.69), 0.983 (11.85), 0.993 (10.59), 0.998 (6.60), 1.008 (4.54), 1.643 (0.88), 1.654 (1.09), 1.657 (1.29), 1.663 (1.13), 1.670 (1.71), 1.674 (1.40), 1.678 (1.37), 1.682 (1.45), 1.685 (1.54), 1.688 (1.55), 1.691 (1.52), 1.696 (1.13), 1.702 (1.30), 1.705 (1.14), 1.717 (0.85), 1.876 (1.21), 1.883 (1.40), 1.886 (1.47), 1.891 (1.56), 1.898 (1.66), 1.902 (1.71), 1.906 (1.44), 1.911 (1.53), 1.918 (1.18), 1.921 (0.99), 1.926 (0.88), 2.076 (0.84), 2.345 (3.82), 2.348 (3.60), 2.380 (4.31), 2.383 (4.02), 2.909 (4.60), 2.920 (4.73), 2.943 (4.34), 2.955 (4.16), 3.354 (3.09), 3.377 (5.05), 3.401 (2.58), 3.572 (2.04), 3.581 (2.57), 3.590 (2.42), 3.595 (2.49), 3.600 (3.01), 3.605 (1.86), 3.614 (2.31), 3.624 (1.88), 4.249 (3.61), 4.767 (1.64), 4.777 (1.52), 5.327 (1.59), 7.572 (1.57), 7.574 (1.63), 7.586 (1.95), 7.589 (3.77), 7.591 (3.44), 7.603 (2.47), 7.607 (3.70), 7.610 (2.16), 7.621 (1.59), 7.624 (1.62), 7.661 (2.54), 7.663 (1.64), 7.675 (4.62), 7.677 (5.15), 7.680 (2.34), 7.691 (4.43), 7.693 (2.60), 7.724 (3.27), 7.736 (3.47), 7.741 (4.77), 7.753 (4.66), 7.758 (2.03), 7.769 (1.86), 8.532 (11.77), 8.550 (13.29), 8.722 (13.08), 8.740 (10.70), 8.796 (0.68), 8.992 (14.83), 8.994 (16.00), 10.136 (3.78), 10.140 (4.00), 10.155 (3.69), 10.159 (3.79).

LC-MS (Method 1): $R_t$=1.00 min; MS (ESIpos): m/z=527 [M+H]$^+$

Example 352

1-(2-Chloro-6-fluorophenyl)-N-[(1S)-1-cyclopropyl-2,2,2-trifluoroethyl]-7-[(4S)-4-hydroxy-2-oxopyrrolidin-1-yl]-4-oxo-1,4-dihydro-1,8-naphthyridine-3-carboxamide

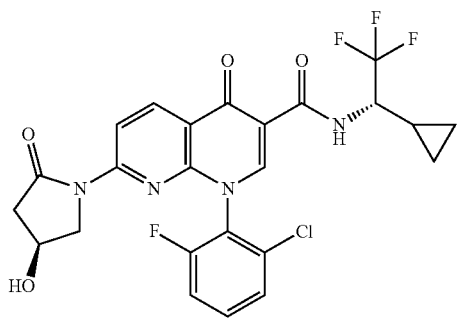 [SMILES: O=C(N[C@@H](C1CC1)C(F)(F)F)c1cn(-c2c(F)cccc2Cl)c2nc(N3C[C@@H](O)CC3=O)ccc2c1=O]

According to GP2, 100 mg (211 μmol) of the compound from Example 120A were reacted with 23.5 mg (232 μmol) of (4S)-4-hydroxypyrrolidin-2-one in the presence of 43.7 mg (316 μmol) of potassium carbonate, 2.4 mg (11 μmol) of palladium(II) acetate and 12.2 mg (21.1 μmol) of Xantphos in 1.9 ml of 1,4-dioxane. Subsequently, 100 mg of N-acetylcysteine were added and the mixture was stirred at RT for a further 0.5 h. After adding 20 ml of ethyl acetate, the mixture was extracted with saturated aqueous sodium hydrogencarbonate solution. The organic phase was concentrated and the residue was purified by means of preparative HPLC (column: Chromatorex C18, 10 μm, 125×30 mm, solvent: acetonitrile/0.05% formic acid gradient; 0 to 3 min 10% acetonitrile, to 35 min 90% acetonitrile and for a further 3 min 90% acetonitrile). 63.8 mg (56% of theory, 99% purity) of the title compound were obtained.

$^1$H-NMR (400 MHz, DMSO-d6) δ[ppm]: −0.149 (0.89), −0.008 (7.91), 0.008 (7.20), 0.146 (0.94), 0.343 (2.06), 0.356 (2.46), 0.368 (1.92), 0.379 (1.30), 0.549 (2.06), 0.563 (2.91), 0.578 (2.77), 0.588 (2.55), 0.598 (1.92), 0.608 (1.65), 0.622 (1.07), 0.638 (0.85), 0.648 (1.34), 0.659 (1.70), 0.669 (2.10), 0.684 (1.52), 0.689 (1.16), 1.208 (0.89), 1.215 (1.12), 1.227 (2.10), 1.248 (2.06), 1.260 (1.12), 2.337 (3.44), 2.366 (1.65), 2.380 (3.71), 2.670 (0.63), 2.710 (1.52), 2.899 (3.49), 2.914 (3.58), 2.942 (3.13), 2.957 (3.08), 3.287 (5.45), 3.345 (2.32), 3.374 (2.95), 3.398 (1.83), 3.563 (1.34), 3.574 (1.83), 3.582 (2.01), 3.593 (3.22), 3.605 (1.25), 3.611 (1.88), 3.624 (1.56), 4.239 (2.59), 4.382 (1.30), 4.402 (1.79), 4.420 (1.52), 5.318 (7.60), 5.327 (7.37), 7.563 (1.21), 7.567 (1.39), 7.576 (1.07), 7.579 (1.21), 7.587 (2.82), 7.599 (2.06), 7.607 (1.79), 7.610 (1.79), 7.623 (1.25), 7.654 (1.61), 7.665 (2.23), 7.669 (1.70), 7.675 (2.91), 7.686 (4.07), 7.689 (2.46), 7.715 (2.99), 7.729 (3.13), 7.736 (4.07), 7.750 (3.89), 7.757 (1.65), 7.771 (1.47), 8.529 (9.25), 8.551 (10.99), 8.722 (11.22), 8.744 (8.98), 8.984 (16.00), 10.277 (4.83), 10.301 (4.65).

LC-MS (Method 3): $R_t$=1.05 min; MS (ESIpos): m/z=539 [M+H]$^+$

Example 353

7-[(3R,4R)-3,4-Dihydroxypyrrolidin-1-yl]-4-oxo-N-[(2S)-1-(trifluoromethoxy)propan-2-yl]-1-(2,4,6-trifluorophenyl)-1,4-dihydro-1,8-naphthyridine-3-carboxamide

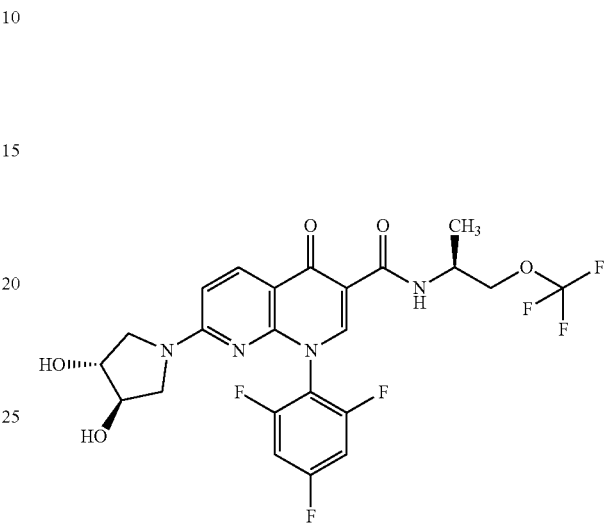

According to GP3, 50.0 mg (104 μmol) of the compound from Example 118A were reacted with 16.0 mg (115 μmol) of (3R,4R)-pyrrolidine-3,4-diol hydrochloride in the presence of 63.5 μl (365 μmol) of N,N-diisopropylethylamine in 1.0 ml of dimethylformamide. The reaction mixture was diluted with 2 ml of acetonitrile, acidified with aqueous 1N hydrochloric acid and purified by means of preparative HPLC (column: Chromatorex C18, 10 μm, 125×30 mm, solvent: acetonitrile/0.05% formic acid gradient; 0 to 3 min 10% acetonitrile, to 35 min 90% acetonitrile and for a further 3 min 90% acetonitrile). 47.9 mg (84% of theory, 100% purity) of the title compound were obtained.

$^1$H-NMR (500 MHz, DMSO-d6) δ[ppm]: 1.244 (16.00), 1.258 (15.83), 2.073 (7.16), 3.057 (2.15), 3.082 (2.68), 3.229 (1.66), 3.237 (1.86), 3.254 (1.49), 3.262 (1.42), 3.338 (3.21), 3.596 (1.49), 3.604 (1.66), 3.618 (1.42), 3.626 (1.26), 3.925 (2.55), 4.047 (2.55), 4.139 (0.89), 4.149 (1.29), 4.159 (4.41), 4.167 (7.16), 4.176 (4.90), 4.186 (1.03), 4.196 (1.09), 4.316 (0.70), 4.325 (1.23), 4.339 (1.62), 4.354 (1.13), 5.137 (3.41), 5.144 (3.38), 5.226 (3.35), 5.234 (3.25), 6.747 (6.92), 6.765 (6.96), 7.539 (1.89), 7.543 (2.09), 7.555 (3.48), 7.561 (3.54), 7.567 (1.62), 7.573 (2.09), 7.578 (1.76), 8.260 (8.68), 8.278 (8.08), 8.722 (12.99), 10.091 (4.07), 10.107 (3.84).

LC-MS (Method 3): $R_t$=1.63 min; MS (ESIpos): m/z=547 [M+H]$^+$

Example 354

1-(2,4-Difluorophenyl)-7-[1-hydroxy-3-azabicyclo[4.1.0]hept-3-yl]-4-oxo-N-[(2R)-1,1,1-trifluorobutan-2-yl]-1,4-dihydro-1,8-naphthyridine-3-carboxamide (diastereomer mixture)

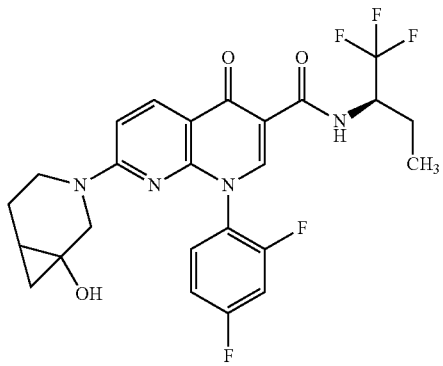 [SMILES: CC[C@@H](NC(=O)c1cn(-c2ccc(F)cc2F)c2nc(N3CCC4CC4(O)C3)ccc2c1=O)C(F)(F)F]

According to GP3, 50.0 mg (112 μmol) of the compound from Example 67A were reacted with 21.2 mg (95% purity, 135 μmol) of 5-azaspiro[2.4]heptan-7-ol hydrochloride in the presence of 68.0 μl (390 μmol) of N,N-diisopropylethylamine in 0.5 ml of dimethylformamide. The reaction mixture was diluted with 1 ml of acetonitrile and 0.1 ml of 1N aqueous hydrochloric acid and purified by means of preparative HPLC (column: Chromatorex C18, 10 μm, 125× 30 mm, solvent: acetonitrile/0.1% formic acid gradient; 0 to 5 min 10% acetonitrile, over 14 min to 90% acetonitrile and for a further 4 min 90% acetonitrile). 49.9 mg (84% of theory, 99% purity) of the title compound were obtained.

$^1$H-NMR (400 MHz, DMSO-d6) δ[ppm]: −0.011 (2.18), −0.008 (5.18), 0.008 (3.42), 0.146 (0.60), 0.178 (1.43), 0.204 (1.20), 0.219 (1.62), 0.232 (0.90), 0.666 (1.84), 0.679 (1.99), 0.690 (2.10), 0.704 (1.77), 0.945 (7.51), 0.963 (16.00), 0.982 (7.70), 1.101 (1.92), 1.110 (1.77), 1.119 (1.80), 1.477 (1.01), 1.596 (1.20), 1.614 (1.54), 1.621 (1.43), 1.630 (1.88), 1.639 (1.65), 1.649 (1.58), 1.656 (1.73), 1.674 (1.28), 1.848 (1.35), 1.858 (1.62), 1.867 (1.58), 1.877 (1.77), 1.883 (1.58), 1.893 (1.39), 1.902 (1.24), 1.912 (1.13), 1.966 (1.05), 2.367 (1.28), 2.478 (1.95), 2.519 (3.15), 2.523 (3.64), 2.710 (1.20), 3.103 (0.79), 3.288 (5.07), 3.384 (1.77), 3.399 (1.50), 3.416 (1.50), 4.013 (2.85), 4.046 (2.55), 4.730 (1.46), 4.751 (1.31), 5.603 (2.70), 6.978 (2.74), 7.001 (2.74), 7.309 (1.46), 7.331 (2.63), 7.352 (1.39), 7.544 (1.50), 7.550 (1.58), 7.569 (2.52), 7.573 (2.48), 7.592 (1.46), 7.599 (1.35), 7.805 (1.80), 7.814 (1.69), 7.828 (1.69), 8.267 (10.07), 8.290 (9.31), 8.613 (7.25), 10.467 (5.07), 10.491 (4.77).

LC-MS (Method 3): $R_t$=2.02 min; MS (ESIpos): m/z=523 [M+H]$^+$

Example 355

1-(2,4-Difluorophenyl)-7-[7-hydroxy-5-azaspiro[2.4]hept-5-yl]-4-oxo-N-[(2R)-1,1,1-trifluorobutan-2-yl]-1,4-dihydro-1,8-naphthyridine-3-carboxamide (diastereomer mixture)

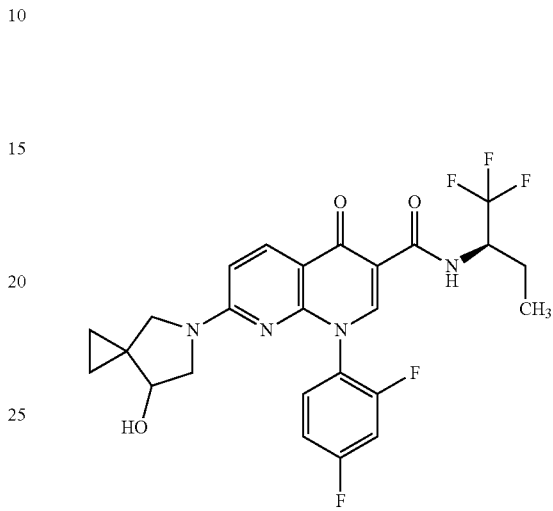

According to GP3, 50.0 mg (112 μmol) of the compound from Example 67A were reacted with 21.2 mg (95% purity, 135 μmol) of 3-azabicyclo[4.1.0]heptan-1-ol hydrochloride in the presence of 68.0 μl (393 μmol) of N,N-diisopropylethylamine in 0.5 ml of dimethylformamide. The reaction mixture was diluted with 1 ml of acetonitrile and 0.1 ml of 1N aqueous hydrochloric acid and purified by means of preparative HPLC (column: Chromatorex C18, 10 μm, 125× 30 mm, solvent: acetonitrile/0.1% formic acid gradient; 0 to 5 min 10% acetonitrile, over 14 min to 90% acetonitrile and for a further 4 min 90% acetonitrile). 48.8 mg (82% of theory, 99% purity) of the title compound were obtained.

$^1$H-NMR (400 MHz, DMSO-d6) δ[ppm]: −0.008 (3.32), 0.008 (3.21), 0.470 (1.19), 0.585 (4.12), 0.818 (1.66), 0.949 (7.22), 0.968 (16.00), 0.986 (7.77), 1.598 (1.12), 1.616 (1.44), 1.624 (1.34), 1.633 (1.77), 1.642 (1.63), 1.651 (1.52), 1.659 (1.73), 1.677 (1.30), 1.850 (1.30), 1.860 (1.52), 1.869 (1.52), 1.879 (1.73), 1.885 (1.52), 1.895 (1.30), 1.904 (1.16), 1.913 (0.98), 2.367 (1.23), 2.563 (1.05), 2.711 (1.26), 3.168 (0.87), 3.202 (1.12), 3.228 (1.08), 3.288 (3.36), 3.298 (2.93), 3.334 (1.52), 3.344 (1.34), 3.355 (1.26), 3.624 (1.59), 3.668 (1.08), 3.741 (1.16), 4.734 (1.34), 4.753 (1.30), 4.942 (0.76), 4.987 (0.79), 6.655 (1.48), 6.677 (1.55), 6.776 (0.79), 6.798 (0.76), 7.326 (1.55), 7.571 (1.23), 7.812 (1.52), 8.277 (4.19), 8.300 (4.05), 8.614 (2.96), 10.504 (5.24), 10.528 (5.06).

LC-MS (Method 3): $R_t$=2.05 min; MS (ESIpos): m/z=523 [M+H]$^+$

Example 356

1-(2,4-Difluorophenyl)-7-[4-hydroxy-3,3-dimethyl-pyrrolidin-1-yl]-4-oxo-N-[(2R)-1,1,1-trifluorobutan-2-yl]-1,4-dihydro-1,8-naphthyridine-3-carboxamide (diastereomer mixture)

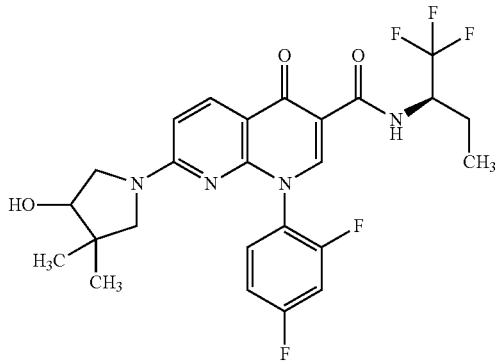 [SMILES: CC[C@@H](NC(=O)c1cn(-c2ccc(F)cc2F)c2nc(N3CC(O)C(C)(C)C3)ccc2c1=O)C(F)(F)F]

According to GP3, 50.0 mg (112 µmol) of the compound from Example 67A were reacted with 21.5 mg (95% purity, 135 µmol) of 4,4-dimethylpyrrolidin-3-ol hydrochloride in the presence of 68.0 µl (393 µmol) of N,N-diisopropylethylamine in 0.5 ml of dimethylformamide. The reaction mixture was diluted with 1 ml of acetonitrile and 0.1 ml of 1N aqueous hydrochloric acid and purified by means of preparative HPLC (column: Chromatorex C18, 10 µm, 125×30 mm, solvent: acetonitrile/0.1% formic acid gradient; 0 to 5 min 10% acetonitrile, over 14 min to 90% acetonitrile and for a further 4 min 90% acetonitrile). 52.4 mg (88% of theory, 99% purity) of the title compound were obtained.

$^1$H-NMR (400 MHz, DMSO-d6) δ[ppm]=10.51 (d, 1H), 8.60 (s, 1H), 8.27 (d, 1H), 7.86-7.76 (m, 1H), 7.63-7.56 (m, 1H), 7.37-7.29 (m, 1H), 6.73 (d, 1H), 5.21-5.00 (m, 1H), 4.81-4.67 (m, 1H), 3.86-3.64 (m, 1.5H), 3.07-2.82 (m, 1.5H), 1.93-1.82 (m, 1H), 1.70-1.57 (m, 1H), 1.04-0.84 (m, 9H), 2H under the water signal.

LC-MS (Method 3): $R_t$=2.13 min; MS (ESIpos): m/z=525 [M+H]$^+$

Example 357

7-[(4S)-4-Hydroxy-2-oxopyrrolidin-1-yl]-4-oxo-N-[(2R)-1,1,1-trifluoro-3,3-dimethylbutan-2-yl]-1-(2,4,6-trifluorophenyl)-1,4-dihydro-1,8-naphthyridine-3-carboxamide

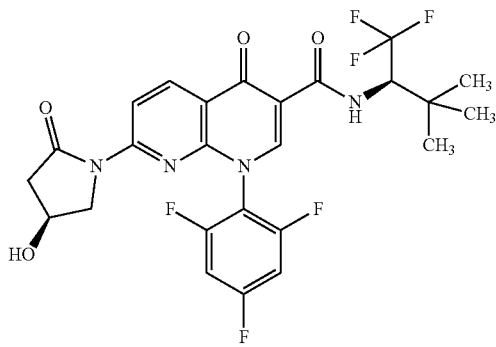 [SMILES: CC(C)(C)[C@@H](NC(=O)c1cn(-c2c(F)cc(F)cc2F)c2nc(N3C[C@@H](O)CC3=O)ccc2c1=O)C(F)(F)F]

According to GP1, 50.0 mg (119 µmol) of the compound from Example 117A were reacted with 22.2 mg (143 µmol) of (2R)-1,1,1-trifluoro-3,3-dimethylbutan-2-amine in the presence of 68.0 mg (179 µmol) of HATU and 41.5 µl (240 µmol) of N,N-diisopropylethylamine in 1.2 ml of dimethylformamide. The reaction mixture was diluted with 2 ml of acetonitrile and 1 ml of water and purified by means of preparative HPLC (column: Chromatorex C18, 10 µm, 125×30 mm, solvent: acetonitrile/0.1% formic acid gradient; 0 to 5 min 10% acetonitrile, over 14 min to 90% acetonitrile and for a further 4 min 90% acetonitrile). 56.2 mg (84% of theory, 99% purity) of the title compound were obtained.

$^1$H-NMR (400 MHz, DMSO-d6) δ[ppm]: −0.008 (0.93), 0.008 (0.57), 1.103 (16.00), 2.358 (0.92), 2.401 (1.06), 2.918 (0.90), 2.933 (0.92), 2.961 (0.82), 2.976 (0.78), 3.289 (1.34), 3.465 (0.91), 3.495 (1.09), 3.674 (0.83), 3.686 (0.99), 3.704 (0.76), 3.716 (0.65), 4.291 (0.70), 4.300 (0.67), 4.626 (0.57), 4.651 (0.73), 5.336 (2.14), 5.345 (2.04), 7.596 (0.65), 7.601 (0.72), 7.616 (1.15), 7.624 (1.13), 7.639 (0.68), 8.535 (3.00), 8.557 (3.38), 8.739 (3.49), 8.761 (2.76), 9.087 (3.75), 10.467 (1.27), 10.492 (1.18).

LC-MS (Method 3): $R_t$=2.05 min; MS (ESIpos): m/z=557 [M+H]$^+$

Example 358

N-(Bicyclo[1.1.1]pent-1-yl)-7-[(4S)-4-hydroxy-2-oxopyrrolidin-1-yl]-4-oxo-1-(2,4,6-trifluorophenyl)-1,4-dihydro-1,8-naphthyridine-3-carboxamide

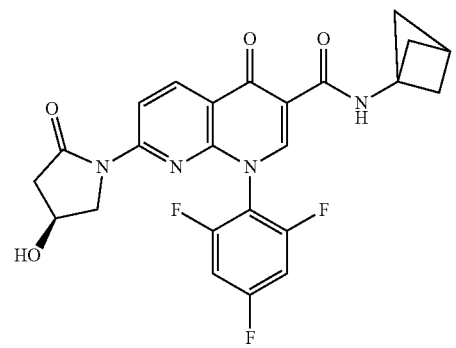 [SMILES: O=C(NC12CC(C1)C2)c1cn(-c2c(F)cc(F)cc2F)c2nc(N3C[C@@H](O)CC3=O)ccc2c1=O]

According to GP1, 45.0 mg (107 µmol) of the compound from Example 117A were reacted with 15.4 mg (129 µmol) of bicyclo[1.1.1]pentan-1-amine hydrochloride in the presence of 61.2 mg (161 µmol) of HATU and 37.4 µl (210 µmol) of N,N-diisopropylethylamine in 2.0 ml of dimethylformamide. The reaction mixture was diluted with 2 ml of acetonitrile and 1 ml of water and purified by means of preparative HPLC (column: Chromatorex C18, 10 µm, 125×30 mm, solvent: acetonitrile/0.1% formic acid gradient; 0 to 5 min 10% acetonitrile, over 14 min to 90% acetonitrile and for a further 4 min 90% acetonitrile). 31.9 mg (61% of theory, 100% purity) of the title compound were obtained.

$^1$H-NMR (400 MHz, DMSO-d6) δ[ppm]: 2.113 (16.00), 2.392 (0.81), 2.910 (0.63), 2.925 (0.66), 3.456 (0.70), 3.486 (0.85), 3.678 (0.73), 5.326 (0.89), 5.335 (0.88), 8.505 (1.28), 8.527 (1.65), 8.663 (1.35), 8.665 (1.49), 8.687 (1.16), 8.927 (2.46), 10.002 (1.75).

LC-MS (Method 3): $R_t$=1.76 min; MS (ESIpos): m/z=485 [M+H]$^+$

Example 359

4-Oxo-7-(2-oxoimidazolidin-1-yl)-N-[(2S)-1,1,1-trifluoro-3,3-dimethylbutan-2-yl]-1-(2,4,6-trifluorophenyl)-1,4-dihydro-1,8-naphthyridine-3-carboxamide

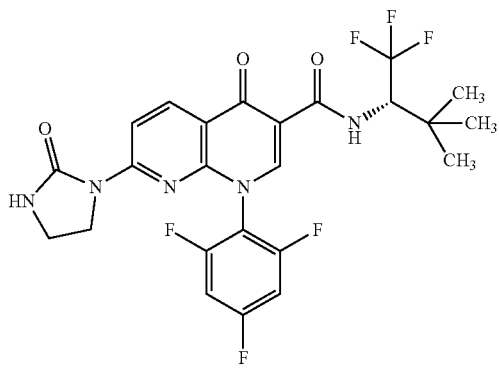 [SMILES: CC(C)(C)[C@H](NC(=O)c1cn(-c2c(F)cc(F)cc2F)c2nc(N3CCNC3=O)ccc2c1=O)C(F)(F)F]

According to GP1, 30.0 mg (74.2 µmol) of the compound from Example 113A were reacted with 13.8 mg (89.0 µmol) of (2S)-1,1,1-trifluoro-3,3-dimethylbutan-2-amine in the presence of 33.9 mg (89.0 µmol) of HATU and 32.0 µl (190 µmol) of N,N-diisopropylethylamine in 1.0 ml of dimethylformamide. The reaction mixture was diluted with 2 ml of DMSO, water and 1 ml of aqueous 1N hydrochloric acid and purified by means of preparative HPLC (column: Chromatorex C18, 10 µm, 125×30 mm, solvent: acetonitrile/0.1% formic acid gradient; 0 to 5 min 10% acetonitrile, over 14 min to 90% acetonitrile and for a further 4 min 90% acetonitrile). 31.5 mg (78% of theory, 99% purity) of the title compound were obtained.

$^1$H-NMR (400 MHz, DMSO-d6) δ[ppm]: 1.098 (16.00), 3.351 (1.68), 3.372 (1.25), 3.581 (1.30), 3.597 (1.13), 3.602 (1.65), 3.621 (0.93), 4.642 (0.74), 7.556 (1.06), 7.578 (1.77), 7.599 (1.05), 7.674 (1.85), 8.434 (2.49), 8.456 (3.12), 8.581 (3.18), 8.603 (2.40), 9.009 (3.62), 10.558 (1.22), 10.584 (1.17).

LC-MS (Method 3): $R_t$=2.12 min; MS (ESIpos): m/z=542 [M+H]$^+$

Example 360

4-Oxo-7-(2-oxoimidazolidin-1-yl)-N-[(2S)-1,1,1-trifluoro-3,3-dimethylbutan-2-yl]-1-(2,4,6-trifluorophenyl)-1,4-dihydro-1,8-naphthyridine-3-carboxamide

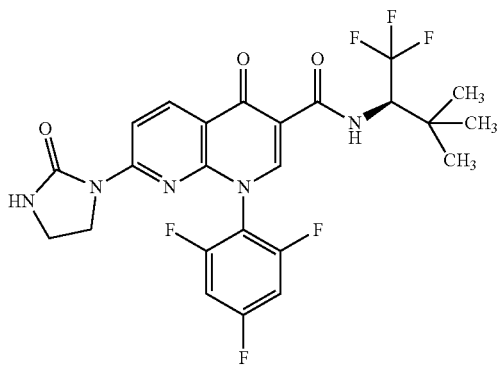 [SMILES: CC(C)(C)[C@@H](NC(=O)c1cn(-c2c(F)cc(F)cc2F)c2nc(N3CCNC3=O)ccc2c1=O)C(F)(F)F]

According to GP1, 30.0 mg (74.2 µmol) of the compound from Example 113A were reacted with 13.8 mg (89.0 µmol) of (2R)-1,1,1-trifluoro-3,3-dimethylbutan-2-amine in the presence of 33.9 mg (89.0 µmol) of HATU and 32.0 µl (190 µmol) of N,N-diisopropylethylamine in 1.0 ml of dimethylformamide. The reaction mixture was diluted with 2 ml of DMSO, water and 1 ml of aqueous 1N hydrochloric acid and purified by means of preparative HPLC (column: Chromatorex C18, 10 µm, 125×30 mm, solvent: acetonitrile/0.1% formic acid gradient; 0 to 5 min 10% acetonitrile, over 14 min to 90% acetonitrile and for a further 4 min 90% acetonitrile). 33.2 mg (82% of theory, 99% purity) of the title compound were obtained.

$^1$H-NMR (400 MHz, DMSO-d6) δ[ppm]: −0.008 (0.92), 0.008 (0.92), 1.098 (16.00), 3.351 (1.77), 3.371 (1.30), 3.580 (1.30), 3.596 (1.15), 3.601 (1.65), 3.620 (0.92), 4.641 (0.74), 7.555 (1.03), 7.578 (1.74), 7.599 (1.00), 7.673 (1.83), 8.433 (2.33), 8.455 (2.98), 8.580 (2.95), 8.603 (2.27), 9.009 (3.42), 10.558 (1.21), 10.583 (1.15).

LC-MS (Method 3): $R_t$=2.13 min; MS (ESIpos): m/z=542 [M+H]$^+$

Example 361

7-[3-(2-Hydroxyethyl)-2-oxoimidazolidin-1-yl]]-4-oxo-N-[(2R)-1,1,1-trifluoro-3,3-dimethylbutan-2-yl]-1-(2,4,6-trifluorophenyl)-1,4-dihydro-1,8-naphthyridine-3-carboxamide

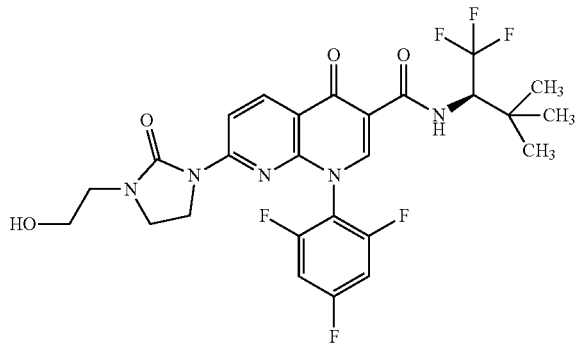 [SMILES: CC(C)(C)[C@@H](NC(=O)c1cn(-c2c(F)cc(F)cc2F)c2nc(N3CCN(CCO)C3=O)ccc2c1=O)C(F)(F)F]

According to GP1, 30 mg (67 μmol) of the compound from Example 123A were reacted with 12.5 mg (80.3 μmol) of (2R)-1,1,1-trifluoro-3,3-dimethylbutan-2-amine in the presence of 30.5 mg (80.3 μmol) of HATU and 29 μl (0.17 mmol) of N,N-diisopropylethylamine in 1.0 ml of dimethylformamide. The reaction mixture was diluted with 2 ml of DMSO, water and 1 ml of aqueous 1N hydrochloric acid and purified by means of preparative HPLC (column: Chromatorex C18, 10 μm, 125×30 mm, solvent: acetonitrile/0.1% formic acid gradient; 0 to 5 min 10% acetonitrile, over 14 min to 90% acetonitrile and for a further 4 min 90% acetonitrile). 33.3 mg (85% of theory, 100% purity) of the title compound were obtained.

$^1$H-NMR (400 MHz, DMSO-d6) δ[ppm]: 1.098 (16.00), 3.260 (1.13), 3.275 (2.52), 3.288 (1.60), 3.490 (1.10), 3.505 (2.50), 3.519 (2.79), 3.526 (2.42), 3.533 (2.77), 3.545 (1.40), 4.641 (0.73), 4.727 (0.93), 4.741 (2.09), 4.755 (0.89), 7.558 (1.06), 7.580 (1.87), 7.602 (1.03), 8.437 (2.12), 8.459 (2.61), 8.594 (2.67), 8.616 (1.99), 9.009 (3.66), 10.554 (1.19), 10.579 (1.13).

LC-MS (Method 3): R$_t$=2.03 min; MS (ESIpos): m/z=586 [M+H]$^+$

Example 362

7-[3-(2-Hydroxyethyl)-2-oxoimidazolidin-1-yl]]-4-oxo-N-[(2S)-1,1,1-trifluorobutan-2-yl]-1-(2,4,6-trifluorophenyl)-1,4-dihydro-1,8-naphthyridine-3-carboxamide

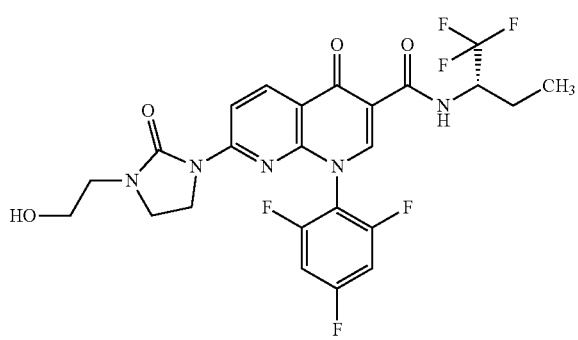 [SMILES: CC[C@H](NC(=O)c1cn(-c2c(F)cc(F)cc2F)c2nc(N3CCN(CCO)C3=O)ccc2c1=O)C(F)(F)F]

According to GP1, 30 mg (67 μmol) of the compound from Example 123A were reacted with 13.1 mg (80.3 μmol) of (2S)-1,1,1-trifluorobutan-2-amine hydrochloride in the presence of 38.2 mg (100 μmol) of HATU and 29 μl (0.17 mmol) of N,N-diisopropylethylamine in 1.0 ml of dimethylformamide. The mixture was diluted with 1 ml of water and 2 ml of acetonitrile and the solution was purified by means of preparative HPLC (column: Chromatorex C18, 10 μm, 125×30 mm, solvent: acetonitrile/0.1% formic acid gradient; 0 to 5 min 10% acetonitrile, over 14 min to 90% acetonitrile and for a further 4 min 90% acetonitrile). 33.3 mg (89% of theory, 100% purity) of the title compound were obtained.

$^1$H-NMR (400 MHz, DMSO-d6) δ[ppm]: −0.008 (2.42), 0.008 (2.11), 0.959 (7.16), 0.978 (16.00), 0.996 (7.76), 1.624 (1.00), 1.641 (1.49), 1.659 (1.80), 1.684 (1.69), 1.702 (1.29), 1.881 (1.58), 1.891 (1.67), 1.915 (1.27), 2.328 (1.22), 2.524 (3.47), 2.670 (1.36), 3.259 (4.78), 3.273 (10.56), 3.287 (6.18), 3.489 (4.40), 3.504 (10.07), 3.518 (11.49), 3.524 (9.87), 3.532 (11.36), 3.543 (5.64), 4.727 (4.56), 4.741 (9.96), 4.755 (5.24), 7.558 (4.78), 7.581 (8.69), 7.603 (4.67), 8.434 (9.07), 8.456 (11.67), 8.563 (12.18), 8.586 (8.51), 8.996 (15.76), 10.195 (5.09), 10.219 (5.00).

LC-MS (Method 3): R$_t$=1.86 min; MS (ESIpos): m/z=558 [M+H]$^+$

Example 363

N-[(1S)-1-Cyclopropyl-2,2,2-trifluoroethyl]-7-[3-(2-hydroxyethyl)-2-oxoimidazolidin-1-yl]-4-oxo-1-(2,4,6-trifluorophenyl)-1,4-dihydro-1,8-naphthyridine-3-carboxamide

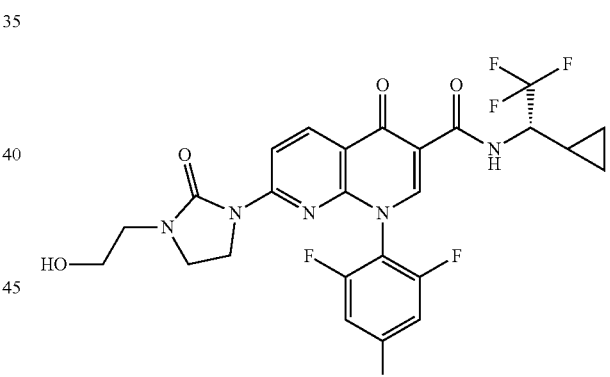

According to GP1, 30.0 mg (66.9 μmol) of the compound from Example 123A were reacted with 14.1 mg (80.3 μmol) of (1S)-1-cyclopropyl-2,2,2-trifluoroethanamine hydrochloride in the presence of 38.2 mg (100 μmol) of HATU and 29 μl (0.17 mmol) of N,N-diisopropylethylamine in 1.0 ml of dimethylformamide. The mixture was diluted with 1 ml of water and 2 ml of acetonitrile and the solution was purified by means of preparative HPLC (column: Chromatorex C18, 10 μm, 125×30 mm, solvent: acetonitrile/0.1% formic acid gradient; 0 to 5 min 10% acetonitrile, over 14 min to 90% acetonitrile and for a further 4 min 90% acetonitrile). 30.9 mg (81% of theory, 100% purity) of the title compound were obtained.

$^1$H-NMR (400 MHz, DMSO-d6) δ[ppm]: −0.008 (1.99), 0.008 (1.85), 0.331 (2.01), 0.342 (3.30), 0.354 (3.18), 0.365 (2.27), 0.377 (1.33), 0.528 (2.08), 0.540 (3.18), 0.553 (3.20), 0.559 (3.65), 0.564 (2.99), 0.577 (3.84), 0.586 (2.81), 0.596

(2.55), 0.607 (2.06), 0.621 (1.24), 0.635 (1.64), 0.645 (1.73), 0.656 (3.35), 0.659 (2.55), 0.666 (2.60), 0.672 (2.22), 0.677 (2.25), 0.680 (2.04), 0.687 (1.19), 0.692 (1.29), 0.699 (0.77), 1.199 (1.29), 1.207 (1.85), 1.220 (3.11), 1.228 (2.27), 1.240 (3.09), 1.252 (1.68), 1.260 (1.15), 2.328 (0.80), 2.524 (2.85), 2.671 (0.87), 3.260 (5.94), 3.274 (13.33), 3.288 (7.79), 3.463 (1.64), 3.478 (2.60), 3.493 (5.80), 3.498 (5.57), 3.504 (12.91), 3.519 (14.90), 3.524 (13.05), 3.532 (14.29), 3.542 (7.18), 3.547 (6.22), 3.566 (1.82), 4.372 (1.61), 4.393 (2.83), 4.415 (2.78), 4.435 (1.50), 4.726 (4.35), 4.740 (10.06), 4.754 (4.33), 7.547 (1.64), 7.555 (5.61), 7.570 (2.67), 7.578 (10.74), 7.585 (2.90), 7.600 (5.68), 7.608 (1.85), 8.435 (10.50), 8.457 (13.99), 8.567 (13.92), 8.590 (10.32), 8.988 (16.00), 10.336 (6.69), 10.360 (6.41).

LC-MS (Method 3): $R_t$=1.88 min; MS (ESIpos): m/z=570 $[M+H]^+$

Example 364

N-[(1S)-1-Cyclopropyl-2,2,2-trifluoroethyl]-7-[3-(2-hydroxyethyl)-2-oxotetrahydropyrimidin-1(2H)-yl]-4-oxo-1-(2,4,6-trifluorophenyl)-1,4-dihydro-1,8-naphthyridine-3-carboxamide

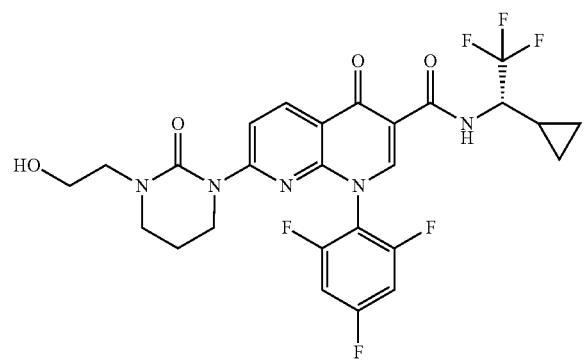 [SMILES: O=C(N[C@@H](C1CC1)C(F)(F)F)c1cn(-c2c(F)cc(F)cc2F)c2nc(N3CCCN(CCO)C3=O)ccc2c1=O]

According to GP1, 54 mg (78% purity, 91 μmol) of the compound from Example 125A were reacted with 19.2 mg (109 μmol) of (1S)-1-cyclopropyl-2,2,2-trifluoroethanamine hydrochloride in the presence of 41.6 mg (109 μmol) of HATU and 40 μl (0.23 mmol) of N,N-diisopropylethylamine in 1.5 ml of dimethylformamide. The mixture was diluted with 1 ml of aqueous 1N hydrochloric acid and 2 ml of DMSO and the solution was purified by means of preparative HPLC (column: Chromatorex C18, 10 μm, 125×30 mm, solvent: acetonitrile/0.1% formic acid gradient; 0 to 5 min 10% acetonitrile, over 14 min to 90% acetonitrile and for a further 2 min 90% acetonitrile). 33.9 mg (63% of theory, 99% purity) of the title compound were obtained.

$^1$H-NMR (400 MHz, DMSO-d6) δ[ppm]: −0.149 (0.60), −0.008 (6.40), 0.008 (4.91), 0.146 (0.64), 0.333 (1.84), 0.343 (3.22), 0.355 (3.03), 0.366 (2.03), 0.378 (1.34), 0.534 (1.96), 0.545 (2.95), 0.560 (3.80), 0.578 (4.09), 0.588 (2.73), 0.599 (2.38), 0.609 (1.93), 0.623 (1.14), 0.637 (1.49), 0.647 (1.71), 0.658 (3.30), 0.668 (2.51), 0.676 (2.16), 0.693 (1.27), 1.187 (0.64), 1.200 (1.27), 1.208 (1.74), 1.220 (2.95), 1.229 (2.16), 1.241 (2.85), 1.253 (1.51), 1.261 (1.09), 1.274 (0.47), 1.878 (1.44), 1.893 (4.09), 1.907 (6.28), 1.922 (4.29), 1.937 (1.56), 2.001 (0.64), 2.323 (1.04), 2.328 (1.44), 2.332 (1.04), 2.366 (0.89), 2.519 (6.57), 2.524 (5.16), 2.665 (1.22), 2.670 (1.64), 2.675 (1.17), 2.710 (1.02), 3.374 (9.15), 3.384 (16.00), 3.398 (9.35), 3.403 (8.04), 3.496 (6.08), 3.511 (8.53), 3.526 (9.23), 3.541 (10.37), 3.555 (9.13), 3.570 (2.98), 4.368 (1.54), 4.389 (2.63), 4.410 (2.60), 4.431 (1.36), 4.695 (3.97), 4.709 (8.81), 4.723 (3.84), 7.571 (5.28), 7.593 (10.15), 7.615 (5.43), 7.623 (1.79), 8.163 (11.66), 8.186 (12.73), 8.500 (12.92), 8.522 (11.44), 9.009 (15.93), 10.318 (6.25), 10.342 (5.98).

LC-MS (Method 3): $R_t$=1.87 min; MS (ESIpos): m/z=584 $[M+H]^+$

Example 365

7-[3-(2-Hydroxyethyl)-2-oxotetrahydropyrimidin-1(2H)-yl]-4-oxo-N-[(2S)-1,1,1-trifluorobutan-2-yl]-1-(2,4,6-trifluorophenyl)-1,4-dihydro-1,8-naphthyridine-3-carboxamide

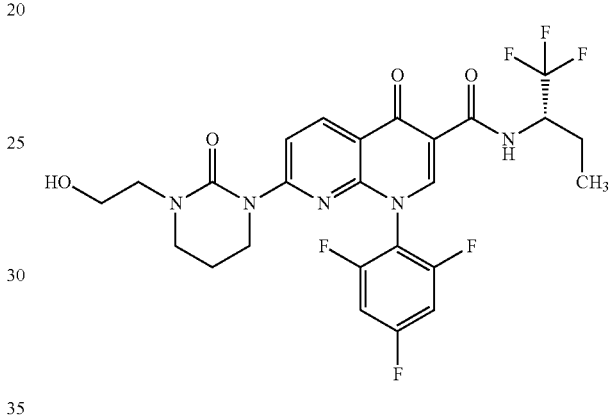

According to GP1, 54 mg (78% purity, 91 μmol) of the compound from Example 125A were reacted with 13.9 mg (109 μmol) of (2S)-1,1,1-trifluorobutan-2-amine in the presence of 41.6 mg (109 μmol) of HATU and 56 μl (0.32 mmol) of N,N-diisopropylethylamine in 1.5 ml of dimethylformamide. The mixture was diluted with 1 ml of aqueous 1N hydrochloric acid and 2 ml of DMSO and the solution was purified by means of preparative HPLC (column: Chromatorex C18, 10 μm, 125×30 mm, solvent: acetonitrile/0.1% formic acid gradient; 0 to 5 min 10% acetonitrile, over 14 min to 90% acetonitrile and for a further 2 min 90% acetonitrile). 34.3 mg (65% of theory, 99% purity) of the title compound were obtained.

$^1$H-NMR (400 MHz, DMSO-d6) δ[ppm]: −0.008 (2.74), 0.008 (2.26), 0.961 (7.23), 0.980 (16.00), 0.998 (7.82), 1.626 (1.06), 1.644 (1.46), 1.651 (1.28), 1.661 (1.79), 1.670 (1.57), 1.679 (1.50), 1.687 (1.72), 1.705 (1.28), 1.863 (1.46), 1.873 (2.05), 1.882 (2.48), 1.892 (5.19), 1.898 (4.38), 1.908 (6.72), 1.917 (3.98), 1.923 (4.27), 1.938 (1.57), 3.369 (5.52), 3.374 (7.82), 3.384 (13.41), 3.389 (11.76), 3.398 (7.96), 3.404 (6.65), 3.497 (5.19), 3.512 (7.27), 3.527 (8.26), 3.541 (9.39), 3.555 (8.26), 3.570 (2.59), 4.693 (4.02), 4.707 (9.13), 4.721 (4.24), 4.759 (1.42), 4.778 (1.35), 7.566 (1.28), 7.574 (4.42), 7.596 (8.15), 7.618 (4.46), 7.625 (1.39), 8.163 (9.86), 8.185 (10.85), 8.497 (10.85), 8.519 (9.64), 9.017 (13.11), 10.174 (5.19), 10.198 (4.97).

LC-MS (Method 3): $R_t$=1.86 min; MS (ESIpos): m/z=572 $[M+H]^+$

Example 366

N-(Bicyclo[1.1.1]pent-1-yl)-7-[(3R,4R)-3,4-dihydroxypyrrolidin-1-yl]-4-oxo-1-(2,4,6-trifluorophenyl)-1,4-dihydro-1,8-naphthyridine-3-carboxamide

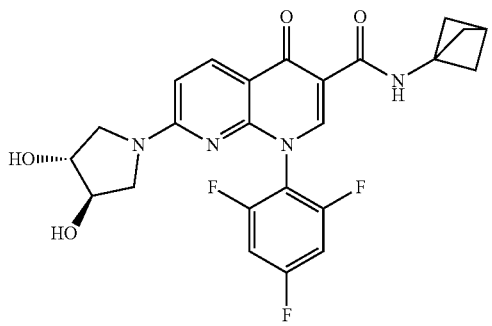 [SMILES: O=C(NC12CC(C1)C2)c1cn(-c2c(F)cc(F)cc2F)c2nc(N3C[C@@H](O)[C@H](O)C3)ccc2c1=O]

According to GP1, 50.0 mg (119 µmol) of the compound from Example 121A were reacted with 17.0 mg (142 µmol) of bicyclo[1.1.1]pentan-1-amine hydrochloride in the presence of 54.1 mg (142 µmol) of HATU and 72 µl (0.42 mmol) of N,N-diisopropylethylamine in 1.5 ml of dimethylformamide. The mixture was diluted with 1 ml of aqueous 1N hydrochloric acid and 2 ml of DMSO and the solution was purified by means of preparative HPLC (column: Chromatorex C18, 10 µm, 125×30 mm, solvent: acetonitrile/0.1% formic acid gradient; 0 to 5 min 10% acetonitrile, over 14 min to 90% acetonitrile and for a further 2 min 90% acetonitrile). 48.8 mg (84% of theory, 99% purity) of the title compound were obtained.

$^1$H-NMR (400 MHz, DMSO-d6) δ[ppm]: −0.008 (1.55), 0.008 (1.50), 2.073 (0.58), 2.093 (16.00), 2.476 (3.02), 5.136 (0.77), 5.218 (0.77), 6.738 (1.36), 6.760 (1.37), 7.568 (0.82), 8.230 (1.64), 8.253 (1.57), 8.660 (2.53), 10.283 (1.64).

LC-MS (Method 1): $R_t$=0.90 min; MS (ESIpos): m/z=487 [M+H]$^+$

Example 367

N-(3-Fluorobicyclo[1.1.1]pent-1-yl)-7-[(4S)-4-hydroxy-2-oxopyrrolidin-1-yl]-4-oxo-1-(2,4,6-trifluorophenyl)-1,4-dihydro-1,8-naphthyridine-3-carboxamide

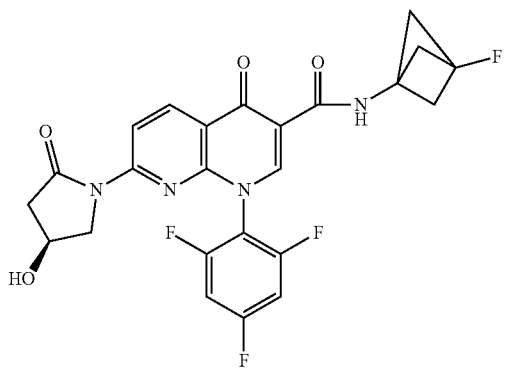 [SMILES: O=C(NC12CC(F)(C1)C2)c1cn(-c2c(F)cc(F)cc2F)c2nc(N3C[C@@H](O)CC3=O)ccc2c1=O]

According to GP1, 50.0 mg (119 µmol) of the compound from Example 117A were reacted with 19.7 mg (143 µmol) of 3-fluorobicyclo[1.1.1]pentan-1-amine hydrochloride in the presence of 54.4 mg (143 µmol) of HATU and 73 µl (0.42 mmol) of N,N-diisopropylethylamine in 1.5 ml of dimethylformamide. The mixture was diluted with 1 ml of aqueous 1N hydrochloric acid and 2 ml of DMSO and the solution was purified by means of preparative HPLC (column: Chromatorex C18, 10 µm, 125×30 mm, solvent: acetonitrile/ 0.05% formic acid gradient; 0 to 3 min 10% acetonitrile, to 35 min 90% acetonitrile and for a further 3 min 90% acetonitrile). 45.1 mg (68% of theory, 90% purity) of the title compound were obtained.

$^1$H-NMR (400 MHz, DMSO-d6) δ[ppm]: −0.149 (0.64), −0.008 (5.57), 0.008 (5.29), 2.073 (2.43), 2.113 (11.93), 2.328 (1.00), 2.332 (0.86), 2.349 (4.57), 2.393 (5.29), 2.670 (1.07), 2.675 (0.79), 2.911 (4.64), 2.926 (4.86), 2.954 (4.36), 2.969 (4.21), 3.339 (1.79), 3.454 (4.64), 3.484 (5.64), 3.665 (4.14), 3.677 (5.14), 3.695 (4.00), 3.707 (3.50), 4.292 (3.43), 5.324 (5.93), 5.332 (6.43), 7.595 (2.71), 7.601 (3.29), 7.614 (4.93), 7.624 (5.00), 7.637 (3.29), 7.644 (2.64), 8.505 (1.43), 8.513 (11.86), 8.527 (1.93), 8.535 (14.64), 8.665 (1.79), 8.672 (14.64), 8.687 (1.50), 8.694 (11.43), 8.926 (1.64), 8.964 (16.00), 10.003 (1.14), 10.119 (12.29).

LC-MS (Method 3): $R_t$=1.74 min; MS (ESIpos): m/z=503 [M+H]$^+$

Example 368

7-[(3R,4R)-3,4-Dihydroxypyrrolidin-1-yl]-N-(3-fluorobicyclo[1.1.1]pent-1-yl)-4-oxo-1-(2,4,6-trifluorophenyl)-1,4-dihydro-1,8-naphthyridine-3-carboxamide

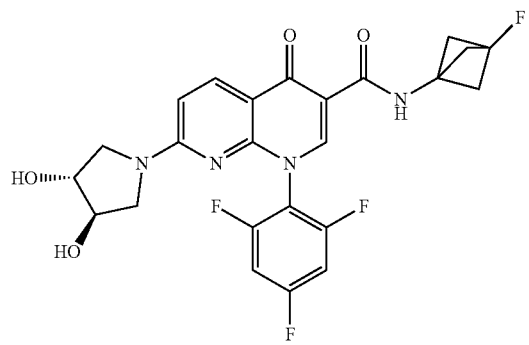 [SMILES: O=C(NC12CC(F)(C1)C2)c1cn(-c2c(F)cc(F)cc2F)c2nc(N3C[C@@H](O)[C@H](O)C3)ccc2c1=O]

According to GP1, 50.0 mg (119 µmol) of the compound from Example 121A were reacted with 19.6 mg (142 µmol) of 3-fluorobicyclo[1.1.1]pentan-1-amine hydrochloride in the presence of 54.1 mg (142 µmol) of HATU and 73 µl (0.420 mmol) of N,N-diisopropylethylamine in 1.2 ml of dimethylformamide. The mixture was diluted with 1 ml of aqueous 1N hydrochloric acid and 2 ml of DMSO and the solution was purified by means of preparative HPLC (column: Chromatorex C18, 10 µm, 125×30 mm, solvent: acetonitrile/0.05% formic acid gradient; 0 to 3 min 10% acetonitrile, to 35 min 90% acetonitrile and for a further 3 min 90% acetonitrile). 50.1 mg (75% of theory, 90% purity) of the title compound were obtained.

$^1$H-NMR (400 MHz, DMSO-d6) δ[ppm]: −0.008 (3.60), 0.008 (3.27), 2.073 (16.00), 2.094 (9.42), 2.476 (2.09), 3.047 (2.50), 3.079 (3.34), 3.222 (2.02), 3.231 (2.25), 3.253

(1.66), 3.264 (1.66), 3.337 (3.32), 3.586 (1.79), 3.595 (2.02), 3.612 (1.63), 3.623 (1.48), 3.922 (3.11), 4.044 (3.06), 5.131 (4.39), 5.139 (4.31), 5.221 (4.39), 5.230 (4.21), 6.738 (0.94), 6.747 (7.09), 6.760 (1.07), 6.770 (7.22), 7.546 (2.58), 7.562 (4.49), 7.569 (4.52), 7.577 (1.68), 7.585 (2.65), 8.231 (1.48), 8.236 (8.55), 8.253 (1.51), 8.258 (8.04), 8.660 (1.38), 8.700 (12.48), 10.283 (0.92), 10.425 (9.08).

LC-MS (Method 3): $R_t$=1.57 min; MS (ESIpos): m/z=505 [M+H]$^+$

Example 369

7-[(3R,4R)-3,4-Dihydroxypyrrolidin-1-yl]-4-oxo-N-[(2S)-1,1,1-trifluoro-3,3-dimethylbutan-2-yl]-1-(2,4,6-trifluorophenyl)-1,4-dihydro-1,8-naphthyridine-3-carboxamide

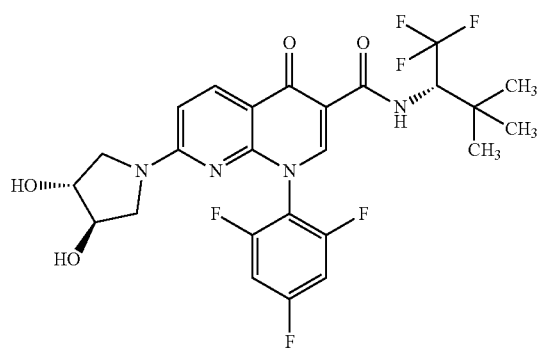 [SMILES: CC(C)(C)[C@H](NC(=O)c1cn(-c2c(F)cc(F)cc2F)c2nc(N3C[C@@H](O)[C@H](O)C3)ccc2c1=O)C(F)(F)F]

According to GP1, 30 mg (71 µmol) of the compound from Example 121A were reacted with 13 mg (85 µmol) of (2S)-1,1,1-trifluoro-3,3-dimethylbutan-2-amine in the presence of 32 mg (85 µmol) of HATU and 43 µl (0.25 mmol) of N,N-diisopropylethylamine in 1.0 ml of dimethylformamide. The mixture was diluted with 1 ml of aqueous 1N hydrochloric acid and 2 ml of DMSO and the solution was purified by means of preparative HPLC (column: Chromatorex C18, 10 µm, 125×30 mm, solvent: acetonitrile/0.05% formic acid gradient; 0 to 3 min 10% acetonitrile, to 35 min 90% acetonitrile and for a further 3 min 90% acetonitrile). 32.4 mg (81% of theory, 100% purity) of the title compound were obtained.

$^1$H-NMR (400 MHz, DMSO-d6) δ[ppm]: −0.008 (2.17), 0.008 (2.14), 1.089 (16.00), 3.059 (0.72), 3.090 (0.96), 3.241 (0.66), 3.328 (1.22), 3.355 (0.91), 3.610 (0.59), 3.929 (0.86), 4.052 (0.86), 4.621 (0.73), 5.138 (1.04), 5.146 (1.08), 5.236 (1.02), 5.245 (1.02), 6.770 (2.04), 6.792 (2.09), 7.548 (0.63), 7.560 (0.95), 7.570 (0.98), 7.583 (0.64), 8.295 (2.41), 8.318 (2.25), 8.815 (3.51), 10.764 (1.24), 10.790 (1.18).

LC-MS (Method 3): $R_t$=1.88 min; MS (ESIpos): m/z=559 [M+H]$^+$

Example 370

7-[(3R,4R)-3,4-Dihydroxypyrrolidin-1-yl]-4-oxo-N-(4,4,4-trifluoro-2-methylbutan-2-yl)-1-(2,4,6-trifluorophenyl)-1,4-dihydro-1,8-naphthyridine-3-carboxamide

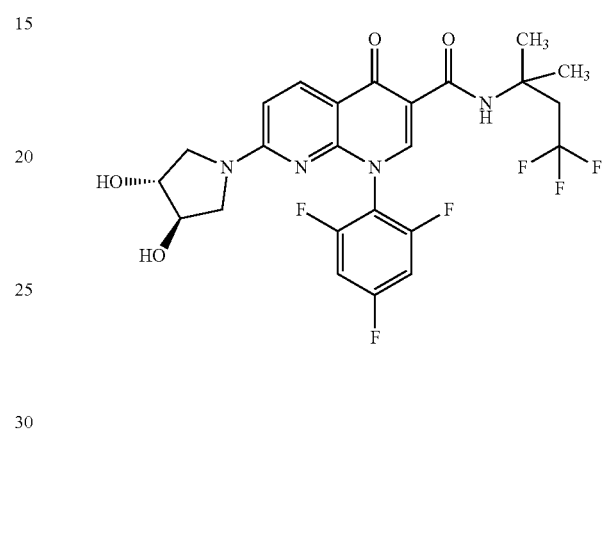

According to GP1, 1.19 g (2.82 mmol) of the compound from Example 121A were reacted with 601 mg (3.38 mmol) of 4,4,4-trifluoro-2-methylbutan-2-amine hydrochloride in the presence of 1.29 g (3.38 mmol) of HATU and 1.72 ml (9.87 mmol) of N,N-diisopropylethylamine in 28 ml of dimethylformamide.

The mixture was admixed with 40 ml of water and 15 ml of aqueous 1 M hydrochloric acid and extracted three times with 40 ml of ethyl acetate. The combined organic phases were washed with 30 ml of saturated aqueous sodium chloride solution, dried and concentrated, and the residue was purified by means of normal phase chromatography (cyclohexane-ethyl acetate gradient). Finally, the product was suspended in 10 ml of acetonitrile and additionally diluted with 15 ml of tert-butyl methyl ether. The mixture was extracted by stirring for 30 min and then filtered. The precipitate was filtered off with suction and dried under high vacuum. 1.20 g (78% of theory, 100% purity) of the title compound were obtained.

$^1$H-NMR (400 MHz, DMSO-d6) δ[ppm]=10.17 (s, 1H), 8.69 (s, 1H), 8.26 (d, 1H), 7.60-7.51 (m, 2H), 6.76 (d, 1H), 5.23 (d, 1H), 5.13 (d, 1H), 4.05 (br. s, 1H), 3.93 (br. s, 1H), 3.61 (dd, 1H), 3.34 (s, 0.5H), 3.25 (dd, 1H), 3.07 (d, 1H), 2.95 (q, 2H), 1.48 (s, 6H).

LC-MS (Method 3): $R_t$=1.71 min; MS (ESIpos): m/z=545 [M+H]$^+$

Example 371

7-[(3R,4R)-3,4-Dihydroxypyrrolidin-1-yl]-4-oxo-N-[3-(trifluoromethyl)bicyclo[1.1.1]pent-1-yl]-1-(2,4,6-trifluorophenyl)-1,4-dihydro-1,8-naphthyridine-3-carboxamide

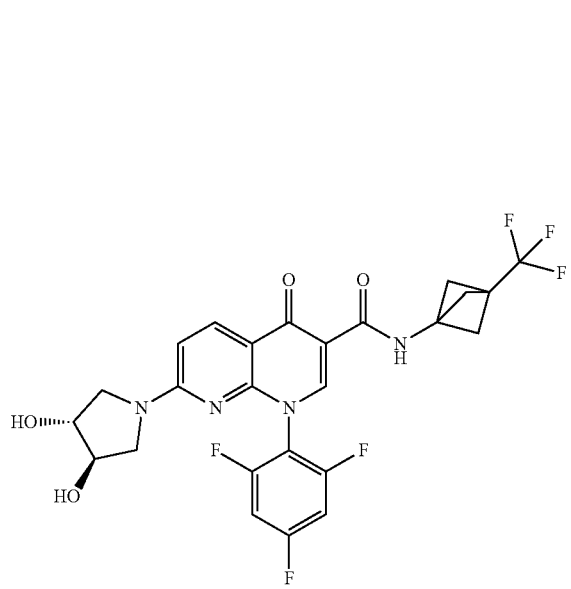 [SMILES: O=C(NC12CC(C(F)(F)F)(C1)C2)c1cn(-c2c(F)cc(F)cc2F)c2nc(N3C[C@@H](O)[C@H](O)C3)ccc2c1=O]

According to GP1, 30 mg (71 µmol) of the compound from Example 121A were reacted with 17 mg (85 µmol) of 3-(trifluoromethyl)bicyclo[1.1.1]pentan-1-amine hydrochloride in the presence of 32.5 mg (85.4 µmol) of HATU and 43 µl (0.25 mmol) of N,N-diisopropylethylamine in 1.0 ml of dimethylformamide.

The mixture was diluted with 1 ml of aqueous 1N hydrochloric acid and 2 ml of DMSO and the solution was purified by means of preparative HPLC (column: Chromatorex C18, 10 µm, 125×30 mm, solvent: acetonitrile/0.05% formic acid gradient; 0 to 3 min 10% acetonitrile, to 35 min 90% acetonitrile and for a further 3 min 90% acetonitrile). 27.6 mg (69% of theory, 99% purity) of the title compound were obtained. 20 $^1$H-NMR (400 MHz, DMSO-d6) δ[ppm]: −0.008 (1.73), 0.008 (1.57), 2.073 (7.45), 2.356 (16.00), 3.077 (0.74), 3.923 (0.74), 4.043 (0.74), 5.132 (1.08), 5.141 (1.08), 5.222 (1.05), 5.232 (1.05), 6.749 (1.73), 6.771 (1.75), 7.568 (1.12), 8.233 (2.13), 8.256 (2.00), 8.711 (3.43), 10.465 (2.33).

LC-MS (Method 3): $R_t$=1.78 min; MS (ESIpos): m/z=555 [M+H]$^+$

Example 372

7-[(4S)-4-Hydroxy-2-oxopyrrolidin-1-yl]-4-oxo-N-[3-(trifluoromethyl)bicyclo[1.1.1]pent-1-yl]-1-(2,4,6-trifluorophenyl)-1,4-dihydro-1,8-naphthyridine-3-carboxamide

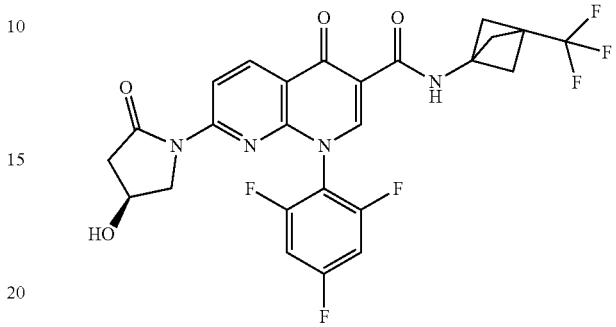

According to GP1, 30 mg (71 µmol) of the compound from Example 117A were reacted with 17 mg (95% purity, 86 µmol) of 3-(trifluoromethyl)bicyclo[1.1.1]pentan-1-amine hydrochloride in the presence of 33 mg (86 µmol) of HATU and 44 µl (0.25 mmol) of N,N-diisopropylethylamine in 1.0 ml of dimethylformamide. The mixture was diluted with 1 ml of aqueous 1N hydrochloric acid and 2 ml of DMSO and the solution was purified by means of preparative HPLC (column: Chromatorex C18, 10 µm, 125×30 mm, solvent: acetonitrile/0.05% formic acid gradient; 0 to 3 min 10% acetonitrile, to 35 min 90% acetonitrile and for a further 3 min 90% acetonitrile). 24.3 mg (61% of theory, 99% purity) of the title compound were obtained.

$^1$H-NMR (400 MHz, DMSO-d6) δ[ppm]: −0.008 (2.13), 0.008 (1.94), 2.349 (0.88), 2.376 (16.00), 2.392 (1.16), 2.911 (0.75), 2.926 (0.78), 2.954 (0.69), 2.969 (0.69), 3.454 (0.78), 3.484 (0.97), 3.666 (0.69), 3.677 (0.85), 3.695 (0.66), 5.324 (1.66), 5.333 (1.66), 7.613 (0.81), 7.622 (0.85), 8.514 (1.85), 8.536 (2.35), 8.671 (2.29), 8.693 (1.78), 8.974 (2.79), 10.159 (2.32).

LC-MS (Method 3): $R_t$=1.95 min; MS (ESIpos): m/z=553 [M+H]$^+$

Example 373

N-[(1S)-1-Cyclopropyl-2,2,2-trifluoroethyl]-7-(1,1-dioxido-1,2,5-thiadiazolidin-2-yl)-4-oxo-1-(2,4,6-trifluorophenyl)-1,4-dihydro-1,8-naphthyridine-3-carboxamide

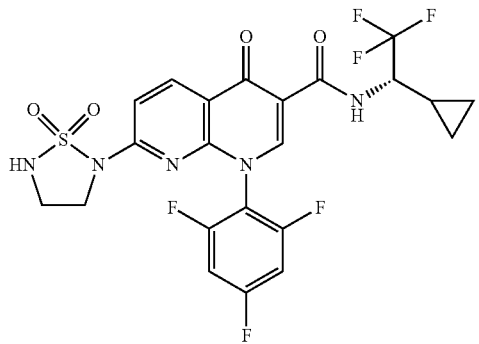 [SMILES: O=C(N[C@@H](C1CC1)C(F)(F)F)c1cn(-c2c(F)cc(F)cc2F)c2nc(N3CCNS3(=O)=O)ccc2c1=O]

104 mg (159 µmol) of the compound from example 127A were dissolved in 10 ml of ethanol. 112 mg (20% purity, 159 µmol) palladium(II) hydroxide on charcoal were added and hydrogenation was effected at standard pressure overnight. The reaction solution was filtered, and the filtrate was concentrated and purified by means of preparative HPLC (column: Chromatorex C18, 10 µm, 125×30 mm, solvent: acetonitrile/0.05% formic acid gradient; 0 to 3 min 10% acetonitrile, to 35 min 90% acetonitrile and for a further 3 min 90% acetonitrile). A further purification was effected by means of chiral preparative HPLC (column: Chiralpak IE 5 µm; flow rate: 15 ml/min; temp.: 35° C.; eluents: 25% ethanol, 75% n-heptane). 23.0 mg (25% of theory, 99% purity) of the title compound were obtained.

$^1$H-NMR (400 MHz, DMSO-d6) δ[ppm]: −0.149 (1.73), −0.008 (16.00), 0.008 (12.76), 0.146 (1.66), 0.341 (2.75), 0.355 (2.60), 0.365 (1.62), 0.377 (1.02), 0.538 (1.62), 0.548 (2.45), 0.562 (3.84), 0.579 (3.61), 0.598 (1.92), 0.609 (1.58), 0.622 (0.98), 0.638 (1.17), 0.647 (1.47), 0.659 (2.56), 0.668 (2.03), 0.680 (1.62), 0.693 (1.05), 1.186 (0.53), 1.198 (1.05), 1.206 (1.43), 1.219 (2.48), 1.239 (2.79), 1.251 (1.51), 1.259 (1.02), 2.327 (1.77), 2.366 (0.83), 2.523 (5.16), 2.665 (1.39), 2.670 (1.88), 2.710 (0.87), 3.457 (3.46), 3.473 (8.24), 3.489 (4.40), 3.752 (4.82), 3.767 (9.04), 3.783 (3.95), 4.368 (1.28), 4.389 (2.22), 4.409 (2.18), 4.429 (1.20), 7.285 (7.98), 7.307 (8.06), 7.513 (4.44), 7.535 (8.43), 7.557 (4.44), 8.037 (4.37), 8.651 (9.56), 8.673 (9.11), 9.002 (13.55), 10.278 (5.12), 10.302 (4.93).

LC-MS (Method 3): $R_t$=1.95 min; MS (ESIpos): m/z=562 [M+H]$^+$

Example 374

N-[(1S)-1-Cyclopropyl-2,2,2-trifluoroethyl]-4-oxo-7-(2-oxo-1,3-oxazolidin-1,3-yl)-1-(2,4,6-trifluorophenyl)-1,4-dihydro-1,8-naphthyridine-3-carboxamide

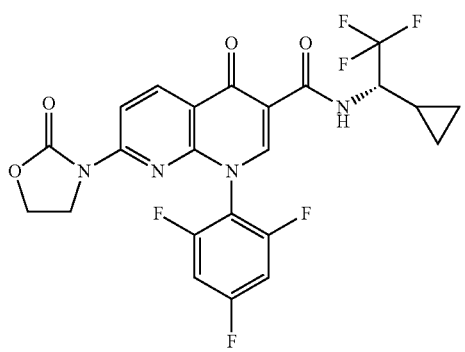 [SMILES: O=C(N[C@@H](C1CC1)C(F)(F)F)c1cn(-c2c(F)cc(F)cc2F)c2nc(N3CCOC3=O)ccc2c1=O]

According to GP2, 50.0 mg (105 µmol) of the compound from Example 126A were reacted with 11.0 mg (126 µmol) of 1,3-oxazolidin-2-one in the presence of 21.8 mg (158 µmol) of potassium carbonate, 2.4 mg (11 µmol) of palladium(II) acetate and 12 mg (21 µmol) of Xantphos in 0.75 ml of 1,4-dioxane. Subsequently, the volume of the mixture was concentrated under reduced pressure, and the residue was taken up with 1 ml of aqueous 1N hydrochloric acid and 2 ml of acetonitrile and purified by means of preparative HPLC (column: Chromatorex C18, 10 µm, 125×30 mm, solvent: acetonitrile/0.05% formic acid gradient; 0 to 3 min 10% acetonitrile, to 35 min 90% acetonitrile and for a further 3 min 90% acetonitrile). 33.6 mg (60% of theory, 99% purity) of the title compound were obtained.

$^1$H-NMR (400 MHz, DMSO-d6) δ[ppm]: −0.008 (1.85), 0.008 (1.34), 0.343 (2.89), 0.357 (2.89), 0.369 (1.83), 0.380 (1.16), 0.541 (1.73), 0.551 (2.65), 0.564 (4.20), 0.582 (4.03), 0.590 (2.61), 0.601 (2.20), 0.611 (1.73), 0.624 (1.06), 0.641 (1.38), 0.650 (1.51), 0.661 (2.74), 0.671 (2.24), 0.682 (1.85), 0.696 (1.19), 1.206 (1.14), 1.215 (1.60), 1.227 (2.57), 1.235 (2.01), 1.248 (2.52), 1.260 (1.47), 1.268 (0.97), 2.073 (1.68), 2.329 (0.69), 2.670 (0.82), 3.745 (4.87), 3.764 (8.60), 3.785 (5.74), 4.372 (7.16), 4.393 (11.23), 4.412 (7.07), 4.437 (1.29), 7.563 (5.18), 7.585 (9.68), 7.608 (5.18), 7.616 (1.64), 8.325 (9.92), 8.347 (10.78), 8.719 (10.89), 8.741 (9.60), 9.063 (16.00), 10.243 (5.50), 10.267 (5.30).

LC-MS (Method 3): $R_t$=2.10 min; MS (ESIpos): m/z=527 [M+H]$^+$

Example 375

7-[3-(2-Hydroxyethyl)-2-oxoimidazolidin-1-yl]-4-oxo-N-(4,4,4-trifluoro-2-methylbutan-2-yl)-1-(2,4,6-trifluorophenyl)-1,4-dihydro-1,8-naphthyridine-3-carboxamide

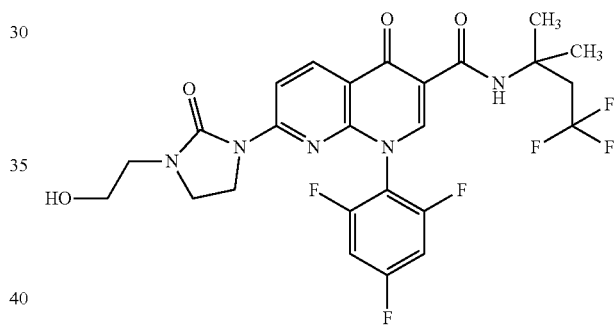

According to GP1, 30 mg (67 µmol) of the compound from Example 123A were reacted with 14 mg (80 µmol) of 4,4,4-trifluoro-2-methylbutan-2-amine hydrochloride in the presence of 38.2 mg (100 µmol) of HATU and 29.1 µl (170 µmol) of N,N-diisopropylethylamine in 2.0 ml of dimethylformamide. The mixture was diluted with 1 ml of 1N aqueous hydrochloric acid, 1 ml of acetonitrile and 1 ml of DMSO and the solution was purified by means of preparative HPLC (column: Chromatorex C18, 10 µm, 125×30 mm, solvent: acetonitrile/0.05% formic acid gradient; 0 to 3 min 10% acetonitrile, to 35 min 90% acetonitrile and for a further 3 min 90% acetonitrile). 29.2 mg (76% of theory, 100% purity) of the title compound were obtained.

$^1$H-NMR (400 MHz, DMSO-d6) δ[ppm]: −0.008 (2.31), 0.008 (1.93), 1.495 (16.00), 2.524 (1.37), 2.670 (0.45), 2.913 (0.72), 2.943 (2.05), 2.973 (1.98), 3.003 (0.60), 3.255 (1.60), 3.270 (3.55), 3.284 (2.02), 3.488 (1.52), 3.501 (3.04), 3.518 (4.32), 3.530 (3.12), 4.739 (1.17), 7.553 (1.55), 7.574 (2.79), 7.596 (1.55), 8.410 (3.01), 8.433 (3.90), 8.542 (4.00), 8.565 (2.88), 8.884 (4.99), 9.980 (3.23).

LC-MS (Method 3): $R_t$=1.89 min; MS (ESIpos): m/z=572 [M+H]$^+$

Example 376

4-Oxo-7-(2-oxoimidazolidin-1-yl)-N-(4,4,4-trifluoro-2-methylbutan-2-yl)-1-(2,4,6-trifluorophenyl)-1,4-dihydro-1,8-naphthyridine-3-carboxamide

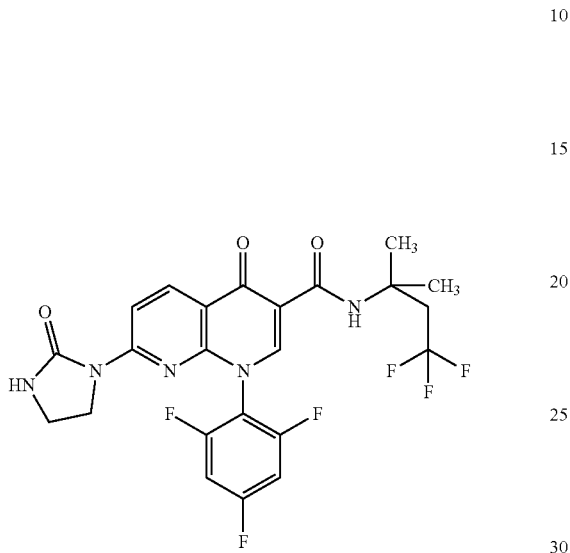

According to GP1, 50.0 mg (124 µmol) of the compound from Example 113A were reacted with 26.4 mg (148 µmol) of 4,4,4-trifluoro-2-methylbutan-2-amine hydrochloride in the presence of 56.4 mg (148 µmol) of HATU and 53.9 µl (309 µmol) of N,N-diisopropylethylamine in 1.5 ml of dimethylformamide. The mixture was diluted with 1 ml of 1N aqueous hydrochloric acid and 1 ml of DMSO and the solution was purified by means of preparative HPLC (column: Chromatorex C18, 10 µm, 125×30 mm, solvent: acetonitrile/0.05% formic acid gradient; 0 to 3 min 10% acetonitrile, to 35 min 90% acetonitrile and for a further 3 min 90% acetonitrile) and final normal phase chromatography (cyclohexane-ethyl acetate gradient). 35.7 mg (55% of theory, 100% purity) of the title compound were obtained.

$^1$H-NMR (400 MHz, DMSO-d6) δ[ppm]: −0.008 (1.14), 0.008 (1.01), 1.495 (16.00), 2.524 (0.93), 2.913 (0.71), 2.943 (2.10), 2.973 (2.00), 3.003 (0.62), 3.325 (1.57), 3.345 (2.21), 3.365 (1.69), 3.572 (1.77), 3.594 (2.24), 3.612 (1.26), 7.550 (1.45), 7.572 (2.62), 7.594 (1.48), 7.649 (2.43), 8.406 (2.75), 8.429 (3.80), 8.528 (3.71), 8.551 (2.69), 8.884 (4.36), 9.985 (3.18).

LC-MS (Method 1): $R_t$=1.04 min; MS (ESIpos): m/z=528 [M+H]$^+$

Example 377

Methyl {1-[5-oxo-6-{[(2S)-1,1,1-trifluorobutan-2-yl]carbamoyl}-8-(2,4,6-trifluorophenyl)-5,8-dihydro-1,8-naphthyridin-2-yl]imidazolidin-2-ylidene}carbamate

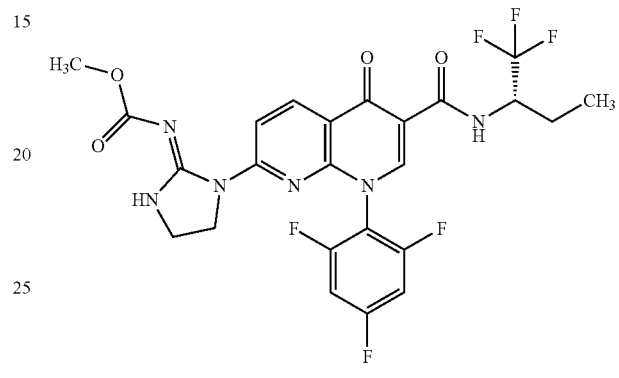

100 mg (205 µmol) of the compound from Example 128A and 57 µl (0.41 mmol) of triethylamine were dissolved in 2.0 ml of dichloromethane. 32.0 mg (205 µmol) of methyl (dichloromethylene)carbamate were added and the mixture was stirred at RT overnight. The reaction mixture was admixed with 20 ml of ethyl acetate and washed three times with saturated aqueous sodium hydrogencarbonate solution. The organic phase was washed with saturated aqueous sodium chloride solution, dried and concentrated. The residue was purified by means of preparative HPLC (column: Chromatorex C18, 10 µm, 125×30 mm, solvent: acetonitrile/0.1% formic acid gradient; 0 to 5 min 10% acetonitrile, over 14 min to 90% acetonitrile and for a further 2 min 90% acetonitrile). 33.7 mg (29% of theory, 100% purity) of the title compound were obtained.

$^1$H-NMR (400 MHz, DMSO-d6) δ[ppm]: 0.008 (1.62), 0.963 (2.65), 0.981 (5.90), 1.000 (2.87), 1.645 (0.55), 1.662 (0.64), 1.670 (0.54), 1.686 (0.62), 1.705 (0.42), 1.865 (0.50), 1.874 (0.56), 1.883 (0.54), 1.893 (0.64), 1.909 (0.50), 1.928 (0.42), 2.329 (0.42), 2.670 (0.48), 3.520 (0.91), 3.541 (2.07), 3.563 (1.92), 3.611 (16.00), 3.655 (2.02), 3.678 (2.20), 3.697 (0.96), 4.757 (0.55), 7.565 (1.66), 7.587 (3.13), 7.609 (1.67), 8.623 (3.35), 8.646 (3.76), 8.918 (4.03), 8.940 (3.39), 8.964 (1.06), 9.027 (5.59), 10.171 (1.83), 10.194 (1.78).

LC-MS (Method 1): $R_t$=1.07 min; MS (ESIpos): m/z=571 [M+H]$^+$

Example 378

N-[(1S)-1-Cyclopropyl-2,2,2-trifluoroethyl]-7-{[(2R)-2-hydroxypropyl]amino}-4-oxo-1-(2,4,6-trifluorophenyl)-1,4-dihydro-1,8-naphthyridine-3-carboxamide

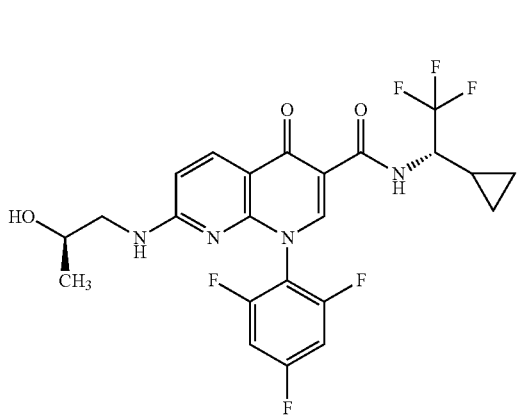 [SMILES: C[C@@H](O)CNc1ccc2c(=O)c(C(=O)N[C@@H](C3CC3)C(F)(F)F)cn(-c3c(F)cc(F)cc3F)c2n1]

According to GP3, 150 mg (315 µmol) of the compound from Example 126A were reacted with 33.2 mg (441 µmol) of (2R)-1-aminopropan-2-ol in the presence of 190 µl (1.10 mmol) of N,N-diisopropylethylamine in 3.1 ml of dimethylformamide. The reaction mixture was diluted with 1 ml of acetonitrile and 0.5 ml of water and purified by means of preparative HPLC (column: Chromatorex C18, 10 µm, 125×30 mm, solvent: acetonitrile/0.1% formic acid gradient; 0 to 5 min 10% acetonitrile, over 14 min to 90% acetonitrile and for a further 2 min 90% acetonitrile). 145 mg (89% of theory, 99% purity) of the title compound were obtained.

$^1$H-NMR (400 MHz, DMSO-d6) δ[ppm]: −0.150 (0.47), −0.008 (4.10), 0.008 (3.55), 0.146 (0.47), 0.307 (1.05), 0.318 (2.37), 0.329 (3.71), 0.341 (3.77), 0.353 (2.84), 0.365 (1.52), 0.490 (0.99), 0.501 (2.60), 0.513 (3.85), 0.525 (3.29), 0.535 (2.80), 0.542 (2.68), 0.549 (2.43), 0.562 (3.79), 0.573 (3.22), 0.583 (2.96), 0.593 (2.41), 0.607 (1.52), 0.622 (1.82), 0.632 (2.17), 0.643 (3.31), 0.653 (3.10), 0.658 (3.00), 0.667 (3.08), 0.675 (1.42), 0.688 (1.03), 0.826 (15.80), 0.842 (16.00), 1.159 (0.79), 1.171 (1.54), 1.179 (2.27), 1.191 (3.91), 1.200 (2.72), 1.212 (3.87), 1.224 (1.99), 1.232 (1.34), 1.244 (0.59), 2.073 (14.17), 2.328 (1.01), 2.333 (0.75), 2.366 (0.79), 2.519 (4.28), 2.524 (3.26), 2.666 (0.79), 2.670 (1.01), 2.710 (0.81), 2.762 (1.12), 2.778 (1.74), 2.795 (2.58), 2.813 (2.31), 2.828 (1.48), 2.984 (1.68), 2.997 (2.51), 3.009 (2.11), 3.029 (1.91), 3.042 (1.40), 3.559 (2.55), 4.330 (0.51), 4.350 (1.93), 4.370 (3.26), 4.392 (3.26), 4.412 (1.74), 4.639 (5.68), 4.650 (5.74), 6.729 (6.67), 6.752 (6.89), 7.535 (6.41), 7.556 (11.17), 7.578 (6.29), 8.137 (6.29), 8.160 (8.19), 8.174 (4.42), 8.188 (2.37), 8.765 (13.93), 10.591 (5.58), 10.615 (5.31).

LC-MS (Method 1): $R_t$=1.00 min; MS (ESIpos): m/z=515 [M+H]$^+$

Example 379

N-(2-Cyclopropylpropan-2-yl)-7-[(3R,4R)-3,4-dihydroxypyrrolidin-1-yl]-4-oxo-1-(2,4,6-trifluorophenyl)-1,4-dihydro-1,8-naphthyridine-3-carboxamide

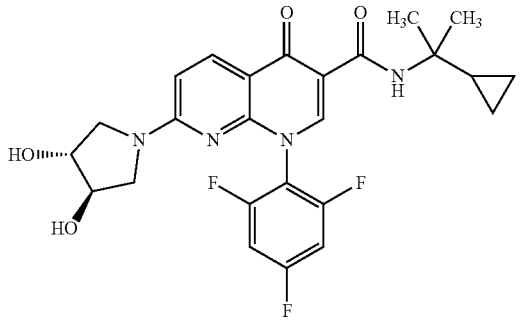 [SMILES: CC(C)(NC(=O)c1cn(-c2c(F)cc(F)cc2F)c2nc(N3C[C@@H](O)[C@H](O)C3)ccc2c1=O)C1CC1]

According to GP1, 30 mg (71 µmol) of the compound from Example 121A were reacted with 8.5 mg (85 µmol) of 2-cyclopropylpropan-2-amine in the presence of 32 mg (85 µmol) of HATU and 43 µl (0.25 µmol) of N,N-diisopropylethylamine in 1.0 ml of dimethylformamide. The mixture was diluted with 1 ml of water and 2 ml of DMSO and the solution was purified by means of preparative HPLC (column: Chromatorex C18, 10 µm, 125×30 mm, solvent: acetonitrile/0.1% formic acid gradient; 0 to 5 min 10% acetonitrile, over 14 min to 90% acetonitrile and for a further 2 min 90% acetonitrile). 21.9 mg (61% of theory, 100% purity) of the title compound were obtained.

$^1$H-NMR (400 MHz, DMSO-d6) δ[ppm]: 0.396 (5.13), 0.414 (4.63), 1.311 (16.00), 2.073 (2.35), 3.049 (0.58), 3.080 (0.80), 3.230 (0.49), 3.253 (0.41), 3.336 (0.74), 3.594 (0.49), 3.921 (0.75), 4.042 (0.75), 5.129 (0.82), 5.221 (0.81), 6.728 (1.58), 6.751 (1.58), 7.536 (0.69), 7.555 (1.16), 7.578 (0.64), 8.256 (1.85), 8.278 (1.73), 8.642 (3.25), 9.938 (2.06).

LC-MS (Method 1): $R_t$=0.89 min; MS (ESIpos): m/z=503 [M+H]$^+$

Example 380

7-(3-Cyano-2-oxotetrahydropyrimidin-1(2H)-yl)-N-[(1S)-1-cyclopropyl-2,2,2-trifluoroethyl]-4-oxo-1-(2,4,6-trifluorophenyl)-1,4-dihydro-1,8-naphthyridine-3-carboxamide

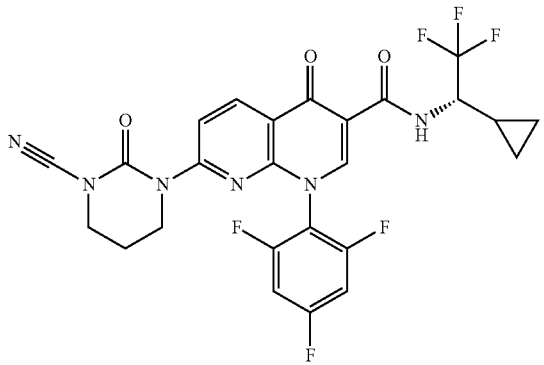 [SMILES: N#CN1CCCN(c2ccc3c(=O)c(C(=O)N[C@@H](C4CC4)C(F)(F)F)cn(-c4c(F)cc(F)cc4F)c3n2)C1=O]

According to GP2, 100 mg (210 µmol) of the compound from Example 126A were reacted with 28.9 mg (231 µmol) of 2-oxotetrahydropyrimidin-1(2H)-carbonitrile in the presence of 43.6 mg (315 µmol) of potassium carbonate, 4.7 mg (21 µmol) of palladium(II) acetate and 24 mg (42 µmol) of Xantphos in 2.1 ml of 1,4-dioxane. Subsequently, 2 ml of water and 3 ml of acetonitrile were added. Purification was effected by means of preparative HPLC (column: Chromatorex C18, 10 µm, 125×30 mm, solvent: acetonitrile/0.1% formic acid gradient; 0 to 5 min 10% acetonitrile, over 14 min to 90% acetonitrile and for a further 2 min 90% acetonitrile). 74.0 mg (62% of theory, 100% purity) of the title compound were obtained.

$^1$H-NMR (400 MHz, DMSO-d6) δ[ppm]: −0.149 (1.15), −0.008 (8.97), 0.008 (8.97), 0.146 (1.12), 0.343 (2.62), 0.356 (2.87), 0.558 (2.55), 0.571 (4.38), 0.584 (3.80), 0.652 (1.63), 0.674 (2.59), 1.232 (2.68), 1.252 (2.40), 2.026 (3.86), 2.040 (5.17), 2.055 (4.09), 2.073 (11.15), 2.328 (1.92), 2.367 (0.93), 2.671 (1.88), 2.710 (0.89), 3.589 (5.05), 3.603 (6.71), 3.617 (5.01), 3.812 (5.43), 3.827 (9.52), 3.841 (5.37), 4.367 (1.31), 4.389 (2.49), 4.409 (2.14), 7.579 (4.89), 7.601 (9.10), 7.624 (5.05), 8.136 (11.08), 8.158 (11.31), 8.695 (11.98), 8.717 (10.57), 9.089 (16.00), 10.195 (5.37), 10.219 (4.89).

LC-MS (Method 1): $R_t$=1.08 min; MS (ESIpos): m/z=565 [M+H]$^+$

Example 381

7-[(4R)-4-Methyl-2-oxoimidazolidin-1-yl]-4-oxo-N-[(2S)-1-(trifluoromethoxy)propan-2-yl]-1-(2,4,6-trifluorophenyl)-1,4-dihydro-1,8-naphthyridine-3-carboxamide

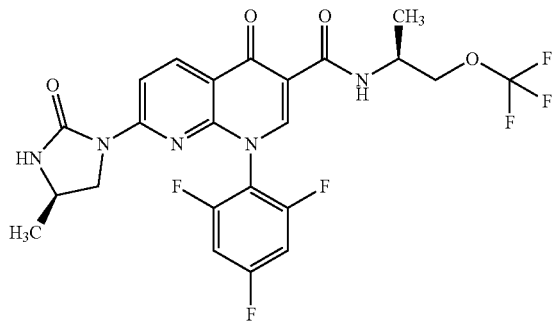

According to GP1, 100 mg (97% purity, 232 µmol) of the compound from Example 129D were reacted with 50.0 mg (278 µmol) of (2S)-1-(trifluoromethoxy)propan-2-amine hydrochloride in the presence of 106 mg (278 µmol) of HATU and 101 µl (580 µmol) of N,N-diisopropylethylamine in 2.3 ml of dimethylformamide. The mixture was diluted with 1 ml of 1N aqueous hydrochloric acid, water and acetonitrile and the solution was purified by means of preparative HPLC (column: Chromatorex C18, 10 µm, 125×30 mm, solvent: acetonitrile/0.1% formic acid gradient; 0 to 5 min 10% acetonitrile, over 14 min to 90% acetonitrile and for a further 2 min 90% acetonitrile). 69.3 mg (55% of theory, 100% purity) of the title compound were obtained.

$^1$H-NMR (500 MHz, DMSO-d6) δ[ppm]: −0.007 (0.71), 0.007 (0.68), 1.120 (10.98), 1.131 (11.18), 1.233 (0.41), 1.256 (16.00), 1.270 (15.96), 2.516 (2.00), 2.520 (1.59), 2.524 (1.18), 3.084 (1.25), 3.093 (2.58), 3.104 (2.65), 3.112 (1.27), 3.711 (1.38), 3.728 (3.72), 3.745 (3.68), 3.749 (3.29), 3.763 (1.38), 3.780 (0.61), 4.157 (0.78), 4.166 (1.11), 4.177 (4.39), 4.184 (5.76), 4.193 (4.96), 4.203 (0.92), 4.213 (1.01), 4.335 (0.64), 4.345 (1.15), 4.359 (1.55), 4.373 (1.09), 4.383 (0.52), 7.550 (1.03), 7.554 (1.02), 7.569 (4.16), 7.587 (4.18), 7.607 (1.02), 7.808 (5.93), 8.406 (8.66), 8.424 (10.07), 8.538 (10.69), 8.556 (8.06), 8.904 (12.01), 9.902 (3.85), 9.917 (3.70).

LC-MS (Method 3): $R_t$=1.91 min; MS (ESIpos): m/z=544 [M+H]$^+$

Example 382

N-(1,1-Difluoro-2-methylpropan-2-yl)-7-[3-(2-hydroxyethyl)-2-oxotetrahydropyrimidin-1(2H)-yl]-4-oxo-1-(2,4,6-trifluorophenyl)-1,4-dihydro-1,8-naphthyridine-3-carboxamide

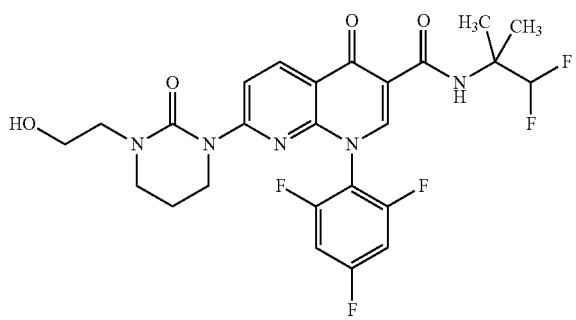 [SMILES: CC(C)(NC(=O)c1cn(-c2c(F)cc(F)cc2F)c2nc(N3CCCN(CCO)C3=O)ccc2c1=O)C(F)F]

According to GP1, 25 mg (97% purity, 52 µmol) of the compound from Example 125A were reacted with 9.2 mg (63 µmol) of 1,1-difluoro-2-methylpropan-2-amine hydrochloride in the presence of 24 mg (63 µmol) of HATU and 23 µl (0.13 mmol) of N,N-diisopropylethylamine in 1.4 ml of dimethylformamide. The mixture was diluted with 1 ml of 1N aqueous hydrochloric acid, water and acetonitrile and the solution was purified by means of preparative HPLC (column: Chromatorex C18, 10 µm, 125×30 mm, solvent: acetonitrile/0.1% formic acid gradient; 0 to 5 min 10% acetonitrile, over 14 min to 90% acetonitrile and for a further 2 min 90% acetonitrile). 16.2 mg (56% of theory, 100% purity) of the title compound were obtained.

$^1$H-NMR (500 MHz, DMSO-d6) δ[ppm]: −0.007 (0.86), 0.006 (0.84), 1.451 (16.00), 1.880 (0.39), 1.891 (1.10), 1.904 (1.70), 1.916 (1.18), 1.927 (0.41), 2.515 (2.23), 2.518 (1.70), 2.522 (1.29), 3.368 (1.68), 3.373 (2.29), 3.380 (4.11), 3.385 (3.51), 3.392 (2.47), 3.397 (2.00), 3.494 (1.65), 3.506 (2.23), 3.518 (1.63), 3.528 (1.16), 3.539 (2.88), 3.551 (2.60), 3.563 (0.84), 4.688 (1.27), 4.699 (2.94), 4.710 (1.25), 6.317 (0.84), 6.431 (1.63), 6.544 (0.76), 7.571 (1.39), 7.588 (2.45), 7.606 (1.37), 8.140 (3.64), 8.158 (3.68), 8.484 (3.92), 8.502 (3.43), 8.927 (5.03), 10.099 (3.13).

LC-MS (Method 3): $R_t$=1.80 min; MS (ESIpos): m/z=554 [M+H]$^+$

Example 383

7-[3-(2-Hydroxyethyl)-2-oxotetrahydropyrimidin-1 (2H)-yl]-4-oxo-N-(4,4,4-trifluoro-2-methylbutan-2-yl)-1-(2,4,6-trifluorophenyl)-1,4-dihydro-1,8-naphthyridine-3-carboxamide

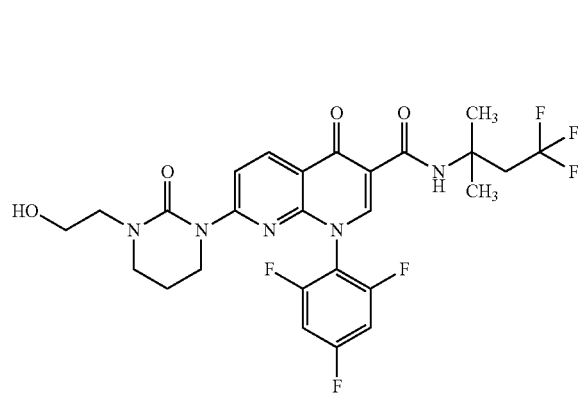 [SMILES: CC(C)(CC(F)(F)F)NC(=O)c1cn(-c2c(F)cc(F)cc2F)c2nc(N3CCCN(CCO)C3=O)ccc2c1=O]

According to GP1, 19 mg (99% purity, 41 μmol) of the compound from Example 125A were reacted with 8.7 mg (49 μmol) of 4,4,4-trifluoro-2-methylbutan-2-amine hydrochloride in the presence of 19 mg (49 μmol) of HATU and 18 μl (0.10 mmol) of N,N-diisopropylethylamine in 1.0 ml of dimethylformamide. The mixture was diluted with 1 ml of aqueous 1N hydrochloric acid, water and acetonitrile and the solution was purified by means of preparative HPLC (column: Chromatorex C18, 10 μm, 125×30 mm, solvent: acetonitrile/0.1% formic acid gradient; 0 to 5 min 10% acetonitrile, over 14 min to 90% acetonitrile and for a further 4 min 90% acetonitrile). 9.30 mg (39% of theory, 100% purity) of the title compound were obtained.

$^1$H-NMR (500 MHz, DMSO-d6) δ[ppm]: 1.497 (16.00), 1.880 (0.42), 1.892 (1.17), 1.904 (1.81), 1.916 (1.24), 1.928 (0.45), 2.519 (0.74), 2.523 (0.56), 2.924 (0.69), 2.948 (2.01), 2.972 (1.89), 2.996 (0.57), 3.369 (1.76), 3.374 (2.47), 3.381 (4.30), 3.386 (3.67), 3.392 (2.62), 3.398 (2.12), 3.495 (1.74), 3.507 (2.38), 3.519 (1.71), 3.529 (1.21), 3.541 (2.97), 3.552 (2.69), 3.564 (0.87), 4.689 (1.27), 4.700 (2.92), 4.711 (1.25), 7.569 (1.48), 7.587 (2.61), 7.604 (1.47), 8.136 (3.98), 8.154 (3.98), 8.478 (4.27), 8.496 (3.72), 8.904 (5.42), 9.962 (3.28).

LC-MS (Method 3): $R_t$=1.88 min; MS (ESIpos): m/z=586 [M+H]$^+$

Example 384

N-[(1S)-1-Cyclopropyl-2,2,2-trifluoroethyl]-7-[(2-hydroxyethyl)(methyl)amino]-4-oxo-1-(2,4,6-trifluorophenyl)-1,4-dihydro-1,8-naphthyridine-3-carboxamide According to GP3, 50.0 mg (105 μmol) of the compound from Example 126A were reacted with 8.7 mg (116 μmol) of 2-(methylamino)ethanol in the presence of 64 μl (0.37 mmol) of N,N-diisopropylethylamine in 0.56 ml of dimethylformamide. The reaction mixture was diluted with 1 ml of acetonitrile and 0.2 ml of 1N aqueous hydrochloric acid and purified by means of preparative HPLC (column: Chromatorex C18, 10 μm, 125×30 mm, solvent: acetonitrile/0.05% formic acid gradient; 0 to 3 min 10% acetonitrile, to 35 min 90% acetonitrile and for a further 3 min 90% acetonitrile). 43.6 mg (81% of theory, 100% purity) of the title compound were obtained.

$^1$H-NMR (400 MHz, DMSO-d6) δ[ppm]: 0.313 (1.08), 0.324 (2.62), 0.334 (4.16), 0.346 (4.12), 0.358 (3.20), 0.370 (1.57), 0.498 (1.08), 0.510 (2.93), 0.521 (4.27), 0.534 (3.75), 0.547 (3.80), 0.556 (3.35), 0.567 (4.19), 0.578 (3.62), 0.588 (3.27), 0.599 (2.68), 0.612 (1.63), 0.626 (2.04), 0.636 (2.30), 0.647 (3.74), 0.658 (3.39), 0.663 (3.25), 0.671 (3.20), 0.679 (1.57), 0.692 (1.03), 1.164 (0.78), 1.176 (1.59), 1.184 (2.37), 1.196 (4.08), 1.205 (3.00), 1.217 (3.98), 1.229 (2.16), 1.237 (1.46), 1.249 (0.63), 2.328 (0.79), 2.366 (0.64), 2.670 (0.91), 2.711 (0.79), 2.833 (1.26), 3.123 (2.01), 3.538 (1.66), 4.332 (0.55), 4.352 (2.17), 4.373 (3.82), 4.394 (3.72), 4.414 (1.97), 4.434 (0.48), 4.615 (0.72), 6.961 (1.39), 7.525 (5.57), 7.547 (10.59), 7.569 (5.53), 8.261 (2.60), 8.280 (2.50), 8.805 (16.00), 10.546 (6.57), 10.570 (6.32).

LC-MS (Method 3): $R_t$=1.93 min; MS (ESIpos): m/z=515 [M+H]$^+$

Example 385

N-[6-{[(1S)-1-Cyclopropyl-2,2,2-trifluoroethyl]carbamoyl}-5-oxo-8-(2,4,6-trifluorophenyl)-5,8-dihydro-1,8-naphthyridin-2-yl]-N-methylglycine

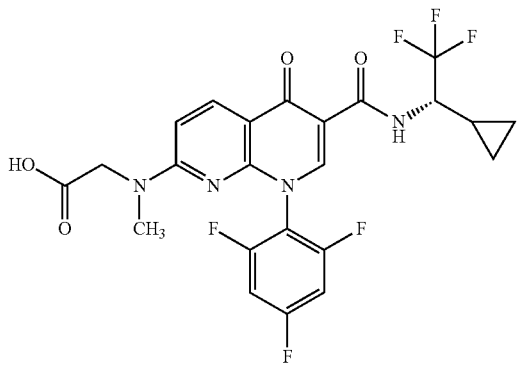 [SMILES: CN(CC(=O)O)c1ccc2c(=O)c(C(=O)N[C@@H](C3CC3)C(F)(F)F)cn(-c3c(F)cc(F)cc3F)c2n1]

According to GP3, 50.0 mg (105 µmol) of the compound from Example 126A were reacted with 50.0 mg (325 µmol) of ethyl N-methylglycinate hydrochloride in the presence of 64 µl (0.37 mmol) of N,N-diisopropylethylamine in 1.0 ml of dimethylformamide. The reaction mixture was diluted with 1 ml of acetonitrile and 0.2 ml of aqueous 1N hydrochloric acid and purified by means of preparative HPLC (column: Chromatorex C18, 10 µm, 125×30 mm, solvent: acetonitrile/0.1% formic acid gradient; 0 to 5 min 10% acetonitrile, over 14 min to 90% acetonitrile and for a further 4 min 90% acetonitrile). 32.0 mg (56% of theory, 96% purity) of the title compound were obtained.

$^1$H-NMR (400 MHz, DMSO-d6) δ[ppm]=12.44 (br. s, 1H), 10.50 (d, 1H), 8.81 (s, 1H), 8.41-8.25 (m, 1H), 7.62-7.35 (m, 2H), 7.08-6.87 (m, 1H), 4.44-4.32 (m, 1H), 3.95 (br. s, 1.4H), 3.15 (br. s, 2.3H), 2.81 (br. s, 0.5H), 1.26-1.16 (m, 1H), 0.70-0.49 (m, 3H), 0.38-0.30 (m, 1H).

LC-MS (Method 3): R$_t$=1.85 min; MS (ESIpos): m/z=529 [M+H]$^+$

Example 386

N-[(1R)-1-Cyclopropyl-2,2,2-trifluoroethyl]-7-[(4S)-4-hydroxy-2-oxopyrrolidin-1-yl]-4-oxo-1-(2,4,6-trifluorophenyl)-1,4-dihydro-1,8-naphthyridine-3-carboxamide

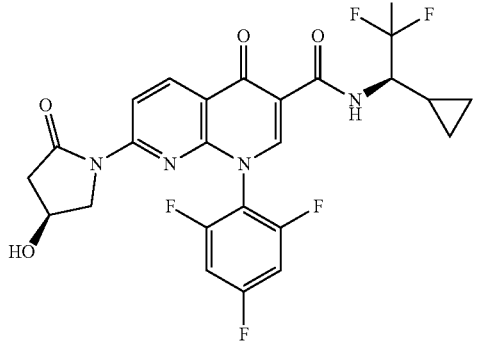

According to GP1, 11.0 g (26.2 mmol) of the compound from Example 117A were reacted with 5.53 g (31.5 mmol) of (1R)-1-cyclopropyl-2,2,2-trifluoroethanamine hydrochloride in the presence of 15.0 g (39.3 mmol) of HATU and 11.4 ml (65.6 mmol) of N,N-diisopropylethylamine in 150 ml of dimethylformamide. The mixture was stirred at room temperature for a further 1.5 h and then the mixture was extracted by stirring in ice-water with a little aqueous hydrochloric acid. The precipitate was filtered off with suction and washed with water. The residue was purified by means of normal phase chromatography (petroleum ether/ethyl acetate 1:1 and dichloromethane/methanol 9:1). 11 g (76% of theory, 99% purity) of the title compound were obtained.

$^1$H-NMR (400 MHz, DMSO-d6) δ[ppm]: −0.008 (2.46), 0.008 (2.09), 0.332 (1.29), 0.337 (1.43), 0.346 (2.78), 0.358 (2.64), 0.371 (1.67), 0.381 (1.15), 0.541 (1.63), 0.551 (2.52), 0.565 (3.70), 0.582 (3.68), 0.591 (2.39), 0.602 (1.99), 0.612 (1.61), 0.626 (1.01), 0.640 (1.25), 0.649 (1.45), 0.661 (2.70), 0.670 (2.11), 0.685 (1.57), 0.696 (1.07), 1.106 (1.49), 1.175 (1.11), 1.193 (1.07), 1.206 (1.09), 1.214 (1.51), 1.227 (2.50), 1.235 (1.85), 1.247 (2.48), 1.259 (1.37), 1.268 (0.95), 1.989 (2.03), 2.356 (3.72), 2.399 (4.35), 2.731 (0.83), 2.891 (1.09), 2.917 (3.56), 2.931 (3.74), 2.960 (3.30), 2.974 (3.20), 3.463 (3.74), 3.493 (4.55), 3.674 (3.26), 3.685 (4.03), 3.703 (3.10), 3.715 (2.74), 4.290 (2.76), 4.299 (2.78), 4.378 (1.33), 4.398 (2.29), 4.420 (2.21), 4.440 (1.21), 5.330 (9.02), 5.339 (8.94), 7.592 (2.15), 7.600 (2.80), 7.611 (4.09), 7.622 (4.09), 7.635 (2.74), 7.642 (2.07), 8.533 (10.41), 8.556 (12.48), 8.710 (12.66), 8.733 (9.92), 9.064 (16.00), 10.249 (5.43), 10.273 (5.21).

LC-MS (Method 3): R$_t$=1.87 min; MS (ESIpos): m/z=541 [M+H]$^+$

Example 387

N-[(1R)-1-Cyclopropyl-2,2,2-trifluoroethyl]-1-(2,6-dichloro-4-fluorophenyl)-7-[(4S)-4-hydroxy-2-oxopyrrolidin-1-yl]-4-oxo-1,4-dihydro-1,8-naphthyridine-3-carboxamide

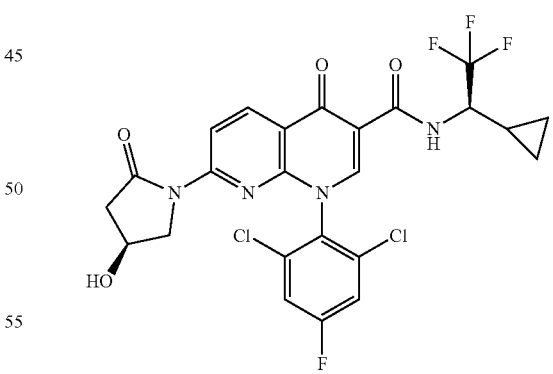

According to GP2, 150 mg (99% purity, 292 µmol) of the compound from Example 130C were reacted with 32.5 mg (321 µmol) of (4S)-4-hydroxypyrrolidin-2-one in the presence of 60.5 mg (438 µmol) of potassium carbonate, 6.6 mg (29 µmol) of palladium(II) acetate and 34 mg (58 µmol) of Xantphos in 3.0 ml of 1,4-dioxane. Subsequently, the reaction mixture was diluted with acetonitrile and filtered, and the solvent was removed under reduced pressure. The residue was taken up in 3 ml of acetonitrile and 0.5 ml of water and purified by means of preparative HPLC (column: Chromatorex C18, 10 μm, 125×30 mm, solvent: acetonitrile/ 0.05% formic acid gradient; 0 to 3 min. 10% acetonitrile to 22 min. 55% acetonitrile, to 35 min. 65% ACN and a further 3 min. 90% acetonitrile), and 25 mg (15% of theory, 97.6% purity) of the title compound were obtained. Subsequently, the mixed fractions were purified again by means of normal phase chromatography (dichloromethane-methanol gradient), and a further 89.2 mg (52% of theory, 97% purity) of the title compound were obtained.

$^1$H-NMR (400 MHz, DMSO-d6) δ[ppm]: −0.008 (3.21), 0.008 (3.00), 0.343 (0.98), 0.353 (1.81), 0.365 (1.66), 0.554 (1.65), 0.569 (2.02), 0.587 (2.18), 0.597 (1.50), 0.607 (1.29), 0.645 (0.88), 0.655 (0.93), 0.666 (1.86), 0.676 (1.40), 1.214 (0.99), 1.227 (1.61), 1.235 (1.22), 1.248 (1.52), 1.259 (0.91), 2.073 (1.27), 2.341 (2.38), 2.386 (2.72), 2.912 (2.30), 2.927 (2.35), 2.956 (2.17), 2.970 (2.05), 3.287 (2.77), 3.375 (2.46), 3.404 (3.01), 3.597 (2.13), 3.610 (2.53), 3.627 (2.05), 3.640 (1.73), 4.270 (1.84), 4.385 (1.48), 4.406 (1.43), 5.329 (5.75), 5.338 (5.59), 7.906 (1.99), 7.913 (5.03), 7.923 (4.69), 7.929 (3.13), 7.934 (4.95), 7.943 (4.50), 7.950 (2.09), 8.531 (7.38), 8.553 (8.44), 8.723 (8.78), 8.746 (6.86), 9.004 (16.00), 10.285 (3.50), 10.309 (3.47).

LC-MS (Method 3): $R_t$=2.01 min; MS (ESIpos): m/z=573 [M+H]$^+$

Example 388

1-(2,6-Dichloro-4-fluorophenyl)-7-[(4S)-4-hydroxy-2-oxopyrrolidin-1-yl]-4-oxo-N-[(2R)-1,1,1-trifluorobutan-2-yl]-1,4-dihydro-1,8-naphthyridine-3-carboxamide

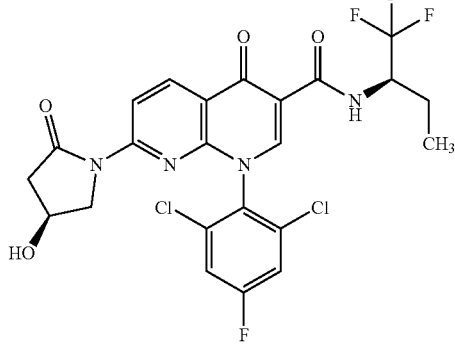

According to GP2, 150 mg (99% purity, 299 μmol) of the compound from Example 131A were reacted with 33.3 mg (329 μmol) of (4S)-4-hydroxypyrrolidin-2-one in the presence of 62.0 mg (448 μmol) of potassium carbonate, 6.7 mg (30 μmol) of palladium(II) acetate and 35 mg (60 μmol) of Xantphos in 3.3 ml of 1,4-dioxane. Subsequently, the reaction mixture was diluted with acetonitrile and filtered, and the solvent was removed under reduced pressure. The residue was taken up in 3.0 ml of acetonitrile and 0.5 ml of water and separated by means of preparative HPLC (column: Chromatorex C18, 10 μm, 125×30 mm, solvent: acetonitrile/ 0.05% formic acid gradient; 0 to 3 min. 10% acetonitrile to 22 min. 55% acetonitrile, to 35 min. 65% ACN and a further 3 min. 90% acetonitrile). The product-containing fractions were combined and purified again by means of normal phase chromatography (dichloromethane-methanol gradient). 65.2 mg (39% of theory, 100% purity) of the title compound were obtained.

$^1$H-NMR (500 MHz, DMSO-d6) δ[ppm]: −0.007 (5.14), 0.007 (4.29), 0.971 (5.91), 0.986 (12.43), 1.001 (6.04), 1.648 (0.89), 1.662 (1.16), 1.667 (1.00), 1.676 (1.35), 1.682 (1.22), 1.690 (1.13), 1.696 (1.26), 1.710 (0.96), 1.875 (0.98), 1.883 (1.18), 1.890 (1.18), 1.898 (1.35), 1.903 (1.18), 1.911 (1.05), 1.918 (0.89), 2.347 (2.86), 2.381 (3.23), 2.919 (2.46), 2.931 (2.64), 2.954 (2.35), 2.965 (2.27), 3.286 (5.71), 3.376 (2.94), 3.400 (3.42), 3.603 (2.38), 3.613 (2.88), 3.627 (2.33), 3.637 (2.05), 4.259 (0.98), 4.269 (2.16), 4.278 (2.07), 4.767 (1.09), 4.783 (1.02), 5.328 (6.02), 5.336 (6.02), 5.754 (16.00), 7.912 (2.07), 7.917 (4.66), 7.927 (5.43), 7.934 (5.84), 7.944 (4.19), 7.949 (2.27), 8.531 (7.28), 8.549 (8.15), 8.721 (8.61), 8.739 (6.95), 9.010 (15.72), 10.140 (3.84), 10.159 (3.71).

LC-MS (Method 3): $R_t$=1.97 min; MS (ESIpos): m/z=561 [M+H]$^+$

Example 389

1-(2,6-Dichloro-4-fluorophenyl)-7-[(4S)-4-hydroxy-2-oxopyrrolidin-1-yl]-4-oxo-N-[(2S)-1,1,1-trifluorobutan-2-yl]-1,4-dihydro-1,8-naphthyridine-3-carboxamide

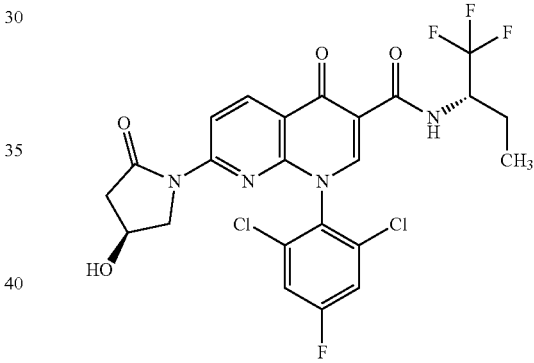

According to GP2, 150 mg (99% purity, 299 μmol) of the compound from Example 132A were reacted with 33.3 mg (329 μmol) of (4S)-4-hydroxypyrrolidin-2-one in the presence of 62.0 mg (448 μmol) of potassium carbonate, 6.7 mg (30 μmol) of palladium(II) acetate and 35 mg (60 μmol) of Xantphos in 3.0 ml of 1,4-dioxane. Subsequently, the reaction mixture was diluted with acetonitrile and filtered, and the solvent was removed under reduced pressure. The residue was taken up in 3.0 ml of acetonitrile and 0.5 ml of water and separated by means of preparative HPLC (column: Chromatorex C18, 10 μm, 125×30 mm, solvent: acetonitrile/ 0.05% formic acid gradient; 0 to 3 min. 10% acetonitrile to 22 min. 55% acetonitrile, to 35 min. 65% ACN and a further 3 min. 90% acetonitrile). The product-containing fractions were combined and purified again by means of normal phase chromatography (dichloromethane-methanol gradient). 13.0 mg (8% of theory, 99% purity) of the title compound were obtained.

$^1$H-NMR (500 MHz, DMSO-d6) δ[ppm]: −0.120 (1.67), −0.013 (2.76), −0.007 (16.00), 0.007 (13.28), 0.117 (1.63), 0.971 (3.73), 0.986 (7.69), 1.001 (3.73), 1.147 (1.17), 1.236 (1.36), 1.662 (0.74), 1.667 (0.66), 1.675 (0.89), 1.682 (0.82), 1.690 (0.78), 1.695 (0.82), 1.710 (0.58), 1.875 (0.62), 1.882

(0.74), 1.890 (0.78), 1.898 (0.85), 1.911 (0.66), 1.917 (0.58), 2.347 (1.75), 2.358 (0.85), 2.362 (1.05), 2.365 (0.82), 2.381 (1.98), 2.632 (0.74), 2.635 (1.05), 2.639 (0.74), 2.919 (1.55), 2.931 (1.63), 2.953 (1.48), 2.965 (1.40), 3.285 (10.17), 3.376 (1.90), 3.399 (2.10), 3.603 (1.51), 3.613 (1.79), 3.627 (1.44), 3.637 (1.24), 4.277 (1.32), 4.767 (0.70), 5.328 (3.77), 5.335 (3.69), 5.754 (4.97), 7.912 (1.32), 7.917 (2.95), 7.927 (3.42), 7.934 (3.65), 7.944 (2.64), 7.949 (1.44), 8.531 (4.58), 8.548 (5.13), 8.721 (5.40), 8.739 (4.35), 9.010 (10.02), 10.140 (2.37), 10.159 (2.29).

LC-MS (Method 3): $R_t$=1.98 min; MS (ESIpos): m/z=561 [M+H]$^+$

Example 390

1-(2-Chloro-4,6-difluorophenyl)-7-[(2R,4S)-4-hydroxy-2,4-dimethylpyrrolidin-1-yl]-4-oxo-N-[(2S)-1,1,1-trifluoropropan-2-yl]-1,4-dihydro-1,8-naphthyridine-3-carboxamide

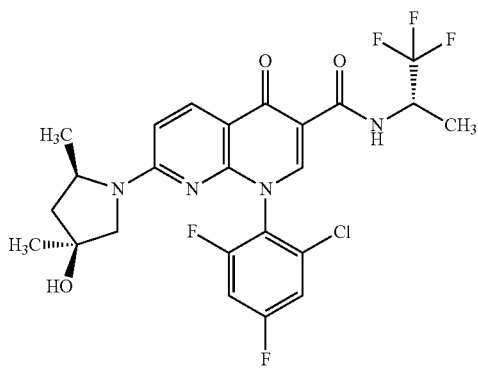 [SMILES: C[C@@H]1C[C@](C)(O)CN1c1ccc2c(=O)c(C(=O)N[C@@H](C)C(F)(F)F)cn(-c3c(F)cc(F)cc3Cl)c2n1]

According to GP3, 18 mg (38 µmol) of the compound from Example 111A were reacted with 10 mg (95% purity, 41 µmol) of the compound from Example 116A in the presence of 23 µl (0.13 mmol) of N,N-diisopropylethylamine in 1.5 ml of dimethylformamide. The reaction mixture was diluted with 4 ml of acetonitrile and 0.5 ml of water and purified by means of preparative HPLC (column: Kromasil C18, 10 µm, 250×20 mm, solvent: acetonitrile/0.05% formic acid gradient; 0 to 3 min 10% acetonitrile, to 35 min 90% acetonitrile and for a further 3 min 90% acetonitrile). 15.9 mg (77% of theory, 99% purity) of the title compound were obtained.

$^1$H-NMR (400 MHz, DMSO-d6) δ[ppm]: −0.149 (0.98), −0.008 (15.59), 0.008 (9.15), 0.146 (0.94), 0.976 (4.35), 1.021 (3.73), 1.267 (12.23), 1.365 (14.65), 1.371 (16.00), 1.382 (14.36), 1.388 (14.61), 1.648 (2.13), 2.001 (1.76), 2.328 (0.90), 2.367 (0.98), 2.711 (1.11), 3.288 (13.09), 3.465 (2.26), 3.752 (1.76), 4.865 (5.87), 4.898 (2.91), 6.702 (2.38), 7.710 (4.76), 7.733 (5.46), 7.749 (3.24), 8.246 (5.91), 8.268 (5.46), 8.761 (5.70), 10.493 (7.30), 10.516 (7.06).

LC-MS (Method 3): $R_t$=2.07 min; MS (ESIpos): m/z=545 [M+H]$^+$

Example 391

1-(2-Chloro-4,6-difluorophenyl)-7-[(3R,4R)-3,4-dihydroxypyrrolidin-1-yl]-4-oxo-N-(4,4,4-trifluoro-2-methylbutan-2-yl)-1,4-dihydro-1,8-naphthyridine-3-carboxamide (atropisomer mixture)

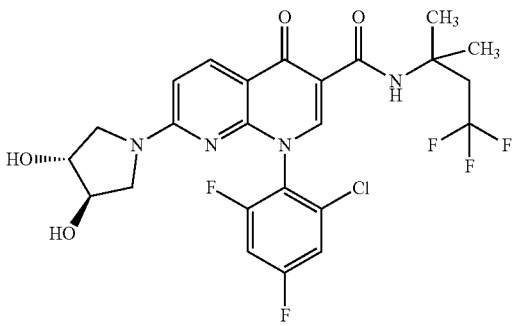 [SMILES: CC(C)(CC(F)(F)F)NC(=O)c1cn(-c2c(F)cc(F)cc2Cl)c2nc(N3C[C@@H](O)[C@H](O)C3)ccc2c1=O]

According to GP3, 100 mg (202 µmol) of the compound from Example 109A were reacted with 33.9 mg (243 µmol) of (3R,4R)-pyrrolidine-3,4-diol hydrochloride in the presence of 123 µl (708 µmol) of N,N-diisopropylethylamine in 2.0 ml of dimethylformamide. The reaction mixture was diluted with 2.0 ml of acetonitrile and acidified with 1N aqueous hydrochloric acid. The solution was purified by means of preparative HPLC (column: Chromatorex C18, 10 µm, 125×30 mm, solvent: acetonitrile/0.1% formic acid gradient; 0 to 5 min 10% acetonitrile, over 14 min to 90% acetonitrile and for a further 4 min 90% acetonitrile). 109 mg (96% of theory, 100% purity) of the title compound were obtained.

LC-MS (Method 3): $R_t$=1.76 min; MS (ESIpos): m/z=561 [M+H]$^+$ $^1$H-NMR (400 MHz, DMSO-d6) δ[ppm]=10.19 (s, 1H), 8.63 (s, 1H), 8.26 (d, 1H), 7.76-7.65 (m, 2H), 6.75 (d, 1H), 5.24-5.19 (m, 1H), 5.15-5.10 (m, 1H), 4.04 (br. s, 1H), 3.91 (br. s, 1H), 3.64-3.56 (m, 1H), 3.24-3.15 (m, 1H), 3.06-2.87 (m, 3H), 1.48 (s, 6H).

109 mg of the title compound (atropisomer mixture) were separated into the atropisomers by chiral SFC (preparative SFC: column: Daicel Chiralpak IE 5 µm 250×20 mm; eluent: 80% isoheptane, 20% ethanol; temperature: 35° C.; flow rate: 15 ml/min; UV detection: 220 nm).

This gave (in the sequence of elution from the column) 45.1 mg of atropisomer 1 from Example 392 (99% de) Rt=5.56 min and 47.9 mg (99% de) of atropisomer 2 from Example 393 $R_t$=6.17 min.

[Analytical SFC: column: Daicel Chiralpak IE 5 µm 250×4.6 mm; eluent: 75% isohexane, 25% ethanol; temperature: 50° C.; flow rate: 1 ml/min; UV detection: 220 nm]

Example 392

1-(2-Chloro-4,6-difluorophenyl)-7-[(3R,4R)-3,4-dihydroxypyrrolidin-1-yl]-4-oxo-N-(4,4,4-trifluoro-2-methylbutan-2-yl)-1,4-dihydro-1,8-naphthyridine-3-carboxamide (atropisomer 1)

LC-MS (Method 3): $R_t$=1.75 min; MS (ESIpos): m/z=561 [M+H]$^+$ $^1$H-NMR (400 MHz, DMSO-d6) δ[ppm]=10.19 (s, 1H), 8.63 (s, 1H), 8.26 (d, 1H), 7.76-7.65 (m, 2H), 6.75 (d, 1H), 5.24-5.19 (m, 1H), 5.15-5.11 (m, 1H), 4.04 (br. s, 1H), 3.91 (br. s, 1H), 3.64-3.56 (m, 1H), 3.23-3.15 (m, 1H), 3.06-2.87 (m, 3H), 1.48 (s, 6H).

Example 393

1-(2-Chloro-4,6-difluorophenyl)-7-[(3R,4R)-3,4-dihydroxypyrrolidin-1-yl]-4-oxo-N-(4,4,4-trifluoro-2-methylbutan-2-yl)-1,4-dihydro-1,8-naphthyridine-3-carboxamide (atropisomer 2)

LC-MS (Method 3): $R_t$=1.75 min; MS (ESIpos): m/z=561 [M+H]$^+$ $^1$H-NMR (400 MHz, DMSO-d6) δ[ppm]=10.19 (s, 1H), 8.63 (s, 1H), 8.26 (d, 1H), 7.76-7.66 (m, 2H), 6.75 (d, 1H), 5.25-5.19 (m, 1H), 5.15-5.11 (m, 1H), 4.04 (br. s, 1H), 3.91 (br. s, 1H), 3.64-3.56 (m, 1H), 3.25-3.17 (m, 1H), 3.04-2.88 (m, 3H), 1.48 (s, 6H).

Example 394

1-(2-Chloro-4,6-difluorophenyl)-4-oxo-7-(2-oxoimidazolidin-1-yl)-N-(4,4,4-trifluoro-2-methylbutan-2-yl)-1,4-dihydro-1,8-naphthyridine-3-carboxamide

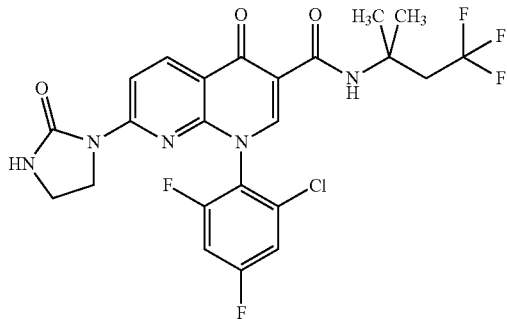 [SMILES: CC(C)(CC(F)(F)F)NC(=O)c1cn(-c2c(F)cc(F)cc2Cl)c2nc(N3CCNC3=O)ccc2c1=O]

According to GP2, 30 mg (61 µmol) of the compound from Example 109A were reacted with 54.4 mg (96% purity, 607 µmol) of imidazolidin-2-one in the presence of 13 mg (91 µmol) of potassium carbonate, 1.4 mg (6.1 µmol) of palladium(II) acetate and 7.0 mg (12 µmol) of Xantphos in 0.6 ml of 1,4-dioxane. This was followed by dilution with 3.0 ml of acetonitrile and 2.0 ml of water. Purification was effected by means of preparative HPLC (column: Chromatorex C18, 10 µm, 125×30 mm, solvent: acetonitrile/0.1% formic acid gradient; 0 to 5 min 10% acetonitrile, over 14 min to 90% acetonitrile and for a further 4 min 90% acetonitrile). 15.6 mg (45% of theory, 96% purity) of the title compound were obtained.

$^1$H-NMR (400 MHz, DMSO-d6) δ[ppm]: −0.149 (0.53), −0.008 (6.12), 0.008 (4.31), 0.146 (0.52), 1.234 (0.65), 1.259 (0.46), 1.496 (16.00), 2.073 (0.62), 2.323 (0.42), 2.328 (0.55), 2.523 (2.22), 2.665 (0.48), 2.670 (0.59), 2.906 (0.49), 2.918 (0.49), 2.937 (1.31), 2.948 (1.32), 2.966 (1.25), 2.978 (1.28), 2.997 (0.42), 3.008 (0.42), 3.335 (3.40), 3.354 (2.11), 3.516 (1.27), 3.526 (1.37), 3.535 (2.07), 3.546 (1.59), 3.567 (0.89), 7.641 (2.91), 7.685 (0.64), 7.691 (0.86), 7.708 (1.01), 7.715 (1.52), 7.731 (1.58), 7.738 (1.88), 7.753 (1.14), 7.763 (0.78), 8.402 (3.40), 8.424 (4.51), 8.532 (4.47), 8.555 (3.26), 8.836 (6.51), 10.001 (3.82).

LC-MS (Method 3): $R_t$=2.01 min; MS (ESIpos): m/z=544 [M+H]$^+$

Example 395

1-(2-Chloro-4,6-difluorophenyl)-7-[(4S)-4-hydroxy-2-oxopyrrolidin-1-yl]-4-oxo-N-(4,4,4-trifluoro-2-methylbutan-2-yl)-1,4-dihydro-1,8-naphthyridine-3-carboxamide

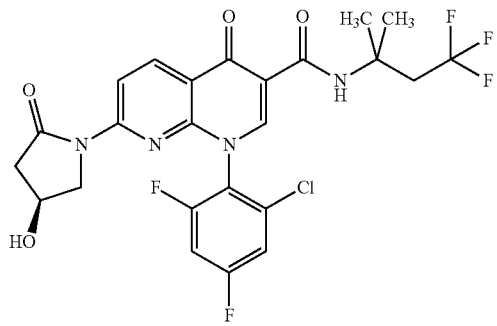 [SMILES: CC(C)(CC(F)(F)F)NC(=O)c1cn(-c2c(F)cc(F)cc2Cl)c2nc(N3C[C@@H](O)CC3=O)ccc2c1=O]

According to GP2, 30 mg (61 µmol) of the compound from Example 109A were reacted with 6.8 mg (67 µmol) of (4S)-4-hydroxypyrrolidin-2-one in the presence of 13 mg (91 µmol) of potassium carbonate, 1.4 mg (6.1 µmol) of palladium(II) acetate and 7.0 mg (12 µmol) of Xantphos in 0.6 ml of 1,4-dioxane. This was followed by dilution with 3.0 ml of acetonitrile and 2.0 ml of water. Separation was effected by means of preparative HPLC (column: Chromatorex C18, 10 µm, 125×30 mm, solvent: acetonitrile/0.05% formic acid gradient; 0 to 3 min 15% acetonitrile, to 15 min 90% acetonitrile and for a further 3 min 90% acetonitrile). The product fractions were combined and purified again by means of normal phase chromatography (ethyl acetate-cyclohexane gradient). 14.2 mg (39% of theory, 93% purity) of the title compound were obtained.

$^1$H-NMR (400 MHz, DMSO-d6) δ[ppm]: −0.149 (0.54), −0.008 (6.50), 0.008 (4.29), 0.146 (0.58), 1.234 (0.80), 1.259 (0.51), 1.501 (16.00), 2.328 (0.70), 2.340 (1.32), 2.383 (1.47), 2.524 (2.20), 2.670 (0.66), 2.905 (1.56), 2.920 (1.76), 2.948 (2.26), 2.963 (1.70), 3.393 (0.71), 3.423 (0.92), 3.443 (0.90), 3.613 (0.70), 3.625 (0.94), 3.632 (0.70), 3.644 (1.25), 3.655 (0.67), 3.662 (0.67), 3.674 (0.50), 4.271 (1.14), 5.318 (3.02), 5.328 (2.85), 7.728 (0.46), 7.743 (0.94), 7.751 (0.83), 7.766 (2.02), 7.777 (1.19), 7.789 (1.98), 7.799 (0.92), 8.507 (3.30), 8.529 (3.96), 8.692 (4.75), 8.714 (3.70), 8.921 (7.11), 9.916 (3.82).

LC-MS (Method 1): $R_t$=1.03 min; MS (ESIpos): m/z=559 [M+H]$^+$

Example 396

N-(Bicyclo[1.1.1]pent-1-yl)-1-(2-chloro-4,6-difluorophenyl)-7-[(4S)-4-hydroxy-2-oxopyrrolidin-1-yl]-4-oxo-1,4-dihydro-1,8-naphthyridine-3-carboxamide

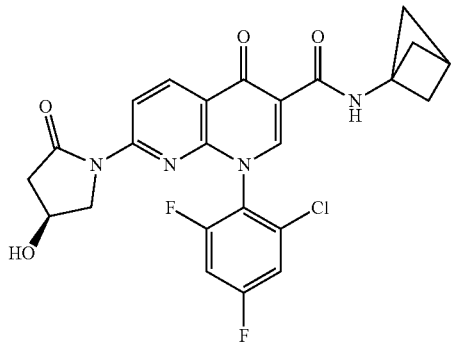 [SMILES: O=C(NC12CC(C1)C2)c1cn(-c2c(F)cc(F)cc2Cl)c2nc(N3C[C@@H](O)CC3=O)ccc2c1=O]

According to GP1, 40 mg (92 µmol) of the compound from Example 133A were reacted with 13.2 mg (110 µmol) of bicyclo[1.1.1]pentan-1-amine hydrochloride in the presence of 41.9 mg (110 µmol) of HATU and 56 µl (0.32 mmol) of N,N-diisopropylethylamine in 0.56 ml of dimethylformamide. The mixture was diluted with 0.1 ml of 1N aqueous hydrochloric acid, 1 ml of acetonitrile, 0.5 ml of DMSO and 0.5 ml of dioxane and the solution was purified by means of preparative HPLC (column: Chromatorex C18, 10 µm, 125×30 mm, solvent: acetonitrile/0.1% formic acid gradient; 0 to 5 min 10% acetonitrile, over 14 min to 90% acetonitrile and for a further 4 min 90% acetonitrile). 34.9 mg (75% of theory, 99% purity) of the title compound were obtained.

$^1$H-NMR (400 MHz, DMSO-d6) δ[ppm]: 2.073 (0.76), 2.114 (16.00), 5.315 (0.76), 5.319 (0.87), 5.324 (0.92), 5.329 (0.77), 7.770 (0.72), 7.793 (0.74), 8.502 (1.41), 8.524 (1.80), 8.671 (1.71), 8.693 (1.35), 8.885 (2.53), 10.018 (1.77).

LC-MS (Method 1): R$_t$=0.98 min; MS (ESIpos): m/z=501 [M+H]$^+$

Example 397

1-(2-Chloro-4,6-difluorophenyl)-N-(3-fluorobicyclo[1.1.1]pent-1-yl)-7-[(4S)-4-hydroxy-2-oxopyrrolidin-1-yl]-4-oxo-1,4-dihydro-1,8-naphthyridine-3-carboxamide

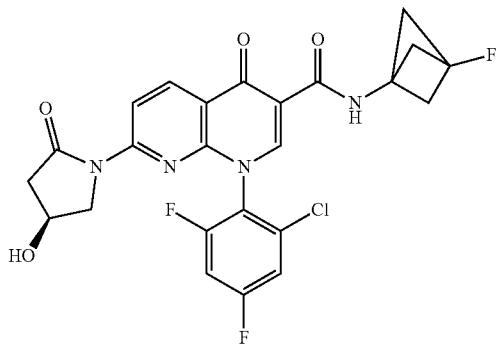 [SMILES: O=C(NC12CC(F)(C1)C2)c1cn(-c2c(F)cc(F)cc2Cl)c2nc(N3C[C@@H](O)CC3=O)ccc2c1=O]

According to GP1, 40 mg (92 µmol) of the compound from Example 133A were reacted with 15.2 mg (110 µmol) of 3-fluorobicyclo[1.1.1]pentan-1-amine hydrochloride in the presence of 41.9 mg (110 µmol) of HATU and 56 µl (0.32 mmol) of N,N-diisopropylethylamine in 0.56 ml of dimethylformamide. The mixture was diluted with 0.1 ml of 1N aqueous hydrochloric acid, 1 ml of acetonitrile, 0.5 ml of DMSO and 0.5 ml of dioxane and the solution was purified by means of preparative HPLC (column: Chromatorex C18, 10 µm, 125×30 mm, solvent: acetonitrile/0.1% formic acid gradient; 0 to 5 min 10% acetonitrile, over 14 min to 90% acetonitrile and for a further 4 min 90% acetonitrile). 28.0 mg (58% of theory, 99% purity) of the title compound were obtained.

$^1$H-NMR (400 MHz, DMSO-d6) δ[ppm]: −0.008 (2.56), 0.008 (2.56), 2.114 (2.50), 2.339 (3.23), 2.382 (3.75), 2.906 (2.85), 2.920 (2.97), 2.949 (2.58), 2.964 (2.56), 3.389 (2.18), 3.419 (2.79), 3.442 (1.96), 3.611 (1.42), 3.623 (1.89), 3.632 (1.95), 3.643 (2.76), 3.653 (1.35), 3.661 (1.82), 3.674 (1.55), 4.272 (2.70), 4.281 (2.70), 5.317 (5.14), 5.322 (4.81), 5.326 (5.55), 5.331 (4.14), 7.726 (0.85), 7.733 (1.24), 7.741 (0.85), 7.748 (2.16), 7.757 (2.14), 7.763 (1.19), 7.771 (3.91), 7.782 (2.76), 7.793 (4.22), 7.804 (2.14), 7.808 (1.69), 7.815 (1.12), 8.510 (9.03), 8.533 (11.06), 8.678 (10.88), 8.701 (8.50), 8.926 (16.00), 10.135 (10.20).

LC-MS (Method 1): R$_t$=0.96 min; MS (ESIpos): m/z=519 [M+H]$^+$

Example 398

1-(2-Chloro-4,6-difluorophenyl)-7-[(4S)-4-hydroxy-2-oxopyrrolidin-1-yl]-4-oxo-N-[(2S)-1,1,1-trifluorobutan-2-yl]-1,4-dihydro-1,8-naphthyridine-3-carboxamide (atropisomer mixture)

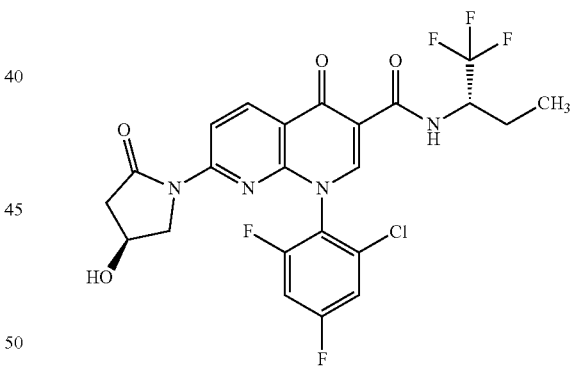

According to GP1, 2.22 g (5.10 mmol) of the compound from Example 133A were reacted with 1.00 g (6.11 mmol) of (2S)-1,1,1-trifluorobutan-2-amine hydrochloride in the presence of 2.91 g (7.64 mmol) of HATU and 2.22 ml (12.7 mmol) of N,N-diisopropylethylamine in 27.8 ml of dimethylformamide. To the reaction solution were added 200 ml of ice-water and 20 ml of 1N aqueous hydrochloric acid, and the precipitate was filtered off with suction and dried under high vacuum. 2.66 g (91% of theory, 95% purity) of the title compound were obtained.

$^1$H-NMR (400 MHz, DMSO-d6) δ[ppm]=10.13 (d, 1H), 9.04 (s, 1H), 8.72 (d, 1H), 8.54 (d, 1H), 7.82-7.72 (m, 2H), 5.33 (d, 1H), 4.84-4.70 (m, 1H), 4.31-4.25 (m, 1H), 3.69-3.61 (m, 1H), 3.47-3.40 (m, 1H), 2.94 (dd, 1H), 2.37 (d, 1H), 1.95-1.84 (m, 1H), 1.75-1.60 (m, 1H), 1.02-0.93 (m, 3H).

LC-MS (Method 4): $R_t$=3.18/3.20 min; MS (ESIpos): m/z=545 [M+H]$^+$ 2.66 g of the title compound (atropisomer mixture) were separated into the atropisomers by chiral SFC (preparative SFC: column: Daicel Chiralcel OX-H 5 µm 250×30 mm; eluent: 0.0-5.5 min 74% carbon dioxide, 26% acetonitrile; 6-12 min 61.1% carbon dioxide, 38.9% acetonitrile, 12.5-14.0 min 74% carbon dioxide, 26% acetonitrile; temperature: 38° C.; flow rate: 180 ml/min; UV detection: 210 nm).

This gave (in the sequence of elution from the column) 857 mg of atropisomer 1 from Example 399 (99% de) Rt=1.00 min and 977 mg (99% de) of atropisomer 2 from Example 400 $R_t$=2.10 min.

[Analytical SFC: column: Daicel Chiralpak OX-H 3 µm 100×4.6 mm; eluent: 80% carbon dioxide, 20% acetonitrile; temperature: 40° C.; flow rate: 3 ml/min; UV detection: 210 nm]

Atropisomer 1 was finally suspended in 5 ml each of ethyl acetate and cyclohexane, the precipitate was filtered off and 494 mg (17.8% of theory, 100% purity) of the compound from Example 399 were obtained.

Atropisomer 2 was finally suspended in 5 ml each of ethyl acetate and cyclohexane, the precipitate was filtered off and 852 mg (30.7% of theory, 100% purity) of the compound from Example 400 were obtained. The mother liquor was concentrated to dryness by rotary evaporation and purified by means of normal phase chromatography (cyclohexane-ethyl acetate gradient), and a further 30.8 mg (1% of theory; 100% purity) of the compound from Example 400 were obtained.

Example 399

1-(2-Chloro-4,6-difluorophenyl)-7-[(4S)-4-hydroxy-2-oxopyrrolidin-1-yl]-4-oxo-N-[(2S)-1,1,1-trifluorobutan-2-yl]-1,4-dihydro-1,8-naphthyridine-3-carboxamide (atropisomer 1)

$^1$H-NMR (400 MHz, DMSO-d6) δ[ppm]=10.13 (d, 1H), 9.04 (s, 1H), 8.72 (d, 1H), 8.54 (d, 1H), 7.83-7.72 (m, 2H), 5.33 (d, 1H), 4.83-4.71 (m, 1H), 4.31-4.25 (m, 1H), 3.66 (dd, 1H), 3.41 (d, 1H), 2.94 (dd, 1H), 2.37 (d, 1H), 1.96-1.83 (m, 1H), 1.74-1.59 (m, 1H), 0.98 (t, 3H).

LC-MS (Method 1): $R_t$=1.00 min; MS (ESIpos): m/z=545 [M+H]$^+$

Example 400

1-(2-Chloro-4,6-difluorophenyl)-7-[(4S)-4-hydroxy-2-oxopyrrolidin-1-yl]-4-oxo-N-[(2S)-1,1,1-trifluorobutan-2-yl]-1,4-dihydro-1,8-naphthyridine-3-carboxamide (atropisomer 2)

$^1$H-NMR (400 MHz, DMSO-d6) δ[ppm]=10.13 (d, 1H), 9.04 (s, 1H), 8.73 (d, 1H), 8.54 (d, 1H), 7.81-7.74 (m, 2H), 5.33 (d, 1H), 4.84-4.70 (m, 1H), 4.32-4.24 (m, 1H), 3.64 (dd, 1H), 3.43 (d, 1H), 2.94 (dd, 1H), 2.37 (d, 1H), 1.96-1.83 (m, 1H), 1.75-1.60 (m, 1H), 0.97 (t, 3H).

LC-MS (Method 1): $R_t$=1.01 min; MS (ESIpos): m/z=545 [M+H]$^+$

Example 401

1-(2-Chloro-4,6-difluorophenyl)-7-[(3R,4R)-3,4-dihydroxypyrrolidin-1-yl]-N-(3-fluorobicyclo[1.1.1]pent-1-yl)-4-oxo-1,4-dihydro-1,8-naphthyridine-3-carboxamide

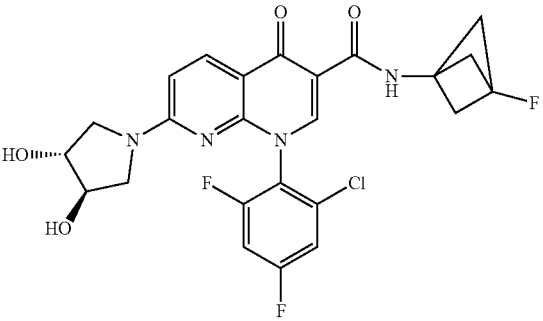 [SMILES: O=C(NC12CC(F)(C1)C2)c1cn(-c2c(F)cc(F)cc2Cl)c2nc(N3C[C@@H](O)[C@H](O)C3)ccc2c1=O]

According to GP1, 50.0 mg (99% purity, 113 µmol) of the compound from Example 134A were reacted with 18.7 mg (136 µmol) of 3-fluorobicyclo[1.1.1]pentan-1-amine hydrochloride in the presence of 51.6 mg (136 µmol) of HATU and 69 µl (0.40 mmol) of N,N-diisopropylethylamine in 1.2 ml of dimethylformamide. The mixture was diluted with 1 ml of 1N aqueous hydrochloric acid and 2.0 ml of DMSO and the solution was purified by means of preparative HPLC (column: Chromatorex C18, 10 µm, 125×30 mm, solvent: acetonitrile/0.1% formic acid gradient; 0 to 5 min 10% acetonitrile, over 14 min to 90% acetonitrile and for a further 4 min 90% acetonitrile). 51.4 mg (86% of theory, 99% purity) of the title compound were obtained.

$^1$H-NMR (400 MHz, DMSO-d6) δ[ppm]: −0.008 (2.40), 0.008 (1.87), 2.073 (14.92), 2.094 (8.32), 2.475 (2.00), 2.988 (1.30), 3.019 (2.12), 3.044 (1.72), 3.178 (1.28), 3.201 (1.88), 3.331 (3.86), 3.587 (2.02), 3.607 (1.63), 3.913 (3.18), 4.039 (3.15), 5.135 (3.79), 5.223 (3.55), 6.731 (0.90), 6.741 (6.39), 6.754 (1.02), 6.763 (6.51), 7.677 (1.08), 7.689 (1.56), 7.700 (2.08), 7.712 (2.36), 7.724 (2.95), 7.753 (2.13), 8.232 (1.47), 8.237 (7.81), 8.259 (7.32), 8.599 (1.82), 8.641 (16.00), 10.305 (0.96), 10.447 (8.86).

LC-MS (Method 3): $R_t$=1.62 min; MS (ESIpos): m/z=521 [M+H]$^+$

Example 402

N-(Bicyclo[1.1.1]pent-1-yl)-1-(2-chloro-4,6-difluorophenyl)-7-[(3R,4R)-3,4-dihydroxypyrrolidin-1-yl]-4-oxo-1,4-dihydro-1,8-naphthyridine-3-carboxamide

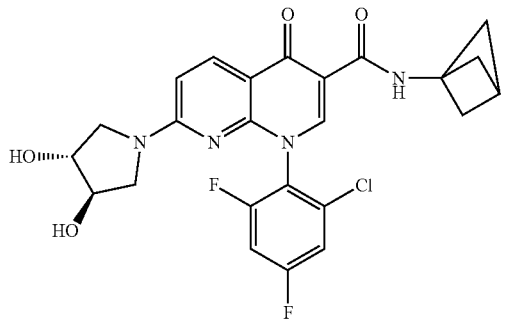 [SMILES: O=C(NC12CC(C1)C2)c1cn(-c2c(F)cc(F)cc2Cl)c2nc(N3C[C@@H](O)[C@H](O)C3)ccc2c1=O]

According to GP1, 50.0 mg (99% purity, 113 µmol) of the compound from Example 134A were reacted with 16.2 mg (136 µmol) of bicyclo[1.1.1]pentan-1-amine hydrochloride in the presence of 51.6 mg (136 µmol) of HATU and 69 µl (0.40 mmol) of N,N-diisopropylethylamine in 1.2 ml of dimethylformamide. The mixture was diluted with 1 ml of 1N aqueous hydrochloric acid and 2.0 ml of DMSO and the solution was purified by means of preparative HPLC (column: Chromatorex C18, 10 µm, 125×30 mm, solvent: acetonitrile/0.1% formic acid gradient; 0 to 5 min 10% acetonitrile, over 14 min to 90% acetonitrile and for a further 4 min 90% acetonitrile). 38.4 mg (67% of theory, 99% purity) of the title compound were obtained.

$^1$H-NMR (400 MHz, DMSO-d6) δ[ppm]: 2.073 (2.07), 2.094 (16.00), 2.475 (2.51), 5.132 (0.78), 6.731 (1.37), 6.754 (1.39), 8.232 (1.63), 8.254 (1.55), 8.599 (2.96), 10.305 (1.69).

LC-MS (Method 3): $R_t$=1.64 min; MS (ESIpos): m/z=503 [M+H]$^+$

Example 403

7-[(3R,4R)-3,4-Dihydroxypyrrolidin-1-yl]-4-oxo-N-(1,1,1-trifluoro-2-methylpropan-2-yl)-1-(2,4,6-trifluorophenyl)-1,4-dihydro-1,8-naphthyridine-3-carboxamide

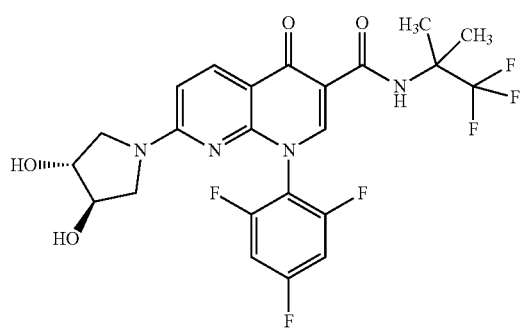 [SMILES: CC(C)(NC(=O)c1cn(-c2c(F)cc(F)cc2F)c2nc(N3C[C@@H](O)[C@H](O)C3)ccc2c1=O)C(F)(F)F]

According to GP1, 100 mg (30% purity, 71.2 µmol) of the compound from Example 121A were reacted with 10.9 mg (85.4 µmol) of 1,1,1-trifluoro-2-methylpropan-2-amine in the presence of 32 mg (85 µmol) of HATU and 31.0 µl (178 µmol) of N,N-diisopropylethylamine in 0.72 ml of dimethylformamide. The mixture was diluted with 1 ml of 1N aqueous hydrochloric acid, water and 2.0 ml of DMSO and the solution was purified by means of preparative HPLC (column: Chromatorex C18, 10 µm, 125×30 mm, solvent: acetonitrile/0.1% formic acid gradient; 0 to 5 min 10% acetonitrile, over 14 min to 90% acetonitrile and for a further 4 min 90% acetonitrile). 25.1 mg (66% of theory, 100% purity) of the title compound were obtained.

$^1$H-NMR (400 MHz, DMSO-d6) δ[ppm]: 0.008 (0.97), 1.633 (16.00), 2.073 (1.22), 3.051 (0.77), 3.083 (1.03), 3.225 (0.61), 3.235 (0.68), 3.257 (0.51), 3.266 (0.48), 3.348 (0.96), 3.593 (0.55), 3.602 (0.62), 3.621 (0.51), 3.630 (0.46), 3.925 (0.94), 4.047 (0.94), 5.135 (1.35), 5.143 (1.37), 5.226 (1.35), 5.235 (1.32), 6.759 (1.96), 6.782 (2.01), 7.545 (0.72), 7.565 (1.29), 7.585 (0.73), 8.266 (2.17), 8.289 (2.07), 8.739 (3.38), 10.653 (2.85).

LC-MS (Method 3): $R_t$=1.71 min; MS (ESIpos): m/z=531 [M+H]$^+$

Example 404

N-[(1S)-1-Cyclopropyl-2,2,2-trifluoroethyl]-7-[(4S)-4-hydroxy-2-oxopyrrolidin-1-yl]-4-oxo-1-(2,4,6-trifluorophenyl)-1,4-dihydro-1,8-naphthyridine-3-carboxamide

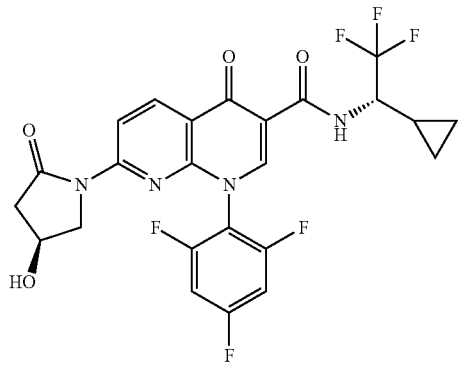 [SMILES: O=C(N[C@@H](C1CC1)C(F)(F)F)c1cn(-c2c(F)cc(F)cc2F)c2nc(N3C[C@@H](O)CC3=O)ccc2c1=O]

According to GP2, 100 mg (210 µmol) of the compound from Example 126A were reacted with 23.4 mg (231 µmol) of (4S)-4-hydroxypyrrolidin-2-one in the presence of 43.6 mg (315 µmol) of potassium carbonate, 2.4 mg (11 µmol) of palladium(II) acetate and 12 mg (21 µmol) of Xantphos in 1.9 ml of 1,4-dioxane. Subsequently, 100 mg of N-acetylcysteine were added and the mixture was stirred at RT for 0.5 h. 20 ml of ethyl acetate were added, and the organic phase was extracted with saturated aqueous sodium hydrogencarbonate solution, dried and concentrated. The residue was purified by means of preparative HPLC (column: Chromatorex C18, 10 µm, 125×30 mm, solvent: acetonitrile/0.05% formic acid gradient; 0 to 3 min. 10% acetonitrile to 22 min. 55% acetonitrile, to 35 min. 65% acetonitrile and a further 3 min. 90% acetonitrile). 60.9 mg (53% of theory, 99% purity) of the title compound were obtained.

$^1$H-NMR (400 MHz, DMSO-d6) δ[ppm]: −0.149 (1.32), −0.008 (11.84), 0.008 (8.55), 0.146 (1.10), 0.342 (1.75), 0.561 (2.41), 0.578 (2.19), 0.659 (1.53), 1.147 (2.63), 1.226 (1.75), 2.327 (1.75), 2.355 (2.41), 2.366 (5.26), 2.399 (2.63), 2.670 (2.19), 2.710 (5.26), 2.916 (1.97), 2.930 (2.19), 2.959 (1.97), 2.974 (1.75), 3.289 (16.00), 3.461 (2.63), 3.490 (3.07), 3.672 (1.97), 3.684 (2.63), 3.701 (2.19), 3.714 (1.75), 4.286 (1.75), 4.416 (1.53), 5.328 (5.26), 5.338 (5.26), 7.611 (2.63), 8.531 (6.14), 8.554 (7.67), 8.709 (7.67), 8.731 (6.14), 9.062 (8.99), 10.247 (3.29), 10.271 (3.07).

LC-MS (Method 1): $R_t$=1.04 min; MS (ESIpos): m/z=541 [M+H]$^+$

Example 405

N-[(1R)-1-Cyclopropyl-2,2,2-trifluoroethyl]-7-[1-hydroxy-3-azabicyclo[3.1.0]hex-3-yl]-4-oxo-1-(2,4,6-trifluorophenyl)-1,4-dihydro-1,8-naphthyridine-3-carboxamide (diastereomer mixture)

Example 406

1-(2-Chloro-4,6-difluorophenyl)-7-[1-hydroxy-3-azabicyclo[3.1.0]hex-3-yl]-4-oxo-N-[(2R)-1,1,1-trifluorobutan-2-yl]-1,4-dihydro-1,8-naphthyridine-3-carboxamide (diastereomer mixture)

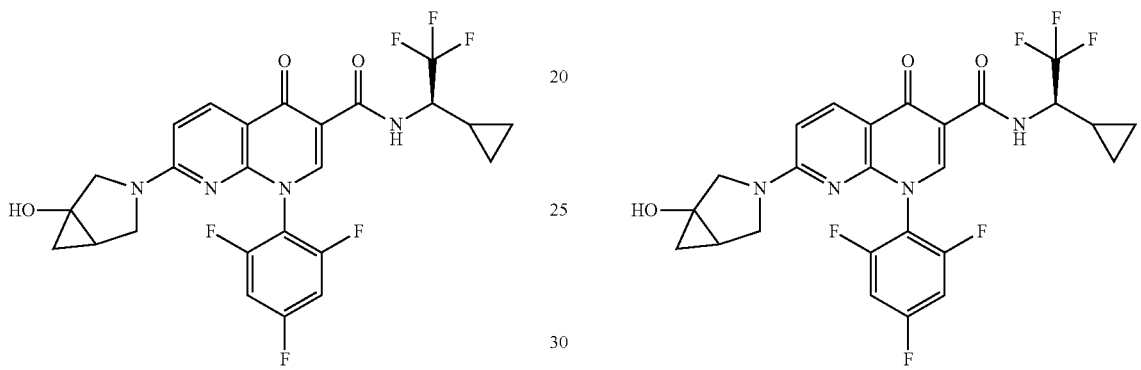

According to GP3, 150 mg (315 µmol) of the compound from Example 135A were reacted with 51.7 mg (347 µmol, 91% purity) of 3-azabicyclo[3.1.0]hexan-1-ol hydrochloride and 192 µl (1.10 µmol) of N,N-diisopropylethylamine in 1.4 ml of dimethylformamide. The reaction solution was diluted with 4 ml of acetonitrile and 0.5 ml of 1N aqueous hydrochloric acid and purified by means of preparative HPLC (column: Chromatorex C18, 10 µm, 125×30 mm, solvent: acetonitrile/0.05% formic acid gradient; (0 to 3 min. 10% acetonitrile to 40 min. 90% acetonitrile and a further 3 min. 90% acetonitrile), and 118.6 mg (69% of theory, 99% purity) of the title compound were obtained.

$^1$H NMR (400 MHz, DMSO-$d_6$): δ [ppm]=10.53 (d, 1H), 8.81 (s, 1H), 8.28 (d, 1H), 7.64-7.50 (m, 2H), 6.84-6.69 (m, 1H), 6.08 (s, 0.5H), 5.96 (s, 0.5H), 4.44-4.32 (m, 1H), 3.93-3.83 (m, 0.5H), 3.70-3.39 (m, 2H), 3.21-3.08 (m, 1H), 1.70-1.51 (m, 1H), 1.26-1.14 (m, 1H), 1.07-0.98 (m, 1H), 0.70-0.29 (m, 5H).

LC-MS (Method 3): $R_t$=2.05 min; MS (ESIpos) m/z 539 [M+H]$^+$.

According to GP3, 150 mg (312 µmol) of the compound from Example 136A were reacted with 51.2 mg (344 µmol, 91% purity) of 3-azabicyclo[3.1.0]hexan-1-ol hydrochloride and 190 µl (1.09 mmol) of N,N-diisopropylethylamine in 3 ml of dimethylformamide. The reaction solution was diluted with 4 ml of acetonitrile and 1 ml of water and purified by means of preparative HPLC (column: Chromatorex C18, 10 µm, 125×30 mm, solvent: acetonitrile/0.05% formic acid gradient; (0 to 3 min. 10% acetonitrile to 40 min. 90% acetonitrile and a further 3 min. 90% acetonitrile), and 104.8 mg (61% of theory, 99% purity) of the title compound were obtained.

$^1$H NMR (400 MHz, DMSO-$d_6$): δ [ppm]=10.41 (d, 1H), 8.77 (s, 1H), 8.28 (d, 1H), 7.81-7.64 (m, 2H), 6.83-6.67 (m, 1H), 6.07 (s, 0.5H), 5.95 (s, 0.5H), 4.80-4.67 (m, 1H), 3.93-3.82 (m, 0.5H), 3.71-3.39 (m, 2H), 3.26-3.03 (m, 1.5H), 1.95-1.81 (m, 1H), 1.72-1.50 (m, 2H), 1.07-0.91 (m, 4H), 0.49-0.37 (m, 1H).

LC-MS (Method 3): $R_t$=2.07 min; MS (ESIpos) m/z 543 [M+H]$^+$.

Example 407

1-(2-Chloro-4,6-difluorophenyl)-7-[(4S)-4-hydroxy-2-oxopyrrolidin-1-yl]-4-oxo-N-[(2R)-1,1,1-trifluorobutan-2-yl]-1,4-dihydro-1,8-naphthyridine-3-carboxamide

Example 408

1-(2-Chloro-4,6-difluorophenyl)-7-[1-hydroxy-3-azabicyclo[3.1.0]hex-3-yl]-4-oxo-N-[(2S)-1,1,1-trifluoropropan-2-yl]-1,4-dihydro-1,8-naphthyridine-3-carboxamide (diastereomer mixture)

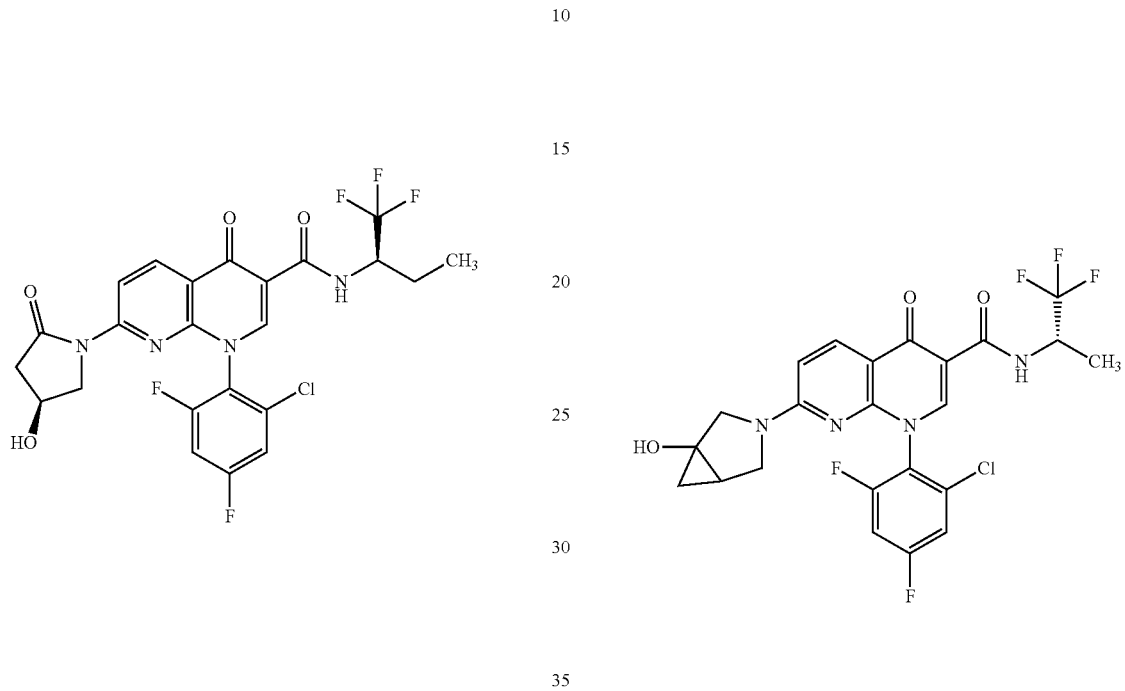

According to GP2, 150 mg (312 µmol) of the compound from Example 136A were reacted with 34.7 mg (344 µmol) of (4S)-4-hydroxypyrrolidin-2-one in the presence of 64.8 mg (469 µmol) of potassium carbonate, 7.0 mg (31 µmol) of palladium(II) acetate and 36 mg (62 µmol) of Xantphos in 3.1 ml of 1,4-dioxane. This was followed by dilution with acetonitrile, filtration and concentration. The residue was dissolved in 3 ml of acetonitrile and 0.5 ml of water and purified twice by means of preparative HPLC (column: Chromatorex C18, 10 µm, 125×30 mm, LM: acetonitrile/0.05% formic acid gradient; 0 to 3 min. 10% acetonitrile to 35 min. 90% acetonitrile and a further 3 min. 90% acetonitrile, and column: Chromatorex C18, 10 µm, 125×30 mm, LM: acetonitrile/0.05% formic acid gradient; 0 to 3 min. 10% acetonitrile to 24 min. 60% acetonitrile; to 35 min 65% acetonitrile, to 44 min 90% acetonitrile and a further 12 min 90% acetonitrile). 91.2 mg (53% of theory, 99% purity) of the title compound were obtained.

$^1$H-NMR (400 MHz, DMSO-d6) δ[ppm]=10.13 (d, 1H), 9.04 (s, 1H), 8.73 (d, 1H), 8.54 (d, 1H), 7.83-7.72 (m, 2H), 5.33 (d, 1H), 4.83-4.71 (m, 1H), 4.31-4.24 (m, 1H), 3.69-3.60 (m, 1H), 3.47-3.38 (m, 1H), 2.94 (dd, 1H), 2.37 (d, 1H), 1.96-1.83 (m, 1H), 1.74-1.61 (m, 1H), 1.03-0.94 (m, 3H).

LC-MS (Method 1): $R_t$=1.07 min; MS (ESIpos): m/z=545 [M+H]$^+$

According to GP3, 150 mg (322 µmol) of the compound from Example 111A were reacted with 52.7 mg (354 µmol, 91% purity) of 3-azabicyclo[3.1.0]hexan-1-ol hydrochloride and 196 µl (1.13 mmol) of N,N-diisopropylethylamine in 3.2 ml of dimethylformamide. The reaction solution was diluted with 4 ml of acetonitrile and 0.5 ml of water and purified by means of preparative HPLC (column: Chromatorex C18, 10 µm, 125×30 mm, solvent: acetonitrile/0.05% formic acid gradient; (0 to 3 min. 10% acetonitrile to 35 min. 90% acetonitrile and a further 3 min. 90% acetonitrile), and 111.8 mg (65% of theory, 99% purity) of the title compound were obtained.

$^1$H NMR (400 MHz, DMSO-d$_6$): δ [ppm]=10.46 (d, 1H), 8.76 (s, 1H), 8.27 (d, 1H), 7.80-7.63 (m, 2H), 6.82-6.68 (m, 1H), 6.07 (s, 0.5H), 5.93 (s, 0.5H), 4.94-4.82 (m, 1H), 3.92-3.81 (m, 0.5H), 3.70-3.39 (m, 2H), 3.26-3.02 (m, 1.5H), 1.70-1.50 (m, 1H), 1.40-1.35 (m, 3H), 1.06-0.99 (m, 1H), 0.47-0.38 (m, 1H).

LC-MS (Method 3): $R_t$=1.98 min; MS (ESIpos) m/z 529 [M+H]$^+$.

Example 409

1-(2-Chloro-4,6-difluorophenyl)-7-[(4S)-4-hydroxy-2-oxopyrrolidin-1-yl]-4-oxo-N-[(2S)-1,1,1-trifluoropropan-2-yl]-1,4-dihydro-1,8-naphthyridine-3-carboxamide

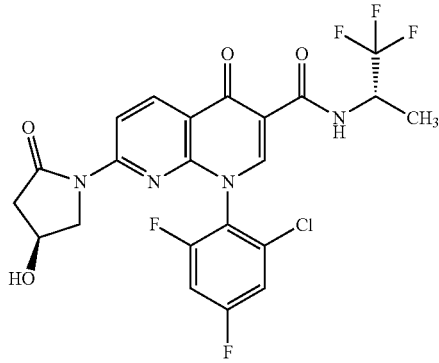 [SMILES: C[C@H](NC(=O)c1cn(-c2c(F)cc(F)cc2Cl)c2nc(N3C[C@@H](O)CC3=O)ccc2c1=O)C(F)(F)F]

According to GP2, 150 mg (322 µmol) of the compound from Example 111A were reacted with 35.7 mg (354 µmol) of (4S)-4-hydroxypyrrolidin-2-one in the presence of 66.7 mg (483 µmol) of potassium carbonate, 7.2 mg (32 µmol) of palladium(II) acetate and 37 mg (64 µmol) of Xantphos in 3.2 ml of 1,4-dioxane. This was followed by dilution with acetonitrile, filtration and concentration. The residue was dissolved in 3 ml of acetonitrile and 0.5 ml of water and purified twice by means of preparative HPLC (column: Chromatorex C18, 10 µm, 125×30 mm, LM: acetonitrile/0.05% formic acid gradient; 0 to 3 min. 10% acetonitrile to 35 min. 90% acetonitrile and a further 3 min. 90% acetonitrile, and column: Chromatorex C18, 10 µm, 125×30 mm, LM: acetonitrile/0.05% formic acid gradient; 0 to 3 min. 10% acetonitrile to 24 min. 60% acetonitrile; to 35 min 65% acetonitrile, to 44 min 90% acetonitrile and a further 12 min 90% acetonitrile). 55.7 mg (32% of theory, 98% purity) of the title compound were obtained.

$^1$H-NMR (400 MHz, DMSO-d6) δ[ppm]=10.18 (d, 1H), 9.04 (d, 1H), 8.72 (d, 1H), 8.54 (d, 1H), 7.82-7.72 (m, 2H), 5.33 (d, 1H), 4.98-4.86 (m, 1H), 4.31-4.24 (m, 1H), 3.68-3.60 (m, 1H), 3.46-3.38 (m, 1H), 2.94 (dd, 1H), 2.37 (d, 1H), 1.42-1.37 (m, 3H).

LC-MS (Method 1): $R_t$=1.01 min; MS (ESIpos): m/z=531 [M+H]$^+$

Example 410

7-[(4S)-4-Hydroxy-2-oxopyrrolidin-1-yl]-4-oxo-N-[1-(trifluoromethoxy)butan-2-yl]-1-(2,4,6-trifluorophenyl)-1,4-dihydro-1,8-naphthyridine-3-carboxamide (diastereomer mixture)

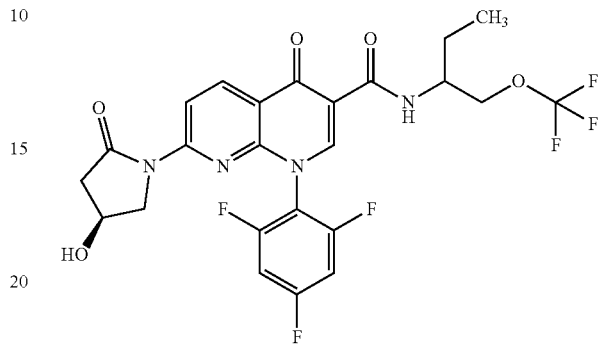

According to GP2, 188 mg (381 µmol) of the compound from Example 137A were reacted with 38.5 mg (381 µmol) of (4S)-4-hydroxypyrrolidin-2-one in the presence of 79.0 mg (572 µmol) of potassium carbonate, 15 mg (69 µmol) of palladium(II) acetate and 79.4 mg (137 µmol) of Xantphos in 3.8 ml of 1,4-dioxane. This was followed by dilution with acetonitrile, filtration and concentration. The residue was dissolved in 3 ml of acetonitrile and 0.5 ml of water and purified by means of preparative HPLC (column: Chromatorex C18, 10 µm, 125×30 mm, solvent: acetonitrile/0.05% formic acid gradient; 0 to 3 min 10% acetonitrile, to 35 min 90% acetonitrile and for a further 3 min 90% acetonitrile). 60.2 mg (28% of theory, 100% purity) of the title compound were obtained.

$^1$H-NMR (400 MHz, DMSO-d6) δ[ppm]=9.81 (d, 1H), 8.99 (s, 1H), 8.71 (d, 1H), 8.53 (d, 1H), 7.66-7.57 (m, 2H), 5.33 (d, 1H), 4.32-4.15 (m, 4H), 3.69 (dd, 1H), 3.48 (d, 1H), 2.94 (dd, 1H), 2.37 (d, 1H), 1.75-1.54 (m, 2H), 0.95 (t, 3H).

LC-MS (Method 3): $R_t$=1.92 min; MS (ESIpos): m/z=559 [M+H]$^+$ 60 mg of the title compound (diastereomer mixture) were separated into the diastereomers by chiral HPLC (preparative HPLC: column: Daicel Chiralcel OZ-H 5 µm 250×20 mm; eluent: 20% ethanol, 80% isohexane; temperature: 25° C.; flow rate: 20 ml/min; UV detection: 220 nm).

This gave (in the sequence of elution from the column) 10.1 mg of diastereomer 1 (99% de) $R_t$=1.77 min and 21 mg (98% de) of diastereomer 2 $R_t$=2.56 min.

[Analytical HPLC: column: Daicel Chiralpak OZ-3 3 µm 20×4.6 mm; eluent: 80% ethanol, 50% isohexane; flow rate: 1 ml/min; UV detection: 220 nm]

Diastereomer 1 was additionally purified by means of preparative HPLC (column: Chromatorex C18, 10 µm, 125×30 mm, solvent: acetonitrile/0.05% formic acid gradient; (0 to 3 min. 10% acetonitrile to 35 min. 90% acetonitrile and a further 3 min. 90% acetonitrile)), and 13.6 mg (6.3% of theory, 99% purity) of the title compound from Example 411 were obtained.

Diastereomer 2 was additionally purified by means of preparative HPLC (column: Chromatorex C18, 10 µm, 125×30 mm, solvent: acetonitrile/0.05% formic acid gradient; (0 to 3 min. 10% acetonitrile to 35 min. 90% acetonitrile and

Example 411

7-[(4S)-4-Hydroxy-2-oxopyrrolidin-1-yl]-4-oxo-N-[1-(trifluoromethoxy)butan-2-yl]-1-(2,4,6-trifluorophenyl)-1,4-dihydro-1,8-naphthyridine-3-carboxamide (diastereomer 1)

$^1$H-NMR (400 MHz, DMSO-d6) δ[ppm]=9.81 (d, 1H), 8.99 (s, 1H), 8.71 (d, 1H), 8.53 (d, 1H), 7.66-7.57 (m, 2H), 5.33 (d, 1H), 4.32-4.15 (m, 4H), 3.69 (dd, 1H), 3.48 (d, 1H), 2.94 (dd, 1H), 2.37 (d, 1H), 1.76-1.55 (m, 2H), 0.95 (t, 3H).

LC-MS (Method 3): $R_t$=1.90 min; MS (ESIpos): m/z=559 [M+H]$^+$

Example 412

7-[(4S)-4-Hydroxy-2-oxopyrrolidin-1-yl]-4-oxo-N-[1-(trifluoromethoxy)butan-2-yl]-1-(2,4,6-trifluorophenyl)-1,4-dihydro-1,8-naphthyridine-3-carboxamide (diastereomer 2)

$^1$H-NMR (400 MHz, DMSO-d6) δ[ppm]=9.81 (d, 1H), 8.99 (s, 1H), 8.71 (d, 1H), 8.53 (d, 1H), 7.66-7.57 (m, 2H), 5.33 (d, 1H), 4.32-4.14 (m, 4H), 3.69 (dd, 1H), 3.48 (d, 1H), 2.94 (dd, 1H), 2.37 (d, 1H), 1.75-1.54 (m, 2H), 0.95 (t, 3H).

LC-MS (Method 3): $R_t$=1.89 min; MS (ESIpos): m/z=559 [M+H]$^+$

Example 413

1-(2-Chloro-4,6-difluorophenyl)-7-[1-hydroxy-3-azabicyclo[3.1.0]hex-3-yl]-4-oxo-N-[(2S)-1,1,1-trifluorobutan-2-yl]-1,4-dihydro-1,8-naphthyridine-3-carboxamide (diastereomer mixture)

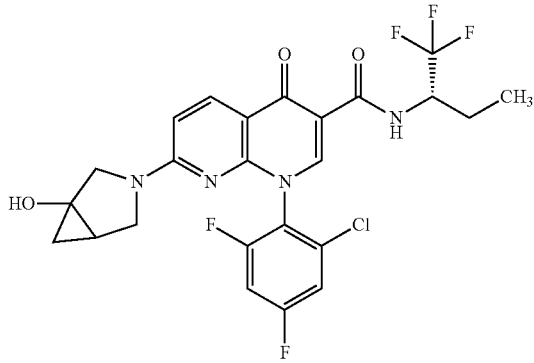

According to GP3, 150 mg (312 µmol) of the compound from Example 108C were reacted with 51.2 mg (344 µmol, 91% purity) of 3-azabicyclo[3.1.0]hexan-1-ol hydrochloride (racemate) and 190 µl (1.09 mmol) of N,N-diisopropylethylamine in 3.1 ml of dimethylformamide. The reaction solution was diluted with 1 ml of acetonitrile and 0.5 ml of water and purified by means of preparative HPLC (column: Chromatorex C18, 10 µm, 125×30 mm, solvent: acetonitrile/0.05% formic acid gradient; (0 to 3 min. 10% acetonitrile to 35 min. 90% acetonitrile and a further 3 min. 90% acetonitrile), and 100.5 mg (59% of theory, 99% purity) of the title compound were obtained.

a further 3 min. 90% acetonitrile)), and 19.6 mg (9.1% of theory, 99% purity) of the title compound from Example 412 were obtained.

$^1$H NMR (400 MHz, DMSO-d$_6$): δ [ppm]=10.42 (d, 1H), 8.76 (s, 1H), 8.28 (d, 1H), 7.80-7.64 (m, 2H), 6.84-6.67 (m, 1H), 6.07 (s, 0.5H), 5.95 (s, 0.5H), 4.80-4.66 (m, 1H), 3.93-3.82 (m, 0.5H), 3.71-3.38 (m, 2H), 3.26-3.02 (m, 1.5H), 1.94-1.82 (m, 1H), 1.72-1.48 (m, 2H), 1.07-0.92 (m, 4H), 0.48-0.37 (m, 1H).

LC-MS (Method 3): $R_t$=2.05 min; MS (ESIpos) m/z 543 [M+H]$^+$.

Example 414

1-(2-Chloro-4,6-difluorophenyl)-N-[(1R)-1-cyclopropyl-2,2,2-trifluoroethyl]-7-[(4S)-4-hydroxy-2-oxopyrrolidin-1-yl]-4-oxo-1,4-dihydro-1,8-naphthyridine-3-carboxamide

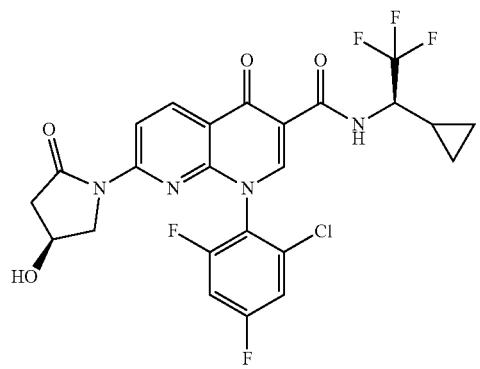 [SMILES: O=C(N[C@H](C1CC1)C(F)(F)F)c1cn(-c2c(F)cc(F)cc2Cl)c2nc(N3C[C@@H](O)CC3=O)ccc2c1=O]

According to GP2, 150 mg (305 µmol) of the compound from Example 138A were reacted with 30.8 mg (305 µmol) of (4S)-4-hydroxypyrrolidin-2-one in the presence of 63.2 mg (457 µmol) of potassium carbonate, 12 mg (55 µmol) of palladium(II) acetate and 63.5 mg (110 µmol) of Xantphos in 2.8 ml of 1,4-dioxane. This was followed by dilution with acetonitrile, filtration and concentration. The residue was dissolved in 3 ml of acetonitrile and 0.5 ml of water and purified twice by means of preparative HPLC (column: Chromatorex C18, 10 µm, 125×30 mm, LM: acetonitrile/0.05% formic acid gradient; 0 to 3 min. 10% acetonitrile to 35 min. 90% acetonitrile and a further 3 min. 90% acetonitrile, and column: Chromatorex C18, 10 µm, 125×30 mm, LM: acetonitrile/0.05% formic acid gradient; 0 to 3 min. 10% acetonitrile to 22 min. 55% acetonitrile; to 35 min 65% acetonitrile, and a further 3 min 90% acetonitrile). Product fractions from both runs were combined, concentrated and purified once again by means of normal phase chromatography (dichloromethane-methanol gradient). 58 mg (34% of theory, 100% purity) of the title compound were obtained.

$^1$H-NMR (400 MHz, DMSO-d6) δ[ppm]=10.27 (d, 1H), 9.03 (s, 1H), 8.73 (d, 1H), 8.54 (d, 1H), 7.82-7.72 (m, 2H), 5.33 (d, 1H), 4.66-4.35 (m, 1H), 4.31-4.25 (m, 1H), 3.69-3.61 (m, 1H), 3.46-3.39 (m, 1H), 2.94 (dd, 1H), 2.37 (d, 1H), 1.28-1.19 (m, 1H), 0.71-0.51 (m, 3H), 0.39-0.31 (m, 1H).

LC-MS (Method 1): $R_t$=1.08 min; MS (ESIpos): m/z=557 [M+H]$^+$

Example 415

1-(2-Chloro-4,6-difluorophenyl)-N-[(1R)-1-cyclopropyl-2,2,2-trifluoroethyl]-7-[1-hydroxy-3-azabicyclo[3.1.0]hex-3-yl]-4-oxo-1,4-dihydro-1,8-naphthyridine-3-carboxamide (diastereomer mixture)

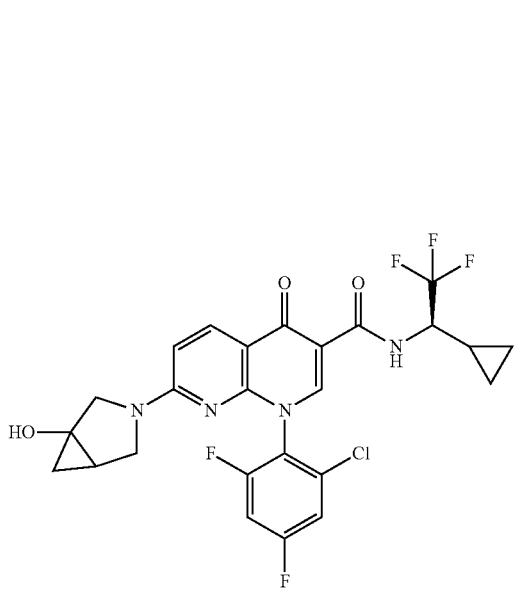 [SMILES: O=C(N[C@H](C1CC1)C(F)(F)F)c1cn(-c2c(F)cc(F)cc2Cl)c2nc(N3CC4CC4(O)C3)ccc2c1=O]

According to GP3, 150 mg (305 μmol) of the compound from Example 138A were reacted with 49.9 mg (335 μmol, 91% purity) of 3-azabicyclo[3.1.0]hexan-1-ol hydrochloride (racemate) and 186 μl (1.07 mmol) of N,N-diisopropylethylamine in 1.4 ml of dimethylformamide. The reaction solution was diluted with 4 ml of acetonitrile, filtered and purified by means of preparative HPLC (column: Chromatorex C18, 10 μm, 125×30 mm, solvent: acetonitrile/0.05% formic acid gradient; (0 to 3 min. 10% acetonitrile to 35 min. 90% acetonitrile and a further 3 min. 90% acetonitrile), and 112 mg (66% of theory, 100% purity) of the title compound were obtained.

$^1$H NMR (400 MHz, DMSO-$d_6$): δ [ppm]=10.55 (d, 1H), 8.76 (s, 1H), 8.29 (d, 1H), 7.80-7.64 (m, 2H), 6.83-6.67 (m, 1H), 6.07 (s, 0.5H), 5.95 (s, 0.5H), 4.45-4.29 (m, 1H), 3.93-3.82 (m, 0.5H), 3.71-3.38 (m, 2H), 3.27-3.01 (m, 1.5H), 1.70-1.49 (m, 1H), 1.26-1.13 (m, 1H), 1.07-0.98 (m, 1H), 0.71-0.29 (m, 5H).

LC-MS (Method 3): $R_t$=2.07 min; MS (ESIpos) m/z 555 [M+H]$^+$.

Example 416

7-[1-Hydroxy-3-azabicyclo[3.1.0]hex-3-yl]-4-oxo-N-[(2S)-1,1,1-trifluorobutan-2-yl]-1-(2,4,6-trifluorophenyl)-1,4-dihydro-1,8-naphthyridine-3-carboxamide (diastereomer mixture)

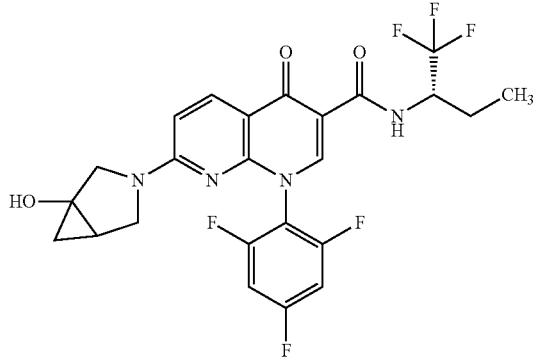 [SMILES: CC[C@H](NC(=O)c1cn(-c2c(F)cc(F)cc2F)c2nc(N3CC4CC4(O)C3)ccc2c1=O)C(F)(F)F]

According to GP3, 150 mg (323 μmol) of the compound from Example 115A were reacted with 53.0 mg (356 μmol, 91% purity) of 3-azabicyclo[3.1.0]hexan-1-ol hydrochloride (racemate) and 197 μl (1.13 mmol) of N,N-diisopropylethylamine in 1.5 ml of dimethylformamide. The reaction solution was diluted with 0.5 ml of acetonitrile and purified by means of preparative HPLC (column: Chromatorex C18, 10 μm, 125×30 mm, solvent: acetonitrile/0.05% formic acid gradient; (0 to 3 min. 10% acetonitrile to 35 min. 90% acetonitrile and a further 3 min. 90% acetonitrile), and 116 mg (67% of theory, 99% purity) of the title compound were obtained.

$^1$H NMR (400 MHz, DMSO-$d_6$): δ [ppm]=10.40 (d, 1H), 8.82 (s, 1H), 8.27 (d, 1H), 7.65-7.49 (m, 2H), 6.83-6.69 (m, 1H), 6.08 (s, 0.5H), 5.96 (s, 0.5H), 4.80-4.67 (m, 1H), 3.93-3.83 (m, 0.5H), 3.71-3.40 (m, 2H), 3.20-3.07 (m, 1H), 1.94-1.81 (m, 1H), 1.71-1.49 (m, 2H), 1.07-0.91 (m, 4H), 0.49-0.41 (m, 1H).

LC-MS (Method 3): $R_t$=2.03 min; MS (ESIpos) m/z 527 [M+H]$^+$.

Example 417

1-(2,6-Difluorophenyl)-7-[1-hydroxy-3-azabicyclo[3.1.0]hex-3-yl]-4-oxo-N-[(2S)-1,1,1-trifluorobutan-2-yl]-1,4-dihydro-1,8-naphthyridine-3-carboxamide (diastereomer mixture)

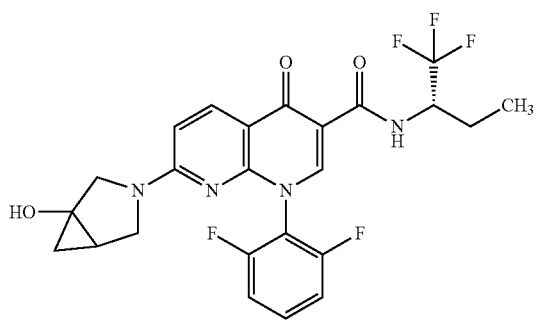 [SMILES: CC[C@H](NC(=O)c1cn(-c2c(F)cccc2F)c2nc(N3CC4CC4(O)C3)ccc2c1=O)C(F)(F)F]

According to GP3, 100 mg (224 µmol) of the compound from Example 114A were reacted with 50.1 mg (336 µmol, 91% purity) of 3-azabicyclo[3.1.0]hexan-1-ol hydrochloride (racemate) and 137 µl (785 µmol) of N,N-diisopropylethylamine in 2.2 ml of dimethylformamide. The reaction solution was diluted with 0.5 ml of acetonitrile and purified by means of preparative HPLC (column: Chromatorex C18, 10 µm, 125×30 mm, solvent: acetonitrile/0.05% formic acid gradient; (0 to 3 min. 10% acetonitrile to 35 min. 90% acetonitrile and a further 3 min. 90% acetonitrile), and 86.4 mg (75% of theory, 99% purity) of the title compound were obtained.

$^1$H NMR (400 MHz, DMSO-d$_6$): δ [ppm]=10.41 (d, 1H), 8.76 (s, 1H), 8.28 (d, 1H), 7.77-7.65 (m, 1H), 7.47-7.36 (m, 2H), 6.83-6.68 (m, 1H), 6.07 (s, 0.5H), 5.93 (s, 0.5H), 4.81-4.67 (m, 1H), 3.93-3.81 (m, 0.5H), 3.71-3.39 (m, 2H), 3.26-3.03 (m, 1.5H), 1.93-1.82 (m, 1H), 1.70-1.47 (m, 2H), 1.06-0.92 (m, 4H), 0.48-0.37 (m, 1H).

LC-MS (Method 3): R$_t$=1.99 min; MS (ESIpos) m/z 509 [M+H]$^+$.

Example 418

1-(2-Chloro-4,6-difluorophenyl)-7-[3-methyl-2-oxopyrrolidin-1-yl]-4-oxo-N-[(2S)-1,1,1-trifluoropropan-2-yl]-1,4-dihydro-1,8-naphthyridine-3-carboxamide (diastereomer mixture)

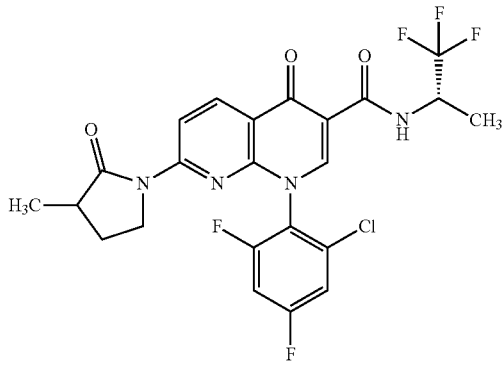 [SMILES: CC1CCN(c2ccc3c(=O)c(C(=O)N[C@@H](C)C(F)(F)F)cn(-c4c(F)cc(F)cc4Cl)c3n2)C1=O]

According to GP2, 100 mg (215 µmol) of the compound from Example 111A were reacted with 23.4 mg (236 µmol) of methylpyrrolidinone (racemate) in the presence of 44.5 mg (322 µmol) of potassium carbonate, 8.7 mg (39 µmol) of palladium(II) acetate and 45 mg (77 µmol) of Xantphos in 2 ml of 1,4-dioxane. Subsequently, the mixture was acidified with 0.5 ml of 1N aqueous hydrochloric acid and the mixture was concentrated. The residue was dissolved in 8 ml of dichloromethane and purified by means of normal phase chromatography (ethyl acetate-cyclohexane gradient). 78.9 mg (69% of theory, 99% purity) of the title compound were obtained.

$^1$H-NMR (400 MHz, DMSO-d6) δ[ppm]=10.18 (d, 1H), 9.04-9.02 (m, 1H), 8.71 (d, 1H), 8.55 (d, 1H), 7.80-7.70 (m, 2H), 4.97-4.86 (m, 1H), 3.59-3.49 (m, 1H), 3.44-3.35 (m, 1H), 2.81-2.70 (m, 1H), 2.24-2.15 (m, 1H), 1.67-1.55 (m, 1H), 1.43-1.36 (m, 3H), 1.17-1.11 (m, 3H).

LC-MS (Method 3): R$_t$=2.31 min; MS (ESIpos): m/z=529 [M+H]$^+$

Example 419

1-(2-Chloro-4,6-difluorophenyl)-4-oxo-7-(2-oxoimidazolidin-1-yl)-N-[(2S)-1,1,1-trifluoropropan-2-yl]-1,4-dihydro-1,8-naphthyridine-3-carboxamide

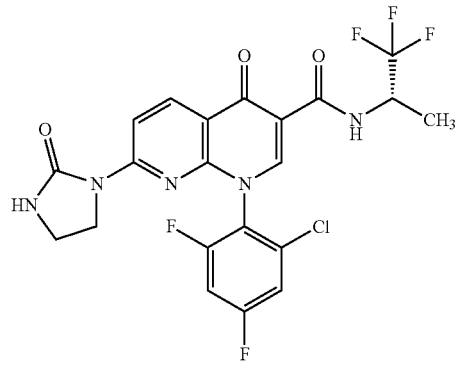 [SMILES: C[C@H](NC(=O)c1cn(-c2c(F)cc(F)cc2Cl)c2nc(N3CCNC3=O)ccc2c1=O)C(F)(F)F]

According to GP2, 100 mg (215 µmol) of the compound from Example 111A were reacted with 92.3 mg (1.07 mmol) of imidazolidin-2-one in the presence of 44.5 mg (322 µmol) of potassium carbonate, 2.4 mg (11 µmol) of palladium(II) acetate and 12 mg (21 µmol) of Xantphos in 6 ml of 1,4-dioxane. Subsequently, the mixture was acidified with 1N aqueous hydrochloric acid and the mixture was concentrated. The residue was dissolved in 8 ml of dichloromethane and purified by means of normal phase chromatography. 68.2 mg (59% of theory, 95% purity) of the title compound were obtained.

$^1$H-NMR (400 MHz, DMSO-d6) δ[ppm]=10.28 (d, 1H), 8.96-8.94 (m, 1H), 8.56 (d, 1H), 8.43 (d, 1H), 7.78-7.64 (m, 3H), 4.97-4.85 (m, 1H), 3.61-3.48 (m, 2H), 1.42-1.35 (m, 3H).

LC-MS (Method 1): R$_t$=1.00 min; MS (ESIpos): m/z=516 [M+H]$^+$

Example 420

N-[(1R)-1-cyclopropyl-2,2,2-trifluoroethyl]-7-[4-methyl-2-oxopyrrolidin-1-yl]-4-oxo-1-(2,4,6-trifluorophenyl)-1,4-dihydro-1,8-naphthyridine-3-carboxamide (diastereomer mixture)

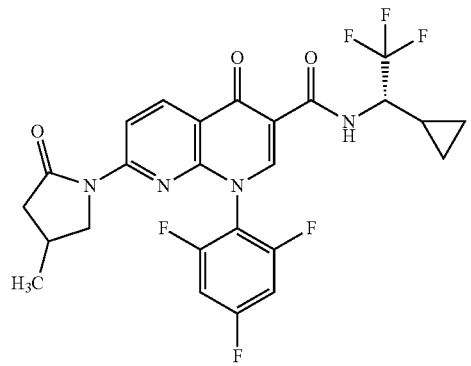 [SMILES: CC1CC(=O)N(c2ccc3c(=O)c(C(=O)N[C@@H](C4CC4)C(F)(F)F)cn(-c4c(F)cc(F)cc4F)c3n2)C1]

According to GP2, 200 mg (420 µmol) of the compound from Example 126A were reacted with 45.8 mg (462 µmol)

of 4-methyl-2-pyrrolidinone (racemate) in the presence of 87.1 mg (631 µmol) of potassium carbonate, 4.7 mg (21 µmol) of palladium(II) acetate and 24 mg (42 µmol) of Xantphos in 3.7 ml of 1,4-dioxane. Subsequently, the mixture was acidified with 1N aqueous hydrochloric acid and the mixture was concentrated. The residue was dissolved in 8 ml of dichloromethane and purified by means of normal phase chromatography (ethyl acetate-cyclohexane gradient). The product fractions were combined and concentrated. The residue was twice stirred in 10 ml of diethyl ether, decanted, dried under high vacuum and finally purified by means of preparative HPLC (column: Chromatorex C18, 10 µm, 125×30 mm, solvent: acetonitrile/0.05% formic acid gradient; 0 to 3 min 10% acetonitrile, to 35 min 90% acetonitrile and for a further 3 min 90% acetonitrile). 159.5 mg (70% of theory, 99% purity) of the title compound were obtained.

$^1$H-NMR (400 MHz, DMSO-d6) δ[ppm]=10.26 (d, 1H), 9.06 (s, 1H), 8.71 (d, 1H), 8.51 (d, 1H), 7.66-7.56 (m, 2H), 4.47-4.35 (m, 1H), 3.72 (dd, 1H), 3.14 (dd, 1H), 2.73 (dd, 1H), 2.48-2.36 (m, 1H), 2.30 (dd, 1H), 1.28-1.18 (m, 1H), 1.03 (d, 3H), 0.71-0.51 (m, 3H), 0.39-0.30 (m, 1H).

LC-MS (Method 3): $R_t$=2.30 min; MS (ESIpos): m/z=539 [M+H]$^+$

Example 421

1-(2-Chloro-4,6-difluorophenyl)-7-[(4S)-4-hydroxy-2-oxopyrrolidin-1-yl]-4-oxo-N-[(2S)-1-(trifluoromethoxy)propan-2-yl]-1,4-dihydro-1,8-naphthyridine-3-carboxamide

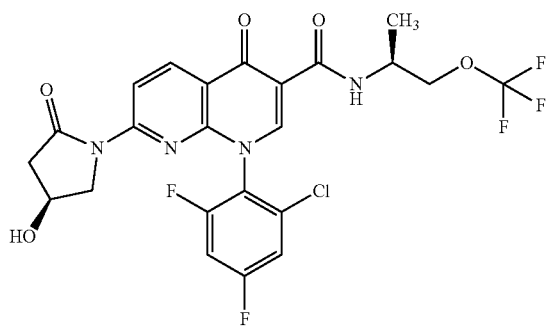 [SMILES: C[C@@H](COC(F)(F)F)NC(=O)c1cn(-c2c(F)cc(F)cc2Cl)c2nc(N3C[C@@H](O)CC3=O)ccc2c1=O]

According to GP2, 80.0 mg (161 µmol) of the compound from Example 112A were reacted with 17.9 mg (177 µmol) of 4-(4S)-4-hydroxypyrrolidin-2-one in the presence of 33.4 mg (242 µmol) of potassium carbonate, 1.8 mg (8.1 µmol) of palladium(II) acetate and 9.3 mg (16 µmol) of Xantphos in 1.6 ml of 1,4-dioxane. Subsequently, 80 mg of N-acetylcysteine were added and the mixture was stirred at RT for 0.5 h. 30 ml of ethyl acetate were added, and the organic phase was washed with saturated aqueous sodium hydrogencarbonate solution, dried over sodium sulphate, filtered and concentrated. The residue was purified by means of preparative HPLC (column: Chromatorex C18, 10 µm, 125×30 mm, solvent: acetonitrile/0.05% formic acid gradient; 0 to 3 min 10% acetonitrile, to 35 min 90% acetonitrile and for a further 3 min 90% acetonitrile). 15.2 mg (17% of theory, 100% purity) of the title compound were obtained.

$^1$H-NMR (400 MHz, DMSO-d6) δ[ppm]=9.85 (dd, 1H), 8.95 (s, 1H), 8.71 (d, 1H), 8.52 (d, 1H), 7.82-7.71 (m, 2H), 5.33 (d, 1H), 4.42-4.14 (m, 4H), 3.69-3.60 (m, 1H), 3.46-3.38 (m, 1H), 2.93 (dd, 1H), 2.37 (d, 1H), 1.27 (dd, 3H).

LC-MS (Method 1): $R_t$=0.98 min; MS (ESIpos): m/z=561 [M+H]$^+$

Example 422

1-(2-Chloro-4,6-difluorophenyl)-7-[3-methyl-2-oxopyrrolidin-1-yl]-4-oxo-N-[(2S)-1,1,1-trifluorobutan-2-yl]-1,4-dihydro-1,8-naphthyridine-3-carboxamide (diastereomer mixture)

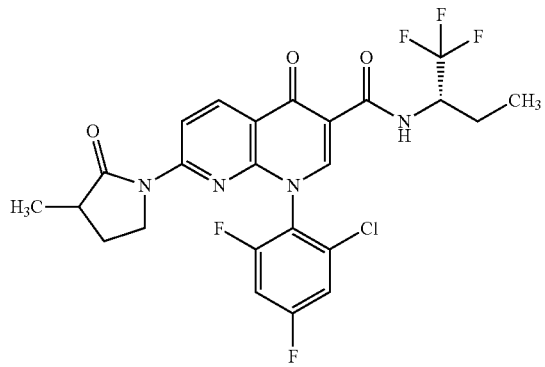 [SMILES: CC[C@H](NC(=O)c1cn(-c2c(F)cc(F)cc2Cl)c2nc(N3CCC(C)C3=O)ccc2c1=O)C(F)(F)F]

According to GP2, 100 mg (208 µmol) of the compound from Example 108C were reacted with 22.7 mg (229 µmol) of methylpyrrolidin-2-one (racemate) in the presence of 43.2 mg (312 µmol) of potassium carbonate, 8.4 mg (37 µmol) of palladium(II) acetate and 43 mg (75 µmol) of Xantphos in 1.9 µl of 1,4-dioxane. Subsequently, the mixture was acidified with 0.5 ml of 1N aqueous hydrochloric acid and the mixture was concentrated. The residue was dissolved in 5 ml of dichloromethane and purified by means of normal phase chromatography (ethyl acetate-cyclohexane gradient). 67.5 mg (59% of theory, 99% purity) of the title compound were obtained.

$^1$H-NMR (400 MHz, DMSO-d6) δ[ppm]=10.13 (d, 1H), 9.04 (s, 1H), 8.72 (d, 1H), 8.55 (d, 1H), 7.80-7.70 (m, 2H), 4.84-4.70 (m, 1H), 3.60-3.48 (m, 1H), 3.45-3.36 (m, 1H), 2.82-2.70 (m, 1H), 2.26-2.14 (m, 1H), 1.96-1.83 (m, 1H), 1.75-1.54 (m, 2H), 1.14 (d, 3H), 1.02-0.94 (m, 3H).

LC-MS (Method 1): $R_t$=1.26 min; MS (ESIpos): m/z=543 [M+H]$^+$ 46 mg of the title compound (diastereomer mixture) were separated into the diastereomers by chiral HPLC (preparative HPLC: column: Daicel Chiralpak IF 5 µm 250×20 mm; eluent: 15% ethanol, 85% isohexane; temperature: 30° C.; flow rate: 15 ml/min; UV detection: 220 nm).

This gave (in the sequence of elution from the column) 35 mg of diastereomer 1 (atropisomer mixture) $R_t$=8.71 min and 16 mg (99% de, atropisomer mixture) of diastereomer 2 $R_t$=9.96/10.69 min.

[Analytical HPLC: column: Daicel Chiralpak IC 5 µm 250×4.6 mm; eluent: 20% ethanol, 80% isohexane; flow rate: 1 ml/min; temp.: 30° C.; UV detection: 220 nm]

Diastereomer 2 was additionally purified by means of preparative HPLC (column: Chromatorex C18, 10 µm, 125×30 mm, solvent: acetonitrile/0.05% formic acid gradient; (0 to 3 min. 10% acetonitrile to 35 min. 90% acetonitrile and a further 3 min. 90% acetonitrile)), and 13.6 mg (12% of theory, 99% purity) of the title compound from Example 423 were obtained.

Diastereomer 1 was purified once again by means of chiral preparative HPLC (column: Daicel Chiralpak IC 5 µm 250×20 mm; eluent: 25% ethanol, 75% isohexane; temperature: 25° C.; flow rate: 15 ml/min; UV detection: 220 nm), and the following were obtained, in the sequence of elution from the column: 10 mg of atropisomer 1 (99% de) $R_t$=10.21 min and 11 mg (96% de) of atropisomer 2 $R_t$=11.11 min.

Atropisomer 1 was additionally purified by means of preparative HPLC (column: Chromatorex C18, 10 μm, 125×30 mm, solvent: acetonitrile/0.05% formic acid gradient; (0 to 3 min. 10% acetonitrile to 35 min. 90% acetonitrile and a further 3 min. 90% acetonitrile)), and 7.8 mg (6.8% of theory, 99% purity) of the title compound from Example 424 were obtained.

Atropisomer 2 was additionally purified by means of preparative HPLC (column: Chromatorex C18, 10 μm, 125×30 mm, solvent: acetonitrile/0.05% formic acid gradient; (0 to 3 min. 10% acetonitrile to 35 min. 90% acetonitrile and a further 3 min. 90% acetonitrile)), and 7.9 mg (6.9% of theory, 99% purity) of the title compound from Example 425 were obtained.

Example 423

1-(2-Chloro-4,6-difluorophenyl)-7-[3-methyl-2-oxopyrrolidin-1-yl]-4-oxo-N-[(2S)-1,1,1-trifluorobutan-2-yl]-1,4-dihydro-1,8-naphthyridine-3-carboxamide (diastereomer 2)

$^1$H-NMR (400 MHz, DMSO-d6) δ[ppm]=10.13 (d, 1H), 9.04 (s, 1H), 8.72 (d, 1H), 8.55 (d, 1H), 7.80-7.70 (m, 2H), 4.84-4.70 (m, 1H), 3.59-3.49 (m, 1H), 3.44-3.35 (m, 1H), 2.82-2.70 (m, 1H), 2.25-2.14 (m, 1H), 1.96-1.84 (m, 1H), 1.75-1.55 (m, 2H), 1.14 (d, 3H), 1.01-0.93 (m, 3H).

LC-MS (Method 1): $R_t$=1.25 min; MS (ESIpos): m/z=543 [M+H]$^+$

Example 424

1-(2-Chloro-4,6-difluorophenyl)-7-[3-methyl-2-oxopyrrolidin-1-yl]-4-oxo-N-[(2S)-1,1,1-trifluorobutan-2-yl]-1,4-dihydro-1,8-naphthyridine-3-carboxamide (atropisomer 1)

$^1$H-NMR (400 MHz, DMSO-d6) δ[ppm]=10.13 (d, 1H), 9.04 (s, 1H), 8.72 (d, 1H), 8.55 (d, 1H), 7.81-7.70 (m, 2H), 4.83-4.71 (m, 1H), 3.57-3.49 (m, 1H), 3.45-3.35 (m, 1H), 2.81-2.71 (m, 1H), 2.25-2.14 (m, 1H), 1.95-1.84 (m, 1H), 1.74-1.55 (m, 2H), 1.14 (d, 3H), 1.02-0.94 (m, 3H).

LC-MS (Method 1): $R_t$=1.26 min; MS (ESIpos): m/z=543 [M+H]$^+$

Example 425

1-(2-Chloro-4,6-difluorophenyl)-7-[3-methyl-2-oxopyrrolidin-1-yl]-4-oxo-N-[(2S)-1,1,1-trifluorobutan-2-yl]-1,4-dihydro-1,8-naphthyridine-3-carboxamide (atropisomer 2)

$^1$H-NMR (400 MHz, DMSO-d6) δ[ppm]=10.13 (d, 1H), 9.03 (s, 1H), 8.72 (d, 1H), 8.55 (d, 1H), 7.80-7.69 (m, 2H), 4.83-4.70 (m, 1H), 3.60-3.51 (m, 1H), 3.42-3.35 (m, 1H), 2.82-2.70 (m, 1H), 2.25-2.14 (m, 1H), 1.97-1.84 (m, 1H), 1.75-1.55 (m, 2H), 1.14 (d, 3H), 1.03-0.94 (m, 3H).

LC-MS (Method 1): $R_t$=1.26 min; MS (ESIpos): m/z=543 [M+H]$^+$

Example 426

1-(2,4-Difluorophenyl)-7-[2-methyl-5-oxopyrrolidin-1-yl]-4-oxo-N-[(2R)-1,1,1-trifluorobutan-2-yl]-1,4-dihydro-1,8-naphthyridine-3-carboxamide (diastereomer mixture)

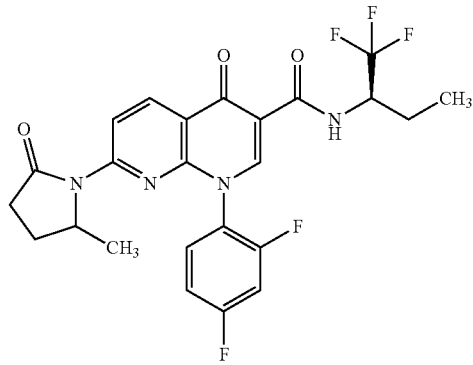 [SMILES: CC[C@@H](NC(=O)c1cn(-c2ccc(F)cc2F)c2nc(N3C(=O)CCC3C)ccc2c1=O)C(F)(F)F]

According to GP2, 200 mg (449 μmol) of the compound from Example 67A were reacted with 48.9 mg (494 μmol) of 5-methylpyrrolidin-2-one (racemate) in the presence of 93.0 mg (673 μmol) of potassium carbonate, 5.0 mg (22 μmol) of palladium(II) acetate and 26 mg (45 μmol) of Xantphos in 4.4 ml of 1,4-dioxane. Subsequently, 80 mg of N-acetylcysteine were added and the mixture was stirred at room temperature for a further 30 min. The reaction mixture was admixed with 30 ml of ethyl acetate and washed with saturated aqueous sodium hydrogencarbonate solution, dried over sodium sulphate, filtered and concentrated. The residue was purified by means of preparative HPLC (column: Chromatorex C18, 10 μm, 125×30 mm, solvent: acetonitrile/0.05% formic acid gradient; 0 to 3 min 10% acetonitrile, to 35 min 90% acetonitrile and for a further 3 min 90% acetonitrile). 120 mg (53% of theory, 100% purity) of the title compound were obtained.

$^1$H-NMR (400 MHz, DMSO-d6) δ[ppm]=10.22 (d, 1H), 8.87 (t, 1H), 8.70 (dd, 1H), 8.49 (dd, 1H), 7.93-7.84 (m, 1H), 7.68-7.60 (m, 1H), 7.41-7.33 (m, 1H), 4.83-4.70 (m, 1H), 4.21-4.09 (m, 1H), 2.87-2.73 (m, 1H), 2.24-2.08 (m, 1H), 1.96-1.84 (m, 1H), 1.73-1.59 (m, 2H), 1.07 (d, 1.5H), 0.98 (t, 3H), 0.92 (d, 1.5H).

LC-MS (Method 1): $R_t$=1.17 min; MS (ESIpos): m/z=509 [M+H]$^+$ 120 mg of the title compound (diastereomer mixture) were separated into the diastereomers by chiral HPLC (preparative HPLC: column: Daicel Chiralpak AZ-H 5 μm 250×30 mm; eluent: 60% ethanol, 40% isohexane; temperature: 23° C.; flow rate: 50 ml/min; UV detection: 220 nm).

This gave (in the sequence of elution from the column) diastereomer 1 (99% de) $R_t$=1.41 min and diastereomer 2 (99% de) $R_t$=2.24 min.

[Analytical HPLC: column: Daicel Chiralpak AZ-3 3 μm 50×4.6 mm; eluent: 50% ethanol, 50% isohexane; flow rate: 1 ml/min; UV detection: 220 nm]

Diastereomer 1 was additionally purified by means of preparative HPLC (column: Chromatorex C18, 10 μm, 125×30 mm, solvent: acetonitrile/0.05% formic acid gradient; (0 to 3 min. 10% acetonitrile to 35 min. 90% acetonitrile and a further 3 min. 90% acetonitrile)), and 41 mg (18% of theory, 99% purity) of the title compound from Example 427 were obtained.

Diastereomer 2 was additionally purified by means of preparative HPLC (column: Chromatorex C18, 10 µm, 125× 30 mm, solvent: acetonitrile/0.05% formic acid gradient; (0 to 3 min. 10% acetonitrile to 35 min. 90% acetonitrile and a further 3 min. 90% acetonitrile)), and 35.6 mg (16% of theory, 99% purity) of the title compound from Example 428 were obtained.

Example 427

1-(2,4-Difluorophenyl)-7-[2-methyl-5-oxopyrrolidin-1-yl]-4-oxo-N-[(2R)-1,1,1-trifluorobutan-2-yl]-1,4-dihydro-1,8-naphthyridine-3-carboxamide (diastereomer 1)

$^1$H-NMR (400 MHz, DMSO-d6) δ[ppm]=10.21 (d, 1H), 8.87 (s, 1H), 8.70 (dd, 1H), 8.49 (dd, 1H), 7.92-7.84 (m, 1H), 7.68-7.60 (m, 1H), 7.40-7.33 (m, 1H), 4.84-4.71 (m, 1H), 4.21-4.09 (m, 1H), 2.87-2.73 (m, 1H), 2.24-2.09 (m, 1H), 1.95-1.83 (m, 1H), 1.73-1.60 (m, 2H), 1.07 (d, 1.5H), 0.98 (t, 3H), 0.92 (d, 1.5H).

LC-MS (Method 1): $R_t$=1.17 min; MS (ESIpos): m/z=509 [M+H]$^+$

Example 428

1-(2,4-Difluorophenyl)-7-[2-methyl-5-oxopyrrolidin-1-yl]-4-oxo-N-[(2R)-1,1,1-trifluorobutan-2-yl]-1,4-dihydro-1,8-naphthyridine-3-carboxamide (diastereomer 2)

$^1$H-NMR (400 MHz, DMSO-d6) δ[ppm]=10.22 (d, 1H), 8.87 (d, 1H), 8.70 (dd, 1H), 8.49 (dd, 1H), 7.93-7.83 (m, 1H), 7.67-7.60 (m, 1H), 7.41-7.33 (m, 1H), 4.84-4.70 (m, 1H), 4.21-4.09 (m, 1H), 2.87-2.73 (m, 1H), 2.25-2.06 (m, 1H), 1.96-1.84 (m, 1H), 1.74-1.59 (m, 2H), 1.08 (d, 1.5H), 0.98 (t, 3H), 0.93 (d, 1.5H).

LC-MS (Method 1): $R_t$=1.17 min; MS (ESIpos): m/z=509 [M+H]$^+$

Example 429

1-(2-Chloro-4,6-difluorophenyl)-N-[(1S)-1-cyclopropyl-2,2,2-trifluoroethyl]-7-[4-methyl-2-oxopyrrolidin-1-yl]-4-oxo-1,4-dihydro-1,8-naphthyridine-3-carboxamide (diastereomer mixture)

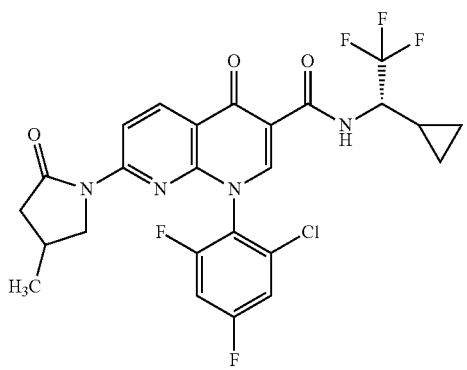 [SMILES: CC1CC(=O)N(c2ccc3c(=O)c(C(=O)N[C@@H](C4CC4)C(F)(F)F)cn(-c4c(F)cc(F)cc4Cl)c3n2)C1]

According to GP2, 200 mg (406 µmol) of the compound from Example 110A were reacted with 44.3 mg (447 µmol) of 4-methylpyrrolidin-2-one (racemate) in the presence of 84.2 mg (609 µmol) of potassium carbonate, 4.6 mg (20 µmol) of palladium(II) acetate and 24 mg (41 µmol) of Xantphos in 3.6 ml of 1,4-dioxane. Subsequently, the mixture was acidified with 1N aqueous hydrochloric acid and the mixture was concentrated. The residue was dissolved in 8 ml of dichloromethane and purified by means of normal phase chromatography (ethyl acetate-cyclohexane gradient). 183 mg (80% of theory, 99% purity) of the title compound were obtained.

$^1$H-NMR (400 MHz, DMSO-d6) δ[ppm]=10.27 (d, 1H), 9.03 (s, 1H), 8.71 (d, 1H), 8.51 (d, 1H), 7.81-7.71 (m, 2H), 4.47-4.33 (m, 1H), 3.71-3.62 (m, 1H), 3.13-3.03 (m, 1H), 2.72 (dd, 1H), 2.46-2.36 (m, 1H), 2.29 (dd, 1H), 1.29-1.18 (m, 1H), 1.01 (d, 3H), 0.72-0.51 (m, 3H), 0.40-0.30 (m, 1H).

LC-MS (Method 3): $R_t$=1.26 min; MS (ESIpos): m/z=555 [M+H]$^+$

Example 430

1-(2-Chloro-4,6-difluorophenyl)-7-[(2R)-2-(hydroxymethyl)-5-oxopyrrolidin-1-yl]-4-oxo-N-[(2S)-1,1,1-trifluorobutan-2-yl]-1,4-dihydro-1,8-naphthyridine-3-carboxamide

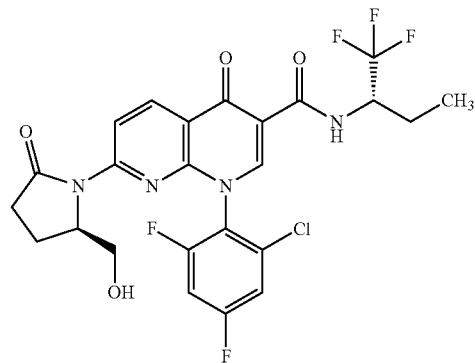 [SMILES: CC[C@H](NC(=O)c1cn(-c2c(F)cc(F)cc2Cl)c2nc(N3C(=O)CC[C@@H]3CO)ccc2c1=O)C(F)(F)F]

According to GP2, 95.2 mg (198 µmol) of the compound from Example 108C were reacted with 50.0 mg (218 µmol) of the compound from Example 139A in the presence of 41.1 mg (297 µmol) of potassium carbonate, 2.2 mg (10 µmol) of palladium(II) acetate and 11 mg (20 µmol) of Xantphos in 2 ml of 1,4-dioxane. Subsequently, 100 mg of N-acetylcysteine were added and the mixture was stirred at room temperature for a further 30 min. The reaction mixture was admixed with 30 ml of ethyl acetate and washed with saturated aqueous sodium hydrogencarbonate solution, dried over magnesium sulphate, filtered and concentrated. The residue was purified by means of preparative HPLC (column: Chromatorex C18, 10 µm, 125×30 mm, solvent: acetonitrile/0.05% formic acid gradient; 0 to 3 min 10% acetonitrile, to 35 min 90% acetonitrile and for a further 3 min 90% acetonitrile). The product-containing fractions were combined and the solvent was removed under reduced pressure. The residue was taken up in 1.5 ml of THF and, while cooling with an ice bath, 57.5 mg (198 µmol) of tris(dimethylamino)sulphur trimethylsilyldifluoride were added. The mixture was stirred at room temperature for a further 1 h. 15 ml of water were added to the reaction solution, and the reaction solution was extracted three times

493 with 15 ml of ethyl acetate. The combined organic phases were washed with saturated aqueous sodium chloride solution, dried over magnesium sulphate, filtered and concentrated. 12 mg (10% of theory, 90% purity) of the title compound were obtained.

$^1$H-NMR (400 MHz, DMSO-d6) δ[ppm]=10.13 (dd, 1H), 9.05 (d, 1H), 8.71 (d, 1H), 8.59 (d, 1H), 7.78-7.68 (m, 2H), 4.84-4.69 (m, 2H), 4.07-4.00 (m, 1H), 3.51-3.40 (m, 1H), 3.22-3.11 (m, 0.5H), 2.81-2.69 (m, 1H), 2.45-2.34 (m, 0.5H), 2.19-1.83 (m, 3H), 1.75-1.58 (m, 1H), 1.02-0.93 (m, 3H).

LC-MS (Method 3): $R_t$=1.96/1.99 min; MS (ESIpos): m/z=559 [M+H]$^+$

Example 431

1-(2,4-Difluorophenyl)-7-[3-methyl-2-oxopyrrolidin-1-yl]-4-oxo-N-[(2R)-1,1,1-trifluorobutan-2-yl]-1,4-dihydro-1,8-naphthyridine-3-carboxamide (diastereomer mixture)

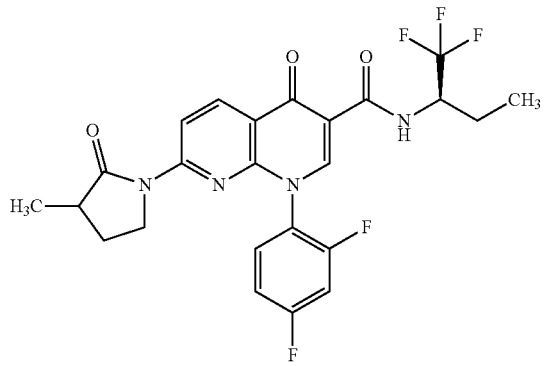 [SMILES: CC[C@@H](NC(=O)c1cn(-c2ccc(F)cc2F)c2nc(N3CCC(C)C3=O)ccc2c1=O)C(F)(F)F]

According to GP2, 150 mg (336 µmol) of the compound from Example 67A were reacted with 36.7 mg (370 µmol) of 3-methylpyrrolidinone in the presence of 69.8 mg (505 µmol) of potassium carbonate, 3.8 mg (17 µmol) of palladium(II) acetate and 19 mg (34 µmol) of Xantphos in 3.4 ml of 1,4-dioxane. Subsequently, the reaction mixture was concentrated and admixed with water and acidified with 1 M aqueous hydrochloric acid. The mixture was extracted three times with 20 ml of ethyl acetate. The combined organic phases were dried over magnesium sulphate, filtered and concentrated by rotary evaporation. The residue was purified by means of normal phase chromatography (ethyl acetate-cyclohexane gradient). 113 mg (66% of theory, 100% purity) of the title compound were obtained.

$^1$H-NMR (400 MHz, DMSO-d6) δ[ppm]=10.22 (d, 1H), 8.85 (s, 1H), 8.70 (d, 1H), 8.53 (dd, 1H), 7.91-7.82 (m, 1H), 7.66-7.57 (m, 1H), 7.40-7.32 (m, 1H), 4.84-4.70 (m, 1H), 3.66-3.52 (m, 1H), 3.48-3.34 (m, 1H), 2.83-2.68 (m, 1H), 2.26-2.15 (m, 1H), 1.95-1.84 (m, 1H), 1.73-1.52 (m, 2H), 1.17-1.11 (m, 3H), 0.98 (t, 3H).

LC-MS (Method 3): $R_t$=2.32 min; MS (ESIpos): m/z=509 [M+H]$^+$

494

Example 432

1-(2,4-Difluorophenyl)-7-[4-methyl-2-oxoimidazolidin-1-yl]-4-oxo-N-[(2R)-1,1,1-trifluorobutan-2-yl]-1,4-dihydro-1,8-naphthyridine-3-carboxamide (diastereomer 1)

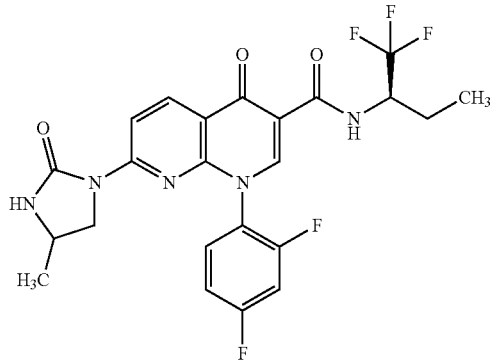 [SMILES: CC[C@@H](NC(=O)c1cn(-c2ccc(F)cc2F)c2nc(N3CC(C)NC3=O)ccc2c1=O)C(F)(F)F]

According to GP2, 250 mg (561 µmol) of the compound from Example 67A were reacted with 61.7 mg (617 µmol) of 4-methylimidazolidin-2-one (racemate) in the presence of 116 mg (841 µmol) of potassium carbonate, 6.3 mg (28 µmol) of palladium(II) acetate and 32 mg (56 µmol) of Xantphos in 5 ml of 1,4-dioxane. Subsequently, 250 mg of N-acetylcysteine were added and the mixture was stirred at room temperature for a further 30 min. The reaction mixture was admixed with 30 ml of ethyl acetate and washed with saturated aqueous sodium hydrogencarbonate solution, dried over sodium sulphate, filtered and concentrated. The residue was taken up in 4 ml of acetonitrile and purified by means of preparative HPLC (column: Chromatorex C18, 10 µm, 125×30 mm, solvent: acetonitrile/0.05% formic acid gradient; 0 to 3 min 10% acetonitrile, to 35 min 90% acetonitrile and for a further 3 min 90% acetonitrile). Purification was additionally effected by means of normal phase chromatography (dichloromethane-methanol 95/5) and another preparative HPLC.

35 mg of the crude product (diastereomer and regioisomer mixture) were separated into the regioisomers and diastereomers by chiral HPLC (preparative HPLC: column: Daicel Chiralpak AD-H 5 µm 250×20 mm; eluent: 20% ethanol, 80% isohexane; temperature: 30° C.; flow rate: 15 ml/min; UV detection: 220 nm).

[Analytical HPLC: column: Daicel Chiralpak IB 5 µm 250×4.6 mm; eluent: 15% ethanol, 85% isohexane; flow rate: 1 ml/min; temp.: 25° C.; UV detection: 220 nm]

This gave (in the sequence of elution from the column) 10 mg of the title compound (diastereomer 1 99% de) $R_t$=10.21 min, 10 mg of diastereomer 2 from Example 433 (99% de) $R_t$=12.52 min and 4 mg of regiosisomer from Example 434 (diastereomer mixture) Rt=10.93/14.93 min.

$^1$H-NMR (400 MHz, DMSO-d6) δ[ppm]=10.31 (d, 1H), 8.78 (s, 1H), 8.56 (d, 1H), 8.41 (d, 1H), 7.90-7.83 (m, 1H), 7.80 (br. s, 1H), 7.65-7.55 (m, 1H), 7.39-7.31 (m, 1H), 4.83-4.69 (m, 1H), 3.81-3.65 (m, 2H), 3.14-3.03 (m, 1H), 1.95-1.84 (m, 1H), 1.72-1.59 (m, 1H), 1.18-1.08 (m, 3H), 0.97 (t, 3H).

LC-MS (Method 1): $R_t$=1.05 min; MS (ESIpos): m/z=510 [M+H]$^+$

Example 433

1-(2,4-Difluorophenyl)-7-[4-methyl-2-oxoimidazolidin-1-yl]-4-oxo-N-[(2R)-1,1,1-trifluorobutan-2-yl]-1,4-dihydro-1,8-naphthyridine-3-carboxamide (diastereomer 2)

$^1$H-NMR (400 MHz, DMSO-d6) δ[ppm]=10.31 (d, 1H), 8.78 (s, 1H), 8.56 (d, 1H), 8.41 (d, 1H), 7.91-7.82 (m, 1H), 7.80 (br. s, 1H), 7.66-7.55 (m, 1H), 7.39-7.31 (m, 1H), 4.82-4.70 (m, 1H), 3.80-3.66 (m, 2H), 3.13-3.02 (m, 1H), 1.95-1.84 (m, 1H), 1.72-1.60 (m, 1H), 1.18-1.07 (m, 3H), 0.97 (t, 3H).

LC-MS (Method 1): $R_t$=1.05 min; MS (ESIpos): m/z=510 [M+H]$^+$

Example 434

1-(2,4-Difluorophenyl)-7-[5-methyl-2-oxoimidazolidin-1-yl]-4-oxo-N-[(2R)-1,1,1-trifluorobutan-2-yl]-1,4-dihydro-1,8-naphthyridine-3-carboxamide (diastereomer mixture)

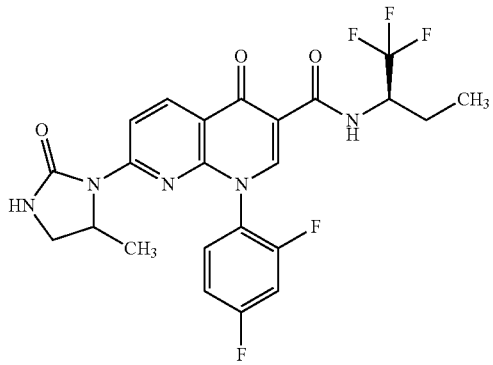 [SMILES: CC[C@@H](NC(=O)c1cn(-c2ccc(F)cc2F)c2nc(N3C(=O)NCC3C)ccc2c1=O)C(F)(F)F]

The title compound was obtained as a regioisomer from Example 432.

$^1$H-NMR (400 MHz, DMSO-d6) δ[ppm]=10.31 (d, 1H), 8.82-8.78 (m, 1H), 8.55 (d, 1H), 8.42-8.36 (m, 1H), 7.92-7.83 (m, 1H), 7.66-7.57 (m, 2H), 7.39-7.32 (m, 1H), 4.81-4.71 (m, 1H), 4.17-4.04 (m, 1H), 3.56-3.44 (m, 1H), 2.91 (dd, 1H), 1.95-1.83 (m, 1H), 1.72-1.61 (m, 1H), 1.08 (d, 1.5H), 0.98 (t, 3H), 0.92 (d, 1.5H).

LC-MS (Method 1): $R_t$=1.04 min; MS (ESIpos): m/z=510 [M+H]$^+$

Example 435

N-[(1S)-1-Cyclopropyl-2,2-difluoroethyl]-7-[(4S)-4-hydroxy-2-oxopyrrolidin-1-yl]-4-oxo-1-(2,4,6-trifluorophenyl)-1,4-dihydro-1,8-naphthyridine-3-carboxamide

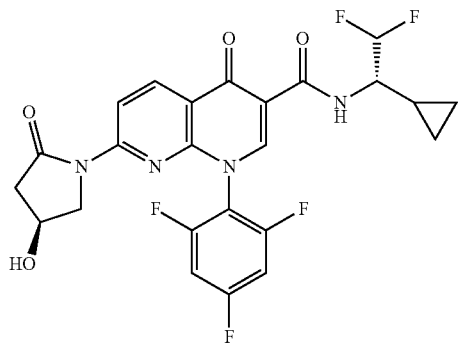 [SMILES: O=C(N[C@H](C(F)F)C1CC1)c1cn(-c2c(F)cc(F)cc2F)c2nc(N3C[C@@H](O)CC3=O)ccc2c1=O]

According to GP1, 40 mg (95 μmol) of the compound from Example 117A were reacted with 16.5 mg (105 μmol) of the compound from Example 140D in the presence of 36 mg (95 μmol) of HATU and 40.0 μl (229 μmol) of N,N-diisopropylethylamine in 0.55 ml of dimethylformamide. The reaction mixture was acidified with 1 ml of aqueous 1N hydrochloric acid, diluted with 1 ml of acetonitrile and purified by means of preparative HPLC (column: Chromatorex C18, 10 μm, 125×30 mm, solvent: acetonitrile/0.1% formic acid gradient; 0 to 5 min 10% acetonitrile, over 14 min to 90% acetonitrile and for a further 4 min 90% acetonitrile). 36.9 mg (72% of theory, 97.5% purity) of the title compound were obtained.

$^1$H-NMR (400 MHz, DMSO-d6) δ[ppm]=10.04 (d, 1H), 9.02 (s, 1H), 8.72 (d, 1H), 8.54 (d, 1H), 7.66-7.56 (m, 2H), 6.25 (dt, 1H), 5.33 (d, 1H), 4.32-4.26 (m, 1H), 4.03-3.88 (m, 1H), 3.70 (dd, 1H), 3.48 (d, 1H), 2.94 (dd, 1H), 2.38 (d, 1H), 1.16-1.04 (m, 1H), 0.63-0.41 (m, 3H), 0.37-0.29 (m, 1H).

LC-MS (Method 3): $R_t$=1.74 min; MS (ESIpos): nm/z=523 [M+H]$^+$.

Example 436

N-[(1S)-1-Cyclopropyl-2,2,2-trifluoroethyl]-7-[5-methyl-2-oxo-1,3-oxazolidin-3-yl]-4-oxo-1-(2,4,6-trifluorophenyl)-1,4-dihydro-1,8-naphthyridine-3-carboxamide (diastereomer mixture)

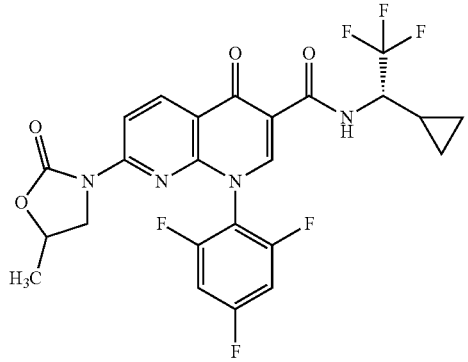 [SMILES: CC1CN(c2ccc3c(=O)c(C(=O)N[C@@H](C4CC4)C(F)(F)F)cn(-c4c(F)cc(F)cc4F)c3n2)C(=O)O1]

According to GP2, 50.0 mg (105 µmol) of the compound from Example 126A were reacted with 12.8 mg (126 µmol) of 5-methyl-1,3-oxazolidin-2-one (racemate) in the presence of 21.8 mg (158 µmol) of potassium carbonate, 2.4 mg (11 µmol) of palladium(II) acetate and 12 mg (21 µmol) of Xantphos in 0.7 ml of 1,4-dioxane. Subsequently, the mixture was diluted with 0.1 ml of 1N aqueous hydrochloric acid and 3 ml of acetonitrile and purified by means of preparative HPLC (column: Chromatorex C18, 10 µm, 125×30 mm, solvent: acetonitrile/0.05% formic acid gradient; 0 to 3 min 10% acetonitrile, to 35 min 90% acetonitrile and for a further 3 min 90% acetonitrile). 40.4 mg (70% of theory, 99% purity) of the title compound were obtained.

$^1$H-NMR (400 MHz, DMSO-d6) δ[ppm]=10.25 (d, 1H), 9.05 (s, 1H), 8.73 (d, 1H), 8.34 (d, 1H), 7.64-7.53 (m, 2H), 4.83-4.73 (m, 1H), 4.46-4.34 (m, 1H), 3.91 (dd, 1H), 1.36 (d, 3H), 1.29-1.19 (m, 1H), 0.71-0.52 (m, 3H), 0.39-0.30 (m, 1H).

LC-MS (Method 3): $R_t$=2.18 min; MS (ESIpos): m/z=541 [M+H]$^+$.

Example 437

N-[(1S)-1-Cyclopropyl-2,2,2-trifluoroethyl]-7-[(4R)-4-methyl-2-oxoimidazolidin-1-yl]-4-oxo-1-(2,4,6-trifluorophenyl)-1,4-dihydro-1,8-naphthyridine-3-carboxamide

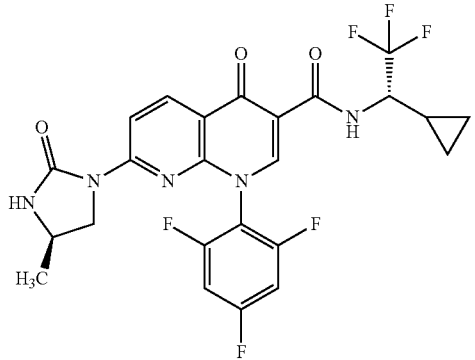 [SMILES: C[C@@H]1CN(c2ccc3c(=O)c(C(=O)N[C@@H](C4CC4)C(F)(F)F)cn(-c4c(F)cc(F)cc4F)c3n2)C(=O)N1]

To a solution of 168 mg (268 µmol) of the compound from Example 141B in 5.9 ml of dimethylformamide were added, at room temperature, 37.0 mg (268 µmol) of potassium carbonate and 109 mg (699 µmol) of 1,1'-carbonyldiimidazole. The mixture was stirred for a further 48 h. Subsequently, the mixture was diluted with 0.1 ml of 1N aqueous hydrochloric acid and 1 ml of acetonitrile and purified by means of preparative HPLC (column: Chromatorex C18, 10 µm, 125×30 mm, solvent: acetonitrile/0.05% formic acid gradient; 0 to 3 min 10% acetonitrile, to 35 min 90% acetonitrile and for a further 3 min 90% acetonitrile). 122 mg (77% of theory, 99% purity) of the title compound were obtained.

$^1$H-NMR (400 MHz, DMSO-d6) δ[ppm]=10.35 (d, 1H), 8.98 (s, 1H), 8.57 (d, 1H), 8.44 (d, 1H), 7.83 (s, 1H), 7.63-7.54 (m, 2H), 4.46-4.34 (m, 1H), 3.81-3.69 (m, 2H), 3.15-3.04 (m, 1H), 1.28-1.17 (m, 1H), 1.12 (d, 3H), 0.71-0.50 (m, 3H), 0.39-0.30 (m, 1H).

LC-MS (Method 3): $R_t$=2.04 min; MS (ESIpos): m/z=540 [M+H]$^+$.

Example 438

N-[1-Cyclopropyl-3,3,3-trifluoropropyl]-7-[(3R,4R)-3,4-dihydroxypyrrolidin-1-yl]-4-oxo-1-(2,4,6-trifluorophenyl)-1,4-dihydro-1,8-naphthyridine-3-carboxamide (diastereomer mixture)

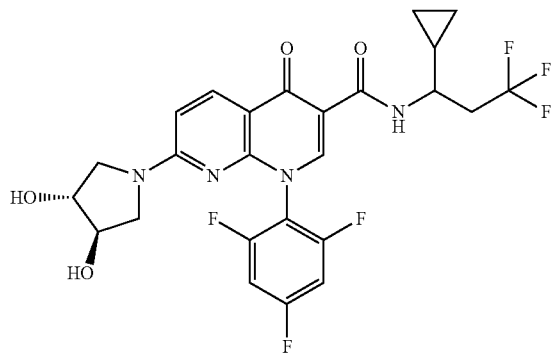 [SMILES: O=C(NC(CC(F)(F)F)C1CC1)c1cn(-c2c(F)cc(F)cc2F)c2nc(N3C[C@@H](O)[C@H](O)C3)ccc2c1=O]

According to GP1, 100 mg (237 µmol) of the compound from Example 121A were reacted with 54.0 mg (285 µmol) of 1-cyclopropyl-3,3,3-trifluoropropan-1-amine hydrochloride (racemate) in the presence of 108 mg (285 µmol) of HATU and 104 µl (593 µmol) of N,N-diisopropylethylamine in 2.4 ml of dimethylformamide. The mixture was diluted with 2 ml of 1 M aqueous hydrochloric acid and 2 ml of DMSO and purified by means of preparative HPLC (column: Chromatorex C18, 10 µm, 125×30 mm, solvent: acetonitrile/0.05% formic acid gradient; 0 to 3 min 10% acetonitrile, to 15 min 90% acetonitrile and for a further 3 min 90% acetonitrile). 111 mg (84% of theory, 100% purity) of the title compound were obtained.

$^1$H-NMR (400 MHz, DMSO-d$_6$): δ [ppm]=10.14 (d, 1H), 8.70 (s, 1H), 8.27 (d, 1H), 7.60-7.51 (m, 2H), 6.75 (d, 1H), 5.23 (d, 1H), 5.13 (d, 1H), 4.05 (br. s, 1H), 3.92 (br. s, 1H), 3.84-3.73 (m, 1H), 3.65-3.56 (m, 1H), 3.25 (dd, 1H), 3.07 (d, 1H), 2.85-2.59 (m, 2H), 1.21-1.10 (m, 1H), 0.57-0.43 (m, 2H), 0.39-0.24 (m, 2H).

LC-MS (Method 1): $R_t$=0.91 min; 557 [M+H]$^+$.

110 mg of the title compound (diastereomer mixture) were separated into the diastereomers by chiral HPLC (preparative HPLC: column: Daicel Chiralpak AD-H 5 µm 250×20 mm; eluent: 20% ethanol, 80% n-heptane; temperature: 23° C.; flow rate: 20 ml/min; UV detection: 220 nm).

This gave (in the sequence of elution from the column) 38.7 mg of diastereomer 1 (99% de) $R_t$=2.49 min and 41.0 mg (92% de) of diastereomer 2 $R_t$=3.09 min.

[Analytical HPLC: column: Daicel IE-3 5 µm 50×4.6 mm; eluent: 20% ethanol, 80% isohexane; UV detection: 220 nm].

Diastereomer 1 was additionally purified by means of preparative HPLC (column: Chromatorex C18, 10 µm, 125×30 mm, solvent: acetonitrile/0.1% formic acid gradient; (0 to 5 min. 10% acetonitrile, over 14 min. to 90% acetonitrile and a further 4 min. 90% acetonitrile)), and 35.4 mg (27% of theory, 100% purity) of the title compound from Example 439 were obtained.

Diastereomer 2 was additionally purified by means of preparative HPLC (column: Chromatorex C18, 10 µm, 125×30 mm, solvent: acetonitrile/0.1% formic acid gradient; (0 to 5 min. 10% acetonitrile, over 14 min. to 90% acetonitrile and a further 4 min. 90% acetonitrile)), and 37.1 mg (28% of theory, 100% purity) of the title compound from Example 440 were obtained.

Example 439

N-[1-Cyclopropyl-3,3,3-trifluoropropyl]-7-[(3R,4R)-3,4-dihydroxypyrrolidin-1-yl]-4-oxo-1-(2,4,6-trifluorophenyl)-1,4-dihydro-1,8-naphthyridine-3-carboxamide (diastereomer 1)

$^1$H-NMR (400 MHz, DMSO-d$_6$): δ [ppm]=10.14 (d, 1H), 8.70 (s, 1H), 8.27 (d, 1H), 7.60-7.51 (m, 2H), 6.76 (d, 1H), 5.23 (d, 1H), 5.14 (d, 1H), 4.05 (br. s, 1H), 3.92 (br. s, 1H), 3.84-3.74 (m, 1H), 3.65-3.57 (m, 1H), 3.25 (dd, 1H), 3.06 (d, 1H), 2.85-2.60 (m, 2H), 1.20-1.10 (m, 1H), 0.57-0.43 (m, 2H), 0.39-0.25 (m, 2H).

LC-MS (Method 1): R$_t$=0.90 min; 557 [M+H]$^+$.

Example 440

N-[1-Cyclopropyl-3,3,3-trifluoropropyl]-7-[(3R,4R)-3,4-dihydroxypyrrolidin-1-yl]-4-oxo-1-(2,4,6-trifluorophenyl)-1,4-dihydro-1,8-naphthyridine-3-carboxamide (diastereomer 2)

$^1$H-NMR (400 MHz, DMSO-d$_6$): δ [ppm]=10.14 (d, 1H), 8.70 (s, 1H), 8.26 (d, 1H), 7.60-7.51 (m, 2H), 6.76 (d, 1H), 5.23 (d, 1H), 5.14 (d, 1H), 4.05 (br. s, 1H), 3.92 (br. s, 1H), 3.83-3.74 (m, 1H), 3.64-3.57 (m, 1H), 3.25 (dd, 1H), 3.07 (d, 1H), 2.82-2.60 (m, 2H), 1.20-1.10 (m, 1H), 0.57-0.43 (m, 2H), 0.39-0.25 (m, 2H).

LC-MS (Method 1): R$_t$=0.90 min; 557 [M+H]$^+$.

Example 441

N-[2-Cyclopropyl-1,1,1-trifluoropropan-2-yl]-7-[(3R,4R)-3,4-dihydroxypyrrolidin-1-yl]-4-oxo-1-(2,4,6-trifluorophenyl)-1,4-dihydro-1,8-naphthyridine-3-carboxamide (diastereomer mixture)

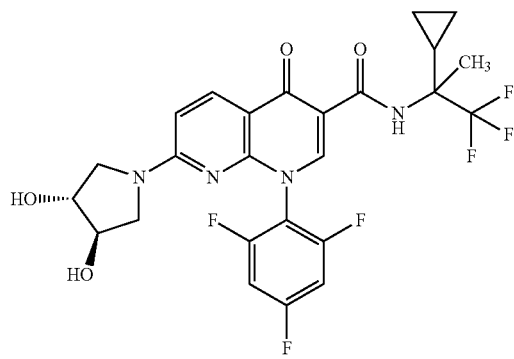 [SMILES: CC(NC(=O)c1cn(-c2c(F)cc(F)cc2F)c2nc(N3C[C@@H](O)[C@H](O)C3)ccc2c1=O)(C1CC1)C(F)(F)F]

According to GP1, 100 mg (237 μmol) of the compound from Example 121A were reacted with 36.3 mg (237 μmol) of 2-cyclopropyl-1,1,1-trifluoropropan-2-amine (racemate) in the presence of 108 mg (285 μmol) of HATU and 104 μl (593 μmol) of N,N-diisopropylethylamine in 3.3 ml of dimethylformamide. The mixture was diluted with 1 ml of 1 M aqueous hydrochloric acid and 2 ml of DMSO and purified by means of preparative HPLC (column: Chromatorex C18, 10 μm, 125×30 mm, solvent: acetonitrile/0.05% formic acid gradient; 0 to 3 min 10% acetonitrile, to 15 min 90% acetonitrile and for a further 3 min 90% acetonitrile). 71.1 mg (54% of theory, 100% purity) of the title compound were obtained.

$^1$H-NMR (400 MHz, DMSO-d$_6$): δ [ppm]=10.38 (s, 1H), 8.73 (s, 1H), 8.28 (d, 1H), 7.61-7.52 (m, 2H), 6.77 (d, 1H), 5.22 (d, 1H), 5.14 (d, 1H), 4.05 (br. s, 1H), 3.92 (br. s, 1H), 3.61 (dd, 1H), 3.25 (dd, 1H), 3.07 (d, 1H), 1.60 (s, 3H), 1.45-1.37 (m, 1H), 0.72-0.66 (m, 1H), 0.59-0.46 (m, 3H).

LC-MS (Method 1): R$_t$=0.96 min; 557 [M+H]$^+$.

70 mg of the title compound (diastereomer mixture) were separated into the diastereomers by chiral HPLC (preparative HPLC: column: Daicel Chiralpak IB 5 μm 250×20 mm; eluent: 25% isopropanol, 75% n-heptane; temperature: 30° C.; flow rate: 15 ml/min; UV detection: 220 nm).

This gave (in the sequence of elution from the column) 33.0 mg of diastereomer 1 (99% de) R$_t$=4.61 min and 32.0 mg (98.5% de) of diastereomer 2 R$_t$=5.24 min.

[Analytical HPLC: column: Daicel Chiralpak IB 5 μm 250×4.6 mm; eluent: 30% isopropanol, 70% n-heptane; flow rate: 1.0 ml/min; temp.: 35° C.; UV detection: 220 nm]

Diastereomer 1 was additionally obtained by means of preparative HPLC (0.1% formic acid; water-acetonitrile gradient), and 29.2 mg (22% of theory, 100% purity) of the title compound from Example 442 were obtained.

Diastereomer 2 was additionally obtained by means of preparative HPLC (0.1% formic acid; water-acetonitrile gradient), and 30.7 mg (23% of theory, 100% purity) of the title compound from Example 443 were obtained.

Example 442

N-[2-Cyclopropyl-1,1,1-trifluoropropan-2-yl]-7-[(3R,4R)-3,4-dihydroxypyrrolidin-1-yl]-4-oxo-1-(2,4,6-trifluorophenyl)-1,4-dihydro-1,8-naphthyridine-3-carboxamide (diastereomer 1)

$^1$H-NMR (400 MHz, DMSO-d$_6$): δ [ppm]=10.38 (s, 1H), 8.73 (s, 1H), 8.29 (d, 1H), 7.61-7.51 (m, 2H), 6.77 (d, 1H), 5.23 (d, 1H), 5.14 (d, 1H), 4.05 (br. s, 1H), 3.92 (br. s, 1H), 3.61 (dd, 1H), 3.25 (dd, 1H), 3.07 (d, 1H), 1.60 (s, 3H), 1.45-1.36 (m, 1H), 0.73-0.65 (m, 1H), 0.60-0.45 (m, 3H).

LC-MS (Method 3): R$_t$=1.82 min; 557 [M+H]$^+$.

Example 443

N-[2-Cyclopropyl-1,1,1-trifluoropropan-2-yl]-7-[(3R,4R)-3,4-dihydroxypyrrolidin-1-yl]-4-oxo-1-(2,4,6-trifluorophenyl)-1,4-dihydro-1,8-naphthyridine-3-carboxamide (diastereomer 1)

$^1$H-NMR (400 MHz, DMSO-d$_6$): δ [ppm]=10.38 (s, 1H), 8.73 (s, 1H), 8.29 (d, 1H), 7.61-7.51 (m, 2H), 6.76 (d, 1H), 5.23 (d, 1H), 5.14 (d, 1H), 4.05 (br. s, 1H), 3.93 (br. s, 1H), 3.61 (dd, 1H), 3.25 (dd, 1H), 3.06 (d, 1H), 1.60 (s, 3H), 1.46-1.37 (m, 1H), 0.73-0.64 (m, 1H), 0.61-0.45 (m, 3H).

LC-MS (Method 3): R$_t$=1.82 min; 557 [M+H]$^+$.

Example 444

N-[(1S)-1-Cyclopropyl-2,2,2-trifluoroethyl]-7-[(5R)-5-methyl-2-oxo-1,3-oxazolidin-3-yl]-4-oxo-1-(2,4,6-trifluorophenyl)-1,4-dihydro-1,8-naphthyridine-3-carboxamide

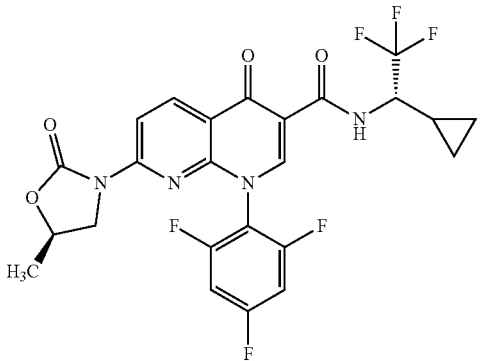 [SMILES: C[C@@H]1CN(c2ccc3c(=O)c(C(=O)N[C@@H](C4CC4)C(F)(F)F)cn(-c4c(F)cc(F)cc4F)c3n2)C(=O)O1]

To a solution of 137 mg (266 µmol) of the compound from Example 378 in 5.9 ml of dimethylformamide were added, at room temperature, 108 mg (666 µmol) of 1,1'-carbonyldiimidazole. The mixture was stirred for a further 6 d. Subsequently, the mixture was diluted with 0.1 ml of 1N aqueous hydrochloric acid and 1 ml of acetonitrile and purified by means of preparative HPLC (column: Chromatorex C18, 10 µm, 125×30 mm, solvent: acetonitrile/0.05% formic acid gradient; 0 to 3 min 10% acetonitrile, to 35 min 90% acetonitrile and for a further 3 min 90% acetonitrile). 90 mg (62% of theory, 99% purity) of the title compound were obtained.

$^1$H-NMR (400 MHz, DMSO-d6) δ[ppm]=10.25 (d, 1H), 9.05 (s, 1H), 8.73 (d, 1H), 8.34 (d, 1H), 7.65-7.53 (m, 2H), 4.83-4.73 (m, 1H), 4.47-4.35 (m, 1H), 3.91 (dd, 1H), 1.37 (d, 3H), 1.29-1.18 (m, 1H), 0.72-0.52 (m, 3H), 0.39-0.31 (m, 1H), a resonance under the water signal.

LC-MS (Method 3): $R_t$=2.20 min; MS (ESIpos): m/z=541 [M+H]$^+$.

Example 445

N-[(1S)-1-Cyclopropyl-2,2,2-trifluoroethyl]-7-[(5S)-5-methyl-2-oxo-1,3-oxazolidin-3-yl]-4-oxo-1-(2,4,6-trifluorophenyl)-1,4-dihydro-1,8-naphthyridine-3-carboxamide

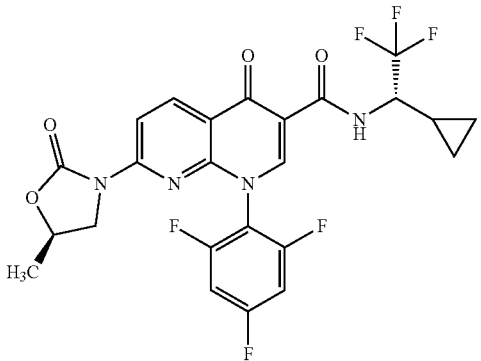 [SMILES: C[C@@H]1CN(c2ccc3c(=O)c(C(=O)N[C@@H](C4CC4)C(F)(F)F)cn(-c4c(F)cc(F)cc4F)c3n2)C(=O)O1]

To a solution of 114 mg (222 µmol) of the compound from Example 142A in 4.9 ml of dimethylformamide were added, at room temperature, 126 mg (775 µmol) of 1,1'-carbonyldiimidazole. The mixture was stirred for a further 7 d. Subsequently, the mixture was diluted with 0.1 ml of 1N aqueous hydrochloric acid and 1 ml of acetonitrile and purified by means of preparative HPLC (column: Chromatorex C18, 10 µm, 125×30 mm, solvent: acetonitrile/0.05% formic acid gradient; 0 to 3 min 10% acetonitrile, to 35 min 90% acetonitrile and for a further 3 min 90% acetonitrile). 45.2 mg (37% of theory, 99% purity) of the title compound were obtained.

$^1$H-NMR (400 MHz, DMSO-d6) δ[ppm]=10.25 (d, 1H), 9.05 (s, 1H), 8.73 (d, 1H), 8.34 (d, 1H), 7.64-7.54 (m, 2H), 4.83-4.73 (m, 1H), 4.47-4.34 (m, 1H), 3.91 (dd, 1H), 1.37 (d, 3H), 1.29-1.19 (m, 1H), 0.71-0.52 (m, 3H), 0.39-0.32 (m, 1H), a resonance under the water signal.

LC-MS (Method 1): $R_t$=1.18 min; MS (ESIpos): m/z=541 [M+H]$^+$.

Example 446

N-[(1S)-1-Cyclopropyl-2,2,2-trifluoroethyl]-7-[4-ethyl-2-oxotetrahydropyrimidin-1(2H)-yl]-4-oxo-1-(2,4,6-trifluorophenyl)-1,4-dihydro-1,8-naphthyridine-3-carboxamide (diastereomer mixture)

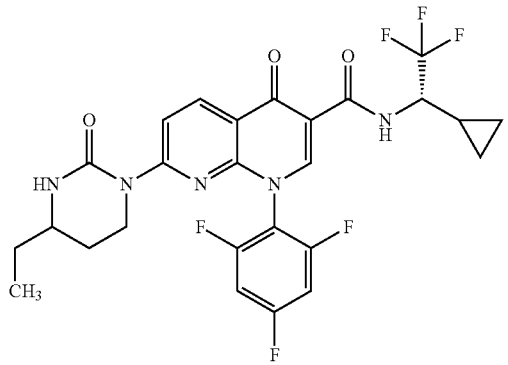 [SMILES: CCC1CCN(c2ccc3c(=O)c(C(=O)N[C@@H](C4CC4)C(F)(F)F)cn(-c4c(F)cc(F)cc4F)c3n2)C(=O)N1]

According to GP2, 100 mg (210 µmol) of the compound from Example 126A were reacted with 29.6 mg (231 µmol) of 4-ethyltetrahydropyrimidin-2(1H)-one (racemate) in the presence of 43.6 mg (315 µmol) of potassium carbonate, 4.7 mg (21 µmol) of palladium(II) acetate and 24 mg (42 µmol) of Xantphos in 2.1 ml of 1,4-dioxane. Subsequently, the mixture was diluted with 3 ml of acetonitrile and 2 ml of water and purified by means of preparative HPLC (column: Chromatorex C18, 10 µm, 125×30 mm, solvent: acetonitrile/ 0.05% formic acid gradient; 0 to 3 min 15% acetonitrile, to 15 min 90% acetonitrile and for a further 3 min 90% acetonitrile). 24.3 mg (20% of theory, 100% purity) of the title compound were obtained.

$^1$H-NMR (400 MHz, DMSO-d6) δ[ppm]=10.33 (d, 1H), 9.01 (s, 1H), 8.53 (d, 1H), 8.31 (d, 1H), 7.64-7.54 (m, 2H), 7.40 (s, 1H), 4.46-4.34 (m, 1H), 3.73-3.65 (m, 1H), 3.27-3.20 (m, 1H), 2.00-1.92 (m, 1H), 1.61-1.46 (m, 2H), 1.41-1.18 (m, 2H), 0.85 (t, 3H), 0.71-0.51 (m, 3H), 0.39-0.31 (m, 1H).

LC-MS (Method 3): $R_t$=2.15 min; MS (ESIpos): m/z=568 [M+H]$^+$.

24 mg of the title compound (diastereomer mixture) were separated into the diastereomers by chiral HPLC (prepara-

Example 447

N-[(1S)-1-Cyclopropyl-2,2,2-trifluoroethyl]-7-[4-ethyl-2-oxotetrahydropyrimidin-1(2H)-yl]-4-oxo-1-(2,4,6-trifluorophenyl)-1,4-dihydro-1,8-naphthyridine-3-carboxamide (diastereomer 1)

$^1$H-NMR (400 MHz, DMSO-d6) δ[ppm]=10.33 (d, 1H), 9.01 (s, 1H), 8.53 (d, 1H), 8.31 (d, 1H), 7.64-7.55 (m, 2H), 7.39 (s, 1H), 4.47-4.33 (m, 1H), 3.75-3.64 (m, 1H), 3.28-3.20 (m, 1H), 2.01-1.90 (m, 1H), 1.61-1.45 (m, 2H), 1.41-1.18 (m, 2H), 0.85 (t, 3H), 0.71-0.49 (m, 3H), 0.39-0.30 (m, 1H).

LC-MS (Method 1): R$_t$=1.16 min; MS (ESIpos): m/z=568 [M+H]$^+$.

Example 448

N-[(1S)-1-Cyclopropyl-2,2,2-trifluoroethyl]-7-[4-ethyl-2-oxotetrahydropyrimidin-1(2H)-yl]-4-oxo-1-(2,4,6-trifluorophenyl)-1,4-dihydro-1,8-naphthyridine-3-carboxamide (diastereomer 2)

$^1$H-NMR (400 MHz, DMSO-d6) δ[ppm]=10.33 (d, 1H), 9.01 (s, 1H), 8.53 (d, 1H), 8.32 (d, 1H), 7.65-7.54 (m, 2H), 7.40 (s, 1H), 4.47-4.33 (m, 1H), 3.74-3.65 (m, 1H), 3.28-3.20 (m, 1H), 2.00-1.91 (m, 1H), 1.61-1.45 (m, 2H), 1.41-1.11 (m, 2H), 0.85 (t, 3H), 0.71-0.50 (m, 3H), 0.39-0.30 (m, 1H).

LC-MS (Method 1): R$_t$=1.16 min; MS (ESIpos): m/z=568 [M+H]$^+$.

Example 449

N-[(1S)-1-Cyclopropyl-2,2,2-trifluoroethyl]-7-[(4S)-4-methyl-2-oxoimidazolidin-1-yl]-4-oxo-1-(2,4,6-trifluorophenyl)-1,4-dihydro-1,8-naphthyridine-3-carboxamide

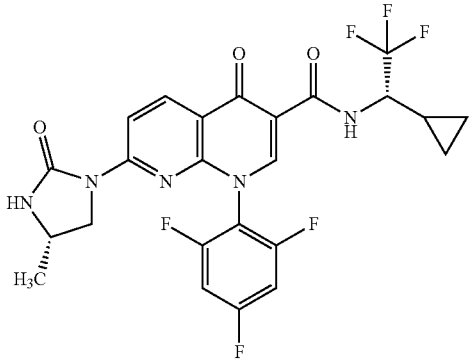

To a solution of 184 mg (292 μmol) of the compound from Example 143B in 6.4 ml of dimethylformamide were added, at room temperature, 40.4 mg (292 μmol) of potassium carbonate and 119 mg (731 μmol) of 1,1'-carbonyldiimidazole. The mixture was stirred for a further 48 h. Subsequently, the mixture was diluted with 0.2 ml of 1N aqueous hydrochloric acid and 1 ml of acetonitrile and purified by means of preparative HPLC (column: Chromatorex C18, 10 μm, 125×30 mm, solvent: acetonitrile/0.1% formic acid gradient; 0 to 5 min 10% acetonitrile, over 14 min to 90% acetonitrile and for a further 4 min 90% acetonitrile). 111 mg (70% of theory, 99% purity) of the title compound were obtained.

$^1$H-NMR (400 MHz, DMSO-d6) δ[ppm]=10.35 (d, 1H), 8.98 (s, 1H), 8.57 (d, 1H), 8.44 (d, 1H), 7.83 (s, 1H), 7.63-7.53 (m, 2H), 4.47-4.34 (m, 1H), 3.82-3.69 (m, 2H), 3.14-3.05 (m, 1H), 1.28-1.18 (m, 1H), 1.13 (d, 3H), 0.71-0.50 (m, 3H), 0.39-0.30 (m, 1H).

LC-MS (Method 1): R$_t$=1.10 min; MS (ESIpos): m/z=540 [M+H]$^+$.

Example 450

N-[(1S)-1-Cyclopropyl-2,2,2-trifluoroethyl]-4-oxo-7-(5-oxo-4,6-diazaspiro[2.4]hept-6-yl)-1-(2,4,6-trifluorophenyl)-1,4-dihydro-1,8-naphthyridine-3-carboxamide

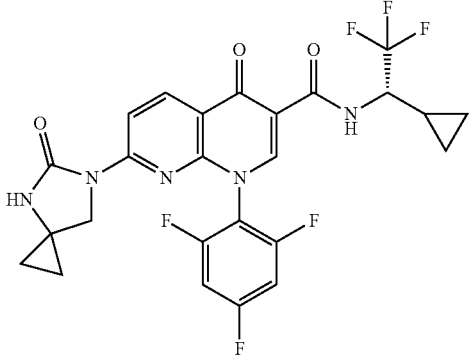 [SMILES: O=C(N[C@@H](C1CC1)C(F)(F)F)c1cn(-c2c(F)cc(F)cc2F)c2nc(N3CC4(CC4)NC3=O)ccc2c1=O]

To a solution of 183 mg (243 μmol) of the compound from Example 144B in 5.4 ml of dimethylformamide were added, at room temperature, 67.1 mg (486 μmol) of potassium carbonate and 98.5 mg (607 μmol) of 1,1'-carbonyldiimidazole. The mixture was stirred for a further 6 h. Subsequently, the mixture was diluted with 0.2 ml of 1N aqueous hydrochloric acid and 1 ml of acetonitrile and purified by means of preparative HPLC (column: Chromatorex C18, 10 μm, 125×30 mm, solvent: acetonitrile/0.1% formic acid gradient; 0 to 5 min 10% acetonitrile, over 14 min to 90% acetonitrile and for a further 4 min 90% acetonitrile). 116 mg (86% of theory, 99% purity) of the title compound were obtained.

$^1$H-NMR (400 MHz, DMSO-d6) δ[ppm]=10.34 (d, 1H), 8.97 (s, 1H), 8.59 (d, 1H), 8.45 (d, 1H), 7.90 (s, 1H), 7.59-7.50 (m, 2H), 4.47-4.34 (m, 1H), 3.60 (s, 2H), 1.28-1.18 (m, 1H), 0.82-0.50 (m, 7H), 0.39-0.30 (m, 1H).

LC-MS (Method 3): R$_t$=2.08 min; MS (ESIpos): m/z=552 [M+H]$^+$.

Example 451

N-[(1S)-1-Cyclopropyl-2,2,2-trifluoroethyl]-7-(4,4-dimethyl-2-oxoimidazolidin-1-yl)-4-oxo-1-(2,4,6-trifluorophenyl)-1,4-dihydro-1,8-naphthyridine-3-carboxamide

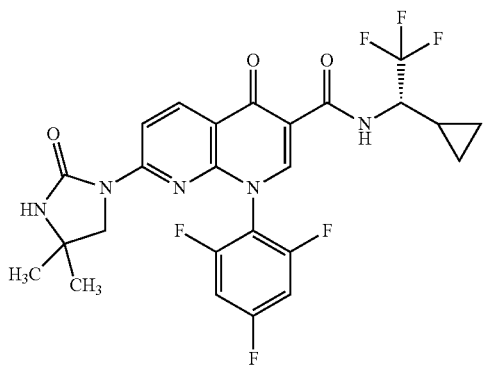 [SMILES: CC1(C)CN(c2ccc3c(=O)c(C(=O)N[C@@H](C4CC4)C(F)(F)F)cn(-c4c(F)cc(F)cc4F)c3n2)C(=O)N1]

To a solution of 190 mg (251 µmol) of the compound from Example 145B in 5.5 ml of dimethylformamide were added, at room temperature, 69.4 mg (502 µmol) of potassium carbonate and 102 mg (628 µmol) of 1,1'-carbonyldiimidazole. The mixture was stirred for a further 4 d. Another 1 equivalent each of 1,1'-carbonyldiimidazole and potassium carbonate were added and the mixture was stirred at room temperature for a further 48 h. Subsequently, the mixture was diluted with 25 ml of 0.5 M aqueous hydrochloric acid and 50 ml of ethyl acetate. The phases were separated and the aqueous phase was extracted three times with 25 ml of ethyl acetate, dried over magnesium sulphate and filtered and the solvent was removed under reduced pressure. The residue was taken up in 0.2 ml of 1N aqueous hydrochloric acid and 1 ml of acetonitrile and purified by means of preparative HPLC (column: Chromatorex C18, 10 µm, 125×30 mm, solvent: acetonitrile/0.1% formic acid gradient; 0 to 5 min 10% acetonitrile, over 14 min to 90% acetonitrile and for a further 4 min 90% acetonitrile). 39.7 mg (28% of theory, 99% purity) of the title compound were obtained.

$^1$H-NMR (400 MHz, DMSO-d6) δ[ppm]=10.35 (d, 1H), 8.98 (s, 1H), 8.57 (d, 1H), 8.44 (d, 1H), 7.89 (s, 1H), 7.64-7.55 (m, 2H), 4.46-4.33 (m, 1H), 1.28-1.14 (m, 7H), 0.70-0.50 (m, 3H), 0.39-0.29 (m, 1H).

LC-MS (Method 3): $R_t$=2.07 min; MS (ESIpos): m/z=554 [M+H]$^+$.

Example 452

N-(1,1-Difluoro-2-methylpropan-2-yl)-7-[(4R)-4-methyl-2-oxoimidazolidin-1-yl]-4-oxo-1-(2,4,6-trifluorophenyl)-1,4-dihydro-1,8-naphthyridine-3-carboxamide

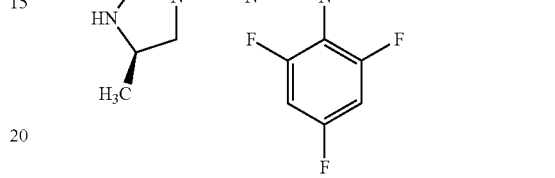

According to GP1, 100 mg (232 µmol, 97% purity) of the compound from Example 146D were reacted with 40.5 mg (278 µmol) of 1,1-difluoro-2-methylpropan-2-amine hydrochloride in the presence of 106 mg (278 µmol) of HATU and 101 µl (580 µmol) of N,N-diisopropylethylamine in 6.2 ml of dimethylformamide. The mixture was diluted with 1 ml of 1 M aqueous hydrochloric acid and acetonitrile and purified by means of preparative HPLC (Chromatorex C18, 10 µm, 125×30 mm, solvent: acetonitrile/0.05% formic acid gradient; 0 to 3 min 10% acetonitrile, to 15 min 90% acetonitrile and for a further 3 min 90% acetonitrile). 47 mg (40% of theory, 100% purity) of the title compound were obtained.

$^1$H-NMR (400 MHz, DMSO-d$_6$): δ [ppm]=10.12 (s, 1H), 8.90 (s, 1H), 8.55 (d, 1H), 8.42 (d, 1H), 7.81 (s, 1H), 7.62-7.53 (m, 2H), 6.43 (t, 1H), 3.80-3.69 (m, 2H), 3.14-3.05 (m, 1H), 1.45 (s, 6H), 1.12 (d, 3H).

LC-MS (Method 3): $R_t$=1.94 min; 510 [M+H]$^+$.

Example 453

7-[(4R)-4-Methyl-2-oxoimidazolidin-1-yl]-4-oxo-N-[(2S)-1-(trifluoromethoxy)butan-2-yl]-1-(2,4,6-trifluorophenyl)-1,4-dihydro-1,8-naphthyridine-3-carboxamide (diastereomer mixture)

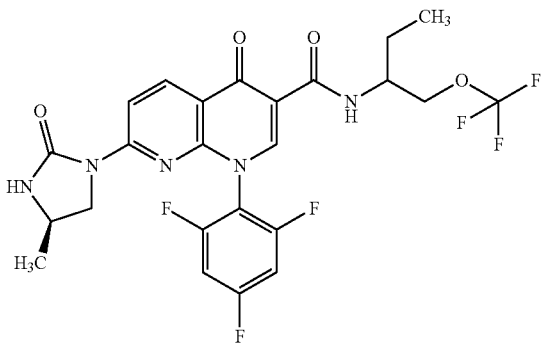 [SMILES: CCC(COC(F)(F)F)NC(=O)c1cn(-c2c(F)cc(F)cc2F)c2nc(N3C[C@@H](C)NC3=O)ccc2c1=O]

According to GP1, 100 mg (232 µmol, 97% purity) of the compound from Example 146D were reacted with 53.9 mg (278 µmol) of 1-(trifluoromethoxy)butan-2-amine hydrochloride in the presence of 106 mg (278 µmol) of HATU and 101 µl (580 µmol) of N,N-diisopropylethylamine in 2.3 ml of dimethylformamide. The mixture was adjusted to pH 1 with 1 M aqueous hydrochloric acid, diluted with 20 ml of water and extracted three times with 20 ml of ethyl acetate. The combined organic phases were washed with saturated aqueous sodium chloride solution, dried over magnesium sulphate, filtered and concentrated. The residue was partly dissolved in acetonitrile, DMSO, dioxane and THF. The insoluble constituents were filtered off with suction and corresponded to the title compound (109 mg, 84% of theory, 100% purity). The mother liquor was purified by means of preparative HPLC (column: Chromatorex C18, 10 µm, 125× 30 mm, solvent: acetonitrile/0.05% formic acid gradient; 0 to 3 min 10% acetonitrile, to 15 min 90% acetonitrile and for a further 3 min 90% acetonitrile). The product fractions were combined, concentrated and lyophilized. 56.8 mg (44% of theory, 100% purity) of the title compound were obtained.

$^1$H-NMR (400 MHz, DMSO-d$_6$): δ [ppm]=9.89 (d, 1H), 8.91 (s, 1H), 8.55 (d, 1H), 8.42 (d, 1H), 7.82 (s, 1H), 7.64-7.52 (m, 2H), 4.26-4.13 (m, 3H), 3.82-3.69 (m, 2H), 3.15-3.04 (m, 1H), 1.76-1.53 (m, 2H), 1.13 (d, 3H), 0.95 (t, 3H).

LC-MS (Method 3): R$_t$=2.03 min; 558 [M+H]$^+$.

166 mg of the title compound (diastereomer mixture) were separated into the diastereomers by chiral HPLC (preparative HPLC: column: YMC Chiralart Cellulose SA 5 µm 250×30 mm; eluent: 20% isopropanol, 80% n-heptane; temperature: 30° C.; flow rate: 30 ml/min; UV detection: 220 nm).

This gave (in the sequence of elution from the column) 27 mg of diastereomer 1 (99% de) R$_t$=7.09 min and 28 mg (98% de) of diastereomer 2 R$_t$=7.87 min.

[Analytical HPLC: column: YMC Chiralart Amylose SA 5 µm 250×4.6 mm; eluent: 20% isopropanol, 80% n-heptane; flow rate: 1.0 ml/min; temp.: 30° C.; UV detection: 220 nm]

Diastereomer 1 was additionally purified by means of preparative HPLC (column: Chromatorex C18, 10 µm, 125× 30 mm, solvent: acetonitrile/0.1% formic acid gradient; (0 to 5 min. 10% acetonitrile, over 14 min. to 90% acetonitrile and a further 4 min. 90% acetonitrile)), and 26.5 mg (20% of theory, 99% purity) of the title compound from Example 454 were obtained.

Diastereomer 2 was additionally purified by means of preparative HPLC (column: Chromatorex C18, 10 µm, 125× 30 mm, solvent: acetonitrile/0.1% formic acid gradient; (0 to 5 min. 10% acetonitrile, over 14 min. to 90% acetonitrile and a further 4 min. 90% acetonitrile)), and 26.5 mg (20% of theory, 99% purity) of the title compound from Example 455 were obtained.

Example 454

7-[(4R)-4-Methyl-2-oxoimidazolidin-1-yl]-4-oxo-N-[(2S)-1-(trifluoromethoxy)butan-2-yl]-1-(2,4,6-trifluorophenyl)-1,4-dihydro-1,8-naphthyridine-3-carboxamide (diastereomer 1)

$^1$H-NMR (400 MHz, DMSO-d$_6$): δ [ppm]=9.89 (d, 1H), 8.91 (s, 1H), 8.55 (d, 1H), 8.42 (d, 1H), 7.82 (s, 1H), 7.63-7.53 (m, 2H), 4.25-4.13 (m, 3H), 3.80-3.69 (m, 2H), 3.14-3.05 (m, 1H), 1.75-1.53 (m, 2H), 1.12 (d, 3H), 0.95 (t, 3H).

LC-MS (Method 3): R$_t$=2.04 min; 558 [M+H]$^+$.

Example 455

7-[(4R)-4-Methyl-2-oxoimidazolidin-1-yl]-4-oxo-N-[(2S)-1-(trifluoromethoxy)butan-2-yl]-1-(2,4,6-trifluorophenyl)-1,4-dihydro-1,8-naphthyridine-3-carboxamide (diastereomer 2)

$^1$H-NMR (400 MHz, DMSO-d$_6$): δ [ppm]=9.89 (d, 1H), 8.91 (s, 1H), 8.56 (d, 1H), 8.42 (d, 1H), 7.82 (s, 1H), 7.63-7.52 (m, 2H), 4.26-4.14 (m, 3H), 3.81-3.69 (m, 2H), 3.15-3.04 (m, 1H), 1.75-1.53 (m, 2H), 1.13 (d, 3H), 0.95 (t, 3H).

LC-MS (Method 3): R$_t$=2.03 min; 558 [M+H]$^+$.

Example 456

7-[(4R)-4-Methyl-2-oxoimidazolidin-1-yl]-4-oxo-N-[(2S)-1,1,1-trifluorobutan-2-yl]-1-(2,4,6-trifluorophenyl)-1,4-dihydro-1,8-naphthyridine-3-carboxamide

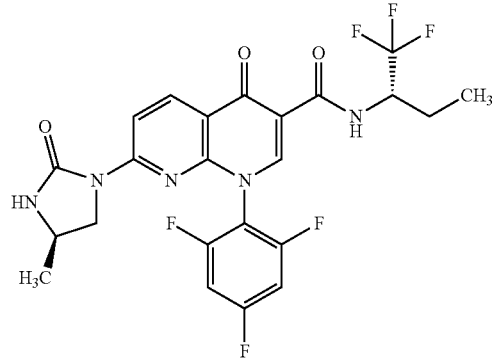 [SMILES: CC[C@H](NC(=O)c1cn(-c2c(F)cc(F)cc2F)c2nc(N3C[C@@H](C)NC3=O)ccc2c1=O)C(F)(F)F]

According to GP1, 100 mg (232 µmol, 97% purity) of the compound from Example 146D were reacted with 45.5 mg (278 µmol) of (2S)-1,1,1-trifluorobutan-2-amine hydrochloride in the presence of 106 mg (278 µmol) of HATU and 101 µl (580 µmol) of N,N-diisopropylethylamine in 2.3 ml of dimethylformamide. The mixture was diluted with 1 ml of 1 M aqueous hydrochloric acid and acetonitrile and purified by means of preparative HPLC (column: Chromatorex C18, 10 µm, 125×30 mm, solvent: acetonitrile/0.05% formic acid gradient; 0 to 3 min 10% acetonitrile, to 15 min 90% acetonitrile and for a further 3 min 90% acetonitrile). The product fractions were combined, concentrated and lyophilized. 57.8 mg (47% of theory, 100% purity) of the title compound were obtained.

$^1$H-NMR (400 MHz, DMSO-d$_6$): δ [ppm]=10.21 (d, 1H), 8.99 (s, 1H), 8.56 (d, 1H), 8.44 (d, 1H), 7.83 (s, 1H), 7.65-7.53 (m, 2H), 4.83-4.68 (m, 1H), 3.81-3.68 (m, 2H), 3.16-3.03 (m, 1H), 1.96-1.82 (m, 1H), 1.74-1.58 (m, 1H), 1.13 (d, 3H), 0.98 (t, 3H).

LC-MS (Method 3): R$_t$=2.00 min; 528 [M+H]$^+$.

Example 457

7-[(4R)-4-Methyl-2-oxoimidazolidin-1-yl]-4-oxo-N-(4,4,4-trifluoro-2-methylbutan-2-yl)-1-(2,4,6-trifluorophenyl)-1,4-dihydro-1,8-naphthyridine-3-carboxamide

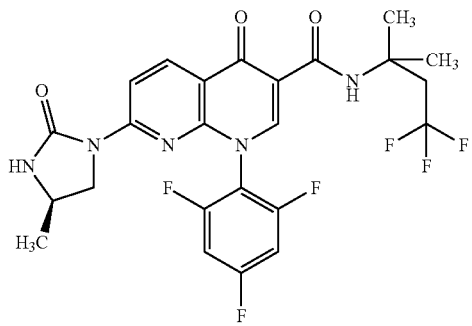 [SMILES: C[C@@H]1CN(c2ccc3c(=O)c(C(=O)NC(C)(C)CC(F)(F)F)cn(-c4c(F)cc(F)cc4F)c3n2)C(=O)N1]

According to GP1, 100 mg (232 μmol, 97% purity) of the compound from Example 146D were reacted with 20.6 mg (116 μmol) of 4,4,4-trifluoro-2-methylbutan-2-amine hydrochloride in the presence of 106 mg (278 μmol) of HATU and 101 μl (580 μmol) of N,N-diisopropylethylamine in 2.3 ml of dimethylformamide. The mixture was diluted with 1 ml of 1 M aqueous hydrochloric acid and acetonitrile and purified by means of preparative HPLC (column: Chromatorex C18, 10 μm, 125×30 mm, solvent: acetonitrile/0.05% formic acid gradient; 0 to 3 min 10% acetonitrile, to 15 min 90% acetonitrile and for a further 3 min 90% acetonitrile). The product fractions were combined, concentrated and lyophilized. 49.8 mg (40% of theory, 100% purity) of the title compound were obtained.

$^1$H-NMR (400 MHz, DMSO-$d_6$): δ [ppm]=9.98 (s, 1H), 8.88 (s, 1H), 8.54 (d, 1H), 8.41 (d, 1H), 7.81 (s, 1H), 7.64-7.53 (m, 2H), 3.82-3.68 (m, 2H), 3.14-3.05 (m, 1H), 2.96 (q, 2H), 1.49 (s, 6H), 1.13 (d, 3H).

LC-MS (Method 3): $R_t$=2.02 min; 542 [M+H]$^+$.

Example 458

7-[(4R)-4-Methyl-2-oxoimidazolidin-1-yl]-4-oxo-N-[3,3,4,4,4-pentafluorobutan-2-yl]-1-(2,4,6-trifluorophenyl)-1,4-dihydro-1,8-naphthyridine-3-carboxamide (diastereomer mixture)

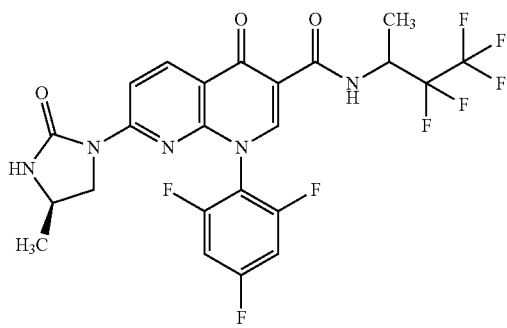 [SMILES: CC(NC(=O)c1cn(-c2c(F)cc(F)cc2F)c2nc(N3C[C@@H](C)NC3=O)ccc2c1=O)C(F)(F)C(F)(F)F]

According to GP1, 100 mg (232 μmol, 97% purity) of the compound from Example 146D were reacted with 53.9 mg (278 μmol) of the compound from Example 147B in the presence of 106 mg (278 μmol) of HATU and 101 μl (580 μmol) of N,N-diisopropylethylamine in 2.3 ml of dimethylformamide. The mixture was diluted with 1 ml of 1 M aqueous hydrochloric acid and acetonitrile and purified by means of preparative HPLC (column: Chromatorex C18, 10 μm, 125×30 mm, solvent: acetonitrile/0.05% formic acid gradient; 0 to 3 min 10% acetonitrile, to 15 min 90% acetonitrile and for a further 3 min 90% acetonitrile). The product fractions were combined, concentrated and lyophilized. 52.6 mg (40% of theory, 100% purity) of the title compound were obtained.

$^1$H-NMR (400 MHz, DMSO-$d_6$): δ [ppm]=10.33 (d, 1H), 8.99 (s, 1H), 8.55 (d, 1H), 8.44 (d, 1H), 7.83 (s, 1H), 7.63-7.53 (m, 2H), 5.11-4.95 (m, 1H), 3.82-3.68 (m, 2H), 3.14-3.04 (m, 1H), 1.41 (d, 3H), 1.13 (d, 3H).

LC-MS (Method 3): $R_t$=2.05 min; 564 [M+H]$^+$.

50 mg of the title compound (diastereomer mixture) were separated into the diastereomers by chiral HPLC (preparative HPLC: column: Daicel Chiralpak AD-H 5 μm 250×20 mm; eluent: 30% ethanol, 70% n-heptane; temperature: 25° C.; flow rate: 15 ml/min; UV detection: 210 nm).

This gave (in the sequence of elution from the column) 20.8 mg of diastereomer 1 (99% de) $R_t$=1.51 min and 20.2 mg (99% de) of diastereomer 2 $R_t$=2.09 min.

[Analytical HPLC: column: Daicel AD-3 3 μm 50×4.6 mm; eluent: 20% ethanol, 80% isohexane; UV detection: 220 nm].

Diastereomer 1 was additionally purified by means of preparative HPLC (column: Chromatorex C18, 10 μm, 125×30 mm, solvent: acetonitrile/0.1% formic acid gradient; (0 to 2.5 min. 10% acetonitrile, over 15.5 min. to 90% acetonitrile and a further 2 min. 90% acetonitrile)), and 19.1 mg (15% of theory, 100% purity) of the title compound from Example 459 were obtained.

Diastereomer 2 was additionally purified by means of preparative HPLC (column: Chromatorex C18, 10 μm, 125×30 mm, solvent: acetonitrile/0.1% formic acid gradient; (0 to 2.5 min. 10% acetonitrile, over 15.5 min. to 90% acetonitrile and a further 2 min. 90% acetonitrile)), and 11.8 mg (9% of theory, 100% purity) of the title compound from Example 460 were obtained.

Example 459

7-[(4R)-4-Methyl-2-oxoimidazolidin-1-yl]-4-oxo-N-[3,3,4,4,4-pentafluorobutan-2-yl]-1-(2,4,6-trifluorophenyl)-1,4-dihydro-1,8-naphthyridine-3-carboxamide (diastereomer 1)

$^1$H-NMR (400 MHz, DMSO-$d_6$): δ [ppm]=10.33 (d, 1H), 8.99 (s, 1H), 8.55 (d, 1H), 8.43 (d, 1H), 7.83 (s, 1H), 7.63-7.53 (m, 2H), 5.10-4.95 (m, 1H), 3.80-3.69 (m, 2H), 3.15-3.05 (m, 1H), 1.41 (d, 3H), 1.13 (d, 3H).

LC-MS (Method 3): $R_t$=2.05 min; 564 [M+H]$^+$.

Example 460

7-[(4R)-4-Methyl-2-oxoimidazolidin-1-yl]-4-oxo-N-[3,3,4,4,4-pentafluorobutan-2-yl]-1-(2,4,6-trifluorophenyl)-1,4-dihydro-1,8-naphthyridine-3-carboxamide (diastereomer 2)

$^1$H-NMR (400 MHz, DMSO-$d_6$): δ [ppm]=10.33 (d, 1H), 8.99 (s, 1H), 8.55 (d, 1H), 8.44 (d, 1H), 7.83 (s, 1H), 7.64-7.53 (m, 2H), 5.11-4.96 (m, 1H), 3.81-3.69 (m, 2H), 3.14-3.03 (m, 1H), 1.41 (d, 3H), 1.12 (d, 3H).

LC-MS (Method 3): $R_t$=2.05 min; 564 [M+H]$^+$.

Example 461

N-[(1S)-1-Cyclopropyl-2,2,2-trifluoroethyl]-7-[4-fluoro-4-(hydroxymethyl)piperidin-1-yl]-4-oxo-1-(2,4,6-trifluorophenyl)-1,4-dihydro-1,8-naphthyridine-3-carboxamide

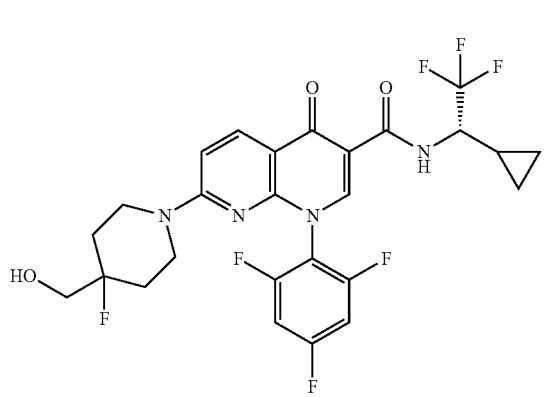 [SMILES: O=C(N[C@@H](C1CC1)C(F)(F)F)c1cn(-c2c(F)cc(F)cc2F)c2nc(N3CCC(F)(CO)CC3)ccc2c1=O]

According to GP3, 100 mg (210 µmol) of the compound from Example 126A were reacted with 39.2 mg (231 µmol) of (4-fluoropiperidin-4-yl)methanol hydrochloride and 128 µl (736 µmol) of N,N-diisopropylethylamine in 2.1 ml of dimethylformamide. The reaction solution was diluted with acetonitrile and 1 ml of 1N aqueous hydrochloric acid and purified by means of preparative HPLC (column: Chromatorex C18, 10 µm, 125×30 mm, solvent: acetonitrile/0.05% formic acid gradient; 0 to 3 min. 10% acetonitrile up to 15 min. to 90% acetonitrile and a further 3 min. 90% acetonitrile), and 102 mg (85% of theory, 100% purity) of the title compound were obtained.

$^1$H NMR (400 MHz, DMSO-d$_6$): δ [ppm]=10.51 (d, 1H), 8.82 (s, 1H), 8.30 (d, 1H), 7.61-7.52 (m, 2H), 7.19 (d, 1H), 4.96 (t, 1H), 4.44-4.32 (m, 1H), 4.05-3.93 (m, 2H), 3.39 (dd, 2H), 3.24-3.10 (m, 2H), 1.78-1.47 (m, 4H), 1.26-1.15 (m, 1H), 0.70-0.47 (m, 3H), 0.39-0.29 (m, 1H).

LC-MS (Method 3): $R_t$=2.01 min; MS (ESIpos) m/z 573 [M+H]$^+$.

Example 462

N-[(1S)-1-Cyclopropyl-2,2,2-trifluoroethyl]-7-[(2R)-2-(hydroxymethyl)piperidin-1-yl]-4-oxo-1-(2,4,6-trifluorophenyl)-1,4-dihydro-1,8-naphthyridine-3-carboxamide

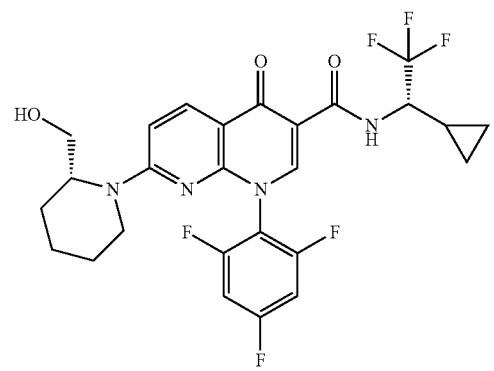 [SMILES: O=C(N[C@@H](C1CC1)C(F)(F)F)c1cn(-c2c(F)cc(F)cc2F)c2nc(N3CCCC[C@@H]3CO)ccc2c1=O]

According to GP3, 100 mg (210 µmol) of the compound from Example 126A were reacted with 35.1 mg (231 µmol) of (2R)-piperidin-2-ylmethanol hydrochloride and 128 µl (736 µmol) of N,N-diisopropylethylamine in 2.1 ml of dimethylformamide. The reaction solution was diluted with acetonitrile and 1 ml of 1N aqueous hydrochloric acid and purified by means of preparative HPLC (column: Chromatorex C18, 10 µm, 125×30 mm, solvent: acetonitrile/0.05% formic acid gradient; 0 to 3 min. 10% acetonitrile up to 15 min. to 90% acetonitrile and a further 3 min. 90% acetonitrile), and 74.1 mg (64% of theory, 100% purity) of the title compound were obtained.

$^1$H NMR (400 MHz, DMSO-d$_6$): δ [ppm]=10.55 (d, 1H), 8.78 (s, 1H), 8.24 (d, 1H), 7.60-7.48 (m, 2H), 7.10 (d, 1H), 4.74-4.63 (m, 1H), 4.44-4.32 (m, 1H), 4.27-4.18 (m, 1H), 4.13-4.03 (m, 1H), 3.57-3.43 (m, 2H), 2.91-2.73 (m, 1H), 1.82-1.72 (m, 1H), 1.64-1.40 (m, 4H), 1.36-1.14 (m, 2H), 0.70-0.48 (m, 3H), 0.38-0.30 (m, 1H).

LC-MS (Method 3): $R_t$=2.14 min; MS (ESIpos) m/z 555 [M+H]$^+$.

Example 463

N-[(1S)-1-Cyclopropyl-2,2,2-trifluoroethyl]-7-[2-(hydroxymethyl)morpholin-4-yl]-4-oxo-1-(2,4,6-trifluorophenyl)-1,4-dihydro-1,8-naphthyridine-3-carboxamide (diastereomer mixture)

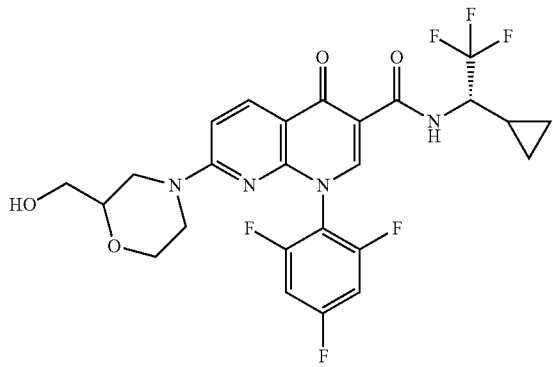 [SMILES: O=C(N[C@@H](C1CC1)C(F)(F)F)c1cn(-c2c(F)cc(F)cc2F)c2nc(N3CCOC(CO)C3)ccc2c1=O]

According to GP3, 100 mg (210 µmol) of the compound from Example 126A were reacted with 37.4 mg (231 µmol, 95% purity) of morpholin-2-ylmethanol hydrochloride and 128 µl (736 µmol) of N,N-diisopropylethylamine in 2.1 ml of dimethylformamide. The reaction solution was diluted with acetonitrile and 1 ml of 1N aqueous hydrochloric acid and purified by means of preparative HPLC (column: Chromatorex C18, 10 µm, 125×30 mm, solvent: acetonitrile/0.05% formic acid gradient; 0 to 3 min. 10% acetonitrile up to 15 min. to 90% acetonitrile and a further 3 min. 90% acetonitrile), and 102 mg (87% of theory, 100% purity) of the title compound were obtained.

$^1$H NMR (400 MHz, DMSO-$d_6$): δ [ppm]=10.50 (d, 1H), 8.83 (s, 1H), 8.33 (d, 1H), 7.59-7.48 (m, 2H), 7.12 (d, 1H), 4.78-4.71 (m, 1H), 4.44-4.32 (m, 1H), 4.10 (d, 1H), 3.96 (d, 1H), 3.86 (d, 1H), 3.48-3.37 (m, 2H), 2.98 (br. s, 1H), 2.72 (br. s, 1H), 1.26-1.15 (m, 1H), 0.71-0.48 (m, 3H), 0.39-0.30.

LC-MS (Method 3): $R_t$=1.88 min; MS (ESIpos) m/z 557 [M+H]$^+$. 100 mg of the title compound (diastereomer mixture) were separated into the diastereomers by chiral HPLC (preparative HPLC: column: Daicel Chiralpak ID 5 µm 250×20 mm; eluent: 20% isopropanol, 80% n-heptane; temperature: 30° C.; flow rate: 15 ml/min; UV detection: 220 nm).

This gave (in the sequence of elution from the column) 45 mg of diastereomer 1 (99% de) $R_t$=13.46 min and 30 mg (99% de) of diastereomer 2 $R_t$=14.69 min.

[Analytical HPLC: column: Daicel Chiralpak ID 5 µm 250×4.6 mm; eluent: 20% isopropanol, 80% isohexane; flow rate: 1 ml/min; temp.: 30° C.; UV detection: 220 nm]

Diastereomer 1 was additionally purified by means of preparative HPLC (column: Chromatorex C18, 10 µm, 125×30 mm, solvent: acetonitrile/0.1% formic acid gradient; (0 to 5 min. 10% acetonitrile, over 14 min. to 90% acetonitrile and a further 4 min. 90% acetonitrile)), and 40.0 mg (34% of theory, 99% purity) of the title compound from Example 464 were obtained.

Diastereomer 2 was additionally purified by means of preparative HPLC (column: Chromatorex C18, 10 µm, 125×30 mm, solvent: acetonitrile/0.1% formic acid gradient; (0 to 5 min. 10% acetonitrile, over 14 min. to 90% acetonitrile and a further 4 min. 90% acetonitrile)), and 24.6 mg (21% of theory, 99% purity) of the title compound from Example 465 were obtained.

Example 464

N-[(1S)-1-Cyclopropyl-2,2,2-trifluoroethyl]-7-[2-(hydroxymethyl)morpholin-4-yl]-4-oxo-1-(2,4,6-trifluorophenyl)-1,4-dihydro-1,8-naphthyridine-3-carboxamide (diastereomer 1)

$^1$H NMR (400 MHz, DMSO-$d_6$): δ [ppm]=10.50 (d, 1H), 8.83 (s, 1H), 8.33 (d, 1H), 7.59-7.48 (m, 2H), 7.12 (d, 1H), 4.78-4.72 (m, 1H), 4.44-4.32 (m, 1H), 4.10 (d, 1H), 3.96 (d, 1H), 3.86 (d, 1H), 3.47-3.38 (m, 2H), 2.98 (br. s, 1H), 2.72 (br. s, 1H), 1.26-1.16 (m, 1H), 0.70-0.48 (m, 3H), 0.38-0.30.

LC-MS (Method 3): $R_t$=1.88 min; MS (ESIpos) m/z 557 [M+H]$^+$.

Example 465

N-[(1S)-1-Cyclopropyl-2,2,2-trifluoroethyl]-7-[2-(hydroxymethyl)morpholin-4-yl]-4-oxo-1-(2,4,6-trifluorophenyl)-1,4-dihydro-1,8-naphthyridine-3-carboxamide (diastereomer 2)

$^1$H NMR (400 MHz, DMSO-$d_6$): δ [ppm]=10.50 (d, 1H), 8.83 (s, 1H), 8.33 (d, 1H), 7.59-7.48 (m, 2H), 7.12 (d, 1H), 4.78-4.71 (m, 1H), 4.45-4.32 (m, 1H), 4.10 (d, 1H), 3.96 (d, 1H), 3.86 (d, 1H), 3.48-3.37 (m, 2H), 2.98 (br. s, 1H), 2.72 (br. s, 1H), 1.26-1.15 (m, 1H), 0.71-0.48 (m, 3H), 0.38-0.30.

LC-MS (Method 3): $R_t$=1.88 min; MS (ESIpos) m/z 557 [M+H]$^+$.

Example 466

N-[(1S)-1-Cyclopropyl-2,2,2-trifluoroethyl]-7-[(3R)-3-hydroxy-2-oxopyrrolidin-1-yl]-4-oxo-1-(2,4,6-trifluorophenyl)-1,4-dihydro-1,8-naphthyridine-3-carboxamide

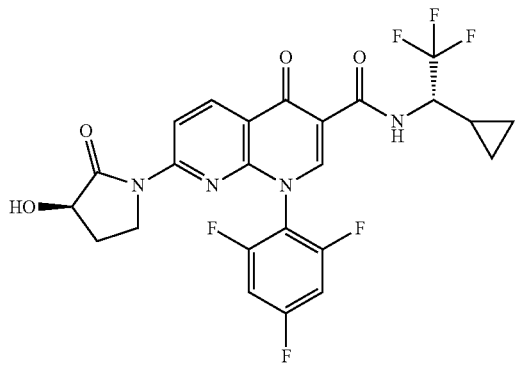 [SMILES: O=C(N[C@@H](C1CC1)C(F)(F)F)c1cn(-c2c(F)cc(F)cc2F)c2nc(N3CC[C@@H](O)C3=O)ccc2c1=O]

According to GP2, 100 mg (210 µmol) of the compound from Example 126A were reacted with 23.4 mg (231 µmol) of (3R)-3-hydroxypyrrolidin-2-one in the presence of 43.6 mg (315 µmol) of potassium carbonate, 4.7 mg (21 µmol) of palladium(II) acetate and 24 mg (42 µmol) of Xantphos in 2.1 ml of 1,4-dioxane. Subsequently, the mixture was diluted with water and acetonitrile and purified by means of preparative HPLC (column: Chromatorex C18, 10 µm, 125×30 mm, solvent: acetonitrile/0.05% formic acid gradient; 0 to 3 min 15% acetonitrile, to 15 min 90% acetonitrile and for a further 3 min 90% acetonitrile). 58.1 mg (51% of theory, 100% purity) of the title compound were obtained.

$^1$H-NMR (400 MHz, DMSO-d6) δ[ppm]=10.25 (d, 1H), 9.07 (s, 1H), 8.74 (d, 1H), 8.55 (d, 1H), 7.64-7.55 (m, 2H), 5.92 (d, 1H), 4.46-4.34 (m, 2H), 3.63-3.53 (m, 1H), 2.37-2.27 (m, 1H), 1.84-1.71 (m, 1H), 1.29-1.19 (m, 1H), 0.71-0.51 (m, 3H), 0.39-0.30 (m, 1H), a resonance partially under the water signal.

LC-MS (Method 3): $R_t$=1.88 min; MS (ESIpos): m/z=541 [M+H]$^+$.

Example 467

N-[(1S)-1-Cyclopropyl-2,2,2-trifluoroethyl]-7-[(3S)-3-hydroxy-2-oxopyrrolidin-1-yl]-4-oxo-1-(2,4,6-trifluorophenyl)-1,4-dihydro-1,8-naphthyridine-3-carboxamide

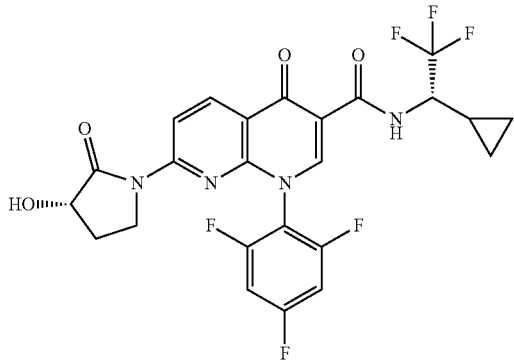 [SMILES: O=C(N[C@@H](C1CC1)C(F)(F)F)c1cn(-c2c(F)cc(F)cc2F)c2nc(N3CC[C@H](O)C3=O)ccc2c1=O]

According to GP2, 100 mg (210 µmol) of the compound from Example 126A were reacted with 23.4 mg (231 µmol) of (3S)-3-hydroxypyrrolidin-2-one in the presence of 43.6 mg (315 µmol) of potassium carbonate, 4.7 mg (21 µmol) of palladium(II) acetate and 24 mg (42 µmol) of Xantphos in 2.1 ml of 1,4-dioxane. Subsequently, the mixture was diluted with water and acetonitrile and purified by means of preparative HPLC (column: Chromatorex C18, 10 µm, 125×30 mm, solvent: acetonitrile/0.05% formic acid gradient; 0 to 3 min 15% acetonitrile, to 15 min 90% acetonitrile and for a further 3 min 90% acetonitrile). 62.1 mg (55% of theory, 100% purity) of the title compound were obtained.

$^1$H-NMR (400 MHz, DMSO-d6) δ[ppm]=10.25 (d, 1H), 9.07 (s, 1H), 8.74 (d, 1H), 8.55 (d, 1H), 7.64-7.55 (m, 2H), 5.92 (d, 1H), 4.47-4.34 (m, 2H), 3.61-3.54 (m, 1H), 2.38-2.27 (m, 1H), 1.84-1.71 (m, 1H), 1.29-1.18 (m, 1H), 0.71-0.51 (m, 3H), 0.39-0.30 (m, 1H), a resonance partially under the water signal.

LC-MS (Method 3): $R_t$=1.88 min; MS (ESIpos): m/z=541 [M+H]$^+$.

Example 468

N-[(1S)-1-Cyclopropyl-2,2,2-trifluoroethyl]-7-[3-(hydroxymethyl)-2-oxopyrrolidin-1-yl]-4-oxo-1-(2,4,6-trifluorophenyl)-1,4-dihydro-1,8-naphthyridine-3-carboxamide (diastereomer mixture)

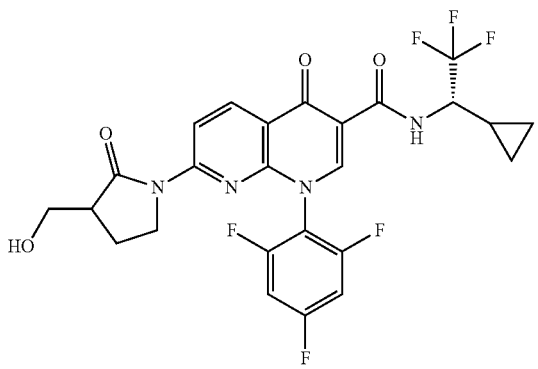 [SMILES: O=C(N[C@@H](C1CC1)C(F)(F)F)c1cn(-c2c(F)cc(F)cc2F)c2nc(N3CCC(CO)C3=O)ccc2c1=O]

According to GP2, 57.3 mg (120 µmol) of the compound from Example 126A were reacted with 30.4 mg (133 µmol) of the compound from Example 148A in the presence of 24.9 mg (181 µmol) of potassium carbonate, 2.7 mg (12 µmol) of palladium(II) acetate and 11 mg (24 µmol) of Xantphos in 3 ml of 1,4-dioxane. Subsequently, the mixture was diluted with 2 ml of water and 3 ml of acetonitrile and purified by means of preparative HPLC (column: Chromatorex C18, 10 µm, 125×30 mm, solvent: acetonitrile/0.05% formic acid gradient; 0 to 3 min 15% acetonitrile, to 15 min 90% acetonitrile and for a further 3 min 90% acetonitrile). The product fractions were concentrated and the residue was taken up in 3 ml of THF. The solution was admixed, while cooling with an ice bath, with 34.9 mg (120 µmol) of tris(dimethylamino)sulphur (trimethylsilyl)difluoride and stirred at 0-5° C. for 30 min and at room temperature for 1 h. The reaction mixture was admixed with 10 ml of water and extracted three times with 15 ml of ethyl acetate. The combined organic phases were washed with saturated aqueous sodium chloride solution, dried over magnesium sulphate, filtered and concentrated. The residue was purified by means of preparative HPLC (column: Chromatorex C18, 10 µm, 125×30 mm, solvent: acetonitrile/0.05% formic acid gradient; 0 to 3 min 10% acetonitrile, to 35 min 90% acetonitrile and for a further 3 min 90% acetonitrile).

The product fractions were combined, concentrated and lyophilized. Finally, the crude product was purified by means of preparative thin-layer chromatography (cyclohexane:ethyl acetate, 1:1, v/v). The product band was scraped off and the product was dissolved in dichloromethane/methanol 9:1 (v/v), filtered and concentrated. The residue was taken up in dichloromethane, filtered through a fine filter, concentrated and lyophilized. 5 mg (7% of theory, 100% purity) of the title compound were obtained.

$^1$H-NMR (400 MHz, DMSO-d6) δ[ppm]=10.26 (d, 1H), 9.06 (s, 1H), 8.72 (d, 1H), 8.56 (d, 1H), 7.64-7.56 (m, 2H), 4.86 (br. s, 1H), 4.46-4.35 (m, 1H), 3.76-3.70 (m, 1H), 3.63-33.54 (m, 2H), 3.52-3.44 (m, 1H), 2.85-2.78 (m, 1H), 2.15-2.06 (m, 1H), 2.02-1.93 (m, 1H), 1.28-1.19 (m, 2H), 0.70-0.52 (m, 3H), 0.38-0.31 (m, 1H).

LC-MS (Method 3): $R_t$=1.93 min; MS (ESIpos): m/z=555 [M+H]$^+$.

Example 469

N-tert-Butyl-7-[(4S)-4-hydroxy-2-oxopyrrolidin-1-yl]-4-oxo-1-(2,4,6-trifluorophenyl)-1,4-dihydro-1,8-naphthyridine-3-carboxamide

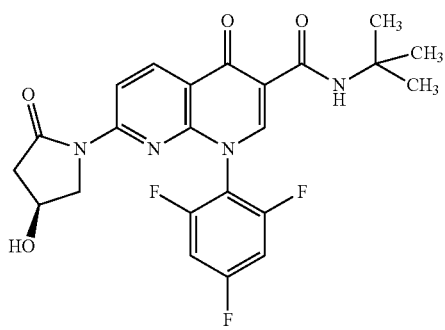 [SMILES: CC(C)(C)NC(=O)c1cn(-c2c(F)cc(F)cc2F)c2nc(N3C[C@@H](O)CC3=O)ccc2c1=O]

According to GP1, 50.0 mg (119 µmol) of the compound from Example 117A were reacted with 10.5 mg (143 µmol) of tert-butylamine in the presence of 54.4 mg (143 µmol) of HATU and 52.0 µl (298 µmol) of N,N-diisopropylethylamine in 2.4 ml of dimethylformamide. The mixture was diluted with 0.3 ml of 1 M aqueous hydrochloric acid and 1 ml of acetonitrile and purified by means of preparative HPLC (column: Chromatorex C18, 10 µm, 125×30 mm, solvent: acetonitrile/0.05% formic acid gradient; 0 to 5 min 10% acetonitrile, to 14 min 90% acetonitrile and for a further 4 min 90% acetonitrile). The product fractions were combined, concentrated and lyophilized. 37.1 mg (65% of theory, 99% purity) of the title compound were obtained.

$^1$H-NMR (400 MHz, DMSO-$d_6$): δ [ppm]=9.70 (s, 1H), 8.92 (s, 1H), 8.69 (d, 1H), 8.51 (d, 1H), 7.66-7.56 (m, 2H), 5.32 (d, 1H), 4.32-4.25 (m, 1H), 3.69 (dd, 1H), 3.47 (d, 1H), 2.93 (dd, 1H), 2.37 (d, 1H), 1.41 (s, 9H).

LC-MS (Method 3): $R_t$=1.74 min; 475 [M+H]$^+$.

Example 470

N-[(1R)-1-Cyclopropylethyl]-7-[(3R,4R)-3,4-dihydroxypyrrolidin-1-yl]-4-oxo-1-(2,4,6-trifluorophenyl)-1,4-dihydro-1,8-naphthyridine-3-carboxamide

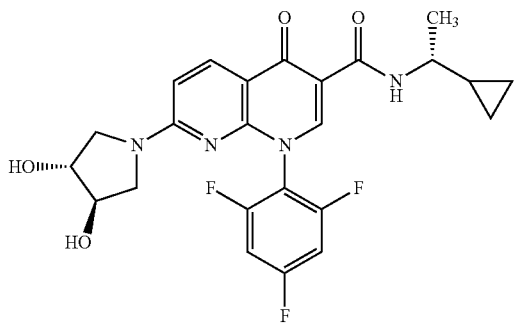 [SMILES: C[C@@H](NC(=O)c1cn(-c2c(F)cc(F)cc2F)c2nc(N3C[C@@H](O)[C@H](O)C3)ccc2c1=O)C1CC1]

According to GP1, 50.0 mg (119 µmol) of the compound from Example 121A were reacted with 12.1 mg (142 µmol) of (1R)-1-cyclopropylethanamine in the presence of 54.1 mg (142 µmol) of HATU and 52.0 µl (297 µmol) of N,N-diisopropylethylamine in 2.4 ml of dimethylformamide. The mixture was diluted with 0.3 ml of 1 M aqueous hydrochloric acid and 1 ml of acetonitrile and purified by means of preparative HPLC (column: Chromatorex C18, 10 µm, 125×30 mm, solvent: acetonitrile/0.05% formic acid gradient; 0 to 2.5 min 10% acetonitrile, to 16 min 90% acetonitrile and for a further 2 min 90% acetonitrile). The product fractions were combined, concentrated and lyophilized. 38.8 mg (67% of theory, 100% purity) of the title compound were obtained.

$^1$H-NMR (400 MHz, DMSO-$d_6$): δ [ppm]=9.95 (d, 1H), 8.67 (s, 1H), 8.26 (d, 1H), 7.60-7.51 (m, 2H), 6.75 (d, 1H), 5.23 (d, 1H), 5.13 (d, 1H), 4.05 (br. s, 1H), 3.92 (br. s, 1H), 3.65-3.47 (m, 2H), 3.25 (dd, 1H), 3.07 (d, 1H), 1.22 (d, 3H), 1.03-0.93 (m, 1H), 0.51-0.38 (m, 2H), 0.33-0.20 (m, 2H).

LC-MS (Method 3): $R_t$=1.50 min; 489 [M+H]$^+$.

Example 471

N-[1-Cyclobutylethyl]-7-[(4S)-4-hydroxy-2-oxopyrrolidin-1-yl]-4-oxo-1-(2,4,6-trifluorophenyl)-1,4-dihydro-1,8-naphthyridine-3-carboxamide (diastereomer mixture)

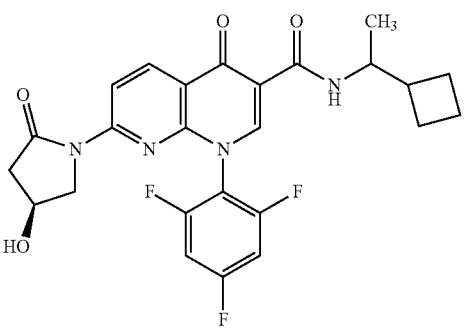 [SMILES: CC(NC(=O)c1cn(-c2c(F)cc(F)cc2F)c2nc(N3C[C@@H](O)CC3=O)ccc2c1=O)C1CCC1]

According to GP1, 50.0 mg (119 µmol) of the compound from Example 117A were reacted with 19.4 mg (143 µmol) of 1-cyclobutylethanamine hydrochloride (racemate) in the presence of 54.4 mg (143 µmol) of HATU and 73.0 µl (417 µmol) of N,N-diisopropylethylamine in 2.4 ml of dimethylformamide. The mixture was diluted with 0.3 ml of 1 M aqueous hydrochloric acid and 1 ml of acetonitrile and purified by means of preparative HPLC (column: Chromatorex C18, 10 µm, 125×30 mm, solvent: acetonitrile/0.05% formic acid gradient; 0 to 5 min 10% acetonitrile, to 14 min 90% acetonitrile and for a further 4 min 90% acetonitrile). The product fractions were combined, concentrated and lyophilized. 30.7 mg (51% of theory, 99% purity) of the title compound were obtained.

$^1$H-NMR (400 MHz, DMSO-$d_6$): δ [ppm]=9.61 (d, 1H), 8.96 (s, 1H), 8.70 (d, 1H), 8.51 (d, 1H), 7.65-7.56 (m, 2H), 5.36-5.30 (m, 1H), 4.29 (br. s, 1H), 4.07-3.95 (m, 1H), 3.69 (dd, 1H), 3.48 (d, 1H), 2.94 (dd, 1H), 2.47-2.34 (m, 2H), 2.03-1.69 (m, 6H), 1.07 (d, 3H).

LC-MS (Method 3): $R_t$=1.86 min; 501 [M+H]$^+$.

Example 472

7-[(3R,4R)-3,4-Dihydroxypyrrolidin-1-yl]-N-[(2S)-3-methylbutan-2-yl]-4-oxo-1-(2,4,6-trifluorophenyl)-1,4-dihydro-1,8-naphthyridine-3-carboxamide

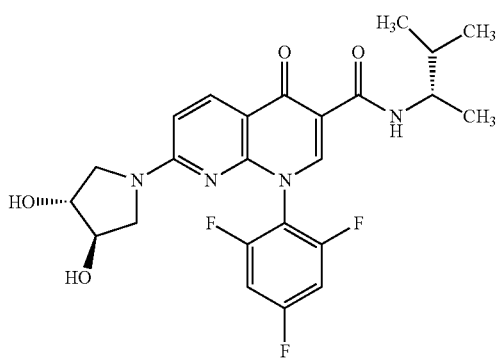 [SMILES: CC(C)[C@H](C)NC(=O)c1cn(-c2c(F)cc(F)cc2F)c2nc(N3C[C@@H](O)[C@H](O)C3)ccc2c1=O]

According to GP1, 50.0 mg (119 µmol) of the compound from Example 121A were reacted with 12.4 mg (142 µmol) of (2S)-3-methylbutan-2-amine in the presence of 54.1 mg (142 µmol) of HATU and 52.0 µl (297 µmol) of N,N-diisopropylethylamine in 2.4 ml of dimethylformamide. The mixture was diluted with 0.3 ml of 1 M aqueous hydrochloric acid and 1 ml of acetonitrile and purified by means of preparative HPLC (column: Chromatorex C18, 10 µm, 125× 30 mm, solvent: acetonitrile/0.05% formic acid gradient; 0 to 5 min 10% acetonitrile, to 14 min 90% acetonitrile and for a further 4 min 90% acetonitrile). 36.0 mg (61% of theory, 99% purity) of the title compound were obtained.

$^1$H-NMR (400 MHz, DMSO-$d_6$): δ [ppm]=9.96 (d, 1H), 8.67 (s, 1H), 8.27 (d, 1H), 7.61-7.51 (m, 2H), 6.75 (d, 1H), 5.22 (d, 1H), 5.14 (d, 1H), 4.05 (br. s, 1H), 3.96-3.86 (m, 2H), 3.61 (dd, 1H), 3.25 (dd, 1H), 3.07 (d, 1H), 1.82-1.72 (m, 1H), 1.11 (d, 3H), 0.97-0.88 (m, 6H).

LC-MS (Method 3): $R_t$=1.57 min; 491 [M+H]$^+$.

Example 473

7-[(4S)-4-Hydroxy-2-oxopyrrolidin-1-yl]-N-[(2R)-3-methylbutan-2-yl]-4-oxo-1-(2,4,6-trifluorophenyl)-1,4-dihydro-1,8-naphthyridine-3-carboxamide

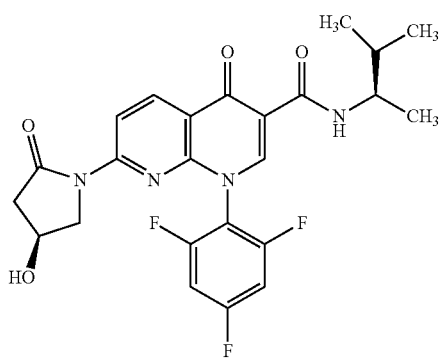 [SMILES: CC(C)[C@@H](C)NC(=O)c1cn(-c2c(F)cc(F)cc2F)c2nc(N3C[C@@H](O)CC3=O)ccc2c1=O]

According to GP1, 50.0 mg (119 µmol) of the compound from Example 117A were reacted with 12.5 mg (143 µmol) of (2R)-3-methylbutan-2-amine in the presence of 54.4 mg (143 µmol) of HATU and 52.0 µl (298 µmol) of N,N-diisopropylethylamine in 2.4 ml of dimethylformamide. The mixture was diluted with 0.3 ml of 1 M aqueous hydrochloric acid and 1 ml of acetonitrile and purified by means of preparative HPLC (column: Chromatorex C18, 10 µm, 125× 30 mm, solvent: acetonitrile/0.05% formic acid gradient; 0 to 5 min 10% acetonitrile, to 14 min 90% acetonitrile and for a further 4 min 90% acetonitrile). 41.7 mg (71% of theory, 99% purity) of the title compound were obtained.

$^1$H-NMR (400 MHz, DMSO-$d_6$): δ [ppm]=9.71 (d, 1H), 8.95 (s, 1H), 8.71 (d, 1H), 8.52 (d, 1H), 7.66-7.56 (m, 2H), 5.33 (br. s, 1H), 4.29 (br. s, 1H), 3.99-3.89 (m, 1H), 3.69 (dd, 1H), 3.48 (d, 1H), 2.94 (dd, 1H), 2.37 (d, 1H), 1.85-1.74 (m, 1H), 1.13 (d, 3H), 0.98-0.89 (m, 6H).

LC-MS (Method 3): $R_t$=1.78 min; 489 [M+H]$^+$.

Example 474

7-[(3R,4R)-3,4-Dihydroxypyrrolidin-1-yl]-N-(2,4-dimethylpentan-3-yl)-4-oxo-1-(2,4,6-trifluorophenyl)-1,4-dihydro-1,8-naphthyridine-3-carboxamide

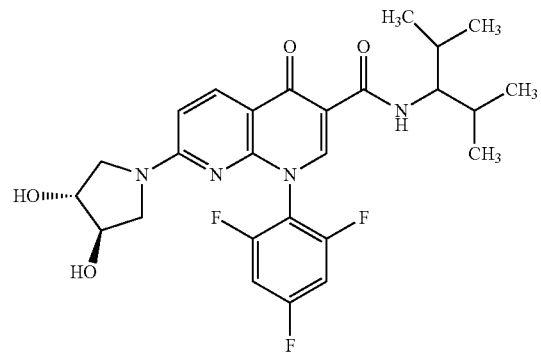 [SMILES: CC(C)C(NC(=O)c1cn(-c2c(F)cc(F)cc2F)c2nc(N3C[C@@H](O)[C@H](O)C3)ccc2c1=O)C(C)C]

According to GP1, 50.0 mg (119 µmol) of the compound from Example 121A were reacted with 16.4 mg (142 µmol) of 2,4-dimethylpentan-3-amine in the presence of 54.1 mg (142 µmol) of HATU and 52.0 µl (297 µmol) of N,N-diisopropylethylamine in 2.4 ml of dimethylformamide. The mixture was diluted with 0.3 ml of 1 M aqueous hydrochloric acid and 1 ml of acetonitrile and purified by means of preparative HPLC (column: Chromatorex C18, 10 µm, 125× 30 mm, eluent: acetonitrile/0.05% formic acid gradient; 0 to 5 min 10% acetonitrile, to 14 min 90% acetonitrile and for a further 4 min 90% acetonitrile). 37.8 mg (61% of theory, 99% purity) of the title compound were obtained.

$^1$H-NMR (400 MHz, DMSO-$d_6$): δ [ppm]=9.85 (d, 1H), 8.69 (s, 1H), 8.29 (d, 1H), 7.61-7.51 (m, 2H), 6.75 (d, 1H), 5.23 (d, 1H), 5.14 (d, 1H), 4.05 (br. s, 1H), 3.93 (br. s, 1H), 3.71-3.56 (m, 2H), 3.25 (dd, 1H), 3.07 (d, 1H), 1.91-1.80 (m, 2H), 0.91-0.85 (m, 12H).

LC-MS (Method 1): $R_t$=0.94 min; 519 [M+H]$^+$.

Example 475

N-(2,4-Dimethylpentan-3-yl)-7-[(4S)-4-hydroxy-2-oxopyrrolidin-1-yl]-4-oxo-1-(2,4,6-trifluorophenyl)-1,4-dihydro-1,8-naphthyridine-3-carboxamide

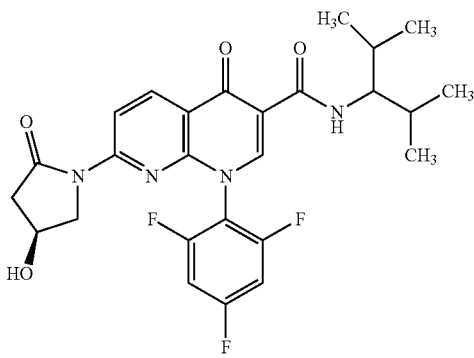 [SMILES: CC(C)C(NC(=O)c1cn(-c2c(F)cc(F)cc2F)c2nc(N3C[C@@H](O)CC3=O)ccc2c1=O)C(C)C]

According to GP1, 50.0 mg (119 μmol) of the compound from Example 117A were reacted with 16.5 mg (143 μmol) of 2,4-dimethylpentan-3-amine in the presence of 54.4 mg (143 μmol) of HATU and 52.0 μl (298 μmol) of N,N-diisopropylethylamine in 2.4 ml of dimethylformamide. The mixture was diluted with 0.3 ml of 1 M aqueous hydrochloric acid and 1 ml of acetonitrile and purified by means of preparative HPLC (column: Chromatorex C18, 10 μm, 125×30 mm, eluent: acetonitrile/0.05% formic acid gradient; 0 to 5 min 10% acetonitrile, to 14 min 90% acetonitrile and for a further 4 min 90% acetonitrile). Finally, purification was effected by means of normal phase chromatography (cyclohexane-ethyl acetate gradient). 37.9 mg (61% of theory, 99% purity) of the title compound were obtained.

$^1$H-NMR (400 MHz, DMSO-$d_6$): δ [ppm]=9.60 (d, 1H), 8.96 (s, 1H), 8.72 (d, 1H), 8.52 (d, 1H), 7.66-7.56 (m, 2H), 5.33 (s, 1H), 4.29 (br. s, 1H), 3.73-3.65 (m, 2H), 3.48 (d, 1H), 2.95 (dd, 1H), 2.37 (d, 1H), 1.93-1.81 (m, 2H), 0.94-0.84 (m, 12H).

LC-MS (Method 3): $R_t$=1.99 min; 517 [M+H]$^+$.

Example 476

N-[1-Cyclobutylethyl]-7-[(3R,4R)-3,4-dihydroxy-pyrrolidin-1-yl]-4-oxo-1-(2,4,6-trifluorophenyl)-1,4-dihydro-1,8-naphthyridine-3-carboxamide (diastereomer mixture)

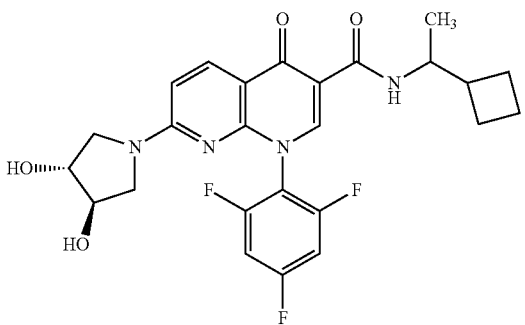 [SMILES: CC(NC(=O)c1cn(-c2c(F)cc(F)cc2F)c2nc(N3C[C@@H](O)[C@H](O)C3)ccc2c1=O)C1CCC1]

According to GP1, 50.0 mg (119 μmol) of the compound from Example 121A were reacted with 19.3 mg (142 μmol) of 1-cyclobutylethanamine hydrochloride (racemate) in the presence of 54.1 mg (142 μmol) of HATU and 72.0 μl (415 μmol) of N,N-diisopropylethylamine in 2.4 ml of dimethylformamide. The mixture was diluted with 0.3 ml of 1 M aqueous hydrochloric acid and 1 ml of acetonitrile and purified by means of preparative HPLC (column: Chromatorex C18, 10 μm, 125×30 mm, solvent: acetonitrile/0.05% formic acid gradient; 0 to 5 min 10% acetonitrile, to 14 min 90% acetonitrile and for a further 4 min 90% acetonitrile). 40.9 mg (68% of theory, 99% purity) of the title compound were obtained.

$^1$H-NMR (400 MHz, DMSO-$d_6$): δ [ppm]=9.86 (d, 1H), 8.68 (s, 1H), 8.27 (d, 1H), 7.60-7.50 (m, 2H), 6.75 (d, 1H), 5.22 (br. s, 1H), 5.13 (br. s, 1H), 4.08-3.89 (m, 3H), 3.65-3.55 (m, 1H), 3.25 (m, 1H), 3.07 (d, 1H), 2.45-2.34 (m, 1H), 2.02-1.67 (m, 6H), 1.05 (d, 3H).

LC-MS (Method 3): $R_t$=1.64 min; 503 [M+H]$^+$.

Example 477

N-[(1S)-1-Cyclopropylethyl]-7-[(3R,4R)-3,4-dihydroxypyrrolidin-1-yl]-4-oxo-1-(2,4,6-trifluorophenyl)-1,4-dihydro-1,8-naphthyridine-3-carboxamide

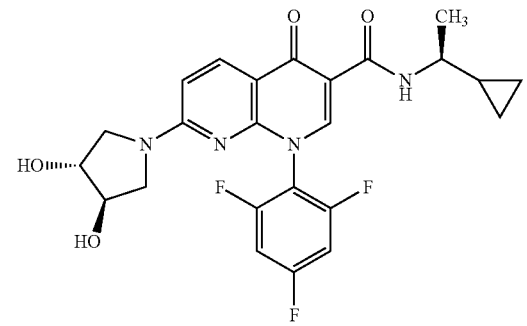 [SMILES: C[C@H](NC(=O)c1cn(-c2c(F)cc(F)cc2F)c2nc(N3C[C@@H](O)[C@H](O)C3)ccc2c1=O)C1CC1]

According to GP1, 50.0 mg (119 μmol) of the compound from Example 121A were reacted with 12.1 mg (142 μmol) of (1S)-1-cyclopropylethanamine in the presence of 54.1 mg (142 μmol) of HATU and 52.0 μl (297 μmol) of N,N-diisopropylethylamine in 2.4 ml of dimethylformamide. The mixture was diluted with 0.3 ml of 1 M aqueous hydrochloric acid and 1 ml of acetonitrile and purified by means of preparative HPLC (column: Chromatorex C18, 10 μm, 125×30 mm, solvent: acetonitrile/0.05% formic acid gradient; 0 to 2.5 min 10% acetonitrile, to 15.5 min 90% acetonitrile and for a further 2 min 90% acetonitrile). 38.9 mg (66% of theory, 99% purity) of the title compound were obtained.

$^1$H-NMR (400 MHz, DMSO-$d_6$): δ [ppm]=9.95 (d, 1H), 8.67 (s, 1H), 8.26 (d, 1H), 7.60-7.51 (m, 2H), 6.75 (d, 1H), 5.22 (br. s, 1H), 5.13 (br. s, 1H), 4.05 (br. s, 1H), 3.93 (br. s, 1H), 3.64-3.48 (m, 2H), 3.25 (m, 1H), 3.07 (d, 1H), 1.22 (d, 3H), 1.03-0.93 (m, 1H), 0.51-0.39 (m, 2H), 0.33-0.20 (m, 2H).

LC-MS (Method 3): $R_t$=1.50 min; 489 [M+H]$^+$.

Example 478

N-[(1S)-1-Cyclopropylethyl]-7-[(4S)-4-hydroxy-2-oxopyrrolidin-1-yl]-4-oxo-1-(2,4,6-trifluorophenyl)-1,4-dihydro-1,8-naphthyridine-3-carboxamide

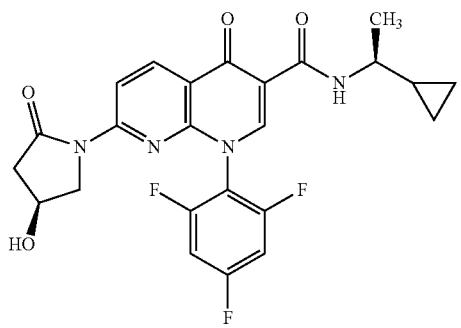 [SMILES: C[C@H](NC(=O)c1cn(-c2c(F)cc(F)cc2F)c2nc(N3C[C@@H](O)CC3=O)ccc2c1=O)C1CC1]

According to GP1, 50.0 mg (119 µmol) of the compound from Example 117A were reacted with 12.2 mg (143 µmol) of (1S)-1-cyclopropylethanamine in the presence of 54.4 mg (143 µmol) of HATU and 52.0 µl (298 µmol) of N,N-diisopropylethylamine in 2.4 ml of dimethylformamide. The mixture was diluted with 0.3 ml of 1 M aqueous hydrochloric acid and 1 ml of acetonitrile and purified by means of preparative HPLC (column: Chromatorex C18, 10 µm, 125×30 mm, solvent: acetonitrile/0.05% formic acid gradient; 0 to 2.5 min 10% acetonitrile, to 15.5 min 90% acetonitrile and for a further 2 min 90% acetonitrile). 26.5 mg (46% of theory, 100% purity) of the title compound were obtained.

$^1$H-NMR (400 MHz, DMSO-$d_6$): δ [ppm]=9.70 (d, 1H), 8.94 (s, 1H), 8.69 (d, 1H), 8.52 (d, 1H), 7.66-7.56 (m, 2H), 5.33 (d, 1H), 4.33-4.25 (m, 1H), 3.69 (dd, 1H), 3.60-3.44 (m, 2H), 2.94 (dd, 1H), 2.37 (d, 1H), 1.24 (d, 1H), 1.06-0.96 (m, 1H), 0.52-0.40 (m, 2H), 0.35-0.21 (m, 2H).

LC-MS (Method 3): $R_t$=1.70 min; 487 [M+H]$^+$.

Example 479

N-tert-Butyl-7-[(3R,4R)-3,4-dihydroxypyrrolidin-1-yl]-4-oxo-1-(2,4,6-trifluorophenyl)-1,4-dihydro-1,8-naphthyridine-3-carboxamide

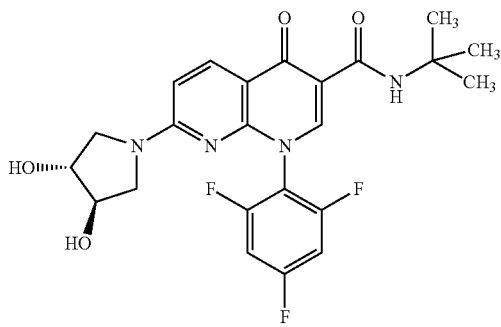 [SMILES: CC(C)(C)NC(=O)c1cn(-c2c(F)cc(F)cc2F)c2nc(N3C[C@@H](O)[C@H](O)C3)ccc2c1=O]

According to GP1, 50.0 mg (119 µmol) of the compound from Example 121A were reacted with 10.4 mg (142 µmol) of 2-methylpropan-2-amine in the presence of 54.1 mg (142 µmol) of HATU and 52.0 µl (297 µmol) of N,N-diisopropylethylamine in 2.4 ml of dimethylformamide. The mixture was diluted with 0.3 ml of 1 M aqueous hydrochloric acid and 1 ml of acetonitrile and purified by means of preparative HPLC (column: Chromatorex C18, 10 µm, 125×30 mm, solvent: acetonitrile/0.05% formic acid gradient; 0 to 2.5 min 10% acetonitrile, to 15.5 min 90% acetonitrile and for a further 2 min 90% acetonitrile). 43.1 mg (76% of theory, 100% purity) of the title compound were obtained.

$^1$H-NMR (400 MHz, DMSO-$d_6$): δ [ppm]=9.95 (s, 1H), 8.65 (s, 1H), 8.26 (d, 1H), 7.60-7.51 (m, 2H), 6.74 (d, 1H), 5.22 (d, 1H), 5.13 (d, 1H), 4.04 (br. s, 1H), 3.92 (br. s, 1H), 3.60 (dd, 1H), 3.24 (dd, 1H), 3.06 (d, 1H), 1.39 (s, 9H).

LC-MS (Method 3): $R_t$=1.51 min; 477 [M+H]$^+$.

Example 480

N-[(1R)-1-Cyclopropylethyl]-7-[(4S)-4-hydroxy-2-oxopyrrolidin-1-yl]-4-oxo-1-(2,4,6-trifluorophenyl)-1,4-dihydro-1,8-naphthyridine-3-carboxamide

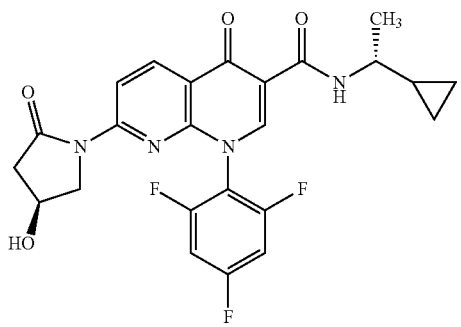 [SMILES: C[C@@H](NC(=O)c1cn(-c2c(F)cc(F)cc2F)c2nc(N3C[C@@H](O)CC3=O)ccc2c1=O)C1CC1]

According to GP1, 50.0 mg (119 µmol) of the compound from Example 117A were reacted with 12.2 mg (143 µmol) of (1R)-1-cyclopropylethanamine in the presence of 54.4 mg (143 µmol) of HATU and 52.0 µl (298 µmol) of N,N-diisopropylethylamine in 2.4 ml of dimethylformamide. The mixture was diluted with 0.3 ml of 1 M aqueous hydrochloric acid and 1 ml of acetonitrile and purified by means of preparative HPLC (column: Chromatorex C18, 10 µm, 125×30 mm, solvent: acetonitrile/0.05% formic acid gradient; 0 to 2.5 min 10% acetonitrile, to 15.5 min 90% acetonitrile and for a further 2 min 90% acetonitrile). 25.7 mg (44% of theory, 100% purity) of the title compound were obtained.

$^1$H-NMR (400 MHz, DMSO-$d_6$): δ [ppm]=9.70 (d, 1H), 8.95 (s, 1H), 8.69 (d, 1H), 8.52 (d, 1H), 7.65-7.57 (m, 2H), 5.33 (d, 1H), 4.32-4.26 (m, 1H), 3.69 (dd, 1H), 3.59-3.44 (m, 2H), 2.94 (dd, 1H), 2.37 (d, 1H), 1.25 (d, 1H), 1.05-0.96 (m, 1H), 0.53-0.40 (m, 2H), 0.35-0.21 (m, 2H).

LC-MS (Method 3): $R_t$=1.70 min; 487 [M+H]$^+$.

Example 481

N-(2-Cyclopropylpropan-2-yl)-7-[(4S)-4-hydroxy-2-oxopyrrolidin-1-yl]-4-oxo-1-(2,4,6-trifluorophenyl)-1,4-dihydro-1,8-naphthyridine-3-carboxamide

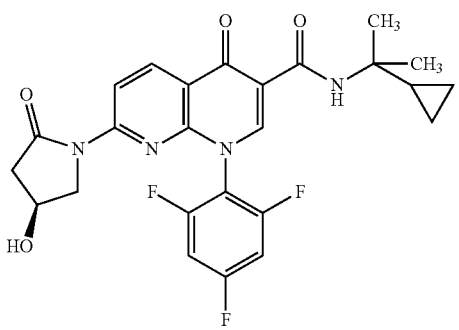 [SMILES: CC(C)(NC(=O)c1cn(-c2c(F)cc(F)cc2F)c2nc(N3C[C@@H](O)CC3=O)ccc2c1=O)C1CC1]

According to GP1, 50.0 mg (119 µmol) of the compound from Example 117A were reacted with 14.2 mg (143 µmol) of 2-cyclopropylpropan-2-amine in the presence of 54.4 mg (143 µmol) of HATU and 52.0 µl (298 µmol) of N,N-diisopropylethylamine in 2.4 ml of dimethylformamide. The mixture was diluted with 0.3 ml of 1 M aqueous hydrochloric acid and 1 ml of acetonitrile and purified by means of preparative HPLC (column: Chromatorex C18, 10 µm, 125× 30 mm, eluent: acetonitrile/0.05% formic acid gradient; 0 to 5 min 10% acetonitrile, to 14 min 90% acetonitrile and for a further 4 min 90% acetonitrile). 41.4 mg (69% of theory, 99% purity) of the title compound were obtained.

$^1$H-NMR (400 MHz, DMSO-$d_6$): δ [ppm]=9.71 (s, 1H), 8.92 (s, 1H), 8.70 (d, 1H), 8.51 (d, 1H), 7.66-7.57 (m, 2H), 5.32 (d, 1H), 4.32-4.26 (m, 1H), 3.69 (dd, 1H), 3.48 (d, 1H), 2.94 (dd, 1H), 2.37 (d, 1H), 1.33 (s, 6H), 0.43 (s, 2H), 0.41 (s, 2H).

LC-MS (Method 3): $R_t$=1.87 min; 501 [M+H]$^+$.

Example 482

7-[(4S)-4-Hydroxy-2-oxopyrrolidin-1-yl]-N-[(2R)-3-methylbutan-2-yl]-4-oxo-1-(2,4,6-trifluorophenyl)-1,4-dihydro-1,8-naphthyridine-3-carboxamide

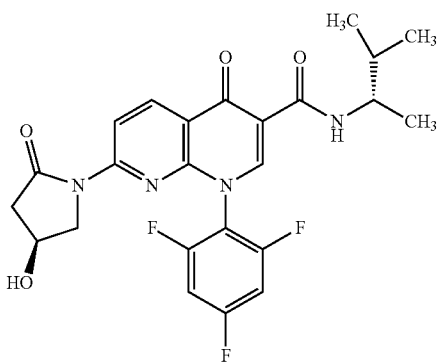 [SMILES: CC(C)[C@H](C)NC(=O)c1cn(-c2c(F)cc(F)cc2F)c2nc(N3C[C@@H](O)CC3=O)ccc2c1=O]

According to GP1, 50.0 mg (119 µmol) of the compound from Example 117A were reacted with 12.5 mg (143 µmol) of (2S)-3-methylbutan-2-amine in the presence of 54.4 mg (143 µmol) of HATU and 52.0 µl (298 µmol) of N,N-diisopropylethylamine in 2.4 ml of dimethylformamide. The mixture was diluted with 0.3 ml of 1 M aqueous hydrochloric acid and 1 ml of acetonitrile and purified by means of preparative HPLC (column: Chromatorex C18, 10 µm, 125× 30 mm, solvent: acetonitrile/0.05% formic acid gradient; 0 to 5 min 10% acetonitrile, to 14 min 90% acetonitrile and for a further 4 min 90% acetonitrile). 37.4 mg (64% of theory, 99% purity) of the title compound were obtained.

$^1$H-NMR (400 MHz, DMSO-$d_6$): δ [ppm]=9.70 (d, 1H), 8.95 (s, 1H), 8.71 (d, 1H), 8.52 (d, 1H), 7.66-7.57 (m, 2H), 5.33 (d, 1H), 4.32-4.26 (m, 1H), 3.99-3.88 (m, 1H), 3.69 (dd, 1H), 3.48 (d, 1H), 2.94 (dd, 1H), 2.37 (d, 1H), 1.84-1.74 (m, 1H), 1.12 (d, 3H), 0.98-0.89 (m, 6H).

LC-MS (Method 3): $R_t$=1.77 min; 489 [M+H]$^+$.

Example 483

7-[(3R,4R)-3,4-Dihydroxypyrrolidin-1-yl]-N-[(2R)-3-methylbutan-2-yl]-4-oxo-1-(2,4,6-trifluorophenyl)-1,4-dihydro-1,8-naphthyridine-3-carboxamide

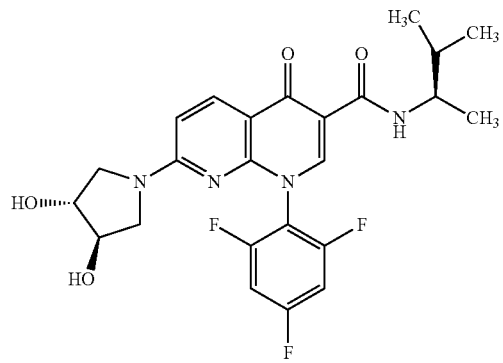 [SMILES: CC(C)[C@@H](C)NC(=O)c1cn(-c2c(F)cc(F)cc2F)c2nc(N3C[C@@H](O)[C@H](O)C3)ccc2c1=O]

According to GP1, 50.0 mg (119 µmol) of the compound from Example 121A were reacted with 12.4 mg (142 µmol) of (2R)-3-methylbutan-2-amine in the presence of 54.1 mg (142 µmol) of HATU and 52.0 µl (297 µmol) of N,N-diisopropylethylamine in 2.4 ml of dimethylformamide. The mixture was diluted with 0.3 ml of 1 M aqueous hydrochloric acid and 1 ml of acetonitrile and purified by means of preparative HPLC (0.05% formic acid, water-acetonitrile gradient). 30.1 mg (51% of theory, 99% purity) of the title compound were obtained.

$^1$H-NMR (400 MHz, DMSO-$d_6$): δ [ppm]=9.96 (d, 1H), 8.68 (s, 1H), 8.27 (d, 1H), 7.60-7.50 (m, 2H), 6.75 (d, 1H), 5.23 (d, 1H), 5.13 (d, 1H), 4.05 (br. s, 1H), 3.97-3.86 (m, 2H), 3.61 (dd, 1H), 3.25 (dd, 1H), 3.07 (d, 1H), 1.82-1.72 (m, 1H), 1.11 (d, 3H), 0.96-0.86 (m, 6H).

LC-MS (Method 3): $R_t$=1.56 min; 491 [M+H]$^+$.

Example 484

7-[(4S)-4-Hydroxy-2-oxopyrrolidin-1-yl]-N-[2-methylpentan-3-yl]-4-oxo-1-(2,4,6-trifluorophenyl)-1,4-dihydro-1,8-naphthyridine-3-carboxamide (diastereomer mixture)

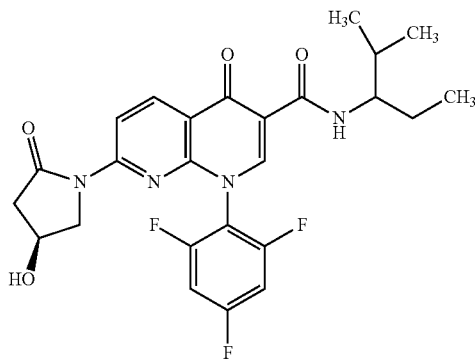 [SMILES: CCC(NC(=O)c1cn(-c2c(F)cc(F)cc2F)c2nc(N3C[C@@H](O)CC3=O)ccc2c1=O)C(C)C]

According to GP1, 100 mg (238 µmol) of the compound from Example 117A were reacted with 39.4 mg (286 µmol) of 2-methylpentan-3-amine hydrochloride (racemate) in the presence of 109 mg (286 µmol) of HATU and 145 µl (835 µmol) of N,N-diisopropylethylamine in 4.6 ml of dimethylformamide. The mixture was diluted with 0.3 ml of 1 M aqueous hydrochloric acid and 1 ml of acetonitrile and purified by means of preparative HPLC (column: Chromatorex C18, 10 µm, 125×30 mm, solvent: acetonitrile/0.05% formic acid gradient; 0 to 5.5 min 10% acetonitrile, to 34 min 90% acetonitrile and for a further 7.5 min 90% acetonitrile). 83.4 mg (69% of theory, 99% purity) of the title compound were obtained.

$^1$H-NMR (400 MHz, DMSO-d$_6$): δ [ppm]=9.61 (d, 1H), 8.95 (s, 1H), 8.71 (d, 1H), 8.52 (d, 1H), 7.66-7.56 (m, 2H), 5.33 (d, 1H), 4.32-4.26 (m, 1H), 3.87-3.77 (m, 1H), 3.69 (dd, 1H), 3.48 (d, 1H), 2.95 (dd, 1H), 2.37 (d, 1H), 1.89-1.78 (m, 1H), 1.65-1.53 (m, 1H), 1.50-1.37 (m, 1H), 0.96-0.82 (m, 9H).

LC-MS (Method 3): R$_t$=1.89 min; 503 [M+H]$^+$.

80 mg of the title compound (diastereomer mixture) were separated into the diastereomers by chiral HPLC (preparative HPLC: column: Daicel Chiralcel OX-H 5 µm 250×20 mm; eluent: 25% ethanol, 75% n-heptane; temperature: 23° C.; flow rate: 30 ml/min; UV detection: 260 nm).

This gave (in the sequence of elution from the column) 30.7 mg of diastereomer 1 (99% de) R$_t$=4.00 min and 31.7 mg (99% de) of diastereomer 2 R$_t$=4.99 min.

[Analytical HPLC: column: Daicel OX-3 50×4.6 mm; eluent: 20% ethanol, 80% isohexane; UV detection: 220 nm].

Diastereomer 1 was additionally obtained by means of preparative HPLC (water-acetonitrile gradient), and 29.8 mg (25% of theory, 99% purity) of the title compound from Example 485 were obtained.

Diastereomer 2 was additionally obtained by means of preparative HPLC (water-acetonitrile gradient), and 28.6 mg (24% of theory, 99% purity) of the title compound from Example 486 were obtained.

Example 485

7-[(4S)-4-Hydroxy-2-oxopyrrolidin-1-yl]-N-[2-methylpentan-3-yl]-4-oxo-1-(2,4,6-trifluorophenyl)-1,4-dihydro-1,8-naphthyridine-3-carboxamide (diastereomer 1)

$^1$H-NMR (400 MHz, DMSO-d$_6$): δ [ppm]=9.60 (d, 1H), 8.95 (s, 1H), 8.71 (d, 1H), 8.52 (d, 1H), 7.66-7.56 (m, 2H), 5.33 (d, 1H), 4.32-4.26 (m, 1H), 3.86-3.78 (m, 1H), 3.69 (dd, 1H), 3.48 (d, 1H), 2.94 (dd, 1H), 2.37 (d, 1H), 1.89-1.78 (m, 1H), 1.65-1.53 (m, 1H), 1.50-1.37 (m, 1H), 0.96-0.83 (m, 9H).

LC-MS (Method 3): R$_t$=1.91 min; 503 [M+H]$^+$.

Example 486

7-[(4S)-4-Hydroxy-2-oxopyrrolidin-1-yl]-N-[2-methylpentan-3-yl]-4-oxo-1-(2,4,6-trifluorophenyl)-1,4-dihydro-1,8-naphthyridine-3-carboxamide (diastereomer 2)

$^1$H-NMR (400 MHz, DMSO-d$_6$): δ [ppm]=9.60 (d, 1H), 8.95 (s, 1H), 8.71 (d, 1H), 8.52 (d, 1H), 7.66-7.57 (m, 2H), 5.33 (d, 1H), 4.32-4.26 (m, 1H), 3.87-3.78 (m, 1H), 3.69 (dd, 1H), 3.48 (d, 1H), 2.94 (dd, 1H), 2.37 (d, 1H), 1.88-1.78 (m, 1H), 1.65-1.53 (m, 1H), 1.50-1.37 (m, 1H), 0.95-0.84 (m, 9H).

LC-MS (Method 3): R$_t$=1.91 min; 503 [M+H]$^+$.

Example 487

7-[(3R,4R)-3,4-Dihydroxypyrrolidin-1-yl]-N-[2-methylpentan-3-yl]-4-oxo-1-(2,4,6-trifluorophenyl)-1,4-dihydro-1,8-naphthyridine-3-carboxamide (diastereomer mixture)

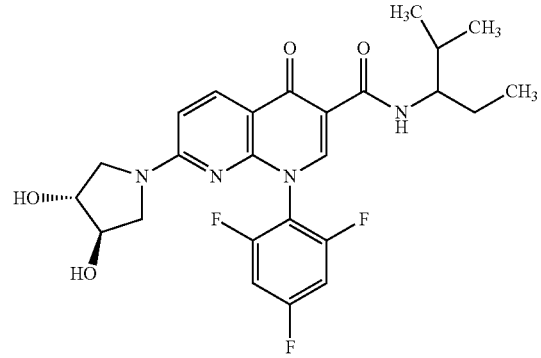 [SMILES: CCC(NC(=O)c1cn(-c2c(F)cc(F)cc2F)c2nc(N3C[C@@H](O)[C@H](O)C3)ccc2c1=O)C(C)C]

According to GP1, 100 mg (237 µmol) of the compound from Example 121A were reacted with 39.2 mg (285 µmol) of 2-methylpentan-3-amine hydrochloride (racemate) in the presence of 108 mg (285 µmol) of HATU and 145 µl (835 µmol) of N,N-diisopropylethylamine in 4.6 ml of dimethylformamide. The mixture was diluted with 0.3 ml of 1 M aqueous hydrochloric acid and 1 ml of acetonitrile and purified by means of preparative HPLC (column: Chromatorex C18, 10 µm, 125×30 mm, solvent: acetonitrile/0.05% formic acid gradient; 0 to 5 min 10% acetonitrile, to 14 min 90% acetonitrile and for a further 4 min 90% acetonitrile). 80.7 mg (67% of theory, 99% purity) of the title compound were obtained.

¹H-NMR (400 MHz, DMSO-d₆): δ [ppm]=9.86 (d, 1H), 8.68 (s, 1H), 8.28 (d, 1H), 7.60-7.51 (m, 2H), 6.75 (d, 1H), 5.23 (d, 1H), 5.13 (d, 1H), 4.05 (br. s, 1H), 3.92 (br. s, 1H), 3.84.3.75 (m, 1H), 3.61 (dd, 1H), 3.25 (dd, 1H), 3.07 (d, 1H), 1.87-1.76 (m, 1H), 1.63-1.51 (m, 1H), 1.48-1.35 (m, 1H), 0.94-0.84 (m, 9H).

LC-MS (Method 3): $R_t$=1.69 min; 505 [M+H]⁺.

Example 488

7-[(3R)-3-Hydroxy-2-oxopyrrolidin-1-yl]-4-oxo-N-(1,1,1-trifluoro-2-methylpropan-2-yl)-1-(2,4,6-trifluorophenyl)-1,4-dihydro-1,8-naphthyridine-3-carboxamide

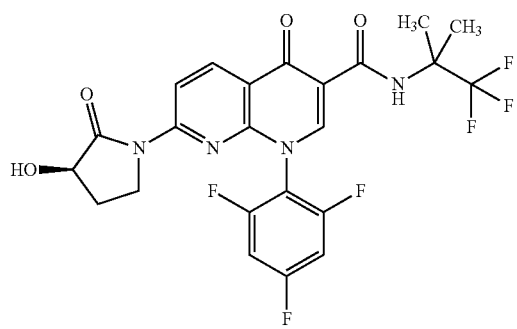 [SMILES: CC(C)(NC(=O)c1cn(-c2c(F)cc(F)cc2F)c2nc(N3CC[C@@H](O)C3=O)ccc2c1=O)C(F)(F)F]

According to GP1, 63.0 mg (150 µmol) of the compound from Example 149A were reacted with 21.0 mg (165 µmol) of 1,1,1-trifluoro-2-methylpropan-2-amine in the presence of 68.6 mg (180 µmol) of HATU and 65.0 µl (376 µmol) of N,N-diisopropylethylamine in 2.1 ml of dimethylformamide. The mixture was diluted with 0.1 ml of 1 M aqueous hydrochloric acid and 1 ml of acetonitrile and purified by means of preparative HPLC (column: Chromatorex C18, 10 µm, 125×30 mm, solvent: acetonitrile/0.05% formic acid gradient; 0 to 5 min 10% acetonitrile, to 14 min 90% acetonitrile and for a further 4 min 90% acetonitrile). 64.8 mg (81% of theory, 99% purity) of the title compound were obtained.

¹H-NMR (400 MHz, DMSO-d₆): δ [ppm]=10.34 (s, 1H), 9.02 (s, 1H), 8.74 (d, 1H), 8.54 (d, 1H), 7.64-7.54 (m, 2H), 5.91 (d, 1H), 4.43-4.35 (m, 1H), 3.62-3.54 (m, 1H), 2.38-2.27 (m, 1H), 1.83-1.70 (m, 1H), 1.65 (s, 6H).

LC-MS (Method 3): $R_t$=1.91 min; 529 [M+H]⁺.

Example 489

7-[4,4-Bis(hydroxymethyl)piperidin-1-yl]-N-[(1S)-1-cyclopropyl-2,2,2-trifluoroethyl]-4-oxo-1-(2,4,6-trifluorophenyl)-1,4-dihydro-1,8-naphthyridine-3-carboxamide

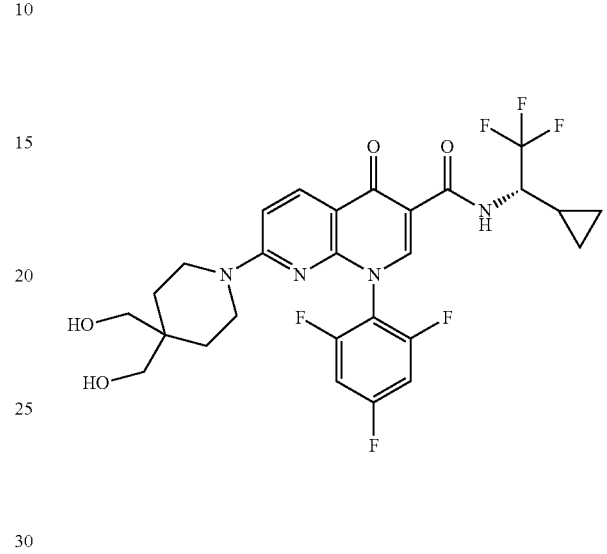

The compound from Example 126A (60.0 mg, 126 µmol) was initially charged in 1.3 ml of DMF, 4,4-piperidinediyldimethanol hydrochloride (32 mg, 177 µmol) and N,N-diisopropylethylamine (99 µl, 567 µmol) were added, and the mixture was stirred at room temperature overnight. The reaction solution was admixed with acetonitrile/water/TFA and purified by means of preparative HPLC (RP18 column, eluent: acetonitrile/water gradient with addition of 0.1% TFA). The product fractions were concentrated, and the residue was dissolved in dichloromethane and washed twice with saturated aqueous sodium hydrogencarbonate solution. The combined aqueous phases were re-extracted once with dichloromethane. The combined organic phases were dried over sodium sulphate, filtered and concentrated by rotary evaporation. This gave 67 mg of the target compound (89% of theory, purity 98%).

LC-MS (Method 3): $R_t$=1.83 min; MS (ESIpos): m/z=585 [M+H]⁺

¹H-NMR (400 MHz, DMSO-d₆) δ [ppm]: −0.008 (0.91), 0.006 (0.40), 0.008 (0.59), 1.334 (0.64), 2.519 (0.77), 2.524 (0.69), 3.276 (1.91), 3.290 (1.96), 3.310 (16.00), 3.475 (0.57), 4.399 (0.74), 4.412 (1.55), 4.426 (0.61), 7.078 (0.69), 7.101 (0.69), 7.542 (0.48), 7.564 (0.88), 7.586 (0.48), 8.244 (0.95), 8.267 (0.87), 8.792 (1.45), 10.539 (0.54), 10.562 (0.51).

In analogy to Example 489, the example compounds shown in Table 23 were prepared by reacting the respected starting compounds Example 126A or Example 115A with the appropriate amines (or salts thereof; 1.2-4 equivalents) under the reaction conditions described (1.5 h to 18 h at room temperature).

TABLE 23

| Ex. | IUPAC name<br>Structure<br>Amine used<br>Yield | LC-MS method<br>Retention time<br>Mass detected<br>NMR data |
|---|---|---|
| 490 | N-[(1S)-1-Cyclopropyl-2,2,2-trifluoroethyl]-7-(4-methylpiperazin-1-yl)-4-oxo-1-(2,4,6-trifluorophenyl)-1,4-dihydro-1,8-naphthyridine-3-carboxamide<br>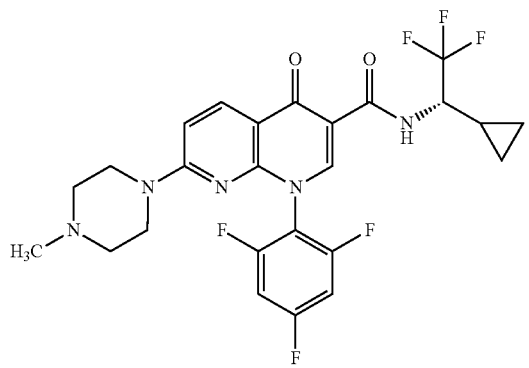<br>with 1-methylpiperazine<br>(84% of theory) | LC-MS (Method 3):<br>$R_t$ = 1.34 min<br>m/z = 540 [M + H]$^+$<br>$^1$H-NMR (400 MHz, DMSO-d$_6$) δ [ppm]:<br>0.008 (2.50), 0.320 (0.77), 0.330 (1.18), 0.343 (1.15), 0.355 (0.91), 0.366 (0.44), 0.511 (0.83), 0.523 (1.21), 0.535 (1.10), 0.547 (1.19), 0.555 (0.93), 0.566 (1.24), 0.577 (1.01), 0.587 (0.92), 0.597 (0.75), 0.611 (0.46), 0.626 (0.65), 0.636 (0.63), 0.647 (1.12), 0.657 (0.98), 0.663 (0.93), 0.670 (0.89), 0.678 (0.44), 1.177 (0.50), 1.185 (0.71), 1.197 (1.20), 1.206 (0.87), 1.217 (1.15), 1.229 (0.69), 1.238 (0.50), 2.073 (0.92), 2.159 (16.00), 2.276 (3.99), 2.288 (5.69), 2.299 (4.00), 2.323 (0.63), 2.328 (0.70), 2.366 (0.42), 2.524 (1.74), 2.670 (0.54), 3.494 (4.95), 4.350 (0.61), 4.371 (1.07), 4.392 (1.03), 4.412 (0.56), 5.754 (1.16), 7.126 (3.15), 7.149 (3.22), 7.543 (2.11), 7.565 (4.02), 7.587 (2.14), 8.284 (3.99), 8.306 (3.73), 8.811 (6.22), 10.498 (2.43), 10.521 (2.35). |
| 491 | N-[(1S)-1-Cyclopropyl-2,2,2-trifluoroethyl]-7-{[(2S)-2,3-dihydroxypropyl](methyl)amino}-4-oxo-1-(2,4,6-trifluorophenyl)-1,4-dihydro-1,8-naphthyridine-3-carboxamide<br>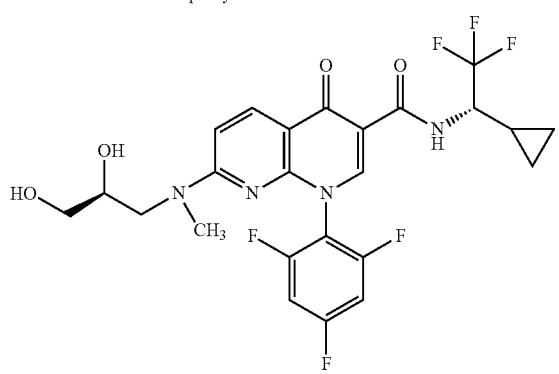<br>with (2S)-3-(methylamino)propane-1,2-diol<br>(74% of theory) | LC-MS (Method 3):<br>$R_t$ = 1.76 min<br>m/z = 545 [M + H]$^+$<br>$^1$H-NMR (400 MHz, DMSO-d$_6$) δ [ppm]:<br>-0.149 (0.45), -0.008 (4.12), 0.008 (3.53), 0.146 (0.46), 0.322 (1.80), 0.333 (2.84), 0.346 (2.88), 0.357 (2.23), 0.369 (1.13), 0.509 (1.97), 0.520 (2.93), 0.533 (2.58), 0.547 (2.54), 0.555 (2.30), 0.567 (2.93), 0.577 (2.52), 0.588 (2.25), 0.598 (1.89), 0.612 (1.13), 0.626 (1.39), 0.636 (1.63), 0.646 (2.58), 0.657 (2.36), 0.662 (2.26), 0.671 (2.23), 0.682 (1.10), 0.691 (0.72), 1.163 (0.59), 1.175 (1.21), 1.183 (1.76), 1.195 (3.01), 1.204 (2.17), 1.216 (3.01), 1.228 (1.78), 1.236 (1.60), 2.328 (1.08), 2.366 (0.67), 2.524 (3.51), 2.670 (1.28), 2.710 (0.85), 2.832 (1.95), 3.136 (2.77), 3.371 (1.04), 3.488 (1.45), 3.690 (0.58), 4.352 (1.52), 4.372 (2.82), 4.394 (3.08), 4.414 (2.02), 4.608 (0.82), 4.744 (0.67), 4.937 (0.61), 6.935 (0.85), 7.541 (3.01), 8.273 (1.43), 8.793 (16.00), 10.551 (3.17), 10.575 (3.08). |
| 492 | N-[(1S)-1-Cyclopropyl-2,2,2-trifluoroethyl]-7-(2-oxa-6-azaspiro[3.3]hept-6-yl)-4-oxo-1-(2,4,6-trifluorophenyl)-1,4-dihydro-1,8-naphthyridine-3-carboxamide<br>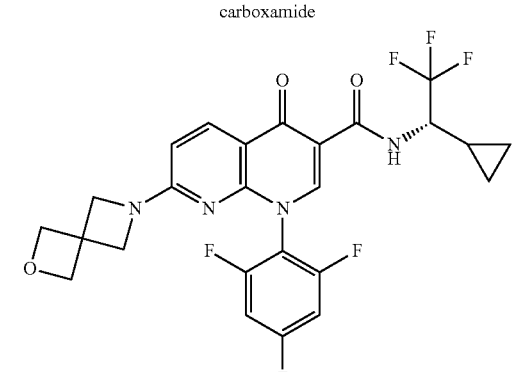<br>with 2-oxa-6-azaspiro[3.3]heptane-ethanedioic acid<br>(74% of theory) | LC-MS (Method 3):<br>$R_t$ = 2.06 min<br>m/z = 539 [M + H]$^+$<br>$^1$H-NMR (400 MHz, DMSO-d$_6$) δ [ppm]:<br>-0.008 (1.90), 0.008 (1.59), 0.314 (0.60), 0.325 (0.95), 0.337 (0.94), 0.348 (0.72), 0.505 (0.67), 0.517 (0.97), 0.530 (0.86), 0.541 (0.95), 0.549 (0.73), 0.560 (0.98), 0.571 (0.79), 0.581 (0.74), 0.591 (0.60), 0.622 (0.51), 0.632 (0.53), 0.642 (0.86), 0.653 (0.77), 0.659 (0.76), 0.666 (0.73), 1.172 (0.40), 1.181 (0.55), 1.193 (1.00), 1.201 (0.71), 1.213 (0.98), 1.225 (0.52), 1.233 (0.47), 2.073 (7.30), 2.328 (0.46), 2.524 (1.43), 2.670 (0.46), 4.348 (0.62), 4.368 (0.92), 4.390 (0.90), 4.410 (0.48), 4.658 (16.00), 5.754 (1.18), 6.593 (3.51), 6.615 (3.56), 7.530 (1.77), 7.552 (3.33), 7.574 (1.80), 8.272 (3.89), 8.294 (3.66), 8.796 (5.72), 10.506 (1.93), 10.530 (1.84). |

TABLE 23-continued

| Ex. | IUPAC name<br>Structure<br>Amine used<br>Yield | LC-MS method<br>Retention time<br>Mass detected<br>NMR data |
|---|---|---|
| 493 | N-[(1S)-1-Cyclopropyl-2,2,2-trifluoroethyl]-7-{[(2S)-2-hydroxypropyl](methyl)amino}-4-oxo-1-(2,4,6-trifluorophenyl)-1,4-dihydro-1,8-naphthyridine-3-carboxamide<br>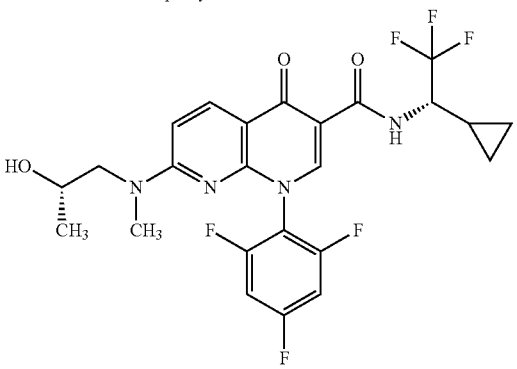<br>with (2S)-1-(methylamino)propan-2-ol<br>(81% of theory) | LC-MS (Method 3):<br>$R_t$ = 2.01 min<br>m/z = 529 [M + H]$^+$<br>$^1$H-NMR (400 MHz, DMSO-d$_6$) δ [ppm]:<br>−0.149 (0.59), −0.008 (8.10), 0.008 (5.14),<br>0.146 (0.65), 0.322 (2.70), 0.333 (3.90),<br>0.345 (3.93), 0.357 (2.97), 0.369 (1.47),<br>0.508 (2.94), 0.520 (4.26), 0.532 (3.73),<br>0.546 (3.67), 0.554 (3.38), 0.566 (4.17),<br>0.576 (3.61), 0.587 (3.29), 0.597 (2.73),<br>0.611 (1.85), 0.625 (2.23), 0.635 (2.58),<br>0.646 (3.76), 0.656 (3.58), 0.661 (3.46),<br>0.670 (3.38), 0.678 (1.94), 0.691 (1.73),<br>0.737 (4.79), 1.076 (1.32), 1.163 (1.20),<br>1.175 (2.03), 1.183 (2.70), 1.195 (4.37),<br>1.204 (3.14), 1.216 (4.23), 1.228 (2.64),<br>1.236 (2.44), 2.328 (1.41), 2.366 (1.14),<br>2.524 (8.46), 2.670 (1.73), 2.710 (1.32),<br>2.834 (2.14), 3.142 (5.58), 3.420 (2.79),<br>3.602 (1.32), 3.865 (0.47), 4.354 (2.32),<br>4.375 (3.64), 4.396 (3.29), 4.416 (1.88),<br>4.631 (1.79), 4.825 (0.50), 5.754 (0.53),<br>6.927 (1.61), 7.546 (5.55), 7.568 (9.95),<br>7.590 (5.40), 8.281 (2.08), 8.804 (16.00),<br>10.546 (4.40), 10.569 (4.20). |
| 494 | N-[(1S)-1-Cyclopropyl-2,2,2-trifluoroethyl]-7-{[(2S)-2-hydroxypropyl](methyl)amino}-4-oxo-1-(2,4,6-trifluorophenyl)-1,4-dihydro-1,8-naphthyridine-3-carboxamide<br>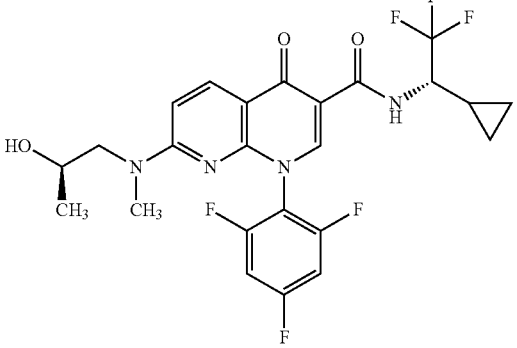<br>with (2S)-1-(methylamino)propan-2-ol<br>(75% of theory) | LC-MS (Method 3):<br>$R_t$ = 2.01 min<br>m/z = 529 [M + H]$^+$<br>$^1$H-NMR (400 MHz, DMSO-d$_6$) δ [ppm]:<br>−0.149 (0.60), −0.008 (5.76), 0.008 (5.76),<br>0.146 (0.70), 0.323 (2.44), 0.334 (3.89),<br>0.346 (3.91), 0.358 (3.04), 0.369 (1.55),<br>0.510 (2.67), 0.522 (3.96), 0.534 (3.49),<br>0.547 (3.66), 0.555 (3.17), 0.567 (3.99),<br>0.578 (3.41), 0.588 (3.17), 0.599 (2.59),<br>0.612 (1.67), 0.626 (2.02), 0.637 (2.27),<br>0.647 (3.64), 0.658 (3.29), 0.663 (3.24),<br>0.671 (3.26), 0.683 (1.82), 0.693 (1.60),<br>0.742 (4.64), 1.079 (1.25), 1.163 (0.90),<br>1.175 (1.72), 1.183 (2.52), 1.195 (4.06),<br>1.204 (2.99), 1.216 (4.04), 1.228 (2.49),<br>1.236 (2.12), 1.249 (0.85), 2.073 (0.47),<br>2.328 (1.42), 2.366 (1.05), 2.523 (5.73),<br>2.670 (1.69), 2.710 (1.17), 2.835 (1.99),<br>3.140 (5.51), 3.420 (2.77), 3.452 (1.87),<br>3.606 (1.25), 3.877 (0.45), 4.330 (0.50),<br>4.350 (2.02), 4.372 (3.59), 4.392 (3.46),<br>4.413 (1.87), 4.625 (1.72), 4.826 (0.47),<br>6.925 (1.57), 7.546 (5.38), 7.568 (10.14),<br>7.590 (5.53), 8.281 (1.94), 8.804 (16.00),<br>10.546 (4.54) , 10.569 (4.46). |

TABLE 23-continued

| Ex. | IUPAC name<br>Structure<br>Amine used<br>Yield | LC-MS method<br>Retention time<br>Mass detected<br>NMR data |
|---|---|---|
| 495 | 7-{[(2R)-2-Hydroxypropyl](methyl)amino}-4-oxo-N-[(2S)-1,1,1-trifluorobutan-2-yl]-1-(2,4,6-trifluorophenyl)-1,4-dihydro-1,8-naphthyridine-3-carboxamide<br>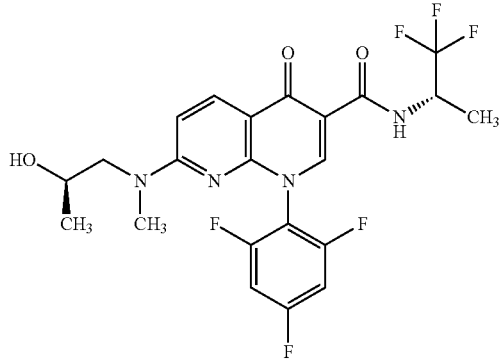<br>with (2R)-1-(methylamino)propan-2-ol<br>(84% of theory) | LC-MS (Method 1):<br>$R_t$ = 1.06 min<br>m/z = 517 [M + H]$^+$<br>$^1$H-NMR (400 MHz, DMSO-d$_6$) δ [ppm]:<br>0.008 (1.41), 0.744 (2.98), 0.953 (7.32),<br>0.971 (16.00), 0.989 (8.01), 1.072 (0.79),<br>1.233 (0.48), 1.603 (1.07), 1.621 (1.44),<br>1.628 (1.30), 1.638 (1.76), 1.646 (1.56),<br>1.656 (1.51), 1.663 (1.70), 1.682 (1.28),<br>1.832 (0.43), 1.851 (1.32), 1.861 (1.53),<br>1.869 (1.55), 1.879 (1.73), 1.886 (1.56),<br>1.896 (1.35), 1.904 (1.16), 1.914 (0.98),<br>2.672 (0.42), 2.837 (1.27), 3.140 (3.52),<br>3.423 (1.78), 3.455 (1.21), 3.606 (0.79),<br>4.626 (1.12), 4.732 (1.60), 4.752 (1.51),<br>6.925 (1.01), 7.549 (3.71), 7.571 (7.04),<br>7.593 (3.75), 8.277 (1.34), 8.814 (11.16),<br>10.413 (2.70), 10.437 (2.70). |
| 496 | 7-(4-Methylpiperazin-1-yl)-4-oxo-N-[(2S)-1,1,1-trifluorobutan-2-yl]-1-(2,4,6-trifluorophenyl)-1,4-dihydro-1,8-naphthyridine-3-carboxamide<br>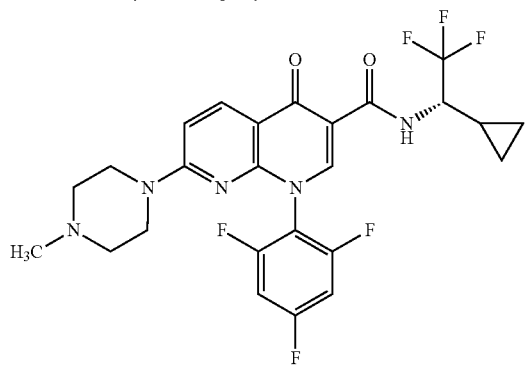<br>with 1-methylpiperazine<br>(83% of theory) | LC-MS (Method 3):<br>$R_t$ = 1.29 min<br>m/z = 528 [M + H]$^+$<br>$^1$H-NMR (400 MHz, DMSO-d$_6$) δ [ppm]:<br>−0.008 (2.46), 0.008 (1.22), 0.949 (3.48),<br>0.968 (7.30), 0.986 (3.51), 1.602 (0.53),<br>1.620 (0.71), 1.627 (0.64), 1.637 (0.86),<br>1.646 (0.74), 1.655 (0.73), 1.662 (0.79),<br>1.681 (0.59), 1.850 (0.66), 1.859 (0.74),<br>1.868 (0.76), 1.878 (0.82), 1.884 (0.72),<br>1.894 (0.63), 1.903 (0.55), 1.913 (0.44),<br>2.074 (2.23), 2.159 (16.00), 2.275 (4.12),<br>2.287 (5.55), 2.299 (3.79), 2.324 (0.52),<br>2.329 (0.50), 2.520 (1.93), 2.524 (1.72),<br>2.671 (0.41), 3.494 (4.82), 4.732 (0.68),<br>4.744 (0.64), 7.125 (3.28), 7.148 (3.25),<br>7.546 (2.19), 7.568 (3.87), 7.590 (2.11),<br>8.281 (4.40), 8.303 (4.08), 8.820 (6.90),<br>10.361 (2.35), 10.385 (2.20). |
| 497 | 7-{[(2R)-2-Hydroxypropyl](methyl)amino}-4-oxo-N-[(2S)-1,1,1-trifluorobutan-2-yl]-1-(2,4,6-trifluorophenyl)-1,4-dihydro-1,8-naphthyridine-3-carboxamide<br>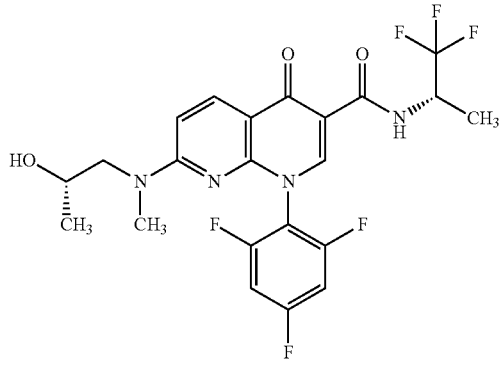<br>with (2R)-1-(methylamino)propan-2-ol<br>(65% of theory) | LC-MS (Method 1):<br>$R_t$ = 1.06 min<br>m/z = 517 [M + H]$^+$<br>$^1$H-NMR (400 MHz, DMSO-d$_6$) δ [ppm]:<br>0.008 (1.19), 0.741 (2.95), 0.951 (7.33),<br>0.969 (16.00), 0.988 (7.97), 1.075 (0.77),<br>1.601 (1.08), 1.619 (1.44), 1.626 (1.29),<br>1.636 (1.75), 1.645 (1.57), 1.655 (1.49),<br>1.662 (1.69), 1.680 (1.28), 1.832 (0.43),<br>1.841 (0.55), 1.850 (1.31), 1.860 (1.52),<br>1.868 (1.53), 1.878 (1.73), 1.885 (1.53),<br>1.895 (1.33), 1.903 (1.15), 1.913 (0.96),<br>2.524 (1.06), 2.835 (1.25), 3.140 (3.53),<br>3.422 (1.68), 3.454 (1.12), 3.610 (0.78),<br>4.633 (1.10), 4.677 (0.40), 4.708 (0.94),<br>4.723 (1.49), 4.732 (1.56), 4.752 (1.47),<br>4.767 (0.90), 6.927 (1.00), 7.550 (3.12),<br>7.571 (5.75), 7.593 (3.15), 8.279 (1.27),<br>8.815 (9.96), 10.413 (2.71), 10.437 (2.67). |

TABLE 23-continued

| Ex. | IUPAC name<br>Structure<br>Amine used<br>Yield | LC-MS method<br>Retention time<br>Mass detected<br>NMR data |
|---|---|---|
| 498 | 7-(2-Oxa-6-azaspiro[3.3]hept-6-yl)-4-oxo-N-[(2S)-1,1,1-trifluorobutan-2-yl]-1-(2,4,6-trifluorophenyl)-1,4-dihydro-1,8-naphthyridine-3-carboxamide<br><br>with 2-oxa-6-azaspiro[3.3]heptane-ethanedioic acid<br>(63% of theory) | LC-MS (Method 1):<br>$R_t$ = 1.09 min<br>m/z = 527 [M + H]$^+$<br>$^1$H-NMR (400 MHz, DMSO-d$_6$) δ [ppm]:<br>−0.062 (5.60), −0.008 (0.86), 0.945 (2.72), 0.963 (6.04), 0.981 (2.96), 1.597 (0.40), 1.615 (0.55), 1.622 (0.49), 1.632 (0.65), 1.640 (0.59), 1.650 (0.56), 1.658 (0.65), 1.676 (0.49), 1.846 (0.49), 1.855 (0.56), 1.864 (0.58), 1.874 (0.65), 1.880 (0.58), 1.891 (0.50), 1.899 (0.43), 2.074 (1.54), 4.660 (16.00), 4.727 (0.57), 4.747 (0.55), 6.592 (3.38), 6.614 (3.40), 7.533 (1.68), 7.555 (3.05), 7.577 (1.68), 8.269 (3.76), 8.291 (3.59), 8.806 (5.71), 10.371 (1.89), 10.395 (1.83). |
| 499 | 7-(tert-Butylamino)-4-oxo-N-[(2S)-1,1,1-trifluorobutan-2-yl]-1-(2,4,6-trifluorophenyl)-1,4-dihydro-1,8-naphthyridine-3-carboxamide<br><br>with 2-methylpropan-2-amine<br>(69% of theory) | LC-MS (Method 3):<br>$R_t$ = 2.30 min<br>m/z = 501 [M + H]$^+$<br>$^1$H-NMR (400 MHz, DMSO-d$_6$) δ [ppm]:<br>0.947 (1.18), 0.966 (2.54), 0.984 (1.25), 1.101 (16.00), 5.756 (1.58), 6.696 (1.28), 6.718 (1.30), 7.564 (0.71), 7.586 (1.32), 7.608 (0.71), 7.706 (1.31), 8.099 (1.42), 8.121 (1.33), 8.793 (2.57), 10.463 (0.78), 10.487 (0.76). |

TABLE 23-continued

| Ex. | IUPAC name<br>Structure<br>Amine used<br>Yield | LC-MS method<br>Retention time<br>Mass detected<br>NMR data |
|---|---|---|
| 500 | 7-[4,4-Bis(hydroxymethyl)piperidin-1-yl]-4-oxo-N-[(2S)-1,1,1-trifluorobutan-2-yl]-1-(2,4,6-trifluorophenyl)-1,4-dihydro-1,8-naphthyridine-3-carboxamide<br>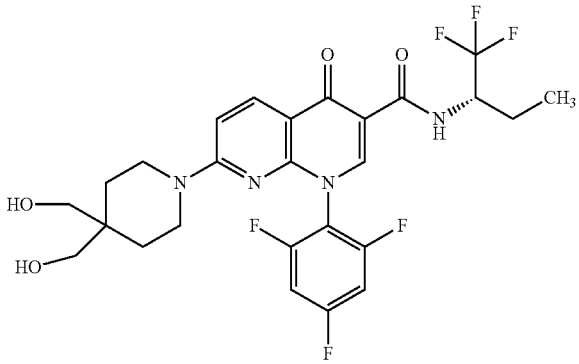<br>with piperidine-4,4-diyldimethanol hydrochloride<br>(71% of theory) | LC-MS (Method 3):<br>$R_t$ = 1.79 min<br>m/z = 573 [M + H]$^+$<br>$^1$H-NMR (400 MHz, DMSO-$d_6$) δ [ppm]:<br>−0.149 (0.46), 0.008 (4.07), 0.146 (0.50), 0.949 (6.73), 0.967 (14.80), 0.986 (7.36), 1.236 (0.98), 1.334 (5.59), 1.600 (1.00), 1.618 (1.26), 1.635 (1.55), 1.643 (1.41), 1.660 (1.55), 1.679 (1.26), 1.849 (1.11), 1.858 (1.35), 1.867 (1.39), 1.877 (1.61), 1.894 (1.22), 1.912 (0.94), 2.328 (1.37), 2.366 (0.87), 2.670 (1.39), 2.710 (0.91), 3.276 (15.39), 3.290 (16.00), 3.471 (5.03), 4.291 (1.07), 4.399 (5.14), 4.412 (11.69), 4.425 (4.99), 4.724 (1.35), 4.811 (0.44), 5.754 (1.89), 7.076 (5.44), 7.099 (5.70), 7.127 (0.54), 7.544 (4.24), 7.566 (7.79), 7.588 (4.11), 8.241 (7.03), 8.263 (6.70), 8.291 (0.57), 8.801 (12.73), 8.815 (1.11), 10.404 (4.64), 10.428 (4.22). |
| 501 | 7-(3-Fluoroazetidin-1-yl)-4-oxo-N-[(2S)-1,1,1-trifluorobutan-2-yl]-1-(2,4,6-trifluorophenyl)-1,4-dihydro-1,8-naphthyridine-3-carboxamide<br>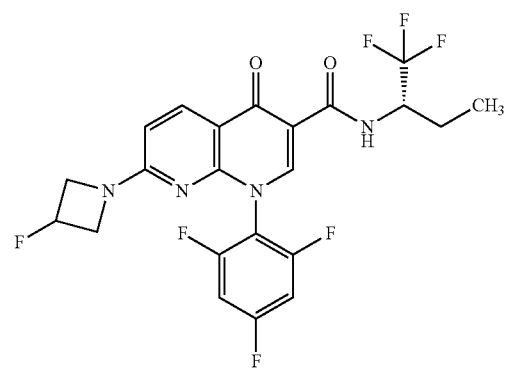<br>with 3-fluoroazetidine<br>(56% of theory) | LC-MS (Method 3):<br>$R_t$ = 2.19 min<br>m/z = 503 [M + H]$^+$<br>$^1$H-NMR (400 MHz, DMSO-$d_6$) δ [ppm]:<br>−0.149 (0.53), 0.147 (0.78), 0.949 (7.00), 0.968 (16.00), 0.986 (7.76), 1.235 (3.76), 1.398 (2.13), 1.603 (1.09), 1.621 (1.51), 1.639 (1.71), 1.663 (1.60), 1.681 (1.22), 1.868 (1.53), 1.879 (1.71), 1.895 (1.38), 2.073 (0.87), 2.328 (1.18), 2.367 (0.71), 2.670 (1.42), 2.711 (0.73), 3.997 (1.27), 4.276 (1.38), 4.747 (1.51), 5.378 (1.67), 5.522 (1.69), 6.671 (8.96), 6.693 (8.89), 7.524 (4.58), 7.546 (8.47), 7.568 (4.60), 8.318 (9.71), 8.340 (9.11), 8.834 (14.82), 10.344 (4.87), 10.369 (4.64). |

Example 502

7-[3,3-Bis(hydroxymethyl)azetidin-1-yl]-N-[(1S)-1-cyclopropyl-2,2,2-trifluoroethyl]-4-oxo-1-(2,4,6-trifluorophenyl)-1,4-dihydro-1,8-naphthyridine-3-carboxamide

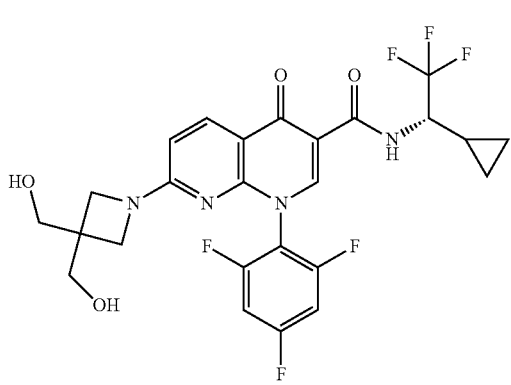 [SMILES: O=C(N[C@@H](C1CC1)C(F)(F)F)c1cn(-c2c(F)cc(F)cc2F)c2nc(N3CC(CO)(CO)C3)ccc2c1=O]

The compound from Example 492 (86.0 mg, 160 μmol) was initially charged in 1 ml of trifluoroacetic acid, 1 ml of water and 1 ml of acetonitrile were added, and the mixture was stirred at room temperature over the weekend. The mixture was purified by means of preparative HPLC (RP18 column, eluent: acetonitrile/water gradient with addition of 0.1% TFA). The product fractions were very substantially concentrated by rotary evaporation; the residue was extracted twice with dichloromethane. The combined organic phases were washed twice with saturated aqueous sodium hydrogencarbonate solution. The combined aqueous phases were re-extracted once with dichloromethane. The combined organic phases were dried over sodium sulphate, filtered and concentrated by rotary evaporation. 86 mg of the target compound (97% of theory) were obtained.

LC-MS (Method 3): $R_t$=1.75 min; MS (ESIpos): m/z=557 [M+H]$^+$ $^1$H-NMR (400 MHz, DMSO-d$_6$) δ [ppm]: −0.008 (2.85), 0.008 (2.81), 0.319 (1.20), 0.330 (1.93), 0.342 (1.91), 0.354 (1.47), 0.366 (0.73), 0.495 (0.49), 0.507 (1.35), 0.518 (1.98), 0.531 (1.75), 0.544 (1.78), 0.553 (1.55), 0.564 (1.94), 0.575 (1.69), 0.585 (1.52), 0.596 (1.25), 0.609 (0.79), 0.623 (0.98), 0.634 (1.10), 0.645 (1.77), 0.655 (1.61), 0.660 (1.54), 0.668 (1.55), 0.676 (0.78), 0.689 (0.54), 0.835 (0.50), 0.853 (0.53), 1.161 (0.74), 1.173 (1.24), 1.182 (1.63), 1.194 (2.31), 1.202 (1.75), 1.214 (2.20), 1.226 (1.46), 1.234 (1.53), 2.074 (1.23), 2.328 (0.58), 2.367 (0.46), 2.671 (0.59), 2.710 (0.43), 3.471 (16.00), 3.484 (15.15), 3.820 (2.70), 4.349 (0.99), 4.370 (1.73), 4.391 (1.70), 4.412 (0.88), 4.823 (4.75), 4.836 (11.08), 4.850 (4.63), 5.754 (0.48), 6.588 (6.33), 6.610 (6.39), 7.519 (3.46), 7.541 (6.53), 7.564 (3.44), 8.246 (6.51), 8.268 (6.21), 8.777 (10.05), 10.542 (4.05), 10.565 (3.86).

Example 503

7-[3,3-Bis(hydroxymethyl)azetidin-1-yl]-4-oxo-N-[(2S)-1,1,1-trifluorobutan-2-yl]-1-(2,4,6-trifluorophenyl)-1,4-dihydro-1,8-naphthyridine-3-carboxamide

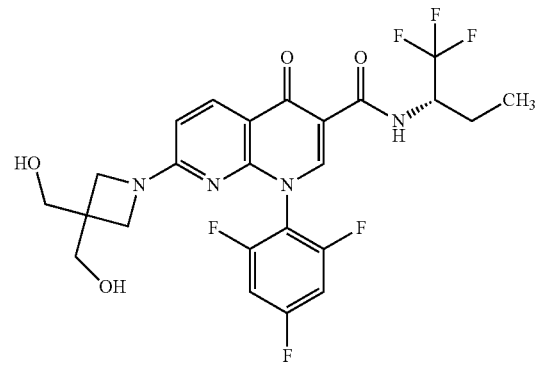 [SMILES: CC[C@H](NC(=O)c1cn(-c2c(F)cc(F)cc2F)c2nc(N3CC(CO)(CO)C3)ccc2c1=O)C(F)(F)F]

The compound from Example 498 (80.0 mg, 150 μmol) was initially charged in 0.94 ml of trifluoroacetic acid, 0.94 ml of water and 0.94 ml of acetonitrile were added, and the mixture was stirred at room temperature for 2 days. The reaction mixture was concentrated and purified by means of preparative HPLC (RP18 column, mobile phase: acetonitrile/water gradient with addition of 0.1% TFA). The product fractions were very substantially concentrated by rotary evaporation; the residue was extracted twice with dichloromethane. The combined organic phases were washed twice with saturated aqueous sodium hydrogencarbonate solution. The combined aqueous phases were re-extracted once with dichloromethane. The combined organic phases were dried over sodium sulphate, filtered and concentrated by evaporation. 63 mg of the target compound (76% of theory) were obtained.

LC-MS (Method 3): $R_t$=1.72 min; MS (ESIpos): m/z=545 [M+H]$^+$

Example 504

7-[(4S)-4-Hydroxy-2-oxopyrrolidin-1-yl]-4-oxo-N-[(2S)-1,1,1-trifluoro-3,3-dimethylbutan-2-yl]-1-(2,4,6-trifluorophenyl)-1,4-dihydro-1,8-naphthyridine-3-carboxamide

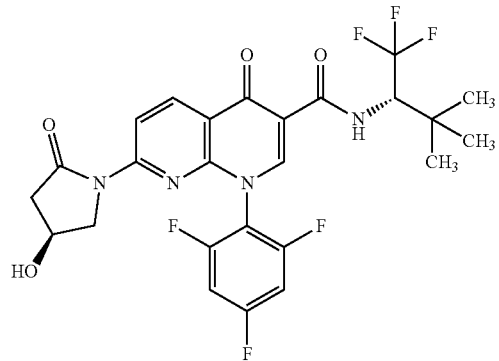 [SMILES: CC(C)(C)[C@H](NC(=O)c1cn(-c2c(F)cc(F)cc2F)c2nc(N3C[C@@H](O)CC3=O)ccc2c1=O)C(F)(F)F]

The compound from Example 117A (35.0 mg, 83.5 µmol) was initially charged in 1.0 ml of dimethylformamide, and HATU (38.1 mg, 100 µmol) and N,N-diisopropylethylamine (44 µl, 250 µmol) were added. The reaction mixture was stirred at RT for 10 min, and (2S)-1,1,1-trifluoro-3,3-dimethylbutan-2-amine (19.4 mg, 125 µmol) dissolved in 1.0 ml of dimethylformamide was added. The mixture was stirred for a further 10 min, diluted with acetonitrile/water, filtered through a syringe filter and purified by means of preparative RP-HPLC (column: Reprosil 125×30; 10µ, flow rate 50 ml/min, MeCN/water/0.1% TFA).

The volatile constituents were removed under reduced pressure and the residue was dried under high vacuum. This gave 40.5 mg (100% purity, 87% of theory) of the title compound.

LC-MS (Method 3): $R_t$=2.04 min; MS (ESIpos): m/z=557 [M+H]$^+$ $^1$H-NMR (400 MHz, DMSO-d6) δ[ppm]: 1.102 (16.00), 2.359 (0.89), 2.403 (1.04), 2.921 (0.87), 2.936 (0.91), 2.964 (0.80), 2.979 (0.79), 3.465 (1.13), 3.495 (1.20), 3.677 (0.80), 3.689 (0.97), 3.707 (0.75), 3.719 (0.65), 4.296 (0.86), 4.652 (0.73), 7.604 (0.76), 7.613 (0.92), 7.627 (0.92), 7.636 (0.77), 8.535 (2.24), 8.557 (2.68), 8.738 (2.64), 8.760 (2.19), 9.086 (3.22), 10.465 (1.20), 10.490 (1.15).

Example 505

N-[1-Cyclobutyl-2,2,2-trifluoroethyl]-7-[(4S)-4-hydroxy-2-oxopyrrolidin-1-yl]-4-oxo-1-(2,4,6-trifluorophenyl)-1,4-dihydro-1,8-naphthyridine-3-carboxamide (diastereomer mixture)

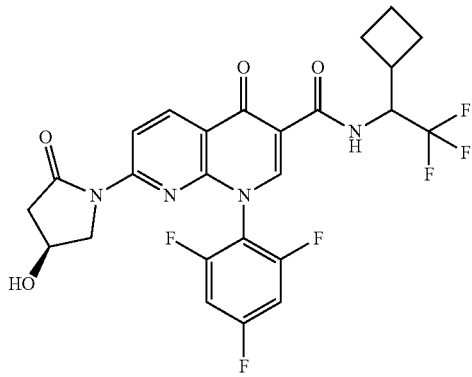 [SMILES: O=C(NC(C1CCC1)C(F)(F)F)c1cn(-c2c(F)cc(F)cc2F)c2nc(N3C[C@@H](O)CC3=O)ccc2c1=O]

The compound from Example 117A (40.0 mg, 95.4 µmol) was initially charged in 1.0 ml of dimethylformamide, and HATU (43.5 mg, 114 µmol) and N,N-diisopropylethylamine (49.5 µl, 295 µmol) were added. The reaction mixture was stirred at RT for 10 min, and rac-1-cyclobutyl-2,2,2-trifluoroethanamine hydrochloride (27.1 mg, 143 µmol) dissolved in 1.0 ml of dimethylformamide and N,N-diisopropylethylamine (16.5 µl, 95 µmol) was added. The mixture was stirred for a further 10 min, diluted with acetonitrile/water, filtered through a syringe filter and purified by means of preparative RP-HPLC (column: Reprosil 125×30; 10µ, flow rate 50 ml/min, MeCN/water/0.1% TFA). The volatile constituents were removed under reduced pressure and the residue was dried under high vacuum. This gave 42.0 mg (100% purity, 79% of theory) of the title compound.

LC-MS (Method 3): $R_t$=2.04 min; MS (ESIpos): m/z=555 [M+H]$^+$ $^1$H-NMR (400 MHz, DMSO-d6) δ[ppm]: −0.008 (3.58), 0.008 (3.53), 1.762 (2.39), 1.789 (0.95), 1.883 (1.62), 1.891 (1.42), 1.904 (3.54), 1.916 (4.79), 1.926 (6.49), 1.933 (5.05), 1.940 (5.04), 1.960 (3.53), 1.990 (3.65), 2.005 (4.84), 2.019 (3.84), 2.040 (1.04), 2.074 (0.76), 2.358 (4.51), 2.402 (5.27), 2.814 (1.33), 2.834 (2.24), 2.857 (1.87), 2.876 (1.04), 2.919 (3.64), 2.933 (3.83), 2.962 (3.27), 2.977 (3.23), 3.467 (4.50), 3.496 (5.56), 3.676 (3.62), 3.688 (4.30), 3.706 (3.25), 3.718 (2.96), 4.297 (3.95), 4.787 (1.50), 4.806 (2.49), 4.829 (2.58), 4.849 (1.47), 5.337 (2.09), 7.597 (2.46), 7.604 (3.04), 7.617 (4.69), 7.626 (4.84), 7.634 (2.83), 7.640 (2.96), 7.647 (2.43), 8.536 (11.34), 8.559 (13.70), 8.728 (13.13), 8.750 (10.68), 9.090 (16.00), 10.272 (5.16), 10.296 (4.99).

25.8 mg of the title compound (diastereomer mixture) were separated into the diastereomers by chiral HPLC (preparative HPLC: column: Daicel Chiralpak IE-H 5 µm 250×25 mm; eluent: 15% ethanol, 75% n-heptane; flow rate: 20 ml/min; UV detection: 220 nm).

This gave (in the sequence of elution from the column) 8 mg of diastereomer 1 from Example 506 (99% de) $R_t$=7.20 min and 15 mg (99% de) of diastereomer 2 from Example 507 $R_t$=8.83 min.

[Analytical HPLC: column: Chiralpak IE-3 5 µm 250×4.6 mm; eluent: 25% ethanol, 75% isohexane; temperature: 30° C.; flow rate: 1.0 ml/min; UV detection: 220 nm]

Example 506

N-[1-Cyclobutyl-2,2,2-trifluoroethyl]-7-[(4S)-4-hydroxy-2-oxopyrrolidin-1-yl]-4-oxo-1-(2,4,6-trifluorophenyl)-1,4-dihydro-1,8-naphthyridine-3-carboxamide (diastereomer 1)

LC-MS (Method 3): $R_t$=2.03 min; MS (ESIpos): m/z=555 [M+H]$^+$

Example 507

N-[1-Cyclobutyl-2,2,2-trifluoroethyl]-7-[(4S)-4-hydroxy-2-oxopyrrolidin-1-yl]-4-oxo-1-(2,4,6-trifluorophenyl)-1,4-dihydro-1,8-naphthyridine-3-carboxamide (diastereomer 2)

LC-MS (Method 3): $R_t$=2.02 min; MS (ESIpos): m/z=555 [M+H]$^+$

Example 508

N-[2-Cyclopropyl-1,1,1-trifluoropropan-2-yl]-7-[(4S)-4-hydroxy-2-oxopyrrolidin-1-yl]-4-oxo-1-(2,4,6-trifluorophenyl)-1,4-dihydro-1,8-naphthyridine-3-carboxamide (diastereomer mixture)

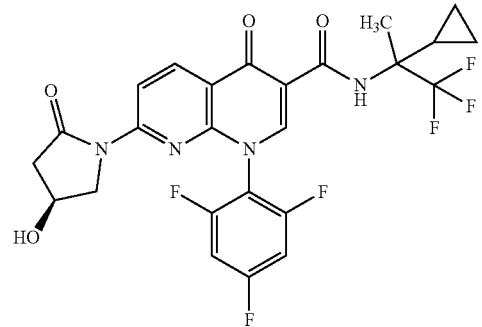 [SMILES: CC(NC(=O)c1cn(-c2c(F)cc(F)cc2F)c2nc(N3C[C@@H](O)CC3=O)ccc2c1=O)(C1CC1)C(F)(F)F]

The compound from Example 117A (35.0 mg, 83.5 µmol) was initially charged in 1.0 ml of dimethylformamide, and HATU (38.1 mg, 100 µmol) and N,N-diisopropylethylamine (44 µl, 250 µmol) were added. The reaction mixture was stirred at RT for 10 min, and rac-2-cyclopropyl-1,1,1-trifluoropropan-2-amine hydrochloride (23.7 mg, 125 µmol) dissolved in 1.0 ml of dimethylformamide and N,N-diisopropylethylamine (15 µl, 83.5 µmol) was added. The mixture was stirred for a further 10 min, diluted with acetonitrile/water, filtered through a syringe filter and purified by means of preparative RP-HPLC (column: Reprosil 125×30; 10µ, flow rate 50 ml/min, MeCN/water/0.1% TFA). The volatile constituents were removed under reduced pressure and the residue was dried under high vacuum. This gave 31.1 mg (100% purity, 67% of theory) of the title compound.

LC-MS (Method 3): $R_t$=1.98 min; MS (ESIpos): m/z=555 [M+H]$^+$ $^1$H-NMR (400 MHz, DMSO-d6) δ[ppm]: −0.149 (0.61), −0.008 (5.62), 0.008 (4.93), 0.146 (0.60), 0.512 (1.29), 0.576 (3.31), 0.597 (3.28), 0.696 (1.33), 1.415 (0.99), 1.422 (0.99), 1.432 (1.47), 1.435 (1.43), 1.444 (1.03), 1.609 (16.00), 2.355 (2.29), 2.398 (2.68), 2.914 (2.19), 2.929 (2.31), 2.957 (2.01), 2.972 (1.93), 3.460 (2.44), 3.490 (2.91), 3.670 (2.01), 3.682 (2.46), 3.700 (1.89), 3.712 (1.65), 4.279 (1.30), 4.292 (2.20), 7.592 (1.30), 7.599 (1.69), 7.611 (2.45), 7.621 (2.55), 7.634 (1.67), 7.642 (1.30), 8.521 (5.65), 8.543 (6.72), 8.717 (6.71), 8.739 (5.41), 8.999 (9.09), 10.088 (6.29).

30 mg of the title compound (diastereomer mixture) were separated into the diastereomers by chiral HPLC (preparative HPLC: column: Daicel IB 5 µm 250×30 mm; eluent: 20% ethanol, 70% n-heptane; flow rate: 20 ml/min; UV detection: 220 nm).

This gave (in the sequence of elution from the column) 2.8 mg of diastereomer 1 from Example 509 (99% de) $R_t$=1.58 min and 3.7 mg (99% de) of diastereomer 2 from Example 510 $R_t$=2.86 min.

[Analytical HPLC: column: Chiralpak IB-3 3 µm 250×4.6 mm; eluent: 20% ethanol, 80% n-heptane; temperature: 30° C.; flow rate: 1.0 ml/min; UV detection: 220 nm]

Example 509

N-[2-Cyclopropyl-1,1,1-trifluoropropan-2-yl]-7-[(4S)-4-hydroxy-2-oxopyrrolidin-1-yl]-4-oxo-1-(2,4,6-trifluorophenyl)-1,4-dihydro-1,8-naphthyridine-3-carboxamide (diastereomer 1)

LC-MS (Method 3): $R_t$=1.99 min; MS (ESIpos): m/z=555 [M+H]$^+$

Example 510

N-[2-Cyclopropyl-1,1,1-trifluoropropan-2-yl]-7-[(4S)-4-hydroxy-2-oxopyrrolidin-1-yl]-4-oxo-1-(2,4,6-trifluorophenyl)-1,4-dihydro-1,8-naphthyridine-3-carboxamide (diastereomer 2)

LC-MS (Method 3): $R_t$=2.00 min; MS (ESIpos): m/z=555 [M+H]$^+$

Example 511

7-[(4S)-4-Hydroxy-2-oxopyrrolidin-1-yl]-4-oxo-N-(4,4,4-trifluoro-2-methylbutan-2-yl)-1-(2,4,6-trifluorophenyl)-1,4-dihydro-1,8-naphthyridine-3-carboxamide

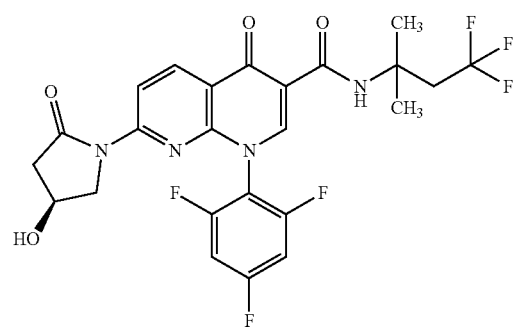 [SMILES: CC(C)(CC(F)(F)F)NC(=O)c1cn(-c2c(F)cc(F)cc2F)c2nc(N3C[C@@H](O)CC3=O)ccc2c1=O]

The compound from Example 117A (120 mg, 286 µmol) was initially charged in 4.0 ml of dimethylformamide, and HATU (131 mg, 343 µmol) and N,N-diisopropylethylamine (150 µl, 870 µmol) were added. The reaction mixture was stirred at RT for 10 min, and 4,4,4-trifluoro-2-methylbutan-2-amine hydrochloride (1:1) (76.2 mg, 429 µmol) dissolved in 1.0 ml of dimethylformamide and N,N-diisopropylethylamine (50 µl, 290 µmol) was added. The mixture was stirred for a further 10 min, diluted with acetonitrile/water, filtered through a syringe filter and purified by means of preparative RP-HPLC (column: Reprosil 125×30; 10µ, flow rate 50 ml/min, MeCN/water/0.1% TFA). The volatile constituents were removed under reduced pressure and the residue was dried under high vacuum. This gave 84.4 mg (100% pure, 54% of theory) of the title compound.

LC-MS (Method 3): $R_t$=1.89 min; MS (ESIpos): m/z=543 [M+H]$^+$ $^1$H-NMR (400 MHz, DMSO-d6) δ[ppm]: −0.008 (0.78), 1.500 (16.00), 2.351 (1.25), 2.395 (1.44), 2.912 (1.44), 2.918 (0.93), 2.927 (1.42), 2.948 (2.18), 2.955 (1.57), 2.970 (1.54), 2.978 (2.05), 3.007 (0.63), 3.459 (1.24), 3.489 (1.53), 3.669 (1.11), 3.681 (1.35), 3.699 (1.04), 3.711 (0.90), 4.290 (0.98), 5.325 (0.99), 7.589 (0.69), 7.596 (0.88), 7.609 (1.31), 7.619 (1.31), 7.627 (0.77), 7.632 (0.86), 7.639 (0.68), 8.510 (3.14), 8.533 (3.85), 8.686 (3.77), 8.708 (2.99), 8.963 (4.50), 9.902 (3.32).

Example 512

N-[1-Cyclopropyl-3,3,3-trifluoropropyl]-7-[(4S)-4-hydroxy-2-oxopyrrolidin-1-yl]-4-oxo-1-(2,4,6-trifluorophenyl)-1,4-dihydro-1,8-naphthyridine-3-carboxamide (diastereomer mixture)

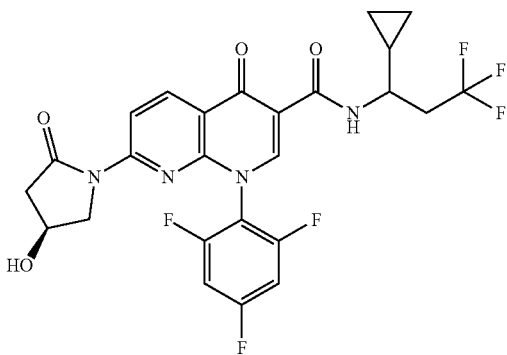 [SMILES: O=C(NC(CC(F)(F)F)C1CC1)c1cn(-c2c(F)cc(F)cc2F)c2nc(N3C[C@@H](O)CC3=O)ccc2c1=O]

The compound from Example 117A (45.0 mg, 107 µmol) was initially charged in 1.0 ml of dimethylformamide, and HATU (38.1 mg, 100 µmol) and N,N-diisopropylethylamine (57 µl, 321 µmol) were added.

The reaction mixture was stirred at RT for 10 min, and rac-1-cyclopropyl-3,3,3-trifluoropropan-1-amine hydrochloride (30.5 mg, 161 µmol) dissolved in 1.0 ml of dimethylformamide and N,N-diisopropylethylamine (19 µl, 107 µmol) was added. The mixture was stirred for a further 10 min, diluted with acetonitrile/water, filtered through a syringe filter and purified by means of preparative RP-HPLC (column: Reprosil 125×30; 10µ, flow rate 50 ml/min, MeCN/water/0.1% TFA). The volatile constituents were removed under reduced pressure and the residue was dried under high vacuum. This gave 45.1 mg (100% purity, 76% of theory) of the title compound.

LC-MS (Method 3): $R_t$=1.85 min; MS (ESIpos): m/z=555 [M+H]$^+$ $^1$H-NMR (400 MHz, DMSO-d6) δ[ppm]: 0.008 (2.32), 0.295 (1.35), 0.304 (2.35), 0.316 (3.52), 0.327 (3.43), 0.346 (3.20), 0.359 (3.36), 0.370 (2.17), 0.381 (1.35), 0.457 (1.08), 0.466 (2.14), 0.478 (2.89), 0.488 (2.87), 0.498 (2.48), 0.507 (2.64), 0.515 (2.35), 0.528 (3.32), 0.536 (2.78), 0.549 (2.23), 0.557 (1.06), 1.150 (1.06), 1.159 (1.62), 1.170 (2.69), 1.179 (2.12), 1.191 (2.60), 1.203 (1.40), 1.211 (0.93), 2.329 (0.79), 2.352 (4.49), 2.367 (1.13), 2.395 (5.21), 2.520 (3.20), 2.524 (2.93), 2.636 (1.02), 2.648 (1.42), 2.666 (1.65), 2.675 (2.84), 2.687 (1.78), 2.704 (1.87), 2.711 (1.76), 2.715 (1.67), 2.769 (1.58), 2.789 (1.81), 2.798 (1.92), 2.807 (1.26), 2.818 (1.78), 2.828 (1.53), 2.836 (1.08), 2.856 (0.99), 2.913 (3.95), 2.928 (4.08), 2.956 (3.59), 2.971 (3.50), 3.462 (5.84), 3.492 (7.00), 3.672 (4.08), 3.684 (4.85), 3.701 (3.77), 3.714 (3.29), 3.770 (0.95), 3.783 (1.15), 3.792 (2.53), 3.803 (2.57), 3.813 (2.55), 3.825 (2.35), 3.834 (1.04), 3.846 (0.81), 4.279 (2.60), 4.292 (4.36), 4.305 (2.41), 6.947 (1.38), 7.074 (1.47), 7.202 (1.33), 7.586 (2.53), 7.593 (3.14), 7.606 (4.74), 7.616 (4.74), 7.629 (3.11), 7.636 (2.41), 8.515 (9.59), 8.537 (11.96), 8.689 (12.12), 8.711 (9.66), 8.970 (16.00), 9.869 (6.05), 9.890 (5.84).

40 mg of the title compound (diastereomer mixture) were separated into the diastereomers by chiral HPLC (preparative HPLC: column: Daicel Chiralpak IE-H 5 µm 250×20 mm; eluent: 50% ethanol, 50% n-heptane; temperature: 25° C.; flow rate: 15 ml/min; UV detection: 210 nm).

This gave (in the sequence of elution from the column) 13.2 mg of diastereomer 1 (99% de) $R_t$=2.50 min and 13.3 mg (95% de) of diastereomer 2 $R_t$=2.91 min.

[Analytical HPLC: column: Chiraltek IE-3 3 µm 250×4.6 mm; eluent: 25% ethanol, 75% isohexane; temperature: 30° C.; flow rate: 1.0 ml/min; UV detection: 220 nm]

Example 513

N-[1-Cyclopropyl-3,3,3-trifluoropropyl]-7-[(4S)-4-hydroxy-2-oxopyrrolidin-1-yl]-4-oxo-1-(2,4,6-trifluorophenyl)-1,4-dihydro-1,8-naphthyridine-3-carboxamide (diastereomer 1)

LC-MS (Method 3): $R_t$=1.84 min; MS (ESIpos): m/z=555 [M+H]$^+$

Example 514

N-[1-Cyclopropyl-3,3,3-trifluoropropyl]-7-[(4S)-4-hydroxy-2-oxopyrrolidin-1-yl]-4-oxo-1-(2,4,6-trifluorophenyl)-1,4-dihydro-1,8-naphthyridine-3-carboxamide (diastereomer 2)

LC-MS (Method 3): $R_t$=1.84 min; MS (ESIpos): m/z=555 [M+H]$^+$

Example 515

7-[(4S)-4-Hydroxy-2-oxopyrrolidin-1-yl]-4-oxo-N-[1-(trifluoromethyl)cyclobutyl]-1-(2,4,6-trifluorophenyl)-1,4-dihydro-1,8-naphthyridine-3-carboxamide

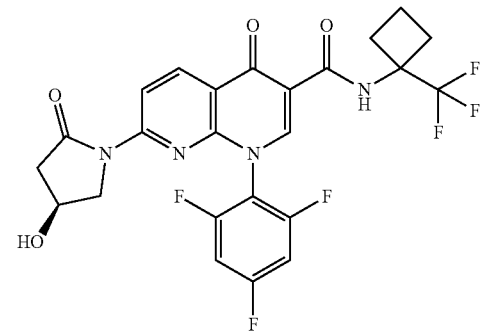 [SMILES: O=C(NC1(C(F)(F)F)CCC1)c1cn(-c2c(F)cc(F)cc2F)c2nc(N3C[C@@H](O)CC3=O)ccc2c1=O]

The compound from Example 117A (35.0 mg, 83.5 µmol) was initially charged in 1.0 ml of dimethylformamide, and HATU (38.1 mg, 100 µmol) and N,N-diisopropylethylamine (44.0 µl, 246 µmol) were added. The reaction mixture was stirred at RT for 10 min, and 1-(trifluoromethyl)cyclobutanamine hydrochloride (22.0 mg, 125 µmol) dissolved in 1.0 ml of dimethylformamide and N,N-diisopropylethylamine (15 µl, 84 µmol) was added. The mixture was stirred for a further 10 min, diluted with acetonitrile/water, filtered through a syringe filter and purified by means of preparative RP-HPLC (column: Reprosil 125×30; 10µ, flow rate 50 ml/min, MeCN/water/0.1% TFA). The volatile constituents were removed under reduced pressure and the residue was dried under high vacuum. This gave 35.8 mg (100% pure, 79% of theory) of the title compound.

LC-MS (Method 3): R$_t$=1.89 min; MS (ESIpos): m/z=541 [M+H]$^+$ $^1$H-NMR (400 MHz, DMSO-d6) δ[ppm]: 1.943 (2.33), 1.964 (2.95), 1.985 (2.04), 2.038 (2.61), 2.051 (2.53), 2.073 (5.69), 2.355 (4.96), 2.398 (5.89), 2.561 (6.85), 2.576 (7.95), 2.599 (6.71), 2.622 (4.45), 2.914 (4.08), 2.929 (4.26), 2.958 (3.72), 2.972 (3.66), 3.462 (5.03), 3.491 (6.09), 3.672 (3.95), 3.684 (4.67), 3.702 (3.59), 3.713 (3.21), 4.293 (4.61), 5.335 (4.12), 7.615 (6.03), 8.527 (8.73), 8.549 (10.88), 8.700 (10.72), 8.723 (8.55), 9.016 (16.00), 10.219 (12.50).

Example 516

N-(1,1-Difluoro-2-methylpropan-2-yl)-7-[(4S)-4-hydroxy-2-oxopyrrolidin-1-yl]-4-oxo-1-(2,4,6-trifluorophenyl)-1,4-dihydro-1,8-naphthyridine-3-carboxamide

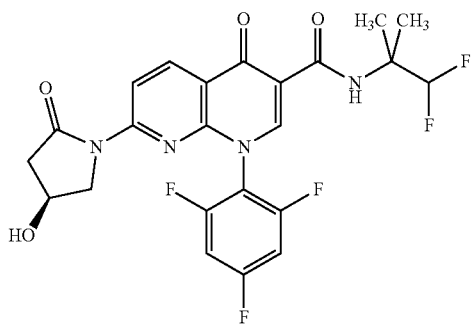 [SMILES: CC(C)(NC(=O)c1cn(-c2c(F)cc(F)cc2F)c2nc(N3C[C@@H](O)CC3=O)ccc2c1=O)C(F)F]

The compound from Example 117A (40.0 mg, 95.4 µmol) was initially charged in 1.0 ml of dimethylformamide, and HATU (43.5 mg, 114 µmol) and N,N-diisopropylethylamine (49.5 µl, 285 µmol) were added. The reaction mixture was stirred at RT for 10 min, and 1,1-difluoro-2-methylpropan-2-amine hydrochloride (20.8 mg, 143 µmol) dissolved in 1.0 ml of dimethylformamide and N,N-diisopropylethylamine (16.5 µl, 95 µmol) was added. The mixture was stirred for a further 10 min, diluted with acetonitrile/water, filtered through a syringe filter and purified by means of preparative RP-HPLC (column: Reprosil 125×30; 10µ, flow rate 50 ml/min, MeCN/water/0.1% TFA). The volatile constituents were removed under reduced pressure and the residue was dried under high vacuum. This gave 46.4 mg (100% purity, 95% of theory) of the title compound.

LC-MS (Method 3): R$_t$=1.82 min; MS (ESIpos): m/z=511 [M+H]$^+$ $^1$H-NMR (400 MHz, DMSO-d6) δ[ppm]: 1.455 (16.00), 2.074 (9.78), 2.353 (1.20), 2.396 (1.40), 2.911 (1.02), 2.926 (1.06), 2.955 (0.93), 2.970 (0.91), 3.459 (1.18), 3.489 (1.46), 3.669 (0.98), 3.681 (1.16), 3.699 (0.89), 3.711 (0.80), 4.292 (1.02), 5.325 (1.11), 5.332 (1.09), 6.289 (0.85), 6.432 (1.58), 6.574 (0.73), 7.591 (0.69), 7.599 (0.86), 7.611 (1.32), 7.621 (1.33), 7.634 (0.86), 7.641 (0.69), 8.517 (2.07), 8.539 (2.63), 8.693 (2.51), 8.715 (2.03), 8.986 (3.49), 10.038 (2.99).

Example 517

7-[(4S)-4-Acetamido-2-oxopyrrolidin-1-yl]-4-oxo-N-[(2S)-1,1,1-trifluorobutan-2-yl]-1-(2,4,6-trifluorophenyl)-1,4-dihydro-1,8-naphthyridine-3-carboxamide (diastereomer mixture)

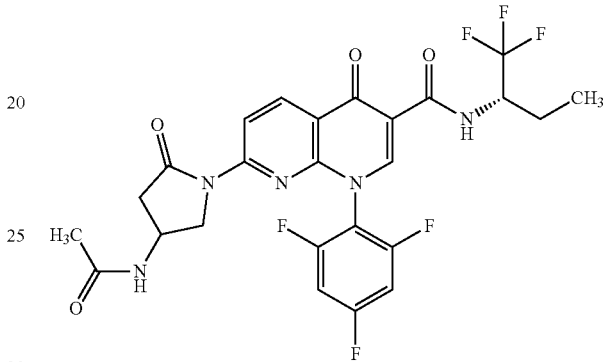

To an initial charge of Example 151C (25.7 mg, 34.0 µmol) in 2.0 ml of dichloromethane was added triethylamine (14 µl, 100 µmol). Acetyl chloride (2.9 µl, 41 µmol) was added slowly to the reaction mixture at 0° C., and then the reaction mixture was stirred at RT overnight. The volatile constituents were removed under reduced pressure and the residue was diluted with acetonitrile/water and purified by means of preparative RP-HPLC (column: Reprosil 125×30; 10µ, flow rate: 50 ml/min, MeCN/water/0.1% TFA). The volatile constituents were removed under reduced pressure and the residue was dried under high vacuum. This gave 16.6 mg (100% purity, 86% of theory) of the title compound.

LC-MS (Method 3): R$_t$=1.77 min; MS (ESIpos): m/z=570 [M+H]$^+$ $^1$H-NMR (400 MHz, DMSO-d6) δ[ppm]: 0.964 (3.36), 0.982 (6.75), 1.000 (3.60), 1.633 (0.51), 1.655 (0.80), 1.667 (0.95), 1.691 (0.94), 1.710 (0.66), 1.776 (16.00), 1.876 (0.94), 1.885 (0.96), 1.895 (1.03), 1.911 (0.83), 2.404 (1.58), 2.453 (2.17), 2.969 (1.38), 2.988 (1.50), 3.012 (1.28), 3.032 (1.25), 3.437 (1.58), 3.463 (1.75), 3.777 (1.40), 3.793 (1.73), 3.806 (1.45), 3.823 (1.29), 4.274 (2.02), 4.765 (1.03), 4.776 (1.01), 7.582 (1.88), 7.603 (3.43), 7.625 (1.86), 8.328 (2.08), 8.344 (2.05), 8.510 (2.75), 8.532 (3.34), 8.723 (3.32), 8.745 (2.77), 9.073 (4.94), 10.091 (2.30), 10.115 (2.24).

Example 518

7-[4-(Acetamidomethyl)-2-oxopyrrolidin-1-yl]-4-oxo-N-[(2S)-1,1,1-trifluorobutan-2-yl]-1-(2,4,6-trifluorophenyl)-1,4-dihydro-1,8-naphthyridine-3-carboxamide (diastereomer mixture)

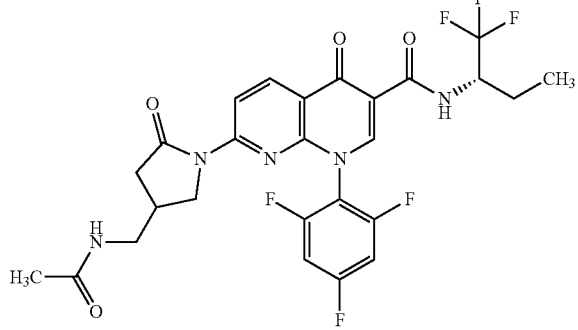

Potassium carbonate (12.9 mg, 93.6 µmol), palladium(II) acetate (2.80 mg, 12.5 µmol) and 9,9-dimethyl-4,5-bis(diphenylphosphino)xanthene (7.22 mg, 12.5 µmol) were stirred in 3.0 ml of dioxane under argon at RT for 10 minutes. Then the compound from 115A (29.0 mg, 62.4 µmol) and the compound from Example 152A (11.7 mg) were added and the mixture was stirred at 80° C. for 4 h. The mixture was purified directly by preparative RP-HPLC (column: Reprosil 125×30; 10µ, flow rate: 50 ml/min, MeCN/water, 0.1% TFA). The volatile constituents were removed under reduced pressure and the residue was dried under high vacuum. This gave 1.70 mg (100% purity, 5% of theory) of the title compound.

LC-MS (Method 1): $R_t$=0.97 min; MS (ESIpos): m/z=584 [M+H]$^+$

Example 519

7-[(4S)-4-Hydroxy-2-oxopyrrolidin-1-yl]-4-oxo-N-[1,1,1,2,2-pentafluoropentan-3-yl]-1-(2,4,6-trifluorophenyl)-1,4-dihydro-1,8-naphthyridine-3-carboxamide (diastereomer mixture)

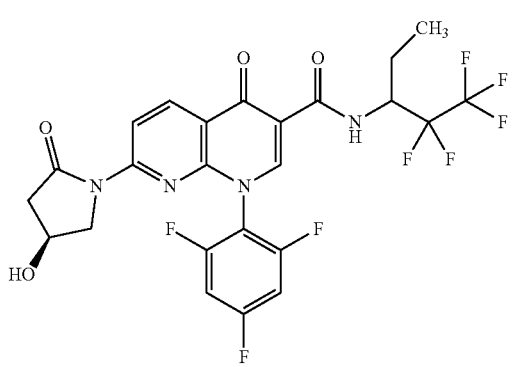 [SMILES: CCC(NC(=O)c1cn(-c2c(F)cc(F)cc2F)c2nc(N3C[C@@H](O)CC3=O)ccc2c1=O)C(F)(F)C(F)(F)F]

According to GP1, 1.18 g (2.81 mmol) of the compound from Example 117A were reacted with 300 mg (1.40 mmol) of the compound from Example 153B in the presence of 1.28 g (3.37 mmol) of HATU and 2.0 ml (11.0 mmol) of DIPEA in 8.0 ml of DMF. The crude product was purified by means of preparative HPLC (acetonitrile/water/0.1% formic acid). 528 mg (33% of theory, 100% purity) of the title compound were obtained.

LC-MS (Method 3): $R_t$=2.00 min; MS (ESIpos): m/z=579 [M+H]$^+$ $^1$H NMR (400 MHz, DMSO-d$_6$): δ ppm=10.16 (d, 1H), 9.08 (s, 1H), 8.72 (d, 1H), 8.54 (d, 1H), 7.56-7.67 (m, 2H), 5.33 (d, 1H), 4.82-4.96 (m, 1H), 4.27-4.32 (m, 1H), 3.69 (dd, 1H), 3.48 (d, 1H), 2.95 (dd, 1H), 2.38 (d, 1H), 1.88-1.99 (m, 1H), 1.62-1.74 (m, 1H), 0.97 (t, 3H).

523 mg of the title compound (diastereomer mixture) were separated into the diastereomers by chiral HPLC (preparative HPLC: column: Daicel Chiralpak IE 5 µm 250×20 mm; eluent: 80% n-heptane, 20% isopropanol; temperature: 30° C.; flow rate: 15 ml/min; UV detection: 220 nm).

This gave (in the sequence of elution from the column) 249 mg (15% of theory, 100% purity) of diastereomer 1 from Example 520 (99% de) Rt=11.07 min and 241 mg (15% of theory, 100% purity) of diastereomer 2 from Example 521 (99% de) Rt=13.85 min.

[Analytical HPLC: column: Daicel Chiralpak IE 5 µm 250×4.6 mm; eluent: 80% isohexane, 20% isopropanol; temperature: 30° C.; flow rate: 1.0 ml/min; UV detection: 220 nm]

Example 520

7-[(4S)-4-Hydroxy-2-oxopyrrolidin-1-yl]-4-oxo-N-[1,1,1,2,2-pentafluoropentan-3-yl]-1-(2,4,6-trifluorophenyl)-1,4-dihydro-1,8-naphthyridine-3-carboxamide (diastereomer 1)

LC-MS (Method 1): $R_t$=1.08 min; MS (ESIpos): m/z=579 [M+H]$^+$ $^1$H NMR (400 MHz, DMSO-d$_6$): δ ppm=10.16 (d, 1H), 9.08 (s, 1H), 8.72 (d, 1H), 8.54 (d, 1H), 7.56-7.67 (m, 2H), 5.34 (d, 1H), 4.82-4.95 (m, 1H), 4.27-4.32 (m, 1H), 3.69 (dd, 1H), 3.48 (d, 1H), 2.95 (dd, 1H), 2.38 (d, 1H), 1.88-1.98 (m, 1H), 1.62-1.64 (m, 1H), 0.97 (t, 3H).

Example 521

7-[(4S)-4-Hydroxy-2-oxopyrrolidin-1-yl]-4-oxo-N-[1,1,1,2,2-pentafluoropentan-3-yl]-1-(2,4,6-trifluorophenyl)-1,4-dihydro-1,8-naphthyridine-3-carboxamide (diastereomer 2)

LC-MS (Method 1): $R_t$=1.08 min; MS (ESIpos): m/z=579 [M+H]$^+$ $^1$H NMR (400 MHz, DMSO-d$_6$): δ ppm=10.16 (d, 1H), 9.08 (s, 1H), 8.72 (d, 1H), 8.54 (d, 1H), 7.57-7.67 (m, 2H), 5.33 (d, 1H), 4.82-4.96 (m, 1H), 4.27-4.32 (m, 1H), 3.69 (dd, 1H), 3.47 (d, 1H), 2.95 (dd, 1H), 2.38 (d, 1H), 1.88-1.99 (m, 1H), 1.62-1.74 (m, 1H), 0.98 (t, 3H).

Example 522

7-[(3R,4R)-3,4-Dihydroxypyrrolidin-1-yl]-4-oxo-N-[1,1,1,2,2-pentafluoropentan-3-yl]-1-(2,4,6-trifluorophenyl)-1,4-dihydro-1,8-naphthyridine-3-carboxamide (diastereomer mixture)

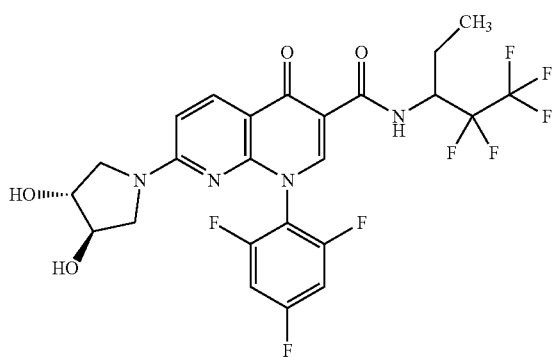 [SMILES: CCC(NC(=O)c1cn(-c2c(F)cc(F)cc2F)c2nc(N3C[C@@H](O)[C@H](O)C3)ccc2c1=O)C(F)(F)C(F)(F)F]

According to GP1, 947 mg (2.25 mmol) of the compound from Example 121A were reacted with 300 mg (1.40 mmol) of the compound from Example 153B in the presence of 1.03 g (2.70 mmol) of HATU and 1.6 ml (9.00 mmol) of DIPEA in 6.4 ml of DMF. The crude product was purified by means of preparative HPLC (acetonitrile/water/0.1% formic acid). 477 mg (37% of theory, 100% purity) of the title compound were obtained.

LC-MS (Method 3): $R_t$=1.83 min; MS (ESIpos): m/z=581 [M+H]$^+$ $^1$H NMR (400 MHz, DMSO-d$_6$): δ ppm=10.48 (d, 1H), 8.81 (s, 1H), 8.28 (d, 1H), 7.53-7.60 (m, 2H), 6.78 (d, 1H), 5.24 (d, 1H), 5.14 (d, 1H), 4.80-4.93 (m, 1H), 4.03-4.07 (m, 1H), 3.90-3.95 (m, 1H), 3.58-3.64 (m, 1H), 3.32-3.37 (m, 1H), 3.21-3.30 (m, 1H), 3.03-3.10 (m, 1H), 1.86-1.97 (m, 1H), 1.60-1.72 (m, 1H), 0.96 (t, 3H).

472 mg of the title compound (diastereomer mixture) were separated into the diastereomers by chiral HPLC (preparative HPLC: column: Daicel Chiralpak IA 5 μm 250×15 mm; eluent: 85% n-heptane, 20% isopropanol; temperature: 30° C.; flow rate: 15 ml/min; UV detection: 220 nm).

This gave (in the sequence of elution from the column) 203 mg (16% of theory, 100% purity) of diastereomer 1 from Example 523 (99% de) Rt=12.94 min and 209 mg (16% of theory, 100% purity) of diastereomer 2 from Example 524 (99% de) Rt=15.48 min.

[Analytical HPLC: column: Daicel Chiralpak IA 5 μm 250×4.6 mm; eluent: 80% isohexane, 20% isopropanol; temperature: 25° C.; flow rate: 1.0 ml/min; UV detection: 220 nm]

Example 523

7-[(3R,4R)-3,4-Dihydroxypyrrolidin-1-yl]-4-oxo-N-[1,1,1,2,2-pentafluoropentan-3-yl]-1-(2,4,6-trifluorophenyl)-1,4-dihydro-1,8-naphthyridine-3-carboxamide (diastereomer 1)

LC-MS (Method 3): $R_t$=1.83 min; MS (ESIpos): m/z=581 [M+H]$^+$ $^1$H NMR (400 MHz, DMSO-d$_6$): δ ppm=10.48 (d, 1H), 8.81 (s, 1H), 8.28 (d, 1H), 7.53-7.60 (m, 2H), 6.78 (d, 1H), 5.23 (d, 1H), 5.14 (d, 1H), 4.80-4.93 (m, 1H), 4.05 (br s, 1H), 3.93 (br s, 1H), 3.62 (dd, 1H), 3.32-3.37 (m, 1H), 3.25 (dd, 1H), 3.07 (d, 1H), 1.87-1.97 (m, 1H), 1.60-1.71 (m, 1H), 0.96 (t, 3H).

Example 524

7-[(3R,4R)-3,4-Dihydroxypyrrolidin-1-yl]-4-oxo-N-[1,1,1,2,2-pentafluoropentan-3-yl]-1-(2,4,6-trifluorophenyl)-1,4-dihydro-1,8-naphthyridine-3-carboxamide (diastereomer 2)

LC-MS (Method 3): $R_t$=1.83 min; MS (ESIpos): m/z=581 [M+H]$^+$ $^1$H NMR (400 MHz, DMSO-d$_6$): δ ppm=10.48 (d, 1H), 8.81 (s, 1H), 8.28 (d, 1H), 7.52-7.60 (m, 2H), 6.78 (d, 1H), 5.24 (d, 1H), 5.14 (d, 1H), 4.79-4.93 (m, 1H), 4.05 (br s, 1H), 3.93 (br s, 1H), 3.61 (br dd, 1H), 3.32-3.37 (m, 1H), 3.20-3.29 (m, 1H), 3.07 (br d, 1H), 1.86-1.97 (m, 1H), 1.59-1.72 (m, 1H), 0.96 (t, 3H).

Example 525

7-[(4S)-4-Hydroxy-2-oxopyrrolidin-1-yl]-4-oxo-N-[(2S)-1,1,1-trifluoro-4-methylpentan-2-yl]-1-(2,4,6-trifluorophenyl)-1,4-dihydro-1,8-naphthyridine-3-carboxamide

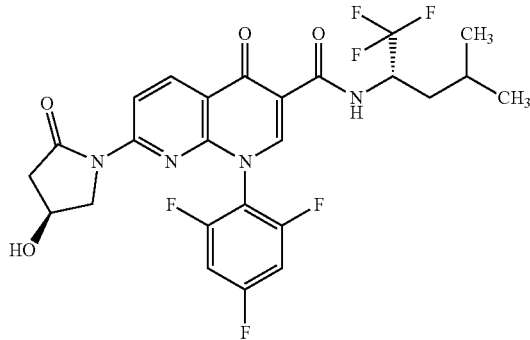 [SMILES: CC(C)C[C@H](NC(=O)c1cn(-c2c(F)cc(F)cc2F)c2nc(N3C[C@@H](O)CC3=O)ccc2c1=O)C(F)(F)F]

According to GP1, 50.0 mg (119 μmol) of the compound from Example 117A were reacted with 27.4 mg (143 μmol) of (2R)-1,1,1-trifluoro-4-methylpentan-2-amine hydrochloride in the presence of 54.4 mg (143 μmol) of HATU and 62 μl (360 μmol) of DIPEA in 460 μl of DMF. The crude product was purified by means of preparative HPLC (acetonitrile/water/0.1% formic acid). 50.3 mg (76% of theory, 100% purity) of the title compound were obtained.

LC-MS (Method 3): $R_t$=2.10 min; MS (ESIpos): m/z=557 [M+H]$^+$ $^1$H NMR (400 MHz, DMSO-d$_6$): δ ppm=10.10 (d, 1H), 9.07 (s, 1H), 8.71 (d, 1H), 8.54 (d, 1H), 7.58-7.66 (m, 2H), 5.33 (d, 1H), 4.80-4.90 (m, 1H), 4.27-4.31 (m, 1H), 3.69 (dd, 1H), 3.47 (d, 1H), 2.94 (dd, 1H), 2.38 (d, 1H), 1.64-1.75 (m, 2H), 1.54-1.62 (m, 1H), 0.95 (d, 3H), 0.90 (d, 3H).

Example 526

7-[(4S)-4-Hydroxy-2-oxopyrrolidin-1-yl]-4-oxo-N-[1,1,1-trifluoro-3-methylbutan-2-yl]-1-(2,4,6-trifluorophenyl)-1,4-dihydro-1,8-naphthyridine-3-carboxamide (diastereomer mixture)

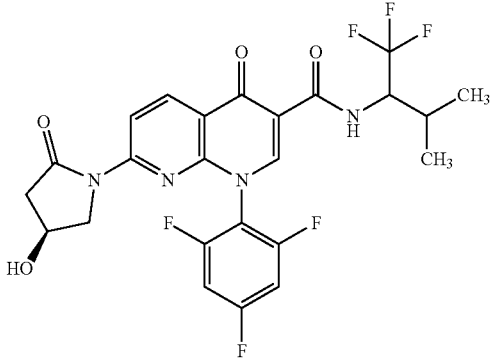 [SMILES: CC(C)C(NC(=O)c1cn(-c2c(F)cc(F)cc2F)c2nc(N3C[C@@H](O)CC3=O)ccc2c1=O)C(F)(F)F]

According to GP1, 80.0 mg (191 µmol) of the compound from Example 117A were reacted with 32.3 mg (229 µmol) of 1,1,1-trifluoro-3-methylbutan-2-amine in the presence of 87.1 mg (229 µmol) of HATU and 100 µl (570 µmol) of DIPEA in 1.4 ml of DMF. The crude product was purified by means of preparative HPLC (acetonitrile/water/0.1% formic acid). 81.5 mg (79% of theory, 100% purity) of the title compound were obtained.

LC-MS (Method 3): $R_t$=1.97 min; MS (ESIpos): m/z=543 [M+H]$^+$ $^1$H NMR (400 MHz, DMSO-d$_6$): δ ppm=10.32 (d, 1H), 9.08 (s, 1H), 8.74 (d, 1H), 8.54 (d, 1H), 7.58-7.66 (m, 2H), 5.33 (dd, 1H), 4.74-4.84 (m, 1H), 4.27-4.32 (m, 1H), 3.69 (dd, 1H), 3.48 (d, 1H), 2.95 (dd, 1H), 2.38 (d, 1H), 2.22-2.31 (m, 1H), 1.04 (d, 3H), 0.98 (d, 3H).

68.0 mg of the title compound (diastereomer mixture) were separated into the diastereomers by chiral HPLC (preparative HPLC: column: Daicel Chiralcel OX-H 5 µm 250×20 mm; eluent: 50% n-heptane, 50% isopropanol; temperature: 40° C.; flow rate: 15 ml/min; UV detection: 220 nm).

This gave (in the sequence of elution from the column) 31.0 mg (30% of theory, 100% purity) of diastereomer 1 from Example 527 (99% de) Rt=4.55 min and 31.0 mg (30% of theory, 100% purity) of diastereomer 2 from Example 528 (99% de) Rt=6.48 min.

[Analytical HPLC: column: Daicel Chiralcel OX-H 5 µm 250×4.6 mm; eluent: 50% isohexane, 50% isopropanol; temperature: 45° C.; flow rate: 1.0 ml/min; UV detection: 220 nm]

Example 527

7-[(4S)-4-Hydroxy-2-oxopyrrolidin-1-yl]-4-oxo-N-[1,1,1-trifluoro-3-methylbutan-2-yl]-1-(2,4,6-trifluorophenyl)-1,4-dihydro-1,8-naphthyridine-3-carboxamide (diastereomer 1)

LC-MS (Method 3): $R_t$=1.94 min; MS (ESIpos): m/z=543 [M+H]$^+$ $^1$H NMR (400 MHz, DMSO-d$_6$): δ ppm=10.32 (d, 1H), 9.08 (s, 1H), 8.74 (d, 1H), 8.54 (d, 1H), 7.58-7.66 (m, 2H), 5.34 (d, 1H), 4.74-4.84 (m, 1H), 4.27-4.32 (m, 1H), 3.69 (dd, 1H), 3.48 (br d, 1H), 2.95 (dd, 1H), 2.38 (br d, 1H), 2.22-2.31 (m, 1H), 1.04 (d, 3H), 0.98 (d, 3H).

Example 528

7-[(4S)-4-Hydroxy-2-oxopyrrolidin-1-yl]-4-oxo-N-[1,1,1-trifluoro-3-methylbutan-2-yl]-1-(2,4,6-trifluorophenyl)-1,4-dihydro-1,8-naphthyridine-3-carboxamide (diastereomer 2)

LC-MS (Method 3): $R_t$=1.95 min; MS (ESIpos): m/z=543 [M+H]$^+$ $^1$H NMR (400 MHz, DMSO-d$_6$): δ ppm=10.32 (d, 1H), 9.08 (s, 1H), 8.74 (d, 1H), 8.54 (d, 1H), 7.58-7.66 (m, 2H), 5.33 (d, 1H), 4.74-4.84 (m, 1H), 4.27-4.32 (m, 1H), 3.70 (dd, 1H), 3.48 (br d, 1H), 2.95 (dd, 1H), 2.38 (br d, 1H), 2.22-2.31 (m, 1H), 1.04 (d, 3H), 0.98 (d, 3H).

Example 529

7-[(4S)-4-Hydroxy-2-oxopyrrolidin-1-yl]-4-oxo-N-[3,3,4,4,4-pentafluorobutan-2-yl]-1-(2,4,6-trifluorophenyl)-1,4-dihydro-1,8-naphthyridine-3-carboxamide (diastereomer mixture)

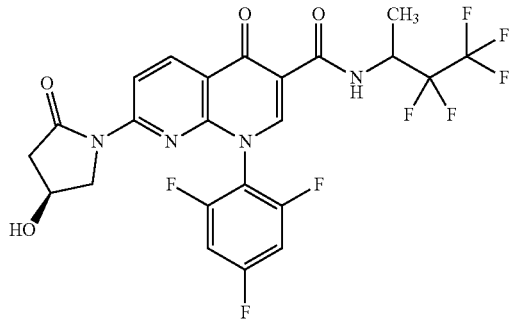 [SMILES: CC(NC(=O)c1cn(-c2c(F)cc(F)cc2F)c2nc(N3C[C@@H](O)CC3=O)ccc2c1=O)C(F)(F)C(F)(F)F]

According to GP1, 500 mg (1.19 mmol) of the compound from Example 117A were reacted with 262 mg (1.31 mmol) of the compound 147B in the presence of 544 mg (1.43 mmol) of HATU and 830 µl (4.80 mmol) of DIPEA in 5.0 ml of DMF. The crude product was purified by means of preparative HPLC (acetonitrile/water/0.1% formic acid). 498 mg (74% of theory, 100% purity) of the title compound were obtained.

LC-MS (Method 3): $R_t$=1.91 min; MS (ESIpos): m/z=565 [M+H]$^+$ $^1$H NMR (400 MHz, DMSO-d$_6$): δ ppm=10.24 (d, 1H), 9.08 (s, 1H), 8.71 (d, 1H), 8.54 (dd, 1H), 7.58-7.65 (m, 2H), 5.33 (t, 1H), 4.97-5.11 (m, 1H), 4.27-4.32 (m, 1H), 3.66-3.72 (m, 1H), 3.45-3.50 (m, 1H), 2.94 (ddd, 1H), 2.37 (br d, 1H), 1.41 (d, 3H).

492 mg of the title compound (diastereomer mixture) were separated into the diastereomers by chiral HPLC (preparative HPLC: column: Daicel Chiralpak AD-H 5 µm 250×20 mm; eluent: 80% n-heptane, 20% isopropanol; temperature: 23° C.; flow rate: 20 ml/min; UV detection: 220 nm).

This gave (in the sequence of elution from the column) 200.4 mg (30% of theory, 100% purity) of diastereomer 1 from Example 530 (99% de) Rt=6.05 min and 199 mg (30% of theory, 100% purity) of diastereomer 2 from Example 531 (99% de) Rt=8.82 min.

[Analytical HPLC: column: Daicel AD-3 3 µm 50×4.6 mm; eluent: 80% isohexane, 20% isopropanol; UV detection: 220 nm].

Example 530

7-[(4S)-4-Hydroxy-2-oxopyrrolidin-1-yl]-4-oxo-N-[3,3,4,4,4-pentafluorobutan-2-yl]-1-(2,4,6-trifluorophenyl)-1,4-dihydro-1,8-naphthyridine-3-carboxamide (diastereomer 1)

LC-MS (Method 3): $R_t$=1.89 min; MS (ESIpos): m/z=565 [M+H]$^+$ $^1$H NMR (400 MHz, DMSO-d$_6$): δ ppm=10.24 (d, 1H), 9.07 (s, 1H), 8.71 (d, 1H), 8.54 (d, 1H), 7.54-7.69 (m, 2H), 5.34 (d, 1H), 4.98-5.12 (m, 1H), 4.26-4.32 (m, 1H), 3.69 (dd, 1H), 3.48 (br d, 1H), 2.94 (dd, 1H), 2.38 (br d, 1H), 1.41 (d, 3H).

Example 531

7-[(4S)-4-Hydroxy-2-oxopyrrolidin-1-yl]-4-oxo-N-[3,3,4,4,4-pentafluorobutan-2-yl]-1-(2,4,6-trifluorophenyl)-1,4-dihydro-1,8-naphthyridine-3-carboxamide (diastereomer 2)

LC-MS (Method 3): $R_t$=1.90 min; MS (ESIpos): m/z=565 [M+H]$^+$ $^1$H NMR (400 MHz, DMSO-d$_6$): δ ppm=10.24 (d, 1H), 9.08 (s, 1H), 8.71 (d, 1H), 8.54 (d, 1H), 7.58-7.65 (m, 2H), 5.33 (d, 1H), 4.98-5.12 (m, 1H), 4.27-4.32 (m, 1H), 3.69 (dd, 1H), 3.47 (br d, 1H), 2.95 (dd, 1H), 2.37 (br d, 1H), 1.41 (d, 3H).

Example 532

N-[1-(2-Chlorophenyl)-2,2,2-trifluoroethyl]-7-[(4S)-4-hydroxy-2-oxopyrrolidin-1-yl]-4-oxo-1-(2,4,6-trifluorophenyl)-1,4-dihydro-1,8-naphthyridine-3-carboxamide (diastereomer mixture)

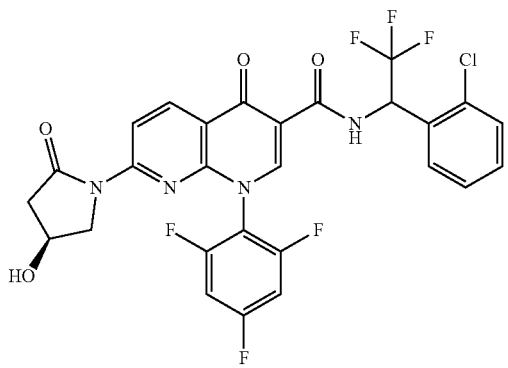 [SMILES: O=C(NC(c1ccccc1Cl)C(F)(F)F)c1cn(-c2c(F)cc(F)cc2F)c2nc(N3C[C@@H](O)CC3=O)ccc2c1=O]

According to GP1, 50.0 mg (119 µmol) of 7-[(4S)-4-hydroxy-2-oxopyrrolidin-1-yl]-4-oxo-1-(2,4,6-trifluorophenyl)-1,4-dihydro-1,8-naphthyridine-3-carboxylic acid were reacted with 30.0 mg (143 µmol) of 1-(2-chlorophenyl)-2,2,2-trifluoroethanamine in the presence of 54.4 mg (143 mmol) of HATU and 62 µl (360 µmol) of DIPEA in 460 µl of DMF. The crude product was purified by means of preparative HPLC (acetonitrile/water/0.1% formic acid). 41.9 mg (58% of theory, 100% purity) of the title compound were obtained.

LC-MS (Method 3): $R_t$=2.14 min; MS (ESIpos): m/z=611 [M+H]$^+$ $^1$H NMR (400 MHz, DMSO-d$_6$): δ ppm=11.21 (d, 1H), 9.09 (s, 1H), 8.76 (d, 1H), 8.56 (d, 1H), 7.44-7.70 (m, 6H), 6.42-6.51 (m, 1H), 5.30-5.37 (m, 1H), 4.27-4.32 (m, 1H), 3.65-3.72 (m, 1H), 3.42-3.51 (m, 1H), 2.94 (ddd, 1H), 2.38 (d, 1H).

35.8 mg of the title compound (diastereomer mixture) were separated into the diastereomers by chiral HPLC (preparative HPLC: column: YMC Chiralart Amylose SA 5 µm 250×30 mm; eluent: 60% n-heptane, 40% isopropanol; temperature: 30° C.; flow rate: 30 ml/min; UV detection: 220 nm).

This gave (in the sequence of elution from the column) 15.0 mg of diastereomer 1 (99% de) Rt=6.50 min and 15.0 mg (99% de) of diastereomer 2 Rt=8.62 min.

[Analytical HPLC: column: YMC Chiralart Amylose SA 5 µm 250×4.6 mm; eluent: 60% isohexane, 40% isopropanol; temperature: 30° C.; flow rate: 1.0 ml/min; UV detection: 220 nm]

Diastereomer 1 was additionally purified by means of preparative HPLC (column: Chromatorex C18, 10 µm, 125*40 mm, solvent: acetonitrile, water, 0.1% formic acid), and 13.4 mg (19% of theory, 100% purity) of the title compound from Example 533 were obtained.

Diastereomer 2 was additionally purified by means of preparative HPLC (column: Chromatorex C18, 10 µm, 125*40 mm, solvent: acetonitrile, water, 0.1% formic acid), and 13.2 mg (18% of theory, 100% purity) of the title compound from Example 534 were obtained.

Example 533

N-[1-(2-Chlorophenyl)-2,2,2-trifluoroethyl]-7-[(4S)-4-hydroxy-2-oxopyrrolidin-1-yl]-4-oxo-1-(2,4,6-trifluorophenyl)-1,4-dihydro-1,8-naphthyridine-3-carboxamide (diastereomer 1)

LC-MS (Method 1): $R_t$=1.13 min; MS (ESIpos): m/z=611 [M+H]$^+$ $^1$H NMR (400 MHz, DMSO-d$_6$): δ ppm=11.21 (d, 1H), 9.09 (s, 1H), 8.76 (d, 1H), 8.56 (d, 1H), 7.46-7.70 (m, 6H), 6.42-6.51 (m, 1H), 5.33 (d, 1H), 4.27-4.32 (m, 1H), 3.69 (dd, 1H), 3.47 (d, 1H), 2.95 (dd, 1H), 2.38 (br d, 1H).

Example 534

N-[1-(2-Chlorophenyl)-2,2,2-trifluoroethyl]-7-[(4S)-4-hydroxy-2-oxopyrrolidin-1-yl]-4-oxo-1-(2,4,6-trifluorophenyl)-1,4-dihydro-1,8-naphthyridine-3-carboxamide (diastereomer 2)

LC-MS (Method 1): $R_t$=1.13 min; MS (ESIpos): m/z=611 [M+H]$^+$ $^1$H NMR (400 MHz, DMSO-d$_6$): δ ppm=11.21 (d, 1H), 9.09 (s, 1H), 8.76 (d, 1H), 8.56 (d, 1H), 7.48-7.66 (m, 6H), 6.42-6.51 (m, 1H), 5.34 (d, 1H), 4.27-4.31 (m, 1H), 3.68 (dd, 1H), 3.47 (br d, 1H), 2.94 (dd, 1H), 2.38 (br d, 1H).

Example 535

N-[(1S)-1-Cyclopropyl-2,2,2-trifluoroethyl]-7-[(3S)-3-methoxypyrrolidin-1-yl]-4-oxo-1-(2,4,6-trifluorophenyl)-1,4-dihydro-1,8-naphthyridine-3-carboxamide

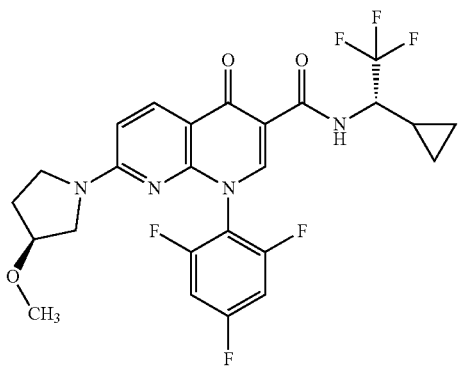 [SMILES: CO[C@H]1CCN(c2ccc3c(=O)c(C(=O)N[C@@H](C4CC4)C(F)(F)F)cn(-c4c(F)cc(F)cc4F)c3n2)C1]

According to GP3, 60.0 mg (126 μmol) of the compound from Example 126A were reacted with 22.6 mg (164 μmol) of (3S)-3-methoxypyrrolidine hydrochloride and 99 μl (570 μmol) of DIPEA in 700 μl of DMF. The crude product was purified by means of preparative HPLC (acetonitrile/water/0.1% formic acid). 58.2 mg (85% of theory, 100% purity) of the title compound were obtained.

LC-MS (Method 3): $R_t$=2.27 min; MS (ESIpos): m/z=541 [M+H]$^+$ $^1$H NMR (400 MHz, DMSO-d$_6$): δ ppm=10.56 (d, 1H), 8.80 (s, 1H), 8.29 (d, 1H), 7.51-7.61 (m, 2H), 6.79 (d, 1H), 4.33-4.43 (m, 1H), 3.94-4.11 (m, 1H), 3.48-3.60 (m, 1.5H), 3.37-3.47 (m, 0.5H), 3.16-3.28 (m, 4.5H), 3.04-3.14 (m, 0.5H), 1.89-2.15 (m, 2H), 1.16-1.25 (m, 1H), 0.50-0.69 (m, 3H), 0.31-0.38 (m, 1H).

Example 536

4-Oxo-7-(2-oxoimidazolidin-1-yl)-N-[1,1,1-trifluoro-3-methylbutan-2-yl]-1-(2,4,6-trifluorophenyl)-1,4-dihydro-1,8-naphthyridine-3-carboxamide (racemate)

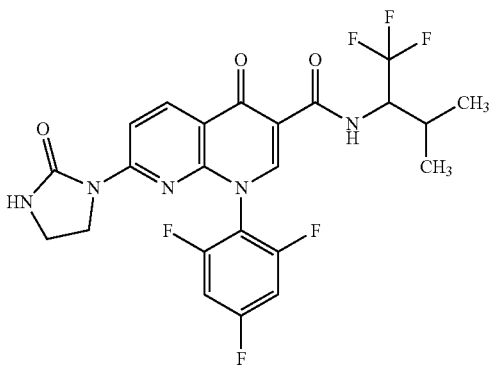 [SMILES: CC(C)C(NC(=O)c1cn(-c2c(F)cc(F)cc2F)c2nc(N3CCNC3=O)ccc2c1=O)C(F)(F)F]

According to GP1, 80.0 mg (198 μmol) of the compound from Example 113A were reacted with 33.5 mg (237 μmol) of 1,1,1-trifluoro-3-methylbutan-2-amine in the presence of 90.3 mg (237 μmol) of HATU and 100 μl (590 μmol) of DIPEA in 1.4 ml of DMF. The crude product was purified by means of preparative HPLC (acetonitrile/water/0.1% formic acid). 68.7 mg (66% of theory, 100% purity) of the title compound were obtained.

LC-MS (Method 3): $R_t$=2.03 min; MS (ESIpos): m/z=528 [M+H]$^+$ $^1$H NMR (400 MHz, DMSO-d$_6$): δ ppm=10.41 (d, 1H), 9.00 (s, 1H), 8.58 (d, 1H), 8.44 (d, 1H), 7.67 (s, 1H), 7.58 (t, 2H), 4.73-4.83 (m, 1H), 3.55-3.63 (m, 2H), 3.32-3.38 (m, 2H), 2.21-2.30 (m, 1H), 1.04 (d, 3H), 0.97 (d, 3H).

57.0 mg of the title compound (racemate) were separated into the enantiomers by chiral HPLC (preparative HPLC: column: Daicel Chiralpak IE 5 μm 250×30 mm; eluent: 70% n-heptane, 20% isopropanol; temperature: 23° C.; flow rate: 20 ml/min; UV detection: 257 nm).

This gave (in the sequence of elution from the column) 23.1 mg of enantiomer 1 (99% de) Rt=14.57 min and 24.4 mg (96% de) of enantiomer 2 Rt=18.53 min.

[Analytical HPLC: column: Daicel Chiralpak IF-3 3 μm 50×4.6 mm; eluent: 80% n-heptane, 20% isopropanol; temperature: 30° C.; flow rate: 1.0 ml/min; UV detection: 255 nm]

Enantiomer 1 was additionally purified by means of preparative HPLC (column: Chromatorex C18, 10 μm, 125*40 mm, solvent: acetonitrile, water, 0.1% formic acid), and 11.0 mg (11% of theory, 100% purity) of the title compound from Example 537 were obtained.

Enantiomer 2 was additionally purified by means of preparative HPLC (column: Chromatorex C18, 10 μm, 125*40 mm, solvent: acetonitrile, water, 0.1% formic acid), and 12.9 mg (12% of theory, 100% purity) of the title compound from Example 538 were obtained.

Example 537

4-Oxo-7-(2-oxoimidazolidin-1-yl)-N-[1,1,1-trifluoro-3-methylbutan-2-yl]-1-(2,4,6-trifluorophenyl)-1,4-dihydro-1,8-naphthyridine-3-carboxamide (enantiomer 1)

LC-MS (Method 3): $R_t$=2.01 min; MS (ESIpos): m/z=528 [M+H]$^+$ $^1$H NMR (400 MHz, DMSO-d$_6$): δ ppm=10.42 (d, 1H), 9.00 (s, 1H), 8.59 (d, 1H), 8.44 (d, 1H), 7.67 (s, 1H), 7.58 (t, 2H), 4.73-4.84 (m, 1H), 3.60 (t, 2H), 3.35 (br t, 2H), 2.21-2.30 (m, 1H), 1.04 (d, 3H), 0.97 (d, 3H).

Example 538

4-Oxo-7-(2-oxoimidazolidin-1-yl)-N-[1,1,1-trifluoro-3-methylbutan-2-yl]-1-(2,4,6-trifluorophenyl)-1,4-dihydro-1,8-naphthyridine-3-carboxamide (enantiomer 2)

LC-MS (Method 3): $R_t$=2.01 min; MS (ESIpos): m/z=528 [M+H]$^+$ $^1$H NMR (400 MHz, DMSO-d$_6$): δ ppm=10.41 (d, 1H), 9.00 (s, 1H), 8.59 (d, 1H), 8.44 (d, 1H), 7.67 (s, 1H), 7.58

(t, 2H), 4.72-4.84 (m, 1H), 3.56-3.63 (m, 2H), 3.31-3.39 (m, 2H), 2.21-2.30 (m, 1H), 1.04 (d, 3H), 0.97 (d, 3H).

Example 539

N-[(1S)-1-Cyclopropyl-2,2,2-trifluoroethyl]-7-(3-ethyl-2-oxotetrahydropyrimidin-1(2H)-yl)-4-oxo-1-(2,4,6-trifluorophenyl)-1,4-dihydro-1,8-naphthyridine-3-carboxamide

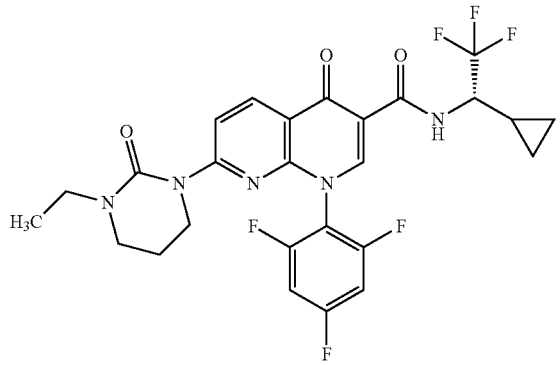 [SMILES: CCN1CCCN(c2ccc3c(=O)c(C(=O)N[C@@H](C4CC4)C(F)(F)F)cn(-c4c(F)cc(F)cc4F)c3n2)C1=O]

According to GP2, 60.0 mg (126 µmol) of the compound from Example 126A were reacted with 19.4 mg (151 µmol) of 1-ethyltetrahydropyrimidin-2(1H)-one in the presence of 26.1 mg (189 µmol) of potassium carbonate, 5.66 mg (25.2 µmol) of palladium acetate and 14.6 mg (25.2 µmol) of Xantphos in 600 µl of 1,4-dioxane. The crude product was purified by means of preparative HPLC (acetonitrile/water/0.1% formic acid). 25.0 mg (35% of theory, 100% purity) of the title compound were obtained.

LC-MS (Method 1): $R_t$=1.20 min; MS (ESIpos): m/z=568 [M+H]$^+$ $^1$H NMR (400 MHz, DMSO-d$_6$): δ ppm=10.33 (d, 1H), 9.00 (s, 1H), 8.51 (d, 1H), 8.18 (d, 1H), 7.56-7.62 (m, 2H), 4.31-4.44 (m, 1H), 3.51 (t, 2H), 3.32-3.39 (m, 3H), 1.87-1.94 (m, 2H), 1.18-1.27 (m, 1H), 1.08 (t, 3H), 0.53-0.70 (m, 3H), 0.30-0.38 (m, 1H).

Example 540

4-Oxo-7-(2-oxoimidazolidin-1-yl)-N-[3,3,4,4,4-pentafluorobutan-2-yl]-1-(2,4,6-trifluorophenyl)-1,4-dihydro-1,8-naphthyridine-3-carboxamide (racemate)

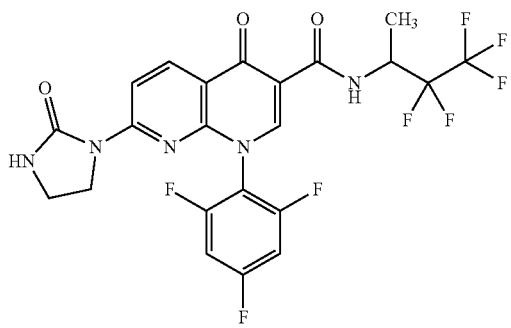 [SMILES: CC(NC(=O)c1cn(-c2c(F)cc(F)cc2F)c2nc(N3CCNC3=O)ccc2c1=O)C(F)(F)C(F)(F)F]

According to GP1, 500 mg (1.24 mmol) of the compound from Example 113A were reacted with 282 mg (1.73 mmol) of the compound from Example 147B in the presence of 564 mg (1.48 mmol) of HATU and 650 µl (3.70 mmol) of DIPEA in 4.6 ml of DMF. The crude product was purified by means of preparative HPLC (acetonitrile/water/0.1% formic acid). 361 mg (53% of theory, 100% purity) of the title compound were obtained.

LC-MS (Method 3): $R_t$=1.97 min; MS (ESIpos): m/z=550 [M+H]$^+$ $^1$H NMR (400 MHz, DMSO-d$_6$): δ ppm=10.33 (d, 1H), 9.00 (s, 1H), 8.55 (d, 1H), 8.44 (d, 1H), 7.67 (s, 1H), 7.54-7.61 (m, 2H), 4.97-5.11 (m, 1H), 3.54-3.65 (m, 2H), 3.32-3.38 (m, 2H), 1.41 (d, 3H).

358 mg of the title compound (racemate) were separated into the enantiomers by chiral SFC (preparative SFC: column: Daicel Chiralcel OD-H 5 µm 250×20 mm; eluent: 88% carbon dioxide, 12% isopropanol; temperature: 40° C.; flow rate: 80 ml/min; UV detection: 210 nm).

This gave (in the sequence of elution from the column) 111 mg (16% of theory, 100% purity) of enantiomer 1 from Example 541 (99% ee) Rt=11.45 min and 124 mg (18% of theory, 100% purity) of enantiomer 2 from Example 542 (99% ee) Rt=13.60 min.

[Analytical SFC: column: OD; eluent: 80% carbon dioxide, 20% isopropanol; flow rate: 3.0 ml/min; UV detection: 210 nm].

Example 541

4-Oxo-7-(2-oxoimidazolidin-1-yl)-N-[3,3,4,4,4-pentafluorobutan-2-yl]-1-(2,4,6-trifluorophenyl)-1,4-dihydro-1,8-naphthyridine-3-carboxamide (enantiomer 1)

LC-MS (Method 3): $R_t$=1.97 min; MS (ESIpos): m/z=550 [M+H]$^+$ $^1$H NMR (400 MHz, DMSO-d$_6$): δ ppm=10.33 (d, 1H), 9.00 (s, 1H), 8.55 (d, 1H), 8.44 (d, 1H), 7.67 (s, 1H), 7.54-7.61 (m, 2H), 4.97-5.10 (m, 1H), 3.55-3.63 (m, 2H), 3.32-3.38 (m, 2H), 1.41 (d, 3H).

Example 542

4-Oxo-7-(2-oxoimidazolidin-1-yl)-N-[3,3,4,4,4-pentafluorobutan-2-yl]-1-(2,4,6-trifluorophenyl)-1,4-dihydro-1,8-naphthyridine-3-carboxamide (enantiomer 2)

LC-MS (Method 3): $R_t$=1.96 min; MS (ESIpos): m/z=550 [M+H]$^+$ $^1$H NMR (400 MHz, DMSO-d$_6$): δ ppm=10.33 (d, 1H), 9.00 (s, 1H), 8.55 (d, 1H), 8.44 (d, 1H), 7.67 (s, 1H), 7.54-7.61 (m, 2H), 4.97-5.10 (m, 1H), 3.55-3.63 (m, 2H), 3.32-3.38 (m, 2H), 1.41 (d, 3H).

Example 543

4-Oxo-7-(2-oxoimidazolidin-1-yl)-N-[(2S)-1,1,1-trifluoro-4-methylpentan-2-yl]-1-(2,4,6-trifluorophenyl)-1,4-dihydro-1,8-naphthyridine-3-carboxamide

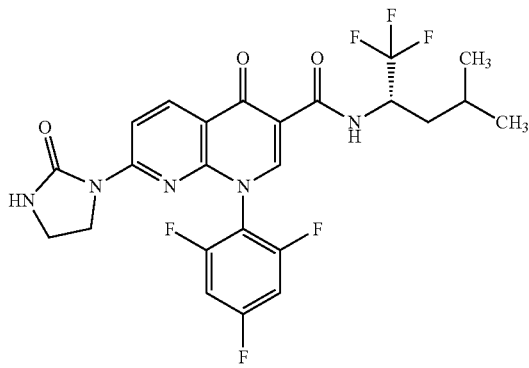 [SMILES: CC(C)C[C@H](NC(=O)c1cn(-c2c(F)cc(F)cc2F)c2nc(N3CCNC3=O)ccc2c1=O)C(F)(F)F]

According to GP1, 26.0 mg (64.3 μmol) of the compound from Example 113A were reacted with 12.0 mg (77.2 μmol) of (2S)-1,1,1-trifluoro-4-methylpentan-2-amine in the presence of 29.3 mg (77.2 μmol) of HATU and 34 μl (190 μmol) of DIPEA in 250 μl of DMF. The crude product was purified by means of preparative HPLC (acetonitrile/water/0.1% formic acid). 22.6 mg (65% of theory, 100% purity) of the title compound were obtained.

LC-MS (Method 3): $R_t$=2.16 min; MS (ESIpos): m/z=542 [M+H]$^+$ $^1$H NMR (400 MHz, DMSO-d$_6$): δ ppm=10.20 (d, 1H), 9.00 (s, 1H), 8.55 (d, 1H), 8.44 (d, 1H), 7.67 (s, 1H), 7.54-7.61 (m, 2H), 4.78-4.89 (m, 1H), 3.55-3.63 (m, 2H), 3.34-3.40 (m, 2H), 1.54-1.73 (m, 3H), 0.95 (d, 3H), 0.90 (d, 3H).

Example 544

7-[(3R,4R)-3,4-Dihydroxypyrrolidin-1-yl]-4-oxo-N-[(2R)-1,1,1-trifluoro-4-methylpentan-2-yl]-1-(2,4,6-trifluorophenyl)-1,4-dihydro-1,8-naphthyridine-3-carboxamide

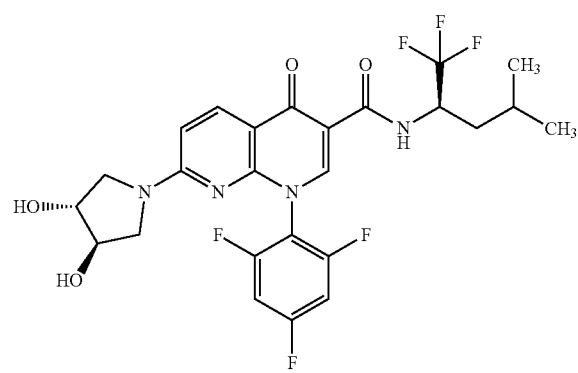 [SMILES: CC(C)C[C@@H](NC(=O)c1cn(-c2c(F)cc(F)cc2F)c2nc(N3C[C@@H](O)[C@H](O)C3)ccc2c1=O)C(F)(F)F]

According to GP1, 50.0 mg (119 μmol) of the compound from Example 121A were reacted with 22.1 mg (142 μmol) of (2S)-1,1,1-trifluoro-4-methylpentan-2-amine in the presence of 54.1 mg (142 μmol) of HATU and 62 μl (360 μmol) of DIPEA in 750 μl of DMF. The crude product was purified by means of preparative HPLC (acetonitrile/water/0.1% formic acid). 47.5 mg (67% of theory, 94% purity) of the title compound were obtained.

LC-MS (Method 3): $R_t$=1.93 min; MS (ESIpos): m/z=559 [M+H]$^+$ $^1$H NMR (400 MHz, DMSO-d$_6$): δ ppm=10.42 (d, 1H), 8.81 (s, 1H), 8.27 (d, 1H), 7.53-7.60 (m, 2H), 6.78 (d, 1H), 5.23 (d, 1H), 5.15 (d, 1H), 4.77-4.88 (m, 1H), 4.05 (br s, 1H), 3.93 (br s, 1H), 3.62 (br dd, 1H), 3.34 (br d, 1H), 3.25 (br dd, 1H), 3.07 (br d, 1H), 1.52-1.72 (m, 3H), 0.95 (d, 3H), 0.89 (d, 3H).

Example 545

7-[(3R,4R)-3,4-Dihydroxypyrrolidin-1-yl]-N-[1,1,1,4,4,4-hexafluorobutan-2-yl]-4-oxo-1-(2,4,6-trifluorophenyl)-1,4-dihydro-1,8-naphthyridine-3-carboxamide (diastereomer mixture)

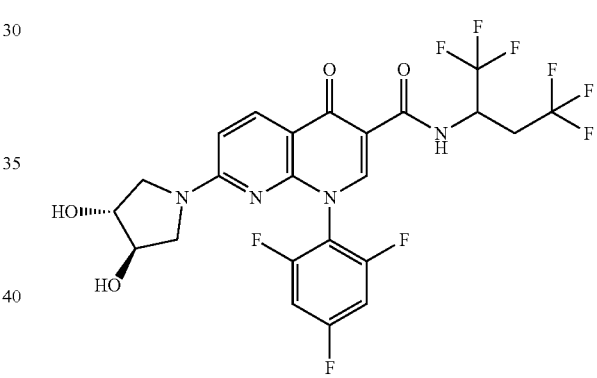

According to GP1, 40.0 mg (94.9 μmol) of the compound from Example 121A were reacted with 28.9 mg (133 μmol) of 1,1,1,4,4,4-hexafluorobutan-2-amine hydrochloride in the presence of 43.3 mg (114 μmol) of HATU and 50 μl (280 μmol) of DIPEA in 350 μl of DMF. The crude product was purified by means of preparative HPLC (acetonitrile/water/0.1% formic acid). 32.0 mg (58% of theory, 100% purity) of the title compound were obtained.

LC-MS (Method 3): $R_t$=1.70 min; MS (ESIpos): m/z=585 [M+H]$^+$ $^1$H NMR (400 MHz, DMSO-d$_6$): δ ppm=10.71 (d, 1H), 8.83 (s, 1H), 8.27 (d, 1H), 7.53-7.60 (m, 2H), 6.78 (d, 1H), 5.10-5.28 (m, 2H), 4.03-4.06 (m, 1H), 3.91-3.94 (m, 1H), 3.58-3.64 (m, 1H), 3.34-3.39 (m, 1H), 3.20-3.28 (m, 2H), 3.02-3.14 (m, 2H), 2.91-3.01 (m, 1H).

Example 546

1-(2-Chloro-4,6-difluorophenyl)-N-[(1 S)-1-cyclopropyl-2,2,2-trifluoroethyl]-7-[(3R,4R)-3,4-dihydroxypyrrolidin-1-yl]-4-oxo-1,4-dihydro-1,8-naphthyridine-3-carboxamide (atropisomer mixture)

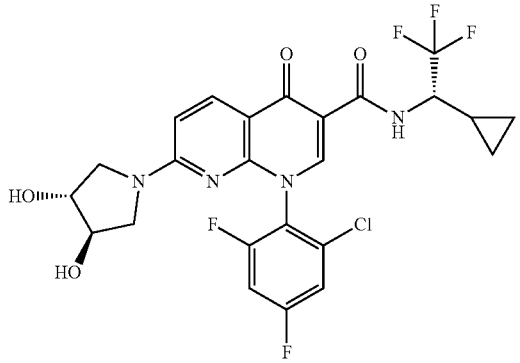 [SMILES: O=C(N[C@@H](C1CC1)C(F)(F)F)c1cn(-c2c(F)cc(F)cc2Cl)c2nc(N3C[C@@H](O)[C@H](O)C3)ccc2c1=O]

According to GP3, 50.0 mg (102 µmol) of the compound from Example 110A were reacted with 17.0 mg (122 µmol) of (3R,4R)-pyrrolidine-3,4-diol hydrochloride and 62 µl (360 µmol) of DIPEA in 500 µl of DMF. The crude product was purified by means of preparative HPLC (acetonitrile/water/0.1% formic acid). 51.6 mg (91% of theory, 100% purity) of the title compound were obtained.

LC-MS (Method 3): $R_t$=1.76 min; MS (ESIpos): m/z=559 [M+H]$^+$ $^1$H NMR (400 MHz, DMSO-d$_6$): δ ppm=10.59 (d, 1H), 8.74 (s, 1H), 8.28 (d, 1H), 7.66-7.76 (m, 2H), 6.78 (d, 1H), 5.20-5.26 (m, 1H), 5.12-5.17 (m, 1H), 4.32-4.43 (m, 1H), 4.01-4.08 (m, 1H), 3.88-3.95 (m, 1H), 3.61 (br dd, 1H), 3.33-3.37 (m, 1H), 3.16-3.26 (m, 1H), 2.97-3.08 (m, 1H), 1.14-1.25 (m, 1H), 0.49-0.69 (m, 3H), 0.34 (dt, 1H).

30.0 mg of the title compound (atropisomer mixture) were separated into the atropisomers by chiral HPLC (preparative HPLC: column: Daicel Chiralcel OX-H 5 µm 250×20 mm; eluent: 75% n-heptane, 25% isopropanol; temperature: 40° C.; flow rate: 15 ml/min; UV detection: 220 nm).

This gave (in the sequence of elution from the column) 14.0 mg (25% of theory, 100% purity) of atropisomer 1 from Example 547 (99% de) Rt=6.08 min and 13.0 mg (23% of theory, 100% purity) of atropisomer 2 from Example 548 (99% de) Rt=8.82 min.

[Analytical HPLC: column: Daicel Chiralcel OX-H 5 µm 250×4.6 mm; eluent: 70% isohexane, 30% isopropanol; temperature: 35° C.; flow rate: 1.0 ml/min; UV detection: 220 nm]

Example 547

1-(2-Chloro-4,6-difluorophenyl)-N-[(1S)-1-cyclopropyl-2,2,2-trifluoroethyl]-7-[(3R,4R)-3,4-dihydroxypyrrolidin-1-yl]-4-oxo-1,4-dihydro-1,8-naphthyridine-3-carboxamide (atropisomer 1)

LC-MS (Method 3): $R_t$=1.77 min; MS (ESIpos): m/z=559 [M+H]$^+$ $^1$H NMR (400 MHz, DMSO-d$_6$): δ ppm=10.59 (d, 1H), 8.74 (s, 1H), 8.28 (d, 1H), 7.66-7.76 (m, 2H), 6.78 (d, 1H), 5.19-5.26 (m, 1H), 5.10-5.19 (m, 1H), 4.33-4.44 (m, 1H), 4.00-4.07 (m, 1H), 3.87-3.96 (m, 1H), 3.61 (br dd, 1H), 3.32-3.36 (m, 1H), 3.17-3.25 (m, 1H), 3.01 (br d, 1H), 1.15-1.28 (m, 1H), 0.49-0.69 (m, 3H), 0.29-0.38 (m, 1H).

Example 548

1-(2-Chloro-4,6-difluorophenyl)-N-[(1S)-1-cyclopropyl-2,2,2-trifluoroethyl]-7-[(3R,4R)-3,4-dihydroxypyrrolidin-1-yl]-4-oxo-1,4-dihydro-1,8-naphthyridine-3-carboxamide (atropisomer 2)

LC-MS (Method 3): $R_t$=1.77 min; MS (ESIpos): m/z=559 [M+H]$^+$ $^1$H NMR (400 MHz, DMSO-d$_6$): δ ppm=10.59 (d, 1H), 8.74 (s, 1H), 8.28 (d, 1H), 7.66-7.77 (m, 2H), 6.78 (d, 1H), 5.19-5.25 (m, 1H), 5.12-5.19 (m, 1H), 4.32-4.42 (m, 1H), 4.04 (br s, 1H), 3.91 (br s, 1H), 3.61 (br dd, 1H), 3.33-3.37 (m, 1H), 3.20 (br dd, 1H), 3.04 (br d, 1H), 1.16-1.26 (m, 1H), 0.50-0.70 (m, 3H), 0.31-0.39 (m, 1H).

Example 549

7-[(3R,4R)-3,4-Dihydroxypyrrolidin-1-yl]-4-oxo-N-[3,3,4,4,4-pentafluorobutan-2-yl]-1-(2,4,6-trifluorophenyl)-1,4-dihydro-1,8-naphthyridine-3-carboxamide (diastereomer mixture)

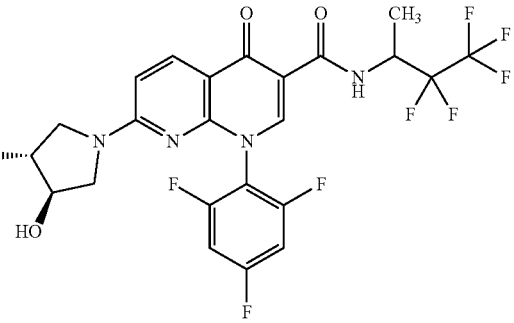

According to GP1, 500 mg (1.19 mmol) of the compound from Example 121A were reacted with 260 mg (1.31 mmol) of the compound from Example 147B in the presence of 541 mg (1.42 mmol) of HATU and 830 µl (4.70 mmol) of DIPEA in 5.0 ml of DMF. The crude product was purified by means of preparative HPLC (acetonitrile/water/0.1% formic acid). 399 mg (59% of theory, 100% purity) of the title compound were obtained.

LC-MS (Method 1): $R_t$=0.93 min; MS (ESIpos): m/z=567 [M+H]$^+$ $^1$H NMR (500 MHz, DMSO-d$_6$): δ ppm=10.56 (d, 1H), 8.80 (s, 1H), 8.27 (d, 1H), 7.53-7.59 (m, 2H), 6.78 (d, 1H), 5.23 (t, 1H), 5.14 (t, 1H), 4.96-5.07 (m, 1H), 4.05 (br s, 1H), 3.93 (br s, 1H), 3.58-3.65 (m, 1H), 3.32-3.37 (m, 1H), 3.25 (dt, 1H), 3.07 (br d, 1H), 1.39 (d, 3H).

395 mg of the title compound (diastereomer mixture) were separated into the diastereomers by chiral HPLC (preparative HPLC: column: Daicel Chiralpak AD-H 5 µm 250×20 mm; eluent: 80% n-heptane, 20% isopropanol; temperature: 23° C.; flow rate: 20 ml/min; UV detection: 220 nm).

This gave (in the sequence of elution from the column) 164.7 mg (24% of theory, 100% purity) of diastereomer 1 from Example 550 (99% de) Rt=4.52 min and 163.7 mg (24% of theory, 100% purity) of diastereomer 2 from Example 551 (97% de) Rt=6.81 min.

[Analytical HPLC: column: Daicel Chiralpak AD-3 3 µm 50×4.6 mm; eluent: 80% n-heptane, 20% isopropanol; flow rate: 1.0 ml/min; UV detection: 220 nm]

Example 550

7-[(3R,4R)-3,4-Dihydroxypyrrolidin-1-yl]-4-oxo-N-[3,3,4,4,4-pentafluorobutan-2-yl]-1-(2,4,6-trifluorophenyl)-1,4-dihydro-1,8-naphthyridine-3-carboxamide (diastereomer 1)

LC-MS (Method 3): $R_t$=1.72 min; MS (ESIpos): m/z=567 [M+H]$^+$ $^1$H NMR (400 MHz, DMSO-d$_6$): δ ppm=10.56 (d, 1H), 8.81 (s, 1H), 8.27 (d, 1H), 7.53-7.60 (m, 2H), 6.78 (d, 1H), 5.23 (d, 1H), 5.15 (d, 1H), 4.95-5.09 (m, 1H), 4.05 (br s, 1H), 3.93 (br s, 1H), 3.62 (dd, 1H), 3.33 (br d, 1H), 3.24 (dd, 1H), 3.07 (br d, 1H), 1.39 (d, 3H).

Example 551

7-[(3R,4R)-3,4-Dihydroxypyrrolidin-1-yl]-4-oxo-N-[3,3,4,4,4-pentafluorobutan-2-yl]-1-(2,4,6-trifluorophenyl)-1,4-dihydro-1,8-naphthyridine-3-carboxamide (diastereomer 2)

LC-MS (Method 3): $R_t$=1.72 min; MS (ESIpos): m/z=567 [M+H]$^+$ $^1$H NMR (400 MHz, DMSO-d$_6$): δ ppm=10.56 (d, 1H), 8.81 (s, 1H), 8.27 (d, 1H), 7.52-7.60 (m, 2H), 6.78 (d, 1H), 5.24 (d, 1H), 5.14 (d, 1H), 4.96-5.09 (m, 1H), 4.05 (br s, 1H), 3.93 (br s, 1H), 3.61 (dd, 1H), 3.32-3.37 (m, 1H), 3.25 (dd, 1H), 3.07 (d, 1H), 1.39 (d, 3H).

Example 552

7-[(3R,4R)-3,4-Dihydroxypyrrolidin-1-yl]-4-oxo-N-[1,1,1-trifluoro-3-methylbutan-2-yl]-1-(2,4,6-trifluorophenyl)-1,4-dihydro-1,8-naphthyridine-3-carboxamide (diastereomer mixture)

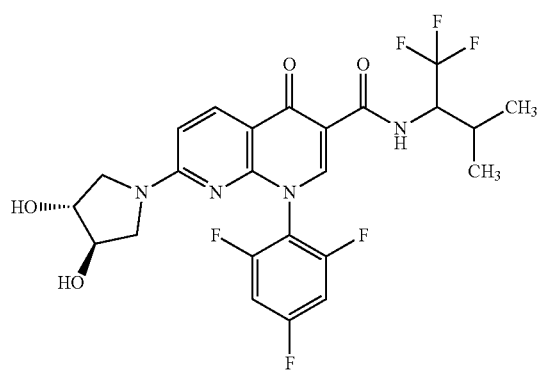 [SMILES: CC(C)C(NC(=O)c1cn(-c2c(F)cc(F)cc2F)c2nc(N3C[C@@H](O)[C@H](O)C3)ccc2c1=O)C(F)(F)F]

According to GP1, 80 mg (190 µmol) of the compound from Example 121A were reacted with 32.2 mg (228 µmol) of 1,1,1-trifluoro-3-methylbutan-2-amine in the presence of 86.6 mg (228 µmol) of HATU and 99 µl (570 µmol) of DIPEA in 1.4 ml of DMF. The crude product was purified by means of preparative HPLC (acetonitrile/water/0.1% formic acid). 73.4 mg (71% of theory, 100% purity) of the title compound were obtained.

LC-MS (Method 3): $R_t$=1.76 min; MS (ESIpos): m/z=545 [M+H]$^+$ $^1$H NMR (400 MHz, DMSO-d$_6$): δ ppm=10.62 (d, 1H), 8.81 (s, 1H), 8.30 (d, 1H), 7.57 (br t, 2H), 6.78 (d, 1H), 5.24 (t, 1H), 5.14 (t, 1H), 4.71-4.81 (m, 1H), 4.05 (br s, 1H), 3.93 (br s, 1H), 3.62 (br dd, 1H), 3.32-3.37 (m, 1H), 3.25 (br dd, 1H), 3.07 (br d, 1H), 2.19-2.29 (m, 1H), 1.03 (d, 3H), 0.96 (d, 3H).

51.0 mg of the title compound (diastereomer mixture) were separated into the diastereomers by chiral HPLC (preparative HPLC: column: Daicel Chiralpak IF 5 µm 250×20 mm; eluent: 80% n-heptane, 20% isopropanol; temperature: 23° C.; flow rate: 20 ml/min; UV detection: 270 nm).

This gave (in the sequence of elution from the column) 7.40 mg of diastereomer 1 (99% de) Rt=7.55 min and 7.30 mg of diastereomer 2 (96% de) Rt=9.20 min.

[Analytical HPLC: column: Daicel Chiralpak IE-3 3 µm 50×4.6 mm; eluent: 80% n-heptane, 20% isopropanol; temperature: 30° C.; flow rate: 1.0 ml/min; UV detection: 220 nm]

Diastereomer 1 was additionally purified by means of preparative HPLC (column: Chromatorex C18, 10 µm, 125*40 mm, solvent: acetonitrile, water, 0.1% formic acid), and 2.40 mg (2.3% of theory, 100% purity) of the title compound from Example 553 were obtained.

Diastereomer 2 was additionally purified by means of preparative HPLC (column: Chromatorex C18, 10 µm, 125*40 mm, solvent: acetonitrile, water, 0.1% formic acid), and 2.30 mg (2.2% of theory, 100% purity) of the title compound from Example 554 were obtained.

Example 553

7-[(3R,4R)-3,4-Dihydroxypyrrolidin-1-yl]-4-oxo-N-[1,1,1-trifluoro-3-methylbutan-2-yl]-1-(2,4,6-trifluorophenyl)-1,4-dihydro-1,8-naphthyridine-3-carboxamide (diastereomer 1)

LC-MS (Method 3): $R_t$=1.77 min; MS (ESIpos): m/z=545 [M+H]$^+$ $^1$H NMR (400 MHz, DMSO-d$_6$): δ ppm=10.62 (d, 1H), 8.81 (s, 1H), 8.30 (d, 1H), 7.53-7.60 (m, 2H), 6.78 (d, 1H), 5.23 (d, 1H), 5.15 (d, 1H), 4.71-4.82 (m, 1H), 4.05 (br s, 1H), 3.93 (br s, 1H), 3.62 (br dd, 1H), 3.32-3.37 (m, 1H), 3.25 (br dd, 1H), 3.07 (d, 1H), 2.19-2.29 (m, 1H), 1.03 (d, 3H), 0.97 (d, 3H).

Example 554

7-[(3R,4R)-3,4-Dihydroxypyrrolidin-1-yl]-4-oxo-N-[1,1,1-trifluoro-3-methylbutan-2-yl]-1-(2,4,6-trifluorophenyl)-1,4-dihydro-1,8-naphthyridine-3-carboxamide (diastereomer 2)

LC-MS (Method 3): $R_t$=1.77 min; MS (ESIpos): m/z=545 [M+H]$^+$ $^1$H NMR (500 MHz, DMSO-d$_6$): δ ppm=10.62 (br d, 1H), 8.81 (s, 1H), 8.30 (br d, 1H), 7.56 (br t, 2H), 6.78 (br d, 1H), 5.19-5.26 (m, 1H), 5.12-5.19 (m, 1H), 4.72-4.81 (m, 1H), 4.05 (br s, 1H), 3.93 (br s, 1H), 3.57-3.66 (m, 1H), 3.33-3.38 (m, 1H), 3.22-3.27 (m, 1H), 3.07 (br d, 1H), 2.19-2.29 (m, 1H), 1.03 (br d, 3H), 0.97 (br d, 3H).

Example 555

N-(1,1,1,3,3,3-Hexafluoropropan-2-yl)-7-[(4S)-4-hydroxy-2-oxopyrrolidin-1-yl]-4-oxo-1-(2,4,6-trifluorophenyl)-1,4-dihydro-1,8-naphthyridine-3-carboxamide

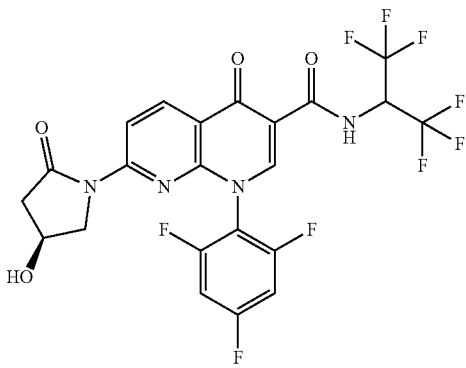 [SMILES: O=C(NC(C(F)(F)F)C(F)(F)F)c1cn(-c2c(F)cc(F)cc2F)c2nc(N3C[C@@H](O)CC3=O)ccc2c1=O]

According to GP2, 60.0 mg (119 μmol) of the compound from Example 154A were reacted with 14.5 mg (143 μmol) of (4S)-4-hydroxypyrrolidin-2-one in the presence of 24.7 mg (179 μmol) of potassium carbonate, 5.35 mg (23.8 μmol) of palladium acetate and 13.8 mg (23.8 μmol) of Xantphos in 1.2 ml of 1,4-dioxane. The crude product was purified by means of preparative HPLC (acetonitrile/water/0.1% formic acid). 42.3 mg (62% of theory, 100% purity) of the title compound were obtained.

LC-MS (Method 3): $R_t$=1.99 min; MS (ESIpos): m/z=569 [M+H]$^+$ $^1$H NMR (400 MHz, DMSO-$d_6$): δ ppm=11.03 (d, 1H), 9.20 (s, 1H), 8.74 (d, 1H), 8.56 (d, 1H), 7.59-7.67 (m, 2H), 6.33-6.43 (m, 1H), 5.34 (d, 1H), 4.27-4.32 (m, 1H), 3.69 (dd, 1H), 3.48 (d, 1H), 2.95 (dd, 1H), 2.38 (d, 1H).

Example 556

1-(2,4-Difluorophenyl)-7-[(4S)-4-hydroxy-2-oxopyrrolidin-1-yl]-4-oxo-N-[1,1,1,2,2-pentafluoropentan-3-yl]-1,4-dihydro-1,8-naphthyridine-3-carboxamide (diastereomer mixture)

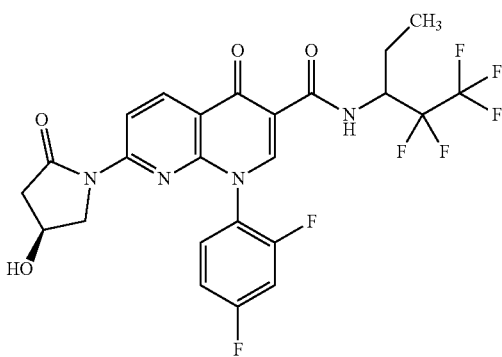 [SMILES: CCC(NC(=O)c1cn(-c2ccc(F)cc2F)c2nc(N3C[C@@H](O)CC3=O)ccc2c1=O)C(F)(F)C(F)(F)F]

According to GP1, 100 mg (249 μmol) of the compound from Example 63A were reacted with 63.9 mg (299 μmol) of the compound from Example 153B in the presence of 114 mg (299 μmol) of HATU and 170 μl (1000 μmol) of DIPEA in 1.0 ml of DMF. The crude product was purified by means of preparative HPLC (acetonitrile/water/0.1% formic acid). 123 mg (88% of theory, 100% purity) of the title compound were obtained.

LC-MS (Method 3): $R_t$=1.96 min; MS (ESIpos): m/z=561 [M+H]$^+$ $^1$H NMR (400 MHz, DMSO-$d_6$): δ ppm=10.27 (d, 1H), 8.86 (d, 1H), 8.71 (d, 1H), 8.52 (br dd, 1H), 7.83-7.94 (m, 1H), 7.63 (br t, 1H), 7.37 (br t, 1H), 5.27-5.37 (m, 1H), 4.82-4.96 (m, 1H), 4.25-4.31 (m, 1H), 3.66 (td, 1H), 3.47 (br t, 1H), 2.88-3.00 (m, 1H), 2.37 (br dd, 1H), 1.88-1.99 (m, 1H), 1.62-1.74 (m, 1H), 0.97 (br t, 3H).

95.0 mg of the title compound (diastereomer mixture) were separated into the diastereomers by chiral HPLC (preparative HPLC: column: Daicel Chiralpak IE 5 μm 250×30 mm; eluent: 70% n-heptane, 20% isopropanol; temperature: 23° C.; flow rate: 20 ml/min; UV detection: 220 nm).

This gave (in the sequence of elution from the column) 35.1 mg (25% of theory, 100% purity) of diastereomer 1 from Example 557 (99% de) Rt=7.05 min and 34.9 mg (25% of theory, 100% purity) of diastereomer 2 from Example 558 (99% de) Rt=9.72 min.

[Analytical HPLC: column: Daicel Chiralpak IE-3 3 μm 50×4.6 mm; eluent: 80% n-heptane, 20% isopropanol; temperature: 30° C.; flow rate: 1.0 ml/min; UV detection: 220 nm]

Example 557

1-(2,4-Difluorophenyl)-7-[(4S)-4-hydroxy-2-oxopyrrolidin-1-yl]-4-oxo-N-[1,1,1,2,2-pentafluoropentan-3-yl]-1,4-dihydro-1,8-naphthyridine-3-carboxamide (diastereomer 1)

LC-MS (Method 3): $R_t$=1.97 min; MS (ESIpos): m/z=561 [M+H]$^+$ $^1$H NMR (400 MHz, DMSO-$d_6$): δ ppm=10.27 (d, 1H), 8.86 (d, 1H), 8.71 (d, 1H), 8.52 (dd, 1H), 7.83-7.94 (m, 1H), 7.59-7.66 (m, 1H), 7.33-7.40 (m, 1H), 5.28-5.37 (m, 1H), 4.83-4.96 (m, 1H), 4.26-4.31 (m, 1H), 3.66 (td, 1H), 3.47 (br t, 1H), 2.89-2.99 (m, 1H), 2.32-2.41 (m, 1H), 1.88-1.98 (m, 1H), 1.62-1.74 (m, 1H), 0.97 (t, 3H).

Example 558

1-(2,4-Difluorophenyl)-7-[(4S)-4-hydroxy-2-oxopyrrolidin-1-yl]-4-oxo-N-[1,1,1,2,2-pentafluoropentan-3-yl]-1,4-dihydro-1,8-naphthyridine-3-carboxamide (diastereomer 2)

LC-MS (Method 3): $R_t$=1.97 min; MS (ESIpos): m/z=561 [M+H]$^+$ $^1$H NMR (400 MHz, DMSO-$d_6$): δ ppm=10.27 (d, 1H), 8.86 (d, 1H), 8.71 (d, 1H), 8.52 (dd, 1H), 7.84-7.92 (m, 1H), 7.63 (br t, 1H), 7.37 (br t, 1H), 5.18-5.43 (m, 1H), 4.82-4.96 (m, 1H), 4.28 (br t, 1H), 3.59-3.72 (m, 1H), 3.42-3.52 (m, 1H), 2.94 (ddd, 1H), 2.32-2.42 (m, 1H), 1.88-1.99 (m, 1H), 1.62-1.74 (m, 1H), 0.97 (t, 3H).

Example 559

7-[(3R,4R)-3,4-Dihydroxypyrrolidin-1-yl]-4-oxo-N-[(2S)-1,1,1-trifluoro-4-methylpentan-2-yl]-1-(2,4,6-trifluorophenyl)-1,4-dihydro-1,8-naphthyridine-3-carboxamide

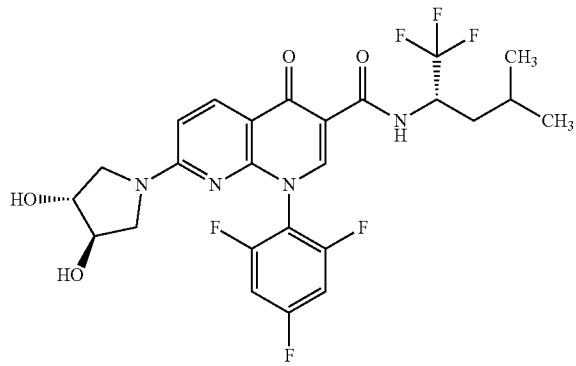 [SMILES: CC(C)C[C@H](NC(=O)c1cn(-c2c(F)cc(F)cc2F)c2nc(N3C[C@@H](O)[C@H](O)C3)ccc2c1=O)C(F)(F)F]

According to GP1, 50.0 mg (119 µmol) of the compound from Example 121A were reacted with 22.1 mg (142 µmol) of (2R)-1,1,1-trifluoro-4-methylpentan-2-amine in the presence of 54.1 mg (142 µmol) of HATU and 62 µl (360 µmol) of DIPEA in 750 µl of DMF. The crude product was purified by means of preparative HPLC (acetonitrile/water/0.1% formic acid). 47.5 mg (72% of theory, 100% purity) of the title compound were obtained.

LC-MS (Method 3): $R_t$=1.93 min; MS (ESIpos): m/z=559 [M+H]$^+$ $^1$H NMR (400 MHz, DMSO-$d_6$): δ ppm=10.42 (d, 1H), 8.81 (s, 1H), 8.27 (d, 1H), 7.52-7.60 (m, 2H), 6.78 (d, 1H), 5.24 (d, 1H), 5.14 (d, 1H), 4.77-4.88 (m, 1H), 4.05 (br s, 1H), 3.93 (br s, 1H), 3.61 (br dd, 1H), 3.34 (br d, 1H), 3.25 (br dd, 1H), 3.07 (br d, 1H), 1.52-1.72 (m, 3H), 0.95 (d, 3H), 0.89 (d, 3H).

Example 560

N-[1-(2-Chlorophenyl)-2,2,2-trifluoroethyl]-7-[(3R,4R)-3,4-dihydroxypyrrolidin-1-yl]-4-oxo-1-(2,4,6-trifluorophenyl)-1,4-dihydro-1,8-naphthyridine-3-carboxamide (diastereomer mixture)

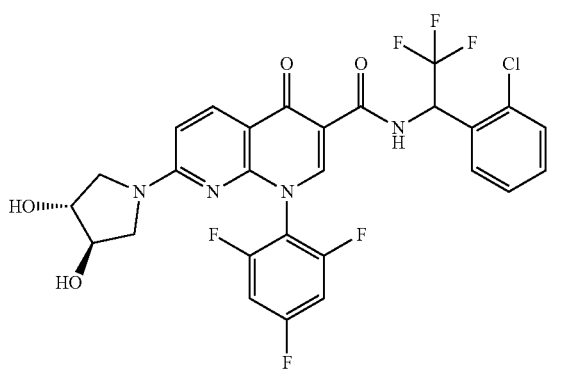 [SMILES: O=C(NC(c1ccccc1Cl)C(F)(F)F)c1cn(-c2c(F)cc(F)cc2F)c2nc(N3C[C@@H](O)[C@H](O)C3)ccc2c1=O]

According to GP1, 50.0 mg (119 µmol) of the compound from Example 121A were reacted with 29.8 mg (142 µmol) of 1-(2-chlorophenyl)-2,2,2-trifluoroethanamine in the presence of 54.1 mg (142 µmol) of HATU and 62 µl (360 µmol) of DIPEA in 460 µl of DMF. The crude product was purified by means of preparative HPLC (acetonitrile/water/0.1% formic acid). 44.9 mg (61% of theory, 100% purity) of the title compound were obtained.

LC-MS (Method 3): $R_t$=1.97 min; MS (ESIpos): m/z=613 [M+H]$^+$ $^1$H NMR (400 MHz, DMSO-$d_6$): δ ppm=11.56 (d, 1H), 8.83 (s, 1H), 8.32 (d, 1H), 7.48-7.64 (m, 6H), 6.80 (d, 1H), 6.40-6.49 (m, 1H), 5.08-5.30 (m, 2H), 4.03-4.07 (m, 1H), 3.90-3.95 (m, 1H), 3.58-3.65 (m, 1H), 3.03-3.10 (m, 1H), 0.97-1.04 (m, 2H).

37.6 mg of the title compound (diastereomer mixture) were separated into the diastereomers by chiral HPLC (preparative HPLC: column: Daicel Chiralcel OX-H 5 µm 250×20 mm; eluent: 45% n-heptane, 55% isopropanol; temperature: 40° C.; flow rate: 15 ml/min; UV detection: 220 nm).

This gave (in the sequence of elution from the column) 14.0 mg (19% of theory, 100% purity) of diastereomer 1 from Example 561 (99% de) Rt=4.83 min and 15.0 mg (20% of theory, 100% purity) of diastereomer 2 from Example 562 (99% de) Rt=6.63 min.

[Analytical HPLC: column: Daicel Chiralcel OX-H 5 µm 250×4.6 mm; eluent: 50% isohexane, 50% isopropanol; temperature: 45° C.; flow rate: 1.0 ml/min; UV detection: 220 nm]

Example 561

N-[1-(2-Chlorophenyl)-2,2,2-trifluoroethyl]-7-[(3R,4R)-3,4-dihydroxypyrrolidin-1-yl]-4-oxo-1-(2,4,6-trifluorophenyl)-1,4-dihydro-1,8-naphthyridine-3-carboxamide (diastereomer 1)

LC-MS (Method 3): $R_t$=1.95 min; MS (ESIpos): m/z=613 [M+H]$^+$ $^1$H NMR (400 MHz, DMSO-$d_6$): δ ppm=11.56 (d, 1H), 8.83 (s, 1H), 8.32 (d, 1H), 7.48-7.64 (m, 6H), 6.80 (d, 1H), 6.40-6.49 (m, 1H), 5.23 (d, 1H), 5.15 (d, 1H), 4.05 (br s, 1H), 3.90-3.95 (m, 1H), 3.62 (dd, 1H), 3.33-3.38 (m, 1H), 3.24 (br dd, 1H), 3.07 (br d, 1H).

Example 562

N-[1-(2-Chlorophenyl)-2,2,2-trifluoroethyl]-7-[(3R,4R)-3,4-dihydroxypyrrolidin-1-yl]-4-oxo-1-(2,4,6-trifluorophenyl)-1,4-dihydro-1,8-naphthyridine-3-carboxamide (diastereomer 2)

LC-MS (Method 3): $R_t$=1.96 min; MS (ESIpos): m/z=613 [M+H]$^+$ $^1$H NMR (400 MHz, DMSO-$d_6$): δ ppm=11.56 (d, 1H), 8.83 (s, 1H), 8.32 (d, 1H), 7.48-7.64 (m, 6H), 6.80 (d, 1H), 6.40-6.49 (m, 1H), 5.24 (d, 1H), 5.14 (d, 1H), 4.05 (br s, 1H), 3.93 (br s, 1H), 3.62 (br dd, 1H), 3.33-3.38 (m, 1H), 3.25 (dd, 1H), 3.06 (d, 1H).

Example 563

N-[1-(2-Chlorophenyl)-2,2,2-trifluoroethyl]-4-oxo-7-(2-oxoimidazolidin-1-yl)-1-(2,4,6-trifluorophenyl)-1,4-dihydro-1,8-naphthyridine-3-carboxamide (racemate)

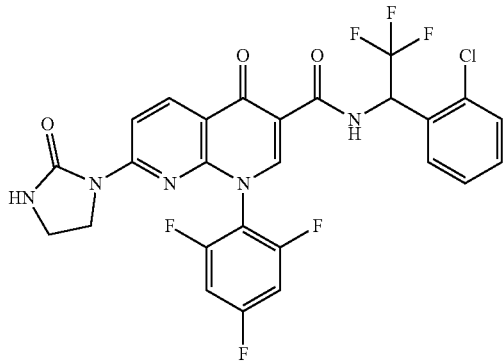 [SMILES: O=C(NC(c1ccccc1Cl)C(F)(F)F)c1cn(-c2c(F)cc(F)cc2F)c2nc(N3CCNC3=O)ccc2c1=O]

According to GP1, 50.0 mg (124 µmol) of 4-oxo-7-(2-oxoimidazolidin-1-yl)-1-(2,4,6-trifluorophenyl)-1,4-dihydro-1,8-naphthyridine-3-carboxylic acid (Example 113A) were reacted with 31.1 mg (148 µmol) of 1-(2-chlorophenyl)-2,2,2-trifluoroethanamine in the presence of 56.4 mg (148 µmol) of HATU and 65 µl (370 µmol) of DIPEA in 480 µl of DMF. The crude product was purified by means of preparative HPLC (acetonitrile/water/0.1% formic acid). 50.6 mg (69% of theory, 100% purity) of the title compound were obtained.

LC-MS (Method 1): $R_t$=1.16 min; MS (ESIpos): m/z=596 [M+H]$^+$ $^1$H NMR (400 MHz, DMSO-d$_6$): δ ppm=11.32 (d, 1H), 9.01 (s, 1H), 8.60 (d, 1H), 8.46 (d, 1H), 7.48-7.69 (m, 7H), 6.41-6.50 (m, 1H), 3.55-3.64 (m, 2H), 3.34-3.38 (m, 2H).

40.4 mg of the title compound (racemate) were separated into the enantiomers by chiral HPLC (preparative HPLC: column: Daicel Chiralpak AZ-H 5 µm 250×20 mm; eluent: 25% n-heptane, 75% isopropanol; temperature: 25° C.; flow rate: 15 ml/min; UV detection: 210 nm).

This gave (in the sequence of elution from the column) 19.3 mg of enantiomer 1 (99% ee) Rt=8.40 min and 16.8 mg of enantiomer 2 (99% ee) Rt=17.95 min.

[Analytical HPLC: column: Chiraltek AZ-3 3 µm; eluent: 50% isohexane, 50% isopropanol; UV detection: 220 nm].

Enantiomer 1 was additionally purified by means of preparative HPLC (column: Chromatorex C18, 10 µm, 125*40 mm, solvent: acetonitrile, water, 0.1% formic acid), and 11.5 mg (16% of theory, 97% purity) of the title compound from Example 564 were obtained.

Enantiomer 2 was additionally purified by means of preparative HPLC (column: Chromatorex C18, 10 µm, 125*40 mm, solvent: acetonitrile, water, 0.1% formic acid), and 9.30 mg (13% of theory, 100% purity) of the title compound from Example 565 were obtained.

Example 564

N-[1-(2-Chlorophenyl)-2,2,2-trifluoroethyl]-4-oxo-7-(2-oxoimidazolidin-1-yl)-1-(2,4,6-trifluorophenyl)-1,4-dihydro-1,8-naphthyridine-3-carboxamide (enantiomer 2)

LC-MS (Method 4): $R_t$=3.81 min; MS (ESIpos): m/z=596 [M+H]$^+$ $^1$H NMR (500 MHz, DMSO-d$_6$): δ ppm=11.32 (d, 1H), 9.01 (s, 1H), 8.60 (d, 1H), 8.46 (d, 1H), 7.49-7.68 (m, 7H), 6.42-6.49 (m, 1H), 3.56-3.62 (m, 2H), 3.33-3.37 (m, 2H).

Example 565

N-[1-(2-Chlorophenyl)-2,2,2-trifluoroethyl]-4-oxo-7-(2-oxoimidazolidin-1-yl)-1-(2,4,6-trifluorophenyl)-1,4-dihydro-1,8-naphthyridine-3-carboxamide (enantiomer 2)

LC-MS (Method 3): $R_t$=2.17 min; MS (ESIpos): m/z=596 [M+H]$^+$ $^1$H NMR (500 MHz, DMSO-d$_6$): δ ppm=11.32 (d, 1H), 9.01 (s, 1H), 8.60 (d, 1H), 8.46 (d, 1H), 7.49-7.68 (m, 7H), 6.42-6.49 (m, 1H), 3.56-3.63 (m, 2H), 3.32-3.37 (m, 2H).

Example 566

1-(2-Chloro-4,6-difluorophenyl)-7-[(3R,4R)-3,4-dihydroxypyrrolidin-1-yl]-4-oxo-N-[(2S)-1,1,1-trifluorobutan-2-yl]-1,4-dihydro-1,8-naphthyridine-3-carboxamide (atropisomer mixture)

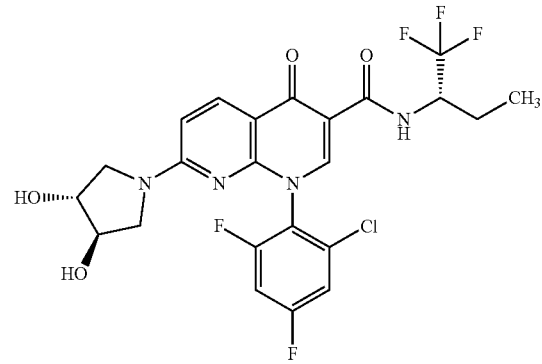

According to GP3, 50.0 mg (104 µmol) of the compound from Example 108C were reacted with 17.4 mg (125 µmol) of (3R,4R)-pyrrolidine-3,4-diol hydrochloride and 63 µl (360 µmol) of DIPEA in 500 µl of DMF. The crude product was purified by means of preparative HPLC (acetonitrile/water/0.1% formic acid). 50.0 mg (88% of theory, 100% purity) of the title compound were obtained.

LC-MS (Method 3): $R_t$=1.72 min; MS (ESIpos): m/z=547 [M+H]$^+$ $^1$H NMR (400 MHz, DMSO-d$_6$): δ ppm=10.46 (dd, 1H), 8.75 (s, 1H), 8.28 (d, 1H), 7.67-7.76 (m, 2H), 6.77 (d, 1H), 5.23 (br d, 1H), 5.14 (d, 1H), 4.68-4.79 (m, 1H), 4.04 (br s, 1H), 3.92 (br s, 1H), 3.61 (br dd, 1H), 3.32-3.37 (m, 1H), 3.17-3.25 (m, 1H), 3.02 (br dd, 1H), 1.83-1.93 (m, 1H), 1.59-1.71 (m, 1H), 0.94-1.00 (m, 3H).

30.0 mg of the title compound (atropisomer mixture) were separated into the atropisomers by chiral HPLC (preparative HPLC: column: Daicel Chiralcel OX-H 5 µm 250×20 mm; eluent: 75% n-heptane, 25% isopropanol; temperature: 40° C.; flow rate: 15 ml/min; UV detection: 220 nm).

This gave (in the sequence of elution from the column) 13.0 mg (23% of theory, 100% purity) of atropisomer 1 from Example 567 (99% de) Rt=6.73 min and 10.0 mg (18% of theory, 100% purity) of atropisomer 2 from Example 568 (99% de) Rt=11.48 min.

Example 567

1-(2-Chloro-4,6-difluorophenyl)-7-[(3R,4R)-3,4-dihydroxypyrrolidin-1-yl]-4-oxo-N-[(2S)-1,1,1-trifluorobutan-2-yl]-1,4-dihydro-1,8-naphthyridine-3-carboxamide (atropisomer 1)

LC-MS (Method 3): $R_t$=1.73 min; MS (ESIpos): m/z=547 [M+H]$^+$ $^1$H NMR (400 MHz, DMSO-d$_6$): δ ppm=10.46 (d, 1H), 8.75 (s, 1H), 8.28 (d, 1H), 7.67-7.76 (m, 2H), 6.77 (d, 1H), 5.23 (d, 1H), 5.14 (d, 1H), 4.68-4.80 (m, 1H), 4.04 (br s, 1H), 3.92 (br s, 1H), 3.61 (dd, 1H), 3.32-3.37 (m, 1H), 3.22 (br dd, 1H), 3.01 (d, 1H), 1.82-1.94 (m, 1H), 1.58-1.70 (m, 1H), 0.97 (t, 3H).

Example 568

1-(2-Chloro-4,6-difluorophenyl)-7-[(3R,4R)-3,4-dihydroxypyrrolidin-1-yl]-4-oxo-N-[(2S)-1,1,1-trifluorobutan-2-yl]-1,4-dihydro-1,8-naphthyridine-3-carboxamide (atropisomer 2)

LC-MS (Method 3): $R_t$=1.73 min; MS (ESIpos): m/z=547 [M+H]$^+$ $^1$H NMR (400 MHz, DMSO-d$_6$): δ ppm=10.45 (d, 1H), 8.75 (s, 1H), 8.28 (d, 1H), 7.68-7.75 (m, 2H), 6.77 (d, 1H), 5.23 (d, 1H), 5.14 (d, 1H), 4.68-4.79 (m, 1H), 4.04 (br s, 1H), 3.87-3.94 (m, 1H), 3.57-3.65 (m, 1H), 3.32-3.38 (m, 1H), 3.20 (br dd, 1H), 3.04 (br d, 1H), 1.83-1.93 (m, 1H), 1.59-1.71 (m, 1H), 0.98 (t, 3H).

Example 569

7-[7-Hydroxy-5-azaspiro[2.4]hept-5-yl]-4-oxo-N-(4,4,4-trifluoro-2-methylbutan-2-yl)-1-(2,4,6-trifluorophenyl)-1,4-dihydro-1,8-naphthyridine-3-carboxamide (racemate)

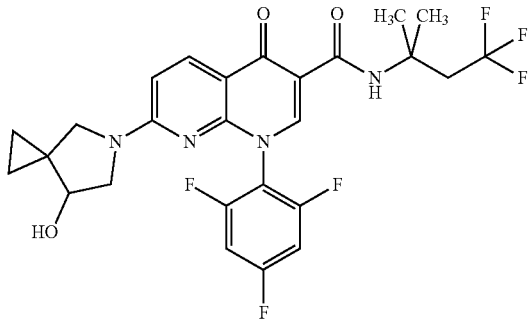 [SMILES: CC(C)(CC(F)(F)F)NC(=O)c1cn(-c2c(F)cc(F)cc2F)c2nc(N3CC(O)C4(CC4)C3)ccc2c1=O]

According to GP1, 80.0 mg (185 μmol) of the compound from Example 155A were reacted with 39.5 mg (223 μmol) of 4,4,4-trifluoro-2-methylbutan-2-amine hydrochloride in the presence of 84.6 mg (223 μmol) of HATU and 97 μl (560 μmol) of DIPEA in 890 μl of DMF. The crude product was purified by means of preparative HPLC (acetonitrile/water/ 0.1% formic acid). 80.9 mg (79% of theory, 100% purity) of the title compound were obtained.

LC-MS (Method 4): $R_t$=3.60 min; MS (ESIpos): m/z=555 [M+H]$^+$ $^1$H NMR (400 MHz, DMSO-d$_6$): δ ppm=10.16 (s, 1H), 8.66-8.71 (m, 1H), 8.27 (d, 1H), 7.49-7.60 (m, 2H), 6.78 (br d, 0.40H), 6.66 (br d, 0.60H), 5.06 (br s, 0.40H), 4.97 (br d, 0.60H), 3.59-3.78 (m, 2H), 3.36-3.49 (m, 1H), 3.10-3.26 (m, 2H), 2.95 (q, 2H), 1.48 (s, 6H), 0.82 (br t, 1H), 0.54-0.62 (m, 2H), 0.48 (br s, 1H).

76.6 mg of the title compound (racemate) were separated into the enantiomers by chiral HPLC (preparative HPLC: column: YMC Chiralart Amylose SA 5 μm 250×30 mm; eluent: 80% n-heptane, 20% ethanol; temperature: 25° C.; flow rate: 30 ml/min; UV detection: 220 nm).

This gave (in the sequence of elution from the column) 30.0 mg (29% of theory, 100% purity) of enantiomer 1 from Example 570 (99% ee) Rt=9.31 min and 32.0 mg (31% of theory, 100% purity) of enantiomer 2 from Example 571 (99% ee) Rt=11.08 min.

[Analytical HPLC: column: YMC Chiralart Amylose SA 5 μm 250×4.6 mm; eluent: 80% isohexane, 20% ethanol; temperature: 25° C.; flow rate: 1.0 ml/min; UV detection: 220 nm]

Example 570

7-[7-Hydroxy-5-azaspiro[2.4]hept-5-yl]-4-oxo-N-(4,4,4-trifluoro-2-methylbutan-2-yl)-1-(2,4,6-trifluorophenyl)-1,4-dihydro-1,8-naphthyridine-3-carboxamide (enantiomer 1)

LC-MS (Method 1): $R_t$=1.12 min; MS (ESIpos): m/z=555 [M+H]$^+$ $^1$H NMR (500 MHz, DMSO-d$_6$): δ ppm=10.16 (s, 1H), 8.66-8.70 (m, 1H), 8.27 (d, 1H), 7.49-7.59 (m, 2H), 6.78 (br d, 0.40H), 6.66 (br d, 0.60H), 5.02-5.08 (m, 0.40H), 4.97 (br d, 0.60H), 3.60-3.78 (m, 2H), 3.31-3.47 (m, 2H), 3.20 (br dd, 1H), 2.95 (q, 2H), 1.48 (s, 6H), 0.77-0.87 (m, 1H), 0.53-0.62 (m, 2H), 0.48 (br s, 1H).

Example 571

7-[7-Hydroxy-5-azaspiro[2.4]hept-5-yl]-4-oxo-N-(4,4,4-trifluoro-2-methylbutan-2-yl)-1-(2,4,6-trifluorophenyl)-1,4-dihydro-1,8-naphthyridine-3-carboxamide (enantiomer 2)

LC-MS (Method 1): $R_t$=1.12 min; MS (ESIpos): m/z=555 [M+H]$^+$ $^1$H NMR (500 MHz, DMSO-d$_6$): δ ppm=10.16 (s, 1H), 8.66-8.70 (m, 1H), 8.27 (d, 1H), 7.49-7.59 (m, 2H), 6.78 (br d, 0.40H), 6.66 (br d, 0.60H), 5.07 (br s, 0.40H), 4.97 (br s, 0.60H), 3.60-3.77 (m, 2H), 3.33-3.47 (m, 2H), 3.20 (br dd, 1H), 2.95 (q, 2H), 1.48 (s, 6H), 0.77-0.86 (m, 1H), 0.54-0.62 (m, 2H), 0.45-0.54 (m, 1H).

Example 572

7-[(3R,4R)-3,4-Dihydroxypyrrolidin-1-yl]-N-(1,1,1,3,3,3-hexafluoropropan-2-yl)-4-oxo-1-(2,4,6-trifluorophenyl)-1,4-dihydro-1,8-naphthyridine-3-carboxamide

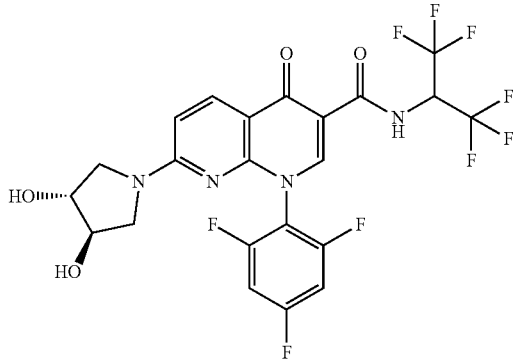 [SMILES: O=C(NC(C(F)(F)F)C(F)(F)F)c1cn(-c2c(F)cc(F)cc2F)c2nc(N3C[C@@H](O)[C@H](O)C3)ccc2c1=O]

According to GP3, 60.0 mg (119 μmol) of the compound from Example 154A were reacted with 20.0 mg (143 μmol) of (3R,4R)-pyrrolidine-3,4-diol hydrochloride and 73 μl (420 μmol) of DIPEA in 600 μl of DMF. The crude product was purified by means of preparative HPLC (acetonitrile/water/0.1% formic acid). 58.9 mg (87% of theory, 100% purity) of the title compound were obtained.

LC-MS (Method 3): $R_t$=1.83 min; MS (ESIpos): m/z=571 [M+H]$^+$ $^1$H NMR (400 MHz, DMSO-d$_6$): δ ppm=11.41 (d, 1H), 8.94 (s, 1H), 8.30 (d, 1H), 7.53-7.62 (m, 2H), 6.81 (d, 1H), 6.24-6.37 (m, 1H), 5.24 (d, 1H), 5.15 (d, 1H), 4.05 (br s, 1H), 3.93 (br s, 1H), 3.62 (br dd, 1H), 3.33-3.39 (m, 1H), 3.20-3.28 (m, 1H), 3.07 (br d, 1H).

Example 573

7-[(3R,4S)-3,4-Dihydroxypyrrolidin-1-yl]-4-oxo-N-[(2S)-1,1,1-trifluoro-4-methylpentan-2-yl]-1-(2,4,6-trifluorophenyl)-1,4-dihydro-1,8-naphthyridine-3-carboxamide

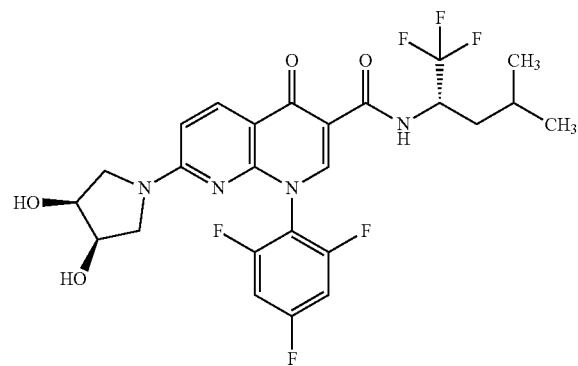 [SMILES: CC(C)C[C@H](NC(=O)c1cn(-c2c(F)cc(F)cc2F)c2nc(N3C[C@@H](O)[C@@H](O)C3)ccc2c1=O)C(F)(F)F]

According to GP1, 60.0 mg (142 μmol) of the compound from Example 156A were reacted with 26.5 mg (171 μmol) of (2S)-1,1,1-trifluoro-4-methylpentan-2-amine in the presence of 65.0 mg (171 μmol) of HATU and 74 μl (430 μmol) of DIPEA in 1.2 ml of DMF. The crude product was purified by means of preparative HPLC (acetonitrile/water/0.1% formic acid). 46.5 mg (58% of theory, 100% purity) of the title compound were obtained.

LC-MS (Method 3): $R_t$=1.97 min; MS (ESIpos): m/z=559 [M+H]$^+$ $^1$H NMR (400 MHz, DMSO-d$_6$): δ ppm=10.41 (br d, 1H), 8.81 (s, 1H), 8.27 (d, 1H), 7.52-7.61 (m, 2H), 6.76 (d, 1H), 4.99-5.07 (m, 1H), 4.94 (br d, 1H), 4.76-4.88 (m, 1H), 4.09-4.17 (m, 1H), 3.99-4.07 (m, 1H), 3.56-3.64 (m, 1H), 3.18-3.28 (m, 2H), 2.96-3.05 (m, 1H), 1.62-1.72 (m, 2H), 1.52-1.62 (m, 1H), 0.95 (br d, 3H), 0.89 (br d, 3H).

Example 574

7-[(3R,4S)-3,4-Dihydroxypyrrolidin-1-yl]-4-oxo-N-[(2R)-1,1,1-trifluoro-4-methylpentan-2-yl]-1-(2,4,6-trifluorophenyl)-1,4-dihydro-1,8-naphthyridine-3-carboxamide

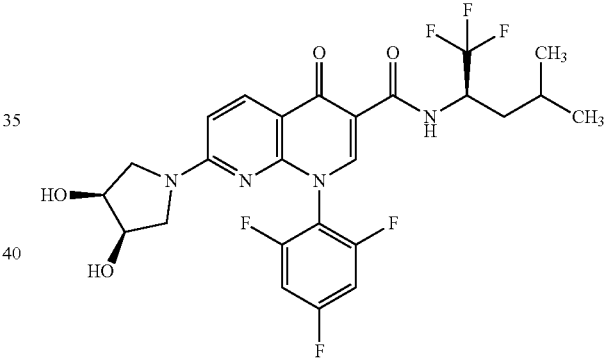

According to GP1, 60.0 mg (142 μmol) of the compound from Example 156A were reacted with 26.5 mg (171 μmol) of (2R)-1,1,1-trifluoro-4-methylpentan-2-amine in the presence of 65.0 mg (171 μmol) of HATU and 74 μl (430 μmol) of DIPEA in 1.2 ml of DMF. The crude product was purified by means of preparative HPLC (acetonitrile/water/0.1% formic acid). 18.2 mg (23% of theory, 100% purity) of the title compound were obtained.

LC-MS (Method 3): $R_t$=1.97 min; MS (ESIpos): m/z=559 [M+H]$^+$ $^1$H NMR (400 MHz, DMSO-d$_6$): δ ppm=10.33-10.50 (m, 1H), 8.81 (br s, 1H), 8.19-8.34 (m, 1H), 7.46-7.66 (m, 2H), 6.68-6.84 (m, 1H), 4.78-5.07 (m, 3H), 3.94-4.21 (m, 2H), 3.53-3.66 (m, 1H), 2.95-3.08 (m, 1H), 1.49-1.76 (m, 3H), 0.82-1.02 (m, 6H).

Example 575

Methyl 4-{5-oxo-6-[(4,4,4-trifluoro-2-methylbutan-2-yl)carbamoyl]-8-(2,4,6-trifluorophenyl)-5,8-dihydro-1,8-naphthyridin-2-yl}piperazine-1-carboxylate

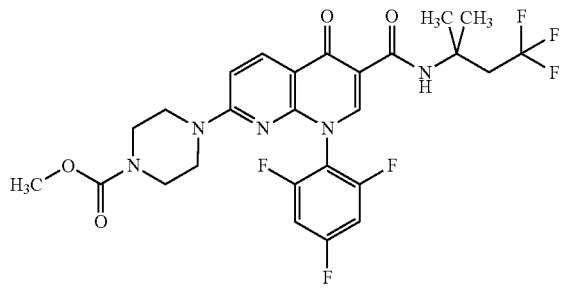 [SMILES: COC(=O)N1CCN(c2ccc3c(=O)c(C(=O)NC(C)(C)CC(F)(F)F)cn(-c4c(F)cc(F)cc4F)c3n2)CC1]

According to GP1, 70.0 mg (151 μmol) of the compound from Example 157A were reacted with 32.3 mg (182 μmol) of 4,4,4-trifluoro-2-methylbutan-2-amine hydrochloride in the presence of 69.1 mg (182 μmol) of HATU and 110 μl (610 μmol) of DIPEA in 580 μl of DMF. The crude product was purified by means of preparative HPLC (acetonitrile/water/0.1% formic acid). 61.1 mg (69% of theory, 100% purity) of the title compound were obtained.

LC-MS (Method 3): $R_t$=2.14 min; MS (ESIpos): m/z=586 [M+H]$^+$ $^1$H NMR (400 MHz, DMSO-d$_6$): δ ppm=10.10 (s, 1H), 8.72 (s, 1H), 8.31 (d, 1H), 7.56 (t, 2H), 7.11 (d, 1H), 3.60 (s, 3H), 3.48-3.55 (m, 4H), 3.36-3.43 (m, 4H), 2.95 (q, 2H), 1.48 (s, 6H).

Example 576

7-[(3R,4R)-3,4-Dihydroxypyrrolidin-1-yl]-4-oxo-N-[1-(trifluoromethoxy)butan-2-yl]-1-(2,4,6-trifluorophenyl)-1,4-dihydro-1,8-naphthyridine-3-carboxamide (diastereomer mixture)

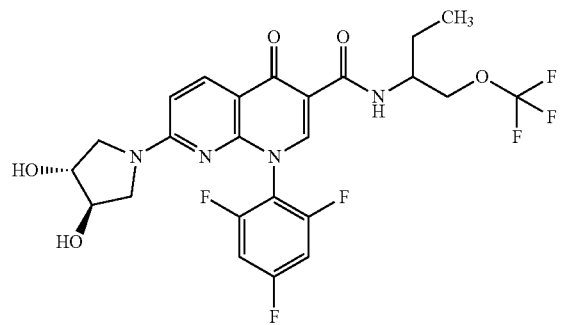 [SMILES: CCC(COC(F)(F)F)NC(=O)c1cn(-c2c(F)cc(F)cc2F)c2nc(N3C[C@@H](O)[C@H](O)C3)ccc2c1=O]

According to GP1, 500 mg (1.19 mmol) of the compound from Example 121A were reacted with 276 mg (1.42 mmol) of 1-(trifluoromethoxy)butan-2-amine hydrochloride in the presence of 541 mg (1.42 mmol) of HATU and 830 μl (4.70 mmol) of DIPEA in 5.0 ml of DMF. The crude product was purified by means of preparative HPLC (acetonitrile/water/0.1% formic acid). 389 mg (58% of theory, 100% purity) of the title compound were obtained.

LC-MS (Method 1): $R_t$=0.94 min; MS (ESIpos): m/z=561 [M+H]$^+$ $^1$H NMR (400 MHz, DMSO-d$_6$): δ ppm=10.08 (br d, 1H), 8.72 (s, 1H), 8.27 (d, 1H), 7.52-7.60 (m, 2H), 6.76 (d, 1H), 5.23 (d, 1H), 5.13 (d, 1H), 4.13-4.23 (m, 3H), 4.05 (br s, 1H), 3.92 (br s, 1H), 3.61 (br dd, 1H), 3.32-3.36 (m, 1H), 3.25 (br dd, 1H), 3.07 (br d, 1H), 1.53-1.73 (m, 2H), 0.94 (t, 3H).

385 mg of the title compound (diastereomer mixture) were separated into the diastereomers by chiral HPLC (preparative HPLC: column: Daicel Chiralcel OZ-H 5 μm 250×20 mm; eluent: 80% n-heptane, 20% isopropanol; temperature: 23° C.; flow rate: 20 ml/min; UV detection: 220 nm).

This gave (in the sequence of elution from the column) 119.4 mg of diastereomer 1 (99% de) Rt=5.13 min and 96.4 mg of diastereomer 2 (95% de) Rt=6.74 min.

[Analytical HPLC: column: Daicel OZ-3 3 μm 50×4.6 mm; eluent: 80% isohexane, 20% isopropanol; UV detection: 220 nm].

Diastereomer 1 was additionally purified by means of preparative HPLC (column: Chromatorex C18, 10 μm, 125*40 mm, solvent: acetonitrile, water, 0.1% formic acid). The isolated substance contained impurities and was further recrystallized from acetonitrile, filtered off with suction, washed with a little acetonitrile and dried. 89.3 mg (13% of theory, 100% purity) of the title compound from Example 577 were obtained.

Diastereomer 2 was additionally purified by means of preparative HPLC (column: Chromatorex C18, 10 μm, 125*40 mm, solvent: acetonitrile, water, 0.1% formic acid). The isolated substance contained impurities and was further recrystallized from acetonitrile, filtered off with suction, washed with a little acetonitrile and dried. 75.5 mg (11% of theory, 100% purity) of the title compound from Example 578 were obtained.

Example 577

7-[(3R,4R)-3,4-Dihydroxypyrrolidin-1-yl]-4-oxo-N-[1-(trifluoromethoxy)butan-2-yl]-1-(2,4,6-trifluorophenyl)-1,4-dihydro-1,8-naphthyridine-3-carboxamide (diastereomer 1)

LC-MS (Method 1): $R_t$=0.92 min; MS (ESIpos): m/z=561 [M+H]$^+$ $^1$H NMR (400 MHz, DMSO-d$_6$): δ ppm=10.04-10.11 (m, 1H), 8.72 (s, 1H), 8.27 (d, 1H), 7.52-7.60 (m, 2H), 6.76 (d, 1H), 5.23 (d, 1H), 5.13 (d, 1H), 4.13-4.23 (m, 3H), 4.05 (br s, 1H), 3.92 (br s, 1H), 3.61 (br dd, 1H), 3.32-3.37 (m, 1H), 3.25 (br dd, 1H), 3.07 (br d, 1H), 1.54-1.73 (m, 2H), 0.94 (t, 3H).

Example 578

7-[(3R,4R)-3,4-Dihydroxypyrrolidin-1-yl]-4-oxo-N-[1-(trifluoromethoxy)butan-2-yl]-1-(2,4,6-trifluorophenyl)-1,4-dihydro-1,8-naphthyridine-3-carboxamide (diastereomer 2)

LC-MS (Method 1): $R_t$=0.92 min; MS (ESIpos): m/z=561 [M+H]$^+$ $^1$H NMR (400 MHz, DMSO-d$_6$): δ ppm=10.08 (br d, 1H), 8.72 (s, 1H), 8.27 (d, 1H), 7.52-7.60 (m, 2H), 6.76 (d, 1H), 5.22 (d, 1H), 5.13 (d, 1H), 4.13-4.23 (m, 3H), 4.05 (br s, 1H), 3.89-3.96 (m, 1H), 3.61 (br dd, 1H), 3.32-3.37 (m, 1H), 3.25 (br dd, 1H), 3.07 (br d, 1H), 1.53-1.73 (m, 2H), 0.94 (t, 3H).

Example 579

N-[(1S)-1-Cyclopropyl-2,2,2-trifluoroethyl]-7-[4-hydroxy-3-methyl-2-oxopyrrolidin-1-yl]-4-oxo-1-(2,4,6-trifluorophenyl)-1,4-dihydro-1,8-naphthyridine-3-carboxamide (diastereomer mixture)

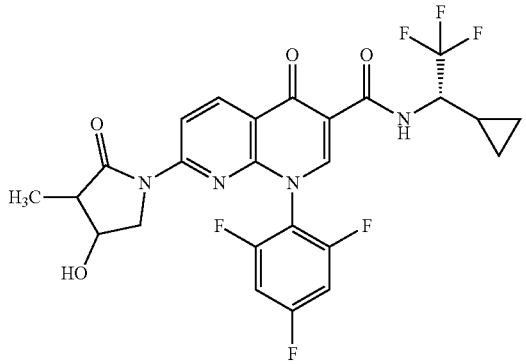 [SMILES: CC1C(=O)N(c2ccc3c(=O)c(C(=O)N[C@@H](C4CC4)C(F)(F)F)cn(-c4c(F)cc(F)cc4F)c3n2)CC1O]

According to GP2, 130 mg (273 µmol) of the compound from Example 126A were reacted with 37.8 mg (328 µmol) of the compound 158D in the presence of 56.6 mg (410 µmol) of potassium carbonate, 12.3 mg (54.6 µmol) of palladium acetate and 31.6 mg (54.6 µmol) of Xantphos in 2.4 ml of 1,4-dioxane. The crude product was purified by means of preparative HPLC (acetonitrile/water/0.1% formic acid). The isolated substance contained impurities and was further recrystallized from acetonitrile, filtered off with suction, washed with a little acetonitrile and dried. 79.6 mg (51% of theory, 97% purity) of the title compound were obtained.

LC-MS (Method 1): $R_t$=1.06 min; MS (ESIpos): m/z=555 [M+H]$^+$ $^1$H NMR (400 MHz, DMSO-d$_6$): δ ppm=10.22-10.30 (m, 1H), 9.06 (s, 1H), 8.71 (d, 1H), 8.51-8.58 (m, 1H), 7.57-7.66 (m, 2H), 5.50 (d, 0.20H), 5.24 (d, 0.80H), 4.40 (sxt, 1H), 4.19 (q, 0.80H), 3.90-3.96 (m, 0.20H), 3.77 (dd, 0.20H), 3.56-3.64 (m, 0.80H), 3.47-3.53 (m, 0.80H), 3.25 (dd, 0.20H), 2.80-2.88 (m, 0.80H), 1.18-1.28 (m, 1H), 1.14 (d, 0.60H), 1.08 (d, 2.40H), 0.52-0.70 (m, 3H), 0.30-0.39 (m, 1H).

Example 580

4-Oxo-7-(2-oxoimidazolidin-1-yl)-N-[(2R)-trifluoro-1,1,1-trifluoro-4-methylpentan-2-yl]-1-(2,4,6-trifluorophenyl)-1,4-dihydro-1,8-naphthyridine-3-carboxamide

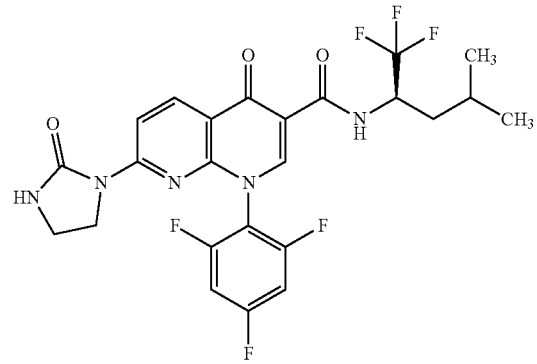 [SMILES: CC(C)C[C@@H](NC(=O)c1cn(-c2c(F)cc(F)cc2F)c2nc(N3CCNC3=O)ccc2c1=O)C(F)(F)F]

According to GP1, 50.0 mg (124 µmol) of the compound from Example 113A were reacted with 23.0 mg (148 µmol) of (2R)-1,1,1-trifluoro-4-methylpentan-2-amine in the presence of 56.4 mg (148 µmol) of HATU and 65 µl (370 µmol) of DIPEA in 480 µl of DMF. The crude product was purified by means of preparative HPLC (acetonitrile/water/0.1% formic acid). 36.2 mg (54% of theory, 100% purity) of the title compound were obtained.

LC-MS (Method 3): $R_t$=2.16 min; MS (ESIpos): m/z=542 [M+H]$^+$ $^1$H NMR (400 MHz, DMSO-d$_6$): δ ppm=10.20 (d, 1H), 9.00 (s, 1H), 8.55 (d, 1H), 8.44 (d, 1H), 7.67 (s, 1H), 7.57 (t, 2H), 4.80-4.89 (m, 1H), 3.56-3.62 (m, 2H), 3.32-3.38 (m, 2H), 1.64-1.74 (m, 2H), 1.53-1.62 (m, 1H), 0.95 (d, 3H), 0.90 (d, 3H).

Example 581

N-(1,1,1,3,3,3-Hexafluoro-2-methylpropan-2-yl)-4-oxo-7-(2-oxoimidazolidin-1-yl)-1-(2,4,6-trifluorophenyl)-1,4-dihydro-1,8-naphthyridine-3-carboxamide

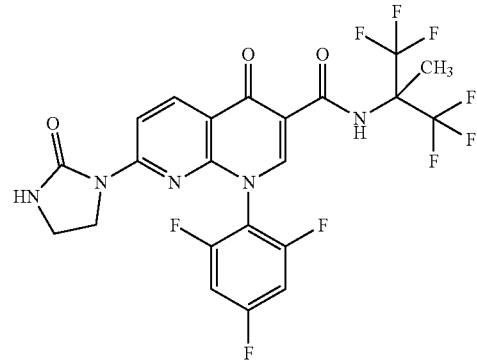 [SMILES: CC(NC(=O)c1cn(-c2c(F)cc(F)cc2F)c2nc(N3CCNC3=O)ccc2c1=O)(C(F)(F)F)C(F)(F)F]

According to GP2, 22.0 mg (42.5 µmol) of the compound from Example 159A were reacted with 36.6 mg (425 µmol) of imidazolidin-2-one in the presence of 8.81 mg (63.7

μmol) of potassium carbonate, 1.91 mg (8.50 μmol) of palladium acetate and 4.92 mg (8.50 μmol) of Xantphos in 430 μl of 1,4-dioxane. The crude product was purified by means of preparative HPLC (acetonitrile/water/0.1% formic acid). 5.30 mg (22% of theory, 100% purity) of the title compound were obtained.

LC-MS (Method 3): $R_t$=2.12 min; MS (ESIpos): m/z=568 [M+H]$^+$ $^1$H NMR (400 MHz, DMSO-d$_6$): δ ppm=11.36 (s, 1H), 9.04 (s, 1H), 8.59 (d, 1H), 8.45 (d, 1H), 7.69 (s, 1H), 7.58 (t, 2H), 3.53-3.65 (m, 2H), 3.32-3.38 (m, 2H), 2.07 (s, 3H).

Example 582

N-[(1S)-1-Cyclopropyl-2,2,2-trifluoroethyl]-7-[trans-3-hydroxy-4-methoxypyrrolidin-1-yl]-4-oxo-1-(2,4,6-trifluorophenyl)-1,4-dihydro-1,8-naphthyridine-3-carboxamide (diastereomer mixture)

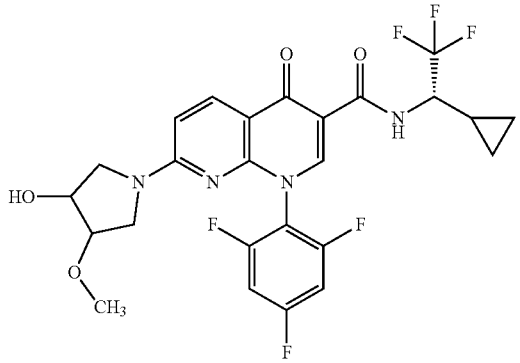 [SMILES: COC1CN(c2ccc3c(=O)c(C(=O)N[C@@H](C4CC4)C(F)(F)F)cn(-c4c(F)cc(F)cc4F)c3n2)CC1O]

According to GP3, 150 mg (315 μmol) of the compound from Example 126A were reacted with 44.3 mg (378 μmol) of 4-methoxypyrrolidin-3-ol and 160 μl (950 μmol) of DIPEA in 1.3 ml of DMF. The crude product was purified by means of preparative HPLC (acetonitrile/water/0.1% formic acid). 147 mg (84% of theory, 100% purity) of the title compound were obtained.

LC-MS (Method 3): $R_t$=1.95 min; MS (ESIpos): m/z=557 [M+H]$^+$ $^1$H NMR (400 MHz, DMSO-d$_6$): δ ppm=10.56 (d, 1H), 8.80 (s, 1H), 8.29 (d, 1H), 7.52-7.60 (m, 2H), 6.80 (t, 1H), 5.35 (br s, 0.45H), 5.25 (br s, 0.55H), 4.33-4.44 (m, 1H), 4.27 (br s, 0.45H), 4.14 (br s, 0.55H), 3.79 (br s, 0.55H), 3.69 (br s, 0.45H), 3.50-3.64 (m, 1.55H), 3.35-3.40 (m, 0.45H), 3.26 (br d, 3.45H), 3.19 (br d, 1H), 3.05-3.12 (m, 0.55H), 1.16-1.25 (m, 1H), 0.50-0.69 (m, 3H), 0.31-0.38 (m, 1H).

138 mg of the title compound (diastereomer mixture) were separated into the diastereomers by chiral HPLC (preparative HPLC: column: Daicel Chiralpak IA 5 μm 250×20 mm; eluent: 85% n-heptane, 15% ethanol; temperature: 25° C.; flow rate: 15 ml/min; UV detection: 210 nm).

This gave (in the sequence of elution from the column) 62.7 mg (36% of theory, 100% purity) of diastereomer 1 from Example 583 (96% de) Rt=12.53 min and 59.6 mg (34% of theory, 100% purity) of diastereomer 2 from Example 584 (96% de) Rt=14.78 min.

[Analytical HPLC: column: Daicel IA-3 3 μm 50×4.6 mm; eluent: 80% isohexane, 20% ethanol; UV detection: 220 nm].

Example 583

N-[(1S)-1-Cyclopropyl-2,2,2-trifluoroethyl]-7-[trans-3-hydroxy-4-methoxypyrrolidin-1-yl]-4-oxo-1-(2,4,6-trifluorophenyl)-1,4-dihydro-1,8-naphthyridine-3-carboxamide (diastereomer 1)

LC-MS (Method 3): $R_t$=1.96 min; MS (ESIpos): m/z=557 [M+H]$^+$ $^1$H NMR (400 MHz, DMSO-d$_6$): δ ppm=10.55 (d, 1H), 8.80 (s, 1H), 8.29 (d, 1H), 7.51-7.61 (m, 2H), 6.80 (br t, 1H), 5.30-5.37 (m, 0.45H), 5.22-5.30 (m, 0.55H), 4.33-4.44 (m, 1H), 4.22-4.31 (m, 0.45H), 4.11-4.20 (m, 0.55H), 3.73-3.82 (m, 0.55H), 3.66-3.71 (m, 0.45H), 3.49-3.64 (m, 1.55H), 3.35-3.41 (m, 0.45H), 3.26 (br d, 3.45H), 3.15-3.22 (m, 1H), 3.06-3.13 (m, 0.55H), 1.15-1.27 (m, 1H), 0.49-0.69 (m, 3H), 0.29-0.37 (m, 1H).

Example 584

N-[(1S)-1-Cyclopropyl-2,2,2-trifluoroethyl]-7-[trans-3-hydroxy-4-methoxypyrrolidin-1-yl]-4-oxo-1-(2,4,6-trifluorophenyl)-1,4-dihydro-1,8-naphthyridine-3-carboxamide (diastereomer 2)

LC-MS (Method 3): $R_t$=1.96 min; MS (ESIpos): m/z=557 [M+H]$^+$ $^1$H NMR (400 MHz, DMSO-d$_6$): δ ppm=10.56 (d, 1H), 8.80 (s, 1H), 8.29 (d, 1H), 7.52-7.60 (m, 2H), 6.80 (br t, 1H), 5.23-5.39 (m, 1H), 4.33-4.43 (m, 1H), 4.25-4.30 (m, 0.45H), 4.14 (br s, 0.55H), 3.75-3.82 (m, 0.55H), 3.66-3.71 (m, 0.45H), 3.50-3.64 (m, 1.55H), 3.35-3.41 (m, 0.45H), 3.26 (br d, 3.45H), 3.19 (br d, 1H), 3.06-3.14 (m, 0.55H), 1.16-1.25 (m, 1H), 0.50-0.69 (m, 3H), 0.31-0.37 (m, 1H).

Example 585

N-(2,6-Dichlorophenyl)-7-[(3R,4R)-3,4-dihydroxypyrrolidin-1-yl]-4-oxo-1-(2,4,6-trifluorophenyl)-1,4-dihydro-1,8-naphthyridine-3-carboxamide

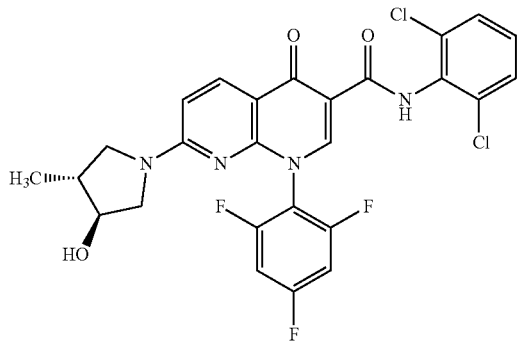 [SMILES: C[C@@H]1CN(c2ccc3c(=O)c(C(=O)Nc4c(Cl)cccc4Cl)cn(-c4c(F)cc(F)cc4F)c3n2)C[C@H]1O]

According to GP3, 60.0 mg (120 μmol) of the compound from Example 160B were reacted with 20.2 mg (144 μmol) of (3R,4R)-pyrrolidine-3,4-diol hydrochloride and 73 μl (420 μmol) of DIPEA in 540 μl of DMF. The crude product was purified by means of preparative HPLC (acetonitrile/water/0.1% formic acid). 53.3 mg (76% of theory, 98% purity) of the title compound were obtained.

LC-MS (Method 1): $R_t$=0.91 min; MS (ESIpos): m/z=565 [M+H]$^+$

¹H NMR (400 MHz, DMSO-d₆): δ ppm=11.95 (s, 1H), 8.89 (s, 1H), 8.34 (d, 1H), 7.48-7.65 (m, 4H), 7.38 (t, 1H), 6.81 (d, 1H), 5.25 (d, 1H), 5.16 (d, 1H), 4.06 (br s, 1H), 3.94 (br s, 1H), 3.63 (br dd, 1H), 3.33-3.39 (m, 1H), 3.23-3.29 (m, 1H), 3.09 (br d, 1H).

Example 586

N-[1,1,1,4,4,4-Hexafluorobutan-2-yl]-4-oxo-7-(2-oxoimidazolidin-1-yl)-1-(2,4,6-trifluorophenyl)-1,4-dihydro-1,8-naphthyridine-3-carboxamide (racemate)

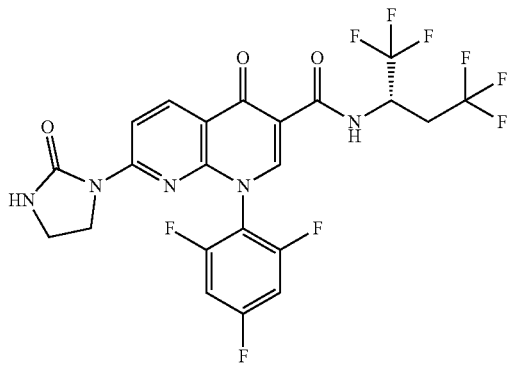 [SMILES: O=C(N[C@@H](CC(F)(F)F)C(F)(F)F)c1cn(-c2c(F)cc(F)cc2F)c2nc(N3CCNC3=O)ccc2c1=O]

According to GP1, 40.0 mg (89.4 µmol, 90% purity) of the compound from Example 113A were reacted with 27.2 mg (125 µmol) of 1,1,1,4,4,4-hexafluorobutan-2-amine hydrochloride in the presence of 40.8 mg (107 µmol) of HATU and 47 µl (270 µmol) of DIPEA in 330 µl of DMF. The crude product was purified by means of preparative HPLC (acetonitrile/water/0.1% formic acid). 33.3 mg (66% of theory, 100% purity) of the title compound were obtained.

LC-MS (Method 3): $R_t$=1.90 min; MS (ESIpos): m/z=568 [M+H]⁺

¹H NMR (400 MHz, DMSO-d₆): δ ppm=10.47 (d, 1H), 9.02 (s, 1H), 8.55 (d, 1H), 8.44 (d, 1H), 7.67 (s, 1H), 7.54-7.61 (m, 2H), 5.21-5.32 (m, 1H), 3.60 (t, 2H), 3.33-3.38 (m, 2H), 3.07-3.20 (dt, 1H), 2.90-3.03 (m, 1H).

25.4 mg of the title compound (racemate) were separated into the enantiomers by chiral HPLC (preparative HPLC: column: Daicel Chiralpak IF 5 µm 250×20 mm; eluent: 80% n-heptane, 20% ethanol; temperature: 25° C.; flow rate: 15 ml/min; UV detection: 220 nm).

This gave (in the sequence of elution from the column) 10.0 mg (20% of theory, 100% purity) of enantiomer 1 from Example 587 (99% ee) Rt=12.96 min and 9.00 mg (18% of theory, 100% purity) of enantiomer 2 from Example 588 (98% ee) Rt=14.19 min.

[Analytical HPLC: column: Daicel Chiralpak IF 5 µm 250×4.6 mm; eluent: 80% isohexane, 20% ethanol; temperature: 30° C.; flow rate: 1.0 ml/min; UV detection: 220 nm]

Example 587

N-[1,1,1,4,4,4-Hexafluorobutan-2-yl]-4-oxo-7-(2-oxoimidazolidin-1-yl)-1-(2,4,6-trifluorophenyl)-1,4-dihydro-1,8-naphthyridine-3-carboxamide (enantiomer 1)

LC-MS (Method 3): $R_t$=1.91 min; MS (ESIpos): m/z=568 [M+H]⁺

¹H NMR (400 MHz, DMSO-d₆): δ ppm=10.47 (d, 1H), 9.02 (s, 1H), 8.55 (d, 1H), 8.44 (d, 1H), 7.67 (br s, 1H), 7.58 (t, 2H), 5.21-5.33 (m, 1H), 3.56-3.63 (m, 2H), 3.32-3.38 (m, 2H), 3.08-3.20 (m, 1H), 2.90-3.03 (m, 1H).

Example 588

N-[1,1,1,4,4,4-Hexafluorobutan-2-yl]-4-oxo-7-(2-oxoimidazolidin-1-yl)-1-(2,4,6-trifluorophenyl)-1,4-dihydro-1,8-naphthyridine-3-carboxamide (enantiomer 2)

LC-MS (Method 3): $R_t$=1.92 min; MS (ESIpos): m/z=568 [M+H]⁺

¹H NMR (400 MHz, DMSO-d₆): δ ppm=10.47 (d, 1H), 9.02 (s, 1H), 8.55 (d, 1H), 8.44 (d, 1H), 7.67 (s, 1H), 7.54-7.61 (m, 2H), 5.23-5.30 (m, 1H), 3.57-3.62 (m, 2H), 3.32-3.37 (m, 2H), 3.09-3.20 (m, 1H), 2.90-3.02 (m, 1H).

Example 589

7-[(3R,4R)-3,4-Dihydroxypyrrolidin-1-yl]-4-oxo-N-[(2S)-1,1,1-trifluorobutan-2-yl]-1-(2,4,6-trifluorophenyl)-1,4-dihydro-1,8-naphthyridine-3-carboxamide

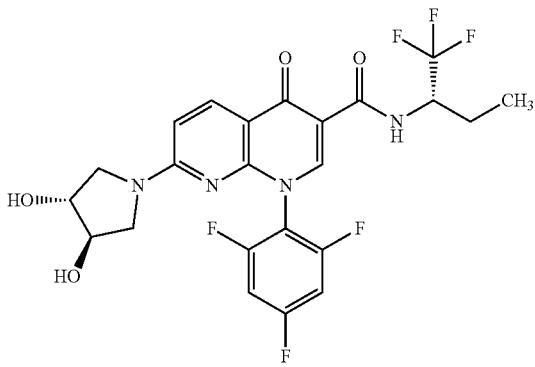 [SMILES: CC[C@H](NC(=O)c1cn(-c2c(F)cc(F)cc2F)c2nc(N3C[C@@H](O)[C@H](O)C3)ccc2c1=O)C(F)(F)F]

According to GP3, 50.0 mg (108 µmol) of the compound from Example 115A were reacted with 18.1 mg (129 µmol) of (3R,4R)-pyrrolidine-3,4-diol hydrochloride and 66 µl (380 µmol) of DIPEA in 500 µl of DMF. The crude product was purified by means of preparative HPLC (acetonitrile/water/0.1% formic acid). 43.1 mg (75% of theory, 100% purity) of the title compound were obtained.

LC-MS (Method 3): $R_t$=1.70 min; MS (ESIpos): m/z=531 [M+H]⁺

¹H NMR (500 MHz, DMSO-d₆): δ ppm=10.43 (d, 1H), 8.81 (s, 1H), 8.28 (d, 1H), 7.53-7.60 (m, 2H), 6.78 (d, 1H), 5.24 (d, 1H), 5.14 (d, 1H), 4.69-4.78 (m, 1H), 4.05 (br s, 1H), 3.93 (br s, 1H), 3.62 (br dd, 1H), 3.33-3.37 (m, 1H), 3.25 (br dd, 1H), 3.07 (br d, 1H), 1.83-1.92 (m, 1H), 1.59-1.69 (m, 1H), 0.97 (t, 3H).

Example 590

N-[(1S)-1-Cyclopropyl-2,2,2-trifluoroethyl]-7-[(3R, 4R)-3,4-dihydroxypyrrolidin-1-yl]-4-oxo-1-(2,4,6-trifluorophenyl)-1,4-dihydro-1,8-naphthyridine-3-carboxamide

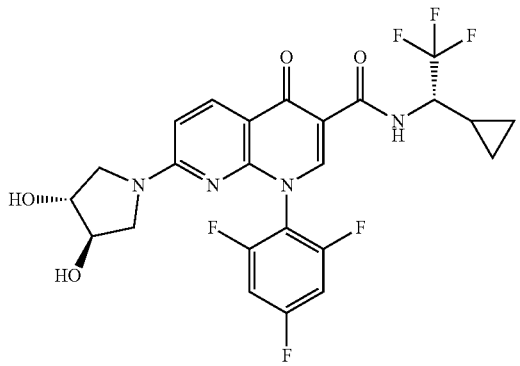 [SMILES: O=C(N[C@@H](C1CC1)C(F)(F)F)c1cn(-c2c(F)cc(F)cc2F)c2nc(N3C[C@@H](O)[C@H](O)C3)ccc2c1=O]

According to GP3, 50.0 mg (105 μmol) of the compound from Example 126A were reacted with 17.6 mg (126 μmol) of (3R,4R)-pyrrolidine-3,4-diol hydrochloride and 64 μl (370 μmol) of DIPEA in 500 μl of DMF. The crude product was purified by means of preparative HPLC (acetonitrile/water/0.1% formic acid). 45.5 mg (80% of theory, 100% purity) of the title compound were obtained.

LC-MS (Method 3): $R_t$=1.73 min; MS (ESIpos): m/z=543 $[M+H]^+$ $^1$H NMR (400 MHz, DMSO-$d_6$): δ ppm=10.57 (d, 1H), 8.80 (s, 1H), 8.28 (d, 1H), 7.52-7.60 (m, 2H), 6.78 (d, 1H), 5.23 (d, 1H), 5.14 (d, 1H), 4.33-4.44 (m, 1H), 4.04-4.07 (m, 1H), 3.93 (br s, 1H), 3.62 (br dd, 1H), 3.32-3.37 (m, 1H), 3.25 (br dd, 1H), 3.07 (br d, 1H), 1.19-1.24 (m, 1H), 0.50-0.69 (m, 3H), 0.30-0.38 (m, 1H).

Example 591

7-[(3R,4R)-3,4-Dihydroxypyrrolidin-1-yl]-N-(1,1,1,3,3,3-hexafluoro-2-methylpropan-2-yl)-4-oxo-1-(2,4,6-trifluorophenyl)-1,4-dihydro-1,8-naphthyridine-3-carboxamide

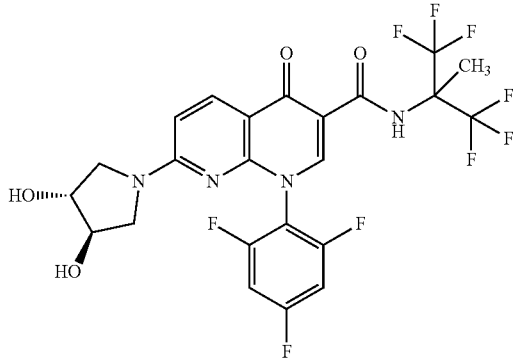 [SMILES: CC(NC(=O)c1cn(-c2c(F)cc(F)cc2F)c2nc(N3C[C@@H](O)[C@H](O)C3)ccc2c1=O)(C(F)(F)F)C(F)(F)F]

According to GP3, 25.0 mg (48.3 μmol) of the compound from Example 159A were reacted with 8.09 mg (57.9 μmol) of (3R,4R)-pyrrolidine-3,4-diol hydrochloride and 29 μl (170 μmol) of DIPEA in 220 μl of DMF. The crude product was purified by means of preparative HPLC (acetonitrile/water/0.1% formic acid). 25.7 mg (91% of theory, 100% purity) of the title compound were obtained.

LC-MS (Method 3): $R_t$=1.91 min; MS (ESIpos): m/z=585 $[M+H]^+$ $^1$H NMR (400 MHz, DMSO-$d_6$): δ ppm=11.61 (s, 1H), 8.84 (s, 1H), 8.30 (d, 1H), 7.54-7.61 (m, 2H), 6.80 (d, 1H), 5.24 (d, 1H), 5.15 (d, 1H), 4.03-4.07 (m, 1H), 3.90-3.95 (m, 1H), 3.62 (dd, 1H), 3.33-3.39 (m, 1H), 3.25 (dd, 1H), 3.07 (d, 1H), 2.06 (br s, 3H).

Example 592

N-(2,6-Dichlorophenyl)-7-[(4S)-4-hydroxy-2-oxopyrrolidin-1-yl]-4-oxo-1-(2,4,6-trifluorophenyl)-1,4-dihydro-1,8-naphthyridine-3-carboxamide

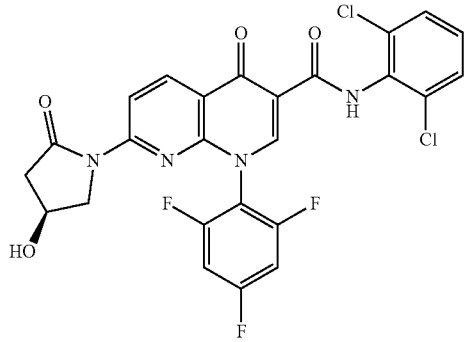 [SMILES: O=C(Nc1c(Cl)cccc1Cl)c1cn(-c2c(F)cc(F)cc2F)c2nc(N3C[C@@H](O)CC3=O)ccc2c1=O]

According to GP2, 60.0 mg (120 μmol) of the compound from Example 160B were reacted with 19.9 mg (144 μmol) of (4S)-4-hydroxypyrrolidin-2-one hydrochloride in the presence of 24.9 mg (180 μmol) of potassium carbonate, 5.40 mg (24.1 μmol) of palladium acetate and 13.9 mg (24.1 μmol) of Xantphos in 1.1 ml of 1,4-dioxane. The crude product was purified by means of preparative HPLC (acetonitrile/water/0.1% formic acid). The substance was recrystallized from acetonitrile, filtered off with suction, washed with a little acetonitrile and dried. The substance was isolated with impurities and was further purified subsequently by means of normal phase chromatography (eluent: cyclohexane-ethyl acetate gradient). 6.20 mg (9% of theory, 100% purity) of the title compound were obtained.

LC-MS (Method 1): $R_t$=1.00 min; MS (ESIpos): m/z=563 $[M+H]^+$ $^1$H NMR (400 MHz, DMSO-$d_6$): δ ppm=11.60 (s, 1H), 9.16 (s, 1H), 8.78 (d, 1H), 8.57 (d, 1H), 7.58-7.66 (m, 4H), 7.39 (t, 1H), 5.35 (br s, 1H), 4.22-4.36 (m, 1H), 3.71 (dd, 1H), 3.49 (d, 1H), 2.96 (dd, 1H).

Example 593

Methyl 4-{6-[(2,6-dichlorophenyl)carbamoyl]-5-oxo-8-(2,4,6-trifluorophenyl)-5,8-dihydro-1,8-naphthyridin-2-yl}piperazine-1-carboxylate

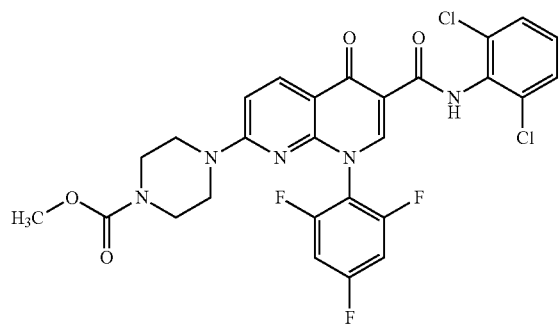 [SMILES: COC(=O)N1CCN(c2ccc3c(=O)c(C(=O)Nc4c(Cl)cccc4Cl)cn(-c4c(F)cc(F)cc4F)c3n2)CC1]

According to GP3, 60.0 mg (120 µmol) of the compound from Example 160B were reacted with 20.8 mg (144 µmol) of methyl piperazine-1-carboxylate and 73 µl (420 µmol) of DIPEA in 540 µl of DMF. The crude product was purified by means of preparative HPLC (acetonitrile/water/0.1% formic acid). 40.3 mg (55% of theory, 100% purity) of the title compound were obtained.

LC-MS (Method 3): $R_t$=2.14 min; MS (ESIpos): m/z=606 [M+H]$^+$ $^1$H NMR (400 MHz, DMSO-d$_6$): δ ppm=11.86 (s, 1H), 8.93 (s, 1H), 8.39 (d, 1H), 7.54-7.61 (m, 4H), 7.38 (t, 1H), 7.16 (d, 1H), 3.61 (s, 3H), 3.50-3.58 (m, 4H), 3.38-3.46 (m, 4H).

Example 594

Methyl 4-[6-{[(1R)-1-cyclopropyl-2,2,2-trifluoroethyl]carbamoyl}-5-oxo-8-(2,4,6-trifluorophenyl)-5,8-dihydro-1,8-naphthyridin-2-yl]piperazine-1-carboxylate

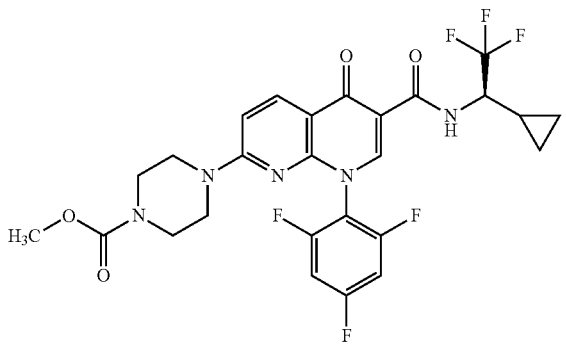 [SMILES: COC(=O)N1CCN(c2ccc3c(=O)c(C(=O)N[C@H](C4CC4)C(F)(F)F)cn(-c4c(F)cc(F)cc4F)c3n2)CC1]

According to GP1, 70.0 mg (151 µmol) of the compound from Example 157A were reacted with 31.9 mg (182 µmol) of (1R)-1-cyclopropyl-2,2,2-trifluoroethanamine hydrochloride in the presence of 69.1 mg (182 µmol) of HATU and 110 µl (610 µmol) of DIPEA in 580 µl of DMF. The crude product was purified by means of preparative HPLC (acetonitrile/water/0.1% formic acid). 50.9 mg (58% of theory, 100% purity) of the title compound were obtained.

LC-MS (Method 3): $R_t$=2.13 min; MS (ESIpos): m/z=584 [M+H]$^+$ $^1$H NMR (400 MHz, DMSO-d$_6$): δ ppm=10.49 (d, 1H), 8.83 (s, 1H), 8.33 (d, 1H), 7.53-7.60 (m, 2H), 7.14 (d, 1H), 4.33-4.43 (m, 1H), 3.61 (s, 3H), 3.50-3.57 (m, 4H), 3.36-3.43 (m, 4H), 1.16-1.25 (m, 1H), 0.50-0.69 (m, 3H), 0.31-0.37 (m, 1H).

Example 595

Methyl 4-[5-oxo-6-{[(2S)-1,1,1-trifluorobutan-2-yl]carbamoyl}-8-(2,4,6-trifluorophenyl)-5,8-dihydro-1,8-naphthyridin-2-yl]piperazine-1-carboxylate

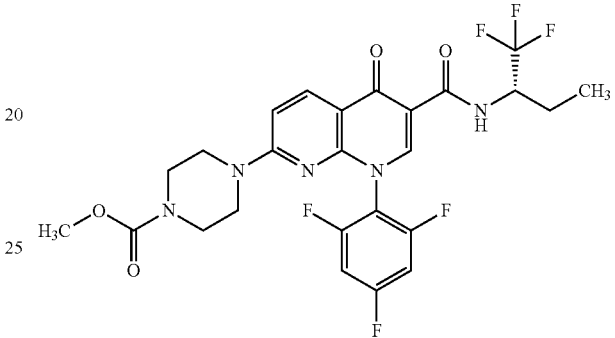

According to GP1, 70.0 mg (151 µmol) of the compound from Example 157A were reacted with 29.7 mg (182 µmol) of (2S)-1,1,1-trifluorobutan-2-amine hydrochloride in the presence of 69.1 mg (182 µmol) of HATU and 79 µl (450 µmol) of DIPEA in 580 µl of DMF. The crude product was purified by means of preparative HPLC (acetonitrile/water/0.1% formic acid). 46.5 mg (54% of theory, 100% purity) of the title compound were obtained.

LC-MS (Method 3): $R_t$=2.11 min; MS (ESIpos): m/z=572 [M+H]$^+$ $^1$H NMR (400 MHz, DMSO-d$_6$): δ ppm=10.36 (d, 1H), 8.84 (s, 1H), 8.33 (d, 1H), 7.57 (t, 2H), 7.14 (d, 1H), 4.69-4.79 (m, 1H), 3.61 (s, 3H), 3.48-3.58 (m, 4H), 3.36-3.44 (m, 4H), 1.83-1.92 (m, 1H), 1.59-1.69 (m, 1H), 0.97 (t, 3H).

Example 596

4-Oxo-7-(2-oxoimidazolidin-1-yl)-N-[1-(trifluoromethyl)cyclobutyl]-1-(2,4,6-trifluorophenyl)-1,4-dihydro-1,8-naphthyridine-3-carboxamide

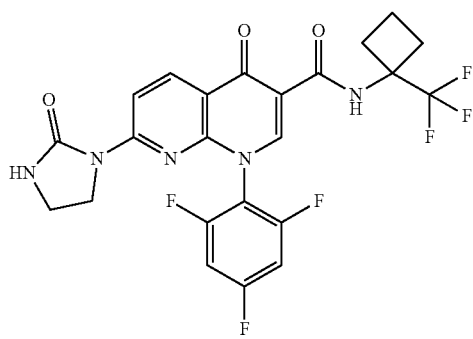 [SMILES: O=C(NC1(C(F)(F)F)CCC1)c1cn(-c2c(F)cc(F)cc2F)c2nc(N3CCNC3=O)ccc2c1=O]

According to GP1, 50.0 mg (124 µmol) of the compound from Example 113A were reacted with 26.1 mg (148 µmol) of 1-(trifluoromethyl)cyclobutanamine hydrochloride in the presence of 56.4 mg (148 µmol) of HATU and 65 µl (370 µmol) of DIPEA in 480 µl of DMF. The crude product was purified by means of preparative HPLC (acetonitrile/water/ 0.1% formic acid). 41.6 mg (64% of theory, 100% purity) of the title compound were obtained.

LC-MS (Method 3): $R_t$=1.97 min; MS (ESIpos): m/z=526 [M+H]$^+$ $^1$H NMR (400 MHz, DMSO-d$_6$): δ ppm=10.31 (s, 1H), 8.94 (s, 1H), 8.55 (d, 1H), 8.43 (d, 1H), 7.66 (s, 1H), 7.58 (t, 2H), 3.56-3.63 (m, 2H), 3.32-3.38 (m, 2H), 2.54-2.66 (m, 4H), 1.90-2.09 (m, 2H).

Example 597

N-(2,6-Dichlorophenyl)-1-(2,4-difluorophenyl)-7-[1-hydroxy-3-azabicyclo[3.1.0]hex-3-yl]-4-oxo-1,4-dihydro-1,8-naphthyridine-3-carboxamide (racemate)

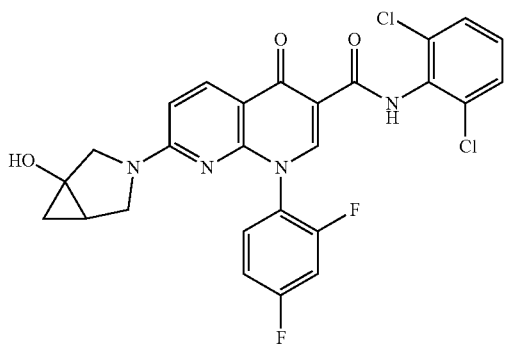 [SMILES: O=C(Nc1c(Cl)cccc1Cl)c1cn(-c2ccc(F)cc2F)c2nc(N3CC4CC4(O)C3)ccc2c1=O]

According to GP3, 90.0 mg (187 µmol) of the compound from Example 81A were reacted with 30.5 mg (225 µmol) of 3-azabicyclo[3.1.0]hexan-1-ol and 110 µl (660 µmol) of DIPEA in 900 µl of DMF. The crude product was purified by means of preparative HPLC (acetonitrile/water/0.1% formic acid). 62.1 mg (61% of theory, 100% purity) of the title compound were obtained.

LC-MS (Method 3): $R_t$=2.02 min; MS (ESIpos): m/z=543 [M+H]$^+$ $^1$H NMR (400 MHz, DMSO-d$_6$): δ ppm=11.99 (s, 1H), 8.69 (s, 1H), 8.34 (d, 1H), 7.78-7.89 (m, 1H), 7.54-7.65 (m, 3H), 7.29-7.40 (m, 2H), 6.70-6.83 (m, 1H), 5.90-6.13 (m, 1H), 3.79-3.95 (m, 0.50H), 3.37-3.75 (m, 2.50H), 3.08-3.23 (m, 1H), 1.52-1.70 (m, 1H), 0.95-1.08 (m, 1H), 0.37-0.50 (m, 1H).

Example 598

7-(3-Methoxy-3-methylazetidin-1-yl)-4-oxo-N-[(2S)-1,1,1-trifluoro-3,3-dimethylbutan-2-yl]-1-(2,4,6-trifluorophenyl)-1,4-dihydro-1,8-naphthyridine-3-carboxamide

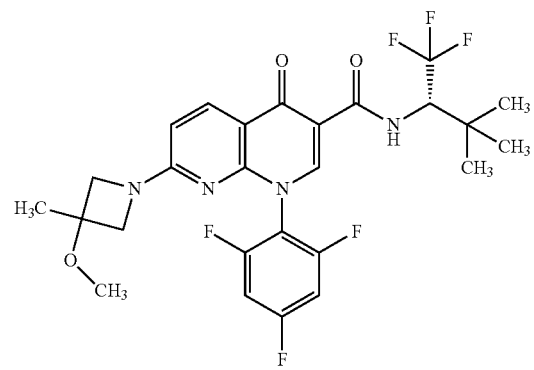 [SMILES: COC1(C)CN(c2ccc3c(=O)c(C(=O)N[C@@H](C(C)(C)C)C(F)(F)F)cn(-c4c(F)cc(F)cc4F)c3n2)C1]

According to GP1, 24.1 mg (57.5 µmol) of the compound from Example 161A were reacted with 13.2 mg (69.0 µmol) of (2S)-1,1,1-trifluoro-3,3-dimethylbutan-2-amine hydrochloride in the presence of 26.3 mg (69.0 µmol) of HATU and 30 µl (170 µmol) of DIPEA in 230 µl of DMF. The crude product was purified by means of preparative HPLC (acetonitrile/water/0.1% formic acid). 23.2 mg (72% of theory, 100% purity) of the title compound were obtained.

LC-MS (Method 3): $R_t$=2.47 min; MS (ESIpos): m/z=557 [M+H]$^+$ $^1$H NMR (400 MHz, DMSO-d$_6$): δ ppm=10.73 (d, 1H), 8.81 (s, 1H), 8.33 (d, 1H), 7.54 (t, 2H), 6.64 (d, 1H), 4.62 (quint, 1H), 3.47-4.12 (m, 4H), 3.16 (s, 3H), 1.41 (s, 3H), 1.08 (s, 9H).

Example 599

N-(1,1,1,3,3,3-Hexafluoropropan-2-yl)-4-oxo-7-(2-oxoimidazolidin-1-yl)-1-(2,4,6-trifluorophenyl)-1,4-dihydro-1,8-naphthyridine-3-carboxamide

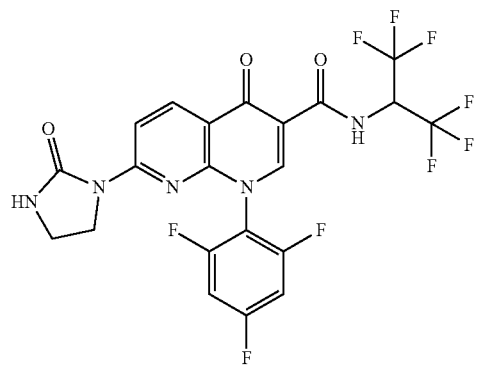 [SMILES: O=C(NC(C(F)(F)F)C(F)(F)F)c1cn(-c2c(F)cc(F)cc2F)c2nc(N3CCNC3=O)ccc2c1=O]

According to GP2, 60.0 mg (119 µmol) of the compound from Example 154A were reacted with 103 mg (1.19 mmol) of imidazolidin-2-one in the presence of 24.7 mg (179 µmol) of potassium carbonate, 5.35 mg (23.8 µmol) of palladium acetate and 13.8 mg (23.8 µmol) of Xantphos in 1.2 ml of 1,4-dioxane. The crude product was purified by means of preparative HPLC (acetonitrile/water/0.1% formic acid). 34.4 mg (52% of theory, 100% purity) of the title compound were obtained.

LC-MS (Method 3): $R_t$=2.05 min; MS (ESIpos): m/z=554 [M+H]$^+$ $^1$H NMR (400 MHz, DMSO-d$_6$): δ ppm=11.15 (d, 1H), 9.12 (s, 1H), 8.58 (d, 1H), 8.46 (d, 1H), 7.69 (s, 1H), 7.59 (t, 2H), 6.33-6.40 (m, 1H), 3.57-3.62 (m, 2H), 3.33-3.38 (m, 2H).

Example 600

N-[(1S)-1-Cyclopropyl-2,2,2-trifluoroethyl]-7-[7-hydroxy-5-azaspiro[2.4]hept-5-yl]-4-oxo-1-(2,4,6-trifluorophenyl)-1,4-dihydro-1,8-naphthyridine-3-carboxamide (diastereomer mixture)

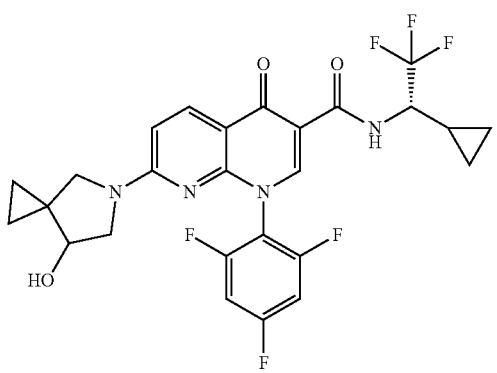 [SMILES: O=C(N[C@@H](C1CC1)C(F)(F)F)c1cn(-c2c(F)cc(F)cc2F)c2nc(N3CC(O)C4(CC4)C3)ccc2c1=O]

According to GP1, 80.0 mg (185 μmol) of the compound from Example 155A were reacted with 39.1 mg (223 μmol) of (1S)-1-cyclopropyl-2,2,2-trifluoroethanamine hydrochloride in the presence of 84.6 mg (223 μmol) of HATU and 97 μl (560 μmol) of DIPEA in 890 μl of DMF. The crude product was purified by means of preparative HPLC (acetonitrile/water/0.1% formic acid). 67.6 mg (66% of theory, 100% purity) of the title compound were obtained.

LC-MS (Method 4): $R_t$=3.62 min; MS (ESIpos): m/z=553 [M+H]$^+$ $^1$H NMR (400 MHz, DMSO-d$_6$): δ ppm=10.56 (d, 1H), 8.77-8.82 (m, 1H), 8.29 (d, 1H), 7.46-7.64 (m, 2H), 6.81 (br d, 0.40H), 6.69 (br d, 0.60H), 4.95-5.11 (m, 1H), 4.33-4.43 (m, 1H), 3.59-3.78 (m, 2H), 3.40-3.48 (m, 1.60H), 3.13-3.27 (m, 1H), 2.89 (s, 0.40H), 1.16-1.25 (m, 1H), 0.77-0.86 (m, 1H), 0.46-0.69 (m, 6H), 0.29-0.38 (m, 1H).

59.0 mg of the title compound (diastereomer mixture) were separated into the diastereomers by chiral HPLC (preparative HPLC: column: YMC Chiralart Amylose SA 5 μm 250×30 mm; eluent: 80% n-heptane, 20% ethanol; temperature: 25° C.; flow rate: 30 ml/min; UV detection: 220 nm).

This gave (in the sequence of elution from the column) 23.0 mg (22% of theory, 100% purity) of diastereomer 1 from Example 601 (99% de) Rt=9.88 min and 22.0 mg (21% of theory, 100% purity) of diastereomer 2 from Example 602 (99% de) Rt=12.57 min.

[Analytical HPLC: column: YMC Chiralart Amylose SA 5 μm 250×4.6 mm; eluent: 80% isohexane, 20% ethanol; temperature: 30° C.; flow rate: 1.0 ml/min; UV detection: 220 nm]

Example 601

N-[(1S)-1-Cyclopropyl-2,2,2-trifluoroethyl]-7-[7-hydroxy-5-azaspiro[2.4]hept-5-yl]-4-oxo-1-(2,4,6-trifluorophenyl)-1,4-dihydro-1,8-naphthyridine-3-carboxamide (diastereomer 1)

LC-MS (Method 3): $R_t$=2.08 min; MS (ESIpos): m/z=553 [M+H]$^+$ $^1$H NMR (400 MHz, DMSO-d$_6$): δ ppm=10.56 (d, 1H), 8.77-8.82 (m, 1H), 8.29 (d, 1H), 7.46-7.64 (m, 2H), 6.81 (br d, 0.40H), 6.69 (br d, 0.60H), 5.07 (br d, 0.40H), 4.98 (br d, 0.60H), 4.33-4.44 (m, 1H), 3.59-3.79 (m, 2H), 3.31-3.47 (m, 1.60H), 3.14-3.27 (m, 1H), 2.88 (br d, 0.40H), 1.14-1.28 (m, 1H), 0.76-0.88 (m, 1H), 0.46-0.69 (m, 6H), 0.29-0.39 (m, 1H).

Example 602

N-[(1S)-1-Cyclopropyl-2,2,2-trifluoroethyl]-7-[7-hydroxy-5-azaspiro[2.4]hept-5-yl]-4-oxo-1-(2,4,6-trifluorophenyl)-1,4-dihydro-1,8-naphthyridine-3-carboxamide (diastereomer 2)

LC-MS (Method 3): $R_t$=2.08 min; MS (ESIpos): m/z=553 [M+H]$^+$ $^1$H NMR (400 MHz, DMSO-d$_6$): δ ppm=10.56 (d, 1H), 8.77-8.82 (m, 1H), 8.29 (d, 1H), 7.49-7.60 (m, 2H), 6.81 (br d, 0.40H), 6.69 (br d, 0.60H), 5.08 (br d, 0.40H), 4.98 (br d, 0.60H), 4.33-4.43 (m, 1H), 3.59-3.79 (m, 2H), 3.31-3.49 (m, 1.60H), 3.21 (br dd, 1H), 2.83-2.93 (m, 0.40H), 1.16-1.26 (m, 1H), 0.76-0.87 (m, 1H), 0.43-0.71 (m, 6H), 0.29-0.39 (m, 1H).

Example 603

Methyl 4-[6-{[(1S)-1-cyclopropyl-2,2,2-trifluoroethyl]carbamoyl}-5-oxo-8-(2,4,6-trifluorophenyl)-5,8-dihydro-1,8-naphthyridin-2-yl]piperazine-1-carboxylate

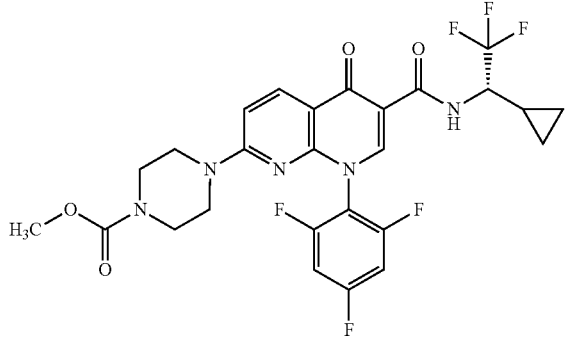 [SMILES: COC(=O)N1CCN(c2ccc3c(=O)c(C(=O)N[C@@H](C4CC4)C(F)(F)F)cn(-c4c(F)cc(F)cc4F)c3n2)CC1]

According to GP1, 70.0 mg (151 μmol) of the compound from Example 157A were reacted with 31.9 mg (182 μmol) of (1S)-1-cyclopropyl-2,2,2-trifluoroethanamine hydrochloride in the presence of 69.1 mg (182 μmol) of HATU and 79 μl (450 μmol) of DIPEA in 580 μl of DMF. The crude product was purified by means of preparative HPLC (acetonitrile/water/0.1% formic acid). 47.9 mg (54% of theory, 100% purity) of the title compound were obtained.

LC-MS (Method 3): $R_t$=2.13 min; MS (ESIpos): m/z=584 [M+H]$^+$

¹H NMR (400 MHz, DMSO-d₆): δ ppm=10.49 (d, 1H), 8.83 (s, 1H), 8.33 (d, 1H), 7.53-7.60 (m, 2H), 7.14 (d, 1H), 4.33-4.43 (m, 1H), 3.61 (s, 3H), 3.49-3.57 (m, 4H), 3.36-3.44 (m, 4H), 1.16-1.25 (m, 1H), 0.50-0.69 (m, 3H), 0.30-0.38 (m, 1H).

Example 604

N-[(1S)-1-Cyclopropyl-2,2,2-trifluoroethyl]-4-oxo-7-(2-oxotetrahydropyrimidin-1(2H)-yl)-1-(2,4,6-trifluorophenyl)-1,4-dihydro-1,8-naphthyridine-3-carboxamide

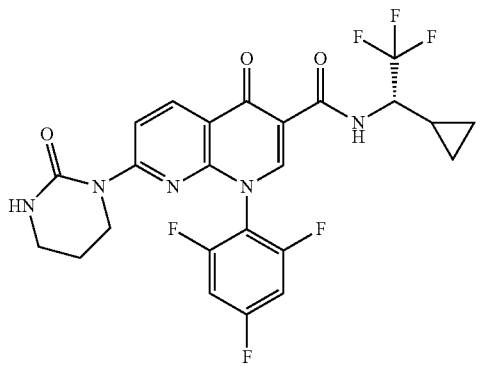 [SMILES: O=C(N[C@@H](C1CC1)C(F)(F)F)c1cn(-c2c(F)cc(F)cc2F)c2nc(N3CCCNC3=O)ccc2c1=O]

According to GP2, 60.0 mg (126 µmol) of the compound from Example 126A were reacted with 126 mg (1.26 mmol) of tetrahydropyrimidin-2(1H)-one in the presence of 26.1 mg (189 µmol) of potassium carbonate, 5.66 mg (25.2 µmol) of palladium acetate and 14.6 mg (25.2 µmol) of Xantphos in 1.2 ml of 1,4-dioxane. The crude product was purified by means of preparative HPLC (acetonitrile/water/0.1% formic acid). 46.0 mg (68% of theory, 100% purity) of the title compound were obtained.

LC-MS (Method 3): R$_t$=1.94 min; MS (ESIpos): m/z=540 [M+H]⁺

¹H NMR (400 MHz, DMSO-d₆): δ ppm=10.33 (d, 1H), 9.01 (s, 1H), 8.52 (d, 1H), 8.30 (d, 1H), 7.60 (t, 2H), 7.38-7.41 (m, 1H), 4.35-4.45 (m, 1H), 3.50 (br t, 2H), 3.15 (td, 2H), 1.80-1.88 (m, 2H), 1.19-1.27 (m, 1H), 0.52-0.70 (m, 3H), 0.31-0.38 (m, 1H).

Example 605

N-[(1R)-1-Cyclopropyl-2,2,2-trifluoroethyl]-7-(3-methoxy-3-methylazetidin-1-yl)-4-oxo-1-(2,4,6-trifluorophenyl)-1,4-dihydro-1,8-naphthyridine-3-carboxamide

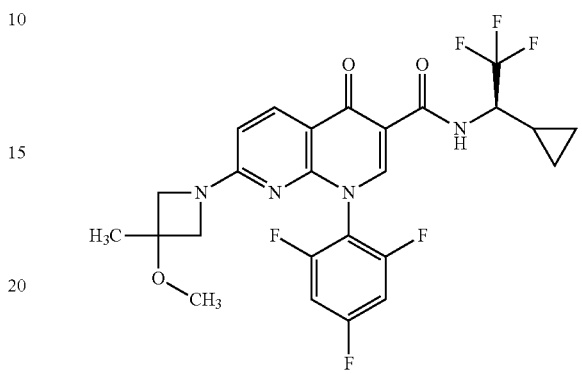

According to GP1, 24.0 mg (57.2 µmol) of the compound from Example 161A were reacted with 12.1 mg (68.7 µmol) of (1R)-1-cyclopropyl-2,2,2-trifluoroethanamine hydrochloride in the presence of 26.1 mg (68.7 µmol) of HATU and 30 µl (170 µmol) of DIPEA in 230 µl of DMF. The crude product was purified by means of preparative HPLC (acetonitrile/water/0.1% formic acid). 23.9 mg (77% of theory, 100% purity) of the title compound were obtained.

LC-MS (Method 3): R$_t$=2.32 min; MS (ESIpos): m/z=541 [M+H]⁺

¹H NMR (400 MHz, DMSO-d₆): δ ppm=10.52 (d, 1H), 8.80 (s, 1H), 8.30 (d, 1H), 7.50-7.58 (m, 2H), 6.64 (d, 1H), 4.33-4.43 (m, 1H), 3.50-4.11 (m, 3H), 3.16 (s, 3H), 1.41 (s, 3H), 1.16-1.25 (m, 1H), 0.49-0.69 (m, 3H), 0.30-0.37 (m, 1H).

Example 606

N-[1,1,1,4,4,4-Hexafluorobutan-2-yl]-7-[(4S)-4-hydroxy-2-oxopyrrolidin-1-yl]-4-oxo-1-(2,4,6-trifluorophenyl)-1,4-dihydro-1,8-naphthyridine-3-carboxamide (diastereomer mixture)

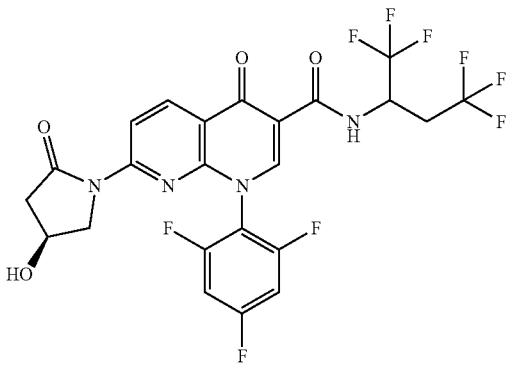 [SMILES: O=C(NC(CC(F)(F)F)C(F)(F)F)c1cn(-c2c(F)cc(F)cc2F)c2nc(N3C[C@@H](O)CC3=O)ccc2c1=O]

According to GP1, 40.0 mg (95.4 µmol) of the compound from Example 117A were reacted with 29.1 mg (134 µmol)

of 1,1,1,4,4,4-hexafluorobutan-2-amine hydrochloride in the presence of 43.5 mg (114 μmol) of HATU and 50 μl (290 μmol) of DIPEA in 350 μl of DMF. The crude product was purified by means of preparative HPLC (acetonitrile/water/ 0.1% formic acid). 36.5 mg (66% of theory, 100% purity) of the title compound were obtained.

LC-MS (Method 1): $R_t$=1.00 min; MS (ESIpos): m/z=583 [M+H]$^+$ $^1$H NMR (400 MHz, DMSO-d$_6$): δ ppm=10.37 (d, 1H), 9.09 (s, 1H), 8.71 (d, 1H), 8.55 (d, 1H), 7.58-7.66 (m, 2H), 5.21-5.37 (m, 2H), 4.29 (br s, 1H), 3.69 (dd, 1H), 3.47 (d, 1H), 3.11-3.22 (m, 1H), 2.90-3.03 (m, 2H), 2.38 (br d, 1H).

36.0 mg of the title compound (diastereomer mixture) were separated into the diastereomers by chiral HPLC (preparative HPLC: column: Daicel Chiralcel OX-H 5 μm 250×20 mm; eluent: 80% n-heptane, 20% isopropanol; temperature: 23° C.; flow rate: 20 ml/min; UV detection: 220 nm).

This gave (in the sequence of elution from the column) 10.50 mg (19% of theory, 100% purity) of diastereomer 1 from Example 607 (99% de) Rt=6.32 min and 6.90 mg (12% of theory, 100% purity) of diastereomer 2 from Example 608 (94% de) Rt=7.62 min.

[Analytical HPLC: column: Daicel OX-3 3 μm 50×4.6 mm; eluent: 80% isohexane, 20% isopropanol; UV detection: 220 nm].

Example 607

N-[1,1,1,4,4,4-Hexafluorobutan-2-yl]-7-[(4S)-4-hydroxy-2-oxopyrrolidin-1-yl]-4-oxo-1-(2,4,6-trifluorophenyl)-1,4-dihydro-1,8-naphthyridine-3-carboxamide (diastereomer 1)

LC-MS (Method 3): $R_t$=1.86 min; MS (ESIpos): m/z=583 [M+H]$^+$ $^1$H NMR (400 MHz, DMSO-d$_6$): δ ppm=10.37 (d, 1H), 9.09 (s, 1H), 8.71 (d, 1H), 8.54 (d, 1H), 7.58-7.66 (m, 2H), 5.22-5.34 (m, 1H), 4.29 (br t, 1H), 3.69 (dd, 1H), 3.44-3.52 (m, 2H), 3.10-3.23 (m, 1H), 2.90-3.01 (m, 2H), 2.38 (d, 1H).

Example 608

N-[1,1,1,4,4,4-Hexafluorobutan-2-yl]-7-[(4S)-4-hydroxy-2-oxopyrrolidin-1-yl]-4-oxo-1-(2,4,6-trifluorophenyl)-1,4-dihydro-1,8-naphthyridine-3-carboxamide (diastereomer 2)

LC-MS (Method 3): $R_t$=1.85 min; MS (ESIpos): m/z=583 [M+H]$^+$ $^1$H NMR (400 MHz, DMSO-d$_6$): δ ppm=10.37 (d, 1H), 9.09 (s, 1H), 8.71 (d, 1H), 8.55 (d, 1H), 7.57-7.66 (m, 2H), 5.21-5.34 (m, 1H), 4.27-4.31 (m, 1H), 3.69 (dd, 1H), 3.11-3.22 (m, 1H), 2.91-3.02 (m, 2H), 2.38 (br d, 1H).

Example 609

4-Oxo-7-(2-oxoimidazolidin-1-yl)-N-[1-(trifluoromethoxy)butan-2-yl]-1-(2,4,6-trifluorophenyl)-1,4-dihydro-1,8-naphthyridine-3-carboxamide (racemate)

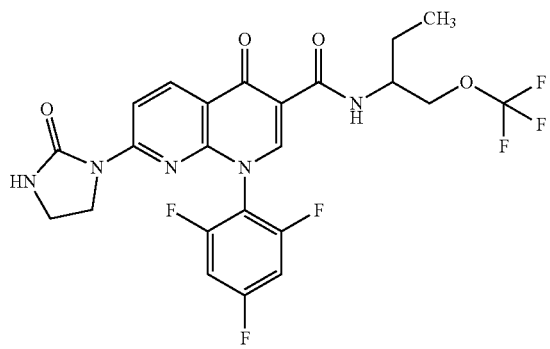 [SMILES: CCC(COC(F)(F)F)NC(=O)c1cn(-c2c(F)cc(F)cc2F)c2nc(N3CCNC3=O)ccc2c1=O]

According to GP1, 300 mg (742 μmol) of the compound from Example 113A were reacted with 201 mg (1.04 mmol) of 1-(trifluoromethoxy)butan-2-amine hydrochloride in the presence of 339 mg (890 μmol) of HATU and 390 μl (2.20 mmol) of DIPEA in 2.8 ml of DMF. The crude product was purified by means of preparative HPLC (acetonitrile/water/ 0.1% formic acid). 224 mg (52% of theory, 94% purity) of the title compound were obtained.

LC-MS (Method 3): $R_t$=1.92 min; MS (ESIpos): m/z=544 [M+H]$^+$ $^1$H NMR (400 MHz, DMSO-d$_6$): δ ppm=9.89 (br d, 1H), 8.92 (s, 1H), 8.55 (d, 1H), 8.42 (d, 1H), 7.65 (s, 1H), 7.53-7.63 (m, 2H), 4.15-4.25 (m, 3H), 3.54-3.64 (m, 2H), 3.32-3.38 (m, 2H), 1.55-1.74 (m, 2H), 0.95 (t, 3H).

216 mg of the title compound (racemate) were separated into the enantiomers by chiral HPLC (preparative HPLC: column: YMC Chiralart Cellulose SB 5 μm 250×20 mm; eluent: 70% n-heptane, 30% isopropanol; temperature: 30° C.; flow rate: 15 ml/min; UV detection: 220 nm).

This gave (in the sequence of elution from the column) 91.0 mg (21% of theory, 100% purity) of enantiomer 1 from Example 610 (99% ee) Rt=12.46 min and 88.0 mg (20% of theory, 100% purity) of enantiomer 2 from Example 611 (98% ee) Rt=14.51 min.

[Analytical HPLC: column: YMC Chiralart Amylose SB 5 μm 250×4.6 mm; eluent: 70% isohexane, 30% isopropanol; temperature: 40° C.; flow rate: 1.0 ml/min; UV detection: 220 nm]

Example 610

4-Oxo-7-(2-oxoimidazolidin-1-yl)-N-[1-(trifluoromethoxy)butan-2-yl]-1-(2,4,6-trifluorophenyl)-1,4-dihydro-1,8-naphthyridine-3-carboxamide (enantiomer 1)

LC-MS (Method 3): $R_t$=1.94 min; MS (ESIpos): m/z=544 [M+H]$^+$ $^1$H NMR (400 MHz, DMSO-d$_6$): δ ppm=9.89 (br d, 1H), 8.92 (s, 1H), 8.55 (d, 1H), 8.42 (d, 1H), 7.65 (s, 1H), 7.54-7.61 (m, 2H), 4.15-4.24 (m, 3H), 3.55-3.63 (m, 2H), 3.32-3.38 (m, 2H), 1.55-1.74 (m, 2H), 0.95 (t, 3H).

Example 611

4-Oxo-7-(2-oxoimidazolidin-1-yl)-N-[1-(trifluoromethoxy)butan-2-yl]-1-(2,4,6-trifluorophenyl)-1,4-dihydro-1,8-naphthyridine-3-carboxamide (enantiomer 2)

LC-MS (Method 3): $R_t$=1.94 min; MS (ESIpos): m/z=544 [M+H]$^+$ $^1$H NMR (400 MHz, DMSO-d$_6$): δ ppm=9.89 (br d, 1H), 8.92 (s, 1H), 8.55 (d, 1H), 8.42 (d, 1H), 7.65 (s, 1H), 7.53-7.62 (m, 2H), 4.15-4.24 (m, 3H), 3.55-3.63 (m, 2H), 3.32-3.38 (m, 2H), 1.54-1.74 (m, 2H), 0.95 (t, 3H).

Example 612

7-[(3R,4S)-3,4-Dihydroxypyrrolidin-1-yl]-4-oxo-N-(4,4,4-trifluoro-2-methylbutan-2-yl)-1-(2,4,6-trifluorophenyl)-1,4-dihydro-1,8-naphthyridine-3-carboxamide

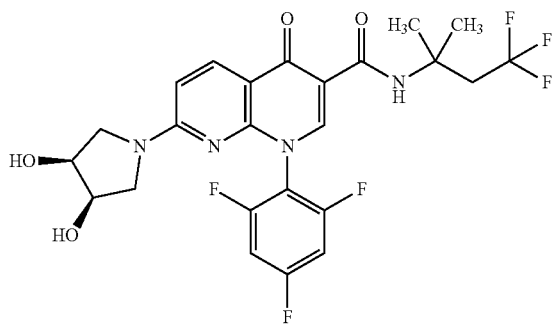 [SMILES: CC(C)(CC(F)(F)F)NC(=O)c1cn(-c2c(F)cc(F)cc2F)c2nc(N3C[C@@H](O)[C@@H](O)C3)ccc2c1=O]

According to GP1, 60.0 mg (142 μmol) of the compound from Example 156A were reacted with 30.3 mg (171 μmol) of 4,4,4-trifluoro-2-methylbutan-2-amine hydrochloride in the presence of 65.0 mg (171 μmol) of HATU and 99 μl (570 μmol) of DIPEA in 1.2 ml of DMF. The crude product was purified by means of preparative HPLC (acetonitrile/water/0.1% formic acid). 56.0 mg (72% of theory, 100% purity) of the title compound were obtained.

LC-MS (Method 3): $R_t$=1.75 min; MS (ESIpos): m/z=545 [M+H]$^+$ $^1$H NMR (400 MHz, DMSO-d$_6$): δ ppm=10.16 (s, 1H), 8.69 (s, 1H), 8.25 (d, 1H), 7.52-7.60 (m, 2H), 6.73 (d, 1H), 5.03 (d, 1H), 4.93 (d, 1H), 4.09-4.17 (m, 1H), 3.99-4.07 (m, 1H), 3.55-3.63 (m, 1H), 3.19-3.30 (m, 2H), 2.89-3.04 (m, 3H), 1.48 (s, 6H).

Example 613

N-(2,6-Dichlorophenyl)-4-oxo-7-(2-oxoimidazolidin-1-yl)-1-(2,4,6-trifluorophenyl)-1,4-dihydro-1,8-naphthyridine-3-carboxamide

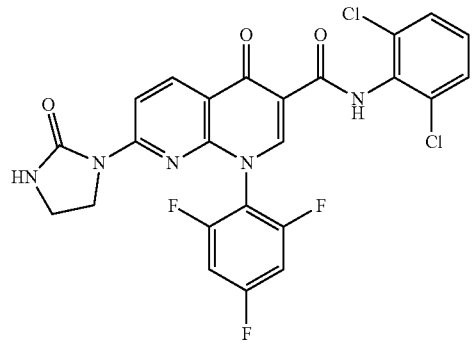 [SMILES: O=C(Nc1c(Cl)cccc1Cl)c1cn(-c2c(F)cc(F)cc2F)c2nc(N3CCNC3=O)ccc2c1=O]

According to GP2, 60.0 mg (120 μmol) of the compound from Example 160B were reacted with 147 mg (1.20 mmol) of imidazolidin-2-one hydrochloride in the presence of 24.9 mg (180 μmol) of potassium carbonate, 5.40 mg (24.1 μmol) of palladium acetate and 13.9 mg (24.1 μmol) of Xantphos in 1.1 ml of 1,4-dioxane. The crude product was purified by means of preparative HPLC (acetonitrile/water/0.1% formic acid). The substance was isolated with impurities and was further recrystallized from acetonitrile, filtered off with suction, washed with a little acetonitrile and dried. 38.5 mg (58% of theory, 100% purity) of the title compound were obtained.

LC-MS (Method 3): $R_t$=1.95 min; MS (ESIpos): m/z=548 [M+H]$^+$ $^1$H NMR (400 MHz, DMSO-d$_6$): δ ppm=11.70 (s, 1H), 9.08 (s, 1H), 8.62 (d, 1H), 8.47 (d, 1H), 7.68 (s, 1H), 7.54-7.63 (m, 4H), 7.39 (t, 1H), 3.57-3.65 (m, 2H), 3.33-3.39 (m, 2H).

Example 614

N-(1,1-Difluoro-2-methylpropan-2-yl)-4-oxo-7-(2-oxoimidazolidin-1-yl)-1-(2,4,6-trifluorophenyl)-1,4-dihydro-1,8-naphthyridine-3-carboxamide

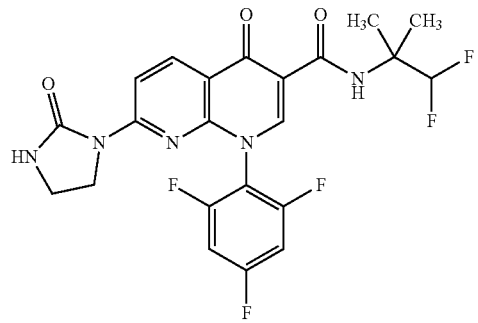 [SMILES: CC(C)(NC(=O)c1cn(-c2c(F)cc(F)cc2F)c2nc(N3CCNC3=O)ccc2c1=O)C(F)F]

According to GP1, 50.0 mg (124 μmol) of the compound from Example 113A were reacted with 25.2 mg (173 μmol) of 1,1-difluoro-2-methylpropan-2-amine hydrochloride in the presence of 56.4 mg (148 μmol) of HATU and 65 μl (370

μmol) of DIPEA in 460 μl of DMF. The crude product was purified by means of preparative HPLC (acetonitrile/water/0.1% formic acid). 34.9 mg (57% of theory, 100% purity) of the title compound were obtained.

LC-MS (Method 3): $R_t$=1.86 min; MS (ESIpos): m/z=496 [M+H]$^+$ $^1$H NMR (400 MHz, DMSO-$d_6$): δ ppm=10.12 (s, 1H), 8.91 (s, 1H), 8.55 (d, 1H), 8.42 (d, 1H), 7.65 (s, 1H), 7.53-7.61 (m, 2H), 6.43 (t, 1H), 3.53-3.65 (m, 2H), 3.32-3.38 (m, 2H), 1.45 (s, 6H).

Example 615

N-[(1S)-1-Cyclopropyl-2,2,2-trifluoroethyl]-7-[trans-3,4-dihydroxypiperidin-1-yl]-4-oxo-1-(2,4,6-trifluorophenyl)-1,4-dihydro-1,8-naphthyridine-3-carboxamide (diastereomer mixture)

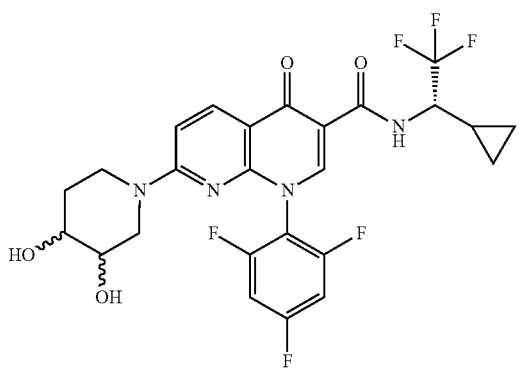 [SMILES: O=C(N[C@@H](C1CC1)C(F)(F)F)c1cn(-c2c(F)cc(F)cc2F)c2nc(N3CCC(O)C(O)C3)ccc2c1=O]

According to GP3, 150 mg (315 μmol) of the compound from Example 126A were reacted with 58.1 mg (378 μmol) of piperidine-3,4-diol hydrochloride and 160 μl (950 μmol) of DIPEA in 1.3 ml of DMF. The crude product was purified by means of preparative HPLC (acetonitrile/water/0.1% formic acid). 153 mg (87% of theory, 100% purity) of the title compound were obtained.

LC-MS (Method 4): $R_t$=2.95 min; MS (ESIpos): m/z=557 [M+H]$^+$ $^1$H NMR (400 MHz, DMSO-$d_6$): δ ppm=10.53 (d, 1H), 8.80 (s, 1H), 8.22-8.28 (m, 1H), 7.52-7.60 (m, 2H), 7.12 (d, 1H), 4.98 (br s, 1H), 4.86 (br s, 1H), 4.33-4.43 (m, 1H), 3.75-3.87 (m, 1H), 3.56-3.75 (m, 1H), 3.39-3.47 (m, 1H), 3.10-3.27 (m, 3H), 1.72-1.82 (m, 1H), 1.16-1.27 (m, 2H), 0.49-0.69 (m, 3H), 0.31-0.37 (m, 1H).

142 mg of the title compound (diastereomer mixture) were separated into the diastereomers by chiral HPLC (preparative SFC: column: Chiralpak AD 250×20 mm; eluent: 85% carbon dioxide, 15% ethanol; temperature: 40° C.; flow rate: 80 ml/min; UV detection: 210 nm).

This gave (in the sequence of elution from the column) 63.80 mg (15% of theory, 100% purity) of diastereomer 1 from Example 616 (99% de) Rt=7.56 min and 62.10 mg (18% of theory, 100% purity) of diastereomer 2 from Example 617 (96% de) Rt=9.25 min.

[Analytical SFC: column: AD; eluent: 80% carbon dioxide, 20% ethanol; flow rate: 3.0 ml/min; UV detection: 210 nm].

Example 616

N-[(1S)-1-Cyclopropyl-2,2,2-trifluoroethyl]-7-[trans-3,4-dihydroxypiperidin-1-yl]-4-oxo-1-(2,4,6-trifluorophenyl)-1,4-dihydro-1,8-naphthyridine-3-carboxamide (diastereomer 1)

LC-MS (Method 1): $R_t$=0.96 min; MS (ESIpos): m/z=557 [M+H]$^+$ $^1$H NMR (600 MHz, DMSO-$d_6$): δ ppm=10.54 (d, 1H), 8.80 (s, 1H), 8.26 (d, 1H), 7.54-7.60 (m, 2H), 7.12 (d, 1H), 4.96-5.03 (m, 1H), 4.88 (d, 1H), 4.34-4.41 (m, 1H), 3.76-3.84 (m, 1H), 3.52-3.74 (m, 1H), 3.39-3.46 (m, 1H), 3.05-3.29 (m, 2H), 1.71-1.82 (m, 1H), 1.17-1.26 (m, 2H), 0.63-0.68 (m, 1H), 0.51-0.60 (m, 2H), 0.31-0.35 (m, 1H).

Example 617

N-[(1S)-1-Cyclopropyl-2,2,2-trifluoroethyl]-7-[trans-3,4-dihydroxypiperidin-1-yl]-4-oxo-1-(2,4,6-trifluorophenyl)-1,4-dihydro-1,8-naphthyridine-3-carboxamide (diastereomer 2)

LC-MS (Method 1): $R_t$=0.96 min; MS (ESIpos): m/z=557 [M+H]$^+$ $^1$H NMR (600 MHz, DMSO-$d_6$): δ ppm=10.54 (d, 1H), 8.80 (s, 1H), 8.26 (d, 1H), 7.54-7.60 (m, 2H), 7.12 (d, 1H), 5.00 (br d, 1H), 4.88 (d, 1H), 4.34-4.41 (m, 1H), 3.77-3.84 (m, 1H), 3.68 (br s, 1H), 3.38-3.48 (m, 2H), 3.18-3.26 (m, 2H), 1.76 (br s, 1H), 1.21-1.28 (m, 1H), 1.16-1.26 (m, 1H), 0.63-0.68 (m, 1H), 0.51-0.60 (m, 2H), 0.33 (br dd, 1H).

Example 618

1-(2,6-Difluorophenyl)-7-[(3R,4R)-3,4-dihydroxy-pyrrolidin-1-yl]-4-oxo-N-[(2R)-1,1,1-trifluorobutan-2-yl]-1,4-dihydro-1,8-naphthyridine-3-carboxamide

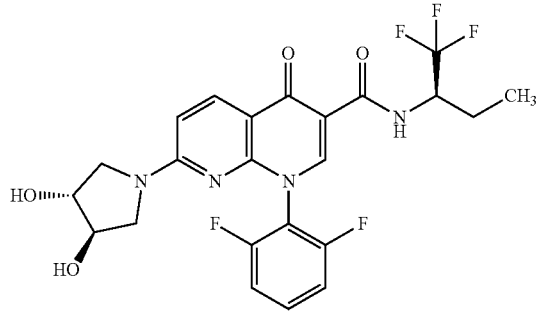 [SMILES: CC[C@@H](NC(=O)c1cn(-c2c(F)cccc2F)c2nc(N3C[C@@H](O)[C@H](O)C3)ccc2c1=O)C(F)(F)F]

To a solution of 115 mg (155 μmol) of the compound from Example 165A in 1.3 ml of THF were added 350 μl (1.0 M in THF, 350 μmol) of tetra-n-butylammonium fluoride, and the reaction mixture was stirred at room temperature for 2 h. The solvent was removed under reduced pressure and the residue was purified by means of normal phase chromatography (ethyl acetate-cyclohexane gradient). The substance was isolated with impurities and was purified further by means of preparative HPLC (acetonitrile/water/0.1% formic acid). 26 mg (33% of theory, 100% purity) of the title compound were obtained.

LC-MS (Method 3): $R_t$=1.63 min; MS (ESIpos): m/z=513 [M+H]$^+$ $^1$H NMR (400 MHz, DMSO-d$_6$): δ ppm=10.45 (d, 1H), 8.75 (s, 1H), 8.28 (d, 1H), 7.67-7.75 (m, 1H), 7.42 (t, 2H), 6.78 (d, 1H), 5.22 (d, 1H), 5.13 (d, 1H), 4.68-4.79 (m, 1H), 4.04 (br s, 1H), 3.89 (br s, 1H), 3.57-3.64 (m, 1H), 3.32-3.37 (m, 1H), 3.19 (dd, 1H), 3.02 (d, 1H), 1.83-1.93 (m, 1H), 1.59-1.70 (m, 1H), 0.97 (t, 3H).

Example 619

7-[7-Hydroxy-5-azaspiro[2.4]hept-5-yl]-4-oxo-N-[(2S)-1,1,1-trifluorobutan-2-yl]-1-(2,4,6-trifluorophenyl)-1,4-dihydro-1,8-naphthyridine-3-carboxamide (diastereomer mixture)

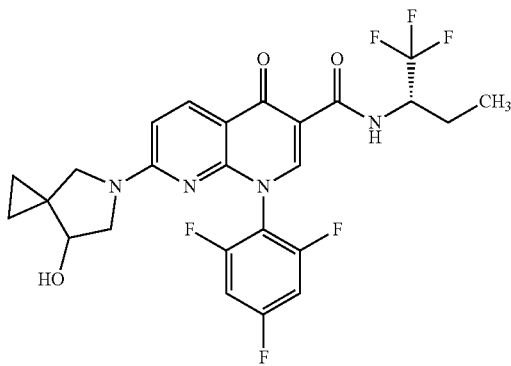 [SMILES: CC[C@H](NC(=O)c1cn(-c2c(F)cc(F)cc2F)c2nc(N3CC(O)C4(CC4)C3)ccc2c1=O)C(F)(F)F]

According to GP1, 80.0 mg (185 μmol) of the compound from Example 155A were reacted with 36.4 mg (223 μmol) of (2S)-1,1,1-trifluorobutan-2-amine hydrochloride in the presence of 84.6 mg (223 μmol) of HATU and 97 μl (560 μmol) of DIPEA in 890 μl of DMF. The crude product was purified by means of preparative HPLC (acetonitrile/water/0.1% formic acid). 90.2 mg (90% of theory, 100% purity) of the title compound were obtained.

LC-MS (Method 4): R$_t$=3.57 min; MS (ESIpos): m/z=541 [M+H]$^+$ $^1$H NMR (400 MHz, DMSO-d$_6$): δ ppm=10.43 (d, 1H), 8.77-8.82 (m, 1H), 8.28 (d, 1H), 7.49-7.61 (m, 2H), 6.80 (br d, 0.40H), 6.69 (d, 0.60H), 5.04-5.11 (m, 0.40H), 4.95-5.02 (m, 0.60H), 4.68-4.78 (m, 1H), 3.61-3.78 (m, 2H), 3.34-3.49 (m, 1.60H), 3.14-3.26 (m, 1H), 2.84-2.92 (m, 0.40H), 1.83-1.92 (m, 1H), 1.58-1.70 (m, 1H), 0.97 (t, 3H), 0.77-0.86 (m, 1H), 0.44-0.63 (m, 3H).

78.7 mg of the title compound (diastereomer mixture) were separated into the diastereomers by chiral HPLC (preparative HPLC: column: Daicel Chiralpak IA 5 μm 250×20 mm; eluent: 80% n-heptane, 20% ethanol; temperature: 25° C.; flow rate: 15 ml/min; UV detection: 210 nm).

This gave (in the sequence of elution from the column) 33.4 mg (33% of theory, 100% purity) of diastereomer 1 from Example 620 (99% de) Rt=8.04 min and 34.5 mg (34% of theory, 100% purity) of diastereomer 2 from Example 621 (98% de) Rt=9.82 min.

[Analytical HPLC: column: Daicel IA-3 3 μm 50×4.6 mm; eluent: 80% isohexane, 20% ethanol; UV detection: 220 nm].

Example 620

7-[7-Hydroxy-5-azaspiro[2.4]hept-5-yl]-4-oxo-N-[(2S)-1,1,1-trifluorobutan-2-yl]-1-(2,4,6-trifluorophenyl)-1,4-dihydro-1,8-naphthyridine-3-carboxamide (diastereomer 1)

LC-MS (Method 1): R$_t$=1.10 min; MS (ESIpos): m/z=541 [M+H]$^+$ $^1$H NMR (400 MHz, DMSO-d$_6$): δ ppm=10.43 (d, 1H), 8.78-8.83 (m, 1H), 8.28 (d, 1H), 7.49-7.61 (m, 2H), 6.81 (br d, 0.40H), 6.69 (br d, 0.60H), 4.93-5.13 (m, 1H), 4.68-4.79 (m, 1H), 3.60-3.78 (m, 2H), 3.32-3.48 (m, 1.60H), 3.14-3.27 (m, 1H), 2.88 (br d, 0.40H), 1.83-1.93 (m, 1H), 1.58-1.70 (m, 1H), 0.97 (t, 3H), 0.76-0.88 (m, 1H), 0.44-0.63 (m, 3H).

Example 621

7-[7-Hydroxy-5-azaspiro[2.4]hept-5-yl]-4-oxo-N-[(2S)-1,1,1-trifluorobutan-2-yl]-1-(2,4,6-trifluorophenyl)-1,4-dihydro-1,8-naphthyridine-3-carboxamide (diastereomer 2)

LC-MS (Method 1): R$_t$=1.10 min; MS (ESIpos): m/z=541 [M+H]$^+$ $^1$H NMR (400 MHz, DMSO-d$_6$): δ ppm=10.43 (d, 1H), 8.78-8.83 (m, 1H), 8.28 (d, 1H), 7.49-7.61 (m, 2H), 6.81 (br d, 0.40H), 6.69 (br d, 0.60H), 4.92-5.19 (m, 1H), 4.68-4.79 (m, 1H), 3.59-3.78 (m, 2H), 3.33-3.48 (m, 1.60H), 3.14-3.27 (m, 1H), 2.88 (br d, 0.40H), 1.83-1.93 (m, 1H), 1.58-1.70 (m, 1H), 0.97 (t, 3H), 0.76-0.88 (m, 1H), 0.44-0.63 (m, 3H).

Example 622

1-(2,4-Difluorophenyl)-7-[(4S)-4-hydroxy-2-oxopyrrolidin-1-yl]-4-oxo-N-[3,3,4,4,4-pentafluorobutan-2-yl]-1,4-dihydro-1,8-naphthyridine-3-carboxamide (diastereomer mixture)

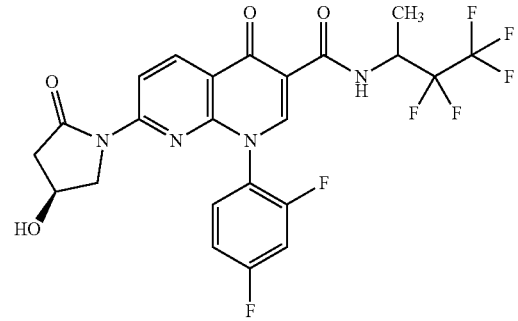 [SMILES: CC(NC(=O)c1cn(-c2ccc(F)cc2F)c2nc(N3C[C@@H](O)CC3=O)ccc2c1=O)C(F)(F)C(F)(F)F]

According to GP1, 150 mg (374 μmol) of the compound from Example 63A were reacted with 89.5 mg (449 μmol) of 3,3,4,4,4-pentafluorobutan-2-amine hydrochloride in the presence of 171 mg (449 μmol) of HATU and 260 μl (1.50 mmol) of DIPEA in 1.5 ml of DMF. The crude product was purified by means of preparative HPLC (acetonitrile/water/0.1% formic acid). 177 mg (87% of theory, 100% purity) of the title compound were obtained.

LC-MS (Method 1): R$_t$=1.03 min; MS (ESIpos): m/z=547 [M+H]$^+$ $^1$H NMR (400 MHz, DMSO-d$_6$): δ ppm=10.35 (br d, 1H), 8.85 (d, 1H), 8.70 (d, 1H), 8.52 (dd, 1H), 7.81-7.93 (m, 1H), 7.63 (br t, 1H), 7.37 (br t, 1H), 5.28-5.36 (m, 1H), 4.98-5.11 (m, 1H), 4.26-4.31 (m, 1H), 3.62-3.71 (m, 1H), 3.42-3.51 (m, 1H), 2.89-2.99 (m, 1H), 2.32-2.41 (m, 1H), 1.41 (d, 3H).

167 mg of the title compound (diastereomer mixture) were separated into the diastereomers by chiral HPLC (preparative HPLC: column: Chiralpak AD-H 5 µm 250×30 mm; eluent: 80% n-heptane, 20% isopropanol; temperature: 23° C.; flow rate: 50 ml/min; UV detection: 220 nm).

This gave (in the sequence of elution from the column) 74.1 mg of diastereomer 1 (99% de) Rt=6.33 min and 71.3 mg of diastereomer 2 (95% de) Rt=9.54 min.

[Analytical HPLC: column: Daicel AD-3 3 µm 50×4.6 mm; eluent: 80% isohexane, 20% isopropanol; UV detection: 220 nm].

Diastereomer 1 was additionally purified by means of preparative HPLC (column: Chromatorex C18, 10 µm, 125*40 mm, solvent: acetonitrile, water, 0.1% formic acid), and 60.3 mg (30% of theory, 100% purity) of the title compound from Example 623 were obtained.

Diastereomer 2 was additionally purified by means of preparative HPLC (column: Chromatorex C18, 10 µm, 125*40 mm, solvent: acetonitrile, water, 0.1% formic acid), and 60.2 mg (30% of theory, 100% purity) of the title compound from Example 624 were obtained.

Example 623

1-(2,4-Difluorophenyl)-7-[(4S)-4-hydroxy-2-oxopyrrolidin-1-yl]-4-oxo-N-[3,3,4,4,4-pentafluorobutan-2-yl]-1,4-dihydro-1,8-naphthyridine-3-carboxamide (diastereomer 1)

LC-MS (Method 3): $R_t$=1.88 min; MS (ESIpos): m/z=547 [M+H]$^+$ $^1$H NMR (400 MHz, DMSO-d$_6$): δ ppm=10.35 (d, 1H), 8.83-8.87 (m, 1H), 8.70 (d, 1H), 8.51 (dd, 1H), 7.80-7.93 (m, 1H), 7.63 (br t, 1H), 7.37 (br t, 1H), 5.28-5.37 (m, 1H), 4.98-5.11 (m, 1H), 4.26-4.31 (m, 1H), 3.66 (td, 1H), 3.47 (br t, 1H), 2.88-2.99 (m, 1H), 2.32-2.42 (m, 1H), 1.41 (d, 3H).

Example 624

1-(2,4-Difluorophenyl)-7-[(4S)-4-hydroxy-2-oxopyrrolidin-1-yl]-4-oxo-N-[3,3,4,4,4-pentafluorobutan-2-yl]-1,4-dihydro-1,8-naphthyridine-3-carboxamide (diastereomer 2)

LC-MS (Method 3): $R_t$=1.88 min; MS (ESIpos): m/z=547 [M+H]$^+$ $^1$H NMR (400 MHz, DMSO-d$_6$): δ ppm=10.35 (br dd, 1H), 8.85 (d, 1H), 8.70 (d, 1H), 8.52 (dd, 1H), 7.82-7.92 (m, 1H), 7.62 (br t, 1H), 7.37 (br t, 1H), 5.27-5.36 (m, 1H), 4.98-5.12 (m, 1H), 4.26-4.31 (m, 1H), 3.62-3.72 (m, 1H), 3.46 (br t, 1H), 2.89-3.00 (m, 1H), 2.37 (br dd, 1H), 1.41 (d, 3H).

Example 625

7-[(3R,4R)-3,4-Dihydroxypyrrolidin-1-yl]-4-oxo-N-[1-(trifluoromethyl)cyclobutyl]-1-(2,4,6-trifluorophenyl)-1,4-dihydro-1,8-naphthyridine-3-carboxamide

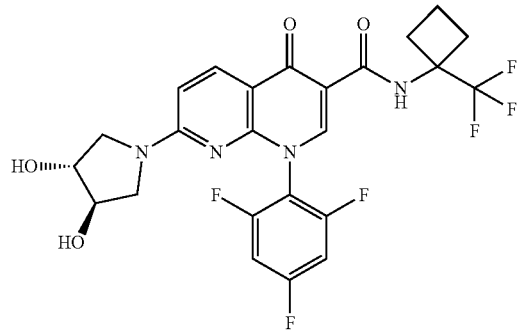 [SMILES: O=C(NC1(C(F)(F)F)CCC1)c1cn(-c2c(F)cc(F)cc2F)c2nc(N3C[C@@H](O)[C@H](O)C3)ccc2c1=O]

According to GP1, 50.0 mg (119 µmol) of the compound from Example 121A were reacted with 25.0 mg (142 µmol) of 1-(trifluoromethyl)cyclobutanamine hydrochloride in the presence of 54.1 mg (142 µmol) of HATU and 62 µl (360 µmol) of DIPEA in 460 µl of DMF. The crude product was purified by means of preparative HPLC (acetonitrile/water/0.1% formic acid). 48.7 mg (76% of theory, 100% purity) of the title compound were obtained.

LC-MS (Method 3): $R_t$=1.73 min; MS (ESIpos): m/z=543 [M+H]$^+$ $^1$H NMR (400 MHz, DMSO-d$_6$): δ ppm=10.54 (s, 1H), 8.75 (s, 1H), 8.27 (d, 1H), 7.53-7.60 (m, 2H), 6.77 (d, 1H), 5.10-5.31 (m, 2H), 4.05 (br s, 1H), 3.93 (br s, 1H), 3.57-3.64 (m, 1H), 3.33-3.37 (m, 2H), 3.21-3.28 (m, 2H), 3.07 (br d, 1H), 2.56-2.65 (m, 2H), 1.90-2.06 (m, 2H).

Example 626

N-(Bicyclo[1.1.1]pent-1-yl)-7-[7-hydroxy-5-azaspiro[2.4]hept-5-yl]-4-oxo-1-(2,4,6-trifluorophenyl)-1,4-dihydro-1,8-naphthyridine-3-carboxamide (racemate)

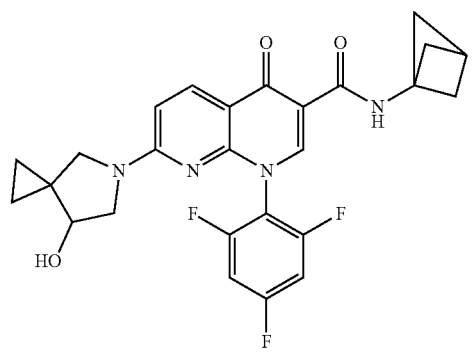 [SMILES: O=C(NC12CC(C1)C2)c1cn(-c2c(F)cc(F)cc2F)c2nc(N3CC(O)C4(CC4)C3)ccc2c1=O]

According to GP1, 80.0 mg (119 µmol) of the compound from Example 155A were reacted with 26.6 mg (223 µmol) of bicyclo[1.1.1]pentan-1-amine hydrochloride in the presence of 84.6 mg (223 µmol) of HATU and 97 µl (560 µmol) of DIPEA in 890 µl of DMF. The crude product was purified by means of preparative HPLC (acetonitrile/water/0.1% formic acid). 57.8 mg (63% of theory, 100% purity) of the title compound were obtained.

LC-MS (Method 4): $R_t$=3.34 min; MS (ESIpos): m/z=497 [M+H]$^+$ $^1$H NMR (400 MHz, DMSO-d$_6$): δ ppm=10.28 (s, 1H), 8.63-8.68 (m, 1H), 8.25 (d, 1H), 7.49-7.61 (m, 2H), 6.78 (br d, 0.40H), 6.66 (br d, 0.60H), 5.02-5.11 (m, 0.40H), 4.95-5.02 (m, 0.60H), 3.58-3.78 (m, 2H), 3.33-3.47 (m, 2H), 3.11-3.25 (m, 1H), 2.87 (br d, 0.40H), 2.09 (s, 6H), 0.77-0.87 (m, 1H), 0.52-0.62 (m, 2H), 0.43-0.52 (m, 1H).

53.4 mg of the title compound (racemate) were separated into the enantiomers by chiral HPLC (preparative HPLC: column: YMC Chiralart Amylose SA 5 μm 250×30 mm; eluent: 85% n-heptane, 15% ethanol; temperature: 25° C.; flow rate: 30 ml/min; UV detection: 220 nm).

This gave (in the sequence of elution from the column) 22.0 mg (24% of theory, 100% purity) of enantiomer 1 from Example 627 (99% ee) Rt=15.56 min and 23.0 mg (25% of theory, 100% purity) of enantiomer 2 from Example 628 (99% ee) Rt=18.15 min.

[Analytical HPLC: column: YMC Chiralart Amylose SA 5 μm 250×4.6 mm; eluent: 80% isohexane, 20% ethanol; temperature: 25° C.; flow rate: 1.0 ml/min; UV detection: 220 nm]

Example 627

N-(Bicyclo[1.1.1]pent-1-yl)-7-[7-hydroxy-5-azaspiro [2.4]hept-5-yl]-4-oxo-1-(2,4,6-trifluorophenyl)-1,4-dihydro-1,8-naphthyridine-3-carboxamide (enantiomer 1)

LC-MS (Method 3): $R_t$=1.99 min; MS (ESIpos): m/z=497 [M+H]$^+$ $^1$H NMR (400 MHz, DMSO-d$_6$): δ ppm=10.28 (s, 1H), 8.63-8.68 (m, 1H), 8.25 (d, 1H), 7.49-7.61 (m, 2H), 6.77 (br d, 0.40H), 6.66 (br d, 0.60H), 5.02-5.09 (m, 0.40H), 4.94-5.02 (m, 0.60H), 3.60-3.77 (m, 2H), 3.31-3.47 (m, 1.60H), 3.14-3.25 (m, 1H), 2.87 (d, 0.40H), 2.09 (s, 6H), 0.77-0.87 (m, 1H), 0.52-0.62 (m, 2H), 0.43-0.52 (m, 1H).

Example 628

N-(Bicyclo[1.1.1]pent-1-yl)-7-[7-hydroxy-5-azaspiro [2.4]hept-5-yl]-4-oxo-1-(2,4,6-trifluorophenyl)-1,4-dihydro-1,8-naphthyridine-3-carboxamide (enantiomer 2)

LC-MS (Method 3): $R_t$=1.99 min; MS (ESIpos): m/z=497 [M+H]$^+$ $^1$H NMR (400 MHz, DMSO-d$_6$): δ ppm=10.28 (s, 1H), 8.63-8.68 (m, 1H), 8.25 (d, 1H), 7.49-7.61 (m, 2H), 6.78 (br d, 0.40H), 6.66 (br d, 0.60H), 5.02-5.09 (m, 0.40H), 4.97 (br d, 0.60H), 3.59-3.78 (m, 2H), 3.32-3.47 (m, 1.60H), 3.13-3.25 (m, 1H), 2.87 (br d, 0.40H), 2.09 (s, 6H), 0.77-0.87 (m, 1H), 0.44-0.63 (m, 3H).

Example 629

N-[(1R)-1-Cyclopropyl-2,2,2-trifluoroethyl]-1-(2,6-difluorophenyl)-4-oxo-7-(2-oxoimidazolidin-1-yl)-1,4-dihydro-1,8-naphthyridine-3-carboxamide

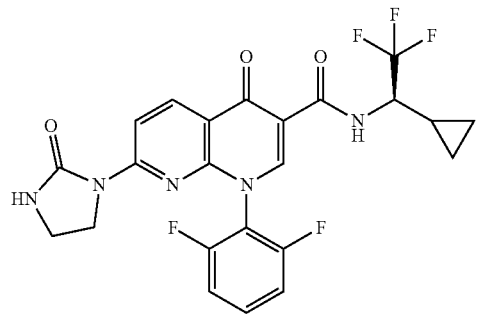 [SMILES: O=C(N[C@H](C1CC1)C(F)(F)F)c1cn(-c2c(F)cccc2F)c2nc(N3CCNC3=O)ccc2c1=O]

According to GP2, 60.0 mg (131 μmol) of the compound from Example 103A were reacted with 113 mg (1.31 mmol) of imidazolidin-2-one in the presence of 27.2 mg (197 μmol) of potassium carbonate, 5.88 mg (26.2 μmol) of palladium acetate and 15.2 mg (26.2 μmol) of Xantphos in 1.2 ml of 1,4-dioxane. The crude product was purified by means of preparative HPLC (acetonitrile/water/0.1% formic acid). The substance was isolated with impurities and was further recrystallized from acetonitrile, filtered off with suction, washed with a little cold acetonitrile and dried. 39.6 mg (60% of theory, 100% purity) of the title compound were obtained.

LC-MS (Method 3): $R_t$=1.91 min; MS (ESIpos): m/z=508 [M+H]$^+$ $^1$H NMR (400 MHz, DMSO-d$_6$): δ ppm=10.36 (d, 1H), 8.94 (s, 1H), 8.57 (d, 1H), 8.44 (d, 1H), 7.68-7.76 (m, 1H), 7.66 (br s, 1H), 7.43 (t, 2H), 4.35-4.45 (m, 1H), 3.50-3.58 (m, 2H), 3.32-3.36 (m, 2H), 1.18-1.27 (m, 1H), 0.51-0.70 (m, 3H), 0.32-0.39 (m, 1H).

Example 630

N-[(1S)-1-Cyclopropyl-2,2,2-trifluoroethyl]-7-[(3R,4S)-3,4-dihydroxypyrrolidin-1-yl]-4-oxo-1-(2,4,6-trifluorophenyl)-1,4-dihydro-1,8-naphthyridine-3-carboxamide

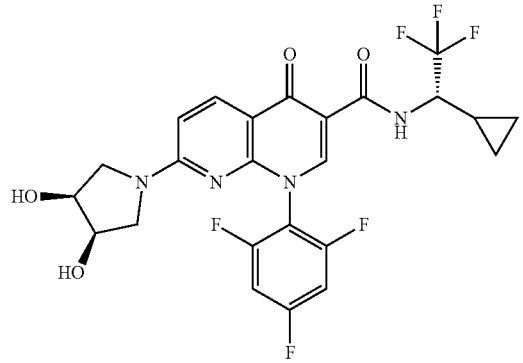 [SMILES: O=C(N[C@@H](C1CC1)C(F)(F)F)c1cn(-c2c(F)cc(F)cc2F)c2nc(N3C[C@@H](O)[C@@H](O)C3)ccc2c1=O]

According to GP3, 60.0 mg (126 µmol) of the compound from Example 126A were reacted with 21.1 mg (151 µmol) of (3R,4S)-pyrrolidine-3,4-diol hydrochloride and 77 µl (440 µmol) of DIPEA in 600 µl of DMF. The crude product was purified by means of preparative HPLC (acetonitrile/water/0.1% formic acid). 61.2 mg (89% of theory, 100% purity) of the title compound were obtained.

LC-MS (Method 3): $R_t$=1.77 min; MS (ESIpos): m/z=543 [M+H]$^+$ $^1$H NMR (400 MHz, DMSO-$d_6$): δ ppm=10.56 (d, 1H), 8.80 (s, 1H), 8.28 (d, 1H), 7.52-7.60 (m, 2H), 6.76 (d, 1H), 5.04 (d, 1H), 4.94 (d, 1H), 4.33-4.43 (m, 1H), 4.10-4.16 (m, 1H), 3.99-4.05 (m, 1H), 3.60 (br dd, 1H), 3.20-3.30 (m, 2H), 2.97-3.04 (m, 1H), 1.16-1.25 (m, 1H), 0.49-0.68 (m, 3H), 0.29-0.37 (m, 1H).

Example 631

N-(2,6-Dichlorophenyl)-1-(2,4-difluorophenyl)-7-[(3R,4R)-3,4-dihydroxypyrrolidin-1-yl]-4-oxo-1,4-dihydro-1,8-naphthyridine-3-carboxamide

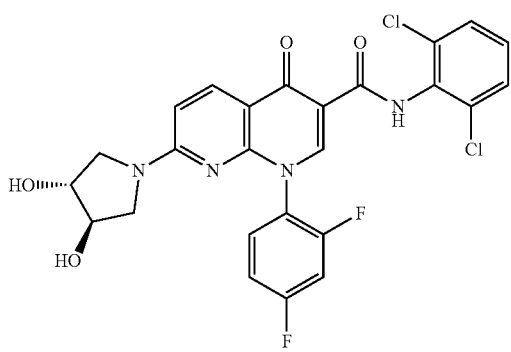 [SMILES: O=C(Nc1c(Cl)cccc1Cl)c1cn(-c2ccc(F)cc2F)c2nc(N3C[C@@H](O)[C@H](O)C3)ccc2c1=O]

According to GP3, 40.0 mg (83.2 µmol) of the compound from Example 81A were reacted with 13.9 mg (99.9 µmol) of (3R,4R)-pyrrolidine-3,4-diol hydrochloride and 51 µl (290 µmol) of DIPEA in 400 µl of DMF. The crude product was purified by means of preparative HPLC (acetonitrile/water/0.1% formic acid). 31.2 mg (68% of theory, 100% purity) of the title compound were obtained.

LC-MS (Method 3): $R_t$=1.68 min; MS (ESIpos): m/z=547 [M+H]$^+$ $^1$H NMR (400 MHz, DMSO-$d_6$): δ ppm=12.04 (s, 1H), 8.68 (s, 1H), 8.34 (d, 1H), 7.85 (td, 1H), 7.55-7.61 (m, 2H), 7.30-7.40 (m, 2H), 6.78 (d, 1H), 5.07-5.29 (m, 2H), 4.01-4.09 (m, 1H), 3.93 (br s, 1H), 3.57-3.66 (m, 1H), 3.16-3.28 (m, 2H), 3.03-3.14 (m, 1H).

Example 632

7-[(4S)-4-Hydroxy-2-oxopyrrolidin-1-yl]-4-oxo-N-[1-(2,2,2-trifluoroethyl)cyclopropyl]-1-(2,4,6-trifluorophenyl)-1,4-dihydro-1,8-naphthyridine-3-carboxamide

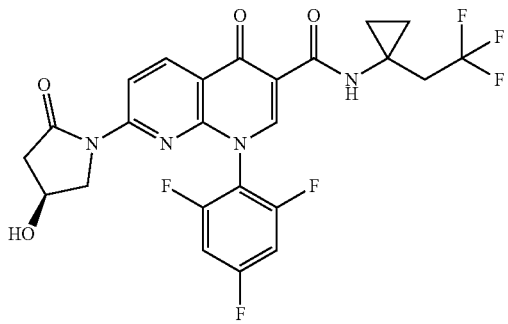 [SMILES: O=C(NC1(CC(F)(F)F)CC1)c1cn(-c2c(F)cc(F)cc2F)c2nc(N3C[C@@H](O)CC3=O)ccc2c1=O]

According to GP1, 23.7 mg (56.4 µmol) of the compound from Example 117A were reacted with 10.4 mg (59.2 µmol) of 1-(2,2,2-trifluoroethyl)cyclopropanamine hydrochloride in the presence of 25.7 mg (67.7 µmol) of HATU and 39 µl (500 µmol) of DIPEA in 500 µl of DMF. The crude product was purified by means of preparative HPLC (acetonitrile/water/0.1% formic acid). 20.1 mg (66% of theory, 100% purity) of the title compound were obtained.

LC-MS (Method 3): $R_t$=1.72 min; MS (ESIpos): m/z=541 [M+H]$^+$ $^1$H NMR (400 MHz, DMSO-$d_6$): δ ppm=9.99 (s, 1H), 8.97 (s, 1H), 8.67 (d, 1H), 8.51 (d, 1H), 7.57-7.65 (m, 2H), 5.32 (d, 1H), 4.26-4.31 (m, 1H), 3.68 (dd, 1H), 3.47 (d, 1H), 2.94 (dd, 1H), 2.68 (q, 2H), 2.37 (d, 1H), 0.86-0.95 (m, 4H).

Example 633

Methyl 4-[6-(bicyclo[1.1.1]pent-1-ylcarbamoyl)-5-oxo-8-(2,4,6-trifluorophenyl)-5,8-dihydro-1,8-naphthyridin-2-yl]piperazine-1-carboxylate

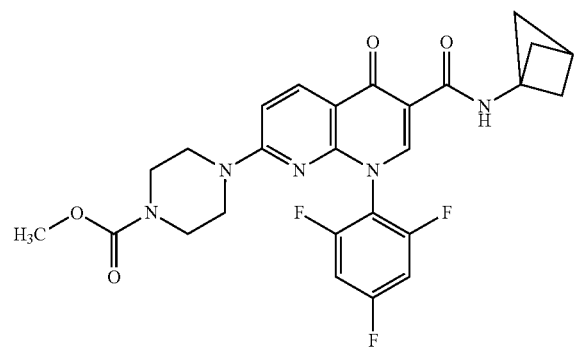 [SMILES: COC(=O)N1CCN(c2ccc3c(=O)c(C(=O)NC45CC(C4)C5)cn(-c4c(F)cc(F)cc4F)c3n2)CC1]

According to GP1, 70.0 mg (151 µmol) of the compound from Example 157A were reacted with 21.7 mg (182 µmol) of bicyclo[1.1.1]pentan-1-amine hydrochloride in the presence of 69.1 mg (182 µmol) of HATU and 79 µl (450 µmol) of DIPEA in 580 µl of DMF. The crude product was purified by means of preparative HPLC (acetonitrile/water/0.1% formic acid). 4.80 mg (6% of theory, 100% purity) of the title compound were obtained.

LC-MS (Method 3): $R_t$=2.05 min; MS (ESIpos): m/z=528 [M+H]+

$^1$H NMR (400 MHz, DMSO-d$_6$): δ ppm=10.22 (s, 1H), 8.69 (s, 1H), 8.29 (d, 1H), 7.57 (t, 2H), 7.11 (d, 1H), 3.60 (s, 3H), 3.47-3.56 (m, 4H), 3.33-3.43 (m, 4H), 2.09 (s, 6H).

Example 634

N-(1,1-Difluoro-2-methylpropan-2-yl)-7-[(3R,4R)-3,4-dihydroxypyrrolidin-1-yl]-4-oxo-1-(2,4,6-trifluorophenyl)-1,4-dihydro-1,8-naphthyridine-3-carboxamide

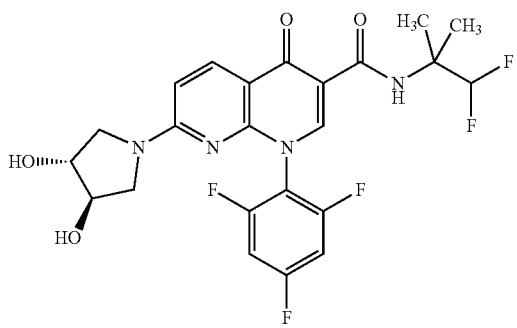 [SMILES: CC(C)(NC(=O)c1cn(-c2c(F)cc(F)cc2F)c2nc(N3C[C@@H](O)[C@H](O)C3)ccc2c1=O)C(F)F]

According to GP1, 30.0 mg (119 μmol) of the compound from Example 121A were reacted with 12.4 mg (85.4 μmol) of 1,1-difluoro-2-methylpropan-2-amine hydrochloride in the presence of 32.5 mg (85.4 μmol) of HATU and 37 μl (210 μmol) of DIPEA in 340 μl of DMF. The crude product was purified by means of preparative HPLC (acetonitrile/water/0.1% formic acid). 10.3 mg (28% of theory, 100% purity) of the title compound were obtained.

LC-MS (Method 3): $R_t$=1.61 min; MS (ESIpos): m/z=513 [M+H]+

$^1$H NMR (400 MHz, DMSO-d$_6$): δ ppm=10.32 (s, 1H), 8.71 (s, 1H), 8.26 (d, 1H), 7.52-7.60 (m, 2H), 6.76 (d, 1H), 6.43 (t, 1H), 5.23 (d, 1H), 5.13 (d, 1H), 4.04 (br s, 1H), 3.88-3.97 (m, 1H), 3.61 (br dd, 1H), 3.32-3.36 (m, 1H), 3.21-3.27 (m, 1H), 3.06 (br d, 1H), 1.43 (s, 6H).

Example 635

7-[(3R,4R)-3,4-Dihydroxypyrrolidin-1-yl]-4-oxo-N-[1-(2,2,2-trifluoroethyl)cyclopropyl]-1-(2,4,6-trifluorophenyl)-1,4-dihydro-1,8-naphthyridine-3-carboxamide

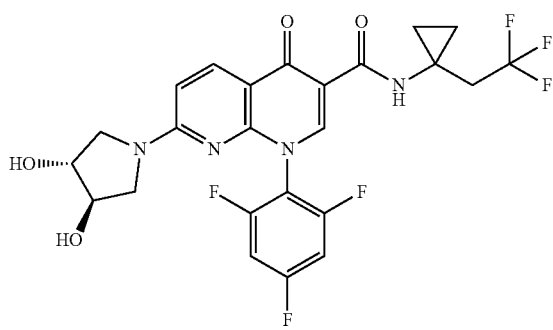 [SMILES: O=C(NC1(CC(F)(F)F)CC1)c1cn(-c2c(F)cc(F)cc2F)c2nc(N3C[C@@H](O)[C@H](O)C3)ccc2c1=O]

According to GP1, 23.8 mg (56.4 μmol) of the compound from Example 121A were reacted with 10.4 mg (59.2 μmol) of 1-(2,2,2-trifluoroethyl)cyclopropanamine hydrochloride in the presence of 25.7 mg (67.7 μmol) of HATU and 39 μl (230 μmol) of DIPEA in 500 μl of DMF. The crude product was purified by means of preparative HPLC (acetonitrile/water/0.1% formic acid). 18.9 mg (62% of theory, 100% purity) of the title compound were obtained.

LC-MS (Method 3): $R_t$=1.53 min; MS (ESIpos): m/z=543 [M+H]+

$^1$H NMR (400 MHz, DMSO-d$_6$): δ ppm=10.25 (s, 1H), 8.70 (s, 1H), 8.24 (d, 1H), 7.52-7.59 (m, 2H), 6.75 (d, 1H), 5.22 (d, 1H), 5.13 (d, 1H), 4.02-4.06 (m, 1H), 3.90-3.94 (m, 1H), 3.57-3.63 (m, 1H), 3.32-3.35 (m, 1H), 3.21-3.27 (m, 1H), 3.06 (br d, 1H), 2.62-2.71 (m, 2H), 0.84-0.93 (m, 4H).

Example 636

7-[(3R,4R)-3,4-Dihydroxypyrrolidin-1-yl]-N-(2,6-dichlorophenyl)-4-oxo-1-(2,4,6-trifluorophenyl)-1,4-dihydro-1,8-naphthyridine-3-carboxamide

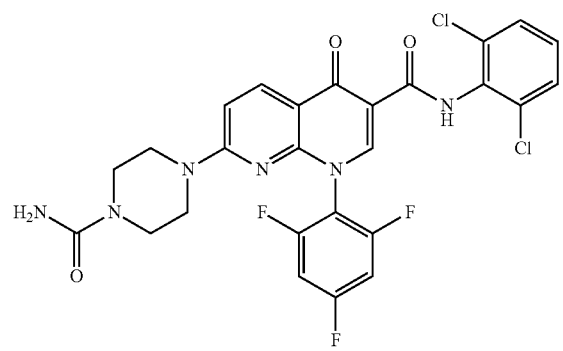 [SMILES: NC(=O)N1CCN(c2ccc3c(=O)c(C(=O)Nc4c(Cl)cccc4Cl)cn(-c4c(F)cc(F)cc4F)c3n2)CC1]

According to GP3, 60.0 mg (120 μmol) of the compound from Example 160B were reacted with 18.6 mg (144 μmol) of piperazine-1-carboxamide and 73 μl (420 μmol) of DIPEA in 540 μl of DMF. The crude product was purified by means of preparative HPLC (acetonitrile/water/0.1% formic acid). 44.1 mg (62% of theory, 100% purity) of the title compound were obtained.

LC-MS (Method 3): $R_t$=1.73 min; MS (ESIpos): m/z=591 [M+H]+

$^1$H NMR (400 MHz, DMSO-d$_6$): δ ppm=11.88 (s, 1H), 8.92 (s, 1H), 8.37 (d, 1H), 7.55-7.62 (m, 4H), 7.35-7.41 (m, 1H), 7.18 (d, 1H), 6.04 (s, 2H), 3.43-3.54 (m, 4H), 3.32-3.38 (m, 4H).

Example 637

1-(2,6-Difluorophenyl)-4-oxo-7-(2-oxoimidazolidin-1-yl)-N-[(2S)-1,1,1-trifluorobutan-2-yl]-1,4-dihydro-1,8-naphthyridine-3-carboxamide

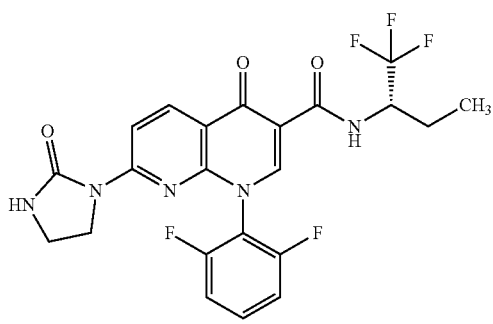 [SMILES: CC[C@H](NC(=O)c1cn(-c2c(F)cccc2F)c2nc(N3CCNC3=O)ccc2c1=O)C(F)(F)F]

According to GP2, 60.0 mg (135 µmol) of the compound from Example 114A were reacted with 116 mg (1.35 mmol) of imidazolidin-2-one in the presence of 27.9 mg (202 µmol) of potassium carbonate, 6.04 mg (26.9 µmol) of palladium acetate and 15.6 mg (26.9 µmol) of Xantphos in 1.2 ml of 1,4-dioxane. The crude product was purified by means of preparative HPLC (acetonitrile/water/0.1% formic acid). The substance was isolated with impurities and was further recrystallized from acetonitrile, filtered off with suction, washed with a little acetonitrile and dried. 33.5 mg (50% of theory, 100% purity) of the title compound were obtained.

LC-MS (Method 3): $R_t$=1.88 min; MS (ESIpos): m/z=496 [M+H]$^+$ $^1$H NMR (400 MHz, DMSO-d$_6$): δ ppm=10.23 (d, 1H), 8.95 (s, 1H), 8.57 (d, 1H), 8.44 (d, 1H), 7.68-7.76 (m, 1H), 7.65 (s, 1H), 7.43 (t, 2H), 4.70-4.81 (m, 1H), 3.51-3.57 (m, 2H), 3.32-3.36 (m, 2H), 1.84-1.94 (m, 1H), 1.61-1.72 (m, 1H), 0.98 (t, 3H).

Example 638

1-(2,6-Difluorophenyl)-4-oxo-7-(2-oxoimidazolidin-1-yl)-N-[(2R)-1,1,1-trifluorobutan-2-yl]-1,4-dihydro-1,8-naphthyridine-3-carboxamide

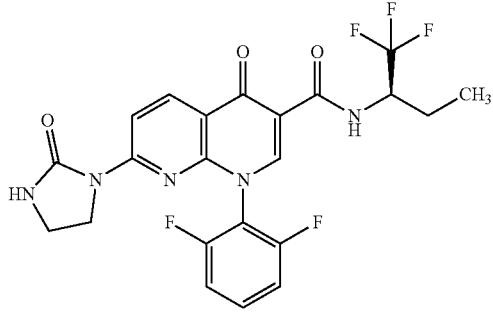 [SMILES: CC[C@@H](NC(=O)c1cn(-c2c(F)cccc2F)c2nc(N3CCNC3=O)ccc2c1=O)C(F)(F)F]

According to GP2, 60.0 mg (135 µmol) of the compound from Example 86A were reacted with 116 mg (1.35 mmol) of imidazolidin-2-one in the presence of 27.9 mg (202 µmol) of potassium carbonate, 6.04 mg (26.9 µmol) of palladium acetate and 15.6 mg (26.9 µmol) of Xantphos in 1.2 ml of 1,4-dioxane. The crude product was purified by means of preparative HPLC (acetonitrile/water/0.1% formic acid). The substance was isolated with impurities and was further recrystallized from acetonitrile, filtered off with suction, washed with a little cold acetonitrile and dried. 27.5 mg (41% of theory, 100% purity) of the title compound were obtained.

LC-MS (Method 3): $R_t$=1.88 min; MS (ESIpos): m/z=496 [M+H]$^+$ $^1$H NMR (600 MHz, DMSO-d$_6$): δ ppm=10.23 (d, 1H), 8.95 (s, 1H), 8.56 (d, 1H), 8.44 (d, 1H), 7.69-7.76 (m, 1H), 7.67 (s, 1H), 7.43 (t, 2H), 4.72-4.80 (m, 1H), 3.49-3.58 (m, 2H), 3.33-3.35 (m, 1H), 3.31-3.33 (m, 1H), 1.86-1.93 (m, 1H), 1.62-1.70 (m, 1H), 0.98 (t, 3H).

Example 639

1-(2,4-Difluorophenyl)-7-[(3R,4S)-3,4-dihydroxy-pyrrolidin-1-yl]-4-oxo-N-[(2R)-1,1,1-trifluorobutan-2-yl]-1,4-dihydro-1,8-naphthyridine-3-carboxamide

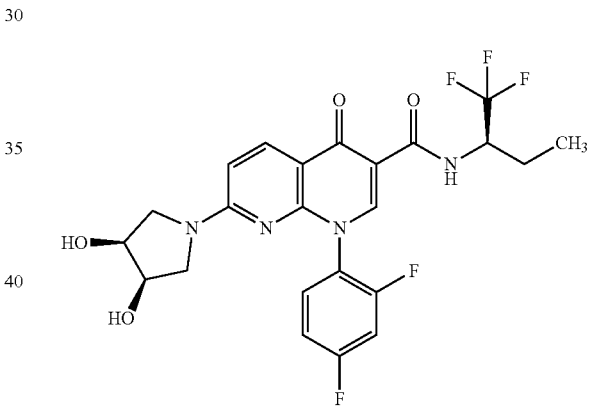

According to GP3, 100 mg (224 µmol) of the compound from Example 67A were reacted with 37.6 mg (269 µmol) of (3R,4S)-pyrrolidine-3,4-diol hydrochloride and 140 µl (790 µmol) of DIPEA in 1.0 ml of DMF. The crude product was purified by means of preparative HPLC (acetonitrile/water/0.1% formic acid). 105 mg (91% of theory, 100% purity) of the title compound were obtained.

LC-MS (Method 3): $R_t$=1.71 min; MS (ESIpos): m/z=513 [M+H]$^+$ $^1$H NMR (400 MHz, DMSO-d$_6$): δ ppm=10.51 (d, 1H), 8.61 (s, 1H), 8.28 (d, 1H), 7.76-7.85 (m, 1H), 7.58 (br t, 1H), 7.33 (br t, 1H), 6.74 (d, 1H), 5.02 (br dd, 1H), 4.89-4.96 (m, 1H), 4.67-4.79 (m, 1H), 4.13 (br s, 1H), 3.97-4.07 (m, 1H), 3.53-3.65 (m, 1H), 3.16-3.30 (m, 2H), 2.93-3.09 (m, 1H), 1.83-1.93 (m, 1H), 1.58-1.69 (m, 1H), 0.97 (t, 3H).

Example 640

1-(2,4-Difluorophenyl)-7-[3-hydroxy-2-methyl-5-oxopyrrolidin-1-yl]-4-oxo-N-[(2R)-1,1,1-trifluorobutan-2-yl]-1,4-dihydro-1,8-naphthyridine-3-carboxamide (diastereomer mixture)

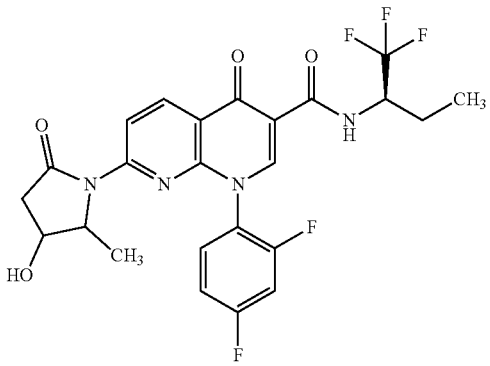 [SMILES: CC[C@@H](NC(=O)c1cn(-c2ccc(F)cc2F)c2nc(N3C(=O)CC(O)C3C)ccc2c1=O)C(F)(F)F]

According to GP2, 60.0 mg (135 µmol) of the compound from Example 67A were reacted with 18.6 mg (162 µmol) of the compound from Example 163C in the presence of 27.9 mg (202 µmol) of potassium carbonate, 6.04 mg (26.9 µmol) of palladium acetate and 15.6 mg (26.9 µmol) of Xantphos in 1.0 ml of 1,4-dioxane. The crude product was purified by means of preparative HPLC (acetonitrile/water/0.1% formic acid). The substance was isolated with impurities and was further purified subsequently by means of normal phase chromatography (eluent: cyclohexane-ethyl acetate gradient). 21.6 mg (31% of theory, 100% purity) of the title compound were obtained.

LC-MS (Method 3): $R_t$=1.90 min; MS (ESIpos): m/z=525 [M+H]$^+$ $^1$H NMR (400 MHz, DMSO-d$_6$): δ ppm=10.17-10.27 (m, 1H), 8.84-8.90 (m, 1H), 8.67-8.73 (m, 1H), 8.54 (t, 0.80H), 8.44 (t, 0.20H), 7.84-7.94 (m, 1H), 7.59-7.69 (m, 1H), 7.33-7.42 (m, 1H), 5.31-5.41 (m, 1H), 4.71-4.83 (m, 1H), 3.88-4.13 (m, 2H), 3.05-3.17 (m, 1H), 2.28 (br dd, 1H), 1.83-1.95 (m, 1H), 1.60-1.73 (m, 1H), 0.93-1.05 (m, 5H), 0.84-0.90 (m, 1H).

Example 641

N-(Bicyclo[1.1.1]pent-1-yl)-7-(3-methoxy-3-methylazetidin-1-yl)-4-oxo-1-(2,4,6-trifluorophenyl)-1,4-dihydro-1,8-naphthyridine-3-carboxamide

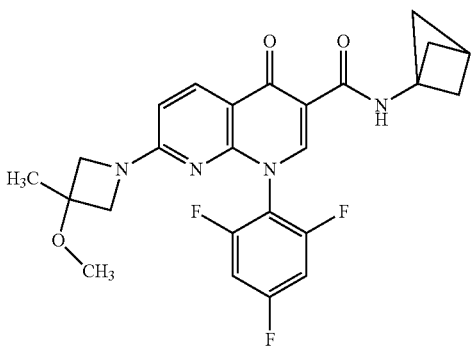 [SMILES: COC1(C)CN(c2ccc3c(=O)c(C(=O)NC45CC(C4)C5)cn(-c4c(F)cc(F)cc4F)c3n2)C1]

According to GP1, 24.1 mg (57.5 µmol) of the compound from Example 161A were reacted with 8.26 mg (69.0 µmol) of bicyclo[1.1.1]pentan-1-amine hydrochloride in the presence of 26.3 mg (69.0 µmol) of HATU and 30 µl (170 µmol) of DIPEA in 230 µl of DMF. The crude product was purified by means of preparative HPLC (acetonitrile/water/0.1% formic acid). 14.0 mg (50% of theory, 100% purity) of the title compound were obtained.

LC-MS (Method 1): $R_t$=1.17 min; MS (ESIpos): m/z=485 [M+H]$^+$ $^1$H NMR (400 MHz, DMSO-d$_6$): δ ppm=10.24 (s, 1H), 8.66 (s, 1H), 8.26 (d, 1H), 7.51-7.58 (m, 2H), 6.61 (d, 1H), 3.53-4.02 (m, 4H), 3.15 (s, 3H), 2.09 (s, 6H), 1.41 (s, 3H).

Example 642

N-[(1S)-1-Cyclopropyl-2,2,2-trifluoroethyl]-7-[(3S,4S)-3,4-dihydroxypyrrolidin-1-yl]-4-oxo-1-(2,4,6-trifluorophenyl)-1,4-dihydro-1,8-naphthyridine-3-carboxamide

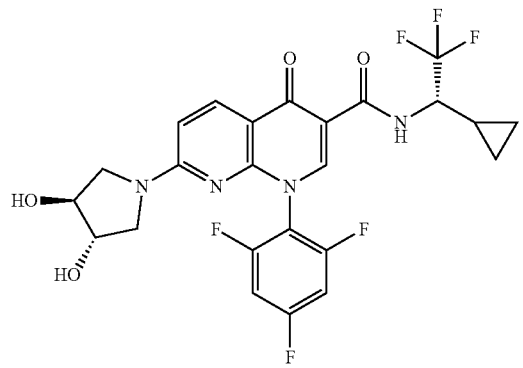 [SMILES: O=C(N[C@@H](C1CC1)C(F)(F)F)c1cn(-c2c(F)cc(F)cc2F)c2nc(N3C[C@H](O)[C@@H](O)C3)ccc2c1=O]

According to GP3, 60.0 mg (126 µmol) of the compound from Example 126A were reacted with 15.6 mg (151 µmol) of (3S,4S)-pyrrolidine-3,4-diol and 55 µl (320 µmol) of DIPEA in 600 µl of DMF. The crude product was purified by means of preparative HPLC (acetonitrile/water/0.1% formic acid). 60.6 mg (89% of theory, 100% purity) of the title compound were obtained.

LC-MS (Method 3): $R_t$=1.72 min; MS (ESIpos): m/z=543 [M+H]$^+$ $^1$H NMR (400 MHz, DMSO-d$_6$): δ ppm=10.57 (d, 1H), 8.80 (s, 1H), 8.28 (d, 1H), 7.56 (br t, 2H), 6.78 (d, 1H), 5.23 (d, 1H), 5.14 (d, 1H), 4.33-4.43 (m, 1H), 4.05 (br s, 1H), 3.93 (br s, 1H), 3.62 (br dd, 1H), 3.32-3.38 (m, 1H), 3.25 (br dd, 1H), 3.07 (br d, 1H), 1.16-1.25 (m, 1H), 0.50-0.69 (m, 3H), 0.31-0.38 (m, 1H).

Example 643

1-(2,6-Dichloro-4-fluorophenyl)-7-[(3R,4R)-3,4-dihydroxypyrrolidin-1-yl]-4-oxo-N-[(2R)-1,1,1-trifluorobutan-2-yl]-1,4-dihydro-1,8-naphthyridine-3-carboxamide

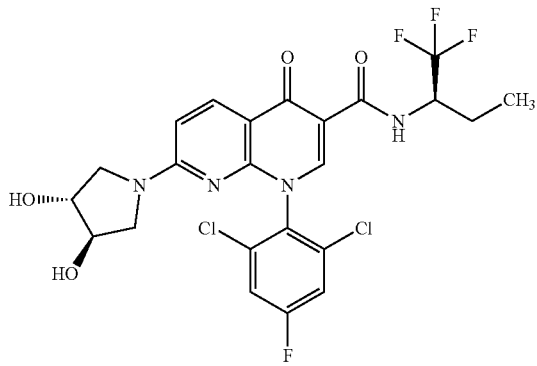 [SMILES: CC[C@@H](NC(=O)c1cn(-c2c(Cl)cc(F)cc2Cl)c2nc(N3C[C@@H](O)[C@H](O)C3)ccc2c1=O)C(F)(F)F]

According to GP3, 60.0 mg (121 μmol) of the compound from Example 131A were reacted with 20.2 mg (145 μmol) of (3R,4R)-pyrrolidine-3,4-diol hydrochloride and 74 μl (420 μmol) of DIPEA in 540 μl of DMF. The crude product was purified by means of preparative HPLC (acetonitrile/water/0.1% formic acid). 56.8 mg (83% of theory, 100% purity) of the title compound were obtained.

LC-MS (Method 3): $R_t$=1.78 min; MS (ESIpos): m/z=563 [M+H]$^+$ $^1$H NMR (400 MHz, DMSO-d$_6$): δ ppm=10.48 (d, 1H), 8.70 (s, 1H), 8.28 (d, 1H), 7.88 (dq, 2H), 6.77 (d, 1H), 5.23 (br d, 1H), 5.15 (br d, 1H), 4.68-4.79 (m, 1H), 4.04 (br s, 1H), 3.91 (br s, 1H), 3.61 (br dd, 1H), 3.33-3.38 (m, 1H), 3.18 (br dd, 1H), 2.99 (br d, 1H), 1.83-1.93 (m, 1H), 1.59-1.71 (m, 1H), 0.98 (t, 3H).

Example 644

N-[(1S)-1-Cyclopropyl-2,2,2-trifluoroethyl]-1-(2,6-difluorophenyl)-4-oxo-7-(2-oxoimidazolidin-1-yl)-1,4-dihydro-1,8-naphthyridine-3-carboxamide

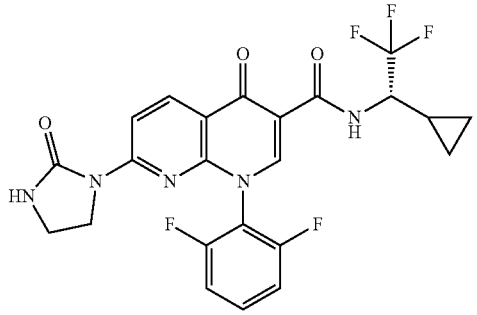 [SMILES: O=C(N[C@@H](C1CC1)C(F)(F)F)c1cn(-c2c(F)cccc2F)c2nc(N3CCNC3=O)ccc2c1=O]

According to GP2, 60.0 mg (131 μmol) of the compound from Example 104A were reacted with 113 mg (1.31 mmol) of imidazolidin-2-one in the presence of 27.2 mg (197 μmol) of potassium carbonate, 5.88 mg (26.2 μmol) of palladium acetate and 15.2 mg (26.2 μmol) of Xantphos in 1.2 ml of 1,4-dioxane. The crude product was purified by means of preparative HPLC (acetonitrile/water/0.1% formic acid). The substance was isolated with impurities and was further recrystallized from acetonitrile, filtered off with suction, washed with a little cold acetonitrile and dried. 34.7 mg (52% of theory, 100% purity) of the title compound were obtained.

LC-MS (Method 3): $R_t$=1.91 min; MS (ESIpos): m/z=508 [M+H]$^+$ $^1$H NMR (400 MHz, DMSO-d$_6$): δ ppm=10.36 (d, 1H), 8.94 (s, 1H), 8.57 (d, 1H), 8.44 (d, 1H), 7.68-7.76 (m, 1H), 7.65 (s, 1H), 7.43 (t, 2H), 4.35-4.45 (m, 1H), 3.50-3.58 (m, 2H), 3.31-3.36 (m, 2H), 1.18-1.27 (m, 1H), 0.51-0.70 (m, 3H), 0.32-0.39 (m, 1H).

Example 645

1-(2,6-Dichlorophenyl)-7-[(4S)-4-hydroxy-2-oxopyrrolidin-1-yl]-4-oxo-N-[(2R)-1,1,1-trifluorobutan-2-yl]-1,4-dihydro-1,8-naphthyridine-3-carboxamide

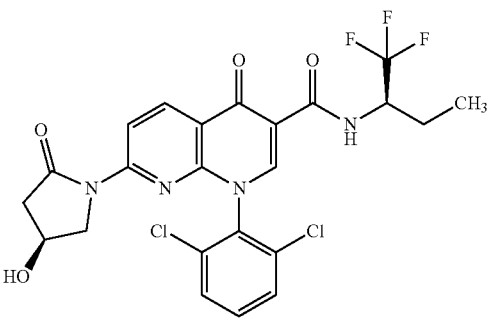 [SMILES: CC[C@@H](NC(=O)c1cn(-c2c(Cl)cccc2Cl)c2nc(N3C[C@@H](O)CC3=O)ccc2c1=O)C(F)(F)F]

According to GP2, 60.0 mg (125 μmol) of the compound from Example 166C were reacted with 15.2 mg (150 μmol) of (4S)-4-hydroxypyrrolidin-2-one in the presence of 26.0 mg (188 μmol) of potassium carbonate, 5.63 mg (25.1 μmol) of palladium acetate and 14.5 mg (25.1 μmol) of Xantphos in 1.0 ml of 1,4-dioxane. The crude product was purified by means of preparative HPLC (acetonitrile/water/0.1% formic acid). 5.00 mg (7% of theory, 100% purity) of the title compound were obtained.

LC-MS (Method 3): $R_t$=1.94 min; MS (ESIpos): m/z=543 [M+H]$^+$ $^1$H NMR (500 MHz, DMSO-d$_6$): δ ppm=10.16 (d, 1H), 8.95 (s, 1H), 8.73 (d, 1H), 8.54 (d, 1H), 7.78-7.84 (m, 2H), 7.70 (t, 1H), 5.33 (d, 1H), 4.73-4.82 (m, 1H), 4.22-4.26 (m, 1H), 3.56 (dd, 1H), 3.32-3.36 (m, 1H), 2.93 (dd, 1H), 2.35 (br d, 1H), 1.86-1.94 (m, 1H), 1.63-1.73 (m, 1H), 0.99 (t, 3H).

Example 646

1-(2,4-Difluorophenyl)-7-[(3R,4R)-3,4-dihydroxy-pyrrolidin-1-yl]-4-oxo-N-[(2R)-1,1,1-trifluorobutan-2-yl]-1,4-dihydro-1,8-naphthyridine-3-carboxamide

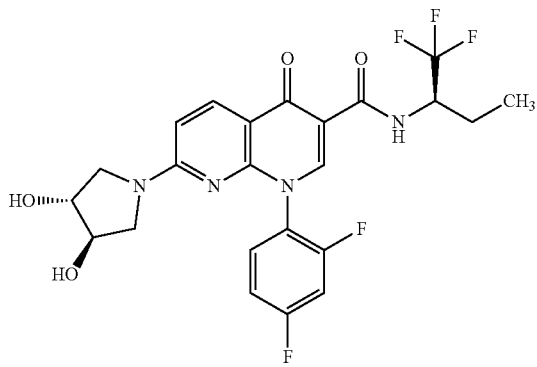 [SMILES: CC[C@@H](NC(=O)c1cn(-c2ccc(F)cc2F)c2nc(N3C[C@@H](O)[C@H](O)C3)ccc2c1=O)C(F)(F)F]

To a solution of 170 mg (229 μmol) of the compound from 167A in 1.9 ml of THF were added 500 μl (1.0 M in THF, 500 μmol) of tetra-n-butylammonium fluoride, and the reaction mixture was stirred at room temperature for 2 h. The solvent was removed under reduced pressure and the residue was purified by means of preparative HPLC (acetonitrile/water/0.1% formic acid). 42.0 mg (36% of theory, 100% purity) of the title compound were obtained.

LC-MS (Method 3): $R_t$=1.65 min; MS (ESIpos): m/z=513 [M+H]$^+$ $^1$H NMR (400 MHz, DMSO-d$_6$): δ ppm=10.52 (d, 1H), 8.61 (s, 1H), 8.28 (d, 1H), 7.73-7.85 (m, 1H), 7.52-7.62 (m, 1H), 7.25-7.37 (m, 1H), 6.76 (d, 1H), 5.08-5.26 (m, 2H), 4.67-4.79 (m, 1H), 4.04 (br s, 1H), 3.92 (br s, 1H), 3.55-3.65 (m, 1H), 3.16-3.28 (m, 2H), 3.00-3.14 (min, 1H), 1.80-1.94 (m, 1H), 1.56-1.70 (m, 1H), 0.97 (t, 3H).

Example 647

N-[(1R)-1-Cyclopropyl-2,2,2-trifluoroethyl]-1-(2,6-dichloro-4-fluorophenyl)-4-oxo-7-(2-oxoimidazolidin-1-yl)-1,4-dihydro-1,8-naphthyridine-3-carboxamide

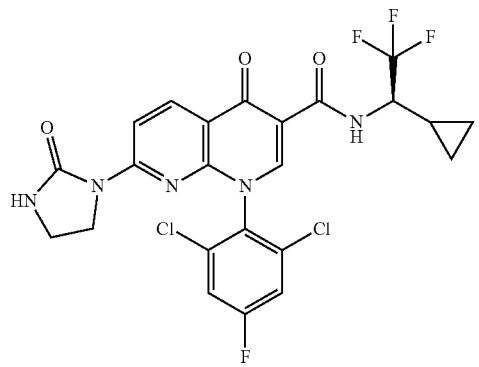 [SMILES: O=C(N[C@H](C1CC1)C(F)(F)F)c1cn(-c2c(Cl)cc(F)cc2Cl)c2nc(N3CCNC3=O)ccc2c1=O]

According to GP2, 60.0 mg (118 μmol) of the compound from Example 130C were reacted with 102 mg (1.18 mmol) of imidazolidin-2-one in the presence of 24.5 mg (177 μmol) of potassium carbonate, 5.30 mg (23.6 μmol) of palladium acetate and 13.6 mg (23.6 μmol) of Xantphos in 1.1 ml of 1,4-dioxane. The crude product was purified by means of preparative HPLC (acetonitrile/water/0.1% formic acid). The substance was isolated with impurities and was further recrystallized from acetonitrile, filtered off with suction, washed with a little acetonitrile and dried. 33.9 mg (51% of theory, 100% purity) of the title compound were obtained.

LC-MS (Method 3): $R_t$=2.05 min; MS (ESIpos): m/z=558 [M+H]$^+$ $^1$H NMR (400 MHz, DMSO-d$_6$): δ ppm=10.39 (d, 1H), 8.91 (s, 1H), 8.57 (d, 1H), 8.44 (d, 1H), 7.89 (d, 2H), 7.66 (s, 1H), 4.34-4.44 (m, 1H), 3.46-3.56 (m, 2H), 3.32-3.37 (m, 2H), 1.18-1.27 (m, 1H), 0.52-0.70 (m, 3H), 0.32-0.39 (m, 1H).

Example 648

1-(2,6-Difluorophenyl)-7-[(3R,4S)-3,4-dihydroxy-pyrrolidin-1-yl]-4-oxo-N-[(2R)-1,1,1-trifluorobutan-2-yl]-1,4-dihydro-1,8-naphthyridine-3-carboxamide

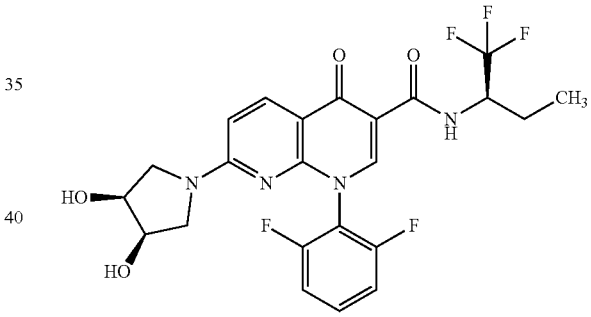

According to GP3, 40.0 mg (89.7 μmol) of the compound from Example 86A were reacted with 15.0 mg (108 μmol) of (3R,4S)-pyrrolidine-3,4-diol hydrochloride and 55 μl (310 μmol) of DIPEA in 410 μl of DMF. The crude product was purified by means of preparative HPLC (acetonitrile/water/0.1% formic acid). 20.0 mg (43% of theory, 100% purity) of the title compound were obtained.

LC-MS (Method 3): $R_t$=1.72 min; MS (ESIpos): m/z=513 [M+H]$^+$ $^1$H NMR (400 MHz, DMSO-d$_6$): δ ppm=10.44 (d, 1H), 8.75 (s, 1H), 8.28 (d, 1H), 7.67-7.75 (m, 1H), 7.38-7.45 (m, 2H), 6.76 (d, 1H), 5.03 (d, 1H), 4.91 (d, 1H), 4.68-4.78 (m, 1H), 4.08-4.15 (m, 1H), 3.97-4.05 (m, 1H), 3.56-3.63 (m, 1H), 3.24-3.30 (m, 1H), 3.14-3.22 (m, 1H), 2.92-3.01 (m, 1H), 1.83-1.93 (m, 1H), 1.58-1.70 (m, 1H), 0.97 (t, 3H).

Example 649

1-(2,6-Dichloro-4-fluorophenyl)-4-oxo-7-(2-oxoimidazolidin-1-yl)-N-[(2R)-1,1,1-trifluorobutan-2-yl]-1,4-dihydro-1,8-naphthyridine-3-carboxamide

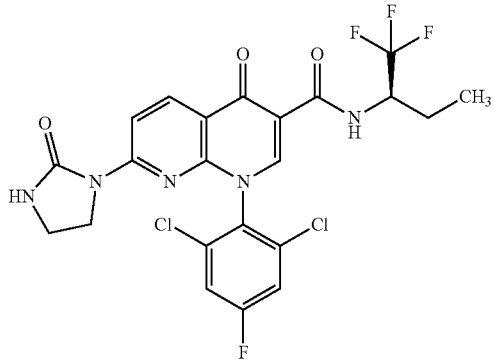 [SMILES: CC[C@@H](NC(=O)c1cn(-c2c(Cl)cc(F)cc2Cl)c2nc(N3CCNC3=O)ccc2c1=O)C(F)(F)F]

According to GP2, 60.0 mg (121 µmol) of the compound from Example 131A were reacted with 104 mg (1.21 mmol) of imidazolidin-2-one in the presence of 25.0 mg (181 µmol) of potassium carbonate, 5.42 mg (24.2 µmol) of palladium acetate and 14.0 mg (24.2 µmol) of Xantphos in 1.1 ml of 1,4-dioxane. The crude product was purified by means of preparative HPLC (acetonitrile/water/0.1% formic acid). The substance was isolated with impurities and was further recrystallized from acetonitrile, filtered off with suction, washed with a little acetonitrile and dried. 24.3 mg (37% of theory, 100% purity) of the title compound were obtained.

LC-MS (Method 3): $R_t$=2.03 min; MS (ESIpos): m/z=546 [M+H]$^+$ $^1$H NMR (400 MHz, DMSO-d$_6$): δ ppm=10.25 (d, 1H), 8.92 (s, 1H), 8.57 (d, 1H), 8.43 (d, 1H), 7.89 (d, 2H), 7.66 (s, 1H), 4.71-4.82 (m, 1H), 3.47-3.55 (m, 2H), 3.32-3.37 (m, 2H), 1.84-1.94 (m, 1H), 1.61-1.73 (m, 1H), 0.98 (t, 3H).

Example 650

7-(4-Carbamoylpiperazin-1-yl)-N-[(1R)-1-cyclopropyl-2,2,2-trifluoroethyl]-4-oxo-1-(2,4,6-trifluorophenyl)-1,4-dihydro-1,8-naphthyridine-3-carboxamide

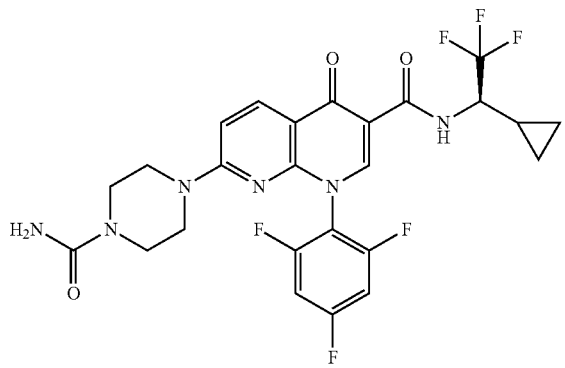 [SMILES: NC(=O)N1CCN(c2ccc3c(=O)c(C(=O)N[C@H](C4CC4)C(F)(F)F)cn(-c4c(F)cc(F)cc4F)c3n2)CC1]

According to GP1, 80.0 mg (179 µmol) of the compound from Example 168A were reacted with 37.7 mg (215 µmol) of (1R)-1-cyclopropyl-2,2,2-trifluoroethanamine hydrochloride in the presence of 81.6 mg (215 µmol) of HATU and 120 µl (720 µmol) of DIPEA in 690 µl of DMF. The crude product was purified by means of preparative HPLC (acetonitrile/water/0.1% formic acid). 74.1 mg (73% of theory, 100% purity) of the title compound were obtained.

LC-MS (Method 3): $R_t$=1.74 min; MS (ESIpos): m/z=569 [M+H]$^+$ $^1$H NMR (400 MHz, DMSO-d$_6$): δ ppm=10.50 (d, 1H), 8.83 (s, 1H), 8.32 (d, 1H), 7.54-7.61 (m, 2H), 7.15 (d, 1H), 6.03 (s, 2H), 4.33-4.43 (m, 1H), 3.44-3.52 (m, 4H), 3.31-3.35 (m, 4H), 1.16-1.25 (m, 1H), 0.50-0.69 (m, 3H), 0.30-0.38 (m, 1H).

Example 651

N-(2,6-Dichlorophenyl)-1-(2,4-difluorophenyl)-7-[(3R,4S)-3,4-dihydroxypyrrolidin-1-yl]-4-oxo-1,4-dihydro-1,8-naphthyridine-3-carboxamide

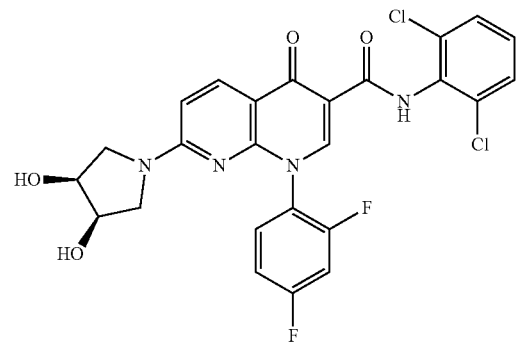 [SMILES: O=C(Nc1c(Cl)cccc1Cl)c1cn(-c2ccc(F)cc2F)c2nc(N3C[C@@H](O)[C@@H](O)C3)ccc2c1=O]

According to GP3, 40.0 mg (83.2 µmol) of the compound from Example 81A were reacted with 13.9 mg (99.9 µmol) of (3R,4S)-pyrrolidine-3,4-diol hydrochloride and 51 µl (290 µmol) of DIPEA in 400 µl of DMF. The crude product was purified by means of preparative HPLC (acetonitrile/water/0.1% formic acid). 32.8 mg (72% of theory, 100% purity) of the title compound were obtained.

LC-MS (Method 3): $R_t$=1.74 min; MS (ESIpos): m/z=547 [M+H]$^+$ $^1$H NMR (400 MHz, DMSO-d$_6$): δ ppm=12.03 (s, 1H), 8.68 (s, 1H), 8.33 (d, 1H), 7.80-7.89 (m, 1H), 7.53-7.63 (m, 3H), 7.30-7.40 (m, 2H), 6.76 (d, 1H), 4.99-5.07 (m, 1H), 4.91-4.98 (m, 1H), 4.10-4.18 (m, 1H), 3.98-4.09 (m, 1H), 3.55-3.66 (m, 1H), 3.17-3.29 (m, 2H), 2.95-3.09 (m, 1H).

Example 652

1-(2,6-Dichlorophenyl)-7-[1-hydroxy-3-azabicyclo[3.1.0]hex-3-yl]-4-oxo-N-[(2R)-1,1,1-trifluorobutan-2-yl]-1,4-dihydro-1,8-naphthyridine-3-carboxamide (diastereomer mixture)

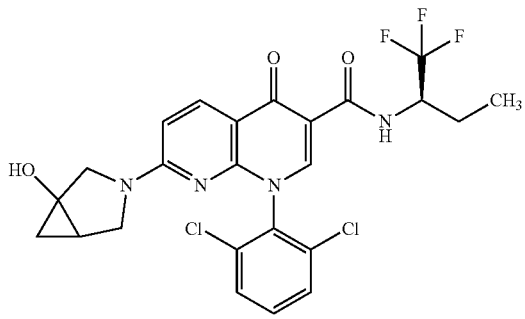 [SMILES: CC[C@@H](NC(=O)c1cn(-c2c(Cl)cccc2Cl)c2nc(N3CC4CC4(O)C3)ccc2c1=O)C(F)(F)F]

According to GP3, 72.7 mg (152 μmol) of the compound from Example 166C were reacted with 27.2 mg (182 μmol, 91% purity) of 3-azabicyclo[3.1.0]hexan-1-ol and 93 μl (530 μmol) of DIPEA in 640 μl of DMF. The crude product was purified by means of preparative HPLC (acetonitrile/water/0.1% formic acid). 62.6 mg (76% of theory, 100% purity) of the title compound were obtained.

LC-MS (Method 1): $R_t$=1.09 min; MS (ESIpos): m/z=541 [M+H]$^+$ $^1$H NMR (400 MHz, DMSO-d$_6$): δ ppm=10.45 (d, 1H), 8.65 (s, 1H), 8.29 (d, 1H), 7.72-7.81 (m, 2H), 7.61-7.72 (m, 1H), 6.69-6.81 (m, 1H), 5.87-6.08 (m, 1H), 4.68-4.79 (m, 1H), 3.82-3.90 (m, 0.40H), 3.58-3.70 (m, 0.60H), 3.35-3.55 (m, 1.60H), 3.13-3.21 (m, 0.40H), 2.96-3.10 (m, 1H), 1.83-1.93 (m, 1H), 1.48-1.71 (m, 2H), 0.92-1.04 (m, 4H), 0.36-0.44 (m, 1H).

Example 653

N-(Bicyclo[1.1.1]pent-1-yl)-4-oxo-7-(2-oxoimidazolidin-1-yl)-1-(2,4,6-trifluorophenyl)-1,4-dihydro-1,8-naphthyridine-3-carboxamide

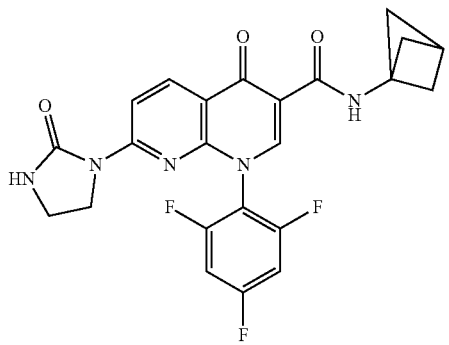 [SMILES: O=C(NC12CC(C1)C2)c1cn(-c2c(F)cc(F)cc2F)c2nc(N3CCNC3=O)ccc2c1=O]

According to GP1, 50.0 mg (124 μmol) of the compound from Example 113A were reacted with 17.7 mg (148 μmol) of bicyclo[1.1.1]pentan-1-amine hydrochloride in the presence of 56.4 mg (148 μmol) of HATU and 86 μl (490 μmol) of DIPEA in 750 μl of DMF. The crude product was purified by means of preparative HPLC (acetonitrile/water/0.1% formic acid). 36.5 mg (63% of theory, 100% purity) of the title compound were obtained.

LC-MS (Method 3): $R_t$=1.84 min; MS (ESIpos): m/z=470 [M+H]$^+$ $^1$H NMR (400 MHz, DMSO-d$_6$): δ ppm=10.08 (s, 1H), 8.85 (s, 1H), 8.52 (d, 1H), 8.41 (d, 1H), 7.65 (s, 1H), 7.57 (t, 2H), 3.55-3.62 (m, 2H), 3.32-3.37 (m, 2H), 2.11 (s, 6H).

Example 654

1-(2,6-Dichloro-4-fluorophenyl)-4-oxo-7-(2-oxoimidazolidin-1-yl)-N-[(2S)-1,1,1-trifluorobutan-2-yl]-1,4-dihydro-1,8-naphthyridine-3-carboxamide

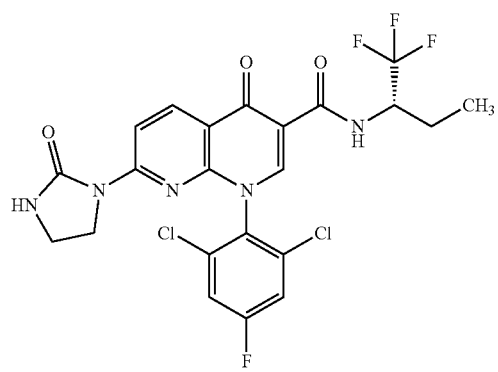 [SMILES: CC[C@H](NC(=O)c1cn(-c2c(Cl)cc(F)cc2Cl)c2nc(N3CCNC3=O)ccc2c1=O)C(F)(F)F]

According to GP2, 60.0 mg (121 μmol) of the compound from Example 132A were reacted with 104 mg (1.21 mmol) of imidazolidin-2-one in the presence of 25.0 mg (181 μmol) of potassium carbonate, 5.42 mg (24.2 μmol) of palladium acetate and 14.0 mg (24.2 μmol) of Xantphos in 1.1 ml of 1,4-dioxane. The crude product was purified by means of preparative HPLC (acetonitrile/water/0.1% formic acid). The substance was isolated with impurities and was further recrystallized from acetonitrile, filtered off with suction, washed with a little acetonitrile and dried. 46.6 mg (71% of theory, 100% purity) of the title compound were obtained.

LC-MS (Method 3): $R_t$=2.03 min; MS (ESIpos): m/z=546 [M+H]$^+$ $^1$H NMR (400 MHz, DMSO-d$_6$): δ ppm=10.25 (d, 1H), 8.92 (s, 1H), 8.57 (d, 1H), 8.43 (d, 1H), 7.89 (d, 2H), 7.66 (s, 1H), 4.70-4.81 (m, 1H), 3.47-3.55 (m, 2H), 3.32-3.37 (m, 2H), 1.84-1.95 (m, 1H), 1.61-1.73 (m, 1H), 0.98 (t, 3H).

Example 655

N-(3,3-Difluoro-1-methylcyclobutyl)-7-[(3R,4R)-3,4-dihydroxypyrrolidin-1-yl]-4-oxo-1-(2,4,6-trifluorophenyl)-1,4-dihydro-1,8-naphthyridine-3-carboxamide

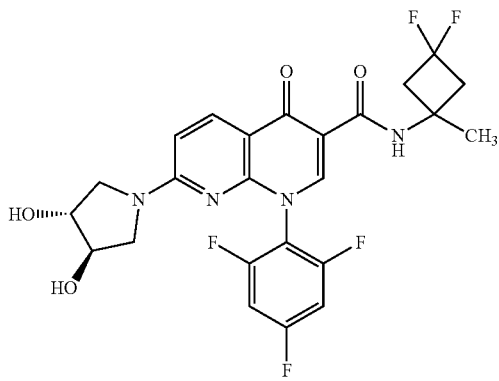 [SMILES: CC1(NC(=O)c2cn(-c3c(F)cc(F)cc3F)c3nc(N4C[C@@H](O)[C@H](O)C4)ccc3c2=O)CC(F)(F)C1]

According to GP1, 50.0 mg (119 µmol) of the compound 121A were reacted with 22.4 mg (142 µmol) of 3,3-difluoro-1-methylcyclobutanamine hydrochloride in the presence of 54.1 mg (142 µmol) of HATU and 83 µl (470 µmol) of DIPEA in 750 µl of DMF. The crude product was purified by means of preparative HPLC (acetonitrile/water/0.1% formic acid). 39.6 mg (64% of theory, 100% purity) of the title compound were obtained.

LC-MS (Method 3): $R_t$=1.59 min; MS (ESIpos): m/z=525 [M+H]$^+$ $^1$H NMR (400 MHz, DMSO-d$_6$): δ ppm=10.28 (s, 1H), 8.70 (s, 1H), 8.26 (d, 1H), 7.53-7.60 (m, 2H), 6.76 (d, 1H), 5.23 (d, 1H), 5.14 (d, 1H), 4.04 (br s, 1H), 3.92 (br s, 1H), 3.61 (br dd, 1H), 3.32-3.36 (m, 1H), 3.24 (br dd, 1H), 2.97-3.10 (m, 3H), 2.70 (td, 2H), 1.55 (s, 3H).

Example 656

N-(3,3-Difluoro-1-methylcyclobutyl)-4-oxo-7-(2-oxoimidazolidin-1-yl)-1-(2,4,6-trifluorophenyl)-1,4-dihydro-1,8-naphthyridine-3-carboxamide

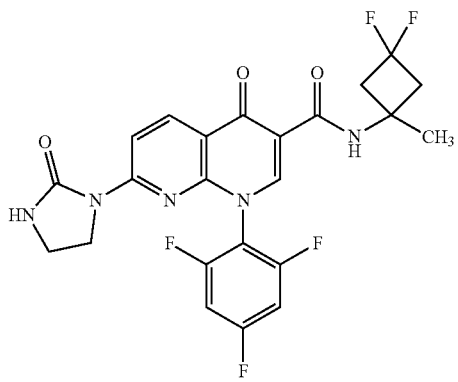 [SMILES: CC1(NC(=O)c2cn(-c3c(F)cc(F)cc3F)c3nc(N4CCNC4=O)ccc3c2=O)CC(F)(F)C1]

According to GP1, 50.0 mg (124 µmol) of the compound from Example 113A were reacted with 23.4 mg (148 µmol) of 3,3-difluoro-1-methylcyclobutanamine hydrochloride in the presence of 56.4 mg (148 µmol) of HATU and 86 µl (490 µmol) of DIPEA in 750 µl of DMF. The crude product was purified by means of preparative HPLC (acetonitrile/water/0.1% formic acid). 37.9 mg (60% of theory, 100% purity) of the title compound were obtained.

LC-MS (Method 3): $R_t$=1.83 min; MS (ESIpos): m/z=508 [M+H]$^+$ $^1$H NMR (400 MHz, DMSO-d$_6$): δ ppm=10.08 (s, 1H), 8.89 (s, 1H), 8.54 (d, 1H), 8.42 (d, 1H), 7.65 (s, 1H), 7.57 (t, 2H), 3.55-3.62 (m, 2H), 3.32-3.38 (m, 2H), 2.98-3.10 (m, 2H), 2.68-2.77 (m, 2H), 1.57 (s, 3H).

Example 657

1-(2,4-Difluorophenyl)-7-[4-hydroxy-3,3,5-trimethyl-2-oxopyrrolidin-1-yl]-4-oxo-N-[(2R)-1,1,1-trifluorobutan-2-yl]-1,4-dihydro-1,8-naphthyridine-3-carboxamide (diastereomer mixture)

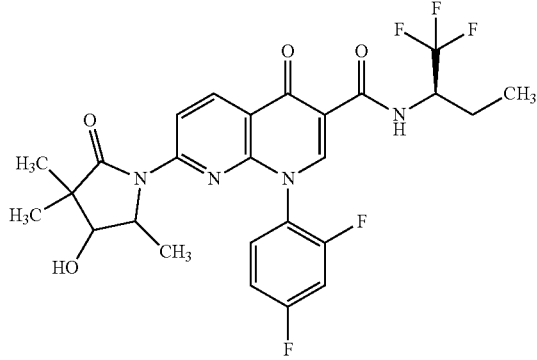 [SMILES: CC[C@@H](NC(=O)c1cn(-c2ccc(F)cc2F)c2nc(N3C(=O)C(C)(C)C(O)C3C)ccc2c1=O)C(F)(F)F]

According to GP2, 31.1 mg (69.8 µmol) of the compound from Example 67A were reacted with 12.0 mg (83.8 µmol) of the compound from Example 164C in the presence of 14.5 mg (105 µmol) of potassium carbonate, 3.14 mg (14.0 µmol) of palladium acetate and 8.08 mg (14.0 µmol) of Xantphos in 620 µl of 1,4-dioxane. The crude product was purified by means of preparative HPLC (acetonitrile/water/0.1% formic acid). 20.0 mg (52% of theory, 100% purity) of the title compound were obtained.

LC-MS (Method 4): $R_t$=3.72 min; MS (ESIpos): m/z=553 [M+H]$^+$ $^1$H NMR (400 MHz, DMSO-d$_6$): δ ppm=10.21 (br d, 1H), 8.84-8.89 (m, 1H), 8.70 (dd, 1H), 8.49 (dd, 1H), 7.84-7.93 (m, 1H), 7.49-7.75 (m, 1H), 7.29-7.41 (m, 1H), 5.40 (d, 1H), 4.71-4.83 (m, 1H), 4.03-4.13 (m, 1H), 3.93-4.03 (m, 1H), 1.82-1.95 (m, 1H), 1.60-1.73 (m, 1H), 0.85-1.11 (m, 12H).

Example 658

7-[(4S)-4-Hydroxy-2-oxopyrrolidin-1-yl]-4-oxo-N-[(2R)-1,1,1-trifluoro-4-methylpentan-2-yl]-1-(2,4,6-trifluorophenyl)-1,4-dihydro-1,8-naphthyridine-3-carboxamide

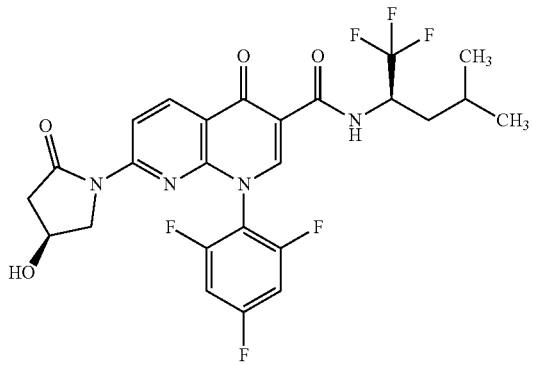 [SMILES: CC(C)C[C@@H](NC(=O)c1cn(-c2c(F)cc(F)cc2F)c2nc(N3C[C@@H](O)CC3=O)ccc2c1=O)C(F)(F)F]

According to GP1, 50.0 mg (119 µmol) of the compound from Example 117A were reacted with 27.4 mg (143 µmol) of (2S)-1,1,1-trifluoro-4-methylpentan-2-amine hydrochloride in the presence of 54.4 mg (143 µmol) of HATU and 62 µl (360 µmol) of DIPEA in 460 µl of DMF. The crude product was purified by means of preparative HPLC (acetonitrile/water/0.1% formic acid). 42.5 mg (62% of theory, 97% purity) of the title compound were obtained.

LC-MS (Method 3): $R_t$=2.10 min; MS (ESIpos): m/z=557 [M+H]$^+$ $^1$H NMR (400 MHz, DMSO-d$_6$): δ ppm=10.10 (d, 1H), 9.08 (s, 1H), 8.71 (d, 1H), 8.54 (d, 1H), 7.58-7.65 (m, 2H), 5.34 (d, 1H), 4.81-4.89 (m, 1H), 4.27-4.31 (m, 1H), 3.69 (dd, 1H), 3.48 (d, 1H), 2.94 (dd, 1H), 2.38 (br d, 1H), 1.65-1.74 (m, 2H), 1.54-1.62 (m, 1H), 0.95 (d, 3H), 0.90 (d, 3H).

Example 659

N-[(1S)-1-Cyclopropyl-2,2,2-trifluoroethyl]-7-[5-(hydroxymethyl)-2-oxo-1,3-oxazolidin-3-yl]-4-oxo-1-(2,4,6-trifluorophenyl)-1,4-dihydro-1,8-naphthyridine-3-carboxamide (diastereomer mixture)

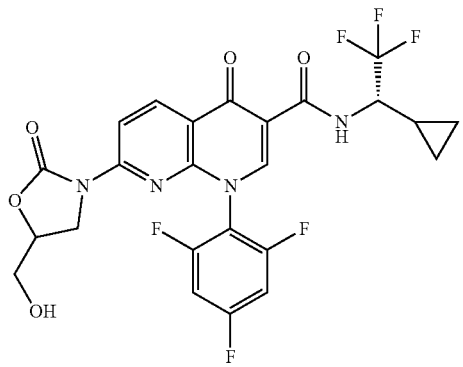 [SMILES: O=C(N[C@@H](C1CC1)C(F)(F)F)c1cn(-c2c(F)cc(F)cc2F)c2nc(N3CC(CO)OC3=O)ccc2c1=O]

According to GP2, 150.0 mg (315 µmol) of the compound from Example 126A were reacted with 44.3 mg (378 µmol) of 5-(hydroxymethyl)-1,3-oxazolidin-2-one (racemate) in the presence of 65.4 mg (473 µmol) of potassium carbonate, 14.2 mg (63.1 µmol) of palladium acetate and 36.5 mg (63.1 µmol) of Xantphos in 1.5 ml of 1,4-dioxane. The crude product was purified by means of preparative HPLC (acetonitrile/water/0.1% formic acid). 17.4 mg (10% of theory, 100% purity) of the title compound were obtained.

LC-MS (Method 3): $R_t$=1.92 min; MS (ESIpos): m/z=557 [M+H]$^+$ $^1$H NMR (400 MHz, DMSO-d$_6$): δ ppm=10.53 (d, 1H), 8.81 (s, 1H), 8.32-8.44 (m, 1H), 8.24 (d, 1H), 7.50-7.59 (m, 2H), 6.78 (br d, 1H), 4.67-4.78 (m, 1H), 4.33-4.44 (m, 2H), 4.02 (br t, 1H), 3.32-3.46 (m, 2H), 1.16-1.25 (m, 1H), 0.49-0.69 (m, 3H), 0.30-0.37 (m, 1H).

Example 660

N-[(1S)-1-Cyclopropyl-2,2,2-trifluoroethyl]-7-[(2S)-2-(hydroxymethyl)pyrrolidin-1-yl]-4-oxo-1-(2,4,6-trifluorophenyl)-1,4-dihydro-1,8-naphthyridine-3-carboxamide

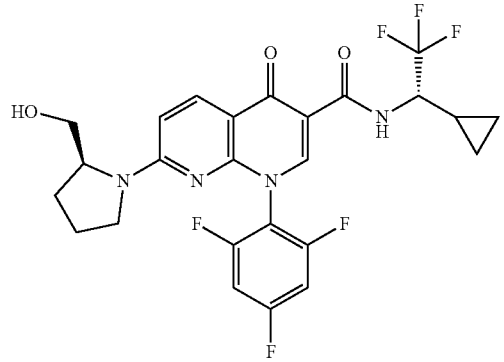 [SMILES: O=C(N[C@@H](C1CC1)C(F)(F)F)c1cn(-c2c(F)cc(F)cc2F)c2nc(N3CCC[C@H]3CO)ccc2c1=O]

According to GP3, 100 mg (210 µmol) of the compound from Example 126A were reacted with 25.5 mg (250 µmol) of (2S)-pyrrolidin-2-ylmethanol and 110 µl (630 µmol) of DIPEA in 850 µl of DMF. The crude product was purified by means of preparative HPLC (acetonitrile/water/0.1% formic acid). 93.6 mg (82% of theory, 100% purity) of the title compound were obtained.

LC-MS (Method 3): $R_t$=2.05 min; MS (ESIpos): m/z=541 [M+H]$^+$ $^1$H NMR (400 MHz, DMSO-d$_6$): δ ppm=10.57 (d, 1H), 8.80 (s, 1H), 8.28 (br d, 1H), 7.46-7.57 (m, 2H), 6.72-6.97 (m, 1H), 4.85-4.94 (m, 0.40H), 4.42-4.50 (m, 0.60H), 4.31-4.42 (m, 1H), 3.94-4.04 (br d, 0.40H), 3.66-3.76 (m, 0.60H), 3.34-3.54 (m, 2H), 3.05-3.28 (m, 2H), 1.75-2.07 (m, 4H), 1.16-1.25 (m, 1H), 0.49-0.69 (m, 3H), 0.30-0.37 (m, 1H).

Example 661

N-[(1S)-1-Cyclopropyl-2,2,2-trifluoroethyl]-7-[(2R)-2-(hydroxymethyl)pyrrolidin-1-yl]-4-oxo-1-(2,4,6-trifluorophenyl)-1,4-dihydro-1,8-naphthyridine-3-carboxamide

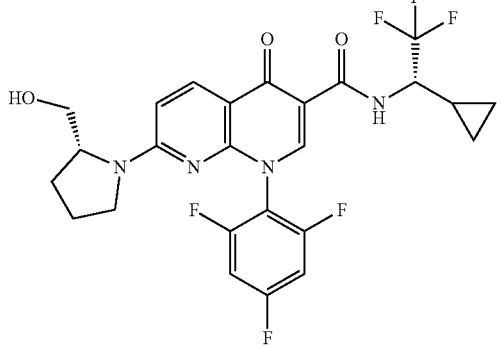

According to GP3, 100 mg (210 μmol) of the compound from Example 126A were reacted with 29.8 mg (294 μmol) of (2R)-pyrrolidin-2-ylmethanol and 110 μl (630 μmol) of DIPEA in 850 μl of DMF. The crude product was purified by means of preparative HPLC (acetonitrile/water/0.1% formic acid). 109 mg (96% of theory, 100% purity) of the title compound were obtained.

LC-MS (Method 3): $R_t$=2.06 min; MS (ESIpos): m/z=541 [M+H]$^+$ $^1$H NMR (400 MHz, DMSO-d$_6$): δ ppm=10.57 (br d, 1H), 8.80 (s, 1H), 8.28 (br d, 1H), 7.46-7.58 (m, 2H), 6.85-6.98 (m, 0.40H), 6.72-6.85 (m, 0.60H), 4.83-4.96 (m, 0.40H), 4.43-4.50 (m, 0.60H), 4.32-4.43 (m, 1H), 3.94-4.04 (m, 0.40H), 3.66-3.78 (m, 0.60H), 3.34-3.55 (m, 2H), 3.03-3.27 (m, 2H), 1.76-2.06 (m, 4H), 1.15-1.26 (m, 1H), 0.50-0.69 (m, 3H), 0.31-0.38 (m, 1H).

Example 662

N-[(1S)-1-Cyclopropyl-2,2,2-trifluoroethyl]-7-(3-hydroxyazetidin-1-yl)-4-oxo-1-(2,4,6-trifluorophenyl)-1,4-dihydro-1,8-naphthyridine-3-carboxamide

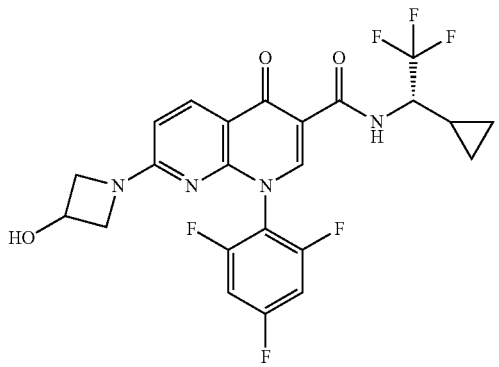 [SMILES: O=C(N[C@@H](C1CC1)C(F)(F)F)c1cn(-c2c(F)cc(F)cc2F)c2nc(N3CC(O)C3)ccc2c1=O]

According to GP3, 200 mg (420 μmol) of the compound from Example 126A were reacted with 64.5 mg (589 μmol) of azetidin-3-ol hydrochloride and 220 μl (1.30 mmol) of DIPEA in 1.7 ml of DMF. The crude product was purified by means of preparative HPLC (acetonitrile/water/0.1% formic acid). 180 mg (83% of theory, 100% purity) of the title compound were obtained.

LC-MS (Method 3): $R_t$=1.91 min; MS (ESIpos): m/z=513 [M+H]$^+$ $^1$H NMR (400 MHz, DMSO-d$_6$): δ ppm=10.53 (d, 1H), 8.79 (s, 1H), 8.28 (d, 1H), 7.50-7.58 (m, 2H), 6.61 (d, 1H), 5.73 (d, 1H), 4.49-4.57 (m, 1H), 4.34-4.42 (m, 1H), 3.89-4.30 (m, 2H), 3.47-3.85 (m, 2H), 1.16-1.25 (m, 1H), 0.49-0.69 (m, 3H), 0.30-0.37 (m, 1H).

Example 663

N-[(1S)-1-Cyclopropyl-2,2,2-trifluoroethyl]-7-[4-hydroxy-4-(hydroxymethyl)piperidin-1-yl]-4-oxo-1-(2,4,6-trifluorophenyl)-1,4-dihydro-1,8-naphthyridine-3-carboxamide

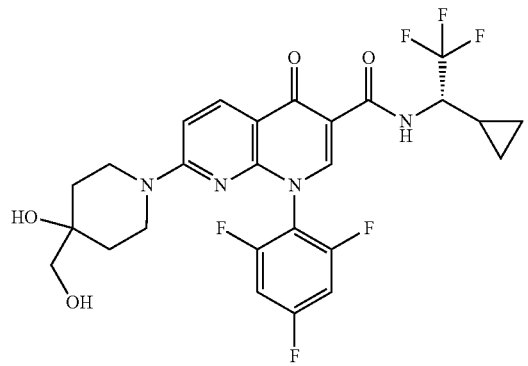 [SMILES: O=C(N[C@@H](C1CC1)C(F)(F)F)c1cn(-c2c(F)cc(F)cc2F)c2nc(N3CCC(O)(CO)CC3)ccc2c1=O]

According to GP3, 100 mg (210 μmol) of the compound from Example 126A were reacted with 38.6 mg (294 μmol) of 4-(hydroxymethyl)piperidin-4-ol and 110 μl (630 μmol) of DIPEA in 850 μl of DMF. The crude product was purified by means of preparative HPLC (acetonitrile/water/0.1% formic acid). 78.7 mg (66% of theory, 100% purity) of the title compound were obtained.

LC-MS (Method 3): $R_t$=1.80 min; MS (ESIpos): m/z=571 [M+H]$^+$ $^1$H NMR (400 MHz, DMSO-d$_6$): δ ppm=10.54 (d, 1H), 8.80 (s, 1H), 8.26 (d, 1H), 8.16 (s, 1H), 7.56 (t, 2H), 7.14 (d, 1H), 4.47-4.68 (m, 1H), 4.23-4.47 (m, 2H), 3.93 (br d, 2H), 3.15 (s, 2H), 1.27-1.52 (m, 4H), 1.16-1.25 (m, 1H), 0.49-0.69 (m, 3H), 0.34 (dq, 1H).

Example 664

7-[Bis(2-hydroxyethyl)amino]-N-[(1S)-1-cyclopropyl-2,2,2-trifluoroethyl]-4-oxo-1-(2,4,6-trifluorophenyl)-1,4-dihydro-1,8-naphthyridine-3-carboxamide

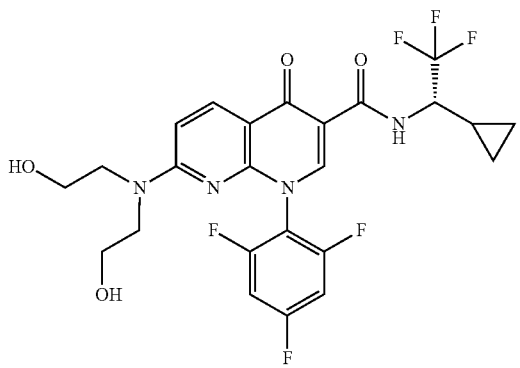 [SMILES: O=C(N[C@@H](C1CC1)C(F)(F)F)c1cn(-c2c(F)cc(F)cc2F)c2nc(N(CCO)CCO)ccc2c1=O]

According to GP3, 100 mg (210 µmol) of the compound from Example 126A were reacted with 30.9 mg (294 µmol) of 2,2'-iminodiethanol and 110 µl (630 µmol) of DIPEA in 850 µl of DMF. The crude product was purified by means of preparative HPLC (acetonitrile/water/0.1% formic acid). 87.5 mg (76% of theory, 100% purity) of the title compound were obtained.

LC-MS (Method 3): $R_t$=1.71 min; MS (ESIpos): m/z=545 [M+H]$^+$ $^1$H NMR (400 MHz, DMSO-d$_6$) δ ppm 10.56 (d, 1H), 8.81 (s, 1H), 8.25 (d, 1H), 7.50-7.57 (m, 2H), 7.01 (d, 1H), 4.72-4.90 (m, 1H), 4.54-4.72 (m, 1H), 4.33-4.43 (m, 1H), 3.52-3.68 (m, 4H), 3.18-3.29 (m, 2H), 1.16-1.25 (m, 1H), 0.50-0.69 (m, 3H), 0.30-0.38 (m, 1H).

Example 665

N-[(1S)-1-Cyclopropyl-2,2,2-trifluoroethyl]-7-[3-hydroxy-3-methylpiperidin-1-yl]-4-oxo-1-(2,4,6-trifluorophenyl)-1,4-dihydro-1,8-naphthyridine-3-carboxamide (diastereomer mixture)

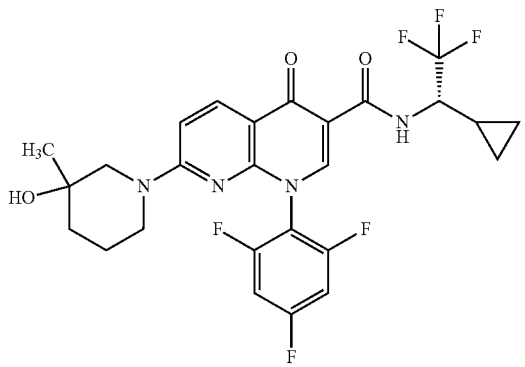 [SMILES: CC1(O)CCCN(c2ccc3c(=O)c(C(=O)N[C@@H](C4CC4)C(F)(F)F)cn(-c4c(F)cc(F)cc4F)c3n2)C1]

According to GP3, 200 mg (420 µmol) of the compound from Example 126A were reacted with 67.8 mg (589 µmol) of 3-methylpiperidin-3-ol and 220 µl (1.3 mmol) of DIPEA in 1.7 ml of DMF. The crude product was purified by means of preparative HPLC (acetonitrile/water/0.1% formic acid). 220 mg (94% of theory, 100% purity) of the title compound were obtained.

LC-MS (Method 3): $R_t$=2.11 min; MS (ESIpos): m/z=555 [M+H]$^+$ $^1$H NMR (400 MHz, DMSO-d$_6$): δ ppm=10.56 (s, 1H), 8.78 (s, 1H), 8.22 (d, 1H), 7.53-7.60 (m, 2H), 7.09 (d, 1H), 4.33-4.44 (m, 2H), 3.34-3.80 (m, 2H), 1.45-1.68 (m, 3H), 1.28-1.42 (m, 1H), 1.15-1.25 (m, 1H), 0.90-1.09 (m, 3H), 0.49-0.69 (m, 3H), 0.29-0.37 (m, 1H).

Example 666

Methyl (5S)-3-[6-{[(1S)-1-cyclopropyl-2,2,2-trifluoroethyl]carbamoyl}-5-oxo-8-(2,4,6-trifluorophenyl)-5,8-dihydro-1,8-naphthyridin-2-yl]-2-oxo-1,3-oxazolidine-5-carboxylate

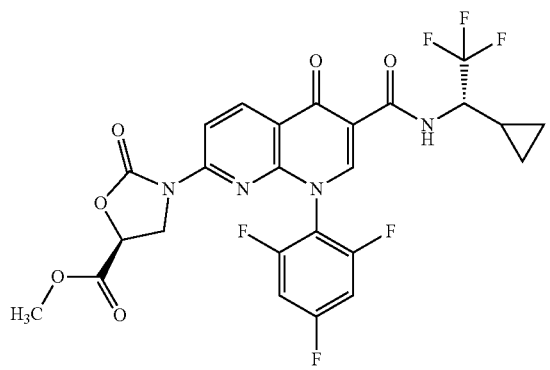 [SMILES: COC(=O)[C@@H]1CN(c2ccc3c(=O)c(C(=O)N[C@@H](C4CC4)C(F)(F)F)cn(-c4c(F)cc(F)cc4F)c3n2)C(=O)O1]

According to GP2, 1.00 g (2.10 mmol) of the compound from Example 126A were reacted with 366 mg (2.52 mmol) of methyl (5S)-2-oxo-1,3-oxazolidine-5-carboxylate in the presence of 436 mg (3.15 mmol) of potassium carbonate, 94.4 mg (420 µmol) of palladium acetate and 243 mg (420 µmol) of Xantphos in 10 ml of 1,4-dioxane. The crude product was purified by means of preparative HPLC (acetonitrile/water/0.1% formic acid). The substance was isolated with impurities and was further recrystallized from acetonitrile, filtered off with suction and dried. 515 mg (42% of theory, 100% purity) of the title compound were obtained.

LC-MS (Method 3): $R_t$=2.11 min; MS (ESIpos): m/z=585 [M+H]$^+$ $^1$H NMR (400 MHz, DMSO-d$_6$): δ ppm=10.23 (d, 1H), 9.07 (s, 1H), 8.76 (d, 1H), 8.29 (d, 1H), 7.57-7.65 (m, 2H), 5.27 (dd, 1H), 4.35-4.45 (m, 1H), 4.04 (t, 1H), 3.85 (dd, 1H), 3.73 (s, 3H), 1.19-1.28 (m, 1H), 0.53-0.70 (m, 3H), 0.31-0.39 (m, 1H).

Example 667

(5S)-3-[6-{[(1S)-1-Cyclopropyl-2,2,2-trifluoroethyl]carbamoyl}-5-oxo-8-(2,4,6-trifluorophenyl)-5,8-dihydro-1,8-naphthyridin-2-yl]-2-oxo-1,3-oxazolidine-5-carboxylic acid

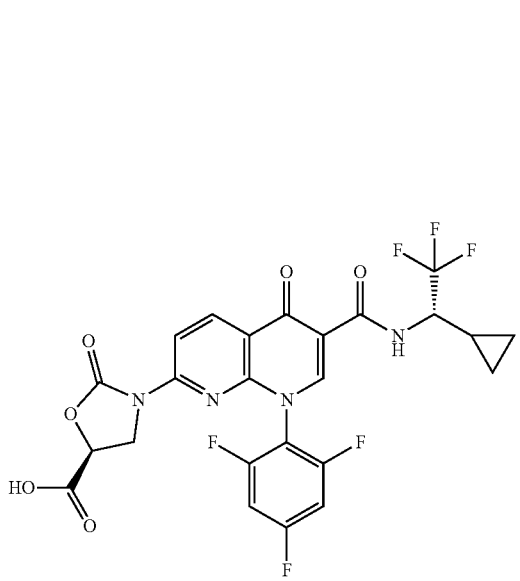 [SMILES: O=C(N[C@@H](C1CC1)C(F)(F)F)c1cn(-c2c(F)cc(F)cc2F)c2nc(N3C[C@@H](C(=O)O)OC3=O)ccc2c1=O]

To a solution of 470 mg (804 µmol) of the compound from Example 666 in 21.4 ml of a mixture of THF and water (3:1, v/v) were added, at 0° C., 33.7 mg (804 µmol) of lithium hydroxide monohydrate dissolved in water. The mixture was stirred at 0° C. for 1 h. Subsequently, the reaction solution was added to water containing a little 1N aqueous hydrochloric acid and extracted three times with ethyl acetate. The combined organic phases were washed with saturated aqueous sodium chloride solution and dried over sodium sulphate. The solvent was removed under reduced pressure, and the substance was recrystallized from a little acetonitrile and dried under high vacuum. 363 mg (79% of theory, 100% purity) of the title compound were obtained.

LC-MS (Method 3): $R_t$=1.75 min; MS (ESIpos): m/z=571 [M+H]$^+$ $^1$H NMR (400 MHz, DMSO-d$_6$): δ ppm=13.73 (br s, 1H), 10.23 (d, 1H), 9.07 (s, 1H), 8.75 (d, 1H), 8.29 (d, 1H), 7.57-7.65 (m, 2H), 5.16 (dd, 1H), 4.35-4.45 (m, 1H), 4.04 (t, 1H), 3.77 (dd, 1H), 1.19-1.28 (m, 1H), 0.52-0.70 (m, 3H), 0.31-0.38 (m, 1H).

Example 668

7-[(5S)-5-Carbamoyl-2-oxo-1,3-oxazolidin-3-yl]-N-[(1S)-1-cyclopropyl-2,2,2-trifluoroethyl]-4-oxo-1-(2,4,6-trifluorophenyl)-1,4-dihydro-1,8-naphthyridine-3-carboxamide

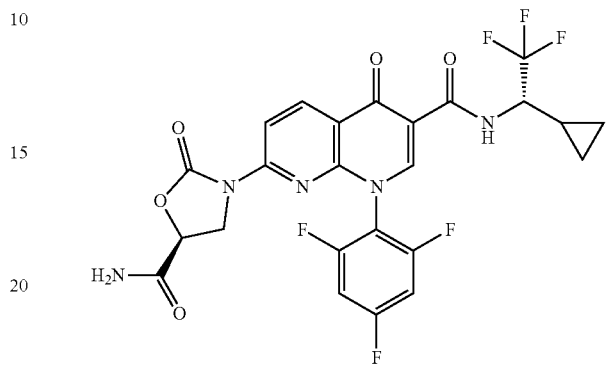

To a solution of 327 mg (556 µmol) of the compound from Example 169A in 12 ml of THF were added dropwise 11 ml (0.50 M in dioxane, 5.60 mmol) of ammonia, and the reaction mixture was stirred at room temperature for 1 h. The solvent was removed under reduced pressure and the residue was purified by means of preparative HPLC (acetonitrile/water/0.1% formic acid). 311 mg (98% of theory, 100% purity) of the title compound were obtained.

LC-MS (Method 3): $R_t$=1.80 min; MS (ESIpos): m/z=570 [M+H]$^+$ $^1$H NMR (400 MHz, DMSO-d$_6$): δ ppm=10.23 (d, 1H), 9.06 (s, 1H), 8.75 (d, 1H), 8.31 (d, 1H), 7.83 (s, 1H), 7.54-7.65 (m, 3H), 4.99 (dd, 1H), 4.35-4.46 (m, 1H), 3.99 (t, 1H), 3.67 (dd, 1H), 1.19-1.28 (m, 1H), 0.53-0.70 (m, 3H), 0.31-0.39 (m, 1H).

Example 669

Methyl (5R)-3-[6-{[(1S)-1-cyclopropyl-2,2,2-trifluoroethyl]carbamoyl}-5-oxo-8-(2,4,6-trifluorophenyl)-5,8-dihydro-1,8-naphthyridin-2-yl]-2-oxo-1,3-oxazolidine-5-carboxylate

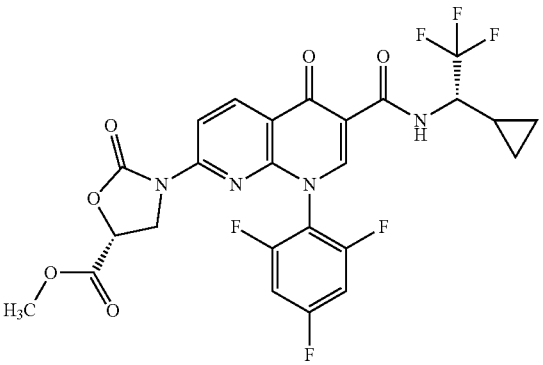 [SMILES: COC(=O)[C@H]1CN(c2ccc3c(=O)c(C(=O)N[C@@H](C4CC4)C(F)(F)F)cn(-c4c(F)cc(F)cc4F)c3n2)C(=O)O1]

According to GP2, 1.00 g (2.10 mmol) of the compound from Example 126A were reacted with 366 mg (2.52 mmol) of methyl (5R)-2-oxo-1,3-oxazolidine-5-carboxylate in the presence of 436 mg (3.15 mmol) of potassium carbonate, 94.4 mg (420 μmol) of palladium acetate and 243 mg (420 μmol) of Xantphos in 10 ml of 1,4-dioxane. The crude product was purified by means of preparative HPLC (acetonitrile/water/0.1% formic acid). The substance was isolated with impurities and was further recrystallized from acetonitrile, filtered off with suction and dried. 631 mg (51% of theory, 99% purity) of the title compound were obtained.

LC-MS (Method 3): $R_t$=2.11 min; MS (ESIpos): m/z=585 $[M+H]^+$ $^1$H NMR (400 MHz, DMSO-$d_6$): δ ppm=10.22 (d, 1H), 9.07 (s, 1H), 8.76 (d, 1H), 8.28 (d, 1H), 7.58-7.65 (m, 2H), 5.27 (dd, 1H), 4.35-4.45 (m, 1H), 4.04 (t, 1H), 3.85 (dd, 1H), 3.73 (s, 3H), 1.19-1.28 (m, 1H), 0.53-0.70 (m, 3H), 0.31-0.38 (m, 1H).

Example 670

(5R)-3-[6-{[(1S)-1-Cyclopropyl-2,2,2-trifluoroethyl]carbamoyl}-5-oxo-8-(2,4,6-trifluorophenyl)-5,8-dihydro-1,8-naphthyridin-2-yl]-2-oxo-1,3-oxazolidine-5-carboxylic acid

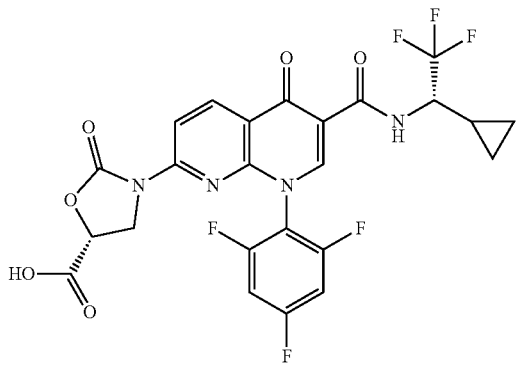 [SMILES: O=C(N[C@@H](C1CC1)C(F)(F)F)c1cn(-c2c(F)cc(F)cc2F)c2nc(N3C[C@H](C(=O)O)OC3=O)ccc2c1=O]

To a solution of 589 mg (1.01 mmol) of the compound from Example 669 in 26.8 ml of a mixture of THF and water (3:1, v/v) were added, at 0° C., 42.3 mg (1.01 mmol) of lithium hydroxide monohydrate dissolved in water. The mixture was stirred at 0° C. for 1 h. Subsequently, the reaction solution was added to water containing a little 1N aqueous hydrochloric acid and extracted three times with ethyl acetate. The combined organic phases were washed with a little saturated aqueous sodium chloride solution and dried over sodium sulphate. The solvent was removed under reduced pressure, and the substance was recrystallized from a little acetonitrile and dried under high vacuum. 485 mg (84% of theory, 100% purity) of the title compound were obtained.

LC-MS (Method 3): $R_t$=1.75 min; MS (ESIpos): m/z=571 $[M+H]^+$ $^1$H NMR (400 MHz, DMSO-$d_6$): δ ppm=13.73 (br s, 1H), 10.23 (d, 1H), 9.07 (s, 1H), 8.75 (d, 1H), 8.29 (d, 1H), 7.58-7.65 (m, 2H), 5.16 (dd, 1H), 4.35-4.45 (m, 1H), 4.04 (t, 1H), 3.77 (dd, 1H), 1.19-1.28 (m, 1H), 0.53-0.70 (m, 3H), 0.31-0.38 (m, 1H).

Example 671

7-[(5R)-5-Carbamoyl-2-oxo-1,3-oxazolidin-3-yl]-N-[(1S)-1-cyclopropyl-2,2,2-trifluoroethyl]-4-oxo-1-(2,4,6-trifluorophenyl)-1,4-dihydro-1,8-naphthyridine-3-carboxamide

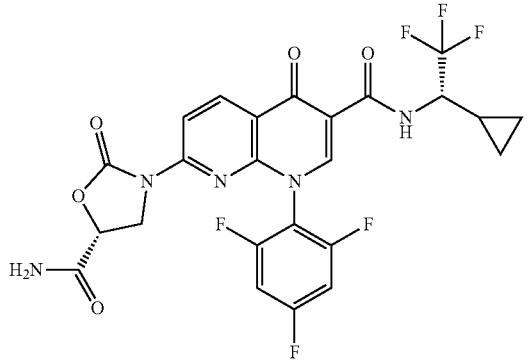 [SMILES: NC(=O)[C@H]1CN(c2ccc3c(=O)c(C(=O)N[C@@H](C4CC4)C(F)(F)F)cn(-c4c(F)cc(F)cc4F)c3n2)C(=O)O1]

To a solution of 454 mg (771 μmol) of the compound from Example 170A in 18 ml of THF were added 15 ml (0.50 M in dioxane, 7.70 mmol) of ammonia, and the reaction mixture was stirred at room temperature for 1 h. The solvent was removed under reduced pressure and the residue was purified by means of preparative HPLC (acetonitrile/water/0.1% formic acid). 421 mg (96% of theory, 100% purity) of the title compound were obtained.

LC-MS (Method 3): $R_t$=1.79 min; MS (ESIpos): m/z=570 $[M+H]^+$ $^1$H NMR (400 MHz, DMSO-$d_6$) δ ppm 10.23 (d, 1H), 9.06 (s, 1H), 8.75 (d, 1H), 8.31 (d, 1H), 7.83 (s, 1H), 7.54-7.65 (m, 3H), 4.99 (dd, 1H), 4.35-4.45 (m, 1H), 3.99 (t, 1H), 3.67 (dd, 1H), 1.19-1.28 (m, 1H), 0.53-0.70 (m, 3H), 0.31-0.38 (m, 1H).

B. ASSESSMENT OF PHARMACOLOGICAL EFFICACY

The pharmacological activity of the compounds according to the invention can be demonstrated by in vitro and in vivo studies, as known to the person skilled in the art. The application examples which follow describe the biological action of the compounds according to the invention, without restricting the invention to these examples.

Abbreviations and Acronyms $B_{Max}$ number of specific binding sites of the radioligand
CAFTY calcium free tyrode
CHO chinese hamster ovary
CRE cAMP-responsive element
DMEM Dulbecco's modified eagle medium
DMSO dimethyl sulphoxide
FCS foetal calf serum
FRET fluorescence resonance energy transfer
GIRK1/4 G-protein-coupled inward rectifier potassium channel, member 1/4
HEPES hydroxyethylpiperazine-ethanesulphonic acid
HTRF homogeneous time resolved fluorescence
$K_d$ equilibrium dissociation constant
$K_i$ equilibrium inhibitor constant
$k_{off}$ rate of dissociation $k_{on}$ rate of association
nM nanomolar
MEM minimum essential medium
µl microliters
µM micromolar
ml milliliters
mM millimolar
mtClytin mitochondrial clytin
mnun minutes
NMS N-Me-scopolamine
PAM positive allosteric modulator
PEI polyethyleneimine
Pen/Strep penicillin/streptomycin
sec seconds B-1. Functional M2-GIRK1/4 Activation Test Both the activation of the M2 receptor by orthosteric agonists alone and the allosteric boosting of orthosterically induced activation by positive allosteric modulators (PAMs) can be determined by means of a cell-based functional GIRK1/4 activity test. The binding of orthosteric agonists (endogenous ligand: acetylcholine) to the M2 receptor leads to receptor activation or a change in conformation of the receptor in the manner of a shift in equilibrium in favour of the active receptor conformation. The binding of the orthosteric agonists to the M2 receptor and hence the activation thereof can be boosted by positive allosteric modulators which bind not to the orthosteric binding site of the agonists but to a separate allosteric binding site.

The agonist-induced change in conformation of the M2 receptor results in a Gαi protein activation. The activation of the Gα subunit leads in turn to dissociation and hence release of the Gβγ subunits from the Gα subunit and the activation of separate downstream signal transduction cascades. The heterodimeric Gβγ complex released binds to the GIRK1/4 potassium channel and induces a ligand-controlled channel activation or opening (Reuveny et al., Nature, July 1994, 370, 143-146). Under physiological conditions, the result is then a selective efflux of potassium from the cell along the electrochemical gradient. The export of positive charge leads to lowering of the transmembrane potential and hence to hyperpolarization of the cell. The extent of hyperpolarization can therefore be regarded as a measure of the activation of the M2 receptor.

The test cell used is a recombinant CHO-DUKX cell line which has been stably transfected with cDNA coding for the human M2 receptor and with cDNA coding for both GIRK1/4 subunits (CHO-DUKX-M2-GIRK). The transmembrane potential, or the relative changes in the transmembrane potential as a function of substance addition or M2 activation, is determined by means of a voltage-sensitive dye (FLIPR Membrane Potential Assay Kit Blue, Molecular Devices # R8034) and the measurement of cell fluorescence using a proprietary fluorescence imaging instrument.

B-1.1. Determination of the Allosteric Potency of the Test Substances ($EC_{50}$ Value)

The test substances are dissolved in dimethyl sulphoxide (DMSO) at a concentration of 10 mM and serially diluted with DMSO in steps of 1:3.16 for a 10-point dose/activity analysis. In accordance with the desired test concentrations, the substances are pre-diluted in loading buffer (composition: 0.6 ml of FLIPR Membrane Potential Assay Kit Blue (10 mg/ml), 0.6 ml of Brilliant Black (10 mg/ml), 2 mM $CaCl_2$ and 2 mM KCl ad 50 ml sodium gluconate Tyrode (PAA, #T21-155)).

The reporter cells cultivated in MEM alpha medium (supplemented with 10% FCS, 2% Glutamax, 1 mg/ml genticin) were sown with 2000 cells (measurement after 48 h) or 4000 cells (measurement after 24 h) in 30 µl per 384-well in pCLEAR/schwarz Greiner cell culture plates (#781092) and incubated at 37° C. for 24 h or 48 h. The sowing medium consisted of MEM alpha medium (supplemented with 5% FCS, 2% Glutamax, no genticin).

For the particular measurement, the medium was removed and the cells were laden with the voltage-sensitive dye for at least 6 min at room temperature (30 µl of loading buffer per 384-well). This was followed, in a first measurement, by the determination of the fluorescence for the resting transmembrane potential for a period of 5 sec. Thereafter, 10 µl in each case of the test substances diluted in loading buffer were added, followed by a second measurement to determine the transmembrane potential for a period of 50 sec. Finally, the cells were admixed with 10 µl of agonist solution (acetylcholine dissolved in loading buffer). Acetylcholine was used at the concentration corresponding to the $EC_{20}$, which had been determined in a preliminary test. The M2-mediated GIRK1/4 activation or hyperpolarization was then monitored in a third measurement over a period of 60 sec. The $EC_{50}$ value (degree of allosteric potency of test compound) and the efficiency (measure of the boosting of the acetylcholine effect at an $EC_{20}$ acetylcholine concentration) were determined with the aid of a 4-parameter logistic function (Hill function).

B-1.2. Determination of Positive Cooperativity (α Factor)

The test substances were dissolved in DMSO at a concentration of 10 mM and serially diluted with DMSO in steps of 1:3.16 for a 10-point dose/activity analysis. In accordance with the desired test concentrations, the substances were pre-diluted in loading buffer (see above).

The reporter cells cultivated in MEM alpha medium (supplemented with 10% FCS, 2% Glutamax, 1 mg/ml genticin) are sown with 2000 cells (measurement after 48 h) or 4000 cells (measurement after 24 h) in 30 µl per 384-well in pCLEAR/schwarz Greiner cell culture plates (#781092) and incubated at 37° C. for 24 h or 48 h. The sowing medium consisted of MEM alpha medium (supplemented with 5% FCS, 2% Glutamax, no genticin).

For the particular measurement, the medium was removed and the cells were laden with the voltage-sensitive dye for at least 6 min at room temperature (30 µl of loading buffer per 384-well). This was followed, in a first measurement, by the determination of the resting transmembrane potential for a period of 5 sec in 1 sec increments. Thereafter, 10 µl in each case of the test substances diluted in loading buffer are added, followed by a second measurement to determine the transmembrane potential for a period of 50 sec in 1 sec increments.

Finally, the cells are admixed with 10 µl of agonist solution (acetylcholine dissolved in loading buffer). In contrast to the $EC_{50}$ determination of the test substances (see B-1.1), however, this is not done using one acetylcholine concentration; instead, every concentration of the test substance is combined with an acetylcholine 8-point dose-response curve. For the acetylcholine dilution series, the agonist is serially prediluted in loading buffer in accordance with the desired end concentrations, starting with a maximum end concentration of 3 µM in steps of 1:3.16. The M2-mediated GIRK1/4 activation or hyperpolarization is then monitored in a third measurement over a period of 60 sec in 1 sec increments. The shift in the acetylcholine dose-response curve in the presence of increasing concentrations of the test substance is analysed and quantified by means of GraphPad PRISM (Allosteric $EC_{50}$ shift). The a factor determined is a measure of the strength and direction of the allosteric effect. α values >1 reflect a lowering of the EC$_{50}$ value or an increase in the potency of the agonist (acetylcholine) in the presence of allosterics and mean positive cooperativity between orthosterics (acetylcholine) and allosterics (test substance). Positive cooperativity is the hallmark of a positive allosteric modulator. Conversely, α values <1 are indicative of negative cooperativity between orthosterics and allosterics, and hence characterize negative allosteric modulators. α values=1 mean no cooperativity between orthosteric and allosteric, meaning that the binding affinities of orthosteric and allosteric to the receptor do not affect one another. The greater the magnitude of the α value, the greater the extent of cooperativity between orthosteric and allosteric.

Table 1 below lists, for individual working examples, the EC$_{50}$ and efficiency values thus determined and the α values from this assay (in some cases as mean values from two or more independent individual determinations):

TABLE 1

| Ex. No. | Receptor activity EC$_{50}$ [μmol/l] | Efficiency [%] | Cooperativity (alpha factor) |
|---|---|---|---|
| 1 | 0.014 | 97.5 | 11 |
| 2 | 0.017 | 100.0 | 24 |
| 3 | 0.017 | 99.8 | 30 |
| 4 | 0.024 | 99.8 | 30 |
| 5 | 0.031 | 98.7 | |
| 6 | 0.034 | 98.8 | 15 |
| 7 | 0.034 | 100.0 | 34 |
| 8 | 0.038 | 98.0 | |
| 9 | 0.040 | 96.5 | 11 |
| 10 | 0.060 | 98.5 | 12 |
| 11 | 0.061 | 99.3 | 10 |
| 12 | 0.064 | 95.0 | |
| 13 | 0.071 | 95.8 | 6 |
| 14 | 0.082 | 97.7 | |
| 15 | 0.085 | 90.5 | 8 |
| 16 | 0.090 | 97.3 | |
| 17 | 0.159 | 97.3 | |
| 18 | 0.117 | 97.3 | |
| 19 | 0.058 | 95.0 | 12 |
| 20 | 0.042 | 98.4 | 34 |
| 21 | 0.145 | 100.0 | |
| 22 | 0.131 | 97.7 | |
| 23 | 0.096 | 99.3 | 20 |
| 24 | 0.063 | 100.0 | 25 |
| 25 | 0.084 | 100.0 | 20 |
| 26 | 0.164 | 97.0 | |
| 27 | 0.089 | 97.7 | 20 |
| 28 | 0.023 | 100.0 | 25 |
| 29 | 0.112 | 95.3 | 4 |
| 30 | 0.095 | 93.3 | 11 |
| 31 | 0.040 | 97.0 | 13 |
| 32 | 0.173 | 93.5 | |
| 33 | 0.091 | 96.7 | 20 |
| 34 | 0.095 | 99.7 | |
| 35 | 0.062 | 98.8 | 24 |
| 36 | 0.019 | 96.1 | 16 |
| 37 | 0.023 | 96.3 | |
| 38 | 0.041 | 100.0 | 14 |
| 39 | 0.088 | 92.1 | 14 |
| 40 | 0.106 | 94.2 | |
| 41 | 0.039 | 99.4 | |
| 42 | 0.017 | 94.5 | |
| 43 | 0.141 | 96.6 | |
| 44 | 0.111 | 98.3 | 12 |
| 45 | 0.028 | 99.7 | |
| 46 | 0.127 | 98.7 | |
| 47 | 0.043 | 100.0 | |
| 48 | 0.110 | 94.8 | |
| 49 | 0.089 | 86.0 | |
| 50 | 0.158 | 95.0 | |
| 51 | 0.100 | 95.0 | |
| 52 | 0.104 | 98.5 | |
| 53 | 0.058 | 100.0 | |
| 54 | 0.085 | 98.3 | |
| 55 | 0.036 | 99.8 | 25 |
| 56 | 0.056 | 100.0 | 15 |
| 57 | 0.082 | 93.8 | 7 |
| 58 | 0.077 | 100.0 | 9 |
| 59 | 0.094 | 97.0 | 11 |
| 60 | 0.155 | 100.0 | 8 |
| 61 | 0.016 | 98.2 | |
| 62 | 0.017 | 95.5 | |
| 63 | 0.040 | 88.0 | |
| 64 | 0.012 | 89.7 | 28 |
| 65 | 0.007 | 93.7 | 36 |
| 66 | 0.010 | 92.0 | |
| 67 | 0.138 | 78.0 | |
| 68 | 0.058 | 97.5 | |
| 69 | 0.013 | 99.5 | |
| 70 | 0.076 | 97.4 | 29 |
| 71 | 0.039 | 95.0 | 30 |
| 72 | 0.053 | 94.0 | |
| 73 | 0.073 | 91.9 | |
| 74 | 0.058 | 87.0 | |
| 75 | 0.073 | 87.0 | |
| 76 | 0.069 | 96.0 | |
| 77 | 0.666 | 100.0 | |
| 78 | 0.079 | 94.3 | |
| 79 | 0.144 | 92.2 | |
| 80 | 0.073 | 94.0 | |
| 81 | 0.102 | 89.7 | |
| 82 | 0.060 | 100.0 | |
| 83 | 0.110 | 88.9 | |
| 84 | 0.077 | 100.0 | |
| 85 | 0.118 | 98.5 | 26 |
| 86 | 0.108 | 94.5 | |
| 87 | 0.129 | 94.0 | 26 |
| 88 | 0.042 | 95.0 | |
| 89 | 0.413 | 96.6 | 20 |
| 90 | 0.298 | 94.7 | 11 |
| 91 | 0.058 | 90.5 | |
| 92 | 0.174 | 95.5 | |
| 93 | 0.213 | 85.7 | 8 |
| 94 | 0.164 | 98.7 | |
| 95 | 0.144 | 90.0 | |
| 96 | 0.134 | 92.3 | |
| 97 | 0.209 | 95.0 | 9 |
| 98 | 0.061 | 97.4 | 14 |
| 99 | 0.182 | 92.7 | |
| 100 | 0.143 | 96.3 | |
| 101 | 0.026 | 76.8 | |
| 102 | 0.031 | 94.0 | |
| 103 | 0.050 | 95.7 | |
| 104 | 0.028 | 96.0 | 15 |
| 105 | 0.146 | 97.7 | |
| 106 | 0.032 | 100.0 | |
| 107 | 0.057 | 91.8 | 14 |
| 108 | 0.024 | 95.0 | |
| 109 | 0.187 | 95.0 | |
| 110 | 0.062 | 98.0 | |
| 111 | 0.035 | 100.0 | 26 |
| 112 | 0.029 | 85.5 | |
| 113 | 0.141 | 91.0 | |
| 114 | 0.098 | 93.3 | |
| 115 | 0.073 | 91.0 | |
| 116 | 0.059 | 93.7 | |
| 117 | 0.089 | 90.5 | |
| 118 | 0.091 | 91.0 | |
| 119 | 0.090 | 94.3 | |
| 120 | 0.062 | 86.5 | |
| 121 | 0.295 | 88.3 | 8 |
| 122 | 0.094 | 87.7 | |
| 123 | 0.115 | 97.7 | 14 |
| 124 | 0.155 | 88.5 | |
| 125 | 0.116 | 93.0 | |
| 126 | 0.180 | 81.0 | |
| 127 | 0.077 | 86.5 | |

TABLE 1-continued

| Ex. No. | Receptor activity EC$_{50}$ [μmol/l] | Efficiency [%] | Cooperativity (alpha factor) |
|---|---|---|---|
| 128 | 0.057 | 91.7 | 18 |
| 129 | 0.045 | 88.1 | |
| 130 | 0.113 | 90.0 | |
| 131 | 0.157 | 89.8 | |
| 132 | 0.010 | 98.0 | 7 |
| 133 | 0.019 | 94.0 | |
| 134 | 0.032 | 92.5 | |
| 135 | 0.017 | 91.0 | 8 |
| 136 | 0.024 | 81.5 | |
| 137 | 0.016 | 97.0 | |
| 138 | 0.068 | 100.0 | |
| 139 | 0.065 | 100.0 | |
| 140 | 0.068 | 99.0 | |
| 141 | 0.083 | 99.4 | |
| 142 | 0.110 | 100.0 | |
| 143 | 0.037 | 95.5 | |
| 144 | 0.032 | 92.7 | |
| 145 | 0.030 | 100.0 | |
| 146 | 0.026 | 95.8 | |
| 147 | 0.082 | 94.9 | |
| 148 | 0.041 | 94.9 | |
| 149 | 0.085 | 100.0 | |
| 150 | 0.072 | 90.5 | |
| 151 | 0.023 | 86.4 | |
| 152 | 0.010 | 97.0 | |
| 153 | 0.104 | 100.0 | |
| 154 | 0.158 | 97.6 | |
| 155 | 0.173 | 97.7 | |
| 156 | 0.086 | 84.7 | |
| 157 | 0.067 | 100.0 | |
| 158 | 0.184 | 100.0 | |
| 159 | 0.117 | 88.9 | |
| 160 | 0.085 | 92.5 | |
| 161 | 0.137 | 99.5 | |
| 162 | 0.038 | 93.2 | |
| 163 | 0.173 | 92.8 | 13 |
| 164 | 0.031 | 97.3 | 21 |
| 165 | 0.011 | 40.5 | |
| 166 | 0.014 | 99.0 | |
| 167 | 0.047 | 95.0 | |
| 168 | 0.060 | 95.0 | 13 |
| 169 | 0.101 | 79.5 | |
| 170 | 0.019 | 96.5 | |
| 171 | 0.030 | 90.5 | |
| 172 | 0.083 | 87.3 | |
| 173 | 0.088 | 100.0 | |
| 174 | 0.113 | 98.6 | 25 |
| 175 | 0.069 | 97.3 | 33 |
| 176 | 0.095 | 94.1 | 28 |
| 177 | 0.138 | 82.4 | 5 |
| 178 | 0.197 | 81.3 | |
| 179 | 0.169 | 63.3 | |
| 180 | 0.115 | 96.6 | |
| 181 | 0.059 | 94.5 | 36 |
| 182 | 0.182 | 94.8 | |
| 183 | 0.166 | 98.0 | |
| 184 | 0.129 | 99.0 | |
| 185 | 0.156 | 97.6 | |
| 186 | 0.030 | 94.0 | |
| 187 | 0.098 | 93.5 | 10 |
| 188 | 0.113 | 98.5 | 9 |
| 189 | 0.023 | 90.5 | 24 |
| 190 | 0.046 | 93.7 | 12 |
| 191 | 0.060 | 85.3 | 7 |
| 192 | 0.054 | 91.7 | 9 |
| 193 | 0.036 | 100.0 | 50 |
| 194 | 0.140 | 96.0 | 16 |
| 195 | 0.343 | 96.3 | |
| 196 | 0.137 | 98.0 | |
| 197 | 0.120 | 92.0 | 10 |
| 198 | 0.113 | 96.0 | 13 |
| 199 | 0.263 | 96.0 | 15 |
| 200 | 0.293 | 83.3 | |
| 201 | 0.039 | 94.8 | 39 |
| 202 | 0.089 | 93.3 | 18 |
| 203 | 0.062 | 92.5 | 8 |
| 204 | 0.034 | 92.5 | 8 |
| 205 | 0.105 | 85.0 | 4 |
| 206 | 0.107 | 95.8 | 14 |
| 207 | 0.035 | 100.0 | 18 |
| 208 | 0.115 | 97.5 | 23 |
| 209 | 0.163 | 94.7 | |
| 210 | 0.285 | 93.5 | |
| 211 | 0.021 | 94.8 | 35 |
| 212 | 0.041 | 99.4 | 54 |
| 213 | 0.019 | 99.6 | 55 |
| 214 | 0.107 | 97.0 | 43 |
| 215 | 0.178 | 100.0 | |
| 216 | 0.089 | 100.0 | 35 |
| 217 | 0.036 | 96.3 | 18 |
| 218 | 0.153 | 93.5 | 33 |
| 219 | 0.106 | 97.0 | 33 |
| 220 | 0.116 | 93.0 | 29 |
| 221 | 0.106 | 97.5 | 24 |
| 222 | 0.200 | 100.0 | |
| 223 | 0.084 | 99.0 | 30 |
| 224 | 0.157 | 97.5 | 31 |
| 225 | 0.363 | 99.7 | 33 |
| 226 | 0.083 | 100.0 | 35 |
| 227 | 0.073 | 89.5 | 14 |
| 228 | 0.051 | 98.7 | 12 |
| 229 | 0.052 | 100.0 | 13 |
| 230 | 0.203 | 66.3 | |
| 231 | 0.120 | 95.4 | 12 |
| 232 | 0.097 | 91.8 | 8 |
| 233 | 0.057 | 100.0 | 41 |
| 234 | 0.075 | 89.8 | 28 |
| 235 | 0.207 | 98.3 | |
| 236 | 0.860 | 100.0 | |
| 237 | 0.751 | 100.0 | |
| 238 | 1.640 | 92.3 | |
| 239 | 0.112 | 99.3 | 30 |
| 240 | 0.110 | 90.7 | 10 |
| 241 | 0.021 | 95.8 | 18 |
| 242 | 0.090 | 96.7 | 10 |
| 243 | 0.015 | 98.0 | 33 |
| 244 | 0.022 | 93.7 | 58 |
| 245 | 0.112 | 98.0 | 42 |
| 246 | 0.023 | 100.0 | 53 |
| 247 | 0.160 | 93.0 | |
| 248 | 0.330 | 91.7 | |
| 249 | 0.505 | 89.0 | |
| 250 | 0.101 | 95.5 | 27 |
| 251 | 0.163 | 100.0 | |
| 252 | 0.109 | 95.5 | |
| 253 | 0.483 | 100.0 | |
| 254 | 0.337 | 94.0 | |
| 255 | 0.083 | 96.7 | 31 |
| 256 | 0.147 | 95.0 | |
| 257 | 0.138 | 100.0 | |
| 258 | 0.147 | 99.3 | 30 |
| 259 | 0.560 | 94.5 | 14 |
| 260 | 0.280 | 96.5 | |
| 261 | 0.075 | 95.7 | 13 |
| 262 | 0.072 | 89.0 | 27 |
| 263 | 0.440 | 68.5 | |
| 264 | 0.530 | 76.3 | |
| 265 | 23.700 | 100.0 | |
| 266 | 0.743 | 100.0 | |
| 267 | 0.024 | 100.0 | 28 |
| 269 | 0.210 | 98.0 | |
| 270 | 1.600 | 94.0 | |
| 271 | 0.040 | 91.0 | 43 |
| 272 | 0.033 | 98.0 | 55 |
| 273 | 0.044 | 100.0 | |
| 274 | 0.049 | 99.8 | |
| 275 | 0.018 | 92.8 | 38 |
| 276 | 0.080 | 100.0 | 28 |
| 277 | 0.078 | 98.5 | |
| 278 | 0.077 | 97.5 | |

TABLE 1-continued

| Ex. No. | Receptor activity EC$_{50}$ [µmol/l] | Efficiency [%] | Cooperativity (alpha factor) |
|---|---|---|---|
| 279 | 0.066 | 92.5 | 34 |
| 280 | 0.044 | 96.5 | 24 |
| 281 | 0.034 | 100.0 | 44 |
| 282 | 0.021 | 99.5 | 32 |
| 283 | 0.040 | 97.0 | |
| 284 | 0.061 | 97.8 | 41 |
| 285 | 0.598 | 79.9 | 23 |
| 286 | 0.094 | 40.0 | 3 |
| 287 | 0.145 | 94.8 | 24 |
| 288 | 0.040 | 84.0 | 12 |
| 289 | 0.061 | 94.3 | |
| 290 | 0.312 | 100.0 | |
| 291 | 0.673 | 99.5 | |
| 292 | 0.059 | 90.5 | |
| 293 | 0.073 | 88.5 | |
| 294 | 0.065 | 92.5 | 31 |
| 295 | 0.021 | 100.0 | 71 |
| 296 | 0.028 | 97.4 | 49 |
| 297 | 0.037 | 97.3 | 47 |
| 298 | 0.074 | 94.0 | |
| 299 | 0.056 | 92.0 | |
| 300 | 0.054 | 95.0 | |
| 301 | 0.030 | 95.5 | 12 |
| 302 | 0.017 | 96.0 | |
| 303 | 0.060 | 95.0 | |
| 304 | 0.009 | 93.0 | 24 |
| 305 | 0.012 | 98.5 | 23 |
| 306 | 0.052 | 98.5 | 21 |
| 307 | 0.014 | 99.5 | 36 |
| 308 | 0.030 | 100.0 | |
| 309 | 0.040 | 96.0 | |
| 310 | 0.014 | 94.5 | 21 |
| 311 | 0.025 | 95.0 | 20 |
| 312 | 0.072 | 97.0 | |
| 313 | 0.071 | 80.0 | |
| 314 | 0.027 | 100.0 | 24 |
| 315 | 0.038 | 96.3 | 25 |
| 316 | 0.028 | 97.0 | |
| 317 | 0.026 | 88.0 | |
| 318 | 0.014 | 86.0 | |
| 319 | 0.025 | 95.5 | |
| 320 | 0.130 | 90.0 | 6 |
| 321 | 0.043 | 58.5 | |
| 322 | 0.040 | 96.0 | |
| 323 | 0.014 | 94.6 | 16 |
| 324 | 0.034 | 97.3 | |
| 325 | 0.007 | 93.0 | 56 |
| 326 | 0.047 | 100.0 | |
| 327 | 0.069 | 95.5 | |
| 328 | 0.079 | 100.0 | |
| 329 | 0.076 | 95.0 | 16 |
| 330 | 0.041 | 93.3 | 29 |
| 331 | 0.033 | 96.0 | 7 |
| 332 | 0.020 | 99.2 | 37 |
| 333 | 0.031 | 94.5 | 28 |
| 334 | 0.007 | 84.0 | |
| 335 | 0.023 | 94.5 | 7 |
| 336 | 0.012 | 92.0 | 13 |
| 337 | 0.036 | 68.0 | |
| 338 | 0.007 | 99.0 | 24 |
| 339 | 0.044 | 94.0 | 26 |
| 340 | 0.010 | 100.0 | 22 |
| 341 | 0.056 | 86.0 | |
| 342 | 0.011 | 93.7 | 13 |
| 343 | 0.025 | 90.5 | |
| 344 | 0.054 | 95.5 | |
| 345 | 0.059 | 100.0 | |
| 346 | 0.050 | 96.0 | |
| 347 | 0.034 | 92.5 | |
| 348 | 0.061 | 100.0 | |
| 349 | 0.004 | 100.0 | 52 |
| 350 | 0.006 | 98.5 | 42 |
| 351 | 0.017 | 100.0 | |
| 352 | 0.017 | 100.0 | |
| 353 | 0.050 | 99.0 | |
| 354 | 0.038 | 93.0 | |
| 355 | 0.085 | 99.5 | |
| 356 | 0.094 | 92.5 | |
| 357 | 0.004 | 100.0 | 63 |
| 358 | 0.024 | 95.0 | 31 |
| 359 | 0.013 | 98.5 | |
| 360 | 0.006 | 100.0 | 36 |
| 361 | 0.017 | 100.0 | |
| 362 | 0.077 | 97.0 | 27 |
| 363 | 0.045 | 95.0 | 28 |
| 364 | 0.016 | 93.0 | 25 |
| 365 | 0.021 | 97.0 | 20 |
| 366 | 0.035 | 100.0 | 36 |
| 367 | 0.100 | 93.0 | |
| 368 | 0.091 | 100.0 | |
| 369 | 0.008 | 95.0 | 39 |
| 370 | 0.014 | 97.2 | 32 |
| 371 | 0.018 | 97.5 | 36 |
| 372 | 0.020 | 100.0 | 34 |
| 373 | 0.089 | 100.0 | |
| 374 | 0.049 | 60.0 | |
| 375 | 0.040 | 96.0 | |
| 376 | 0.016 | 93.0 | |
| 377 | 0.048 | 99.0 | 34 |
| 378 | 0.081 | 76.8 | |
| 379 | 0.035 | 95.5 | |
| 380 | 0.046 | 88.0 | |
| 381 | 0.023 | 87.0 | |
| 382 | 0.072 | 91.0 | |
| 383 | 0.018 | 85.5 | |
| 384 | 0.028 | 88.0 | 22 |
| 385 | 0.068 | 72.5 | 11 |
| 386 | 0.009 | 97.8 | 39 |
| 387 | 0.042 | 95.5 | |
| 388 | 0.052 | 89.0 | |
| 389 | 0.038 | 85.5 | |
| 390 | 0.014 | 88.0 | |
| 391 | 0.008 | 97.0 | |
| 392 | 0.006 | 100.0 | |
| 393 | 0.125 | 100.0 | |
| 394 | 0.007 | 100.0 | |
| 395 | 0.007 | 100.0 | |
| 396 | 0.017 | 92.0 | 29 |
| 397 | 0.032 | 90.0 | |
| 398 | 0.010 | 100.0 | 26 |
| 399 | 0.040 | 96.5 | 11 |
| 400 | 0.005 | 100.0 | 32 |
| 401 | 0.041 | 95.5 | |
| 402 | 0.025 | 97.5 | 18 |
| 403 | 0.032 | 100.0 | |
| 404 | 0.007 | 98.3 | 35 |
| 405 | 0.008 | 95.5 | |
| 406 | 0.009 | 88.0 | |
| 407 | 0.007 | 98.5 | 32 |
| 408 | 0.009 | 94.0 | |
| 409 | 0.019 | 99.5 | 22 |
| 410 | 0.009 | 87.0 | 36 |
| 411 | 0.021 | 100.0 | |
| 412 | 0.016 | 98.0 | 34 |
| 413 | 0.010 | 100.0 | |
| 414 | 0.009 | 100.0 | 40 |
| 415 | 0.006 | 96.0 | |
| 416 | 0.008 | 92.0 | |
| 417 | 0.024 | 100.0 | |
| 418 | 0.017 | 89.0 | 7 |
| 419 | 0.046 | 91.5 | |
| 420 | 0.016 | 97.5 | |
| 421 | 0.048 | 100.0 | |
| 422 | 0.006 | 79.0 | 16 |
| 423 | 3.150 | 53.5 | |
| 424 | 0.007 | 99.0 | 15 |
| 425 | 0.005 | 90.5 | 9 |
| 426 | 0.048 | 92.0 | |
| 427 | 0.019 | 91.5 | |
| 428 | 0.072 | 86.0 | |

TABLE 1-continued

| Ex. No. | Receptor activity EC$_{50}$ [μmol/l] | Efficiency [%] | Cooperativity (alpha factor) |
|---|---|---|---|
| 429 | 0.016 | 99.0 | |
| 430 | 0.061 | 90.0 | |
| 431 | 0.092 | 98.0 | |
| 432 | 0.040 | 94.0 | 26 |
| 433 | 0.170 | 100.0 | |
| 434 | 0.061 | 92.0 | |
| 435 | 0.084 | 100.0 | |
| 436 | 0.081 | 94.0 | |
| 437 | 0.009 | 98.4 | 29 |
| 438 | 0.037 | 99.5 | |
| 439 | 0.020 | 100.0 | 35 |
| 440 | 0.023 | 98.5 | |
| 441 | 0.015 | 100.0 | |
| 442 | 0.010 | 100.0 | |
| 443 | 0.009 | 100.0 | |
| 444 | 0.051 | 100.0 | |
| 445 | 0.096 | 97.5 | |
| 446 | 0.050 | 85.0 | 21 |
| 447 | 0.024 | 93.0 | |
| 448 | 0.019 | 97.0 | 22 |
| 449 | 0.015 | 91.0 | 34 |
| 450 | 0.019 | 78.5 | |
| 451 | 0.008 | 91.0 | 21 |
| 452 | 0.013 | 100.0 | 25 |
| 453 | 0.011 | 98.5 | |
| 454 | 0.007 | 100.0 | 28 |
| 455 | 0.010 | 100.0 | 17 |
| 456 | 0.009 | 92.0 | 32 |
| 457 | 0.004 | 82.0 | 36 |
| 458 | 0.003 | 100.0 | |
| 459 | 0.004 | 95.0 | |
| 460 | 0.005 | 98.0 | |
| 461 | 0.039 | 89.0 | |
| 462 | 0.018 | 88.0 | 17 |
| 463 | 0.054 | 89.0 | |
| 464 | 0.128 | 82.5 | |
| 465 | 0.076 | 89.0 | |
| 466 | 0.026 | 100.0 | |
| 467 | 0.042 | 97.5 | |
| 468 | 0.023 | 98.5 | |
| 469 | 0.020 | 100.0 | |
| 470 | 0.104 | 98.5 | |
| 471 | 0.010 | 89.0 | |
| 472 | 0.029 | 90.0 | |
| 473 | 0.031 | 100.0 | |
| 474 | 0.005 | 100.0 | 44 |
| 475 | 0.002 | 100.0 | 68 |
| 476 | 0.018 | 98.0 | |
| 477 | 0.073 | 89.0 | |
| 478 | 0.024 | 100.0 | |
| 479 | 0.038 | 100.0 | |
| 480 | 0.046 | 100.0 | |
| 481 | 0.010 | 100.0 | |
| 482 | 0.013 | 98.5 | |
| 483 | 0.054 | 92.5 | |
| 484 | 0.006 | 99.5 | 44 |
| 485 | 0.006 | 100.0 | |
| 486 | 0.004 | 100.0 | |
| 487 | 0.012 | 96.5 | |
| 488 | 0.024 | 96.0 | 53 |
| 489 | 0.027 | 100.0 | 23 |
| 490 | 0.103 | 91.5 | |
| 491 | 0.106 | 85.5 | |
| 492 | 0.044 | 97.5 | |
| 493 | 0.016 | 94.5 | 14 |
| 494 | 0.028 | 78.0 | 20 |
| 495 | 0.031 | 99.5 | |
| 496 | 0.067 | 89.0 | |
| 497 | 0.029 | 92.0 | |
| 498 | 0.060 | 83.5 | |
| 499 | 0.063 | 96.0 | |
| 500 | 0.076 | 100.0 | |
| 501 | 0.058 | 98.0 | |
| 502 | 0.030 | 91.0 | |
| 503 | 0.028 | 88.5 | 24 |
| 504 | 0.004 | 100.0 | 47 |
| 505 | 0.006 | 100.0 | |
| 506 | 0.007 | 100.0 | 57 |
| 507 | 0.006 | 98.0 | 37 |
| 508 | 0.007 | 93.5 | |
| 509 | 0.007 | 88.0 | |
| 510 | 0.006 | 94.0 | 46 |
| 511 | 0.009 | 100.0 | 30 |
| 512 | 0.010 | 100.0 | |
| 513 | 0.010 | 91.0 | |
| 514 | 0.010 | 99.0 | 30 |
| 515 | 0.012 | 99.3 | 37 |
| 516 | 0.020 | 100.0 | 35 |
| 517 | 0.085 | 88.5 | |
| 518 | 0.470 | 99.5 | |
| 519 | 0.003 | 96.7 | |
| 520 | 0.002 | 100.0 | 36 |
| 521 | 0.002 | 100.0 | 72 |
| 522 | 0.004 | 92.8 | |
| 523 | 0.001 | 100.0 | 41 |
| 524 | 0.002 | 100.0 | 60 |
| 525 | 0.005 | 100.0 | |
| 526 | 0.009 | 100.0 | |
| 527 | 0.005 | 100.0 | 61 |
| 528 | 0.006 | 100.0 | 66 |
| 529 | 0.006 | 96.0 | |
| 530 | 0.006 | 98.7 | 44 |
| 531 | 0.009 | 97.0 | |
| 532 | 0.018 | 92.0 | |
| 533 | 0.024 | 100.0 | |
| 534 | 0.006 | 100.0 | |
| 535 | 0.007 | 100.0 | 27 |
| 536 | 0.016 | 99.5 | |
| 537 | 0.010 | 92.0 | 31 |
| 538 | 0.007 | 100.0 | 40 |
| 539 | 0.007 | 86.5 | 21 |
| 540 | 0.009 | 90.0 | |
| 541 | 0.007 | 92.2 | 31 |
| 542 | 0.019 | 98.5 | 36 |
| 543 | 0.008 | 100.0 | 28 |
| 544 | 0.008 | 98.0 | |
| 545 | 0.008 | 99.0 | |
| 546 | 0.010 | 100.0 | |
| 547 | 0.120 | 90.0 | |
| 548 | 0.009 | 100.0 | 37 |
| 549 | 0.009 | 100.0 | |
| 550 | 0.009 | 100.0 | 34 |
| 551 | 0.018 | 100.0 | |
| 552 | 0.014 | 96.0 | |
| 553 | 0.013 | 97.5 | 49 |
| 554 | 0.010 | 94.5 | 54 |
| 555 | 0.010 | 100.0 | |
| 556 | 0.010 | 100.0 | |
| 557 | 0.011 | 100.0 | 44 |
| 558 | 0.022 | 100.0 | |
| 559 | 0.010 | 99.0 | |
| 560 | 0.017 | 100.0 | |
| 561 | 0.004 | 95.0 | 62 |
| 562 | 0.010 | 100.0 | 40 |
| 563 | 0.020 | 100.0 | |
| 564 | 0.042 | 89.0 | |
| 565 | 0.010 | 99.5 | |
| 566 | 0.016 | 96.5 | |
| 567 | 0.140 | 80.0 | |
| 568 | 0.011 | 100.0 | |
| 569 | 0.049 | 100.0 | |
| 570 | 0.056 | 100.0 | |
| 571 | 0.012 | 94.0 | 33 |
| 572 | 0.012 | 100.0 | |
| 573 | 0.012 | 100.0 | 57 |
| 574 | 0.012 | 100.0 | 36 |
| 575 | 0.013 | 96.0 | |
| 576 | 0.013 | 99.5 | |
| 577 | 0.020 | 100.0 | |
| 578 | 0.017 | 100.0 | 29 |

TABLE 1-continued

| Ex. No. | Receptor activity EC$_{50}$ [μmol/l] | Efficiency [%] | Cooperativity (alpha factor) |
|---|---|---|---|
| 579 | 0.014 | 97.5 | |
| 580 | 0.014 | 100.0 | |
| 581 | 0.014 | 98.0 | |
| 582 | 0.014 | 100.0 | |
| 583 | 0.019 | 100.0 | |
| 584 | 0.016 | 98.0 | |
| 585 | 0.014 | 95.5 | |
| 586 | 0.015 | 100.0 | |
| 587 | 0.014 | 93.5 | |
| 588 | 0.009 | 100.0 | |
| 589 | 0.015 | 100.0 | 34 |
| 590 | 0.015 | 100.0 | 43 |
| 591 | 0.016 | 100.0 | |
| 592 | 0.016 | 99.5 | |
| 593 | 0.017 | 89.5 | 29 |
| 594 | 0.018 | 100.0 | |
| 595 | 0.019 | 94.0 | 36 |
| 596 | 0.021 | 98.5 | 19 |
| 597 | 0.021 | 95.5 | |
| 598 | 0.021 | 100.0 | |
| 599 | 0.023 | 90.0 | |
| 600 | 0.028 | 96.9 | |
| 601 | 0.073 | 100.0 | |
| 602 | 0.023 | 91.5 | |
| 603 | 0.025 | 89.5 | |
| 604 | 0.025 | 93.5 | |
| 605 | 0.025 | 98.0 | |
| 606 | 0.027 | 98.0 | |
| 607 | 0.005 | 100.0 | 32 |
| 608 | 0.022 | 100.0 | |
| 609 | 0.028 | 99.0 | |
| 610 | 0.011 | 100.0 | |
| 611 | 0.017 | 90.0 | |
| 612 | 0.029 | 100.0 | |
| 613 | 0.033 | 95.5 | |
| 614 | 0.036 | 94.5 | |
| 615 | 0.053 | 99.3 | |
| 616 | 0.037 | 90.5 | |
| 617 | 0.096 | 98.0 | |
| 618 | 0.039 | 99.0 | 30 |
| 619 | 0.040 | 88.6 | |
| 620 | 0.047 | 100.0 | |
| 621 | 0.010 | 100.0 | 44 |
| 622 | 0.043 | 93.0 | |
| 623 | 0.067 | 97.0 | |
| 624 | 0.140 | 96.5 | |
| 625 | 0.043 | 100.0 | |
| 626 | 0.044 | 93.5 | |
| 627 | 0.140 | 83.5 | |
| 628 | 0.032 | 89.5 | |
| 629 | 0.044 | 100.0 | |
| 630 | 0.048 | 100.0 | |
| 631 | 0.049 | 86.0 | 23 |
| 632 | 0.049 | 100.0 | |
| 633 | 0.052 | 93.8 | |
| 634 | 0.054 | 100.0 | 48 |
| 635 | 0.059 | 100.0 | |
| 636 | 0.060 | 98.1 | |
| 637 | 0.060 | 93.0 | |
| 638 | 0.063 | 100.0 | |
| 639 | 0.068 | 96.5 | 25 |
| 640 | 0.069 | 91.3 | |
| 641 | 0.071 | 100.0 | |
| 642 | 0.072 | 100.0 | |
| 643 | 0.073 | 92.0 | |
| 644 | 0.074 | 85.0 | |
| 645 | 0.074 | 83.0 | |
| 646 | 0.074 | 100.0 | 30 |
| 647 | 0.077 | 92.0 | |
| 648 | 0.081 | 96.5 | 49 |
| 649 | 0.083 | 94.0 | |
| 650 | 0.083 | 100.0 | |
| 651 | 0.086 | 95.0 | |
| 652 | 0.089 | 80.0 | |
| 653 | 0.089 | 86.5 | |
| 654 | 0.093 | 84.0 | |
| 655 | 0.097 | 98.0 | |
| 656 | 0.100 | 91.5 | |
| 657 | 0.100 | 85.3 | |
| 658 | 0.006 | 100.0 | |
| 659 | 0.081 | 98.0 | |
| 660 | 0.102 | 84.5 | |
| 661 | 0.048 | 95.5 | |
| 662 | 0.038 | 100.0 | |
| 663 | 0.030 | 90.5 | |
| 664 | 0.100 | 98.0 | |
| 665 | 0.073 | 92.5 | |
| 666 | 0.022 | 100.0 | 60 |
| 667 | 3.850 | 100.0 | |
| 668 | 0.089 | 100.0 | |
| 669 | 0.106 | 84.9 | |
| 670 | 1.450 | 66.5 | |
| 671 | 0.100 | 94.0 | |

B-2. Functional Ca2+ Release Test by Means of M2-Gα16 Reporter Cells

Any potentially agonistic or else potentially allosteric effect of the test substances on the M2 receptor can be determined by a functional Ca$^{2+}$ release test. The activation of the M2 receptor by binding of orthosteric agonists (acetylcholine) or other substances having an agonistic effect leads to a change in conformation of the receptor, which, in the endogenous state, results in Gαi protein activation. However, coupling of the M2 receptor to the exogenously expressed promiscuous Gαq protein Gα16 results in Gα16 protein activation after activation of the M2 receptor, which causes—via a downstream signal transduction cascade—intracellular Ca$^{2+}$ release. The extent of intracellular Ca$^{2+}$ mobilization can therefore be regarded as a measure of the activation of the M2 receptor.

The test cell used is a recombinant CHO cell line which has been stably transfected with cDNA coding for the human M2 receptor and the Gα16 protein and with cDNA coding for the mitochondrially expressed photoprotein clytin (mt-Clytin) (CHO mtClytin Gα16 M2). The determination of the intracellular Ca$^{2+}$ release as a function of substance addition or M2 activation is effected by means of a Ca$^{2+}$-sensitive dye (Fluo-8) and the measurement of cell fluorescence using a FLIPR$^{TETRA}$ instrument (Molecular Devices).

B-2.1. Agonism Assay

The test substances are dissolved in DMSO at a concentration of 10 mM and serially diluted with DMSO in steps of 1:3.16 for a 10-point dose/activity analysis. In accordance with the desired test concentrations, the substances are prediluted in Fluo-8 buffer (composition per 100 ml: 500 μl probenecid, 2 ml Brilliant Black (20 mg/ml), 440 μl Fluo-8, 2 mM CaCl$_2$ ad 100 ml CAFTY Tyrode (130 mM NaCl, 5 mM KCl, 20 mM HEPES, 1 mM MgCl$_2$, 5 mM NaHCO$_3$, pH 7.4)).

The reporter cells cultivated in MEM alpha medium (supplemented with 10% FCS, 2% Glutamax) were sown with 3000 cells in 30 μl of sowing medium per 384-well in pCLEAR/schwarz Greiner cell culture plates (#781092) and incubated at 37° C. for 24 h. The sowing medium consists of MEM alpha medium (supplemented with 5% FCS, 2% Glutamax). For the respective measurement, the medium is removed and the cells, after addition of 20 μl in each case of Fluo-8 buffer per 384-well, were incubated in an incubator at 37° C. for 1 h. After addition of 10 μl in each case per 384-well of the prediluted test substances, cell fluorescence was measured for a period of 5 min in 1 sec increments. The relative degree of maximum activation of the M2 receptor by the respective test substances is calculated by normalizing the test signal to the signal corresponding to the $E_{Max}$ concentration of acetylcholine (3 μM).

B-2.2. Determination of the Positive Allosteric Modulator Effect

In order to be able to determine the positive cooperativity of the test substances in relation to the acetylcholine-mediated M2 receptor activation, reference agonist (acetylcholine) is then added for a full dose-response analysis. For this purpose, acetylcholine is serially diluted in Fluo-8 buffer in steps of 1:3.16 beginning with a maximum final concentration of 1 μM. After addition of 10 μl in each case of agonist solution per 384-well, cell fluorescence is again measured for a period of 5 min in 1 sec increments. The same assay plate is used as immediately before for the M2 agonism assay. The shift in the acetylcholine dose-response curve in the presence of increasing concentrations of the test substance is analysed and quantified by means of GraphPad PRISM (Allosteric $EC_{50}$ shift) (see above).

B-3. Selectivity Test with Respect to Human Muscarinic Acetylcholine Receptors

Any potentially agonistic effect, or else positive allosteric effect, of the test substances on other human muscarinic acetylcholine receptors can be determined in a functional $Ca^{2+}$ release test (Eurofins; GPCRProfiler® Services in agonistic and allosteric mode for Mx Receptors; cat#: HTS600GPCR).

The test cells used were the Chem-1 or Chem-4 cell lines transfected with the particular receptor (ChemiScreen™ M1 Calcium-Optimized FLIPR Cell Lines, Eurofins; M1: HTSO44C; ChemiScreen™ Calcium-Optimized Stable Cell Line Human Recombinant M2 Muscarininc Acetylcholine Receptor, Eurofins; M2: HTS115C; ChemiScreen™ Human Recombinant M3 Muscarinic Acetylcholine Receptor Calcium-Optimized Stable Cell Line, Eurofins; M3: HTS116C; ChemiScreen™ Human Recombinant M4 Muscarinic Acetylcholine Receptor Calcium-Optimized Stable Cell Line, Eurofins; M4: HTS117C; ChemiScreen™ M5 Calcium-Optimized FLIPR Cell Lines, Eurofins; M5: HTS075C). The substance test is conducted with a FLIPR$^{TETRA}$ instrument (Molecular Devices).

B-3.1. Agonism Assay

In order to determine any potential agonistic effect of the test substances, the respective test substances were added with a final test concentration of 10 μM or 1 μM. $Ca^{2+}$ release or cell fluorescence is measured over a period of 180 sec. The positive control used for normalization of the substance effect to the receptor activation is a concentration of acetylcholine corresponding to the $E_{Max}$ value.

After the agonism assay has ended, the assay plate is incubated at 25° C. for 7 min. After the incubation period, the positive allosteric modulator assay is initialized.

B-3.2. Allosteric Modulator Assay

In order to examine any positive or negative allosteric effect of the test substances on other human muscarinic acetylcholine receptors and the M2 receptor itself, every substance concentration is combined with an acetylcholine 8-point dose-response curve. Addition of agonist solution is again followed in turn by the measurement of cell fluorescence for a period of 180 sec. The shift in the acetylcholine dose-response curve (maximum shift in the $EC_{50}$ of acetylcholine) is analysed and quantified by means of GraphPad PRISM (Sigmoidal dose-response (variable slope)—$EC_{50}$). Finally, quotients of the allosteric shift for the M2 receptor and M4 receptor are formed, which function in turn as a measure of the respective selectivity.

Tables 2 and 3 below list, for individual working examples, the quotients thus determined using selected molecules from this assay:

TABLE 2

| Ex. No. | $EC_{50}$ ACh M2 [nM] | $EC_{50}$ ACh M4 [nM] | Concentration [μM] | Shift $EC_{50}$ M2 | Shift $EC_{50}$ M4 | Selectivity (Shift $EC_{50}$ M2/Shift $EC_{50}$ M4) |
|---|---|---|---|---|---|---|
| Ref. (LY2119620) | 440 | 100 | 10 | 46 | 56 | 0.8 |
| Ref. (LY2119620) | 440 | 100 | 1 | 24 | 83 | 0.3 |
| 175 | 440 | 100 | 10 | 76 | 0.9 | 83 |
| 175 | 440 | 100 | 1 | 21 | 0.7 | 29 |
| 323 | 323 | 110 | 10 | 40 | 0.9 | 44 |
| 323 | 350 | 110 | 1 | 48 | 0.9 | 52 |
| 590 | 350 | 110 | 10 | 39 | 1.2 | 33 |
| 590 | 350 | 110 | 1 | 7 | 1.1 | 7 |

More particularly, it is clear from Table 2 that the selectivity of the above-addressed molecule LY2119620 has a clear tendency in favour of M4, whereas the selectivity of the molecules according to the invention is balanced or biased to M2.

TABLE 3

| Ex. No. | $EC_{50}$ ACh M2 [nM] | $EC_{50}$ ACh M4 [nM] | Concentration [μM] | Shift $EC_{50}$ M2 | Shift $EC_{50}$ M1 | Selectivity (Shift $EC_{50}$ M2/Shift $EC_{50}$ M1) |
|---|---|---|---|---|---|---|
| Ref. (LY2119620) | 18 | 100 | 10 | 46 | 11 | 4 |
| 175 | 18 | 100 | 10 | 76 | 0.3 | 287 |

TABLE 3-continued

| Ex. No. | EC$_{50}$ ACh M2 [nM] | EC$_{50}$ ACh M4 [nM] | Concentration [µM] | Shift EC$_{50}$ M2 | Shift EC$_{50}$ M1 | Selectivity (Shift EC$_{50}$ M2/Shift EC$_{50}$ M1) |
|---|---|---|---|---|---|---|
| 323 | 18 | 100 | 10 | 40 | 1.3 | 31 |
| 590 | 18 | 100 | 10 | 39 | 1.3 | 30 |

It is clear from Table 3 that the molecules according to the invention have a very much greater selectivity for M2 compared to M1 than the above-addressed molecule LY2119620.

B-4. In Vitro M2 PAM Gi Assay

For the characterization of the test substances on positive allosteric modulation of the human M2 receptor, the carbachol-induced inhibition of the rise in cAMP due to forskolin in recombinant M2 receptor-expressing CHO cells is measured, these additionally expressing a luciferase gene under the control of a cAMP-responsive element (CRE): 3000 cells in 25 µl of full medium (DMEM F12 PAN medium, 10% FCS, 1.35 mM Na pyruvate, 20 mM Hepes, 4 mM Glutamax, 2% sodium bicarbonate, 1% Pen/Strep, 1% 100× non-essential amino acids) are sown per well of a 384 multititre plate (Greiner, TC Platte, black with clear base) and incubated at 37° C., 5% CO$_2$ for 24 hours. Before the measurement, the medium is replaced by 30 µl of test medium (Optimem) and incubated at 37° C., 5% CO$_2$ for 10 minutes. The test substance is prepared in DMSO in various concentrations (starting concentration 10 mM, dilution factor 3.16) as a dose-response curve and pre-diluted 1:50 with calcium-free Tyrode, 2 mM CaCl$_2$, 0.01% BSA. 10 µl of the prediluted substance solution are added to the cells and incubated at 37° C., 5% CO$_2$ for 10 minutes.

The M2 receptor is activated by adding 10 µl of carbachol in various concentrations in calcium-free Tyrode, 2 mM CaCl$_2$ and incubated at 37° C., 5% CO$_2$ for 5 minutes. Adenylyl cyclase is activated by adding 10 µl of 1 µM (final concentration) forskolin in calcium-free Tyrode, 2 mM CaCl$_2$ and incubated at 37° C., 5% CO$_2$ for 5 hours. After removing the cell supernatant and adding 20 µl of Luci/Triton buffer (1:1), luminescence is determined in a luminometer for 60 seconds.

Calcium-free Tyrode: 130 mM NaCl, 5 mM KCl, 20 mM HEPES, 1 mM MgCl$_2$, 4.8 mM NaHCO$_3$, pH 7.4

Luci/Triton buffer (1:1): Luci buffer (20 mM tricine, pH 7.8, 2.67 mM magnesium sulphate, 0.1 mM EDTA, 4 mM DTT, 270 µM coenzyme A, 470 µM D-luciferin, 530 µM ATP) mixed 1:1 with triton buffer (25 mM Tris aqueous hydrochloric acid, pH 7.8, 25 mM Na$_2$HPO$_4$, 2 mM dithiothreitol, 3% Triton X-100, 10% glycerin).

The EC$_{50}$ value was determined with the aid of a 4-parameter logistic function (Hill function).

B-5. Competitive Binding Test for Human M2 and M4 Receptors

The direct binding of the test substances to the M2 receptor and the boosting of the binding (increasing affinity) of the natural agonist acetylcholine to the M2 receptor in the presence of the test substances (positive allosteric effect) is determined by means of a FRET-based binding assay (HTRF Tag-lite® binding assay, Cisbio). For control of selectivity, the binding of the test substances to the structurally related M4 receptor is examined analogously. The HTRF Tag-lite® assay is a homogeneous binding assay and is based on the competitive binding of a fluorescent ligand (probe) and the unlabelled test substance to the receptor, which is expressed in living cells. The receptor in turn is derivatized with a fluorescent donor dye (terbium cryptate), such that excitation of the donor dye gives rise to a FRET signal between the receptor and probe (acceptor) when the probe is bound to the receptor. The acceptor probe used was a telenzepine derivative conjugated with an HTRF fluorescent dye (red ligand; L0040RED). The probe therefore binds in the conserved orthosteric binding site both of the M2 and of the M4 receptor. The allosteric binding site of the M2 receptor has been characterized by x-ray crystallography and is postulated as being directly above the orthosteric binding pocket (Kruse et al., *Nature*, 2013, 504, 101-106). Both the binding of unlabelled orthosteric agonists (acetylcholine) to the orthosteric binding site and the binding of allosteric modulators (test substances) to the allosteric binding site therefore leads to a concentration-dependent competitive displacement of the probe and hence to a decrease in the FRET-based fluorescence signal.

All binding tests are conducted on white 384 microtitre plates (small volume) in a total volume of 20 µl. The HTRF measurements are undertaken with a PHERAstar instrument (BMG Labtech). For the muscarinic M2 or M4 receptor binding test, SNAPed-M2-expressing cells (C1TT1M2) or SNAPed-M4-expressing cells (C1TT1M4) are used, which have been labelled with a donor fluorophore (Lumi4Tb; CELLCUST). The cells are incubated with the acceptor probe in Tag-lite binding buffer (LABMED) in the presence of test substance or acetylcholine. Subsequently, the fluorescence signal is measured at wavelengths of 665 nm and 620 nm and the HTRF quotient (signal at 665 nm/signal at 620 nm) is determined. The relative specific signal is determined by subtracting the HTRF quotient of negative control (Tag-lite buffer only without probe).

B-5.1. Binding of the Test Substances

In order to determine the binding of the test substances to the M2 or M4 receptor in the absence of orthosteric agonist, a dose-response analysis of the test substances is undertaken in the competitive format of the M2-Tag-lite® or M4-Tag-lite® binding assay. The test substances are dissolved in DMSO at a concentration of 10 mM and serially diluted with DMSO in steps of 1:3.16 for a dose-response analysis. The maximum test concentration corresponds to 10 µM. The molar concentration of the test substance that brought about a half-maximum reduction in the HTRF signal in relation to the maximum and remaining HTRF signal at the highest substance concentration (EC$_{50}$ of the binding) is determined by means of GraphPad PRISM (Sigmoidal dose response). At the same time, the strength of the competition effect is determined by calculating the maximum decrease in the specific HTRF signal at the highest substance concentration (% max. competition).

B-5.2. Binding of the Test Substances in Allosteric Mode

To examine the allosteric modulation of the M2 receptor by the test compounds, firstly, a dose-response analysis of the test substances in the competitive format of the M2-Taglite® or M4-Tag-lite® binding assay in the presence of a concentration of acetylcholine corresponding to the $EC_{20}$ value is undertaken, the latter being determined in a separate 11-point acetylcholine dose-response analysis (3 µM). The test substances are dissolved in DMSO at a concentration of 10 mM and serially diluted with DMSO in steps of 1:3.16 for a 10-point dose/activity analysis. The maximum test concentration corresponds to 10 µM. The molar concentration of the test substance that brought about a half-maximum reduction in the HTRF signal in relation to the maximum and remaining HTRF signal at the highest substance concentration in the presence of an acetylcholine concentration corresponding to the EC20 value ($EC_{50}$ of the binding) is determined by means of GraphPad PRISM (Sigmoidal dose response). At the same time, the strength of the competition effect is determined by calculating the maximum decrease in the specific HTRF signal at the highest substance concentration (% max. competition).

In order to examine the boosting of the binding of acetylcholine to the M2 or M4 receptor, in addition, secondly, an 11-point dose-response analysis of acetylcholine in the competitive format of the M2-Tag-lite® or M4-Tag-lite® binding assay was undertaken in the absence or in the presence of 1 µM or 10 µM test substance. The shift in the acetylcholine dose-response curve (maximum shift in the EC50 value of acetylcholine) was analysed and quantified by means of GraphPad PRISM (Sigmoidal dose-response).

B-6. Radioligand Binding Assay for Human M2 Receptors

The allosteric mechanism of action of the test substances can be further investigated in detail and be quantified by various radioligand binding assays. The binding of the allostere to the allosteric binding site of the M2 receptor results in an increase in the binding affinity of the orthosteric ligand for the M2 receptor in the case of positive cooperativity. The increase in the binding affinity of the orthosteric ligand by the allostere in the ternary complex consisting of orthostere, allostere and M2 receptor is in turn due to modulation of the binding kinetics of the orthostere. The allostere can alter the association and/or dissociation rate of the orthostere at the M2 receptor. A lowering of the dissociation rate reflects in this case a stabilization of the ternary complex and accompanies therefore a lowering of the dissociation constant of the orthosteric ligand under equilibrium conditions (Lazareno, Determination of Allosteric Interactions Using Radioligand-Binding Techniques in *Methods in Molecular Biology*, vol. 259, Receptor Signal Transduction Protocols, 2nd ed.; Kostenis and Mohr, *Trends Pharmacol. Sci.* 1996, 17(8), 280-283).

B-6.1. Radioligand Binding Assay Under Equilibrium Conditions

In order to check and to quantify the influence of the test substances on the binding affinity of orthosteric agonists for the M2 receptor, a radioligand binding assay under equilibrium conditions can be conducted. In this case, the binding of the radiolabelled M2 receptor agonist $^3$H-oxotremorine M to the M2 receptor is investigated at different concentrations of $^3$H-oxotremorine M in the binding equilibrium (Croy et al., *Mol. Pharmacol.* 2014, 86, 106-115). Based on the amount of radioactive agonist specifically bound to the M2 receptor as a function of the agonist concentration (graphically represented as the so-called Langmuir isotherm), firstly the equilibrium dissociation constant $K_d$ of the agonist can be calculated as a quantitative measure of its binding affinity for the M2 receptor and secondly the concentration or number of specific binding sites of the radioligand (agonist) $B_{max}$ in the absence or presence of different concentrations of the test substances (positive allosteric modulators) (Hulme and Trevethick, *Brit. J. Pharmacol.* 2010, 161, 1219-1237).

The radioligand binding assay for the M2 receptor (Euroscreen, FAST-0261B) is carried out by means of $^3$H-labelled oxotremorine M (NET671) as agonist. The agonist binding to the M2 receptor is carried out in triplicate on 96-well microtitre plates (Master Block, Greiner, 786201) in binding buffer (sodium/potassium phosphate buffer, pH 7.4). For this purpose, each assay of M2 membrane extracts (20 µg of protein/96 well) are incubated with various concentrations of radiolabelled agonists (0.2-100 nM) alone or in the presence of 1 µM or 10 µM test substance or binding buffer alone in a total volume of 0.1 mL at 37° C. for 60 min. The non-specific binding of $^3$H-labelled oxotremorine M to the membrane is determined by co-incubating with N-methylscopolamine (NMS), an orthosteric antagonist of the M2 receptor, in a 200-fold excess. In order to stop the binding reaction, the samples are then filtered via GF/C filter (Perkin Elmer, 6005174), which had previously been wetted with 0.5% polyethylenimine (PEI) solution, for 2 h at room temperature. The filters are washed six times each with 0.5 mL of ice-cold wash buffer (10 mM sodium/potassium phosphate buffer, pH 7.4) and 50 µL of Microscint 20 scintillation solution (Packard) added per assay. The samples are then incubated for 15 min on an orbital shaker before the radioactivity is measured by means of a TopCount™ instrument (1 min/well).

The test substances are dissolved in DMSO at a concentration of 10 mM and further diluted in DMSO corresponding to the final test concentration in order to obtain a 100-fold dilution of the DMSO solution used in binding buffer.

The $K_d$ and $B_{max}$ of $^3$H-oxotremorine M for the M2 receptor are determined with the aid of a "one-site" specific binding model (Croy et al., *Mol. Pharmacol.* 2014, 86, 106-115).

B-6.2. Competitive Radioligand Binding Assay Under Equilibrium Conditions

In order to check and to quantify further the influence of the test substances on the binding affinity of orthosteric agonists for the M2 receptor, a competitive radioligand binding assay under equilibrium conditions is also conducted. In this case, the binding of the antagonistic radioligand $^3$H—N-methylscopolamine ($^3$H-NMS) to the M2 receptor is determined in the absence or presence of various concentrations of non-radiolabelled agonist oxotremorine M (Croy et al., *Mol. Pharmacol.* 2014, 86, 106-115; Schober et al., *Mol. Pharmacol.* 2014, 86, 116-123). The radiolabelled probe (antagonist) and the non-labelled agonist compete for the binding to the orthosteric binding site of the M2 receptor. The ability to displace the radiolabelled probe therefore serves as a measure of the binding affinity of the agonist for the receptor and can be quantified in accordance with the Cheng-Prusoff equation as an equilibrium inhibition constant ($K_i$) (Cheng and Prusoff, *Biochem. Pharmacol.* 1973, 22(23), 3099-3108). In order to further investigate the allosteric effect of the test substances, the influence of the test substances on the $K_i$ of oxotremorine M is determined.

The antagonist inhibition binding assay for the M2 receptor (Euroscreen, FAST-0261B) is carried out on 96-well microtitre plates (Master Block, Greiner, 786201) in binding buffer (50 mM Tris buffer pH 7.4, 1 mM EDTA, 10 µg/ml saponin) using $^3$H-NMS as M2 receptor antagonist. To adjust the binding equilibrium, each assay of M2 membrane extracts (20 µg of protein/96 well) are incubated with a defined concentration of radiolabelled antagonist (0.5 nM)

alone or in the presence of various concentrations of non-labelled agonists (oxotremorine M; 0.001 nM to 1 mM) with or without 1 µM or 10 µM test substance or binding buffer alone in a total volume of 0.1 mL at 25° C. for 2 h. The non-specific binding of $^3$H-labelled NMS to the membrane is determined by co-incubating with non-radiolabelled acetylcholine in a 200-fold excess. In order to stop the binding reaction, the samples are then filtered over GF/C filters (Perkin Elmer, 6005174), which had previously been wetted with 0.5% PEI solution, for 2 h at room temperature. The filters are washed six times each with 0.5 mL of ice-cold wash buffer (10 mM sodium/potassium phosphate buffer, pH 7.4) and 50 µL of Microscint 20 scintillation solution (Packard) is added per assay. The samples were then incubated for 15 min on an orbital shaker before the radioactivity is measured by means of a TopCount™ instrument (1 min/well).

The test substances are dissolved in DMSO at a concentration of 10 mM and further diluted in DMSO corresponding to the final test concentration in order to obtain a 100-fold dilution of the DMSO solution used in binding buffer.

The $K_i$ values in the presence or absence of test substance are quantified with the aid of the Cheng-Prusoff equation (Cheng and Prusoff, *Biochem. Pharmacol.* 1973, 22(23), 3099-3108). In this case, the $IC_{50}$ values of the substances are determined according to a four parameter logistic equation and the $K_d$ of NMS determined in a radioligand binding assay under equilibrium conditions (Schober et al., *Mol. Pharmacol.* 2014, 86, 116-123).

B-6.3. Kinetic Radioligand Binding Assay

By means of a kinetic radioligand binding assay, the kinetics of the dissociation of the radiolabelled agonist $^3$H-oxotremorine M for the M2 receptor in the presence or absence of test substance can be investigated. By these means, the influence of the allosteric activity of the test substances on the dissociation constant ($k_{off}$-rate) of the M2 agonist can be determined and thus the allosteric mechanism of the test substances can be further characterized (Lazareno, Determination of Allosteric Interactions Using Radioligand-Binding Techniques in *Methods in Molecular Biology*, vol. 259, Receptor Signal Transduction Protocols, 2nd ed.; Schrage et al.).

The radioligand dissociation binding assay for the M2 receptor (Euroscreen, FAST-0261B) is carried out with $^3$H-labelled oxotremorine M (NET671) as agonist. The binding reaction is carried out in binding buffer (sodium/potassium phosphate buffer, pH 7.4) on 96-well microtitre plates (Master Block, Greiner, 786201). For this purpose, each assay of M2 membrane extracts (20 µg of protein/96 well) are preincubated with a defined concentration of radiolabelled agonist (9.65 nM) alone or in the presence of 1 µM or 10 µM test substance or binding buffer alone at 37° C. for 60 min. NMS is then added in 200-fold excess at various time points (one time point per assay) and the mixtures incubated in a total volume of 0.1 mL at 37° C. In order to stop the binding reaction, the samples are then filtered over GF/C filters (Perkin Elmer, 6005174), which had previously been wetted with 0.5% PEI solution, for 2 h at room temperature. The filters are washed six times each with 0.5 mL of ice-cold wash buffer (10 mM sodium/potassium phosphate buffer, pH 7.4) and 50 µL of Microscint 20 scintillation solution (Packard) is added per assay. The samples are then incubated for 15 min on an orbital shaker before the radioactivity is measured by means of a Top-Count™ instrument (1 min/well).

The test substances are dissolved in DMSO at a concentration of 10 mM and further diluted in DMSO corresponding to the final test concentration in order to obtain a 100-fold dilution of the DMSO solution used in binding buffer.

The $k_{off}$ was determined with the aid of a "one phase" exponential decay model of the dissociation (Hulme and Trevethick, *Brit. J. Pharmacol.* 2010, 161, 1219-1237; Kostenis and Mohr, *Trends Pharmacol. Sci.* 1996, 17(8), 280-283).

B-7. Effects of the Test Substances on Acetylcholine-Mediated GIRK1/4 Channel Currents in Primary Atrial Rat Cardiomyocytes The substance testing is carried out in accordance with a patch clamp protocol described in the literature for the electrophysiological measurement of acetylcholine-induced GIRK1/4 membrane currents in native rat atrial myocytes (see e.g. Beckmann and Rinne et al., G Protein-Activated (GIRK) Current in Rat Ventricular Myocytes is Masked by Constitutive Inward Rectifier Current (IK1), Cell Physiol Biochem 2008; 21:259-268).

An acetylcholine dose-response curve for GIRK1/4 activity is initially determined in the absence of test substance (DMSO control) by perfusing test solutions with increasing acetylcholine concentration and measuring the resulting membrane currents. The membrane currents or change in the membrane currents are measured for a given ACh concentration for approx. 10 to 20 seconds. After application of the maximum ACh concentration within a DRC series, a solution of atropine (10 µM) is perfused followed by washing out of the substance solutions in order to ensure the M2 selectivity and reversibility of M2 activation. Changes of the membrane currents are appropriately recorded. Here, each acetylcholine concentration of the membrane current measured is in each case normalized to the maximum acetylcholine-induced membrane current (I/IMax). An acetylcholine dose-response curve comprises in this case five different concentrations (1 nM, 10 nM, 100 nM, 1 µM, 10 µM). The EC50 value is determined with the aid of a 4-parameter logistic function (Hill function).

In order to determine the allosteric effect of the test substances on the M2 receptor, the acetylcholine dose-response curve is determined for the GIRK1/4 membrane current in the presence of a constant concentration of the respective test substance (e.g. 1 µM). For this purpose, after pre-incubation of the cell with the test substance for approx. 20 seconds and measurement of the membrane currents, a test solution comprising the same substance concentration and a defined ACh concentration is perfused for approx. 10 to 20 seconds and the membrane currents are measured. After application of the maximum acetylcholine concentration within a measurement series, the perfusion of a solution with atropine (10 µM) is in turn carried out in order to check the M2 selectivity of the substance effect. The EC50 value in the presence of test substance is determined analogously with the aid of a 4-parameter logistic function (Hill function) (see above).

The shift in the acetylcholine dose-response curve is determined and quantified by the change in the EC50 value for acetylcholine in the absence or presence of the test substance.

B-8. Effects of the Test Substances on Isolated Perfused Rat Heart

Male Wistar rats (strain: (HsdCpb:WU) with a body weight of 200-250 g are anaesthetized with Narcoren (100 mg/kg). The thorax is opened and the heart is then exposed, excised and connected to a Langendorff apparatus by placing a cannula into the aorta. The heart is perfused retrogradely at 9 ml/min at constant flow with a Krebs-Henseleit buffer solution (gassed with 95% $O_2$ and 5% $CO_2$, pH 7.4, 35° C.; with the following composition in mmol/l: NaCl 118; KCl 3; $NaHCO_3$ 22; $KH_2PO_4$ 1.2; magnesium sulphate 1.2; $CaCl_2$ 1.8; glucose 10; Na pyruvate 2). To measure the contractility of the heart, a balloon, made of thin plastic film, which is attached to a PE tube and filled with water is introduced via an opening in the left auricle of the heart into the left ventricle. The balloon is connected to a pressure transducer. The end-diastolic pressure is adjusted to 5-10 mmHg via the balloon volume. The data are enhanced by a bridge amplifier and registered on a computer using the LabChart software (ADInstruments).

To investigate the allosteric effect of the test substances, the hearts are perfused with addition of 300 nmol/l of the test substance. After 15 min, carbachol is added cumulatively to the perfusion solution in increasing concentrations. Lowering of the heart rate resulting therefrom is compared, as dose-response curve, with effects on hearts which had been treated with solvent in place of test substance. The shift in the carbachol dose-response curve is analysed and quantified by GraphPad PRISM (sigmoidal dose-response).

B-9. Effects of the Test Substances on the Heart Rate in Anaesthetized Rats

Male rats of the strain (WI) WU Br from the breeder Charles River are anaesthetized initially with a 4-5% isoflurane inhalation for approx. 3 min. Subsequently, anaesthesia is maintained using a 1.5% isoflurane inhalation. For this purpose, the anaesthetized animals are fixed on a heated operating plate. By means of visual inspection and between toe reflex, the depth of anaesthesia is checked.

For the application of the test substance, an i.v. route into the jugular vein is used. A caudal to cranial skin incision is then made longitudinally and both the cervical musculature and the salivary glands are severed. The right common carotid artery is exposed and blood supply is arrested both proximally and distally. Using microinstrumentation, a TIP catheter (1.2 F) is introduced into the vessel in order to measure the arterial pressure and the heart rate.

Initially, both parameters are monitored for 10 min in the basal state without substance addition. The substances to be investigated are dissolved in suitable solvent mixtures and subsequently administered at various dosages to a group of animals in each case via the jugular vein by an infusion pump over 5 min. A solvent-treated group is used as control under the same experimental conditions. The arterial blood pressure and heart rate with substance addition is determined for 20 min. The data are registered with the PowerLab system (AD instruments) and evaluated using the LabChart program (AD instruments).

The values determined in this manner for the percentage decrease in heart rate for individual working examples are given in Table 4 below (in some cases as means of a plurality of independent individual determinations):

TABLE 4

| Ex. No. | Reduction in heart rate (%) |
|---|---|
| 28 | 9 |
| 174 | 7 |
| 175 | 6 |
| 189 | 7 |
| 201 | 6 |
| 212 | 11 |
| 213 | 14 |

TABLE 4-continued

| Ex. No. | Reduction in heart rate (%) |
|---|---|
| 271 | 8 |
| 275 | 9 |
| 284 | 11 |
| 296 | 11 |
| 297 | 10 |
| 323 | 13 |
| 325 | 13 |
| 330 | 9 |
| 332 | 11 |
| 342 | 10 |
| 349 | 14 |
| 370 | 12 |
| 386 | 13 |
| 400 | 11 |
| 404 | 9 |
| 407 | 13 |
| 414 | 16 |
| 511 | 10 |
| 520 | 15 |
| 523 | 15 |
| 530 | 13 |
| 541 | 14 |
| 550 | 13 |
| 590 | 13 |

B-10. Radiotelemetric Measurement of Blood Pressure and Heart Rate of Conscious Rats A commercially available telemetry system from Data Sciences International DSI, USA, is employed for the measurements on conscious rats described below. The system consists of 3 main components: (1) implantable transmitters (PhysioTel® telemetry transmitter), (2) receivers (PhysioTel® receiver), which are linked via a multiplexer (DSI Data Exchange Matrix) to a (3) data acquisition computer. The telemetry system makes it possible to continuously record blood pressure, heart rate and body motion of conscious animals in their usual habitat.

The studies are conducted on adult female rats (Wistar Unilever/WU or Spontaneous Hypertensive Rat/SHR) with a body weight of >200 g. After transmitter implantation, the experimental animals are housed singly in type III Makrolon® cages. They have free access to standard feed and water. The day/night rhythm in the test laboratory is set by changing the illumination of the room.

Transmitter Implantation:

The telemetry transmitters used (e.g. PA-C40 HD-S10, DSI) are surgically implanted under aseptic conditions in the experimental animals at least 14 days before the first experimental use. For the implantation, the fasted animals are anaesthetized with isoflurane (IsoFlo®, Abbott, initiation 5%, maintenance 2%) and shaved and disinfected over a large area of their abdomens. After the abdominal cavity has been opened along the linea alba, the liquid-filled measuring catheter of the system is inserted into the descending aorta in the cranial direction above the bifurcation and fixed with tissue glue (Vetbond™, 3M). The transmitter housing is fixed intraperitoneally to the abdominal wall muscle, and the wound is closed layer by layer. Post-operatively, an antibiotic (Ursocyclin® 10%, 60 mg/kg s.c., 0.06 ml/100 g body weight, Serumwerk Bernburg AG, Germany) for infection prophylaxis and an analgesic (Rimadyl®, 4 mg/kg s.c., Pfizer, Germany) are administered.

Substances and Solutions:

Unless stated otherwise, the substances to be studied are administered orally to a group of animals in each case (M=6). In accordance with an administration volume of 2 ml/kg of body weight, the test substances are dissolved in suitable solvent mixtures. A solvent-treated group of animals is used as control.

Experimental Outline:

The telemetry measuring system is configured for 24 animals. Each of the instrumented rats living in the system is assigned a separate receiving antenna (RPC-1 Receiver, DSI). The implanted senders can be activated externally via an installed magnetic switch and are switched to transmission during the pre-run of the experiment. The signals emitted can be detected online by a data acquisition system (Dataquest™ A.R.T. for Windows, DSI or Ponemah, DSI) and processed accordingly. In the standard procedure, the following are measured for 10-second periods in each case: (1) systolic blood pressure (SBP), (2) diastolic blood pressure (DBP), (3) mean arterial pressure (MAP), (4) heart rate (HR) and (5) activity (ACT). These parameters are measured over 24 hours after administration. The acquisition of measurements is repeated under computer control at 5-minute intervals. The source data obtained as absolute values are corrected in the diagram with the currently measured barometric pressure (Ambient Pressure Reference Monitor, APR-1, DSI).

Evaluation:

After the end of the experiment, the acquired individual data are sorted using the analysis software (Dataquest™ A.R.T. 4.1 Analysis or Ponemah, DSI). The 2 hour time point before substance application is assumed as the blank value. The data are smoothed over a presettable period by determination of the means (30 minute mean).

B-11. Effects of the Test Substances on the Heart Rate in Anaesthetized Dogs

Male or female cross-breeds (Mongrels, Marshall BioResources, USA) with a body weight between 20 and 30 kg are anaesthetized with pentobarbital (30 mg/kg iv, Narcoren®, Merial, Germany). Pancuronium chloride (Pancuronium-Actavis®, Actavis, Germany, 1 mg/animal iv) serves here additionally as muscle relaxant. The dogs are intubated and ventilated with an oxygen-air mixture (40/60%) (approximately 5-6 L/min). The ventilation is conducted using a ventilation device from GE Healthcare (Avance), which also serves as anaesthesia monitor (CO2 analyser). The anaesthesia is maintained by a constant infusion of pentobarbital (50 µg/kg/min); fentanyl (10 g/kg/h) serves as analgesic. An alternative to pentobarbital consists of using isoflurane (1-2% by volume).

The dog is provided with the following:
bladder catheter for bladder emptying or measurement of urine flow
ECG leads to the extremities (for ECG measurement)
insertion of a NaCl-filled Fluidmedic-PE-300 loop into the *A. femoralis*. This is linked to a pressure sensor (Braun Melsungen, Melsungen, Germany) for measuring the systemic blood pressure
insertion of a NaCl-filled venous catheter (Vygon, Germany) into the *V. femoralis* for infusing test substances or withdrawing blood.
insertion of a Millar Tip catheter (Typ 350 PC, Millar Instruments, Houston, USA) via the left atrium or via a sluice for measuring the heart haemodynamics incorporated into the *A. carotis*
insertion of a Swan-Ganz catheter (CCOmbo 7.5F, Edwards, Irvine, USA) via the *V. jugularis* into the *A. pulmonalis* for measuring cardiac output, oxygen saturation, pulmonary arterial pressures and central venous pressure.
provision of an ultrasound flowmeter probe (Transsonic Systems, Ithaka, USA) to the Aorta descendens for measuring aorta flow
provision of an ultrasound flowmeter probe (Transsonic Systems, Ithaka, USA) to the left Aorta *coronaria* for measuring coronary flow
placement of a Braunille into the *Venae cephalicae* for infusing pentobarbital, liquid substitution and for withdrawing blood (determination of the substance plasma levels or other clinical blood values)
placement of a Braunille into the *Venae saphenae* for infusing fentanyl and substance application The primary signals are possibly amplified (Gould Amplifier, Gould Instrument Systems, Valley View, USA) or Edwards Vigilance Monitor (Edwards, Irvine, USA) and subsequently fed into the Ponemah system (DataSciences Inc, Minneapolis, USA) for evaluation. The signals are recorded continuously over the whole experimental time course, further processed digitally by this software and averaged over 30 s.

B-12. Effects of the Test Substances on the Heart Rate and Heart Rate Variability in Healthy, Conscious Dogs To characterize test substances with regard to their effect on heart rate, heart rate variability (HRV) and blood pressure, telemetric measurements are conducted in healthy, male Beagle dogs. Under isoflurane anaesthesia, a telemetry transmitter (model L21, from Data Sciences International, USA) is firstly implanted in the animals. After left-sided thoracotomy, pressure sensors are then placed in the aorta and in the left ventricle. To record an electrocardiogram (ECG), further electrodes are placed on the heart. For wound healing, the animals are then placed back in the pen under antiobiotic (clindamycin, Zoetis, Germany) and analgesic (fentanyl, Janssen, Germany) aftercare. By means of the antennae installed in the animal pen, the blood pressure and ECG signals are forwarded to a data acquistion computer and evaluated by analysis software (Ponemah, Data Sciences International, USA). The telemetry system makes it possible to continuously monitor blood pressures and ECG signals in conscious animals. Technical details can be found in the documentation from the manufacturing company (Data Sciences International, USA).

The substances to be investigated are administered orally to the healthy dogs in suitable solvent mixtures by means of a gelatine capsule. A vehicle-treated group of animals is employed as control. The telemetry measurement is started before substance administration and recorded for a time period of several hours. The time course is displayed graphically by means of data smoothed by determination of means with the aid of the GraphPadPrism software (GraphPad, USA). To analyse the HRV, the ECG data are subjected to a frequency-domain heart rate variability analysis. For this purpose, the R-R intervals of the recorded ECGs are used. Data outside the previously defined range of 0.2 s-1.5 s are excluded from the analysis. The excluded data are replaced by values which had been obtained by linear interpolation. These data are converted by spline interpolation into equally-spaced supporting points. To analyse the heart rate variability, the data are further subdivided in 30 s steps to packets of 300 s length. For each data packet, a Fourier transformation is calculated. The power is further calculated in three frequency bands (vlf=0.0033-0.04 1/s; lf=0.04-0.15 1/s; hf=0.15-0.5 1/s). To characterize the test substance, the total power (sum total of all three frequency bands) of the HRV analysis is used.

The invention claimed is:
1. A compound of formula (I)

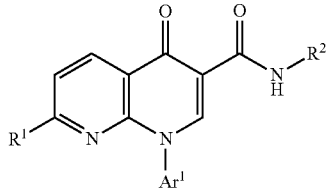

wherein
$R^1$ is $NR^4R^5$,
wherein
$R^4$ is hydrogen, methyl, $(C_2\text{-}C_4)$-alkyl, or $(C_3\text{-}C_6)$-cycloalkyl,
wherein $(C_2\text{-}C_4)$-alkyl may be substituted by hydroxyl or up to trisubstituted by fluorine; and
$R^5$ is $(C_1\text{-}C_6)$-alkyl, $(C_3\text{-}C_6)$-cycloalkyl, 3- to 6-membered saturated heterocyclyl or $(C_1\text{-}C_4)$-alkylsulphonyl,
wherein $(C_1\text{-}C_6)$-alkyl, $(C_3\text{-}C_6)$-cycloalkyl and 3- to 6-membered saturated heterocyclyl may be up to trisubstituted, identically or differently, by methyl, difluoromethyl, trifluoromethyl, hydroxyl, hydroxycarbonyl, oxo, methoxy, difluoromethoxy, trifluoromethoxy and cyano, and additionally up to tetrasubstituted by fluorine; or
$R^4$ and $R^5$ together with the nitrogen atom to which they are bonded form a saturated or partially unsaturated, 3- to 6-membered monocyclic or 6- to 10-membered bicyclic heterocycle which may contain one or two further, identical or different heteroatoms from the group of N, O, S, SO and/or $SO_2$ as ring members,
wherein the 3- to 6-membered monocyclic and the 6- to 10-membered bicyclic heterocycle may each be substituted by 1 to 5 substituents independently selected from the group of $(C_1\text{-}C_4)$-alkyl, difluoromethyl, trifluoromethyl, 3ydroxyl, hydroxycarbonyl, oxo, $(C_1\text{-}C_3)$-alkoxy, difluoromethoxy, trifluoromethoxy, cyano, $(C_1\text{-}C_3)$-alkoxycarbonyl, aminocarbonyl, mono-$(C_1\text{-}C_3)$-alkylaminocarbonyloxy, —NHC(=O)$R^{22A}$ and $CH_2NHC(=O)R^{22B}$, and additionally up to tetrasubstituted by fluorine, wherein
$R^{22A}$ and $R^{22B}$ are independently $(C_1\text{-}C_3)$-alkyl or cyclopropyl, and
wherein $(C_1\text{-}C_4)$-alkyl may be mono- or disubstituted, identically or differently, by hydroxyl and $(C_1\text{-}C_3)$-alkoxy, and up to tetrasubstituted by fluorine;
$R^2$ is a group of the formula

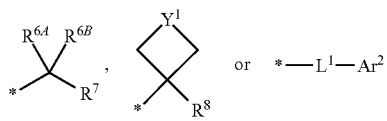

wherein
* marks the bonding site to the nitrogen atom of the amide moiety;

$R^{6A}$ is hydrogen or $(C_1\text{-}C_4)$-alkyl;
$R^{6B}$ is hydrogen, $(C_1\text{-}C_4)$-alkyl, cyclopropyl, trifluoromethyl, methoxymethyl, or trifluoromethoxymethyl;
$R^7$ is $(C_1\text{-}C_4)$-alkyl, cyclopropyl, or cyclobutyl,
wherein $(C_1\text{-}C_4)$-alkyl may be up to pentasubstituted and cyclopropyl and cyclobutyl up to tetrasubstituted by fluorine;
$Y^1$ is $(CH_2)_k$—, —$CF_2$—, —O—$CH_2$—, —$CH_2$—O—, or —$CH_2$—O—$CH_2$—,
wherein
k is 0, 1, 2, or 3;
$R^8$ is up to penta-fluorine-substituted $(C_1\text{-}C_2)$-alkyl or trifluoromethoxymethyl;
$L^1$ is a bond or a group of the formula —$C(R^{9A}R^{9B})$—$(C(R^{10A}R^{10B}))_m$—,
wherein
m is 0 or 1;
$R^{9A}$ is hydrogen or methyl;
$R^{9B}$ is hydrogen, methyl, trifluoromethyl, pentafluoroethyl or trifluoromethoxymethyl;
$R^{10A}$ and $R^{10B}$ are independently hydrogen or methyl;
$Ar^2$ is phenyl,
wherein phenyl may be mono- to trisubstituted, identically or differently, by fluorine, chlorine, $(C_1\text{-}C_3)$-alkyl, difluoromethoxymethyl, trifluoromethoxymethyl and/or trifluoromethyl, or
is a 5- to 10-membered bicyclic or tricyclic carbocycle,
wherein the 5- to 10-membered bicyclic or tricyclic carbocycle may be up to trisubstituted, identically or differently, by $(C_1\text{-}C_3)$-alkyl and trifluoromethyl, and additionally up to tetrasubstituted by fluorine;
$Ar^1$ is a group of the formula

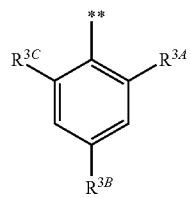

wherein
** marks the bonding site to the nitrogen atom;
$R^{3A}$ is fluorine, chlorine or trifluoromethyl;
$R^{3B}$ is hydrogen or fluorine; and
$R^{3C}$ is hydrogen, fluorine, or chlorine,
or an N-oxide, a salt, a solvate, a salt of an N-oxide, a solvate of an N-oxide, or a solvate of a salt thereof.
2. The compound according to claim 1,
wherein
$R^1$ is $NR^4R^5$,
wherein
$R^4$ is hydrogen or methyl; and
$R^5$ is $(C_1\text{-}C_4)$-alkyl or methylsulphonyl,
wherein $(C_1\text{-}C_4)$-alkyl may be up to disubstituted by hydroxyl and additionally up to trisubstituted by fluorine; or
$R^4$ and $R^5$ together with the nitrogen atom to which they are bonded form a saturated or partially unsaturated, 4- to 6-membered monocyclic or 6- to 10-membered bicyclic heterocycle which may contain one or two further heteroatoms from the group of N, O, S, SO and $SO_2$ as ring member, wherein the 4- to 6-membered monocyclic and the 6- to 10-membered bicyclic heterocycle may each be substituted by 1 to 5 substituents independently selected from the group consisting of $(C_1-C_3)$-alkyl, difluoromethyl, trifluoromethyl, hydroxymethyl, hydroxyethyl, hydroxyl, oxo, methoxy, difluoromethoxy, trifluoromethoxy, methoxymethyl, cyano, methoxycarbonyl, aminocarbonyl and monomethylaminocarbonyloxy, and additionally up to tetrasubstituted by fluorine;

$R^2$ is a group of the formula

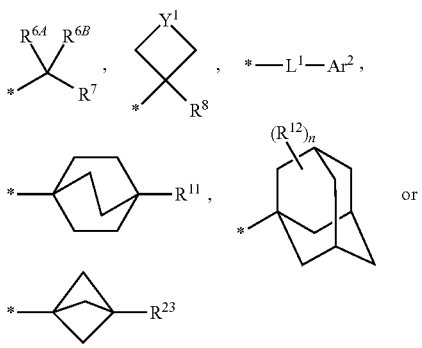

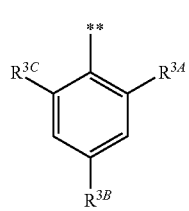

wherein
* marks the bonding site to the nitrogen atom of the amide moiety;
$R^{6A}$ is hydrogen or methyl;
$R^{6B}$ is hydrogen, $(C_1-C_4)$-alkyl, cyclopropyl, trifluoromethyl or trifluoromethoxymethyl;
$R^7$ is $(C_1-C_4)$-alkyl, cyclopropyl, or cyclobutyl,
  wherein $(C_1-C_4)$-alkyl may be up to penta substituted by fluorine;
$Y^1$ is $-(CH_2)_k-$, $-CF_2-$, $-O-CH_2-$, $-CH_2-O-$, or $-CH_2-O-CH_2-$,
  wherein
  k is 0, 1, 2 or 3;
$R^8$ is methyl, trifluoromethyl, or 2,2,2-trifluoroethyl;
$L^1$ is a bond or a group of the formula $-CR^{9A}R^{9B}-$,
  wherein
  $R^{9A}$ is hydrogen or methyl;
  $R^{9B}$ is hydrogen, methyl, trifluoromethyl, or trifluoromethoxymethyl;
$Ar^2$ is phenyl,
  which may be mono- or disubstituted, identically or differently, by fluorine, chlorine, methyl and/or trifluoromethyl;
$R^{11}$, $R^{12}$ and $R^{23}$ are each independently hydrogen, fluorine, methyl, ethyl, or trifluoroethyl;
n is the number 1 or 2,
wherein, if one of the substituents $R^{11}$, $R^{12}$ or $R^{23}$ occurs twice in each case, its definitions may independently be the same or different;
$Ar^1$ is a group of the formula

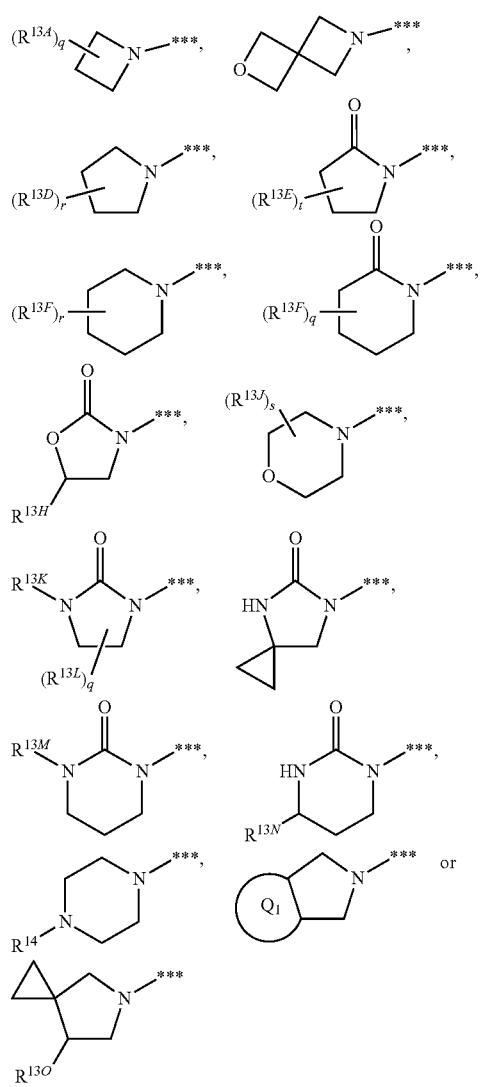

wherein
** marks the bonding site to the nitrogen atom;
$R^{3A}$ is fluorine, chlorine or trifluoromethyl;
$R^{3B}$ is hydrogen or fluorine; and
$R^{3C}$ is hydrogen, fluorine, or chlorine,
or a salt, a solvate, or a solvate of a salt thereof.

3. The compound according to claim 1,
wherein
$R^1$ is $NR^4R^5$,
  wherein
  $R^4$ is hydrogen or methyl; and
  $R^5$ is methyl, isopropyl, 2,2-difluoroethyl, 2,2,2-trifluoroethyl, 2-hydroxyethyl or 2-hydroxypropyl, or
  is a 4- to 6-membered monocyclic or 6- to 8-membered bicyclic heterocycle which is bonded via a nitrogen atom and is of the formula wherein
*** marks the bonding site to the carbon atom of the pyridine ring;
the ring $Q_i$ is a group of the formula wherein
¹ and #² mark the bonding site to the carbon atom of the pyrrolidine ring; and
Y⁷ is —CF₂— or —CHR¹⁵—,
wherein
R¹⁵ is methoxymethyl; and
R¹⁶ is hydroxyl;
$R^{13A}$ is fluorine, hydroxyl, hydroxymethyl, methyl, trifluoromethyl, or methoxy;
$R^{13D}$ is hydrogen, fluorine, methyl, hydroxyl, hydroxymethyl, methoxy or difluoromethoxy;
$R^{13E}$ is hydrogen, fluorine, methyl, hydroxyl, hydroxymethyl, or methoxy;
$R^{13F}$ is fluorine, methyl, hydroxyl, hydroxymethyl or cyano;
$R^{13G}$ is fluorine or hydroxyl;
$R^{13H}$ is hydrogen, methyl, hydroxymethyl, aminocarbonyl, or methoxycarbonyl;
$R^{13J}$ is oxo, hydroxymethyl, or difluoromethyl;
$R^{13K}$ is hydrogen, methyl, or 2-hydroxyethyl;
$R^{13L}$ is hydrogen or methyl;
$R^{13M}$ is ethyl, 2-hydroxyethyl, or cyano;
$R^{13N}$ is hydrogen or ethyl;
$R^{13O}$ is hydrogen or hydroxyl;
$R^{14}$ is methyl, methoxycarbonyl, or aminocarbonyl;
q is the number 0, h or 2;
r is the number 0, 1, 2, or 3;
s is the number 0 or 1;
t is the number 0, 1, 2, 3 or 4;
wherein, in the case that the substituents $R^{13A}$, $R^{13D}$, $R^{13E}$, $R^{13F}$, $R^{13G}$, $R^{13J}$, and $R^{13L}$ occur more than once, the definitions thereof may each be the same or different;
$R^2$ is a group of the formula wherein
* marks the bonding site to the nitrogen atom of the amide moiety;
$R^{6A}$ is hydrogen or methyl;
$R^{6B}$ is methyl, ethyl, cyclopropyl, trifluoromethyl, or trifluoromethoxymethyl;

$R^7$ is methyl, ethyl, n-propyl, isopropyl, tert-butyl, 2-methylprop-1-yl, trifluoromethyl, difluoromethyl, pentafluoroethyl, 2,2,2-trifluoroethyl, or cyclopropyl;
$R^8$ is 2,2,2-trifluoroethyl;
$L^1$ is a bond or a group of the formula —$CR^{9A}R^{9B}$—,
wherein
$R^{9A}$ is hydrogen or methyl;
$R^{9B}$ is hydrogen, methyl, trifluoromethyl, or trifluoromethoxymethyl;
$Ar^2$ is phenyl,
which may be mono- or disubstituted, identically or differently, by fluorine, chlorine, methyl, and/or trifluoromethyl;
$R^{11}$ is hydrogen, fluorine or methyl;
$R^{12A}$ is hydrogen, fluorine, methyl, ethyl, or trifluoromethyl;
$R^{12B}$ is hydrogen or fluorine;
$R^{23}$ is hydrogen, fluorine or trifluoromethyl; and
$Ar^1$ is a group of the formula wherein
** marks the bonding site to the nitrogen atom;
$R^{3A}$ is fluorine or chlorine;
$R^{3B}$ is hydrogen or fluorine; and
$R^{3C}$ is hydrogen, fluorine, or chlorine,
or a salt, a solvate, or a solvate of a salt thereof.

4. The compound according to claim 1,
wherein
$R^1$ is a group of the formula -continued

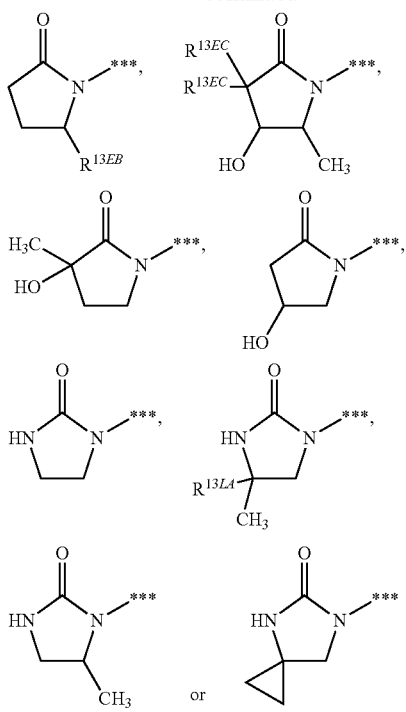

wherein

*** marks the bonding site to the carbon atom of the pyridine ring;

$R^{13DA}$ is hydrogen or methyl;

$R^{13EA}$ is hydroxyl or hydroxymethyl;

$R^{13EB}$ is methyl or hydroxymethyl;

$R^{13EC}$ is hydrogen or methyl;

$R^{13LA}$ is hydrogen or methyl;

$R^2$ is a group of the formula

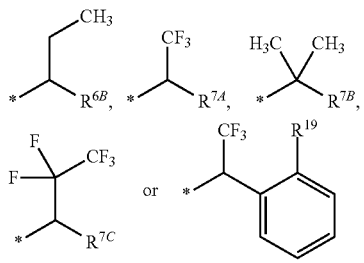

wherein

* marks the bonding site to the nitrogen atom of the amide moiety;

$R^{6B}$ is trifluoromethoxymethyl;

$R^{7A}$ is methyl, ethyl, trifluoromethyl, or cyclopropyl;

$R^{7B}$ is trifluoromethyl, difluoromethyl, or 2,2,2-trifluoroethyl;

$R^{7C}$ is methyl or ethyl;

$R^{19}$ is chlorine; and $Ar^1$ is a group of the formula

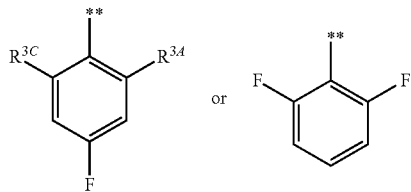

wherein

** marks the bonding site to the nitrogen atom;

$R^{3A}$ is fluorine or chlorine; and $R^{3C}$ is hydrogen or fluorine, or a salt, a solvate, or a solvate of a salt thereof.

5. The compound according to claim 1, wherein $R^1$ is a group of the formula

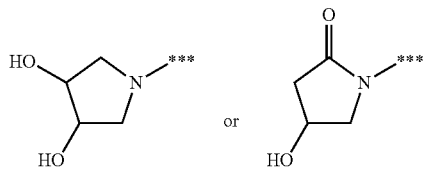

wherein

*** marks the bonding site to the carbon atom of the pyridine ring;

$R^2$ is a group of the formula

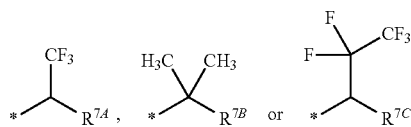

wherein

* marks the bonding site to the nitrogen atom of the amide moiety;

$R^{7A}$ is ethyl, trifluoromethyl, or cyclopropyl;

$R^{7B}$ is trifluoromethyl;

$R^{7C}$ is methyl or ethyl; and $Ar^1$ is a group of the formula

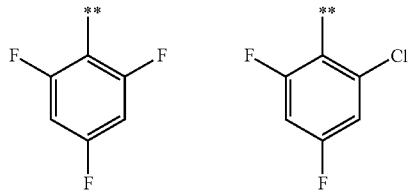

wherein

** marks the bonding site to the nitrogen atom, or a salt, a solvate, or a solvate of a salt thereof.

6. A process for preparing a compound of formula (I) according to claim 1, wherein

[A] a compound of the formula (II)

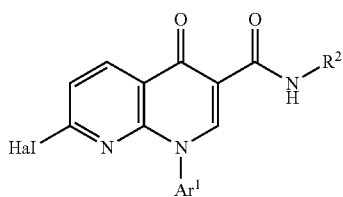

wherein $R^2$ and $Ar^1$ are as defined in claim 1, and Hal is fluorine, chlorine, bromine or iodine, is reacted with a compound of the formula (III)

$R^1$—H   (III)

wherein $R^1$ is as defined in claim 1, to give the carboxamide of the formula (I)

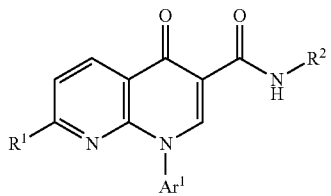

wherein $R^1$, $R^2$ and $Ar^1$ are as defined in claim 1, or [B] a compound of the formula (IV)

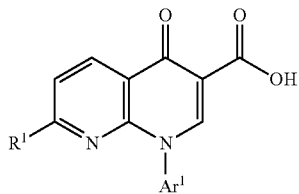

wherein $R^1$ and $Ar^1$ are as defined in claim 1, is reacted with a compound of the formula (V)

$R^2$—$NH_2$   (V)

wherein $R^2$ is as defined in claim 1, to give the compound of the formula (I)

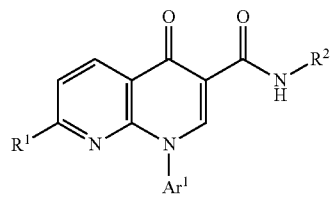

wherein $R^1$, $R^2$ and $Ar^1$ are as defined in claim 1, and wherein the compound of formula (I) is optionally separated into enantiomers and/or diastereomers and/or converted with the appropriate (i) solvents and/or (ii) bases or acids to a solvate, a salt, or a solvate of a salt thereof.

7. A pharmaceutical combination comprising a compound according to claim 1 in combination with one or more further active ingredients selected from the group consisting of active hypotensive ingredients, active antiarrhythmic ingredients, vasopressin receptor antagonists, PDE 5 inhibitors, platelet aggregation inhibitors, sGC activators and sGC stimulators.

8. A pharmaceutical composition comprising a compound according to claim 1 in combination with an inert, non-toxic, pharmaceutically suitable excipient.

* * * * *